US012553031B2

(12) United States Patent
Simpson-Abelson et al.

(10) Patent No.: US 12,553,031 B2
(45) **Date of Patent: *Feb. 17, 2026**

(54) METHODS AND COMPOSITIONS FOR T-CELL COCULTURE POTENCY ASSAYS AND USE WITH CELL THERAPY PRODUCTS

(71) Applicant: Iovance Biotherapeutics, Inc., San Carlos, CA (US)

(72) Inventors: Michelle R. Simpson-Abelson, Lithia, FL (US); Matthew J. Frigault, Dorchester, MA (US); Wayne P. Rothbaum, New York, NY (US); Michael Weiser, Miami, FL (US)

(73) Assignee: Iovance Biotherapeutics, Inc., San Carlos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/668,092

(22) Filed: May 17, 2024

(65) Prior Publication Data

US 2024/0325509 A1 Oct. 3, 2024

Related U.S. Application Data

(63) Continuation of application No. 18/477,810, filed on Sep. 29, 2023, which is a continuation of application No. 17/705,159, filed on Mar. 25, 2022.

(60) Provisional application No. 63/309,919, filed on Feb. 14, 2022, provisional application No. 63/286,145, filed on Dec. 6, 2021, provisional application No. 63/246,890, filed on Sep. 22, 2021, provisional application No. 63/233,035, filed on Aug. 13, 2021, provisional application No. 63/212,933, filed on Jun. 21, 2021, provisional application No. 63/189,829, filed on May 18, 2021, provisional application No. 63/166,210, filed on Mar. 25, 2021.

(51) Int. Cl.

| | |
|---|---|
| ***C12N 5/0783*** | (2010.01) |
| ***A61K 39/00*** | (2006.01) |
| ***A61K 40/11*** | (2025.01) |
| ***A61K 40/42*** | (2025.01) |
| ***G01N 33/50*** | (2006.01) |
| ***G01N 33/68*** | (2006.01) |

(52) U.S. Cl.

CPC ........ *C12N 5/0638* (2013.01); *A61K 39/0011* (2013.01); *A61K 40/11* (2025.01); *A61K 40/42* (2025.01); *G01N 33/5008* (2013.01); *G01N 33/505* (2013.01); *G01N 33/6866* (2013.01); *A61K 2039/5158* (2013.01); *A61K 2039/545* (2013.01); *A61K 2039/55533* (2013.01); *A61K 2239/38* (2023.05); *A61K 2239/48* (2023.05); *A61K 2239/55* (2023.05); *C12N 2501/2302* (2013.01); *C12N 2502/1114* (2013.01); *C12N 2502/30* (2013.01); *C12N 2503/00* (2013.01); *G01N 2333/57* (2013.01); *G01N 2500/10* (2013.01)

(58) Field of Classification Search

CPC .................... C12N 2502/1114; G01N 2333/57

See application file for complete search history.

(56) References Cited

U.S. PATENT DOCUMENTS

| | | | |
|---|---|---|---|
| 4,660,971 | A | 4/1987 | Sage et al. |
| 4,662,742 | A | 5/1987 | Chupp |
| 4,710,635 | A | 12/1987 | Chupp |
| 4,766,106 | A | 8/1988 | Katre et al. |
| 4,818,103 | A | 4/1989 | Thomas et al. |
| 4,897,355 | A | 1/1990 | Eppstein et al. |
| 4,902,502 | A | 2/1990 | Nitecki et al. |
| 5,019,034 | A | 5/1991 | Weaver et al. |
| 5,057,413 | A | 10/1991 | Terstappen et al. |
| 5,089,261 | A | 2/1992 | Nitecki et al. |
| 5,126,132 | A | 6/1992 | Rosenberg |
| 5,128,257 | A | 7/1992 | Baer |
| 5,137,817 | A | 8/1992 | Busta et al. |
| 5,173,158 | A | 12/1992 | Schmukler |
| 5,206,344 | A | 4/1993 | Katre et al. |
| 5,232,856 | A | 8/1993 | Firth |
| 5,273,525 | A | 12/1993 | Hofmann |
| 5,279,833 | A | 1/1994 | Rose |

(Continued)

FOREIGN PATENT DOCUMENTS

| | | |
|---|---|---|
| CN | 102816734 | 12/2012 |
| CN | 106244538 A | 12/2016 |

(Continued)

OTHER PUBLICATIONS

Salerno et al. Critical role of post-transcriptional regulation for IFN-γ in tumor-infiltrating T cells. Oncoimmunology. Oct. 22, 2018;8(2):e1532762. (Year: 2018).*

(Continued)

*Primary Examiner* — Valarie E Bertoglio
*Assistant Examiner* — Briana N Ebbinghaus
(74) *Attorney, Agent, or Firm* — Melissa J. Brayman

(57) ABSTRACT

The present invention provides novel processes, compositions, and methods for analyzing or assaying the potency and/or functionality of tumor infiltrating lymphocyte (TIL) products for use in therapy, including human cancer therapy, and analyzing or assaying the potency and/or functionality of other polyclonal products, such as marrow infiltrating lymphocyte (MIL) and peripheral blood lymphocyte (PBL) products. Compositions, methods, and kits for preparing and treating cancer using TIL, MIL, and PBL products are also provided.

13 Claims, 217 Drawing Sheets

Specification includes a Sequence Listing.

(56) References Cited

U.S. PATENT DOCUMENTS 5,304,120 A 4/1994 Crandell et al.
5,318,514 A 6/1994 Hofmann
5,443,983 A 8/1995 Ochoa et al.
5,593,875 A 1/1997 Wurm et al.
5,620,842 A 4/1997 Davis et al.
5,641,457 A 6/1997 Vardanega et al.
5,648,260 A 7/1997 Winter et al.
5,714,350 A 2/1998 Co et al.
5,739,277 A 4/1998 Presta et al.
5,766,902 A 6/1998 Craig et al.
5,811,097 A 9/1998 Allison et al.
5,824,778 A 10/1998 Ishikawa et al.
5,834,250 A 11/1998 Wells et al.
5,849,902 A 12/1998 Arrow et al.
5,855,887 A 1/1999 Allison et al.
5,869,046 A 2/1999 Presta et al.
5,898,031 A 4/1999 Crooke
5,908,635 A 6/1999 Thierry
5,928,893 A 7/1999 Kang et al.
5,977,318 A 11/1999 Linsley et al.
5,985,216 A 11/1999 Rens et al.
6,010,613 A 1/2000 Walters et al.
6,025,337 A 2/2000 Truong et al.
6,051,227 A 4/2000 Allison et al.
6,056,938 A 5/2000 Unger et al.
6,078,490 A 6/2000 Walters
6,079,836 A 6/2000 Burr et al.
6,096,871 A 8/2000 Presta et al.
6,107,094 A 8/2000 Crooke
6,110,490 A 8/2000 Thierry
6,121,022 A 9/2000 Presta et al.
6,194,551 B1 2/2001 Idusogie et al.
6,207,156 B1 3/2001 Kuchroo et al.
6,210,669 B1 4/2001 Aruffo et al.
6,242,195 B1 6/2001 Idusogie et al.
6,256,096 B1 7/2001 Johnson
6,277,375 B1 8/2001 Ward
6,303,121 B1 10/2001 Kwon
6,312,700 B1 11/2001 Weinberg
6,350,861 B1 2/2002 Co et al.
6,352,694 B1 3/2002 June et al.
6,362,325 B1 3/2002 Kwon
6,410,517 B1 6/2002 Truong et al.
6,475,994 B2 11/2002 Tomalia et al.
6,479,626 B1 11/2002 Kim et al.
6,482,652 B2 11/2002 Furlong et al.
6,489,458 B2 12/2002 Hackett et al.
6,495,333 B1 12/2002 Willmann et al.
6,506,559 B1 1/2003 Fire et al.
6,528,624 B1 3/2003 Idusogie et al.
6,534,055 B1 3/2003 June et al.
6,534,261 B1 3/2003 Cox et al.
6,534,484 B1 3/2003 Wheeler et al.
6,538,124 B1 3/2003 Idusogie et al.
6,569,997 B1 5/2003 Kwon
6,607,882 B1 8/2003 Cox et al.
6,627,442 B1 9/2003 Humeau et al.
6,682,736 B1 1/2004 Hanson et al.
6,700,130 B2 3/2004 Fritz
6,706,289 B2 3/2004 Lewis et al.
6,737,056 B1 5/2004 Presta
6,746,838 B1 6/2004 Choo et al.
6,794,136 B1 9/2004 Eisenberg et al.
6,821,505 B2 11/2004 Ward
6,824,978 B1 11/2004 Cox et al.
6,866,997 B1 3/2005 Choo et al.
6,867,041 B2 3/2005 Berenson et al.
6,887,466 B2 5/2005 June et al.
6,887,673 B2 5/2005 Kunkel et al.
6,903,185 B2 6/2005 Kim et al.
6,905,680 B2 6/2005 June et al.
6,905,681 B1 6/2005 June et al.
6,905,685 B2 6/2005 Kwon
6,933,113 B2 8/2005 Case et al.
6,974,863 B2 12/2005 Kwon
6,979,539 B2 12/2005 Cox et al.
6,984,720 B1 1/2006 Korman et al.
6,998,253 B1 2/2006 Presta et al.
7,013,219 B2 3/2006 Case et al.
7,030,215 B2 4/2006 Liu et al.
7,056,704 B2 6/2006 Tuschl et al.
7,078,196 B2 7/2006 Tuschl et al.
7,083,784 B2 8/2006 Dall'Acqua et al.
7,109,003 B2 9/2006 Hanson et al.
7,132,281 B2 11/2006 Hanson et al.
7,144,575 B2 12/2006 June et al.
7,175,843 B2 2/2007 June et al.
7,189,705 B2 3/2007 Lam et al.
7,214,493 B2 5/2007 Kunkel et al.
7,220,719 B2 5/2007 Case et al.
7,232,566 B2 6/2007 June et al.
7,241,573 B2 7/2007 Choo et al.
7,241,574 B2 7/2007 Choo et al.
7,282,564 B2 10/2007 Mello et al.
7,288,638 B2 10/2007 Jure-Kunkel et al.
7,432,249 B2 10/2008 Crooke
7,432,250 B2 10/2008 Crooke
7,479,269 B2 1/2009 June et al.
7,504,101 B2 3/2009 Weinberg
7,538,095 B2 5/2009 Fire et al.
7,550,140 B2 6/2009 Bakker et al.
7,560,438 B2 7/2009 Fire et al.
7,572,631 B2 8/2009 Berenson et al.
7,585,849 B2 9/2009 Liu et al.
7,595,376 B2 9/2009 Kim et al.
7,622,444 B2 11/2009 Weinberg
7,687,070 B2 3/2010 Gebeyehu et al.
7,696,175 B2 4/2010 Epstein et al.
7,855,078 B2 12/2010 Evans
7,943,743 B2 5/2011 Korman et al.
7,951,365 B2 5/2011 Winqvist et al.
7,960,515 B2 6/2011 Min et al.
7,990,525 B2 8/2011 Kanda
8,007,785 B2 8/2011 Winqvist et al.
8,008,449 B2 8/2011 Korman et al.
8,034,334 B2 10/2011 Dudley et al.
8,133,983 B2 3/2012 Bakker et al.
8,168,757 B2 5/2012 Finnefrock et al.
8,206,702 B2 6/2012 Winqvist et al.
8,211,424 B2 7/2012 Winqvist et al.
8,211,425 B2 7/2012 Winqvist et al.
8,217,149 B2 7/2012 Irving et al.
8,236,930 B2 8/2012 Min et al.
8,287,856 B2 10/2012 Li et al.
8,287,857 B2 10/2012 Dudley et al.
8,337,850 B2 12/2012 Ahrens et al.
8,354,509 B2 1/2013 Carven et al.
8,383,099 B2 2/2013 Dudley et al.
8,450,460 B2 5/2013 Hill et al.
8,580,247 B2 11/2013 Li et al.
8,586,526 B2 11/2013 Gregory et al.
8,617,884 B2 12/2013 Berenson et al.
8,686,119 B2 4/2014 Rotem-Yehudar et al.
8,697,359 B1 4/2014 Zhang
8,735,553 B1 5/2014 Li et al.
8,771,945 B1 7/2014 Zhang
8,779,108 B2 7/2014 Queva et al.
8,795,965 B2 8/2014 Zhang
8,809,050 B2 8/2014 Vera et al.
8,821,867 B2 9/2014 Ahrens et al.
8,865,406 B2 10/2014 Zhang et al.
8,871,445 B2 10/2014 Cong et al.
8,889,356 B2 11/2014 Zhang
8,895,308 B1 11/2014 Zhang et al.
8,906,616 B2 12/2014 Zhang et al.
8,907,053 B2 12/2014 Sasikumar et al.
8,921,519 B2 12/2014 Hill et al.
8,932,814 B2 1/2015 Zhang et al.
8,945,839 B2 2/2015 Zhang
8,956,860 B2 2/2015 Vera et al.
8,962,804 B2 2/2015 Williams et al.
8,993,233 B2 3/2015 Zhang et al.
8,999,641 B2 4/2015 Zhang et al.
9,006,399 B2 4/2015 Liu et al.

(56) References Cited

U.S. PATENT DOCUMENTS

| | | | |
|---|---|---|---|
| 9,028,824 | B2 | 5/2015 | Min et al. |
| 9,044,442 | B2 | 6/2015 | Sasikumar et al. |
| 9,074,185 | B2 | 7/2015 | Dudley et al. |
| 9,080,171 | B2 | 7/2015 | Khvorova et al. |
| 9,096,642 | B2 | 8/2015 | Sasikumar et al. |
| 9,163,085 | B2 | 10/2015 | Liu et al. |
| 9,340,599 | B2 | 5/2016 | Hill et al. |
| 9,341,562 | B2 | 5/2016 | Martini et al. |
| 9,359,420 | B2 | 6/2016 | Hill et al. |
| 9,453,791 | B2 | 9/2016 | Schreuder et al. |
| 9,468,678 | B2 | 10/2016 | Ahrens et al. |
| 9,476,028 | B2 | 10/2016 | Karlsson-Parra et al. |
| 9,528,088 | B2 | 12/2016 | Berenson et al. |
| 9,631,225 | B2 | 4/2017 | Hawkins et al. |
| 9,645,010 | B2 | 5/2017 | Lo et al. |
| 9,677,989 | B2 | 6/2017 | Sklar et al. |
| 9,687,510 | B2 | 6/2017 | Borrello et al. |
| 9,790,490 | B2 | 10/2017 | Zhang et al. |
| 9,844,569 | B2 | 12/2017 | Gros et al. |
| 9,914,783 | B1 | 3/2018 | Afar et al. |
| 10,130,659 | B2 | 11/2018 | Wardell et al. |
| 10,137,479 | B2 | 11/2018 | Sinha et al. |
| 10,144,779 | B2 | 12/2018 | van Dijk et al. |
| 10,166,257 | B2 | 1/2019 | Wardell et al. |
| 10,183,979 | B2 | 1/2019 | Alvarez et al. |
| 10,272,113 | B2 | 4/2019 | Wardell et al. |
| 10,363,273 | B2 | 7/2019 | Wardell et al. |
| 10,398,734 | B2 | 9/2019 | Wardell et al. |
| 10,415,015 | B2 | 9/2019 | Veerapathran et al. |
| 10,420,799 | B2 | 9/2019 | Wardell et al. |
| 10,436,698 | B2 | 10/2019 | Bandura et al. |
| 10,463,697 | B2 | 11/2019 | Wardell et al. |
| 10,537,595 | B2 | 1/2020 | Wardell et al. |
| 10,639,330 | B2 | 5/2020 | Wardell et al. |
| 10,646,517 | B2 | 5/2020 | Wardell et al. |
| 10,648,900 | B2 | 5/2020 | Mach et al. |
| 10,653,723 | B1 | 5/2020 | Wardell et al. |
| 10,695,372 | B2 | 6/2020 | Wardell et al. |
| 10,816,550 | B2 | 10/2020 | Cho et al. |
| 10,894,063 | B2 | 1/2021 | Wardell et al. |
| 10,905,718 | B2 | 2/2021 | Wardell et al. |
| 10,918,666 | B2 | 2/2021 | Wardell et al. |
| 10,935,482 | B2 | 3/2021 | Diebold et al. |
| 11,026,974 | B2 | 6/2021 | Frank et al. |
| 11,083,752 | B2 | 8/2021 | Wardell et al. |
| 11,168,303 | B2 | 11/2021 | Wardell et al. |
| 11,168,304 | B2 | 11/2021 | Wardell et al. |
| 2001/0006416 | A1 | 7/2001 | Johnson |
| 2002/0039581 | A1 | 4/2002 | Carreno et al. |
| 2002/0086014 | A1 | 7/2002 | Korman et al. |
| 2002/0186375 | A1 | 12/2002 | Asbury et al. |
| 2003/0051263 | A1 | 3/2003 | Fire et al. |
| 2003/0055020 | A1 | 3/2003 | Fire et al. |
| 2003/0056235 | A1 | 3/2003 | Fire et al. |
| 2004/0110704 | A1 | 6/2004 | Yamane et al. |
| 2004/0265839 | A1 | 12/2004 | Mello et al. |
| 2005/0095244 | A1 | 5/2005 | Jure-Kunkel et al. |
| 2005/0100913 | A1 | 5/2005 | Mello et al. |
| 2005/0106717 | A1 | 5/2005 | Wilson et al. |
| 2005/0201994 | A1 | 9/2005 | Korman et al. |
| 2006/0024798 | A1 | 2/2006 | Mello et al. |
| 2008/0050342 | A1 | 2/2008 | Fire et al. |
| 2008/0055443 | A1 | 3/2008 | Okamoto et al. |
| 2008/0081373 | A1 | 4/2008 | Fire et al. |
| 2008/0248576 | A1 | 10/2008 | Fire et al. |
| 2009/0028857 | A1 | 1/2009 | Li et al. |
| 2010/0136030 | A1 | 6/2010 | Salah-Eddine et al. |
| 2010/0203056 | A1 | 8/2010 | Irving et al. |
| 2010/0266617 | A1 | 10/2010 | Carven et al. |
| 2010/0285013 | A1 | 11/2010 | Li et al. |
| 2011/0008369 | A1 | 1/2011 | Finnefrock et al. |
| 2011/0027218 | A1 | 2/2011 | Hill et al. |
| 2011/0039914 | A1 | 2/2011 | Pavco et al. |
| 2011/0052530 | A1 | 3/2011 | Dudley et al. |
| 2011/0111494 | A1 | 5/2011 | Hill et al. |
| 2011/0136228 | A1 | 6/2011 | Vera et al. |
| 2011/0201118 | A1 | 8/2011 | Yang et al. |
| 2012/0244133 | A1 | 9/2012 | Rosenberg et al. |
| 2013/0022600 | A1 | 1/2013 | Li et al. |
| 2013/0034559 | A1 | 2/2013 | Queva et al. |
| 2013/0045200 | A1 | 2/2013 | Irving et al. |
| 2013/0045201 | A1 | 2/2013 | Irving et al. |
| 2013/0045202 | A1 | 2/2013 | Irving et al. |
| 2013/0102075 | A1 | 4/2013 | Vera et al. |
| 2013/0108651 | A1 | 5/2013 | Carven et al. |
| 2013/0109843 | A1 | 5/2013 | Carven et al. |
| 2013/0115617 | A1 | 5/2013 | Wilson |
| 2013/0117869 | A1 | 5/2013 | Duchateau et al. |
| 2013/0131141 | A1 | 5/2013 | Khvorova et al. |
| 2013/0131142 | A1 | 5/2013 | Libertine et al. |
| 2013/0315884 | A1 | 11/2013 | Galetto et al. |
| 2014/0065135 | A1 | 3/2014 | Irving et al. |
| 2014/0227237 | A1 | 8/2014 | June et al. |
| 2014/0294898 | A1 | 10/2014 | Miller et al. |
| 2014/0295426 | A1 | 10/2014 | Albelda et al. |
| 2014/0328791 | A1 | 11/2014 | Bossard et al. |
| 2014/0341917 | A1 | 11/2014 | Nastri et al. |
| 2014/0377284 | A1 | 12/2014 | Simons et al. |
| 2014/0377739 | A1 | 12/2014 | Welch et al. |
| 2015/0073024 | A1 | 3/2015 | Sasikumar et al. |
| 2015/0073042 | A1 | 3/2015 | Sasikumar et al. |
| 2015/0087581 | A1 | 3/2015 | Sasikumar et al. |
| 2015/0110734 | A1 | 4/2015 | Hill et al. |
| 2015/0125491 | A1 | 5/2015 | Sasikumar et al. |
| 2015/0126709 | A1 | 5/2015 | Hill et al. |
| 2015/0126710 | A1 | 5/2015 | Hill et al. |
| 2015/0132288 | A1 | 5/2015 | Simons et al. |
| 2015/0175966 | A1 | 6/2015 | Vera et al. |
| 2015/0190506 | A1 | 7/2015 | Cheung et al. |
| 2015/0203871 | A1 | 7/2015 | Juillerat et al. |
| 2015/0320798 | A1 | 11/2015 | Borrello et al. |
| 2016/0010058 | A1 | 1/2016 | Gros et al. |
| 2016/0120906 | A1 | 5/2016 | Galetto et al. |
| 2016/0208216 | A1 | 7/2016 | Vera et al. |
| 2016/0215262 | A1 | 7/2016 | Powell |
| 2016/0304873 | A1 | 10/2016 | Wolfson et al. |
| 2017/0044496 | A1 | 2/2017 | Sarnaik et al. |
| 2017/0081635 | A1 | 3/2017 | Sarnaik et al. |
| 2017/0107490 | A1 | 4/2017 | Maeurer |
| 2017/0114321 | A1 | 4/2017 | Berenson et al. |
| 2017/0152478 | A1 | 6/2017 | Rosenberg et al. |
| 2017/0258838 | A1 | 9/2017 | Borrello et al. |
| 2018/0127715 | A1 | 5/2018 | Veerapathran et al. |
| 2018/0148690 | A1 | 5/2018 | Gros et al. |
| 2018/0187150 | A1 | 7/2018 | De Larichaudy |
| 2018/0207201 | A1 | 7/2018 | Wardell et al. |
| 2018/0228841 | A1 | 8/2018 | Frank et al. |
| 2018/0280436 | A1 | 10/2018 | Wardell et al. |
| 2018/0282694 | A1 | 10/2018 | Wardell et al. |
| 2019/0000070 | A1 | 1/2019 | De Larichaudy et al. |
| 2019/0048096 | A1 | 2/2019 | Hermann et al. |
| 2019/0062706 | A1 | 2/2019 | Almaasbak et al. |
| 2019/0083536 | A1 | 3/2019 | Wardell et al. |
| 2019/0136186 | A1 | 5/2019 | Germeroth et al. |
| 2019/0201334 | A1 | 7/2019 | Hakim et al. |
| 2019/0276802 | A1 | 9/2019 | Simpson-Abelson et al. |
| 2020/0018120 | A1 | 1/2020 | Riddel et al. |
| 2020/0024350 | A1 | 1/2020 | van Dijk et al. |
| 2020/0181220 | A1 | 6/2020 | Ptacin et al. |
| 2020/0223907 | A1 | 7/2020 | Balakrishnan et al. |
| 2020/0224161 | A1 | 7/2020 | Karyampudi et al. |
| 2020/0270334 | A1 | 8/2020 | Deane et al. |
| 2020/0277573 | A1 | 9/2020 | Simpson-Abelson et al. |
| 2020/0330601 | A1 | 10/2020 | Ptacin et al. |
| 2021/0038684 | A1 | 2/2021 | Losey et al. |

FOREIGN PATENT DOCUMENTS

| | | | |
|---|---|---|---|
| CN | 106591232 | A | 4/2017 |
| CN | 107384867 | A | 11/2017 |
| EP | 0154316 | A2 | 9/1985 |
| EP | 0401384 | A1 | 12/1990 |
| EP | 0404097 | A2 | 12/1990 |
| EP | 0672141 | B1 | 9/1995 |

(56) References Cited

FOREIGN PATENT DOCUMENTS

| | | | |
|---|---|---|---|
| EP | 0928290 | B9 | 11/2005 |
| EP | 1212422 | B1 | 2/2007 |
| EP | 1309726 | B2 | 12/2009 |
| EP | 1539929 | B1 | 4/2013 |
| EP | 2925329 | A1 | 10/2015 |
| EP | 3188740 | A1 | 7/2017 |
| EP | 3365434 | A1 | 8/2018 |
| EP | 3368659 | A1 | 9/2018 |
| EP | 3487990 | A1 | 5/2019 |
| WO | WO 1988007089 | A1 | 9/1988 |
| WO | WO 1990014074 | A1 | 11/1990 |
| WO | WO 1991016024 | A1 | 10/1991 |
| WO | WO 1991017424 | A1 | 11/1991 |
| WO | WO 1993011161 | A1 | 6/1993 |
| WO | WO 1995012673 | A1 | 5/1995 |
| WO | WO 1995021925 | A1 | 8/1995 |
| WO | WO 1996014339 | A1 | 5/1996 |
| WO | WO 1996040915 | A2 | 12/1996 |
| WO | WO 1997020574 | A1 | 6/1997 |
| WO | WO 1998030679 | A1 | 1/1998 |
| WO | WO 1998005787 | A1 | 2/1998 |
| WO | WO 1998013526 | A1 | 4/1998 |
| WO | WO 1998023289 | A1 | 6/1998 |
| WO | WO 1998042752 | A1 | 10/1998 |
| WO | WO 1999032619 | A1 | 7/1999 |
| WO | WO 1999051642 | A1 | 10/1999 |
| WO | WO 1999054342 | A1 | 10/1999 |
| WO | WO 1999058572 | A1 | 11/1999 |
| WO | WO 2000009560 | A2 | 2/2000 |
| WO | WO 2000032767 | A2 | 6/2000 |
| WO | WO 2000037504 | A2 | 6/2000 |
| WO | WO 2000042072 | A2 | 7/2000 |
| WO | WO 2001014424 | A3 | 3/2001 |
| WO | WO 2001029058 | A1 | 4/2001 |
| WO | WO 2002044215 | A2 | 6/2002 |
| WO | WO 2002060919 | A2 | 8/2002 |
| WO | WO 2003035835 | A3 | 5/2003 |
| WO | WO 2003074569 | A2 | 9/2003 |
| WO | WO 2003086459 | A1 | 10/2003 |
| WO | WO 2004016750 | A2 | 2/2004 |
| WO | WO 2004029207 | A2 | 4/2004 |
| WO | WO 2004031370 | A1 | 4/2004 |
| WO | WO 2004035607 | A2 | 4/2004 |
| WO | WO 2004035752 | A2 | 4/2004 |
| WO | WO 2004063351 | A2 | 7/2004 |
| WO | WO 2004074455 | A2 | 9/2004 |
| WO | WO 2004081021 | A2 | 9/2004 |
| WO | WO 2004099249 | A2 | 11/2004 |
| WO | WO 2005040217 | A2 | 5/2005 |
| WO | WO 2005070963 | A1 | 8/2005 |
| WO | WO 2005077981 | A2 | 8/2005 |
| WO | WO 2005092380 | A2 | 10/2005 |
| WO | WO 2005092925 | A2 | 10/2005 |
| WO | WO 2005123780 | A2 | 12/2005 |
| WO | WO 2006009649 | A2 | 1/2006 |
| WO | WO 2006019447 | A1 | 2/2006 |
| WO | WO 2006029219 | A2 | 3/2006 |
| WO | WO 2006047350 | A2 | 5/2006 |
| WO | WO 2006085967 | A2 | 8/2006 |
| WO | WO 2006121168 | A1 | 11/2006 |
| WO | WO 2006121810 | A2 | 11/2006 |
| WO | WO 2007067959 | A2 | 6/2007 |
| WO | WO 2008025516 | A2 | 3/2008 |
| WO | WO 2007123737 | A3 | 10/2008 |
| WO | WO 2008156712 | A1 | 12/2008 |
| WO | WO 2009007120 | A2 | 1/2009 |
| WO | WO 2009040789 | A2 | 4/2009 |
| WO | WO 2009045457 | A2 | 4/2009 |
| WO | WO 2009100140 | A1 | 8/2009 |
| WO | WO 2009102427 | A2 | 8/2009 |
| WO | WO 2010003766 | A2 | 1/2010 |
| WO | WO 2010010051 | A1 | 1/2010 |
| WO | WO 2010033246 | A1 | 3/2010 |
| WO | WO 2010033247 | A2 | 3/2010 |
| WO | WO 2010042433 | A1 | 4/2010 |
| WO | WO 2010078966 | A1 | 7/2010 |
| WO | WO 2011072088 | A2 | 6/2011 |
| WO | WO 2011119852 | A1 | 9/2011 |
| WO | WO 2011119887 | A1 | 9/2011 |
| WO | WO 2012027328 | A2 | 3/2012 |
| WO | WO 2012032433 | A1 | 3/2012 |
| WO | WO 2012065086 | A1 | 5/2012 |
| WO | WO 2012177788 | A1 | 6/2012 |
| WO | WO 2012120125 | A1 | 9/2012 |
| WO | WO 2012129201 | A1 | 9/2012 |
| WO | WO 2013028231 | A1 | 2/2013 |
| WO | WO 2013038191 | A2 | 3/2013 |
| WO | WO 2013057500 | A1 | 4/2013 |
| WO | WO 2013059343 | A1 | 4/2013 |
| WO | WO 2013088147 | A1 | 6/2013 |
| WO | WO 2013173835 | A1 | 11/2013 |
| WO | WO 2013188427 | A1 | 12/2013 |
| WO | WO 2014148895 | A1 | 9/2014 |
| WO | WO 2014210036 | A1 | 12/2014 |
| WO | WO 2015009604 | A1 | 1/2015 |
| WO | WO 2015119923 | A1 | 2/2015 |
| WO | WO 2015033301 | A1 | 3/2015 |
| WO | WO 2015036927 | A1 | 3/2015 |
| WO | WO 2015157636 | A1 | 10/2015 |
| WO | WO 2015188839 | A1 | 12/2015 |
| WO | WO 2015189356 | A1 | 12/2015 |
| WO | WO 2015189357 | A1 | 12/2015 |
| WO | WO 2016053338 | A1 | 4/2016 |
| WO | WO 2016096903 | A1 | 6/2016 |
| WO | WO 2017008063 | A1 | 1/2017 |
| WO | WO 2017048614 | A1 | 3/2017 |
| WO | WO 2017070151 | A1 | 4/2017 |
| WO | WO 2017123663 | A1 | 7/2017 |
| WO | WO 2018005712 | A1 | 1/2018 |
| WO | WO 2018081473 | A1 | 5/2018 |
| WO | WO 2018102761 | A1 | 6/2018 |
| WO | WO 2018129332 | A1 | 7/2018 |
| WO | WO 2018170188 | A2 | 9/2018 |
| WO | WO 2018182817 | A1 | 10/2018 |
| WO | WO 2018204760 | A1 | 11/2018 |
| WO | WO 2018209115 | A1 | 11/2018 |
| WO | WO 2018226714 | A1 | 12/2018 |
| WO | WO 2019136456 | A1 | 7/2019 |
| WO | WO 2019145711 | A1 | 8/2019 |
| WO | WO 2019160829 | A1 | 8/2019 |
| WO | WO 2019210131 | A1 | 10/2019 |
| WO | WO 2020096988 | A1 | 5/2020 |
| WO | WO 2020152451 | A1 | 7/2020 |
| WO | WO 2021123832 | A1 | 6/2021 |

OTHER PUBLICATIONS

Pimentel et al. A novel co-culture assay to assess anti-tumor cos+ T cell cytotoxicity via luminescence and multicolor flow cytometry . J Immunol Methods. Dec. 2020:487:112899. (Year: 2020).*

Stonehouse et al. Molecular characterization of U937-dependent T-cell co-stimulation. Immunology. Jan. 1999;96(1):35-4. (Year: 1999).*

Isogai et al. Preparation of Induced Pluripotent Stem Cells Using Human Peripheral Blood Monocytes. Cell Reprogram. Dec. 2018;20(6):347-355. (Year: 2018).*

Bragança et al. Induced pluripotent stem cells, a giant leap for mankind therapeutic applications. World J Stem Cells. Jul. 2, 20196; 11(7): 421-430. Published online Jul. 2, 20196. (Year: 2019).*

Ahmad, Zuhaida Asra et al. "scFv antibody: principles and clinical application." *Clinical & developmental immunology* vol. 2012 (2012): 980250. doi:10.1155/2012/980250.

Akkök, C. A. et al. "Use of different DMSO concentrations for cryopreservation of autologous peripheral blood stem cell grafts does not have any major impact on levels of leukocyte- and platelet-derived soluble mediators." Cytotherapy vol. 11,6 (2009): 749-60. doi:10.3109/14653240902980443.

Andersen, Rikke et al. "Long-Lasting Complete Responses in Patients with Metastatic Melanoma after Adoptive Cell Therapy with Tumor-Infiltrating Lymphocytes and an Attenuated IL2 Regimen." *Clinical cancer research : an official journal of the American Association for Cancer Research* vol. 22,15 (2016): 3734-45. doi:10.1158/1078-0432.CCR-15-1879.

(56) References Cited

OTHER PUBLICATIONS

Annunziato, F et al. "Expression and release of LAG-3-encoded protein by human CD4+ T cells are associated with IFN-gamma production ." *FASEB journal : official publication of the Federation of American Societies for Experimental Biology* vol. 10,7 (1996): 769-76. doi:10.1096/fasebj.10.7.8635694.
Augustyns, K et al. "Incorporation of hexose nucleoside analogues into oligonucleotides: synthesis, base-pairing properties and enzymatic stability." *Nucleic acids research* vol. 20,18 (1992): 4711-6. doi:10.1093/nar/20.18.4711.
Axelsson et al., "Cryopreserved peripheral blood mononuclear cells are suitable for the assessment of immunological markers in type 1 diabetic children", Cryobiology, Aug. 2008, 57, 201-208.
Bajgain, P. et al., "Optimizing the production of suspension cells using the G-Rex "M" series", Molecular Therapy—Methods and Clinical Development, vol. 1, Jan. 1, 2014.
Baldan, V et al. "Efficient and reproducible generation of tumour-infiltrating lymphocytes for renal cell carcinoma." British journal of cancer vol. 112,9 (2015): 1510-8. doi:10.1038/bjc.2015.96.
Baruch et al., "Adoptive T cell therapy: An overview of obstacles and opportunities : ACT Obstacles and Opportunities", Cancer, vol. 123, No. S11, May 19, 2017, pp. 2154-2162.
Beane, Joal D et al. "Clinical Scale Zinc Finger Nuclease-mediated Gene Editing of PD-1 in Tumor Infiltrating Lymphocytes for the Treatment of Metastatic Melanoma." *Molecular therapy : the journal of the American Society of Gene Therapy* vol. 23,8 (2015): 1380-1390. doi:10.1038/mt.2015.71.
Benjamin, D. et al. "Immunoglobulin secretion by cell lines derived from African and American undifferentiated lymphomas of Burkitt's and non-Burkitt's type." J Immunol Sep. 1, 1982, 129 (3) 1336-1342.
Bergan, R et al. "Electroporation enhances c-myc antisense oligodeoxynucleotide efficacy." *Nucleic acids research* vol. 21,15 (1993): 3567-73. doi: 10.1093/nar/21.15.3567.
Besser, Michal J et al. "Adoptive transfer of tumor-infiltrating lymphocytes in patients with metastatic melanoma: intent-to-treat analysis and efficacy after failure to prior immunotherapies." *Clinical cancer research : an official journal of the American Association for Cancer Research* vol. 19,17 (2013): 4792-800. doi:10.1158/1078-0432.CCR-13-0380.
Besser, Michal J et al. "Clinical responses in a phase II study using adoptive transfer of short-term cultured tumor infiltration lymphocytes in metastatic melanoma patients." Clinical cancer research : an official journal of the American Association for Cancer Research vol. 16,9 (2010): 2646-55. doi:10.1158/1078-0432.CCR-10-0041.
Besser, Michal J et al. "Minimally cultured or selected autologous tumor-infiltrating lymphocytes after a lympho-depleting chemotherapy regimen in metastatic melanoma patients." *Journal of immunotherapy* (*Hagerstown, Md. : 1997*) vol. 32,4 (2009): 415-23. doi:10.1097/CJI.0b013e31819c8bda.
Bird, R E et al. "Single-chain antigen-binding proteins." *Science* (*New York, N. Y.*) vol. 242,4877 (1988): 423-6. doi:10.1126/science.3140379.
Borovsky, Zipora et al. "Serial triggering of T cell receptors results in incremental accumulation of signaling intermediates." *The Journal of biological chemistry* vol. 277,24 (2002): 21529-36. doi:10.1074/jbc.M201613200.
Bosshart, Herbert, and Michael Heinzelmann. "THP-1 cells as a model for human monocytes." *Annals of translational medicine* vol. 4,21 (2016): 438. doi:10.21037/atm.2016.08.53.
Brahmer, et al., J. Clin. Oncol. 2014, 32, 5s (supplement, abstract 8021).
Byrne, Michael et al. "Novel hydrophobically modified asymmetric RNAi compounds (sd-rxRNA) demonstrate robust efficacy in the eye." *Journal of ocular pharmacology and therapeutics : the official journal of the Association for Ocular Pharmacology and Therapeutics* vol. 29,10 (2013): 855-64. doi:10.1089/jop.2013.0148.
Callahan JD, Sajjadi NC. "Testing the Null Hypothesis for a Specified Difference—The Right Way to Test for Parallelism." BioProcess J, 2003; 2(2): 71-77. https://doi.org/10.12665/J22.Callahan.
Camacho, L. H. et al., "Phase 1 clinical trial of anti-CTLA4 human monoclonal antibody CP-675,206 in patients (pts) with advanced solid malignancies" Journal of Clinical Oncology (2004) 22:14_suppl, p. 2505-2505.
Campbell, Brittany B et al. "Comprehensive Analysis of Hypermutation in Human Cancer." *Cell* vol. 171,5 (2017): 1042-1056.e10. doi:10.1016/j.cell.2017.09.048.
Cancer Genome Atlas Network. "Comprehensive molecular characterization of human colon and rectal cancer." *Nature* vol. 487,7407 330-7. Jul. 18, 2012, doi:10.1038/nature11252.
Cancer Genome Atlas Research Network et al. "Integrated genomic characterization of endometrial carcinoma." *Nature* vol. 497,7447 (2013): 67-73. doi:10.1038/nature12113.
Cepko, C, and W Pear. "Overview of the retrovirus transduction system." *Current protocols in molecular biology* vol. Chapter 9 (2001): Unit9.9. doi: 10.1002/0471142727.mb0909s36.
Chacon et al., "Co-stimulation through 4-1BB/CD137 Improves the Expansion and Fundtion of CD8+ Melanoma Tumor-Infiltrating Lymphocytes for Adoptive T-Cell Therapy", PLOS ONE, vol. 8, No. 4, Apr. 1, 2013, 25 pages.
Chang C.-H. et al., "Metabolic competition in the tumor microenvironment is a driver of cancer progression", Cell., Sep. 10, 2015, vol. 162, No. 6, pp. 1229-1241.
Chang et al., "Emerging concepts in immunotherapy T-cell metabolism as a therapeutic target", Nat. Immunol., Apr. 2016, 17(4), 364-368.
Chen, C, and H Okayama. "High-efficiency transformation of mammalian cells by plasmid DNA." *Molecular and cellular biology* vol. 7,8 (1987): 2745-52. doi:10.1128/mcb.7.8.2745-2752.1987.
Cieri, Nicoletta et al. "IL-7 and IL-15 instruct the generation of human memory stem T cells from naive precursors." *Blood* vol. 121,4 (2013): 573-84. doi:10.1182/blood-2012-05-431718.
Cox, David Benjamin Turitz et al. "Therapeutic genome editing: prospects and challenges." *Nature medicine* vol. 21,2 (2015): 121-31. doi:10.1038/nm.3793.
Curti, Brendan D et al. "OX40 is a potent immune-stimulating target in late-stage cancer patients." *Cancer research* vol. 73,24 (2013): 7189-7198. doi:10.1158/0008-5472.CAN-12-4174.
Damsky, William E Jr, and Marcus Bosenberg. "Mouse melanoma models and cell lines." *Pigment cell & melanoma research* vol. 23,6 (2010): 853-9. doi:10.1111/j.1755-148X.2010.00777.x.
De Marco, Ario. "Biotechnological applications of recombinant single-domain antibody fragments." *Microbial cell factories* vol. 10 44. Jun. 9, 2011, doi:10.1186/1475-2859-10-44.
De Wolf, Charlotte et al. "Regulatory perspective on in vitro potency assays for human dendritic cells used in anti-tumor immunotherapy." Cytotherapy vol. 20,11 (2018): 1289-1308. doi:10.1016/j.jcyt.2018.07.006.
Donia, M et al. "Characterization and comparison of 'standard' and 'young' tumour-infiltrating lymphocytes for adoptive cell therapy at a Danish translational research institution." *Scandinavian journal of immunology* vol. 75,2 (2012): 157-67. doi:10.1111/j.1365-3083.2011.02640.x.
Donia, M., et al. "Simplified protocol for clinical-grade tumor-infiltrating lymphocyte manufacturing with use of the Wave bioreactor", Cytotherapy. Aug. 2014;16(8):1117-20. doi: 10.1016/j.jcyt.2014.02.004; PubMed PMID: 24831841.
Dudley, Mark E et al. "Adoptive cell therapy for patients with metastatic melanoma: evaluation of intensive myeloablative chemoradiation preparative regimens." *Journal of clinical oncology : official journal of the American Society of Clinical Oncology* vol. 26,32 (2008): 5233-9. doi: 10.1200/JCO.2008.16.5449.
Dudley, Mark E et al. "Adoptive cell transfer therapy following non-myeloablative but lymphodepleting chemotherapy for the treatment of patients with refractory metastatic melanoma." *Journal of clinical oncology : official journal of the American Society of Clinical Oncology* vol. 23,10 (2005): 2346-57. doi:10.1200/JCO.2005.00.240.

(56) References Cited

OTHER PUBLICATIONS

Dudley, Mark E et al. "Cancer regression and autoimmunity in patients after clonal repopulation with antitumor lymphocytes." *Science* (*New York, N.Y.*) vol. 298,5594 (2002): 850-4. doi:10.1126/science. 1076514.

Dudley, Mark E et al. "CD8+ enriched "young" tumor infiltrating lymphocytes can mediate regression of metastatic melanoma." *Clinical cancer research : an official journal of the American Association for Cancer Research* vol. 16,24 (2010): 6122-31. doi:10.1158/1078-0432.CCR-10-1297.

Dudley, Mark E et al. "Generation of tumor-infiltrating lymphocyte cultures for use in adoptive transfer therapy for melanoma patients." *Journal of immunotherapy* (Hagerstown, Md. : 1997) vol. 26,4 (2003): 332-42. doi:10.1097/00002371-200307000-00005.

Dull, T et al. "A third-generation lentivirus vector with a conditional packaging system." *Journal of virology* vol. 72,11 (1998): 8463-71. doi:10.1128/JVI.72.11.8463-8471.1998.

Eton, O et al. "A phase II study of "decrescendo" interleukin-2 plus interferon-alpha-2a in patients with progressive metastatic melanoma after chemotherapy." *Cancer* vol. 88,7 (2000): 1703-9.

Fantozzi, Anna, and Gerhard Christofori. "Mouse models of breast cancer metastasis." *Breast cancer research : BCR* vol. 8,4 (2006): 212. doi:10.1186/bcr1530.

Farber, Donna L et al. "Human memory T cells: generation, compartmentalization and homeostasis." *Nature reviews. Immunology* vol. 14,1 (2014): 24-35. doi:10.1038/nri3567.

Fehniger, T A, and M A Caligiuri. "Interleukin 15: biology and relevance to human disease." *Blood* vol. 97,1 (2001): 14-32. doi:10.1182/blood.v97.1.14.

Felgner, P L et al. "Lipofection: a highly efficient, lipid-mediated DNA-transfection procedure." *Proceedings of the National Academy of Sciences of the United States of America* vol. 84,21 (1987): 7413-7. doi:10.1073/pnas.84.21.7413.

Felix, Nathan J, and Paul M Allen. "Specificity of T-cell alloreactivity." *Nature reviews. Immunology* vol. 7,12 (2007): 942-53. doi:10.1038/nri2200.

Findlay, J W et al. "Validation of immunoassays for bioanalysis: a pharmaceutical industry perspective." *Journal of pharmaceutical and biomedical analysis* vol. 21,6 (2000): 1249-73. doi:10.1016/s0731-7085(99)00244-7.

Fisher, Timothy S et al. "Targeting of 4-1BB by monoclonal antibody PF-05082566 enhances T-cell function and promotes anti-tumor activity." *Cancer immunology, immunotherapy : CII* vol. 61,10 (2012): 1721-33. doi:10.1007/s00262-012-1237-1.

Fong, Miranda Y, and Sham S Kakar. "Ovarian cancer mouse models: a summary of current models and their limitations." *Journal of ovarian research* vol. 2,1 12. Sep. 28, 2009, doi:10.1186/1757-2215-2-12.

Forget et al., "Activation and propagation of tumor infiltrating lymphocytes on clinical-grade designer artificial antigen presenting cells for adoptive immunotherapy of melanoma", Journal of Immunotherapy, vol. 37 No.9, Nov. 1, 2014, pp. 448-460.

Forget, Marie-Andrée et al. "The beneficial effects of a gas-permeable flask for expansion of Tumor-Infiltrating lymphocytes as reflected in their mitochondrial function and respiration capacity." Oncoimmunology vol. 5,2 e1057386. Jun. 5, 2015, doi:10.1080/2162402X.2015.1057386.

Frank et al., "Remarkably Stable Tumor-Infiltrating Lymphocytes (TIL) for Infusion Phenotype Following Cryopreservation", Nov. 6, 2016, Retrieved from the Internet: http://www.iovance.com/wp-content/uploads/2017/05/LION16701_Frank_POSTER3_final-0005.

Fry, Terry J, and Crystal L Mackall. "Interleukin-7: from bench to clinic." *Blood* vol. 99,11 (2002): 3892-904. doi:10.1182/blood.v99.11.3892.

Fuerst, Mark "Metastatic Melanoma Immunotherapy with Pembrolizumab Induces Durable Responses," *Oncology Times* vol. 36, 13 (2014): 35-36. doi: 10.1097/01.COT.0000452086.09862.55.

Gao, Y et al. "Induction of an exceptionally high-level, nontranslated, Epstein-Barr virus-encoded polyadenylated transcript in the Burkitt's lymphoma line Daudi." *Journal of virology* vol. 71,1 (1997): 84-94. doi:10.1128/JVI.71.1.84-94.1997.

Garaud, Soizic et al. "A simple and rapid protocol to non-enzymatically dissociate fresh human tissues for the analysis of infiltrating lymphocytes." Journal of visualized experiments : JoVE , 94 52392. Dec. 6, 2014, doi: 10.3791/52392.

Gassner, Franz Josef et al. "Fludarabine modulates composition and function of the T cell pool in patients with chronic lymphocytic leukaemia." *Cancer immunology, immunotherapy : CII* vol. 60,1 (2011): 75-85. doi:10.1007/s00262-010-0920-3.

Gattinoni, Luca et al. "A human memory T cell subset with stem cell-like properties." *Nature medicine* vol. 17,10 1290-7. Sep. 18, 2011, doi:10.1038/nm.2446.

Gattinoni, Luca et al. "Adoptive immunotherapy for cancer: building on success." *Nature reviews. Immunology* vol. 6,5 (2006): 383-93. doi:10.1038/nri1842.

Gattinoni, Luca et al. "Paths to stemness: building the ultimate antitumour T cell." *Nature reviews. Cancer* vol. 12,10 (2012): 671-84. doi:10.1038/nrc3322.

Gieffers, Christian et al. "APG350 induces superior clustering of TRAIL receptors and shows therapeutic antitumor efficacy independent of cross-linking via Fcγ receptors." *Molecular cancer therapeutics* vol. 12,12 (2013): 2735-47. doi:10.1158/1535-7163.MCT-13-0323.

Gladstone, D E et al. "Infusion of cryopreserved autologous lymphocytes using a standard peripheral i.v. catheter." Bone marrow transplantation vol. 49,8 (2014): 1119-20. doi:10.1038/bmt.2014.98.

Glassman, A B, and C E Bennett. "Cryopreservation of human lymphocytes: a brief review and evaluation of an automated liquid nitrogen freezer." Transfusion vol. 19,2 (1979): 178-81. doi:10.1046/j.1537-2995.1979.19279160289.x.

Goff, Stephanie L et al. "Randomized, Prospective Evaluation Comparing Intensity of Lymphodepletion Before Adoptive Transfer of Tumor-Infiltrating Lymphocytes for Patients With Metastatic Melanoma." *Journal of clinical oncology : official journal of the American Society of Clinical Oncology* vol. 34,20 (2016): 2389-97. doi:10.1200/JCO.2016.66.7220.

Goff, Stephanie L et al. "Tumor infiltrating lymphocyte therapy for metastatic melanoma: analysis of tumors resected for TIL." *Journal of immunotherapy* (Hagerstown, Md. : 1997) vol. 33,8 (2010): 840-7. doi:10.1097/CJI.0b013e3181f05b91.

Gottschalk, Paul G, and John R Dunn. "Measuring parallelism, linearity, and relative potency in bioassay and immunoassay data." *Journal of biopharmaceutical statistics* vol. 15,3 (2005): 437-63. doi:10.1081/BIP-200056532.

Graham, FL, and A J van der Eb. "A new technique for the assay of infectivity of human adenovirus 5 DNA." *Virology* vol. 52,2 (1973): 456-67. doi:10.1016/0042-6822(73)90341-3.

Griesbeck, Morgane et al. "Sex Differences in Plasmacytoid Dendritic Cell Levels of IRF5 Drive Higher IFN-α Production in Women." *Journal of immunology* (Baltimore, Md. : 1950) vol. 195,11 (2015): 5327-36. doi:10.4049/jimmunol.1501684.

Hackett, Perry B et al. "A transposon and transposase system for human application." *Molecular therapy : the journal of the American Society of Gene Therapy* vol. 18,4 (2010): 674-83. doi:10.1038/mt.2010.2.

Hall et al., "Expansion of tumor-infiltrating lymphocytes (TIL) from human pancreatic tumors", Journal for Immuno Therapy of Cancer, vol. 4, No. 1, pp. 1-12.

Hasan et al., "Artificial Antigen Presenting Cells: An Off the Shelf Approach for Generation of Desirable T-Cell Populations for Broad Application of Adoptive Immunotherapy", Adv Genet Eng, 2015, 4:3.

Hauck, Walter W et al. "Assessing parallelism prior to determining relative potency." *PDA journal of pharmaceutical science and technology* vol. 59,2 (2005): 127-37.

He, Jia et al., "Ex vivo expansion of tumor-infiltrating lymphocytes from nasopharyngeal carcinoma patients for adoptive immunotherapy," Chinese Journal of Cancer, vol. 31, No. 6, Jun. 5, 2012.

(56) References Cited

OTHER PUBLICATIONS

Henning AL, et al.. Measurement of T-Cell Telomere Length Using Amplified-Signal FISH Staining and Flow Cytometry. Curr Protoc Cytom. Jan. 5, 2017;79:7.47.1-7.47.10. doi: 10.1002/cpcy.11. PubMed PMID 28055115.
Henson, Sian M et al. "KLRG1 signaling induces defective Akt (ser473) phosphorylation and proliferative dysfunction of highly differentiated CD8+ T cells." *Blood* vol. 113,26 (2009): 6619-28. doi:10.1182/blood-2009-01-199588.
Hernandez-Chacon et al., "Costimulation through the CD137/4-1BB Pathway Protects Human Melanoma Tumor-infiltrating Lymphocytes from Activation-induced Cell Death and Enhances Anti-tumor Effector Function", Journal of Immuno Therapy, vol. 34, No. 3, Apr. 1, 2011, pp. 236-250.
Herndler-Brandstetter, Dietmar et al. "KLRG1+ Effector CD8+ T Cells Lose KLRG1, Differentiate into All Memory T Cell Lineages, and Convey Enhanced Protective Immunity." *Immunity* vol. 48,4 (2018): 716-729.e8. doi:10.1016/j.immuni.2018.03.015.
Herreros-Villanueva, Marta et al. "Mouse models of pancreatic cancer." *World journal of gastroenterology* vol. 18,12 (2012): 1286-94. doi:10.3748/wjg.v18.i12.1286.
Hinrichs CS, Rosenberg SA. Exploiting the curative potential of adoptive T-cell therapy for cancer. Immunol Rev. Jan. 2014;257(1):56-71. doi: 10.1111/imr. 12132. Review. PubMed PMID: 24329789; PubMed Central PMCID: PMC3920180.
Holliger, P et al. "Diabodies: small bivalent and bispecific antibody fragments." *Proceedings of the National Academy of Sciences of the United States of America* vol. 90,14 (1993): 6444-8. doi:10.1073/pnas.90.14.6444.
Hopewell, Emily L et al. "Tumor-infiltrating lymphocytes: Streamlining a complex manufacturing process." *Cytotherapy* vol. 21,3 (2019): 307-314. doi:10.1016/j.jcyt.2018.11.004.
Huang, Jianping et al. "Survival, persistence, and progressive differentiation of adoptively transferred tumor-reactive T cells associated with tumor regression." *Journal of immunotherapy* (Hagerstown, Md.: 1997) vol. 28,3 (2005): 258-67. doi:10.1097/01.cji.0000158855.92792.7a.
Hurwitz, A A et al. "CTLA-4 blockade synergizes with tumor-derived granulocyte- macrophage colony-stimulating factor for treatment of an experimental mammary carcinoma." *Proceedings of the National Academy of Sciences of the United States of America* vol. 95,17 (1998): 10067-71. doi:10.1073/pnas.95.17.10067.
Huston, J S et al. "Protein engineering of antibody binding sites: recovery of specific activity in an anti-digoxin single-chain Fv analogue produced in *Escherichia coli.*" *Proceedings of the National Academy of Sciences of the United States of America* vol. 85,16 (1988): 5879-83. doi:10.1073/pnas.85.16.5879.
Ikarashi, H et al., "Solid-phase anti-CD3 antibody activation and cryopreservation of human tumor-infiltrating lymphocytes derived from epithelial ovarian cancer", *Japanese Journal of Cancer Research*, vol. 83, No. 12, Dec. 1, 1992.
International Search Report and Written Opinion for International Patent Application No. PCT/US2017/058610 dated Mar. 8, 2018, 13 pages.
International Search Report and Written Opinion for International Patent Application No. PCT/US2018/012633 dated May 25, 2018, 14 pages.
International Search Report and Written Opinion for International Patent Application No. PCT/US2018/040474 dated Nov. 14, 2018, 17 pages.
Invitation to Pay Additional Fees for International Patent Application No. PCT/US2022/022030 dated Jul. 18, 2022, 16 pages.
Itzhaki, Orit et al. "Establishment and large-scale expansion of minimally cultured "young" tumor infiltrating lymphocytes for adoptive transfer therapy." Journal of immunotherapy (Hagerstown, Md. : 1997) vol. 34,2 (2011): 212-20. doi:10.1097/CJI.0b013e318209c94c.
Iyer, R.K. et al., "Industrializing Autologous Adoptive Immunotherapies: Manufacturing Advances and Challenges", Frontiers in Medicine, vol. 5, May 23, 2018.
Jaeger, H M, and S R Nagel. "Physics of the granular state." *Science* (New York, N.Y.) vol. 255,5051 (1992): 1523-31. doi:10.1126/science.255.5051.1523.
Jin et al., "Enhanced clinical-scale manufacturing of TCR transduced T-cells using closed culture system modules", Journal of Translational Medicine, col. 16. No. 1, Jan. 24, 2018.
Jin, Jianjian et al. "Simplified method of the growth of human tumor infiltrating lymphocytes in gas-permeable flasks to Nos. needed for patient treatment." *Journal of immunotherapy* (Hagerstown, Md. : 1997) vol. 35,3 (2012): 283-92. doi:10.1097/CJI.0b013e31824e801f.
Jones, P T et al. "Replacing the complementarity-determining regions in a human antibody with those from a mouse." *Nature* vol. 321,6069 (1986): 522-5. doi:10.1038/321522a0.
Junker, Niels et al. "Bimodal ex vivo expansion of T cells from patients with head and neck squamous cell carcinoma: a prerequisite for adoptive cell transfer." Cytotherapy vol. 13,7 (2011): 822-34. doi:10.3109/14653249.2011.563291.
Keir, Mary E et al. "PD-1 and its ligands in tolerance and immunity." *Annual review of immunology* vol. 26 (2008): 677-704. doi:10.1146/annurev.immunol.26.021607.090331.
Khvorova, Anastasia, and Jonathan K Watts. "The chemical evolution of oligonucleotide therapies of clinical utility." *Nature biotechnology* vol. 35,3 (2017): 238-248. doi:10.1038/nbt.3765.
Kim, Seungwon. "Animal models of cancer in the head and neck region." *Clinical and experimental otorhinolaryngology* vol. 2,2 (2009): 55-60. doi:10.3342/ceo.2009.2.2.55.
Klapper, J.A. et al., "Single-pass, closed-system rapid expansion of lymphocyte cultures for adoptive cell therapy", Journal of Immunological Methods, vol. 345, No. 1-2, Jun. 30, 2009.
Kraus, Annette A et al. "Comparison of plaque- and flow cytometry-based methods for measuring dengue virus neutralization." *Journal of clinical microbiology* vol. 45,11 (2007): 3777-80. doi:10.1128/JCM.00827-07.
Kverneland, Anders Handrup et al. "Adoptive cell therapy in combination with checkpoint inhibitors in ovarian cancer." Oncotarget vol. 11,22 2092-2105. Jun. 2, 2020, doi:10.18632/oncotarget.27604.
Lee et al., "Tumor-Infiltrating Lymphocytes in Melanoma", Curr Oncol Rep. Aug. 2012, 14, 468-474.
Lee, Do Y et al. "4-1BB signaling activates the t cell factor 1 effector/β-catenin pathway with delayed kinetics via ERK signaling and delayed PI3K/AKT activation to promote the proliferation of CD8+ T Cells." *PloS one* vol. 8,7 e69677. Jul. 11, 2013, doi:10.1371/journal.pone.0069677.
Levine, Bruce L et al. "Gene transfer in humans using a conditionally replicating lentiviral vector." *Proceedings of the National Academy of Sciences of the United States of America* vol. 103,46 (2006): 17372-7. doi:10.1073/pnas.0608138103.
Li et al. MART-1-specific melanoma tumor-infiltrating lymphocytes maintaining CD28 expression have improved survival and expansion capability following antigenic restimulation in vitro. J Immunol. Jan. 1, 2010;184(1):452-65. doi: 10.4049/jimmunol.0901101. Epub Nov. 30, 2009. PubMed PMID: 19949105.
Ligtenberg, Maarten A et al. "Self-Delivering RNAi Targeting PD-1 Improves Tumor-Specific T Cell Functionality for Adoptive Cell Therapy of Malignant Melanoma." *Molecular therapy : the journal of the American Society of Gene Therapy* vol. 26,6 (2018): 1482-1493. doi:10.1016/j.ymthe.2018.04.015.
Lozzio, C B, and B B Lozzio. "Human chronic myelogenous leukemia cell-line with positive Philadelphia chromosome." *Blood* vol. 45,3 (1975): 321-34.
Malek, Thomas R. "The biology of interleukin-2." *Annual review of immunology* vol. 26 (2008): 453-79. doi:10.1146/annurev.immunol.26.021607.090357.
Matzinger, P, and M J Bevan. "Hypothesis: why do so many lymphocytes respond to major histocompatibility antigens ?. " *Cellular immunology* vol. 29,1 (1977): 1-5. doi:10.1016/0008-8749(77)90269-6.
McDermott, David et al. "Durable benefit and the potential for long-term survival with immunotherapy in advanced melanoma." *Cancer treatment reviews* vol. 40,9 (2014): 1056-64. doi:10.1016/j.ctrv.2014.06.012.
Merhavi-Shoham et al., "Adoptive Cell Therapy for Metastatic Melanoma", Cancer Journal, vol. 23, No. 1, Jan. 1, 2017.

(56) References Cited

OTHER PUBLICATIONS

Meuwissen, Ralph, and Anton Berns. "Mouse models for human lung cancer." *Genes & development* vol. 19,6 (2005): 643-64. doi:10.1101/gad.1284505.
Mokyr, M B et al. "Realization of the therapeutic potential of CTLA-4 blockade in low-dose chemotherapy-treated tumor-bearing mice." *Cancer research* vol. 58,23 (1998): 5301-4.
Monnier, Philippe, et al. "In Vivo Applications of Single Chain Fv (Variable Domain) (ScFv) Fragments." *Antibodies*, vol. 2, No. 4, Apr. 2013, pp. 193-208. https://doi.org/10.3390/antib2020193.
Mullany, Lisa K, and JoAnne S Richards. "Minireview: animal models and mechanisms of ovarian cancer development." *Endocrinology* vol. 153,4 (2012): 1585-92. doi:10.1210/en.2011-2121.
Mullinax et al., "Combination of Ipilimumab and Adoptive Cell Therapy with Tumor-Infiltrating Lymphocytes for Patients with Metastatic Melanoma", *Frontiers in Oncology*, vol. 8, Mar. 2, 2018.
Muranski, Pawel et al. "Increased intensity lymphodepletion and adoptive immunotherapy—how far can we go ?." *Nature clinical practice. Oncology* vol. 3,12 (2006): 668-81. doi:10.1038/ncponc0666.
Nelson, Brad H. "IL-2, regulatory T cells, and tolerance." *Journal of immunology* (Baltimore, Md. : 1950) vol. 172,7 (2004): 3983-8. doi:10.4049/jimmunol. 172.7.3983.
Nguyen, Linh T et al. "Expansion and characterization of human melanoma tumor-infiltrating lymphocytes (TILs)." PloS one vol. 5,11 e13940. Nov. 10, 2010, doi:10.1371/journal.pone.0013940.
O. R. Musin (2003). "The problem of the twenty-five spheres". Russ. Math. Surv. 58 (4): 794-795.
O'Day, S J et al. "Advantages of concurrent biochemotherapy modified by decrescendo interleukin-2, granulocyte colony-stimulating factor, and tamoxifen for patients with metastatic melanoma." *Journal of clinical oncology : official journal of the American Society of Clinical Oncology* vol. 17,9 (1999): 2752-61. doi: 10.1200/JCO.1999.17.9.2752.
Page, David B et al. "Immune modulation in cancer with antibodies." *Annual review of medicine* vol. 65 (2014): 185-202. doi:10.1146/annurev-med-092012-112807.
Pfeifer, Gerd P et al. "Mutations induced by ultraviolet light." *Mutation research* vol. 571, 1-2 (2005): 19-31. doi:10.1016/j.mrfmmm.2004.06.057.
Pleasance, Erin D et al. "A small-cell lung cancer genome with complex signatures of tobacco exposure." *Nature* vol. 463,7278 (2010): 184-90. doi:10.1038/nature08629.
Presta, L G. "Antibody engineering." *Current Opinion in Structural Biology* (1992) 2:593-6. doi:10.1016/0958-1669(92)90168-i.
Riddell, S R et al. "Restoration of viral immunity in immunodeficient humans by the adoptive transfer of T cell clones." *Science* (New York, N.Y.) vol. 257,5067 (1992): 238-41. doi:10.1126/science.1352912.
Riechmann, L et al. "Reshaping human antibodies for therapy." *Nature* vol. 332,6162 (1988): 323-7. doi:10.1038/332323a0.
Robbins, Paul F et al. "Cutting edge: persistence of transferred lymphocyte clonotypes correlates with cancer regression in patients receiving cell transfer therapy." *Journal of immunology* (Baltimore, Md. : 1950) vol. 173,12 (2004): 7125-30. doi:10.4049/jimmunol.173.12.7125.
Robert, Caroline et al. "Anti-programmed-death-receptor-1 treatment with pembrolizumab in ipilimumab-refractory advanced melanoma: a randomised dose-comparison cohort of a phase 1 trial." *Lancet* (London, England) vol. 384,9948 (2014): 1109-17. doi:10.1016/S0140-6736(14)60958-2.
Roberts, Steven A et al. "An APOBEC cytidine deaminase mutagenesis pattern is widespread in human cancers." *Nature genetics* vol. 45,9 (2013): 970-6. doi:10.1038/ng.2702.
Rohaan et al., "Adoptive transfer of tumor-infiltrating lymphocytes in melanoma: a viable treatment option", Journal for Immunotherapy of Cancer, vol. 6, No. 1, Oct. 3, 2018, pp. 1-16.
Rose, J K et al. "A new cationic liposome reagent mediating nearly quantitative transfection of animal cells." *BioTechniques* vol. 10,4 (1991): 520-5.
Rosenberg SA, Dudley ME. Adoptive cell therapy for the treatment of patients with metastatic melanoma. Curr Opin Immunol. Apr. 2009;21(2):233-40.
Rosenberg SA, et al. "Durable Complete Responses in Heavily Pretreated Patients with Metastatic Melanoma Using T Cell Transfer Immunotherapy", Clinical Cancer research, vol. 17, No. 13, Jul. 1, 2011 pp. 4550-4557.
Rosenberg, "IL-2: The First Effective Immunotherapy for Human Cancer," The Journal of Immunology, col. 192, No. 12, Jun. 6, 2014.
Rosenberg, S A et al. "A new approach to the adoptive immunotherapy of cancer with tumor-infiltrating lymphocytes." Science (New York, N.Y.) vol. 233,4770 (1986): 1318-21. doi:10.1126/science.3489291.
Rosenberg, S A et al. "Treatment of patients with metastatic melanoma with autologous tumor-infiltrating lymphocytes and interleukin 2." Journal of the National Cancer Institute vol. 86, 15 (1994): 1159-66. doi:10.1093/jnci/86.15.1159.
Rosenberg, S A et al. "Use of tumor-infiltrating lymphocytes and interleukin-2 in the immunotherapy of patients with metastatic melanoma. A preliminary report." *The New England journal of medicine* vol. 319,25 (1988): 1676-80. doi:10.1056/NEJM198812223192527.
Rosenberg, Steven A et al. "Durable complete responses in heavily pretreated patients with metastatic melanoma using T-cell transfer immunotherapy." *Clinical cancer research : an official journal of the American Association for Cancer Research* vol. 17,13 (2011): 4550-7. doi:10.1158/1078-0432.CCR-11-0116.
Rufer N, et al., "Telomere length dynamics in human lymphocyte subpopulations measured by flow cytometry", Nat Biotechnol. Aug. 1998;16(8):743-7. PubMed PMID: 9702772.
Sadeghi, Arian et al. "Rapid expansion of T cells: Effects of culture and cryopreservation and importance of short-term cell recovery." *Acta oncologica* (Stockholm, Sweden) vol. 52,5 (2013): 978-86. doi:10.3109/0284186X.2012.737020.
Sadun, et al., J. Immunother. 2009, 182, 1481-89.
Sallusto, Federica et al. "Central memory and effector memory T cell subsets: function, generation, and maintenance." *Annual review of immunology* vol. 22 (2004): 745-63. doi:10.1146/annurev.immunol.22.012703.104702.
Sano, Daisuke, and Jeffrey N Myers. "Xenograft models of head and neck cancers." *Head & neck oncology* vol. 1 32. Aug. 13, 2009, doi:10.1186/1758-3284-1-32.
Schiltz, P M et al. "Characterization of tumor-infiltrating lymphocytes derived from human tumors for use as adoptive immunotherapy of cancer." *Journal of immunotherapy* (Hagerstown, Md. : 1997) vol. 20,5 (1997): 377-86. doi:10.1097/00002371-199709000-00007.
Segal, Neil H et al. "Results from an Integrated Safety Analysis of Urelumab, an Agonist Anti-CD137 Monoclonal Antibody." *Clinical cancer research : an official journal of the American Association for Cancer Research* vol. 23,8 (2017): 1929-1936. doi:10.1158/1078-0432.CCR-16-1272.
Seitter, Samantha J et al. "Impact of Prior Treatment on the Efficacy of Adoptive Transfer of Tumor-Infiltrating Lymphocytes in Patients with Metastatic Melanoma." *Clinical cancer research : an official journal of the American Association for Cancer Research* vol. 27,19 (2021): 5289-5298. doi: 10.1158/1078-0432.CCR-21-1171.
Sharei, Armon et al. "A vector-free microfluidic platform for intracellular delivery." *Proceedings of the National Academy of Sciences of the United States of America* vol. 110,6 (2013): 2082-7. doi:10.1073/pnas.1218705110.
Sharei, Armon et al. "Ex vivo cytosolic delivery of functional macromolecules to immune cells." *PloS one* vol. 10,4 e0118803. Apr. 13, 2015, doi:10.1371/journal.pone.0118803.
Shedlock, Devon J, and Hao Shen. "Requirement for CD4 T cell help in generating functional CD8 T cell memory." *Science* (New York, N.Y.) vol. 300,5617 (2003): 337-9. doi:10.1126/science.1082305.
Shen, Xinglei et al. "Persistence of tumor infiltrating lymphocytes in adoptive immunotherapy correlates with telomere length." *Journal of immunotherapy* (Hagerstown, Md. : 1997) vol. 30,1 (2007): 123-9. doi:10.1097/01.cji.0000211321.07654.b8.
Shields, Robert L et al. "Lack of fucose on human IgG1 N-linked oligosaccharide improves binding to human Fcgamma RIII and

(56) References Cited

OTHER PUBLICATIONS antibody-dependent cellular toxicity." *The Journal of biological chemistry* vol. 277,30 (2002): 26733-40. doi:10.1074/jbc. M202069200.
Simpson-Abelson, et al., *Ann. Oncol.*, 2020, 31, S720.
Simpson-Abelson, et al., Iovance Generation-2 Tumor-infiltrating Lymphocyte (TIL) Product Is Reinvigorated During the Manufacturing Process ESMO Congress, Sep. 19-21, 2020, poster 1053P.
Smith, Corey et al. "Ex vivo expansion of human T cells for adoptive immunotherapy using the novel Xeno-free CTS Immune Cell Serum Replacement." *Clinical & translational immunology* vol. 4,1 e31. Jan. 16, 2015, doi:10.1038/cti.2014.31.
Sobel and Bokisch, Fed. Proc. 1975, 34, 965.
Somerville RP, et al.. Clinical scale rapid expansion of lymphocytes for adoptive cell transfer therapy in the WAVE® bioreactor. J Transl Med. Apr. 4, 2012;10:69.
Spiess, P J et al. "In vivo antitumor activity of tumor-infiltrating lymphocytes expanded in recombinant interleukin-2." *Journal of the National Cancer Institute* vol. 79,5 (1987): 1067-75.
Spolski, Rosanne, and Warren J Leonard. "Interleukin-21: a double-edged sword with therapeutic potential." *Nature reviews. Drug discovery* vol. 13,5 (2014): 379-95. doi:10.1038/nrd4296.
Steinke, J W, and L Borish. "Th2 cytokines and asthma. Interleukin-4: its role in the pathogenesis of asthma, and targeting it for asthma treatment with interleukin-4 receptor antagonists." *Respiratory research* vol. 2,2 (2001): 66-70. doi:10.1186/rr40.
Sun, Joseph C, and Michael J Bevan. "Defective CD8 T cell memory following acute infection without CD4 T cell help." Science (New York, N. Y.) vol. 300,5617 (2003): 339-42. doi:10. 1126/science.1083317.
Swartz, Melody A et al. "Tumor microenvironment complexity: emerging roles in cancer therapy." *Cancer research* vol. 72,10 (2012): 2473-80. doi:10.1158/0008-5472.CAN-12- 0122.
Tarentino, A L et al. "The isolation and structure of the core oligosaccharide sequences of IgM." *Biochemistry* vol. 14,25 (1975): 5516-23. doi:10.1021/bi00696a021.
Theofilopoulos, A N et al. "Binding of soluble immune complexes to human lymphoblastoid cells. II. Use of Raji cells to detect circulating immune complexes in animal and human sera." *The Journal of experimental medicine* vol. 140,5 (1974): 1230-44. doi:10.1084/jem.140.5.1230.
Theofilopoulos, A N et al. "The Raji cell radioimmune assay for detecting immune complexes in human sera." *The Journal of clinical investigation* vol. 57,1 (1976): 169-82. doi:10.1172/ JCI108257.
Thomas, Anish, and Marko Jakopovic. "Immunotherapy for non-small-cell lung cancer." *Expert opinion on biological therapy* vol. 14,8 (2014): 1061-4. doi:10.1517/14712598.2014.925874.
Topalian, Suzanne L et al. "Safety, activity, and immune correlates of anti-PD-1 antibody in cancer." *The New England journal of medicine* vol. 366,26 (2012): 2443-54. doi:10.1056/NEJMoa1200690.
Tran, Khoi Q et al. "Minimally cultured tumor-infiltrating lymphocytes display optimal characteristics for adoptive cell therapy." *Journal of immunotherapy* (Hagerstown, Md. : 1997) vol. 31,8 (2008): 742-51. doi:10.1097/CJI.0b013e31818403d5.
Tsong, T Y. "Electroporation of cell membranes." *Biophysical journal* vol. 60,2 (1991): 297-306. doi:10.1016/S0006-3495(91)82054-9.
Tsoukas, C D et al. "Activation of resting T lymphocytes by anti-CD3 (T3) antibodies in the absence of monocytes." *Journal of immunology* (Baltimore, Md. : 1950) vol. 135,3 (1985): 1719-23.
Tsuchiya, S et al. "Establishment and characterization of a human acute monocytic leukemia cell line (THP-1)." *International journal of cancer* vol. 26,2 (1980): 171-6. doi:10.1002/ijc.2910260208.
Umaña, P et al. "Engineered glycoforms of an antineuroblastoma IgG1 with optimized antibody-dependent cellular cytotoxic activity." *Nature biotechnology* vol. 17,2 (1999): 176-80. doi:10.1038/ 6179.
Van den Bossche, J. et al. "Metabolic Characterization of Polarized M1 and M2 Bone Marrow-derived Macrophages Using Real-time Extracellular Flux Analysis." Journal of visualized experiments : JoVE , 105 53424. Nov. 28, 2015, doi: 10.3791/53424.
USP Pharmacopeial Convention (chapter 1032) Design and Development of Biological Assays 1-36 2013 (USP) [retrieved on Nov. 28, 2022]. retrieved from the internet :< URL: http://www. ipqpubs .com/wp-content/uploads/2010/06/U SP_ 1032 .pdf> (Year: 2013).
Wang & Riviere, "Manufacture of tumor- and virus-specific T lymphocytes for adoptive cell therapies", Cancer Gene Therapy, 2015, 22: 85-94.
Wang, Changyu et al. "In vitro characterization of the anti-PD-1 antibody nivolumab, BMS-936558, and in vivo toxicology in non-human primates." *Cancer immunology research* vol. 2,9 (2014): 846-56. doi:10.1158/2326-6066.CIR-14-0040.
Ward, E S et al. "Binding activities of a repertoire of single immunoglobulin variable domains secreted from *Escherichia coli.*" *Nature* vol. 341,6242 (1989): 544-6. doi:10.1038/341544a0.
Wardell et al., "A cryopreserved tumor infiltrating lymphocyte (TIL) product for LN-44", Nov. 8, 2017, retrieved from the Internet: URL: http://www.iovance.com/wp-content/uploads/2017/11/SITC2017_Seth_poster_FINAL_SWDE_PRINT_7Nov2017.pdf.
Weber, Jeffrey S et al. "Safety, efficacy, and biomarkers of nivolumab with vaccine in ipilimumab-refractory or -naive melanoma." *Journal of clinical oncology : official journal of the American Society of Clinical Oncology* vol. 31,34 (2013): 4311-8. doi:10.1200/JCO. 2013.51.4802.
Weinberg, Andrew D et al. "Anti-OX40 (CD134) administration to nonhuman primates: immunostimulatory effects and toxicokinetic study." *Journal of immunotherapy* (Hagerstown, Md. : 1997) vol. 29,6 (2006): 575-85. doi:10.1097/01.cji.0000211319.00031.fc.
Wigler, M et al. "DNA-mediated transfer of the adenine phosphoribosyltransferase locus into mammalian cells." *Proceedings of the National Academy of Sciences of the United States of America* vol. 76,3 (1979): 1373-6. doi:10.1073/pnas.76.3.1373.
Wilson Wolf—Superior Cell Culture Devices, G-Rex, Oct. 31, 2016.
Wu, Richard et al. "Adoptive T-cell therapy using autologous tumor-infiltrating lymphocytes for metastatic melanoma: current status and future outlook." Cancer journal (Sudbury, Mass.) vol. 18,2 (2012): 160-75. doi:10.1097/PPO.0b013e31824d4465.
Yamane-Ohnuki, Naoko et al. "Establishment of FUT8 knockout Chinese hamster ovary cells: an ideal host cell line for producing completely defucosylated antibodies with enhanced antibody-dependent cellular cytotoxicity." *Biotechnology and bioengineering* vol. 87,5 (2004): 614-22. doi:10.1002/bit.20151.
Ye, et al., "Engineered Artificial antigen presenting cells facilitate direct and efficient expansion of tumor infiltrating lymphocytes", J. Translat. Med. 2011, 9(131), 13 pages.
Zhou J, et al.. Telomere length of transferred lymphocytes correlates with in vivo persistence and tumor regression in melanoma patients receiving cell transfer therapy. J Immunol. Nov. 15, 2005;175(10):7046-52. PubMed PMID: 16272366; PubMed Central PMCID: PMC135131.
Zhou, Juhua et al. "Persistence of multiple tumor-specific T-cell clones is associated with complete tumor regression in a melanoma patient receiving adoptive cell transfer therapy." *Journal of immunotherapy* (Hagerstown, Md. : 1997) vol. 28,1 (2005): 53-62. doi:10.1097/00002371-200501000-00007.
Zufferey, R et al. "Multiply attenuated lentiviral vector achieves efficient gene delivery in vivo." *Nature biotechnology* vol. 15,9 (1997): 871-5. doi:10.1038/nbt0997-871.
Zuliani, T. et al., "Value of large scale expansion of tumor infiltrating lymphocytes in a compartmentalised gas-permiable bag: interests for adoptive immunotherapy", Journal of Translational Medicine, vol. 9, No. 1, May 16, 2011.
Declaration of Dr. Michelle Simpson-Abelson Under 37 C.F.R. § 1.132.
Poschke, Isabel et al. "Identification of a tumor-reactive T-cell repertoire in the immune infiltrate of patients with resectable pancreatic ductal adenocarcinoma." Oncoimmunology vol. 5,12 e1240859. Oct. 7, 2016, doi:10.1080/2162402X.2016.1240859.
International Preliminary Report on Patentability for International Patent Application No. PCT/US22/22030 dated Sep. 12, 2023, 16 pages.

(56) References Cited

OTHER PUBLICATIONS

International Search Report and Written Opinion for International Patent Application No. PCT/US22/22030 dated Oct. 11, 2022, 21 pages.
Baust, J M et al. "A molecular basis of cryopreservation failure and its modulation to improve cell survival." Cell transplantation vol. 10,7 (2001): 561-71.
Butler, Marcus O et al. "Ex vivo expansion of human CD8+ T cells using autologous CD4+ T cell help." PloS one vol. 7,1 (2012): e30229. doi:10.1371/journal.pone.0030229.
Simpson-Abelson, Michelle R. et al., "Emigrant Tumor Infiltrating Lymphocytes (TIL) Profoundly Differ from Remnant T cells," AACR 32nd annual meeting, Apr. 1-5, 2017.
Choudhary. Importance of Negative and Positive Controls in Microbial Analysis. Pharmaceutical Guidelines. (accessed at: https://web.archive.org/web/20170515082209/https://www.pharmaguideline.com/2017 /05/importance-of-negative-and-positive-controls.html) (Year: 2017).

* cited by examiner

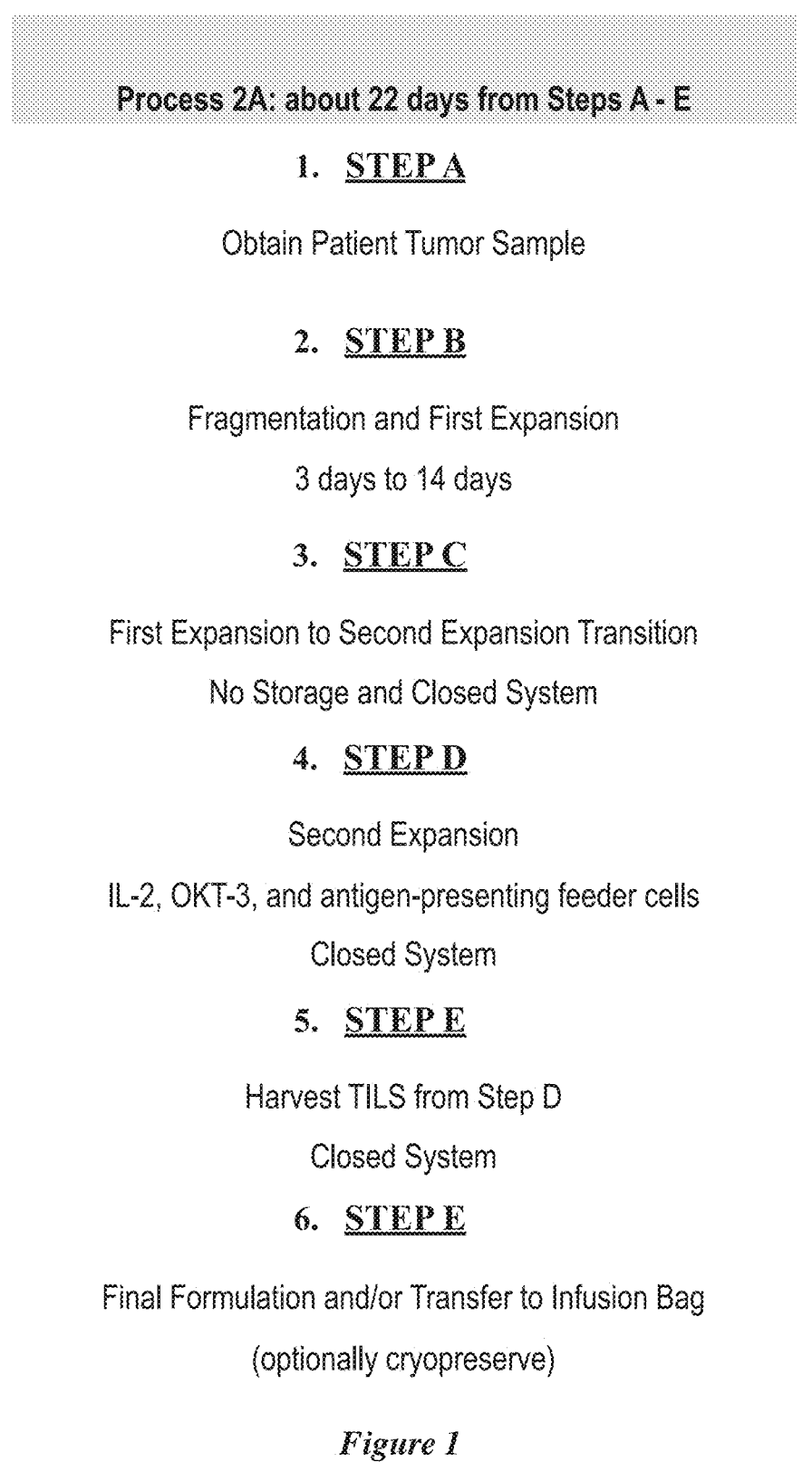

Process 2A: about 22 days from Steps A - E

1. STEP A

Obtain Patient Tumor Sample

2. STEP B

Fragmentation and First Expansion 3 days to 14 days

3. STEP C

First Expansion to Second Expansion Transition

No Storage and Closed System

4. STEP D

Second Expansion

IL-2, OKT-3, and antigen-presenting feeder cells

Closed System

5. STEP E

Harvest TILS from Step D

Closed System

6. STEP E

Final Formulation and/or Transfer to Infusion Bag (optionally cryopreserve)

*Figure 1*

| Process 1C: 43-55 Days for Steps A - E | Process 2A: about 22 days from Steps A - E |
|---|---|
| 1. STEP A<br>Obtain Patient Tumor Sample | 1. STEP A<br>Obtain Patient Tumor Sample |
| 2. STEP B<br>Fragmentation and First Expansion<br>11 days to 21 days | 2. STEP B<br>Fragmentation and First Expansion<br>3 days to 14 days |
| 3. STEP C<br>First Expansion to Second Expansion Transition<br>Optional Storage until Selection | 3. STEP C<br>First Expansion to Second Expansion Transition<br>No Storage and Closed System |
| 4. STEP D<br>Second Expansion<br>IL-2, OKT-3, antigen-presenting feeder cells<br>Optionally repeat one or more times | 4. STEP D<br>Second Expansion<br>IL-2, OKT-3, antigen-presenting feeder cells<br>Closed System |
| 5. STEP E<br>Harvest TILs from Step D | 5. STEP E<br>Harvest TILs from Step D<br>Closed System |
| 6. STEP F<br>Final Formulation and/or Transfer to Infusion Bag | 6. STEP F<br>Final Formulation and/or Transfer to Infusion Bag<br>(optionally cryopreserve) |

*Figure 5*

| Process Step | Process 1C Embodiment | Process 2A Embodiment | Advantages |
|---|---|---|---|
| Pre-REP | • 4 fragments per 10 GREX-10 flasks<br>• 11-21 day duration | • 40 fragments per 1 GREX-100M flask<br>• 11 day duration | • Increased tumor fragments per flask<br>• Shortened culture time<br>• Reduced number of steps<br>• Amenable to closed system |
| Pre-REP to REP Transition | • Pre-REP TIL are frozen until phenotyped for selection then thawed to proceed to the REP (~day 30)<br>• REP requires >40x10$^6$ TIL | • Pre-REP TIL directly move to REP on day 11<br>• REP requires 25-200x10$^6$ TIL | • Shortened pre-REP-to-REP process<br>• Reduced number of steps<br>• Eliminated phenotyping selection<br>• Amenable to closed system |
| REP | • 6 GREX-100M flasks on REP day 0<br>• 5x10$^6$ TIL and 5x10$^8$ PBMC feeders per flask on REP day 0<br>• Split to 18-36 flasks on REP day 7<br>• 14 day duration | • 1 GREX-500M flask on day 11<br>• 25-200x10$^6$ TIL and 5x10$^9$ PBMC feeders on day 11<br>• Split to ≤ 6 GREX-500M flasks on day 16<br>• 11 day duration | • Reduced number of steps<br>• Shorter REP duration<br>• Closed system transfer of TIL between flasks<br>• Closed system media exchanges |
| Harvest | • TIL harvested via centrifugation | • TIL harvested via LOVO automated cell washing system | • Reduced number of steps<br>• Automated cell washing<br>• Closed system<br>• Reduced loss of product during wash |
| Final Formulation | • Fresh product in Hypothermosol<br>• Single infusion bag<br>• Limited shipping stability | • Cryopreserved product in PlasmaLyte-A + 1% HSA and CS10 stored in $LN_2$<br>• Multiple aliquots<br>• Longer shipping stability | • Shipping flexibility<br>• Flexible patient scheduling<br>• More timely release testing |
| Overall Estimated Process Time | • 43 -55 days | • 22 days | • Faster turnaround to patient |

*Figure 6*

| Process 2A/Gen 2: about 22 days from Steps A -E | Process Gen 3: about 14-18 days from Steps A -E |
|---|---|
| **STEP A**<br>Obtain Patient Tumor Sample<br>(optionally can be frozen before Step B) | **STEP A**<br>Obtain Patient Tumor Sample<br>(optionally can be frozen before Step B) |
| **STEP B**<br>First Expansion<br>(physical fragmentation to at least 40 fragments per container grown for about 3 days to 14 days with media comprising IL-2) | **STEP B**<br>Priming First Expansion<br>(physical fragmentation of up to 60 fragments per container grown for about 1 days to 7 days with media comprising IL-2, OKT-3, and antigen-presenting feeder cells) |
| **STEP C**<br>First Expansion to Second Expansion Transition<br>(Step B TILs directly move to Step D, optionally on Step B day 11) | **STEP C**<br>Priming First Expansion to Rapid Second Expansion Transition<br>(Step B TILs directly move to Step D on day 7) |
| **STEP D**<br>Second Expansion<br>(TILs grown in growth media medium comprising IL-2, OKT-3, and antigen-presenting feeder cells in a closed container) | **STEP D**<br>Rapid Second Expansion<br>(TILs grown in growth media medium comprising IL-2, OKT-3, and 2X antigen-presenting feeder cells; Days 10-11 scale up and add additional IL-2) |
| **STEP E**<br>Harvest TILS from Step D<br>(TILs harvested via closed system) | **STEP E**<br>Harvest TILS from Step D |
| **STEP F**<br>Examine the potency and/or functionality of TIL s from Step E | **STEP F**<br>Examine the potency and/or functionality of TILs from Step E |
| **STEP G**<br>Final Formulation and/or Transfer to Infusion Bag<br>(optionally cryopreserve) | **STEP G**<br>Final Formulation and/or Transfer to Infusion Bag<br>(optionally cryopreserve) |

*Figure 8A*

Process Gen 3: about 14-18 days from Steps A-E

STEP A
Obtain Patient Tumor Sample
(optionally can be frozen before Step B)

STEP B
Priming First Expansion
(physical fragmentation of up to 60 fragments per container grown for about 1 days to 7 days with media comprising IL-2, OKT-3, and antigen-presenting feeder cells)

STEP C
Priming First Expansion to Rapid Second Expansion Transition
(Step B TILs directly move to Step D on day 7)

STEP D
Rapid Second Expansion
(TILs grown in growth media medium comprising IL-2, OKT-3, and 2X antigen-presenting feeder cells; Days 10-11 scale up and add additional IL-2)

STEP E
Harvest TILS from Step D

STEP F
Examine the potency and/or functionality of TILs from Step E

STEP G
Final Formulation and/or Transfer to Infusion Bag
(optionally cryopreserve)

*Figure 8B*

| Embodiment Gen 3.0: about 14-18 days from Steps A - E | Embodiment Gen 3.1 control: about 14-18 days from Steps A - E | Embodiment Gen 3.1 Test/F: about 14-18 days from Steps A - E |
|---|---|---|
| **STEP A**<br>Obtain Patient Tumor Sample (optionally can be frozen before Step B) | **STEP A**<br>Obtain Patient Tumor Sample (optionally can be frozen before Step B) | **STEP A**<br>Obtain Patient Tumor Sample (optionally can be frozen before Step B) |
| **STEP B**<br>Priming First Expansion (physical fragmentation of up to 60 fragments per container grown for about 1 days to 7/8 days with media comprising IL-2) | **STEP B**<br>Priming First Expansion (physical fragmentation of up to 60 fragments per container grown for about 1 days to 7/8 days with media comprising IL-2, and OKT-3) | **STEP B**<br>Priming First Expansion (physical fragmentation of up to 60 fragments per container grown for about 1 days to 7/8 days with media comprising IL-2, OKT-3, and antigen-presenting feeder cells) |
| **STEP C**<br>Priming First Expansion to Rapid Second Expansion Transition (Step B TILs directly move to Step D on day 7/8) | **STEP C**<br>Priming First Expansion to Rapid Second Expansion Transition (Step B TILs directly move to Step D on day 7/8) | **STEP C**<br>Priming First Expansion to Rapid Second Expansion Transition (Step B TILs directly move to Step D on day 7/8) |
| **STEP D**<br>Rapid Second Expansion (TILs grown in growth media medium comprising IL-2, OKT-3, and antigen-presenting feeder cells; Days 10-11 scale up and add additional IL-2) | **STEP D**<br>Rapid Second Expansion (TILs grown in growth media medium comprising IL-2, OKT-3, and 2X antigen-presenting feeder cells; Days 10-11 scale up and add additional IL-2) | **STEP D**<br>Rapid Second Expansion (TILs grown in growth media medium comprising IL-2, OKT-3, and 2X antigen-presenting feeder cells; Days 10-11 scale up and add additional IL-2) |
| **STEP E**<br>Harvest TILS from Step D | **STEP E**<br>Harvest TILS from Step D | **STEP E**<br>Harvest TILS from Step D |
| **STEP F**<br>Examine the potency and/or functionality of TILs from Step E | **STEP F**<br>Examine the potency and/or functionality of TILs from Step E | **STEP F**<br>Examine the potency and/or functionality of TILs from Step E |
| **STEP G**<br>Final Formulation and/or Transfer to Infusion Bag (optionally cryopreserve) | **STEP G**<br>Final Formulation and/or Transfer to Infusion Bag (optionally cryopreserve) | **STEP G**<br>Final Formulation and/or Transfer to Infusion Bag (optionally cryopreserve) |

*Figure 8C*

Modified Gen 2-like Process: about 22 days from Steps A - E

STEP A
Obtain Patient Tumor Sample
(optionally can be frozen before Step B;
optionally tumor sample can be a core/small biopsy)

STEP B1
Initial Culture
physical fragmentation of up to 60 tumor fragments or up to 10 cores/small biopsies per container, TILs grown for 3 days in growth medium comprising IL-2

STEP B2
Priming First Expansion
TILs grown for 8 days in growth medium comprising IL-2, OKT-3, and antigen-presenting feeder cells)

STEP C
Priming First Expansion to Rapid Second Expansion Transition
(Step B TILs directly move to Step D on day 11)

STEP D
Rapid Second Expansion
(volume reduced; TILs grown in growth media medium comprising IL-2, OKT-3, and 50X antigen-presenting feeder cells; Day 16 scale up and add additional IL-2)

STEP E
Harvest TILS from Step D

STEP F
Examine the potency and/or functionality of TILs from Step E

STEP G
Final Formulation and/or Transfer to Infusion Bag
(optionally cryopreserve)

*Figure 8D*

| STEP | Gen 2 | Gen 2.1 | Gen 3.0 Optimized |
|---|---|---|---|
| **Pre REP-day 0** | ≤ 50 fragments/ 1 G-Rex 100MCS - **11 days** | ≤ 180 fragments/ 3 G-Rex, Pre-formulated CM1 warmed media<br>100MCS - **11 days** | ***Fresh or Frozen Tumor***<br>Whole tumor with ≤ 30 fragments up to 60 fragments per 1 G-Rex.<br>100MCS (up to 4 G-Rex),<br>preformulated warmed media - **7 days. Pre REP, Feeders 2.5 E8 cells + OKT-3 (30ng/mL)** |
| **REP Initiation** | Direct to REP- Day 11-<br>**<200 E6 TIL**<br>1 G-Rex 500MCS | Direct to REP- Day 11-<br>**<200 E6 TIL**<br>Pre-formulated CM2 warmed media in one G-Rex 500MCS | Direct to REP - Day **7-all cells TIL- same G-Rex 100MCS (100MCS up to 4 GREX), Standard media or Defined Media (Serum free). Addition Feeders 5 E8 cells +OKT-3 (30ng/mL)** |
| **TIL propagation or Scale up** | 1 to 5 G-REX 500MCS<br>**Split day 16** | 2 to 5 G-REX 500MCS<br>Pre-formulated CM4 warmed media<br>**Split day 16** | From G-REX 100MCS transfer TIL suspension to G-REX 500MCS, up to 4 GREX 500 MCS- Standard media or Defined Media (Serum Free)<br>**Scale up on day 10 or 11** |
| **Harvest** | **Harvest day 22,**<br>LOVO-automated cell washer | **Harvest day 22,**<br>LOVO-automated cell washer (5 wash cycle) | **Harvest day 14 or 16**<br>LOVO- automated cell washer (5 wash cycle) |
| **Final formulation** | Cryopreserved Product 300IU/ml IL2- CS10 in $LN_2$, multiple aliquots | Cryopreserved Product 300IU/ml IL2- CS10 in $LN_2$, multiple aliquots | Cryopreserved product 300IU/ml IL-2- CS10 in $LN_2$, multiple aliquots |
| **Process time** | **22 days** | **22 days** | **16 days** |

*Figure 11*

| Process Day | Conditions | Gen 3.1 |
|---|---|---|
| Day 0- pre REP initiation | Media CM1 | 500 mL |
| | IL-2 (6000 IU/mL) | + |
| | OKT-3 (30ng/mL) | + |
| | Feeders (250 E+06) | + |

| Process Day | Conditions | Gen 3.1 |
|---|---|---|
| Day 7- REP initiation | Media CM2 | 500 mL |
| | IL-2 (6000 IU/mL) | + |
| | OKT-3 (30ng/mL) added on Day 7 | + |
| | Feeders Added on Day 7 | 500 E06 |
| | Total Feeders at Day | 750 E+06 |

| Process Day | Conditions | Gen 3.1 |
|---|---|---|
| Day 9-11 - Scale Up | From G-REX 100MCS transfer TIL suspension to 1 G-REX 500MCS (up to 3 GREX 500MCS) | Yes |
| Day 16 - Harvest | LOVO- automated cell washer | Yes |

*Figure 12*

| Process Comparison | Key Process Changes | Benefit |
|---|---|---|
| Gen 2 : Gen 2.1 | • Initiate process with two flasks instead of one flask<br>• Divide REP initiation feeder layer between 2 G-Rex500MCS Flasks<br>• Pre-formulate media and warm prior to use | • Potential doubling of final cell count (dose) with increased TIL repertoire.<br>• Process redundancy throughout process |
| Gen 2.1 : Gen 3.1 | • Fresh or Frozen tumor<br>• 14-16 day process (from 22 day)<br>• Reduce total feeder layer on process<br>• Feeder layer and OKT3 present at Day 0<br>• REP initiated with fragments<br>• 100MCS scales to 500MCS<br>• Scales to multiple pre-REP flasks<br>• Standard Media and Defined Media (Serum Free) | • Increased potency<br>• Improved phenotype<br>• Decreased process time<br>• Reduced reagent testing<br>• Decreased process variability<br>• Defined reagents<br>• Increased repertoire<br>• Reduce impurities (feeder)<br>• Comparable or Higher Dose. |

*Figure 13*

| Process Comparison | Key Process Changes | Desired Improvement | Criteria for Success | Outcome |
| --- | --- | --- | --- | --- |
| Gen 2 : Gen 3.0 | • 14-16 days<br>• Initiate REP with fragments up to 4 flask.<br>• 100MCS scales to 500MCS | • Increased potency<br>• Improved phenotype<br>• Decreased process time | • Increase potency as measured by INF-g ✓<br>• Comparable phenotype ✓<br>• Comparable Dose ✓<br>• Comparable purity ✓ (feeder cell)<br>• Maintain clonal diversity ✓ | • Potency increased over Gen2<br>• Improved expression of CD28 on CD8 cells<br>• Maximum capacity of flask reached by day 16 on Gen 3.1<br>• Reduced feeder cell usage<br>• Increased diversity |

*Figure 14*

| Process | Gen 2 | Gen 3 |
| --- | --- | --- |
| L4054 | Standard Media | Standard Media |
| L4055 | Standard Media | Standard Media |
| M1085T | Standard Media | Standard Media |

Standard Media:
Pre REP: CM1
REP initiation : CM2
Split or Scale up : CM4

| Process | Gen 3 | Gen 3.1 control | Gen 3.1 |
| --- | --- | --- | --- |
| L4063 | Standard Media | Standard Media | Standard Media |
| L4064 | Defined Media | Defined Media | Defined Media |

Defined Media:
CTS Optimizer (Serum Free Media) in each day of the process

*Figure 15*

| Process Day | Conditions | Gen 3.1 Test |
|---|---|---|
| Day 0- pre REP initiation | Media CM1 | 500 mL |
| | IL-2 (6000 IU/mL) | + |
| | OKT-3 (15ug) | + |
| | Feeders (250 E+06) | + |

| Process Day | Conditions | Gen 3.1 Test |
|---|---|---|
| Day 7- REP initiation | Media CM2 | 500 mL |
| | IL-2 (6000 IU/mL) | + |
| | OKT-3 (30ug) added on Day 7 | + |
| | Feeders Added on Day 7 | 500 E06 |
| | Total Feeders at Day | 750 E+06 |

| Process Day | Conditions | Gen 3.1 Test |
|---|---|---|
| Day 9-11 - Scale Up | From G-REX 100MCS transfer TIL suspension to 1 G-REX 500MCS (up to 3 GREX 500MCS) | Yes |
| Day 16 - Harvest | LOVO- automated cell washer | Yes |

*Figure 20*

| | Gen 2 | Gen 3 |
|---|---|---|
| Total culture time | 22 days | 16-17 days (or 16 days) |
| Pre-REP | | |
| Fragments/flask | ≤ 60 fragments in one flask | ≤ 60 fragments in up to 4 flasks |
| Media volume | 1L – single addition | 1L – 2 x 500 mL additions |
| Target pre-REP cell numbers | <200 x $10^6$ TIL | All cells carried through continuous process |
| Screening | No screen | No screen |
| Selection of flasks | No selection | Bact-T sterility, visual inspection for contaminants |
| REP/Scale up | | |
| Feeders | | Reduced by ≥ 40% |
| Media | Contains HSAB | Defined medium |
| Scale up | Pooled culture; volume reduce to 500 mL on Day 5 split up to 5 flasks (2500 $cm^2$) | Flasks scaled linearly and treated as subcomponents |
| OKT3 | 150 μg | ≤ 180 μg |
| IL-2 | High dose | High dose |
| Number of flasks | 1-5 | 1-4 |
| Final steps | | |
| Harvest/volume reduction | Closed 10:1 | Closed 10:1 |
| Concentrate/wash | LOVO 100:1 | LOVO 1000:1 |
| Formulation conditions | 1:1 CS10 (5% DMSO) | 1:1 CS10 (5% DMSO) |
| Shipment conditions | Vapor phase liquid nitrogen | Vapor phase liquid nitrogen |
| Infusion | Thawed IV gravity | Thawed IV gravity |

*Figure 23*

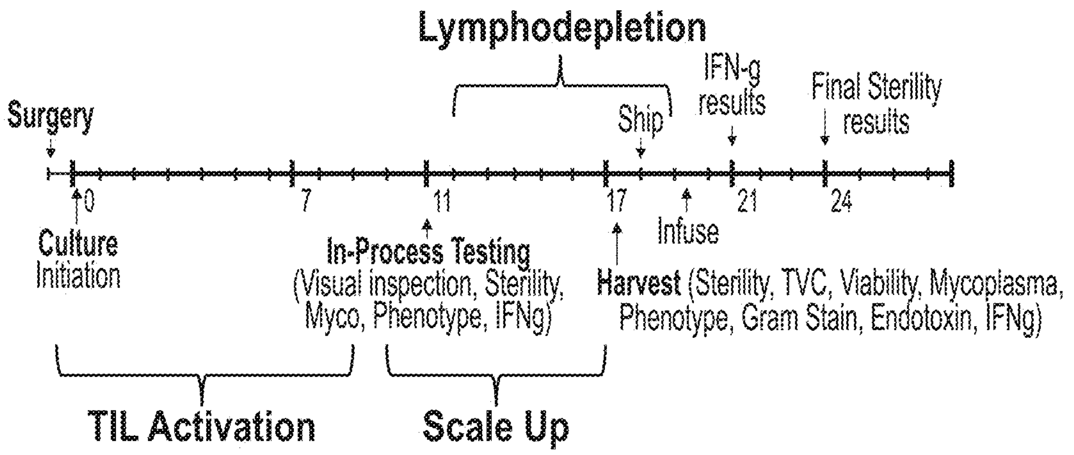

LD on:
Day 10-11 Viability
Day 10-11 Phenotype
Day 10-11 myco
Day 10-11 IFNg*

Release for infusion on:
Gram Stain
Day 10-11 Sterility
Day 16-17 Mycoplasma
Day 16-17 Endotoxin
Day 16-17 Phenotyping
Day 16-17 TVC count
Day 16-17 Viability

Final Release (CoA)
Day 16-17 Frozen:Thawed IFNg (ELISA)
Day 16-17 Endotoxin
Day 16-17 Phenotyping
Day 16-17 TVC count
Day 16-17 Viability
Day 16-17 Sterility

* Restimulation for ELISA on Day 10-11 will be from a fresh / frozen in-process sample reportable On Day 14

*Figure 24*

| STEP | Gen 2 | Gen 2.1 | Gen 3.0 |
|---|---|---|---|
| **Pre REP- day 0** | ≤ 50 fragments/ 1 G-Rex 100MCS - **11 days** | ≤ 180 fragments/ 3 G-Rex, Pre-formulated CM1 warmed media 100MCS - **11 days** | ***Fresh or Frozen Tumor*** Whole tumor with ≤ 30 fragments up to 60 fragments per 1 G-Rex. 100MCS (up to 4 G-Rex), preformulated warmed media - **7 days. Pre REP, Feeders 250e$^6$ cells + OKT-3 (15ug)** |
| **REP Initiation** | Direct to REP- Day 11- **<200e$^6$ TIL** 1 G-Rex 500MCS | Direct to REP- Day 11- **<200e$^6$ TIL** Pre-formulated CM2 warmed media in one G-Rex 500MCS | Direct to REP - Day **7-all cells TIL- same G-Rex 100MCS (100MCS up to 4 GREX), Standard media or Defined Media (Serum free). Addition Feeders 500e$^6$ cells +OKT-3 (30ug)** |
| **TIL propagation or Scale up** | 1 to 5 G-REX 500MCS **Split day 16** | 2 to 5 G-REX 500MCS Pre-formulated CM4 warmed media **Split day 16** | From G-REX 100MCS transfer TIL suspension to G-REX 500MCS, up to 4 GREX 500 MCS- Standard media or Defined Media (Serum Free) **Scale up on day 10 or 11** |
| **Harvest** | **Harvest day 22,** LOVO-automated cell washer | **Harvest day 22,** LOVO-automated cell washer (5 wash cycle) | **Harvest day 14 or 16** LOVO- automated cell washer (5 wash cycle) |
| **Final formulation** | Cryopreserved Product 300IU/ml IL2- CS10 in $LN_2$, multiple aliquots | Cryopreserved Product 300IU/ml IL2- CS10 in $LN_2$, multiple aliquots | Cryopreserved product 300IU/ml IL-2- CS10 in $LN_2$, multiple aliquots |
| **Process time** | **22 days** | **22 days** | **16 days** |

*Figure 28*

| Process Comparison | Process Changes | Differences |
|---|---|---|
| Gen 2 : Gen 2.1 | • Initiate process with two flasks instead of one flask<br>• Divide REP initiation feeder layer between 2 G-Rex500MCS Flasks<br>• Pre-formulate media and warm prior to use | • Potential doubling of final cell count (dose with increased TIL repertoire.<br>• Process redundancy throughout process |
| Gen 2.1 : Gen 3.1 | • Fresh or Frozen tumor<br>• 14-16 day process (from 22 day)<br>• Reduce total feeder layer on process<br>• Feeder layer and OKT3 present at Day 0<br>• REP initiated with fragments<br>• 100MCS scales to 500MCS<br>• Scales to multiple pre-REP flasks<br>• Standard Media and Defined Media (Serum Free) | • Increased potency<br>• Improved phenotype<br>• Decreased process time<br>• Reduced reagent testing<br>• Decreased process variability<br>• Defined reagents<br>• Increased repertoire<br>• Reduce impurities (feeder)<br>• Comparable or Higher Dose. |

*Figure 29*

Table 2. Description of Gen 3 optimization conditions.

| Process Day | Conditions | Gen 3.0 | Gen 3.1 control | Gen 3.1 Test |
|---|---|---|---|---|
| **Day 0 :** Tumor Fragment Isolation and Activation | Media (*) | 500 mL | 500 mL | 500 mL |
| | IL-2 | 6000 IU/mL | 6000 IU/mL | 6000 IU/mL |
| | OKT-3 | - | 15 ug | 15 ug |
| | Feeders | - | - | 2.5E+06 |
| **Process Day** | **Conditions** | **Gen 3.0** | **Gen 3.1 control** | **Gen 3.1 Test** |
| **Day 7 - 8 :** TIL Culture Reactivation | Media (*) | 500 mL | 500 mL | 500 mL |
| | IL-2 | 6000 IU/mL | 6000 IU/mL | 6000 IU/mL |
| | OKT-3 | 30 ug | 30 ug | 30 ug |
| | Feeders | 1 E+09 | 500 E+06 | 500E+06 |
| | Total Feeders added through Day 7 | 1 E+09 | 500 E+06 | 750E+06 |
| **Process Day** | **Conditions** | **Gen 3.0** | **Gen 3.1 control** | **Gen 3.1 Test** |
| **Day 10-11 : Culture Scale Up** | From GREX 100 transfer whole TIL suspension to 1 GREX 500 containing 4L media with IL-2 (3000 IU/mL) | | | |
| **Process Day** | **Conditions** | **Gen 3.0** | **Gen 3.1 control** | **Gen 3.1 Test** |
| **Day 16-17: Harvest/Wash/Formulate** | LOVO automated cell washer and cryopreservation with CS10. | | | |

(*) Media can be standard media or CTS serum free media.

*Figure 30*

| Step | Process Gen 3-Optimized |
| --- | --- |
| **Day 0**<br>**Tumor isolation and Activation** | ≤240 fragments<br>≤60 fragments/flask<br>≤4 flasks<br>≤2L media (500mL/flask)<br>IL-2 (6000IU/mL)<br>$2.5 \times 10^8$ feeder cells/flask<br>15ug OKT3/flask |
| **Day 7 - 8**<br>**Reactivation** | Fresh TIL direct to REP<br>Activate entire culture<br>$5 \times 10^8$ feeder cells<br>30 ug OKT3/flask<br>G-Rex 100MCS<br>Add 500mL media+ IL-2(6000IU/mL) |
| **Day 10 - 11**<br>**Scale up or TIL Sub-culture** | ≤4 G-REX 500MCS<br>Scale up entire culture transferring 1L from GREX 100MCS into GREX 500MCS<br>and add 4L of media +IL-2 (3000 IU/mL) /flask |
| **Day 16 - 17**<br>**Harvest** | Harvest<br>LOVO- automated cell washer<br>Cryopreservation on Plasmalyte 1% HSA: CS10 |

*Figure 32*

| Test | Acceptance Criteria | Gen 3.1 Test vs Gen 3.0 Process |
|---|---|---|
| Cell Count (TVC) | Gen 3.1 > 30% to Process Gen 3.0 | Met |
| % Viability | ≥70% Viability | Met |
| Immunophenotyping (%CD3+/ %CD45+) | ≤5% difference between Gen 3.1 and Gen 3.0 process | Met |
| IFNγ secretion | Gen 3.1 ≥ to Process Gen 3.0 | Met |

*Figure 33*

| Cytokine | Number (Samples) | TIL:Target Ratio | Mean | Median | Minimum | Maximum |
|---|---|---|---|---|---|---|
| IFNγ | 6 | 5:1 | 1039 | 174 | 53 | 3998 |
| | | 1:1 | 855 | 269 | 42 | 3708 |
| | | 1:5 | 481 | 61 | 23 | 1813 |
| Granzyme B | 6 | 5:1 | 3296 | 1877 | 738 | 11011 |
| | | 1:1 | 2569 | 1527 | 568 | 8721 |
| | | 1:5 | 1167 | 683 | 317 | 3745 |

*Figure 55*

*Solid gray line = 12 hours; aCD3/aCD28/a41BB beads*
*Dotted gray line = 12 hours unstimulated TIL*
*Solid black line = 18 hours; aCD3/aCD28/a41BB beads*
*Dotted black line = 18 hours unstimulated TIL*

*Solid gray line = 12 hours: aCD3/aCD28/a41BB beads*
*Dotted gray line = 12 hours unstimulated TIL*
*Solid black line = 18 hours: aCD3/aCD28/a41BB beads*
*Dotted black line = 18 hours unstimulated TIL*

*Solid black line: 5-fold change*
*Dotted black line: 3-fold change*

*Solid black line: 5-fold change*
*Dotted black line: 3-fold change*

*Solid black line: 5-fold change*
*Dotted black line: 3-fold change*
*Dotted black and white line: 2-fold change*

*Solid gray line =12 hours: aCD3/aCD28/a41BB beads*
*Dotted gray line = 12 hours unstimulated TIL*
*Solid blackline =18 hours: aCD3/aCD28/a41BB beads*
*Dotted black line = 18 hours unstimulated TIL*

*Solid gray line =12 hours: aCD3/aCD28/a41BB beads*
*Dotted gray line = 12 hours unstimulated TIL*
*Solid black line =18 hours: aCD3/aCD28/a41BB beads*
*Dotted black line = 18 hours unstimulated TIL*

*Solid black line: 5-fold change*
*Dotted black line: 3-fold change*

*Solid black line: 5-fold change*
*Dotted black line: 3-fold change*

*Solid black line: 5-fold change*
*Dotted black line: 3-fold change*
*Dotted black and white line: 2-fold change*

*Solid gray line =12 hours: aCD3/aCD28/a41BB beads*
*Dotted gray line = 12 hours unstimulated TIL*
*Solid black line =18 hours: aCD3/aCD28/a41BB beads*
*Dotted black line = 18 hours unstimulated TIL*

*Solid gray line =12 hours: aCD3/aCD28/a41BB beads*
*Dotted gray line = 12 hours unstimulated TIL*
*Solid black line =18 hours: aCD3/aCD28/a41BB beads*
*Dotted black line = 18 hours unstimulated TIL*

*Solid gray line =12 hours: aCD3/aCD28/a41BB beads*
*Dotted gray line = 12 hours unstimulated TIL*
*Solid black line =18 hours: aCD3/aCD28/a41BB beads*
*Dotted black line = 18 hours unstimulated TIL*

| Cytokine | Timepoint | Group | Mean | STDEV | Min | LQ | Median | UQ | Max | CV (%) |
|---|---|---|---|---|---|---|---|---|---|---|
| Granzyme B | 12 hr | K562 (pg/mL) | 171.8 | 87.3 | 52.7 | 115.7 | 146.0 | 210.7 | 369.7 | 50.8 |
| | | Raji (pg/mL) | 782.5 | 458.5 | 239.0 | 431.0 | 703.0 | 972.7 | 1746.3 | 40.4 |
| | | K562 Fold Change over TIL | 1.6 | 0.7 | 0.4 | 1.1 | 1.5 | 2.0 | 2.9 | 58.6 |
| | | Raji Fold Change over TIL | 7.1 | 3.1 | 2.1 | 5.3 | 6.9 | 8.1 | 16.5 | 43.1 |
| | | K562 over K562 | 1 | 0 | 1 | 1 | 1 | 1 | 1 | 0.0 |
| | | Raji over K562 | 4.8 | 1.9 | 2.2 | 3.7 | 4.6 | 4.9 | 10.8 | 39.4 |
| | 18 hr | K562 (pg/mL) | 337.8 | 175.8 | 119.0 | 217.0 | 311.5 | 378.0 | 853.0 | 52.0 |
| | | Raji (pg/mL) | 2105.1 | 1297.4 | 603.3 | 1185.3 | 1672.7 | 3051.3 | 5383.7 | 54.6 |
| | | K562 Fold Change over TIL | 0.9 | 0.5 | 0.3 | 0.5 | 0.9 | 1.2 | 2.3 | 61.6 |
| | | Raji Fold Change over TIL | 5.4 | 2.6 | 1.7 | 3.4 | 5.7 | 6.4 | 11.5 | 48.6 |
| | | K562 over K562 | 1 | 0 | 1 | 1 | 1 | 1 | 1 | 0.0 |
| | | Raji over K562 | 6.4 | 3.0 | 2.8 | 4.8 | 5.5 | 8.2 | 14.6 | 46.2 |
| IFN-γ | 12 hr | K562 (pg/mL) | 16.0 | 18.4 | 1.8 | 6.3 | 10.5 | 16.2 | 69.1 | 114.8 |
| | | Raji (pg/mL) | 198.4 | 245.3 | 19.5 | 50.7 | 106.5 | 196.0 | 1022.7 | 194.1 |
| | | K562 Fold Change over TIL | 3.0 | 5.8 | 0.4 | 0.9 | 1.2 | 1.7 | 26.3 | 123.7 |
| | | Raji Fold Change over TIL | 26.7 | 26.2 | 2.0 | 7.9 | 14.1 | 46.2 | 92.9 | 97.8 |
| | | K562 over K562 | 1 | 0 | 1 | 1 | 1 | 1 | 1 | 0.0 |
| | | Raji over K562 | 20.3 | 22.9 | 1.0 | 5.0 | 12.9 | 25.1 | 83.7 | 112.5 |
| | 18 hr | K562 (pg/mL) | 17.7 | 20.0 | 1.9 | 7.4 | 12.7 | 17.4 | 77.9 | 113.2 |
| | | Raji (pg/mL) | 379.8 | 526.0 | 26.6 | 99.9 | 164.0 | 430.7 | 2112.7 | 194.0 |
| | | K562 Fold Change over TIL | 3.1 | 6.0 | 0.3 | 0.9 | 1.0 | 2.0 | 27.1 | 138.5 |
| | | Raji Fold Change over TIL | 45.3 | 49.1 | 2.8 | 12.3 | 23.0 | 73.4 | 154.7 | 108.3 |
| | | K562 over K562 | 1 | 0 | 1 | 1 | 1 | 1 | 1 | 0.0 |
| | | Raji over K562 | 36.8 | 47.7 | 1.5 | 6.2 | 14.4 | 44.1 | 157.5 | 129.7 |

Figure 97

Fit Curve

Model Comparison

| Model | AICc | BIC | SSE | MSE | RMSE | R-Square |
|---|---|---|---|---|---|---|
| Linear | -234.6697 | -211.3489 | 0.1034374 | 0.001724 | 0.0415206 | 0.9947651 |

Plot

Fit Curve

Model Comparison

| Model | AICc | BIC | SSE | MSE | RMSE | R-Square |
|---|---|---|---|---|---|---|
| Linear | -216.8738 | -193.553 | 0.1324404 | 0.0022073 | 0.0469823 | 0.9943524 |

Plot

METHODS AND COMPOSITIONS FOR T-CELL COCULTURE POTENCY ASSAYS AND USE WITH CELL THERAPY PRODUCTS

CROSS-REFERENCES TO RELATED APPLICATIONS

This instant application is a continuation application of U.S. patent application Ser. No. 18/477,810 filed Sep. 29, 2023, which is a continuation application of U.S. patent application Ser. No. 17/705,159 filed Mar. 25, 2022, and which claims the benefit of U.S. Provisional Application No. 63/166,210 filed Mar. 25, 2021, U.S. Provisional Application No. 63/189,829 filed May 18, 2021, U.S. Provisional Application No. 63/212,933 filed Jun. 21, 2021, U.S. Provisional Application No. 63/233,035 filed Aug. 13, 2021, U.S. Provisional Application No. 63/246,890 filed Sep. 22, 2021, U.S. Provisional Application No. 63/286,145 filed Dec. 6, 2021, and U.S. Provisional Application No. 63/309,919 filed Feb. 14, 2022, which are expressly incorporated herein by reference in their entirety for all purposes.

REFERENCE TO A "SEQUENCE LISTING," A TABLE, OR A COMPUTER PROGRAM, LISTING APPENDIX SUBMITTED ON A COMPACT DISK

The instant application contains a Sequence Listing which has been submitted electronically in XML file format and is hereby incorporated by reference in its entirety. Said XML file, created on May 17, 2024, is named 116983-5089-US02 Sequence Listing.xml and is 319,262 bytes in size.

BACKGROUND OF THE INVENTION

Treatment of bulky, refractory cancers using adoptive autologous transfer of tumor infiltrating lymphocytes (TILs) represents a powerful approach to therapy for patients with poor prognoses. Gattinoni, et al., *Nat. Rev. Immunol.* 2006, 6, 383-393. TILs are dominated by T cells, and IL-2-based TIL expansion followed by a "rapid expansion process" (REP) has become a preferred method for TIL expansion because of its speed and efficiency. Dudley, et al., *Science* 2002, 298, 850-54; Dudley, et al., *J. Clin. Oncol.* 2005, 23, 2346-57; Dudley, et al., *J. Clin. Oncol.* 2008, 26, 5233-39; Riddell, et al., *Science* 1992, 257, 238-41; Dudley, et al., *J. Immunother.* 2003, 26, 332-42. A number of approaches to improve responses to TIL therapy in melanoma and to expand TIL therapy to other tumor types have been explored with limited success, and the field remains challenging. Goff, et al., *J. Clin. Oncol.* 2016, 34, 2389-97; Dudley, et al., *J. Clin. Oncol.* 2008, 26, 5233-39; Rosenberg, et al., *Clin. Cancer Res.* 2011, 17, 4550-57. Combination studies with single immune checkpoint inhibitors have also been described, but further studies are ongoing and additional methods of treatment are needed (Kverneland, et al., *Oncotarget,* 2020, 11 (22), 2092-2105).

Furthermore, current TIL manufacturing and treatment processes are limited by length, cost, sterility concerns, and other factors described herein such that the potential to treat patients which are refractory other checkpoint inhibitor therapies have been severely limited. There is an urgent need to provide quality control processes for TIL manufacturing processes and therapies based on such processes that are appropriate for use in treating patients for whom very few or no viable treatment options remain. The present invention meets this need by providing a shortened manufacturing process for use in generating TILs with an additional step providing a mechanism for assessing potency and/or functionality of the expanded TILs.

The present invention provides improved processes, methods, and compositions for preparing and assessing the potency and/or functionality of T cells, including TILs, in order, for example, to prepare therapeutic populations of TILs with increased therapeutic efficacy for the treatment of cancer. These potency assays capable of providing superior performance, better control over T cell product potency, and increased biological relevance, among other improvements, in comparison to assays known in the art. Processes for manufacturing, methods of administration, and pharmaceutical compositions using potency assays are also described. These processes and methods may additionally be used with the administration of TILs in combination with CTLA-4 and PD-1 inhibitors and/or PD-L1 inhibitors as described herein.

BRIEF SUMMARY OF THE INVENTION

Provided herein are methods for assessing the potency and/or functionality of expanded TILs and other polyclonal T cell products, including marrow infiltrating lymphocytes (MILs) and peripheral blood lymphocytes (PBLs), which can then be employed in the treatment of cancer by administering TILs, MILs, PBLs, or other polyclonal T cell products assessed by these methods.

In one aspect, the present invention provides for a method of determining the potency of a T cell product, the method comprising the steps of:

a. performing a co-culture of a target cell with a T cell product cell for a first period;
b. obtaining a harvest from the co-culture; and
c. assessing the harvest for (1) expression of one or more markers on the T cell product cell or (2) one or more analytes secreted from the T cell product cell to obtain one or more observed values to determine the potency for the T cell product.

In some embodiments, the method comprises the additional steps of:

d. performing a second co-culture of a negative control comprising (i) a negative control cell or (ii) a human leukocyte antigen (HLA) blocking antibody and the target cell with the T cell product cell for a second period;
e. obtaining a second harvest from the second co-culture;
f. assessing the second harvest for (1) the expression of the one or more markers on the T cell product cell or (2) the one or more analytes secreted from the T cell product cell to obtain one or more control values; and
g. comparing the one or more observed values from step c with the one or more control values from step f, where each observed value is compared to its corresponding control value, to determine the potency of the T cell product.

In some embodiments, the T cell product is selected from the group consisting of a tumor-infiltrating lymphocyte (TIL) product, a marrow-infiltrating lymphocyte (MIL) product, or a peripheral blood lymphocyte (PBL) product.

In some embodiments, the T cell product is a TIL product from a human, and wherein the TIL product is obtained by resection of a tumor or fragmentation or digestion of a tumor and manufactured by a TIL expansion process comprising a rapid expansion protocol step.

In some embodiments, the method comprises the step of releasing the T cell product for use in the treatment of a human patient.

In some embodiment, the target cell is an irradiated Raji cell or a derivative, variant, modification, or progeny thereof.

In some embodiments, the negative control cell lacks MHC or HLA Class I and MHC or HLA Class II expression.

In some embodiments, the negative control cell is an irradiated K562 cell or a derivative, variant, modification, or progeny thereof.

In some embodiments, the HLA blocking antibody comprises an HLA-I blocking antibody, an HLA-II blocking antibody, or a combination thereof.

In some embodiments, the ratio between the number of TIL product cells to the number of target cells is between 5:1 and 1:5.

In some embodiments, the ratio between the number of TIL product cells to the number of negative control cells is between 5:1 and 1:5.

In some embodiments, the ratio between the number of TIL product cells to the number of target cells is between 3:1 and 1:3.

In some embodiments, the ratio between the number of TIL product cells to the number of negative control cells is between 3:1 and 1:3.

In some embodiments, the ratio between the number of TIL product cells to the number of target cells is between 1:2 and 1:4.

In some embodiments, the ratio between the number of TIL product cells to the number of negative control cells is between 1:2 and 1:4.

In some embodiments, the ratio between the number of TIL product cells to the number of target cells is between 1:25 and 1:35.

In some embodiments, the ratio between the number of TIL product cells to the number of negative control cells is between 1:25 and 1:35.

In some embodiments, the ratio between the number of TIL product cells to the number of target cells is about 1:2.

In some embodiments, the ratio between the number of TIL product cells to the number of negative control cells is about 1:2.

In some embodiments, the ratio between the number of TIL product cells to the number of target cells is about 1:3.

In some embodiments, the ratio between the number of TIL product cells to the number of negative control cells is about 1:3.

In some embodiments, the ratio between the number of TIL product cells to the number of target cells is about 1:4.

In some embodiments, the ratio between the number of TIL product cells to the number of negative control cells is about 1:4.

In some embodiments, the co-culture is performed after thawing a cryopreserved TIL product, MIL product, or PBL product, and allowing the thawed TIL product, MIL product, or PBL product to recover under incubation for a period selected from the group consisting of 12 hours, 24 hours, 36 hours, 48 hours, 60 hours, and 72 hours.

In some embodiments, the first period is from about 6 hours to about 48 hours.

In some embodiments, the second period is from about 6 hours to about 48 hours.

In some embodiments, the first period is selected from the group consisting of about 12 hours, about 18 hours, and about 24 hours.

In some embodiments, the second period is selected from the group consisting of about 12 hours, about 18 hours, and about 24 hours.

In some embodiments, the first period and the second period are the same duration.

In some embodiments, the one or more markers on the T cell product are selected from the group consisting of CD25, CD69, CD134, CD137, CD150, KLRG1, or combinations thereof.

In some embodiments, the one or more analytes secreted from the T cell product is selected from the group consisting of IFN-α, IFN-β, IFN-γ, granzyme B, perforin, TNF-α, IL-1α, IL-1 β, IL-2, IL-3, IL-4, IL-5, IL-6, IL-8, IL-9, IL-10, IL-13, IL-14, IL-16, IL-17, IL-18, IL-22, IL-25, IL-26, MIP-1β, and combinations thereof.

In some embodiments, the one or more analytes secreted from the TIL product is selected from the group consisting of IFN-α, IFN-β, IFN-γ, granzyme B, perforin, TNF-α, IL-1α, IL-1 β, IL-2, IL-3, IL-4, IL-5, IL-6, IL-8, IL-9, IL-10, IL-13, IL-14, IL-16, IL-17, IL-18, IL-22, IL-25, IL-26, MIP-1β, and combinations thereof, wherein the quantity of the observed value is normalized to the quantity of the control value for each of the one or more analytes, and wherein the increase in observed value over the control value for each of the one or more analytes is selected from the group consisting of at least 1-fold, at least 1.5-fold, at least 2-fold, at least 2.5-fold, at least 3-fold, at least 3.5-fold, at least 4-fold, at least 4.5-fold, and at least 5-fold.

In some embodiments, the TIL product is manufactured from a tumor obtained by surgical resection, needle biopsy, core biopsy, small biopsy, or other means for obtaining a sample that contains a mixture of tumor and TIL cells from a human patient.

In another aspect, the present invention provides a method of treating a cancer in a patient in need thereof with a population of tumor infiltrating lymphocytes (TILs), the method comprising the steps of:

(a) obtaining and/or receiving a first population of TILs from a tumor resected from the patient by surgical resection, needle biopsy, core biopsy, small biopsy, or other means by processing a tumor sample obtained from the patient into (i) multiple tumor fragments or (ii) a tumor digest;

(b) adding the first population of TILs into a closed system;

(c) performing a first expansion by culturing the first population of TILs in a cell culture medium comprising IL-2 to produce a second population of TILs, wherein the first expansion is performed in a closed container providing a first gas-permeable surface area, wherein the first expansion is performed for about 3-14 days to obtain the second population of TILs, and wherein the transition from step (b) to step (c) occurs without opening the system;

(d) performing a second expansion by supplementing the cell culture medium of the second population of TILs with additional IL-2, OKT-3, and antigen presenting cells (APCs), to produce a third population of TILs, wherein the second expansion is performed for about 7-14 days to obtain the third population of TILs, wherein the third population of TILs is a therapeutic population of TILs, wherein the second expansion is performed in a closed container providing a second gas-permeable surface area, and wherein the transition from step (c) to step (d) occurs without opening the system;

(e) harvesting the therapeutic population of TILs obtained from step (d), wherein the transition from step (d) to step (e) occurs without opening the system;

(f) determining the potency of the therapeutic population of TILs by:

i. performing a co-culture of a target cell with a portion of the therapeutic population of TILs for a first period;

ii. obtaining a harvest from the co-culture;

iii. assessing the harvest for (1) expression of one or more markers on the portion of the therapeutic population of TILs or (2) one or more analytes secreted from the portion of the therapeutic population of TILs to obtain one or more observed values to determine the potency for the therapeutic population of TILs;

iv. performing a second co-culture of a negative control cell or (i) a negative control cell or (ii) a human leukocyte antigen blocking antibody with a second portion of the therapeutic population of TILs for a second period;

v. obtaining a second harvest from the second co-culture;

vi. assessing the second harvest for (1) the expression of the one or more markers on the second portion of the therapeutic population of TILs or (2) the one or more analytes secreted from the second portion of the therapeutic population of TILs to obtain one or more control values; and vii. comparing the one or more observed values with the one or more control values, where each observed value is compared to its corresponding control value, to determine the potency of the therapeutic population of TILs;

(g) transferring the therapeutic population of TILs from step (e) to an infusion bag, wherein the transfer from step (e) to (g) occurs without opening the system;

(h) optionally cryopreserving the infusion bag comprising the therapeutic population of TILs from step (g) using a cryopreservation process; and (i) if the therapeutic population of TILs is determined to be potent, administering a therapeutically effective dosage of the therapeutic population of TILs from the infusion bag in step (g) or (h) to the patient.

In some embodiments, examining the potency and/or functionality of the TILs harvested occurs after cryopreservation, or optionally before and after a cryopreservation step.

In some embodiments, the patient has a tumor that is unresectable, metastatic, resistant, or refractory to a CTLA-4 inhibitor, PD-1 inhibitor, or a PD-L1 inhibitor, and optionally wherein the patient has been previously treated with a CTLA-4 inhibitor, a PD-1 inhibitor, or a PD-L1 inhibitor.

In some embodiments, the second population of TILs in step (c) is at least 50-fold greater in number than the first population of TILs.

In some embodiments, the first expansion is performed over a period of about 10 to about 12 days.

In some embodiments, the second expansion is performed over a period of about 10 to about 12 days.

In some embodiments, the first expansion is performed over a period of about 11 days.

In some embodiments, the second expansion is performed over a period of about 11 days.

In some embodiments, the IL-2 is present at an initial concentration of between 1000 IU/mL and 6000 IU/mL in the cell culture medium in the first expansion.

In some embodiments, in the second expansion step, the IL-2 is present at an initial concentration of between 1000 IU/mL and 6000 IU/mL and the OKT-3 antibody is present at an initial concentration of about 30 ng/mL.

In some embodiments, the method further comprises the step of treating the patient with a non-myeloablative lymphodepletion regimen prior to administering the TILs to the patient.

In some embodiments, the non-myeloablative lymphodepletion regimen comprises the steps of administration of cyclophosphamide at a dose of 60 mg/m$^2$/day for two days followed by administration of fludarabine at a dose of 25 mg/m$^2$/day for five days.

In some embodiments, the non-myeloablative lymphodepletion regimen comprises the steps of administration of cyclophosphamide at a dose of 60 mg/m$^2$/day and fludarabine at a dose of 25 mg/m$^2$/day for two days followed by administration of fludarabine at a dose of 25 mg/m$^2$/day for three days.

In some embodiments, the method further comprises the step of treating the patient with an IL-2 regimen starting on the day after the administration of the therapeutic population of TILs to the patient.

In some embodiments, the method further comprises the step of treating the patient with an IL-2 regimen starting on the same day as administration of the therapeutic population of TILs to the patient.

In some embodiments, the IL-2 regimen is administered about 3 to about 24 hours after completion of the administration of the therapeutic population of TILs to the patient.

In some embodiments, the IL-2 regimen is a high-dose IL-2 regimen comprising 600,000 or 720,000 IU/kg of aldesleukin, or a biosimilar or variant thereof, administered as a 15-minute bolus intravenous infusion every eight hours until tolerance.

In some embodiments, processing a tumor sample obtained from the patient into a tumor digest in step (a) further comprises incubating the tumor sample in an enzymatic media.

In some embodiments, processing a tumor sample obtained from the patient into a tumor digest in step (a) further comprises disrupting the tumor sample mechanically so as to dissociate the tumor sample.

In some embodiments, processing a tumor sample obtained from the patient into a tumor digest in step (a) further comprises purifying the disassociated tumor sample using a density gradient separation.

In some embodiments, the enzymatic media comprises DNase.

In some embodiments, the enzymatic media comprises about 30 units/mL of DNase.

In some embodiments, the enzymatic media comprises collagenase.

In some embodiments, the enzymatic media comprises about 1.0 mg/ml of collagenase.

In some embodiments, the cancer is selected from the group consisting of melanoma, ovarian cancer, pancreatic cancer, endometrial cancer, thyroid cancer, cervical cancer, non-small-cell lung cancer, small-cell lung cancer, bladder cancer, breast cancer, head and neck cancer, glioblastoma, gastrointestinal cancer, renal cancer, sarcoma, and renal cell carcinoma.

In some embodiments, the method comprises the step of administering a PD-1 inhibitor, PD-L1 inhibitor, or CTLA-4 inhibitor to the patient.

In another aspect, the present invention provides a method of determining the potency of a T cell product, the method comprising the steps of:

a. performing at least three co-cultures of target cells with T cell product cells at different target cell concentrations;
b. performing at least three co-cultures of target cells with T cell reference standard cells at different target cell concentrations;
c. extracting supernatants from each of the co-cultures; and
d. assessing the supernatants for a cytokine secreted from the T cell product cells and T cell reference standard cells to obtain dose-concentrations to determine the potency of the T cell product;

wherein the target cells are monocyte cells.

In some embodiments, the T cell product is a tumor infiltrating lymphocyte (TIL) product, a marrow infiltrating lymphocyte (MIL) product, or a peripheral blood lymphocyte (PBL) product.

In some embodiments, the monocyte cells are U937 or Thp1 cells, or a derivative, variant, modification, or progeny thereof, and wherein the cytokine is interferon-γ.

In some embodiments, the co-cultures are performed for a time period selected from the group consisting of about 6 hours, about 12 hours, about 18 hours, about 24 hours, about 30 hours, about 36 hours, about 42 hours, and about 48 hours.

In some embodiments, the T cell product is a TIL product, and wherein four target cell dose-concentrations of about $4\times10^5$, about $2\times10^5$, about $1\times10^5$, and about $0.5\times10^5$ target cells per well and a single TIL cell concentration of about $1.5\times10^6$ TIL per well are used.

In some embodiments, at least four co-cultures of target cells with T cell product cells and at least four co-cultures of target cells with T cell reference standard cells are used, parallel line analysis is performed, and one outlier target cell dose-concentration is discarded.

In some embodiments, the method is a component of a potency assay matrix.

In some embodiments, the potency assay matrix comprises one or more assays selected from the group consisting of a bead- or plate-based assay using CD3, CD28, and/or CD137 stimulation and reporting interferon-γ, granzyme B, or tumor necrosis factor-α, an assay for total viable cells, an assay for percentage viable cells, an assay for $CD4^+$ cell content, an assay for $CD8^+$ cell content, an assay for $T_{EM}$ cell content, an assay for $T_{CM}$ cell content, an assay for $LAG3^+$ cell content, and an assay for $KLRG1^+$ cell content, an assay for $CD101^+$ cell content, an assay for $CD69^+$ cell content, an assay for $T_{SCM}$ cell content, an assay for $T_{EMRA}$ cell content, an assay for $T_{reg}$ cell content, an assay for $PD\text{-}1^+$ cell content, an assay for $TIM3^+$ cell content, an assay for $CD25^+$ cell content, an assay for $CD27^+$ cell content, an assay for $CD28^+$ cell content, an assay for $CD56^+$ cell content, an assay for $CTLA\text{-}4^+$ cell content, an assay for $TIGIT^+$ cell content, and an assay for $CD57^+$ cell content.

In another aspect, the present invention provides a method for treating a subject with a cancer, the method comprising administering an expanded tumor infiltrating lymphocytes (TILs) comprising:

(a) adding a tumor digest or tumor fragments into a closed system, wherein the tumor digest or tumor fragments comprise a first population of TILs and are obtained from a tumor that was resected from the subject;
(b) performing a first expansion by culturing the first population of TILs in a cell culture medium comprising IL-2 to produce a second population of TILs, wherein the first expansion is performed in a closed container providing a first gas-permeable surface area, wherein the first expansion is performed for about 3-11 days to obtain the second population of TILs, and wherein the transition from step (b) to step (c) occurs without opening the system;
(c) performing a second expansion by supplementing additional cell culture medium comprising IL-2, OKT-3, and antigen presenting cells (APCs), to produce a third population of TILs, wherein the second expansion is performed for about 7-11 days to obtain the third population of TILs, wherein the second expansion is performed in a closed container providing a second gas-permeable surface area, and wherein the transition from step (b) to step (c) occurs without opening the system;
(d) harvesting the third population of TILs obtained from step (c), wherein the transition from step (c) to step (d) occurs without opening the system;
(e) transferring the harvested third TIL population from step (d) to an infusion bag, wherein the transfer from step (d) to (e) occurs without opening the system;
(f) cryopreserving the infusion bag comprising the harvested TIL population from step (e) using a cryopreservation process; and
(g) administering a therapeutically effective dosage of the third population of TILs from the infusion bag in step (f) to the subject;

wherein the APCs are selected from the group consisting of Raji, Ramos, Daudi, U937, or Thp1 cells, or a derivative, variant, modification, or progeny thereof.

In some embodiments, the cancer is selected from the group consisting of melanoma (including metastatic melanoma and uveal melanoma), ovarian cancer, cervical cancer, non-small-cell lung cancer (NSCLC), small cell lung cancer, bladder cancer, breast cancer, cancer caused by human papilloma virus, head and neck cancer (including head and neck squamous cell carcinoma (HNSCC)), esophageal cancer, esophagogastric junction cancer, gastric cancer, gastrointestinal cancer, renal cancer, and renal cell carcinoma.

In some embodiments, the first expansion in step (a) and the second expansion in step (b) are each individually performed within a period of 11 days.

In some embodiments, steps (a) through (d) are performed in about 10 days to about 22 days.

In some embodiments, the potency of the TILs has been determined using the method as described herein.

In some embodiments, the potency of the TILs has been determined using the method as described herein.

BRIEF DESCRIPTION OF THE DRAWINGS

FIG. 1: Exemplary Gen 2 (process 2A) chart providing an overview of Steps A through F.

FIG. 5: Comparison table of Steps A through F from exemplary embodiments of process 1C and Gen 2 (process 2A) for TIL manufacturing.

FIG. 6: Detailed comparison of an embodiment of process 1C and an embodiment of Gen 2 (process 2A) for TIL manufacturing.

FIG. 8A-8D: A) Shows a comparison between the 2A process (approximately 22-day process) and an embodiment of the Gen 3 process for TIL manufacturing (approximately 14-days to 16-days process). B) Exemplary Process Gen 3 chart providing an overview of Steps A through F (approximately 14-days to 16-days process). C) Chart providing three exemplary Gen 3 processes with an overview of Steps A through F (approximately 14-days to 16-days process) for each of the three process variations. D) Exemplary modified Gen 2-like process providing an overview of Steps A through F (approximately 22-days process).

FIG. 11: Table describing various features of embodiments of the Gen 2, Gen 2.1 and Gen 3.0 process.

FIG. 12: Overview of the media conditions for an embodiment of the Gen 3 process, referred to as Gen 3.1.

FIG. 13: Table describing various features of embodiments of the Gen 2, Gen 2.1 and Gen 3.0 process.

FIG. 14: Table comparing various features of embodiments of the Gen 2 and Gen 3.0 processes.

FIG. 15: Table providing media uses in the various embodiments of the described expansion processes.

FIG. 20: Provides a process overview for an exemplary embodiment of the Gen 3.1 process (a 16 day process).

FIG. 23: Comparison table for exemplary Gen 2 and exemplary Gen 3 processes.

FIG. 24: Schematic of an exemplary embodiment of the Gen 3 process (a 16-17 day process) preparation timeline.

FIG. 28: Comparison of Gen 2, Gen 2.1 and an embodiment of the Gen 3 process (a 16 day process).

FIG. 29: Comparison of Gen 2, Gen 2.1 and an embodiment of the Gen 3 process (a 16 day process).

FIG. 30: Gen 3 embodiment components.

FIG. 32: Shown are the components of an exemplary embodiment of the Gen 3 process (a 16-17 day process).

FIG. 33: Acceptance criteria table.

FIG. 55: IFN-γ and granzyme B secretion summary table.

FIG. 97: Summary table for granzyme B and IFN-γ results for 22 samples tested using an embodiment of a Raji cell co-culture assay.

Figure 120:
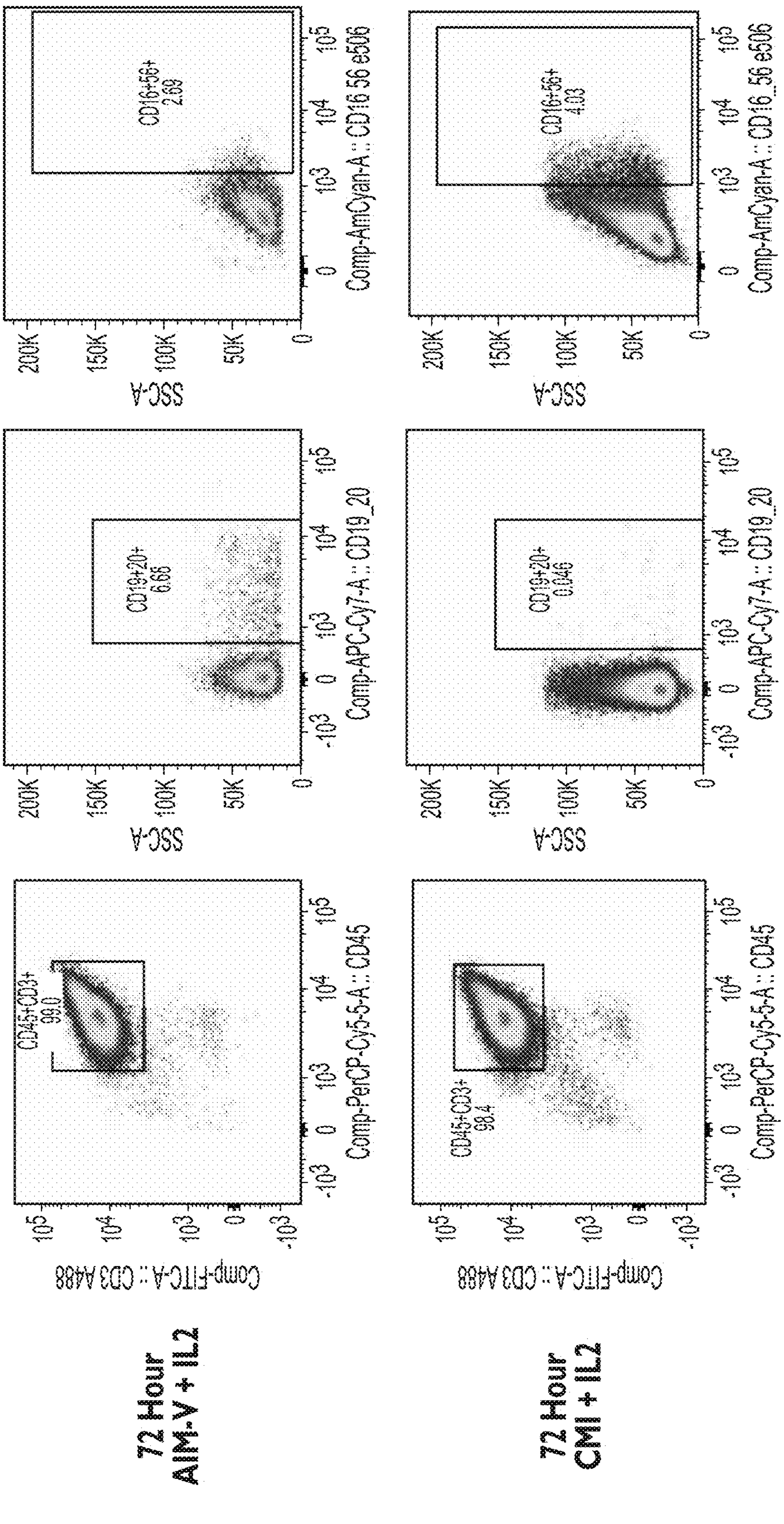

FIG. 120: Flow cytometry analysis of residual cell populations of parent live populations for TIL line M1179 in two embodiments of the co-culture conditions at 72 hour resting periods.

Figure 121:
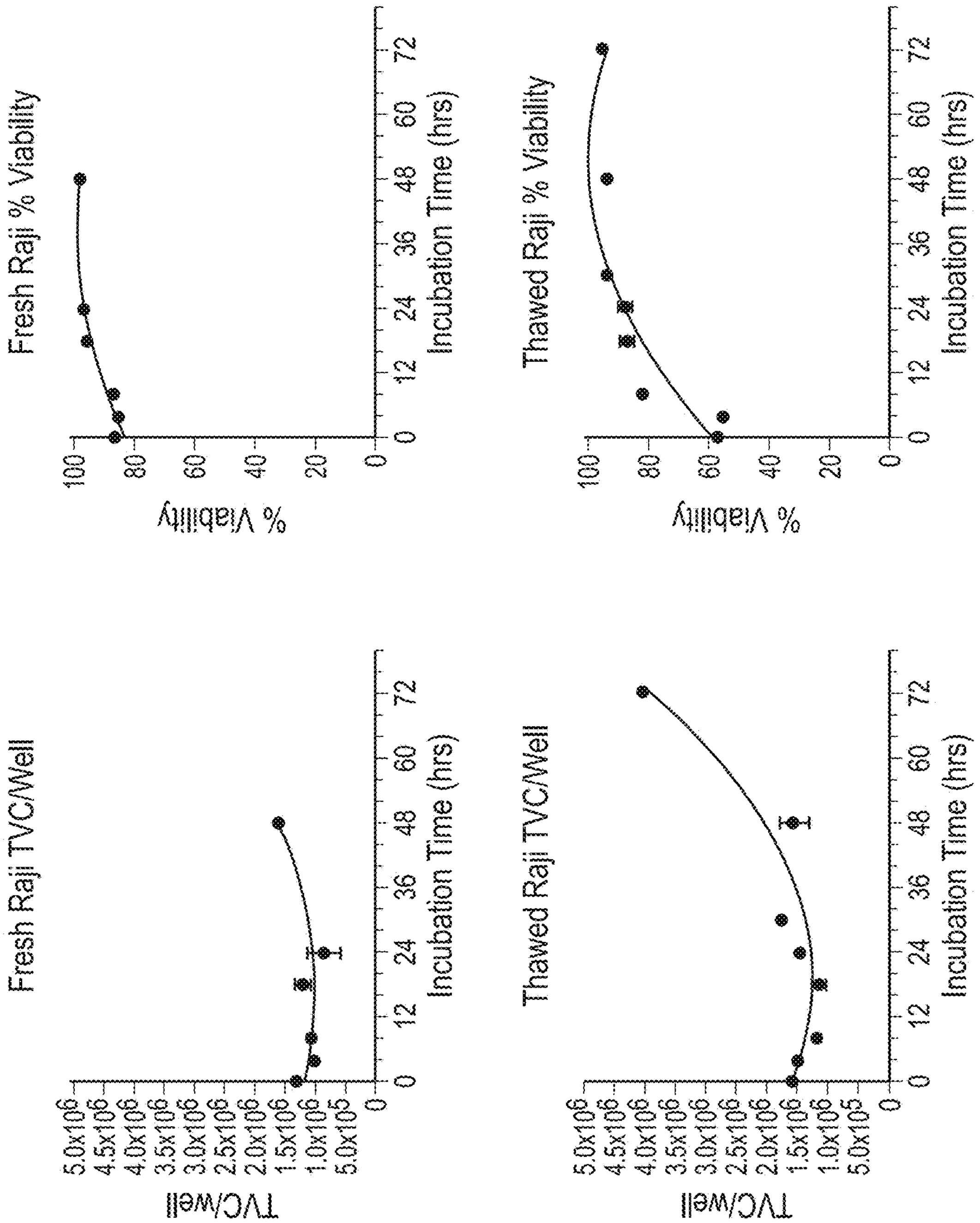

FIG. 121: Proliferation profiles of Raji cell lines.

Figure 122:
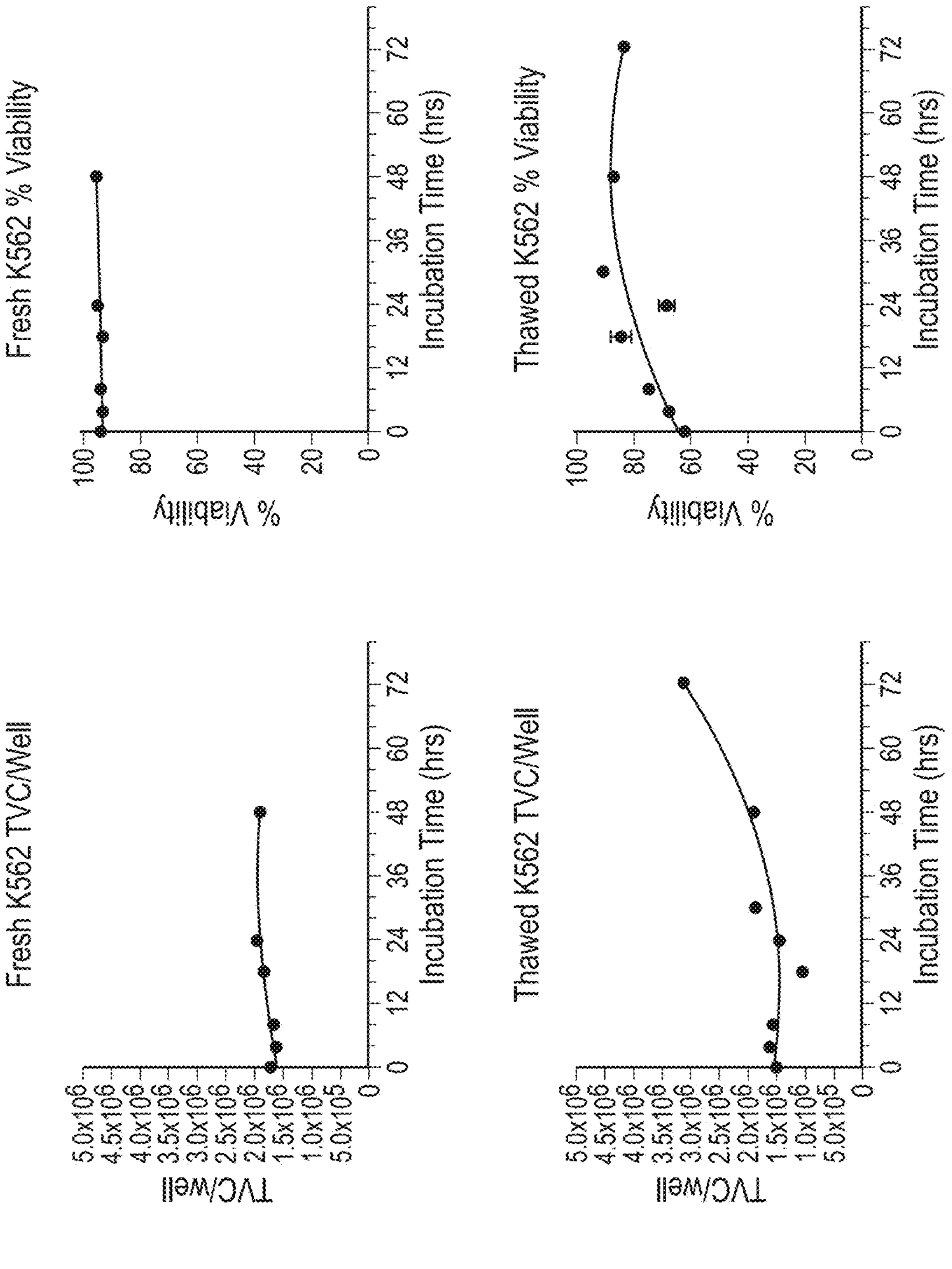

FIG. 122: Proliferation profiles of K562 cell lines.

Figure 123:
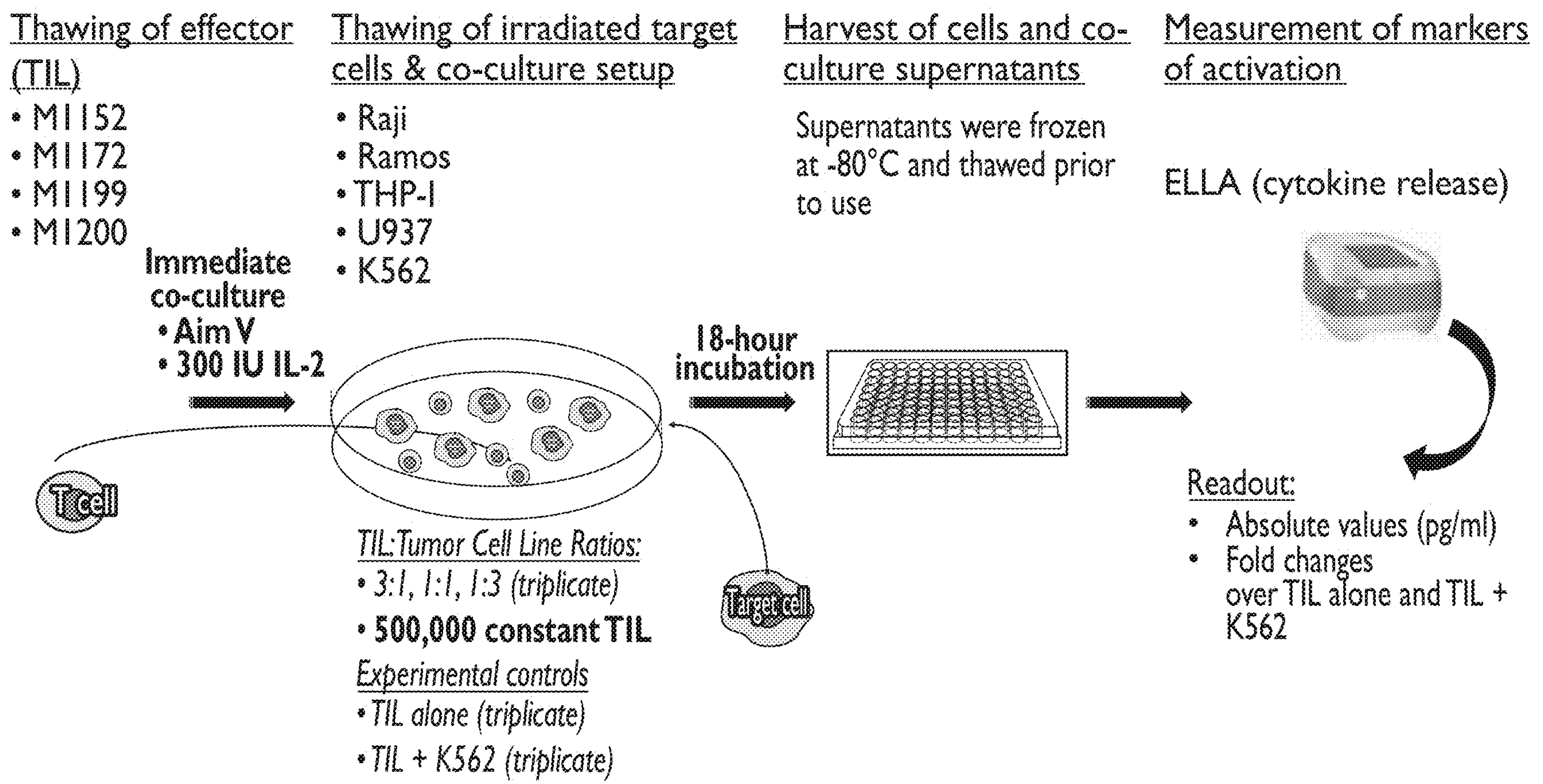

FIG. 123: Diagram of an experimental plan for TIL:tumor cell line co-culture assays, which are also embodiments of the present invention.

Figure 124:
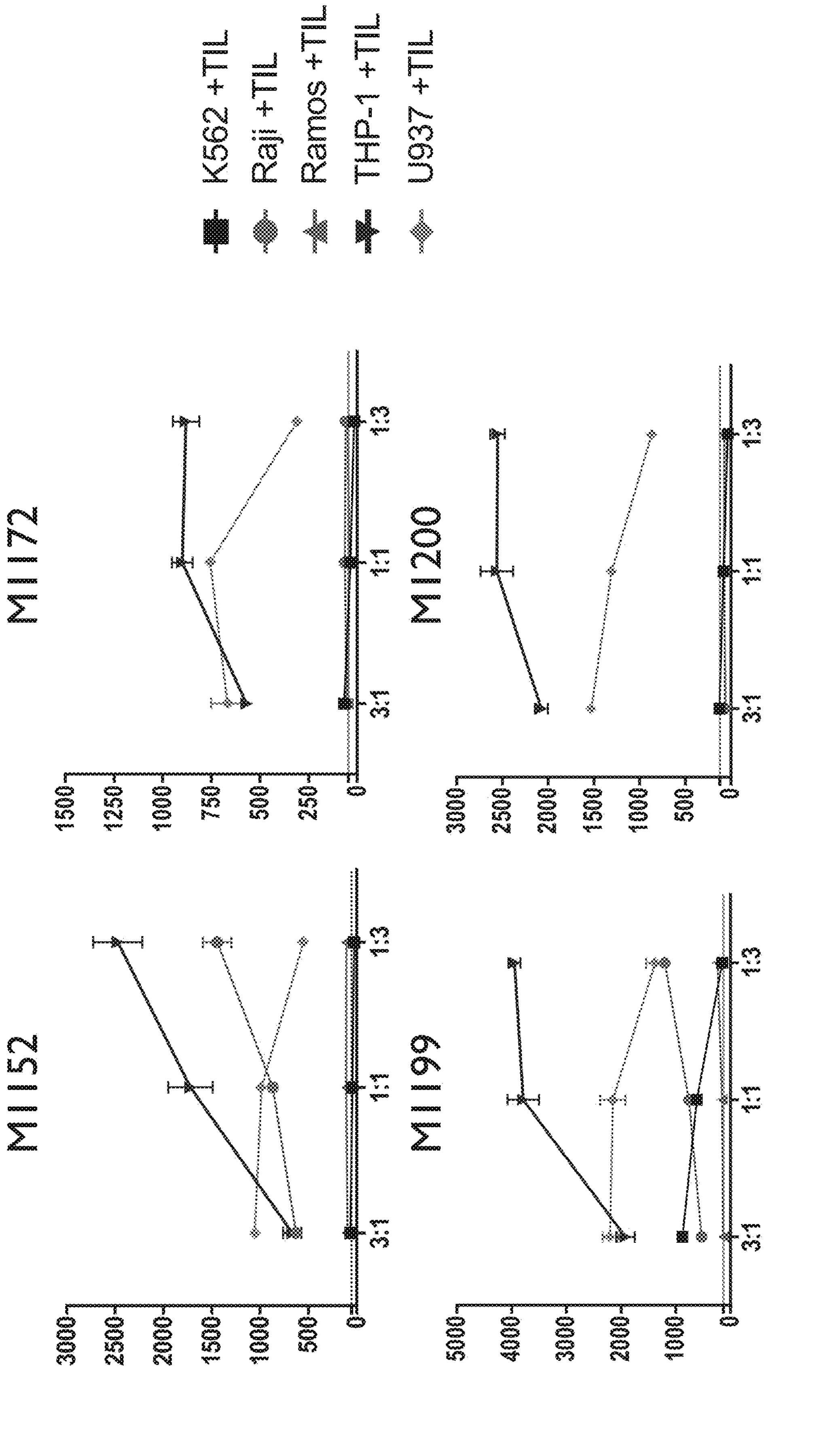

FIG. 124: IFN-γ secretion for the tested target (Raji, Ramos, Thp1 and U937) cell lines and negative control (K562) cell lines (pg/mL, absolute values) at three ratios of TILs to target cells (3:1, 1:1, and 1:3), which are embodiments of the present invention.

Figure 125:
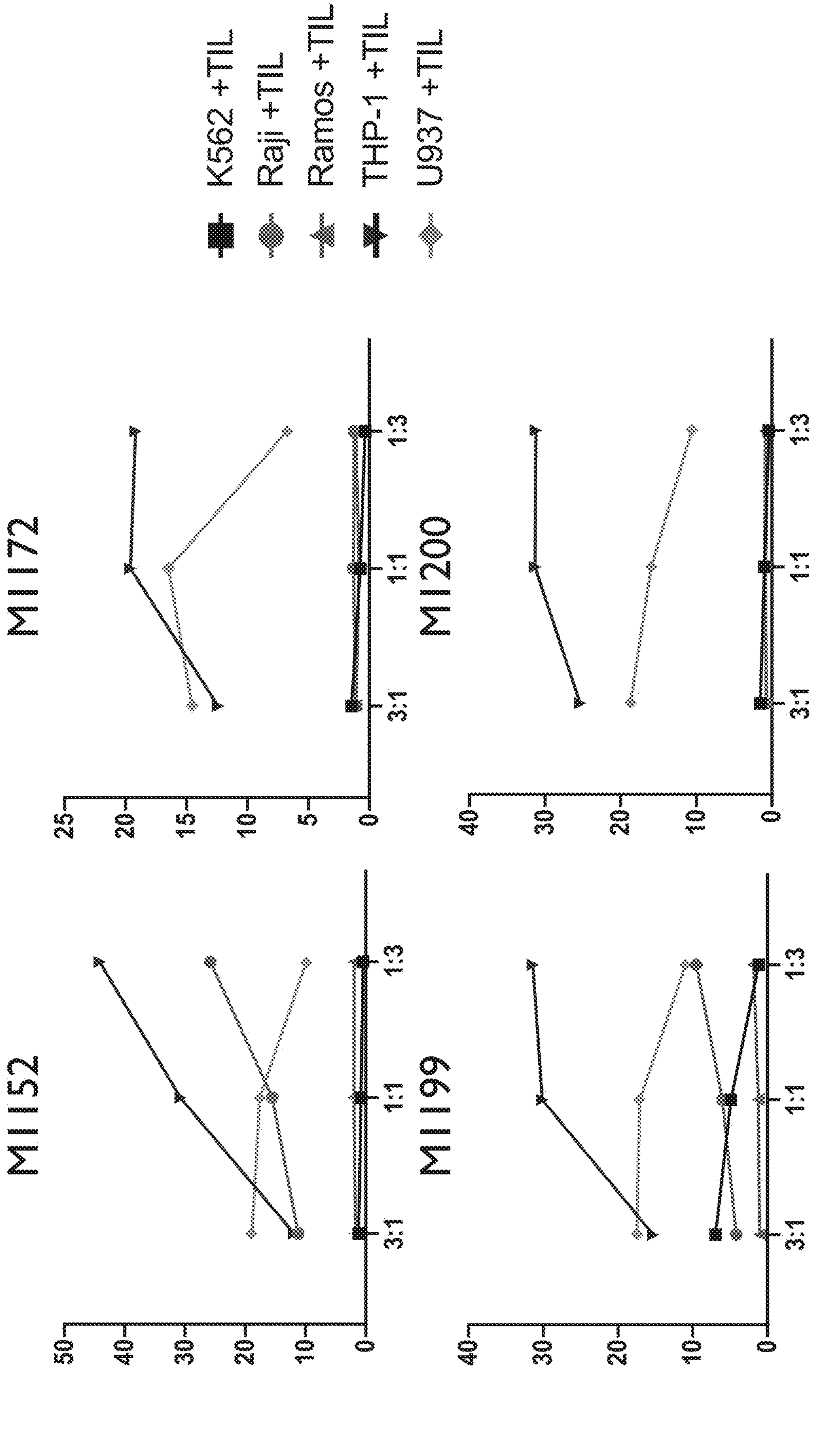

FIG. 125: IFN-γ secretion for the tested target (Raji, Ramos, Thp1 and U937) cell lines and negative control (K562) cell lines (fold change of [TIL+target]/[TIL alone])

at three ratios of TILs to target cells (3:1, 1:1, and 1:3), which are embodiments of the present invention.

Figure 126:
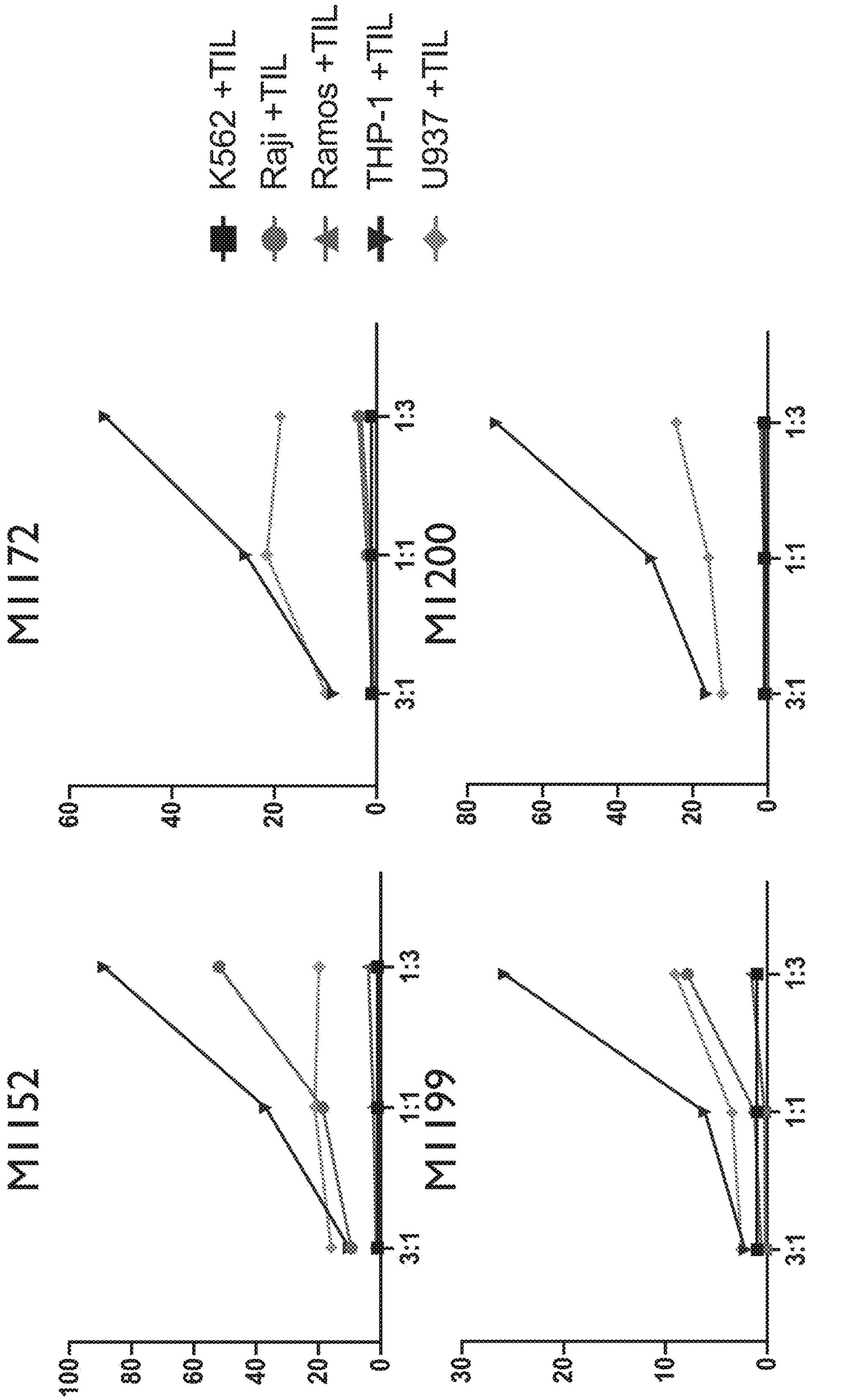

FIG. 126: IFN-γ secretion for the tested target (Raji, Ramos, Thp1 and U937) cell lines and negative control (K562) cell lines (fold change of [TIL+target]/[TIL+K562]) at three ratios of TILs to target cells (3:1, 1:1, and 1:3), which are embodiments of the present invention.

Figure 127:
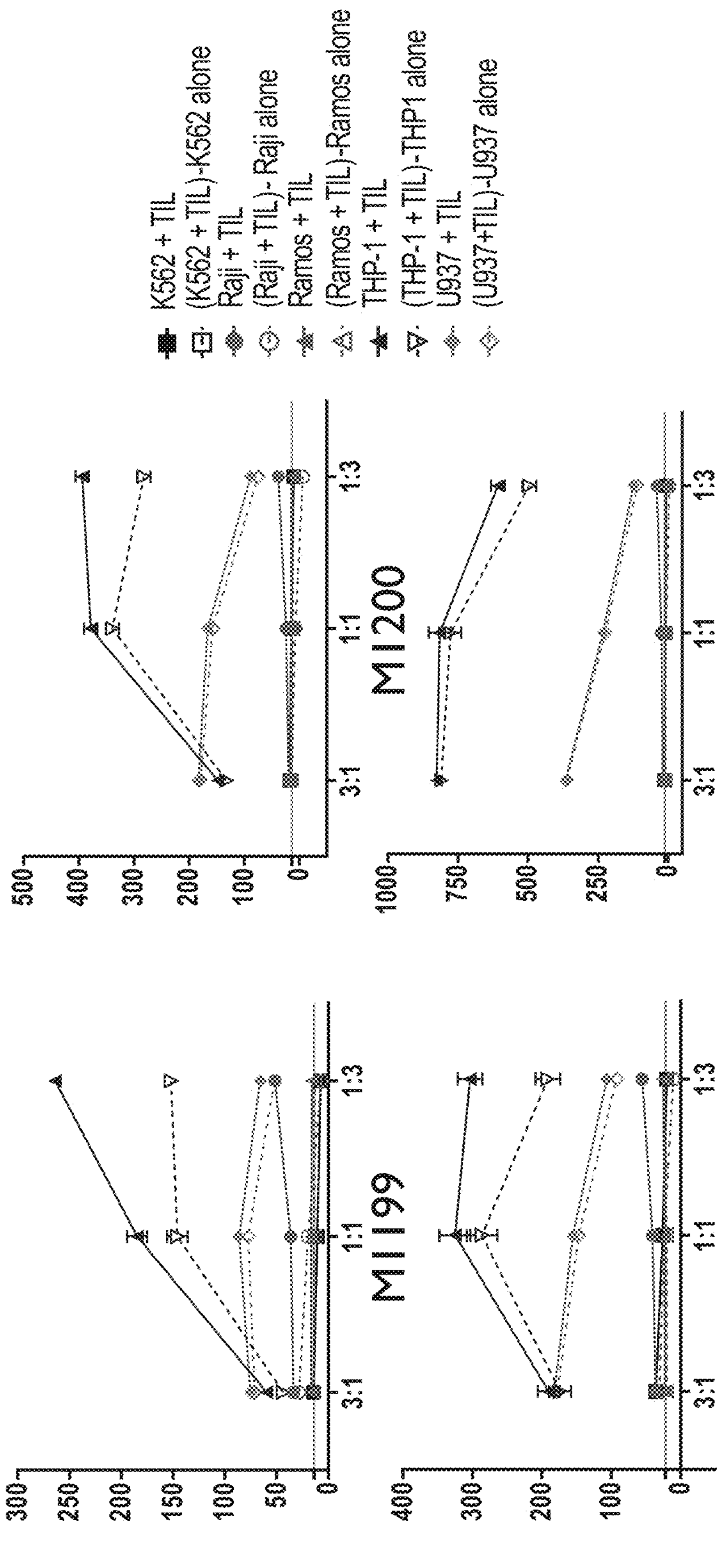

FIG. 127: TNF-α secretion for the tested target (Raji, Ramos, Thp1 and U937) cell lines and negative control (K562) cell lines (pg/mL, absolute values) at three ratios of TILs to target cells (3:1, 1:1, and 1:3), which are embodiments of the present invention.

Figure 128:
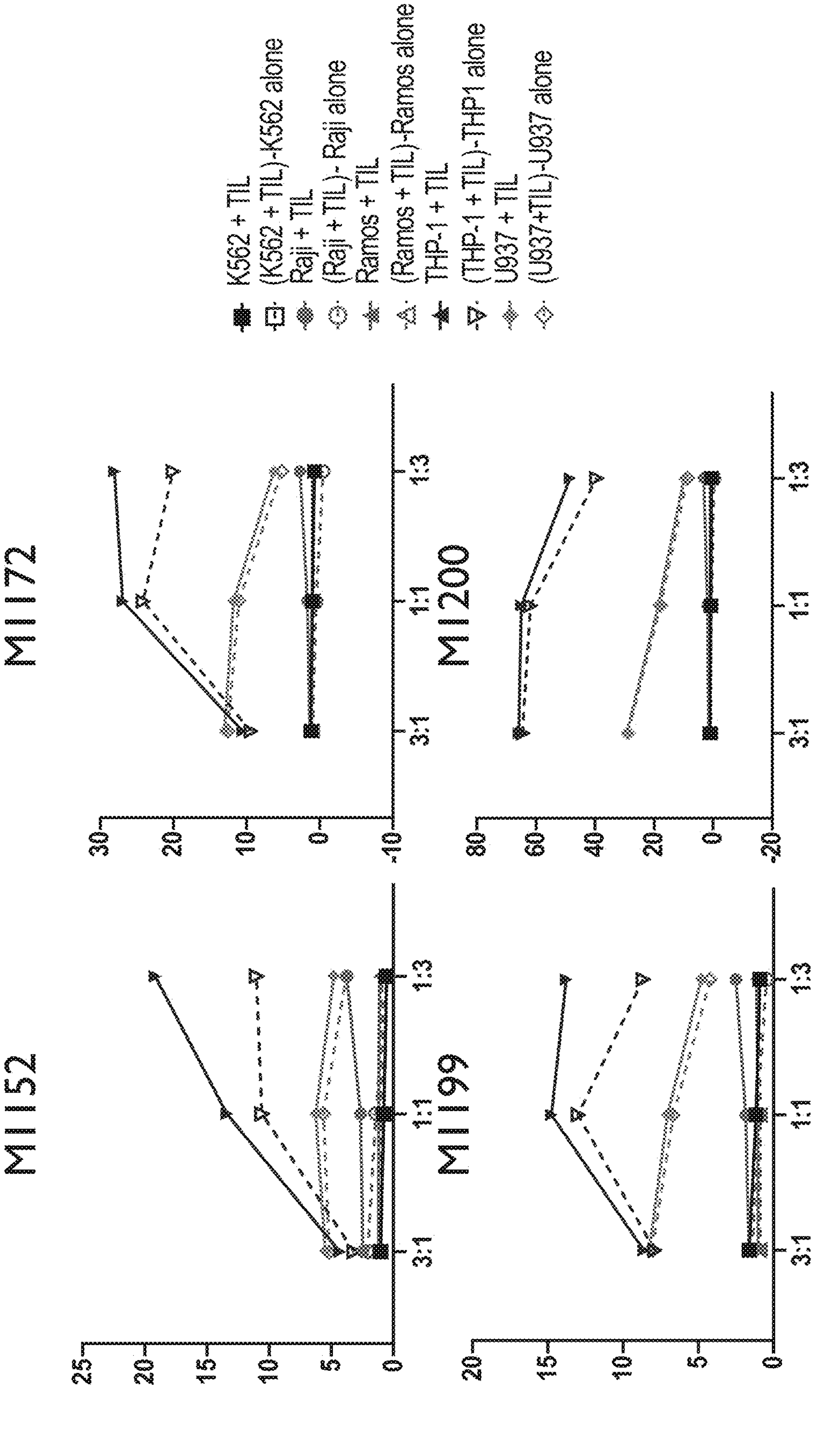

FIG. 128: TNF-α secretion for the tested target (Raji, Ramos, Thp1 and U937) cell lines and negative control (K562) cell lines (fold change of [TIL+target]/[TIL alone]) at three ratios of TILs to target cells (3:1, 1:1, and 1:3), which are embodiments of the present invention.

Figure 129:
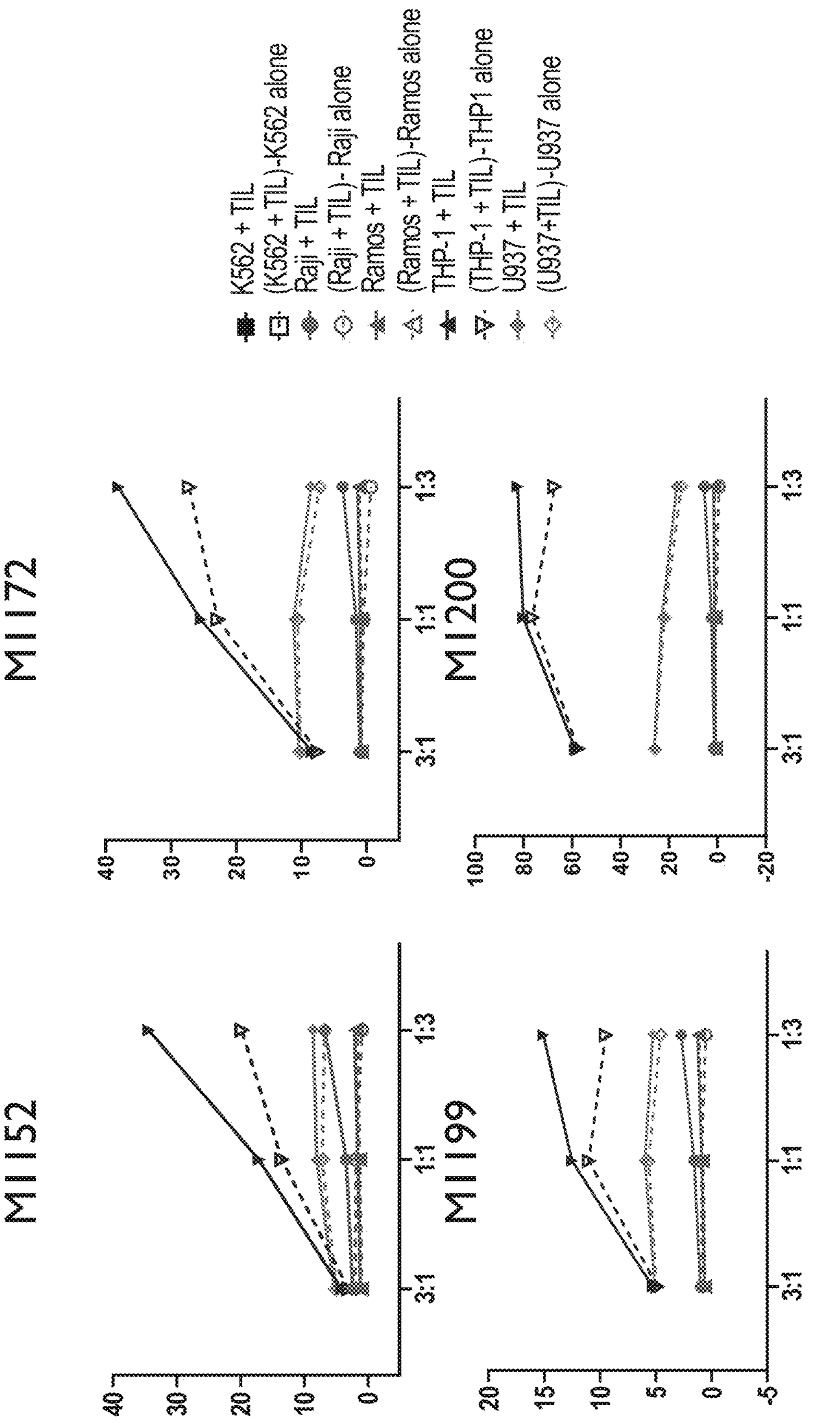

FIG. 129: TNF-α secretion for the tested target (Raji, Ramos, Thp1 and U937) cell lines and negative control (K562) cell lines (fold change of [TIL+target]/[TIL+K562]) at three ratios of TILs to target cells (3:1, 1:1, and 1:3), which are embodiments of the present invention.

Figure 130:
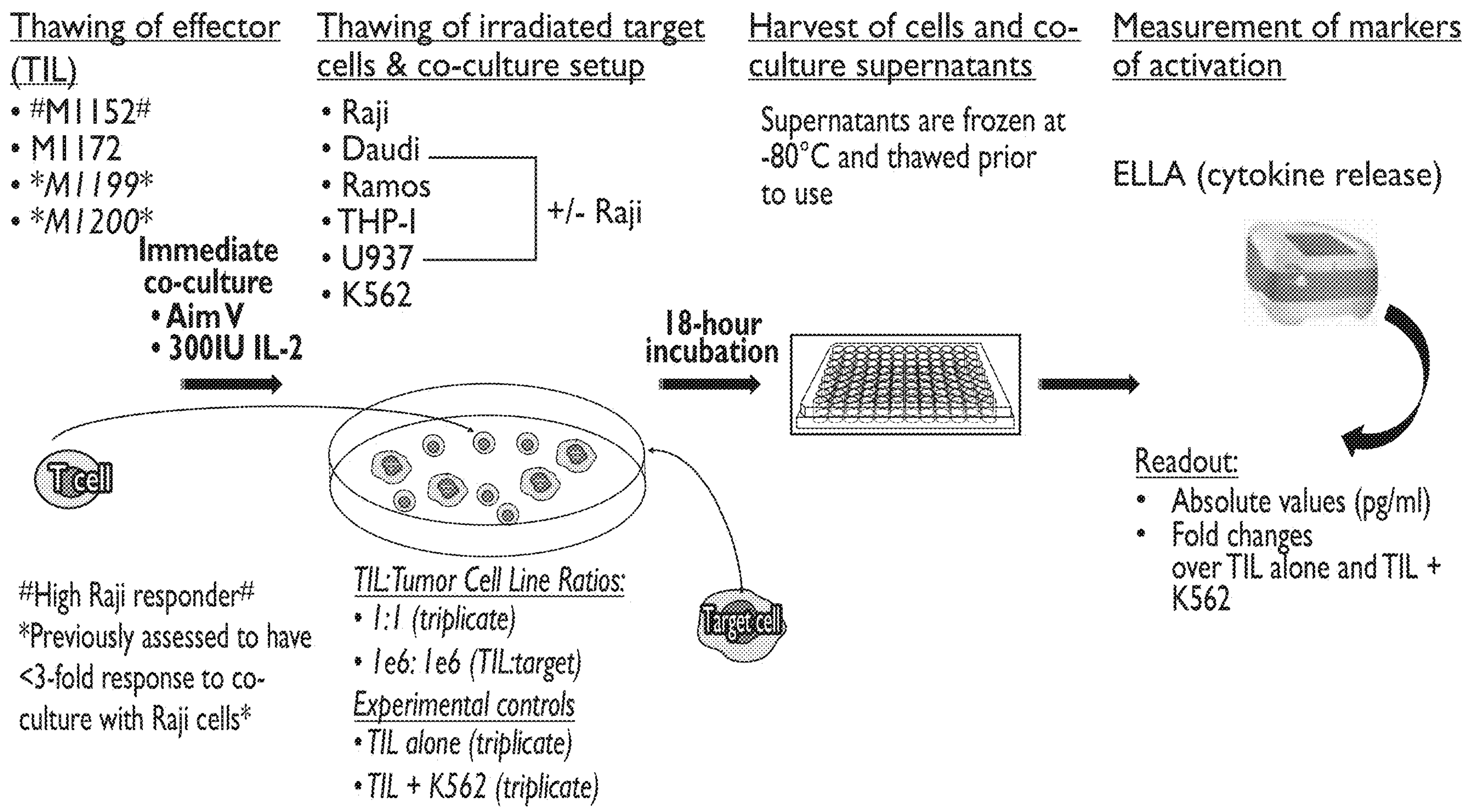

FIG. 130: Diagram of an experimental plan for TIL:tumor cell line co-culture assays, which are also embodiments of the present invention.

Figure 131:
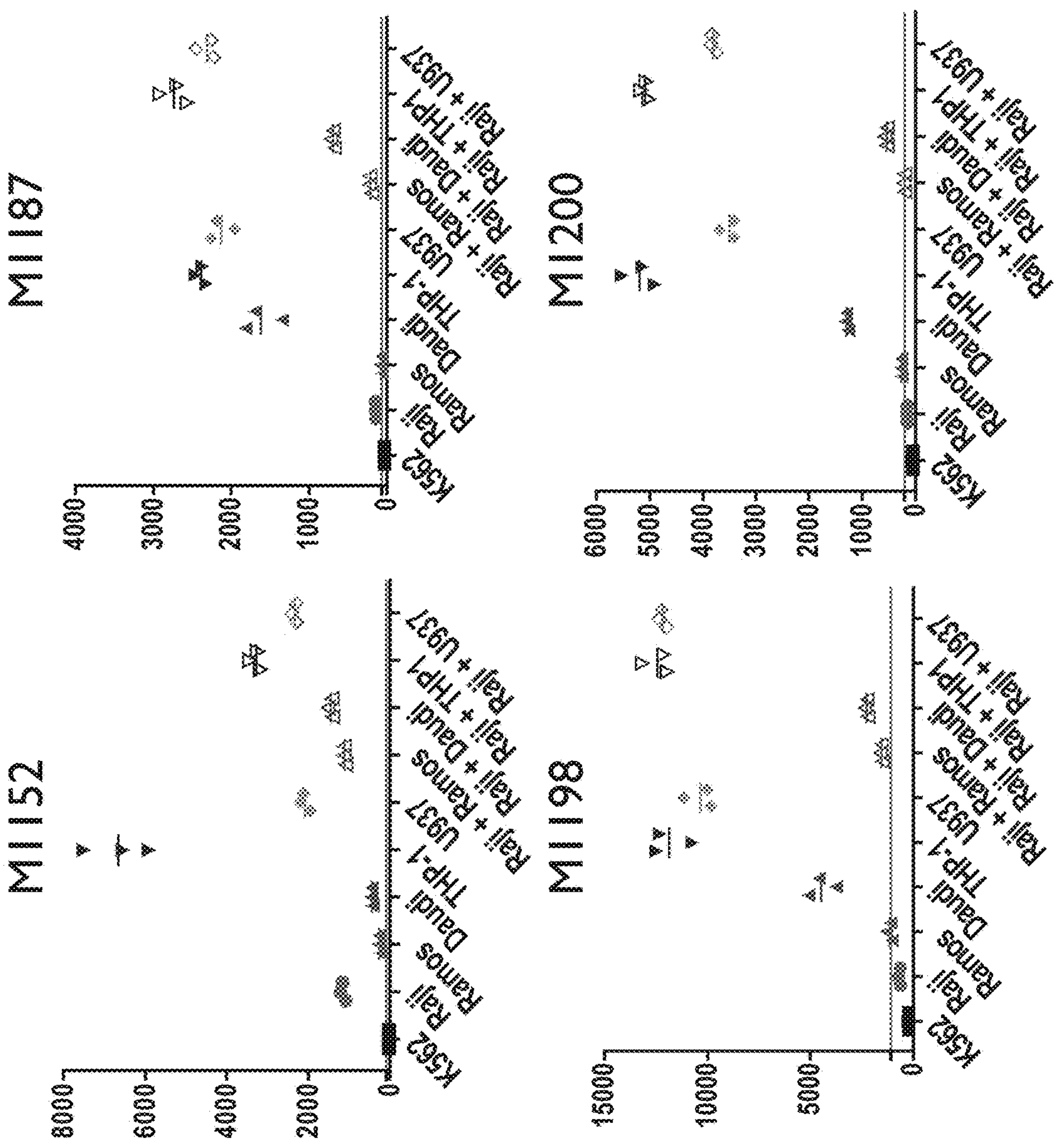

FIG. 131: IFN-γ secretion for tested target and negative control (K562) cell lines (pg/mL), which are embodiments of the present invention.

Figure 132:
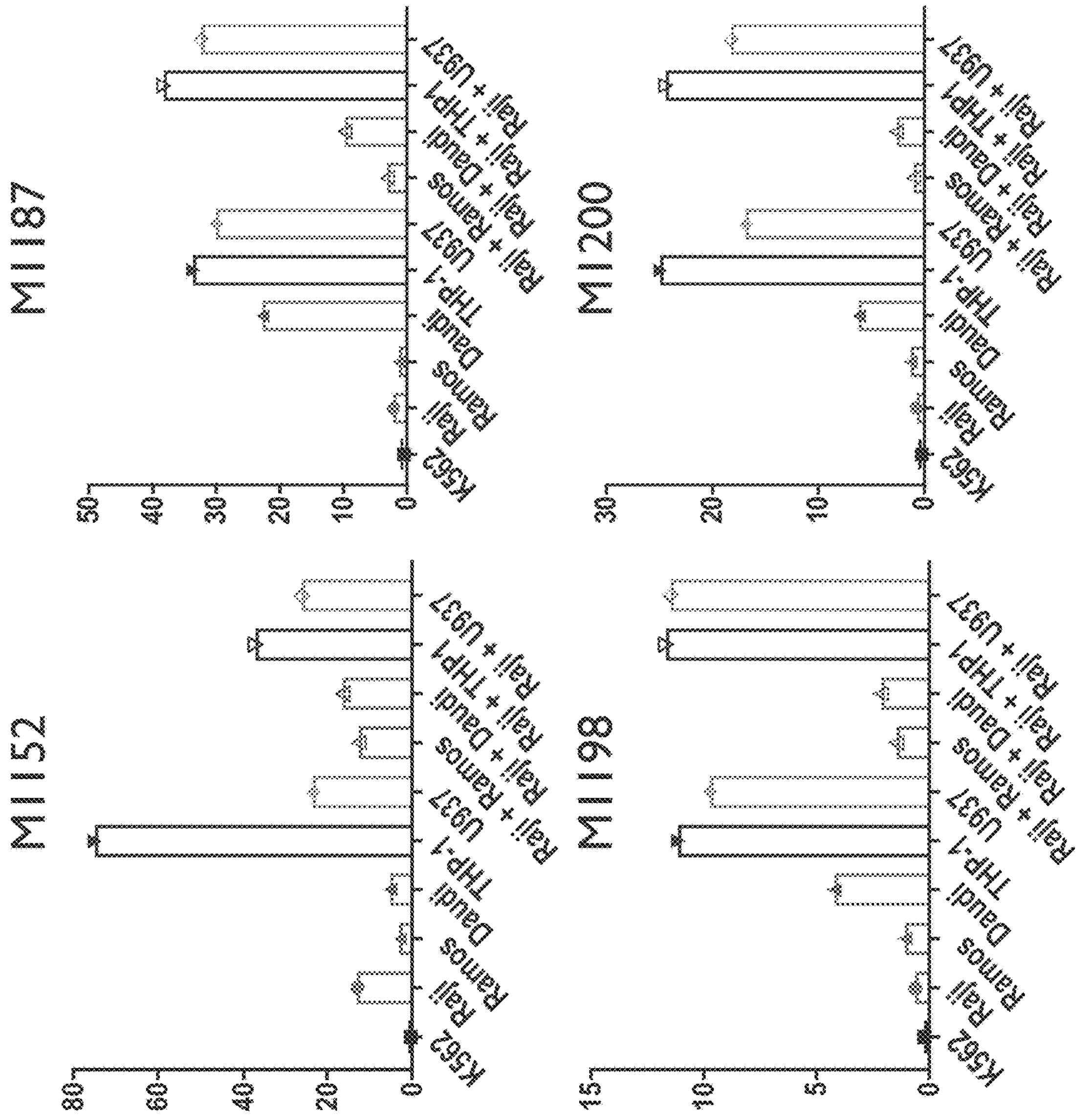

FIG. 132: IFN-γ secretion for tested target and negative control (K562) cell lines (fold change of [TIL+target]/[TIL alone]), which are embodiments of the present invention.

Figure 133:
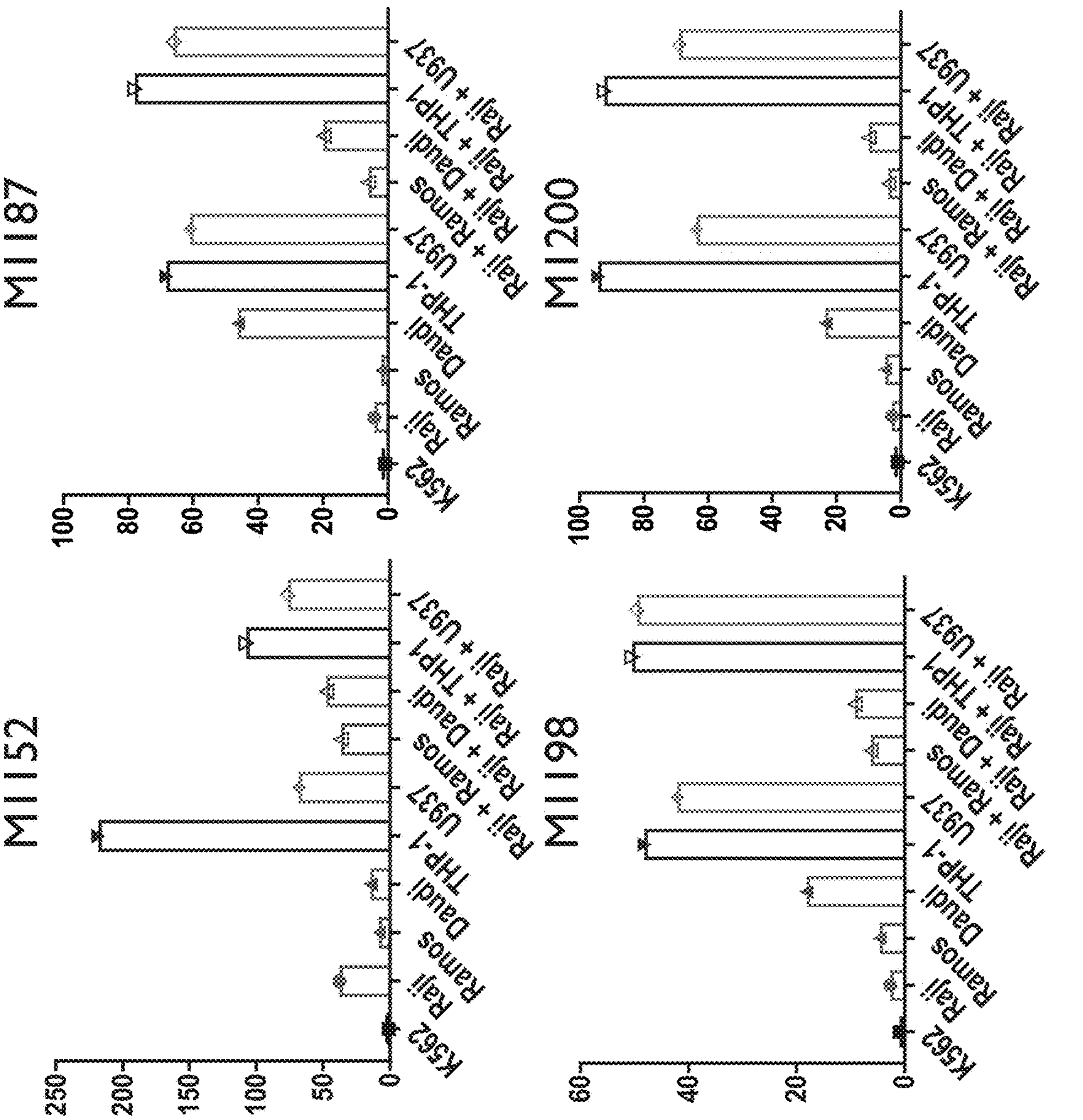

FIG. 133: IFN-γ secretion for tested target and negative control (K562) cell lines (fold change of [TIL+target]/[TIL+K562]), which are embodiments of the present invention.

Figure 134:
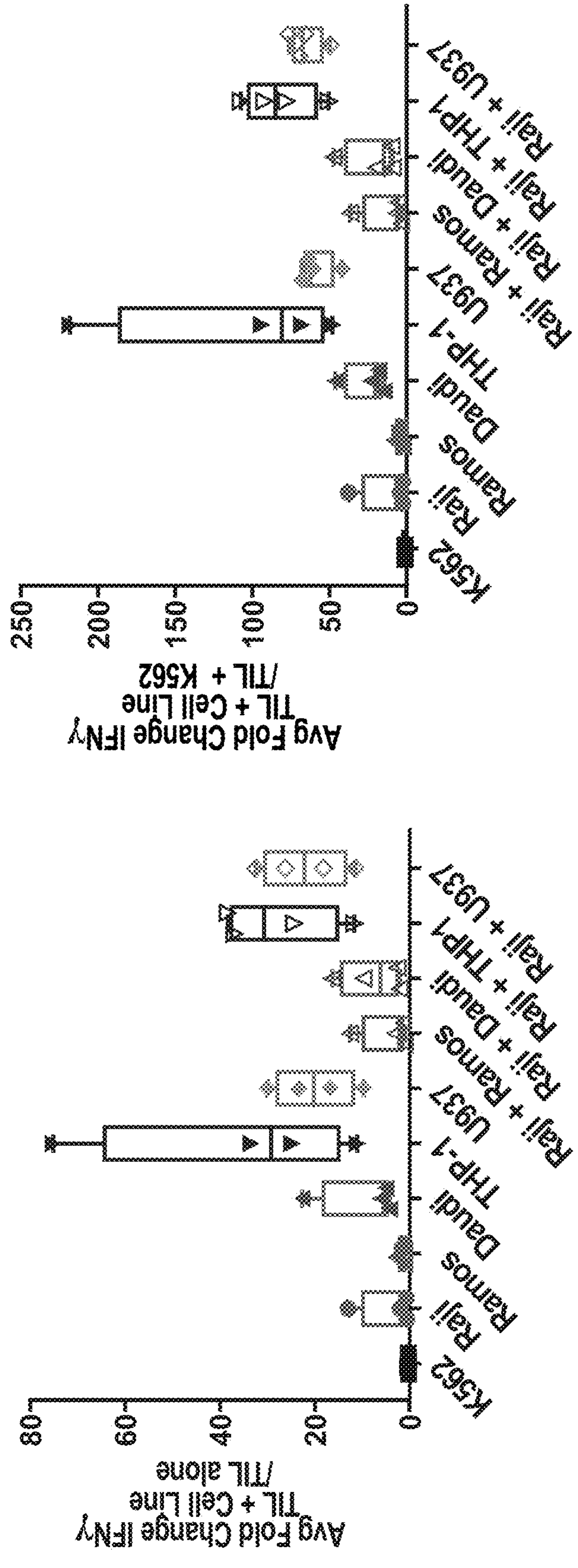

FIG. 134: Averages and ranges of fold change of TIL+target cell line (or combination) over TIL alone (left panel) and TIL+target cell line (or combination) over TIL+K562 (right panel).

Figure 135:
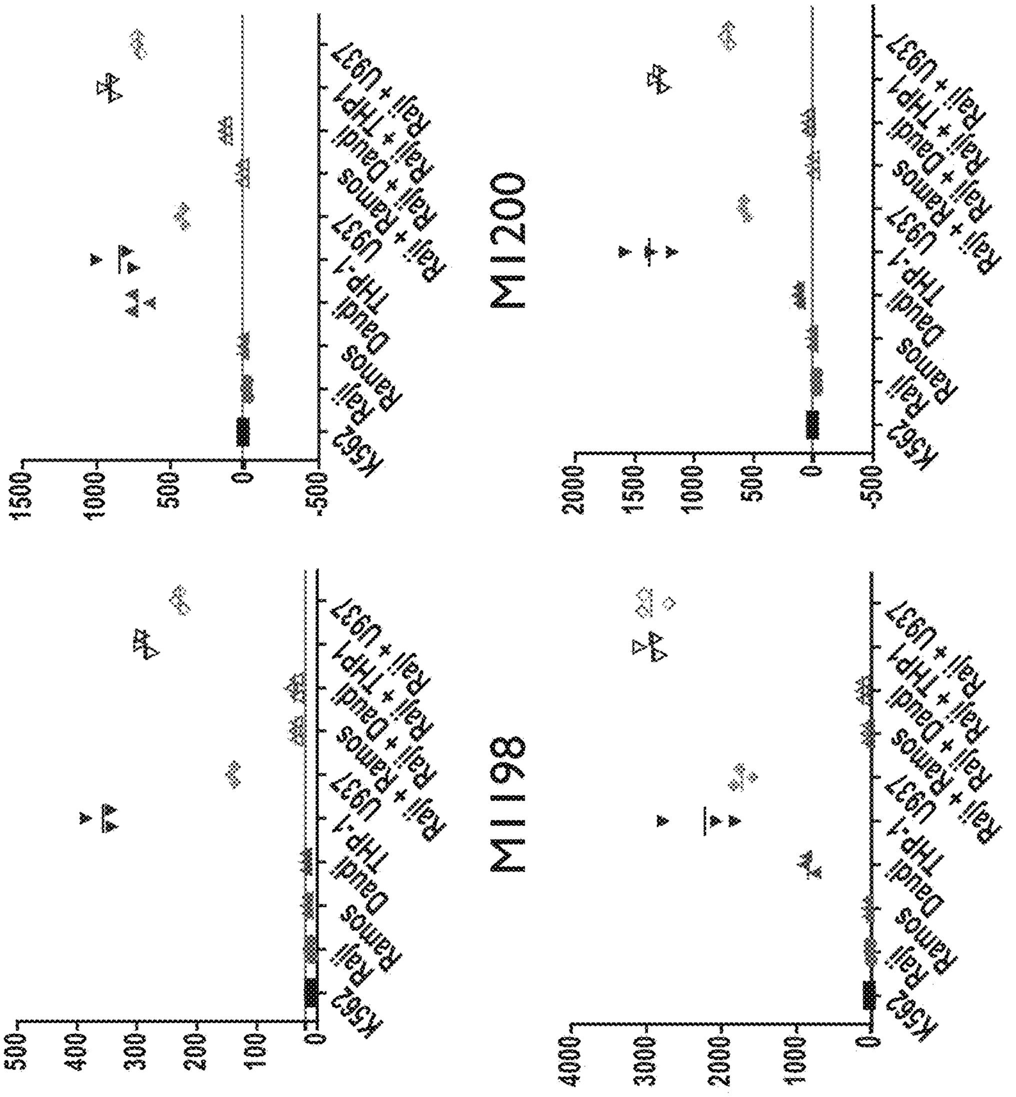

FIG. 135: TNF-α secretion (pg/mL) for tested target and negative control cell lines, including combination target cell lines, for melanoma TIL lines M1152, M1187, M1198, and M1200.

Figure 136:
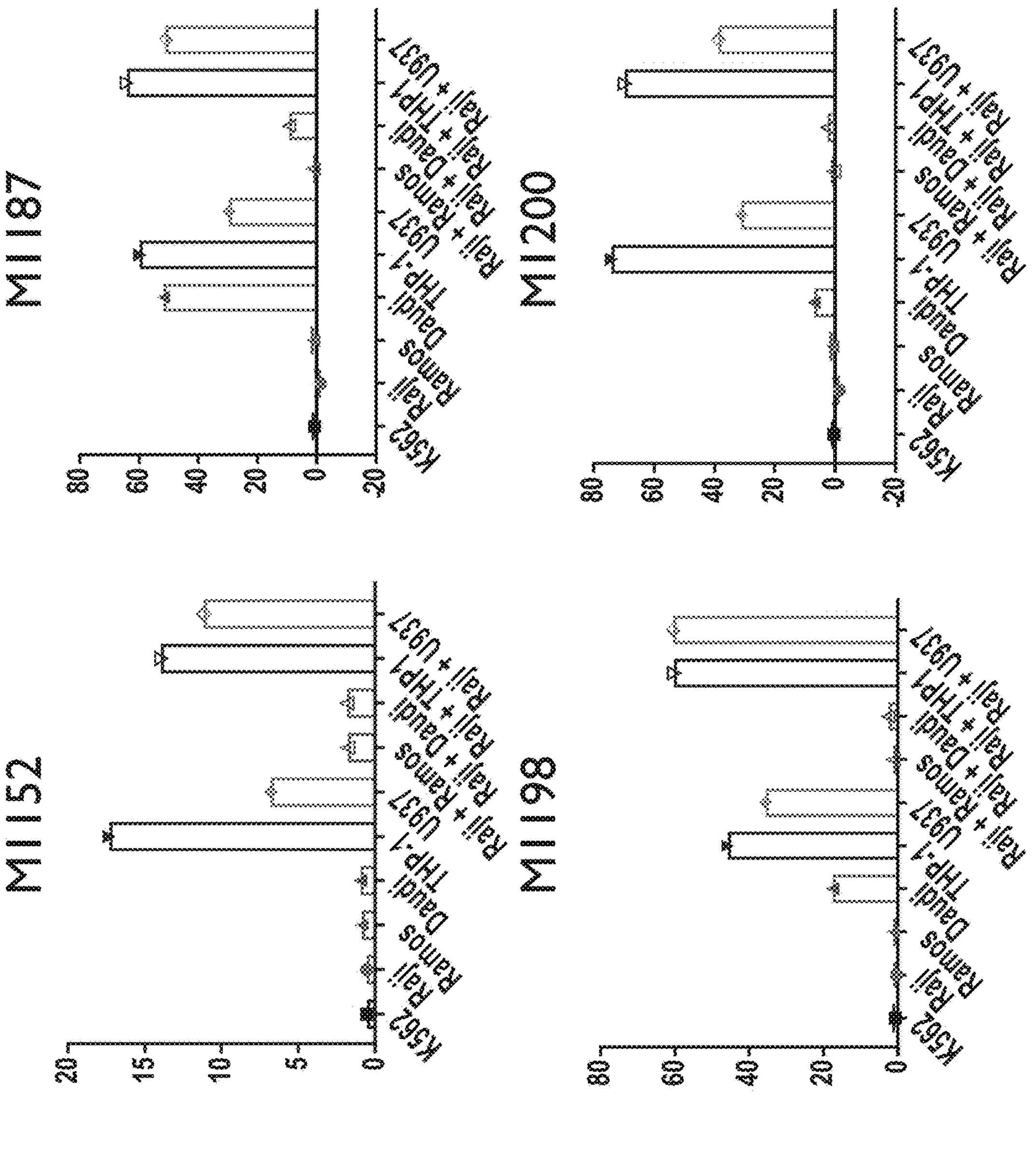

FIG. 136: TNF-α secretion (fold change of [TIL+tumor cell line or combination]/[TIL alone]) for tested target and negative control cell lines, including combination target cell lines, for melanoma TIL lines M1152, M1187, M1198, and M1200.

Figure 137:
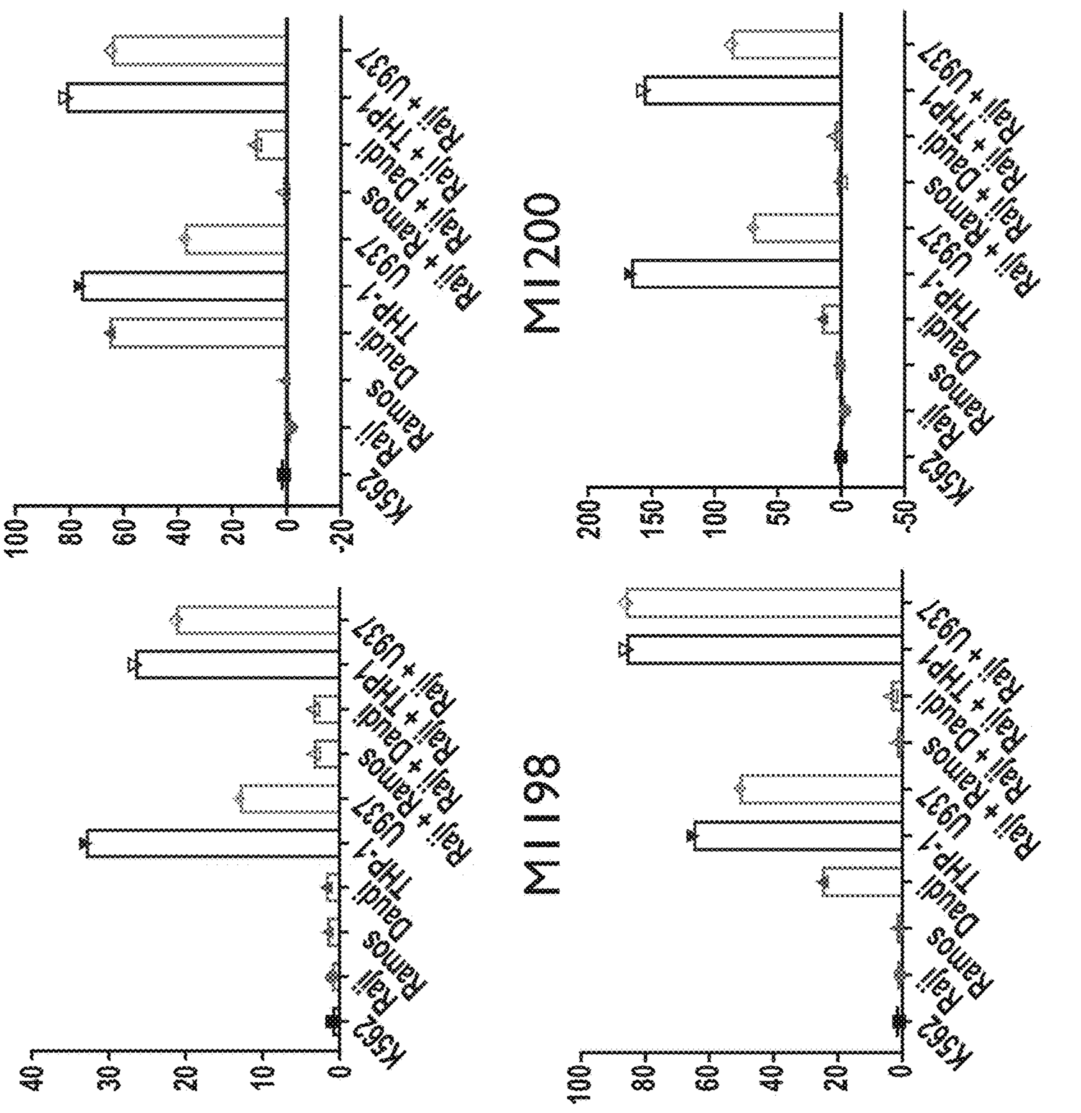

FIG. 137: TNF-α secretion (fold change of [TIL+tumor cell line or combination]/[TIL+K562]) for tested target and negative control cell lines, including combination target cell lines, for melanoma TIL lines M1152, M1187, M1198, and M1200.

Figure 138:
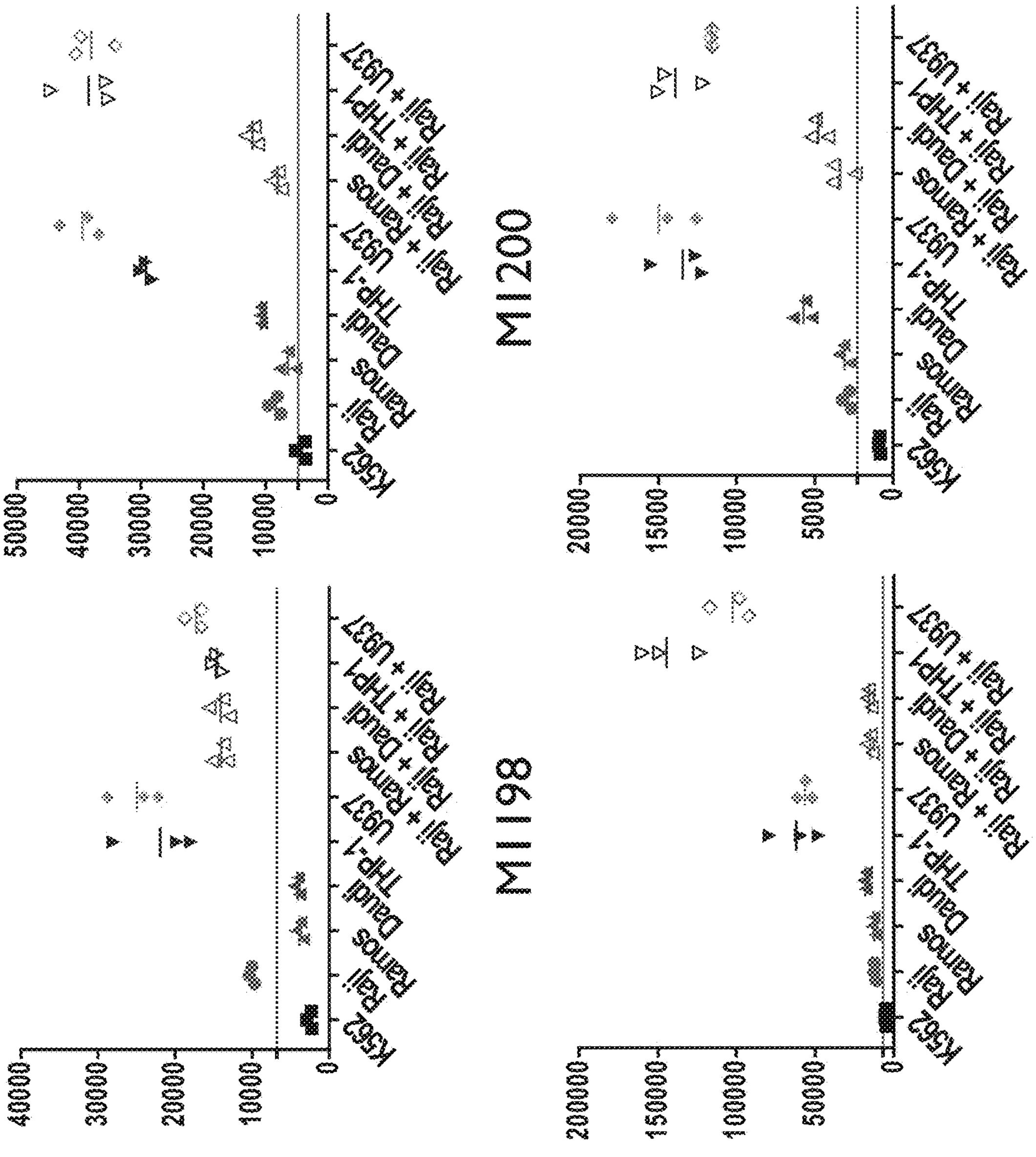

FIG. 138: Granzyme B secretion (pg/mL) for tested target and negative control cell lines, including combination target cell lines, for melanoma TIL lines M1152, M1187, M1198, and M1200.

Figure 139:
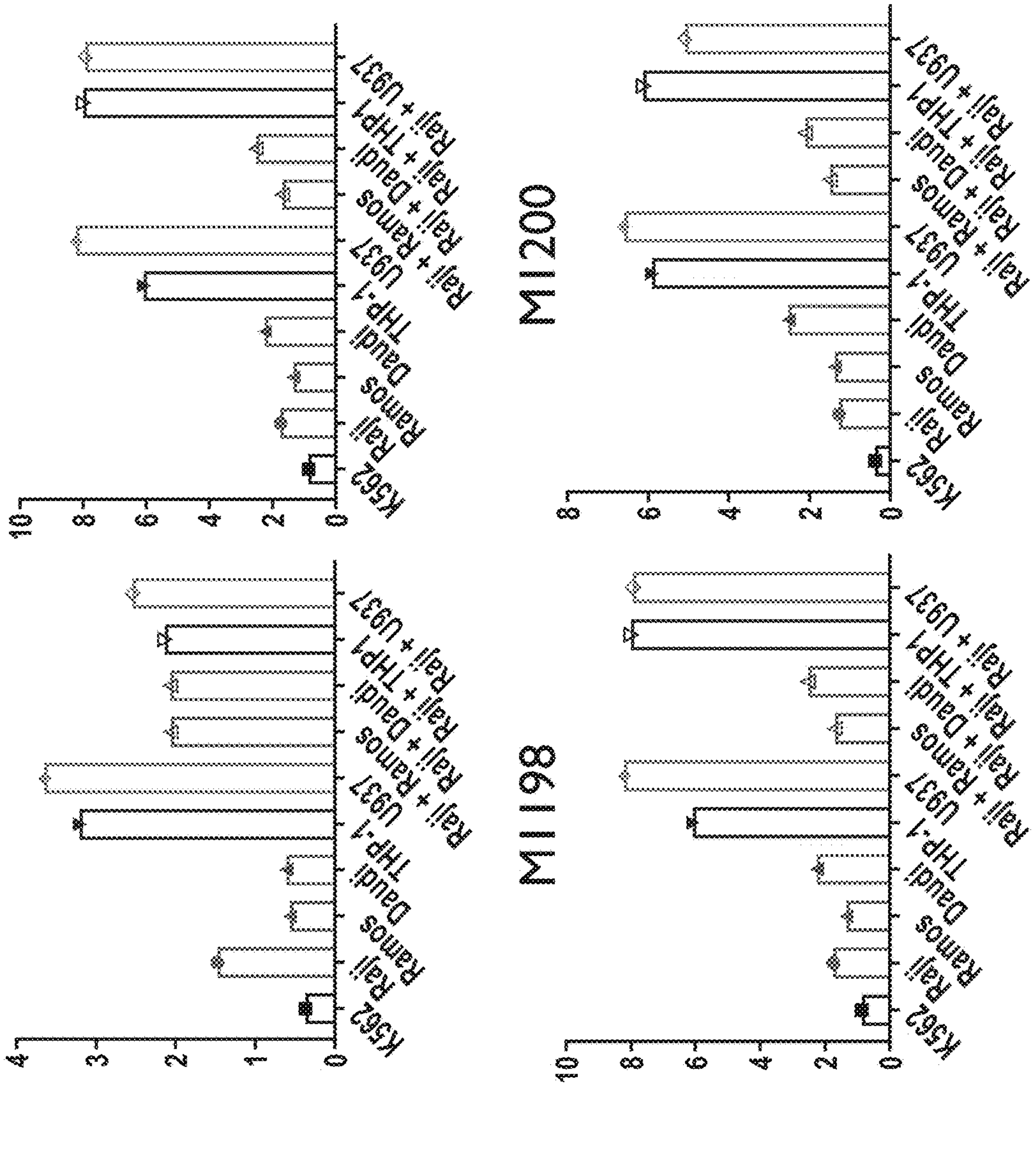

FIG. 139: Granzyme B secretion (fold change of [TIL+tumor cell line or combination]/[TIL alone]) for tested target and negative control cell lines, including combination target cell lines, for melanoma TIL lines M1152, M1187, M1198, and M1200.

Figure 140:
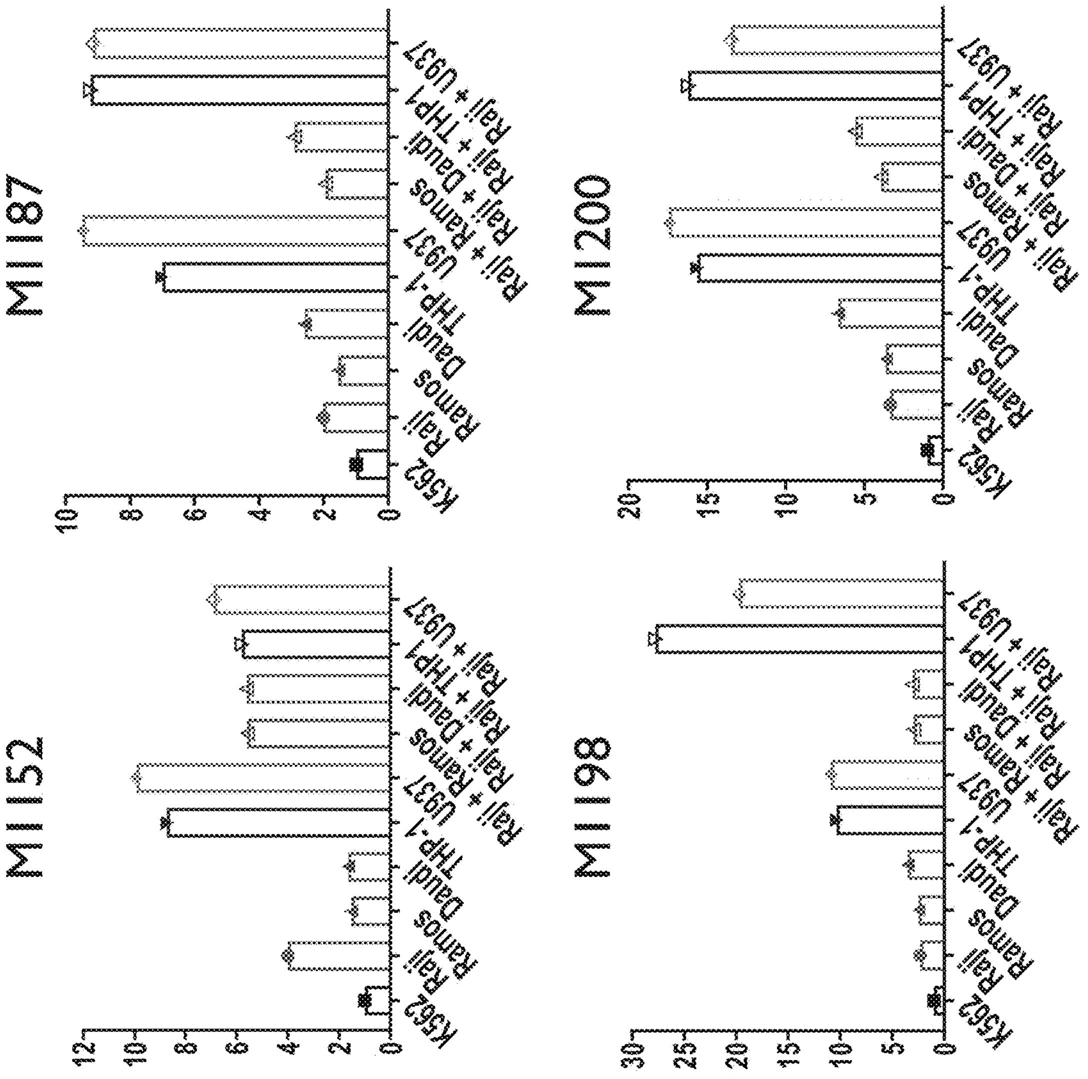

FIG. 140: Granzyme B secretion (fold change of [TIL+tumor cell line or combination]/[TIL+K562]) for tested target and negative control cell lines, including combination target cell lines, for melanoma TIL lines M1152, M1187, M1198, and M1200.

Figure 141:
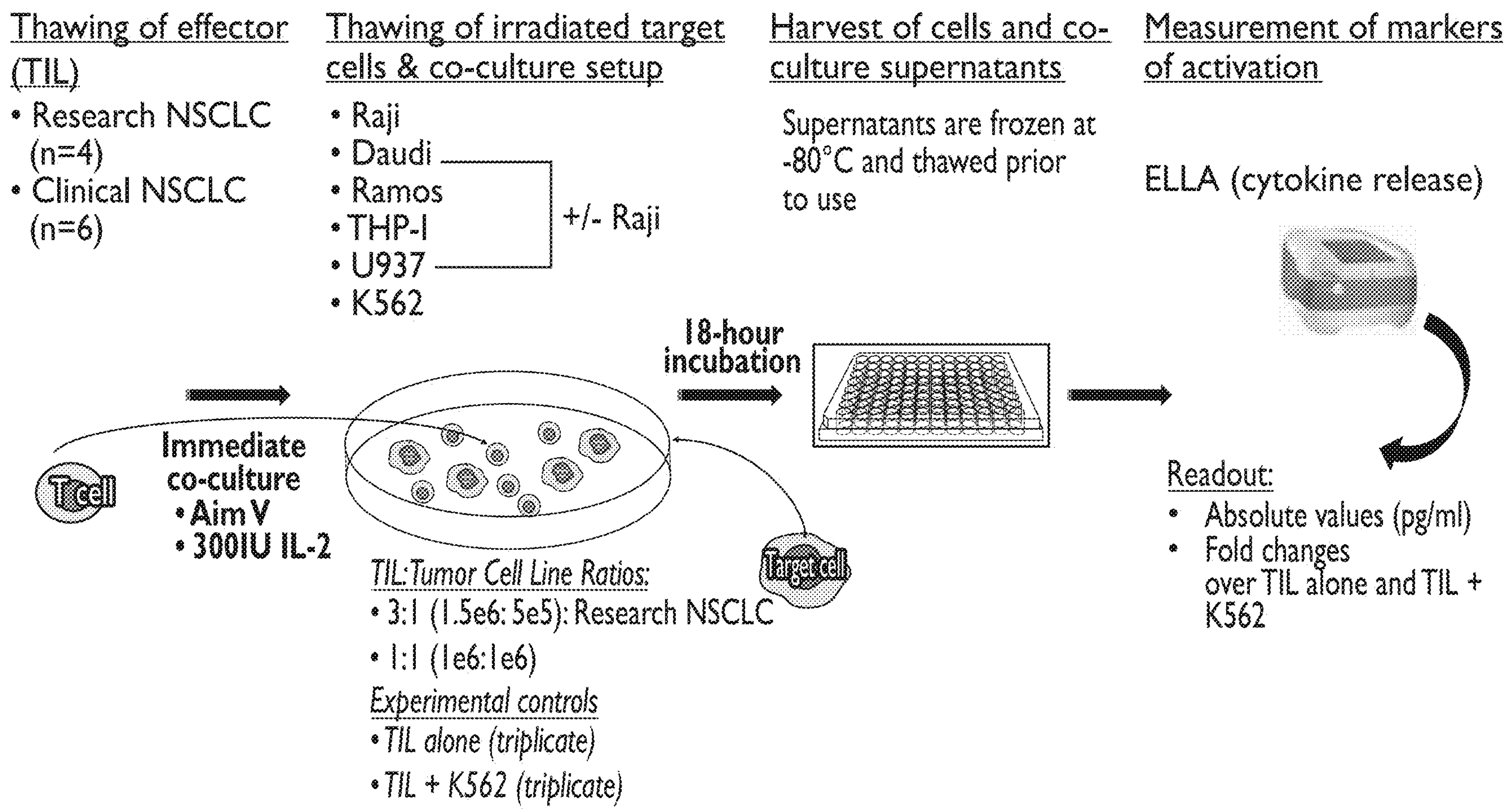

FIG. 141: Diagram of an experimental plan for TIL:tumor cell line co-culture assays, which are also embodiments of the present invention.

Figure 142:
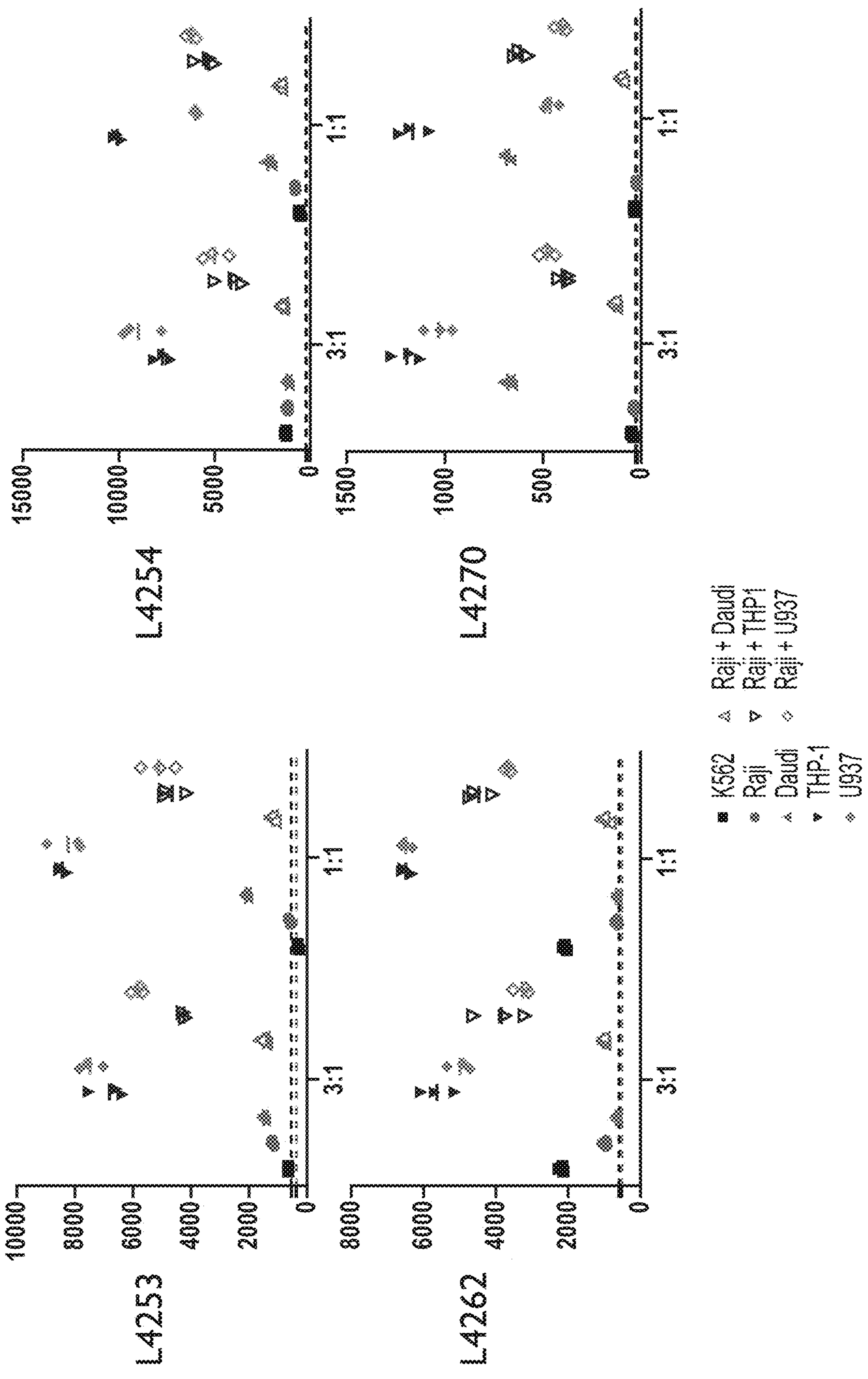

FIG. 142: IFN-γ secretion (pg/mL) for tested target and negative control cell lines, including combination target cell lines, for research NSCLC TIL lines L4253, L4254. L4262, and L4270. Black dotted line: 3:1 TIL alone. Grey dotted line: 1:1 TIL alone.

Figure 143:
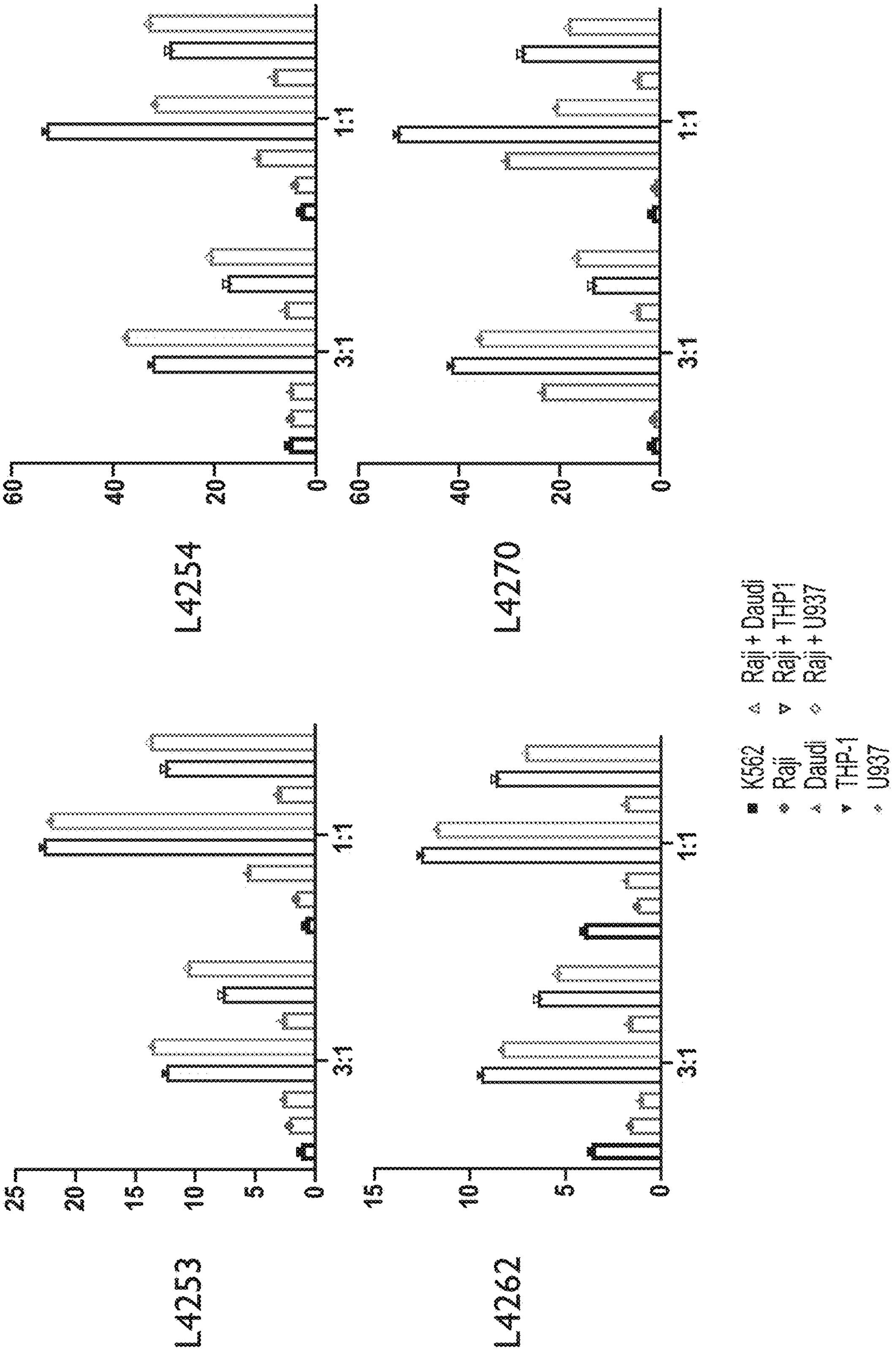

FIG. 143: Fold IFN-γ secretion (TIL+tumor cell line/TIL alone) for tested target NSCLC cell lines, including combination target cell lines, for research NSCLC TIL lines L4253, L4254, L4262, and L4270).

Figure 144:
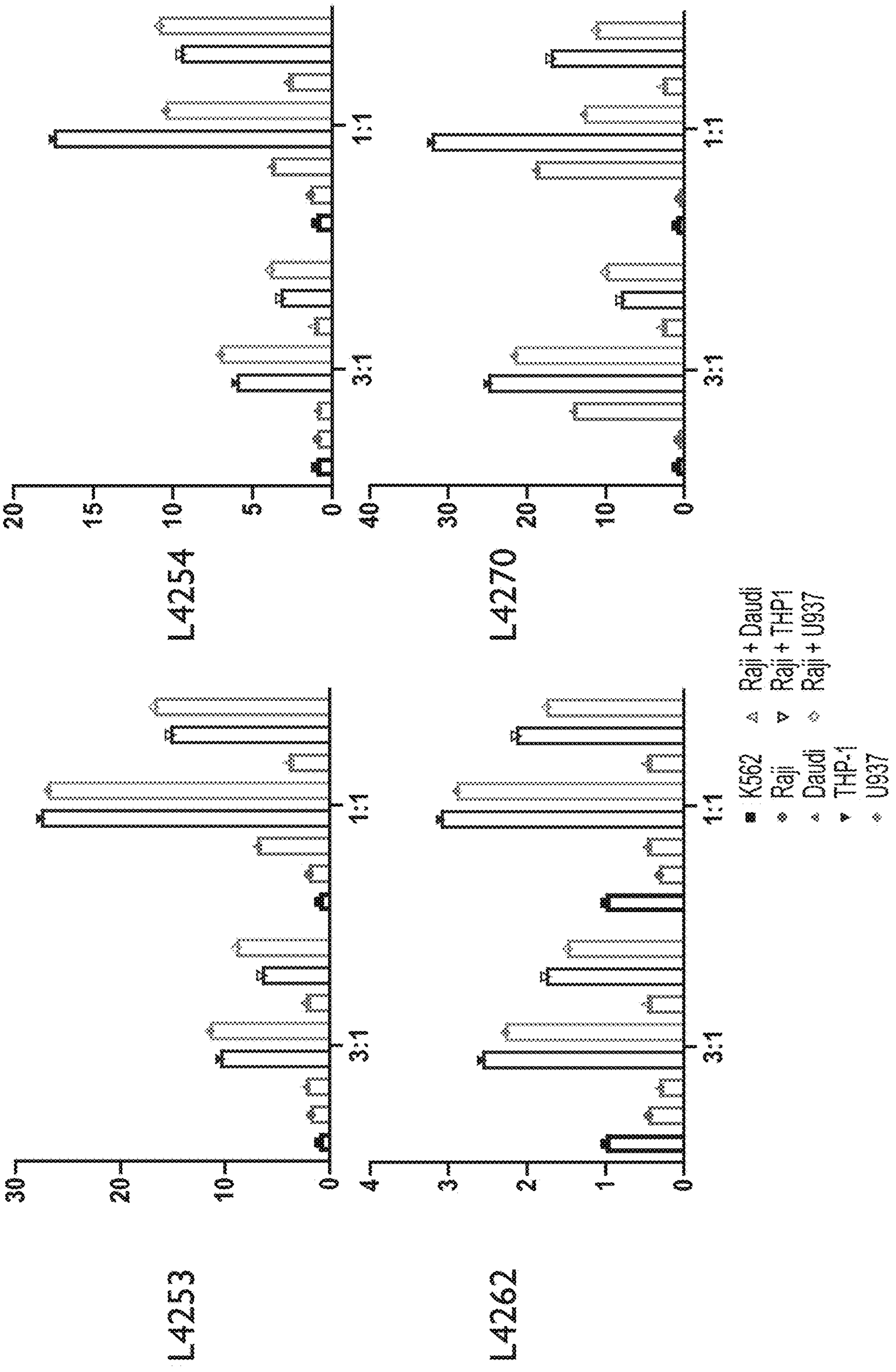

FIG. 144: Fold IFN-γ secretion (TIL+tumor cell line/[TIL+K562]) for tested target NSCLC cell lines, including combination target cell lines, for research NSCLC TIL lines L4253, L4254, L4262, and L4270).

Figure 145:
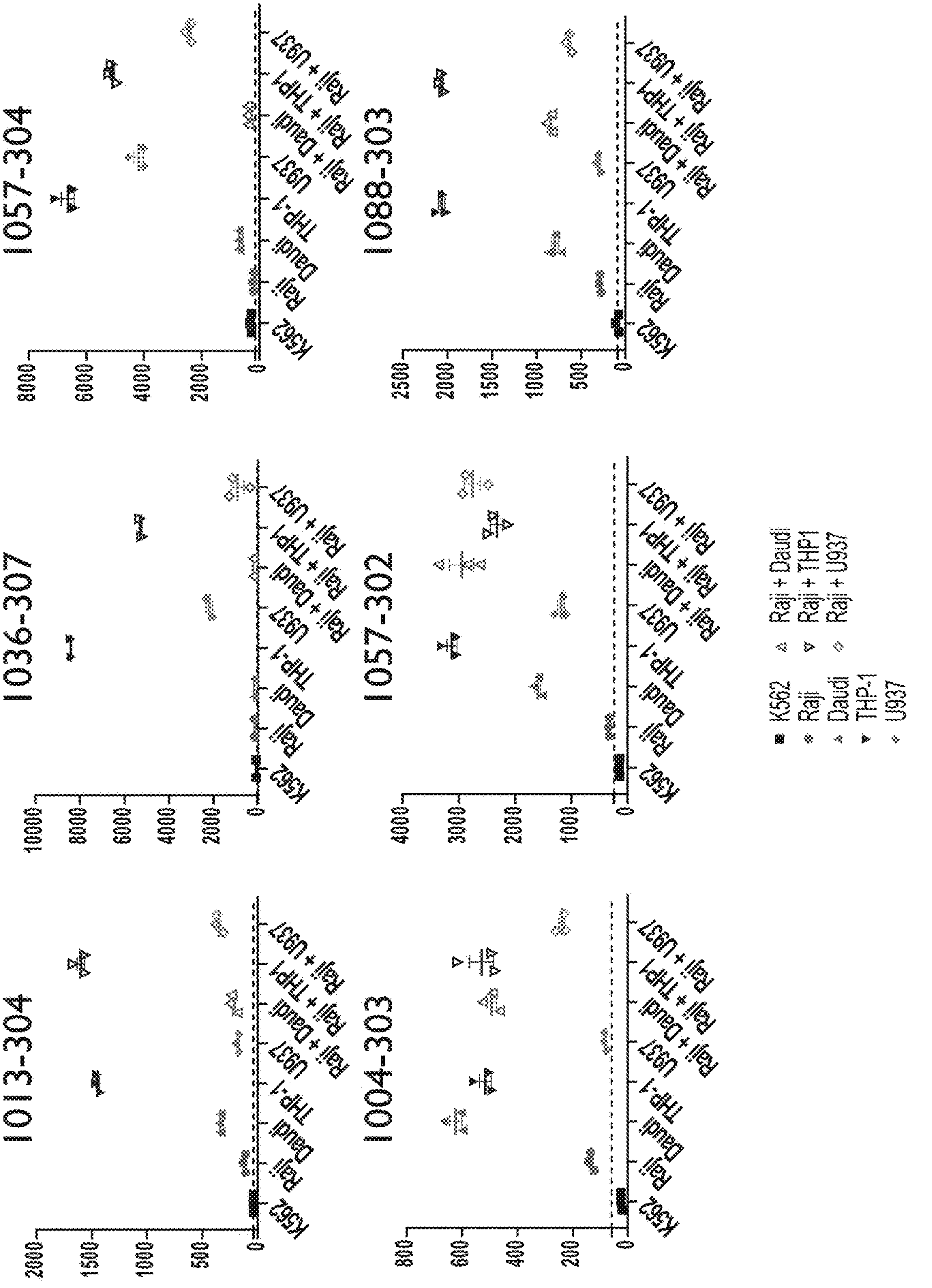

FIG. 145: IFN-γ secretion (pg/mL) for tested target and negative control cell lines, including combination target cell lines, for clinical NSCLC TIL lines 1013-304, 1036-307, 1057-304, 1004-303, 1057-302, and 1088-303. Black dotted line: TIL alone. Data was obtained at a 1:1 TIL:target ratio.

Figure 146:
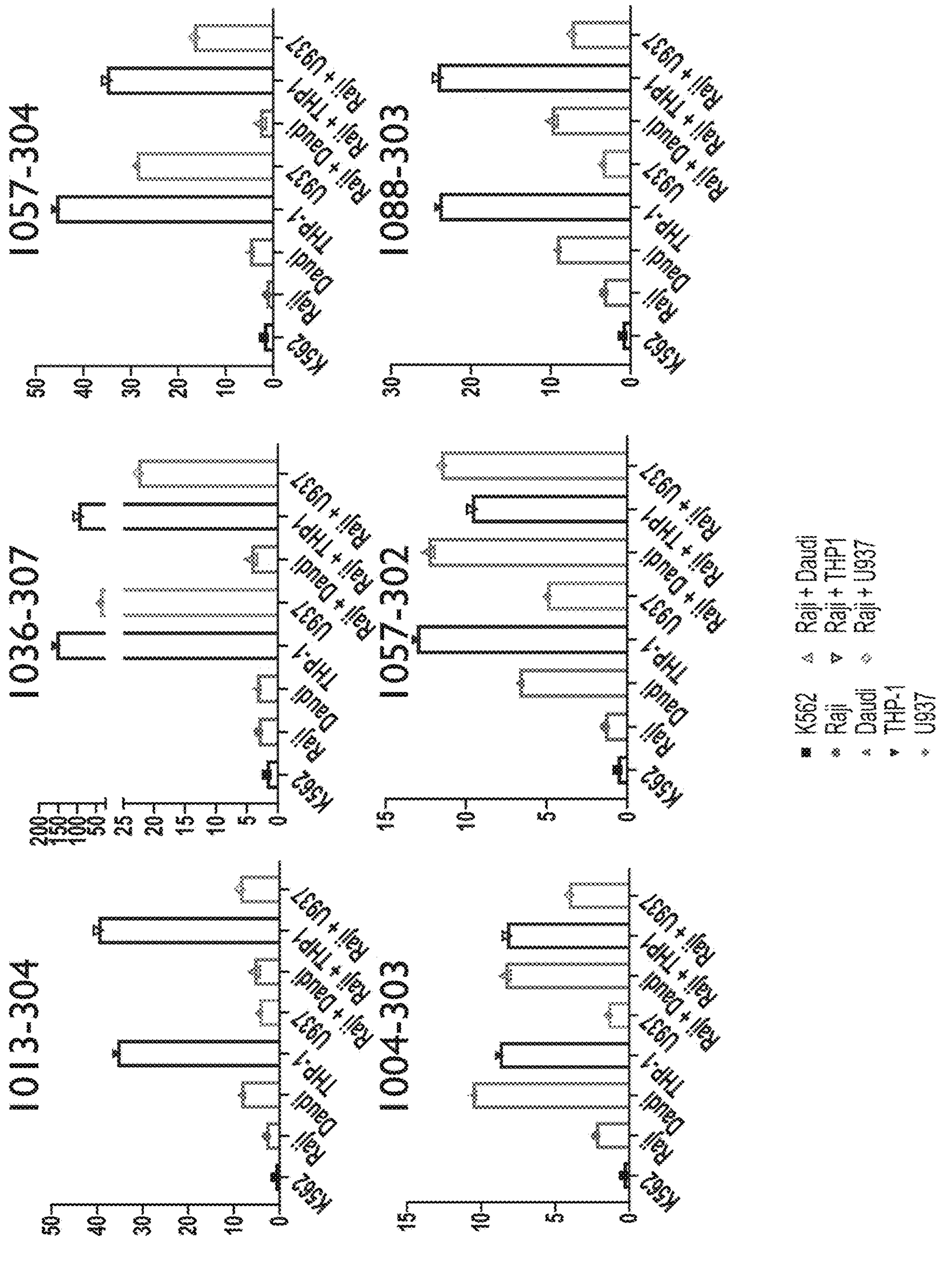

FIG. 146: Fold IFN-γ secretion (TIL+tumor cell line/TIL alone) for tested target and negative control cell lines, including combination target cell lines, for clinical NSCLC TIL lines 1013-304, 1036-307, 1057-304, 1004-303, 1057-302, and 1088-303. Black dotted line: TIL alone. Data was obtained at a 1:1 TIL:target ratio.

Figure 147:
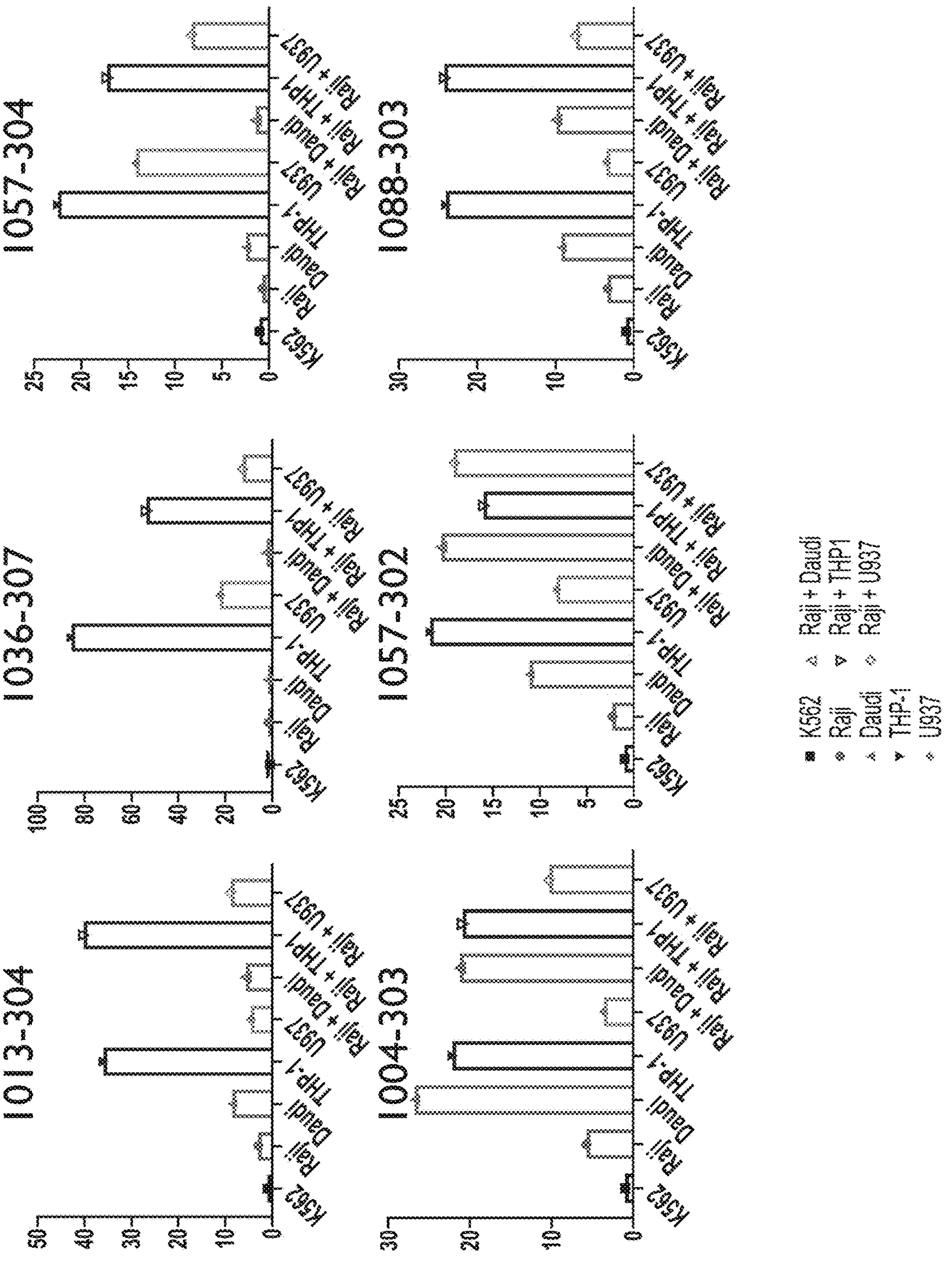

FIG. 147: Fold IFN-γ secretion (TIL+tumor cell line/[TIL+K562]) for tested target and negative control cell lines, including combination target cell lines, for clinical NSCLC TIL lines 1013-304, 1036-307, 1057-304, 1004-303, 1057-302, and 1088-303. Black dotted line: TIL alone. Data was obtained at a 1:1 TIL:target ratio.

Figure 148:
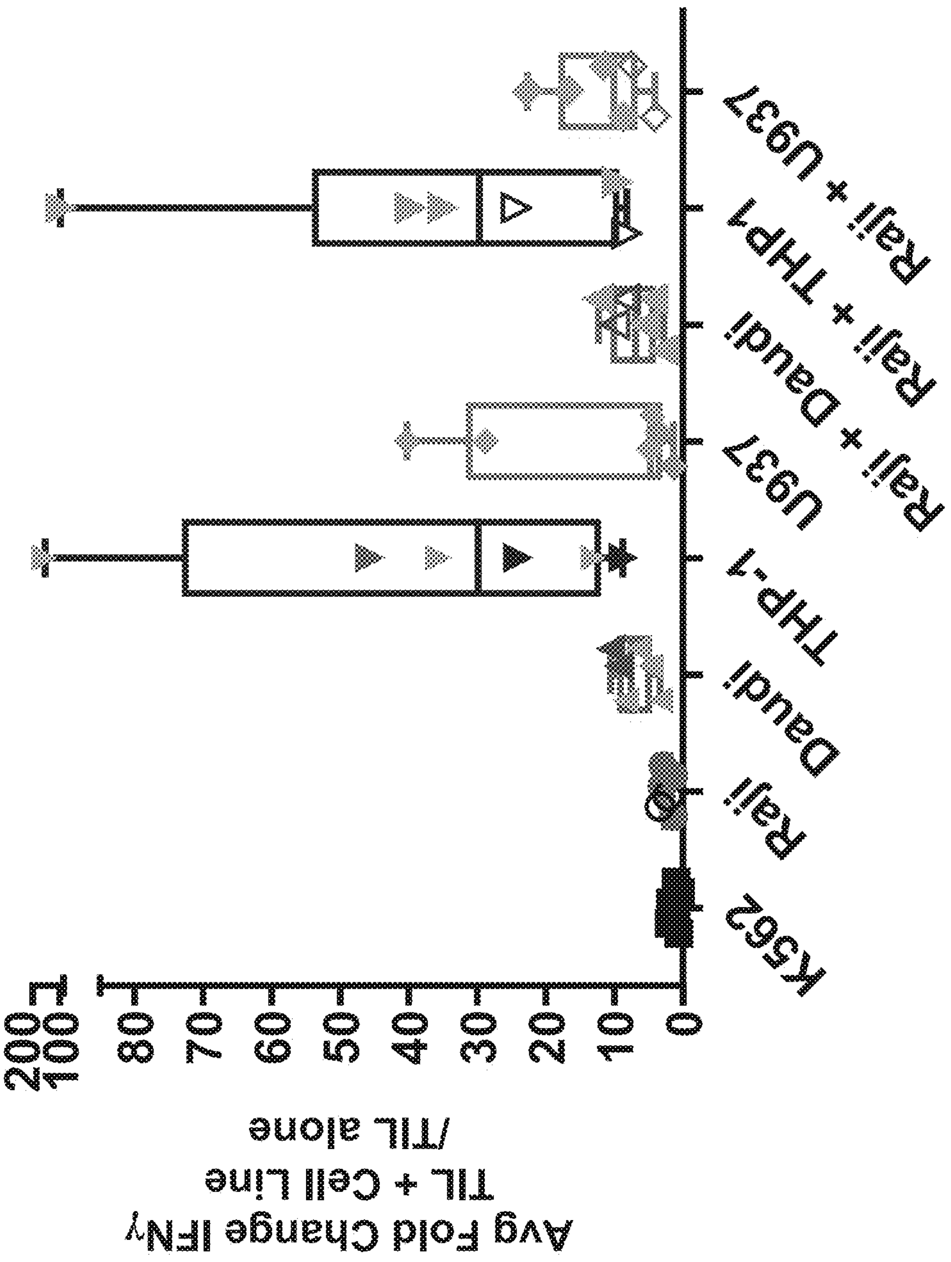

FIG. 148: Summary of fold change in IFN-γ secretion (TIL+tumor cell line/TIL alone) for tested target and negative control cell lines for clinical NSCLC TIL lines 1013-304, 1036-307, 1057-304, 1004-303, 1057-302, and 1088-303. Filled red symbols represent clinical partial responses while remaining symbols represent clinical stable disease responses.

Figure 149:
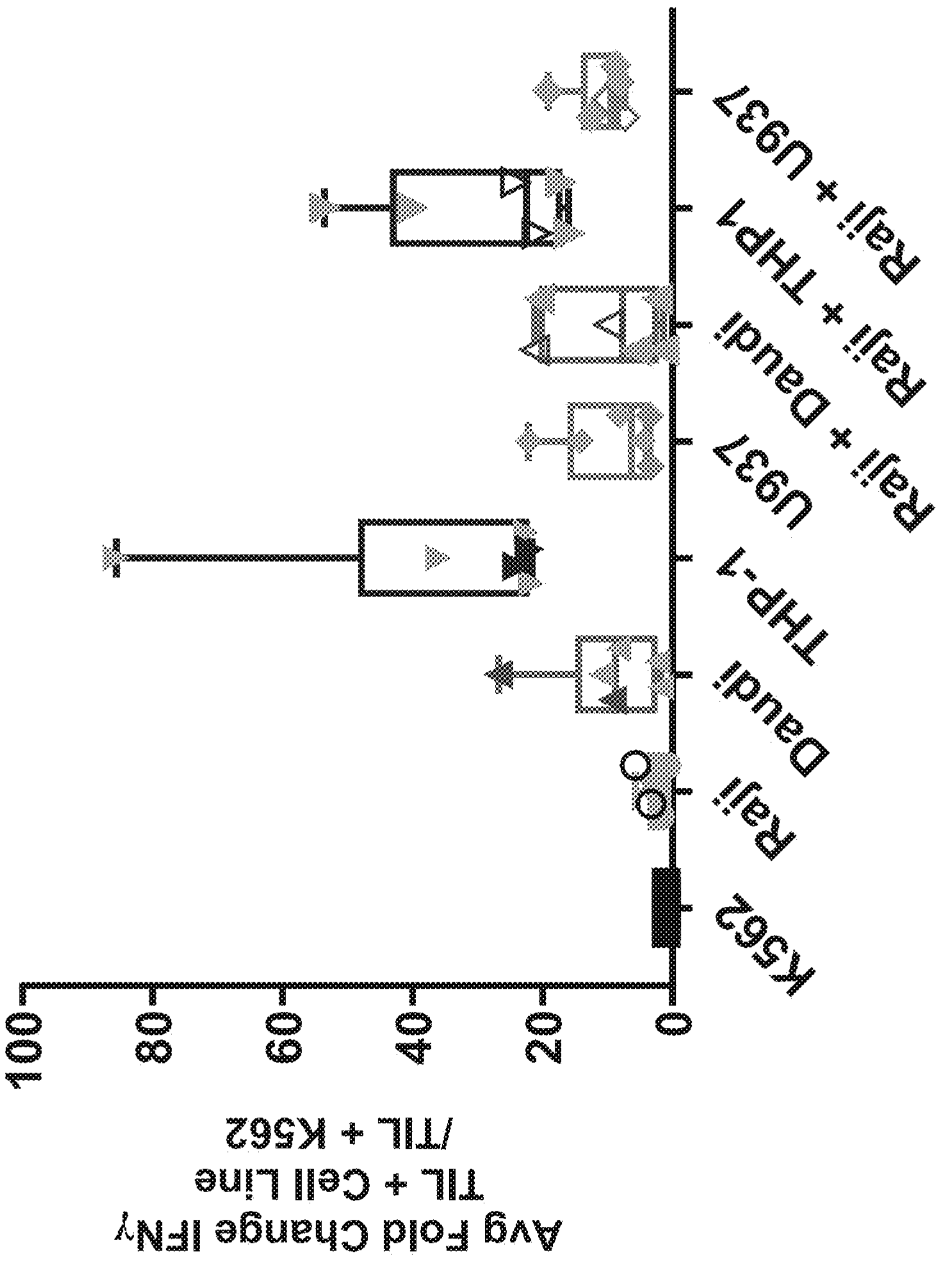

FIG. 149: Summary of fold change in IFN-γ secretion (TIL+tumor cell line/[TIL+K562]) for tested target and negative control cell lines for clinical NSCLC TIL lines 1013-304, 1036-307, 1057-304, 1004-303, 1057-302, and 1088-303. Filled red symbols represent clinical partial responses while remaining symbols represent clinical stable disease responses.

Figure 150:
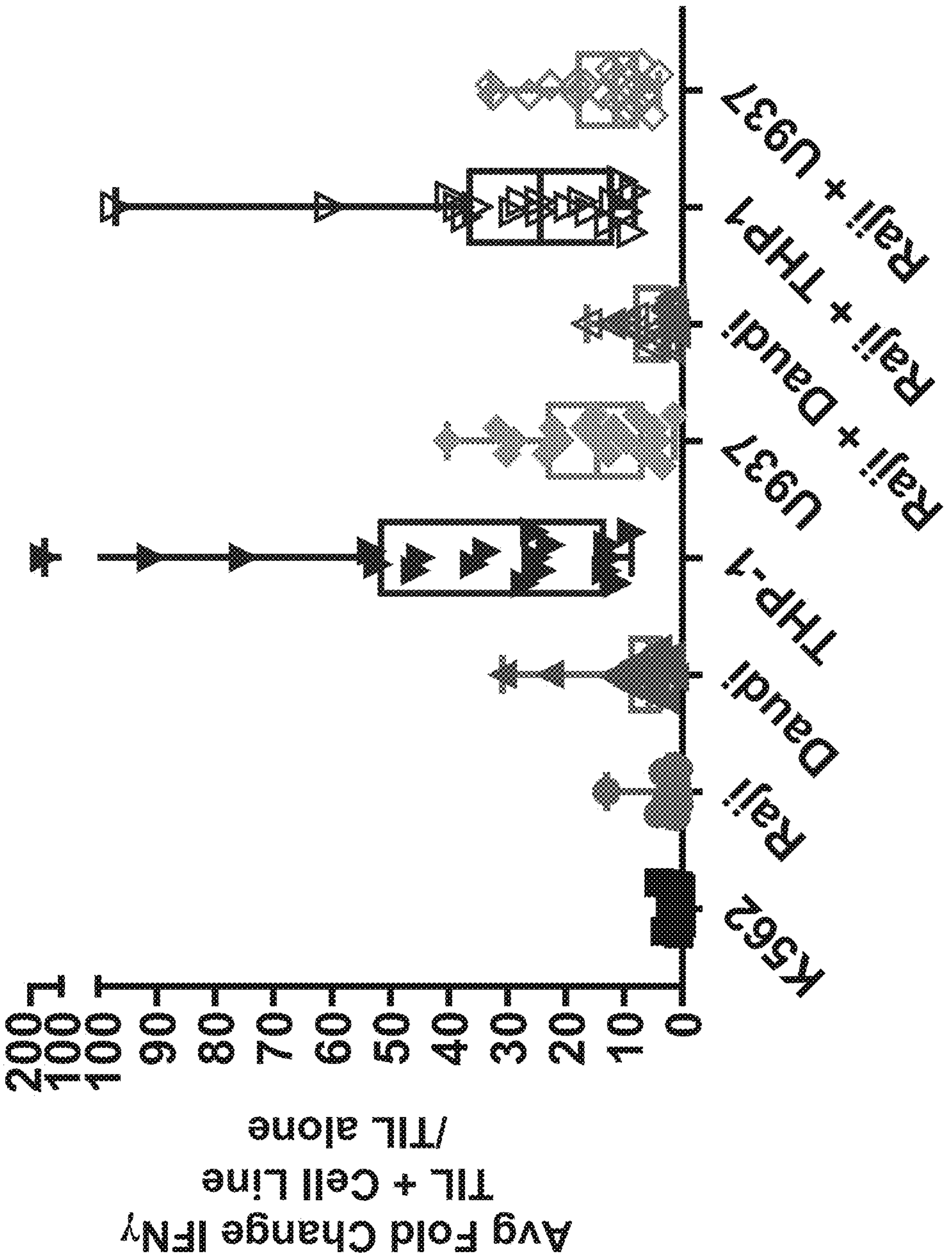

FIG. 150: Summary of fold change in IFN-γ secretion (TIL+tumor cell line/TIL alone) for tested target and negative control cell lines for 19 research and clinical melanoma and NSCLC TIL lines. Boxes represent one standard deviation on either side of the average, which is denoted by a line.

Figure 151:
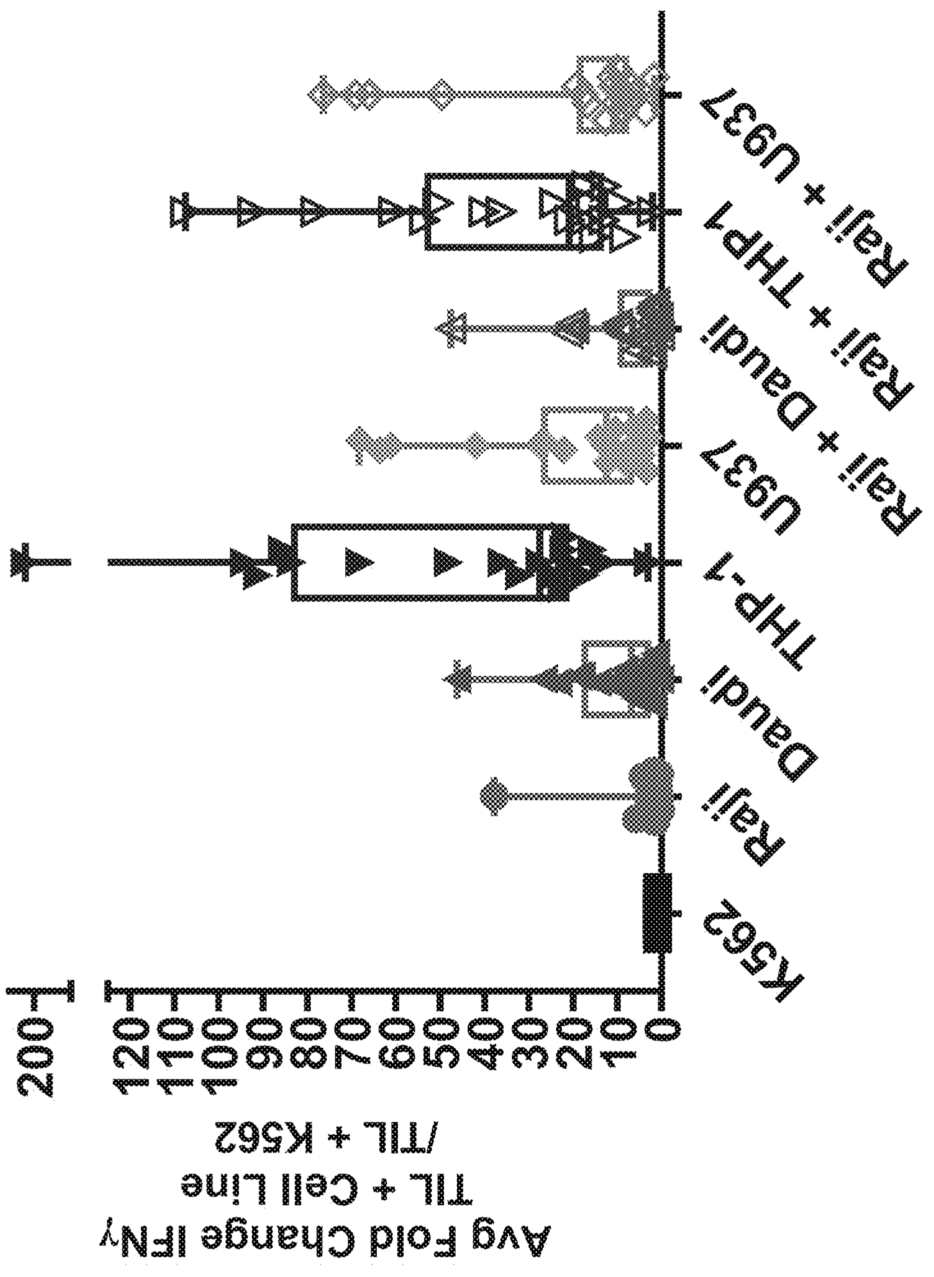

FIG. 151: Summary of fold change in IFN-γ secretion (TIL+tumor cell line/[TIL+K562]) for tested target and negative control cell lines for 19 research and clinical melanoma and NSCLC TIL lines. Boxes represent one standard deviation on either side of the average, which is denoted by a line.

Figure 152:
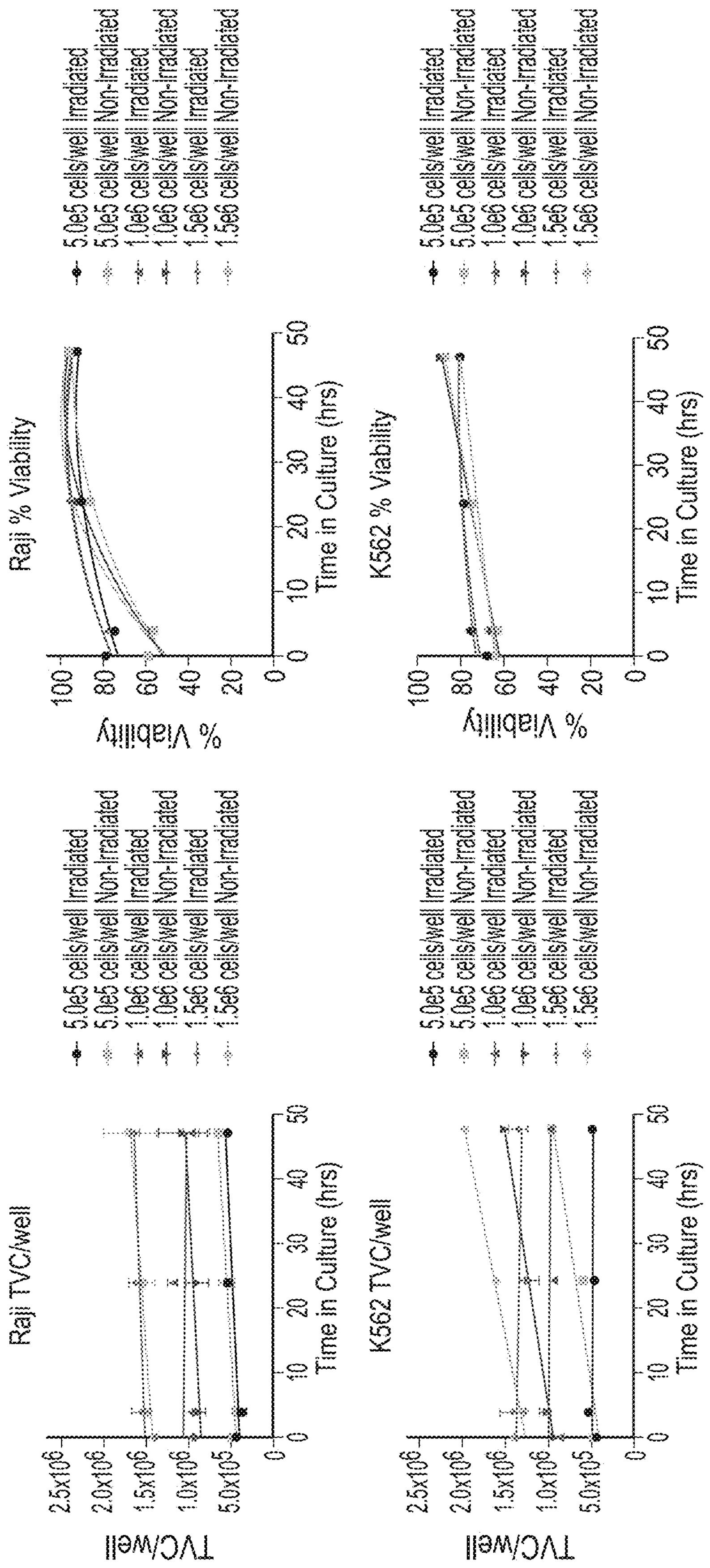

FIG. 152: Impact of irradiation upon proliferation (total viable cells, TVC) of Raji and K562 cells during 24 hours of co-culture.

Figure 153:
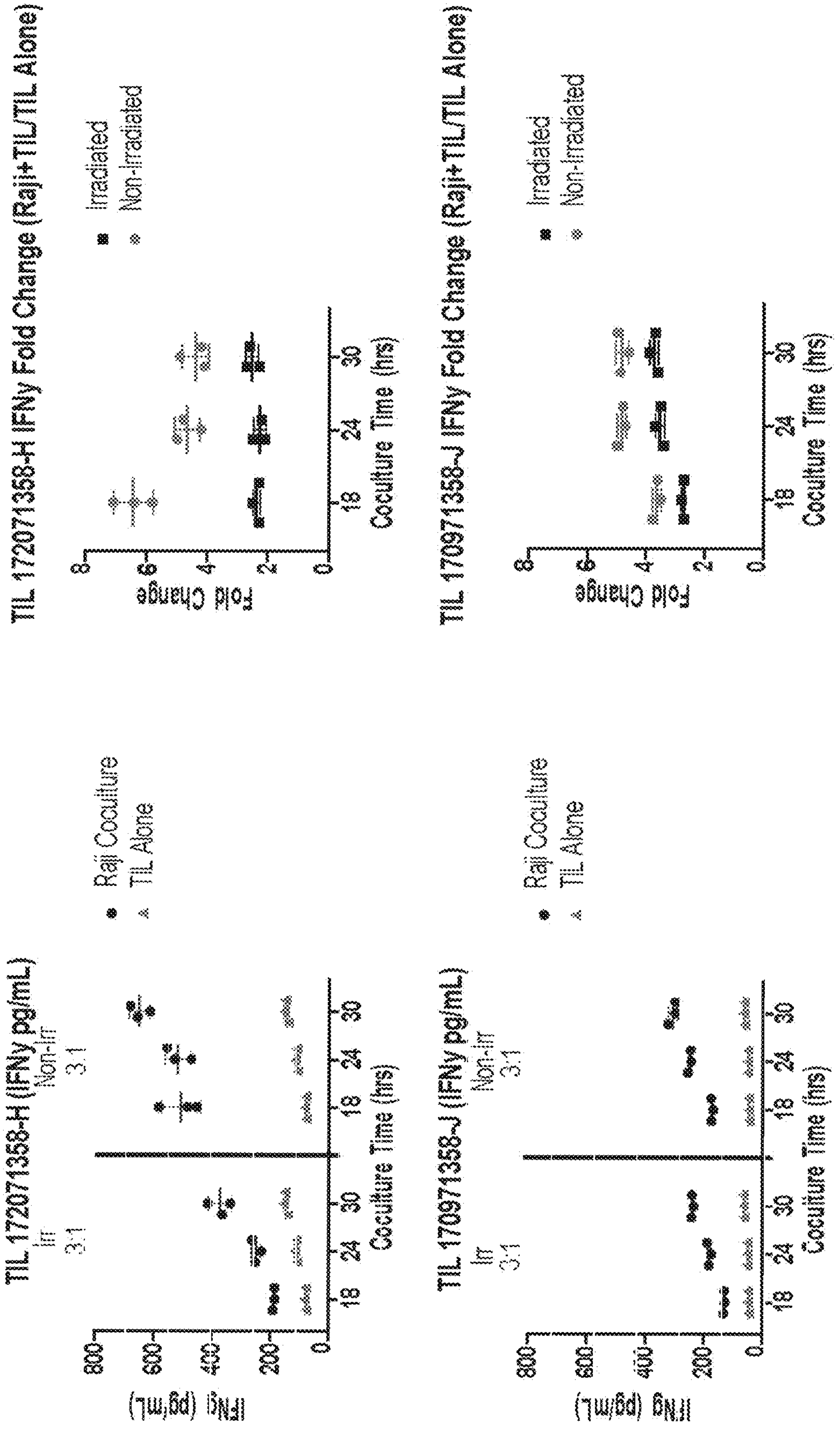

FIG. 153: Concentration of secreted IFN-γ upon co-culture with non-irradiated and irradiated Raji cells for two cervical cancer TIL lots.

Figure 154:
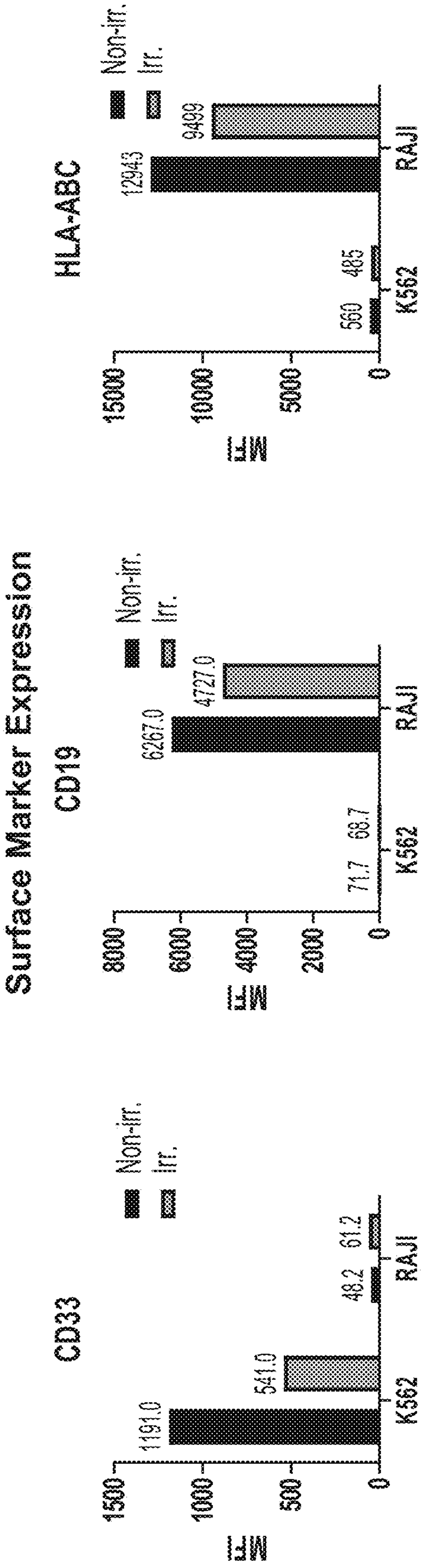

FIG. 154: Surface marker expression on K562 and Raji cells determined by flow cytometry for three markers with irradiation ("Irr.") and without irradiation ("Non-irr.").

Figure 155:
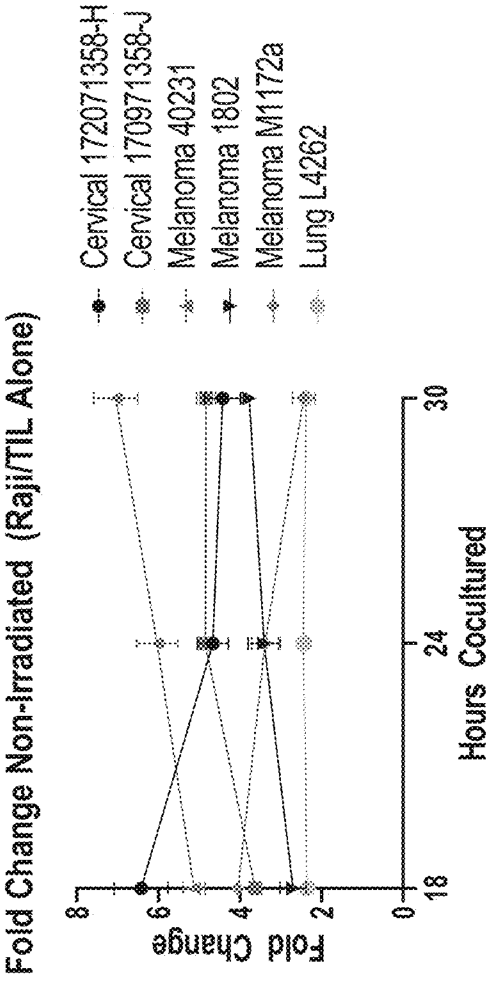

FIG. 155: IFN-γ fold change (triplicate samples) versus assay co-culture period in hours over TIL alone using for three melanoma, two cervical, and one NSCLC TIL lines.

Figure 156:
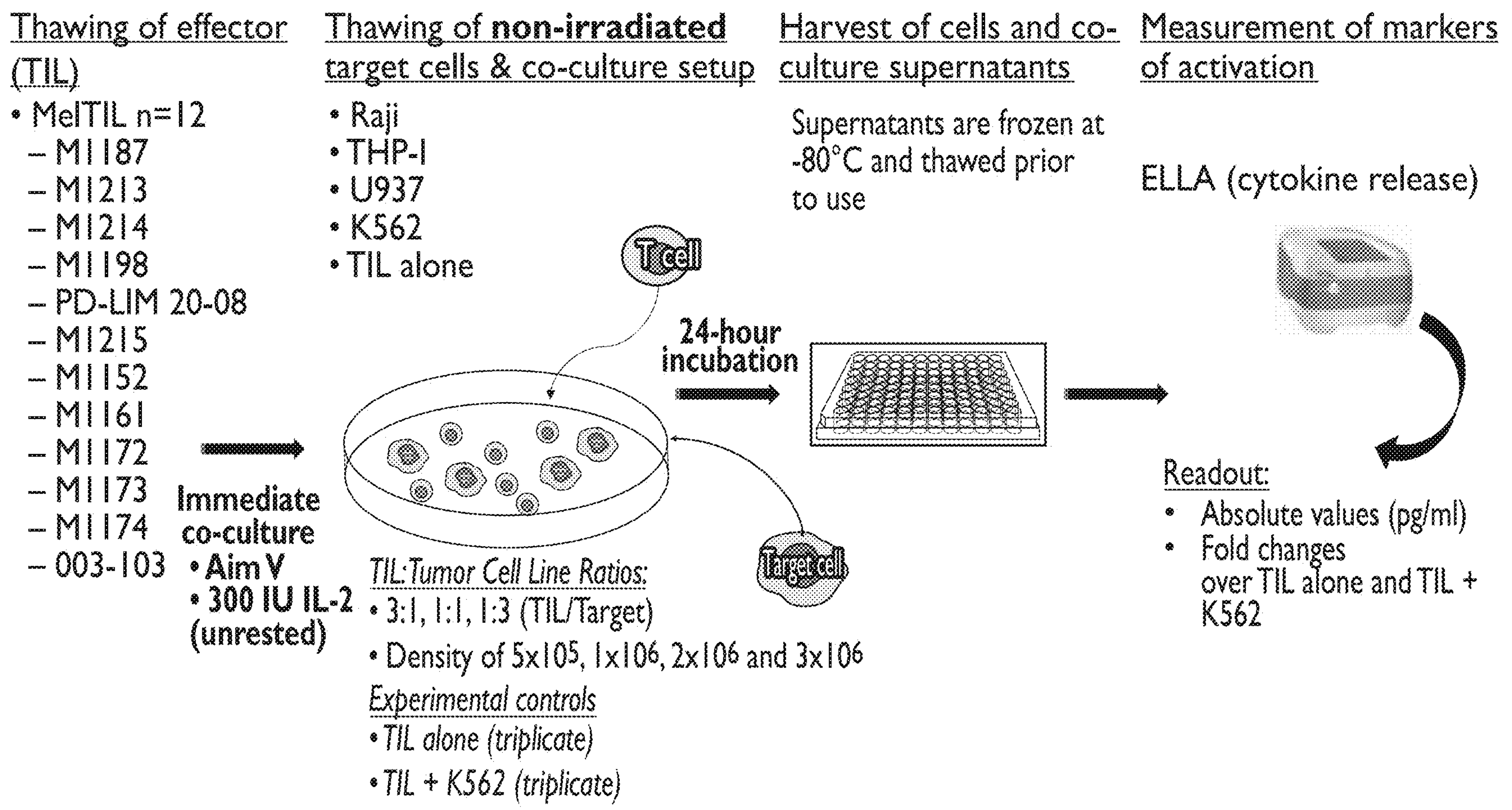

FIG. 156: Diagram of an experimental plan for TIL:tumor cell line co-culture assays, which are also embodiments of the present invention.

Figure 157:
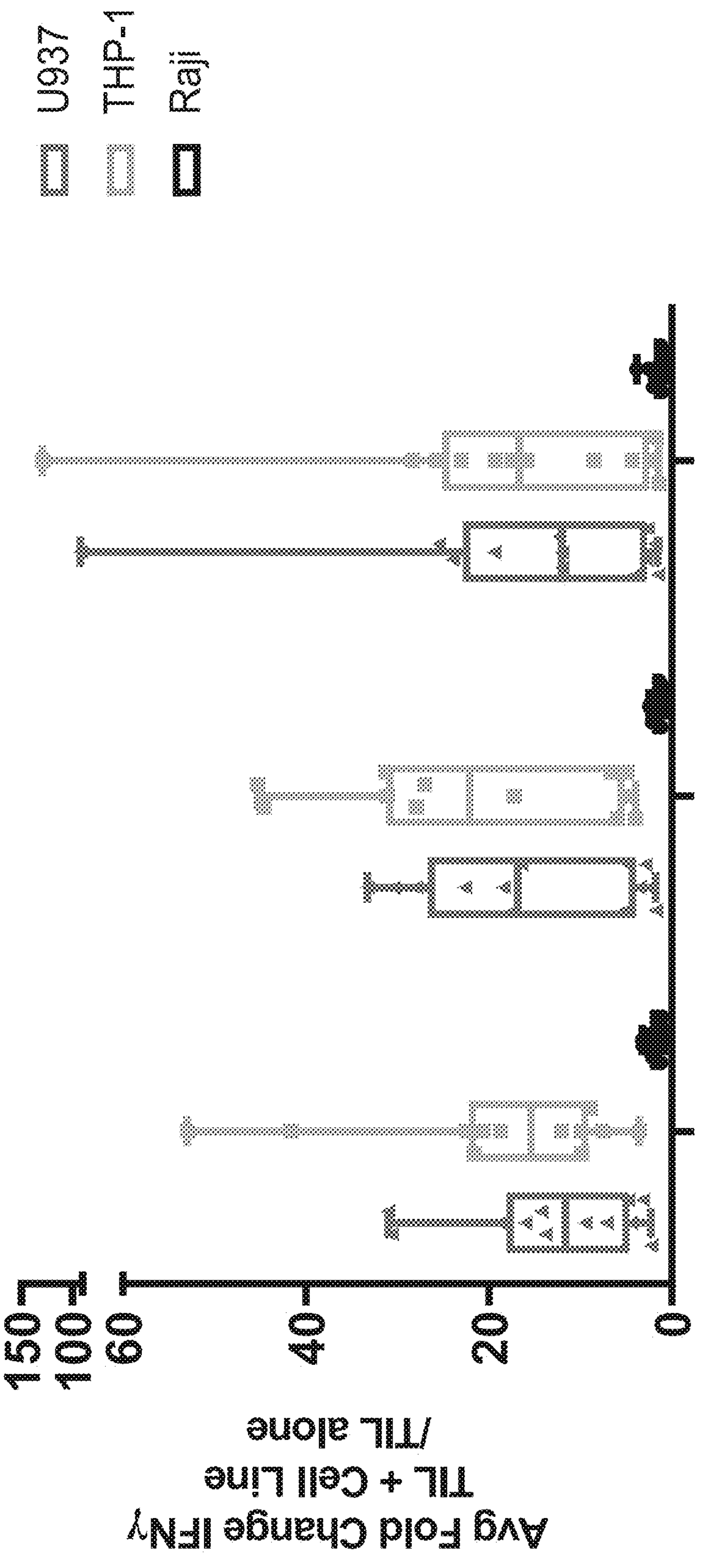

FIG. 157: Average fold change for IFN-γ of tumor cell line plus TIL over TIL alone for $1.0\times10^6$ TVC/well for 12 melanoma TIL lines. Boxes represent one standard deviation on either side of the average, which is denoted by a line.

Figure 158:
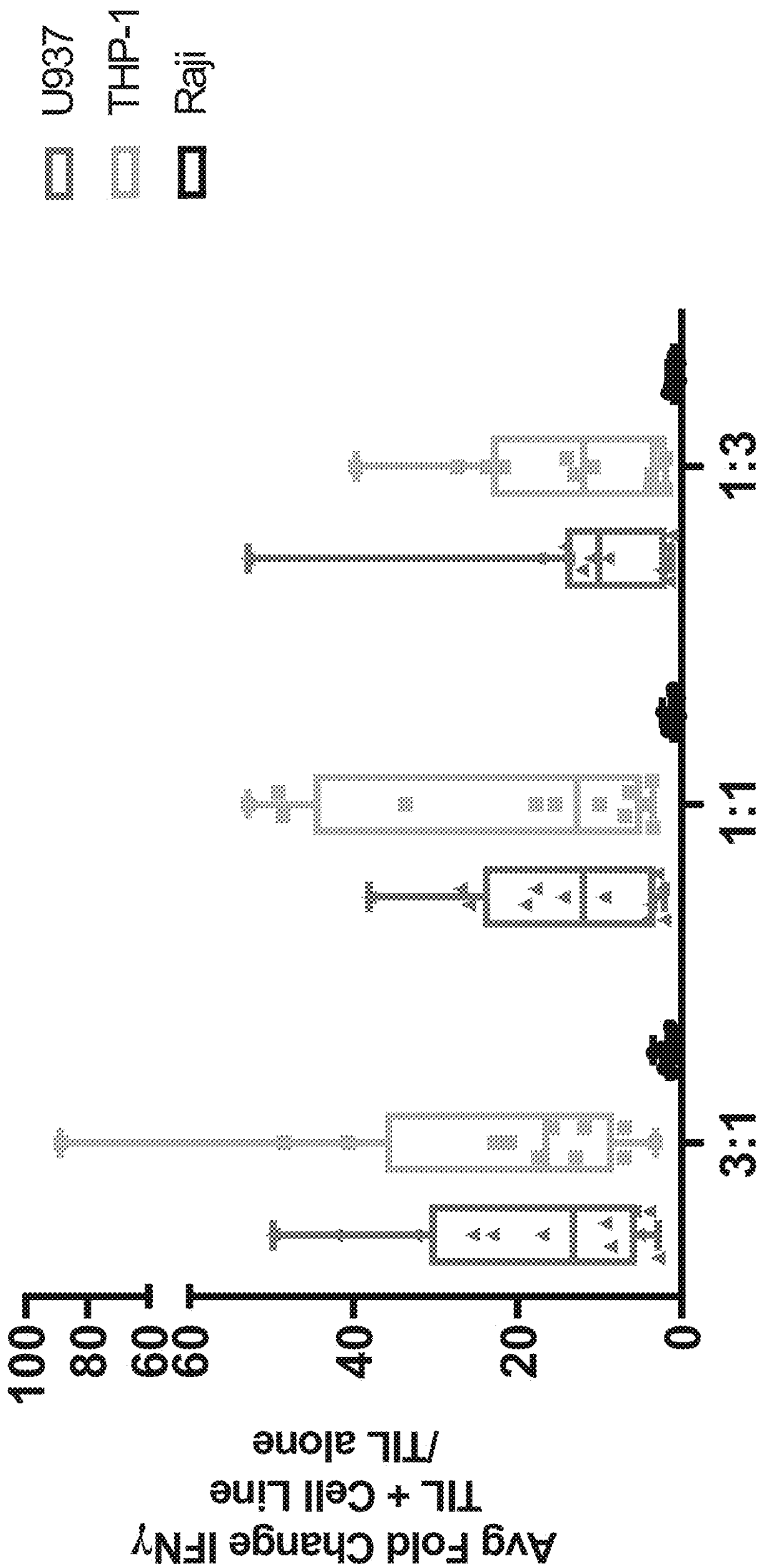

FIG. 158: Average fold change for IFN-γ of tumor cell line plus TIL over TIL alone for $2.0\times10^6$ TVC/well for 12 melanoma TIL lines. Boxes represent one standard deviation on either side of the average, which is denoted by a line.

Figure 159:
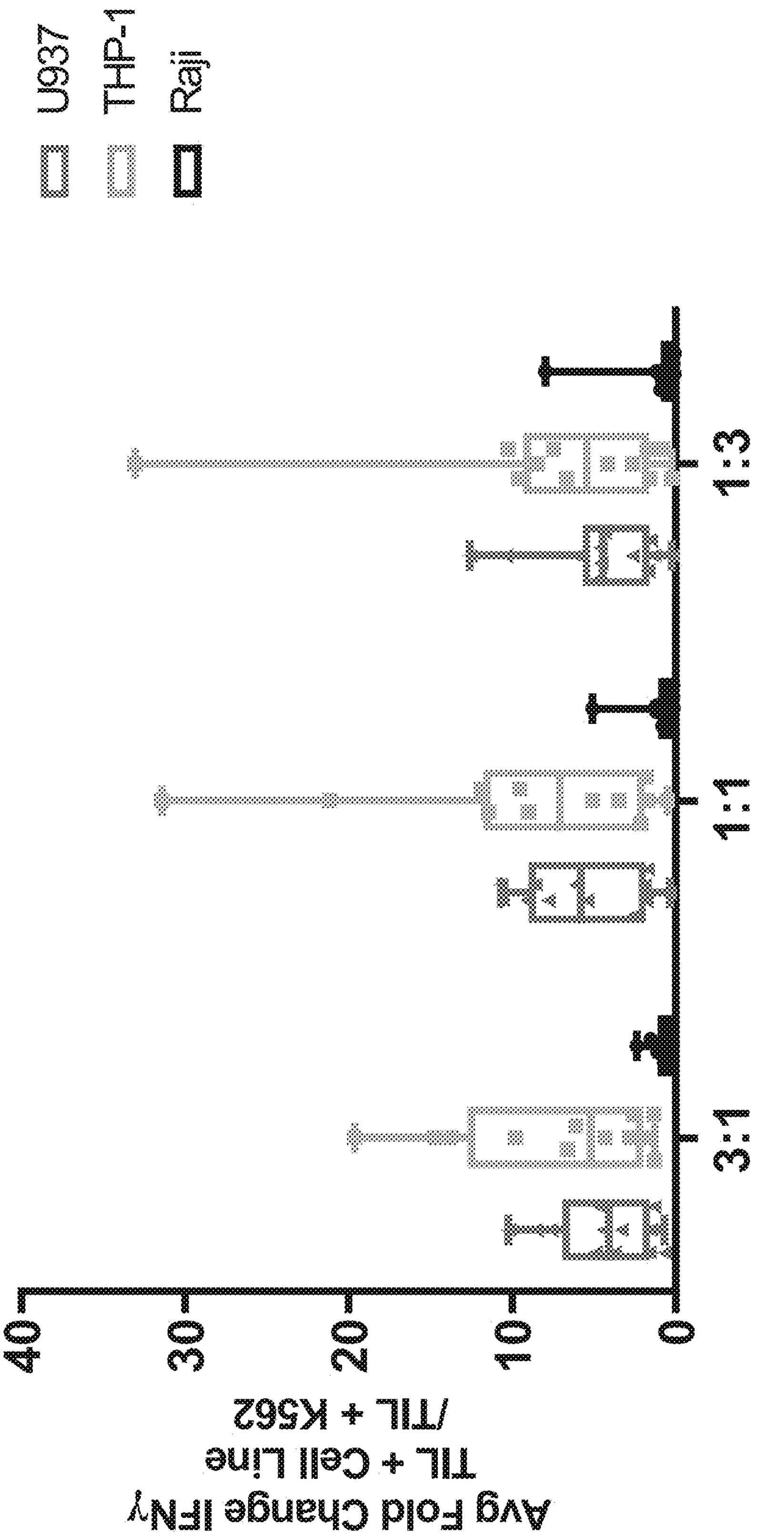

FIG. 159: Average fold change for IFN-γ of tumor cell line plus TIL over K562 negative control cells for $1.0\times10^6$ TVC/well for 12 melanoma TIL lines. Boxes represent one standard deviation on either side of the average, which is denoted by a line.

Figure 160:
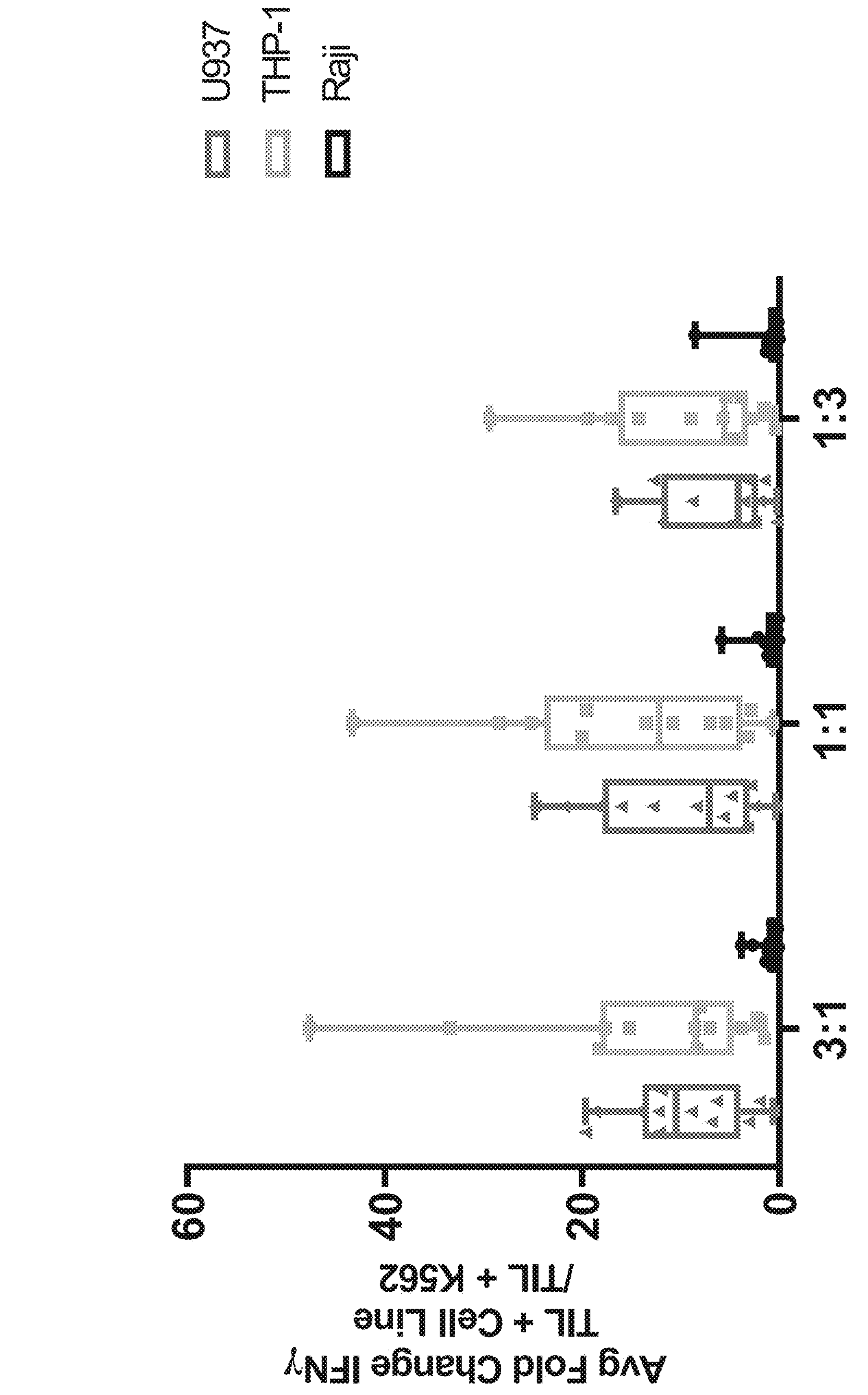

FIG. 160: Average fold change for IFN-γ of tumor cell line plus TIL over K562 negative control cells for $2.0\times10^6$ TVC/well for 12 melanoma TIL lines. Boxes represent one standard deviation on either side of the average, which is denoted by a line.

Figure 161:
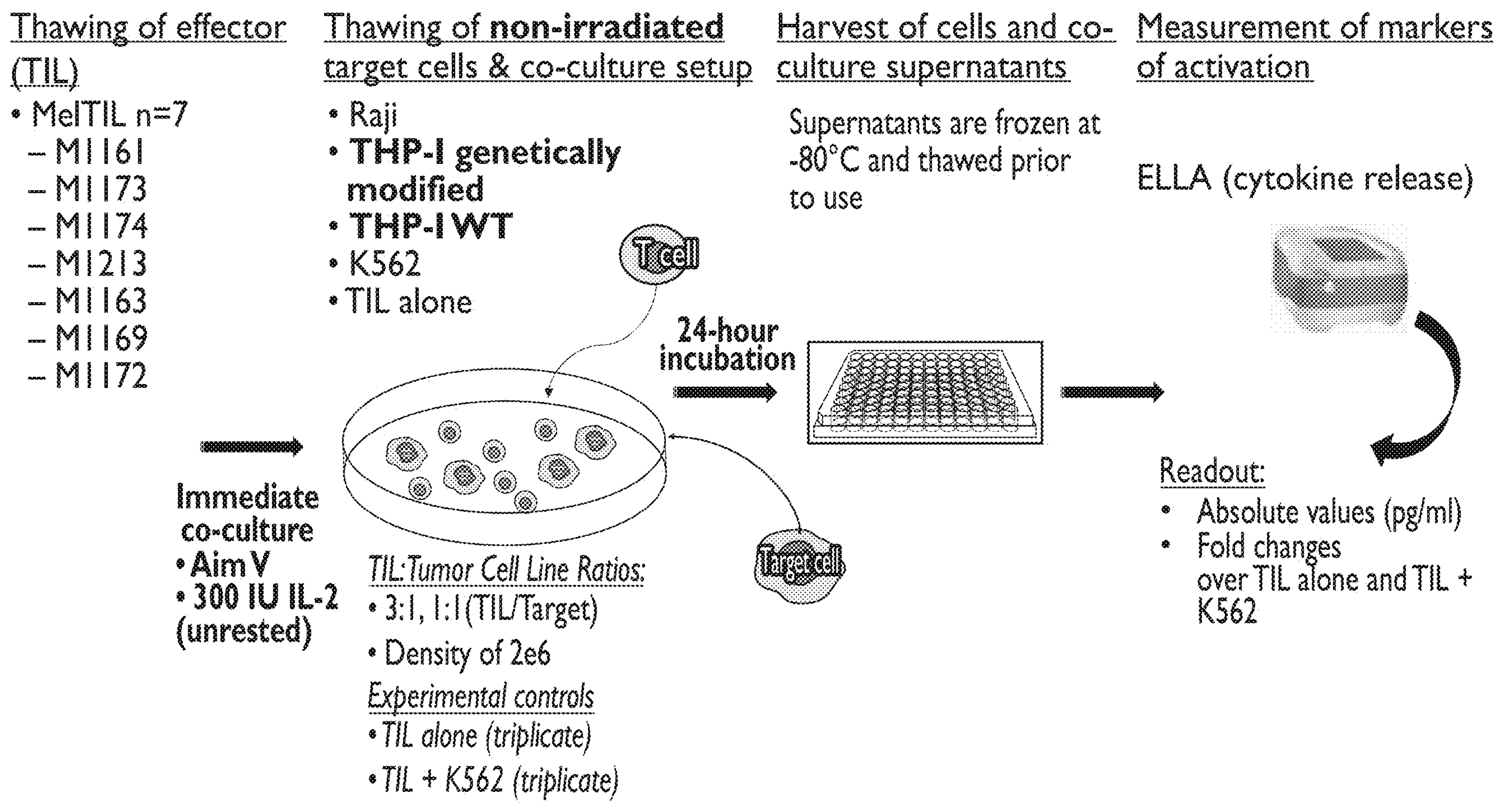

FIG. 161: Diagram of an experimental plan for TIL:tumor cell line co-culture assays for two types of the Thp1 (THP-1) monocytic cell line, wildtype (WT) and genetically modified, which are also embodiments of the present invention.

Figure 162:
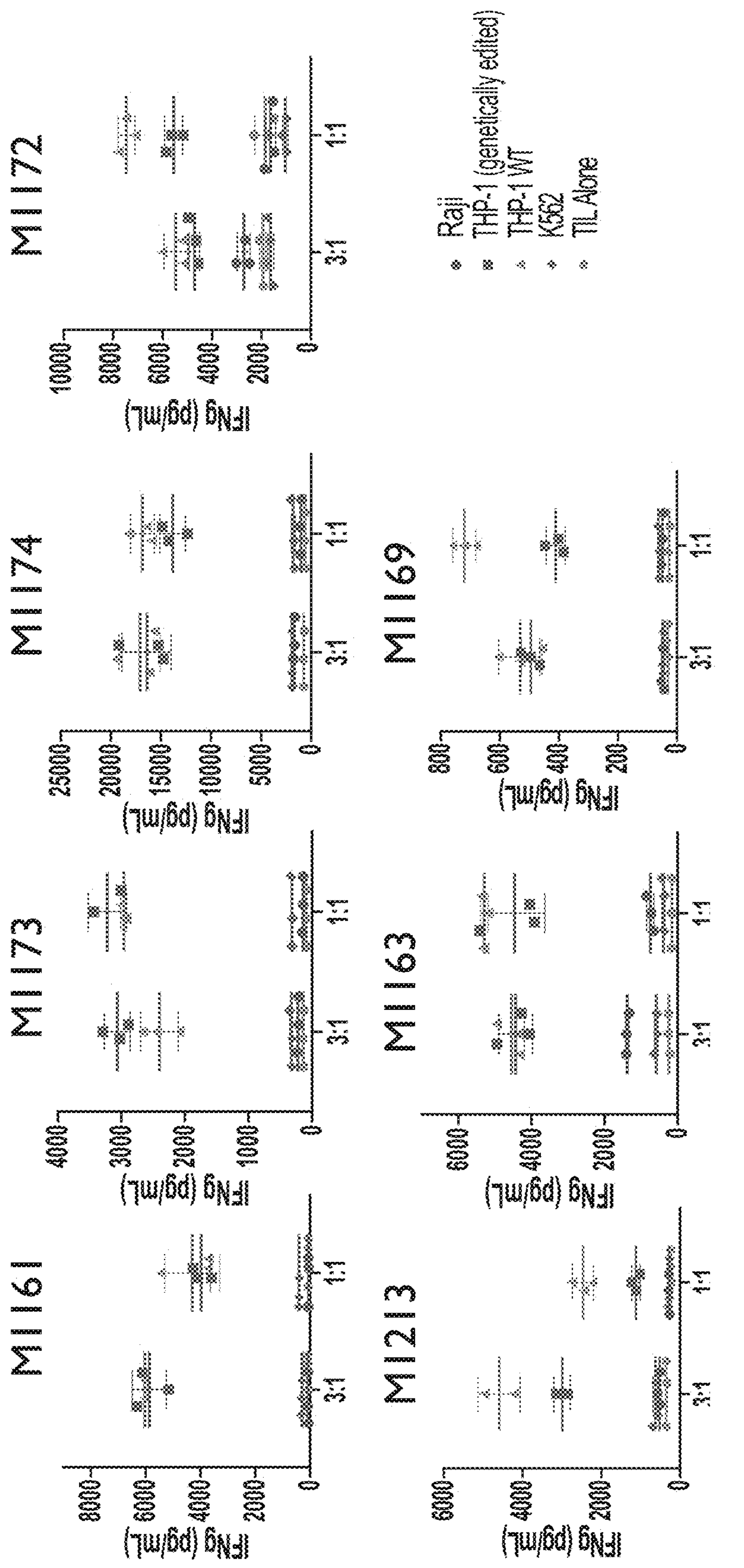

FIG. 162: Comparison of IFN-γ values (pg/mL) obtained for WT and genetically modified Thp1 target cells.

Figure 163:
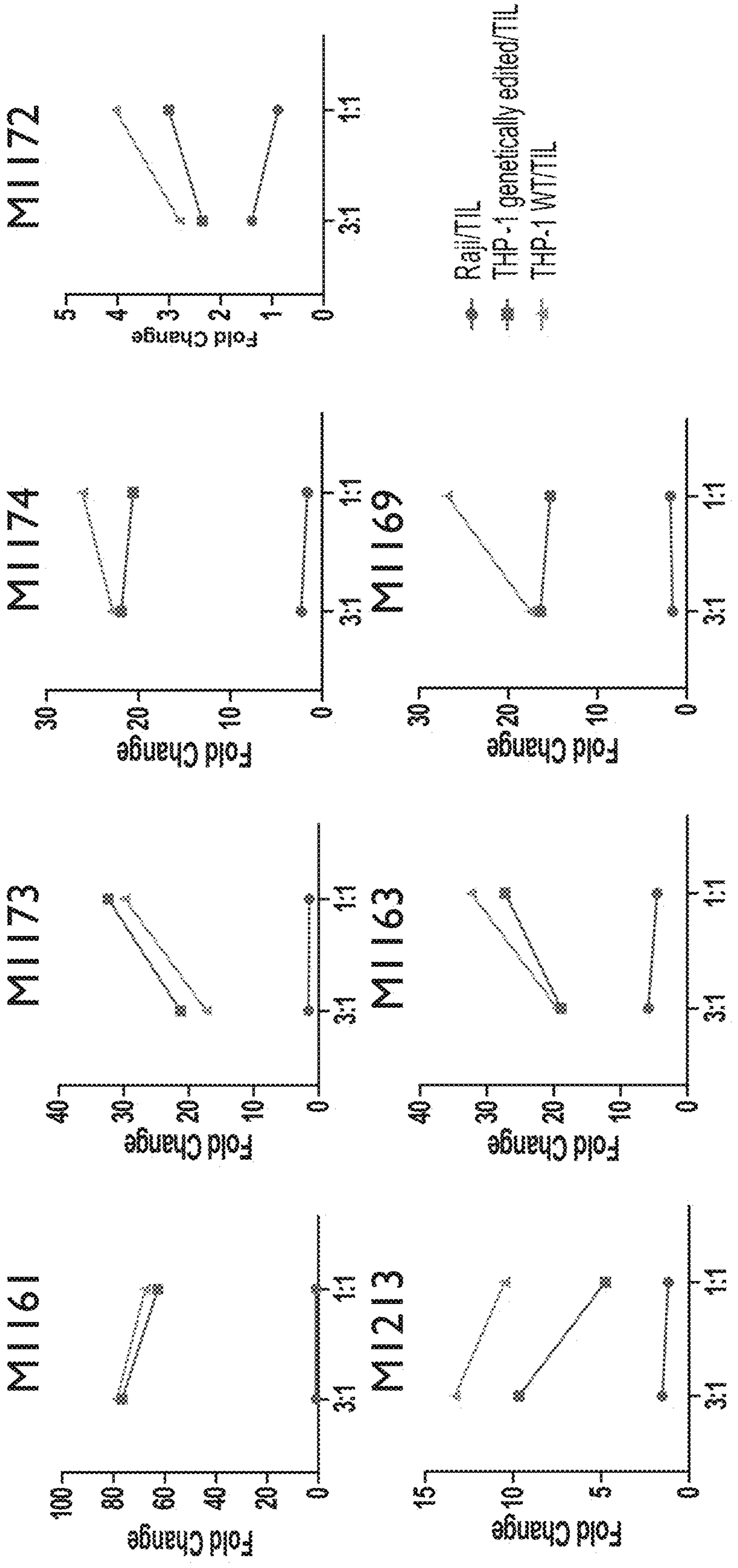

FIG. 163: Comparison of IFN-γ fold change over TIL alone values obtained for WT and genetically modified Thp1 target cells.

Figure 164:
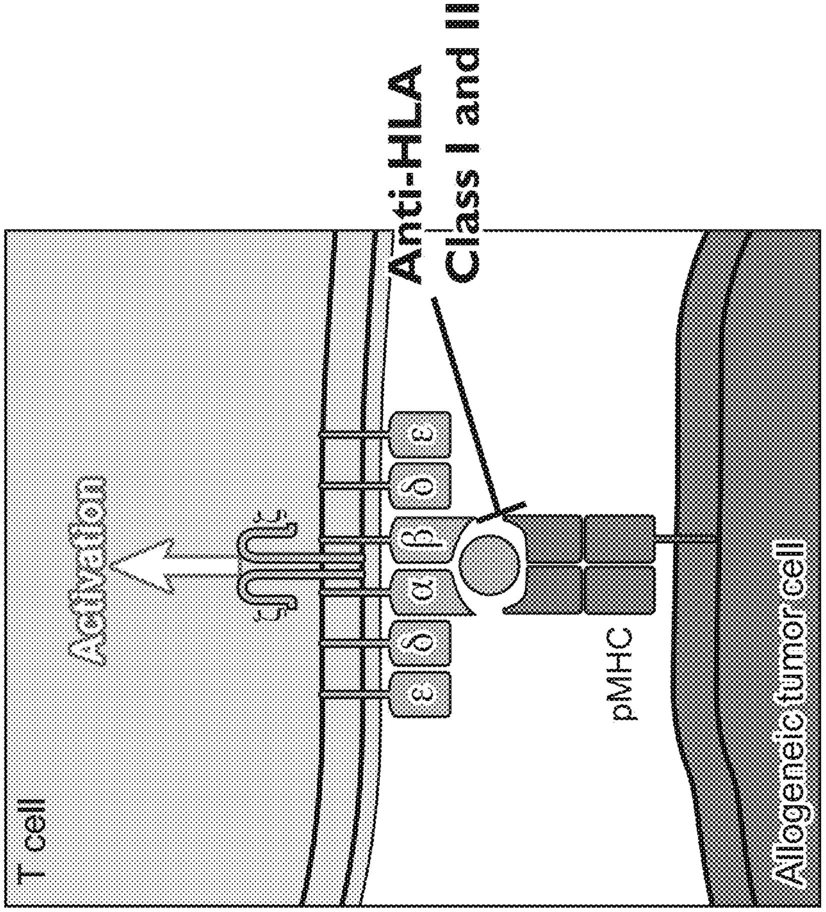

FIG. 164: Diagram illustrating HLA blockade, which is a negative control for the assays of the present invention in certain embodiments.

Figure 165:
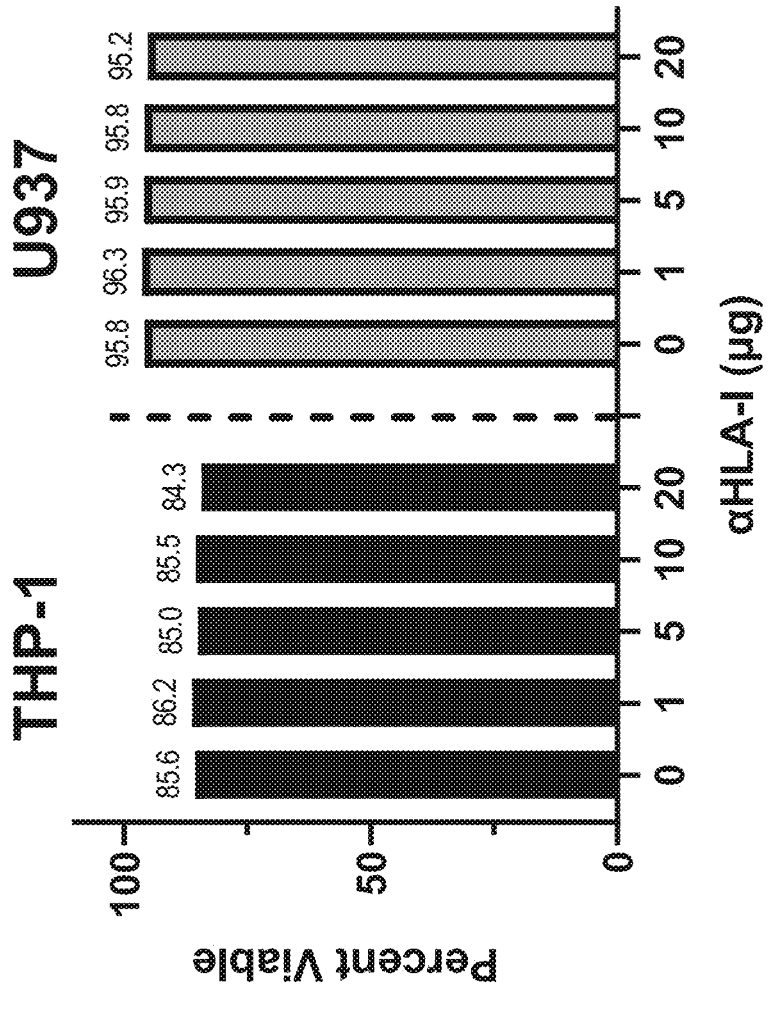

FIG. 165: Effects of HLA-I blockade on Thp1 (THP-1) and U937 monocyte cell lines at different antibody concentrations, as measured by percent viability for each monocyte cell line.

Figure 166:
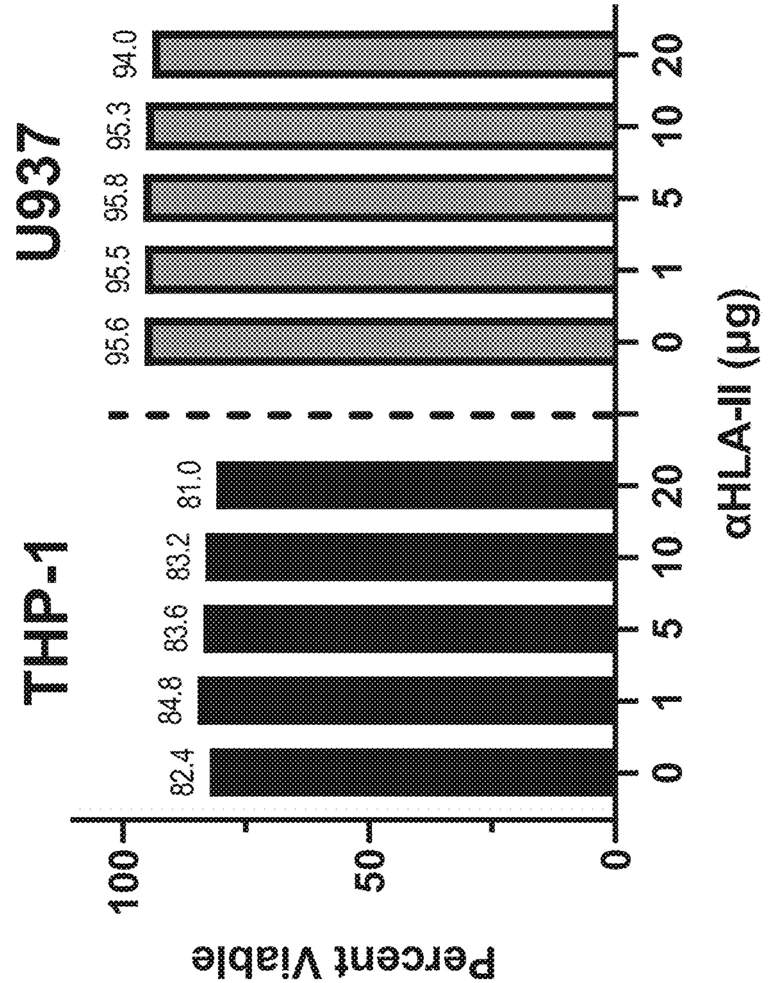

FIG. 166: Effects of HLA-II blockade on Thp1 (THP-1) and U937 monocyte cell lines at different antibody concentrations, as measured by percent viability for each monocyte cell line.

Figure 167:
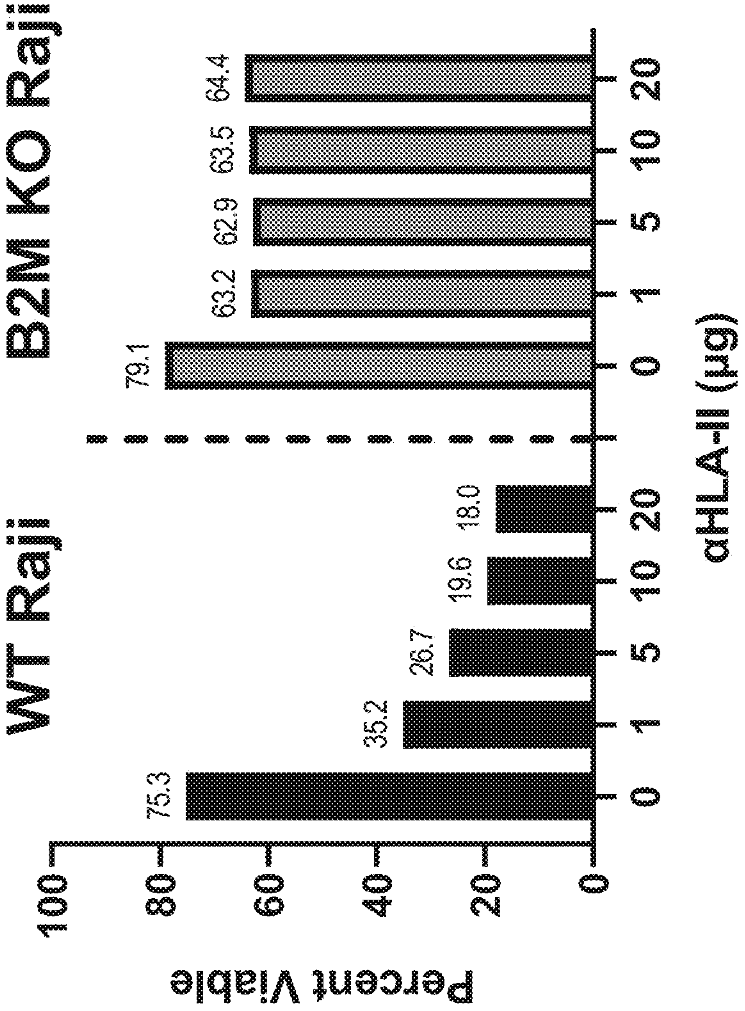

FIG. 167: Effects of HLA-II blockade on Raji cells at different antibody concentrations, as measured by percent viability for Raji cells and genetically modified Raji cells (B2M KO).

Figure 168:
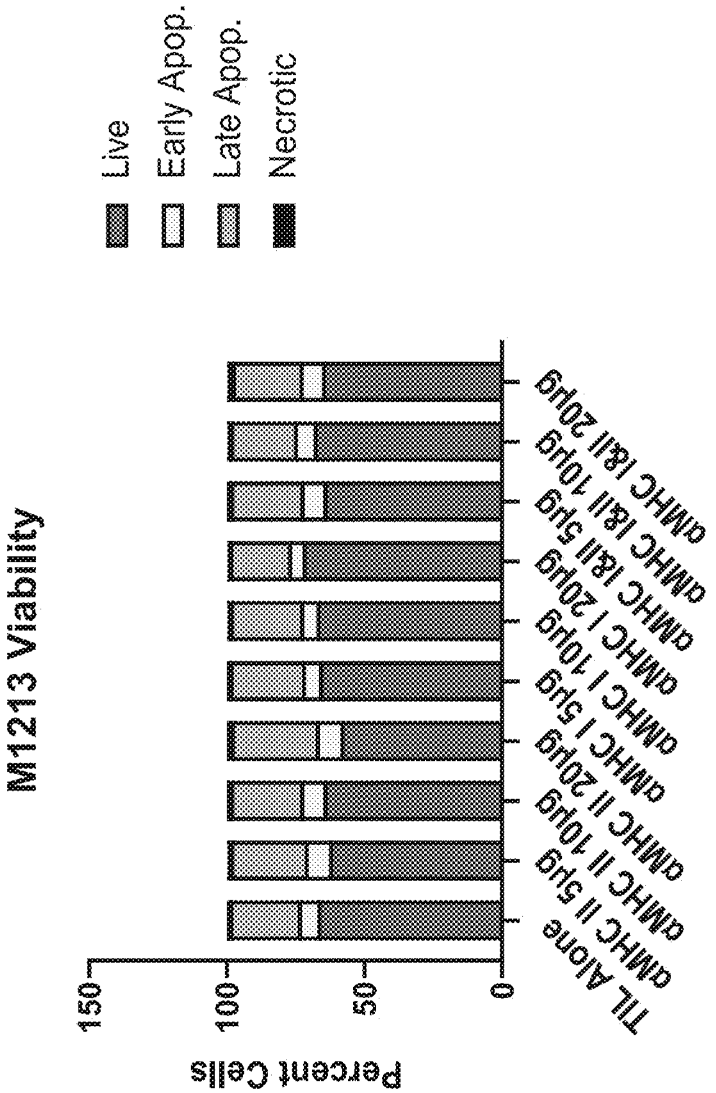

FIG. 168: Effects of HLA-I (aMHC I) and HLA-II (aMHC II) antibody blockade on TIL cell line M1213.

Figure 169:
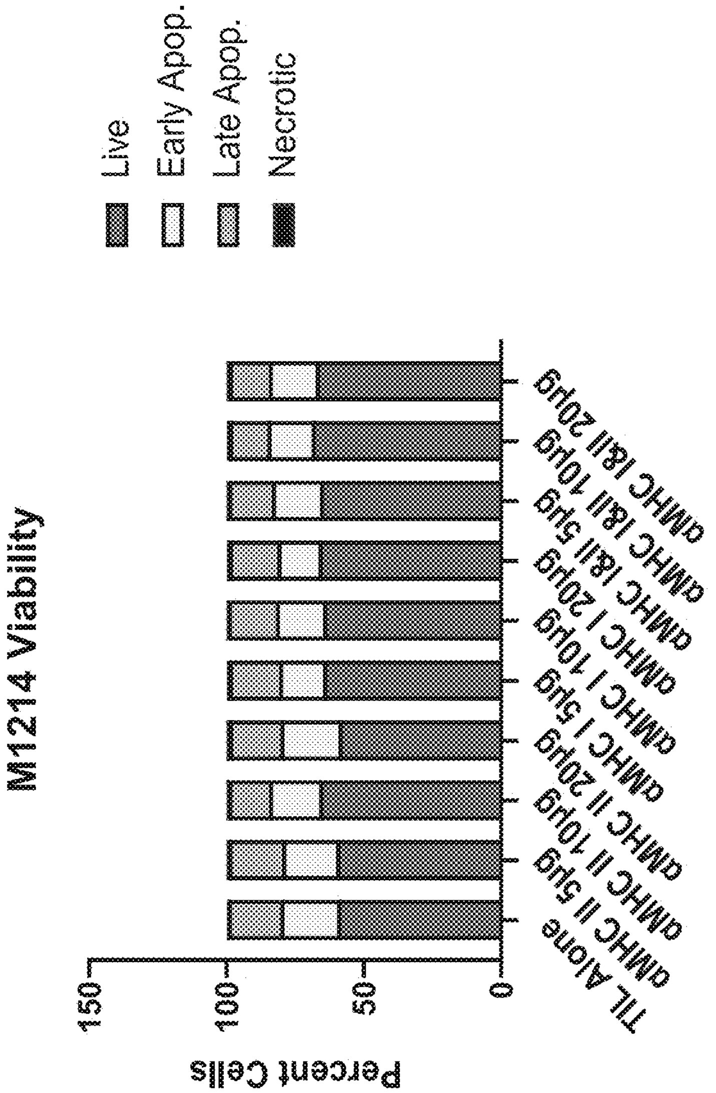

FIG. 169: Effects of HLA-I (aMHC I) and HLA-II (aMHC II) antibody blockade on TIL cell line M1214.

Figure 170:
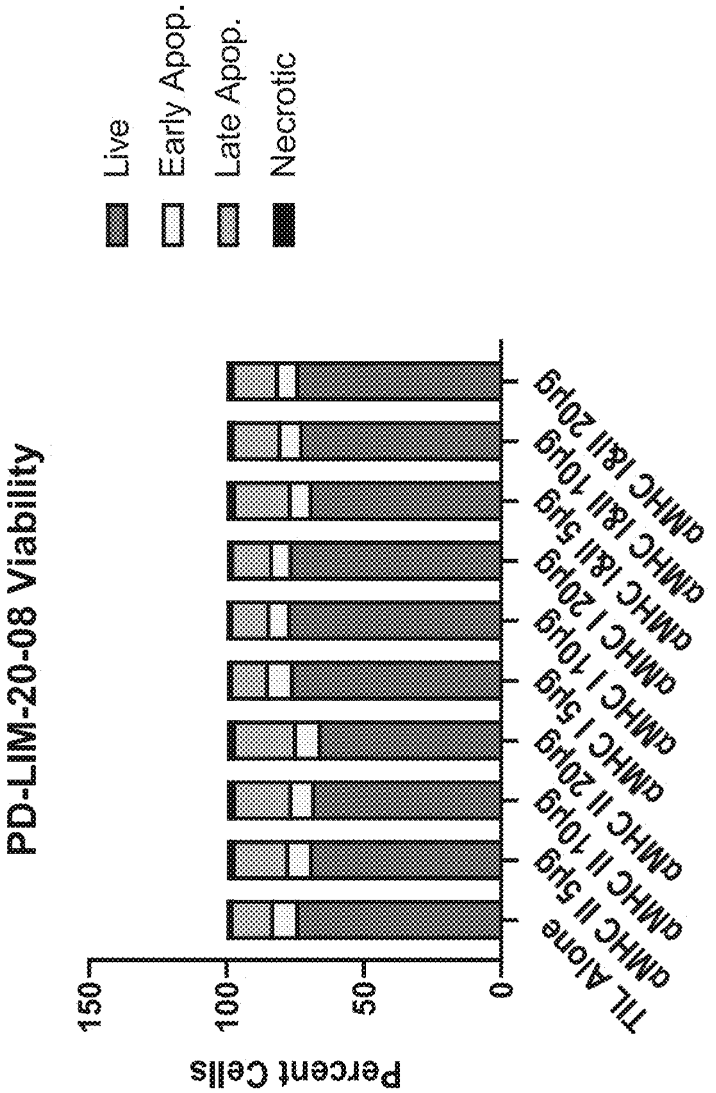

FIG. 170: Effects of HLA-I (aMHC I) and HLA-II (aMHC II) antibody blockade on TIL cell line PD-LIM-20-08.

Figure 171:
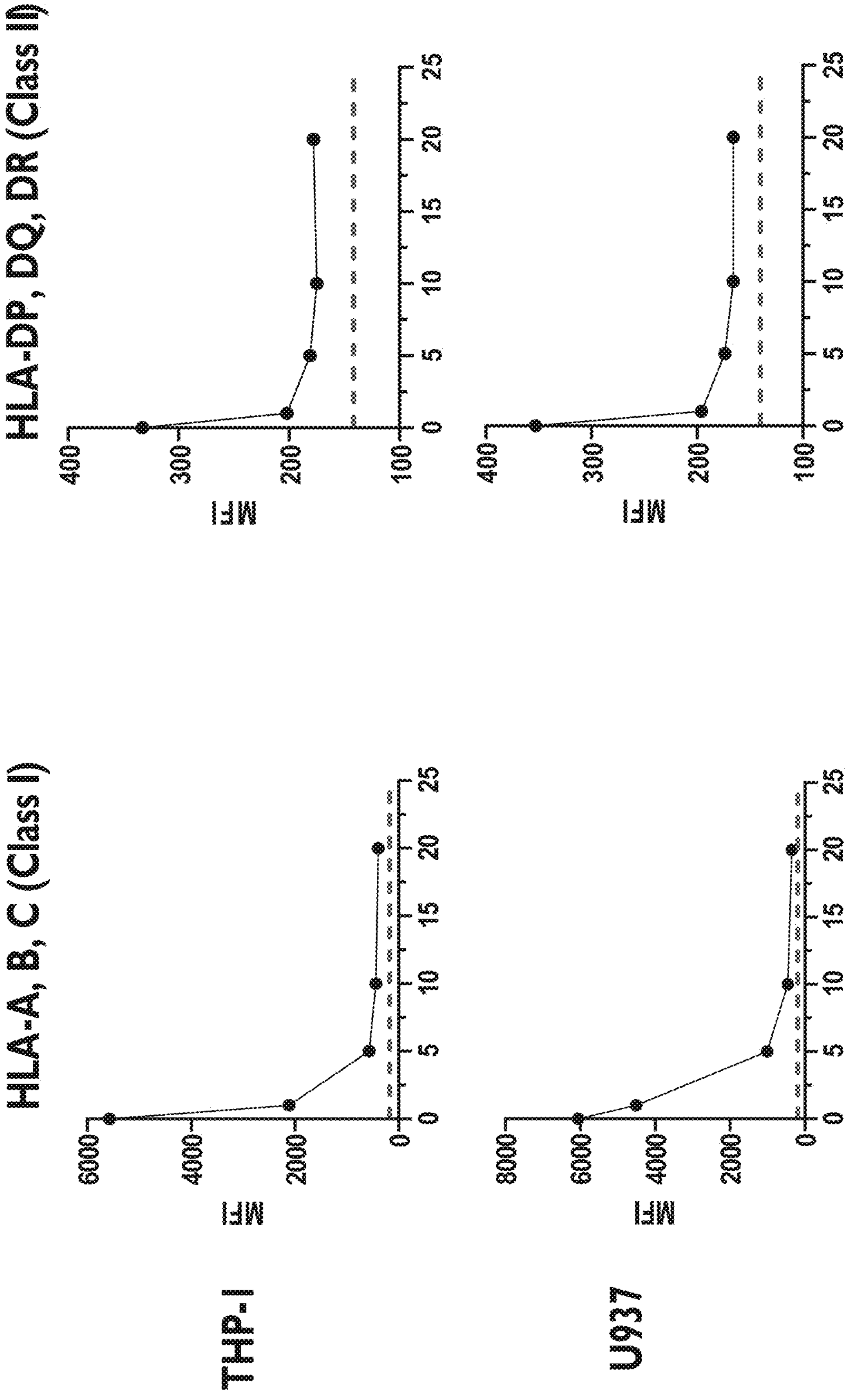

FIG. 171: Results of HLA (MHC) Class I and II antibody dose titrations. Embodiment I of the HLA blocking negative control method was performed using 20 μg/mL of HLA-I blocking antibody and 10 μg/mL of HLA-II blocking antibody. Embodiment II of the HLA blocking negative control method was performed using 10 μg/mL of HLA-I blocking antibody and 5 μg/mL of HLA-II blocking antibody.

Figure 172:
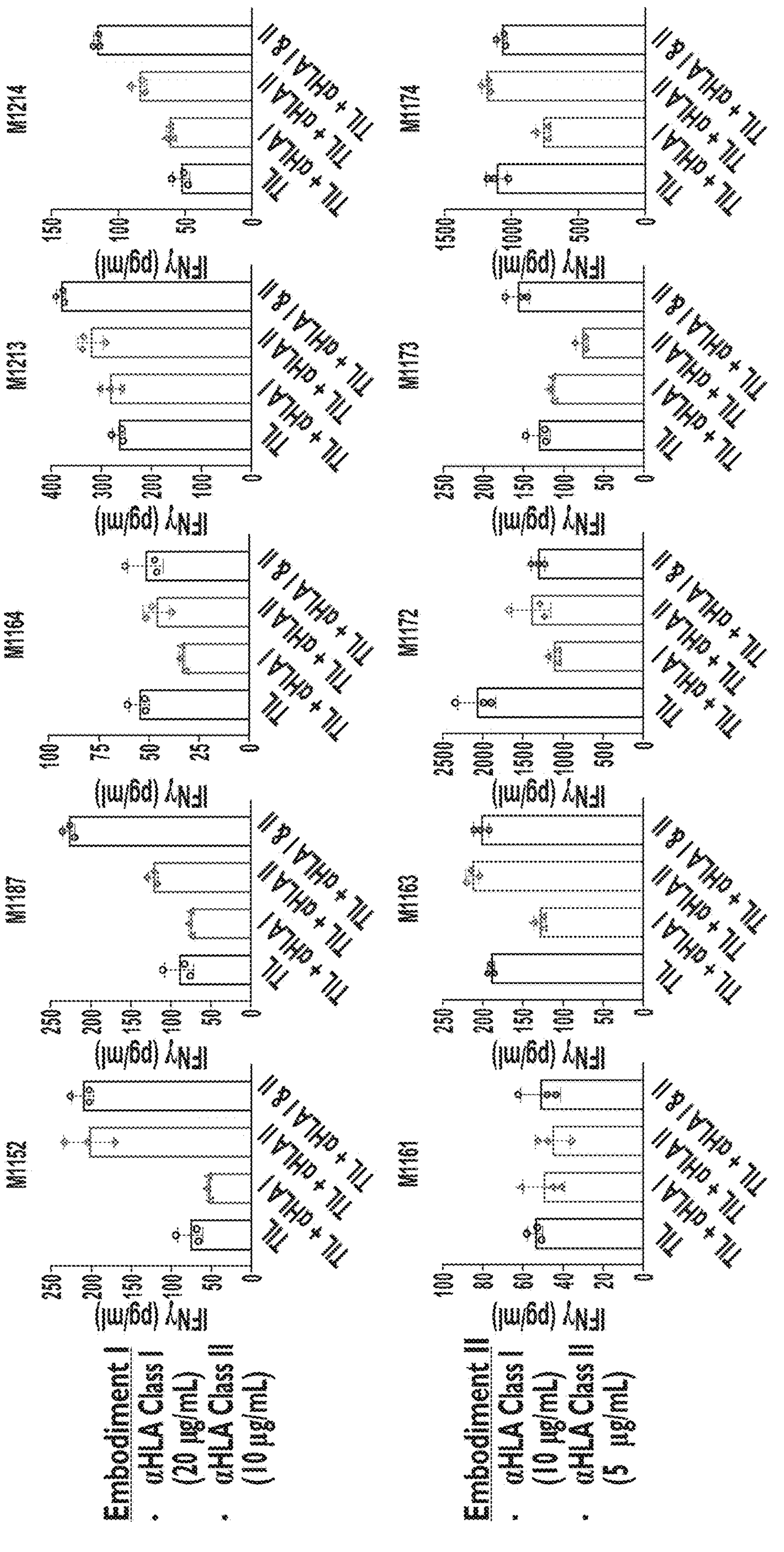

FIG. 172: Results of background IFN-γ secretion from ten TIL lines upon addition of anti-HLA-I antibody (denoted αMHC I) and anti-HLA-II antibody (denoted αMHC II), each performed in triplicate. Embodiment I and Embodiment II refer to the experimental embodiments shown in FIG. 173 and FIG. 184, respectively, and described elsewhere herein, including use of 20 μg/mL HLA-I blocking antibody and 10 μg/mL HLA-II blocking antibody for Embodiment I and 10 μg/mL HLA-I blocking antibody and 5 μg/mL HLA-II blocking antibody for Embodiment II.

Figure 173:
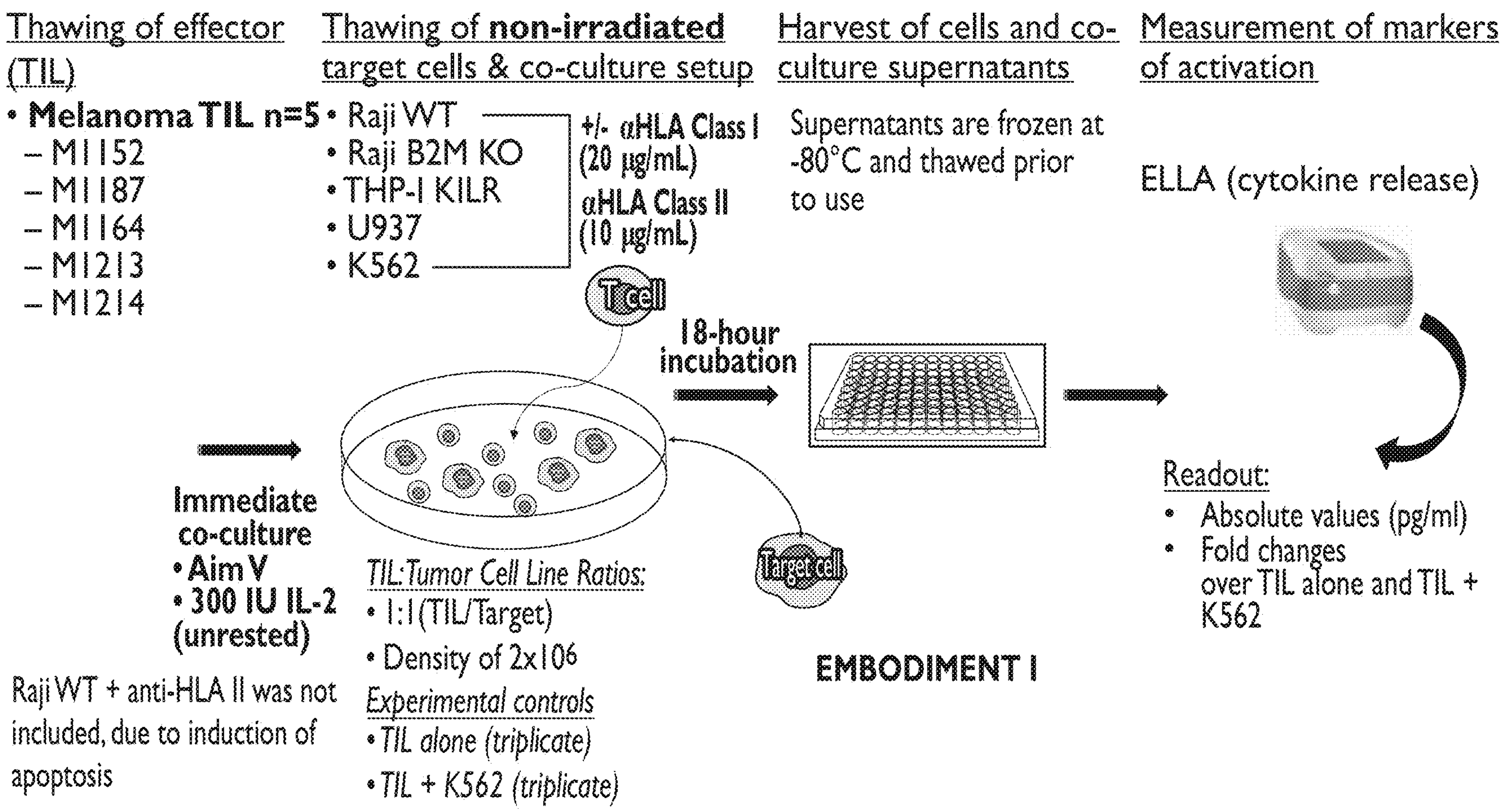

FIG. 173: Diagram of an experimental plan for TIL:tumor cell line co-culture assays using HLA blocking antibodies as negative controls in place of negative control cell lines, which are collectively referred to herein as "Embodiment I" where applicable and which are also embodiments of the present invention.

Figure 174:
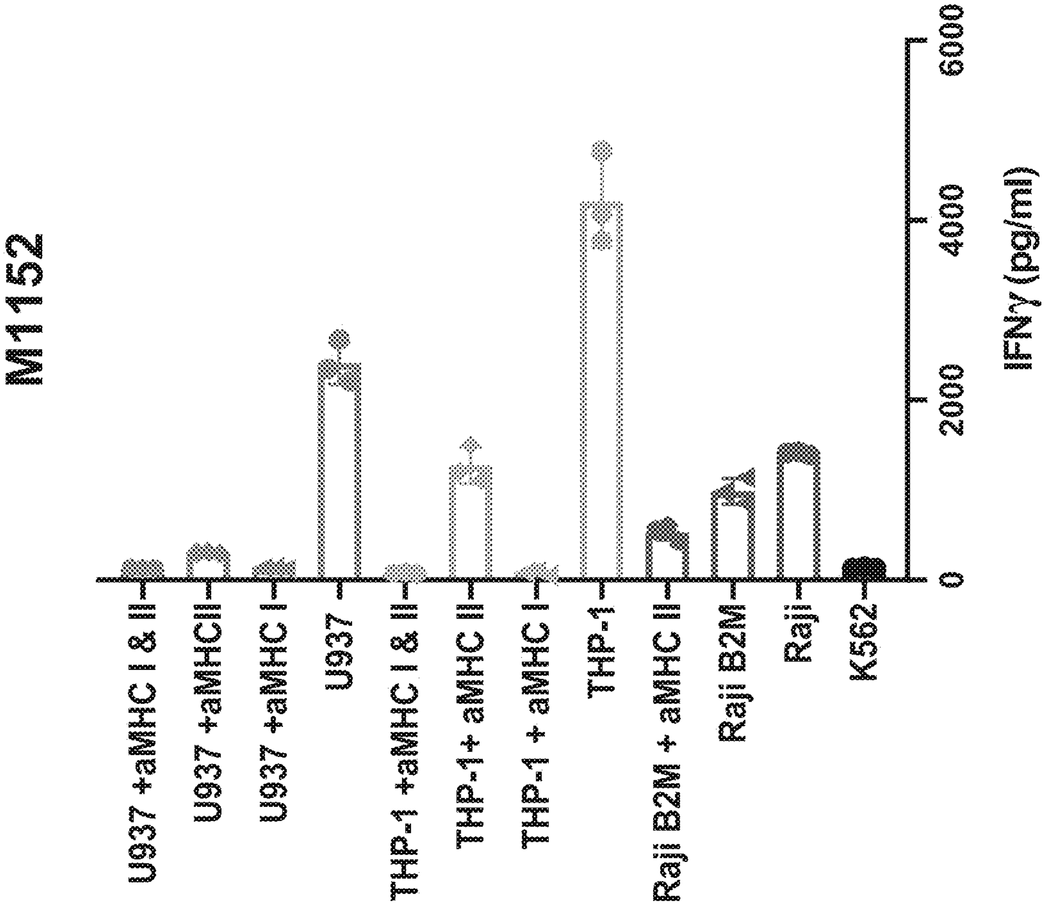

FIG. 174: Results of HLA blocking negative control experiments for melanoma TIL line M1152 co-cultured with target cells and K562 cells as a control, reported as pg/mL of IFN-γ.

Figure 175:
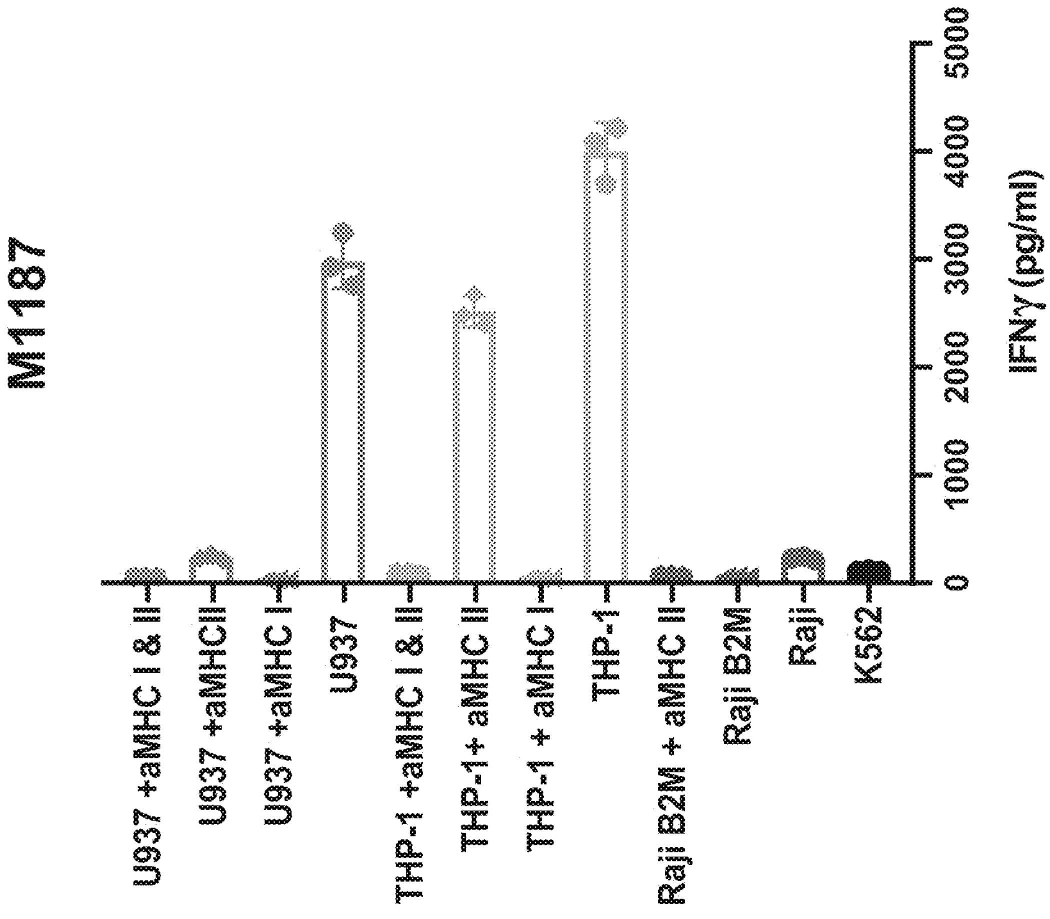

FIG. 175: Results of HLA blocking negative control experiments for melanoma TIL line M1187 co-cultured with target cells and K562 cells as a control, reported as pg/mL of IFN-γ.

Figure 176:
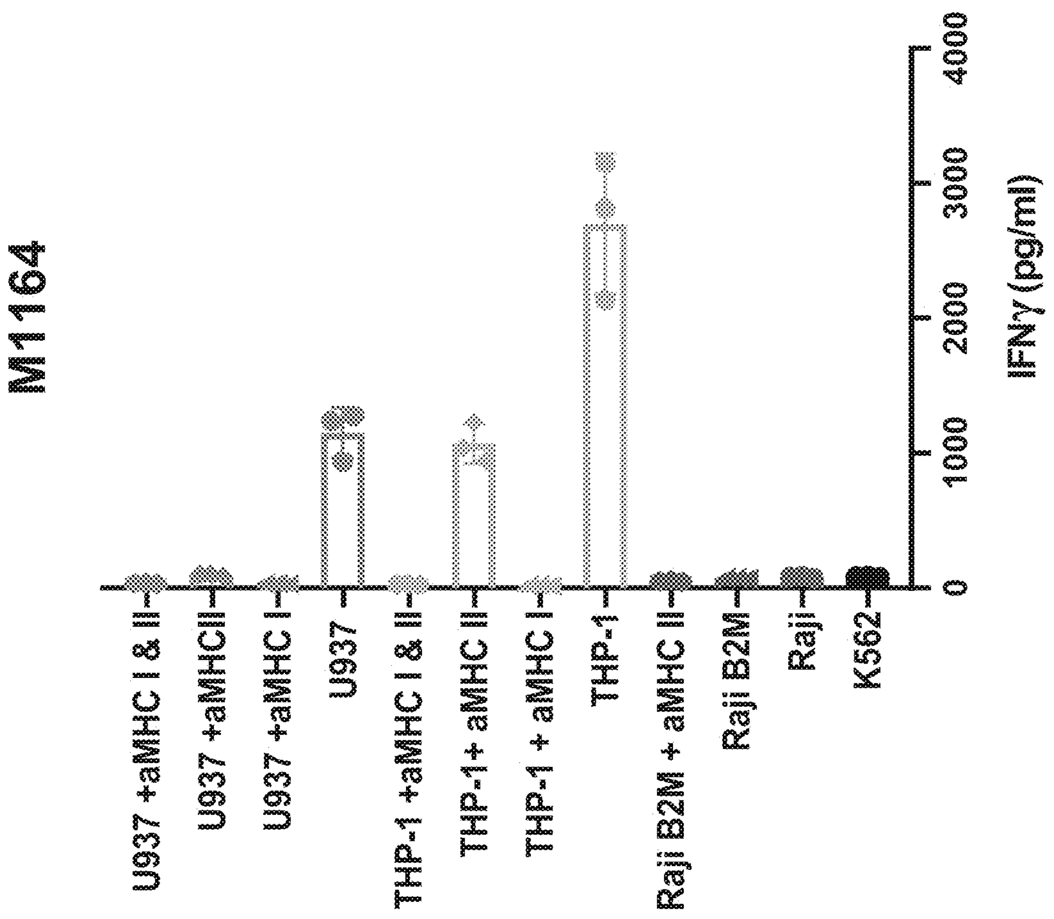

FIG. 176: Results of HLA blocking negative control experiments for melanoma TIL line M1164 co-cultured with target cells and K562 cells as a control, reported as pg/mL of IFN-γ.

Figure 177:
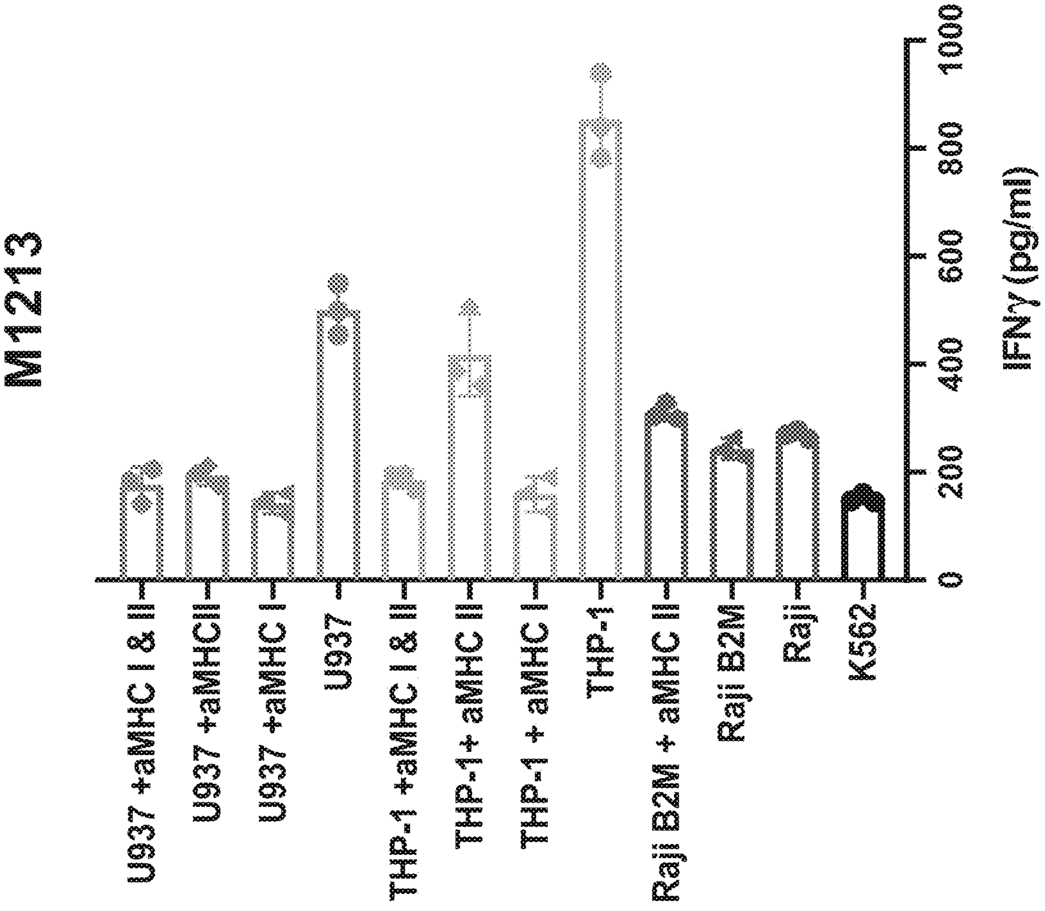

FIG. 177: Results of HLA blocking negative control experiments for melanoma TIL line M1213 co-cultured with target cells and K562 cells as a control, reported as pg/mL of IFN-γ.

Figure 178:
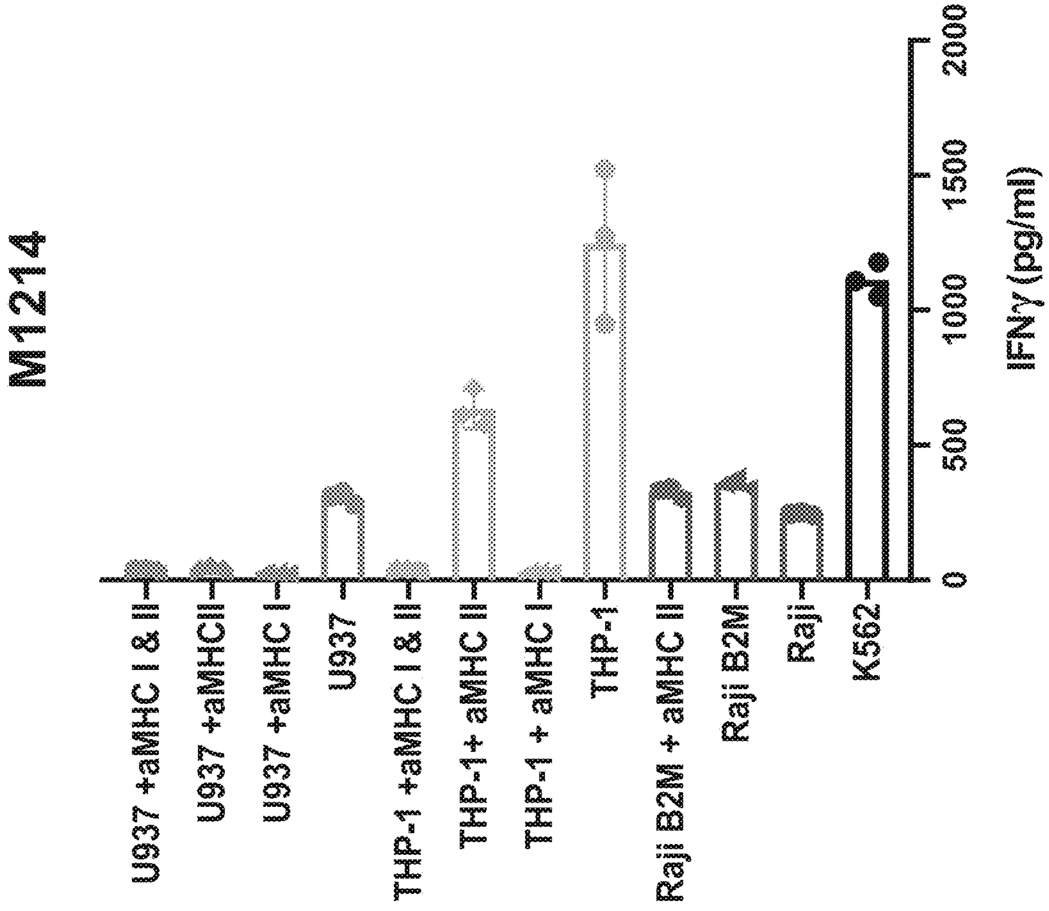

FIG. 178: Results of HLA blocking negative control experiments for melanoma TIL line M1214 co-cultured with target cells and K562 cells as a control, reported as pg/mL of IFN-γ.

Figure 179:
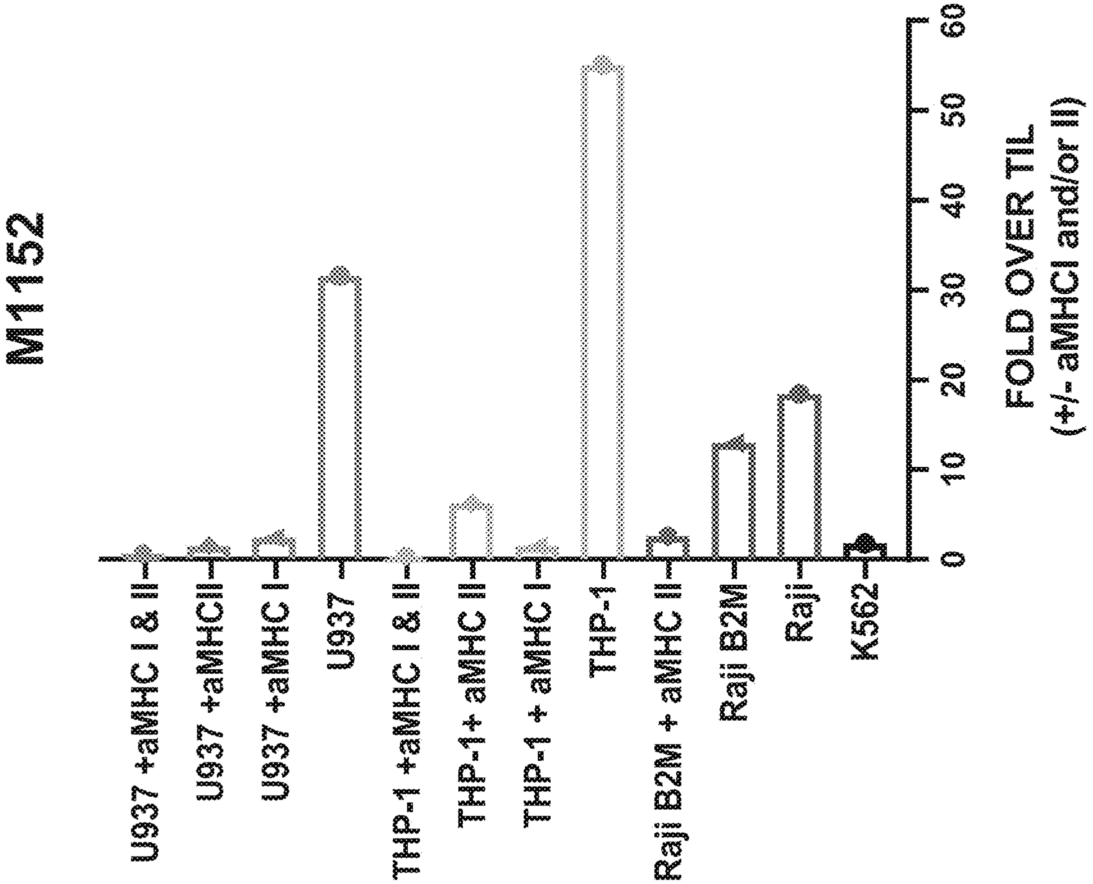

FIG. 179: Results of HLA blocking negative control experiments for melanoma TIL line M1152 co-cultured with target cells and K562 cells as a control, reported as fold enhancement in IFN-γ release over TIL alone.

Figure 180:
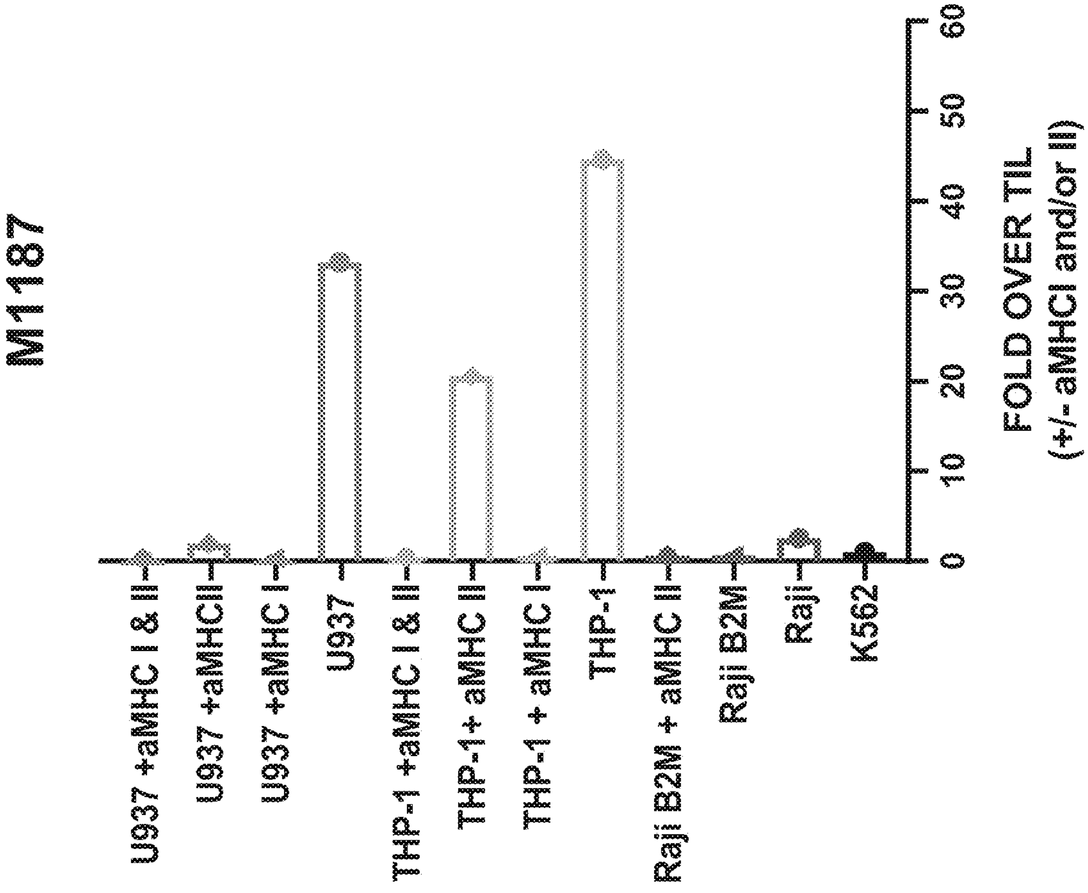

FIG. 180: Results of HLA blocking negative control experiments for melanoma TIL line M1187 co-cultured with target cells and K562 cells as a control, reported as fold enhancement in IFN-γ release over TIL alone.

Figure 181:
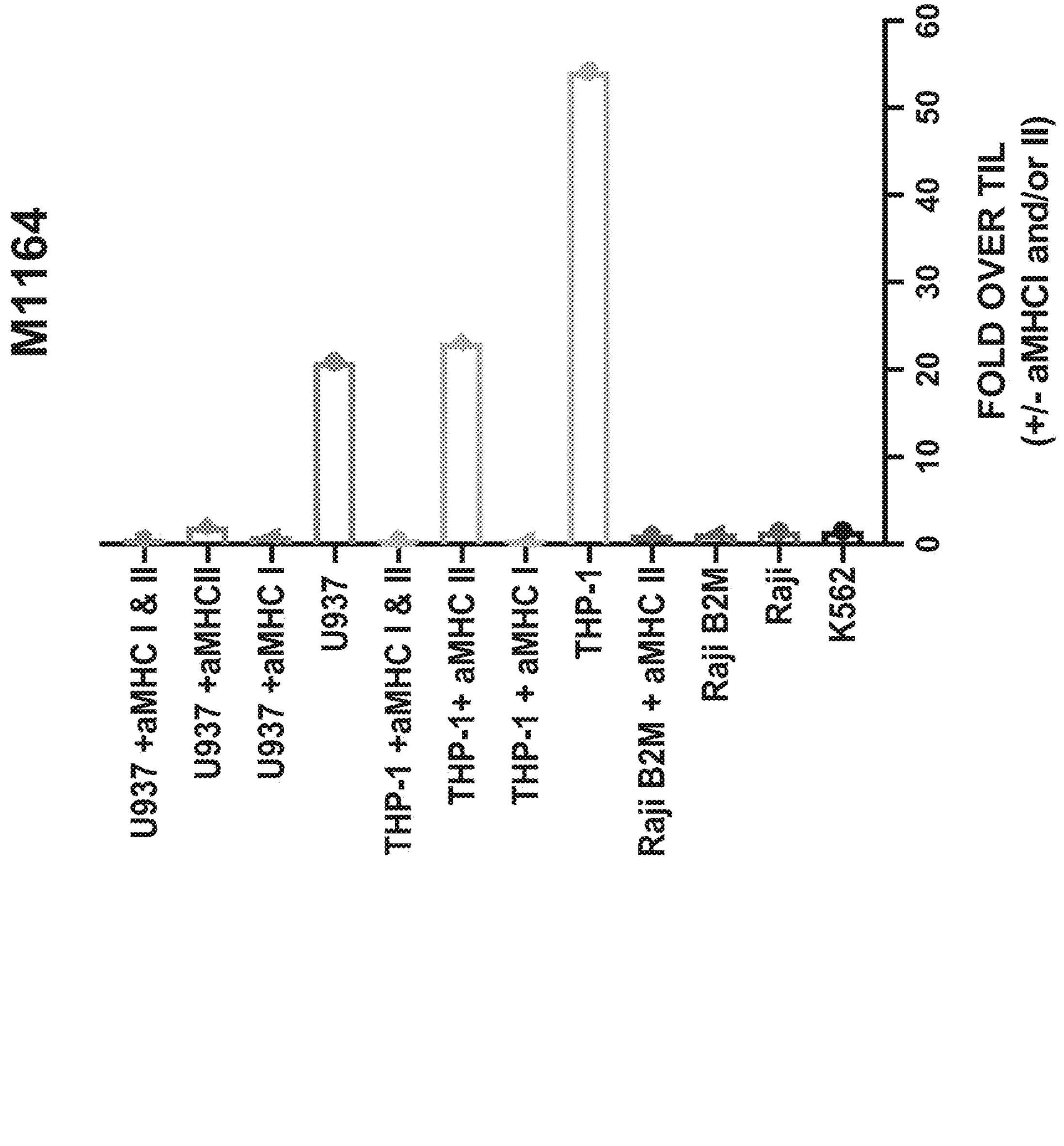

FIG. 181: Results of HLA blocking negative control experiments for melanoma TIL line M1164 co-cultured with target cells and K562 cells as a control, reported as fold enhancement in IFN-γ release over TIL alone.

Figure 182:
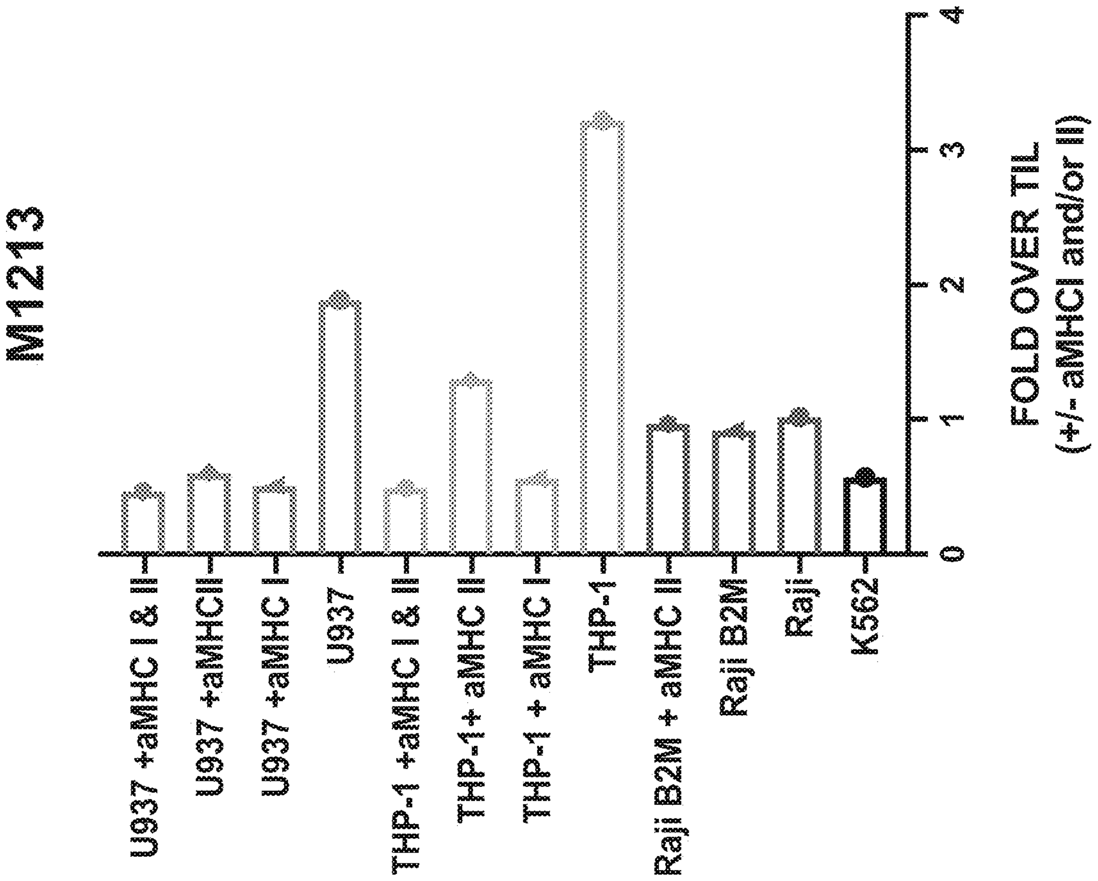

FIG. 182: Results of HLA blocking negative control experiments for melanoma TIL line M1213 co-cultured with target cells and K562 cells as a control, reported as fold enhancement in IFN-γ release over TIL alone.

Figure 183:
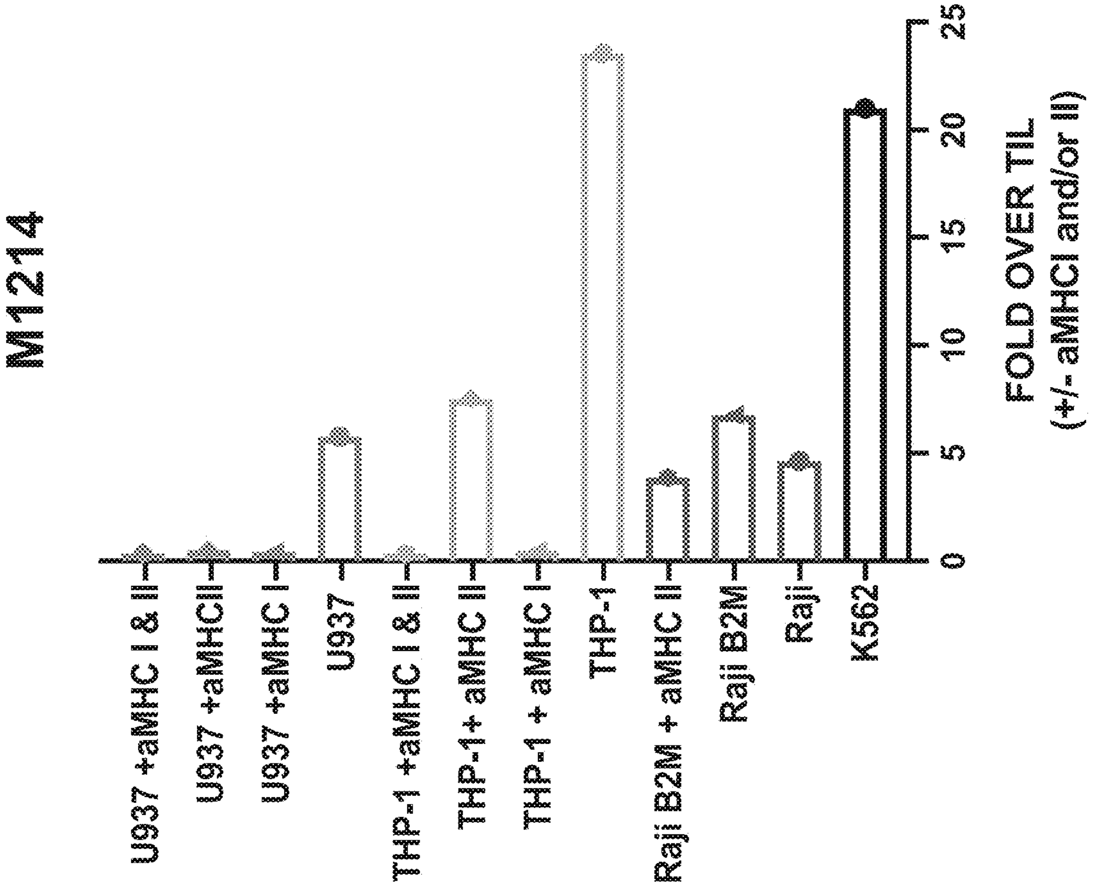

FIG. 183: Results of HLA blocking negative control experiments for melanoma TIL line M1214 co-cultured with target cells and K562 cells as a control, reported as fold enhancement in IFN-γ release over TIL alone.

Figure 184:
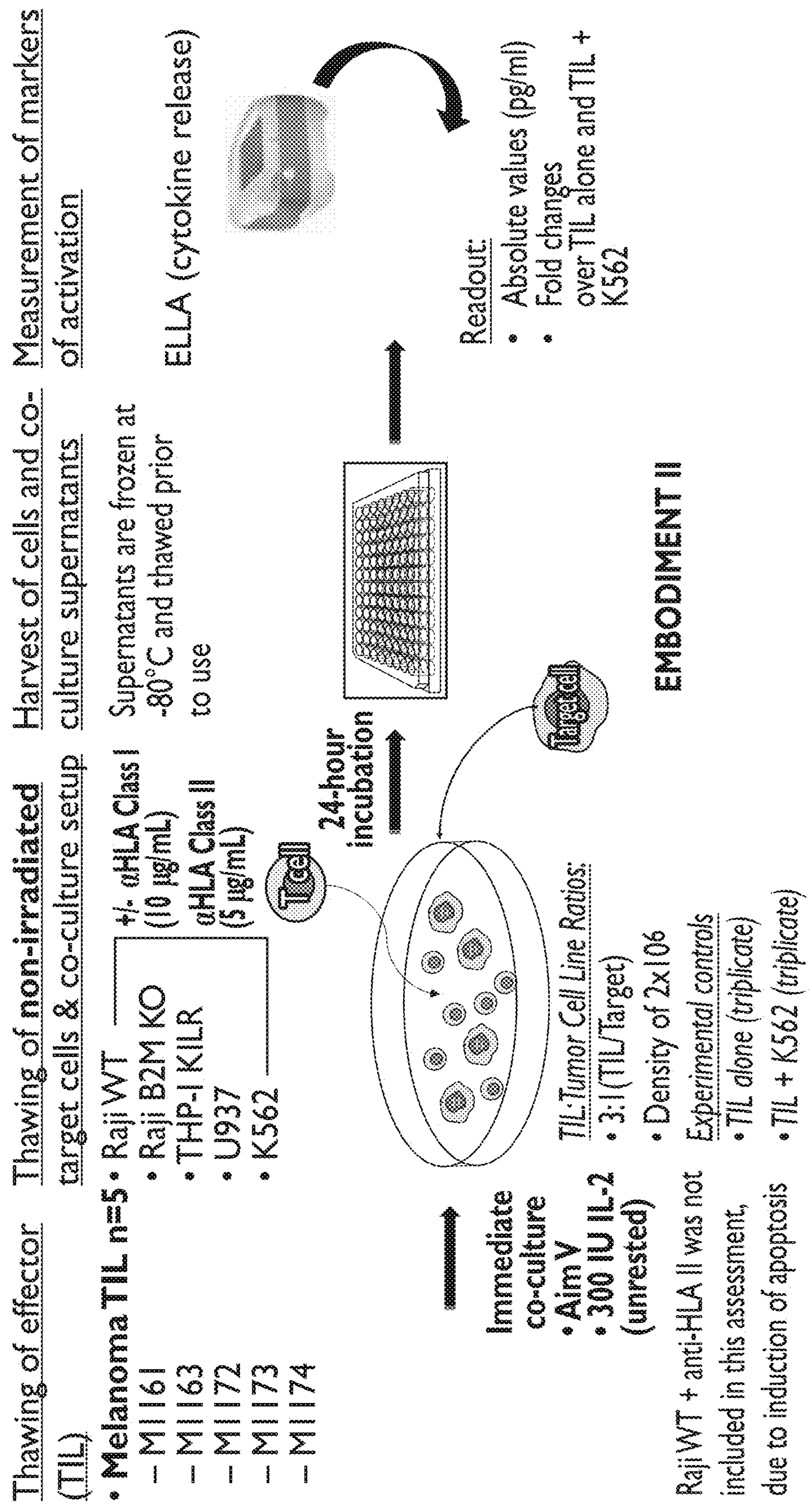

FIG. 184: Diagram of an experimental plan for TIL:tumor cell line co-culture assay's using HLA blocking antibodies as negative controls in place of negative control cell lines, which are collectively referred to herein as "Embodiment II" where applicable and which are also embodiments of the present invention.

Figure 185:
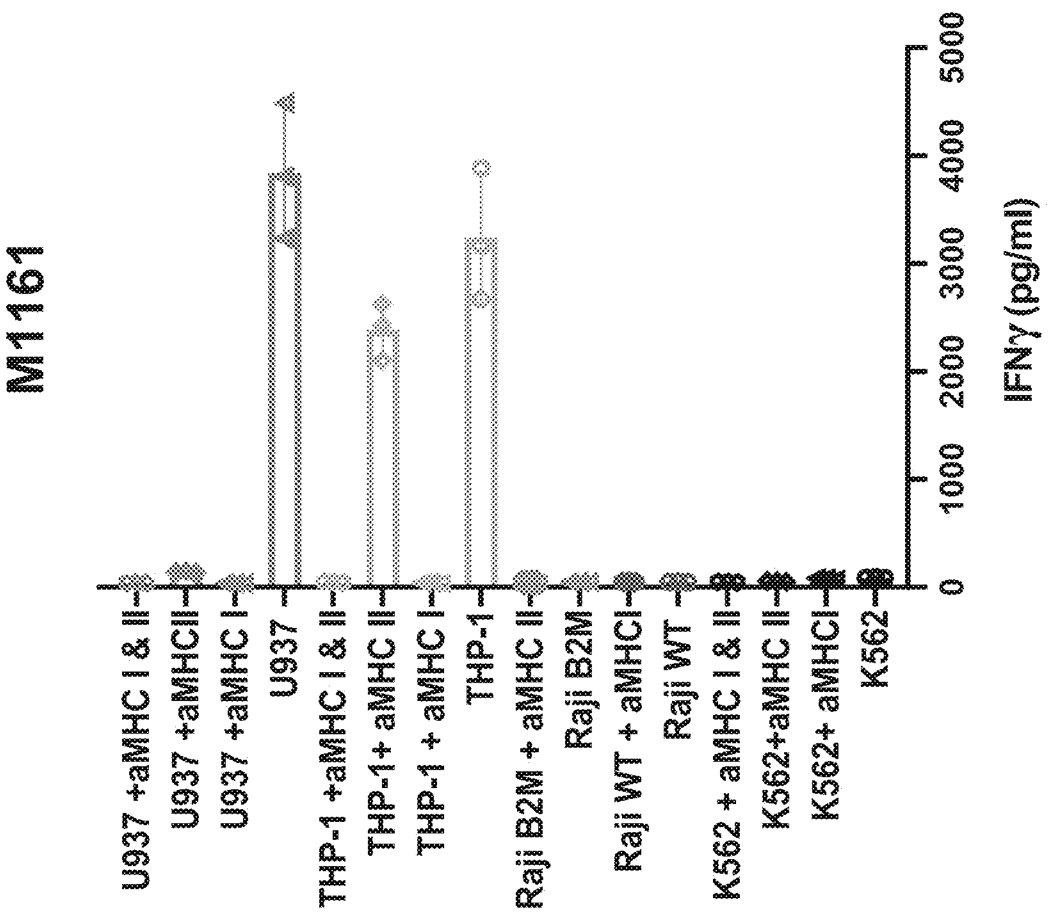

FIG. 185: Results of HLA blocking negative control experiments for melanoma TIL line M1161 co-cultured with target cells and K562 cells as a control, reported as pg/mL of IFN-γ. The $CD4^+$ and $CD8^+$ populations for M1161 were determined by flow cytometry to be 1.4% and 97.6%, respectively.

Figure 186:
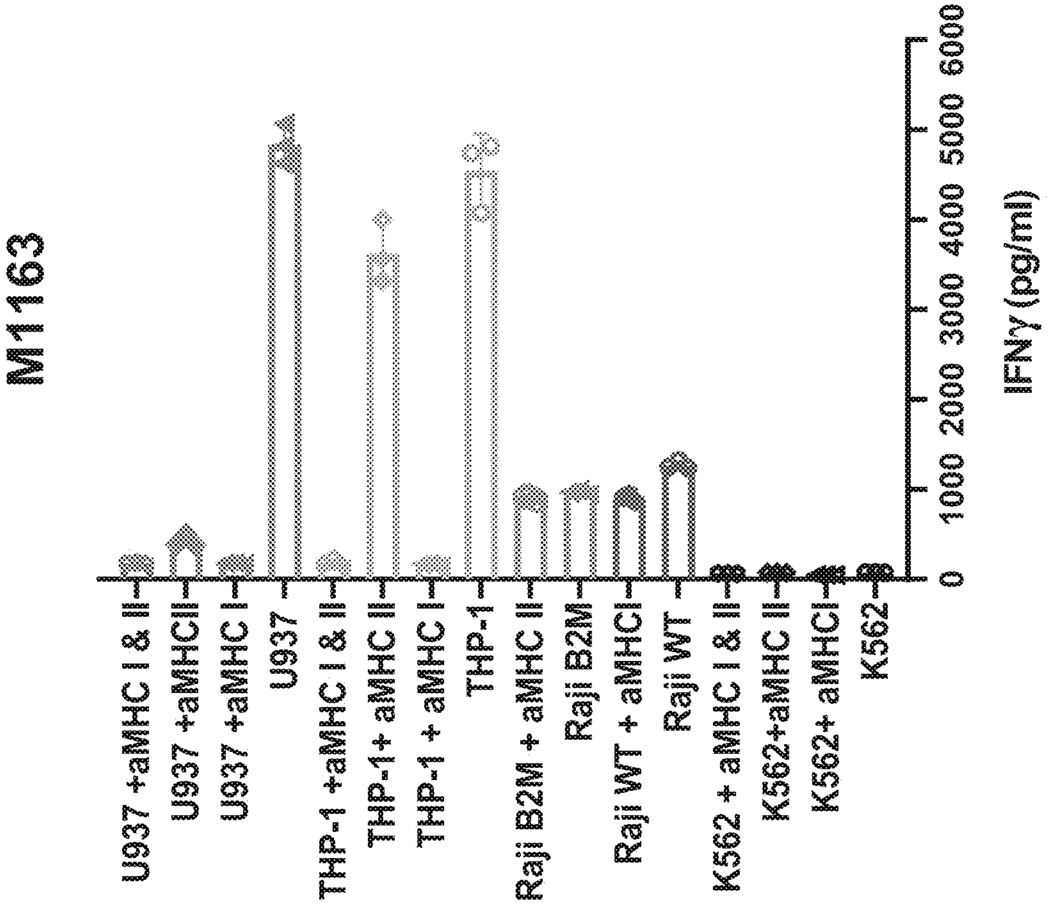

FIG. 186: Results of HLA blocking negative control experiments for melanoma TIL line M1163 co-cultured with target cells and K562 cells as a control, reported as pg/mL of IFN-γ. The $CD4^+$ and $CD8^+$ populations for M1163 were determined by flow cytometry to be 60.6% and 34.9%, respectively.

Figure 187:
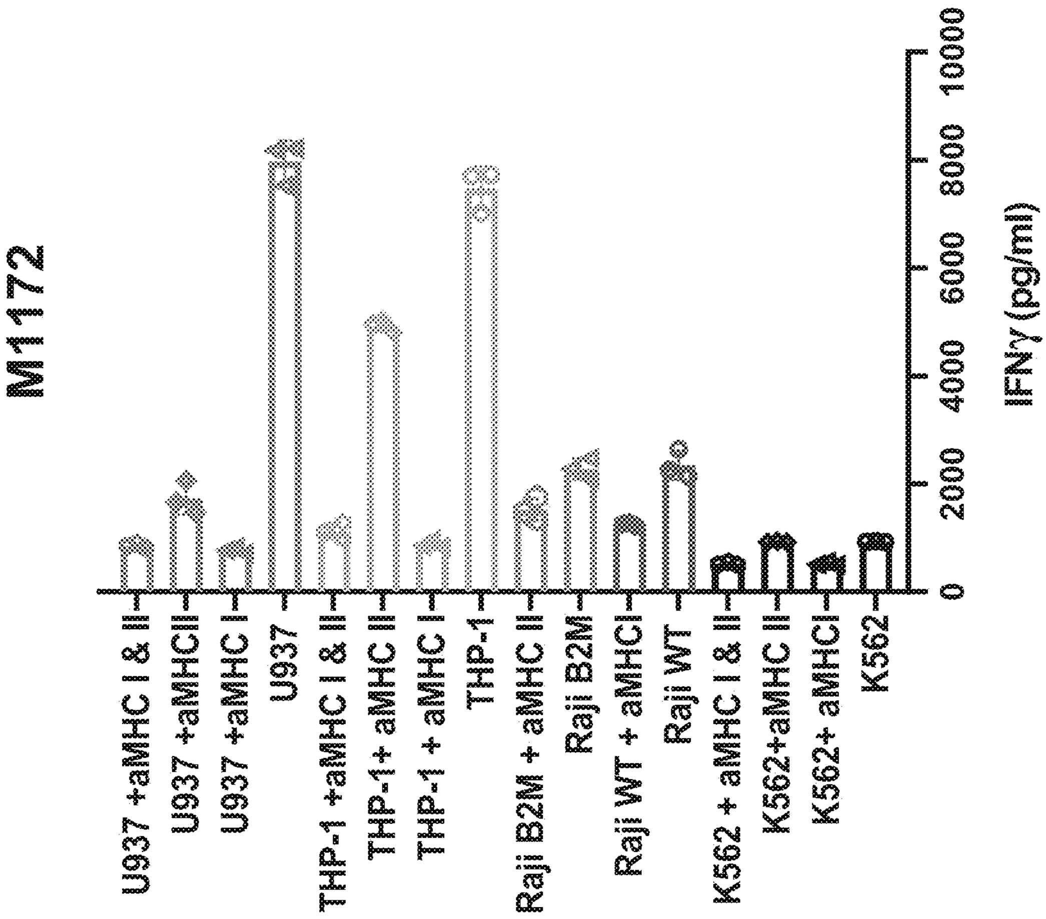

FIG. 187: Results of HLA blocking negative control experiments for melanoma TIL line M1172 co-cultured with target cells and K562 cells as a control, reported as pg/mL of IFN-γ. The $CD4^+$ and $CD8^+$ populations for M1172 were determined by flow cytometry to be 71.8% and 22.2%, respectively.

Figure 188:
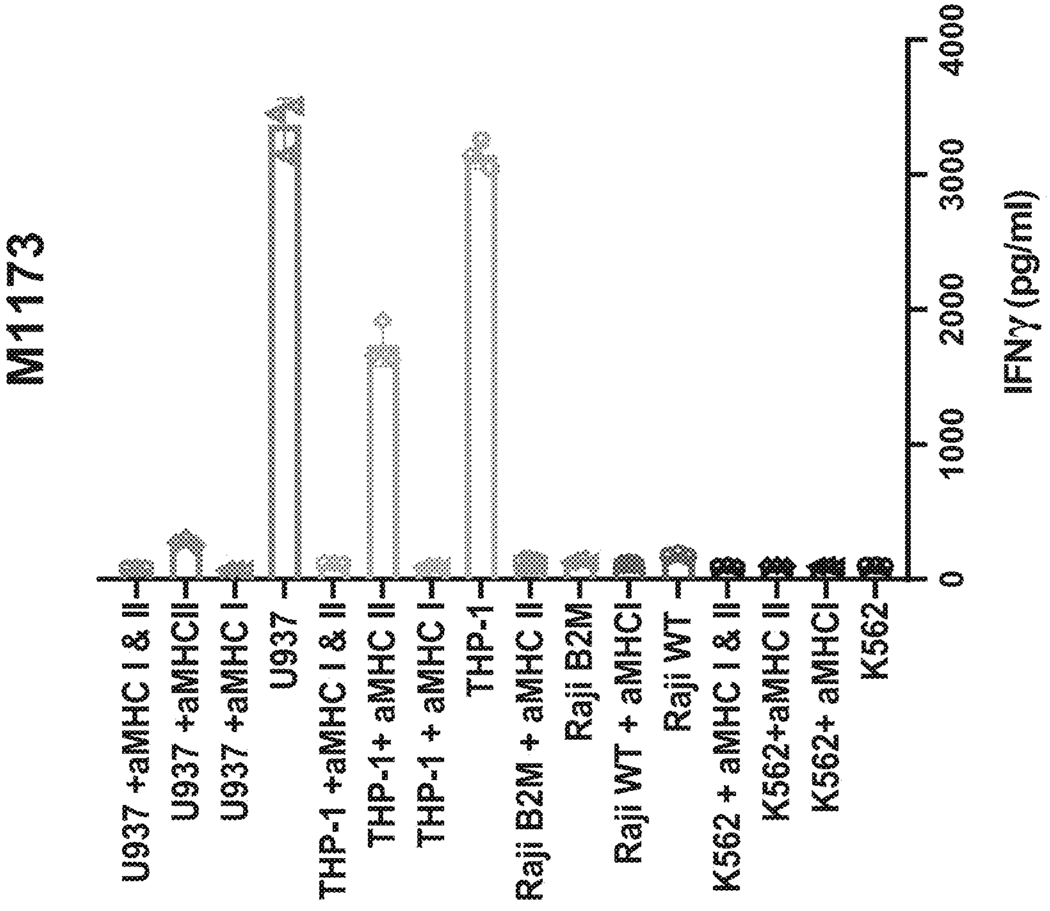

FIG. 188: Results of HLA blocking negative control experiments for melanoma TIL line M1173 co-cultured with target cells and K562 cells as a control, reported as pg/mL of IFN-γ. The $CD4^+$ and $CD8^+$ populations for M1173 were determined by flow cytometry to be 13.4% and 81.6%, respectively.

Figure 189:
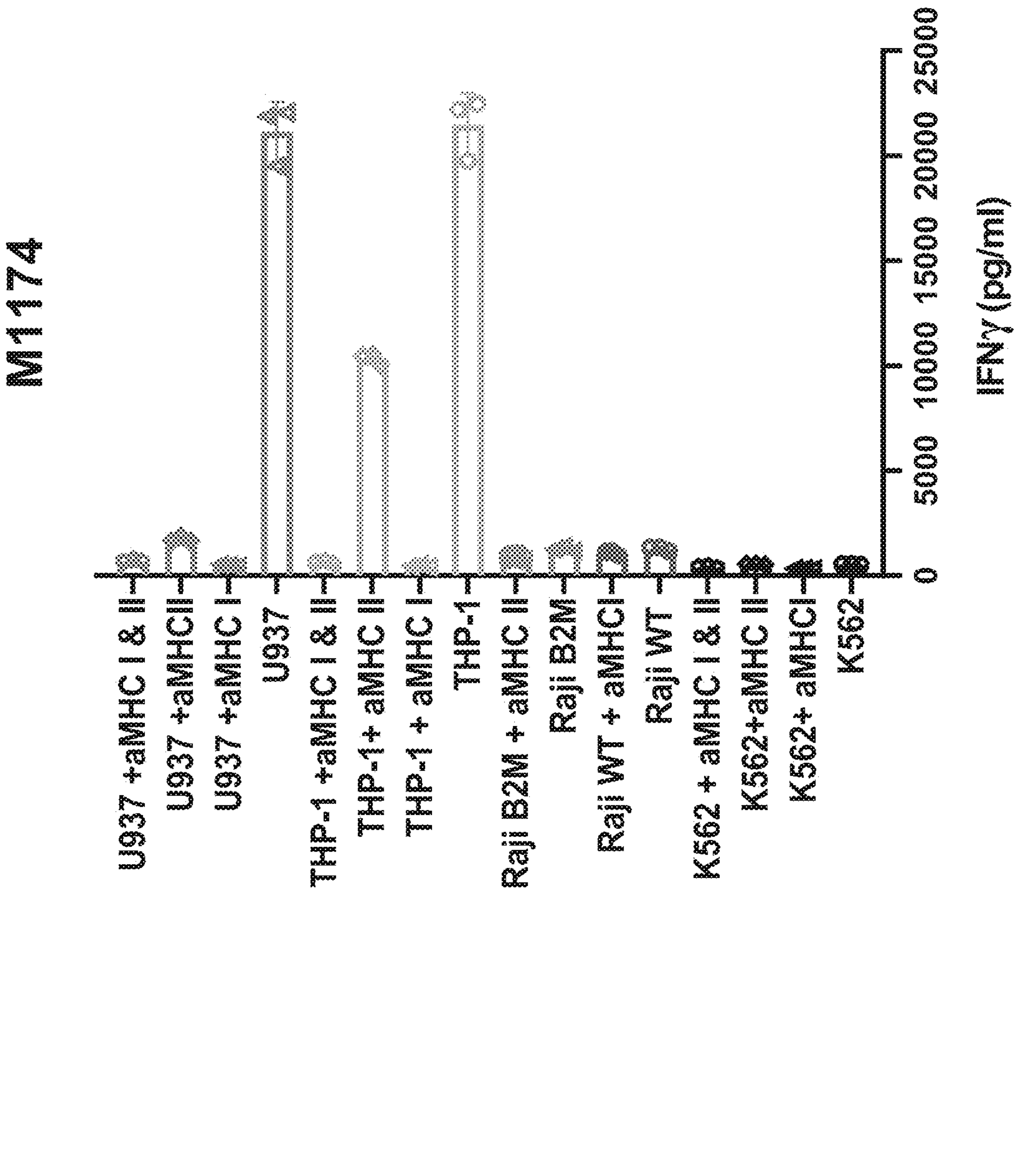

FIG. 189: Results of HLA blocking negative control experiments for melanoma TIL line M1174 co-cultured with target cells and K562 cells as a control, reported as pg/mL of IFN-γ. The $CD4^+$ and $CD8^+$ populations for M1174 were determined by flow cytometry to be 92.3% and 6.2%, respectively.

Figure 190:
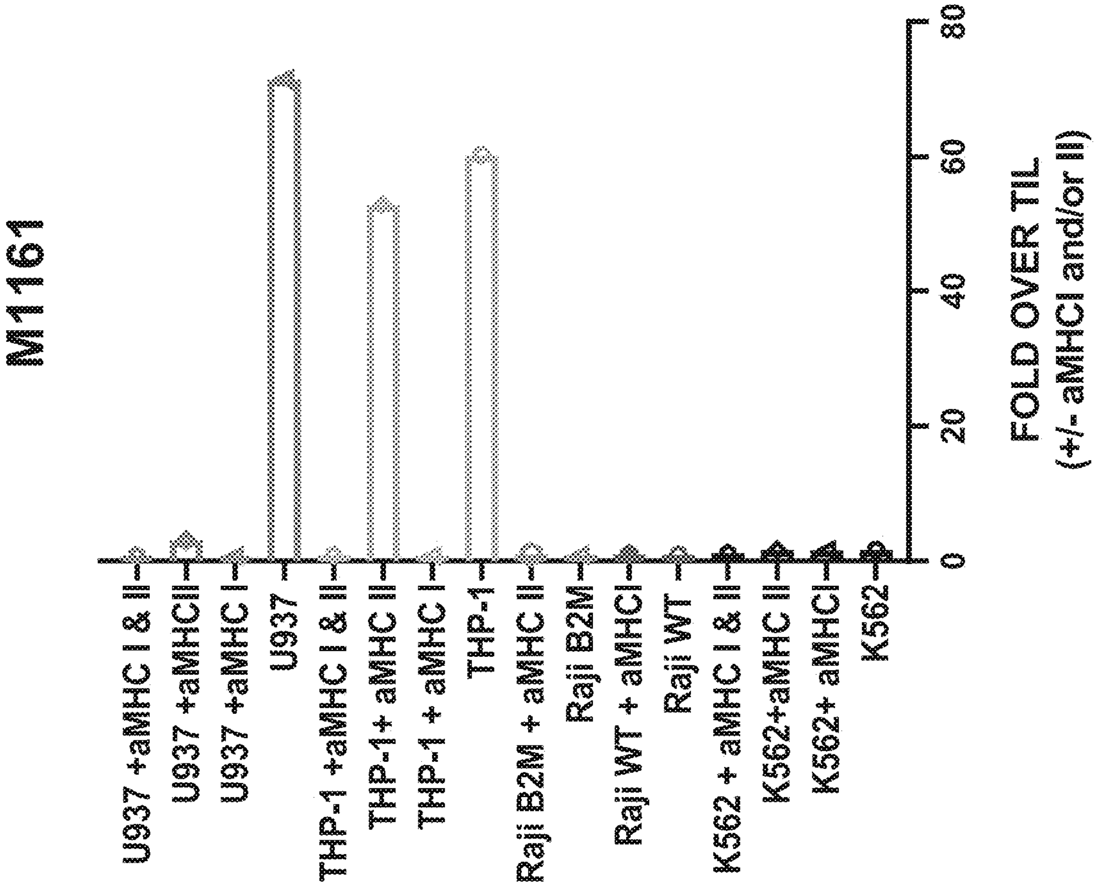

FIG. 190: Results of HLA blocking negative control experiments for melanoma TIL line M1161 co-cultured with target cells and K562 cells as a control, reported as fold enhancement in IFN-γ release over TIL alone. The $CD4^+$ and $CD8^+$ populations for M1161 were determined by flow cytometry to be 1.4% and 97.6%, respectively.

Figure 191:
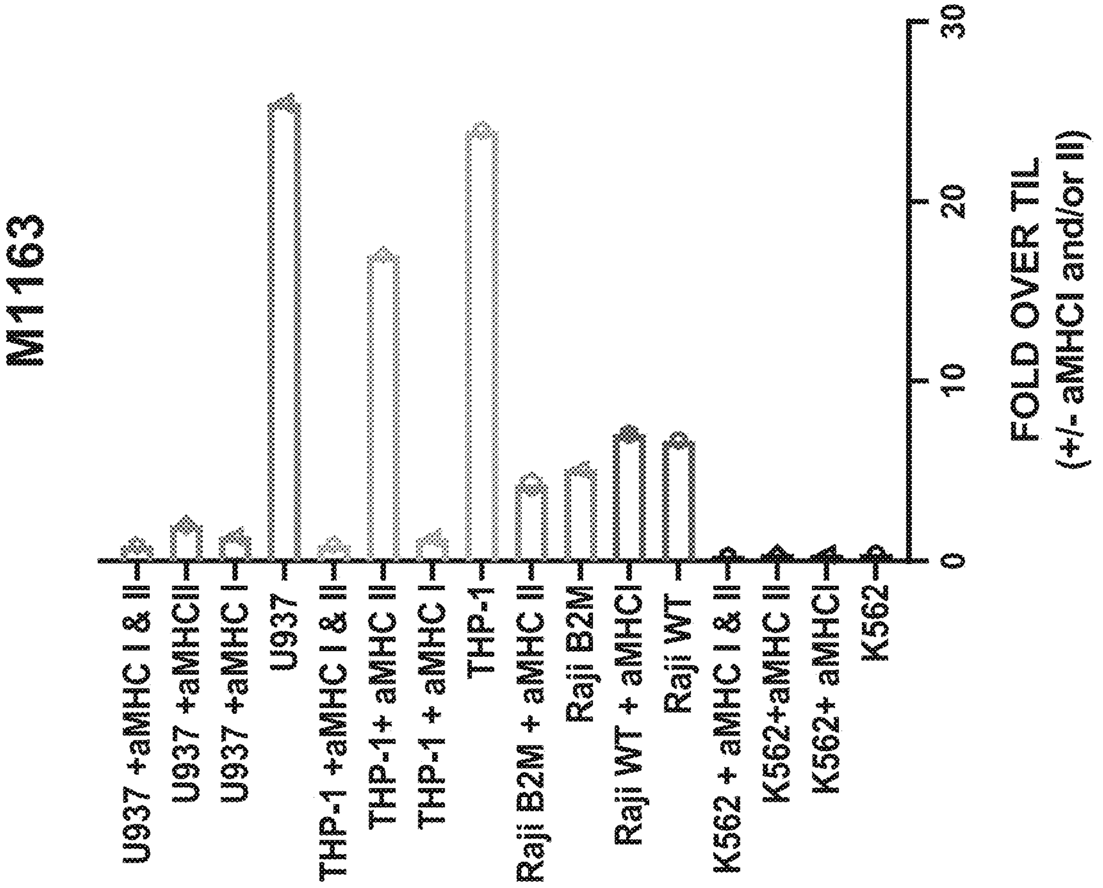

FIG. 191: Results of HLA blocking negative control experiments for melanoma TIL line M1163 co-cultured with target cells and K562 cells as a control, reported as fold enhancement in IFN-γ release over TIL alone. The $CD4^+$ and $CD8^+$ populations for M1163 were determined by flow cytometry to be 60.6% and 34.9%, respectively.

Figure 192:
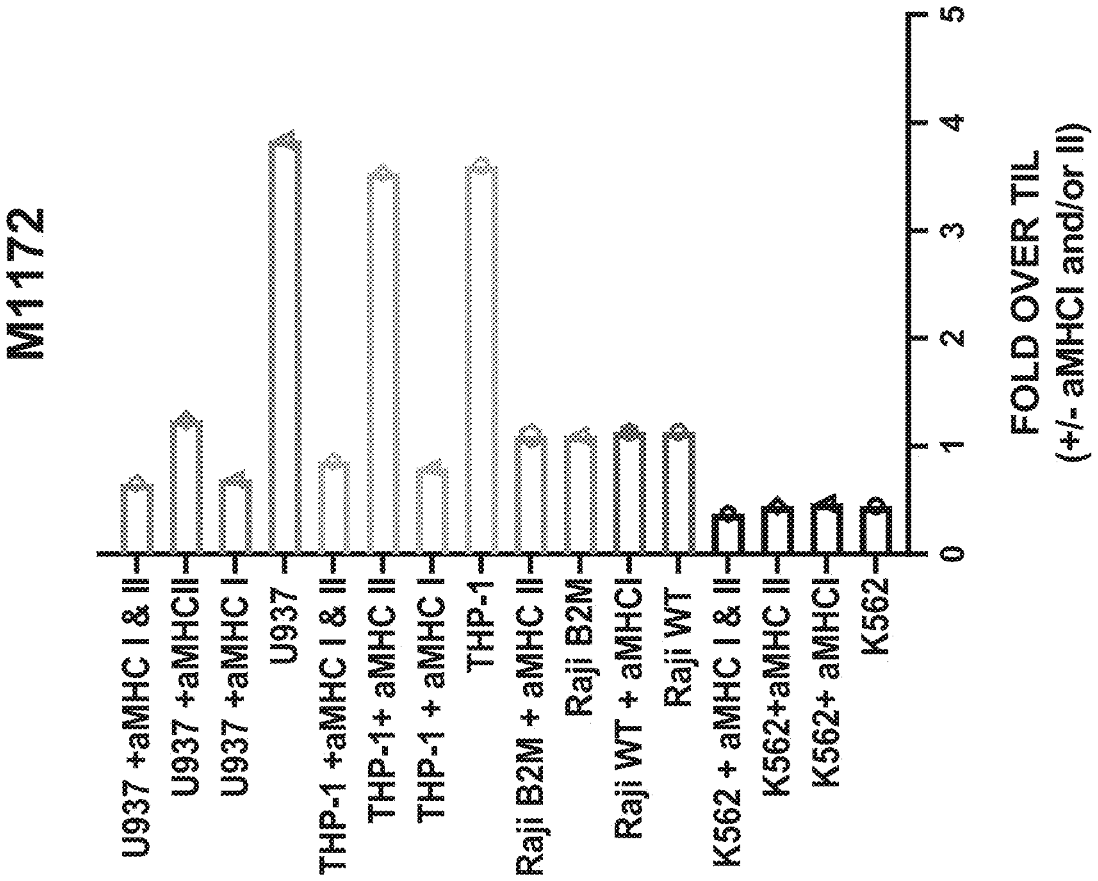

FIG. 192: Results of HLA blocking negative control experiments for melanoma TIL line M1172 co-cultured with target cells and K562 cells as a control, reported as fold enhancement in IFN-γ release over TIL alone. The $CD4^+$ and $CD8^+$ populations for M1172 were determined by flow cytometry to be 71.8% and 22.2%, respectively.

Figure 193:
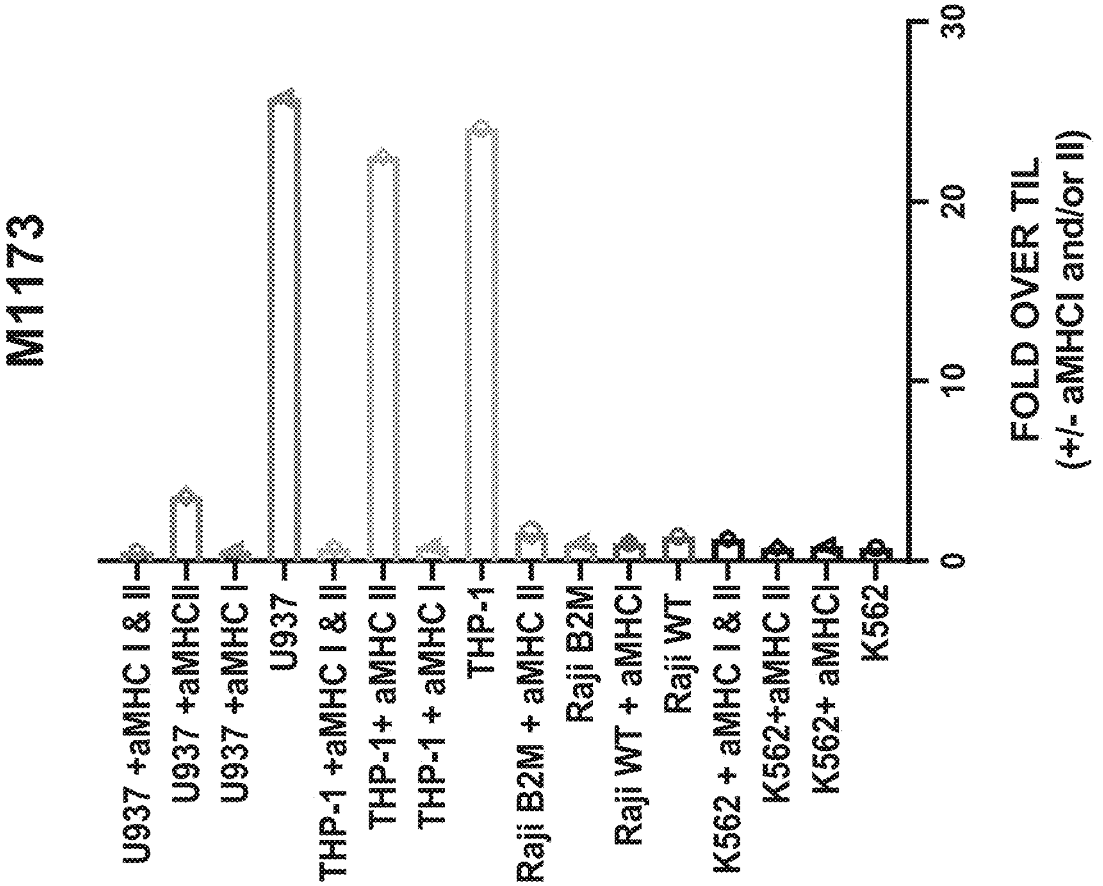

FIG. 193: Results of HLA blocking negative control experiments for melanoma TIL line M1173 co-cultured with target cells and K562 cells as a control, reported as fold enhancement in IFN-γ release over TIL alone. The $CD4^+$ and $CD8^+$ populations for M1173 were determined by flow cytometry to be 13.4% and 81.6%, respectively.

Figure 194:
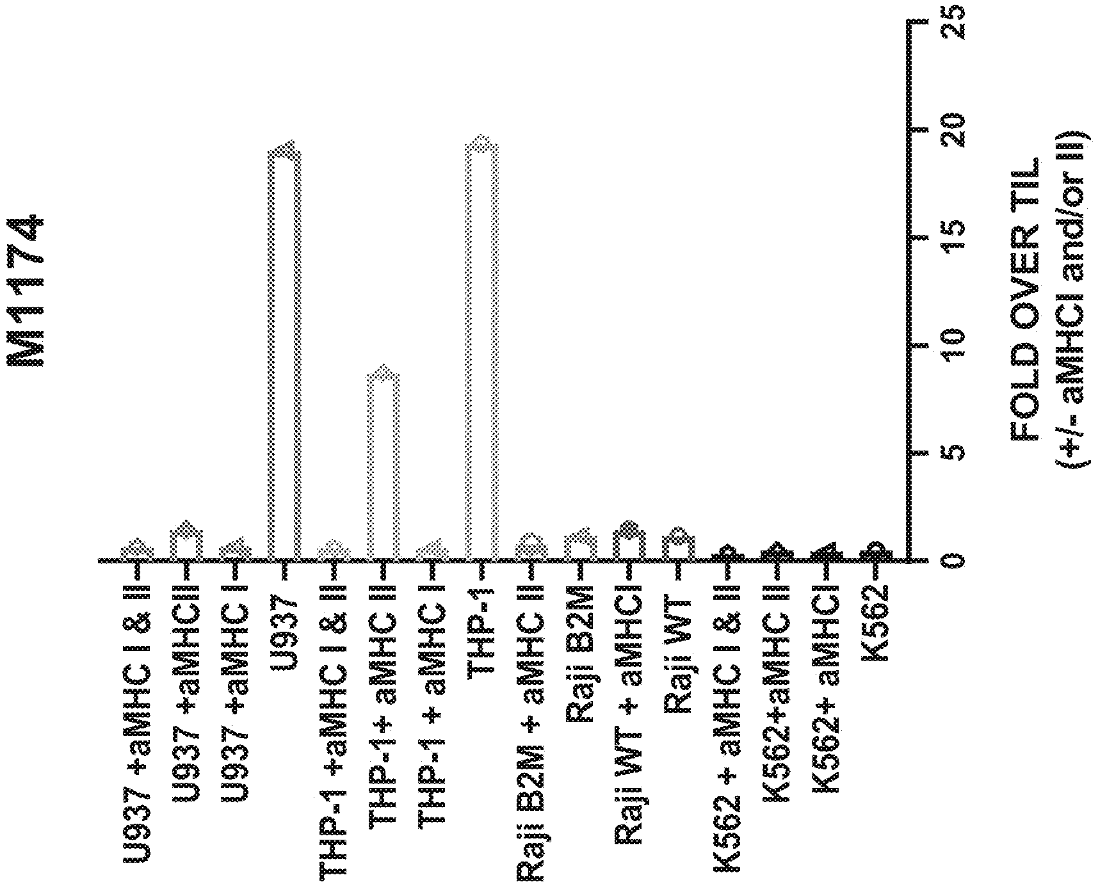

FIG. 194: Results of HLA blocking negative control experiments for melanoma TIL line M1174 co-cultured with target cells and K562 cells as a control, reported as fold enhancement in IFN-γ release over TIL alone. The $CD4^+$ and $CD8^+$ populations for M1174 were determined by flow cytometry to be 92.3% and 6.2%, respectively.

Figure 195:
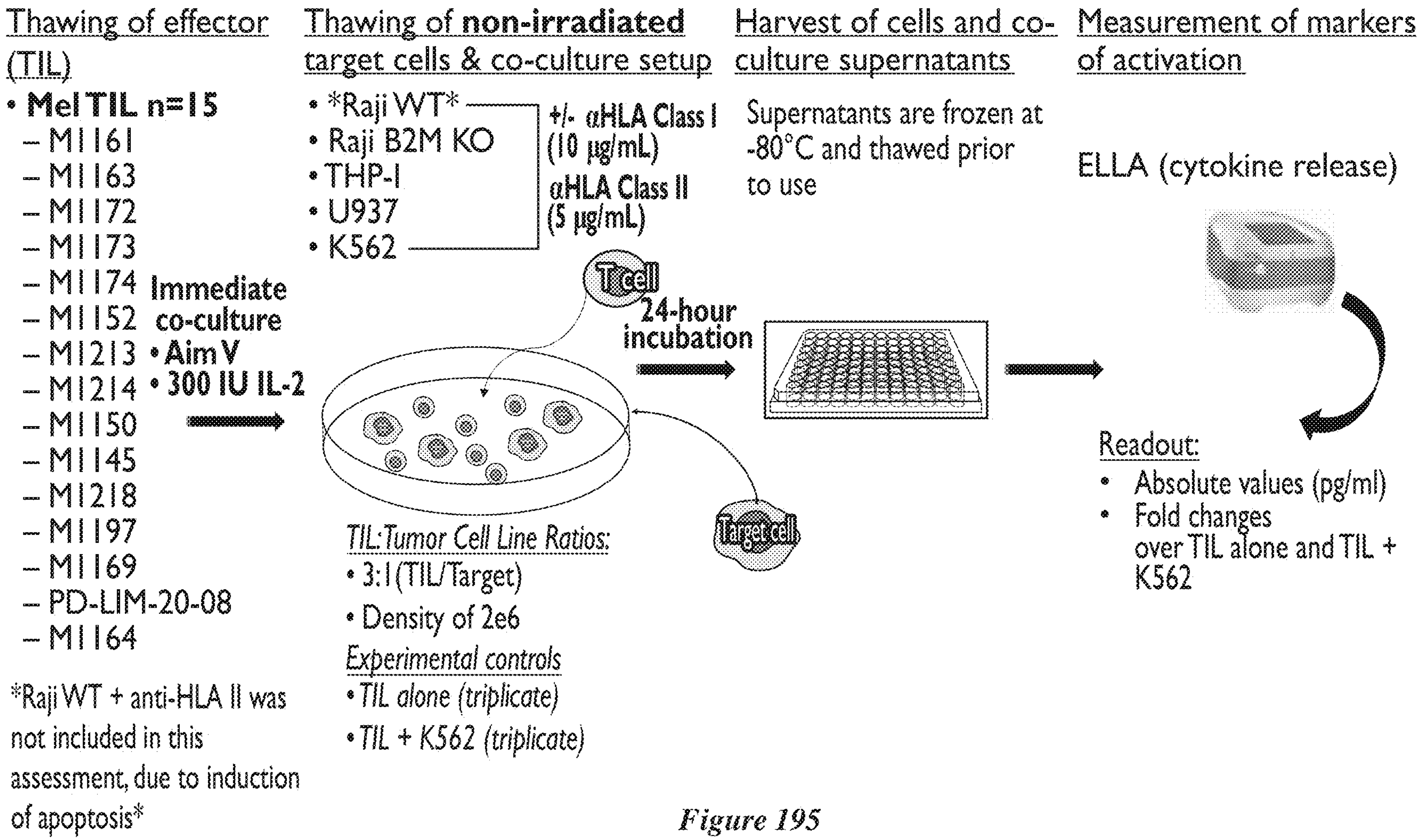

FIG. 195: Diagram of an experimental plan for TIL:tumor cell line co-culture assays using HLA blocking antibodies as negative controls in place of negative control cell lines, or in addition to TIL alone control experiments, all of which are also embodiments of the present invention. Fifteen melanoma cell lines are used.

Figure 196:
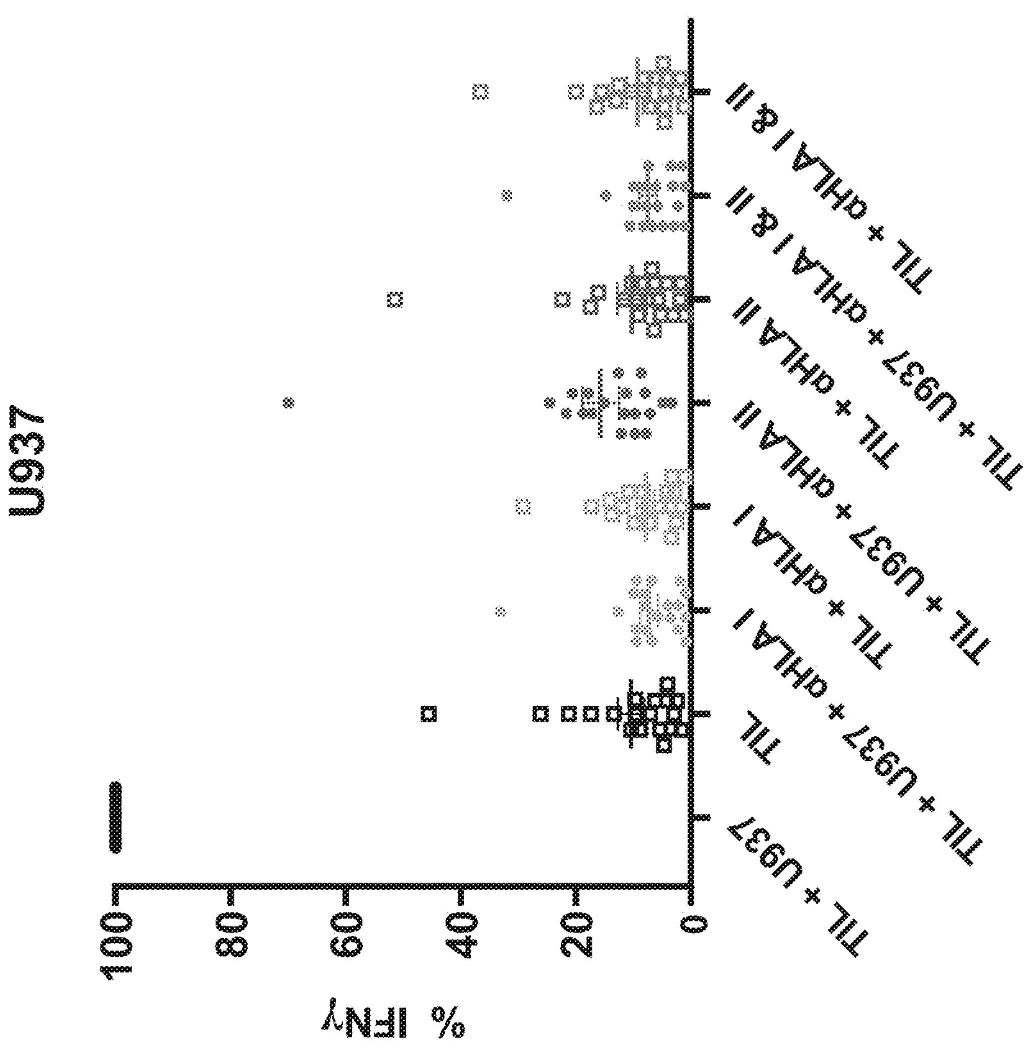

FIG. 196: Results of HLA blocking negative control experiments for 15 melanoma TIL lines co-cultured with U937 target cells.

Figure 197:
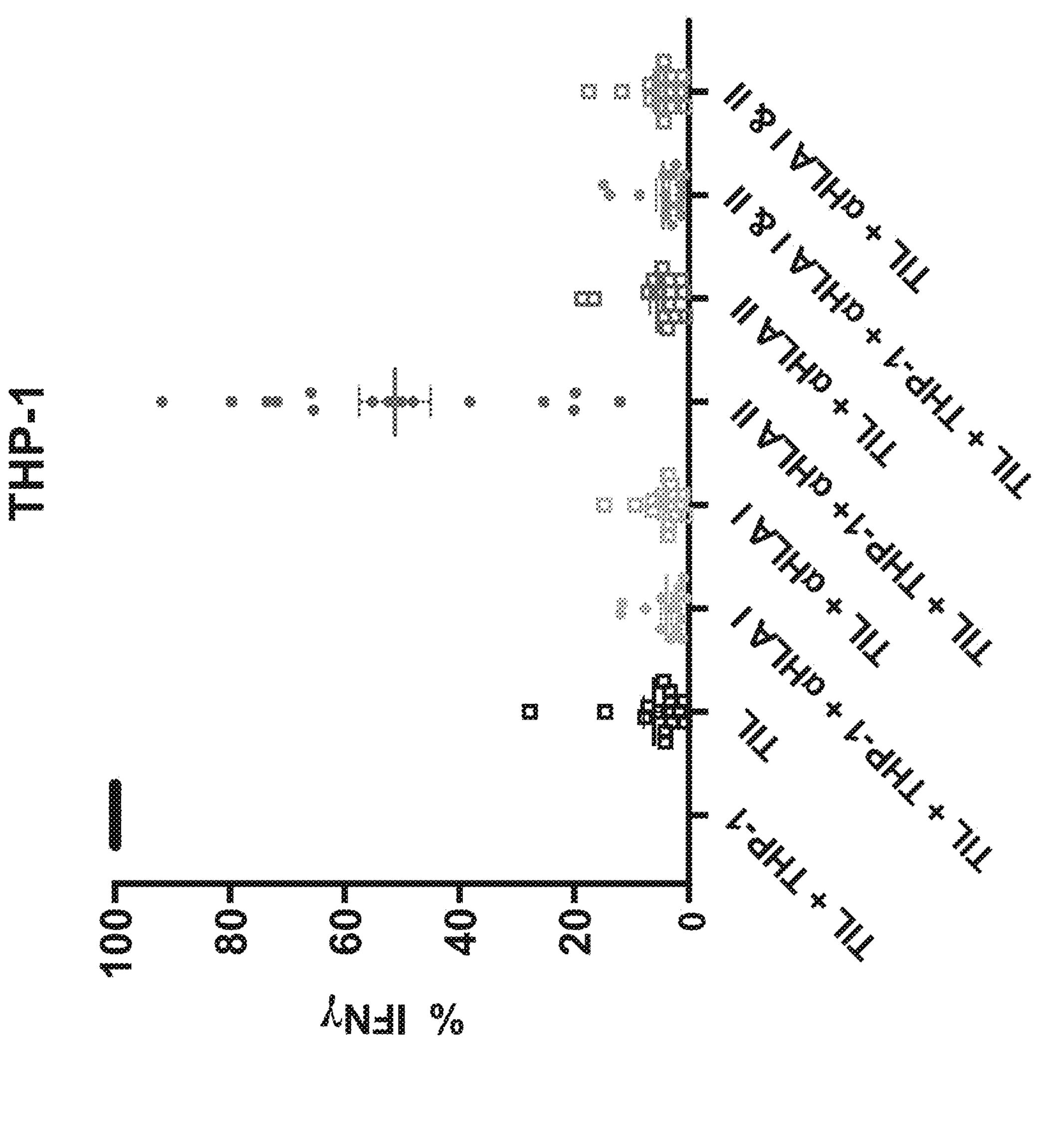

FIG. 197: Results of HLA blocking negative control experiments for 15 melanoma TIL lines co-cultured with Thp1 (THP-1) target cells.

Figure 198:
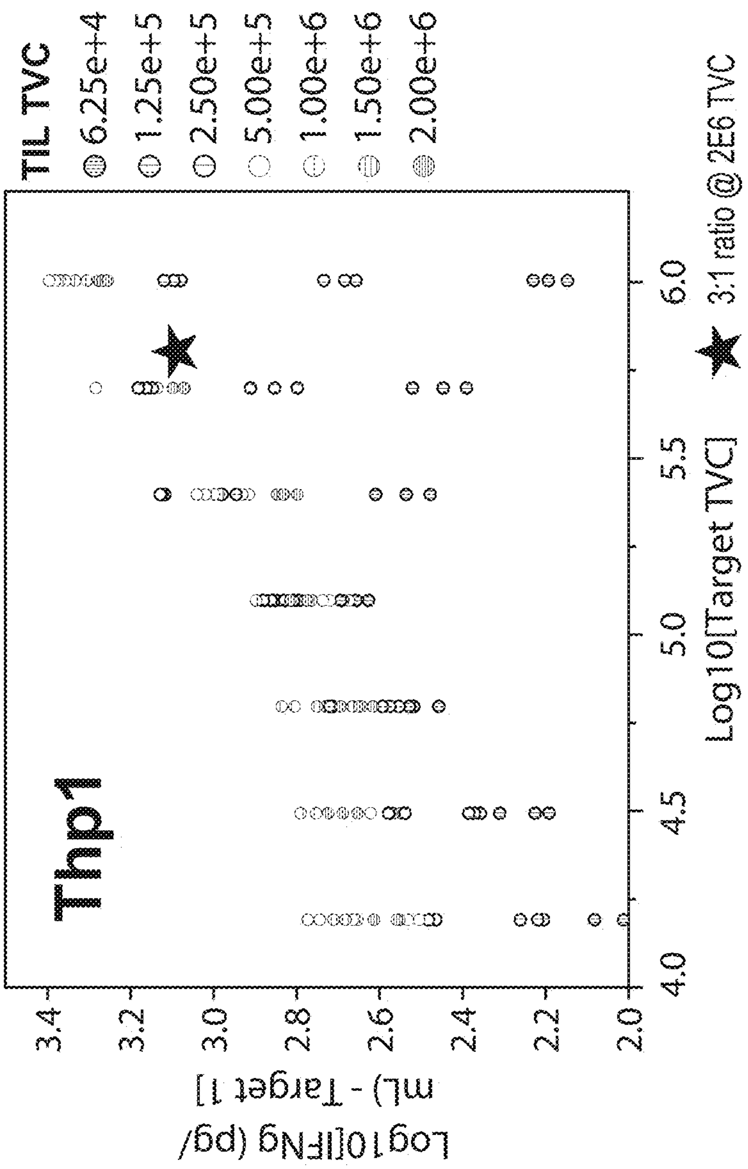

FIG. 198: Determination of effective TIL concentration for Thp1 cells. The star indicates a 3:1 TIL:Thp1 ratio at $2\times10^6$ TVC.

Figure 199:
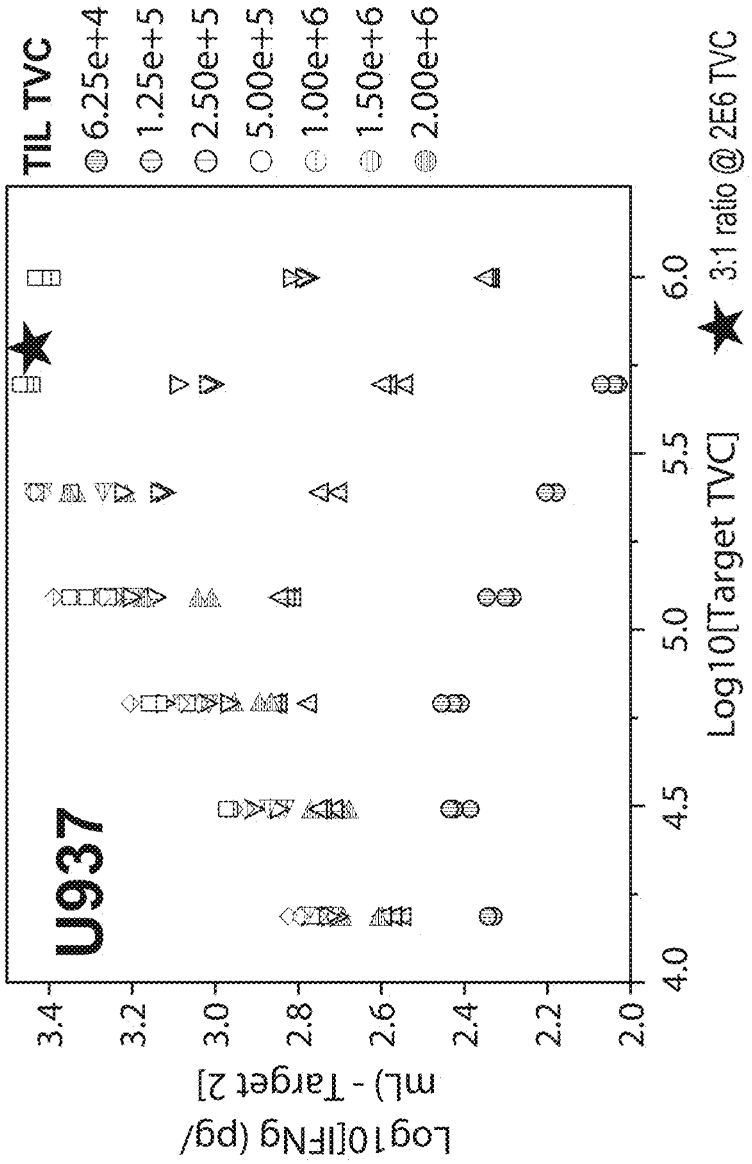

FIG. 199: Determination of effective TIL concentration for U937 cells. The star indicates a 3:1 TIL:U937 ratio at $2\times10^6$ TVC.

Figure 200:
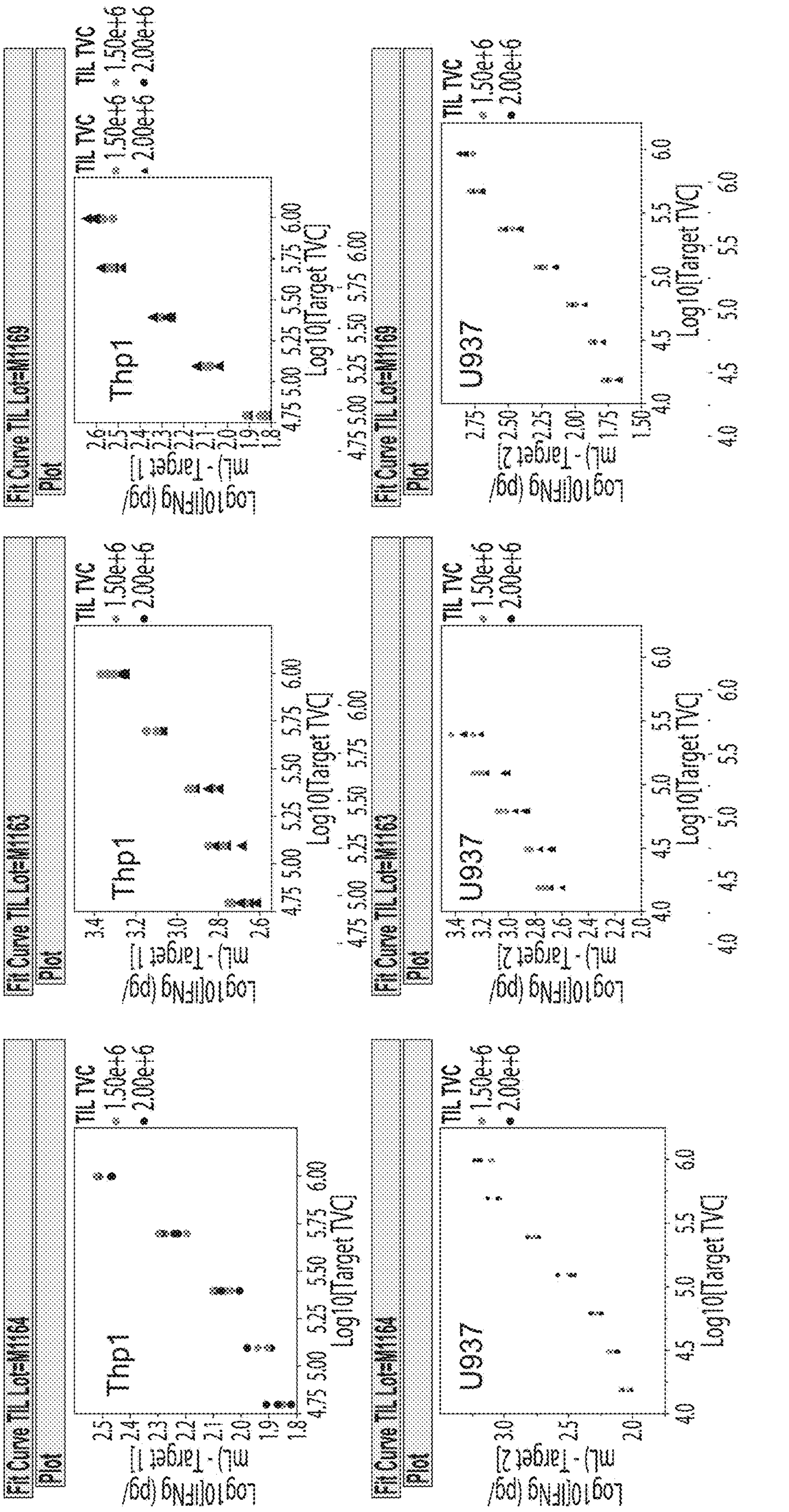

FIG. 200: Dose-response curves for three TIL lots (M1164, M1163, and M1169) using Thp1 and U937 target cells.

Figure 201:
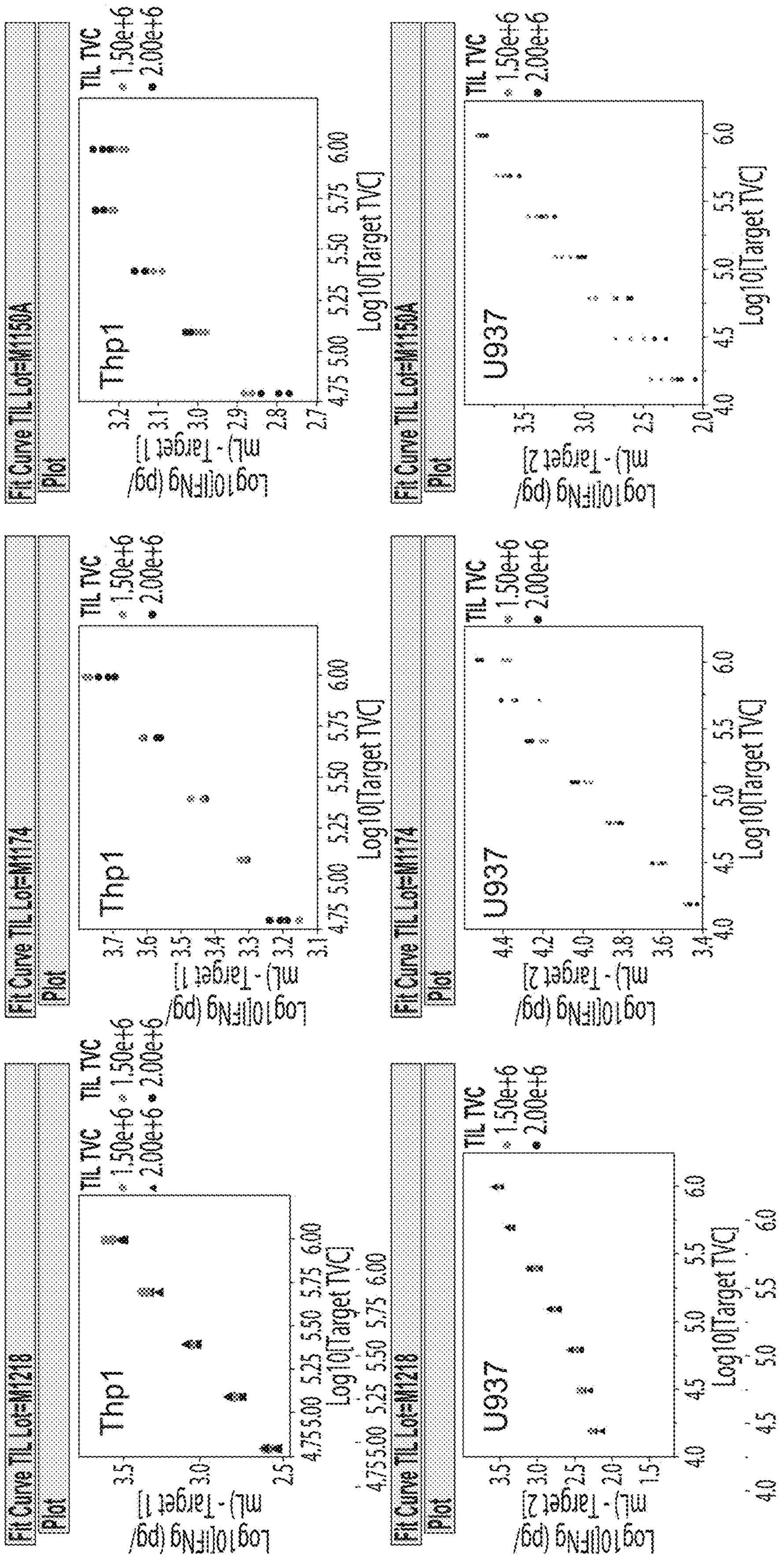

FIG. 201: Dose-response curves for three additional TIL lots (M1218, M1174, and M1150A) using Thp1 and U937 target cells.

Figure 202:
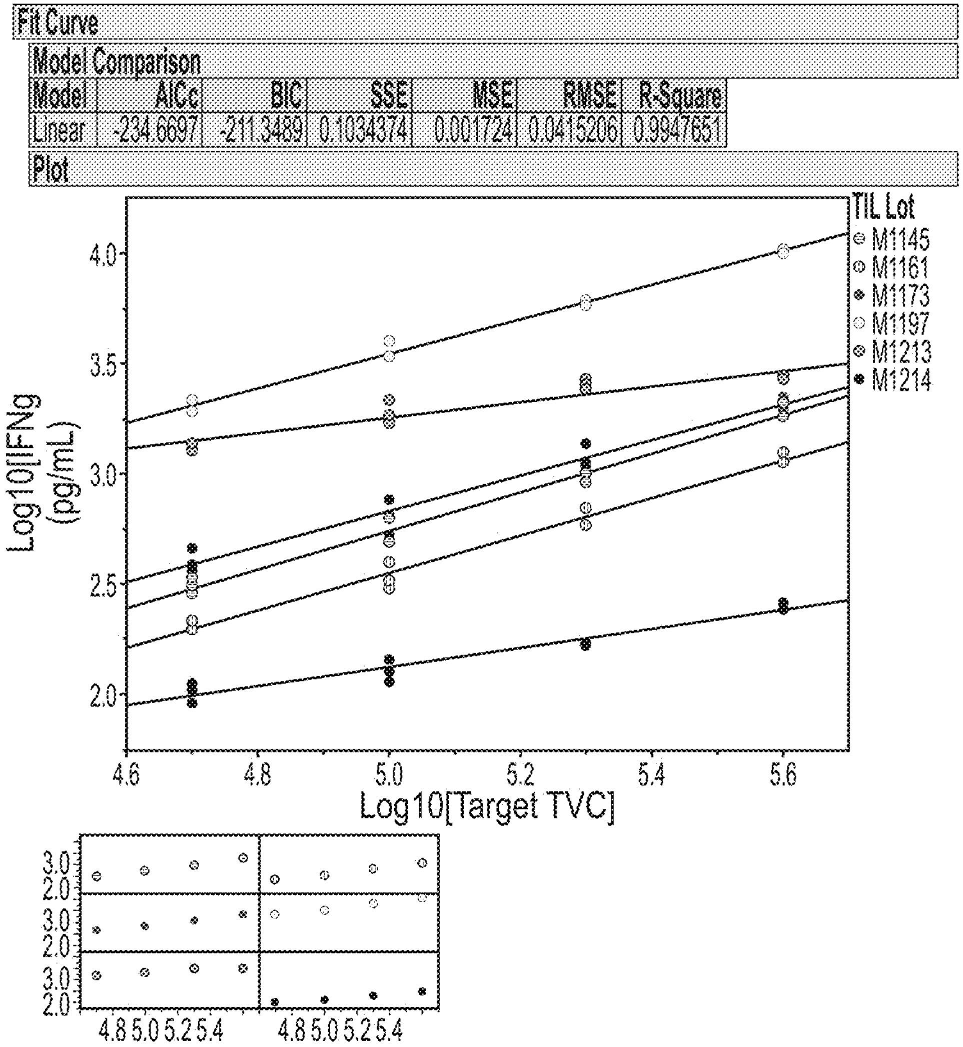

FIG. 202: Parallel line analysis for six TIL lots using U937 target cells. All six TILs demonstrate a clear dose response.

Figure 203:
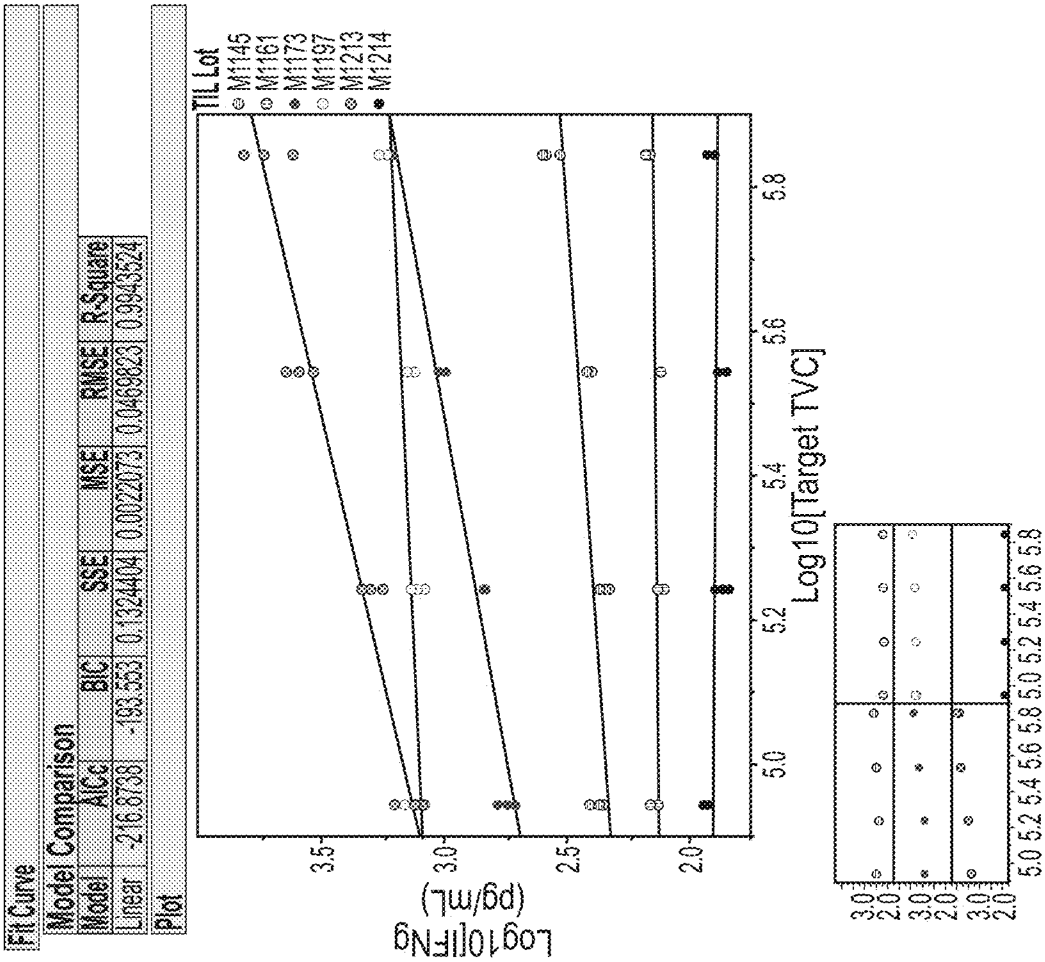

FIG. 203: Parallel line analysis for six TIL lots using Thp1 target cells. TIL M1173 and TIL M1213 demonstrate a clear dose response.

Figure 204:
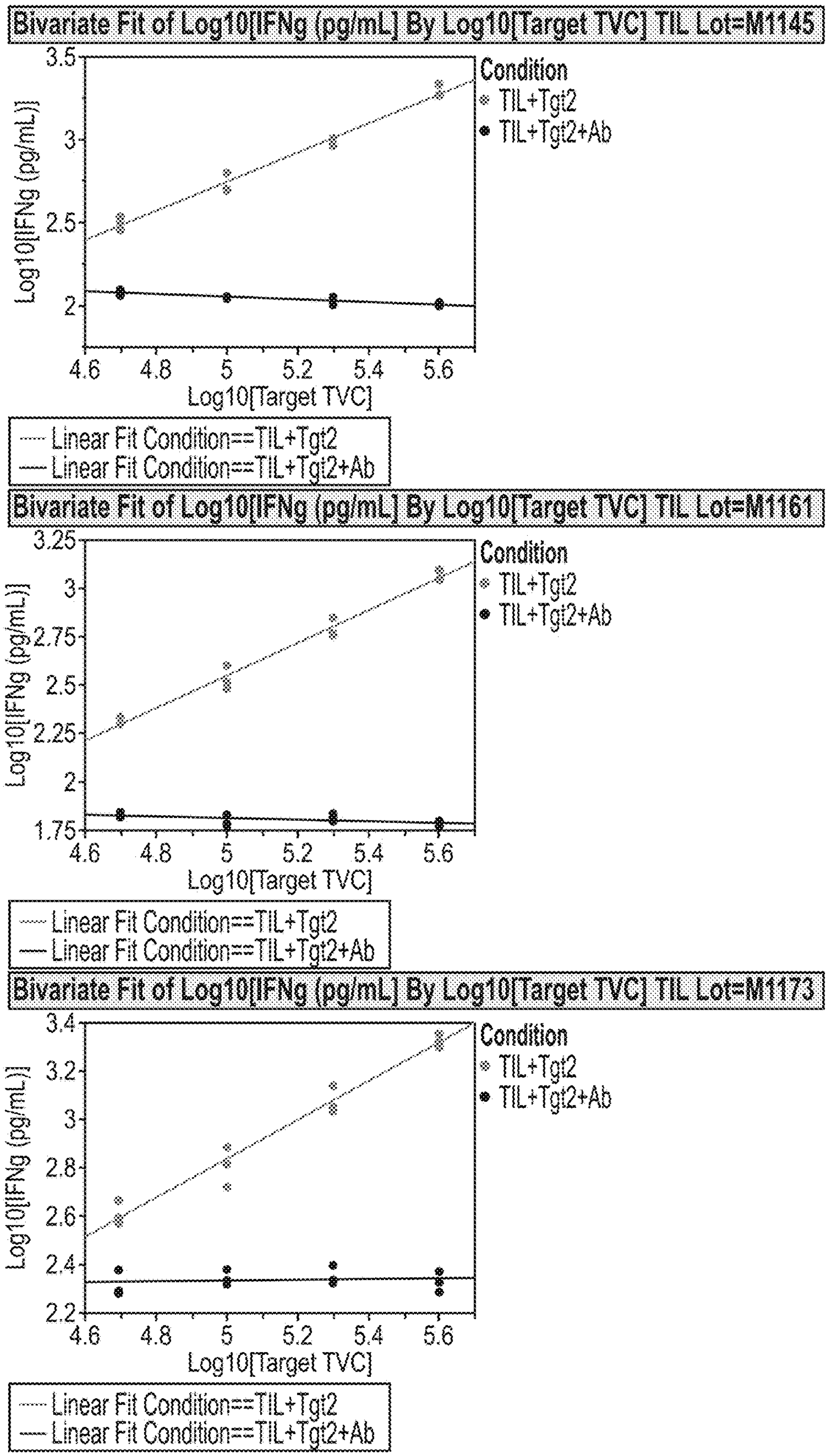

FIG. 204: Dose-response curves for three TIL lots (M1145, M1161, and M1173) at $1.5\times10^6$ TIL concentration with and without HLA blocking antibodies using U937 target cells. All three TIL lots demonstrate a clear dose response and also show complete inhibition of signal with antibody treatment (specific inhibition).

Figure 205:
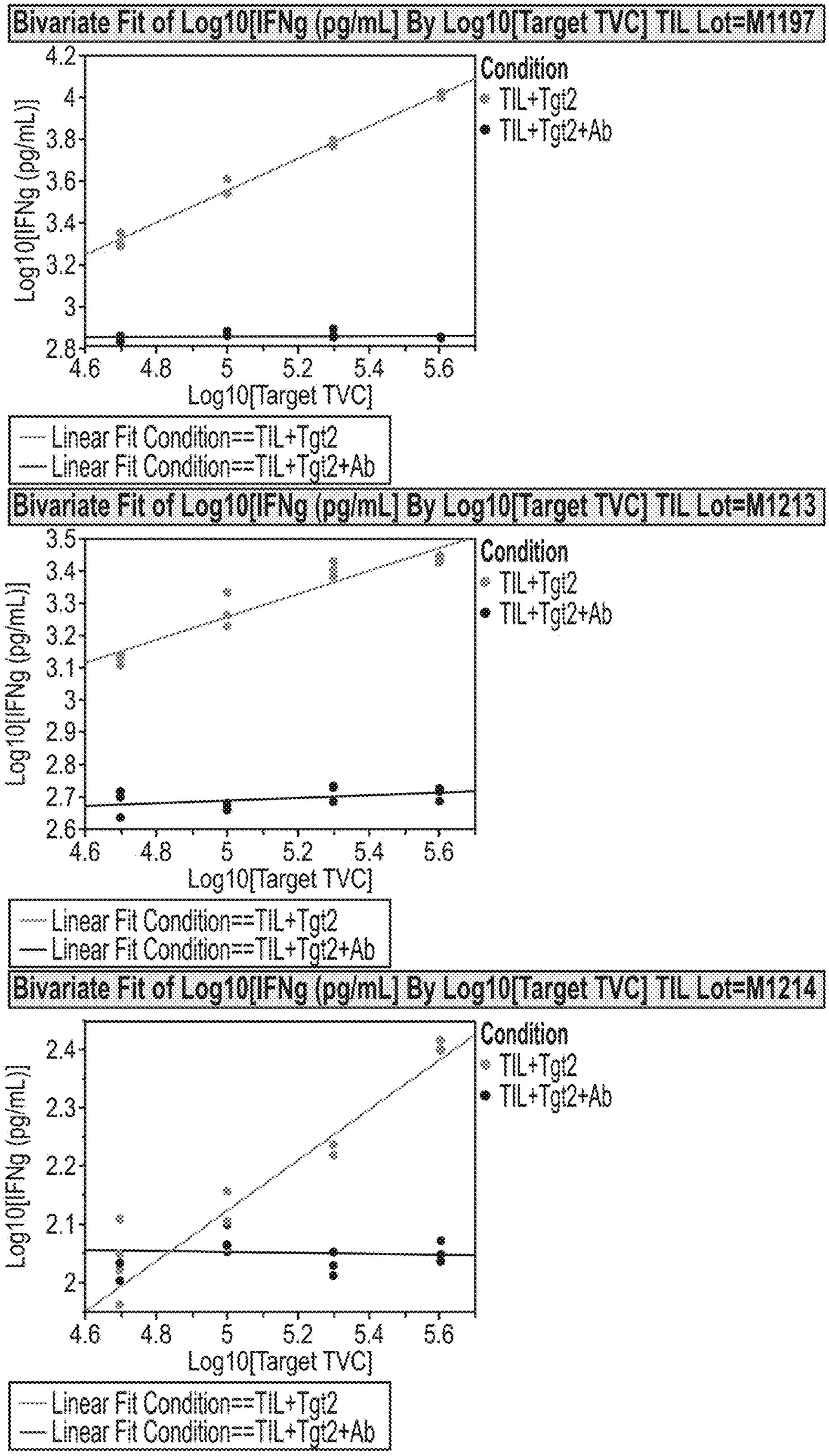

FIG. 205: Dose-response curves for three TIL lots (M1197, M1213, and M1214) at $1.5\times10^6$ TIL concentration with and without HLA blocking antibodies using U937 target cells. All three TIL lots demonstrate a clear dose response and also show complete inhibition of signal with antibody treatment (specific inhibition).

Figure 206:
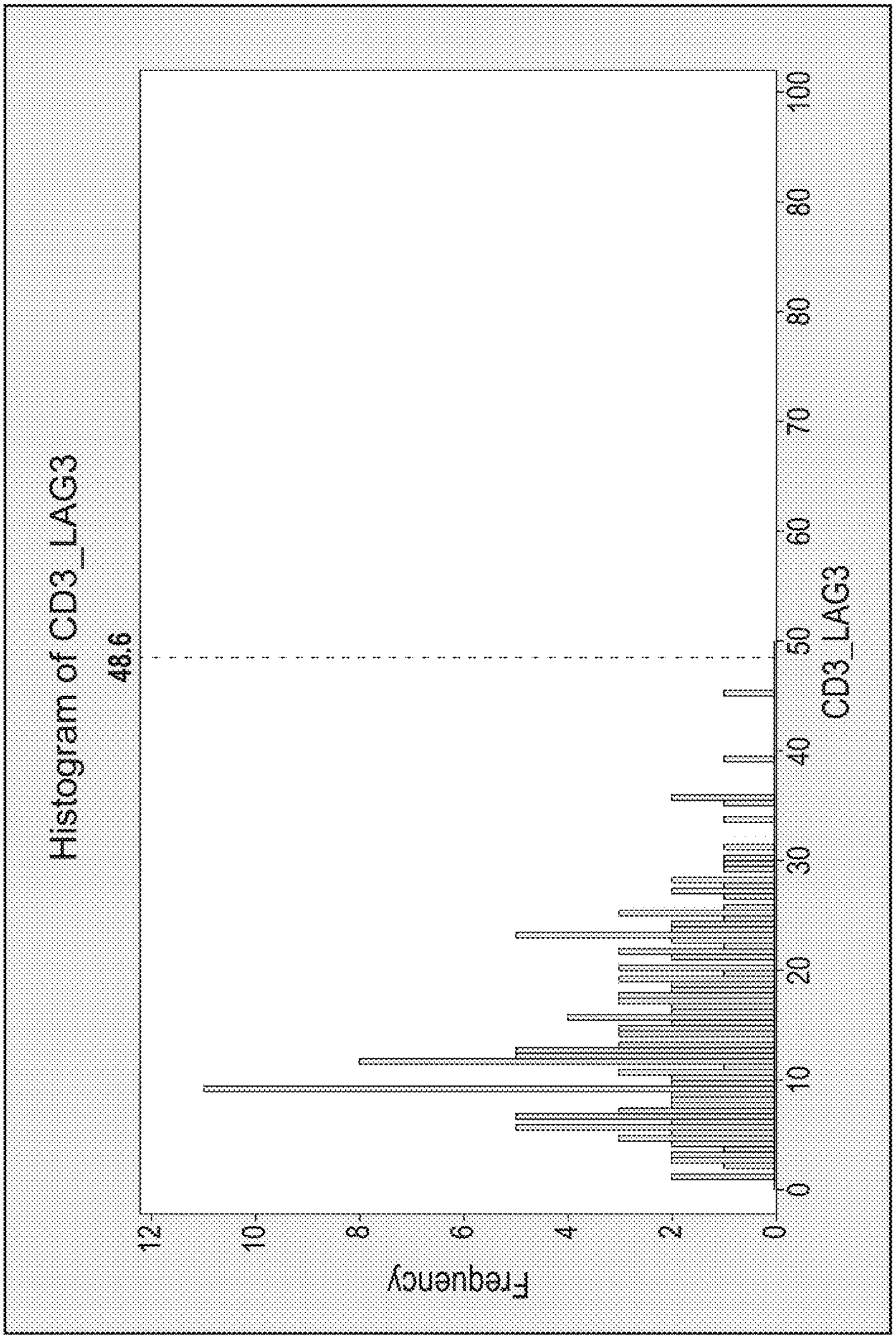

FIG. 206: Histogram of LAG3 expression by flow cytometry for melanoma TIL clinical samples.

Figure 207:
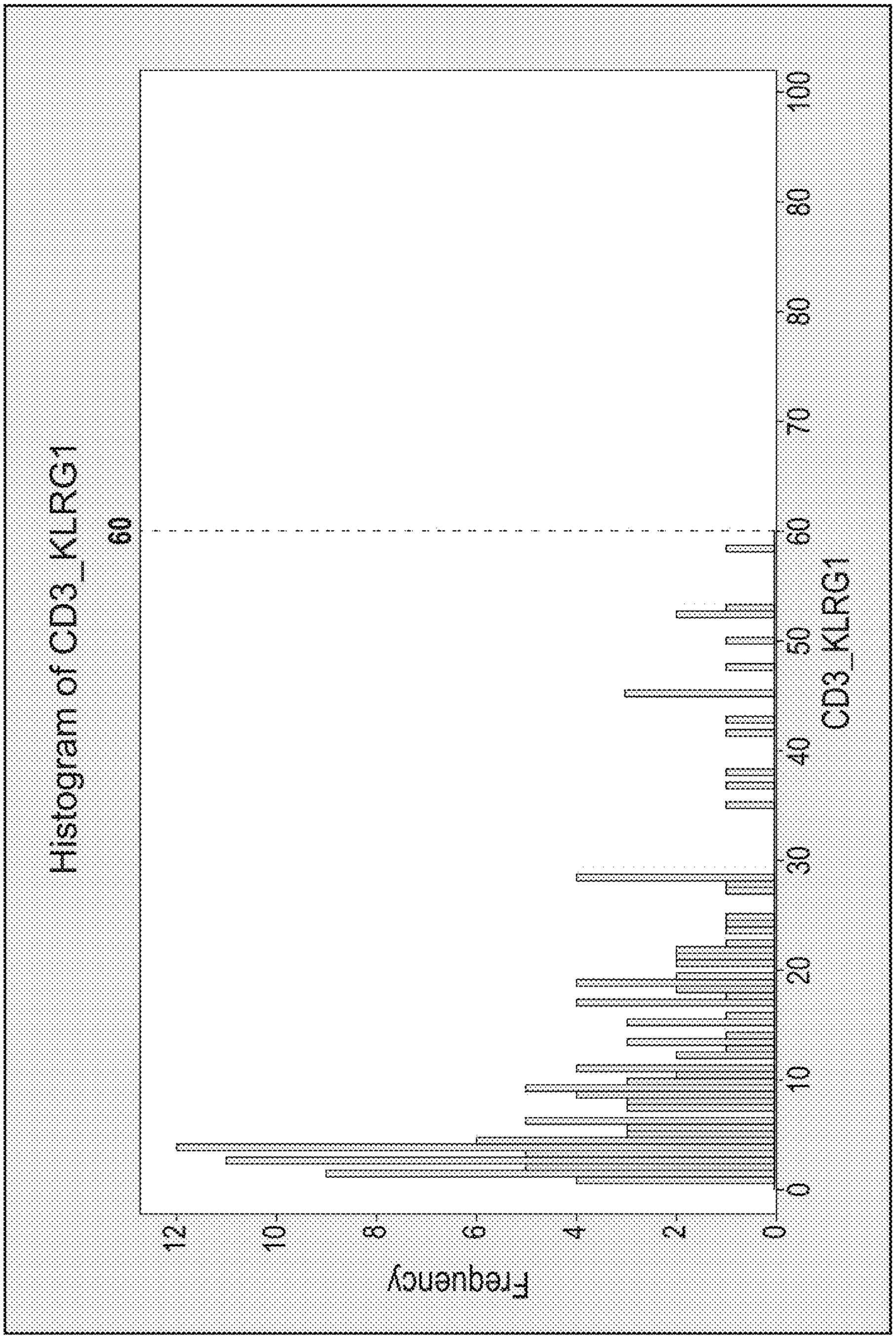

FIG. 207: Histogram of KLRG1 expression by flow cytometry for melanoma TIL clinical samples.

Figure 208:
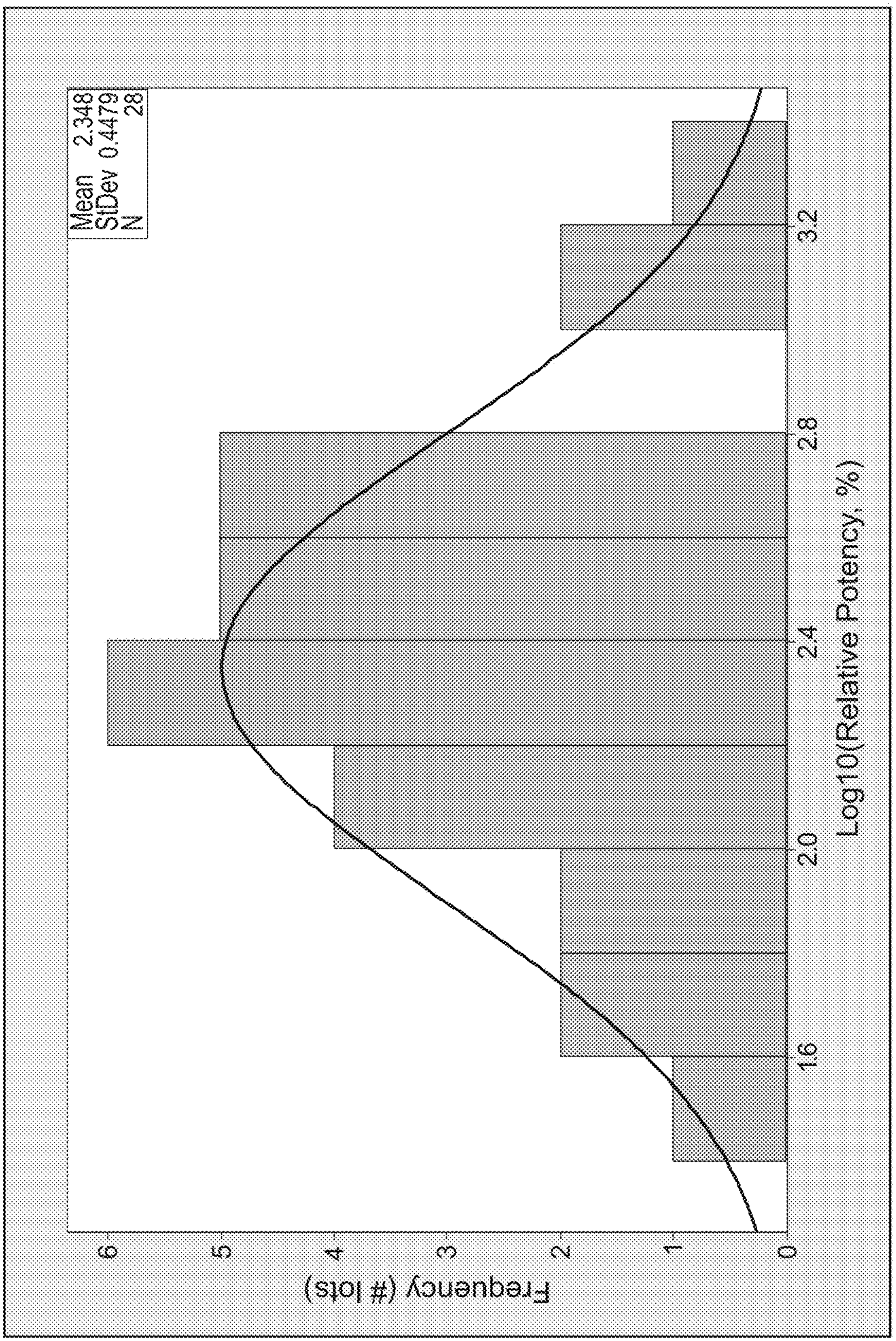

FIG. 208: Logarithmic distribution assessment of a histogram of relative potency of 28 historical clinical lots using a U937 alloreactive co-culture assay. Relative potency measurements calculated for each TIL lot were log-transformed, and the resulting distribution is normally distributed, indicating that the underlying distribution is log-normally distributed.

Figure 209:
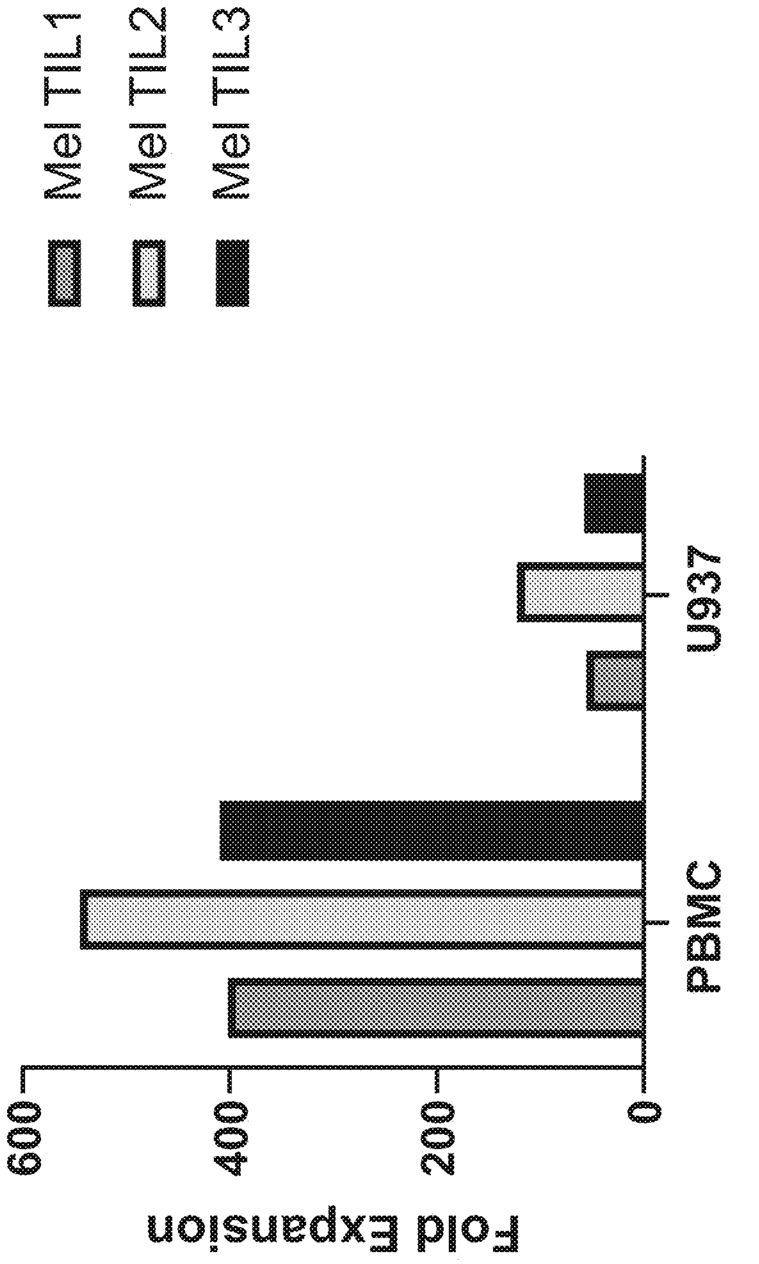

FIG. 209: Expansion of TILs incubated with U937 cells or allogeneic PBMCs during REP.

Figure 210:
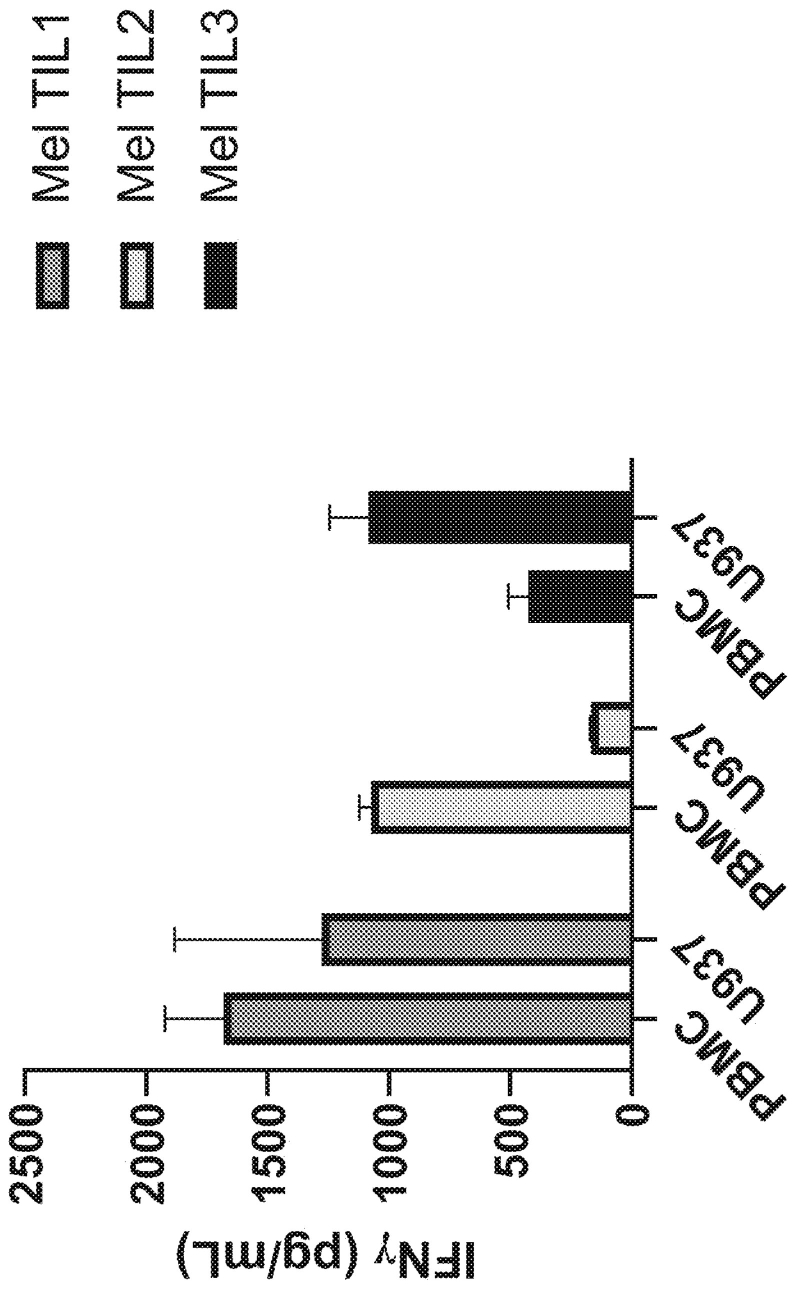

FIG. 210: IFN-γ secretion in TILs stimulated with anti-CD3 and anti-CD28 beads after REP with U937 cells or allogeneic PBMCs.

Figure 211:
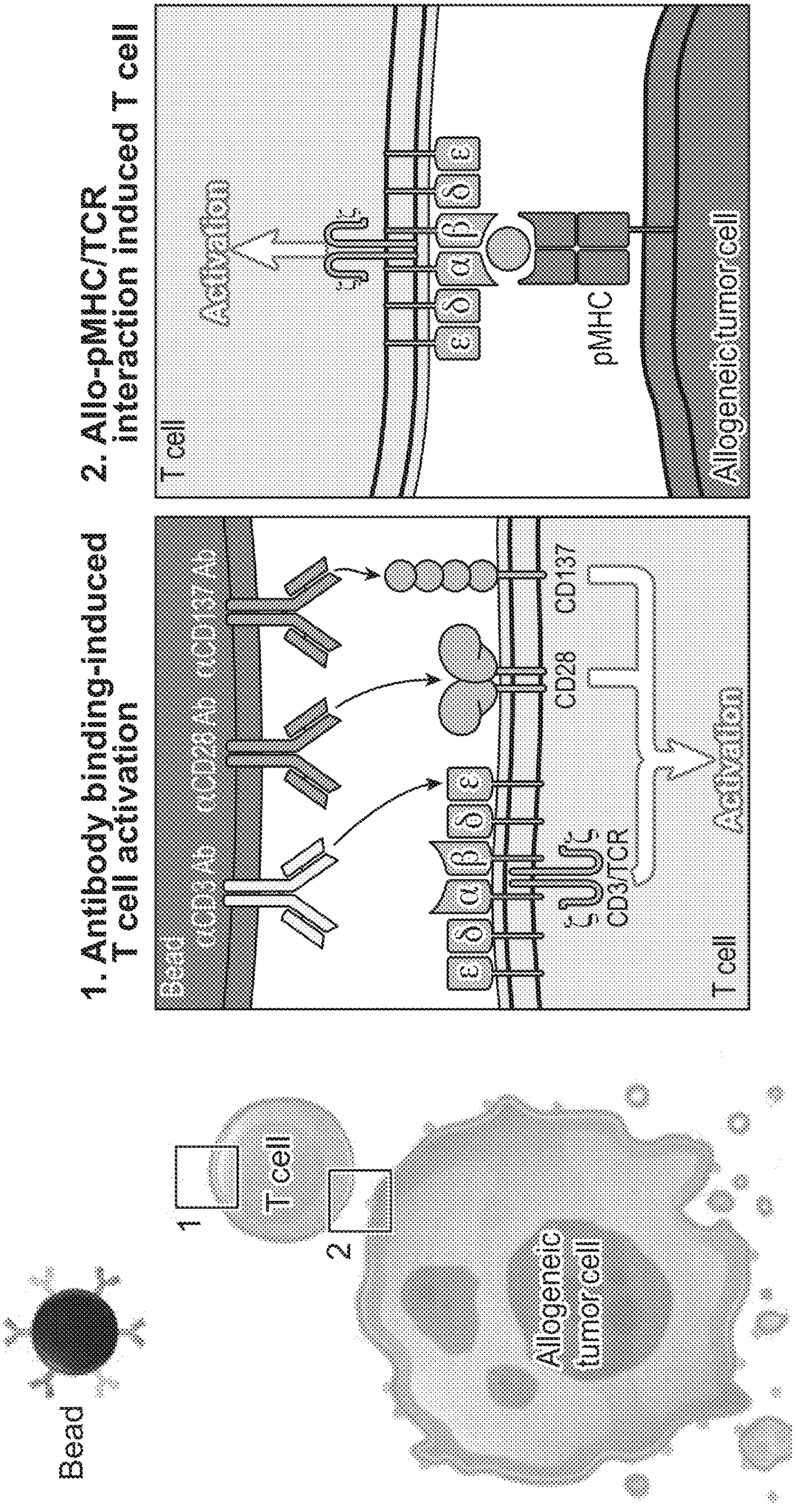

FIG. 211: Comparison of embodiments of the alloreactivity co-culture assays (denoted "allo-pMHC-TCR interaction induced T cell") of the present invention with traditional antibody bead-based assays for T cell potency testing.

BRIEF DESCRIPTION OF THE SEQUENCE LISTING

SEQ ID NO:1 is the amino acid sequence of the heavy chain of muromonab.

SEQ ID NO:2 is the amino acid sequence of the light chain of muromonab.

SEQ ID NO:3 is the amino acid sequence of a recombinant human IL-2 protein.

SEQ ID NO:4 is the amino acid sequence of aldesleukin.

SEQ ID NO:5 is an IL-2 form.

SEQ ID NO:6 is an IL-2 form.

SEQ ID NO: 7 is an IL-2 form.

SEQ ID NO:8 is a mucin domain polypeptide.

SEQ ID NO:9 is the amino acid sequence of a recombinant human IL-4 protein.

SEQ ID NO:10 is the amino acid sequence of a recombinant human IL-7 protein.

SEQ ID NO: 11 is the amino acid sequence of a recombinant human IL-15 protein.

SEQ ID NO: 12 is the amino acid sequence of a recombinant human IL-21 protein.

SEQ ID NO:13 is an IL-2 sequence.

SEQ ID NO: 14 is an IL-2 mutein sequence.

SEQ ID NO: 15 is an IL-2 mutein sequence.

SEQ ID NO:16 is the HCDR1_IL-2 for IgG.IL2R67A.H1.

SEQ ID NO: 17 is the HCDR2 for IgG.IL2R67A.H1.

SEQ ID NO: 18 is the HCDR3 for IgG.IL2R67A.H1.

SEQ ID NO: 19 is the HCDR1_IL-2 kabat for IgG.IL2R67A.H1.

SEQ ID NO:20 is the HCDR2 kabat for IgG.IL2R67A.H1.

SEQ ID NO:21 is the HCDR3 kabat for IgG.IL2R67A.H1.

SEQ ID NO:22 is the HCDR1_IL-2 clothia for IgG.IL2R67A.H1.

SEQ ID NO:23 is the HCDR2 clothia for IgG.IL2R67A.H1.

SEQ ID NO:24 is the HCDR3 clothia for IgG.IL2R67A.H1.

SEQ ID NO:25 is the HCDR1_IL-2 IMGT for IgG.IL2R67A.H1.

SEQ ID NO:26 is the HCDR2 IMGT for IgG.IL2R67A.H1.

SEQ ID NO:27 is the HCDR3 IMGT for IgG.IL2R67A.H1.

SEQ ID NO:28 is the $V_H$ chain for IgG.IL2R67A.H1.

SEQ ID NO:29 is the heavy chain for IgG.IL2R67A.H1.

SEQ ID NO:30 is the LCDR1 kabat for IgG.IL2R67A.H1.

SEQ ID NO:31 is the LCDR2 kabat for IgG.IL2R67A.H1.

SEQ ID NO:32 is the LCDR3 kabat for IgG.IL2R67A.H1.

SEQ ID NO:33 is the LCDR1 chothia for IgG.IL2R67A.H1.

SEQ ID NO:34 is the LCDR2 chothia for IgG.IL2R67A.H1.

SEQ ID NO:35 is the LCDR3 chothia for IgG.IL2R67A.H1.

SEQ ID NO:36 is a $V_L$ chain.

SEQ ID NO:37 is a light chain.

SEQ ID NO:38 is a light chain.

SEQ ID NO:39 is a light chain.

SEQ ID NO:40 is the amino acid sequence of human 4-1BB.

SEQ ID NO:41 is the amino acid sequence of murine 4-1BB.

SEQ ID NO:42 is the heavy chain for the 4-1BB agonist monoclonal antibody utomilumab (PF-05082566).

SEQ ID NO:43 is the light chain for the 4-1BB agonist monoclonal antibody utomilumab (PF-05082566).

SEQ ID NO:44 is the heavy chain variable region ($V_H$) for the 4-1BB agonist monoclonal antibody utomilumab (PF-05082566).

SEQ ID NO:45 is the light chain variable region ($V_L$) for the 4-1BB agonist monoclonal antibody utomilumab (PF-05082566).

SEQ ID NO:46 is the heavy chain CDR1 for the 4-1BB agonist monoclonal antibody utomilumab (PF-05082566).

SEQ ID NO:47 is the heavy chain CDR2 for the 4-1BB agonist monoclonal antibody utomilumab (PF-05082566).

SEQ ID NO:48 is the heavy chain CDR3 for the 4-1BB agonist monoclonal antibody utomilumab (PF-05082566).

SEQ ID NO:49 is the light chain CDR1 for the 4-1BB agonist monoclonal antibody utomilumab (PF-05082566).

SEQ ID NO:50 is the light chain CDR2 for the 4-1BB agonist monoclonal antibody utomilumab (PF-05082566).

SEQ ID NO:51 is the light chain CDR3 for the 4-1BB agonist monoclonal antibody utomilumab (PF-05082566).

SEQ ID NO:52 is the heavy chain for the 4-1BB agonist monoclonal antibody urelumab (BMS-663513).

SEQ ID NO:53 is the light chain for the 4-1BB agonist monoclonal antibody urelumab (BMS-663513).

SEQ ID NO:54 is the heavy chain variable region ($V_H$) for the 4-1BB agonist monoclonal antibody urelumab (BMS-663513).

SEQ ID NO:55 is the light chain variable region ($V_L$) for the 4-1BB agonist monoclonal antibody urelumab (BMS-663513).

SEQ ID NO:56 is the heavy chain CDR1 for the 4-1BB agonist monoclonal antibody urelumab (BMS-663513).

SEQ ID NO:57 is the heavy chain CDR2 for the 4-1BB agonist monoclonal antibody urelumab (BMS-663513).

SEQ ID NO:58 is the heavy chain CDR3 for the 4-1BB agonist monoclonal antibody urelumab (BMS-663513).

SEQ ID NO:59 is the light chain CDR1 for the 4-1BB agonist monoclonal antibody urelumab (BMS-663513).

SEQ ID NO:60 is the light chain CDR2 for the 4-1BB agonist monoclonal antibody urelumab (BMS-663513).

SEQ ID NO:61 is the light chain CDR3 for the 4-1BB agonist monoclonal antibody urelumab (BMS-663513).

SEQ ID NO:62 is an Fc domain for a TNFRSF agonist fusion protein.

SEQ ID NO:63 is a linker for a TNFRSF agonist fusion protein.

SEQ ID NO:64 is a linker for a TNFRSF agonist fusion protein.

SEQ ID NO:65 is a linker for a TNFRSF agonist fusion protein.

SEQ ID NO:66 is a linker for a TNFRSF agonist fusion protein.

SEQ ID NO:67 is a linker for a TNFRSF agonist fusion protein.

SEQ ID NO:68 is a linker for a TNFRSF agonist fusion protein.

SEQ ID NO:69 is a linker for a TNFRSF agonist fusion protein.

SEQ ID NO:70 is a linker for a TNFRSF agonist fusion protein.

SEQ ID NO:71 is a linker for a TNFRSF agonist fusion protein.

SEQ ID NO: 72 is a linker for a TNFRSF agonist fusion protein.

SEQ ID NO:73 is an Fc domain for a TNFRSF agonist fusion protein.

SEQ ID NO: 74 is a linker for a TNFRSF agonist fusion protein.

SEQ ID NO: 75 is a linker for a TNFRSF agonist fusion protein.

SEQ ID NO:76 is a linker for a TNFRSF agonist fusion protein.

SEQ ID NO: 77 is a 4-1BB ligand (4-1BBL) amino acid sequence.

SEQ ID NO: 78 is a soluble portion of 4-1BBL polypeptide.

SEQ ID NO: 79 is a heavy chain variable region ($V_H$) for the 4-1BB agonist antibody 4B4-1-1 version 1.

SEQ ID NO:80 is a light chain variable region ($V_L$) for the 4-1BB agonist antibody 4B4-1-1 version 1.

SEQ ID NO:81 is a heavy chain variable region ($V_H$) for the 4-1BB agonist antibody 4B4-1-1 version 2.

SEQ ID NO:82 is a light chain variable region ($V_L$) for the 4-1BB agonist antibody 4B4-1-1 version 2.

SEQ ID NO:83 is a heavy chain variable region ($V_H$) for the 4-1BB agonist antibody H39E3-2.

SEQ ID NO:84 is a light chain variable region ($V_L$) for the 4-1BB agonist antibody H39E3-2.

SEQ ID NO:85 is the amino acid sequence of human OX40.

SEQ ID NO:86 is the amino acid sequence of murine OX40.

SEQ ID NO:87 is the heavy chain for the OX40 agonist monoclonal antibody tavolixizumab (MEDI-0562).

SEQ ID NO:88 is the light chain for the OX40 agonist monoclonal antibody tavolixizumab (MEDI-0562).

SEQ ID NO:89 is the heavy chain variable region ($V_H$) for the OX40 agonist monoclonal antibody tavolixizumab (MEDI-0562).

SEQ ID NO:90 is the light chain variable region ($V_L$) for the OX40 agonist monoclonal antibody tavolixizumab (MEDI-0562).

SEQ ID NO:91 is the heavy chain CDR1 for the OX40 agonist monoclonal antibody tavolixizumab (MEDI-0562).

SEQ ID NO: 92 is the heavy chain CDR2 for the OX40 agonist monoclonal antibody tavolixizumab (MEDI-0562).

SEQ ID NO:93 is the heavy chain CDR3 for the OX40 agonist monoclonal antibody tavolixizumab (MEDI-0562).

SEQ ID NO:94 is the light chain CDR1 for the OX40 agonist monoclonal antibody tavolixizumab (MEDI-0562).

SEQ ID NO:95 is the light chain CDR2 for the OX40 agonist monoclonal antibody tavolixizumab (MEDI-0562).

SEQ ID NO:96 is the light chain CDR3 for the OX40 agonist monoclonal antibody tavolixizumab (MEDI-0562).

SEQ ID NO:97 is the heavy chain for the OX40 agonist monoclonal antibody 11D4.

SEQ ID NO:98 is the light chain for the OX40 agonist monoclonal antibody 11D4.

SEQ ID NO:99 is the heavy chain variable region ($V_H$) for the OX40 agonist monoclonal antibody 11D4.

SEQ ID NO:100 is the light chain variable region ($V_L$) for the OX40 agonist monoclonal antibody 11D4.

SEQ ID NO: 101 is the heavy chain CDR1 for the OX40 agonist monoclonal antibody 11D4.

SEQ ID NO: 102 is the heavy chain CDR2 for the OX40 agonist monoclonal antibody 11D4.

SEQ ID NO: 103 is the heavy chain CDR3 for the OX40 agonist monoclonal antibody 11D4.

SEQ ID NO: 104 is the light chain CDR1 for the OX40 agonist monoclonal antibody 11D4.

SEQ ID NO: 105 is the light chain CDR2 for the OX40 agonist monoclonal antibody 11D4.

SEQ ID NO: 106 is the light chain CDR3 for the OX40 agonist monoclonal antibody 11D4.

SEQ ID NO: 107 is the heavy chain for the OX40 agonist monoclonal antibody 18D8.

SEQ ID NO: 108 is the light chain for the OX40 agonist monoclonal antibody 18D8.

SEQ ID NO: 109 is the heavy chain variable region ($V_H$) for the OX40 agonist monoclonal antibody 18D8.

SEQ ID NO:110 is the light chain variable region ($V_L$) for the OX40 agonist monoclonal antibody 18D8.

SEQ ID NO: 111 is the heavy chain CDR1 for the OX40 agonist monoclonal antibody 18D8.

SEQ ID NO: 112 is the heavy chain CDR2 for the OX40 agonist monoclonal antibody 18D8.

SEQ ID NO: 113 is the heavy chain CDR3 for the OX40 agonist monoclonal antibody 18D8.

SEQ ID NO:114 is the light chain CDR1 for the OX40 agonist monoclonal antibody 18D8.

SEQ ID NO: 115 is the light chain CDR2 for the OX40 agonist monoclonal antibody 18D8.

SEQ ID NO: 116 is the light chain CDR3 for the OX40 agonist monoclonal antibody 18D8.

SEQ ID NO: 117 is the heavy chain variable region ($V_H$) for the OX40 agonist monoclonal antibody Hu119-122.

SEQ ID NO:118 is the light chain variable region ($V_L$) for the OX40 agonist monoclonal antibody Hu119-122.

SEQ ID NO: 119 is the heavy chain CDR1 for the OX40 agonist monoclonal antibody Hu119-122.

SEQ ID NO: 120 is the heavy chain CDR2 for the OX40 agonist monoclonal antibody Hu119-122.

SEQ ID NO: 121 is the heavy chain CDR3 for the OX40 agonist monoclonal antibody Hu119-122.

SEQ ID NO: 122 is the light chain CDR1 for the OX40 agonist monoclonal antibody Hu119-122.

SEQ ID NO: 123 is the light chain CDR2 for the OX40 agonist monoclonal antibody Hu119-122.

SEQ ID NO: 124 is the light chain CDR3 for the OX40 agonist monoclonal antibody Hu119-122.

SEQ ID NO: 125 is the heavy chain variable region ($V_H$) for the OX40 agonist monoclonal antibody Hu106-222.

SEQ ID NO: 126 is the light chain variable region ($V_L$) for the OX40 agonist monoclonal antibody Hu106-222.

SEQ ID NO: 127 is the heavy chain CDR1 for the OX40 agonist monoclonal antibody Hu106-222.

SEQ ID NO: 128 is the heavy chain CDR2 for the OX40 agonist monoclonal antibody Hu106-222.

SEQ ID NO: 129 is the heavy chain CDR3 for the OX40 agonist monoclonal antibody Hu106-222.

SEQ ID NO: 130 is the light chain CDR1 for the OX40 agonist monoclonal antibody Hu106-222.

SEQ ID NO: 131 is the light chain CDR2 for the OX40 agonist monoclonal antibody Hu106-222.

SEQ ID NO: 132 is the light chain CDR3 for the OX40 agonist monoclonal antibody Hu106-222.

SEQ ID NO:133 is an OX40 ligand (OX40L) amino acid sequence.

SEQ ID NO: 134 is a soluble portion of OX40L polypeptide.

SEQ ID NO:135 is an alternative soluble portion of OX40L polypeptide.

SEQ ID NO: 136 is the heavy chain variable region ($V_H$) for the OX40 agonist monoclonal antibody 008.

SEQ ID NO: 137 is the light chain variable region ($V_L$) for the OX40 agonist monoclonal antibody 008.

SEQ ID NO: 138 is the heavy chain variable region ($V_H$) for the OX40 agonist monoclonal antibody 011.

SEQ ID NO: 139 is the light chain variable region ($V_L$) for the OX40 agonist monoclonal antibody 011.

SEQ ID NO: 140 is the heavy chain variable region ($V_H$) for the OX40 agonist monoclonal antibody 021.

SEQ ID NO: 141 is the light chain variable region ($V_L$) for the OX40 agonist monoclonal antibody 021.

SEQ ID NO: 142 is the heavy chain variable region ($V_H$) for the OX40 agonist monoclonal antibody 023.

SEQ ID NO: 143 is the light chain variable region ($V_L$) for the OX40 agonist monoclonal antibody 023.

SEQ ID NO:144 is the heavy chain variable region ($V_H$) for an OX40 agonist monoclonal antibody.

SEQ ID NO: 145 is the light chain variable region ($V_L$) for an OX40 agonist monoclonal antibody.

SEQ ID NO: 146 is the heavy chain variable region ($V_H$) for an OX40 agonist monoclonal antibody.

SEQ ID NO: 147 is the light chain variable region ($V_L$) for an OX40 agonist monoclonal antibody.

SEQ ID NO: 148 is the heavy chain variable region ($V_H$) for a humanized OX40 agonist monoclonal antibody.

SEQ ID NO: 149 is the heavy chain variable region ($V_H$) for a humanized OX40 agonist monoclonal antibody.

SEQ ID NO: 150 is the light chain variable region ($V_L$) for a humanized OX40 agonist monoclonal antibody.

SEQ ID NO:151 is the light chain variable region ($V_L$) for a humanized OX40 agonist monoclonal antibody.

SEQ ID NO: 152 is the heavy chain variable region ($V_H$) for a humanized OX40 agonist monoclonal antibody.

SEQ ID NO: 153 is the heavy chain variable region ($V_H$) for a humanized OX40 agonist monoclonal antibody.

SEQ ID NO:154 is the light chain variable region ($V_L$) for a humanized OX40 agonist monoclonal antibody.

SEQ ID NO:155 is the light chain variable region ($V_L$) for a humanized OX40 agonist monoclonal antibody.

SEQ ID NO: 156 is the heavy chain variable region ($V_H$) for an OX40 agonist monoclonal antibody.

SEQ ID NO: 157 is the light chain variable region ($V_L$) for an OX40 agonist monoclonal antibody.

SEQ ID NO: 158 is the heavy chain amino acid sequence of the PD-1 inhibitor nivolumab.

SEQ ID NO: 159 is the light chain amino acid sequence of the PD-1 inhibitor nivolumab.

SEQ ID NO: 160 is the heavy chain variable region ($V_H$) amino acid sequence of the PD-1 inhibitor nivolumab.

SEQ ID NO: 161 is the light chain variable region ($V_L$) amino acid sequence of the PD-1 inhibitor nivolumab.

SEQ ID NO: 162 is the heavy chain CDR1 amino acid sequence of the PD-1 inhibitor nivolumab.

SEQ ID NO: 163 is the heavy chain CDR2 amino acid sequence of the PD-1 inhibitor nivolumab.

SEQ ID NO: 164 is the heavy chain CDR3 amino acid sequence of the PD-1 inhibitor nivolumab.

SEQ ID NO: 165 is the light chain CDR1 amino acid sequence of the PD-1 inhibitor nivolumab.

SEQ ID NO: 166 is the light chain CDR2 amino acid sequence of the PD-1 inhibitor nivolumab.

SEQ ID NO: 167 is the light chain CDR3 amino acid sequence of the PD-1 inhibitor nivolumab.

SEQ ID NO: 168 is the heavy chain amino acid sequence of the PD-1 inhibitor pembrolizumab.

SEQ ID NO: 169 is the light chain amino acid sequence of the PD-1 inhibitor pembrolizumab.

SEQ ID NO: 170 is the heavy chain variable region ($V_H$) amino acid sequence of the PD-1 inhibitor pembrolizumab.

SEQ ID NO: 171 is the light chain variable region ($V_L$) amino acid sequence of the PD-1 inhibitor pembrolizumab.

SEQ ID NO: 172 is the heavy chain CDR1 amino acid sequence of the PD-1 inhibitor pembrolizumab.

SEQ ID NO: 173 is the heavy chain CDR2 amino acid sequence of the PD-1 inhibitor pembrolizumab.

SEQ ID NO: 174 is the heavy chain CDR3 amino acid sequence of the PD-1 inhibitor pembrolizumab.

SEQ ID NO: 175 is the light chain CDR1 amino acid sequence of the PD-1 inhibitor pembrolizumab.

SEQ ID NO: 176 is the light chain CDR2 amino acid sequence of the PD-1 inhibitor pembrolizumab.

SEQ ID NO: 177 is the light chain CDR3 amino acid sequence of the PD-1 inhibitor pembrolizumab.

SEQ ID NO: 178 is the heavy chain amino acid sequence of the PD-L1 inhibitor durvalumab.

SEQ ID NO: 179 is the light chain amino acid sequence of the PD-L1 inhibitor durvalumab.

SEQ ID NO: 180 is the heavy chain variable region ($V_H$) amino acid sequence of the PD-L1 inhibitor durvalumab.

SEQ ID NO: 181 is the light chain variable region ($V_L$) amino acid sequence of the PD-L1 inhibitor durvalumab.

SEQ ID NO: 182 is the heavy chain CDR1 amino acid sequence of the PD-L1 inhibitor durvalumab.

SEQ ID NO: 183 is the heavy chain CDR2 amino acid sequence of the PD-L1 inhibitor durvalumab.

SEQ ID NO: 184 is the heavy chain CDR3 amino acid sequence of the PD-L1 inhibitor durvalumab.

SEQ ID NO: 185 is the light chain CDR1 amino acid sequence of the PD-L1 inhibitor durvalumab.

SEQ ID NO: 186 is the light chain CDR2 amino acid sequence of the PD-L1 inhibitor durvalumab.

SEQ ID NO: 187 is the light chain CDR3 amino acid sequence of the PD-L1 inhibitor durvalumab.

SEQ ID NO: 188 is the heavy chain amino acid sequence of the PD-L1 inhibitor avelumab.

SEQ ID NO: 189 is the light chain amino acid sequence of the PD-L1 inhibitor avelumab.

SEQ ID NO: 190 is the heavy chain variable region ($V_H$) amino acid sequence of the PD-L1 inhibitor avelumab.

SEQ ID NO: 191 is the light chain variable region ($V_L$) amino acid sequence of the PD-L1 inhibitor avelumab.

SEQ ID NO: 192 is the heavy chain CDR1 amino acid sequence of the PD-L1 inhibitor avelumab.

SEQ ID NO: 193 is the heavy chain CDR2 amino acid sequence of the PD-L1 inhibitor avelumab.

SEQ ID NO: 194 is the heavy chain CDR3 amino acid sequence of the PD-L1 inhibitor avelumab.

SEQ ID NO: 195 is the light chain CDR1 amino acid sequence of the PD-L1 inhibitor avelumab.

SEQ ID NO: 196 is the light chain CDR2 amino acid sequence of the PD-L1 inhibitor avelumab.

SEQ ID NO: 197 is the light chain CDR3 amino acid sequence of the PD-L1 inhibitor avelumab.

SEQ ID NO: 198 is the heavy chain amino acid sequence of the PD-L1 inhibitor atezolizumab.

SEQ ID NO: 199 is the light chain amino acid sequence of the PD-L1 inhibitor atezolizumab.

SEQ ID NO:200 is the heavy chain variable region ($V_H$) amino acid sequence of the PD-L1 inhibitor atezolizumab.

SEQ ID NO:201 is the light chain variable region ($V_L$) amino acid sequence of the PD-L1 inhibitor atezolizumab.

SEQ ID NO:202 is the heavy chain CDR1 amino acid sequence of the PD-L1 inhibitor atezolizumab.

SEQ ID NO:203 is the heavy chain CDR2 amino acid sequence of the PD-L1 inhibitor atezolizumab.

SEQ ID NO:204 is the heavy chain CDR3 amino acid sequence of the PD-L1 inhibitor atezolizumab.

SEQ ID NO: 205 is the light chain CDR1 amino acid sequence of the PD-L1 inhibitor atezolizumab.

SEQ ID NO:206 is the light chain CDR2 amino acid sequence of the PD-L1 inhibitor atezolizumab.

SEQ ID NO:207 is the light chain CDR3 amino acid sequence of the PD-L1 inhibitor atezolizumab.

SEQ ID NO:208 is the heavy chain amino acid sequence of the CTLA-4 inhibitor ipilimumab.

SEQ ID NO:209 is the light chain amino acid sequence of the CTLA-4 inhibitor ipilimumab.

SEQ ID NO:210 is the heavy chain variable region ($V_H$) amino acid sequence of the CTLA-4 inhibitor ipilimumab.

SEQ ID NO:211 is the light chain variable region ($V_L$) amino acid sequence of the CTLA-4 inhibitor ipilimumab.

SEQ ID NO: 212 is the heavy chain CDR1 amino acid sequence of the CTLA-4 inhibitor ipilimumab.

SEQ ID NO:213 is the heavy chain CDR2 amino acid sequence of the CTLA-4 inhibitor ipilimumab.

SEQ ID NO:214 is the heavy chain CDR3 amino acid sequence of the CTLA-4 inhibitor ipilimumab.

SEQ ID NO:215 is the light chain CDR1 amino acid sequence of the CTLA-4 inhibitor ipilimumab.

SEQ ID NO:216 is the light chain CDR2 amino acid sequence of the CTLA-4 inhibitor ipilimumab.

SEQ ID NO:217 is the light chain CDR3 amino acid sequence of the CTLA-4 inhibitor ipilimumab.

SEQ ID NO:218 is the heavy chain amino acid sequence of the CTLA-4 inhibitor tremelimumab.

SEQ ID NO:219 is the light chain amino acid sequence of the CTLA-4 inhibitor tremelimumab.

SEQ ID NO:220 is the heavy chain variable region ($V_H$) amino acid sequence of the CTLA-4 inhibitor tremelimumab.

SEQ ID NO:221 is the light chain variable region ($V_L$) amino acid sequence of the CTLA-4 inhibitor tremelimumab.

SEQ ID NO: 222 is the heavy chain CDR1 amino acid sequence of the CTLA-4 inhibitor tremelimumab.

SEQ ID NO: 223 is the heavy chain CDR2 amino acid sequence of the CTLA-4 inhibitor tremelimumab.

SEQ ID NO:224 is the heavy chain CDR3 amino acid sequence of the CTLA-4 inhibitor tremelimumab.

SEQ ID NO:225 is the light chain CDR1 amino acid sequence of the CTLA-4 inhibitor tremelimumab.

SEQ ID NO:226 is the light chain CDR2 amino acid sequence of the CTLA-4 inhibitor tremelimumab.

SEQ ID NO: 227 is the light chain CDR3 amino acid sequence of the CTLA-4 inhibitor tremelimumab.

SEQ ID NO:228 is the heavy chain amino acid sequence of the CTLA-4 inhibitor zalifrelimab.

SEQ ID NO:229 is the light chain amino acid sequence of the CTLA-4 inhibitor zalifrelimab.

SEQ ID NO:230 is the heavy chain variable region ($V_H$) amino acid sequence of the CTLA-4 inhibitor zalifrelimab.

SEQ ID NO:231 is the light chain variable region ($V_L$) amino acid sequence of the CTLA-4 inhibitor zalifrelimab.

SEQ ID NO:232 is the heavy chain CDR1 amino acid sequence of the CTLA-4 inhibitor zalifrelimab.

SEQ ID NO:233 is the heavy chain CDR2 amino acid sequence of the CTLA-4 inhibitor zalifrelimab.

SEQ ID NO: 234 is the heavy chain CDR3 amino acid sequence of the CTLA-4 inhibitor zalifrelimab.

SEQ ID NO:235 is the light chain CDR1 amino acid sequence of the CTLA-4 inhibitor zalifrelimab.

SEQ ID NO:236 is the light chain CDR2 amino acid sequence of the CTLA-4 inhibitor zalifrelimab.

SEQ ID NO: 237 is the light chain CDR3 amino acid sequence of the CTLA-4 inhibitor zalifrelimab.

DETAILED DESCRIPTION OF THE INVENTION

I. Introduction

Adoptive cell therapy utilizing TILs cultured ex vivo by the rapid expansion protocol (REP) has produced successful adoptive cell therapy following host immunosuppression in patients with cancer such as melanoma. Current infusion acceptance parameters rely on readouts of the composition of TILs (e.g., CD28, CD8, or CD4 positivity), the expression of various cytokines and other markers upon stimulation in bead-based potency assays (such as IFN-γ), and on the numerical folds of expansion and viability of the REP product. Described herein are potency assays capable of providing superior performance, better control over T cell product potency, and increased biological relevance, among other improvements, in comparison to assays known in the art.

II. Definitions

Unless defined otherwise, all technical and scientific terms used herein have the same meaning as is commonly understood by one of skill in the art to which this invention belongs. All patents and publications referred to herein are incorporated by reference in their entireties.

The terms "co-administration," "co-administering," "administered in combination with," "administering in combination with," "simultaneous," and "concurrent," as used herein, encompass administration of two or more active pharmaceutical ingredients (in a preferred embodiment of the present invention, for example, a plurality of TILs) to a subject or patient so that both active pharmaceutical ingredients and/or their metabolites are present in the subject or patient at the same time. Co-administration includes simultaneous administration in separate compositions, administration at different times in separate compositions, or administration in a composition in which two or more active pharmaceutical ingredients are present. Simultaneous administration in separate compositions and administration in a composition in which both agents are present are preferred.

The term "in vivo" refers to an event that takes place in a subject's body or a patient's body.

The term "in vitro" refers to an event that takes places outside of a subject's body or patient's body. In vitro assays encompass cell-based assays in which cells alive or dead are employed and may also encompass a cell-free assay in which no intact cells are employed.

The term "ex vivo" refers to an event which involves treating or performing a procedure on a cell, tissue and/or organ which has been removed from a subject's body or a patient's body. Aptly, the cell, tissue and/or organ may be returned to the subject's body or a patient's body in a method of surgery or treatment.

The term "rapid expansion" means an increase in the number of antigen-specific TILs of at least about 3-fold (or 4-, 5-, 6-, 7-, 8-, or 9-fold) over a period of a week, more preferably at least about 10-fold (or 20-, 30-, 40-, 50-, 60-, 70-, 80-, or 90-fold) over a period of a week, or most preferably at least about 100-fold over a period of a week. A number of rapid expansion protocols are described herein.

By "tumor infiltrating lymphocytes" or "TILs" herein is meant a population of cells originally obtained as white blood cells that have left the bloodstream of a subject and migrated into a tumor. TILs include, but are not limited to, $CD8^+$ cytotoxic T cells (lymphocytes), Th1 and Th17 CD4+ T cells, natural killer cells, dendritic cells and M1 macrophages. TILs include both primary and secondary TILs. "Primary TILs" are those that are obtained from patient tissue samples as outlined herein (sometimes referred to as "freshly harvested"), and "secondary TILs" are any TIL cell populations that have been expanded or proliferated as discussed herein, including, but not limited to bulk TILs and expanded TILs ("REP TILs" or "post-REP TILs"). TIL cell populations can include genetically modified TILs.

By "population of cells" (including TILs) herein is meant a number of cells that share common traits. In general, populations generally range from $1\times10^6$ to $1\times10^{10}$ in number, with different TIL populations comprising different numbers. For example, initial growth of primary TILs in the presence of IL-2 results in a population of bulk TILs of roughly $1\times10^8$ cells. REP expansion is generally done to provide populations of $1.5\times10^9$ to $1.5\times10^{10}$ cells for infusion.

By "cryopreserved TILs" herein is meant that TILs, either primary, bulk, or expanded (REP TILs), are treated and stored in the range of about −150° C. to −60° C. General methods for cryopreservation are also described elsewhere herein, including in the Examples. For clarity, "cryopreserved TILs" are distinguishable from frozen tissue samples which may be used as a source of primary TILs.

By "thawed cryopreserved TILs" herein is meant a population of TILs that was previously cryopreserved and then treated to return to room temperature or higher, including but not limited to cell culture temperatures or temperatures wherein TILs may be administered to a patient.

TILs can generally be defined either biochemically, using cell surface markers, or functionally, by their ability to infiltrate tumors and effect treatment. TILs can be generally categorized by expressing one or more of the following biomarkers: CD4, CD8, TCR αβ. CD27, CD28, CD56, CCR7, CD45Ra, CD95, PD-1, and CD25. Additionally and alternatively, TILs can be functionally defined by their ability to infiltrate solid tumors upon reintroduction into a patient.

The term "cryopreservation media" or "cryopreservation medium" refers to any medium that can be used for cryopreservation of cells. Such media can include media comprising 7% to 10% DMSO. Exemplary media include CryoStor CS10, Hypothermasol, as well as combinations thereof. The term "CS10" refers to a cryopreservation medium which is obtained from Stemcell Technologies or from Biolife Solutions. The CS10 medium may be referred to by the trade name "CryoStor®; CS10". The CS10 medium is a serum-free, animal component-free medium which comprises DMSO.

The term "central memory T cell," "central memory T-cell," or "$T_{CM}$" refers to a subset of T cells that in the human are CD45R0+ and constitutively express CCR7 (CCR7hi or $CCR7^+$) and CD62L (CD62hi). The surface phenotype of central memory T cells also includes TCR, CD3, CD127 (IL-7R), and IL-15R. Transcription factors for central memory T cells include BCL-6, BCL-6B, MBD2, and BMI1. Central memory T cells primarily secret IL-2 and CD40L as effector molecules after TCR triggering. Central memory T cells are predominant in the CD4 compartment in blood, and in the human are proportionally enriched in lymph nodes and tonsils. Self-renewing stem memory T cells, or "$T_{SCM}$", are a subset which can differentiate into $T_{EM}$ or $T_{EM}$ cells, and are described in Gattinoni, et al., *Nature Med.* 2011, 17, 1290-97.

The term "effector memory T cell," "effector memory T-cell," or "$T_{EM}$" refers to a subset of human or mammalian T cells that, like central memory T cells, are CD45R0)+, but have lost the constitutive expression of CCR7 (CCR7lo or $CCR^-$) and are heterogeneous or low for CD62L expression (CD62Llo). The surface phenotype of central memory T cells also includes TCR, CD3, CD127 (IL-7R), and IL-15R. Transcription factors for central memory T cells include BLIMP1. Effector memory T cells rapidly secret high levels of inflammatory cytokines following antigenic stimulation, including interferon-γ, IL-4, and IL-5. Effector memory T cells are predominant in the CD8 compartment in blood, and in the human are proportionally enriched in the lung, liver, and gut. $CD8^+$ effector memory T cells carry large amounts of perforin. Terminally differentiated $T_{EM}$ cells which re-express the CD45RA marker are referred to as "$T_{EMRA}$" or "TEMRA" cells.

The term "closed system" refers to a system that is closed to the outside environment. Any closed system appropriate for cell culture methods can be employed with the methods of the present invention. Closed systems include, for example, but are not limited to, closed G-containers. Once a tumor segment is added to the closed system, the system is no opened to the outside environment until the TILs are ready to be administered to the patient.

The terms "fragmenting," "fragment," and "fragmented," as used herein to describe processes for disrupting a tumor, includes mechanical fragmentation methods such as crushing, slicing, dividing, and morcellating tumor tissue as well as any other method for disrupting the physical structure of tumor tissue.

The terms "peripheral blood mononuclear cells" and "PBMCs" refers to a peripheral blood cell having a round nucleus, including lymphocytes (T cells, B cells, NK cells) and monocytes. When used as an antigen presenting cell (PBMCs are a type of antigen-presenting cell), the peripheral blood mononuclear cells are preferably irradiated allogeneic peripheral blood mononuclear cells.

The terms "peripheral blood lymphocytes" and "PBLs" refer to T cells expanded from peripheral blood. In some embodiments, PBLs are separated from whole blood or apheresis product from a donor. In some embodiments, PBLs are separated from whole blood or apheresis product from a donor by positive or negative selection of a T cell phenotype, such as the T cell phenotype of CD3+ CD45+.

The terms "major histocompatibility complex" or "MHC" refer to a large locus on vertebrate DNA containing a set of closely linked polymorphic genes that code for cell surface proteins, known as MHC molecules, that are essential for the function of the adaptive immune system. MHC genes are highly polymorphic, and yield two major products, MHC Class I and MHC Class II molecules. MHC Class I proteins present endogenous antigens that originate from the cytoplasm. MHC Class II proteins present exogenous antigens that originate extracellularly from foreign bodies such as bacteria.

The term "MHC dominant recognition" refers to an allogeneic interaction of the T cell's TCR complex with a target cell's HLA-peptide complex. MHC dominant recognition is described in Felix and Allen, *Nat. Rev. Immunol.,* 2007, 7 (12), 942-53: Matzinger and Bevan. *Cell Immunol.,* 1977, 29 (1), 1-5, and Janeway. The Major Histocompatibility Complex and Its Functions in Immunobiology: The Immune System in Health and Disease. 5th edition. Garland Science. 2001, the disclosures of each of which are incorporated by reference herein. In MHC dominant recognition, the allogeneic MHC molecule may provide a better fit to the T cell receptor, giving a tight binding that is less dependent on the peptide that is bound to the MHC molecule.

The terms "human leukocyte antigens" or "HLA" or "HLA complex" refer to MHC molecules expressed on the surface of human cells. Human leukocyte antigens are encoded by the MHC gene complex in humans.

The terms "target cell" and "target cell line" refers to a cell that is the assay target of a T cell, such as a TIL, MIL, or PBL. In an embodiment, a target cell expresses MHC Class I and/or Class II. In an embodiment, a target cell includes a Raji cell and derivatives, variants, modifications, and progeny thereof, as well as other cells that express MHC Class I and/or Class II. In an embodiment, a target cell includes a Thp1 cell and derivatives, variants, modifications, and progeny thereof. In an embodiment, a target cell includes a Ramos cell and derivatives, variants, modifications, and progeny thereof. In an embodiment, a target cell includes a U937 cell and derivatives, variants, modifications, and progeny thereof. In an embodiment, a target cell includes a Daudi cell and derivatives, variants, modifications, and progeny thereof. In an embodiment, the target cell is irradiated. In an embodiment, the target cell is not irradiated. In an embodiment, the target cell line is a combination of any two of a Raji cell line, a Thp1 cell line, a Ramos cell line, a U937 cell line, and a Daudi cell line. In an embodiment, the target cell line is a combination of any three of a Raji cell line, a Thp1 cell line, a Ramos cell line, a U937 cell line, and a Daudi cell line. In an embodiment, the target cell line is a combination of any four of a Raji cell line, a Thp1 cell line, a Ramos cell line, a U937 cell line, and a Daudi cell line. In an embodiment, the target cell line is a combination of a Raji cell line, a Thp1 cell line, a Ramos cell line, a U937 cell line, and a Daudi cell line. In an embodiment, a target cell line is a mixed tumor target cell line. In an embodiment, a target cell line is an alloreactive target cell line. In an embodiment, a target cell line is a mixed tumor alloreactive target cell line. In an embodiment, a target cell line is a mixed tumor alloreactive target cell line comprising a combination of at least two of the following cell lines: a Raji cell line, a Ramos cell line, a Thp1 cell line, a U937 cell line, and a Daudi cell line.

The terms "Raji cell" or "Raji cell line" mean a Burkitt's lymphoma cell line with B cell characteristics, available from multiple vendors, including the American Type Culture Collection (Manassas, VA, USA), and derivatives, variants, modifications, and progeny thereof. Raji cells are described in Theofilopoulos, et al., *J. Clin. Invest.* 1976, 57, 169-182: Sobel and Bokisch, *Fed. Proc.* 1975, 34, 965; and Theofilopoulos, et al., *J. Exp. Med.* 1974, 140, 1230-1244; the disclosures of each of which is incorporated by reference herein. Raji cells lack membrane-bound immunoglobulin, but have receptors for IgG Fc, C3b, C3d, and Clq. In an embodiment, a Raji cell or a derivative, variant, modification, or progeny thereof is a target cell. In an embodiment, a Raji cell is genetically modified to express a fluorescent, phosphorescent, chemiluminescent, or bioluminescent label, such that when its cell membrane is disrupted, the fluorescent, phosphorescent, chemiluminescent, or bioluminescent label is released to the media for potential use in detection. For example, the genetic modification approach described for bioluminescence detection in U.S. Pat. No. 10,415,015, the disclosures of which are incorporated by reference herein, may be employed in the modification of a Raji cell.

The terms "Thp1 cell" or "Thp1 cell line" mean a human acute monocytic leukemia cell line, also referred to as "THP-1 cell" or "THP-1 cell line" and available from multiple vendors, including the American Type Culture Collection (Manassas, VA, USA), and derivatives, variants, modifications, and progeny thereof. The Thp1 cell line is described in Tsuchiya, et al., *Int. J. Cancer* 1980, 26, 171-176 and Bosshart and Heinzelmann, *Ann. Transl. Med.* 2016, 4 (21), 438, the disclosures of each of which are incorporated by reference herein. In an embodiment, a Thp1 cell or a derivative, variant, modification, or progeny thereof is a target cell. In an embodiment, a Thp1 cell is genetically modified to express a fluorescent, phosphorescent, chemiluminescent, or bioluminescent label, such that when its cell membrane is disrupted, the fluorescent, phosphorescent, chemiluminescent, or bioluminescent label is released to the media for potential use in detection. For example, the genetic modification approach described for bioluminescence detection in U.S. Pat. No. 10,415,015, the disclosures of which are incorporated by reference herein, may be employed in the modification of a Thp1 cell.

The terms "Ramos cell" or "Ramos cell line" mean a human Burkitt's lymphoma cell line, which is available from multiple vendors, including the American Type Culture Collection (Manassas, VA, USA), and derivatives, variants, modifications, and progeny thereof. The Ramos cell line is described in Benjamin, et al. *J. Immunol.* 1982, 129, 1336-1342, the disclosures of which are incorporated by reference herein. In an embodiment, a Ramos cell or a derivative, variant, modification, or progeny thereof is a target cell. In an embodiment, a Ramos cell is genetically modified to express a fluorescent, phosphorescent, chemiluminescent, or bioluminescent label, such that when its cell membrane is disrupted, the fluorescent, phosphorescent, chemiluminescent, or bioluminescent label is released to the media for potential use in detection. For example, the genetic modification approach described for bioluminescence detection in U.S. Pat. No. 10,415,015, the disclosures of which are incorporated by reference herein, may be employed in the modification of a Ramos cell.

The terms "U937 cell" or "U937 cell line" mean a human histiocytic lymphoma cell line, which is available from multiple vendors, including the American Type Culture Collection (Manassas, VA, USA), and derivatives, variants, modifications, and progeny thereof. The U937 cell line is described in Kraus, et al., *J. Clin. Microbiol.* 2007, 45, 3777-3780, the disclosures of which are incorporated by reference herein. In an embodiment, a U937 cell or a derivative, variant, modification, or progeny thereof is a target cell. In an embodiment, a U937 cell is genetically modified to express a fluorescent, phosphorescent, chemiluminescent, or bioluminescent label, such that when its cell membrane is disrupted, the fluorescent, phosphorescent, chemiluminescent, or bioluminescent label is released to the media for potential use in detection. For example, the genetic modification approach described for bioluminescence detection in U.S. Pat. No. 10,415,015, the disclosures of which are incorporated by reference herein, may be employed in the modification of a U937 cell.

The terms "Daudi cell" or "Daudi cell line" mean a human Burkitt's lymphoma cell line, which is available from multiple vendors, including the American Type Culture Collection (Manassas, VA, USA), and derivatives, variants, modifications, and progeny thereof. The Daudi cell line is described in Gao, et al., *J. Virol.* 1997, 71, 84-94, the disclosures of which are incorporated by reference herein. In an embodiment, a Daudi cell or a derivative, variant, modification, or progeny thereof is a target cell. In an embodiment, a Daudi cell is genetically modified to express a fluorescent, phosphorescent, chemiluminescent, or bioluminescent label, such that when its cell membrane is disrupted, the fluorescent, phosphorescent, chemiluminescent, or bioluminescent label is released to the media for potential use in detection. For example, the genetic modification approach described for bioluminescence detection in U.S. Pat. No. 10,415,015, the disclosures of which are incorporated by reference herein, may be employed in the modification of a Daudi cell.

The terms "negative control," "negative control cell," and "negative control cell line" refers to a cell that is used as a negative control for a T cell assay, including a TIL, MIL, or PBL assay. In an embodiment, a target cell lacks MHC Class I and Class II expression. In an embodiment, a target cell lacks MHC Class I expression. In an embodiment, a target cell lacks MHC or HLA Class I expression. In an embodiment, a target cell expresses MHC or HLA Class I and/or Class II at a minimal level.

The terms "K562 cell" or "K562 cell line" mean a human Caucasian chronic myelogenous leukemia cell line with lymphoblastic morphology, available from multiple vendors, including the American Type Culture Collection (Manassas, VA, USA), and derivatives, variants, modifications, and progeny thereof. K562 cells are described in Lozzio and Lozzio, *Blood.* 1975, 45, 321-34, In an embodiment, a negative control cell includes a K562 cell and derivatives, variants, modifications, and progeny thereof, as well as other cells that do not express MHC or HLA Class I or Class II.

The term "anti-CD3 antibody" refers to an antibody or variant thereof, e.g., a monoclonal antibody and including human, humanized, chimeric or murine antibodies which are directed against the CD3 receptor in the T cell antigen receptor of mature T cells. Anti-CD3 antibodies include OKT-3, also known as muromonab. Anti-CD3 antibodies also include the UHCT1 clone, also known as T3 and CD3ε. Other anti-CD3 antibodies include, for example, otelixizumab, teplizumab, and visilizumab.

The term "OKT-3" (also referred to herein as "OKT3") refers to a monoclonal antibody or biosimilar or variant thereof, including human, humanized, chimeric, or murine antibodies, directed against the CD3 receptor in the T cell antigen receptor of mature T cells, and includes commercially-available forms such as OKT-3 (30 ng/ml, MACS GMP CD3 pure, Miltenyi Biotech, Inc., San Diego, CA, USA) and muromonab or variants, conservative amino acid substitutions, glycoforms, or biosimilars thereof. The amino acid sequences of the heavy and light chains of muromonab are given in Table 1 (SEQ ID NO: 1 and SEQ ID NO: 2). A hybridoma capable of producing OKT-3 is deposited with the American Type Culture Collection and assigned the ATCC accession number CRL 8001. A hybridoma capable of producing OKT-3 is also deposited with European Collection of Authenticated Cell Cultures (ECACC) and assigned Catalogue No. 86022706.

the term IL-2 encompasses human, recombinant forms of IL-2 such as aldesleukin (PROLEUKIN, available commercially from multiple suppliers in 22 million IU per single use vials), as well as the form of recombinant IL-2 commercially supplied by CellGenix, Inc., Portsmouth, NH, USA (CELLGRO GMP) or ProSpec-Tany TechnoGene Ltd., East Brunswick, NJ, USA (Cat. No. CYT-209-b) and other commercial equivalents from other vendors. Aldesleukin (des-alanyl-1, serine-125 human IL-2) is a nonglycosylated human recombinant form of IL-2 with a molecular weight of approximately 15 kDa. The amino acid sequence of aldesleukin suitable for use in the invention is given in Table 2 (SEQ ID NO:4). The term IL-2 also encompasses pegylated forms of IL-2, as described herein, including the pegylated IL2 prodrug NKTR-214, available from Nektar Therapeutics, South San Francisco, CA, USA. NKTR-214 and pegylated IL-2 suitable for use in the invention is described in U.S. Patent Application Publication No. US 2014/0328791 A1 and International Patent Application Publication No. WO 2012/065086 A1, the disclosures of which are incorporated by reference herein. Alternative forms of conjugated IL-2 suitable for use in the invention are described in U.S. Pat. Nos. 4,766,106, 5,206,344, 5,089,261 and 4,902,502, the disclosures of which are incorporated by reference herein. Formulations of IL-2 suitable for use in the invention are described in U.S. Pat. No. 6,706,289, the disclosure of which is incorporated by reference herein.

In some embodiments, an IL-2 form suitable for use in the invention is THOR-707. Additional alternative forms of IL-2 suitable for use in the invention are described in U.S. Patent Application Publication No. US 2020/0181220 A1 and U.S. Patent Application Publication No. US 2020/0330601 A1, the disclosures of which are incorporated by reference herein. In some embodiments, an IL-2 form suitable for use in the invention is ALKS-4230). Additional alternative forms of IL-2 suitable for use in the invention are also described in U.S. Patent Application Publication No. US 2021/0038684 A1 and U.S. Pat. No. 10,183,979, the disclosures of which are incorporated by reference herein. In

TABLE 1

Amino acid sequences of muromonab.

| Identifier | Sequence (One-Letter Amino Acid Symbols) |
|---|---|
| SEQ ID NO: 1 Muromonab heavy chain | QVQLQQSGAE LARPGASVKM SCKASGYTFT RYTMHWVKQR PGQGLEWIGY INPSRGYTNY 60<br>NQKFKDKATL TTDKSSSTAY MQLSSLTSED SAVYYCARYY DDHYCLDYWG QGTTLTVSSA 120<br>KTTAPSVYPL APVCGGTTGS SVTLGCLVKG YFPEPVTLTW NSGSLSSGVH TFPAVLQSDL 180<br>YTLSSSVTVT SSTWPSQSIT CNVAHPASST KVDKKIEPRP KSCDKTHTCP PCPAPELLGG 240<br>PSVFLFPPKP KDTLMISRTP EVTCVVVDVS HEDPEVKFNW YVDGVEVHNA KTKPREEQYN 300<br>STYRVVSVLT VLHQDWLNGK EYKCKVSNKA LPAPIEKTIS KAKGQPREPQ VYTLPPSRDE 360<br>LTKNQVSLTC LVKGFYPSDI AVEWESNGQP ENNYKTTPPV LDSDGSFFLY SKLTVDKSRW 420<br>QQGNVFSCSV MHEALHNHYT QKSLSLSPGK 450 |
| SEQ ID NO: 2 Muromonab light chain | QIVLTQSPAI MSASPGEKVT MTCSASSSVS YMNWYQQKSG TSPKRWIYDT SKLASGVPAH 60<br>FRGSGSGTSY SLTISGMEAE DAATYYCQQW SSNPFTFGSG TKLEINRADT APTVSIFPPS 120<br>SEQLTSGGAS VVCFLNNFYP KDINVKWKID GSERQNGVLN SWTDQDSKDS TYSMSSTLTL 180<br>TKDEYERHNS YTCEATHKTS TSPIVKSFNR NEC 213 |

The term "IL-2" (also referred to herein as "IL2") refers to the T cell growth factor known as interleukin-2, and includes all forms of IL-2 including human and mammalian forms, conservative amino acid substitutions, glycoforms, biosimilars, and variants thereof. IL-2 is described, e.g., in Nelson, *J. Immunol.* 2004, 172, 3983-88 and Malek, *Annu. Rev. Immunol.* 2008, 26, 453-79, the disclosures of which are incorporated by reference herein. The amino acid sequence of recombinant human IL-2 suitable for use in the invention is given in Table 2 (SEQ ID NO:3). For example, some embodiments, and IL-2 form suitable for use in the invention is an interleukin 2 (IL-2) conjugate comprising: an isolated and purified IL-2 polypeptide; and a conjugating moiety that binds to the isolated and purified IL-2 polypeptide at an amino acid position selected from K35, T37, R38, T41, F42, K43, F44, Y45, E61, E62, E68, K64, P65, V69, L72, and Y107, wherein the numbering of the amino acid residues corresponds to SEQ ID NO: 1 in U.S. Patent Application Publication No. US 2020/018120. In some embodiments, the amino acid position is selected from T37, R38, T41, F42, F44, Y45, E61, E62, E68, K64, P65, V69, L72, and Y107. In some embodiments, the amino acid position is selected from T37, R38, T41, F42, F44, Y45, E61, E62, E68, P65, V69, L72, and Y107. In some embodiments, the amino acid position is selected from T37, T41, F42, F44, Y45, P65, V69, L72, and Y107. In some embodiments, the amino acid position is selected from R38 and K64. In some embodiments, the amino acid position is selected from E61, E62, and E68. In some embodiments, the amino acid position is at E62. In some embodiments, the amino acid residue selected from K35, T37, R38, T41, F42, K43, F44, Y45, E61, E62, E68, K64, P65, V69, L72, and Y107 is further mutated to lysine, cysteine, or histidine. In some embodiments, the amino acid residue is mutated to cysteine. In some embodiments, the amino acid residue is mutated to lysine. In some embodiments, the amino acid residue selected from K35, T37, R38, T41, F42, K43, F44, Y45, E61, E62, E68, K64, P65, V69, L72, and Y107 is further mutated to an unnatural amino acid. In some embodiments, the unnatural amino acid comprises N6-azidoethoxy-L-lysine (AzK), N6-propargylethoxy-L-lysine (PraK), BCN-L-lysine, norbornene lysine, TCO-lysine, methyltetrazine lysine, allyloxycarbonyllysine, 2-amino-8-oxononanoic acid, 2-amino-8-oxooctanoic acid, p-acetyl-L-phenylalanine, p-azidomethyl-L-phenylalanine (pAMF), p-iodo-L-phenylalanine, m-acetylphenylalanine, 2-amino-8-oxononanoic acid, p-propargyloxyphenylalanine, p-propargyl-phenylalanine, 3-methyl-phenylalanine, L-Dopa, fluorinated phenylalanine, isopropyl-L-phenylalanine, p-azido-L-phenylalanine, p-acyl-L-phenylalanine, p-benzoyl-L-phenylalanine, p-bromophenylalanine, p-amino-L-phenylalanine, isopropyl-L-phenylalanine, O-allyltyrosine, O-methyl-L-tyrosine, O-4-allyl-L-tyrosine, 4-propyl-L-tyrosine, phosphonotyrosine, tri-O-acetyl-GlcNAcp-serine, L-phosphoserine, phosphonoserine, L-3-(2-naphthyl)alanine, 2-amino-3-((2-((3-(benzyloxy)-3-oxopropyl)amino)ethyl)selanyl)propanoic acid, 2-amino-3-(phenylselanyl)propanoic, or selenocysteine. In some embodiments, the IL-2 conjugate has a decreased affinity to IL-2 receptor α (IL-2Rα) subunit relative to a wild-type IL-2 polypeptide. In some embodiments, the decreased affinity is about 10%, 20%, 30%, 40%, 50%, 60%, 70%, 80%, 90%, 95%, 99%, or greater than 99% decrease in binding affinity to IL-2Rα relative to a wild-type IL-2 polypeptide. In some embodiments, the decreased affinity is about 1-fold, 2-fold, 3-fold, 4-fold, 5-fold, 6-fold, 7-fold, 8-fold, 9-fold. 10-fold, 30-fold, 50-fold, 100-fold, 200-fold, 300-fold, 500-fold, 1000-fold, or more relative to a wild-type IL-2 polypeptide. In some embodiments, the conjugating moiety impairs or blocks the binding of IL-2 with IL-2Rα. In some embodiments, the conjugating moiety comprises a water-soluble polymer. In some embodiments, the additional conjugating moiety comprises a water-soluble polymer. In some embodiments, each of the water-soluble polymers independently comprises polyethylene glycol (PEG), poly(propylene glycol) (PPG), copolymers of ethylene glycol and propylene glycol, poly(oxyethylated polyol), poly(olefinic alcohol), poly(vinylpyrrolidone), poly(hydroxyalkylmethacrylamide), poly(hydroxyalkylmethacrylate), poly(saccharides), poly(α-hydroxy acid), poly(vinyl alcohol), polyphosphazene, polyoxazolines (POZ), poly(N-acryloylmorpholine), or a combination thereof. In some embodiments, each of the water-soluble polymers independently comprises PEG. In some embodiments, the PEG is a linear PEG or a branched PEG. In some embodiments, each of the water-soluble polymers independently comprises a polysaccharide. In some embodiments, the polysaccharide comprises dextran, polysialic acid (PSA), hyaluronic acid (HA), amylose, heparin, heparan sulfate (HS), dextrin, or hydroxyethyl-starch (HES). In some embodiments, each of the water-soluble polymers independently comprises a glycan. In some embodiments, each of the water-soluble polymers independently comprises polyamine. In some embodiments, the conjugating moiety comprises a protein. In some embodiments, the additional conjugating moiety comprises a protein. In some embodiments, each of the proteins independently comprises an albumin, a transferrin, or a transthyretin. In some embodiments, each of the proteins independently comprises an Fc portion. In some embodiments, each of the proteins independently comprises an Fc portion of IgG. In some embodiments, the conjugating moiety comprises a polypeptide. In some embodiments, the additional conjugating moiety comprises a polypeptide. In some embodiments, each of the polypeptides independently comprises a XTEN peptide, a glycine-rich homoamino acid polymer (HAP), a PAS polypeptide, an elastin-like polypeptide (ELP), a CTP peptide, or a gelatin-like protein (GLK) polymer. In some embodiments, the isolated and purified IL-2 polypeptide is modified by glutamylation. In some embodiments, the conjugating moiety is directly bound to the isolated and purified IL-2 polypeptide. In some embodiments, the conjugating moiety is indirectly bound to the isolated and purified IL-2 polypeptide through a linker. In some embodiments, the linker comprises a homobifunctional linker. In some embodiments, the homobifunctional linker comprises Lomant's reagent dithiobis (succinimidylpropionate) DSP. 3'3'-dithiobis(sulfosuccinimidyl proprionate) (DTSSP), disuccinimidyl suberate (DSS), bis(sulfosuccinimidyl) suberate (BS), disuccinimidyl tartrate (DST), disulfosuccinimidyl tartrate (sulfo DST), ethylene glycobis (succinimidylsuccinate) (EGS), disuccinimidyl glutarate (DSG), N,N'-disuccinimidyl carbonate (DSC), dimethyl adipimidate (DMA), dimethyl pimelimidate (DMP), dimethyl suberimidate (DMS), dimethyl-3,3'-dithiobispropionimidate (DTBP), 1,4-di-(3'-(2'-pyridyldithio) propionamido) butane (DPDPB), bismaleimidohexane (BMH), aryl halide-containing compound (DFDNB), such as e.g. 1,5-difluoro-2,4-dinitrobenzene or 1,3-difluoro-4,6-dinitrobenzene, 4,4'-difluoro-3,3'-dinitrophenylsulfone (DFDNPS), bis-[β-(4-azidosalicylamido)ethyl]disulfide (BASED), formaldehyde, glutaraldehyde, 1,4-butanediol diglycidyl ether, adipic acid dihydrazide, carbohydrazide, o-toluidine, 3,3'-dimethylbenzidine, benzidine, α,α'-p-diaminodiphenyl, diiodo-p-xylene sulfonic acid, N,N'-ethylene-bis(iodoacetamide), or N,N'-hexamethylene-bis(iodoacetamide). In some embodiments, the linker comprises a heterobifunctional linker. In some embodiments, the heterobifunctional linker comprises N-succinimidyl 3-(2-pyridyldithio)propionate (sPDP), long-chain N-succinimidyl 3-(2-pyridyldithio)propionate (LC-sPDP), water-soluble-long-chain N-succinimidyl 3-(2-pyridyldithio)propionate (sulfo-LC-sPDP), succinimidyloxycarbonyl-α-methyl-α-(2-pyridyldithio)toluene (sMPT), sulfosuccinimidyl-6-[α-methyl-α-(2-pyridyldithio)toluamido]hexanoate (sulfo-LC-sMPT), succinimidyl-4-(N-maleimidomethyl)cyclohexane-1-carboxylate (sMCC), sulfosuccinimidyl-4-(N-maleimidomethyl)cyclohexane-1-carboxylate (sulfo-sMCC), m-maleimidobenzoyl-N-hydroxysuccinimide ester (MBs), m-maleimidobenzoyl-N-hydroxysulfosuccinimide ester (sulfo-MBs), N-succinimidyl(4-iodoacteyl)aminobenzoate (sIAB), sulfosuccinimidyl(4-iodoacteyl)aminobenzoate (sulfo-sIAB), succinimidyl-4-(p-maleimidophenyl)butyrate (SMPB), sulfosuccinimidyl-4-(p-maleimidophenyl)butyrate (sulfo-sMPB), N-(γ-maleimidobutyryloxy)succinimide ester (GMBs), N-(γ-maleimidobutyryloxy)sulfosuccinimide ester (sulfo-GMBs), succinimidyl 6-((iodoacetyl)amino)hexanoate (sIAX), succinimidyl 6-[6-(((iodoacetyl)amino) hexanoyl)amino]hexanoate (slAXX), succinimidyl 4-(((iodoacetyl)amino)methyl)cyclohexane-1-carboxylate (sIAC), succinimidyl 6-(((((4-iodoacetyl)amino)methyl)cyclohexane-1-carbonyl)amino)hexanoate (sIACX), p-nitrophenyl iodoacetate (NPIA), carbonyl-reactive and sulfhydryl-reactive cross-linkers such as 4-(4-N-maleimidophenyl) butyric acid hydrazide (MPBH), 4-(N-maleimidomethyl) cyclohexane-1-carboxyl-hydrazide-8 (M2C2H), 3-(2-pyridyldithio) propionyl hydrazide (PDPH), N-hydroxysuccinimidyl-4-azidosalicylic acid (NHS-AsA), N-hydroxysulfosuccinimidyl-4-azidosalicylic acid (sulfo-NHs-AsA), sulfosuccinimidyl-(4-azidosalicylamido) hexanoate (sulfo-NHs-LC-AsA), sulfosuccinimidyl-2-(p-azidosalicylamido)ethyl-1,3'-dithiopropionate (sAsD), N-hydroxysuccinimidyl-4-azidobenzoate (HsAB), N-hydroxysulfosuccinimidyl-4-azidobenzoate (sulfo-HsAB), N-succinimidyl-6-(4$^{+}$-azido-2'-nitrophenyl amino)hexanoate (SANPAH), sulfosuccinimidyl-6-(4$^{+}$-azido-2'-nitrophenylamino)hexanoate (sulfo-sANPAH). N-5-azido-2-nitrobenzoyloxysuccinimide (ANB-NOs), sulfosuccinimidyl-2-(m-azido-o-nitrobenzamido)-ethyl-1,3'-dithiopropionate (sAND), N-succinimidyl-4 (4-azidophenyl) 1,3'-dithiopropionate (sADP), N-sulfosuccinimidyl(4-azidophenyl)-1,3'-dithiopropionate (sulfo-SADP), sulfosuccinimidyl 4-(p-azidophenyl)butyrate (sulfo-sAPB), sulfosuccinimidyl 2-(7-azido-4-methylcoumarin-3-acetamide)ethyl-1,3'-dithiopropionate (sAED), sulfosuccinimidyl 7-azido-4-methylcoumain-3-acetate (sulfo-sAMCA), p-nitrophenyl diazopyruvate (pNPDP), p-nitrophenyl-2-diazo-3,3,3-trifluoropropionate (PNP-DTP), 1-(ρ-Azidosalicylamido)-4-(iodoacetamido) butane (AsIB), N-[4-(ρ-azidosalicylamido) butyl]-3'-(2'-pyridyldithio) propionamide (APDP), benzophenone-4-iodoacetamide, p-azidobenzoyl hydrazide (ABH), 4-(ρ-azidosalicylamido)butylamine (AsBA), or p-azidophenyl glyoxal (APG). In some embodiments, the linker comprises a cleavable linker, optionally comprising a dipeptide linker. In some embodiments, the dipeptide linker comprises Val-Cit, Phe-Lys, Val-Ala, or Val-Lys. In some embodiments, the linker comprises a non-cleavable linker. In some embodiments, the linker comprises a maleimide group, optionally comprising maleimidocaproyl (mc), succinimidyl-4-(N-maleimidomethyl)cyclohexane-1-carboxylate (sMCC), or sulfosuccinimidyl-4-(N-maleimidomethyl) cyclohexane-1-carboxylate (sulfo-sMCC). In some embodiments, the linker further comprises a spacer. In some embodiments, the spacer comprises p-aminobenzyl alcohol (PAB), p-aminobenzyoxycarbonyl (PABC), a derivative, or an analog thereof. In some embodiments, the conjugating moiety is capable of extending the serum half-life of the IL-2 conjugate. In some embodiments, the additional conjugating moiety is capable of extending the serum half-life of the IL-2 conjugate. In some embodiments, the IL-2 form suitable for use in the invention is a fragment of any of the IL-2 forms described herein. In some embodiments, the IL-2 form suitable for use in the invention is pegylated as disclosed in U.S. Patent Application Publication No. US 2020/0181220 A1 and U.S. Patent Application Publication No. US 2020/0330601 A1. In some embodiments, the IL-2 form suitable for use in the invention is an IL-2 conjugate comprising: an IL-2 polypeptide comprising an N6-azidoethoxy-L-lysine (AzK) covalently attached to a conjugating moiety comprising a polyethylene glycol (PEG), wherein: the IL-2 polypeptide comprises an amino acid sequence having at least 80% sequence identity to SEQ ID NO: 1 in U.S. Patent Application Publication No. 2020/0330601 (listed herein as SEQ ID NO:5 in Table 2); and the AzK substitutes for an amino acid at position K35, F42, F44, K43, E62, P65, R38, T41, E68, Y45, V69, or L72 in reference to the amino acid positions within SEQ ID NO: 1 in U.S. Patent Publication Application No. US 2020/0330601 (listed herein as SEQ ID NO: 5 in Table 2). In some embodiments, the IL-2 polypeptide comprises an N-terminal deletion of one residue relative to SEQ ID NO: 1 in U.S. Patent Publication Application No. US 2020/0330601 (listed herein as SEQ ID NO:5 in Table 2). In some embodiments, the IL-2 form suitable for use in the invention lacks IL-2R alpha chain engagement but retains normal binding to the intermediate affinity IL-2R beta-gamma signaling complex. In some embodiments, an IL-2 form suitable for use in the invention is ALKS-4230. A form of IL-2 suitable for use in the invention is described in U.S. Patent Application Publication No. US 2021/0038684 A1 as SEQ ID NO: 1 (listed herein as SEQ ID NO:6 in Table 2). In some embodiments, an IL-2 form suitable for use in the invention is a fusion protein comprising amino acids 24-452 of SEQ ID NO:2 in U.S. Pat. No. 10,183,979 (SEQ ID NO:2 in U.S. Pat. No. 10,183,979 listed herein as SEQ ID NO: 7 in Table 2). In some embodiments, an IL-2 form suitable for use in the invention is a fusion protein comprising amino acids 24-452 of SEQ ID NO: 2 in U.S. Pat. No. 10,183,979 or an amino acid sequence homologous to amino acids 24-452 of SEQ ID NO:2 in U.S. Pat. No. 10,183,979 with at least 98% amino acid sequence identity over the entire length of amino acids 24-452 of SEQ ID NO:2 in U.S. Pat. No. 10,183,979 and having the receptor antagonist activity of amino acids 24-452 of SEQ ID NO: 2 in U.S. Pat. No. 10,183,979. Optionally, in some embodiments, an IL-2 form suitable for use in the invention is a fusion protein comprising a first fusion partner that is linked to a second fusion partner by a mucin domain polypeptide linker, wherein the first fusion partner is IL-1Rα or a protein having at least 98% amino acid sequence identity to IL-1Rα and having the receptor antagonist activity of IL-Rα, and wherein the second fusion partner comprises all or a portion of an immunoglobulin comprising an Fc region, wherein the mucin domain polypeptide linker comprises SEQ ID NO:14 in U.S. Pat. No. 10,183,979 (listed herein as SEQ ID NO:8 in Table 2) or an amino acid sequence having at least 90% sequence identity to SEQ ID NO:14 in U.S. Pat. No. 10,183,979 (listed herein as SEQ ID NO:8 in Table 2) and wherein the half-life of the fusion protein is improved as compared to a fusion of the first fusion partner to the second fusion partner in the absence of the mucin domain polypeptide linker.

TABLE 2

Amino acid sequences of interleukins.

| Identifier | Sequence (One-Letter Amino Acid Symbols) |
|---|---|
| SEQ ID NO: 3<br>recombinant<br>human IL-2<br>(rhIL-2) | MAPTSSSTKK TQLQLEHLLL DLQMILNGIN NYKNPKLTRM LTFKFYMPKK ATELKHLQCL 60<br>EEELKPLEEV LNLAQSKNFH LRPRDLISNI NVIVLELKGS ETTFMCEYAD ETATIVEFLN 120<br>RWITFCQSII STLT 134 |

TABLE 2-continued

Amino acid sequences of interleukins.

| Identifier | Sequence (One-Letter Amino Acid Symbols) | |
|---|---|---|
| SEQ ID NO: 4<br>Aldesleukin | PTSSSTKKTQ LQLEHLLLDL QMILNGINNY KNPKLTRMLT FKFYMPKKAT ELKHLQCLEE<br>ELKPLEEVLN LAQSKNFHLR PRDLISNINV IVLELKGSET TFMCEYADET ATIVEFLNRW<br>ITFSQSIIST LT | 60<br>120<br>132 |
| SEQ ID NO: 5<br>IL-2 form | APTSSSTKKT QLQLEHLLLD LQMILNGINN YKNPKLTRML TFKFYMPKKA TELKHLQCLE<br>EELKPLEEVL NLAQSKNFHL RPRDLISNIN VIVLELKGSE TTFMCEYADE TATIVEFLNR<br>WITFCQSIIS TLT | 60<br>120<br>133 |
| SEQ ID NO: 6<br>IL-2 form | SKNFELRPRD LISNINVIVL ELKGSETTFM CEYADETATI VEFLNRWITF SQSIISTLTG<br>GSSSTKKTQL QLEHLLLDLQ MILNGINNYK NPKLTRMLTF KFYMPKKATE LKHLQCLEEE<br>LKPLEEVLNL AQGSGGGSEL CDDDPPEIPH ATFKAMAYKE GTMLNCECKR GFRRIKSGSL<br>YMLCTGNSSH SSWDNQCQCT SSATRNTTKQ VTPQPEEQKE RKTTEMQSPM QPVDQASLPG<br>HCREPPPWEN EATERIYHFV VGQMVYYQCV QGYRALHRGP AESVCKMTHG KTRWTQPQLI<br>CTG | 60<br>120<br>180<br>240<br>300<br>303 |
| SEQ ID NO: 7<br>IL-2 form | MDAMKRGLCC VLLLCGAVFV SARRPSGRKS SKMQAFRIWD VNQKTFYLRN NQLVAGYLQG<br>PNVNLEEKID VVPIEPHALF LGIHGGKMCL SCVKSGDETR LQLEAVNITD LSENRKQDKR<br>FAFIRSDSGP TTSFESAACP GWFLCTAMEA DQPVSLTNMP DEGVMVTKFY FQEDESGSGG<br>ASSESSASSD GPHPVITESR ASSESSASSD GPHPVITESR EPKSSDKTKT CPPCPAPELL<br>GGPSVFLFPP KPKDTLMISR TPEVTCVVVD VSHEDPEVKF NWYVDGVEVH NAKTKPREEQ<br>YNSTYRVVSV LTVLHQDWLN GKEYKCKVSN KALPAPIEKT ISKAKGQPRE PQVYTLPPSR<br>EEMTKNQVSL TCLVKGFYPS DIAVEWESNG QPENNYKTTP PVLDSDGSFF LYSKLTVDKS<br>RWQQGNVFSC SVMHEALHNH YTQKSLSLSP GK | 60<br>120<br>180<br>240<br>300<br>360<br>420<br>452 |
| SEQ ID NO: 8<br>mucin domain<br>polypeptide | SESSASSDGP HPVITP | 16 |
| SEQ ID NO: 9<br>recombinant<br>human IL-4<br>(rhIL-4) | MKKCDITLQE IIKTLNSLTE QKTLCTELTV TDIFAASKNT TEKETFCRAA TVLRQFYSHH<br>EKDTRCLGAT AQQFHRHKQL IRFLKRLDRN LWGLAGLNSC PVKEANQSTL ENFLERLKTI<br>MREKYSKCSS | 60<br>120<br>130 |
| SEQ ID NO: 10<br>recombinant<br>human IL-7<br>(rhIL-7) | MDCDIEGKDG KQYESVLMVS IDQLLDSMKE IGSNCLNNEF NFFKRHICDA NKEGMFLFRA<br>ARKLRQFLKM NSTGDFDLHL LKVSEGTTIL LNCTGQVKGR KPAALGEAQP TKSLEENKSL<br>KEQKKLNDLC FLKRLLQEIK TCWNKILMGT KEH | 60<br>120<br>153 |
| SEQ ID NO: 11<br>recombinant<br>human IL-15<br>(rhIL-15) | MNWVNVISDL KKIEDLIQSM HIDATLYTES DVHPSCKVTA MKCFLLELQV ISLESGDASI<br>HDTVENLIIL ANNSLSSNGN VTESGCKECE ELEEKNIKEF LQSFVHIVQM FINTS | 60<br>115 |
| SEQ ID NO: 12<br>recombinant<br>human IL-21<br>(rhIL-21) | MQDRHMIRMR QLIDIVDQLK NYVNDLVPEF LPAPEDVETN CEWSAFSCFQ KAQLKSANTG<br>NNERIINVSI KKLKRKPPST NAGRRQKHRL TCPSCDSYEK KPPKEFLERF KSLLQKMIHQ<br>HLSSRTHGSE DS | 60<br>120<br>132 |

In some embodiments, an IL-2 form suitable for use in the invention includes a antibody cytokine engrafted protein comprises a heavy chain variable region ($V_H$), comprising complementarity determining regions HCDR1, HCDR2, HCDR3: a light chain variable region ($V_L$), comprising LCDR1, LCDR2, LCDR3; and an IL-2 molecule or a fragment thereof engrafted into a CDR of the $V_H$ or the $V_L$, wherein the antibody cytokine engrafted protein preferentially expands T effector cells over regulatory T cells. In an embodiment, the antibody cytokine engrafted protein comprises a heavy chain variable region ($V_H$), comprising complementarity determining regions HCDR1, HCDR2, HCDR3; a light chain variable region ($V_L$), comprising LCDR1, LCDR2, LCDR3; and an IL-2 molecule or a fragment thereof engrafted into a CDR of the $V_H$ or the $V_L$, wherein the IL-2 molecule is a mutein, and wherein the antibody cytokine engrafted protein preferentially expands T effector cells over regulatory T cells. In an embodiment, the IL-2 regimen comprises administration of an antibody described in U.S. Patent Application Publication No. US 2020/0270334 A1, the disclosures of which are incorporated by reference herein. In an embodiment, the antibody cytokine engrafted protein comprises a heavy chain variable region ($V_H$), comprising complementarity determining regions HCDR1, HCDR2, HCDR3; a light chain variable region ($V_L$), comprising LCDR1, LCDR2, LCDR3; and an IL-2 molecule or a fragment thereof engrafted into a CDR of the $V_H$ or the $V_L$, wherein the IL-2 molecule is a mutein, wherein the antibody cytokine engrafted protein preferentially expands T effector cells over regulatory T cells, and wherein the antibody further comprises an IgG class heavy chain and an IgG class light chain selected from the group consisting of: a IgG class light chain comprising SEQ ID NO:69 in U.S. Patent Application Publication No. US 2020/0270334 A1 and a IgG class heavy chain comprising SEQ ID NO:53 in U.S. Patent Application Publication No. US 2020/0270334 A1: a IgG class light chain comprising SEQ ID NO: 37 in U.S. Patent Application Publication No. US 2020/0270334 A1 and a IgG class heavy chain comprising SEQ ID NO:21 in U.S. Patent Application Publication No. US 2020/0270334 A1: a IgG class light chain comprising SEQ ID NO:69 in U.S. Patent Application Publication No. US 2020/0270334 A1 and a IgG class heavy chain comprising SEQ ID NO:21 in U.S. Patent Application Publication No. US 2020/0270334 A1; and a IgG class light chain comprising SEQ ID NO:37 and a IgG class heavy chain comprising SEQ ID NO: 53 in U.S. Patent Application Publication No. US 2020/0270334 A1.

In an embodiment, an IL-2 molecule or a fragment thereof is engrafted into HCDR1 of the $V_H$, wherein the IL-2 molecule is a mutein. In an embodiment, an IL-2 molecule or a fragment thereof is engrafted into HCDR2 of the $V_H$, wherein the IL-2 molecule is a mutein. In an embodiment, an IL-2 molecule or a fragment thereof is engrafted into HCDR3 of the $V_H$, wherein the IL-2 molecule is a mutein. In an embodiment, an IL-2 molecule or a fragment thereof is engrafted into LCDR1 of the $V_L$, wherein the IL-2 molecule is a mutein. In an embodiment, an IL-2 molecule or a fragment thereof is engrafted into LCDR2 of the $V_L$, wherein the IL-2 molecule is a mutein. In an embodiment, an IL-2 molecule or a fragment thereof is engrafted into LCDR3 of the $V_L$, wherein the IL-2 molecule is a mutein.

The insertion of the IL-2 molecule can be at or near the N-terminal region of the CDR, in the middle region of the CDR or at or near the C-terminal region of the CDR. In some embodiments, the antibody cytokine engrafted protein comprises an IL-2 molecule incorporated into a CDR, wherein the IL2 sequence does not frameshift the CDR sequence. In some embodiments, the antibody cytokine engrafted protein comprises an IL-2 molecule incorporated into a CDR, wherein the IL-2 sequence replaces all or part of a CDR sequence. The replacement by the IL-2 molecule can be the N-terminal region of the CDR, in the middle region of the CDR or at or near the C-terminal region the CDR. A replacement by the IL-2 molecule can be as few as one or two amino acids of a CDR sequence, or the entire CDR sequences.

In some embodiments, an IL-2 molecule is engrafted directly into a CDR without a peptide linker, with no additional amino acids between the CDR sequence and the IL-2 sequence. In some embodiments, an IL-2 molecule is engrafted indirectly into a CDR with a peptide linker, with one or more additional amino acids between the CDR sequence and the IL-2 sequence.

In some embodiments, the IL-2 molecule described herein is an IL-2 mutein. In some instances, the IL-2 mutein comprising an R67A substitution. In some embodiments, the IL-2 mutein comprises the amino acid sequence SEQ ID NO:4 or SEQ ID NO:6 in U.S. Patent Application Publication No. 2020/0270334 A1. In some embodiments, the IL-2 mutein comprises an amino acid sequence in Table 1 in U.S. Patent Application Publication No. US 2020/0270334 A1, the disclosure of which is incorporated by reference herein.

In an embodiment, the antibody cytokine engrafted protein comprises an HCDR1 selected from the group consisting of SEQ ID NO:7. SEQ ID NO: 10. SEQ ID NO: 13 and SEQ ID NO:16 of U.S. Patent Application Publication No. US 2020/0270334 A1. In an embodiment, the antibody cytokine engrafted protein comprises an HCDR1 selected from the group consisting of SEQ ID NO:7. SEQ ID NO: 10. SEQ ID NO: 13 and SEQ ID NO: 16, and an HCDR2 selected from the group consisting of SEQ ID NO:8. SEQ ID NO: 11. SEQ ID NO: 14, and SEQ ID NO:17 of U.S. Patent Application Publication No. 2020/0270334 A1. In an embodiment, the antibody cytokine engrafted protein comprises an HCDR1 selected from the group consisting of SEQ ID NO: 7. SEQ ID NO: 10. SEQ ID NO: 13 and SEQ ID NO:16, an HCDR2 selected from the group consisting of SEQ ID NO:8. SEQ ID NO: 11. SEQ ID NO: 14, and SEQ ID NO: 17, and an HCDR3 selected from the group consisting of SEQ ID NO: 9. SEQ ID NO: 12. SEQ ID NO: 15, and SEQ ID NO: 18 of U.S. Patent Application Publication No. US 2020/0270334 A1. In an embodiment, the antibody cytokine engrafted protein comprises a $V_H$ region comprising the amino acid sequence of SEQ ID NO: 19 of U.S. Patent Application Publication No. US 2020/0270334 A1. In an embodiment, the antibody cytokine engrafted protein comprises a heavy chain comprising the amino acid sequence of SEQ ID NO:21 of U.S. Patent Application Publication No. US 2020/0270334 A1. In an embodiment, the antibody cytokine engrafted protein comprises a $V_L$ region comprising the amino acid sequence of SEQ ID NO:35 of U.S. Patent Application Publication No. US 2020/0270334 A1. In an embodiment, the antibody cytokine engrafted protein comprises a light chain comprising the amino acid sequence of SEQ ID NO:37 of U.S. Patent Application Publication No. US 2020/0270334 A1. In an embodiment, the antibody cytokine engrafted protein comprises a $V_H$ region comprising the amino acid sequence of SEQ ID NO: 19 and a $V_L$ region comprising the amino acid sequence of SEQ ID NO: 35 of U.S. Patent Application Publication No. 2020/0270334 A1. In an embodiment, the antibody cytokine engrafted protein comprises a heavy chain region comprising the amino acid sequence of SEQ ID NO:21 and a light chain region comprising the amino acid sequence of SEQ ID NO:37 of U.S. Patent Application Publication No. 2020/0270334 A1. In an embodiment, the antibody cytokine engrafted protein comprises IgG.IL2R67A.H1 of U.S. Patent Application Publication No. 2020/0270334 A1. In an embodiment, the antibody components of the antibody cytokine engrafted protein described herein comprise immunoglobulin sequences, framework sequences, or CDR sequences of palivizumab.

In some embodiments, the antibody cytokine engrafted protein described herein has a longer serum half-life that a wild-type IL-2 molecule such as, but not limited to, aldeskeukin (Proleukin®) or a comparable molecule.

In an embodiment, the antibody cytokine engrafted protein described herein has a sequence as set forth in Table 3.

TABLE 3

Sequences of exemplary palivizumab antibody-IL-2 engrafted proteins.

| Identifier in US 2020/0270334 | Identifier | Sequence (One-Letter Amino Acid Symbols) | |
|---|---|---|---|
| SEQ ID | SEQ ID | MYRMQLLSCI ALSLALVTNS APTSSSTKKT QLQLEHLLLD LQMILNGINN YKNPKLTRML | 60 |
| NO: 2 | NO: 13 | TFKFYMPKKA TELKHLQCLE EELKPLEEVL NLAQSKNFHL RPRDLISNIN VIVLELKGSE | 120 |
| IL-2 | IL-2 | TTFMCEYADE TATIVEFLNR WITFCQSIIS TLT | 153 |

TABLE 3-continued

Sequences of exemplary palivizumab antibody-IL-2 engrafted proteins.

| Identifier in US 2020/0270334 | Identifier | Sequence (One-Letter Amino Acid Symbols) | |
|---|---|---|---|
| SEQ ID NO: 4 IL-2 mutein | SEQ ID NO: 14 IL-2 mutein | APTSSSTKKT QLQLEHLLLD LQMILNGINN YKNPKLTAML TFKFYMPKKA TELKHLQCLE<br>EELKPLEEVL NLAQSKNFHL RPRDLISNIN VIVLELKGSE TTFMCEYADE TATIVEFLNR<br>WITFCQSIIS TLT | 60<br>120<br>133 |
| SEQ ID NO: 6 IL-2 mutein | SEQ ID NO: 15 IL-2 mutein | APTSSSTKKT QLQLEHLLLD LQMILNGINN YKNPKLTRML TAKFYMPKKA TELKHLQCLE<br>EELKPLEEVL NLAQSKNFHL RPRDLISNIN VIVLELKGSE TTFMCEYADE TATIVEFLNR<br>WITFCQSIIS TLT | 60<br>120<br>133 |
| SEQ ID NO: 7 HCDR1_IL-2 | SEQ ID NO: 16 HCDR1_IL-2 | GFSLAPTSSS TKKTQLQLEH LLLDLQMILN GINNYKNPKL TAMLTFKFYM PKKATELKHL<br>QCLEEELKPL EEVLNLAQSK NFHLRPRDLI SNINVIVLEL KGSETTFMCE YADETATIVE<br>FLNRWITFCQ SIISTLTSTS GMSVG | 60<br>120<br>145 |
| SEQ ID NO: 8 HCDR2 | SEQ ID NO: 17 HCDR2 | DIWWDDKKDY NPSLKS | 16 |
| SEQ ID NO: 9 HCDR3 | SEQ ID NO: 18 HCDR3 | SMITNWYFDV | 10 |
| SEQ ID NO: 10 HCDR1_IL-2 kabat | SEQ ID NO: 19 HCDR1_IL-2 kabat | APTSSSTKKT QLQLEHLLLD LQMILNGINN YKNPKLTAML TFKFYMPKKA TELKHLQCLE<br>EELKPLEEVL NLAQSKNFHL RPRDLISNIN VIVLELKGSE TTFMCEYADE TATIVEFLNR<br>WITFCQSIIS TLTSTSGMSV G | 60<br>120<br>141 |
| SEQ ID NO: 11 HCDR2 kabat | SEQ ID NO: 20 HCDR2 kabat | DIWWDDKKDY NPSLKS | 16 |
| SEQ ID NO: 12 HCDR3 kabat | SEQ ID NO: 21 HCDR3 kabat | SMITNWYFDV | 10 |
| SEQ ID NO: 13 HCDR1_IL-2 clothia | SEQ ID NO: 22 HCDR1_IL-2 clothia | GFSLAPTSSS TKKTQLQLEH LLLDLQMILN GINNYKNPKL TAMLTFKFYM PKKATELKHL<br>QCLEEELKPL EEVLNLAQSK NFHLRPRDLI SNINVIVLEL KGSETTFMCE YADETATIVE<br>FLNRWITFCQ SIISTLTSTS GM | 60<br>120<br>142 |
| SEQ ID NO: 14 HCDR2 clothia | SEQ ID NO: 23 HCDR2 clothia | WWDDK | 5 |
| SEQ ID NO: 15 HCDR3 clothia | SEQ ID NO: 24 HCDR3 clothia | SMITNWYFDV | 10 |
| SEQ ID NO: 16 HCDR1_IL-2 IMGT | SEQ ID NO: 25 HCDR1_IL-2 IMGT | GFSLAPTSSS TKKTQLQLEH LLLDLQMILN GINNYKNPKL TAMLTFKFYM PKKATELKHL<br>QCLEEELKPL EEVLNLAQSK NFHLRPRDLI SNINVIVLEL KGSETTFMCE YADETATIVE<br>FLNRWITFCQ SIISTLTSTS GMS | 60<br>120<br>143 |
| SEQ ID NO: 17 HCDR2 IMGT | SEQ ID NO: 26 HCDR2 IMGT | IWWDDKK | 7 |
| SEQ ID NO: 18 HCDR3 IMGT | SEQ ID NO: 27 HCDR3 IMGT | ARSMITNWYF DV | 12 |
| SEQ ID NO: 19 VH | SEQ ID NO: 28 VH | QVTLRESGPA LVKPTQTLTL TCTFSGFSLA PTSSSTKKTQ LQLEHLLLDL QMILNGINNY<br>KNPKLTAMLT FKFYMPKKAT ELKHLQCLEE ELKPLEEVLN LAQSKNFHLR PRDLISNINV<br>IVLELKGSET TFMCEYADET ATIVEFLNRW ITFCQSIIST LTSTSGMSVG WIRQPPGKAL<br>EWLADIWWDD KKDYNPSLKS RLTISKDTSK NQVVLKVTNM DPADTATYYC ARSMITNWYF<br>DVWGAGTTVT VSS | 60<br>120<br>180<br>240<br>253 |

TABLE 3-continued

Sequences of exemplary palivizumab antibody-IL-2 engrafted proteins.

| Identifier in US 2020/ 0270334 | Identifier | Sequence (One-Letter Amino Acid Symbols) | |
|---|---|---|---|
| SEQ ID NO: 21 Heavy chain | SEQ ID NO: 29 Heavy chain | QMILNGINNY KNPKLTAMLT FKFYMPKKAT ELKHLQCLEE ELKPLEEVLN LAQSKNFHLR<br>PRDLISNINV IVLELKGSET TFMCEYADET ATIVEFLNRW ITFCQSIIST LTSTSGMSVG<br>WIRQPPGKAL EWLADIWWDD KKDYNPSLKS RLTISKDTSK NQVVLKVTNM DPADTATYYC<br>ARSMITNWYF DVWGAGTTVT VSSASTKGPS VFPLAPSSKS TSGGTAALGC LVKDYFPEPV<br>TVSWNSGALT SGVHTFPAVL QSSGLYSLSS VVTVPSSSLG TQTYICNVNH KPSNTKVDKR<br>VEPKSCDKTH TCPPCPAPEL LGGPSVFLFP PKPKDTLMIS RTPEVTCVVV AVSHEDPEVK<br>FNWYVDGVEV HNAKTKPREE QYNSTYRVVS VLTVLHQDWL NGKEYKCKVS NKALAAPIEK<br>TISKAKGQPR EPQVYTLPPS RBEMTKNQVS LTCLVKGFYP SDIAVEWESN GQPENNYKTT<br>PPVLDSDGSF FLYSKLTVDK SRWQQGNVFS CSVMHEALHN HYTQKSLSLS PGK | 60<br>120<br>180<br>240<br>300<br>360<br>420<br>480<br>533 |
| SEQ ID NO: 26 LCDR1 kabat | SEQ ID NO: 30 LCDR1 kabat | KAQLSVGYMH | 10 |
| SEQ ID NO: 27 LCDR2 kabat | SEQ ID NO: 31 LCDR2 kabat | DTSKLAS | 7 |
| SEQ ID NO: 28 LCDR3 kabat | SEQ ID NO: 32 LCDR3 kabat | FQGSGYPFT | 9 |
| SEQ ID NO: 29 LCDR1 chothia | SEQ ID NO: 33 LCDR1 chothia | QLSVGY | 6 |
| SEQ ID NO: 30 LCDR2 chothia | SEQ ID NO: 34 LCDR2 chothia | DTS | 3 |
| SEQ ID NO: 31 LCDR3 chothia | SEQ ID NO: 35 LCDR3 chothia | GSGYPF | 6 |
| SEQ ID NO: 35 VL | SEQ ID NO: 36 VL | DIQMTQSPST LSASVGDRVT ITCKAQLSVG YMHWYQQKPG KAPKLLIYDT SKLASGVPSR<br>FSGSGSGTEF TLTISSLQPD DFATYYCFQG SGYPFTFGGG TKLEIK | 60<br>106 |
| SEQ ID NO: 37 Light chain | SEQ ID NO: 37 Light chain | DIQMTQSPST LSASVGDRVT ITCKAQLSVG YMHWYQQKPG KAPKLLIYDT SKLASGVPSR<br>FSGSGSGTEF TLTISSLQPD DFATYYCFQG SGYPFTFGGG TKLEIKRTVA APSVFIFPPS<br>DEQLKSGTAS VVCLLNNFYP REAKVQWKVD NALQSGNSQE SVTEQDSKDS TYSLSSTLTL<br>SKADYEKHKV YACEVTHQGL SSPVTKSFNR GEC | 60<br>120<br>180<br>213 |
| SEQ ID NO: 53 Light chain | SEQ ID NO: 38 Light chain | QVTLRESGPA LVKPTQTLTL TCTFSGFSLA PTSSSTKKTQ LQLEHLLLDL QMILNGINNY<br>KNPKLTRMLT AKFYMPKKAT ELKHLQCLEE ELKPLEEVLN LAQSKNFHLR PRDLISNINV<br>IVLELKGSET TFMCEYADET ATIVEFLNRW ITFCQSIIST LTSTSGMSVG WIRQPPGKAL<br>EWLADIWWDD KKDYNPSLKS RLTISKDTSK NQVVLKVTNM DPADTATYYC ARSMITNWYF<br>DVWGAGTTVT VSSASTKGPS VFPLAPSSKS TSGGTAALGC LVKDYFPEPV TVSWNSGALT<br>SGVHTFPAVL QSSGLYSLSS VVTVPSSSLG TQTYICNVNH KPSNTKVDKR VEPKSCDKTH<br>TCPPCPAPEL LGGPSVFLFP PKPKDTLMIS RTPEVTCVVV AVSHEDPEVK FNWYVDGVEV<br>HNAKTKPREE QYNSTYRVVS VLTVLHQDWL NGKEYKCKVS NKALAAPIEK TISKAKGQPR<br>EPQVYTLPPS REEMTKNQVS LTCLVKGFYP SDIAVEWESN GQPENNYKTT PPVLDSDGSF<br>FLYSKLTVDK SRWQQGNVFS CSVMHEALHN HYTQKSLSLS PGK | 60<br>120<br>180<br>240<br>300<br>360<br>420<br>480<br>540<br>583 |
| SEQ ID NO: 69 Light chain | SEQ ID NO: 39 Light chain | DIQMTQSPST LSASVGDRVT ITCKAQLSVG YMHWYQQKPG KAPKLLIYDT SKLASGVPSR<br>FSGSGSGTEF TLTISSLQPD DFATYYCFQG SGYPFTFGGG TKLEIKRTVA APSVFIFPPS<br>DEQLKSGTAS VVCLLNNFYP REAKVQWKVD NALQSGNSQE SVTEQDSKDS TYSLSSTLTL<br>SKADYEKHKV YACEVTHQGL SSPVTKSFNR GEC | 60<br>120<br>180<br>213 |

The term "IL-4" (also referred to herein as "IL4") refers to the cytokine known as interleukin 4, which is produced by Th2 T cells and by eosinophils, basophils, and mast cells. IL-4 regulates the differentiation of naïve helper T cells (Th0 cells) to Th2 T cells. Steinke and Borish, *Respir. Res.* 2001, 2, 66-70. Upon activation by IL-4, Th2 T cells subsequently produce additional IL-4 in a positive feedback loop. IL-4 also stimulates B cell proliferation and class II MHC expression, and induces class switching to IgE and $IgG_1$ expression from B cells. Recombinant human IL-4 suitable for use in the invention is commercially available from multiple suppliers, including ProSpec-Tany TechnoGene Ltd., East Brunswick, NJ, USA (Cat. No. CYT-211) and ThermoFisher Scientific, Inc., Waltham, MA, USA (human IL-15 recombinant protein, Cat. No. Gibco CTP0043). The amino acid sequence of recombinant human IL-4 suitable for use in the invention is given in Table 2 (SEQ ID NO:9).

The term "IL-7" (also referred to herein as "IL7") refers to a glycosylated tissue-derived cytokine known as interleukin 7, which may be obtained from stromal and epithelial cells, as well as from dendritic cells. Fry and Mackall. *Blood* 2002, 99, 3892-904. IL-7 can stimulate the development of T cells. IL-7 binds to the IL-7 receptor, a heterodimer consisting of IL-7 receptor alpha and common gamma chain receptor, which in a series of signals important for T cell development within the thymus and survival within the periphery. Recombinant human IL-7 suitable for use in the invention is commercially available from multiple suppliers, including ProSpec-Tany TechnoGene Ltd., East Brunswick, NJ, USA (Cat. No. CYT-254) and ThermoFisher Scientific. Inc., Waltham, MA, USA (human IL-15 recombinant protein. Cat. No. Gibco PHC0071). The amino acid sequence of recombinant human IL-7 suitable for use in the invention is given in Table 2 (SEQ ID NO:10).

The term "IL-15" (also referred to herein as "IL15") refers to the T cell growth factor known as interleukin-15, and includes all forms of IL-2 including human and mammalian forms, conservative amino acid substitutions, glycoforms, biosimilars, and variants thereof. IL-15 is described, e.g., in Fehniger and Caligiuri. *Blood* 2001, 97, 14-32, the disclosure of which is incorporated by reference herein. IL-15 shares β and γ signaling receptor subunits with IL-2. Recombinant human IL-15 is a single, non-glycosylated polypeptide chain containing 114 amino acids (and an N-terminal methionine) with a molecular mass of 12.8 kDa. Recombinant human IL-15 is commercially available from multiple suppliers, including ProSpec-Tany TechnoGene Ltd., East Brunswick, NJ, USA (Cat. No. CYT-230)-b) and ThermoFisher Scientific. Inc., Waltham. MA, USA (human IL-15 recombinant protein. Cat. No. 34-8159-82). The amino acid sequence of recombinant human IL-15 suitable for use in the invention is given in Table 2 (SEQ ID NO:11).

The term "IL-21" (also referred to herein as "IL21") refers to the pleiotropic cytokine protein known as interleukin-21, and includes all forms of IL-21 including human and mammalian forms, conservative amino acid substitutions, glycoforms, biosimilars, and variants thereof. IL-21 is described, e.g., in Spolski and Leonard. *Nat. Rev. Drug. Disc.* 2014, 13, 379-95, the disclosure of which is incorporated by reference herein. IL-21 is primarily produced by natural killer T cells and activated human $CD4^+$ T cells. Recombinant human IL-21 is a single, non-glycosylated polypeptide chain containing 132 amino acids with a molecular mass of 15.4 kDa. Recombinant human IL-21 is commercially available from multiple suppliers, including ProSpec-Tany TechnoGene Ltd., East Brunswick, NJ, USA (Cat. No. CYT-408-b) and ThermoFisher Scientific. Inc., Waltham, MA, USA (human IL-21 recombinant protein, Cat. No. 14-8219-80). The amino acid sequence of recombinant human IL-21 suitable for use in the invention is given in Table 2 (SEQ ID NO:12).

When "an anti-tumor effective amount", "a tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the tumor infiltrating lymphocytes (e.g., secondary TILs or genetically modified cytotoxic lymphocytes) described herein may be administered at a dosage of $10^4$ to $10^{11}$ cells/kg body weight (e.g., $10^5$ to $10^6$, $10^5$ to $10^{10}$, $10^5$ to $10^{11}$, $10^6$ to $10^{10}$, $10^6$ to $10^{11}$, $10^7$ to $10^{11}$, $10^7$ to $10^{10}$, $10^8$ to $10^{11}$, $10^8$ to $10^{10}$, $10^9$ to $10^{11}$, or $10^9$ to $10^{10}$ cells/kg body weight), including all integer values within those ranges. Tumor infiltrating lymphocytes (including in some cases, genetically modified cytotoxic lymphocytes) compositions may also be administered multiple times at these dosages. The tumor infiltrating lymphocytes (including in some cases, genetically) can be administered by using infusion techniques that are commonly known in immunotherapy (see, e.g., Rosenberg et al., *New Eng. J. of Med.* 319:1676, 1988). The optimal dosage and treatment regime for a particular patient can readily be determined by one skilled in the art of medicine by monitoring the patient for signs of disease and adjusting the treatment accordingly.

The term "hematological malignancy", "hematologic malignancy" or terms of correlative meaning refer to mammalian cancers and tumors of the hematopoietic and lymphoid tissues, including but not limited to tissues of the blood, bone marrow, lymph nodes, and lymphatic system. Hematological malignancies are also referred to as "liquid tumors." Hematological malignancies include, but are not limited to, acute lymphoblastic leukemia (ALL), chronic lymphocytic lymphoma (CLL), small lymphocytic lymphoma (SLL), acute myelogenous leukemia (AML), chronic myelogenous leukemia (CML), acute monocytic leukemia (AMOL), Hodgkin's lymphoma, and non-Hodgkin's lymphomas. The term "B cell hematological malignancy" refers to hematological malignancies that affect B cells.

The term "liquid tumor" refers to an abnormal mass of cells that is fluid in nature. Liquid tumor cancers include, but are not limited to, leukemias, myelomas, and lymphomas, as well as other hematological malignancies. TILs obtained from liquid tumors may also be referred to herein as marrow infiltrating lymphocytes (MILs). TILs obtained from liquid tumors, including liquid tumors circulating in peripheral blood, may also be referred to herein as PBLs. The terms MIL, TIL, and PBL are used interchangeably herein and differ only based on the tissue type from which the cells are derived.

The term "microenvironment," as used herein, may refer to the solid or hematological tumor microenvironment as a whole or to an individual subset of cells within the microenvironment. The tumor microenvironment, as used herein, refers to a complex mixture of "cells, soluble factors, signaling molecules, extracellular matrices, and mechanical cues that promote neoplastic transformation, support tumor growth and invasion, protect the tumor from host immunity, foster therapeutic resistance, and provide niches for dominant metastases to thrive," as described in Swartz, et al., *Cancer Res.*, 2012, 72, 2473. Although tumors express antigens that should be recognized by T cells, tumor clearance by the immune system is rare because of immune suppression by the microenvironment.

In an embodiment, the invention includes a method of treating a cancer with a population of TILs, wherein a patient is pre-treated with non-myeloablative chemotherapy prior to an infusion of TILs according to the invention. In some embodiments, the population of TILs may be provided wherein a patient is pre-treated with nonmyeloablative chemotherapy prior to an infusion of TILs according to the present invention. In an embodiment, the non-myeloablative chemotherapy is cyclophosphamide 60 mg/kg/d for 2 days (days 27 and 26 prior to TIL infusion) and fludarabine 25 mg/m2/d for 5 days (days 27 to 23 prior to TIL infusion). In an embodiment, after non-myeloablative chemotherapy and TIL infusion (at day 0) according to the invention, the patient receives an intravenous infusion of IL-2 intravenously at 720,000 IU/kg every 8 hours to physiologic tolerance.

Experimental findings indicate that lymphodepletion prior to adoptive transfer of tumor-specific T lymphocytes plays a key role in enhancing treatment efficacy by eliminating regulatory T cells and competing elements of the immune system ("cytokine sinks"). Accordingly, some embodiments of the invention utilize a lymphodepletion step (sometimes also referred to as "immunosuppressive conditioning") on the patient prior to the introduction of the TILs of the invention.

The term "effective amount" or "therapeutically effective amount" refers to that amount of a compound or combination of compounds as described herein that is sufficient to effect the intended application including, but not limited to, disease treatment. A therapeutically effective amount may vary depending upon the intended application (in vitro or in vivo), or the subject and disease condition being treated (e.g., the weight, age and gender of the subject), the severity of the disease condition, or the manner of administration. The term also applies to a dose that will induce a particular response in target cells (e.g., the reduction of platelet adhesion and/or cell migration). The specific dose will vary depending on the particular compounds chosen, the dosing regimen to be followed, whether the compound is administered in combination with other compounds, timing of administration, the tissue to which it is administered, and the physical delivery system in which the compound is carried.

The terms "treatment", "treating", "treat", and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment", as used herein, covers any treatment of a disease in a mammal, particularly in a human, and includes: (a) preventing the disease from occurring in a subject which may be predisposed to the disease but has not yet been diagnosed as having it: (b) inhibiting the disease, i.e., arresting its development or progression; and (c) relieving the disease, i.e., causing regression of the disease and/or relieving one or more disease symptoms. "Treatment" is also meant to encompass delivery of an agent in order to provide for a pharmacologic effect, even in the absence of a disease or condition. For example, "treatment" encompasses delivery of a composition that can elicit an immune response or confer immunity in the absence of a disease condition, e.g., in the case of a vaccine.

The term "heterologous" when used with reference to portions of a nucleic acid or protein indicates that the nucleic acid or protein comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source, or coding regions from different sources. Similarly, a heterologous protein indicates that the protein comprises two or more subsequences that are not found in the same relationship to each other in nature (e.g., a fusion protein).

The terms "sequence identity," "percent identity." and "sequence percent identity" (or synonyms thereof, e.g., "99% identical") in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences. Suitable programs to determine percent sequence identity include for example the BLAST suite of programs available from the U.S. Government's National Center for Biotechnology Information BLAST web site. Comparisons between two sequences can be carried using either the BLASTN or BLASTP algorithm. BLASTN is used to compare nucleic acid sequences, while BLASTP is used to compare amino acid sequences. ALIGN, ALIGN-2 (Genentech, South San Francisco, California) or MegAlign, available from DNASTAR, are additional publicly available software programs that can be used to align sequences. One skilled in the art can determine appropriate parameters for maximal alignment by particular alignment software. In certain embodiments, the default parameters of the alignment software are used.

As used herein, the term "variant" encompasses but is not limited to antibodies or fusion proteins which comprise an amino acid sequence which differs from the amino acid sequence of a reference antibody by way of one or more substitutions, deletions and/or additions at certain positions within or adjacent to the amino acid sequence of the reference antibody. The variant may comprise one or more conservative substitutions in its amino acid sequence as compared to the amino acid sequence of a reference antibody. Conservative substitutions may involve, e.g., the substitution of similarly charged or uncharged amino acids. The variant retains the ability to specifically bind to the antigen of the reference antibody. The term variant also includes pegylated antibodies or proteins.

By "tumor infiltrating lymphocytes" or "TILs" herein is meant a population of cells originally obtained as white blood cells that have left the bloodstream of a subject and migrated into a tumor. TILs include, but are not limited to, CD8 cytotoxic T cells (lymphocytes), Th1 and Th17 $CD4^+$ T cells, natural killer cells, dendritic cells and M1 macrophages. TILs include both primary and secondary TILs. "Primary TILs" are those that are obtained from patient tissue samples as outlined herein (sometimes referred to as "freshly harvested"), and "secondary TILs" are any TIL cell populations that have been expanded or proliferated as discussed herein, including, but not limited to bulk TILs, expanded TILs ("REP TILs") as well as "reREP TILs" as discussed herein, reREP TILs can include for example second expansion TILs or second additional expansion TILs (such as, for example, those described in Step D of FIG. 8, including TILs referred to as reREP TILs).

TILs can generally be defined either biochemically, using cell surface markers, or functionally, by their ability to infiltrate tumors and effect treatment. TILs can be generally categorized by expressing one or more of the following biomarkers: CD4, CD8, TCR αβ, CD27, CD28, CD56, CCR7, CD45Ra, CD95, PD-1, and CD25. Additionally, and alternatively, TILs can be functionally defined by their ability to infiltrate solid tumors upon reintroduction into a patient. TILs may further be characterized by potency—for example, TILs may be considered potent if, for example, interferon (IFN) release is greater than about 50 pg/mL, greater than about 100 pg/mL, greater than about 150 pg/mL, or greater than about 200 pg/mL.

The term "deoxyribonucleotide" encompasses natural and synthetic, unmodified and modified deoxyribonucleotides. Modifications include changes to the sugar moiety, to the base moiety and/or to the linkages between deoxyribonucleotide in the oligonucleotide.

The term "RNA" defines a molecule comprising at least one ribonucleotide residue. The term "ribonucleotide" defines a nucleotide with a hydroxyl group at the 2' position of a b-D-ribofuranose moiety. The term RNA includes double-stranded RNA, single-stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Nucleotides of the RNA molecules described herein may also comprise non-standard nucleotides, such as non-naturally occurring nucleotides or chemically synthesized nucleotides or deoxynucleotides. These altered RNAs can be referred to as analogs or analogs of naturally-occurring RNA.

The terms "pharmaceutically acceptable carrier" or "pharmaceutically acceptable excipient" are intended to include any and all solvents, dispersion media, coatings, antibacterial and antifungal agents, isotonic and absorption delaying agents, and inert ingredients. The use of such pharmaceutically acceptable carriers or pharmaceutically acceptable excipients for active pharmaceutical ingredients is well known in the art. Except insofar as any conventional pharmaceutically acceptable carrier or pharmaceutically acceptable excipient is incompatible with the active pharmaceutical ingredient, its use in therapeutic compositions of the invention is contemplated. Additional active pharmaceutical ingredients, such as other drugs, can also be incorporated into the described compositions and methods.

The terms "about" and "approximately" mean within a statistically meaningful range of a value. Such a range can be within an order of magnitude, preferably within 50%, more preferably within 20%, more preferably still within 10%, and even more preferably within 5% of a given value or range. The allowable variation encompassed by the terms "about" or "approximately" depends on the particular system under study, and can be readily appreciated by one of ordinary skill in the art. Moreover, as used herein, the terms "about" and "approximately" mean that dimensions, sizes, formulations, parameters, shapes and other quantities and characteristics are not and need not be exact, but may be approximate and/or larger or smaller, as desired, reflecting tolerances, conversion factors, rounding off, measurement error and the like, and other factors known to those of skill in the art. In general, a dimension, size, formulation, parameter, shape or other quantity or characteristic is "about" or "approximate" whether or not expressly stated to be such. It is noted that embodiments of very different sizes, shapes and dimensions may employ the described arrangements.

The transitional terms "comprising," "consisting essentially of," and "consisting of," when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. All compositions, methods, and kits described herein that embody the present invention can, in alternate embodiments, be more specifically defined by any of the transitional terms "comprising," "consisting essentially of," and "consisting of."

The terms "antibody" and its plural form "antibodies" refer to whole immunoglobulins and any antigen-binding fragment ("antigen-binding portion") or single chains thereof. An "antibody" further refers to a glycoprotein comprising at least two heavy (H) chains and two light (L) chains inter-connected by disulfide bonds, or an antigen-binding portion thereof. Each heavy chain is comprised of a heavy chain variable region (abbreviated herein as $V_H$) and a heavy chain constant region. The heavy chain constant region is comprised of three domains. CH1, CH2 and CH3. Each light chain is comprised of a light chain variable region (abbreviated herein as $V_L$) and a light chain constant region. The light chain constant region is comprised of one domain, $C_L$. The $V_H$ and $V_L$ regions of an antibody may be further subdivided into regions of hypervariability, which are referred to as complementarity determining regions (CDR) or hypervariable regions (HVR), and which can be interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen epitope or epitopes. The constant regions of the antibodies may mediate the binding of the immunoglobulin to host tissues or factors, including various cells of the immune system (e.g., effector cells) and the first component (Clq) of the classical complement system.

The term "antigen" refers to a substance that induces an immune response. In some embodiments, an antigen is a molecule capable of being bound by an antibody or a TCR if presented by major histocompatibility complex (MHC) molecules. The term "antigen", as used herein, also encompasses T cell epitopes. An antigen is additionally capable of being recognized by the immune system. In some embodiments, an antigen is capable of inducing a humoral immune response or a cellular immune response leading to the activation of B lymphocytes and/or T lymphocytes. In some cases, this may require that the antigen contains or is linked to a Th cell epitope. An antigen can also have one or more epitopes (e.g., B- and T-epitopes). In some embodiments, an antigen will preferably react, typically in a highly specific and selective manner, with its corresponding antibody or TCR and not with the multitude of other antibodies or TCRs which may be induced by other antigens.

The terms "monoclonal antibody," "mAb," "monoclonal antibody composition," or their plural forms refer to a preparation of antibody molecules of single molecular composition. A monoclonal antibody composition displays a single binding specificity and affinity for a particular epitope. Monoclonal antibodies specific to certain receptors can be made using knowledge and skill in the art of injecting test subjects with suitable antigen and then isolating hybridomas expressing antibodies having the desired sequence or functional characteristics. DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are then transfected into host cells such as *E. coli* cells, simian COS cells. Chinese hamster ovary (CHO) cells, or myeloma cells that do not otherwise produce immunoglobulin protein, to obtain the synthesis of monoclonal antibodies in the recombinant host cells. Recombinant production of antibodies will be described in more detail below.

The terms "antigen-binding portion" or "antigen-binding fragment" of an antibody (or simply "antibody portion" or "fragment"), as used herein, refers to one or more fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$, and CH1 domains; (ii) a F(ab')2 fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody. (v) a domain antibody (dAb) fragment (Ward, et al., *Nature,* 1989, 341, 544-546), which may consist of a $V_H$ or a $V_L$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules known as single chain Fv (scFv); see, e.g., Bird, et al., *Science* 1988, 242, 423-426; and Huston, et al., *Proc. Natl. Acad. Sci. USA* 1988, 85, 5879-5883). Such scFv antibodies are also intended to be encompassed within the terms "antigen-binding portion" or "antigen-binding fragment" of an antibody. These antibody fragments are obtained using conventional techniques known to those with skill in the art, and the fragments are screened for utility in the same manner as are intact antibodies.

The term "human antibody," as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). The term "human antibody", as used herein, is not intended to include antibodies in which CDR sequences derived from the germline of another mammalian species, such as a mouse, have been grafted onto human framework sequences.

The term "human monoclonal antibody" refers to antibodies displaying a single binding specificity which have variable regions in which both the framework and CDR regions are derived from human germline immunoglobulin sequences. In an embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

The term "recombinant human antibody", as used herein, includes all human antibodies that are prepared, expressed, created or isolated by recombinant means, such as (a) antibodies isolated from an animal (such as a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

As used herein, "isotype" refers to the antibody class (e.g., IgM or IgG1) that is encoded by the heavy chain constant region genes.

The phrases "an antibody recognizing an antigen" and "an antibody specific for an antigen" are used interchangeably herein with the term "an antibody which binds specifically to an antigen."

The term "human antibody derivatives" refers to any modified form of the human antibody, including a conjugate of the antibody and another active pharmaceutical ingredient or antibody. The terms "conjugate," "antibody-drug conjugate", "ADC," or "immunoconjugate" refers to an antibody, or a fragment thereof, conjugated to another therapeutic moiety, which can be conjugated to antibodies described herein using methods available in the art.

The terms "humanized antibody," "humanized antibodies." and "humanized" are intended to refer to antibodies in which CDR sequences derived from the germline of another mammalian species, such as a mouse, have been grafted onto human framework sequences. Additional framework region modifications may be made within the human framework sequences. Humanized forms of non-human (for example, murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a 15 hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. For further details, see Jones, et al., *Nature* 1986, 321, 522-525; Riechmann, et al., *Nature* 1988, 332, 323-329; and Presta. *Curr. Op. Struct. Biol.* 1992, 2, 593-596. The antibodies described herein may also be modified to employ any Fc variant which is known to impart an improvement (e.g., reduction) in effector function and/or FcR binding. The Fc variants may include, for example, any one of the amino acid substitutions disclosed in International Patent Application Publication Nos. WO 1988/07089 A1, WO 1996/14339 A1, WO 1998/05787 A1, WO 1998/23289 A1, WO 1999/51642 A1, WO 99/58572 A1, WO 2000/09560 A2, WO 2000/32767 A1, WO 2000/42072 A2, WO 2002/44215 A2, WO 2002/060919 A2, WO 2003/074569 A2, WO 2004/016750 A2, WO 2004/029207 A2, WO 2004/035752 A2, WO 2004/063351 A2, WO 2004/074455 A2, WO 2004/099249 A2, WO 2005/040217 A2, WO 2005/070963 A1, WO 2005/077981 A2, WO 2005/092925 A2, WO 2005/123780 A2, WO 2006/019447 A1, WO 2006/047350 A2, and WO 2006/085967 A2; and U.S. Pat. Nos. 5,648,260; 5,739,277; 5,834,250; 5,869,046; 6,096,871; 6,121,022; 6,194,551; 6,242,195; 6,277,375; 6,528,624; 6,538,124; 6,737,056; 6,821,505; 6,998,253; and 7,083,784; the disclosures of which are incorporated by reference herein.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

A "diabody" is a small antibody fragment with two antigen-binding sites. The fragments comprises a heavy chain variable domain ($V_H$) connected to a light chain variable domain ($V_L$) in the same polypeptide chain ($V_H$-$V_L$ or $V_L$-$V_H$). By using a linker that is too short to allow pairing between the two domains on the same chain, the domains are forced to pair with the complementary domains of another chain and create two antigen-binding sites. Diabodies are described more fully in, e.g., European Patent No. EP 404,097. International Patent Publication No. WO 93/11161; and Bolliger, et al., *Proc. Natl. Acad. Sci. USA* 1993, 90, 6444-6448.

The term "glycosylation" refers to a modified derivative of an antibody. An aglycoslated antibody lacks glycosylation. Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Aglycosylation may increase the affinity of the antibody for antigen, as described in U.S. Pat. Nos. 5,714,350 and 6,350,861. Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, the cell lines Ms704, Ms705, and Ms709 lack the fucosyltransferase gene. FUT8 (alpha (1,6) fucosyltransferase), such that antibodies expressed in the Ms704, Ms705, and Ms709 cell lines lack fucose on their carbohydrates. The Ms704, Ms705, and Ms709 FUT8−/− cell lines were created by the targeted disruption of the FUT8 gene in CHO/DG44 cells using two replacement vectors (see e.g. U.S. Patent Publication No. 2004/0110704 or Yamane-Ohnuki, et al., *Biotechnol. Bioeng.,* 2004, 87, 614-622). As another example, European Patent No. EP 1,176,195 describes a cell line with a functionally disrupted FUT8 gene, which encodes a fucosyl transferase, such that antibodies expressed in such a cell line exhibit hypofucosylation by reducing or eliminating the alpha 1.6 bond-related enzyme, and also describes cell lines which have a low enzyme activity for adding fucose to the N-acetylglucosamine that binds to the Fc region of the antibody or does not have the enzyme activity, for example the rat myeloma cell line YB2/0) (ATCC CRL 1662). International Patent Publication WO 03/035835 describes a variant CHO cell line. Lec 13 cells, with reduced ability to attach fucose to Asn (297)-linked carbohydrates, also resulting in hypofucosylation of antibodies expressed in that host cell (see also Shields, et al., *J. Biol. Chem.* 2002, 277, 26733-26740). International Patent Publication No. WO 99/54342 describes cell lines engineered to express glycoprotein-modifying glycosyl transferases (e.g., beta(1,4)-N-acetylglucosaminyltransferase III (GnTIII)) such that antibodies expressed in the engineered cell lines exhibit increased bisecting GlcNac structures which results in increased ADCC activity of the antibodies (see also Umana, et al., *Nat. Biotech.* 1999, 17, 176-180). Alternatively, the fucose residues of the antibody may be cleaved off using a fucosidase enzyme. For example, the fucosidase alpha-L-fucosidase removes fucosyl residues from antibodies as described in Tarentino, et al., *Biochem.* 1975, 14, 5516-5523.

"Pegylation" refers to a modified antibody, or a fragment thereof, that typically is reacted with polyethylene glycol (PEG), such as a reactive ester or aldehyde derivative of PEG, under conditions in which one or more PEG groups become attached to the antibody or antibody fragment. Pegylation may, for example, increase the biological (e.g., serum) half life of the antibody. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono ($C_1$-$C_{10}$)alkoxy- or aryloxy-polyethylene glycol or polyethylene glycol-maleimide. The antibody to be pegylated may be an aglycosylated antibody. Methods for pegylation are known in the art and can be applied to the antibodies of the invention, as described for example in European Patent Nos. EP 0154316 and EP 0401384 and U.S. Pat. No. 5,824,778, the disclosures of each of which are incorporated by reference herein.

The term "biosimilar" means a biological product, including a monoclonal antibody or protein, that is highly similar to a U.S. licensed reference biological product notwithstanding minor differences in clinically inactive components, and for which there are no clinically meaningful differences between the biological product and the reference product in terms of the safety, purity, and potency of the product. Furthermore, a similar biological or "biosimilar" medicine is a biological medicine that is similar to another biological medicine that has already been authorized for use by the European Medicines Agency. The term "biosimilar" is also used synonymously by other national and regional regulatory agencies. Biological products or biological medicines are medicines that are made by or derived from a biological source, such as a bacterium or yeast. They can consist of relatively small molecules such as human insulin or erythropoietin, or complex molecules such as monoclonal antibodies. For example, if the reference IL-2 protein is aldesleukin (PROLEUKIN), a protein approved by drug regulatory authorities with reference to aldesleukin is a "biosimilar to" aldesleukin or is a "biosimilar thereof" of aldesleukin. In Europe, a similar biological or "biosimilar" medicine is a biological medicine that is similar to another biological medicine that has already been authorized for use by the European Medicines Agency (EMA). The relevant legal basis for similar biological applications in Europe is Article 6 of Regulation (EC) No 726/2004 and Article 10(4) of Directive 2001/83/EC, as amended and therefore in Europe, the biosimilar may be authorized, approved for authorization or subject of an application for authorization under Article 6 of Regulation (EC) No 726/2004 and Article 10(4) of Directive 2001/83/EC. The already authorized original biological medicinal product may be referred to as a "reference medicinal product" in Europe. Some of the requirements for a product to be considered a biosimilar are outlined in the CHMP Guideline on Similar Biological Medicinal Products. In addition, product specific guidelines, including guidelines relating to monoclonal antibody biosimilars, are provided on a product-by-product basis by the EMA and published on its website. A biosimilar as described herein may be similar to the reference medicinal product by way of quality characteristics, biological activity, mechanism of action, safety profiles and/or efficacy. In addition, the biosimilar may be used or be intended for use to treat the same conditions as the reference medicinal product. Thus, a biosimilar as described herein may be deemed to have similar or highly similar quality characteristics to a reference medicinal product. Alternatively, or in addition, a biosimilar as described herein may be deemed to have similar or highly similar biological activity to a reference medicinal product. Alternatively, or in addition, a biosimilar as described herein may be deemed to have a similar or highly similar safety profile to a reference medicinal product. Alternatively, or in addition, a biosimilar as described herein may be deemed to have similar or highly similar efficacy to a reference medicinal product. As described herein, a biosimilar in Europe is compared to a reference medicinal product which has been authorized by the EMA. However, in some instances, the biosimilar may be compared to a biological medicinal product which has been authorized outside the European Economic Area (a non-EEA authorized "comparator") in certain studies. Such studies include for example certain clinical and in vivo non-clinical studies. As used herein, the term "biosimilar" also relates to a biological medicinal product which has been or may be compared to a non-EEA authorized comparator. Certain biosimilars are proteins such as antibodies, antibody fragments (for example, antigen binding portions) and fusion proteins. A protein biosimilar may have an amino acid sequence that has minor modifications in the amino acid structure (including for example deletions, additions, and/or substitutions of amino acids) which do not significantly affect the function of the polypeptide. The biosimilar may comprise an amino acid sequence having a sequence identity of 97% or greater to the amino acid sequence of its reference medicinal product, e.g., 97%, 98%, 99% or 100%. The biosimilar may comprise one or more post-translational modifications, for example, although not limited to, glycosylation, oxidation, deamidation, and/or truncation which is/are different to the post-translational modifications of the reference medicinal product, provided that the differences do not result in a change in safety and/or efficacy of the medicinal product. The biosimilar may have an identical or different glycosylation pattern to the reference medicinal product. Particularly, although not exclusively, the biosimilar may have a different glycosylation pattern if the differences address or are intended to address safety concerns associated with the reference medicinal product. Additionally, the biosimilar may deviate from the reference medicinal product in for example its strength, pharmaceutical form, formulation, excipients and/or presentation, providing safety and efficacy of the medicinal product is not compromised. The biosimilar may comprise differences in for example pharmacokinetic (PK) and/or pharmacodynamic (PD) profiles as compared to the reference medicinal product but is still deemed sufficiently similar to the reference medicinal product as to be authorized or considered suitable for authorization. In certain circumstances, the biosimilar exhibits different binding characteristics as compared to the reference medicinal product, wherein the different binding characteristics are considered by a Regulatory Authority such as the EMA not to be a barrier for authorization as a similar biological product. The term "biosimilar" is also used synonymously by other national and regional regulatory agencies.

III. Potency Assay Methods and Compositions

Without being limited to any particular theory, it is believed that commercially-viable TIL and T cell potency assays are limited by the unavailability of neoantigen-expressing target cells, the lack of overlap between patients and the neoantigens expressed by their tumors, and the inability to identify all relevant neoantigens in time to construct an assay. As a result, unlike commercial and clinical T cell therapies using transduced chimeric antigen receptors, which have received regulatory approval in some cases using a target-based assay, a target-based assay is not feasible on the timescale needed for an effective cancer therapy for a polyclonal T cell product, such as a TIL, MIL, or PBL therapy or product. At the same time, bead-based assays are limited by their inability to recapitulate the natural activation and killing ability of a TIL or T cell. For example, bead-based or plate-based assays that utilize anti-CD3 coatings bind to the CD3 epsilon chains on a TIL or T cell, which are non-covalently associated with the TCR, when it would be more preferable to bind to the TCR itself. A disadvantage of bead-based assays employing CD3 is thus that they do not use the alpha and beta components of the TCR for their interaction. The presence of other costimulatory molecules, such as CD28 or CD137 (4-1BB) on beads, also leads to an unnatural and less preferable interaction, at least because activation of these costimulatory molecules yields an assay that is less selective for tumor-resident cells such as TILs. The present invention provides a solution to these problems. Without being limited to any particular theory, it is believed that an interaction between MHC or HLA on a target cell with a TCR of a T cell, including a TIL, MIL, or PBL, produces an analyte, which may be compared to the analyte produced by a T cell, including a TIL, MIL, or PBL, co-cultured with a MHC-negative control, in order to assess one or more properties of the T cell, including a TIL, MIL, or PBL, such as its potency, identity, or other useful characteristics to assist in the manufacture or provision of therapy for cancers. Furthermore, again without being limited to any particular theory, it is believed that because T cells such as TILs and MILs are found at the site of a tumor, or PBLs have been activated previously by tumor exposure, such T cells, including TILs, MILs, and PBLs, are already cross-primed or primed T cells, with CD28 and 4-1BB already activated.

In an embodiment, the invention includes a potency assay composition that comprises a Raji cell and a T cell, such as a TIL, cocultured in media. In an embodiment, the invention includes a potency assay composition that comprises a Thp1 cell and a T cell, such as a TIL, cocultured in media. In an embodiment, the invention includes a potency assay composition that comprises a Ramos cell and a T cell, such as a TIL, cocultured in media. In an embodiment, the invention includes a potency assay composition that comprises a U937 cell and a T cell, such as a TIL, cocultured in media. In an embodiment, the invention includes a potency assay composition that comprises a Daudi cell and a T cell, such as a TIL, cocultured in media. In an embodiment, a potency assay composition comprises a K562 cell and a T cell, such as a TIL, cocultured in media, and used as a negative control. In an embodiment, a potency assay composition comprises a peripheral blood mononuclear cell (PBMC) and a T cell, such as a TIL, cocultured in media, and used as a mixed-lymphocyte reaction (MLR) positive control. In an embodiment, the TILs and PBMCs in the foregoing embodiment are from the same patient. In an embodiment, the TILs are manufactured using a Gen 2 or Gen 3 process or other manufacturing process as described herein. In an embodiment, the TILs are manufactured using at least one REP step. In an embodiment, the potency assay is performed using TILs, MILs, or PBLs produced using the expansion or manufacturing processes described herein. In an embodiment, TILs are tested with a potency assay described herein after manufacturing with a process described in U.S. Patent Application Publication No. US 2018/0282694 A1 or in U.S. Pat. Nos. 10,130,659, 10,166,257, 10,272,113, 10,363,273, 10,398,734, 10,420,799, 10,463,697, 10,537,595, 10,646,517, 10,653,723, 10,693,330, 10,695,372, 10,894,063, and 10,905,718, the disclosures of each of which are incorporated herein by reference. In an embodiment, TILs are tested with a potency assay described herein after manufacturing with a process described in U.S. Pat. No. 10,918,666, the disclosures of which are incorporated herein by reference. In an embodiment, TILs are tested with a potency assay described herein after manufacturing with a process described in U.S. Patent Application Publication No. US 2020/0277573 A1, the disclosures of which are incorporated herein by reference. In an embodiment, TILs are tested with a potency assay described herein after manufacturing with a process described in International Patent Application Publication No. WO 2019/210131 A1, the disclosures of which are incorporated herein by reference. In an embodiment, TILs are tested with a potency assay described herein after manufacturing with a process described in International Patent Application Publication No. WO 2019/136456 A1, the disclosures of which are incorporated herein by reference. In an embodiment, TILs are tested with a potency assay described herein after manufacturing with a process described in International Patent Application Publication No. WO 2021/123832 A1, the disclosures of which are incorporated herein by reference. In an embodiment, MILs and PBLs are tested with a potency assay described herein after manufacturing with a process described in U.S. Patent Application Publication No. US 2020/0224161 A1, the disclosures of which are incorporated herein by reference. In an embodiment, TILs are tested with a potency assay described herein after manufacturing with a process described in International Patent Application Publication No. WO 2019/145711 A1, the disclosures of which are incorporated herein by reference. In an embodiment, TILs are tested with a potency assay described herein after manufacturing with a process described in International Patent Application Publication No. WO 2020/152451 A1, the disclosures of which are incorporated herein by reference.

A. Assay Methods

In an embodiment, the invention includes a method for determining the potency of a T cell product using a target cell capable of binding to a T cell receptor. In an embodiment, the invention includes an assay based on the allogeneic interaction of the T cell or TIL, MIL, or PBL TCR complex with the target cell's HLA-peptide complex, also referred to as MHC dominant recognition. In an embodiment, the invention includes an assay utilizing MHC dominant recognition of a T cell or TIL, MIL, or PBL TCR complex with a target cell to produce an analyte, which is compared to the analyte produced by a T cell or TIL co-culture with a MHC-negative control. In an embodiment, the T cell or TIL, MIL, or PBL TCR complex binding to the target cell occurs through its alpha (α) and beta (β) chains. In an embodiment, the target cell expresses HLA. In an embodiment, the target cell is a B cell. In an embodiment, the target cell is a B cell lymphoblastoid cell or B-lymphoblastoid cell. In an embodiment, the target cell is a Burkitt's lymphoma cell. In an embodiment, the target cell is a myeloid lineage cell. In an embodiment, the target cell is a monocyte. In an embodiment, the target cell is an acute monocytic leukemia cell. In an embodiment, the target cell is an M5-subtype acute monocytic leukemia cell. In an embodiment, the target cell is a Raji cell or a derivative, variant, modification, or progeny thereof. In an embodiment, the target cell is a Thp1 cell or a derivative, variant, modification, or progeny thereof. In an embodiment, the target cell is a Ramos cell or a derivative, variant, modification, or progeny thereof. In an embodiment, the target cell is a U937 cell or a derivative, variant, modification, or progeny thereof. In an embodiment, the target cell is a Daudi cell or a derivative, variant, modification, or progeny thereof. In an embodiment, the target cell is a melanocyte cell. In an embodiment, the target cell is an HLA-A-02 positive melanocyte cell. In an embodiment, the target cell is a melanoma cell. In an embodiment, the target cell is an HLA-A-02 positive melanoma cell. In an embodiment, the target cell is a melanoma cell selected from the group consisting of Sk-MEL-5, Malme-3M, SK-MEL-28, SK-MEL-3, SH-4, SK-MEL-24, RPMI-7951, SK-MEL-1, A375, G-361, and combinations thereof.

In an embodiment, the invention includes an assay based upon an alloreactive TCR or HLA recognition occurring between a tumor cell and a T cell, such as a TIL, MIL, or PBL produced using the expansion or manufacturing processes described herein. In an embodiment, the invention includes an assay based upon an alloreactive TCR or HLA recognition occurring between a Raji, Thp1, Ramos, U937, or Daudi cell, or derivative, variant, modification, or progeny thereof, and a T cell, such as a TIL, MIL, or PBL, produced using the expansion or manufacturing processes described herein. In an embodiment, the invention includes the use of the foregoing embodiments in combination with a negative control as described herein. In an embodiment, the negative control serves as a basal or baseline activity level for a T cell, such as a TIL, MIL, or PBL, for comparison with a T cell assay based on MHC dominant recognition. In an embodiment, the negative control is a cell line that lacks HLA Class I and/or HLA Class II expression. In an embodiment, the negative control is a cell line that lacks MHC Class I and/or MHC Class II expression. In an embodiment, the negative control is a cell line that lacks HLA or MHC to control for assay variability. In an embodiment, the negative control is a cell line that lacks HLA or MHC to demonstrate that MHC dominant recognition is the primary variable of a potency assay.

In an embodiment, the invention includes the use of a K562 cell, or a derivative, variant, modification, or progeny thereof, as a negative control as described herein by co-culture of a T cell product, such as a TIL, MIL, or PBL product, with K562 cells. The use of K562 cells as a negative control can be employed with the assays described herein as well as with bead and plate-bound antibody-stimulated bioassays, such as an anti-CD3 plate assay for IFN-γ.

In an embodiment, the invention includes the use of one or more HLA-blocking antibodies, or a fragment, derivative, variant, or modification thereof, as described herein by co-culture of a T cell product, such as a TIL, MIL, or PBL product, with a target cell or combination of target cells as a negative control. The use of an HLA-blocking antibody or multiple HLA-blocking antibodies as a negative control can be employed with the assays described herein.

In some embodiments, the potency and/or functionality of expanded TILs produced by the methods described herein or known in the art is examined. Examining the potency and/or functionality of the expanded TILs allows for characterization of clinical TIL product lots. In an embodiment, TIL potency is defined as increased expression of select surface markers expressed as percentage of marker-positive cells or mean fluorescence intensity (MFI) upon coculture with Raji cells, optionally in comparison to K562 cells. Alternatively, Raji cells, K562 and TIL may be cultured alone. In some embodiments, PBMCs from the same patient from which TILs or MILs are obtained is used as a control. In some embodiments, bead-based CD3/CD28 stimulation may also be used as a control. In some embodiments, bead-based CD3/CD28/CD137 stimulation may also be used as a control. In some embodiments, addition of a mouse monoclonal antibody against CD28 is used to ensure additional co-stimulation to amplify the T cell response. In some embodiments, PBMCs may be co-cultured with each TIL lot as a positive control for the MLR response.

In an embodiment, a potency assay includes a co-culture step wherein the co-culture occurs for a period selected from the group consisting of 30 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 25 hours, 26 hours, 27 hours, 28 hours, 29 hours, 30 hours, 31 hours, 32 hours, 33 hours, 34 hours, 35 hours, 36 hours, 37 hours, 38 hours, 39 hours, 40 hours, 41 hours, 42 hours, 43 hours, 44 hours, 45 hours, 46 hours, 47 hours, 48 hours, 49 hours, and 50 hours. In an embodiment, a potency assay includes a co-culture step wherein the co-culture occurs for a period selected from the group consisting of 6 hours, 12 hours, 18 hours, 24 hours, and 32 hours.

In an embodiment, a potency assay includes a target cell and T cell (including a TIL, MIL or PBL) co-culture step wherein the co-culture occurs for a period selected from the group consisting of 30 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 25 hours, 26 hours, 27 hours, 28 hours, 29 hours, 30 hours, 31 hours, 32 hours, 33 hours, 34 hours, 35 hours, 36 hours, 37 hours, 38 hours, 39 hours, 40 hours, 41 hours, 42 hours, 43 hours, 44 hours, 45 hours, 46 hours, 47 hours, 48 hours, 49 hours, and 50 hours. In an embodiment, a potency assay includes a co-culture step wherein the co-culture occurs for a period selected from the group consisting of 6 hours, 12 hours, 18 hours, 24 hours, and 32 hours.

In an embodiment, a potency assay includes a negative control cell and T cell (including a TIL, MIL or PBL) co-culture step wherein the co-culture occurs for a period selected from the group consisting of 30 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 25 hours, 26 hours, 27 hours, 28 hours, 29 hours, 30 hours, 31 hours, 32 hours, 33 hours, 34 hours, 35 hours, 36 hours, 37 hours, 38 hours, 39 hours, 40 hours, 41 hours, 42 hours, 43 hours, 44 hours, 45 hours, 46 hours, 47 hours, 48 hours, 49 hours, and 50 hours. In an embodiment, a potency assay includes a co-culture step wherein the co-culture occurs for a period selected from the group consisting of 6 hours, 12 hours, 18 hours, 24 hours, and 32 hours.

In an embodiment, the invention includes a potency assay method for determining the potency of a TIL, MIL, PBL or other T cell product that relates to clinical benefits. Clinical benefits can be measured in multiple ways, including but not limited to demonstration of cell function in vitro, disease control rate, overall response rate, duration of response, or other scientific measures of clinical benefit or potential clinical benefit.

In some embodiments, the potency of expanded or formulated TILs, MILs, and PBLs is examined by a co-culture assay described herein. Examining the potency of the expanded or formulated TILs, MILs, and PBLs allows for characterization of TIL, MIL, or PBL product lots. The potency of TILs, MILs, or PBLs, also referred to as activation, is defined as increased expression of select surface markers expressed as percentage of marker-positive cells or mean fluorescence intensity (MFI) upon coculture of TILs, MILs, or PBLs with Raji cells, or derivatives, variants, modifications, or progeny thereof, compared to co-culture of TILs, MILs, or PBLs with K562 cells.

In an embodiment, the invention includes a method for determining the potency of a T cell product using a target cell capable of binding to a T cell receptor, wherein the method for determining potency is an allorecognition assay. In an embodiment, the invention includes a method for determining the potency of a T cell product using a target cell capable of binding to a T cell receptor, wherein the method for determining potency is an allorecognition assay. In an embodiment, the invention includes a method for determining the potency of a T cell product using a Raji cell, or a derivative, variant, modification, or progeny thereof, capable of binding to a T cell receptor, wherein the method for determining potency is an allorecognition assay. In an embodiment, the invention includes a method for determining the potency of a T cell product using a Thp1 cell, or a derivative, variant, modification, or progeny thereof, capable of binding to a T cell receptor, wherein the method for determining potency is an allorecognition assay. In an embodiment, the invention includes a method for determining the potency of a T cell product using a Ramos cell, or a derivative, variant, modification, or progeny thereof, capable of binding to a T cell receptor, wherein the method for determining potency is an allorecognition assay. In an embodiment, the invention includes a method for determining the potency of a T cell product using a U937 cell, or a derivative, variant, modification, or progeny thereof, capable of binding to a T cell receptor, wherein the method for determining potency is an allorecognition assay. In an embodiment, the invention includes a method for determining the potency of a T cell product using a Daudi cell, or a derivative, variant, modification, or progeny thereof, capable of binding to a T cell receptor, wherein the method for determining potency is an allorecognition assay.

In an embodiment, the invention includes a method for determining the potency of a T cell product using a target cell capable of binding to a T cell receptor, wherein the secretion or expression of a protein is detected using an enzyme-linked immunosorbent assay (ELISA) detection method. In a further embodiment, the ELISA method is automated using an automated or robotic system, such as an ELLA system (available from the ProteinSimple division of BioTechne, Inc., San Jose, CA, USA), the ISOPLEXIS system (available from Isoplexis, Inc., Branford, CT, USA), or the LUNARIS system (available from AYOXXA Biosystems GmbH, Cologne, Germany). In an embodiment, the potency assay detection is performed using multiplex assay detection, such as a LUMINEX system (available from the R&D Systems division of BioTechne, Inc., Minnesota, MN, USA). In an embodiment, the invention includes a potency assay method that uses a flow cytometry detection method. In an embodiment, the invention includes a potency assay method for a secreted protein. In an embodiment, the invention includes a potency assay method for a cell-surface or bound protein. In an embodiment, the invention includes a potency assay method that uses a binding assay detection method. In an embodiment, the ELLA system measures IFN-γ concentration post activation of a co-culture assay described herein, wherein supernatants collected from the co-culture are screened for IFN-γ production on each multi-well (such as a 72-well) commercially validated cartridge. In an embodiment, the ELLA automated system performs to the sub-picogram level of sensitivity including four logs of sensitivity in the dynamic range. In an embodiment, the repeatability and precision of the assay is increased by minimizing procedural error using an ELLA system as compared to a traditional ELISA method.

In an embodiment, the invention includes a method for determining the potency of a T cell product using a target cell capable of binding to a T cell receptor, wherein the secretion or expression of an analyte is detected using a detection method. In an embodiment, the analyte detected is a protein. In an embodiment, the analyte detected is a cytokine. In an embodiment, the analyte detected is an interferon. In an embodiment, the analyte detected is interferon-alpha, also referred to as IFN-α or IFNα. In an embodiment, the analyte detected is interferon-alpha, also referred to as IFN-β or IFNβ. In an embodiment, the analyte detected is interferon-gamma, also referred to as IFN-γ or IFNγ. In an embodiment, the analyte detected is granzyme B, also referred to as GzmB. In an embodiment, the analyte detected is perform. In an embodiment, the analyte detected is tumor necrosis factor alpha, also referred to as TNF-α or TNFα. In an embodiment, the analyte detected is an interleukin. In an embodiment, the analyte detected is IL-1α, IL-1 β, IL-2, IL-3, IL-4, IL-5, IL-6, IL-8, IL-9, IL-10, IL-13, IL-14, IL-16, IL-17, IL-18, IL-22, IL-25, or IL-26. In an embodiment, the analyte detected is CD25. In an embodiment, the analyte detected is CD69. In an embodiment, the analyte detected is CD137 (4-1BB). In an embodiment, the analyte detected is CD134 (OX40). In an embodiment, the analyte detected is CCL4. In an embodiment, the analyte detected is CD150, also known as SLAM, SLAM F1, or signaling lymphocytic activation molecule 1. In an embodiment, the analyte detected is KLRG1. In an embodiment, the analyte detected is KLRG1. In an embodiment, the analyte detected is secreted MIP-1β.

In an embodiment, the invention includes a method for determining the potency of a T cell product using a target cell capable of binding to a T cell receptor, wherein the secretion or expression of an analyte is detected using a detection method, wherein the T cell product is a TIL product, and wherein the analyte is a cell surface marker selected from the group consisting of CD25, CD69, CD134, CD137, and CD150.

In an embodiment, the invention includes a method for determining the potency of a T cell product using a cell capable of allogeneic binding to a T cell receptor, wherein a negative control comprising a cell that lacks MHC I and MHC II expression is used for comparison with a co-culture of a T cell product (such as a TIL, MIL or PBL product) with a target cell. In an embodiment, the invention includes a method for determining the potency of a TIL product using a Raji cell capable of allogeneic binding to a T cell receptor, wherein a negative control comprising a K562 cell that lacks MHC I and MHC II expression is used for comparison with a co-culture of the TIL product with the Raji cell.

In some embodiments, the increased expression of select surface markers expressed as percentage of marker-positive cells or mean fluorescence intensity (MFI) upon coculture with Raji cells, compared to K562 cells, is an increase of at least 10%, at least 15%, at least 20%, at least 30%, at least 40%, at least 50%, at least 60%, at least 70%, at least 80%, at least 90%, or at least 100%.

In some embodiments, the increased expression of select surface markers expressed as percentage of marker-positive cells or mean fluorescence intensity (MFI) upon coculture with Raji cells, compared to K562 cells, is an increase of at least 10%, at least 15%, at least 20%, at least 30%, at least 40%, at least 50%, at least 60%, at least 70%, at least 80%, at least 90%, or at least 100%.

In some embodiments, the supernatants from the co-culture methods described herein are tested immediately after removal from co-culture. In an embodiment, the supernatants from the co-culture methods described herein are tested 1 hour, 2 hours, 3 hours, 4 hours, 5 hours, 6 hours, 7 hours, 8 hours, 10 hours, 12 hours, 18 hours, 24 hours, or 48 hours after removal from co-culture. In an embodiment, the supernatants from the co-culture methods described herein are frozen after removal from co-culture and are later thawed for testing. In some embodiments, the supernatants from the co-culture methods described herein are assessed for IFN-γ, granzyme B, TNF-α, CCL4, and/or MIP-1β secretion.

In some embodiments, the present invention provides a method for assaying TIL activity comprising the steps of: a) irradiating Raji cells and K562 cells; (b) co-culturing irradiated Raji cells and irradiated K562 cells with TIL at one or more of the following target ratios (50:1, 25:1, 12.5:1, 6.25:1, 3:1, 1:1, 1:3, 1:6.25, 1:12.5, 1:25), optionally with an agonistic or super-agonistic anti-CD28 antibody; (c) collecting the supernatants from the co-cultured cells in step (b) after 6-24 hours; (d) harvesting the cells from step (b) and measuring surface marker expression of T cell activation; and (e) assaying the supernatants from the cocultured cells collected in step (c) for markers of T cell activation.

In some embodiments, the potency and/or functionality of the expanded TILs is examined before cryopreservation of the TILs. In some embodiments, the potency and/or functionality of the expanded TILs is examined after cryopreservation. In an embodiment, the potency of a TIL, MIL, or PBL product is examined as part of release testing for a pharmaceutical product. In an embodiment, the potency of a TIL, MIL, or PBL product is examined as part of stability testing for a pharmaceutical product, for example, after thawing of a cryopreserved product or after storage of a previously-thawed or never frozen product for a defined period under different environmental conditions.

In some embodiments, the increased expression of select surface markers expressed as a percentage of marker-positive cells or mean fluorescence intensity (MFI) upon coculture with Raji cells, compared to K562 cells, is an increase of at least 10%, at least 15%, at least 20%, at least 30%, at least 40%, at least 50%, at least 60%, at least 70%, at least 80%, at least 90%, or at least 100%.

In some embodiments, the increased expression of select surface markers expressed as a percentage of marker-positive cells or mean fluorescence intensity (MFI) upon coculture with Raji cells, compared to K562 cells, is an increase of at least 1-fold, at least 1.5-fold, at least 2-fold, at least 2.5-fold, at least 3-fold, at least 3.5-fold, at least 4-fold, at least 4.5-fold, at least 5-fold, at least 5.5-fold, at least 6-fold, at least 6.5-fold, at least 7-fold, at least 7.5-fold, at least 8-fold, at least 8.5-fold, at least 9-fold, at least 9.5-fold, at least 10-fold, at least 11-fold, at least 12-fold, at least 13-fold, at least 14-fold, at least 15-fold, at least 16-fold, at least 17-fold, at least 18-fold, at least 19-fold, at least 20-fold, at least 25-fold, at least 30-fold, at least 35-fold, at least 40-fold, at least 45-fold, at least 50-fold, at least 55-fold, at least 60-fold, at least 70-fold, at least 80-fold, at least 90-fold, or at least 100-fold.

In some embodiments, the increased expression of CD25 expressed as a percentage of marker-positive cells or mean fluorescence intensity (MFI) upon coculture with Raji cells, compared to K562 cells, is an increase of at least 10%, at least 15%, at least 20%, at least 30%, at least 40%, at least 50%, at least 60%, at least 70%, at least 80%, at least 90%, or at least 100%.

In some embodiments, the increased expression of CD25 expressed as a percentage of marker-positive cells or mean fluorescence intensity (MFI) upon coculture with Raji cells, compared to K562 cells, is an increase of at least 1-fold, at least 1.5-fold, at least 2-fold, at least 2.5-fold, at least 3-fold, at least 3.5-fold, at least 4-fold, at least 4.5-fold, at least 5-fold, at least 5.5-fold, at least 6-fold, at least 6.5-fold, at least 7-fold, at least 7.5-fold, at least 8-fold, at least 8.5-fold, at least 9-fold, at least 9.5-fold, at least 10-fold, at least 11-fold, at least 12-fold, at least 13-fold, at least 14-fold, at least 15-fold, at least 16-fold, at least 17-fold, at least 18-fold, at least 19-fold, at least 20-fold, at least 25-fold, at least 30-fold, at least 35-fold, at least 40-fold, at least 45-fold, at least 50-fold, at least 55-fold, at least 60-fold, at least 70-fold, at least 80-fold, at least 90-fold, or at least 100-fold.

In some embodiments, the increased expression of CD69 expressed as a percentage of marker-positive cells or mean fluorescence intensity (MFI) upon coculture with Raji cells, compared to K562 cells, is an increase of at least 10%, at least 15%, at least 20%, at least 30%, at least 40%, at least 50%, at least 60%, at least 70%, at least 80%, at least 90%, or at least 100%.

In some embodiments, the increased expression of CD69 expressed as a percentage of marker-positive cells or mean fluorescence intensity (MFI) upon coculture with Raji cells, compared to K562 cells, is an increase of at least 1-fold, at least 1.5-fold, at least 2-fold, at least 2.5-fold, at least 3-fold, at least 3.5-fold, at least 4-fold, at least 4.5-fold, at least 5-fold, at least 5.5-fold, at least 6-fold, at least 6.5-fold, at least 7-fold, at least 7.5-fold, at least 8-fold, at least 8.5-fold, at least 9-fold, at least 9.5-fold, at least 10-fold, at least 11-fold, at least 12-fold, at least 13-fold, at least 14-fold, at least 15-fold, at least 16-fold, at least 17-fold, at least 18-fold, at least 19-fold, at least 20-fold, at least 25-fold, at least 30-fold, at least 35-fold, at least 40-fold, at least 45-fold, at least 50-fold, at least 55-fold, at least 60-fold, at least 70-fold, at least 80-fold, at least 90-fold, or at least 100-fold.

In some embodiments, the increased expression of CD134 expressed as a percentage of marker-positive cells or mean fluorescence intensity (MFI) upon coculture with Raji cells, compared to K562 cells, is an increase of at least 10%, at least 15%, at least 20%, at least 30%, at least 40%, at least 50%, at least 60%, at least 70%, at least 80%, at least 90%, or at least 100%.

In some embodiments, the increased expression of CD134 expressed as a percentage of marker-positive cells or mean fluorescence intensity (MFI) upon coculture with Raji cells, compared to K562 cells, is an increase of at least 1-fold, at least 1.5-fold, at least 2-fold, at least 2.5-fold, at least 3-fold, at least 3.5-fold, at least 4-fold, at least 4.5-fold, at least 5-fold, at least 5.5-fold, at least 6-fold, at least 6.5-fold, at least 7-fold, at least 7.5-fold, at least 8-fold, at least 8.5-fold, at least 9-fold, at least 9.5-fold, at least 10-fold, at least 11-fold, at least 12-fold, at least 13-fold, at least 14-fold, at least 15-fold, at least 16-fold, at least 17-fold, at least 18-fold, at least 19-fold, at least 20-fold, at least 25-fold, at least 30-fold, at least 35-fold, at least 40-fold, at least 45-fold, at least 50-fold, at least 55-fold, at least 60-fold, at least 70-fold, at least 80-fold, at least 90-fold, or at least 100-fold.

In some embodiments, the increased expression of CD137 expressed as a percentage of marker-positive cells or mean fluorescence intensity (MFI) upon coculture with Raji cells, compared to K562 cells, is an increase of at least 10%, at least 15%, at least 20%, at least 30%, at least 40%, at least 50%, at least 60%, at least 70%, at least 80%, at least 90%, or at least 100%.

In some embodiments, the increased expression of CD137 expressed as a percentage of marker-positive cells or mean fluorescence intensity (MFI) upon coculture with Raji cells, compared to K562 cells, is an increase of at least 1-fold, at least 1.5-fold, at least 2-fold, at least 2.5-fold, at least 3-fold, at least 3.5-fold, at least 4-fold, at least 4.5-fold, at least 5-fold, at least 5.5-fold, at least 6-fold, at least 6.5-fold, at least 7-fold, at least 7.5-fold, at least 8-fold, at least 8.5-fold, at least 9-fold, at least 9.5-fold, at least 10-fold, at least 11-fold, at least 12-fold, at least 13-fold, at least 14-fold, at least 15-fold, at least 16-fold, at least 17-fold, at least 18-fold, at least 19-fold, at least 20-fold, at least 25-fold, at least 30-fold, at least 35-fold, at least 40-fold, at least 45-fold, at least 50-fold, at least 55-fold, at least 60-fold, at least 70-fold, at least 80-fold, at least 90-fold, or at least 100-fold.

In some embodiments, the increased expression of CD150 expressed as a percentage of marker-positive cells or mean fluorescence intensity (MFI) upon coculture with Raji cells, compared to K562 cells, is an increase of at least 10%, at least 15%, at least 20%, at least 30%, at least 40%, at least 50%, at least 60%, at least 70%, at least 80%, at least 90%, or at least 100%.

In some embodiments, the increased expression of CD150 expressed as a percentage of marker-positive cells or mean fluorescence intensity (MFI) upon coculture with Raji cells, compared to K562 cells, is an increase of at least 1-fold, at least 1.5-fold, at least 2-fold, at least 2.5-fold, at least 3-fold, at least 3.5-fold, at least 4-fold, at least 4.5-fold, at least 5-fold, at least 5.5-fold, at least 6-fold, at least 6.5-fold, at least 7-fold, at least 7.5-fold, at least 8-fold, at least 8.5-fold, at least 9-fold, at least 9.5-fold, at least 10-fold, at least 11-fold, at least 12-fold, at least 13-fold, at least 14-fold, at least 15-fold, at least 16-fold, at least 17-fold, at least 18-fold, at least 19-fold, at least 20-fold, at least 25-fold, at least 30-fold, at least 35-fold, at least 40-fold, at least 45-fold, at least 50-fold, at least 55-fold, at least 60-fold, at least 70-fold, at least 80-fold, at least 90-fold, or at least 100-fold.

In some embodiments, the increased expression of granzyme B expressed or secreted as a percentage of ELISA-detected analyte or mean fluorescence intensity (MFI) upon coculture with Raji cells, compared to K562 cells, is an increase of at least 10%, at least 15%, at least 20%, at least 30%, at least 40%, at least 50%, at least 60%, at least 70%, at least 80%, at least 90%, or at least 100%.

In some embodiments, the increased expression of granzyme B expressed or secreted as a percentage of ELISA-detected analyte or mean fluorescence intensity (MFI) upon coculture with Raji cells, compared to K562 cells, is an increase of at least 1-fold, at least 1.5-fold, at least 2-fold, at least 2.5-fold, at least 3-fold, at least 3.5-fold, at least 4-fold, at least 4.5-fold, at least 5-fold, at least 5.5-fold, at least 6-fold, at least 6.5-fold, at least 7-fold, at least 7.5-fold, at least 8-fold, at least 8.5-fold, at least 9-fold, at least 9.5-fold, at least 10-fold, at least 11-fold, at least 12-fold, at least 13-fold, at least 14-fold, at least 15-fold, at least 16-fold, at least 17-fold, at least 18-fold, at least 19-fold, at least 20-fold, at least 25-fold, at least 30-fold, at least 35-fold, at least 40-fold, at least 45-fold, at least 50-fold, at least 55-fold, at least 60-fold, at least 70-fold, at least 80-fold, at least 90-fold, or at least 100-fold.

In some embodiments, the increased expression of IFN-γ expressed or secreted as a percentage of ELISA-detected analyte or mean fluorescence intensity (MFI) upon coculture with Raji cells, compared to K562 cells, is an increase of at least 10%, at least 15%, at least 20%, at least 30%, at least 40%, at least 50%, at least 60%, at least 70%, at least 80%, at least 90%, or at least 100%.

In some embodiments, the increased expression of IFN-γ expressed or secreted as a percentage of ELISA-detected analyte or mean fluorescence intensity (MFI) upon coculture with Raji cells, compared to K562 cells, is an increase of at least 1-fold, at least 1.5-fold, at least 2-fold, at least 2.5-fold, at least 3-fold, at least 3.5-fold, at least 4-fold, at least 4.5-fold, at least 5-fold, at least 5.5-fold, at least 6-fold, at least 6.5-fold, at least 7-fold, at least 7.5-fold, at least 8-fold, at least 8.5-fold, at least 9-fold, at least 9.5-fold, at least 10-fold, at least 11-fold, at least 12-fold, at least 13-fold, at least 14-fold, at least 15-fold, at least 16-fold, at least 17-fold, at least 18-fold, at least 19-fold, at least 20-fold, at least 25-fold, at least 30-fold, at least 35-fold, at least 40-fold, at least 45-fold, at least 50-fold, at least 55-fold, at least 60-fold, at least 70-fold, at least 80-fold, at least 90-fold, or at least 100-fold.

In some embodiments, the increased expression of TNF-α expressed or secreted as a percentage of ELISA-detected analyte or mean fluorescence intensity (MFI) upon coculture with Raji cells, compared to K562 cells, is an increase of at least 10%, at least 15%, at least 20%, at least 30%, at least 40%, at least 50%, at least 60%, at least 70%, at least 80%, at least 90%, or at least 100%.

In some embodiments, the increased expression of TNF-α expressed or secreted as a percentage of ELISA-detected analyte or mean fluorescence intensity (MFI) upon coculture with Raji cells, compared to K562 cells, is an increase of at least 1-fold, at least 1.5-fold, at least 2-fold, at least 2.5-fold, at least 3-fold, at least 3.5-fold, at least 4-fold, at least 4.5-fold, at least 5-fold, at least 5.5-fold, at least 6-fold, at least 6.5-fold, at least 7-fold, at least 7.5-fold, at least 8-fold, at least 8.5-fold, at least 9-fold, at least 9.5-fold, at least 10-fold, at least 11-fold, at least 12-fold, at least 13-fold, at least 14-fold, at least 15-fold, at least 16-fold, at least 17-fold, at least 18-fold, at least 19-fold, at least 20-fold, at least 25-fold, at least 30-fold, at least 35-fold, at least 40-fold, at least 45-fold, at least 50-fold, at least 55-fold, at least 60-fold, at least 70-fold, at least 80-fold, at least 90-fold, or at least 100-fold.

In some embodiments, the increased expression of perform expressed or secreted as a percentage of ELISA-detected analyte or mean fluorescence intensity (MFI) upon coculture with Raji cells, compared to K562 cells, is an increase of at least 10%, at least 15%, at least 20%, at least 30%, at least 40%, at least 50%, at least 60%, at least 70%, at least 80%, at least 90%, or at least 100%.

In some embodiments, the increased expression of perform expressed or secreted as a percentage of ELISA-detected analyte or mean fluorescence intensity (MFI) upon coculture with Raji cells, compared to K562 cells, is an increase of at least 1-fold, at least 1.5-fold, at least 2-fold, at least 2.5-fold, at least 3-fold, at least 3.5-fold, at least 4-fold, at least 4.5-fold, at least 5-fold, at least 5.5-fold, at least 6-fold, at least 6.5-fold, at least 7-fold, at least 7.5-fold, at least 8-fold, at least 8.5-fold, at least 9-fold, at least 9.5-fold, at least 10-fold, at least 11-fold, at least 12-fold, at least 13-fold, at least 14-fold, at least 15-fold, at least 16-fold, at least 17-fold, at least 18-fold, at least 19-fold, at least 20-fold, at least 25-fold, at least 30-fold, at least 35-fold, at least 40-fold, at least 45-fold, at least 50-fold, at least 55-fold, at least 60-fold, at least 70-fold, at least 80-fold, at least 90-fold, or at least 100-fold.

In some embodiments, the increased expression of CCL4 expressed or secreted as a percentage of ELISA-detected analyte or mean fluorescence intensity (MFI) upon coculture with Raji cells, compared to K562 cells, is an increase of at least 10%, at least 15%, at least 20%, at least 30%, at least 40%, at least 50%, at least 60%, at least 70%, at least 80%, at least 90%, or at least 100%.

In some embodiments, the increased expression of CCL4 expressed or secreted as a percentage of ELISA-detected analyte or mean fluorescence intensity (MFI) upon coculture with Raji cells, compared to K562 cells, is an increase of at least 1-fold, at least 1.5-fold, at least 2-fold, at least 2.5-fold, at least 3-fold, at least 3.5-fold, at least 4-fold, at least 4.5-fold, at least 5-fold, at least 5.5-fold, at least 6-fold, at least 6.5-fold, at least 7-fold, at least 7.5-fold, at least 8-fold, at least 8.5-fold, at least 9-fold, at least 9.5-fold, at least 10-fold, at least 11-fold, at least 12-fold, at least 13-fold, at least 14-fold, at least 15-fold, at least 16-fold, at least 17-fold, at least 18-fold, at least 19-fold, at least 20-fold, at least 25-fold, at least 30-fold, at least 35-fold, at least 40-fold, at least 45-fold, at least 50-fold, at least 55-fold, at least 60-fold, at least 70-fold, at least 80-fold, at least 90-fold, or at least 100-fold.

In some embodiments, the increased expression of MIP-1β expressed or secreted as a percentage of ELISA-detected analyte or mean fluorescence intensity (MFI) upon coculture with Raji cells, compared to K562 cells, is an increase of at least 10%, at least 15%, at least 20%, at least 30%, at least 40%, at least 50%, at least 60%, at least 70%, at least 80%, at least 90%, or at least 100%.

In some embodiments, the increased expression of MIP-1β expressed or secreted as a percentage of ELISA-detected analyte or mean fluorescence intensity (MFI) upon coculture with Raji cells, compared to K562 cells, is an increase of at least 1-fold, at least 1.5-fold, at least 2-fold, at least 2.5-fold, at least 3-fold, at least 3.5-fold, at least 4-fold, at least 4.5-fold, at least 5-fold, at least 5.5-fold, at least 6-fold, at least 6.5-fold, at least 7-fold, at least 7.5-fold, at least 8-fold, at least 8.5-fold, at least 9-fold, at least 9.5-fold, at least 10-fold, at least 11-fold, at least 12-fold, at least 13-fold, at least 14-fold, at least 15-fold, at least 16-fold, at least 17-fold, at least 18-fold, at least 19-fold, at least 20-fold, at least 25-fold, at least 30-fold, at least 35-fold, at least 40-fold, at least 45-fold, at least 50-fold, at least 55-fold, at least 60-fold, at least 70-fold, at least 80-fold, at least 90-fold, or at least 100-fold.

In some embodiments, the quantity of granzyme B secreted upon coculture with Raji cells is at least 20 pg/mL, at least 30 pg/mL, at least 40 pg/mL, at least 50 pg/mL, at least 60 pg/mL, at least 70 pg/mL, at least 80 pg/mL, at least 90 pg/mL, at least 100 pg/mL, at least 150 pg/mL, at least 200 pg/mL, at least 250 pg/mL, at least 300 pg/mL, at least 350 pg/mL, at least 400 pg/mL, at least 450 pg/mL, at least 500 pg/mL, at least 600 pg/mL, at least 700 pg/mL, at least 800 pg/mL, at least 900 pg/mL, at least 1000 pg/mL, at least 1100 pg/mL, or at least 1200 pg/mL, wherein each mL of test article contains $1\times10^5$ TILs, $2\times10^5$ TILs, $3\times10^5$ TILs, $4\times10^5$ TILs, $5\times10^5$ TILs, $6\times10^5$ TILs, $7\times10^5$ TILs, $8\times10^5$ TILs, $9\times10^5$ TILs, or $10\times10^5$ TILs.

In some embodiments, the quantity of IFN-γ secreted upon coculture with Raji cells is at least 20 pg/mL, at least 30 pg/mL, at least 40 pg/mL, at least 50 pg/mL, at least 60 pg/mL, at least 70 pg/mL, at least 80 pg/mL, at least 90 pg/mL, at least 100 pg/mL, at least 150 pg/mL, at least 200 pg/mL, at least 250 pg/mL, at least 300 pg/mL, at least 350 pg/mL, at least 400 pg/mL, at least 450 pg/mL, at least 500 pg/mL, at least 600 pg/mL, at least 700 pg/mL, at least 800 pg/mL, at least 900 pg/mL, at least 1000 pg/mL, at least 1100 pg/mL, or at least 1200 pg/mL, wherein each mL of test article contains $1\times10^5$ TILs, $2\times10^5$ TILs, $3\times10^5$ TILs, $4\times10^5$ TILs, $5\times10^5$ TILs, $6\times10^5$ TILs, $7\times10^5$ TILs, $8\times10^5$ TILs, $9\times10^5$ TILs, or $10\times10^5$ TILs.

In some embodiments, the quantity of TNF-α secreted upon coculture with Raji cells is at least 20 pg/mL, at least 30 pg/mL, at least 40 pg/mL, at least 50 pg/mL, at least 60 pg/mL, at least 70 pg/mL, at least 80 pg/mL, at least 90 pg/mL, at least 100 pg/mL, at least 150 pg/mL, at least 200 pg/mL, at least 250 pg/mL, at least 300 pg/mL, at least 350 pg/mL, at least 400 pg/mL, at least 450 pg/mL, at least 500 pg/mL, at least 600 pg/mL, at least 700 pg/mL, at least 800 pg/mL, at least 900 pg/mL, at least 1000 pg/mL, at least 1100 pg/mL, or at least 1200 pg/mL, wherein each mL of test article contains $1\times10^5$ TILs, $2\times10^5$ TILs, $3\times10^5$ TILs, $4\times10^5$ TILs, $5\times10^5$ TILs, $6\times10^5$ TILs, $7\times10^5$ TILs, $8\times10^5$ TILs, $9\times10^5$ TILs, or $10\times10^5$ TILs.

In some embodiments, the quantity of perforin secreted upon coculture with Raji cells is at least 20 pg/mL, at least 30 pg/mL, at least 40 pg/mL, at least 50 pg/mL, at least 60 pg/mL, at least 70 pg/mL, at least 80 pg/mL, at least 90 pg/mL, at least 100 pg/mL, at least 150 pg/mL, at least 200 pg/mL, at least 250 pg/mL, at least 300 pg/mL, at least 350 pg/mL, at least 400 pg/mL, at least 450 pg/mL, at least 500 pg/mL, at least 600 pg/mL, at least 700 pg/mL, at least 800 pg/mL, at least 900 pg/mL, at least 1000 pg/mL, at least 1100 pg/mL, or at least 1200 pg/mL, wherein each mL of test article contains $1\times10^5$ TILs, $2\times10^5$ TILs, $3\times10^5$ TILs, $4\times10^5$ TILs, $5\times10^5$ TILs, $6\times10^5$ TILs, $7\times10^5$ TILs, $8\times10^5$ TILs, $9\times10^5$ TILs, or $10\times10^5$ TILs.

In some embodiments, the quantity of CCL4 secreted upon coculture with Raji cells is at least 20 pg/mL, at least 30 pg/mL, at least 40 pg/mL, at least 50 pg/mL, at least 60 pg/mL, at least 70 pg/mL, at least 80 pg/mL, at least 90 pg/mL, at least 100 pg/mL, at least 150 pg/mL, at least 200 pg/mL, at least 250 pg/mL, at least 300 pg/mL, at least 350 pg/mL, at least 400 pg/mL, at least 450 pg/mL, at least 500 pg/mL, at least 600 pg/mL, at least 700 pg/mL, at least 800 pg/mL, at least 900 pg/mL, at least 1000 pg/mL, at least 1100 pg/mL, or at least 1200 pg/mL, wherein each mL of test article contains $1\times10^5$ TILs, $2\times10^5$ TILs, $3\times10^5$ TILs, $4\times10^5$ TILs, $5\times10^5$ TILs, $6\times10^5$ TILs, $7\times10^5$ TILs, $8\times10^5$ TILs, $9\times10^5$ TILs, or $10\times10^5$ TILs.

In some embodiments, the quantity of MIP-1β secreted upon coculture with Raji cells is at least 20 pg/mL, at least 30 pg/mL, at least 40 pg/mL, at least 50 pg/mL, at least 60 pg/mL, at least 70 pg/mL, at least 80 pg/mL, at least 90 pg/mL, at least 100 pg/mL, at least 150 pg/mL, at least 200 pg/mL, at least 250 pg/mL, at least 300 pg/mL, at least 350 pg/mL, at least 400 pg/mL, at least 450 pg/mL, at least 500 pg/mL, at least 600 pg/mL, at least 700 pg/mL, at least 800 pg/mL, at least 900 pg/mL, at least 1000 pg/mL, at least 1100 pg/mL, or at least 1200 pg/mL, wherein each mL of test article contains $1\times10^5$ TILs, $2\times10^5$ TILs, $3\times10^5$ TILs, $4\times10^5$ TILs, $5\times10^5$ TILs, $6\times10^5$ TILs, $7\times10^5$ TILs, $8\times10^5$ TILs, $9\times10^5$ TILs, or $10\times10^5$ TILs.

In an embodiment, the target cell to T cell (including TIL, MIL or PBL) ratio is selected from the group consisting of about 1:1.1, about 1:1.2, about 1:1.3, about 1:1.4, about 1:1.5, about 1:1.6, about 1:1.7, about 1:1.8, about 1:1.9, about 1:2, about 1:2.1, about 1:2.2, about 1:2.3, about 1:2.4, about 1:2.5, about 1:2.6, about 1:2.7, about 1:2.8, about 1:2.9, about 1:3, about 1:3.1, about 1:3.2, about 1:3.3, about 1:3.4, about 1:3.5, about 1:3.6, about 1:3.7, about 1:3.8, about 1:3.9, about 1:4, about 1:4.1, about 1:4.2, about 1:4.3, about 1:4.4, about 1:4.5, about 1:4.6, about 1:4.7, about 1:4.8, about 1:4.9, about 1:5, about 1:5.1, about 1:5.2, about 1:5.3, about 1:5.4, about 1:5.5, about 1:5.6, about 1:5.7, about 1:5.8, about 1:5.9, about 1:6, about 1:6.1, about 1:6.2, about 1:6.25, about 1:6.3, about 1:6.4, about 1:6.5, about 1:6.6, about 1:6.7, about 1:6.8, about 1:6.9, about 1:7, about 1:7.1, about 1:7.2, about 1:7.3, about 1:7.4, about 1:7.5, about 1:7.6, about 1:7.7, about 1:7.8, about 1:7.9, about 1:8, about 1:8.1, about 1:8.2, about 1:8.3, about 1:8.4, about 1:8.5, about 1:8.6, about 1:8.7, about 1:8.8, about 1:8.9, about 1:9, about 1:9.1, about 1:9.2, about 1:9.3, about 1:9.4, about 1:9.5, about 1:9.6, about 1:9.7, about 1:9.8, about 1:9.9, about 1:10, about 1:11, about 1:12, about 1:12.5, about 1:13, about 1:14, about 1:15, about 1:16, about 1:17, about 1:18, about 1:19, about 1:20, about 1:25, about 1:30, about 1:35, about 1:40, about 1:45, about 1:50, about 1:60, about 1:70, about 1:80, about 1:90, or about 1:100.

In an embodiment, the T cell (including TIL, MIL or PBL) to target cell ratio is selected from the group consisting of about 1:1.1, about 1:1.2, about 1:1.3, about 1:1.4, about 1:1.5, about 1:1.6, about 1:1.7, about 1:1.8, about 1:1.9, about 1:2, about 1:2.1, about 1:2.2, about 1:2.3, about 1:2.4, about 1:2.5, about 1:2.6, about 1:2.7, about 1:2.8, about 1:2.9, about 1:3, about 1:3.1, about 1:3.2, about 1:3.3, about 1:3.4, about 1:3.5, about 1:3.6, about 1:3.7, about 1:3.8, about 1:3.9, about 1:4, about 1:4.1, about 1:4.2, about 1:4.3, about 1:4.4, about 1:4.5, about 1:4.6, about 1:4.7, about 1:4.8, about 1:4.9, about 1:5, about 1:5.1, about 1:5.2, about 1:5.3, about 1:5.4, about 1:5.5, about 1:5.6, about 1:5.7, about 1:5.8, about 1:5.9, about 1:6, about 1:6.1, about 1:6.2, about 1:6.25, about 1:6.3, about 1:6.4, about 1:6.5, about 1:6.6, about 1:6.7, about 1:6.8, about 1:6.9, about 1:7, about 1:7.1, about 1:7.2, about 1:7.3, about 1:7.4, about 1:7.5, about 1:7.6, about 1:7.7, about 1:7.8, about 1:7.9, about 1:8, about 1:8.1, about 1:8.2, about 1:8.3, about 1:8.4, about 1:8.5, about 1:8.6, about 1:8.7, about 1:8.8, about 1:8.9, about 1:9, about 1:9.1, about 1:9.2, about 1:9.3, about 1:9.4, about 1:9.5, about 1:9.6, about 1:9.7, about 1:9.8, about 1:9.9, about 1:10, about 1:11, about 1:12, about 1:12.5, about 1:13, about 1:14, about 1:15, about 1:16, about 1:17, about 1:18, about 1:19, about 1:20, about 1:25, about 1:30, about 1:35, about 1:40, about 1:45, about 1:50, about 1:60, about 1:70, about 1:80, about 1:90, or about 1:100.

In an embodiment, the Raji cell to T cell (including TIL, MIL or PBL) ratio is selected from the group consisting of about 1:1.1, about 1:1.2, about 1:1.3, about 1:1.4, about 1:1.5, about 1:1.6, about 1:1.7, about 1:1.8, about 1:1.9, about 1:2, about 1:2.1, about 1:2.2, about 1:2.3, about 1:2.4, about 1:2.5, about 1:2.6, about 1:2.7, about 1:2.8, about 1:2.9, about 1:3, about 1:3.1, about 1:3.2, about 1:3.3, about 1:3.4, about 1:3.5, about 1:3.6, about 1:3.7, about 1:3.8, about 1:3.9, about 1:4, about 1:4.1, about 1:4.2, about 1:4.3, about 1:4.4, about 1:4.5, about 1:4.6, about 1:4.7, about 1:4.8, about 1:4.9, about 1:5, about 1:5.1, about 1:5.2, about 1:5.3, about 1:5.4, about 1:5.5, about 1:5.6, about 1:5.7, about 1:5.8, about 1:5.9, about 1:6, about 1:6.1, about 1:6.2, about 1:6.25, about 1:6.3, about 1:6.4, about 1:6.5, about 1:6.6, about 1:6.7, about 1:6.8, about 1:6.9, about 1:7, about 1:7.1, about 1:7.2, about 1:7.3, about 1:7.4, about 1:7.5, about 1:7.6, about 1:7.7, about 1:7.8, about 1:7.9, about 1:8, about 1:8.1, about 1:8.2, about 1:8.3, about 1:8.4, about 1:8.5, about 1:8.6, about 1:8.7, about 1:8.8, about 1:8.9, about 1:9, about 1:9.1, about 1:9.2, about 1:9.3, about 1:9.4, about 1:9.5, about 1:9.6, about 1:9.7, about 1:9.8, about 1:9.9, about 1:10, about 1:11, about 1:12, about 1:12.5, about 1:13, about 1:14, about 1:15, about 1:16, about 1:17, about 1:18, about 1:19, about 1:20, about 1:25, about 1:30, about 1:35, about 1:40, about 1:45, about 1:50, about 1:60, about 1:70, about 1:80, about 1:90, or about 1:100.

In an embodiment, the T cell (including TIL, MIL or PBL) to Raji cell ratio is selected from the group consisting of about 1:1.1, about 1:1.2, about 1:1.3, about 1:1.4, about 1:1.5, about 1:1.6, about 1:1.7, about 1:1.8, about 1:1.9, about 1:2, about 1:2.1, about 1:2.2, about 1:2.3, about 1:2.4, about 1:2.5, about 1:2.6, about 1:2.7, about 1:2.8, about 1:2.9, about 1:3, about 1:3.1, about 1:3.2, about 1:3.3, about 1:3.4, about 1:3.5, about 1:3.6, about 1:3.7, about 1:3.8, about 1:3.9, about 1:4, about 1:4.1, about 1:4.2, about 1:4.3, about 1:4.4, about 1:4.5, about 1:4.6, about 1:4.7, about 1:4.8, about 1:4.9, about 1:5, about 1:5.1, about 1:5.2, about 1:5.3, about 1:5.4, about 1:5.5, about 1:5.6, about 1:5.7, about 1:5.8, about 1:5.9, about 1:6, about 1:6.1, about 1:6.2, about 1:6.25, about 1:6.3, about 1:6.4, about 1:6.5, about 1:6.6, about 1:6.7, about 1:6.8, about 1:6.9, about 1:7, about 1:7.1, about 1:7.2, about 1:7.3, about 1:7.4, about 1:7.5, about 1:7.6, about 1:7.7, about 1:7.8, about 1:7.9, about 1:8, about 1:8.1, about 1:8.2, about 1:8.3, about 1:8.4, about 1:8.5, about 1:8.6, about 1:8.7, about 1:8.8, about 1:8.9, about 1:9, about 1:9.1, about 1:9.2, about 1:9.3, about 1:9.4, about 1:9.5, about 1:9.6, about 1:9.7, about 1:9.8, about 1:9.9, about 1:10, about 1:11, about 1:12, about 1:12.5, about 1:13, about 1:14, about 1:15, about 1:16, about 1:17, about 1:18, about 1:19, about 1:20, about 1:25, about 1:30, about 1:35, about 1:40, about 1:45, about 1:50, about 1:60, about 1:70, about 1:80, about 1:90, or about 1:100.

In an embodiment, the negative control cell to T cell (including TIL, MIL or PBL) ratio is selected from the group consisting of about 1:1.1, about 1:1.2, about 1:1.3, about 1:1.4, about 1:1.5, about 1:1.6, about 1:1.7, about 1:1.8, about 1:1.9, about 1:2, about 1:2.1, about 1:2.2, about 1:2.3, about 1:2.4, about 1:2.5, about 1:2.6, about 1:2.7, about 1:2.8, about 1:2.9, about 1:3, about 1:3.1, about 1:3.2, about 1:3.3, about 1:3.4, about 1:3.5, about 1:3.6, about 1:3.7, about 1:3.8, about 1:3.9, about 1:4, about 1:4.1, about 1:4.2, about 1:4.3, about 1:4.4, about 1:4.5, about 1:4.6, about 1:4.7, about 1:4.8, about 1:4.9, about 1:5, about 1:5.1, about 1:5.2, about 1:5.3, about 1:5.4, about 1:5.5, about 1:5.6, about 1:5.7, about 1:5.8, about 1:5.9, about 1:6, about 1:6.1, about 1:6.2, about 1:6.25, about 1:6.3, about 1:6.4, about 1:6.5, about 1:6.6, about 1:6.7, about 1:6.8, about 1:6.9, about 1:7, about 1:7.1, about 1:7.2, about 1:7.3, about 1:7.4, about 1:7.5, about 1:7.6, about 1:7.7, about 1:7.8, about 1:7.9, about 1:8, about 1:8.1, about 1:8.2, about 1:8.3, about 1:8.4, about 1:8.5, about 1:8.6, about 1:8.7, about 1:8.8, about 1:8.9, about 1:9, about 1:9.1, about 1:9.2, about 1:9.3, about 1:9.4, about 1:9.5, about 1:9.6, about 1:9.7, about 1:9.8, about 1:9.9, about 1:10, about 1:11, about 1:12, about 1:12.5, about 1:13, about 1:14, about 1:15, about 1:16, about 1:17, about 1:18, about 1:19, about 1:20, about 1:25, about 1:30, about 1:35, about 1:40, about 1:45, about 1:50, about 1:60, about 1:70, about 1:80, about 1:90, or about 1:100.

In an embodiment, the T cell (including TIL, MIL or PBL) to negative control cell ratio is selected from the group consisting of about 1:1.1, 1:1.2, 1:1.3, 1:1.4, 1:1.5, 1:1.6, 1:1.7, 1:1.8, 1:1.9, 1:2, 1:2.1, 1:2.2, 1:2.3, 1:2.4, 1:2.5, 1:2.6, 1:2.7, 1:2.8, 1:2.9, 1:3, 1:3.1, 1:3.2, 1:3.3, 1:3.4, 1:3.5, 1:3.6, 1:3.7, 1:3.8, 1:3.9, 1:4, 1:4.1, 1:4.2, 1:4.3, 1:4.4, 1:4.5, 1:4.6, 1:4.7, 1:4.8, 1:4.9, 1:5, 1:5.1, 1:5.2, 1:5.3, 1:5.4, 1:5.5, 1:5.6, 1:5.7, 1:5.8, 1:5.9, 1:6, 1:6.1, 1:6.2, 1:6.25, 1:6.3, 1:6.4, 1:6.5, 1:6.6, 1:6.7, 1:6.8, 1:6.9, 1:7, 1:7.1, 1:7.2, 1:7.3, 1:7.4, 1:7.5, 1:7.6, 1:7.7, 1:7.8, 1:7.9, 1:8, 1:8.1, 1:8.2, 1:8.3, 1:8.4, 1:8.5, 1:8.6, 1:8.7, 1:8.8, 1:8.9, 1:9, 1:9.1, 1:9.2, 1:9.3, 1:9.4, 1:9.5, 1:9.6, 1:9.7, 1:9.8, 1:9.9, 1:10, 1:11, 1:12, 1:12.5, 1:13, 1:14, 1:15, 1:16, 1:17, 1:18, 1:19, 1:20, 1:25, 1:30, 1:35, 1:40, 1:45, 1:50, 1:60, 1:70, 1:80, 1:90, or 1:100.

In an embodiment, the K562 cell to T cell (including TIL, MIL or PBL) ratio is selected from the group consisting of about 1:1.1, 1:1.2, 1:1.3, 1:1.4, 1:1.5, 1:1.6, 1:1.7, 1:1.8, 1:1.9, 1:2, 1:2.1, 1:2.2, 1:2.3, 1:2.4, 1:2.5, 1:2.6, 1:2.7, 1:2.8, 1:2.9, 1:3, 1:3.1, 1:3.2, 1:3.3, 1:3.4, 1:3.5, 1:3.6, 1:3.7, 1:3.8, 1:3.9, 1:4, 1:4.1, 1:4.2, 1:4.3, 1:4.4, 1:4.5, 1:4.6, 1:4.7, 1:4.8, 1:4.9, 1:5, 1:5.1, 1:5.2, 1:5.3, 1:5.4, 1:5.5, 1:5.6, 1:5.7, 1:5.8, 1:5.9, 1:6, 1:6.1, 1:6.2, 1:6.25, 1:6.3, 1:6.4, 1:6.5, 1:6.6, 1:6.7, 1:6.8, 1:6.9, 1:7, 1:7.1, 1:7.2, 1:7.3, 1:7.4, 1:7.5, 1:7.6, 1:7.7, 1:7.8, 1:7.9, 1:8, 1:8.1, 1:8.2, 1:8.3, 1:8.4, 1:8.5, 1:8.6, 1:8.7, 1:8.8, 1:8.9, 1:9, 1:9.1, 1:9.2, 1:9.3, 1:9.4, 1:9.5, 1:9.6, 1:9.7, 1:9.8, 1:9.9, 1:10, 1:11, 1:12, 1:12.5, 1:13, 1:14, 1:15, 1:16, 1:17, 1:18, 1:19, 1:20, 1:25, 1:30, 1:35, 1:40, 1:45, 1:50, 1:60, 1:70, 1:80, 1:90, or 1:100.

In an embodiment, the T cell (including TIL, MIL or PBL) to K562 cell ratio is selected from the group consisting of about 1:1.1, 1:1.2, 1:1.3, 1:1.4, 1:1.5, 1:1.6, 1:1.7, 1:1.8, 1:1.9, 1:2, 1:2.1, 1:2.2, 1:2.3, 1:2.4, 1:2.5, 1:2.6, 1:2.7, 1:2.8, 1:2.9, 1:3, 1:3.1, 1:3.2, 1:3.3, 1:3.4, 1:3.5, 1:3.6, 1:3.7, 1:3.8, 1:3.9, 1:4, 1:4.1, 1:4.2, 1:4.3, 1:4.4, 1:4.5, 1:4.6, 1:4.7, 1:4.8, 1:4.9, 1:5, 1:5.1, 1:5.2, 1:5.3, 1:5.4, 1:5.5, 1:5.6, 1:5.7, 1:5.8, 1:5.9, 1:6, 1:6.1, 1:6.2, 1:6.25, 1:6.3, 1:6.4, 1:6.5, 1:6.6, 1:6.7, 1:6.8, 1:6.9, 1:7, 1:7.1, 1:7.2, 1:7.3, 1:7.4, 1:7.5, 1:7.6, 1:7.7, 1:7.8, 1:7.9, 1:8, 1:8.1, 1:8.2, 1:8.3, 1:8.4, 1:8.5, 1:8.6, 1:8.7, 1:8.8, 1:8.9, 1:9, 1:9.1, 1:9.2, 1:9.3, 1:9.4, 1:9.5, 1:9.6, 1:9.7, 1:9.8, 1:9.9, 1:10, 1:11, 1:12, 1:12.5, 1:13, 1:14, 1:15, 1:16, 1:17, 1:18, 1:19, 1:20, 1:25, 1:30, 1:35, 1:40, 1:45, 1:50, 1:60, 1:70, 1:80, 1:90, or 1:100.

In an embodiment, the target cell to T cell (including TIL, MIL or PBL) ratio is between 1:1 and 1:2, between 1:2 and 1:3, between 1:3 and 1:4, between 1:4 and 1:5, between 1:5 and 1:6, between 1:6 and 1:7, between 1:7 and 1:8, between 1:8 and 1:9, between 1:9 and 1:10, between 1:10 and 1:11, between 1:11 and 1:12, between 1:12 and 1:13, between 1:13 and 1:14, between 1:14 and 1:15, between 1:15 and 1:16, between 1:16 and 1:17, between 1:17 and 1:18, between 1:18 and 1:19, between 1:19 and 1:20, between 1:20 and 1:25, between 1:25 and 1:30, between 1:30 and 1:35, between 1:35 and 1:40, between 1:40 and 1:45, between 1:45 and 1:50, between 1:50 and 1:55, between 1:55 and 1:60, between 1:60 and 1:70, between 1:70 and 1:80, between 1:80 and 1:90, or between 1:90 and 1:100, or, alternatively, between 1:0.5 and 1:100, between 1:0.5 and 1:50, between 1:0.5 and 1:40, between 1:0.5 and 1:30, between 1:0.5 and 1:25, between 1:0.5 and 1:20, between 1:0.5 and 1:15, between 1:0.5 and 1:10, between 1:0.5 and 1:5, between 1:0.75 and 1:50, between 1:0.75 and 1:40, between 1:0.75 and 1:30, between 1:0.75 and 1:25, between 1:0.75 and 1:20, between 1:0.75 and 1:15, between 1:0.75 and 1:10, between 1:0.75 and 1:5, between 1:0.5 and 1:2.5, between 1:1 and 1:20, between 1:1 and 1:10, between 1:1 and 1:5, between 1:1 and 1:2.5; between 1:2 and 1:5, between 1:2.5 and 1:5, or between 1:3 and 1:5.

In an embodiment, the T cell (including TIL, MIL or PBL) to target cell ratio is between 1:1 and 1:2, between 1:2 and 1:3, between 1:3 and 1:4, between 1:4 and 1:5, between 1:5 and 1:6, between 1:6 and 1:7, between 1:7 and 1:8, between 1:8 and 1:9, between 1:9 and 1:10, between 1:10 and 1:11, between 1:11 and 1:12, between 1:12 and 1:13, between 1:13 and 1:14, between 1:14 and 1:15, between 1:15 and 1:16, between 1:16 and 1:17, between 1:17 and 1:18, between 1:18 and 1:19, between 1:19 and 1:20, between 1:20 and 1:25, between 1:25 and 1:30, between 1:30 and 1:35, between 1:35 and 1:40, between 1:40 and 1:45, between 1:45 and 1:50, between 1:50 and 1:55, between 1:55 and 1:60, between 1:60 and 1:70, between 1:70 and 1:80, between 1:80 and 1:90, or between 1:90 and 1:100, or, alternatively, between 1:0.5 and 1:100, between 1:0.5 and 1:50, between 1:0.5 and 1:40, between 1:0.5 and 1:30, between 1:0.5 and 1:25, between 1:0.5 and 1:20, between 1:0.5 and 1:15, between 1:0.5 and 1:10, between 1:0.5 and 1:5, between 1:0.75 and 1:50, between 1:0.75 and 1:40, between 1:0.75 and 1:30, between 1:0.75 and 1:25, between 1:0.75 and 1:20, between 1:0.75 and 1:15, between 1:0.75 and 1:10, between 1:0.75 and 1:5, between 1:0.5 and 1:2.5, between 1:1 and 1:20, between 1:1 and 1:10, between 1:1 and 1:5, between 1:1 and 1:2.5; between 1:2 and 1:5, between 1:2.5 and 1:5, or between 1:3 and 1:5.

In an embodiment, the Raji cell to T cell (including TIL, MIL or PBL) ratio is between 1:1 and 1:2, between 1:2 and 1:3, between 1:3 and 1:4, between 1:4 and 1:5, between 1:5 and 1:6, between 1:6 and 1:7, between 1:7 and 1:8, between 1:8 and 1:9, between 1:9 and 1:10, between 1:10 and 1:11, between 1:11 and 1:12, between 1:12 and 1:13, between 1:13 and 1:14, between 1:14 and 1:15, between 1:15 and 1:16, between 1:16 and 1:17, between 1:17 and 1:18, between 1:18 and 1:19, between 1:19 and 1:20, between 1:20 and 1:25, between 1:25 and 1:30, between 1:30 and 1:35, between 1:35 and 1:40, between 1:40 and 1:45, between 1:45 and 1:50, between 1:50 and 1:55, between 1:55 and 1:60, between 1:60 and 1:70, between 1:70 and 1:80, between 1:80 and 1:90, or between 1:90 and 1:100, or, alternatively, between 1:0.5 and 1:100, between 1:0.5 and 1:50, between 1:0.5 and 1:40, between 1:0.5 and 1:30, between 1:0.5 and 1:25, between 1:0.5 and 1:20, between 1:0.5 and 1:15, between 1:0.5 and 1:10, between 1:0.5 and 1:5, between 1:0.75 and 1:50, between 1:0.75 and 1:40, between 1:0.75 and 1:30, between 1:0.75 and 1:25, between 1:0.75 and 1:20, between 1:0.75 and 1:15, between 1:0.75 and 1:10, between 1:0.75 and 1:5, between 1:0.5 and 1:2.5, between 1:1 and 1:20, between 1:1 and 1:10, between 1:1 and 1:5, between 1:1 and 1:2.5; between 1:2 and 1:5, between 1:2.5 and 1:5, or between 1:3 and 1:5.

In an embodiment, the T cell (including TIL, MIL or PBL) to Raji cell ratio is between 1:1 and 1:2, between 1:2 and 1:3, between 1:3 and 1:4, between 1:4 and 1:5, between 1:5 and 1:6, between 1:6 and 1:7, between 1:7 and 1:8, between 1:8 and 1:9, between 1:9 and 1:10, between 1:10 and 1:11, between 1:11 and 1:12, between 1:12 and 1:13, between 1:13 and 1:14, between 1:14 and 1:15, between 1:15 and 1:16, between 1:16 and 1:17, between 1:17 and 1:18, between 1:18 and 1:19, between 1:19 and 1:20, between 1:20 and 1:25, between 1:25 and 1:30, between 1:30 and 1:35, between 1:35 and 1:40, between 1:40 and 1:45, between 1:45 and 1:50, between 1:50 and 1:55, between 1:55 and 1:60, between 1:60 and 1:70, between 1:70 and 1:80, between 1:80 and 1:90, or between 1:90 and 1:100, or, alternatively, between 1:0.5 and 1:100, between 1:0.5 and 1:50, between 1:0.5 and 1:40, between 1:0.5 and 1:30, between 1:0.5 and 1:25, between 1:0.5 and 1:20, between 1:0.5 and 1:15, between 1:0.5 and 1:10, between 1:0.5 and 1:5, between 1:0.75 and 1:50, between 1:0.75 and 1:40, between 1:0.75 and 1:30, between 1:0.75 and 1:25, between 1:0.75 and 1:20, between 1:0.75 and 1:15, between 1:0.75 and 1:10, between 1:0.75 and 1:5, between 1:0.5 and 1:2.5, between 1:1 and 1:20, between 1:1 and 1:10, between 1:1 and 1:5, between 1:1 and 1:2.5; between 1:2 and 1:5, between 1:2.5 and 1:5, or between 1:3 and 1:5.

In an embodiment, the negative control cell to T cell (including TIL, MIL or PBL) ratio is between 1:1 and 1:2, between 1:2 and 1:3, between 1:3 and 1:4, between 1:4 and 1:5, between 1:5 and 1:6, between 1:6 and 1:7, between 1:7 and 1:8, between 1:8 and 1:9, between 1:9 and 1:10, between 1:10 and 1:11, between 1:11 and 1:12, between 1:12 and 1:13, between 1:13 and 1:14, between 1:14 and 1:15, between 1:15 and 1:16, between 1:16 and 1:17, between 1:17 and 1:18, between 1:18 and 1:19, between 1:19 and 1:20, between 1:20 and 1:25, between 1:25 and 1:30, between 1:30 and 1:35, between 1:35 and 1:40, between 1:40 and 1:45, between 1:45 and 1:50, between 1:50 and 1:55, between 1:55 and 1:60, between 1:60 and 1:70, between 1:70 and 1:80, between 1:80 and 1:90, or between 1:90 and 1:100, or, alternatively, between 1:0.5 and 1:100, between 1:0.5 and 1:50, between 1:0.5 and 1:40, between 1:0.5 and 1:30, between 1:0.5 and 1:25, between 1:0.5 and 1:20, between 1:0.5 and 1:15, between 1:0.5 and 1:10, between 1:0.5 and 1:5, between 1:0.75 and 1:50, between 1:0.75 and 1:40, between 1:0.75 and 1:30, between 1:0.75 and 1:25, between 1:0.75 and 1:20, between 1:0.75 and 1:15, between 1:0.75 and 1:10, between 1:0.75 and 1:5, between 1:0.5 and 1:2.5, between 1:1 and 1:20, between 1:1 and 1:10, between 1:1 and 1:5, between 1:1 and 1:2.5; between 1:2 and 1:5, between 1:2.5 and 1:5, or between 1:3 and 1:5.

In an embodiment, the T cell (including TIL, MIL or PBL) to negative control cell ratio is between 1:1 and 1:2, between 1:2 and 1:3, between 1:3 and 1:4, between 1:4 and 1:5, between 1:5 and 1:6, between 1:6 and 1:7, between 1:7 and 1:8, between 1:8 and 1:9, between 1:9 and 1:10, between 1:10 and 1:11, between 1:11 and 1:12, between 1:12 and 1:13, between 1:13 and 1:14, between 1:14 and 1:15, between 1:15 and 1:16, between 1:16 and 1:17, between 1:17 and 1:18, between 1:18 and 1:19, between 1:19 and 1:20, between 1:20 and 1:25, between 1:25 and 1:30, between 1:30 and 1:35, between 1:35 and 1:40, between 1:40 and 1:45, between 1:45 and 1:50, between 1:50 and 1:55, between 1:55 and 1:60, between 1:60 and 1:70, between 1:70 and 1:80, between 1:80 and 1:90, or between 1:90 and 1:100, or, alternatively, between 1:0.5 and 1:100, between 1:0.5 and 1:50, between 1:0.5 and 1:40, between 1:0.5 and 1:30, between 1:0.5 and 1:25, between 1:0.5 and 1:20, between 1:0.5 and 1:15, between 1:0.5 and 1:10, between 1:0.5 and 1:5, between 1:0.75 and 1:50, between 1:0.75 and 1:40, between 1:0.75 and 1:30, between 1:0.75 and 1:25, between 1:0.75 and 1:20, between 1:0.75 and 1:15, between 1:0.75 and 1:10, between 1:0.75 and 1:5, between 1:0.5 and 1:2.5, between 1:1 and 1:20, between 1:1 and 1:10, between 1:1 and 1:5, between 1:1 and 1:2.5; between 1:2 and 1:5, between 1:2.5 and 1:5, or between 1:3 and 1:5.

In an embodiment, the K562 cell to T cell (including TIL, MIL or PBL) ratio is between 1:1 and 1:2, between 1:2 and 1:3, between 1:3 and 1:4, between 1:4 and 1:5, between 1:5 and 1:6, between 1:6 and 1:7, between 1:7 and 1:8, between 1:8 and 1:9, between 1:9 and 1:10, between 1:10 and 1:11, between 1:11 and 1:12, between 1:12 and 1:13, between 1:13 and 1:14, between 1:14 and 1:15, between 1:15 and 1:16, between 1:16 and 1:17, between 1:17 and 1:18, between 1:18 and 1:19, between 1:19 and 1:20, between 1:20 and 1:25, between 1:25 and 1:30, between 1:30 and 1:35, between 1:35 and 1:40, between 1:40 and 1:45, between 1:45 and 1:50, between 1:50 and 1:55, between 1:55 and 1:60, between 1:60 and 1:70, between 1:70 and 1:80, between 1:80 and 1:90, or between 1:90 and 1:100, or, alternatively, between 1:0.5 and 1:100, between 1:0.5 and 1:50, between 1:0.5 and 1:40, between 1:0.5 and 1:30, between 1:0.5 and 1:25, between 1:0.5 and 1:20, between 1:0.5 and 1:15, between 1:0.5 and 1:10, between 1:0.5 and 1:5, between 1:0.75 and 1:50, between 1:0.75 and 1:40, between 1:0.75 and 1:30, between 1:0.75 and 1:25, between 1:0.75 and 1:20, between 1:0.75 and 1:15, between 1:0.75 and 1:10, between 1:0.75 and 1:5, between 1:0.5 and 1:2.5, between 1:1 and 1:20, between 1:1 and 1:10, between 1:1 and 1:5, between 1:1 and 1:2.5; between 1:2 and 1:5, between 1:2.5 and 1:5, or between 1:3 and 1:5.

In an embodiment, the T cell (including TIL, MIL or PBL) to K562 cell ratio is between 1:1 and 1:2, between 1:2 and 1:3, between 1:3 and 1:4, between 1:4 and 1:5, between 1:5 and 1:6, between 1:6 and 1:7, between 1:7 and 1:8, between 1:8 and 1:9, between 1:9 and 1:10, between 1:10 and 1:11, between 1:11 and 1:12, between 1:12 and 1:13, between 1:13 and 1:14, between 1:14 and 1:15, between 1:15 and 1:16, between 1:16 and 1:17, between 1:17 and 1:18, between 1:18 and 1:19, between 1:19 and 1:20, between 1:20 and 1:25, between 1:25 and 1:30, between 1:30 and 1:35, between 1:35 and 1:40, between 1:40 and 1:45, between 1:45 and 1:50, between 1:50 and 1:55, between 1:55 and 1:60, between 1:60 and 1:70, between 1:70 and 1:80, between 1:80 and 1:90, or between 1:90 and 1:100, or, alternatively, between 1:0.5 and 1:100, between 1:0.5 and 1:50, between 1:0.5 and 1:40, between 1:0.5 and 1:30, between 1:0.5 and 1:25, between 1:0.5 and 1:20, between 1:0.5 and 1:15, between 1:0.5 and 1:10, between 1:0.5 and 1:5, between 1:0.75 and 1:50, between 1:0.75 and 1:40, between 1:0.75 and 1:30, between 1:0.75 and 1:25, between 1:0.75 and 1:20, between 1:0.75 and 1:15, between 1:0.75 and 1:10, between 1:0.75 and 1:5, between 1:0.5 and 1:2.5, between 1:1 and 1:20, between 1:1 and 1:10, between 1:1 and 1:5, between 1:1 and 1:2.5; between 1:2 and 1:5, between 1:2.5 and 1:5, or between 1:3 and 1:5.

In an embodiment, the TIL to Raji cell ratio in a target cell co-culture is selected from the group consisting of about 15:1, about 14:1, about 13:1, about 12:1, about 11:1, about 10:1, about 9:1, about 8:1, about 7:1, about 6:1, about 5:1, about 4.5:1, about 4:1, about 3.5:1, about 3:1, about 2.5:1, about 2:1, about 1.5:1, about 1:1, about 1:1.5, about 1:2, about 1:2.5, about 1:3, about 1:3.5, about 1:4, about 1:4.5, about 1:5, about 1:6, about 1.7, about 1:8, about 1:9, about 1:10, about 1:11, about 1:12, about 1:13, about 1:14, and about 1:15.

In an embodiment, the TIL to K562 cell ratio in a target cell co-culture is selected from the group consisting of about 15:1, about 14:1, about 13:1, about 12:1, about 11:1, about 10:1, about 9:1, about 8:1, about 7:1, about 6:1, about 5:1, about 4.5:1, about 4:1, about 3.5:1, about 3:1, about 2.5:1, about 2:1, about 1.5:1, about 1:1, about 1:1.5, about 1:2, about 1:2.5, about 1:3, about 1:3.5, about 1:4, about 1:4.5, about 1:5, about 1:6, about 1.7, about 1:8, about 1:9, about 1:10, about 1:11, about 1:12, about 1:13, about 1:14, and about 1:15.

In an embodiment, about $1\times10^5$ to $10\times10^5$ TILs are co-cultured with about $1\times10^5$ to $10\times10^5$ Raji cells. In an embodiment, about $3\times10^5$ to $7\times10^5$ TILs are co-cultured with about $1\times10^5$ to $3\times10^5$ Raji cells. In an embodiment, about $5\times10^5$ to $6\times10^5$ TILs are co-cultured with about $3\times10^5$ to $7\times10^5$ Raji cells. In an embodiment, about $4\times10^5$ TILs are co-cultured with about $5\times10^5$ Raji cells. In an embodiment, about $5\times10^5$ TILs are co-cultured with about $5\times10^5$ Raji cells. In an embodiment, about $5\times10^5$ TILs are co-cultured with about $4\times10^5$ Raji cells. In an embodiment, about $3\times10^5$ to $7\times10^5$ TILs are co-cultured with about $7\times10^5$ to $20\times10^5$ Raji cells. In an embodiment, about $4\times10^5$ to $4\times10^5$ TILs are co-cultured with about $10\times10^5$ to $15\times10^5$ Raji cells. In an embodiment, about $5\times10^5$ TILs are co-cultured with about $15\times10^5$ Raji cells.

In some embodiments, the present invention provides a method for assaying TIL activity comprising the steps of: (a) irradiating Raji cells and K562 cells; (b) co-culturing irradiated Raji cells and irradiated K562 cells with TIL at a target ratios selected from the group consisting of 50:1, 25:1, 12.5:1, 6.25:1, 1:1, 1:6.25, 1:12.5, and 1:25), such co-culture optionally performed using an anti-CD28 antibody; (c) collecting the supernatants from the co-cultured cells in step (b) after 6 to 24 hours; (d) harvesting the cells from step (b) and measuring surface marker expression of T cell activation; and (e) assaying the supernatants from the co-cultured cells collected in step (c) for markers of T cell activation.

In an embodiment, a potency assay includes a recovery step wherein a TIL, MIL, or PBL cryopreserved product is thawed and allowed to recover at ambient or refrigerated temperature for a period selected from the group consisting of 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 25 hours, 26 hours, 27 hours, 28 hours, 29 hours, 30 hours, 31 hours, 32 hours, 33 hours, 34 hours, 35 hours, 36 hours, 37 hours, 38 hours, 39 hours, 40 hours, 41 hours, 42 hours, 43 hours, 44 hours, 45 hours, 46 hours, 47 hours, 48 hours, 49 hours, 50 hours, 51 hours, 52 hours, 53 hours, 54 hours, 55 hours, 56 hours, 57 hours, 58 hours, 59 hours, 60 hours, 61 hours, 62 hours, 63 hours, 64 hours, 65 hours, 66 hours, 67 hours, 68 hours, 69 hours, 70 hours, 71 hours, 72 hours, 73 hours, 74 hours, 75 hours, 76 hours, 77 hours, 78 hours, 79 hours, 80 hours, 85 hours, 90 hours, 95 hours, 100 hours, 110 hours, and 120 hours. I In an embodiment, a potency assay includes a recovery step wherein a TIL, MIL, or PBL cryopreserved product is thawed and allowed to recover at ambient or refrigerated temperature for a period selected from the group consisting of about 12 hours, about 24 hours, about 48 hours, about 72 hours, and about 96 hours. The foregoing durations may be measured from the completion of the thawing process or from the start of the thawing process.

In an embodiment, the invention includes a method of determining the potency of a T cell product, the method comprising the steps of:

a. performing a co-culture of a target cell with a T cell product cell for a first period;
b. obtaining a harvest from the co-culture; and
c. assessing the harvest for (1) expression of one or more markers on the T cell product cell or (2) one or more analytes secreted from the T cell product cell to obtain one or more observed values to determine the potency for the T cell product.

In an embodiment, the invention includes a method of determining the potency of a T cell product, the method comprising the steps of:

a. performing a co-culture of a target cell with a T cell product cell for a first period;
b. obtaining a harvest from the co-culture; and
c. assessing the harvest for (1) expression of one or more markers on the T cell product cell or (2) one or more analytes secreted from the T cell product cell to obtain one or more observed values to determine the potency for the T cell product.

wherein the foregoing method is a component of a potency assay matrix comprising at least one other assay selected from the group consisting of a bead- or plate-based assay using CD3, CD28, and/or CD137 stimulation and reporting interferon-γ, granzyme B, or tumor necrosis factor-α, an assay for total viable cells, an assay for percentage viable cells, an assay for $CD4^+$ cell content, an assay for $CD8^+$ cell content, an assay for $T_{EM}$ cell content, an assay for $T_{CM}$ cell content, an assay for $LAG3^+$ cell content, an assay for $KLRG1^+$ cell content, an assay for $CD101^+$ cell content, an assay for $CD69^+$ cell content, an assay for $T_{SCM}$ cell content, an assay for $T_{EMRA}$ cell content, an assay for $T_{reg}$ cell content, an assay for $PD\text{-}1^+$ cell content, an assay for $TIM3^+$ cell content, an assay for $CD25^+$ cell content, an assay for $CD27^+$ cell content, an assay for $CD28^+$ cell content, an assay for $CD56^+$ cell content, an assay for $CTLA\text{-}4^+$ cell content, an assay for $TIGIT^+$ cell content, and an assay for $CD57^+$ cell content. In an embodiment, the foregoing assays are flow cytometric assays.

In an embodiment, the invention includes a method of determining the potency of a T cell product, the method comprising the steps of:

a. performing a co-culture of a target cell with a T cell product cell for a first period;
b. obtaining a harvest from the co-culture; and
c. assessing the harvest for (1) expression of one or more markers on the T cell product cell or (2) one or more analytes secreted from the T cell product cell to obtain one or more observed values to determine the potency for the T cell product.
d. performing a second co-culture of a negative control cell with the T cell product cell for a second period;
e. obtaining a second harvest from the second co-culture;
f. assessing the second harvest for (1) the expression of the one or more markers on the T cell product cell or (2) the one or more analytes secreted from the T cell product cell to obtain one or more control values; and
g. comparing the one or more observed values from step c with the one or more control values from step f, where each observed value is compared to its corresponding control value, to determine the potency of the T cell product.

In an embodiment, the invention includes a method of determining the potency of a T cell product, the method comprising the steps of:

a. performing a co-culture of a target cell with a T cell product cell for a first period;
b. obtaining a harvest from the co-culture; and
c. assessing the harvest for (1) expression of one or more markers on the T cell product cell or (2) one or more analytes secreted from the T cell product cell to obtain one or more observed values to determine the potency for the T cell product.
d. performing a second co-culture of a negative control cell with the T cell product cell for a second period;
e. obtaining a second harvest from the second co-culture;
f. assessing the second harvest for (1) the expression of the one or more markers on the T cell product cell or (2) the one or more analytes secreted from the T cell product cell to obtain one or more control values; and
g. comparing the one or more observed values from step c with the one or more control values from step f, where each observed value is compared to its corresponding control value, to determine the potency of the T cell product.

wherein the T cell product is selected from the group consisting of a tumor-infiltrating lymphocyte (TIL) product, a marrow-infiltrating lymphocyte (MIL) product, or a peripheral blood lymphocyte (PBL) product.

In an embodiment, the invention includes a method of determining the potency of a T cell product, the method comprising the steps of:

a. performing a co-culture of a target cell with a T cell product cell for a first period;
b. obtaining a harvest from the co-culture; and
c. assessing the harvest for (1) expression of one or more markers on the T cell product cell or (2) one or more analytes secreted from the T cell product cell to obtain one or more observed values to determine the potency for the T cell product.
d. performing a second co-culture of a negative control cell with the T cell product cell for a second period;
e. obtaining a second harvest from the second co-culture;
f. assessing the second harvest for (1) the expression of the one or more markers on the T cell product cell or (2) the one or more analytes secreted from the T cell product cell to obtain one or more control values; and
g. comparing the one or more observed values from step c with the one or more control values from step f, where each observed value is compared to its corresponding control value, to determine the potency of the T cell product.

wherein the T cell product is a TIL product from a human, and wherein the TIL product is obtained by resection of a tumor or fragmentation or digestion of a tumor and manufactured by a TIL expansion process comprising a rapid expansion protocol step.

In an embodiment, the invention includes a method of determining the potency of a T cell product, the method comprising the steps of a. performing a co-culture of a target cell with a T cell product cell for a first period;
b. obtaining a harvest from the co-culture; and
c. assessing the harvest for (1) expression of one or more markers on the T cell product cell or (2) one or more analytes secreted from the T cell product cell to obtain one or more observed values to determine the potency for the T cell product.

d. performing a second co-culture of a negative control cell with the T cell product cell for a second period;

e. obtaining a second harvest from the second co-culture;

f. assessing the second harvest for (1) the expression of the one or more markers on the T cell product cell or (2) the one or more analytes secreted from the T cell product cell to obtain one or more control values;

g. comparing the one or more observed values from step c with the one or more control values from step f, where each observed value is compared to its corresponding control value, to determine the potency of the T cell product; and h. releasing the T cell product for use in the treatment of a human patient.

wherein the T cell product is a TIL product from a human, and wherein the TIL product is obtained by resection of a tumor or fragmentation or digestion of a tumor and manufactured by a TIL expansion process comprising a rapid expansion protocol step.

In an embodiment, the invention includes a method of determining the potency of a T cell product, the method comprising the steps of:

a. performing a co-culture of a target cell with a T cell product cell for a first period;

b. obtaining a harvest from the co-culture; and c. assessing the harvest for (1) expression of one or more markers on the T cell product cell or (2) one or more analytes secreted from the T cell product cell to obtain one or more observed values to determine the potency for the T cell product.

d. performing a second co-culture of a negative control cell with the T cell product cell for a second period;

e. obtaining a second harvest from the second co-culture;

f. assessing the second harvest for (1) the expression of the one or more markers on the T cell product cell or (2) the one or more analytes secreted from the T cell product cell to obtain one or more control values;

g. comparing the one or more observed values from step c with the one or more control values from step f, where each observed value is compared to its corresponding control value, to determine the potency of the T cell product; and h. releasing the T cell product for use in the treatment of a human patient.

wherein the T cell product is a TIL product from a human, and wherein the TIL product is obtained by resection of a tumor or fragmentation or digestion of a tumor and manufactured by a TIL expansion process comprising a rapid expansion protocol step, and wherein the target cell is an irradiated Raji cell, Ramos cell, Daudi cell, U937 cell, or Thp1 cell, or a derivative, variant, modification, or progeny thereof.

In an embodiment, the invention includes a method of determining the potency of a T cell product, the method comprising the steps of:

a. performing a co-culture of a target cell with a T cell product cell for a first period;

b. obtaining a harvest from the co-culture; and c. assessing the harvest for (1) expression of one or more markers on the T cell product cell or (2) one or more analytes secreted from the T cell product cell to obtain one or more observed values to determine the potency for the T cell product.

d. performing a second co-culture of a negative control cell with the T cell product cell for a second period;

e. obtaining a second harvest from the second co-culture;

f. assessing the second harvest for (1) the expression of the one or more markers on the T cell product cell or (2) the one or more analytes secreted from the T cell product cell to obtain one or more control values;

g. comparing the one or more observed values from step c with the one or more control values from step f, where each observed value is compared to its corresponding control value, to determine the potency of the T cell product; and h. releasing the T cell product for use in the treatment of a human patient.

wherein the T cell product is a TIL product from a human, and wherein the TIL product is obtained by resection of a tumor or fragmentation or digestion of a tumor and manufactured by a TIL expansion process comprising a rapid expansion protocol step, wherein the target cell is an irradiated Raji cell, Ramos cell, Daudi cell, U937 cell, or Thp1 cell, or a derivative, variant, modification, or progeny thereof, and wherein the negative control cell lacks MHC Class I and MHC Class II expression.

In an embodiment, the invention includes a method of determining the potency of a T cell product, the method comprising the steps of:

a. performing a co-culture of a target cell with a T cell product cell for a first period;

b. obtaining a harvest from the co-culture; and c. assessing the harvest for (1) expression of one or more markers on the T cell product cell or (2) one or more analytes secreted from the T cell product cell to obtain one or more observed values to determine the potency for the T cell product.

d. performing a second co-culture of a negative control cell with the T cell product cell for a second period;

e. obtaining a second harvest from the second co-culture;

f. assessing the second harvest for (1) the expression of the one or more markers on the T cell product cell or (2) the one or more analytes secreted from the T cell product cell to obtain one or more control values;

g. comparing the one or more observed values from step c with the one or more control values from step f, where each observed value is compared to its corresponding control value, to determine the potency of the T cell product; and h. releasing the T cell product for use in the treatment of a human patient.

wherein the T cell product is a TIL product from a human, and wherein the TIL product is obtained by resection of a tumor or fragmentation or digestion of a tumor and manufactured by a TIL expansion process comprising a rapid expansion protocol step, wherein the target cell is an irradiated Raji cell, Ramos cell, Daudi cell, U937 cell, or Thp1 cell, or a derivative, variant, modification, or progeny thereof, and wherein the negative control cell is an irradiated K562 cell or a derivative, variant, modification, or progeny thereof.

In an embodiment, the invention includes a method of determining the potency of a T cell product, the method comprising the steps of a. performing a co-culture of a target cell with a T cell product cell for a first period;

b. obtaining a harvest from the co-culture; and c. assessing the harvest for (1) expression of one or more markers on the T cell product cell or (2) one or more analytes secreted from the T cell product cell to obtain one or more observed values to determine the potency for the T cell product.

d. performing a second co-culture of a negative control cell with the T cell product cell for a second period;
e. obtaining a second harvest from the second co-culture;
f. assessing the second harvest for (1) the expression of the one or more markers on the T cell product cell or (2) the one or more analytes secreted from the T cell product cell to obtain one or more control values;
g. comparing the one or more observed values from step c with the one or more control values from step f, where each observed value is compared to its corresponding control value, to determine the potency of the T cell product; and
h. releasing the T cell product for use in the treatment of a human patient.

wherein the T cell product is a TIL product from a human, and wherein the TIL product is obtained by resection of a tumor or fragmentation or digestion of a tumor and manufactured by a TIL expansion process comprising a rapid expansion protocol step, wherein the target cell is an irradiated Raji cell, Ramos cell, Daudi cell, U937 cell, or Thp1 cell or a derivative, variant, modification, or progeny thereof, wherein the negative control cell is an irradiated K562 cell or a derivative, variant, modification, or progeny thereof, and wherein the ratio between the number of TIL product cells to the number of target cells is between 5:1 and 1:5.

In an embodiment, the invention includes a method of determining the potency of a T cell product, the method comprising the steps of:

a. performing a co-culture of a target cell with a T cell product cell for a first period;
b. obtaining a harvest from the co-culture; and
c. assessing the harvest for (1) expression of one or more markers on the T cell product cell or (2) one or more analytes secreted from the T cell product cell to obtain one or more observed values to determine the potency for the T cell product.
d. performing a second co-culture of a negative control cell with the T cell product cell for a second period;
e. obtaining a second harvest from the second co-culture;
f. assessing the second harvest for (1) the expression of the one or more markers on the T cell product cell or (2) the one or more analytes secreted from the T cell product cell to obtain one or more control values;
g. comparing the one or more observed values from step c with the one or more control values from step f, where each observed value is compared to its corresponding control value, to determine the potency of the T cell product; and
h. releasing the T cell product for use in the treatment of a human patient.

wherein the T cell product is a TIL product from a human, and wherein the TIL product is obtained by resection of a tumor or fragmentation or digestion of a tumor and manufactured by a TIL expansion process comprising a rapid expansion protocol step, wherein the target cell is an irradiated Raji cell, Ramos cell, Daudi cell, U937 cell, or Thp1 cell, or a derivative, variant, modification, or progeny thereof, wherein the negative control cell is an irradiated K562 cell or a derivative, variant, modification, or progeny thereof, wherein the ratio between the number of TIL product cells to the number of target cells is between 5:1 and 1:5, and wherein the ratio between the number of TIL product cells to the number of negative control cells is between 5:1 and 1:5.

In an embodiment, the invention includes a method of determining the potency of a T cell product, the method comprising the steps of:

a. performing a co-culture of a target cell with a T cell product cell for a first period;
b. obtaining a harvest from the co-culture; and
c. assessing the harvest for (1) expression of one or more markers on the T cell product cell or (2) one or more analytes secreted from the T cell product cell to obtain one or more observed values to determine the potency for the T cell product.
d. performing a second co-culture of a negative control cell with the T cell product cell for a second period;
e. obtaining a second harvest from the second co-culture;
f. assessing the second harvest for (1) the expression of the one or more markers on the T cell product cell or (2) the one or more analytes secreted from the T cell product cell to obtain one or more control values;
g. comparing the one or more observed values from step c with the one or more control values from step f, where each observed value is compared to its corresponding control value, to determine the potency of the T cell product; and
h. releasing the T cell product for use in the treatment of a human patient.

wherein the T cell product is a TIL product from a human, and wherein the TIL product is obtained by resection of a tumor or fragmentation or digestion of a tumor and manufactured by a TIL expansion process comprising a rapid expansion protocol step, wherein the target cell is an irradiated Raji cell, Ramos cell, Daudi cell, U937 cell, or Thp1 cell, or a derivative, variant, modification, or progeny thereof, wherein the negative control cell is an irradiated K562 cell or a derivative, variant, modification, or progeny thereof, wherein the first period is from about 6 hours to about 48 hours and the second period is from about 6 hours to about 48 hours.

In an embodiment, the invention includes a method of determining the potency of a T cell product, the method comprising the steps of:

a. performing a co-culture of a target cell with a T cell product cell for a first period;
b. obtaining a harvest from the co-culture; and
c. assessing the harvest for (1) expression of one or more markers on the T cell product cell or (2) one or more analytes secreted from the T cell product cell to obtain one or more observed values to determine the potency for the T cell product.
d. performing a second co-culture of a negative control cell with the T cell product cell for a second period;
e. obtaining a second harvest from the second co-culture;
f. assessing the second harvest for (1) the expression of the one or more markers on the T cell product cell or (2) the one or more analytes secreted from the T cell product cell to obtain one or more control values;
g. comparing the one or more observed values from step c with the one or more control values from step f, where each observed value is compared to its corresponding control value, to determine the potency of the T cell product; and
h. releasing the T cell product for use in the treatment of a human patient.

wherein the T cell product is a TIL product from a human, and wherein the TIL product is obtained by resection of a tumor or fragmentation or digestion of a tumor and manufactured by a TIL expansion process comprising a rapid expansion protocol step, wherein the target cell is an irradiated Raji cell, Ramos cell, Daudi cell, U937 cell, or Thp1 cell, or a derivative, variant, modification, or progeny thereof, wherein the negative control cell is an irradiated K562 cell or a derivative, variant, modification, or progeny thereof, wherein the first period is selected from the group consisting of about 12 hours, about 18 hours, and about 24 hours and wherein the second period is selected from the group consisting of about 12 hours, about 18 hours, and about 24 hours.

In an embodiment, the invention includes a method of determining the potency of a T cell product, the method comprising the steps of a. performing a co-culture of a target cell with a T cell product cell for a first period;
b. obtaining a harvest from the co-culture; and
c. assessing the harvest for (1) expression of one or more markers on the T cell product cell or (2) one or more analytes secreted from the T cell product cell to obtain one or more observed values to determine the potency for the T cell product.
d. performing a second co-culture of a negative control cell with the T cell product cell for a second period;
e. obtaining a second harvest from the second co-culture;
f. assessing the second harvest for (1) the expression of the one or more markers on the T cell product cell or (2) the one or more analytes secreted from the T cell product cell to obtain one or more control values;
g. comparing the one or more observed values from step c with the one or more control values from step f, where each observed value is compared to its corresponding control value, to determine the potency of the T cell product; and
h. releasing the T cell product for use in the treatment of a human patient.

wherein the T cell product is a TIL product from a human, and wherein the TIL product is obtained by resection of a tumor or fragmentation or digestion of a tumor and manufactured by a TIL expansion process comprising a rapid expansion protocol step, wherein the target cell is an irradiated Raji cell, Ramos cell, Daudi cell, U937 cell, or Thp1 cell, or a derivative, variant, modification, or progeny thereof, wherein the negative control cell is an irradiated K562 cell or a derivative, variant, modification, or progeny thereof, wherein the one or more markers on the T cell product are selected from the group consisting of CD25, CD69, CD134, CD137, CD150, KLRG1, or combinations thereof.

In an embodiment, the invention includes a method of determining the potency of a T cell product, the method comprising the steps of:

a. performing a co-culture of a target cell with a T cell product cell for a first period;
b. obtaining a harvest from the co-culture; and
c. assessing the harvest for (1) expression of one or more markers on the T cell product cell or (2) one or more analytes secreted from the T cell product cell to obtain one or more observed values to determine the potency for the T cell product.
d. performing a second co-culture of a negative control cell with the T cell product cell for a second period;
e. obtaining a second harvest from the second co-culture;
f. assessing the second harvest for (1) the expression of the one or more markers on the T cell product cell or (2) the one or more analytes secreted from the T cell product cell to obtain one or more control values;
g. comparing the one or more observed values from step c with the one or more control values from step f, where each observed value is compared to its corresponding control value, to determine the potency of the T cell product; and
h. releasing the T cell product for use in the treatment of a human patient.

wherein the T cell product is a TIL product from a human, and wherein the TIL product is obtained by resection of a tumor or fragmentation or digestion of a tumor and manufactured by a TIL expansion process comprising a rapid expansion protocol step, wherein the target cell is an irradiated Raji cell, Ramos cell, Daudi cell, U937 cell, or Thp1 cell, or a derivative, variant, modification, or progeny thereof, wherein the negative control cell is an irradiated K562 cell or a derivative, variant, modification, or progeny thereof, wherein the one or more analytes secreted from the T cell product is selected from the group consisting of IFN-α, IFN-β, IFN-γ, granzyme B, perforin, TNF-α, IL-1α, IL-1 β, IL-2, IL-3, IL-4, IL-5, IL-6, IL-8, IL-9, IL-10, IL-13, IL-14, IL-16, IL-17, IL-18, IL-22, IL-25, IL-26, MIP-1β, and combinations thereof.

In an embodiment, the invention includes a method of determining the potency of a T cell product, the method comprising the steps of:

a. performing a co-culture of a target cell with a T cell product cell for a first period;
b. obtaining a harvest from the co-culture; and
c. assessing the harvest for (1) expression of one or more markers on the T cell product cell or (2) one or more analytes secreted from the T cell product cell to obtain one or more observed values to determine the potency for the T cell product.
d. performing a second co-culture of a negative control cell with the T cell product cell for a second period;
e. obtaining a second harvest from the second co-culture;
f. assessing the second harvest for (1) the expression of the one or more markers on the T cell product cell or (2) the one or more analytes secreted from the T cell product cell to obtain one or more control values;
g. comparing the one or more observed values from step c with the one or more control values from step f, where each observed value is compared to its corresponding control value, to determine the potency of the T cell product; and
h. releasing the T cell product for use in the treatment of a human patient.

wherein the T cell product is a TIL product from a human, and wherein the TIL product is obtained by resection of a tumor or fragmentation or digestion of a tumor and manufactured by a TIL expansion process comprising a rapid expansion protocol step, wherein the target cell is an irradiated Raji cell, Ramos cell, Daudi cell, U937 cell, or Thp1 cell, or a derivative, variant, modification, or progeny thereof, wherein the negative control cell is an irradiated K562 cell or a derivative, variant, modification, or progeny thereof, wherein the one or more analytes secreted from the T cell product is selected from the group consisting of IFN-α, IFN-β, IFN-γ, granzyme B, perforin, TNF-α, IL-1α, IL-1 β, IL-2, IL-3, IL-4, IL-5, IL-6, IL-8, IL-9, IL-10, IL-13, IL-14, IL-16, IL-17, IL-18, IL-22, IL-25, IL-26, MIP-1β, and combinations thereof, wherein the one or more analytes secreted from the TIL product is selected from the group consisting of IFN-α, IFN-0, IFN-γ, granzyme B, perforin, TNF-α, IL-1α, IL-1 β, IL-2, IL-3, IL-4, IL-5, IL-6, IL-8, IL-9, IL-10, IL-13, IL-14, IL-16, IL-17, IL-18, IL-22, IL-25, IL-26, MIP-1β, and combinations thereof, wherein the quantity of the observed value is normalized to the quantity of the control value for each of the one or more analytes, and wherein the increase in observed value over the control value for each of the one or more analytes is selected from the group consisting of at least 1-fold, at least 1.5-fold, at least 2-fold, at least 2.5-fold, at least 3-fold, at least 3.5-fold, at least 4-fold, at least 4.5-fold, and at least 5-fold.

In any of the foregoing embodiments, tumor digestion may be performed by methods described herein or known in the art. In any of the foregoing embodiments, tumor is digestion is performed according to the methods or using the compositions or devices described in International Patent Publication No. WO 2021/123832 A1, the disclosures of which are incorporated by reference herein.

In some embodiments, the present invention provides a method for assaying TIL polyfunctional activity to assess the potency and/or functionality of expanded TILs and other polyclonal T cell products, including MILs and PBLs, which can then be employed in the treatment of cancer by administering TILs, MILs, PBLs, or other polyclonal T cell products assessed, the method comprising the steps of.

a. performing a co-culture of a target cell with a T cell product cell for a first period;
b. obtaining a harvest from the co-culture; and
c. assessing the harvest for (1) expression of one or more markers on the T cell product cell or (2) two or more analytes secreted from the T cell product cell to obtain one or more observed values to determine the potency for the T cell product.

In some embodiments, the method comprises the additional steps of:

d. performing a second co-culture of a negative control cell with the T cell product cell for a second period;
e. obtaining a second harvest from the second co-culture;
f. assessing the second harvest for (1) the expression of the one or more markers on the T cell product cell or (2) the two or more analytes secreted from the T cell product cell to obtain one or more control values; and
g. comparing the one or more observed values from step c with the one or more control values from step f, where each observed value is compared to its corresponding control value, to determine the potency of the T cell product, wherein the two or more analytes secreted from the TIL product is selected from the group consisting of IFN-α, IFN-β, IFN-γ, granzyme B, perform, TNF-α, IL-1α, IL-1 β, IL-2, IL-3, IL-4, IL-5, IL-6, IL-8, IL-9, IL-10, IL-13, IL-14, IL-16, IL-17, IL-18, IL-22, IL-25, IL-26, MIP-1β, and combinations thereof, wherein the quantity of the observed value is normalized to the quantity of the control value for each of the two or more analytes, and wherein the increase in observed value over the control value for each of the two or more analytes is selected from the group consisting of at least 1-fold, at least 1.5-fold, at least 2-fold, at least 2.5-fold, at least 3-fold, at least 3.5-fold, at least 4-fold, at least 4.5-fold, at least 5-fold, at least 6-fold, at least 7-fold, at least 8-fold, at least 9-fold, and at least 10-fold.

In some embodiments, the present invention provides a method for assaying TIL polyfunctional activity to assess the potency and/or functionality of expanded TILs and other polyclonal T cell products, including MILs and PBLs, which can then be employed in the treatment of cancer by administering TILs, MILs, PBLs, or other polyclonal T cell products assessed, the method comprising the steps of:

a. performing a co-culture of a target cell with a T cell product cell for a first period;
b. obtaining a harvest from the co-culture; and
c. assessing the harvest for (1) expression of one or more markers on the T cell product cell or (2) three or more analytes secreted from the T cell product cell to obtain one or more observed values to determine the potency for the T cell product.

In some embodiments, the method comprises the additional steps of:

d. performing a second co-culture of a negative control cell with the T cell product cell for a second period;
e. obtaining a second harvest from the second co-culture;
f. assessing the second harvest for (1) the expression of the one or more markers on the T cell product cell or (2) the three or more analytes secreted from the T cell product cell to obtain one or more control values; and
g. comparing the one or more observed values from step c with the one or more control values from step f, where each observed value is compared to its corresponding control value, to determine the potency of the T cell product, wherein the three or more analytes secreted from the TIL product is selected from the group consisting of IFN-α, IFN-β, IFN-γ, granzyme B, perform, TNF-α, IL-1α, IL-1 β, IL-2, IL-3, IL-4, IL-5, IL-6, IL-8, IL-9, IL-10, IL-13, IL-14, IL-16, IL-17, IL-18, IL-22, IL-25, IL-26, MIP-1β, and combinations thereof, wherein the quantity of the observed value is normalized to the quantity of the control value for each of the three or more analytes, and wherein the increase in observed value over the control value for each of the three or more analytes is selected from the group consisting of at least 1-fold, at least 1.5-fold, at least 2-fold, at least 2.5-fold, at least 3-fold, at least 3.5-fold, at least 4-fold, at least 4.5-fold, and at least 5-fold, at least 6-fold, at least 7-fold, at least 8-fold, at least 9-fold, and at least 10-fold.

In some embodiments, the present invention provides a method for assaying TIL polyfunctional activity to assess the potency and/or functionality of expanded TILs and other polyclonal T cell products, including MILs and PBLs, which can then be employed in the treatment of cancer by administering TILs, MILs, PBLs, or other polyclonal T cell products assessed, the method comprising the steps of:

a. performing a co-culture of a plurality of target cells with a plurality of T cell product cell for a first period;
b. obtaining a harvest from the co-culture; and
c. assessing the harvest for (1) expression of one or more markers on the T cell product cells or (2) one or more analytes secreted from the T cell product cells to obtain one or more observed values to determine the potency for the T cell product.

In some embodiments, the method comprises the additional steps of:

d. performing a second co-culture of a plurality of negative control cells with the T cell product cells for a second period;
e. obtaining a second harvest from the second co-culture;
f. assessing the second harvest for (1) the expression of the one or more markers on the T cell product cells or (2) the one or more analytes secreted from the T cell product cells to obtain one or more control values; and
g. comparing the one or more observed values from step c with the one or more control values from step f, where each observed value is compared to its corresponding control value, to determine the potency of the T cell product, wherein the one or more analytes secreted from the TIL product is selected from the group consisting of IFN-α, IFN-β, IFN-γ, granzyme B, perform, TNF-α, IL-1α, IL-1 β, IL-2, IL-3, IL-4, IL-5, IL-6, IL-8, IL-9, IL-10, IL-13, IL-14, IL-16, IL-17, IL-18, IL-22, IL-25, IL-26, MIP-1β, and combinations thereof, wherein the quantity of the observed value is normalized to the quantity of the control value for each of the one or more analytes, and wherein the increase in observed value over the control value for each of the one or more analytes is selected from the group consisting of at least 1-fold, at least 1.5-fold, at least 2-fold, at least 2.5-fold, at least 3-fold, at least 3.5-fold, at least 4-fold, at least 4.5-fold, and at least 5-fold, at least 6-fold, at least 7-fold, at least 8-fold, at least 9-fold, and at least 10-fold.

In an embodiment, the invention includes the foregoing methods, wherein the target cell is selected from the group consisting of Raji cell, a Thp1 cell, a Ramos cell, a U937 cell, a Daudi cell, and combinations thereof. In an embodiment, the target cells are a combination of two or more cell lines. In an embodiment, the target cells are a 1:1 combination of two or more cell lines. In an embodiment, the target cells are a 1:1 combination of two or more cell lines, wherein the two or more cell lines are different and are each independently selected from the group consisting of Raji cell, a Thp1 cell, a Ramos cell, a U937 cell, and a Daudi cell. In an embodiment, the target cells are a 1:1:1 combination of three or more cell lines, wherein the three or more cell lines are different and are each independently selected from the group consisting of Raji cell, a Thp1 cell, a Ramos cell, a U937 cell, and a Daudi cell. In an embodiment, the target cells are a 1:1:1:1 combination of four or more cell lines, wherein the four or more cell lines are different and are each independently selected from the group consisting of Raji cell, a Thp1 cell, a Ramos cell, a U937 cell, and a Daudi cell. In an embodiment, the target cells are a 1:1:1:1:1 combination of two or more cell lines, wherein the two or more cell lines are different and are each independently selected from the group consisting of Raji cell, a Thp1 cell, a Ramos cell, a U937 cell, and a Daudi cell.

In an embodiment, the target cells are a combination of a Raji cells and Thp1 cells, wherein the ratio of Raji cells to Thp1 cells is selected from the group consisting of 5:1, 4:1, 3:1, 2:1, 1:1, 1:2, 1:3, 1:4, and 1:5. In an embodiment, the target cells are a combination of a Raji cells and Ramos cells, wherein the ratio of Raji cells to Ramos cells is selected from the group consisting of 5:1, 4:1, 3:1, 2:1, 1:1, 1:2, 1:3, 1:4, and 1:5. In an embodiment, the target cells are a combination of a Raji cells and U937 cells, wherein the ratio of Raji cells to U937 cells is selected from the group consisting of 5:1, 4:1, 3:1, 2:1, 1:1, 1:2, 1:3, 1:4, and 1:5. In an embodiment, the target cells are a combination of a Raji cells and Daudi cells, wherein the ratio of Raji cells to Daudi cells is selected from the group consisting of 5:1, 4:1, 3:1, 2:1, 1:1, 1:2, 1:3, 1:4, and 1:5.

In an embodiment, the invention includes the foregoing methods, wherein the co-culture comprises cell culture media. In an embodiment, the invention includes the foregoing methods, wherein the co-culture comprises CM1 media. In an embodiment, the invention includes the foregoing methods, wherein the co-culture comprises AIM-V media (L-glutamine, 50 μM streptomycin sulfate, and 10 μM gentamicin sulfate), also referred to as AIM V medium, which is commercially available from Invitrogen (Carlsbad, CA). In an embodiment, the invention includes the foregoing methods, wherein the co-culture and second co-culture comprise cell culture media. In an embodiment, the invention includes the foregoing methods, wherein the co-culture and second co-culture each comprise CM1 media. In an embodiment, the invention includes the foregoing methods, wherein the co-culture and second co-culture each comprise AIM-V media. In an embodiment, the co-culture comprises IL-2, wherein the IL-2 is added continuously during co-culture, and wherein the IL-2 is maintained at a concentration between 50 IU/mL and 1000 IU/mL during the co-culture. In an embodiment, the co-culture comprises IL-2, wherein the IL-2 is added continuously during co-culture, and wherein the IL-2 is maintained at a concentration between 100 IU/mL and 500 IU/mL during the co-culture. In an embodiment, the co-culture comprises IL-2, wherein the IL-2 is added continuously during co-culture, and wherein the IL-2 is maintained at a concentration between 200 IU/mL and 400 IU/mL during the co-culture. In an embodiment, the co-culture comprises IL-2, wherein the IL-2 is added continuously during co-culture, and wherein the IL-2 is maintained at a concentration selected from the group consisting of about 50 IU/mL, about 100 IU/mL, about 150 IU/mL, about 200 IU/mL, about 250 IU/mL, about 300 IU/mL, about 350 IU/mL, about 400 IU/mL, about 450 IU/mL and about 500 IU/mL.

In an embodiment, the invention includes a method of determining the potency of a T cell product, the method comprising the steps of:

a. performing a co-culture of a target cell with a T cell product cell for a first period;
b. obtaining a harvest from the co-culture; and
c. assessing the harvest for (1) expression of one or more markers on the T cell product cell or (2) one or more analytes secreted from the T cell product cell to obtain one or more observed values to determine the potency for the T cell product, wherein IL-2 is added continuously during the co-culture, and wherein the IL-2 is maintained at a concentration in the co-culture selected from the group consisting of about 50 IU/mL, about 100 IU/mL, about 150 IU/mL, about 200 IU/mL, about 250 IU/mL, about 300 IU/mL, about 350 IU/mL, about 400 IU/mL, about 450 IU/mL and about 500 IU/mL.

In an embodiment, the invention includes a method of determining the potency of a T cell product, the method comprising the steps of:

a. performing a co-culture of a target cell with a T cell product cell for a first period;
b. obtaining a harvest from the co-culture;
c. assessing the harvest for (1) expression of one or more markers on the T cell product cell or (2) one or more analytes secreted from the T cell product cell to obtain one or more observed values to determine the potency for the T cell product;
d. performing a second co-culture of a negative control cell with the T cell product cell for a second period;
e. obtaining a second harvest from the second co-culture;
f. assessing the second harvest for (1) the expression of the one or more markers on the T cell product cell or (2) the one or more analytes secreted from the T cell product cell to obtain one or more control values; and
g. comparing the one or more observed values from step c with the one or more control values from step f, where each observed value is compared to its corresponding control value, to determine the potency of the T cell product.

wherein IL-2 is added continuously during the co-culture and the second co-culture, and wherein the IL-2 is maintained at a concentration in each of the co-culture and the second co-culture at a concentration selected from the group consisting of about 50 IU/mL, about 100 IU/mL, about 150 IU/mL, about 200 IU/mL, about 250 IU/mL, about 300 IU/mL, about 350 IU/mL, about 400 IU/mL, about 450 IU/mL and about 500 IU/mL.

In an embodiment, the invention includes a method of determining the potency of a T cell product, the method comprising the steps of:

a. performing a co-culture of a target cell with a T cell product cell for a first period;
b. obtaining a harvest from the co-culture; and
c. assessing the harvest for (1) expression of one or more markers on the T cell product cell or (2) one or more analytes secreted from the T cell product cell to obtain one or more observed values to determine the potency for the T cell product, wherein IL-2 is added continuously during the co-culture, and wherein the IL-2 is maintained at a concentration in the co-culture of between 50 IU/mL and 1000 IU/mL.

In an embodiment, the invention includes a method of determining the potency of a T cell product, the method comprising the steps of:

a. performing a co-culture of a target cell with a T cell product cell for a first period;
b. obtaining a harvest from the co-culture; and
c. assessing the harvest for (1) expression of one or more markers on the T cell product cell or (2) one or more analytes secreted from the T cell product cell to obtain one or more observed values to determine the potency for the T cell product.
d. performing a second co-culture of a negative control cell with the T cell product cell for a second period;
e. obtaining a second harvest from the second co-culture;
f. assessing the second harvest for (1) the expression of the one or more markers on the T cell product cell or (2) the one or more analytes secreted from the T cell product cell to obtain one or more control values; and
g. comparing the one or more observed values from step c with the one or more control values from step f, where each observed value is compared to its corresponding control value, to determine the potency of the T cell product.

wherein IL-2 is added continuously during the co-culture and the second co-culture, and wherein the IL-2 is maintained in each of the co-culture and the second co-culture at a concentration of between 50 IU/mL and 1000 IU/mL.

In some embodiments, the present invention provides a method for assaying TIL, MIL, or PBL activity, wherein a killing assay is used. In some embodiments, the present invention provides a method for assaying TIL, MIL, or PBL activity, wherein a killing assay is used, and wherein a cell lysis endpoint is detected. In some embodiments, the present invention provides a method for assaying TIL, MIL, or PBL activity, wherein a killing assay is used. In some embodiments, the present invention provides a method for assaying TIL, MIL, or PBL activity, wherein a killing assay is used, and a cell lysis endpoint is detected through genetic modification of the target cell line to express fluorescent, chemiluminescent, or bioluminescent protein when lysed. Suitable genetic modifications and assays include luciferase assays, such as those described in U.S. Pat. No. 9,631,225, the disclosures of which are incorporated by reference herein. For example, the genetic modification approach described for bioluminescence detection in U.S. Pat. No. 10,415,015, the disclosures of which are incorporated by reference herein, may be employed in the modification of a target cell, such as a Raji cell, K562 cell, Daudi cell, Ramos cell, U937 cell, or Thp1 cell.

In an embodiment, the present invention provides a method for assaying the potency of a T cell product, the method further comprising the step of pre-irradiating the target cell to arrest proliferation. In an embodiment, the present invention provides a method for assaying the potency of a T cell product, the method comprising the use of a target cell that is not irradiated to arrest proliferation. In an embodiment, the present invention provides a method for assaying the potency of a T cell product, the method further comprising the step of chemically or biologically treating the target cell to arrest proliferation.

In an embodiment, the present invention provides a method for assaying the potency of a T cell product, the method further comprising the step of pre-irradiating the negative control cell to arrest proliferation. In an embodiment, the present invention provides a method for assaying the potency of a T cell product, the method comprising the use of a negative control cell that is not irradiated to arrest proliferation. In an embodiment, the present invention provides a method for assaying the potency of a T cell product, the method further comprising the step of chemically or biologically treating the negative control cell to arrest proliferation.

In an embodiment, the target cell is irradiated using X-rays or gamma rays to a total absorbed dose of radiation of about 5 Gy, 10 Gy, 15 Gy, 20 Gy, 25 Gy, 30 Gy, 35 Gy, 40 Gy, 45 Gy, 50 Gy, 55 Gy, 60 Gy. 65 Gy, 70 Gy, 75 Gy, 80 Gy, 85 Gy, 90 Gy, 95 Gy, 100 Gy, 105 Gy, 110 Gy, 115 Gy, 120 Gy, 125 Gy, 130 Gy, 135 Gy, 140 Gy, 145 Gy, 150 Gy, 155 Gy, 160 Gy, 165 Gy, 170 Gy, 175 Gy, 180 Gy, 185 Gy, 190 Gy, or 200 Gy.

In an embodiment, the target cell is irradiated using X-rays or gamma rays to a total absorbed dose of radiation of about 100 rads, 200 rads, 300 rads, 400 rads, 500 rads, 600 rads, 700 rads, 800 rads, 900 rads, 1000 rads, 1100 rads, 1200 rads, 1300 rads, 1400 rads, 1500 rads, 1600 rads, 1700 rads, 1800 rads, 1900 rads, 2000 rads, 2100 rads, 2200 rads, 2300 rads, 2400 rads, 2500 rads, 2600 rads, 2700 rads, 2800 rads, 2900 rads, 3000 rads, 3100 rads, 3200 rads, 3300 rads, 3400 rads, 3500 rads, 3600 rads, 3700 rads, 3800 rads, 3900 rads, 4000 rads, 4100 rads, 4200 rads, 4300 rads, 4400 rads, 4500 rads, 4600 rads, 4700 rads, 4800 rads, 4900 rads, 5000 rads, 5100 rads, 5200 rads, 5300 rads, 5400 rads, 5500 rads, 5600 rads, 5700 rads, 5800 rads, 5900 rads, 6000 rads, 6100 rads, 6200 rads, 6300 rads, 6400 rads, 6500 rads, 6600 rads, 6700 rads, 6800 rads, 6900 rads, 7000 rads, 7500 rads, 8000 rads, 8500 rads, 9000 rads, 9500 rads, or 10000 rads.

In an embodiment, the target cell is irradiated using X-rays or gamma rays at a rate of absorbed dose of radiation of about 20 rads/min, 40 rads/min, 60 rads/min, 80 rads/min, 100 rads/min, 120 rads/min, 140 rads/min, 160 rads/min, 180 rads/min, 200 rads/min, 220 rads/min, 240 rads/min, 260 rads/min, 280 rads/min, 300 rads/min, 320 rads/min, 340 rads/min, 360 rads/min, 380 rads/min, 400 rads/min, 420 rads/min, 440 rads/min, 460 rads/min, 480 rads/min, 500 rads/min, 520 rads/min, 540 rads/min, 560 rads/min, 580 rads/min, 600 rads/min, 620 rads/min, 640 rads/min, 660 rads/min, 680 rads/min, or 700 rads/min. In an embodiment, the target cell is irradiated using X-rays or gamma rays at a rate of absorbed dose of radiation of about 50 rads/min, 100 rads/min, 150 rads/min, 200 rads/min, 250 rads/min, 300 rads/min, 350 rads/min, 400 rads/min, 450 rads/min, 500 rads/min, 550 rads/min, 600 rads/min, 650 rads/min, 700 rads/min, 750 rads/min, 800 rads/min, 850 rads/min, 900 rads/min, 950 rads/min, 1000 rads/min, 1050 rads/min, 1100 rads/min, 1150 rads/min, 1200 rads/min, 1250 rads/min, 1300 rads/min, 1350 rads/min, 1400 rads/min, 1450 rads/min, 1500 rads/min, 1550 rads/min, 1600 rads/min, 1650 rads/min, 1700 rads/min, 1750 rads/min, 1800 rads/min, 1850 rads/min, 1900 rads/min, 1950 rads/min, or 2000 rads/min.

In an embodiment, the invention includes a method for performing a mixed tumor alloreactivity assay method disclosure to determine the potency of a T cell product, such as a TIL, MIL, or PBL product. In an embodiment, the invention includes a method of determining the potency of a T cell product, the method comprising the steps of:

a. performing a co-culture of a mixed tumor alloreactive cell line with a T cell product cell for a first period;
b. obtaining a harvest from the co-culture; and
c. assessing the harvest for (1) expression of one or more markers on the T cell product cell or (2) one or more analytes secreted from the T cell product cell to obtain one or more observed values to determine the potency for the T cell product, wherein IL-2 is added continuously during the co-culture, and wherein the IL-2 is maintained at a concentration in the co-culture selected from the group consisting of about 50 IU/mL, about 100 IU/mL, about 150 IU/mL, about 200 IU/mL, about 250 IU/mL, about 300 IU/mL, about 350 IU/mL, about 400 IU/mL, about 450 IU/mL and about 500 IU/mL.

In an embodiment, the invention includes a method of determining the potency of a T cell product, the method comprising the steps of:

a. performing a co-culture of a mixed tumor alloreactive cell line with a T cell product cell for a first period, wherein the mixed tumor alloreactive cell line is a mixed tumor cell line;
b. obtaining a harvest from the co-culture;
c. assessing the harvest for (1) expression of one or more markers on the T cell product cell or (2) one or more analytes secreted from the T cell product cell to obtain one or more observed values to determine the potency for the T cell product;
d. performing a second co-culture of a negative control cell with the T cell product cell for a second period;
e. obtaining a second harvest from the second co-culture;
f. assessing the second harvest for (1) the expression of the one or more markers on the T cell product cell or (2) the one or more analytes secreted from the T cell product cell to obtain one or more control values; and
g. comparing the one or more observed values from step c with the one or more control values from step f, where each observed value is compared to its corresponding control value, to determine the potency of the T cell product.

wherein IL-2 is added continuously during the co-culture and the second co-culture, and wherein the IL-2 is maintained at a concentration in each of the co-culture and the second co-culture at a concentration selected from the group consisting of about 50 IU/mL, about 100 IU/mL, about 150 IU/mL, about 200 IU/mL, about 250 IU/mL, about 300 IU/mL, about 350 IU/mL, about 400 IU/mL, about 450 IU/mL and about 500 IU/mL.

In an embodiment, the invention includes a method of determining the potency of a T cell product, the method comprising the steps of:

a. performing a co-culture of a mixed tumor alloreactive cell line with a T cell product cell for a first period;
b. obtaining a harvest from the co-culture; and
c. assessing the harvest for (1) expression of one or more markers on the T cell product cell or (2) one or more analytes secreted from the T cell product cell to obtain one or more observed values to determine the potency for the T cell product, wherein IL-2 is added continuously during the co-culture, and wherein the IL-2 is maintained at a concentration in the co-culture of between 50 IU/mL and 1000 IU/mL.

In an embodiment, the invention includes a method of determining the potency of a T cell product, the method comprising the steps of:

a. performing a co-culture of a mixed tumor alloreactive cell line with a T cell product cell for a first period;
b. obtaining a harvest from the co-culture; and
c. assessing the harvest for (1) expression of one or more markers on the T cell product cell or (2) one or more analytes secreted from the T cell product cell to obtain one or more observed values to determine the potency for the T cell product.
d. performing a second co-culture of a negative control cell with the T cell product cell for a second period;
e. obtaining a second harvest from the second co-culture;
f. assessing the second harvest for (1) the expression of the one or more markers on the T cell product cell or (2) the one or more analytes secreted from the T cell product cell to obtain one or more control values; and
g. comparing the one or more observed values from step c with the one or more control values from step f, where each observed value is compared to its corresponding control value, to determine the potency of the T cell product.

wherein IL-2 is added continuously during the co-culture and the second co-culture, and wherein the IL-2 is maintained in each of the co-culture and the second co-culture at a concentration of between 50 IU/mL and 1000 IU/mL.

In an embodiment, the invention includes a method for performing a potency assay wherein the target cell line or combination of target cell lines is optimized for maximal HLA diversity. In an embodiment, the invention includes a method for performing a potency assay wherein the target cell line or combination of target cell lines is optimized for maximal heterozygosity. In an embodiment, the invention includes a method for performing a potency assay wherein the target cell line or combination of target cell lines is optimized for maximal immunogenicity. In an embodiment, the invention includes a method for performing a potency assay wherein the target cell line or combination of target cell lines is optimized for maximal HLA-A2 immunogenicity. In an embodiment, the invention includes a method for performing a potency assay wherein the target cell line or combination of target cell lines are selected based on HLA properties. In an embodiment, the invention includes a method for performing a potency assay wherein the target cell line or combination of target cell lines express HLA-A, HLA-B, HLA-C, HLA-DQ (A1), HLA-DQ (A2), HLA-DR (B1), HLA-DP (B1), HLA-DP (B2), or combinations thereof. In an embodiment, the invention includes a method for performing a potency assay wherein the target cell line or combination of target cell lines is optimized for maximal allogeneic HLA-TCR interactions. In an embodiment, the invention includes a method for performing a potency assay wherein the target cell line or combination of target cell lines is optimized for maximal non-antigen-specific HLA-TCR interactions.

In an embodiment, the invention includes a method for performing a potency assay wherein the total number of TIL and target cells per vial or well is approximately $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $1.5\times10^6$, $2\times10^6$, $2.5\times10^6$, $3\times10^6$, $3.5\times10^6$, $4\times10^6$, $4.5\times10^6$, or $5\times10^6$. In an embodiment, a vial or well has a volume of about 0.5 mL, 1 mL, 1.5 mL, 2 mL, 2.5 mL, 3 mL, 3.5 mL, 4 mL, 4.5 mL, or 5 mL.

In some embodiments, an HLA-I blocking antibody is used as a negative control at a concentration of about 0.1 μg/mL, about 0.2 μg/mL, about 0.3 μg/mL, about 0.4 μg/mL, about 0.5 μg/mL, about 0.6 μg/mL, about 0.7 μg/mL, about 0.8 μg/mL, about 0.9 μg/mL, about 1 μg/mL, about 2 μg/mL, about 3 μg/mL, about 4 μg/mL, about 5 μg/mL, about 6 μg/mL, about 7 μg/mL, about 8 μg/mL, about 9 μg/mL, about 10 μg/mL, about 11 μg/mL, about 12 μg/mL, about 13 μg/mL, about 14 μg/mL, about 15 μg/mL, about 16 μg/mL, about 17 μg/mL, about 18 μg/mL, about 19 μg/mL, about 20 μg/mL, about 21 μg/mL, about 22 μg/mL, about 23 μg/mL, about 24 μg/mL, about 25 μg/mL, about 26 μg/mL, about 27 μg/mL, about 28 μg/mL, about 29 μg/mL, about 30 μg/mL, about 35 μg/mL, about 40 μg/mL, about 45 μg/mL, or about 50 μg/mL. In any of the foregoing embodiments, the HLA-I blocking antibody is Clone W6/32 (anti-HLA-ABC), available from Biolegend, Inc. (San Diego, CA, USA).

In some embodiments, an HLA-II blocking antibody is used as a negative control at a concentration of about 0.1 μg/mL, about 0.2 μg/mL, about 0.3 μg/mL, about 0.4 μg/mL, about 0.5 μg/mL, about 0.6 μg/mL, about 0.7 μg/mL, about 0.8 μg/mL, about 0.9 μg/mL, about 1 μg/mL, about 2 μg/mL, about 3 μg/mL, about 4 μg/mL, about 5 μg/mL, about 6 μg/mL, about 7 μg/mL, about 8 μg/mL, about 9 μg/mL, about 10 μg/mL, about 11 μg/mL, about 12 μg/mL, about 13 μg/mL, about 14 μg/mL, about 15 μg/mL, about 16 μg/mL, about 17 μg/mL, about 18 μg/mL, about 19 μg/mL, about 20 μg/mL, about 21 μg/mL, about 22 μg/mL, about 23 μg/mL, about 24 μg/mL, about 25 μg/mL, about 26 μg/mL, about 27 μg/mL, about 28 μg/mL, about 29 μg/mL, about 30 μg/mL, about 35 μg/mL, about 40 μg/mL, about 45 μg/mL, or about 50 μg/mL. In any of the foregoing embodiments, the HLA-II blocking antibody is Clone TU39 (HLA-DR, DP, DQ), available from BD Biosciences, Inc. (Franklin Lakes, NJ, USA).

In an embodiment, the invention comprises a method of determining the potency of a TIL product, the method comprising the steps of:

a. performing a co-culture of a target cell with a TIL cell for a first period;
b. obtaining a harvest or extracting a supernatant from the co-culture; and
c. assessing (1) the harvest for expression of one or more markers on the TIL cell or (2) the supernatant for one or more analytes secreted from the TIL cell to obtain one or more observed values to determine the potency for the TIL product, wherein the TIL to target cell ratio is about 3:1, wherein the target cell is a monocyte cell, and wherein the total cells in the co-culture of step (a) is about $1\times10^6$ per mL.

In an embodiment, the invention comprises a method of determining the potency of a TIL product, the method comprising the steps of:

a. performing a co-culture of a target cell with a TIL cell for a first period;
b. obtaining a harvest or extracting a supernatant from the co-culture; and
c. assessing (1) the harvest for expression of one or more markers on the TIL cell or (2) the supernatant for one or more analytes secreted from the TIL cell to obtain one or more observed values to determine the potency for the TIL product, wherein the TIL to target cell ratio is about 3:1, wherein the target cell is a monocyte cell, wherein the total cells in the co-culture of step (a) is about $1\times10^6$ per mL, and wherein the foregoing method is a component of a potency assay matrix comprising at least one other assay selected from the group consisting of a bead- or plate-based assay for a cytokine, an assay for total viable cells, an assay for percentage viable cells, an assay for $CD4^+$ cell content, an assay for $CD8^+$ cell content, an assay for $T_{EM}$ cell content, an assay for $T_{CM}$ cell content, an assay for $LAG3^+$ cell content, and an assay for $KLRG1^+$ cell content, an assay for $CD101^+$ cell content, an assay for $CD69^+$ cell content, an assay for $T_{SCM}$ cell content, an assay for $T_{EMRA}$ cell content, an assay for $T_{reg}$ cell content, an assay for PD-$1^+$ cell content, an assay for $TIM3^+$ cell content, an assay for $CD25^+$ cell content, an assay for $CD27^+$ cell content, an assay for $CD28^+$ cell content, an assay for $CD56^+$ cell content, an assay for CTLA-$4^+$ cell content, an assay for $TIGIT^+$ cell content, and an assay for $CD57^+$ cell content. In an embodiment, the foregoing assays are flow cytometric assays.

In an embodiment, the invention comprises a method of determining the potency of a TIL product, the method comprising the steps of:

a. performing a co-culture of a target cell with a TIL cell for a first period;
b. obtaining a harvest or extracting a supernatant from the co-culture; and
c. assessing (1) the harvest for expression of one or more markers on the TIL cell or (2) the supernatant for one or more analytes secreted from the TIL cell to obtain one or more observed values to determine the potency for the TIL product, wherein the TIL to target cell ratio is about 3:1, wherein the target cell is a monocyte cell, and wherein the total cells in the co-culture of step (a) is about $2\times10^6$ per mL.

In an embodiment, the invention comprises a method of determining the potency of a TIL product, the method comprising the steps of:

a. performing a co-culture of a target cell with a TIL cell for a first period;
b. obtaining a harvest or extracting a supernatant from the co-culture; and
c. assessing (1) the harvest for expression of one or more markers on the TIL cell or (2) the supernatant for one or more analytes secreted from the TIL cell to obtain one or more observed values to determine the potency for the TIL product, wherein the TIL to target cell ratio is about 3:1, wherein the target cell is a monocyte cell, wherein the total cells in the co-culture of step (a) is about $2\times10^6$ per mL, and wherein the foregoing method is a component of a potency assay matrix comprising at least one other assay selected from the group consisting of a bead- or plate-based assay using CD3, CD28, and/or CD137 stimulation and reporting interferon-γ, granzyme B, or tumor necrosis factor-α, an assay for total viable cells, an assay for percentage viable cells, an assay for $CD4^+$ cell content, an assay for $CD8^+$ cell content, an assay for $T_{EM}$ cell content, an assay for $T_{CM}$ cell content, an assay for $LAG3^+$ cell content, and an assay for $KLRG1^+$ cell content, an assay for $CD101^+$ cell content, an assay for $CD69^+$ cell content, an assay for $T_{SCM}$ cell content, an assay for $T_{EMRA}$ cell content, an assay for $T_{reg}$ cell content, an assay for PD-$1^+$ cell content, an assay for $TIM3^+$ cell content, an assay for $CD25^+$ cell content, an assay for $CD27^+$ cell content, an assay for $CD28^+$ cell content, an assay for $CD56^+$ cell content, an assay for CTLA-$4^+$ cell content, an assay for TIGIT$^+$ cell content, and an assay for CD57$^+$ cell content. In an embodiment, the foregoing assays are flow cytometric assays.

In an embodiment, the invention comprises a method of determining the potency of a TIL product, the method comprising the steps of:

a. performing a co-culture of a target cell with a TIL cell for a first period;
b. obtaining a harvest or extracting a supernatant from the co-culture; and
c. assessing (1) the harvest for expression of one or more markers on the TIL cell or (2) the supernatant for one or more analytes secreted from the TIL cell to obtain one or more observed values to determine the potency for the TIL product, wherein the TIL to target cell ratio is about 1:1, wherein the target cell is a monocyte cell, and wherein the total cells in the co-culture of step (a) is about $1\times10^6$ per mL.

In an embodiment, the invention comprises a method of determining the potency of a TIL product, the method comprising the steps of:

a. performing a co-culture of a target cell with a TIL cell for a first period;
b. obtaining a harvest or extracting a supernatant from the co-culture; and
c. assessing (1) the harvest for expression of one or more markers on the TIL cell or (2) the supernatant for one or more analytes secreted from the TIL cell to obtain one or more observed values to determine the potency for the TIL product, wherein the target cell is a monocyte cell, wherein the total cells in the co-culture of step (a) is about $1\times10^6$ per mL, and wherein the foregoing method is a component of a potency assay matrix comprising at least one other assay selected from the group consisting of a bead- or plate-based assay using CD3, CD28, and/or CD137 stimulation and reporting interferon-γ, granzyme B, or tumor necrosis factor-α, an assay for total viable cells, an assay for percentage viable cells, an assay for CD4$^+$ cell content, an assay for CD8$^+$ cell content, an assay for $T_{EM}$ cell content, an assay for $T_{CM}$ cell content, an assay for LAG3$^+$ cell content, and an assay for KLRG1$^+$ cell content, an assay for CD101$^+$ cell content, an assay for CD69$^+$ cell content, an assay for $T_{SCM}$ cell content, an assay for $T_{EMRA}$ cell content, an assay for $T_{reg}$ cell content, an assay for PD-1$^+$ cell content, an assay for TIM3$^+$ cell content, an assay for CD25$^+$ cell content, an assay for CD27$^+$ cell content, an assay for CD28$^+$ cell content, an assay for CD56$^+$ cell content, an assay for CTLA-4$^+$ cell content, an assay for TIGIT$^+$ cell content, and an assay for CD57$^+$ T cell content. In an embodiment, the foregoing assays are flow cytometric assays.

In an embodiment, the invention comprises a method of determining the potency of a TIL product, the method comprising the steps of:

a. performing a co-culture of a target cell with a TIL cell for a first period;
b. obtaining a harvest or extracting a supernatant from the co-culture; and
c. assessing (1) the harvest for expression of one or more markers on the TIL cell or (2) the supernatant for one or more analytes secreted from the TIL cell to obtain one or more observed values to determine the potency for the TIL product, wherein the TIL to target cell ratio is about 1:1, wherein the target cell is a monocyte cell, and wherein the total cells in the co-culture of step (a) is about $2\times10^6$ per mL.

In an embodiment, the invention comprises a method of determining the potency of a TIL product, the method comprising the steps of:

a. performing a co-culture of a target cell with a TIL cell for a first period;
b. obtaining a harvest or extracting a supernatant from the co-culture; and
c. assessing (1) the harvest for expression of one or more markers on the TIL cell or (2) the supernatant for one or more analytes secreted from the TIL cell to obtain one or more observed values to determine the potency for the TIL product,
d. performing a second co-culture of a negative control comprising a human leukocyte antigen (HLA) blocking antibody with the TIL cell and the target cell, for a second period, such second period optionally occurring simultaneously with the first period;
e. obtaining a second harvest or extracting a second supernatant from the second co-culture;
f. assessing (1) the second harvest for the expression of the one or more markers on the TIL cell or (2) the second supernatant for one or more analytes secreted from the TIL cell to obtain one or more control values; and
g. comparing the one or more observed values from step c with the one or more control values from step f, where each observed value is compared to its corresponding control value, to determine the potency of the TIL product, wherein the TIL to target cell ratio is between 3:1 and 1:1, wherein the target cell is a monocyte cell, wherein the total cells in the co-culture of step (a) and second co-culture of step (d) is between $0.5\times10^6$ per mL and $3\times10^6$ per mL, and wherein the HLA blocking antibody is selected from the group consisting of an HLA-I blocking antibody, an HLA-II blocking antibody, and combinations thereof.

In an embodiment, the invention comprises a method of determining the potency of a TIL product, the method comprising the steps of:

a. performing a co-culture of a target cell with a TIL cell for a first period;
b. obtaining a harvest or extracting a supernatant from the co-culture; and
c. assessing (1) the harvest for expression of one or more markers on the TIL cell or (2) the supernatant for one or more analytes secreted from the TIL cell to obtain one or more observed values to determine the potency for the TIL product,
d. performing a second co-culture of a negative control comprising a human leukocyte antigen (HLA) blocking antibody with the TIL cell and the target cell, for a second period, such second period optionally occurring simultaneously with the first period;
e. obtaining a second harvest or extracting a second supernatant from the second co-culture;
f. assessing (1) the second harvest for the expression of the one or more markers on the TIL cell or (2) the second supernatant for one or more analytes secreted from the TIL cell to obtain one or more control values; and
g. comparing the one or more observed values from step c with the one or more control values from step f, where each observed value is compared to its corresponding control value, to determine the potency of the TIL product, wherein the TIL to target cell ratio is between 3:1 and 1:1, wherein the target cell is a Thp1 cell, or a derivative, variant, modification, or progeny thereof, wherein the total cells in the co-culture of step (a) and second co-culture of step (d) is between $0.5\times10^6$ per mL and $3\times10^6$ per mL, and wherein the HLA blocking antibody is selected from the group consisting of an HLA-I blocking antibody, an HLA-II blocking antibody, and combinations thereof.

In an embodiment, the invention comprises a method of determining the potency of a TIL product, the method comprising the steps of:

a. performing a co-culture of a target cell with a TIL cell for a first period;
b. obtaining a harvest or extracting a supernatant from the co-culture; and
c. assessing (1) the harvest for expression of one or more markers on the TIL cell or (2) the supernatant for one or more analytes secreted from the TIL cell to obtain one or more observed values to determine the potency for the TIL product,
d. performing a second co-culture of a negative control comprising a human leukocyte antigen (HLA) blocking antibody with the TIL cell and the target cell, for a second period, such second period optionally occurring simultaneously with the first period;
e. obtaining a second harvest or extracting a second supernatant from the second co-culture;
f. assessing (1) the second harvest for the expression of the one or more markers on the TIL cell or (2) the second supernatant for one or more analytes secreted from the TIL cell to obtain one or more control values; and
g. comparing the one or more observed values from step c with the one or more control values from step f, where each observed value is compared to its corresponding control value, to determine the potency of the TIL, wherein the TIL to target cell ratio is between 3:1 and 1:1, wherein the target cell is a U937 cell, or a derivative, variant, modification, or progeny thereof, wherein the total cells in the co-culture of step (a) and second co-culture of step (d) is between $0.5\times10^6$ per mL and $3\times10^6$ per mL, and wherein the HLA blocking antibody is selected from the group consisting of an HLA-I blocking antibody, an HLA-II blocking antibody, and combinations thereof.

In an embodiment, the invention comprises a method of determining the potency of a TIL product, the method comprising the steps of:

a. performing a co-culture of a target cell with a TIL cell for a first period;
b. obtaining a harvest or extracting a supernatant from the co-culture; and
c. assessing (1) the harvest for expression of one or more markers on the TIL cell or (2) the supernatant for one or more analytes secreted from the TIL cell to obtain one or more observed values to determine the potency for the TIL product,
d. performing a second co-culture of a negative control comprising a human leukocyte antigen class I (HLA-I) blocking antibody and a human leukocyte antigen class II (HLA-II) blocking antibody with the TIL cell and the target cell, for a second period, such second period optionally occurring simultaneously with the first period;
e. obtaining a second harvest or extracting a second supernatant from the second co-culture;
f. assessing (1) the second harvest for the expression of the one or more markers on the TIL cell or (2) the second supernatant for one or more analytes secreted from the TIL cell to obtain one or more control values; and
g. comparing the one or more observed values from step c with the one or more control values from step f, where each observed value is compared to its corresponding control value, to determine the potency of the TIL product, wherein the TIL to target cell ratio is between 3:1 and 1:1, wherein the target cell is a Thp1 cell, or a derivative, variant, modification, or progeny thereof, wherein the total cells in the co-culture of step (a) and second co-culture of step (d) is between $0.5\times10^6$ per mL and $3\times10^6$ per mL, and wherein the concentration of the HLA-I blocking antibody is between 5 μg/mL and 20 μg/mL and the concentration of the HLA-II blocking antibody is between 5 μg/mL and 10 μg/mL.

In an embodiment, the invention comprises a method of determining the potency of a TIL product, the method comprising the steps of:

a. performing a co-culture of a target cell with a TIL cell for a first period;
b. obtaining a harvest or extracting a supernatant from the co-culture; and
c. assessing (1) the harvest for expression of one or more markers on the TIL cell or (2) the supernatant for one or more analytes secreted from the TIL cell to obtain one or more observed values to determine the potency for the TIL product,
d. performing a second co-culture of a negative control comprising a human leukocyte antigen class I (HLA-I) blocking antibody and a human leukocyte antigen class II (HLA-II) blocking antibody with the TIL cell and the target cell, for a second period, such second period optionally occurring simultaneously with the first period;
e. obtaining a second harvest or extracting a second supernatant from the second co-culture;
f. assessing (1) the second harvest for the expression of the one or more markers on the TIL cell or (2) the second supernatant for one or more analytes secreted from the TIL cell to obtain one or more control values; and
g. comparing the one or more observed values from step c with the one or more control values from step f, where each observed value is compared to its corresponding control value, to determine the potency of the TIL product, wherein the TIL to target cell ratio is between 3:1 and 1:1, wherein the target cell is a Thp1 cell, or a derivative, variant, modification, or progeny thereof, wherein the total cells in the co-culture of step (a) and second co-culture of step (d) is between $0.5\times10^6$ per mL and $3\times10^6$ per mL, and wherein the concentration of the HLA-I blocking antibody is between 5 μg/mL and 20 μg/mL and the concentration of the HLA-II blocking antibody is between 5 μg/mL and 10 μg/mL.

In an embodiment, the invention comprises a method of determining the potency of a TIL product, the method comprising the steps of:

a. performing a co-culture of a target cell with a TIL cell for a first period;
b. obtaining a harvest or extracting a supernatant from the co-culture; and
c. assessing (1) the harvest for expression of one or more markers on the TIL cell or (2) the supernatant for one or more analytes secreted from the TIL cell to obtain one or more observed values to determine the potency for the TIL product, d. performing a second co-culture of a negative control comprising a human leukocyte antigen class I (HLA-I) blocking antibody and a human leukocyte antigen class II (HLA-II) blocking antibody with the TIL cell and the target cell, for a second period, such second period optionally occurring simultaneously with the first period;

e. obtaining a second harvest or extracting a second supernatant from the second co-culture;

f. assessing (1) the second harvest for the expression of the one or more markers on the TIL cell or (2) the second supernatant for one or more analytes secreted from the TIL cell to obtain one or more control values; and g. comparing the one or more observed values from step c with the one or more control values from step f, where each observed value is compared to its corresponding control value, to determine the potency of the TIL product, wherein the TIL to target cell ratio is between 3:1 and 1:1, wherein the target cell is a Thp1 cell, or a derivative, variant, modification, or progeny thereof, wherein the total cells in the co-culture of step (a) and second co-culture of step (d) is between $0.5\times10^6$ per mL and $3\times10^6$ per mL, wherein the concentration of the HLA-I blocking antibody is between 5 μg/mL and 20 μg/mL and the concentration of the HLA-II blocking antibody is between 5 μg/mL and 10 μg/mL, and wherein the one or more analytes secreted from the TIL cell comprises interferon-γ.

In an embodiment, the invention comprises a method of determining the potency of a TIL product, the method comprising the steps of:

a. performing a co-culture of a target cell with a TIL cell for a first period;

b. obtaining a harvest or extracting a supernatant from the co-culture; and c. assessing (1) the harvest for expression of one or more markers on the TIL cell or (2) the supernatant for one or more analytes secreted from the TIL cell to obtain one or more observed values to determine the potency for the TIL product, d. performing a second co-culture of a negative control comprising a human leukocyte antigen class I (HLA-I) blocking antibody and a human leukocyte antigen class II (HLA-II) blocking antibody with the TIL cell and the target cell, for a second period, such second period optionally occurring simultaneously with the first period;

e. obtaining a second harvest or extracting a second supernatant from the second co-culture;

f. assessing (1) the second harvest for the expression of the one or more markers on the TIL cell or (2) the second supernatant for one or more analytes secreted from the TIL cell to obtain one or more control values; and g. comparing the one or more observed values from step c with the one or more control values from step f, where each observed value is compared to its corresponding control value, to determine the potency of the TIL product, wherein the TIL to target cell ratio is between 3:1 and 1:1, wherein the target cell is a Thp1 cell, or a derivative, variant, modification, or progeny thereof, wherein the total cells in the co-culture of step (a) and second co-culture of step (d) is between $0.5\times10^6$ per mL and $3\times10^6$ per mL, wherein the concentration of the HLA-I blocking antibody is between 5 μg/mL and 20 μg/mL and the concentration of the HLA-II blocking antibody is between 5 μg/mL and 10 μg/mL, and wherein the one or more analytes secreted from the TIL cell comprises interferon-γ.

In an embodiment, the invention comprises a method of determining the potency of a TIL product, the method comprising the steps of:

a. performing a co-culture of a target cell with a TIL cell from the TIL product for a first period;

b. extracting a supernatant from the co-culture; and c. assessing the supernatant for interferon-γ secreted from the TIL cell to obtain an observed value, d. performing a second co-culture of a negative control comprising a human leukocyte antigen class I (HLA-I) blocking antibody and a human leukocyte antigen class II (HLA-II) blocking antibody with the TIL cell from the TIL product and the target cell, for a second period, such second period optionally occurring simultaneously with the first period;

e. extracting a second supernatant from the second co-culture;

f. assessing the second supernatant for interferon-γ secreted from the TIL cell to obtain a control value; and g. comparing the observed value from step c with the control value from step f, wherein fold enhancement is calculated, to determine the potency of the TIL product, wherein the TIL to target cell ratio is between 3:1 and 1:1, wherein the target cell is a Thp1 cell, or a derivative, variant, modification, or progeny thereof, wherein the total cells in the co-culture of step (a) and second co-culture of step (d) is between $0.5\times10^6$ per mL and $3\times10^6$ per mL, and wherein the concentration of the HLA-I blocking antibody is between 5 μg/mL and 20 μg/mL and the concentration of the HLA-II blocking antibody is between 5 μg/mL and 10 μg/mL.

In an embodiment, the invention comprises a method of determining the potency of a TIL product, the method comprising the steps of:

a. performing a co-culture of a target cell with a TIL cell from the TIL product for a first period;

b. extracting a supernatant from the co-culture; and c. assessing the supernatant for interferon-γ secreted from the TIL cell to obtain an observed value, d. performing a second co-culture of a negative control comprising a human leukocyte antigen class I (HLA-I) blocking antibody and a human leukocyte antigen class II (HLA-II) blocking antibody with the TIL cell from the TIL product and the target cell, for a second period, such second period optionally occurring simultaneously with the first period;

e. extracting a second supernatant from the second co-culture;

f. assessing the second supernatant for interferon-γ secreted from the TIL cell to obtain a control value; and g. comparing the observed value from step c with the control value from step f, wherein fold enhancement is calculated, to determine the potency of the TIL product, wherein the TIL to target cell ratio is between 3:1 and 1:1, wherein the target cell is a U937 cell, or a derivative, variant, modification, or progeny thereof, wherein the total cells in the co-culture of step (a) is between $0.5\times10^6$ per mL and $3\times10^6$ per mL, and wherein the concentration of the HLA-I blocking antibody is between 5 μg/mL and 20 μg/mL and the concentration of the HLA-II blocking antibody is between 5 μg/mL and 10 μg/mL.

In an embodiment, the invention comprises a method of determining the potency of a TIL product, the method comprising the steps of:

a. performing a co-culture of a target cell with a TIL cell from the TIL product for a first period;
b. extracting a supernatant from the co-culture; and
c. assessing the supernatant for interferon-γ secreted from the TIL cell to obtain an observed value,
d. performing a second co-culture of a negative control comprising a human leukocyte antigen class I (HLA-I) blocking antibody and a human leukocyte antigen class II (HLA-II) blocking antibody with the TIL cell from the TIL product and the target cell, for a second period, such second period optionally occurring simultaneously with the first period;
e. extracting a second supernatant from the second co-culture;
f. assessing the second supernatant for interferon-γ secreted from the TIL cell to obtain a control value; and
g. comparing the observed value from step c with the control value from step f, wherein fold enhancement is calculated, to determine the potency of the TIL product, wherein the TIL to target cell ratio is between 3:1 and 1:1, wherein the target cell is a Thp1 cell, or a derivative, variant, modification, or progeny thereof, wherein the total cells in the co-culture of step (a) and second co-culture of step (d) is between $1\times10^6$ per mL and $3\times10^6$ per mL, wherein the concentration of the HLA-I blocking antibody is between 5 μg/mL and 20 μg/mL and the concentration of the HLA-II blocking antibody is between 5 μg/mL and 10 μg/mL, wherein IL-2 is added continuously during the co-culture and the second co-culture, wherein the IL-2 is maintained in each of the co-culture and the second co-culture at a concentration of between 100 IU/mL and 500 IU/m, and wherein the co-culture and second co-culture are performed using AIM-V media.

In an embodiment, the invention comprises a method of determining the potency of a TIL product, the method comprising the steps of:

a. performing a co-culture of a target cell with a TIL cell from the TIL product for a first period;
b. extracting a supernatant from the co-culture; and
c. assessing the supernatant for interferon-γ secreted from the TIL cell to obtain an observed value,
d. performing a second co-culture of a negative control comprising a human leukocyte antigen class I (HLA-I) blocking antibody and a human leukocyte antigen class II (HLA-II) blocking antibody with the TIL cell from the TIL product and the target cell, for a second period, such second period optionally occurring simultaneously with the first period;
e. extracting a second supernatant from the second co-culture;
f. assessing the second supernatant for interferon-γ secreted from the TIL cell to obtain a control value; and
g. comparing the observed value from step c with the control value from step f, wherein fold enhancement is calculated, to determine the potency of the TIL product, wherein the TIL to target cell ratio is between 3:1 and 1:1, wherein the target cell is a U937 cell, or a derivative, variant, modification, or progeny thereof, wherein the total cells in the co-culture of step (a) and second co-culture of step (d) is between $1\times10^6$ per mL and $3\times10^6$ per mL, wherein the concentration of the HLA-I blocking antibody is between 5 μg/mL and 20 μg/mL and the concentration of the HLA-II blocking antibody is between 5 μg/mL and 10 μg/mL, wherein IL-2 is added continuously during the co-culture and the second co-culture, wherein the IL-2 is maintained in each of the co-culture and the second co-culture at a concentration of between 100 IU/mL and 500 IU/m, and wherein the co-culture and second co-culture are performed using AIM-V media.

In an embodiment, the invention comprises a method of determining the potency of a TIL product, the method comprising the steps of:

a. performing a co-culture of a target cell with a TIL cell from the TIL product for a first period;
b. extracting a supernatant from the co-culture; and
c. assessing the supernatant for interferon-γ secreted from the TIL cell to obtain an observed value,
d. performing a second co-culture of a negative control comprising a human leukocyte antigen class I (HLA-I) blocking antibody and a human leukocyte antigen class II (HLA-II) blocking antibody with the TIL cell from the TIL product and the target cell, for a second period, such second period optionally occurring simultaneously with the first period;
e. extracting a second supernatant from the second co-culture;
f. assessing the second supernatant for interferon-γ secreted from the TIL cell to obtain a control value; and
g. comparing the observed value from step c with the control value from step f, wherein fold enhancement is calculated, to determine the potency of the TIL product, wherein the TIL to target cell ratio is between 3:1 and 1:1, wherein the target cell is a U937 cell, or a derivative, variant, modification, or progeny thereof, wherein the total cells in the co-culture of step (a) and second co-culture of step (d) is between $1\times10^6$ per mL and $3\times10^6$ per mL, wherein the concentration of the HLA-I blocking antibody is between 5 μg/mL and 20 μg/mL and the concentration of the HLA-II blocking antibody is between 5 μg/mL and 10 μg/mL, wherein IL-2 is added continuously during the co-culture and the second co-culture, wherein the IL-2 is maintained in each of the co-culture and the second co-culture at a concentration of between 100 IU/mL and 500 IU/m, wherein the co-culture and second co-culture are performed using AIM-V media, and wherein the foregoing method is a component of a potency assay matrix comprising at least one other assay selected from the group consisting of a bead- or plate-based assay using CD3, CD28, and/or CD137 stimulation and reporting interferon-γ, granzyme B, or tumor necrosis factor-α, an assay for total viable cells, an assay for percentage viable cells, an assay for $CD4^+$ cell content, an assay for $CD8^+$ cell content, an assay for $T_{EM}$ cell content, an assay for $T_{CM}$ cell content, an assay for $LAG3^+$ cell content, and an assay for $KLRG1^+$ cell content, an assay for $CD101^+$ cell content, an assay for $CD69^+$ cell content, an assay for $T_{SCM}$ cell content, an assay for $T_{EMRA}$ cell content, an assay for $T_{reg}$ cell content, an assay for $PD\text{-}1^+$ cell content, an assay for $TIM3^+$ cell content, an assay for $CD25^+$ cell content, an assay for $CD27^+$ cell content, an assay for $CD28^+$ cell content, an assay for $CD56^+$ cell content, an assay for $CTLA\text{-}4^+$ cell content, an assay for $TIGIT^+$ cell content, and an assay for $CD57^+$ cell content. In an embodiment, the foregoing assays are flow cytometric assays.

In some embodiments, the target cell line is prepared from a master cell bank passaged not greater than two times, not greater than three times, not greater than four times, not greater than five times, not greater than six times, not greater than seven times, not greater than eight times, not greater than nine times, or not greater than ten times. In another embodiment of the foregoing embodiments, the total number of passages may be determined by comparison to the number of passages reported by the provider of the target cell line.

In some embodiments, the Raji, Ramos, Daudi, U937, or Thp1 cell line, or combinations thereof, is prepared from a master cell bank passaged not greater than two times, not greater than three times, not greater than four times, not greater than five times, not greater than six times, not greater than seven times, not greater than eight times, not greater than nine times, or not greater than ten times. In another embodiment of the foregoing embodiments, the total number of passages may be determined by comparison to the number of passages reported by the provider or providers of the Raji, Ramos, Daudi, U937, or Thp1 cell line or combinations thereof.

In some embodiments, the negative control cell line is prepared from a master cell bank passaged not greater than two times, not greater than three times, not greater than four times, not greater than five times, not greater than six times, not greater than seven times, not greater than eight times, not greater than nine times, or not greater than ten times. In another embodiment of the foregoing embodiments, the total number of passages may be determined by comparison to the number of passages reported by the provider of the negative control cell line.

In some embodiments, the K562 cell line is prepared from a master cell bank passaged not greater than two times, not greater than three times, not greater than four times, not greater than five times, not greater than six times, not greater than seven times, not greater than eight times, not greater than nine times, or not greater than ten times. In another embodiment of the foregoing embodiments, the total number of passages may be determined by comparison to the number of passages reported by the provider of the K562 cell line.

In some embodiments, the target cell line is prepared from a working cell bank passaged not greater than two times, not greater than three times, not greater than four times, not greater than five times, not greater than six times, not greater than seven times, not greater than eight times, not greater than nine times, or not greater than ten times. In another embodiment of the foregoing embodiments, the total number of passages may be determined by comparison to the number of passages reported by the provider of the target cell line.

In some embodiments, the Raji, Ramos, Daudi, U937, or Thp1 cell line, or combinations thereof, is prepared from a working cell bank passaged not greater than two times, not greater than three times, not greater than four times, not greater than five times, not greater than six times, not greater than seven times, not greater than eight times, not greater than nine times, or not greater than ten times. In another embodiment of the foregoing embodiments, the total number of passages may be determined by comparison to the number of passages reported by the provider or providers of the Raji, Ramos, Daudi, U937, or Thp1 cell line or combinations thereof.

In some embodiments, the negative control cell line is prepared from a working cell bank passaged not greater than two times, not greater than three times, not greater than four times, not greater than five times, not greater than six times, not greater than seven times, not greater than eight times, not greater than nine times, or not greater than ten times. In another embodiment of the foregoing embodiments, the total number of passages may be determined by comparison to the number of passages reported by the provider of the negative control cell line.

In some embodiments, the K562 cell line is prepared from a working cell bank passaged not greater than two times, not greater than three times, not greater than four times, not greater than five times, not greater than six times, not greater than seven times, not greater than eight times, not greater than nine times, or not greater than ten times. In another embodiment of the foregoing embodiments, the total number of passages may be determined by comparison to the number of passages reported by the provider of the K562 cell line.

In some embodiments, the negative control cell line is a TIL cell line tested for the secretion or expression of a protein (such as IFN-γ or granzyme B) after culture under conditions as used in the co-culture with a target cell line (such as a monocyte cell line, or a Raji, Ramos, Daudi, U937, or Thp1 cell line), except that the target cell line is not included with the TIL cell line. These negative control experiments are referred to herein in some cases as “TIL alone” control experiments. Fold enhancement and parallel line analysis calculations may be employed in conjunction with a TIL alone negative control experiment. For example, a co-culture of a TIL line may be performed according to the methods described herein with a monocyte target cell line, and in a separate experiment run under the same conditions and at the same time, the TIL line may be cultured alone. Both experiments may then be analyzed for IFN-γ expression, and compared to calculate a fold-enhancement or used in the calculation of parallel line analysis slopes or other analytical criteria.

In some of the foregoing embodiments, a positive control TIL cell line is also included, which is measured using the methods described herein (e.g., steps (a) through (c) in the relevant foregoing embodiments) to ensure reproducibility on an interexperiment, interday, interanalyst, or interlaboratory basis.

In some embodiments, the foregoing methods are used with a data analysis step. In some embodiments, the data analysis step is a fold-enhancement calculation, as described elsewhere herein in detail. In some embodiments, the data analysis step is a parallel line analysis calculation, as described elsewhere herein in detail. A parallel line analysis approach to statistical analysis and pass/fail release or stability determinations may be used with any of the foregoing assay embodiments, including in conjunction with the measurement of two, three, four, or five target cell concentrations against a single TIL lot concentration to determine dose response, with optional removal of one or two outliers (for example, four target cell concentrations with removal of one outlier). Parallel line analysis is also described in USP Chapter <1032> Design and Development of Biological Assays. USP Pharmacopeial Convention: Rockville, MD, 2013; USP Chapter <111> Design and Analysis of Biological Assays. US Pharmacopeial Convention: Rockville, MD, 2014; USP Chapter <1033> Biological Assay Validation. USP Pharmacopeial Convention: Rockville, MD, 2013; USP Chapter <1034> Analysis of Biological Assays. US Pharmacopeial Convention: Rockville, MD, 2013; Hauck, et al., *PDA J. Pharma. Sci. Technol.* 2005, 59(2), 127-137; Callahan and Sajjadi, *BioProcessing J.* 2003, 2(2), 71-77; Findlay, et al., *J. Pharm. Biomed. Anal.* 2000, 21, 1249-1273; and Gottschalk and Dunn, *J. Biopharm. Stat.* 2005, 15(3), 437-463; the disclosures of each of which are incorporated by reference herein.

In some embodiments, the foregoing methods are used with a data analysis step performed per USP <1032> Design and Development of Biological Assays, the disclosures of which are incorporated by reference herein. In some embodiments, the foregoing methods are used with a data analysis step wherein data are log transformed according to USP <1032> Design and Development of Biological Assays and USP <1033> Biological Assay Validation, the disclosures of each of which are incorporated by reference herein, to meet requirements for symmetry, normal distribution, and homogeneity of variability in measurements across the potency range. In some embodiments, the foregoing methods are used with a data analysis step wherein outliers are assessed and omitted from analysis as described in USP <1034> Analysis of Biological Assays, the disclosures of which are incorporated by reference herein. In some embodiments, the foregoing methods are used with a data analysis step wherein linear regression is performed across the four-point dose curve with masking (if needed) of either the highest or lowest concentration due to saturation of the curve. In some embodiments, the foregoing methods are used with a data analysis step wherein at least three and preferably four adjacent [dose-]concentrations are used. In some embodiments, the foregoing methods are used with a data analysis step wherein it is required that the slope of the linear segment is sufficiently steep. In some embodiments, the foregoing methods are used with a data analysis step wherein it is required that the lines fit to standard and test samples are straight and that the lines are parallel. In some embodiments, the foregoing methods are used with a data analysis step wherein parallel line analysis is performed between the TIL test article and the reference standard according to USP <1032> Design and Development of Biological Assays, the disclosures of which are incorporated by reference herein. In some embodiments, the foregoing methods are used with a data analysis step wherein statistical similarity between the reference standard and the TIL test article measured by parallelism demonstrates the biological similarity of the TIL test article to the reference standard. In some embodiments, the foregoing methods are used with a data analysis step wherein the parallelism slope ratio, linearity ratio, regression ($R^2$) and root mean square error (RMSE) are calculated and reported. In some embodiments, the foregoing methods are used with a data analysis step wherein assay suitability and validity of parallelism and linearity is ranked and determined to either "pass" or "fail" the validity criterion within limits according to USP <1033> Biological Assay Validation, the disclosures of which are incorporated by reference herein. In some embodiments, the foregoing methods are used with a data analysis step wherein the relative potency within the 95% confidence interval as a range of percent of tolerance is determined as "reportable" or "inconclusive". While not being bound by theory, according to USP <1032> Design and Development of Biological Assays, relative potency is preferred over potency, which is derived from an absolute value, because it is a calibrator that nulls out the effect of variability inherent of biological samples and cellular behavior over time.

In some embodiments, the invention includes one of the foregoing methods for determining TIL, MIL, or PBL product potency, and further includes the use of one of the foregoing methods in conjunction with other potency assays and/or identity assays to form a potency assay (or potency and identity assay) matrix. Such a matrix includes multiple steps for determining the potency (or potency and identity) of a TIL, MIL, or PBL product. Potency assay matrices are described in the U.S. Food and Drug Administration's *Guidance for Industry: Potency Tests for Cellular and Gene Therapy Products,* 2011, 76 Fed. Reg. 9028, the disclosures of which are incorporated by reference herein. In some embodiments, the invention includes a matrix that comprises an allogeneic co-culture assay, such as an allogeneic co-culture assay using Raji, Ramos, Daudi, U937, or Thp1 target cells, as well as at least one additional assay. In some embodiments, the invention includes a matrix that comprises an allogeneic co-culture assay, such as an allogeneic co-culture assay using Raji, Ramos, Daudi, U937, or Thp1 target cells, as well as at least two additional assays. In some embodiments, the invention includes a matrix that comprises an allogeneic co-culture assay, such as an allogeneic co-culture assay using Raji, Ramos, Daudi, U937, or Thp1 target cells, as well as at least three additional assays. In some embodiments, the invention includes a matrix that comprises an allogeneic co-culture assay, such as an allogeneic co-culture assay using Raji, Ramos, Daudi, U937, or Thp1 target cells, as well as at least four additional assays. In some embodiments, the invention includes a matrix that comprises an allogeneic co-culture assay, such as an allogeneic co-culture assay using Raji, Ramos, Daudi, U937, or Thp1 target cells, as well as at least five additional assays. In some embodiments, the invention includes a matrix that comprises an allogeneic co-culture assay, such as an allogeneic co-culture assay using Raji, Ramos, Daudi, U937, or Thp1 target cells, as well as at least six additional assays. In some embodiments, the invention includes a matrix that comprises an allogeneic co-culture assay, such as an allogeneic co-culture assay using Raji, Ramos, Daudi, U937, or Thp1 target cells, as well as at least seven additional assays. In some embodiments, the invention includes a matrix that comprises an allogeneic co-culture assay, such as an allogeneic co-culture assay using Raji, Ramos, Daudi, U937, or Thp1 target cells, as well as at least eight additional assays. In some embodiments, the invention includes a matrix that comprises an allogeneic co-culture assay, such as an allogeneic co-culture assay using Raji, Ramos, Daudi, U937, or Thp1 target cells, as well as at least nine additional assays. In some embodiments, the invention includes a matrix that comprises an allogeneic co-culture assay, such as an allogeneic co-culture assay using Raji, Ramos, Daudi, U937, or Thp1 target cells, as well as at least ten additional assays. In some embodiments, the invention includes a matrix that comprises an allogeneic co-culture assay, such as an allogeneic co-culture assay using Raji, Ramos, Daudi, U937, or Thp1 target cells, as well as at least eleven additional assays. In some embodiments, the invention includes a matrix that comprises an allogeneic co-culture assay, such as an allogeneic co-culture assay using Raji, Ramos, Daudi, U937, or Thp1 target cells, as well as at least twelve additional assays.

In some embodiments, the invention includes a method for determining the potency of a T cell product wherein the level of IFN-γ, granzyme B, or TNF-α is measured by a bead- or plate-based stimulation method, including stimulation by anti-CD3, anti-CD28, and/or anti-CD137 antibodies. Such methods are orthogonal to the allogeneic co-culture assays described herein in that they detect TIL, MIL, or PBL activation through a different mechanism and further report on the functionality or activity of a TIL, MIL, or PBL therapeutic product. Such methods may therefore be included in a potency assay matrix as described herein, alone or in combination with the allogeneic co-culture assays described herein. Suitable bead and plate-based methods are described in U.S. Pat. Nos. 10,130,659; 11,083,752; 10,918,666; 11,168,303; and 11,026,974 and U.S. Patent Application Publication No. US 2019/0276802 A1, the disclosures of which are incorporated by reference herein.

In some embodiments, the invention includes a method for determining the potency of a T cell product wherein the number or percentage of $T_{CM}$ cells is measured. In some embodiments, the invention includes a method for determining the potency of a T cell product wherein the number or percentage of $T_{EM}$ cells is measured. In some embodiments, the invention includes a method for determining the potency of a T cell product wherein the number or percentage of $T_{SCM}$ cells is measured. In some embodiments, the invention includes a method for determining the potency of a T cell product wherein the number or percentage of $T_{EMRA}$ cells is measured. In some embodiments, TIL, MIL, or PBL product potency is determined by measurement of $T_{EM}$ cells through the percentage of $CD45RA^{-}CCR7^{-}$ expressing cells by flow cytometry, wherein the expression of $CD45RA^{-}CCR7^{-}$ is detected on greater than 5%, greater than 10%, greater than 15%, greater than 20%, greater than 25%, greater than 30%, greater than 35%, greater than 40%, greater than 45%, greater than 50%, greater than 55%, greater than 60%, greater than 65%, greater than 70%, greater than 75%, greater than 80%, greater than 85%, greater than 90%, or greater than 95% of the $CD3^{+}$ cells or $TCR_{\alpha\beta}$-positive cells. In some embodiments, TIL, MIL, or PBL product potency is determined by measurement of $T_{CM}$ cells through the percentage of $CD45RA^{-}$ CCR7T expressing cells by flow cytometry, wherein the expression of $CD45RA^{-}CCR7^{+}$ is detected on greater than 5%, greater than 10%, greater than 15%, greater than 20%, greater than 25%, greater than 30%, greater than 35%, greater than 40%, greater than 45%, greater than 50%, greater than 55%, greater than 60%, greater than 65%, greater than 70%, greater than 75%, greater than 80%, greater than 85%, greater than 90%, or greater than 95% of the $CD3^{+}$ cells or $TCR_{\alpha\beta}$-positive cells. In some embodiments, the invention includes a method for determining the potency of a T cell product wherein the total $T_{EM}$ and $T_{CM}$ cell population is greater than $100\times10^6$, greater than $150\times10^6$, greater than $200\times10^6$, greater than $250\times10^6$, greater than $300\times10^6$, greater than $350\times10^6$, greater than $400\times10^6$, greater than $450\times10^6$, greater than $500\times10^6$, greater than $550\times10^6$, greater than $600\times10^6$, greater than $650\times10^6$, greater than $700\times10^6$, greater than $750\times10^6$, greater than $800\times10^6$, greater than $850\times10^6$, greater than $900\times10^6$, greater than $950\times10^6$, greater than $1\times10^9$, greater than $1.5\times10^9$, greater than $2.0\times10^9$, greater than $2.5\times10^9$, greater than $3.0\times10^9$, greater than $3.5\times10^9$, greater than $4.0\times10^9$, greater than $5.0\times10^9$, greater than $6.0\times10^9$, greater than $7.0\times10^9$, greater than $8.0\times10^9$, greater than $9.0\times10^9$, or greater than $10\times10^9$ cells.

In some embodiments, the invention includes a method for determining the potency of a T cell product wherein the percentage expression of CD8 is measured. In some embodiments, the measurement of CD8 is by flow cytometry. In some embodiments, TIL, MIL, or PBL product potency is determined by measurement of CD8 by flow cytometry. In some embodiments, TIL, MIL, or PBL product potency is determined by measurement of CD8 by flow cytometry, wherein the measurement is part of a series of measurements performed according to an assay matrix. In some embodiments, TIL, MIL, or PBL product potency is determined by measurement of CD8 by flow cytometry, wherein the measurement is part of a series of measurements performed according to an assay matrix, and further wherein the assay matrix also comprises an alloreactive co-culture assay as described elsewhere herein. In some embodiments, TIL, MIL, or PBL product potency is determined by measurement of CD8 by flow cytometry, wherein the expression of CD8 is detected on greater than 5%, greater than 10%, greater than 15%, greater than 20%, greater than 25%, greater than 30%, greater than 35%, greater than 40%, greater than 45%, greater than 50%, greater than 55%, greater than 60%, greater than 65%, greater than 70%, greater than 75%, greater than 80%, greater than 85%, greater than 90%, or greater than 95% of the $CD3^{+}$ cells or $TCR_{\alpha\beta}$-positive cells.

In some embodiments, the invention includes a method for determining the potency of a T cell product wherein the percentage expression of CD8 is measured. In some embodiments, the measurement of CD8 is by flow cytometry. In some embodiments, TIL, MIL, or PBL product potency is determined by measurement of CD8 by flow cytometry. In some embodiments, TIL, MIL, or PBL product potency is determined by measurement of CD8 by flow cytometry, wherein the measurement is part of a series of measurements performed according to an assay matrix. In some embodiments, TIL, MIL, or PBL product potency is determined by measurement of CD8 by flow cytometry, wherein the measurement is part of a series of measurements performed according to an assay matrix, and further wherein the assay matrix also comprises an alloreactive co-culture assay as described elsewhere herein. In some embodiments, TIL, MIL, or PBL product potency is determined by measurement of CD8 by flow cytometry, wherein the expression of CD8 is detected on greater than 2%, greater than 3%, greater than 4%, greater than 5%, greater than 10%, greater than 15%, greater than 20%, greater than 25%, greater than 30%, greater than 35%, greater than 40%, greater than 45%, greater than 50%, greater than 55%, greater than 60%, greater than 65%, greater than 70%, greater than 75%, greater than 80%, greater than 85%, greater than 90%, or greater than 95% of the $CD3^{+}$ cells or $TCR_{\alpha\beta}$-positive cells.

In some embodiments, the invention includes a method for determining the potency of a T cell product wherein the percentage expression of CD4 is measured. In some embodiments, the measurement of CD4 is by flow cytometry. In some embodiments, TIL, MIL, or PBL product potency is determined by measurement of CD4 by flow cytometry. In some embodiments, TIL, MIL, or PBL product potency is determined by measurement of CD8 by flow cytometry, wherein the measurement is part of a series of measurements performed according to an assay matrix. In some embodiments, TIL, MIL, or PBL product potency is determined by measurement of CD4 by flow cytometry, wherein the measurement is part of a series of measurements performed according to an assay matrix, and further wherein the assay matrix also comprises an alloreactive co-culture assay as described elsewhere herein. In some embodiments, TIL, MIL, or PBL product potency is determined by measurement of CD4 by flow cytometry, wherein the expression of CD4 is detected on greater than 2%, greater than 3%, greater than 4%, greater than 5%, greater than 10%, greater than 15%, greater than 20%, greater than 25%, greater than 30%, greater than 35%, greater than 40%, greater than 45%, greater than 50%, greater than 55%, greater than 60%, greater than 65%, greater than 70%, greater than 75%, greater than 80%, greater than 85%, greater than 90%, or greater than 95% of the $CD3^{+}$ cells or $TCR_{\alpha\beta}$-positive cells.

In some embodiments, the invention includes a method for determining the potency of a T cell product wherein the percentage expression of both CD4 and CD8 is measured. In some embodiments, the measurement of both CD4 and CD8 is by flow cytometry. In some embodiments, TIL, MIL, or PBL product potency is determined by measurement of both CD4 and CD8 by flow cytometry. In some embodiments, TIL, MIL, or PBL product potency is determined by measurement of both CD4 and CD8 by flow cytometry, wherein the measurement is part of a series of measurements performed according to an assay matrix. In some embodiments, TIL, MIL, or PBL product potency is determined by measurement of both CD4 and CD8 by flow cytometry, wherein the measurement is part of a series of measurements performed according to an assay matrix, and further wherein the assay matrix also comprises an alloreactive co-culture assay as described elsewhere herein. In some embodiments, TIL, MIL, or PBL product potency is determined by measurement of both CD4 and CD8 by flow cytometry, wherein the expression of CD4 plus CD8 is detected on greater than 50%, greater than 55%, greater than 60%, greater than 65%, greater than 70%, greater than 75%, greater than 80%, greater than 85%, greater than 90%, or greater than 95% of the $CD3^+$ cells or $TCR_{\alpha\beta}$-positive cells.

In some embodiments, the invention includes a method for determining the potency of a T cell product wherein the total $CD4^+$ and $CD8^+$ cell population, including singly-positive CD4, singly-positive CD8, and doubly-positive subsets, is greater than $100\times10^6$, greater than $150\times10^6$, greater than $200\times10^6$, greater than $250\times10^6$, greater than $300\times10^6$, greater than $350\times10^6$, greater than $400\times10^6$, greater than $450\times10^6$, greater than $500\times10^6$, greater than $550\times10^6$, greater than $600\times10^6$, greater than $650\times10^6$, greater than $700\times10^6$, greater than $750\times10^6$, greater than $800\times10^6$, greater than $850\times10^6$, greater than $900\times10^6$, greater than $950\times10^6$, greater than $1\times10^9$, greater than $1.5\times10^9$, greater than $2.0\times10^9$, greater than $2.5\times10^9$, greater than $3.0\times10^9$, greater than $3.5\times10^9$, greater than $4.0\times10^9$, greater than $5.0\times10^9$, greater than $6.0\times10^9$, greater than $7.0\times10^9$, greater than $8.0\times10^9$, greater than $9.0\times10^9$, or greater than $10\times10^9$ cells.

In some embodiments, the invention includes a method for determining the potency of a T cell product wherein the percentage expression of LAG3 is measured. In some embodiments, the measurement of LAG3 is by flow cytometry. In some embodiments, TIL, MIL, or PBL product potency is determined by measurement of LAG3 by flow cytometry. In some embodiments, TIL, MIL, or PBL product potency is determined by measurement of LAG3 by flow cytometry, wherein the measurement is part of a series of measurements performed according to an assay matrix. In some embodiments, TIL, MIL, or PBL product potency is determined by measurement of LAG3 by flow cytometry, wherein the measurement is part of a series of measurements performed according to an assay matrix, and further wherein the assay matrix also comprises an alloreactive co-culture assay as described elsewhere herein. In some embodiments, TIL, MIL, or PBL product potency is determined by measurement of LAG3 by flow cytometry, wherein the expression of LAG3 is detected on less than 5%, less than 10%, less than 15%, less than 20%, less than 25%, less than 30%, less than 35%, less than 40%, less than 45%, less than 50%, less than 55%, less than 60%, less than 65%, less than 70%, less than 75%, less than 80%, less than 85%, less than 90%, or less than 95% of the $CD3^+$ cells or $TCR_{\alpha\beta}$-positive cells. In some embodiments, TIL, MIL, or PBL product potency is determined by measurement of LAG3 by flow cytometry, wherein the expression of LAG3 is detected on greater than 5%, greater than 10%, greater than 15%, greater than 20%, greater than 25%, greater than 30%, greater than 35%, greater than 40%, greater than 45%, greater than 50%, greater than 55%, greater than 60%, greater than 65%, greater than 70%, greater than 75%, greater than 80%, greater than 85%, greater than 90%, or greater than 95% of the $CD3^+$ cells or $TCR_{\alpha\beta}$-positive cells. In some embodiments, TIL, MIL, or PBL product potency is determined by measurement of the total number of $LAG3^+$ cells, wherein the total number of $LAG3^+$ cells is greater than $50\times10^6$, greater than $100\times10^6$, greater than $150\times10^6$, greater than $200\times10^6$, greater than $250\times10^6$, greater than $300\times10^6$, greater than $350\times10^6$, greater than $400\times10^6$, greater than $450\times10^6$, greater than $500\times10^6$, greater than $550\times10^6$, greater than $600\times10^6$, greater than $650\times10^6$, greater than $700\times10^6$, greater than $750\times10^6$, greater than $800\times10^6$, greater than $850\times10^6$, greater than $900\times10^6$, greater than $950\times10^6$, greater than $1\times10^9$, greater than $1.5\times10^9$, greater than $2.0\times10^9$, greater than $2.5\times10^9$, greater than $3.0\times10^9$, greater than $3.5\times10^9$, greater than $4.0\times10^9$, greater than $5.0\times10^9$, greater than $6.0\times10^9$, greater than $7.0\times10^9$, greater than $8.0\times10^9$, greater than $9.0\times10^9$, or greater than $10\times10^9$ cells.

In some embodiments, the invention includes a method for determining the potency of a T cell product wherein the percentage expression of KLRG1 is measured. In some embodiments, the measurement of KLRG1 is by flow cytometry. In some embodiments, TIL, MIL, or PBL product potency is determined by measurement of KLRG1 by flow cytometry. In some embodiments, TIL, MIL, or PBL product potency is determined by measurement of KLRG1 by flow cytometry, wherein the measurement is part of a series of measurements performed according to an assay matrix. In some embodiments, TIL, MIL, or PBL product potency is determined by measurement of KLRG1 by flow cytometry, wherein the measurement is part of a series of measurements performed according to an assay matrix, and further wherein the assay matrix also comprises an alloreactive co-culture assay as described elsewhere herein. In some embodiments, TIL, MIL, or PBL product potency is determined by measurement of KLRG1 by flow cytometry, wherein the expression of KLRG1 is detected on less than 5%, less than 10%, less than 15%, less than 20%, less than 25%, less than 30%, less than 35%, less than 40%, less than 45%, less than 50%, less than 55%, less than 60%, less than 65%, less than 70%, less than 75%, less than 80%, less than 85%, less than 90%, or less than 95% of the $CD3^+$ cells or $TCR_{\alpha\beta}$-positive cells. In some embodiments, TIL, MIL, or PBL product potency is determined by measurement of KLRG1 by flow cytometry, wherein the expression of KLRG1 is detected on greater than 5%, greater than 10%, greater than 15%, greater than 20%, greater than 25%, greater than 30%, greater than 35%, greater than 40%, greater than 45%, greater than 50%, greater than 55%, greater than 60%, greater than 65%, greater than 70%, greater than 75%, greater than 80%, greater than 85%, greater than 90%, or greater than 95% of the $CD3^+$ cells or $TCR_{\alpha\beta}$-positive cells. In some embodiments, TIL, MIL, or PBL product potency is determined by measurement of the total number of $KLRG1^+$ cells, wherein the total number of $KLRG1^+$ cells is greater than $50\times10^6$, greater than $100\times10^6$, greater than $150\times10^6$, greater than $200\times10^6$, greater than $250\times10^6$, greater than $300\times10^6$, greater than $350\times10^6$, greater than $400\times10^6$, greater than $450\times10^6$, greater than $500\times10^6$, greater than $550\times10^6$, greater than $600\times10^6$, greater than $650\times10^6$, greater than $700\times10^6$, greater than $750\times10^6$, greater than $800\times10^6$, greater than $850\times10^6$, greater than $900\times10^6$, greater than $950\times10^6$, greater than $1\times10^9$, greater than $1.5\times10^9$, greater than $2.0\times10^9$, greater than $2.5\times10^9$, greater than $3.0\times10^9$, greater than $3.5\times10^9$, greater than $4.0\times10^9$, greater than $5.0\times10^9$, greater than $6.0\times10^9$, greater than $7.0\times10^9$, greater than $8.0\times10^9$, greater than $9.0\times10^9$, or greater than $10\times10^9$ cells.

In some embodiments, the invention includes a method for determining the potency of a T cell product wherein the percentage expression of CD101 is measured. In some embodiments, the measurement of CD101 is by flow cytometry. In some embodiments, TIL, MIL, or PBL product potency is determined by measurement of CD101 by flow cytometry. In some embodiments, TIL, MIL, or PBL product potency is determined by measurement of CD101 by flow cytometry, wherein the measurement is part of a series of measurements performed according to an assay matrix. In some embodiments, TIL, MIL, or PBL product potency is determined by measurement of CD101 by flow cytometry, wherein the measurement is part of a series of measurements performed according to an assay matrix, and further wherein the assay matrix also comprises an alloreactive co-culture assay as described elsewhere herein. In some embodiments, TIL, MIL, or PBL product potency is determined by measurement of CD101 by flow cytometry, wherein the expression of CD101 is detected on less than 5%, less than 10%, less than 15%, less than 20%, less than 25%, less than 30%, less than 35%, less than 40%, less than 45%, less than 50%, less than 55%, less than 60%, less than 65%, less than 70%, less than 75%, less than 80%, less than 85%, less than 90%, or less than 95% of the $CD3^+$ cells or $TCR_{\alpha\beta}$-positive cells. In some embodiments, TIL, MIL, or PBL product potency is determined by measurement of CD101 by flow cytometry, wherein the expression of CD101 is detected on greater than 5%, greater than 10%, greater than 15%, greater than 20%, greater than 25%, greater than 30%, greater than 35%, greater than 40%, greater than 45%, greater than 50%, greater than 55%, greater than 60%, greater than 65%, greater than 70%, greater than 75%, greater than 80%, greater than 85%, greater than 90%, or greater than 95% of the $CD3^+$ cells or $TCR_{\alpha\beta}$-positive cells. In some embodiments, TIL, MIL, or PBL product potency is determined by measurement of the total number of $CD101^+$ cells, wherein the total number of $CD101^+$ cells is greater than $50\times10^6$, greater than $100\times10^6$, greater than $150\times10^6$, greater than $200\times10^6$, greater than $250\times10^6$, greater than $300\times10^6$, greater than $350\times10^6$, greater than $400\times10^6$, greater than $450\times10^6$, greater than $500\times10^6$, greater than $550\times10^6$, greater than $600\times10^6$, greater than $650\times10^6$, greater than $700\times10^6$, greater than $750\times10^6$, greater than $800\times10^6$, greater than $850\times10^6$, greater than $900\times10^6$, greater than $950\times10^6$, greater than $1\times10^9$, greater than $1.5\times10^9$, greater than $2.0\times10^9$, greater than $2.5\times10^9$, greater than $3.0\times10^9$, greater than $3.5\times10^9$, greater than $4.0\times10^9$, greater than $5.0\times10^9$, greater than $6.0\times10^9$, greater than $7.0\times10^9$, greater than $8.0\times10^9$, greater than $9.0\times10^9$, or greater than $10\times10^9$ cells.

In some embodiments, the invention includes a method for determining the potency of a T cell product wherein the percentage expression of CD69 is measured. In some embodiments, the measurement of CD69 is by flow cytometry. In some embodiments, TIL, MIL, or PBL product potency is determined by measurement of CD69 by flow cytometry. In some embodiments, TIL, MIL, or PBL product potency is determined by measurement of CD69 by flow cytometry, wherein the measurement is part of a series of measurements performed according to an assay matrix. In some embodiments, TIL, MIL, or PBL product potency is determined by measurement of CD69 by flow cytometry, wherein the measurement is part of a series of measurements performed according to an assay matrix, and further wherein the assay matrix also comprises an alloreactive co-culture assay as described elsewhere herein. In some embodiments, TIL, MIL, or PBL product potency is determined by measurement of CD69 by flow cytometry, wherein the expression of CD69 is detected on less than 5%, less than 10%, less than 15%, less than 20%, less than 25%, less than 30%, less than 35%, less than 40%, less than 45%, less than 50%, less than 55%, less than 60%, less than 65%, less than 70%, less than 75%, less than 80%, less than 85%, less than 90%, or less than 95% of the $CD3^+$ cells or $TCR_{\alpha\beta}$-positive cells. In some embodiments, TIL, MIL, or PBL product potency is determined by measurement of CD69 by flow cytometry, wherein the expression of CD69 is detected on greater than 5%, greater than 10%, greater than 15%, greater than 20%, greater than 25%, greater than 30%, greater than 35%, greater than 40%, greater than 45%, greater than 50%, greater than 55%, greater than 60%, greater than 65%, greater than 70%, greater than 75%, greater than 80%, greater than 85%, greater than 90%, or greater than 95% of the $CD3^+$ cells or $TCR_{\alpha\beta}$-positive cells. In some embodiments, TIL, MIL, or PBL product potency is determined by measurement of the total number of $CD69^+$ cells, wherein the total number of $CD69^+$ cells is greater than $50\times10^6$, greater than $100\times10^6$, greater than $150\times10^6$, greater than $200\times10^6$, greater than $250\times10^6$, greater than $300\times10^6$, greater than $350\times10^6$, greater than $400\times10^6$, greater than $450\times10^6$, greater than $500\times10^6$, greater than $550\times10^6$, greater than $600\times10^6$, greater than $650\times10^6$, greater than $700\times10^6$, greater than $750\times10^6$, greater than $800\times10^6$, greater than $850\times10^6$, greater than $900\times10^6$, greater than $950\times10^6$, greater than $1\times10^9$, greater than $1.5\times10^9$, greater than $2.0\times10^9$, greater than $2.5\times10^9$, greater than $3.0\times10^9$, greater than $3.5\times10^9$, greater than $4.0\times10^9$, greater than $5.0\times10^9$, greater than $6.0\times10^9$, greater than $7.0\times10^9$, greater than $8.0\times10^9$, greater than $9.0\times10^9$, or greater than $10\times10^9$ cells.

In some embodiments, the invention includes a method for determining the potency of a T cell product wherein the percentage expression of PD-1 is measured. In some embodiments, the measurement of PD-1 is by flow cytometry. In some embodiments, TIL, MIL, or PBL product potency is determined by measurement of PD-1 by flow cytometry. In some embodiments, TIL, MIL, or PBL product potency is determined by measurement of PD-1 by flow cytometry, wherein the measurement is part of a series of measurements performed according to an assay matrix. In some embodiments, TIL, MIL, or PBL product potency is determined by measurement of PD-1 by flow cytometry, wherein the measurement is part of a series of measurements performed according to an assay matrix, and further wherein the assay matrix also comprises an alloreactive co-culture assay as described elsewhere herein. In some embodiments, TIL, MIL, or PBL product potency is determined by measurement of PD-1 by flow cytometry, wherein the expression of PD-1 is detected on less than 5%, less than 10%, less than 15%, less than 20%, less than 25%, less than 30%, less than 35%, less than 40%, less than 45%, less than 50%, less than 55%, less than 60%, less than 65%, less than 70%, less than 75%, less than 80%, less than 85%, less than 90%, or less than 95% of the $CD3^+$ cells or $TCR_{\alpha\beta}$-positive cells. In some embodiments, TIL, MIL, or PBL product potency is determined by measurement of PD-1 by flow cytometry, wherein the expression of PD-1 is detected on greater than 5%, greater than 10%, greater than 15%, greater than 20%, greater than 25%, greater than 30%, greater than 35%, greater than 40%, greater than 45%, greater than 50%, greater than 55%, greater than 60%, greater than 65%, greater than 70%, greater than 75%, greater than 80%, greater than 85%, greater than 90%, or greater than 95% of the $CD3^+$ cells or $TCR_{\alpha\beta}$-positive cells. In some embodiments, TIL, MIL, or PBL product potency is determined by measurement of the total number of $PD\text{-}1^+$ cells, wherein the total number of PD-1 cells is greater than $50\times10^6$, greater than $100\times10^6$, greater than $150\times10^6$, greater than $200\times10^6$, greater than $250\times10^6$, greater than $300\times10^6$, greater than $350\times10^6$, greater than $400\times10^6$, greater than $450\times10^6$, greater than $500\times10^6$, greater than $550\times10^6$, greater than $600\times10^6$, greater than $650\times10^6$, greater than $700\times10^6$, greater than $750\times10^6$, greater than $800\times10^6$, greater than $850\times10^6$, greater than $900\times10^6$, greater than $950\times10^6$, greater than $1\times10^9$, greater than $1.5\times10^9$, greater than $2.0\times10^9$, greater than $2.5\times10^9$, greater than $3.0\times10^9$, greater than $3.5\times10^9$, greater than $4.0\times10^9$, greater than $5.0\times10^9$, greater than $6.0\times10^9$, greater than $7.0\times10^9$, greater than $8.0\times10^9$, greater than $9.0\times10^9$, or greater than $10\times10^9$ cells.

In some embodiments, the invention includes a method for determining the potency of a T cell product wherein the percentage expression of TIM3 is measured. In some embodiments, the measurement of TIM3 is by flow cytometry. In some embodiments, TIL, MIL, or PBL product potency is determined by measurement of TIM3 by flow cytometry. In some embodiments, TIL, MIL, or PBL product potency is determined by measurement of TIM3 by flow cytometry, wherein the measurement is part of a series of measurements performed according to an assay matrix. In some embodiments, TIL, MIL, or PBL product potency is determined by measurement of TIM3 by flow cytometry, wherein the measurement is part of a series of measurements performed according to an assay matrix, and further wherein the assay matrix also comprises an alloreactive co-culture assay as described elsewhere herein. In some embodiments, TIL, MIL, or PBL product potency is determined by measurement of TIM3 by flow cytometry, wherein the expression of TIM3 is detected on less than 5%, less than 10%, less than 15%, less than 20%, less than 25%, less than 30%, less than 35%, less than 40%, less than 45%, less than 50%, less than 55%, less than 60%, less than 65%, less than 70%, less than 75%, less than 80%, less than 85%, less than 90%, or less than 95% of the $CD3^+$ cells or $TCR_{\alpha\beta}$-positive cells. In some embodiments, TIL, MIL, or PBL product potency is determined by measurement of TIM3 by flow cytometry, wherein the expression of TIM3 is detected on greater than 5%, greater than 10%, greater than 15%, greater than 20%, greater than 25%, greater than 30%, greater than 35%, greater than 40%, greater than 45%, greater than 50%, greater than 55%, greater than 60%, greater than 65%, greater than 70%, greater than 75%, greater than 80%, greater than 85%, greater than 90%, or greater than 95% of the $CD3^+$ cells or $TCR_{\alpha\beta}$-positive cells. In some embodiments, TIL, MIL, or PBL product potency is determined by measurement of the total number of $TIM3^+$ cells, wherein the total number of $TIM3^+$ cells is greater than $50\times10^6$, greater than $100\times10^6$, greater than $150\times10^6$, greater than $200\times10^6$, greater than $250\times10^6$, greater than $300\times10^6$, greater than $350\times10^6$, greater than $400\times10^6$, greater than $450\times10^6$, greater than $500\times10^6$, greater than $550\times10^6$, greater than $600\times10^6$, greater than $650\times10^6$, greater than $700\times10^6$, greater than $750\times10^6$, greater than $800\times10^6$, greater than $850\times10^6$, greater than $900\times10^6$, greater than $950\times10^6$, greater than $1\times10^9$, greater than $1.5\times10^9$, greater than $2.0\times10^9$, greater than $2.5\times10^9$, greater than $3.0\times10^9$, greater than $3.5\times10^9$, greater than $4.0\times10^9$, greater than $5.0\times10^9$, greater than $6.0\times10^9$, greater than $7.0\times10^9$, greater than $8.0\times10^9$, greater than $9.0\times10^9$, or greater than $10\times10^9$ cells.

In some embodiments, the invention includes a method for determining the potency of a T cell product wherein the percentage expression of CD25 is measured. In some embodiments, the measurement of CD25 is by flow cytometry. In some embodiments, TIL, MIL, or PBL product potency is determined by measurement of CD25 by flow cytometry. In some embodiments, TIL, MIL, or PBL product potency is determined by measurement of CD25 by flow cytometry, wherein the measurement is part of a series of measurements performed according to an assay matrix. In some embodiments, TIL, MIL, or PBL product potency is determined by measurement of CD25 by flow cytometry, wherein the measurement is part of a series of measurements performed according to an assay matrix, and further wherein the assay matrix also comprises an alloreactive co-culture assay as described elsewhere herein. In some embodiments, TIL, MIL, or PBL product potency is determined by measurement of CD25 by flow cytometry, wherein the expression of CD25 is detected on less than 5%, less than 10%, less than 15%, less than 20%, less than 25%, less than 30%, less than 35%, less than 40%, less than 45%, less than 50%, less than 55%, less than 60%, less than 65%, less than 70%, less than 75%, less than 80%, less than 85%, less than 90%, or less than 95% of the $CD3^+$ cells or $TCR_{\alpha\beta}$-positive cells. In some embodiments, TIL, MIL, or PBL product potency is determined by measurement of CD25 by flow cytometry, wherein the expression of CD25 is detected on greater than 5%, greater than 10%, greater than 15%, greater than 20%, greater than 25%, greater than 30%, greater than 35%, greater than 40%, greater than 45%, greater than 50%, greater than 55%, greater than 60%, greater than 65%, greater than 70%, greater than 75%, greater than 80%, greater than 85%, greater than 90%, or greater than 95% of the $CD3^+$ cells or $TCR_{\alpha\beta}$-positive cells. In some embodiments, TIL, MIL, or PBL product potency is determined by measurement of the total number of $CD25^+$ cells, wherein the total number of $CD25^+$ cells is greater than $50\times10^6$, greater than $100\times10^6$, greater than $150\times10^6$, greater than $200\times10^6$, greater than $250\times10^6$, greater than $300\times10^6$, greater than $350\times10^6$, greater than $400\times10^6$, greater than $450\times10^6$, greater than $500\times10^6$, greater than $550\times10^6$, greater than $600\times10^6$, greater than $650\times10^6$, greater than $700\times10^6$, greater than $750\times10^6$, greater than $800\times10^6$, greater than $850\times10^6$, greater than $900\times10^6$, greater than $950\times10^6$, greater than $1\times10^9$, greater than $1.5\times10^9$, greater than $2.0\times10^9$, greater than $2.5\times10^9$, greater than $3.0\times10^9$, greater than $3.5\times10^9$, greater than $4.0\times10^9$, greater than $5.0\times10^9$, greater than $6.0\times10^9$, greater than $7.0\times10^9$, greater than $8.0\times10^9$, greater than $9.0\times10^9$, or greater than $10\times10^9$ cells.

In some embodiments, the invention includes a method for determining the potency of a T cell product wherein the percentage expression of CD27 is measured. In some embodiments, the measurement of CD27 is by flow cytometry. In some embodiments, TIL, MIL, or PBL product potency is determined by measurement of CD27 by flow cytometry. In some embodiments, TIL, MIL, or PBL product potency is determined by measurement of CD27 by flow cytometry, wherein the measurement is part of a series of measurements performed according to an assay matrix. In some embodiments, TIL, MIL, or PBL product potency is determined by measurement of CD27 by flow cytometry, wherein the measurement is part of a series of measurements performed according to an assay matrix, and further wherein the assay matrix also comprises an alloreactive co-culture assay as described elsewhere herein. In some embodiments, TIL, MIL, or PBL product potency is determined by measurement of CD27 by flow cytometry, wherein the expression of CD27 is detected on less than 5%, less than 10%, less than 15%, less than 20%, less than 25%, less than 30%, less than 35%, less than 40%, less than 45%, less than 50%, less than 55%, less than 60%, less than 65%, less than 70%, less than 75%, less than 80%, less than 85%, less than 90%, or less than 95% of the $CD3^+$ cells or $TCR_{\alpha\beta}$-positive cells. In some embodiments, TIL, MIL, or PBL product potency is determined by measurement of CD27 by flow cytometry, wherein the expression of CD27 is detected on greater than 5%, greater than 10%, greater than 15%, greater than 20%, greater than 25%, greater than 30%, greater than 35%, greater than 40%, greater than 45%, greater than 50%, greater than 55%, greater than 60%, greater than 65%, greater than 70%, greater than 75%, greater than 80%, greater than 85%, greater than 90%, or greater than 95% of the $CD3^+$ cells or $TCR_{\alpha\beta}$-positive cells. In some embodiments, TIL, MIL, or PBL product potency is determined by measurement of the total number of $CD27^+$ cells, wherein the total number of $CD27^+$ cells is greater than $50\times10^6$, greater than $100\times10^6$, greater than $150\times10^6$, greater than $200\times10^6$, greater than $250\times10^6$, greater than $300\times10^6$, greater than $350\times10^6$, greater than $400\times10^6$, greater than $450\times10^6$, greater than $500\times10^6$, greater than $550\times10^6$, greater than $600\times10^6$, greater than $650\times10^6$, greater than $700\times10^6$, greater than $750\times10^6$, greater than $800\times10^6$, greater than $850\times10^6$, greater than $900\times10^6$, greater than $950\times10^6$, greater than $1\times10^9$, greater than $1.5\times10^9$, greater than $2.0\times10^9$, greater than $2.5\times10^9$, greater than $3.0\times10^9$, greater than $3.5\times10^9$, greater than $4.0\times10^9$, greater than $5.0\times10^9$, greater than $6.0\times10^9$, greater than $7.0\times10^9$, greater than $8.0\times10^9$, greater than $9.0\times10^9$, or greater than $10\times10^9$ cells.

In some embodiments, the invention includes a method for determining the potency of a T cell product wherein the percentage expression of CD28 is measured. In some embodiments, the measurement of CD28 is by flow cytometry. In some embodiments, TIL, MIL, or PBL product potency is determined by measurement of CD28 by flow cytometry. In some embodiments, TIL, MIL, or PBL product potency is determined by measurement of CD28 by flow cytometry, wherein the measurement is part of a series of measurements performed according to an assay matrix. In some embodiments, TIL, MIL, or PBL product potency is determined by measurement of CD28 by flow cytometry, wherein the measurement is part of a series of measurements performed according to an assay matrix, and further wherein the assay matrix also comprises an alloreactive co-culture assay as described elsewhere herein. In some embodiments, TIL, MIL, or PBL product potency is determined by measurement of CD28 by flow cytometry, wherein the expression of CD28 is detected on less than 5%, less than 10%, less than 15%, less than 20%, less than 25%, less than 30%, less than 35%, less than 40%, less than 45%, less than 50%, less than 55%, less than 60%, less than 65%, less than 70%, less than 75%, less than 80%, less than 85%, less than 90%, or less than 95% of the $CD3^+$ cells or $TCR_{\alpha\beta}$-positive cells. In some embodiments, TIL, MIL, or PBL product potency is determined by measurement of CD28 by flow cytometry, wherein the expression of CD28 is detected on greater than 5%, greater than 10%, greater than 15%, greater than 20%, greater than 25%, greater than 30%, greater than 35%, greater than 40%, greater than 45%, greater than 50%, greater than 55%, greater than 60%, greater than 65%, greater than 70%, greater than 75%, greater than 80%, greater than 85%, greater than 90%, or greater than 95% of the $CD3^+$ cells or $TCR_{\alpha\beta}$-positive cells. In some embodiments, TIL, MIL, or PBL product potency is determined by measurement of the total number of $CD28^+$ cells, wherein the total number of $CD28^+$ cells is greater than $50\times10^6$, greater than $100\times10^6$, greater than $150\times10^6$, greater than $200\times10^6$, greater than $250\times10^6$, greater than $300\times10^6$, greater than $350\times10^6$, greater than $400\times10^6$, greater than $450\times10^6$, greater than $500\times10^6$, greater than $550\times10^6$, greater than $600\times10^6$, greater than $650\times10^6$, greater than $700\times10^6$, greater than $750\times10^6$, greater than $800\times10^6$, greater than $850\times10^6$, greater than $900\times10^6$, greater than $950\times10^6$, greater than $1\times10^9$, greater than $1.5\times10^9$, greater than $2.0\times10^9$, greater than $2.5\times10^9$, greater than $3.0\times10^9$, greater than $3.5\times10^9$, greater than $4.0\times10^9$, greater than $5.0\times10^9$, greater than $6.0\times10^9$, greater than $7.0\times10^9$, greater than $8.0\times10^9$, greater than $9.0\times10^9$, or greater than $10\times10^9$ cells.

In some embodiments, the invention includes a method for determining the potency of a T cell product wherein the percentage expression of CD56 is measured. In some embodiments, the measurement of CD56 is by flow cytometry. In some embodiments, TIL, MIL, or PBL product potency is determined by measurement of CD56 by flow cytometry. In some embodiments, TIL, MIL, or PBL product potency is determined by measurement of CD56 by flow cytometry, wherein the measurement is part of a series of measurements performed according to an assay matrix. In some embodiments, TIL, MIL, or PBL product potency is determined by measurement of CD56 by flow cytometry, wherein the measurement is part of a series of measurements performed according to an assay matrix, and further wherein the assay matrix also comprises an alloreactive co-culture assay as described elsewhere herein. In some embodiments, TIL, MIL, or PBL product potency is determined by measurement of CD56 by flow cytometry, wherein the expression of CD56 is detected on less than 5%, less than 10%, less than 15%, less than 20%, less than 25%, less than 30%, less than 35%, less than 40%, less than 45%, less than 50%, less than 55%, less than 60%, less than 65%, less than 70%, less than 75%, less than 80%, less than 85%, less than 90%, or less than 95% of the $CD3^+$ cells or $TCR_{\alpha\beta}$-positive cells. In some embodiments, TIL, MIL, or PBL product potency is determined by measurement of CD56 by flow cytometry, wherein the expression of CD56 is detected on greater than 5%, greater than 10%, greater than 15%, greater than 20%, greater than 25%, greater than 30%, greater than 35%, greater than 40%, greater than 45%, greater than 50%, greater than 55%, greater than 60%, greater than 65%, greater than 70%, greater than 75%, greater than 80%, greater than 85%, greater than 90%, or greater than 95% of the $CD3^+$ cells or $TCR_{\alpha\beta}$-positive cells. In some embodiments, TIL, MIL, or PBL product potency is determined by measurement of the total number of $CD56^+$ cells, wherein the total number of $CD56^+$ cells is greater than $50\times10^6$, greater than $100\times10^6$, greater than $150\times10^6$, greater than $200\times10^6$, greater than $250\times10^6$, greater than $300\times10^6$, greater than $350\times10^6$, greater than $400\times10^6$, greater than $450\times10^6$, greater than $500\times10^6$, greater than $550\times10^6$, greater than $600\times10^6$, greater than $650\times10^6$, greater than $700\times10^6$, greater than $750\times10^6$, greater than $800\times10^6$, greater than $850\times10^6$, greater than $900\times10^6$, greater than $950\times10^6$, greater than $1\times10^9$, greater than $1.5\times10^9$, greater than $2.0\times10^9$, greater than $2.5\times10^9$, greater than $3.0\times10^9$, greater than $3.5\times10^9$, greater than $4.0\times10^9$, greater than $5.0\times10^9$, greater than $6.0\times10^9$, greater than $7.0\times10^9$, greater than $8.0\times10^9$, greater than $9.0\times10^9$, or greater than $10\times10^9$ cells.

In some embodiments, the invention includes a method for determining the potency of a T cell product wherein the percentage expression of CD57 is measured. In some embodiments, the measurement of CD57 is by flow cytometry. In some embodiments, TIL, MIL, or PBL product potency is determined by measurement of CD57 by flow cytometry. In some embodiments, TIL, MIL, or PBL product potency is determined by measurement of CD57 by flow cytometry, wherein the measurement is part of a series of measurements performed according to an assay matrix. In some embodiments, TIL, MIL, or PBL product potency is determined by measurement of CD57 by flow cytometry, wherein the measurement is part of a series of measurements performed according to an assay matrix, and further wherein the assay matrix also comprises an alloreactive co-culture assay as described elsewhere herein. In some embodiments, TIL, MIL, or PBL product potency is determined by measurement of CD57 by flow cytometry, wherein the expression of CD57 is detected on less than 5%, less than 10%, less than 15%, less than 20%, less than 25%, less than 30%, less than 35%, less than 40%, less than 45%, less than 50%, less than 55%, less than 60%, less than 65%, less than 70%, less than 75%, less than 80%, less than 85%, less than 90%, or less than 95% of the $CD3^+$ cells or $TCR_{\alpha\beta}$-positive cells. In some embodiments, TIL, MIL, or PBL product potency is determined by measurement of CD57 by flow cytometry, wherein the expression of CD57 is detected on greater than 5%, greater than 10%, greater than 15%, greater than 20%, greater than 25%, greater than 30%, greater than 35%, greater than 40%, greater than 45%, greater than 50%, greater than 55%, greater than 60%, greater than 65%, greater than 70%, greater than 75%, greater than 80%, greater than 85%, greater than 90%, or greater than 95% of the CD3T cells or $TCR_{\alpha\beta}$-positive cells. In some embodiments, TIL, MIL, or PBL product potency is determined by measurement of the total number of $CD57^+$ cells, wherein the total number of $CD57^+$ cells is greater than $50\times10^6$, greater than $100\times10^6$, greater than $150\times10^6$, greater than $200\times10^6$, greater than $250\times10^6$, greater than $300\times10^6$, greater than $350\times10^6$, greater than $400\times10^6$, greater than $450\times10^6$, greater than $500\times10^6$, greater than $550\times10^6$, greater than $600\times10^6$, greater than $650\times10^6$, greater than $700\times10^6$, greater than $750\times10^6$, greater than $800\times10^6$, greater than $850\times10^6$, greater than $900\times10^6$, greater than $950\times10^6$, greater than $1\times10^9$, greater than $1.5\times10^9$, greater than $2.0\times10^9$, greater than $2.5\times10^9$, greater than $3.0\times10^9$, greater than $3.5\times10^9$, greater than $4.0\times10^9$, greater than $5.0\times10^9$, greater than $6.0\times10^9$, greater than $7.0\times10^9$, greater than $8.0\times10^9$, greater than $9.0\times10^9$, or greater than $10\times10^9$ cells.

In some embodiments, the invention includes a method for determining the potency of a T cell product wherein the percentage expression of CTLA-4 is measured. In some embodiments, the measurement of CTLA-4 is by flow cytometry. In some embodiments, TIL, MIL, or PBL product potency is determined by measurement of CTLA-4 by flow cytometry. In some embodiments, TIL, MIL, or PBL product potency is determined by measurement of CTLA-4 by flow cytometry, wherein the measurement is part of a series of measurements performed according to an assay matrix. In some embodiments, TIL, MIL, or PBL product potency is determined by measurement of CTLA-4 by flow cytometry, wherein the measurement is part of a series of measurements performed according to an assay matrix, and further wherein the assay matrix also comprises an alloreactive co-culture assay as described elsewhere herein. In some embodiments, TIL, MIL, or PBL product potency is determined by measurement of CTLA-4 by flow cytometry, wherein the expression of CTLA-4 is detected on less than 5%, less than 10%, less than 15%, less than 20%, less than 25%, less than 30%, less than 35%, less than 40%, less than 45%, less than 50%, less than 55%, less than 60%, less than 65%, less than 70%, less than 75%, less than 80%, less than 85%, less than 90%, or less than 95% of the $CD3^+$ cells or $TCR_{\alpha\beta}$-positive cells. In some embodiments, TIL, MIL, or PBL product potency is determined by measurement of CTLA-4 by flow cytometry, wherein the expression of CTLA-4 is detected on greater than 5%, greater than 10%, greater than 15%, greater than 20%, greater than 25%, greater than 30%, greater than 35%, greater than 40%, greater than 45%, greater than 50%, greater than 55%, greater than 60%, greater than 65%, greater than 70%, greater than 75%, greater than 80%, greater than 85%, greater than 90%, or greater than 95% of the $CD3^+$ cells or $TCR_{\alpha\beta}$-positive cells. In some embodiments, TIL, MIL, or PBL product potency is determined by measurement of the total number of CTLA-$4^+$ cells, wherein the total number of CTLA-$4^+$ cells is greater than $50\times10^6$, greater than $100\times10^6$, greater than $150\times10^6$, greater than $200\times10^6$, greater than $250\times10^6$, greater than $300\times10^6$, greater than $350\times10^6$, greater than $400\times10^6$, greater than $450\times10^6$, greater than $500\times10^6$, greater than $550\times10^6$, greater than $600\times10^6$, greater than $650\times10^6$, greater than $700\times10^6$, greater than $750\times10^6$, greater than $800\times10^6$, greater than $850\times10^6$, greater than $900\times10^6$, greater than $950\times10^6$, greater than $1\times10^9$, greater than $1.5\times10^9$, greater than $2.0\times10^9$, greater than $2.5\times10^9$, greater than $3.0\times10^9$, greater than $3.5\times10^9$, greater than $4.0\times10^9$, greater than $5.0\times10^9$, greater than $6.0\times10^9$, greater than $7.0\times10^9$, greater than $8.0\times10^9$, greater than $9.0\times10^9$, or greater than $10\times10^9$ cells.

In some embodiments, the invention includes a method for determining the potency of a T cell product wherein the percentage expression of TIGIT is measured. In some embodiments, the measurement of TIGIT is by flow cytometry. In some embodiments, TIL, MIL, or PBL product potency is determined by measurement of TIGIT by flow cytometry. In some embodiments, TIL, MIL, or PBL product potency is determined by measurement of TIGIT by flow cytometry, wherein the measurement is part of a series of measurements performed according to an assay matrix. In some embodiments, TIL, MIL, or PBL product potency is determined by measurement of TIGIT by flow cytometry, wherein the measurement is part of a series of measurements performed according to an assay matrix, and further wherein the assay matrix also comprises an alloreactive co-culture assay as described elsewhere herein. In some embodiments, TIL, MIL, or PBL product potency is determined by measurement of TIGIT by flow cytometry, wherein the expression of TIGIT is detected on less than 5%, less than 10%, less than 15%, less than 20%, less than 25%, less than 30%, less than 35%, less than 40%, less than 45%, less than 50%, less than 55%, less than 60%, less than 65%, less than 70%, less than 75%, less than 80%, less than 85%, less than 90%, or less than 95% of the $CD3^+$ cells or $TCR_{\alpha\beta}$-positive cells. In some embodiments, TIL, MIL, or PBL product potency is determined by measurement of TIGIT by flow cytometry, wherein the expression of TIGIT is detected on greater than 5%, greater than 10%, greater than 15%, greater than 20%, greater than 25%, greater than 30%, greater than 35%, greater than 40%, greater than 45%, greater than 50%, greater than 55%, greater than 60%, greater than 65%, greater than 70%, greater than 75%, greater than 80%, greater than 85%, greater than 90%, or greater than 95% of the $CD3^+$ cells or $TCR_{\alpha\beta}$-positive cells. In some embodiments, TIL, MIL, or PBL product potency is determined by measurement of the total number of $TIGIT^+$ cells, wherein the total number of $TIGIT^+$ cells is greater than $50\times10^6$, greater than $100\times10^6$, greater than $150\times10^6$, greater than $200\times10^6$, greater than $250\times10^6$, greater than $300\times10^6$, greater than $350\times10^6$, greater than $400\times10^6$, greater than $450\times10^6$, greater than $500\times10^6$, greater than $550\times10^6$, greater than $600\times10^6$, greater than $650\times10^6$, greater than $700\times10^6$, greater than $750\times10^6$, greater than $800\times10^6$, greater than $850\times10^6$, greater than $900\times10^6$, greater than $950\times10^6$, greater than $1\times10^9$, greater than $1.5\times10^9$, greater than $2.0\times10^9$, greater than $2.5\times10^9$, greater than $3.0\times10^9$, greater than $3.5\times10^9$, greater than $4.0\times10^9$, greater than $5.0\times10^9$, greater than $6.0\times10^9$, greater than $7.0\times10^9$, greater than $8.0\times10^9$, greater than $9.0\times10^9$, or greater than $10\times10^9$ cells.

In some embodiments, the invention includes a potency or identity assay matrix which includes an assay wherein the content of $T_{reg}$ cells is measured, including by an intracellular staining flow cytometry assay for FoxP3+ cells, as is known in the art.

In an embodiment, the invention includes a method for determining the potency of a T cell product using a target cell capable of binding to a T cell receptor, wherein the method is used in a potency assay matrix comprising at least one other potency assay. In an embodiment, the invention includes an assay based on the allogeneic interaction of the T cell or TIL, MIL, or PBL TCR complex with the target cell's HLA-peptide complex, also referred to as MHC dominant recognition, wherein the assay is used in a potency assay matrix comprising at least one other potency assay.

In an embodiment, the invention comprises a method of determining the potency of a TIL product, the method comprising the steps of:

a. performing at least three co-cultures of target cells with TIL cells from the TIL product for a period of 12 to 48 hours at different target cell concentrations;
b. extracting supernatants from each of the co-cultures; and
c. assessing the supernatants for interferon-γ secreted from the TIL cells to obtain a dose-concentration to determine the potency of the TIL product;

wherein the target cells are Raji, Ramos, Daudi, U937, or Thp1 cells, or a derivative, variant, modification, or progeny thereof.

In an embodiment, the invention comprises a method of determining the potency of a TIL product, the method comprising the steps of:

a. performing at least three co-cultures of target cells with TIL cells from the TIL product for a period of 12 to 48 hours at different target cell concentrations;
b. extracting supernatants from each of the co-cultures; and
c. assessing the supernatants for interferon-γ secreted from the TIL cells to obtain a dose-concentration to determine the potency of the TIL product;

wherein the target cells are monocyte lineage cells.

In an embodiment, the invention comprises a method of determining the potency of a TIL product, the method comprising the steps of:

a. performing at least three co-cultures of target cells with TIL cells from the TIL product for a period of about 24 hours using at least three different target cell concentrations;
b. extracting supernatants from each of the co-cultures; and
c. assessing the supernatants for interferon-γ secreted from the TIL cells to obtain a dose-concentration to determine the potency of the TIL product;

wherein the target cells are Thp1 cells or U937 cells, or a derivative, variant, modification, or progeny thereof, and wherein relative potency is determined by parallel line analysis using a TIL reference standard.

In an embodiment, the invention comprises a method of determining the potency of a TIL product, the method comprising the steps of a. performing four co-cultures of target cells with TIL cells from the TIL product for a period of 12 to 48 hours at four different target cell concentrations;
b. extracting supernatants from each of the co-cultures; and
c. assessing the supernatants for interferon-γ secreted from the TIL cells to obtain a dose-concentration to determine the potency of the TIL product;

wherein the target cells are Raji, Ramos, Daudi, U937, or Thp1 cells, or a derivative, variant, modification, or progeny thereof, wherein relative potency is determined by parallel line analysis using a TIL reference standard in a separate series of experiments replicating steps a through c.

In an embodiment, the invention comprises a method of determining the potency of a TIL product, the method comprising the steps of d. performing four co-cultures of target cells with TIL cells from the TIL product for a period of 12 to 48 hours at four different target cell concentrations;
e. extracting supernatants from each of the co-cultures; and
f. assessing the supernatants for interferon-γ secreted from the TIL cells to obtain a dose-concentration to determine the potency of the TIL product;

wherein the target cells are Raji, Ramos, Daudi, U937, or Thp1 cells, or a derivative, variant, modification, or progeny thereof, wherein relative potency is determined by parallel line analysis using a TIL reference standard in a separate series of experiments replicating steps a through c, and wherein four target cell dose-concentrations of $4\times10^5$, $2\times10^5$, $1\times10^5$, and $0.5\times10^5$ cells per well and a single TIL cell concentration of $1.5\times10^6$ TIL per well are used.

In an embodiment, the invention comprises a method of determining the potency of a TIL product, the method comprising the steps of.

a. performing four co-cultures of target cells with TIL cells from the TIL product for a period of 12 to 48 hours at four different target cell concentrations;
b. extracting supernatants from each of the co-cultures; and
c. assessing the supernatants for interferon-γ secreted from the TIL cells to obtain a dose-concentration to determine the potency of the TIL product;

wherein the target cells are Raji, Ramos, Daudi, U937, or Thp1 cells, or a derivative, variant, modification, or progeny thereof, wherein relative potency is determined by parallel line analysis using a TIL reference standard in a separate series of experiments replicating steps a through c, wherein four target cell dose-concentrations of $4\times10^5$, $2\times10^5$, $1\times10^5$, and $0.5\times10^5$ cells per well and a single TIL cell concentration of $1.5\times10^6$ TIL per well are used, and wherein the foregoing method is a component of a potency assay matrix comprising at least one other assay selected from the group consisting of a bead- or plate-based assay for a cytokine, an assay for total viable cells, an assay for percentage viable cells, an assay for $CD4^+$ cell content, an assay for $CD8^+$ cell content, an assay for $T_{EM}$ cell content, an assay for $T_{CM}$ cell content, an assay for $LAG3^+$ cell content, and an assay for $KLRG1^+$ cell content, an assay for $CD101^+$ cell content, an assay for $CD69^\times$ cell content, an assay for $T_{SCM}$ cell content, an assay for $T_{EMRA}$ cell content, an assay for $T_{reg}$ cell content, an assay for $PD\text{-}1^+$ cell content, an assay for $TIM3^+$ cell content, an assay for $CD25^+$ cell content, an assay for $CD27^+$ cell content, an assay for $CD28^+$ cell content, an assay for $CD56^+$ cell content, an assay for CTLA-$4^+$ cell content, an assay for $TIGIT^+$ cell content, and an assay for $CD57^+$ T cell content.

In an embodiment, the invention comprises a method of determining the potency of a TIL product, the method comprising the steps of:

a. performing four co-cultures of target cells with TIL cells from the TIL product for a period of 12 to 48 hours at four different target cell concentrations;
b. extracting supernatants from each of the co-cultures; and
c. assessing the supernatants for interferon-γ secreted from the TIL cells to obtain a dose-concentration to determine the potency of the TIL product;

wherein the target cells are Raji, Ramos, Daudi, U937, or Thp1 cells, or a derivative, variant, modification, or progeny thereof, wherein relative potency is determined by parallel line analysis using a TIL reference standard in a separate series of experiments replicating steps a through c, wherein four target cell dose-concentrations of $4\times10^5$, $2\times10^5$, $1\times10^5$, and $0.5\times10^5$ cells per well and a single TIL cell concentration of $1.5\times10^6$ TIL per well are used, and wherein the foregoing method is a component of a potency assay matrix comprising at least one other assay selected from the group consisting of a bead- or plate-based assay using CD3, CD28, and/or CD137 stimulation and reporting interferon-γ, granzyme B, or tumor necrosis factor-α, an assay for total viable cells, an assay for percentage viable cells, an assay for $CD4^+$ cell content, an assay for $CD8^+$ cell content, an assay for $T_{EM}$ cell content, an assay for $T_{CM}$ cell content, an assay for $LAG3^+$ cell content, and an assay for $KLRG1^+$ cell content, an assay for $CD101^+$ cell content, an assay for $CD69^+$ cell content, an assay for $T_{SCM}$ cell content, an assay for $T_{EMRA}$ cell content, an assay for $T_{reg}$ cell content, an assay for PD-$1^+$ cell content, an assay for $TIM3^+$ cell content, an assay for $CD25^+$ cell content, an assay for $CD27^+$ cell content, an assay for $CD28^+$ cell content, an assay for $CD56^+$ cell content, an assay for CTLA-$4^+$ cell content, an assay for $TIGIT^+$ cell content, and an assay for $CD57^+$ T cell content.

In an embodiment, the invention comprises a method of determining the potency of a TIL product, the method comprising the steps of.

a. performing four co-cultures of target cells with TIL cells from the TIL product for a period of about 24 hours at four different target cell concentrations;
b. extracting supernatants from each of the co-cultures; and
c. assessing the supernatants for interferon-γ secreted from the TIL cells to obtain a dose-concentration to determine the potency of the TIL product;

wherein the target cells are Raji, Ramos, Daudi, U937, or Thp1 cells, or a derivative, variant, modification, or progeny thereof, wherein relative potency is determined by parallel line analysis using a TIL reference standard in a separate series of experiments replicating steps a through c, wherein four target cell dose-concentrations of $4\times10^5$, $2\times10^5$, $1\times10^5$, and $0.5\times10^5$ cells per well and a single TIL cell concentration of $1.5\times10^6$ TIL per well are used, wherein one outlier dose-concentration may be discarded, and wherein the foregoing method is a component of a potency assay matrix comprising at least one other assay selected from the group consisting of a bead- or plate-based assay using CD3, CD28, and/or CD137 stimulation and reporting interferon-γ, granzyme B, or tumor necrosis factor-α, an assay for total viable cells, an assay for percentage viable cells, an assay for $CD4^+$ cell content, an assay for $CD8^+$ cell content, an assay for $T_{EM}$ cell content, an assay for $T_{CM}$ cell content, an assay for $LAG3^+$ cell content, and an assay for $KLRG1^+$ cell content, an assay for $CD101^+$ cell content, an assay for $CD69^+$ cell content, an assay for $T_{SCM}$ cell content, an assay for $T_{EMRA}$ cell content, an assay for $T_{reg}$ cell content, an assay for PD-$1^+$ cell content, an assay for $TIM3^+$ cell content, an assay for $CD25^+$ cell content, an assay for $CD27^+$ cell content, an assay for $CD28^+$ cell content, an assay for $CD56^+$ cell content, an assay for CTLA-$4^+$ cell content, an assay for $TIGIT^+$ cell content, and an assay for $CD57^+$ cell content.

In an embodiment, the invention comprises a method of determining the potency of a TIL product, the method comprising the steps of.

a. performing at least three co-cultures of target cells with TIL cells from the TIL product for a period of 12 to 48 hours at different target cell concentrations;
b. extracting supernatants from each of the co-cultures; and
c. assessing the supernatants for interferon-γ secreted from the TIL cells to obtain a dose-concentration to determine the potency of the TIL product;

wherein the target cells are monocyte lineage cells, wherein relative potency is determined by parallel line analysis using a TIL reference standard in a separate series of experiments replicating steps a through c, wherein four target cell dose-concentrations of $4\times10^5$, $2\times10^5$, $1\times10^5$, and $0.5\times10^5$ cells per well and a single TIL cell concentration of $1.5\times10^6$ TIL per well are used, wherein one outlier dose-concentration may be discarded, and wherein the foregoing method is a component of a potency assay matrix comprising at least one other assay selected from the group consisting of a bead- or plate-based assay using CD3, CD28, and/or CD137 stimulation and reporting interferon-γ, granzyme B, or tumor necrosis factor-α, an assay for total viable cells, an assay for percentage viable cells, an assay for $CD4^+$ cell content, an assay for $CD8^+$ cell content, an assay for $T_{EM}$ cell content, an assay for $T_{CM}$ cell content, an assay for $LAG3^+$ cell content, and an assay for $KLRG1^+$ cell content, an assay for $CD101^+$ cell content, an assay for $CD69^+$ cell content, an assay for $T_{SCM}$ cell content, an assay for $T_{EMRA}$ cell content, an assay for $T_{reg}$ cell content, an assay for PD-$1^+$ cell content, an assay for $TIM3^+$ cell content, an assay for $CD25^+$ cell content, an assay for $CD27^+$ cell content, an assay for $CD28^+$ cell content, an assay for $CD56^+$ cell content, an assay for CTLA-$4^+$ cell content, an assay for $TIGIT^+$ cell content, and an assay for $CD57^+$ T cell content.

In an embodiment, the invention comprises a method of determining the potency of a TIL product, the method comprising the steps of:

a. performing multiple co-cultures of target cells with TIL product cells at different target cell or TIL product cell concentrations;
b. performing multiple co-cultures of target cells with TIL reference standard cells at different target cell or TIL reference standard cell concentrations;
c. extracting supernatants from each of the co-cultures; and
d. assessing the supernatants for a cytokine secreted from the TIL product cells and TIL reference standard cells to obtain dose-concentrations to determine the potency of the TIL product;

wherein the target cells are monocyte lineage cells.

In an embodiment, the invention comprises a method of determining the potency of a TIL product, the method comprising the steps of a. performing multiple co-cultures of target cells with TIL product cells at different target cell concentrations;

b. performing multiple co-cultures of target cells with TIL reference standard cells at different target cell concentrations;

c. extracting supernatants from each of the co-cultures; and d. assessing the supernatants for a cytokine secreted from the TIL product cells and TIL reference standard cells to obtain dose-concentrations to determine the potency of the TIL product;

wherein the target cells are monocyte lineage cells.

In an embodiment, the invention comprises a method of determining the potency of a TIL product, the method comprising the steps of a. performing multiple co-cultures of target cells with TIL product cells for a period of 12 to 48 hours at different target cell concentrations;

b. performing multiple co-cultures of target cells with TIL reference standard cells for a period of 12 to 48 hours at different target cell concentrations;

c. extracting supernatants from each of the co-cultures; and d. assessing the supernatants for a cytokine secreted from the TIL product cells and TIL reference standard cells to obtain dose-concentrations to determine the potency of the TIL product;

wherein the target cells are monocyte lineage cells.

In an embodiment, the invention comprises a method of determining the potency of a TIL product, the method comprising the steps of a. performing multiple co-cultures of target cells with TIL product cells for a period of 12 to 48 hours at different target cell concentrations;

b. performing multiple co-cultures of target cells with TIL reference standard cells for a period of 12 to 48 hours at different target cell concentrations;

c. extracting supernatants from each of the co-cultures; and d. assessing the supernatants for interferon-γ secreted from the TIL product cells and TIL reference standard cells to obtain dose-concentrations to determine the potency of the TIL product;

wherein the target cells are U937 or Thp1 cells, or a derivative, variant, modification, or progeny thereof.

In an embodiment, the invention comprises a method of determining the potency of a TIL product, the method comprising the steps of a. performing multiple co-cultures of target cells with TIL product cells for a period of 12 to 48 hours at different target cell concentrations;

b. performing multiple co-cultures of target cells with TIL reference standard cells for a period of 12 to 48 hours at different target cell concentrations;

c. extracting supernatants from each of the co-cultures; and d. assessing the supernatants for interferon-γ secreted from the TIL product cells and TIL reference standard cells to obtain dose-concentrations to determine the potency of the TIL product;

wherein the target cells are monocyte lineage cells, and wherein the foregoing method is a component of a potency assay matrix comprising at least one other assay.

In an embodiment, the invention comprises a method of determining the potency of a TIL product, the method comprising the steps of:

a. performing multiple co-cultures of target cells with TIL product cells for a period of 12 to 48 hours at different target cell concentrations;

b. performing multiple co-cultures of target cells with TIL reference standard cells for a period of 12 to 48 hours at different target cell concentrations;

c. extracting supernatants from each of the co-cultures; and d. assessing the supernatants for interferon-γ secreted from the TIL product cells and TIL reference standard cells to obtain dose-concentrations to determine the potency of the TIL product;

wherein the target cells are U937 or Thp1 cells, or a derivative, variant, modification, or progeny thereof, and wherein the foregoing method is a component of a potency assay matrix comprising at least one other assay.

In an embodiment, the invention comprises a method of determining the potency of a TIL product, the method comprising the steps of a. performing at least three co-cultures of target cells with TIL product cells for a period of 12 to 48 hours at different target cell concentrations;

b. performing at least three co-cultures of target cells with TIL reference standard cells for a period of 12 to 48 hours at different target cell concentrations;

c. extracting supernatants from each of the co-cultures; and d. assessing the supernatants for interferon-γ secreted from the TIL product cells and TIL reference standard cells to obtain dose-concentrations to determine the potency of the TIL product;

wherein the target cells are U937 or Thp1 cells, or a derivative, variant, modification, or progeny thereof, and wherein the foregoing method is a component of a potency assay matrix comprising at least one other assay.

In an embodiment, the invention comprises a method of determining the potency of a TIL product, the method comprising the steps of a. performing at least three co-cultures of target cells with TIL product cells for a period of about 24 hours at different target cell concentrations;

b. performing at least three co-cultures of target cells with TIL reference standard cells for a period of about 24 hours at different target cell concentrations;

c. extracting supernatants from each of the co-cultures; and d. assessing the supernatants for interferon-γ secreted from the TIL product cells and TIL reference standard cells to obtain dose-concentrations to determine the potency of the TIL product;

wherein the target cells are U937 or Thp1 cells, or a derivative, variant, modification, or progeny thereof, and wherein the foregoing method is a component of a potency assay matrix comprising at least one other assay.

In an embodiment, the invention comprises a method of determining the potency of a TIL product, the method comprising the steps of:

a. performing at least three co-cultures of target cells with TIL product cells for a period of about 24 hours at different target cell concentrations;

b. performing at least three co-cultures of target cells with TIL reference standard cells for a period of about 24 hours at different target cell concentrations;

c. extracting supernatants from each of the co-cultures; and d. assessing the supernatants for interferon-γ secreted from the TIL product cells and TIL reference standard cells to obtain dose-concentrations to determine the potency of the TIL product;

wherein the target cells are U937 or Thp1 cells, or a derivative, variant, modification, or progeny thereof, wherein four target cell dose-concentrations of $4\times10^5$, $2\times10^5$, $1\times10^5$, and $0.5\times10^5$ cells per well and a single TIL cell concentration of $1.5\times10^6$ TIL per well are used, wherein one outlier dose-concentration may be discarded, and wherein the foregoing method is a component of a potency assay matrix comprising at least one other assay selected from the group consisting of a bead- or plate-based assay using CD3, CD28, and/or CD137 stimulation and reporting interferon-γ, granzyme B, or tumor necrosis factor-α, an assay for total viable cells, an assay for percentage viable cells, an assay for $CD4^+$ cell content, an assay for $CD8^+$ cell content, an assay for $T_{EM}$ cell content, an assay for $T_{CM}$ cell content, an assay for $LAG3^+$ cell content, and an assay for $KLRG1^+$ cell content, an assay for $CD101^+$ cell content, an assay for $CD69^+$ cell content, an assay for $T_{SCM}$ cell content, an assay for $T_{EMRA}$ cell content, an assay for $T_{reg}$ cell content, an assay for PD-$1^+$ cell content, an assay for $TIM3^+$ cell content, an assay for $CD25^+$ cell content, an assay for $CD27^+$ cell content, an assay for $CD28^+$ cell content, an assay for $CD56^+$ cell content, an assay for CTLA-$4^+$ cell content, an assay for $TIGIT^+$ cell content, and an assay for $CD57^+$ cell content.

In an embodiment, the invention comprises a method of determining the potency of a TIL product, the method comprising the steps of.

a. performing at least three co-cultures of target cells with TIL product cells for a period of about 24 hours at different target cell concentrations;
b. performing at least three co-cultures of target cells with TIL reference standard cells for a period of about 24 hours at different target cell concentrations;
c. extracting supernatants from each of the co-cultures; and
d. assessing the supernatants for interferon-γ secreted from the TIL product cells and TIL reference standard cells to obtain dose-concentrations to determine the potency of the TIL product;

wherein the target cells are U937 or Thp1 cells, or a derivative, variant, modification, or progeny thereof, wherein four target cell dose-concentrations of $4\times10^5$, $2\times10^5$, $1\times10^5$, and $0.5\times10^5$ cells per well and a single TIL cell concentration of $1.5\times10^6$ TIL per well are used each of which is performed with at least two replicates, wherein one outlier dose-concentration may be discarded, and wherein the foregoing method is a component of a potency assay matrix comprising at least one other assay selected from the group consisting of a bead- or plate-based assay using CD3, CD28, and/or CD137 stimulation and reporting interferon-γ, granzyme B, or tumor necrosis factor-α, an assay for total viable cells, an assay for percentage viable cells, an assay for $CD4^+$ cell content, an assay for $CD8^+$ cell content, an assay for $T_{EM}$ cell content, an assay for $T_{CM}$ cell content, an assay for $LAG3^+$ cell content, and an assay for KLRG1 cell content, an assay for $CD101^+$ cell content, an assay for $CD69^+$ cell content, an assay for $T_{SCM}$ cell content, an assay for $T_{EMRA}$ cell content, an assay for $T_{reg}$ cell content, an assay for PD-$1^+$ cell content, an assay for $TIM3^+$ cell content, an assay for $CD25^+$ cell content, an assay for $CD27^+$ cell content, an assay for $CD28^+$ cell content, an assay for $CD56^+$ cell content, an assay for CTLA-$4^+$ cell content, an assay for $TIGIT^+$ cell content, and an assay for $CD57^+$ T cell content.

In an embodiment, the invention comprises a method of determining the potency of a TIL product, the method comprising the steps of:

a. performing at least three co-cultures of target cells with TIL product cells for a period of about 24 hours at different target cell concentrations;
b. performing at least three co-cultures of target cells with TIL reference standard cells for a period of about 24 hours at different target cell concentrations;
c. extracting supernatants from each of the co-cultures; and
d. assessing the supernatants for interferon-γ secreted from the TIL product cells and TIL reference standard cells to obtain dose-concentrations to determine the potency of the TIL product;

wherein the target cells are U937 or Thp1 cells, or a derivative, variant, modification, or progeny thereof, wherein four target cell dose-concentrations of $4\times10^5$, $2\times10^5$, $1\times10^5$, and $0.5\times10^5$ cells per well and a single TIL cell concentration of $1.5\times10^6$ TIL per well are used each of which is performed with at least two replicates, wherein one outlier dose-concentration may be discarded, and wherein the foregoing method is a component of a potency assay matrix comprising at least three other assays selected from the group consisting of a bead- or plate-based assay using CD3, CD28, and/or CD137 stimulation and reporting interferon-γ, granzyme B, or tumor necrosis factor-α, an assay for total viable cells, an assay for percentage viable cells, an assay for $CD4^+$ cell content, an assay for $CD8^+$ cell content, an assay for $T_{EM}$ cell content, an assay for $T_{CM}$ cell content, an assay for $LAG3^+$ cell content, and an assay for $KLRG1^+$ cell content, an assay for $CD101^+$ cell content, an assay for $CD69^+$ cell content, an assay for $T_{SCM}$ cell content, an assay for $T_{EMRA}$ cell content, an assay for $T_{reg}$ cell content, an assay for PD-$1^+$ cell content, an assay for $TIM3^+$ cell content, an assay for $CD25^+$ cell content, an assay for $CD27^+$ cell content, an assay for $CD28^+$ cell content, an assay for $CD56^+$ cell content, an assay for CTLA-$4^+$ cell content, an assay for $TIGIT^+$ cell content, and an assay for $CD57^+$ cell content.

In an embodiment, the invention comprises a method of determining the potency of a TIL product, the method comprising the steps of:

a. performing at least three co-cultures of target cells with TIL product cells for a period of about 24 hours at different target cell concentrations;
b. performing at least three co-cultures of target cells with TIL reference standard cells for a period of about 24 hours at different target cell concentrations;
c. extracting supernatants from each of the co-cultures; and
d. assessing the supernatants for interferon-γ secreted from the TIL product cells and TIL reference standard cells to obtain dose-concentrations to determine the potency of the TIL product;

wherein the target cells are U937 or Thp1 cells, or a derivative, variant, modification, or progeny thereof, wherein four target cell dose-concentrations of $4\times10^5$, $2\times10^5$, $1\times10^5$, and $0.5\times10^5$ cells per well and a single TIL cell concentration of $1.5\times10^6$ TIL per well are used each of which is performed with at least two replicates, wherein one outlier dose-concentration may be discarded, and wherein the foregoing method is a component of a potency assay matrix comprising at least five other assays selected from the group consisting of a bead- or plate-based assay using CD3, CD28, and/or CD137 stimulation and reporting interferon-γ, granzyme B, or tumor necrosis factor-α, an assay for total viable cells, an assay for percentage viable cells, an assay for $CD4^+$ cell content, an assay for $CD8^+$ cell content, an assay for $T_{EM}$ cell content, an assay for $T_{CM}$ cell content, an assay for LAG3$^+$ cell content, and an assay for KLRG1$^+$ cell content, an assay for CD101$^+$ cell content, an assay for CD69$^+$ cell content, an assay for $T_{SCM}$ cell content, an assay for $T_{EMRA}$ cell content, an assay for $T_{reg}$ cell content, an assay for PD-1$^+$ cell content, an assay for TIM3$^+$ cell content, an assay for CD25$^+$ cell content, an assay for CD27$^+$ cell content, an assay for CD28$^+$ cell content, an assay for CD56$^+$ cell content, an assay for CTLA-4$^+$ cell content, an assay for TIGIT$^+$ cell content, and an assay for CD57$^+$ cell content.

In some embodiments, the invention comprises a method of determining the potency of a TIL product, the method comprising the steps of performing a flow cytometric analysis using a flow cytometer, including multichannel and multicolor flow cytometers. Suitable flow cytometers and methods are described in the art, including in U.S. Pat. Nos. 9,645,010; 10,816,550; 10,137,479; 9,453,791; 10,935,482; 10,648,900; 9,341,562; 9,677,989; 4,710,635; 4,662,742; 4,660,971; 4,818,103; 5,057,413; 5,641,457; 5,620,842; 5,985,216; 6,079,836; 6,495,333; 6,256,096; 6,482,652; 6,700,130; 7,855,078; 7,990,525; and 10,436,698; and U.S. Patent Application Publication Nos. US 2001/0006416 A1 and US 2002/0186375 A1, the disclosures of which are incorporated by reference herein. In some embodiments, the foregoing flow cytometry methods are combined with an allogeneic co-culture assay as described herein. In some embodiments, the foregoing flow cytometry methods are combined with a bead- or plate-based assay using CD3, CD28, and/or CD137 stimulation and reporting interferon-γ, granzyme B, or tumor necrosis factor-α by an ELISA-based method.

In some embodiments, the foregoing co-cultures are performed in an incubator. In some embodiments, the foregoing co-cultures are performed in an incubator at about 40° C. In some embodiments, the foregoing co-cultures are performed in an incubator at about 35° C. In some embodiments, the foregoing co-cultures are performed in an incubator at about 37° C. In some embodiments, the foregoing co-cultures are performed in an incubator with about 5% $CO_2$ gas. In some embodiments, the foregoing co-cultures are performed in an incubator with about 10% $CO_2$ gas. In some embodiments, the foregoing co-cultures are performed in an incubator with about 15% $CO_2$ gas. In some embodiments, the foregoing co-cultures are performed in an incubator with about 20% $CO_2$ gas. In some embodiments, the foregoing co-cultures are performed in an incubator with humidification.

B. Assay Compositions

In some embodiments, the invention includes compositions comprising a TIL, such as a TIL, MIL, or PBL product and a target cell. In some embodiments, the invention includes compositions comprising a TIL, such as a TIL, MIL, or PBL product and a target cell in a medium. In some embodiments, the invention includes compositions comprising a TIL, such as a TIL, MIL, or PBL product and a target cell, wherein the target cell is an Raji cell or a derivative, variant, modification, or progeny thereof. In some embodiments, the invention includes compositions comprising a TIL, such as a TIL, MIL, or PBL product and a negative control cell. In some embodiments, the invention includes compositions comprising a TIL, such as a TIL, MIL, or PBL product and a negative control cell in a medium. In some embodiments, the invention includes compositions comprising a TIL, such as a TIL, MIL, or PBL product and a target cell, wherein the negative control cell is an K562 cell or a derivative, variant, modification, or progeny thereof. In an embodiment, the invention includes compositions comprising a supernatant obtained from a co-culture assay as described herein, optionally containing secreted proteins.

In an embodiment, the invention includes a composition comprising media (such as AIM-V media), at least one cell from a cell line selected from the group consisting of a Raji cell line, a Thp1 cell line, a Ramos cell line, a U937 cell line, a Daudi cell line, and combinations thereof, and IL-2. In an embodiment, the invention includes a composition comprising AIM-V media, at least one cell from a cell line selected from the group consisting of a Raji cell line, a Thp1 cell line, a Ramos cell line, a U937 cell line, a Daudi cell line, and combinations thereof, and IL-2, wherein the IL-2 is added continuously during co-culture. In an embodiment, the invention includes a composition comprising AIM-V media, at least one cell from a cell line selected from the group consisting of a Raji cell line, a Thp1 cell line, a Ramos cell line, a U937 cell line, a Daudi cell line, and combinations thereof, and IL-2, wherein the IL-2 is added continuously during co-culture, and wherein the IL-2 is maintained at a concentration between 50 IU/mL and 1000 IU/mL during the co-culture. In an embodiment, the invention includes a composition comprising AIM-V media, at least one cell from a cell line selected from the group consisting of a Raji cell line, a Thp1 cell line, a Ramos cell line, a U937 cell line, a Daudi cell line, and combinations thereof, and IL-2, wherein the IL-2 is added continuously during co-culture, and wherein the IL-2 is maintained at a concentration between 100 IU/mL and 500 IU/mL during the co-culture. In an embodiment, the invention includes a composition comprising AIM-V media, at least one cell from a cell line selected from the group consisting of a Raji cell line, a Thp1 cell line, a Ramos cell line, a U937 cell line, a Daudi cell line, and combinations thereof, and IL-2, wherein the IL-2 is added continuously during co-culture, and wherein the IL-2 is maintained at a concentration between 200 IU/mL and 400 IU/mL during the co-culture. In an embodiment, the invention includes a composition comprising AIM-V media, at least one cell from a cell line selected from the group consisting of a Raji cell line, a Thp1 cell line, a Ramos cell line, a U937 cell line, a Daudi cell line, and combinations thereof, and IL-2 at a concentration selected from the group consisting of about 50 IU/mL, about 100 IU/mL, about 150 IU/mL, about 200 IU/mL, about 250 IU/mL, about 300 IU/mL, about 350 IU/mL, about 400 IU/mL, about 450 IU/mL and about 500 IU/mL. In an embodiment, the invention includes a composition comprising target cells, wherein the target cells are a combination of a Raji cells and Thp1 cells, wherein the ratio of Raji cells to Thp1 cells is selected from the group consisting of 5:1, 4:1, 3:1, 2:1, 1:1, 1:2, 1:3, 1:4, and 1:5. In an embodiment, the invention includes a composition comprising target cells, wherein the target cells are a combination of a Raji cells and Ramos cells, wherein the ratio of Raji cells to Ramos cells is selected from the group consisting of 5:1, 4:1, 3:1, 2:1, 1:1, 1:2, 1:3, 1:4, and 1:5. In an embodiment, the invention includes a composition comprising target cells, wherein the target cells are a combination of a Raji cells and U937 cells, wherein the ratio of Raji cells to U937 cells is selected from the group consisting of 5:1, 4:1, 3:1, 2:1, 1:1, 1:2, 1:3, 1:4, and 1:5. In an embodiment, the invention includes a composition comprising target cells, wherein the target cells are a combination of a Raji cells and Daudi cells, wherein the ratio of Raji cells to Daudi cells is selected from the group consisting of 5:1, 4:1, 3:1, 2:1, 1:1, 1:2, 1:3, 1:4, and 1:5.

In an embodiment, the invention includes a composition comprising media (such as AIM-V media), at least one cell from a cell line selected from the group consisting of a B cell line, a B cell lymphoblastoid cell line, a Burkitt's lymphoma cell line, a myeloid lineage cell line, a monocyte cell line, an acute monocytic leukemia cell, an M5-subtype acute monocytic leukemia cell, a melanocyte cell line, a melanoma cell line, and combinations thereof, and IL-2. In an embodiment, the invention includes a composition comprising AIM-V media, at least one cell from a cell line selected from the group consisting of a B cell line, a B cell lymphoblastoid cell line, a Burkitt's lymphoma cell line, a myeloid lineage cell line, a monocyte cell line, an acute monocytic leukemia cell, an M5-subtype acute monocytic leukemia cell, a melanocyte cell line, a melanoma cell line and combinations thereof, and IL-2, wherein the IL-2 is added continuously during co-culture. In an embodiment, the invention includes a composition comprising AIM-V media, at least one cell from a cell line selected from the group consisting of a B cell line, a B cell lymphoblastoid cell line, a Burkitt's lymphoma cell line, a myeloid lineage cell line, a monocyte cell line, an acute monocytic leukemia cell, an M5-subtype acute monocytic leukemia cell, a melanocyte cell line, a melanoma cell line, and combinations thereof, and IL-2, wherein the IL-2 is added continuously during co-culture, and wherein the IL-2 is maintained at a concentration between 50 IU/mL and 1000 IU/mL during the co-culture. In an embodiment, the invention includes a composition comprising AIM-V media, at least one cell from a cell line selected from the group consisting of a B cell line, a B cell lymphoblastoid cell line, a Burkitt's lymphoma cell line, a myeloid lineage cell line, a monocyte cell line, an acute monocytic leukemia cell, an M5-subtype acute monocytic leukemia cell, a melanocyte cell line, a melanoma cell line and combinations thereof, and IL-2, wherein the IL-2 is added continuously during co-culture, and wherein the IL-2 is maintained at a concentration between 100 IU/mL and 500 IU/mL during the co-culture. In an embodiment, the invention includes a composition comprising AIM-V media, at least one cell from a cell line selected from the group consisting of a B cell line, a B cell lymphoblastoid cell line, a Burkitt's lymphoma cell line, a myeloid lineage cell line, a monocyte cell line, an acute monocytic leukemia cell, an M5-subtype acute monocytic leukemia cell, a melanocyte cell line, a melanoma cell line and combinations thereof, and IL-2, wherein the IL-2 is added continuously during co-culture, and wherein the IL-2 is maintained at a concentration between 200 IU/mL and 400 IU/mL during the co-culture. In an embodiment, the invention includes a composition comprising AIM-V media, at least one cell from a cell line selected from the group consisting of a B cell line, a B cell lymphoblastoid cell line, a Burkitt's lymphoma cell line, a myeloid lineage cell line, a monocyte cell line, an acute monocytic leukemia cell, an M5-subtype acute monocytic leukemia cell, a melanocyte cell line, a melanoma cell line, and combinations thereof, and IL-2 at a concentration selected from the group consisting of about 50 IU/mL, about 100 IU/mL, about 150 IU/mL, about 200 IU/mL, about 250 IU/mL, about 300 IU/mL, about 350 IU/mL, about 400 IU/mL, about 450 IU/mL and about 500 IU/mL.

In an embodiment, any of the prior embodiments of target cells comprise irradiated target cells. In an embodiment, any of the prior embodiments of target cells comprise non-irradiated target cells. In an embodiment, any of the prior embodiments of negative control cells comprise irradiated negative control cells. In an embodiment, any of the prior embodiments of negative control cells comprise non-irradiated negative control cells.

In an embodiment, the invention includes a composition comprising a target cell line or combination of target cell lines that express HLA-A, HLA-B, HLA-C, HLA-DQ (A1), HLA-DQ (A2), HLA-DR (B1), HLA-DP (B1), HLA-DP (B2), or combinations thereof. In an embodiment, the invention includes a method for performing a potency assay wherein the target cell line or combination of target cell lines express HLA-A, HLA-B, HLA-C, HLA-DQ (A1), HLA-DQ (A2), HLA-DR (B1), HLA-DP (B1), HLA-DP (B2), or combinations thereof, and further comprise a population of TILs, MILs, or PBLs prepared by the methods described herein. In some embodiments, the invention includes a method for performing a potency assay wherein the target cell line or combination of target cell lines express HLA-A, HLA-B, HLA-C, HLA-DQ (A1), HLA-DQ (A2), HLA-DR (B1), HLA-DP (B1), HLA-DP (B2), or combinations thereof, and further comprise a population of TILs, MILs, or PBLs prepared by the Gen 2 processes described herein. In some embodiments, the invention includes a method for performing a potency assay wherein the target cell line or combination of target cell lines express HLA-A, HLA-B, HLA-C, HLA-DQ (A1), HLA-DQ (A2), HLA-DR (B1), HLA-DP (B1), HLA-DP (B2), or combinations thereof, and further comprise a population of TILs, MILs, or PBLs prepared by the Gen 3 processes described herein. In an embodiment, the invention includes a method for performing a potency assay wherein the target cell line or combination of target cell lines express HLA-A, HLA-B, HLA-C, HLA-DQ (A1), HLA-DQ (A2), HLA-DR (B1), HLA-DP (B1), HLA-DP (B2), or combinations thereof, and further comprise a population of TILs, MILs, or PBLs according to the compositions disclosed or claimed in U.S. Pat. Nos. 10,894,063; 10,398,734; 10,537,595; 10,695,372; and 10,653,723, the disclosures of which are incorporated by reference herein.

In an embodiment, the invention includes a composition comprising a target cell line or combination of target cell lines that includes a B cell. In an embodiment, the invention includes a composition comprising a target cell line or combination of target cell lines that includes a B cell lymphoblastoid cell. In an embodiment, the invention includes a composition comprising a target cell line or combination of target cell lines that includes a Burkitt's lymphoma cell. In an embodiment, the invention includes a composition comprising a target cell line or combination of target cell lines that includes a myeloid lineage cell. In an embodiment, the invention includes a composition comprising a target cell line or combination of target cell lines that includes a monocyte. In an embodiment, the invention includes a composition comprising a target cell line or combination of target cell lines that includes an acute monocytic leukemia cell. In an embodiment, the invention includes a composition comprising a target cell line or combination of target cell lines that includes an M5-subtype acute monocytic leukemia cell. In an embodiment, the invention includes a composition comprising a target cell line or combination of target cell lines that includes a Raji cell or a derivative, variant, modification, or progeny thereof, including a Raji B2M cell. In an embodiment, the invention includes a composition comprising a target cell line or combination of target cell lines that includes a Thp1 cell or a derivative, variant, modification, or progeny thereof, including genetically modified Thp1 cells suitable for killing assays. In an embodiment, the invention includes a composition comprising a target cell line or combination of target cell lines that includes a Ramos cell or a derivative, variant, modification, or progeny thereof, including genetically modified Ramos cells suitable for killing assays. In an embodiment, the invention includes a composition comprising a target cell line or combination of target cell lines that includes a U937 cell or a derivative, variant, modification, or progeny thereof, including genetically modified U937 cells suitable for killing assays. In an embodiment, the invention includes a composition comprising a target cell line or combination of target cell lines that includes a Daudi cell or a derivative, variant, modification, or progeny thereof, including genetically modified Daudi cells suitable for killing assays. In an embodiment, the invention includes a composition comprising a target cell line or combination of target cell lines that includes a melanocyte cell. In an embodiment, the invention includes a composition comprising a target cell line or combination of target cell lines that includes an HLA-A-02 positive melanocyte cell. In an embodiment, the invention includes a composition comprising a target cell line or combination of target cell lines that includes a melanoma cell. In an embodiment, the invention includes a composition comprising a target cell line or combination of target cell lines that includes an HLA-A-02 positive melanoma cell. In an embodiment, the invention includes a composition comprising a target cell line or combination of target cell lines that includes a melanoma cell selected from the group consisting of Sk-MEL-5, Malme-3M, SK-MEL-28, SK-MEL-3, SH-4, SK-MEL-24, RPMI-7951, SK-MEL-1, A375, G-361, and combinations thereof.

In an embodiment, the invention includes a composition comprising media, a target cell, and an HLA-I blocking antibody. In an embodiment, the invention includes a composition comprising media, a target cell, and an HLA-II blocking antibody. In an embodiment, the invention includes a composition comprising media, a target cell, an HLA-I blocking antibody, and an HLA-II blocking antibody. In an embodiment, the invention includes a composition comprising media, IL-2, a target cell, and an HLA-I blocking antibody. In an embodiment, the invention includes a composition comprising media, IL-2, a target cell, and an HLA-II blocking antibody. In an embodiment, the invention includes a composition comprising media, IL-2, a target cell, an HLA-I blocking antibody, and an HLA-II blocking antibody. In any of the foregoing embodiments, the composition further comprises a secreted cytokine, the level of which may be compared to the level obtained without the presence of the HLA-I and/or HLA-II blocking antibody. In any of the foregoing embodiments, the HLA-I blocking antibody is present at a concentration of between 1 μg/mL and 50 μg/mL. In any of the foregoing embodiments, the HLA-I blocking antibody is present at a concentration of between 5 μg/mL and 20 μg/mL. In any of the foregoing embodiments, the HLA-II blocking antibody is present at a concentration of between 1 μg/mL and 50 μg/mL. In any of the foregoing embodiments, the HLA-II blocking antibody is present at a concentration of between 5 μg/mL and 20 μg/mL.

In some embodiments, potency assays described herein may be used to determine the potency of T cell compositions, including TIL, MIL, and PBL compositions, described in U.S. Patent Application Publication Nos. US 2018/0282694 A1; US 2020/0224161 A1; and US 2020/0277573 A1; International Patent Application Publication Nos. WO 2019/210131 A1; WO 2019/136456 A1; WO 2019/145711 A1; WO 2019/210131 A1; WO 2020/152451 A1; and WO 2021/123832 A1; and in U.S. Pat. Nos. 10,130,659, 10,166,257, 10,272,113, 10,363,273, 10,398,734, 10,420,799, 10,463,697, 10,537,595, 10,646,517, 10,653,723, 10,693,330, 10,695,372, 10,894,063, 10,905,718, and 10,918,666, the disclosures of each of which are incorporated herein by reference.

In some of the foregoing embodiments, target cells for potency assays are prepared as working cell banks. In some of the foregoing embodiments, target cells for potency assays are prepared as master cell banks.

C. Assay Kits

In an embodiment, the invention includes kits for testing potency of a TIL, such as a TIL, MIL, or PBL product. In some embodiments, kits include a target cell as described herein. In an embodiment, the kit includes a Raji cell, a Thp1 cell, a Ramos cell, a U937 cell, a Daudi cell, a combination thereof, or a derivative, variant, modification, or progeny thereof.

In some embodiments, kits include a negative control cell as described herein. In an embodiment, the kit includes a K562 cell or a derivative, variant, modification, or progeny thereof. In some embodiments, kits include media, immunoassay reagents, ELISA or automated ELISA systems, supernatant liquids comprising secreted proteins, PBMCs, positive controls as described herein, or other test components.

In some embodiments, the invention includes a kit for testing the potency of a TIL, such as a TIL, MIL or PBL product, wherein the kit comprises one to three target cells, media, and a co-culture vessel. In some embodiments, the one to three target cells are selected from the group consisting of a Raji cell, a Thp1 cell, a Ramos cell, a U937 cell, a Daudi cell, and combinations, derivatives, variants, modifications, and progeny thereof. In some embodiments, the media comprises AIM-V media. In some embodiments, the media comprises IL-2.

In some embodiments, the kits comprise a monocytic target cell line. In some embodiments, the kits comprise a myeloid lineage target cell line. In some embodiments, the kits comprise a B cell target cell line. In some embodiments, the kits comprise a B cell lymphoblastoid cell target cell line. In some embodiments, the kits comprise a Burkitt's lymphoma cell target cell line. In some embodiments, the kits comprise an acute monocytic leukemia cell target cell line. In some embodiments, the kits comprise an M5-subtype acute monocytic leukemia cell line.

In an embodiment, any of the prior embodiments of kits comprise irradiated target cells. In an embodiment, any of the prior embodiments of kits comprise non-irradiated target cells. In an embodiment, any of the prior embodiments of kits comprise irradiated negative control cells. In an embodiment, any of the prior embodiments of kits comprise non-irradiated negative control cells. In an embodiment, any of the prior embodiments of kits comprise non-irradiated K562 negative control cells. In an embodiment, any of the prior embodiments of kits comprise irradiated K562 negative control cells.

Exemplary embodiments of proposed methods to assay the potency or functionality of T cells, including TILs, MILs, and PBLs, may also be found in the examples and drawings included herein.

In any of the foregoing embodiments, the kits also include an HLA-I blocking antibody. In any of the foregoing embodiments, the kits also include an HLA-II blocking antibody.

In any of the foregoing embodiments, the kits also include a positive control TIL cell line. Suitable positive control TIL cell lines include those that have been well-characterized, expanded to large cell counts, shown to respond reproducibly in the potency assays of the present invention, and stored carefully under frozen conditions for use later

IV. Gen 2 TIL Manufacturing Processes

Figure 2A:
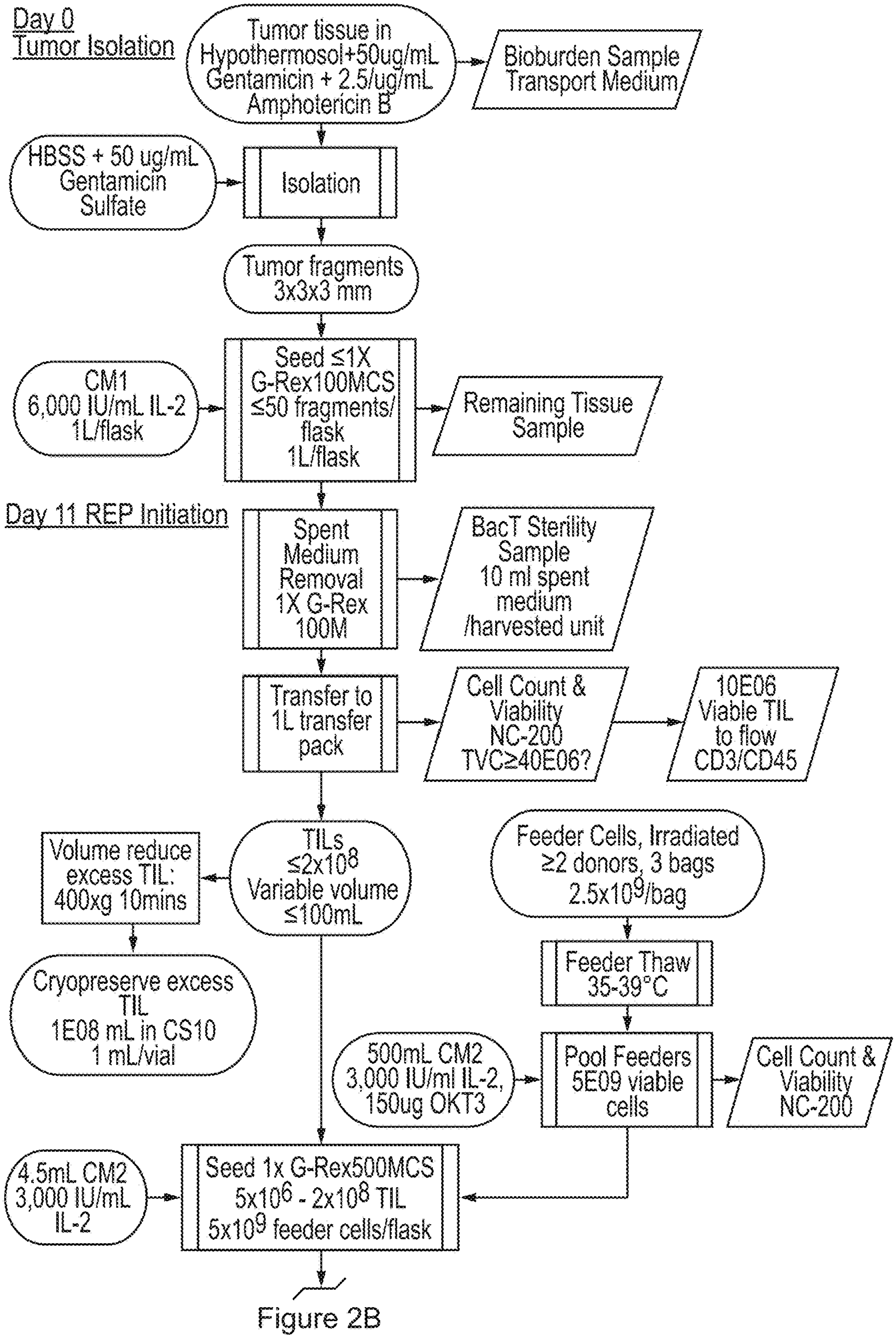
FIG. 2A-2C: Process flow chart of an embodiment of Gen 2 (process 2A) for TIL manufacturing.
Figure 2B:
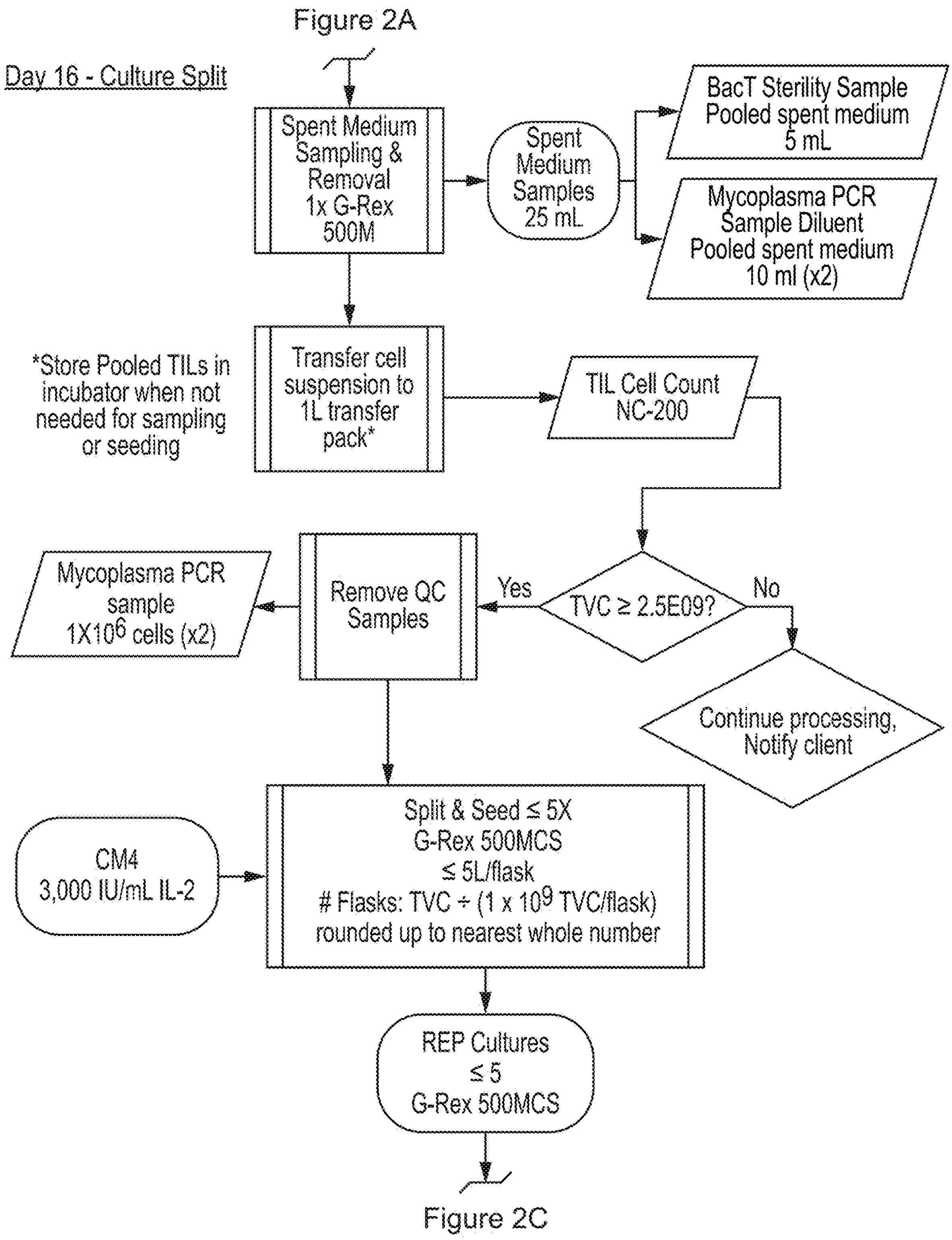
Figure 2C:
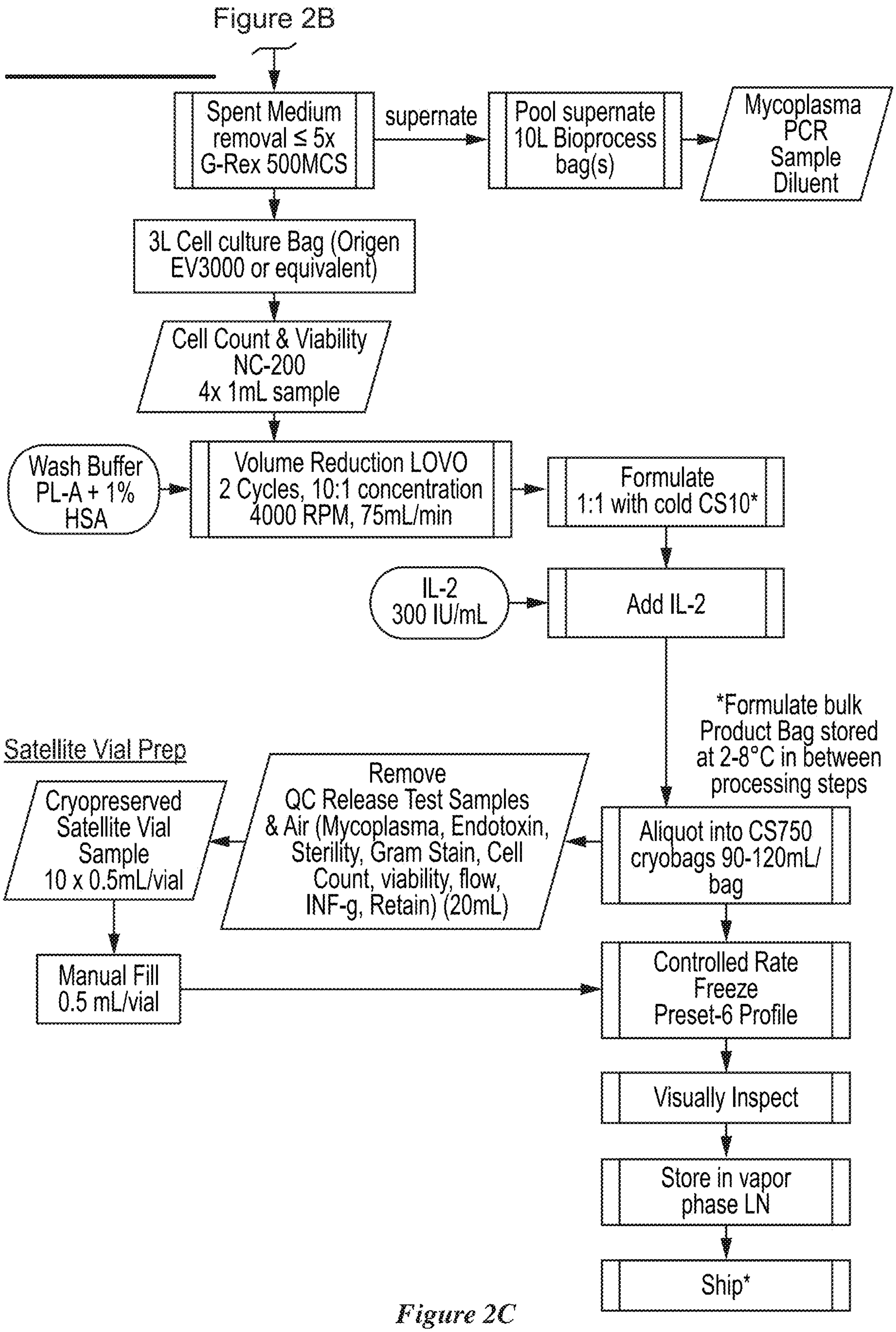
Figure 3:
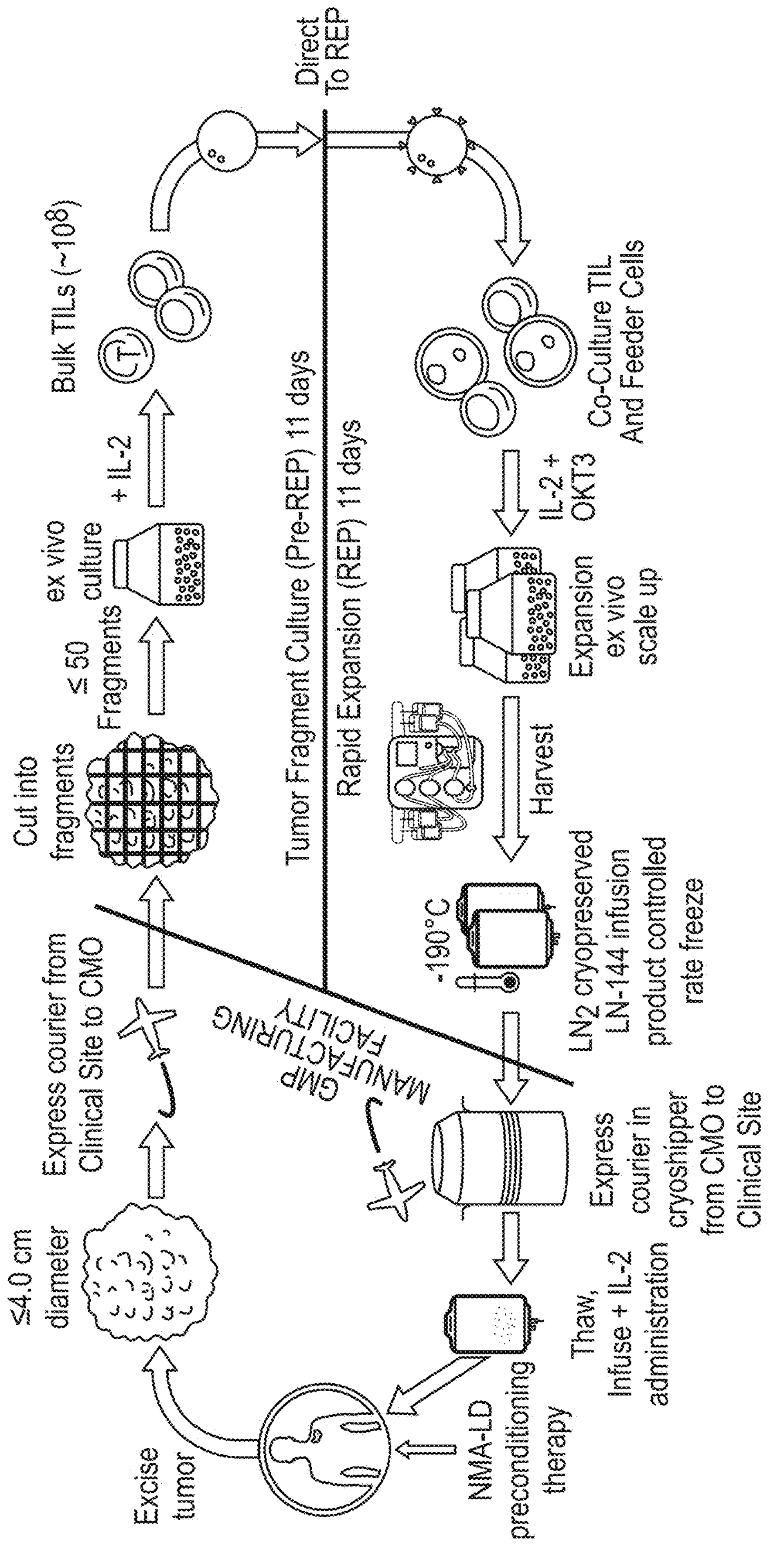
FIG. 3: Shows a diagram of an embodiment of a cryopreserved TIL exemplary manufacturing process (~22 days).

An exemplary family of TIL processes known as Gen 2 (also known as process 2A) containing some of these features is depicted in FIGS. 1 and 2. An embodiment of Gen 2 is shown in FIG. 2. Some of the advantages of this embodiment of the present invention over process 1C are described in International Patent Publication No. WO 2018/081473 A1, incorporated by reference herein.

As discussed herein, the present invention can include a step relating to the restimulation of cryopreserved TILs to increase their metabolic activity and thus relative health prior to transplant into a patient, and methods of testing said metabolic health. As generally outlined herein, TILs are generally taken from a patient sample and manipulated to expand their number prior to transplant into a patient. In some embodiments, the TILs may be optionally genetically manipulated as discussed below.

In some embodiments, the TILs may be cryopreserved. Once thawed, they may also be restimulated to increase their metabolism prior to infusion into a patient.

In some embodiments, the first expansion (including processes referred to as the preREP as well as processes shown in FIG. 1 as Step A) is shortened to 3 to 14 days and the second expansion (including processes referred to as the REP as well as processes shown in FIG. 1 as Step B) is shorted to 7 to 14 days, as discussed in detail below as well as in the examples and figures. In some embodiments, the first expansion (for example, an expansion described as Step B in FIG. 1) is shortened to 11 days and the second expansion (for example, an expansion as described in Step D in FIG. 1) is shortened to 11 days. In some embodiments, the combination of the first expansion and second expansion (for example, expansions described as Step B and Step D in FIG. 1) is shortened to 22 days, as discussed in detail below and in the examples and figures.

The "Step" Designations A, B, C, etc., below are in reference to FIG. 1 and in reference to certain embodiments described herein. The ordering of the Steps below and in FIG. 1 is exemplary and any combination or order of steps, as well as additional steps, repetition of steps, and/or omission of steps is contemplated by the present application and the methods disclosed herein.

A. STEP A: Obtain Patient Tumor Sample

In general, TILs are initially obtained from a patient tumor sample ("primary TILs") and then expanded into a larger population for further manipulation as described herein, optionally cryopreserved, restimulated as outlined herein and optionally evaluated for phenotype and metabolic parameters as an indication of TIL health.

A patient tumor sample may be obtained using methods known in the art, generally via surgical resection, needle biopsy, core biopsy, small biopsy, or other means for obtaining a sample that contains a mixture of tumor and TIL cells. In some embodiments, multilesional sampling is used. In some embodiments, surgical resection, needle biopsy, core biopsy, small biopsy, or other means for obtaining a sample that contains a mixture of tumor and TIL cells includes multilesional sampling (i.e., obtaining samples from one or more tumor cites and/or locations in the patient, as well as one or more tumors in the same location or in close proximity). In general, the tumor sample may be from any solid tumor, including primary tumors, invasive tumors or metastatic tumors. The tumor sample may also be a liquid tumor, such as a tumor obtained from a hematological malignancy. The solid tumor may be of skin tissue. In some embodiments, useful TILs are obtained from a melanoma.

Once obtained, the tumor sample is generally fragmented using sharp dissection into small pieces of between 1 to about 8 $mm^3$, with from about 2-3 $mm^3$ being particularly useful. The TILs are cultured from these fragments using enzymatic tumor digests. Such tumor digests may be produced by incubation in enzymatic media (e.g., Roswell Park Memorial Institute (RPMI) 1640 buffer, 2 mM glutamate, 10 mcg/mL gentamicine, 30 units/mL of DNase and 1.0 mg/mL of collagenase) followed by mechanical dissociation (e.g., using a tissue dissociator). Tumor digests may be produced by placing the tumor in enzymatic media and mechanically dissociating the tumor for approximately 1 minute, followed by incubation for 30 minutes at 37° C. in 5% $CO_2$, followed by repeated cycles of mechanical dissociation and incubation under the foregoing conditions until only small tissue pieces are present. At the end of this process, if the cell suspension contains a large number of red blood cells or dead cells, a density gradient separation using FICOLL branched hydrophilic polysaccharide may be performed to remove these cells. Alternative methods known in the art may be used, such as those described in U.S. Patent Application Publication No. 2012/0244133 A1, the disclosure of which is incorporated by reference herein. Any of the foregoing methods may be used in any of the embodiments described herein for methods of expanding TILs or methods treating a cancer. In some embodiments, the tumor is digested according to the methods or in the form of the compositions described in International Patent Publication No. WO 2021/123832 A1, the disclosures of which are incorporated by reference herein.

As indicated above, in some embodiments, the TILs are derived from solid tumors. In some embodiments, the solid tumors are not fragmented. In some embodiments, the solid tumors are not fragmented and are subjected to enzymatic digestion as whole tumors. In some embodiments, the tumors are digested in in an enzyme mixture comprising collagenase, DNase, and hyaluronidase. In some embodiments, the tumors are digested in in an enzyme mixture comprising collagenase, DNase, and hyaluronidase for 1-2 hours. In some embodiments, the tumors are digested in in an enzyme mixture comprising collagenase, DNase, and hyaluronidase for 1-2 hours at 37° C., 5% $CO_2$. In some embodiments, the tumors are digested in in an enzyme mixture comprising collagenase, DNase, and hyaluronidase for 1-2 hours at 37° C., 5% $CO_2$ with rotation. In some embodiments, the tumors are digested overnight with constant rotation. In some embodiments, the tumors are digested overnight at 37° C., 5% $CO_2$ with constant rotation. In some embodiments, the whole tumor is combined with the enzymes to form a tumor digest reaction mixture.

In some embodiments, the tumor is reconstituted with the lyophilized enzymes in a sterile buffer. In some embodiments, the buffer is sterile HBSS.

In some embodiments, the enzyme mixture comprises collagenase. In some embodiments, the collagenase is collagenase IV. In some embodiments, the working stock for the collagenase is a 100 mg/mL 10× working stock.

In some embodiments, the enzyme mixture comprises DNAse. In some embodiments, the working stock for the DNAse is a 10,000 IU/mL 10× working stock.

In some embodiments, the enzyme mixture comprises hyaluronidase. In some embodiments, the working stock for the hyaluronidase is a 10-mg/mL 10× working stock.

In some embodiments, the enzyme mixture comprises 10 mg/mL collagenase, 1000 IU/mL DNAse, and 1 mg/mL hyaluronidase.

In some embodiments, the enzyme mixture comprises 10 mg/mL collagenase, 500 IU/mL DNAse, and 1 mg/mL hyaluronidase.

In general, the harvested cell suspension is called a "primary cell population" or a "freshly harvested" cell population.

In some embodiments, fragmentation includes physical fragmentation, including for example, dissection as well as digestion. In some embodiments, the fragmentation is physical fragmentation. In some embodiments, the fragmentation is dissection. In some embodiments, the fragmentation is by digestion. In some embodiments, TILs can be initially cultured from enzymatic tumor digests and tumor fragments obtained from patients. In an embodiment, TILs can be initially cultured from enzymatic tumor digests and tumor fragments obtained from patients.

In some embodiments, where the tumor is a solid tumor, the tumor undergoes physical fragmentation after the tumor sample is obtained in, for example, Step A (as provided in FIG. 1). In some embodiments, the fragmentation occurs before cryopreservation. In some embodiments, the fragmentation occurs after cryopreservation. In some embodiments, the fragmentation occurs after obtaining the tumor and in the absence of any cryopreservation. In some embodiments, the tumor is fragmented and 10, 20, 30, 40 or more fragments or pieces are placed in each container for the first expansion. In some embodiments, the tumor is fragmented and 30 or 40 fragments or pieces are placed in each container for the first expansion. In some embodiments, the tumor is fragmented and 40 fragments or pieces are placed in each container for the first expansion. In some embodiments, the multiple fragments comprise about 4 to about 50 fragments, wherein each fragment has a volume of about 27 $mm^3$. In some embodiments, the multiple fragments comprise about 30 to about 60 fragments with a total volume of about 1300 $mm^3$ to about 1500 $mm^3$. In some embodiments, the multiple fragments comprise about 50 fragments with a total volume of about 1350 $mm^3$. In some embodiments, the multiple fragments comprise about 50 fragments with a total mass of about 1 gram to about 1.5 grams. In some embodiments, the multiple fragments comprise about 4 fragments.

In some embodiments, the TILs are obtained from tumor fragments. In some embodiments, the tumor fragment is obtained by sharp dissection. In some embodiments, the tumor fragment is between about 1 $mm^3$ and 10 $mm^3$. In some embodiments, the tumor fragment is between about 1 $mm^3$ and 8 $mm^3$. In some embodiments, the tumor fragment is about 1 $mm^3$. In some embodiments, the tumor fragment is about 2 $mm^3$. In some embodiments, the tumor fragment is about 3 $mm^3$. In some embodiments, the tumor fragment is about 4 $mm^3$. In some embodiments, the tumor fragment is about 5 $mm^3$. In some embodiments, the tumor fragment is about 6 $mm^3$. In some embodiments, the tumor fragment is about 7 $mm^3$. In some embodiments, the tumor fragment is about 8 $mm^3$. In some embodiments, the tumor fragment is about 9 $mm^3$. In some embodiments, the tumor fragment is about 10 $mm^3$. In some embodiments, the tumors are 1-4 mm×1-4 mm×1-4 mm. In some embodiments, the tumors are 1 mm×1 mm×1 mm. In some embodiments, the tumors are 2 mm×2 mm×2 mm. In some embodiments, the tumors are 3 mm×3 mm×3 mm. In some embodiments, the tumors are 4 mm×4 mm×4 mm.

In some embodiments, the tumors are resected in order to minimize the amount of hemorrhagic, necrotic, and/or fatty tissues on each piece. In some embodiments, the tumors are resected in order to minimize the amount of hemorrhagic tissue on each piece. In some embodiments, the tumors are resected in order to minimize the amount of necrotic tissue on each piece. In some embodiments, the tumors are resected in order to minimize the amount of fatty tissue on each piece.

In some embodiments, the tumor fragmentation is performed in order to maintain the tumor internal structure. In some embodiments, the tumor fragmentation is performed without preforming a sawing motion with a scalpel. In some embodiments, the TILs are obtained from tumor digests. In some embodiments, tumor digests were generated by incubation in enzyme media, for example but not limited to RPMI 1640, 2 mM GlutaMAX, 10 mg/mL gentamicin, 30 U/mL DNase, and 1.0 mg/mL collagenase, followed by mechanical dissociation (GentleMACS, Miltenyi Biotec, Auburn, CA). After placing the tumor in enzyme media, the tumor can be mechanically dissociated for approximately 1 minute. The solution can then be incubated for 30 minutes at 37° C. in 5% $CO_2$ and it then mechanically disrupted again for approximately 1 minute. After being incubated again for 30 minutes at 37° C. in 5% $CO_2$, the tumor can be mechanically disrupted a third time for approximately 1 minute. In some embodiments, after the third mechanical disruption if large pieces of tissue were present, 1 or 2 additional mechanical dissociations were applied to the sample, with or without 30 additional minutes of incubation at 37° C. in 5% $CO_2$. In some embodiments, at the end of the final incubation if the cell suspension contained a large number of red blood cells or dead cells, a density gradient separation using Ficoll can be performed to remove these cells.

In some embodiments, the harvested cell suspension prior to the first expansion step is called a "primary cell population" or a "freshly harvested" cell population.

In some embodiments, cells can be optionally frozen after sample harvest and stored frozen prior to entry into the expansion described in Step B, which is described in further detail below, as well as exemplified in FIG. 1, as well as FIG. 8.

1. Pleural Effusion TILs

In some embodiments, the sample is a pleural fluid sample. In some embodiments, the source of the TILs for expansion according to the processes described herein is a pleural fluid sample. In some embodiments, the sample is a pleural effusion derived sample. In some embodiments, the source of the TILs for expansion according to the processes described herein is a pleural effusion derived sample. See, for example, methods described in U.S. Patent Publication US 2014/0295426, incorporated herein by reference in its entirety for all purposes.

In some embodiments, any pleural fluid or pleural effusion suspected of and/or containing TILs can be employed. Such a sample may be derived from a primary or metastatic lung cancer, such as NSCLC or SCLC. In some embodiments, the sample may be secondary metastatic cancer cells which originated from another organ, e.g., breast, ovary, colon or prostate. In some embodiments, the sample for use in the expansion methods described herein is a pleural exudate. In some embodiments, the sample for use in the expansion methods described herein is a pleural transudate. Other biological samples may include other serous fluids containing TILs, including, e.g., ascites fluid from the abdomen or pancreatic cyst fluid. Ascites fluid and pleural fluids involve very similar chemical systems; both the abdomen and lung have mesothelial lines and fluid forms in the pleural space and abdominal spaces in the same matter in malignancies and such fluids in some embodiments contain TILs. In some embodiments, wherein the disclosure exemplifies pleural fluid, the same methods may be performed with similar results using ascites or other cyst fluids containing TILs.

In some embodiments, the pleural fluid is in unprocessed form, directly as removed from the patient. In some embodiments, the unprocessed pleural fluid is placed in a standard blood collection tube, such as an EDTA or Heparin tube, prior to the contacting step. In some embodiments, the unprocessed pleural fluid is placed in a standard CellSave® tube (Veridex) prior to the contacting step. In some embodiments, the sample is placed in the CellSave tube immediately after collection from the patient to avoid a decrease in the number of viable TILs. The number of viable TILs can decrease to a significant extent within 24 hours, if left in the untreated pleural fluid, even at 4° C. In some embodiments, the sample is placed in the appropriate collection tube within 1 hour, 5 hours, 10 hours, 15 hours, or up to 24 hours after removal from the patient. In some embodiments, the sample is placed in the appropriate collection tube within 1 hour, 5 hours, 10 hours, 15 hours, or up to 24 hours after removal from the patient at 4° C.

In some embodiments, the pleural fluid sample from the chosen subject may be diluted. In one embodiment, the dilution is 1:10 pleural fluid to diluent. In another embodiment, the dilution is 1:9 pleural fluid to diluent. In another embodiment, the dilution is 1:8 pleural fluid to diluent. In another embodiment, the dilution is 1:5 pleural fluid to diluent. In another embodiment, the dilution is 1:2 pleural fluid to diluent. In another embodiment, the dilution is 1:1 pleural fluid to diluent. In some embodiments, diluents include saline, phosphate buffered saline, another buffer or a physiologically acceptable diluent. In some embodiments, the sample is placed in the CellSave tube immediately after collection from the patient and dilution to avoid a decrease in the viable TILs, which may occur to a significant extent within 24-48 hours, if left in the untreated pleural fluid, even at 4° C. In some embodiments, the pleural fluid sample is placed in the appropriate collection tube within 1 hour, 5 hours, 10 hours, 15 hours, 24 hours, 36 hours, up to 48 hours after removal from the patient, and dilution. In some embodiments, the pleural fluid sample is placed in the appropriate collection tube within 1 hour, 5 hours, 10 hours, 15 hours, 24 hours, 36 hours, up to 48 hours after removal from the patient, and dilution at 4° C.

In still another embodiment, pleural fluid samples are concentrated by conventional means prior further processing steps. In some embodiments, this pre-treatment of the pleural fluid is preferable in circumstances in which the pleural fluid must be cryopreserved for shipment to a laboratory performing the method or for later analysis (e.g., later than 24-48 hours post-collection). In some embodiments, the pleural fluid sample is prepared by centrifuging the pleural fluid sample after its withdrawal from the subject and resuspending the centrifugate or pellet in buffer. In some embodiments, the pleural fluid sample is subjected to multiple centrifugations and resuspensions, before it is cryopreserved for transport or later analysis and/or processing.

In some embodiments, pleural fluid samples are concentrated prior to further processing steps by using a filtration method. In some embodiments, the pleural fluid sample used in the contacting step is prepared by filtering the fluid through a filter containing a known and essentially uniform pore size that allows for passage of the pleural fluid through the membrane but retains the tumor cells. In some embodiments, the diameter of the pores in the membrane may be at least 4 μM. In another embodiment the pore diameter may be 5 μM or more, and in other embodiment, any of 6, 7, 8, 9, or 10 μM. After filtration, the cells, including TILs, retained by the membrane may be rinsed off the membrane into a suitable physiologically acceptable buffer. Cells, including TILs, concentrated in this way may then be used in the contacting step of the method.

In some embodiments, pleural fluid sample (including, for example, the untreated pleural fluid), diluted pleural fluid, or the resuspended cell pellet, is contacted with a lytic reagent that differentially lyses non-nucleated red blood cells present in the sample. In some embodiments, this step is performed prior to further processing steps in circumstances in which the pleural fluid contains substantial numbers of RBCs. Suitable lysing reagents include a single lytic reagent or a lytic reagent and a quench reagent, or a lytic agent, a quench reagent and a fixation reagent. Suitable lytic systems are marketed commercially and include the BD Pharm Lyse™ system (Becton Dickenson). Other lytic systems include the Versalyse™ system, the FACSlyse™ system (Becton Dickenson), the Immunoprep™ system or Erythrolyse II system (Beckman Coulter, Inc.), or an ammonium chloride system. In some embodiments, the lytic reagent can vary with the primary requirements being efficient lysis of the red blood cells, and the conservation of the TILs and phenotypic properties of the TILs in the pleural fluid. In addition to employing a single reagent for lysis, the lytic systems useful in methods described herein can include a second reagent, e.g., one that quenches or retards the effect of the lytic reagent during the remaining steps of the method, e.g., Stabilyse™ reagent (Beckman Coulter, Inc.). A conventional fixation reagent may also be employed depending upon the choice of lytic reagents or the preferred implementation of the method.

In some embodiments, the pleural fluid sample, unprocessed, diluted or multiply centrifuged or processed as described herein above is cryopreserved at a temperature of about −140° C. prior to being further processed and/or expanded as provided herein.

B. STEP B: First Expansion

In some embodiments, the present methods provide for obtaining young TILs, which are capable of increased replication cycles upon administration to a subject/patient and as such may provide additional therapeutic benefits over older TILs (i.e., TILs which have further undergone more rounds of replication prior to administration to a subject/patient). Features of young TILs have been described in the literature, for example Donia, at al., *Scandinavian Journal of Immunology,* 75:157-167 (2012); Dudley et al., *Clin Cancer Res,* 16:6122-6131 (2010); Huang et al., *J Immunother,* 28(3):258-267 (2005); Besser et al., *Clin Cancer Res,* 19(17):OF1-OF9 (2013); Besser et al., *J Immunother* 32:415-423 (2009); Robbins, et al., *J Immunol* 2004; 173: 7125-7130; Shen et al., J Immunother, 30:123-129 (2007); Zhou, et al., *J Immunother,* 28:53-62 (2005); and Tran, et al., J Immunother, 31:742-751 (2008), all of which are incorporated herein by reference in their entireties.

The diverse antigen receptors of T and B lymphocytes are produced by somatic recombination of a limited, but large number of gene segments. These gene segments: V (variable), D (diversity), J (joining), and C (constant), determine the binding specificity and downstream applications of immunoglobulins and T cell receptors (TCRs). The present invention provides a method for generating TILs which exhibit and increase the T cell repertoire diversity. In some embodiments, the TILs obtained by the present method exhibit an increase in the T cell repertoire diversity. In some embodiments, the TILs obtained by the present method exhibit an increase in the T cell repertoire diversity as compared to freshly harvested TILs and/or TILs prepared using other methods than those provide herein including for example, methods other than those embodied in FIG. 1. In some embodiments, the TILs obtained by the present method exhibit an increase in the T cell repertoire diversity as compared to freshly harvested TILs and/or TILs prepared using methods referred to as process 1C, as exemplified in FIG. 5 and/or FIG. 6. In some embodiments, the TILs obtained in the first expansion exhibit an increase in the T cell repertoire diversity. In some embodiments, the increase in diversity is an increase in the immunoglobulin diversity and/or the T cell receptor diversity. In some embodiments, the diversity is in the immunoglobulin is in the immunoglobulin heavy chain. In some embodiments, the diversity is in the immunoglobulin is in the immunoglobulin light chain. In some embodiments, the diversity is in the T cell receptor. In some embodiments, the diversity is in one of the T cell receptors selected from the group consisting of alpha, beta, gamma, and delta receptors. In some embodiments, there is an increase in the expression of T cell receptor (TCR) alpha and/or beta. In some embodiments, there is an increase in the expression of T cell receptor (TCR) alpha. In some embodiments, there is an increase in the expression of T cell receptor (TCR) beta. In some embodiments, there is an increase in the expression of TCRab (i.e., TCRα/β).

After dissection or digestion of tumor fragments, for example such as described in Step A of FIG. 1, the resulting cells are cultured in serum containing IL-2 under conditions that favor the growth of TILs over tumor and other cells. In some embodiments, the tumor digests are incubated in 2 mL wells in media comprising inactivated human AB serum with 6000 IU/mL of IL-2. This primary cell population is cultured for a period of days, generally from 3 to 14 days, resulting in a bulk TIL population, generally about $1\times10^8$ bulk TIL cells. In some embodiments, this primary cell population is cultured for a period of 7 to 14 days, resulting in a bulk TIL population, generally about $1\times10^8$ bulk TIL cells. In some embodiments, this primary cell population is cultured for a period of 10 to 14 days, resulting in a bulk TIL population, generally about $1\times10^8$ bulk TIL cells. In some embodiments, this primary cell population is cultured for a period of about 11 days, resulting in a bulk TIL population, generally about $1\times10^8$ bulk TIL cells.

In a preferred embodiment, expansion of TILs may be performed using an initial bulk TIL expansion step (for example such as those described in Step B of FIG. 1, which can include processes referred to as pre-REP) as described below and herein, followed by a second expansion (Step D, including processes referred to as rapid expansion protocol (REP) steps) as described below under Step D and herein, followed by optional cryopreservation, and followed by a second Step D (including processes referred to as restimulation REP steps) as described below and herein. The TILs obtained from this process may be optionally characterized for phenotypic characteristics and metabolic parameters as described herein.

In embodiments where TIL cultures are initiated in 24-well plates, for example, using Costar 24-well cell culture cluster, flat bottom (Corning Incorporated, Corning, NY, each well can be seeded with $1\times10^6$ tumor digest cells or one tumor fragment in 2 mL of complete medium (CM) with IL-2 (6000 IU/mL; Chiron Corp., Emeryville, CA). In some embodiments, the tumor fragment is between about 1 $mm^3$ and 10 $mm^3$.

In some embodiments, the first expansion culture medium is referred to as "CM", an abbreviation for culture media. In some embodiments, CM for Step B consists of RPMI 1640 with GlutaMAX, supplemented with 10% human AB serum, 25 mM Hepes, and 10 mg/mL gentamicin. In embodiments where cultures are initiated in gas-permeable flasks with a 40 mL capacity and a 10 $cm^2$ gas-permeable silicon bottom (for example, G-Rex 10; Wilson Wolf Manufacturing, New Brighton, MN), each flask was loaded with $10\text{-}40\times10^6$ viable tumor digest cells or 5-30 tumor fragments in $10^{-40}$ mL of CM with IL-2. Both the G-Rex 10 and 24-well plates were incubated in a humidified incubator at 37° C. in 5% $CO_2$ and 5 days after culture initiation, half the media was removed and replaced with fresh CM and IL-2 and after day 5, half the media was changed every 2-3 days.

After preparation of the tumor fragments, the resulting cells (i.e., fragments) are cultured in serum containing IL-2 under conditions that favor the growth of TILs over tumor and other cells. In some embodiments, the tumor digests are incubated in 2 mL wells in media comprising inactivated human AB serum (or, in some cases, as outlined herein, in the presence of aAPC cell population) with 6000 IU/mL of IL-2. This primary cell population is cultured for a period of days, generally from 10 to 14 days, resulting in a bulk TIL population, generally about $1\times10^8$ bulk TIL cells. In some embodiments, the growth media during the first expansion comprises IL-2 or a variant thereof. In some embodiments, the IL is recombinant human IL-2 (rhIL-2). In some embodiments the IL-2 stock solution has a specific activity of $20\text{-}30\times10^6$ IU/mg for a 1 mg vial. In some embodiments the IL-2 stock solution has a specific activity of $20\times10^6$ IU/mg for a 1 mg vial. In some embodiments the IL-2 stock solution has a specific activity of $25\times10^6$ IU/mg for a 1 mg vial. In some embodiments the IL-2 stock solution has a specific activity of $30\times10^6$ IU/mg for a 1 mg vial. In some embodiments, the IL-2 stock solution has a final concentration of $4\text{-}8\times10^6$ IU/mg of IL-2. In some embodiments, the IL-2 stock solution has a final concentration of $5\text{-}7\times10^6$ IU/mg of IL-2. In some embodiments, the IL-2 stock solution has a final concentration of $6\times10^6$ IU/mg of IL-2. In some embodiments, the IL-2 stock solution is prepare as described in Example 5. In some embodiments, the first expansion culture media comprises about 10,000 IU/mL of IL-2, about 9,000 IU/mL of IL-2, about 8,000 IU/mL of IL-2, about 7,000 IU/mL of IL-2, about 6000 IU/mL of IL-2 or about 5,000 IU/mL of IL-2. In some embodiments, the first expansion culture media comprises about 9,000 IU/mL of IL-2 to about 5,000 IU/mL of IL-2. In some embodiments, the first expansion culture media comprises about 8,000 IU/mL of IL-2 to about 6,000 IU/mL of IL-2. In some embodiments, the first expansion culture media comprises about 7,000 IU/mL of IL-2 to about 6,000 IU/mL of IL-2. In some embodiments, the first expansion culture media comprises about 6,000 IU/mL of IL-2. In an embodiment, the cell culture medium further comprises IL-2. In some embodiments, the cell culture medium comprises about 3000 IU/mL of IL-2. In an embodiment, the cell culture medium further comprises IL-2. In a preferred embodiment, the cell culture medium comprises about 3000 IU/mL of IL-2. In an embodiment, the cell culture medium comprises about 1000 IU/mL, about 1500 IU/mL, about 2000 IU/mL, about 2500 IU/mL, about 3000 IU/mL, about 3500 IU/mL, about 4000 IU/mL, about 4500 IU/mL, about 5000 IU/mL, about 5500 IU/mL, about 6000 IU/mL, about 6500 IU/mL, about 7000 IU/mL, about 7500 IU/mL, or about 8000 IU/mL of IL-2. In an embodiment, the cell culture medium comprises between 1000 and 2000 IU/mL, between 2000 and 3000 IU/mL, between 3000 and 4000 IU/mL, between 4000 and 5000

IU/mL, between 5000 and 6000 IU/mL, between 6000 and 7000 IU/mL, between 7000 and 8000 IU/mL, or about 8000 IU/mL of IL-2.

In some embodiments, first expansion culture media comprises about 500 IU/mL of IL-15, about 400 IU/mL of IL-15, about 300 IU/mL of IL-15, about 200 IU/mL of IL-15, about 180 IU/mL of IL-15, about 160 IU/mL of IL-15, about 140 IU/mL of IL-15, about 120 IU/mL of IL-15, or about 100 IU/mL of IL-15. In some embodiments, the first expansion culture media comprises about 500 IU/mL of IL-15 to about 100 IU/mL of IL-15. In some embodiments, the first expansion culture media comprises about 400 IU/mL of IL-15 to about 100 IU/mL of IL-15. In some embodiments, the first expansion culture media comprises about 300 IU/mL of IL-15 to about 100 IU/mL of IL-15. In some embodiments, the first expansion culture media comprises about 200 IU/mL of IL-15. In some embodiments, the cell culture medium comprises about 180 IU/mL of IL-15. In an embodiment, the cell culture medium further comprises IL-15. In a preferred embodiment, the cell culture medium comprises about 180 IU/mL of IL-15.

In some embodiments, first expansion culture media comprises about 20 IU/mL of IL-21, about 15 IU/mL of IL-21, about 12 IU/mL of IL-21, about 10 IU/mL of IL-21, about 5 IU/mL of IL-21, about 4 IU/mL of IL-21, about 3 IU/mL of IL-21, about 2 IU/mL of IL-21, about 1 IU/mL of IL-21, or about 0.5 IU/mL of IL-21. In some embodiments, the first expansion culture media comprises about 20 IU/mL of IL-21 to about 0.5 IU/mL of IL-21. In some embodiments, the first expansion culture media comprises about 15 IU/mL of IL-21 to about 0.5 IU/mL of IL-21. In some embodiments, the first expansion culture media comprises about 12 IU/mL of IL-21 to about 0.5 IU/mL of IL-21. In some embodiments, the first expansion culture media comprises about 10 IU/mL of IL-21 to about 0.5 IU/mL of IL-21. In some embodiments, the first expansion culture media comprises about 5 IU/mL of IL-21 to about 1 IU/mL of IL-21. In some embodiments, the first expansion culture media comprises about 2 IU/mL of IL-21. In some embodiments, the cell culture medium comprises about 1 IU/mL of IL-21. In some embodiments, the cell culture medium comprises about 0.5 IU/mL of IL-21. In an embodiment, the cell culture medium further comprises IL-21. In a preferred embodiment, the cell culture medium comprises about 1 IU/mL of IL-21.

In an embodiment, the cell culture medium comprises OKT-3 antibody. In some embodiments, the cell culture medium comprises about 30 ng/mL of OKT-3 antibody. In an embodiment, the cell culture medium comprises about 0.1 ng/mL, about 0.5 ng/mL, about 1 ng/mL, about 2.5 ng/mL, about 5 ng/mL, about 7.5 ng/mL, about 10 ng/mL, about 15 ng/mL, about 20 ng/mL, about 25 ng/mL, about 30 ng/mL, about 35 ng/mL, about 40 ng/mL, about 50 ng/mL, about 60 ng/mL, about 70 ng/mL, about 80 ng/mL, about 90 ng/mL, about 100 ng/mL, about 200 ng/mL, about 500 ng/mL, and about 1 μg/mL of OKT-3 antibody. In an embodiment, the cell culture medium comprises between 0.1 ng/mL and 1 ng/mL, between 1 ng/mL and 5 ng/mL, between 5 ng/mL and 10 ng/mL, between 10 ng/mL and 20 ng/mL, between 20 ng/mL and 30 ng/mL, between 30 ng/mL and 40 ng/mL, between 40 ng/mL and 50 ng/mL, and between 50 ng/mL and 100 ng/mL of OKT-3 antibody. In some embodiments, the cell culture medium does not comprise OKT-3 antibody. In some embodiments, the OKT-3 antibody is muromonab.

In some embodiments, the cell culture medium comprises one or more TNFRSF agonists in a cell culture medium. In some embodiments, the TNFRSF agonist comprises a 4-1BB agonist. In some embodiments, the TNFRSF agonist is a 4-1BB agonist, and the 4-1BB agonist is selected from the group consisting of urelumab, utomilumab, EU-101, a fusion protein, and fragments, derivatives, variants, biosimilars, and combinations thereof. In some embodiments, the TNFRSF agonist is added at a concentration sufficient to achieve a concentration in the cell culture medium of between 0.1 μg/mL and 100 μg/mL. In some embodiments, the TNFRSF agonist is added at a concentration sufficient to achieve a concentration in the cell culture medium of between 20 μg/mL and 40 μg/mL.

In some embodiments, in addition to one or more TNFRSF agonists, the cell culture medium further comprises IL-2 at an initial concentration of about 3000 IU/mL and OKT-3 antibody at an initial concentration of about 30 ng/mL, and wherein the one or more TNFRSF agonists comprises a 4-1BB agonist.

In some embodiments, the first expansion culture medium is referred to as "CM", an abbreviation for culture media. In some embodiments, it is referred to as CM1 (culture medium 1). In some embodiments, CM consists of RPMI 1640 with GlutaMAX, supplemented with 10% human AB serum, 25 mM Hepes, and 10 mg/mL gentamicin. In embodiments where cultures are initiated in gas-permeable flasks with a 40 mL capacity and a 10 $cm^2$ gas-permeable silicon bottom (for example, G-Rex 10; Wilson Wolf Manufacturing, New Brighton, MN), each flask was loaded with $10\text{-}40\times10^6$ viable tumor digest cells or 5-30 tumor fragments in $10^{-40}$ mL of CM with IL-2. Both the G-Rex 10 and 24-well plates were incubated in a humidified incubator at 37° C. in 5% $CO_2$ and 5 days after culture initiation, half the media was removed and replaced with fresh CM and IL-2 and after day 5, half the media was changed every 2-3 days. In some embodiments, the CM is the CM1 described in the Examples, see, Example 1. In some embodiments, the first expansion occurs in an initial cell culture medium or a first cell culture medium. In some embodiments, the initial cell culture medium or the first cell culture medium comprises IL-2.

Figure 4:
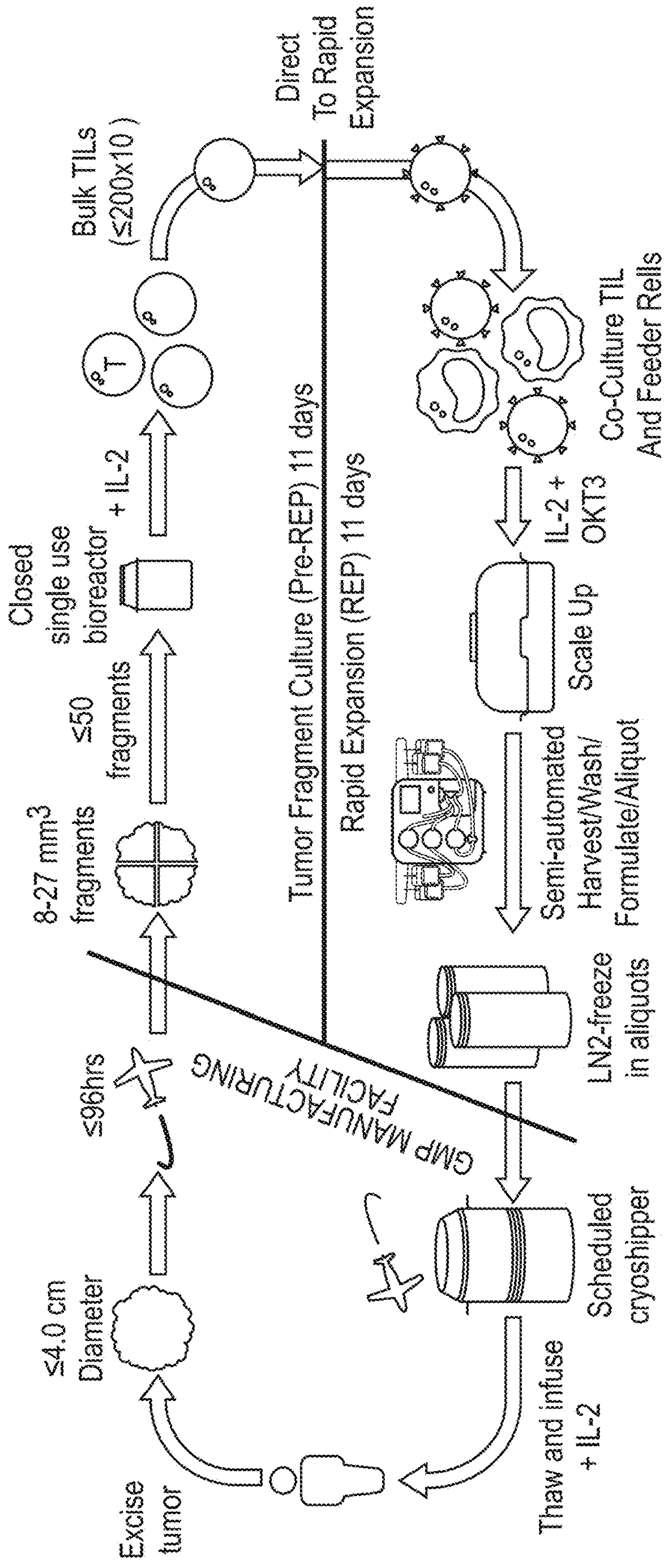
FIG. 4: Shows a diagram of an embodiment of Gen 2 (process 2A), a 22-day process for TIL manufacturing.
Figure 7:
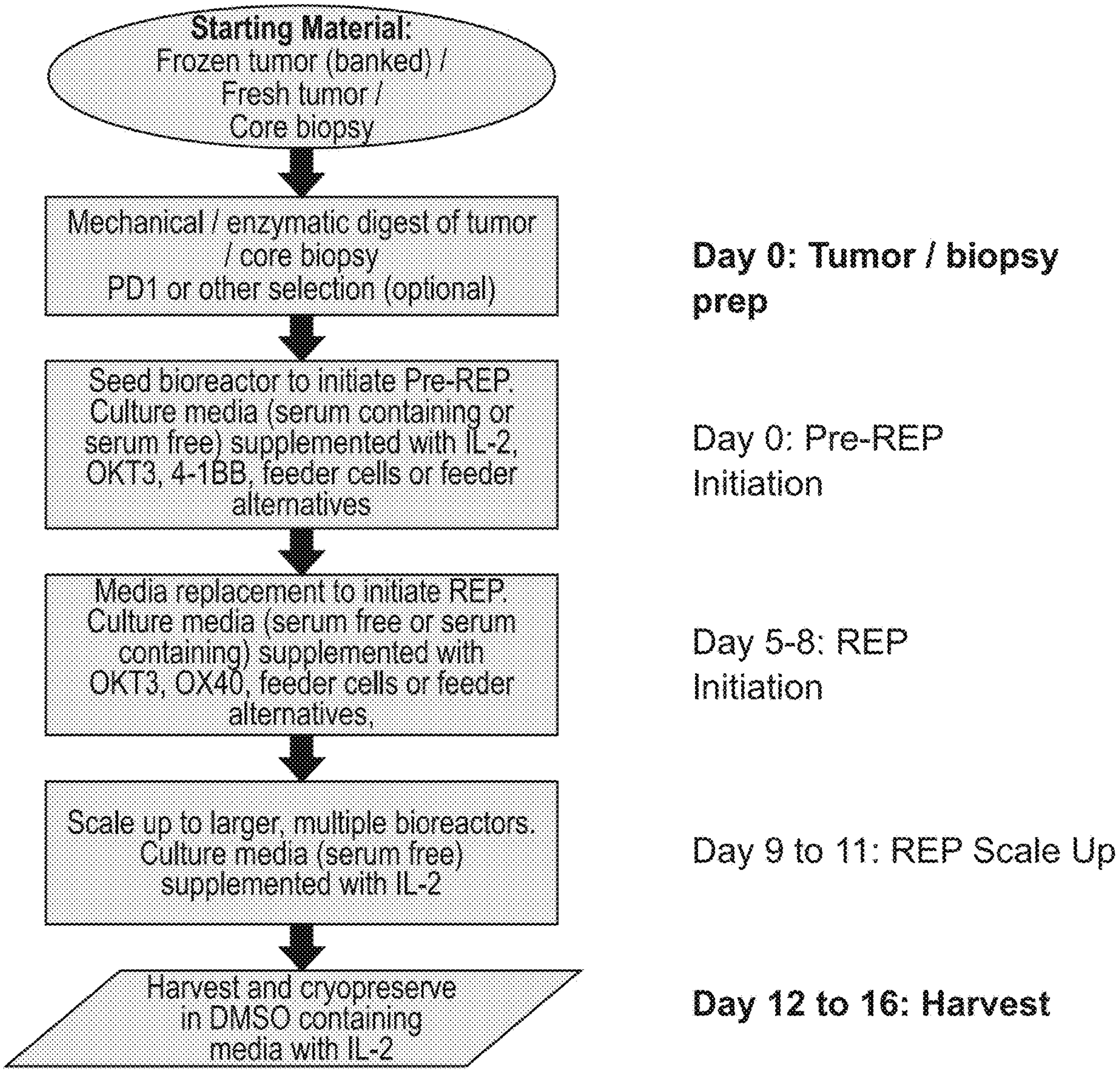
FIG. 7: Exemplary Gen 3 type TIL manufacturing process.
Figure 9:
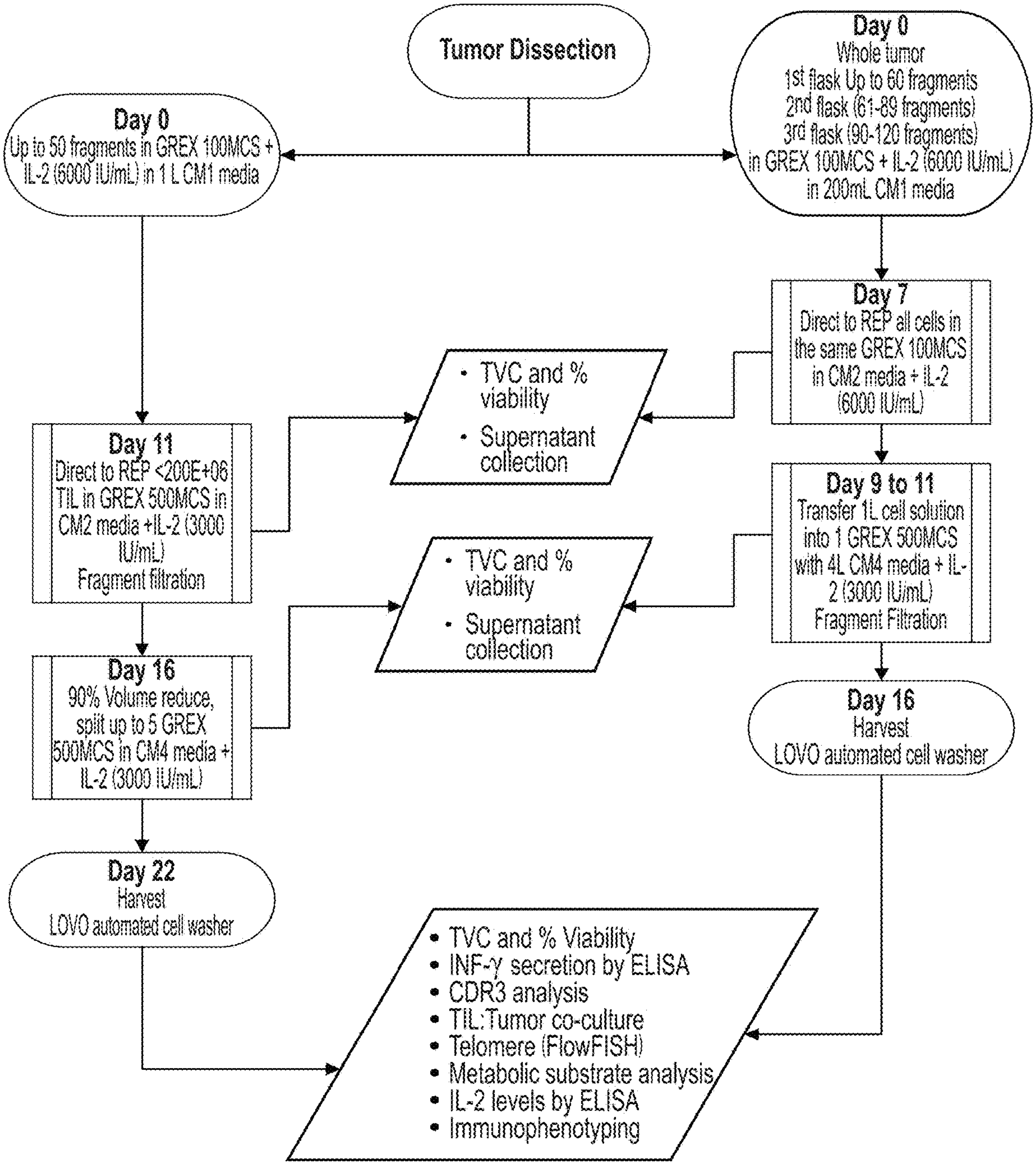
FIG. 9: Provides an experimental flow chart for comparability between Gen 2 (process 2A) versus Gen 3 processes.
Figure 10:
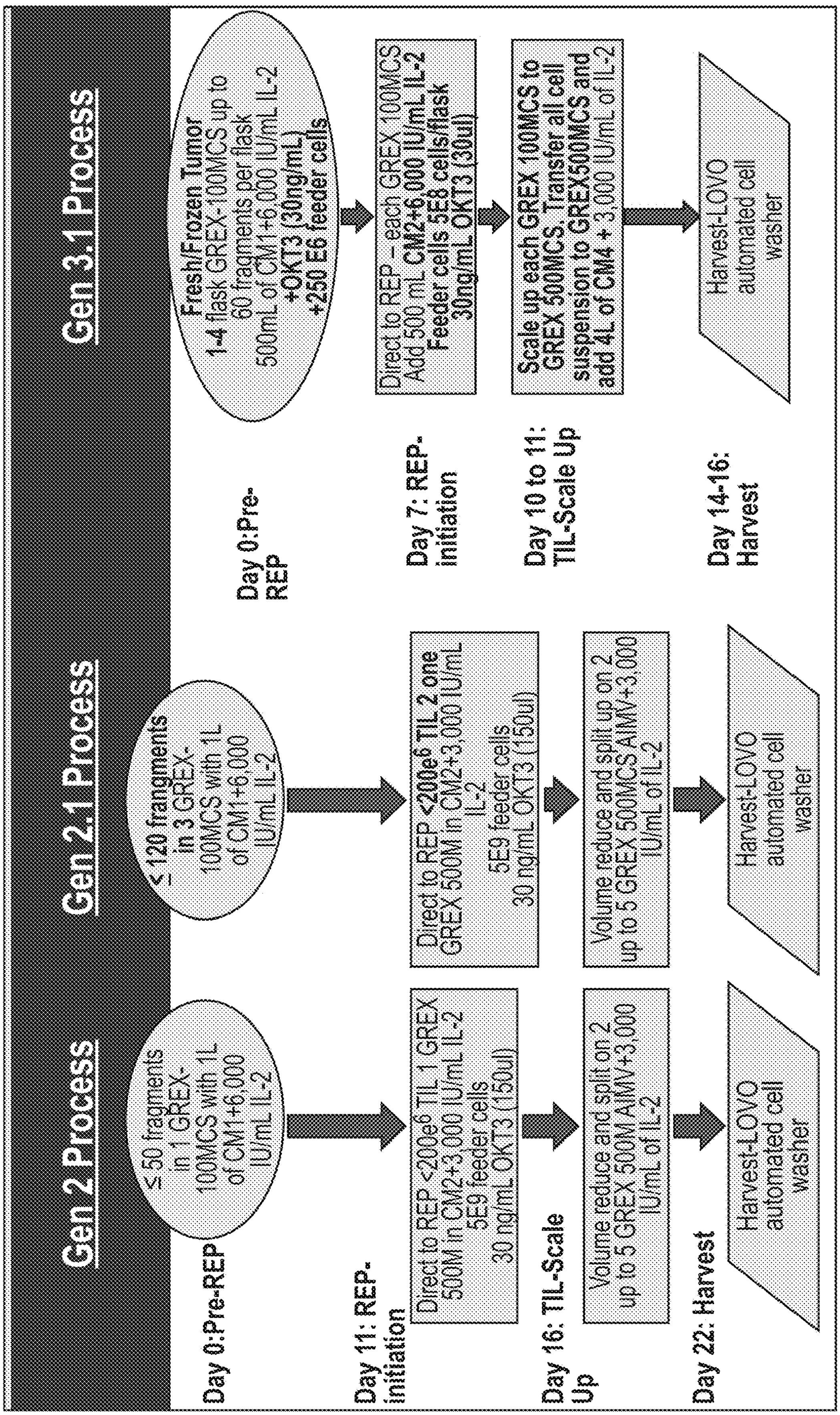
FIG. 10: Shows a comparison between various Gen 2 (process 2A) and the Gen 3.1 process embodiment.
Figure 16:
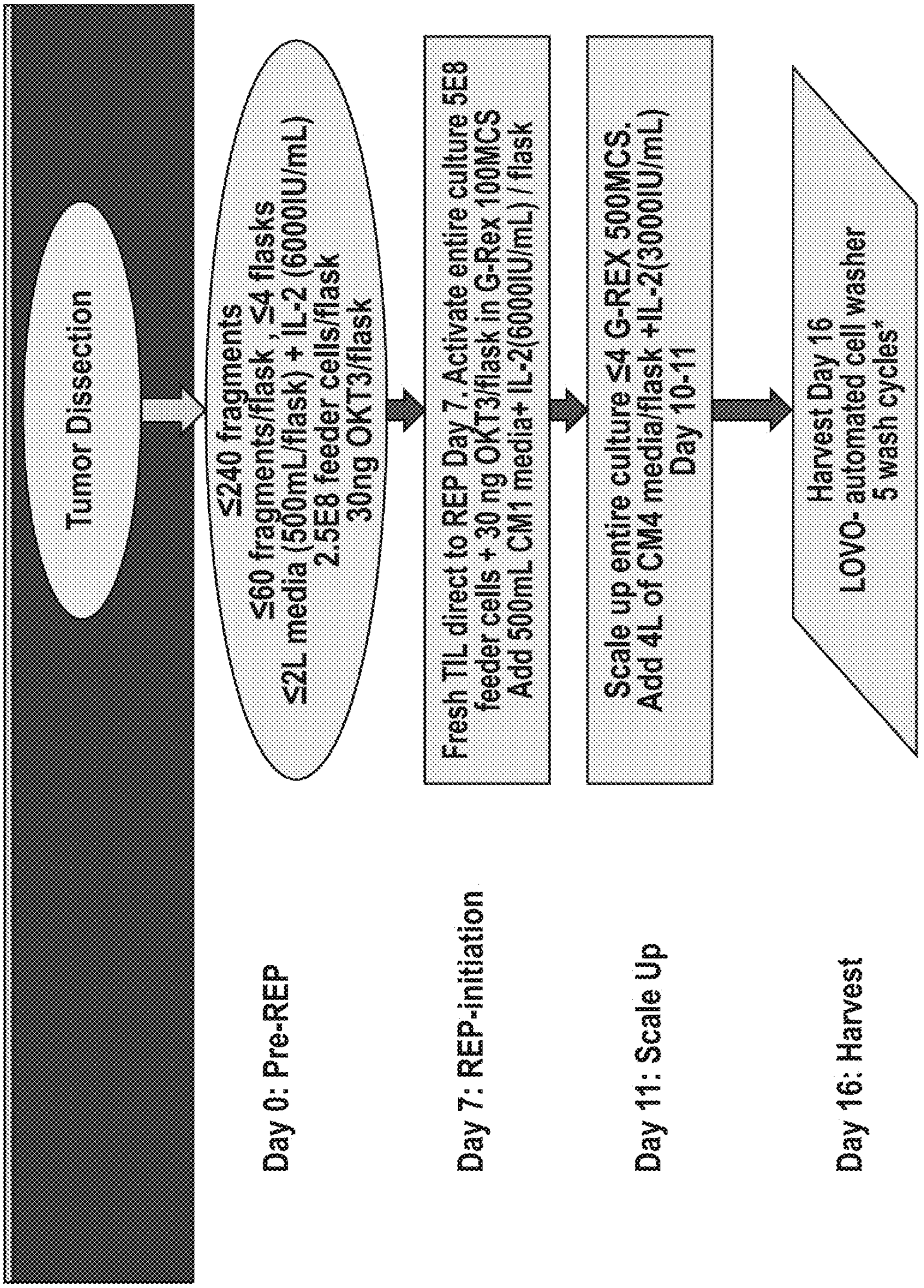
FIG. 16: Schematic of an exemplary embodiment of the Gen 3 process (a 16-day process).
Figure 17:
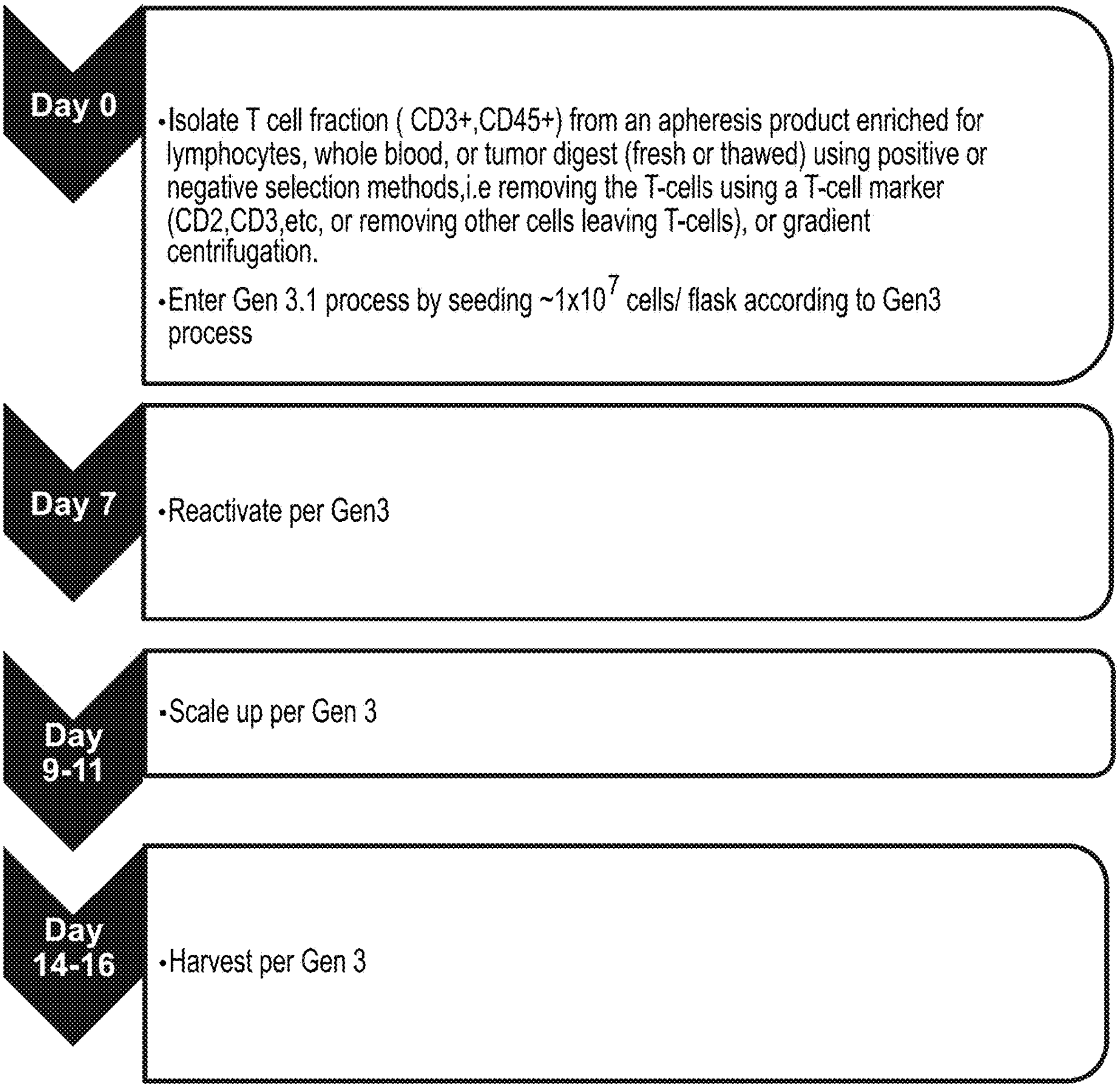
FIG. 17: Schematic of an exemplary embodiment of a method for expanding T cells from hematopoietic malignancies using Gen 3 expansion platform.

In some embodiments, the first expansion (including processes such as for example those described in Step B of FIG. 1, which can include those sometimes referred to as the pre-REP) process is shortened to 3-14 days, as discussed in the examples and figures. In some embodiments, the first expansion (including processes such as for example those described in Step B of FIG. 1, which can include those sometimes referred to as the pre-REP) is shortened to 7 to 14 days, as discussed in the Examples and shown in FIGS. 4 and 5, as well as including for example, an expansion as described in Step B of FIG. 1. In some embodiments, the first expansion of Step B is shortened to $10^{-14}$ days. In some embodiments, the first expansion is shortened to 11 days, as discussed in, for example, an expansion as described in Step B of FIG. 1.

In some embodiments, the first TIL expansion can proceed for 1 day, 2 days, 3 days, 4 days, 5 days, 6 days, 7 days, 8 days, 9 days, 10 days, 11 days, 12 days, 13 days, or 14 days. In some embodiments, the first TIL expansion can proceed for 1 day to 14 days. In some embodiments, the first TIL expansion can proceed for 2 days to 14 days. In some embodiments, the first TIL expansion can proceed for 3 days to 14 days. In some embodiments, the first TIL expansion can proceed for 4 days to 14 days. In some embodiments, the first TIL expansion can proceed for 5 days to 14 days. In some embodiments, the first TIL expansion can proceed for 6 days to 14 days. In some embodiments, the first TIL expansion can proceed for 7 days to 14 days. In some embodiments, the first TIL expansion can proceed for 8 days to 14 days. In some embodiments, the first TIL expansion can proceed for 9 days to 14 days. In some embodiments, the first TIL expansion can proceed for 10 days to 14 days. In some embodiments, the first TIL expansion can proceed for 11 days to 14 days. In some embodiments, the first TIL expansion can proceed for 12 days to 14 days. In some embodiments, the first TIL expansion can proceed for 13 days to 14 days. In some embodiments, the first TIL expansion can proceed for 14 days. In some embodiments, the first TIL expansion can proceed for 1 day to 11 days. In some embodiments, the first TIL expansion can proceed for 2 days to 11 days. In some embodiments, the first TIL expansion can proceed for 3 days to 11 days. In some embodiments, the first TIL expansion can proceed for 4 days to 11 days. In some embodiments, the first TIL expansion can proceed for 5 days to 11 days. In some embodiments, the first TIL expansion can proceed for 6 days to 11 days. In some embodiments, the first TIL expansion can proceed for 7 days to 11 days. In some embodiments, the first TIL expansion can proceed for 8 days to 11 days. In some embodiments, the first TIL expansion can proceed for 9 days to 11 days. In some embodiments, the first TIL expansion can proceed for 10 days to 11 days. In some embodiments, the first TIL expansion can proceed for 11 days.

In some embodiments, a combination of IL-2, IL-7, IL-15, and/or IL-21 are employed as a combination during the first expansion. In some embodiments, IL-2, IL-7, IL-15, and/or IL-21 as well as any combinations thereof can be included during the first expansion, including for example during a Step B processes according to FIG. 1, as well as described herein. In some embodiments, a combination of IL-2, IL-15, and IL-21 are employed as a combination during the first expansion. In some embodiments, IL-2, IL-15, and IL-21 as well as any combinations thereof can be included during Step B processes according to FIG. 1 and as described herein.

In some embodiments, the first expansion (including processes referred to as the pre-REP; for example, Step B according to FIG. 1) process is shortened to 3 to 14 days, as discussed in the examples and figures. In some embodiments, the first expansion of Step B is shortened to 7 to 14 days. In some embodiments, the first expansion of Step B is shortened to 10 to 14 days. In some embodiments, the first expansion is shortened to 11 days.

In some embodiments, the first expansion, for example, Step B according to FIG. 1, is performed in a closed system bioreactor. In some embodiments, a closed system is employed for the TIL expansion, as described herein. In some embodiments, a single bioreactor is employed. In some embodiments, the single bioreactor employed is for example a G-Rex 10 or a G-Rex 100. In some embodiments, the closed system bioreactor is a single bioreactor.

C. STEP C: First Expansion to Second Expansion Transition

In some cases, the bulk TIL population obtained from the first expansion, including for example the TIL population obtained from for example, Step B as indicated in FIG. 1, can be cryopreserved immediately, using the protocols discussed herein below. Alternatively, the TIL population obtained from the first expansion, referred to as the second TIL population, can be subjected to a second expansion (which can include expansions sometimes referred to as REP) and then cryopreserved as discussed below. Similarly, in the case where genetically modified TILs will be used in therapy, the first TIL population (sometimes referred to as the bulk TIL population) or the second TIL population (which can in some embodiments include populations referred to as the REP TIL populations) can be subjected to genetic modifications for suitable treatments prior to expansion or after the first expansion and prior to the second expansion.

In some embodiments, the TILs obtained from the first expansion (for example, from Step B as indicated in FIG. 1) are stored until phenotyped for selection. In some embodiments, the TILs obtained from the first expansion (for example, from Step B as indicated in FIG. 1) are not stored and proceed directly to the second expansion. In some embodiments, the TILs obtained from the first expansion are not cryopreserved after the first expansion and prior to the second expansion. In some embodiments, the transition from the first expansion to the second expansion occurs at about 3 days, 4, days, 5 days, 6 days, 7 days, 8 days, 9 days, 10 days, 11 days, 12 days, 13 days, or 14 days from when fragmentation occurs. In some embodiments, the transition from the first expansion to the second expansion occurs at about 3 days to 14 days from when fragmentation occurs. In some embodiments, the transition from the first expansion to the second expansion occurs at about 4 days to 14 days from when fragmentation occurs. In some embodiments, the transition from the first expansion to the second expansion occurs at about 4 days to 10 days from when fragmentation occurs. In some embodiments, the transition from the first expansion to the second expansion occurs at about 7 days to 14 days from when fragmentation occurs. In some embodiments, the transition from the first expansion to the second expansion occurs at about 14 days from when fragmentation occurs.

In some embodiments, the transition from the first expansion to the second expansion occurs at 1 day, 2 days, 3 days, 4 days, 5 days, 6 days, 7 days, 8 days, 9 days, 10 days, 11 days, 12 days, 13 days, or 14 days from when fragmentation occurs. In some embodiments, the transition from the first expansion to the second expansion occurs 1 day to 14 days from when fragmentation occurs. In some embodiments, the first TIL expansion can proceed for 2 days to 14 days. In some embodiments, the transition from the first expansion to the second expansion occurs 3 days to 14 days from when fragmentation occurs. In some embodiments, the transition from the first expansion to the second expansion occurs 4 days to 14 days from when fragmentation occurs. In some embodiments, the transition from the first expansion to the second expansion occurs 5 days to 14 days from when fragmentation occurs. In some embodiments, the transition from the first expansion to the second expansion occurs 6 days to 14 days from when fragmentation occurs. In some embodiments, the transition from the first expansion to the second expansion occurs 7 days to 14 days from when fragmentation occurs. In some embodiments, the transition from the first expansion to the second expansion occurs 8 days to 14 days from when fragmentation occurs. In some embodiments, the transition from the first expansion to the second expansion occurs 9 days to 14 days from when fragmentation occurs. In some embodiments, the transition from the first expansion to the second expansion occurs 10 days to 14 days from when fragmentation occurs. In some embodiments, the transition from the first expansion to the second expansion occurs 11 days to 14 days from when fragmentation occurs. In some embodiments, the transition from the first expansion to the second expansion occurs 12 days to 14 days from when fragmentation occurs. In some embodiments, the transition from the first expansion to the second expansion occurs 13 days to 14 days from when fragmentation occurs. In some embodiments, the transition from the first expansion to the second expansion occurs 14 days from when fragmentation occurs. In some embodiments, the transition from the first expansion to the second expansion occurs 1 day to 11 days from when fragmentation occurs. In some embodiments, the transition from the first expansion to the second expansion occurs 2 days to 11 days from when fragmentation occurs. In some embodiments, the transition from the first expansion to the second expansion occurs 3 days to 11 days from when fragmentation occurs. In some embodiments, the transition from the first expansion to the second expansion occurs 4 days to 11 days from when fragmentation occurs. In some embodiments, the transition from the first expansion to the second expansion occurs 5 days to 11 days from when fragmentation occurs. In some embodiments, the transition from the first expansion to the second expansion occurs 6 days to 11 days from when fragmentation occurs. In some embodiments, the transition from the first expansion to the second expansion occurs 7 days to 11 days from when fragmentation occurs. In some embodiments, the transition from the first expansion to the second expansion occurs 8 days to 11 days from when fragmentation occurs. In some embodiments, the transition from the first expansion to the second expansion occurs 9 days to 11 days from when fragmentation occurs. In some embodiments, the transition from the first expansion to the second expansion occurs 10 days to 11 days from when fragmentation occurs. In some embodiments, the transition from the first expansion to the second expansion occurs 11 days from when fragmentation occurs.

In some embodiments, the TILs are not stored after the first expansion and prior to the second expansion, and the TILs proceed directly to the second expansion (for example, in some embodiments, there is no storage during the transition from Step B to Step D as shown in FIG. 1). In some embodiments, the transition occurs in closed system, as described herein. In some embodiments, the TILs from the first expansion, the second population of TILs, proceeds directly into the second expansion with no transition period.

In some embodiments, the transition from the first expansion to the second expansion, for example, Step C according to FIG. 1, is performed in a closed system bioreactor. In some embodiments, a closed system is employed for the TIL expansion, as described herein. In some embodiments, a single bioreactor is employed. In some embodiments, the single bioreactor employed is for example a G-Rex 10 or a G-Rex 100. In some embodiments, the closed system bioreactor is a single bioreactor.

1. Cytokines

The expansion methods described herein generally use culture media with high doses of a cytokine, in particular IL-2, as is known in the art.

Alternatively, using combinations of cytokines for the rapid expansion and or second expansion of TILs is additionally possible, with combinations of two or more of IL-2, IL-15 and IL-21 as is described in U.S. Patent Application Publication No. US 2017/0107490 A1 and International Patent Application Publication No. WO 2015/189357, each of which is hereby expressly incorporated by reference in their entirety. Thus, possible combinations include IL-2 and IL-15, IL-2 and IL-21, IL-15 and IL-21 and IL-2, IL-15 and IL-21, with the latter finding particular use in many embodiments. The use of combinations of cytokines specifically favors the generation of lymphocytes, and in particular T cells as described therein.

D. STEP D: Second Expansion

In some embodiments, the TIL cell population is expanded in number after harvest and initial bulk processing for example, after Step A and Step B, and the transition referred to as Step C, as indicated in FIG. 1). This further expansion is referred to herein as the second expansion, which can include expansion processes generally referred to in the art as a rapid expansion process (REP; as well as processes as indicated in Step D of FIG. 1). The second expansion is generally accomplished using a culture media comprising a number of components, including feeder cells, a cytokine source, and an anti-CD3 antibody, in a gas-permeable container.

In some embodiments, the second expansion or second TIL expansion (which can include expansions sometimes referred to as REP; as well as processes as indicated in Step D of FIG. 1) of TIL can be performed using any TIL flasks or containers known by those of skill in the art. In some embodiments, the second TIL expansion can proceed for 7 days, 8 days, 9 days, 10 days, 11 days, 12 days, 13 days, or 14 days. In some embodiments, the second TIL expansion can proceed for about 7 days to about 14 days. In some embodiments, the second TIL expansion can proceed for about 8 days to about 14 days. In some embodiments, the second TIL expansion can proceed for about 9 days to about 14 days. In some embodiments, the second TIL expansion can proceed for about 10 days to about 14 days. In some embodiments, the second TIL expansion can proceed for about 11 days to about 14 days. In some embodiments, the second TIL expansion can proceed for about 12 days to about 14 days. In some embodiments, the second TIL expansion can proceed for about 13 days to about 14 days. In some embodiments, the second TIL expansion can proceed for about 14 days.

In an embodiment, the second expansion can be performed in a gas permeable container using the methods of the present disclosure (including for example, expansions referred to as REP; as well as processes as indicated in Step D of FIG. 1). For example, TILs can be rapidly expanded using non-specific T cell receptor stimulation in the presence of interleukin-2 (IL-2) or interleukin-15 (IL-15). The non-specific T cell receptor stimulus can include, for example, an anti-CD3 antibody, such as about 30 ng/mL of OKT3, a mouse monoclonal anti-CD3 antibody (commercially available from Ortho-McNeil, Raritan, NJ or Miltenyi Biotech, Auburn, CA) or UHCT-1 (commercially available from BioLegend, San Diego, CA, USA). TILs can be expanded to induce further stimulation of the TILs in vitro by including one or more antigens during the second expansion, including antigenic portions thereof, such as epitope(s), of the cancer, which can be optionally expressed from a vector, such as a human leukocyte antigen A2 (HLA-A2) binding peptide, e.g., 0.3 μM MART-1:26-35 (27 L) or gpl 00:209-217 (210M), optionally in the presence of a T cell growth factor, such as 300 IU/mL IL-2 or IL-15. Other suitable antigens may include, e.g., NY-ESO-1, TRP-1, TRP-2, tyrosinase cancer antigen, MAGE-A3, SSX-2, and VEGFR2, or antigenic portions thereof. TIL may also be rapidly expanded by re-stimulation with the same antigen(s) of the cancer pulsed onto HLA-A2-expressing antigen-presenting cells. Alternatively, the TILs can be further re-stimulated with, e.g., example, irradiated, autologous lymphocytes or with irradiated HLA-A2+ allogeneic lymphocytes and IL-2. In some embodiments, the re-stimulation occurs as part of the second expansion. In some embodiments, the second expansion occurs in the presence of irradiated, autologous lymphocytes or with irradiated HLA-A2+ allogeneic lymphocytes and IL-2.

In an embodiment, the cell culture medium further comprises IL-2. In some embodiments, the cell culture medium comprises about 3000 IU/mL of IL-2. In an embodiment, the cell culture medium comprises about 1000 IU/mL, about 1500 IU/mL, about 2000 IU/mL, about 2500 IU/mL, about 3000 IU/mL, about 3500 IU/mL, about 4000 IU/mL, about 4500 IU/mL, about 5000 IU/mL, about 5500 IU/mL, about 6000 IU/mL, about 6500 IU/mL, about 7000 IU/mL, about 7500 IU/mL, or about 8000 IU/mL of IL-2. In an embodiment, the cell culture medium comprises between 1000 and 2000 IU/mL, between 2000 and 3000 IU/mL, between 3000 and 4000 IU/mL, between 4000 and 5000 IU/mL, between 5000 and 6000 IU/mL, between 6000 and 7000 IU/mL, between 7000 and 8000 IU/mL, or between 8000 IU/mL of IL-2.

In an embodiment, the cell culture medium comprises OKT-3 antibody. In some embodiments, the cell culture medium comprises about 30 ng/mL of OKT-3 antibody. In an embodiment, the cell culture medium comprises about 0.1 ng/mL, about 0.5 ng/mL, about 1 ng/mL, about 2.5 ng/mL, about 5 ng/mL, about 7.5 ng/mL, about 10 ng/mL, about 15 ng/mL, about 20 ng/mL, about 25 ng/mL, about 30 ng/mL, about 35 ng/mL, about 40 ng/mL, about 50 ng/mL, about 60 ng/mL, about 70 ng/mL, about 80 ng/mL, about 90 ng/mL, about 100 ng/mL, about 200 ng/mL, about 500 ng/mL, and about 1 μg/mL of OKT-3 antibody. In an embodiment, the cell culture medium comprises between 0.1 ng/mL and 1 ng/mL, between 1 ng/mL and 5 ng/mL, between 5 ng/mL and 10 ng/mL, between 10 ng/mL and 20 ng/mL, between 20 ng/mL and 30 ng/mL, between 30 ng/mL and 40 ng/mL, between 40 ng/mL and 50 ng/mL, and between 50 ng/mL and 100 ng/mL of OKT-3 antibody. In some embodiments, the cell culture medium does not comprise OKT-3 antibody. In some embodiments, the OKT-3 antibody is muromonab.

In some embodiments, the cell culture medium comprises one or more TNFRSF agonists in a cell culture medium. In some embodiments, the TNFRSF agonist comprises a 4-1BB agonist. In some embodiments, the TNFRSF agonist is a 4-1BB agonist, and the 4-1BB agonist is selected from the group consisting of urelumab, utomilumab, EU-101, a fusion protein, and fragments, derivatives, variants, biosimilars, and combinations thereof. In some embodiments, the TNFRSF agonist is added at a concentration sufficient to achieve a concentration in the cell culture medium of between 0.1 μg/mL and 100 μg/mL. In some embodiments, the TNFRSF agonist is added at a concentration sufficient to achieve a concentration in the cell culture medium of between 20 μg/mL and 40 μg/mL.

In some embodiments, in addition to one or more TNFRSF agonists, the cell culture medium further comprises IL-2 at an initial concentration of about 3000 IU/mL and OKT-3 antibody at an initial concentration of about 30 ng/mL, and wherein the one or more TNFRSF agonists comprises a 4-1BB agonist.

In some embodiments, a combination of IL-2, IL-7, IL-15, and/or IL-21 are employed as a combination during the second expansion. In some embodiments, IL-2, IL-7, IL-15, and/or IL-21 as well as any combinations thereof can be included during the second expansion, including for example during a Step D processes according to FIG. 1, as well as described herein. In some embodiments, a combination of IL-2, IL-15, and IL-21 are employed as a combination during the second expansion. In some embodiments, IL-2, IL-15, and IL-21 as well as any combinations thereof can be included during Step D processes according to FIG. 1 and as described herein.

In some embodiments, the second expansion can be conducted in a supplemented cell culture medium comprising IL-2, OKT-3, antigen-presenting feeder cells, and optionally a TNFRSF agonist. In some embodiments, the second expansion occurs in a supplemented cell culture medium. In some embodiments, the supplemented cell culture medium comprises IL-2, OKT-3, and antigen-presenting feeder cells. In some embodiments, the second cell culture medium comprises IL-2, OKT-3, and antigen-presenting cells (APCs; also referred to as antigen-presenting feeder cells). In some embodiments, the second expansion occurs in a cell culture medium comprising IL-2, OKT-3, and antigen-presenting feeder cells (i.e., antigen presenting cells).

In some embodiments, the second expansion culture media comprises about 500 IU/mL of IL-15, about 400 IU/mL of IL-15, about 300 IU/mL of IL-15, about 200 IU/mL of IL-15, about 180 IU/mL of IL-15, about 160 IU/mL of IL-15, about 140 IU/mL of IL-15, about 120 IU/mL of IL-15, or about 100 IU/mL of IL-15. In some embodiments, the second expansion culture media comprises about 500 IU/mL of IL-15 to about 100 IU/mL of IL-15. In some embodiments, the second expansion culture media comprises about 400 IU/mL of IL-15 to about 100 IU/mL of IL-15. In some embodiments, the second expansion culture media comprises about 300 IU/mL of IL-15 to about 100 IU/mL of IL-15. In some embodiments, the second expansion culture media comprises about 200 IU/mL of IL-15. In some embodiments, the cell culture medium comprises about 180 IU/mL of IL-15. In an embodiment, the cell culture medium further comprises IL-15. In a preferred embodiment, the cell culture medium comprises about 180 IU/mL of IL-15.

In some embodiments, the second expansion culture media comprises about 20 IU/mL of IL-21, about 15 IU/mL of IL-21, about 12 IU/mL of IL-21, about 10 IU/mL of IL-21, about 5 IU/mL of IL-21, about 4 IU/mL of IL-21, about 3 IU/mL of IL-21, about 2 IU/mL of IL-21, about 1 IU/mL of IL-21, or about 0.5 IU/mL of IL-21. In some embodiments, the second expansion culture media comprises about 20 IU/mL of IL-21 to about 0.5 IU/mL of IL-21. In some embodiments, the second expansion culture media comprises about 15 IU/mL of IL-21 to about 0.5 IU/mL of IL-21. In some embodiments, the second expansion culture media comprises about 12 IU/mL of IL-21 to about 0.5 IU/mL of IL-21. In some embodiments, the second expansion culture media comprises about 10 IU/mL of IL-21 to about 0.5 IU/mL of IL-21. In some embodiments, the second expansion culture media comprises about 5 IU/mL of IL-21 to about 1 IU/mL of IL-21. In some embodiments, the second expansion culture media comprises about 2 IU/mL of IL-21. In some embodiments, the cell culture medium comprises about 1 IU/mL of IL-21. In some embodiments, the cell culture medium comprises about 0.5 IU/mL of IL-21. In an embodiment, the cell culture medium further comprises IL-21. In a preferred embodiment, the cell culture medium comprises about 1 IU/mL of IL-21.

In some embodiments the antigen-presenting feeder cells (APCs) are PBMCs. In an embodiment, the ratio of TILs to PBMCs and/or antigen-presenting cells in the rapid expansion and/or the second expansion is about 1 to 25, about 1 to 50, about 1 to 100, about 1 to 125, about 1 to 150, about 1 to 175, about 1 to 200, about 1 to 225, about 1 to 250, about 1 to 275, about 1 to 300, about 1 to 325, about 1 to 350, about 1 to 375, about 1 to 400, or about 1 to 500. In an embodiment, the ratio of TILs to PBMCs in the rapid expansion and/or the second expansion is between 1 to 50 and 1 to 300. In an embodiment, the ratio of TILs to PBMCs in the rapid expansion and/or the second expansion is between 1 to 100 and 1 to 200.

In an embodiment, REP and/or the second expansion is performed in flasks with the bulk TILs being mixed with a 100- or 200-fold excess of inactivated feeder cells, 30 mg/mL OKT3 anti-CD3 antibody and 3000 IU/mL IL-2 in 150 mL media. Media replacement is done (generally 2/3 media replacement via respiration with fresh media) until the cells are transferred to an alternative growth chamber. Alternative growth chambers include G-Rex flasks and gas permeable containers as more fully discussed below.

In some embodiments, the second expansion (which can include processes referred to as the REP process) is shortened to 7-14 days, as discussed in the examples and figures. In some embodiments, the second expansion is shortened to 11 days.

In an embodiment, REP and/or the second expansion may be performed using T-175 flasks and gas permeable bags as previously described (Tran, et al., *J. Immunother.* 2008, 31, 742-51; Dudley, et al., *J. Immunother.* 2003, 26, 332-42) or gas permeable cultureware (G-Rex flasks). In some embodiments, the second expansion (including expansions referred to as rapid expansions) is performed in T-175 flasks, and about $1\times10^6$ TILs suspended in 150 mL of media may be added to each T-175 flask. The TILs may be cultured in a 1 to 1 mixture of CM and AIM-V medium, supplemented with 3000 IU per mL of IL-2 and 30 ng per mL of anti-CD3. The T-175 flasks may be incubated at 37° C. in 5% $CO_2$. Half the media may be exchanged on day 5 using 50/50 medium with 3000 IU per mL of IL-2. In some embodiments, on day 7 cells from two T-175 flasks may be combined in a 3 L bag and 300 mL of AIM-V with 5% human AB serum and 3000 IU per mL of IL-2 was added to the 300 mL of TIL suspension. The number of cells in each bag was counted every day or two and fresh media was added to keep the cell count between 0.5 and $2.0\times10^6$ cells/mL.

In an embodiment, the second expansion (which can include expansions referred to as REP, as well as those referred to in Step D of FIG. 1) may be performed in 500 mL capacity gas permeable flasks with 100 cm gas-permeable silicon bottoms (G-Rex 100, commercially available from Wilson Wolf Manufacturing Corporation, New Brighton, MN, USA), $5\times10^6$ or $10\times10^6$ TIL may be cultured with PBMCs in 400 mL of 50/50 medium, supplemented with 5% human AB serum, 3000 IU per mL of IL-2 and 30 ng per mL of anti-CD3 (OKT3). The G-Rex 100 flasks may be incubated at 37° C. in 5% $CO_2$. On day 5, 250 mL of supernatant may be removed and placed into centrifuge bottles and centrifuged at 1500 rpm (491× g) for 10 minutes. The TIL pellets may be re-suspended with 150 mL of fresh medium with 5% human AB serum, 3000 IU per mL of IL-2, and added back to the original G-Rex 100 flasks. When TIL are expanded serially in G-Rex 100 flasks, on day 7 the TIL in each G-Rex 100 may be suspended in the 300 mL of media present in each flask and the cell suspension may be divided into 3 100 mL aliquots that may be used to seed 3 G-Rex 100 flasks. Then 150 mL of AIM-V with 5% human AB serum and 3000 IU per mL of IL-2 may be added to each flask. The G-Rex 100 flasks may be incubated at 37° C. in 5% $CO_2$ and after 4 days 150 mL of AIM-V with 3000 IU per mL of IL-2 may be added to each G-Rex 100 flask. The cells may be harvested on day 14 of culture.

In an embodiment, the second expansion (including expansions referred to as REP) is performed in flasks with the bulk TILs being mixed with a 100- or 200-fold excess of inactivated feeder cells, 30 mg/mL OKT3 anti-CD3 antibody and 3000 IU/mL IL-2 in 150 mL media. In some embodiments, media replacement is done until the cells are transferred to an alternative growth chamber. In some embodiments, 2/3 of the media is replaced by respiration with fresh media. In some embodiments, alternative growth chambers include G-Rex flasks and gas permeable containers as more fully discussed below.

In an embodiment, the second expansion (including expansions referred to as REP) is performed and further comprises a step wherein TILs are selected for superior tumor reactivity. Any selection method known in the art may be used. For example, the methods described in U.S. Patent Application Publication No. 2016/0010058 A1, the disclosures of which are incorporated herein by reference, may be used for selection of TILs for superior tumor reactivity.

Optionally, a cell viability assay can be performed after the second expansion (including expansions referred to as the REP expansion), using standard assays known in the art. For example, a trypan blue exclusion assay can be done on a sample of the bulk TILs, which selectively labels dead cells and allows a viability assessment. In some embodiments, TIL samples can be counted and viability determined using a Cellometer K2 automated cell counter (Nexcelom Bioscience, Lawrence, MA). In some embodiments, viability is determined according to the standard Cellometer K2 Image Cytometer Automatic Cell Counter protocol.

In some embodiments, the second expansion (including expansions referred to as REP) of TIL can be performed using T-175 flasks and gas-permeable bags as previously described (Tran K Q, Zhou J, Durflinger K H, et al., 2008, *J Immunother.*, 31:742-751, and Dudley M E, Wunderlich J R, Shelton T E, et al. 2003, *J Immunother.*, 26:332-342) or gas-permeable G-Rex flasks. In some embodiments, the second expansion is performed using flasks. In some embodiments, the second expansion is performed using gas-permeable G-Rex flasks. In some embodiments, the second expansion is performed in T-175 flasks, and about $1\times10^6$ TILs are suspended in about 150 mL of media and this is added to each T-175 flask. The TIL are cultured with irradiated (50 Gy) allogeneic PBMC as "feeder" cells at a ratio of 1 to 100 and the cells were cultured in a 1 to 1 mixture of CM and AIM-V medium (50/50 medium), supplemented with 3000 IU/mL of IL-2 and 30 ng/mL of anti-CD3. The T-175 flasks are incubated at 37° C. in 5% $CO_2$. In some embodiments, half the media is changed on day 5 using 50/50 medium with 3000 IU/mL of IL-2. In some embodiments, on day 7, cells from 2 T-175 flasks are combined in a 3 L bag and 300 mL of AIM-V with 5% human AB serum and 3000 IU/mL of IL-2 is added to the 300 mL of TIL suspension. The number of cells in each bag can be counted every day or two and fresh media can be added to keep the cell count between about 0.5 and about $2.0\times10^6$ cells/mL.

In some embodiments, the second expansion (including expansions referred to as REP) are performed in 500 mL capacity flasks with 100 $cm^2$ gas-permeable silicon bottoms (G-Rex 100, Wilson Wolf), about $5\times10^6$ or $10\times10^6$ TIL are cultured with irradiated allogeneic PBMC at a ratio of 1 to 100 in 400 mL of 50/50 medium, supplemented with 3000 IU/mL of IL-2 and 30 ng/mL of anti-CD3. The G-Rex 100 flasks are incubated at 37° C. in 5% $CO_2$. In some embodiments, on day 5, 250 mL of supernatant is removed and placed into centrifuge bottles and centrifuged at 1500 rpm (491 g) for 10 minutes. The TIL pellets can then be resuspended with 150 mL of fresh 50/50 medium with 3000 IU/mL of IL-2 and added back to the original G-Rex 100 flasks. In embodiments where TILs are expanded serially in G-Rex 100 flasks, on day 7 the TIL in each G-Rex 100 are suspended in the 300 mL of media present in each flask and the cell suspension was divided into three 100 mL aliquots that are used to seed 3 G-Rex 100 flasks. Then 150 mL of AIM-V with 5% human AB serum and 3000 IU/mL of IL-2 is added to each flask. The G-Rex 100 flasks are incubated at 37° C. in 5% $CO_2$ and after 4 days 150 mL of AIM-V with 3000 IU/mL of IL-2 is added to each G-Rex 100 flask. The cells are harvested on day 14 of culture.

The diverse antigen receptors of T and B lymphocytes are produced by somatic recombination of a limited, but large number of gene segments. These gene segments: V (variable), D (diversity), J (joining), and C (constant), determine the binding specificity and downstream applications of immunoglobulins and T cell receptors (TCRs). The present invention provides a method for generating TILs which exhibit and increase the T cell repertoire diversity. In some embodiments, the TILs obtained by the present method exhibit an increase in the T cell repertoire diversity. In some embodiments, the TILs obtained in the second expansion exhibit an increase in the T cell repertoire diversity. In some embodiments, the increase in diversity is an increase in the immunoglobulin diversity and/or the T cell receptor diversity. In some embodiments, the diversity is in the immunoglobulin is in the immunoglobulin heavy chain. In some embodiments, the diversity is in the immunoglobulin is in the immunoglobulin light chain. In some embodiments, the diversity is in the T cell receptor. In some embodiments, the diversity is in one of the T cell receptors selected from the group consisting of alpha, beta, gamma, and delta receptors. In some embodiments, there is an increase in the expression of T cell receptor (TCR) alpha and/or beta. In some embodiments, there is an increase in the expression of T cell receptor (TCR) alpha. In some embodiments, there is an increase in the expression of T cell receptor (TCR) beta. In some embodiments, there is an increase in the expression of TCRab (i.e., TCRα/β).

In some embodiments, the second expansion culture medium (e.g., sometimes referred to as CM2 or the second cell culture medium), comprises IL-2, OKT-3, as well as the antigen-presenting feeder cells (APCs), as discussed in more detail below.

In some embodiments, the second expansion, for example, Step D according to FIG. 1, is performed in a closed system bioreactor. In some embodiments, a closed system is employed for the TIL expansion, as described herein. In some embodiments, a single bioreactor is employed. In some embodiments, the single bioreactor employed is for example a G-Rex 10 or a G-Rex 100. In some embodiments, the closed system bioreactor is a single bioreactor.

1. Feeder Cells and Antigen Presenting Cells

In an embodiment, the second expansion procedures described herein (for example including expansion such as those described in Step D from FIG. 1, as well as those referred to as REP) require an excess of feeder cells during REP TIL expansion and/or during the second expansion. In many embodiments, the feeder cells are peripheral blood mononuclear cells (PBMCs) obtained from standard whole blood units from healthy blood donors. The PBMCs are obtained using standard methods such as Ficoll-Paque gradient separation.

In general, the allogeneic PBMCs are inactivated, either via irradiation or heat treatment, and used in the REP procedures, as described in the examples, which provides an exemplary protocol for evaluating the replication incompetence of irradiate allogeneic PBMCs.

In some embodiments, PBMCs are considered replication incompetent and accepted for use in the TIL expansion procedures described herein if the total number of viable cells on day 14 is less than the initial viable cell number put into culture on day 0 of the REP and/or day 0 of the second expansion (i.e., the start day of the second expansion).

In some embodiments, PBMCs are considered replication incompetent and accepted for use in the TIL expansion procedures described herein if the total number of viable cells, cultured in the presence of OKT3 and IL-2, on day 7 and day 14 has not increased from the initial viable cell number put into culture on day 0 of the REP and/or day 0 of the second expansion (i.e., the start day of the second expansion). In some embodiments, the PBMCs are cultured in the presence of 30 ng/mL OKT3 antibody and 3000 IU/mL IL-2.

In some embodiments, PBMCs are considered replication incompetent and accepted for use in the TIL expansion procedures described herein if the total number of viable cells, cultured in the presence of OKT3 and IL-2, on day 7 and day 14 has not increased from the initial viable cell number put into culture on day 0 of the REP and/or day 0 of the second expansion (i.e., the start day of the second expansion). In some embodiments, the PBMCs are cultured in the presence of 5-60 ng/mL OKT3 antibody and 1000-6000 IU/mL IL-2. In some embodiments, the PBMCs are cultured in the presence of 10-50 ng/mL OKT3 antibody and 2000-5000 IU/mL IL-2. In some embodiments, the PBMCs are cultured in the presence of 20-40 ng/mL OKT3 antibody and 2000-4000 IU/mL IL-2. In some embodiments, the PBMCs are cultured in the presence of 25-35 ng/mL OKT3 antibody and 2500-3500 IU/mL IL-2.

In some embodiments, the antigen-presenting feeder cells are PBMCs. In some embodiments, the antigen-presenting feeder cells are artificial antigen-presenting feeder cells. In an embodiment, the ratio of TILs to antigen-presenting feeder cells in the second expansion is about 1 to 25, about 1 to 50, about 1 to 100, about 1 to 125, about 1 to 150, about 1 to 175, about 1 to 200, about 1 to 225, about 1 to 250, about 1 to 275, about 1 to 300, about 1 to 325, about 1 to 350, about 1 to 375, about 1 to 400, or about 1 to 500. In an embodiment, the ratio of TILs to antigen-presenting feeder cells in the second expansion is between 1 to 50 and 1 to 300. In an embodiment, the ratio of TILs to antigen-presenting feeder cells in the second expansion is between 1 to 100 and 1 to 200.

In an embodiment, the second expansion procedures described herein require a ratio of about $2.5\times10^9$ feeder cells to about $100\times10^6$ TILs. In another embodiment, the second expansion procedures described herein require a ratio of about $2.5\times10'$ feeder cells to about $50\times10^6$ TILs. In yet another embodiment, the second expansion procedures described herein require about $2.5\times10^9$ feeder cells to about $25\times10^6$ TILs.

In an embodiment, the second expansion procedures described herein require an excess of feeder cells during the second expansion. In many embodiments, the feeder cells are peripheral blood mononuclear cells (PBMCs) obtained from standard whole blood units from healthy blood donors. The PBMCs are obtained using standard methods such as Ficoll-Paque gradient separation. In an embodiment, artificial antigen-presenting cells (aAPCs) are used in place of PBMCs.

In general, the allogeneic PBMCs are inactivated, either via irradiation or heat treatment, and used in the TIL expansion procedures described herein, including the exemplary procedures described in the figures and examples.

In an embodiment, aAPCs are used in the second expansion as a replacement for, or in combination with, PBMCs.

In an embodiment, the antigen presenting cells used in the second expansion of the Gen 2 process are monocyte cells. In an embodiment, the antigen presenting cells are B cells. In an embodiment, the antigen presenting cells are B cell lymphoblastoid cells or B-lymphoblastoid cells. In an embodiment, the antigen presenting cells are Burkitt's lymphoma cells. In an embodiment, the antigen presenting cells are myeloid lineage cells. In an embodiment, the antigen presenting cells are monocytes. In an embodiment, the antigen presenting cells are HLA-A-02 positive monocytes. In an embodiment, the antigen presenting cells are acute monocytic leukemia cells. In an embodiment, the antigen presenting cells are M5-subtype acute monocytic leukemia cells. In an embodiment, the antigen presenting cells are Raji cells or a derivative, variant, modification, or progeny thereof. In an embodiment, the antigen presenting cells are Thp1 cells or a derivative, variant, modification, or progeny thereof. In an embodiment, the antigen presenting cells are Ramos cells or a derivative, variant, modification, or progeny thereof. In an embodiment, the antigen presenting cells are U937 cells or a derivative, variant, modification, or progeny thereof. In an embodiment, the antigen presenting cells are Daudi cells or a derivative, variant, modification, or progeny thereof. In an embodiment, the antigen presenting cells are melanocyte cells. In an embodiment, the antigen presenting cells are HLA-A-02 positive melanocyte cells. In an embodiment, the antigen presenting cells are melanoma cells. In an embodiment, the antigen presenting cells are HLA-A-02 positive melanoma cells. In an embodiment, the antigen presenting cells are selected from the group consisting of Sk-MEL-5, Malme-3M, SK-MEL-28, SK-MEL-3, SH-4, SK-MEL-24, RPMI-7951, SK-MEL-1, A375, G-361, and combinations thereof, or derivatives, variants, modifications, or progeny thereof. In any of the foregoing embodiments, the antigen presenting cells may be irradiated as described elsewhere herein or non-irradiated.

In an embodiment, aAPCs are used in the second expansion of a Gen 2 process. In an embodiment, the aAPCs are genetically modified monocyte cells. In an embodiment, the aAPCs are genetically modified B cells. In an embodiment, the aAPCs are genetically modified B cell lymphoblastoid cells or B-lymphoblastoid cells. In an embodiment, the aAPCs are genetically modified Burkitt's lymphoma cells. In an embodiment, the aAPCs are genetically modified myeloid lineage cells. In an embodiment, the aAPCs are genetically modified monocytes. In an embodiment, the aAPCs are genetically modified HLA-A-02 positive monocyte cells. In an embodiment, the aAPCs are genetically modified acute monocytic leukemia cells. In an embodiment, the aAPCs are genetically modified M5-subtype acute monocytic leukemia cells. In an embodiment, the aAPCs are genetically modified Raji cells or a derivative, variant, modification, or progeny thereof. In an embodiment, the aAPCs are genetically modified Thp1 cells or a derivative, variant, modification, or progeny thereof. In an embodiment, the aAPCs are genetically modified Ramos cells or a derivative, variant, modification, or progeny thereof. In an embodiment, the aAPCs are genetically modified U937 cells or a derivative, variant, modification, or progeny thereof. In an embodiment, the aAPCs are genetically modified Daudi cells or a derivative, variant, modification, or progeny thereof. In an embodiment, the aAPCs are genetically modified melanocyte cells. In an embodiment, the aAPCs are genetically modified HLA-A-02 positive melanocyte cells. In an embodiment, the aAPCs are genetically modified melanoma cells. In an embodiment, the aAPCs are genetically modified HLA-A-02 positive melanoma cells. In an embodiment, the aAPCs are genetically modified antigen presenting cells selected from the group consisting of Sk-MEL-5, Malme-3M, SK-MEL-28, SK-MEL-3, SH-4, SK-MEL-24, RPMI-7951, SK-MEL-1, A375, G-361, and combinations thereof, or derivatives, variants, modifications, or progeny thereof. In an embodiment, the genetically modified cells are modified to express CD86, OX40L, 4-1BBL, an OX-40 agonistic antibody, an 4-1BB agonistic antibody, an antibody capable of binding the Fc chain of OKT-3, and/or ICOS-L, as described in U.S. Pat. No. 10,415,015, the disclosures of which are incorporated by reference herein. In any of the foregoing embodiments, the genetically modified aAPCs may be irradiated as described elsewhere herein or non-irradiated.

2. Cytokines

The expansion methods described herein generally use culture media with high doses of a cytokine, in particular IL-2, as is known in the art.

Alternatively, using combinations of cytokines for the rapid expansion and or second expansion of TILs is additionally possible, with combinations of two or more of IL-2, IL-15 and IL-21 as is described in U.S. Patent Application Publication No. US 2017/0107490 A1 and International Patent Application Publication No. WO 2015/189357, each of which is hereby expressly incorporated by reference in their entirety. Thus, possible combinations include IL-2 and IL-15, IL-2 and IL-21, IL-15 and IL-21 and IL-2, IL-15 and IL-21, with the latter finding particular use in many embodiments. The use of combinations of cytokines specifically favors the generation of lymphocytes, and in particular T cells as described therein.

E. STEP E: Harvest TILs

After the second expansion step, cells can be harvested. In some embodiments the TILs are harvested after one, two, three, four or more expansion steps, for example as provided in FIG. 1. In some embodiments the TILs are harvested after two expansion steps, for example as provided in FIG. 1.

TILs can be harvested in any appropriate and sterile manner, including for example by centrifugation. Methods for TIL harvesting are well known in the art and any such know methods can be employed with the present process. In some embodiments, TILs are harvested using an automated system.

Cell harvesters and/or cell processing systems are commercially available from a variety of sources, including, for example, Fresenius Kabi, Tomtec Life Science, Perkin Elmer, and Inotech Biosystems International, Inc. Any cell based harvester can be employed with the present methods. In some embodiments, the cell harvester and/or cell processing systems is a membrane-based cell harvester. In some embodiments, cell harvesting is via a cell processing system, such as the LOVO system (manufactured by Fresenius Kabi). The term "LOVO cell processing system" also refers to any instrument or device manufactured by any vendor that can pump a solution comprising cells through a membrane or filter such as a spinning membrane or spinning filter in a sterile and/or closed system environment, allowing for continuous flow and cell processing to remove supernatant or cell culture media without pelletization. In some embodiments, the cell harvester and/or cell processing system can perform cell separation, washing, fluid-exchange, concentration, and/or other cell processing steps in a closed, sterile system.

In some embodiments, the harvest, for example, Step E according to FIG. 1, is performed from a closed system bioreactor. In some embodiments, a closed system is employed for the TIL expansion, as described herein. In some embodiments, a single bioreactor is employed. In some embodiments, the single bioreactor employed is for example a G-Rex 10 or a G-Rex 100. In some embodiments, the closed system bioreactor is a single bioreactor.

In some embodiments, Step E according to FIG. 1, is performed according to the processes described in Example 14. In some embodiments, the closed system is accessed via syringes under sterile conditions in order to maintain the sterility and closed nature of the system. In some embodiments, a closed system as described in Example 14 is employed.

In some embodiments, TILs are harvested according to the methods described in Example 14. In some embodiments, TILs between days 1 and 11 are harvested using the methods as described (referred to as the Day 11 TIL harvest in Example 14). In some embodiments, TILs between days 12 and 22 are harvested using the methods as described (referred to as the Day 22 TIL harvest in Example 14).

F. STEP F: Assays of Expanded TILs

In some embodiments, the potency and/or functionality of the expanded TILs from the steps provided above is examined using one of the assay methods described herein.

In an embodiment, the invention includes a method of determining the potency of a Gen 2 TIL product as described herein, the method comprising the steps of:

a. performing a co-culture of a target cell with a Gen 2 TIL product cell for a first period;
b. obtaining a harvest from the co-culture; and
c. assessing the harvest for (1) expression of one or more markers on the Gen 2 TIL product or (2) one or more analytes secreted from the Gen 2 TIL product cell to obtain one or more observed values to determine the potency for the Gen 2 TIL product.

Alternatively, in some embodiments, the expanded TILs are analyzed using a combined assay comprising CD3 or CD3/CD28 bead-based stimulation with ELISA or automated ELISA (e.g., ELLA) detection of at least two analytes selected from the group consisting of IFN-γ, granzyme B, perform, and TNF-α. In an embodiment, the specification for such combined assay is at least 500 pg/mL for the at least two selected analytes, at least 600 pg/mL for the at least two selected analytes, at least 700 pg/mL for the at least two selected analytes, at least 800 pg/mL for the at least two selected analytes, at least 900 pg/mL for the at least two selected analytes, at least 1000 pg/mL for the at least two selected analytes, at least 1100 pg/mL for the at least two selected analytes, or at least 1200 pg/mL for the at least two selected analytes, wherein each mL of test article contains $1\times10^5$ TILs, $2\times10^5$ TILs, $3\times10^5$ TILs, $4\times10^5$ TILs, $5\times10^5$ TILs, $6\times10^5$ TILs, $7\times10^5$ TILs, $8\times10^5$ TILs, $9\times10^5$ TILs, or $10\times10^5$ TILs.

G. STEP G: Final Formulation and Transfer to Infusion Container

After Steps A through E as provided in an exemplary order in FIG. 1, and Step F, as outlined in detail above and herein are complete, cells are transferred to a container for use in administration to a patient. In some embodiments, once a therapeutically sufficient number of TILs are obtained using the expansion methods described above, they are transferred to a container, which may include an infusion bag or sterile vial, for use in administration to a patient as a pharmaceutical composition, including pharmaceutical compositions described herein. TILs may be assessed for potency after transfer to such a container, which may occur immediately after the transfer or after the container has been stored for a period of time, such as for stability testing.

In an embodiment, the pharmaceutical composition is a suspension of TILs in a sterile buffer. TILs expanded using PBMCs of the present disclosure may be administered by any suitable route as known in the art. In some embodiments, the T cells are administered as a single intra-arterial or intravenous infusion, which preferably lasts approximately 30 to 60 minutes. Other suitable routes of administration include intraperitoneal, intrathecal, and intralymphatic administration.

V. Gen 3 TIL Manufacturing Processes

Without being limited to any particular theory, it is believed that the priming first expansion that primes an activation of T cells followed by the rapid second expansion that boosts the activation of T cells as described in the methods of the invention allows the preparation of expanded T cells that retain a "younger" phenotype, and as such the expanded T cells of the invention are expected to exhibit greater cytotoxicity against cancer cells than T cells expanded by other methods. In particular, it is believed that an activation of T cells that is primed by exposure to an anti-CD3 antibody (e.g. OKT-3), IL-2 and optionally antigen-presenting cells (APCs) and then boosted by subsequent exposure to additional anti-CD-3 antibody (e.g. OKT-3), IL-2 and APCs as taught by the methods of the invention limits or avoids the maturation of T cells in culture, yielding a population of T cells with a less mature phenotype, which T cells are less exhausted by expansion in culture and exhibit greater cytotoxicity against cancer cells. Exemplary processes are shown in FIG. 8. In some embodiments, the step of rapid second expansion is split into a plurality of steps to achieve a scaling up of the culture by: (a) performing the rapid second expansion by culturing T cells in a small scale culture in a first container, e.g., a G-Rex 100MCS container, for a period of about 3 to 4 days, and then (b) effecting the transfer of the T cells in the small scale culture to a second container larger than the first container, e.g., a G-Rex 500MCS container, and culturing the T cells from the small scale culture in a larger scale culture in the second container for a period of about 4 to 7 days. In some embodiments, the step of rapid expansion is split into a plurality of steps to achieve a scaling out of the culture by: (a) performing the rapid second expansion by culturing T cells in a first small scale culture in a first container, e.g., a G-Rex 100MCS container, for a period of about 3 to 4 days, and then (b) effecting the transfer and apportioning of the T cells from the first small scale culture into and amongst at least 2, 3, 4, 5, 6, 7, 8, 9, 10, 11, 12, 13, 14, 15, 16, 17, 18, 19, or 20 second containers that are equal in size to the first container, wherein in each second container the portion of the T cells from first small scale culture transferred to such second container is cultured in a second small scale culture for a period of about 4 to 7 days. In some embodiments, the step of rapid expansion is split into a plurality of steps to achieve a scaling out and scaling up of the culture by: (a) performing the rapid second expansion by culturing T cells in a small scale culture in a first container, e.g., a G-Rex 100MCS container, for a period of about 3 to 4 days, and then (b) effecting the transfer and apportioning of the T cells from the small scale culture into and amongst at least 2, 3, 4, 5, 6, 7, 8, 9, 10, 11, 12, 13, 14, 15, 16, 17, 18, 19, or 20 second containers that are larger in size than the first container, e.g., G-Rex 500MCS containers, wherein in each second container the portion of the T cells from the small scale culture transferred to such second container is cultured in a larger scale culture for a period of about 4 to 7 days. In some embodiments, the step of rapid expansion is split into a plurality of steps to achieve a scaling out and scaling up of the culture by: (a) performing the rapid second expansion by culturing T cells in a small scale culture in a first container, e.g., a G-Rex 100MCS container, for a period of about 4 days, and then (b) effecting the transfer and apportioning of the T cells from the small scale culture into and amongst 2, 3 or 4 second containers that are larger in size than the first container, e.g., G-Rex 500MCS containers, wherein in each second container the portion of the T cells from the small scale culture transferred to such second container is cultured in a larger scale culture for a period of about 5 days.

In some embodiments, the rapid second expansion is performed after the activation of T cells effected by the priming first expansion begins to decrease, abate, decay or subside.

In some embodiments, the rapid second expansion is performed after the activation of T cells effected by the priming first expansion has decreased by at or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%.

In some embodiments, the rapid second expansion is performed after the activation of T cells effected by the priming first expansion has decreased by a percentage in the range of at or about 1% to 100%.

In some embodiments, the rapid second expansion is performed after the activation of T cells effected by the priming first expansion has decreased by a percentage in the range of at or about 10% to 10%, 10% to 20%, 20% to 30%, 30% to 40%, 40% to 50%, 50% to 60%, 60% to 70%, 70% to 80%, 80% to 90%, or 90% to 100%.

In some embodiments, the rapid second expansion is performed after the activation of T cells effected by the priming first expansion has decreased by at least at or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99%.

In some embodiments, the rapid second expansion is performed after the activation of T cells effected by the priming first expansion has decreased by up to at or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%.

In some embodiments, the decrease in the activation of T cells effected by the priming first expansion is determined by a reduction in the amount of interferon gamma released by the T cells in response to stimulation with antigen.

In some embodiments, the priming first expansion of T cells is performed during a period of up to at or about 7 days or about 8 days.

In some embodiments, the priming first expansion of T cells is performed during a period of up to at or about 1 day, 2 days, 3 days, 4 days, 5 days, 6 days, 7 days, or 8 days.

In some embodiments, the priming first expansion of T cells is performed during a period of 1 day, 2 days, 3 days, 4 days, 5 days, 6 days, 7 days, or 8 days.

In some embodiments, the rapid second expansion of T cells is performed during a period of up to at or about 11 days.

In some embodiments, the rapid second expansion of T cells is performed during a period of up to at or about 1 day, 2 days, 3 days, 4 days, 5 days, 6 days, 7 days, 8 days, 9 days, 10 days or 11 days.

In some embodiments, the rapid second expansion of T cells is performed during a period of 1 day, 2 days, 3 days, 4 days, 5 days, 6 days, 7 days, 8 days, 9 days, 10 days or 11 days.

In some embodiments, the priming first expansion of T cells is performed during a period of from at or about 1 day to at or about 7 days and the rapid second expansion of T cells is performed during a period of from at or about 1 day to at or about 11 days.

In some embodiments, the priming first expansion of T cells is performed during a period of up to at or about 1 day, 2 days, 3 days, 4 days, 5 days, 6 days, 7 days, or 8 days and the rapid second expansion of T cells is performed during a period of up to at or about 1 day, 2 days, 3 days, 4 days, 5 days, 6 days, 7 days, 8 days, 9 days, 10 days or 11 days.

In some embodiments, the priming first expansion of T cells is performed during a period of from at or about 1 day to at or about 8 days and the rapid second expansion of T cells is performed during a period of from at or about 1 day to at or about 9 days.

In some embodiments, the priming first expansion of T cells is performed during a period of 8 days and the rapid second expansion of T cells is performed during a period of 9 days.

In some embodiments, the priming first expansion of T cells is performed during a period of from at or about 1 day to at or about 7 days and the rapid second expansion of T cells is performed during a period of from at or about 1 day to at or about 9 days.

In some embodiments, the priming first expansion of T cells is performed during a period of 7 days and the rapid second expansion of T cells is performed during a period of 9 days.

In some embodiments, the T cells are tumor infiltrating lymphocytes (TILs).

In some embodiments, the T cells are marrow infiltrating lymphocytes (MILs).

In some embodiments, the T cells are peripheral blood lymphocytes (PBLs).

In some embodiments, the T cells are obtained from a donor suffering from a cancer.

In some embodiments, the T cells are TILs obtained from a tumor excised from a patient suffering from a cancer.

In some embodiments, the T cells are TILs obtained from a tumor excised from a patient suffering from a melanoma.

In some embodiments, the T cells are MILs obtained from bone marrow of a patient suffering from a hematologic malignancy.

In some embodiments, the T cells are PBLs obtained from peripheral blood mononuclear cells (PBMCs) from a donor. In some embodiments, the donor is suffering from a cancer. In some embodiments, the cancer is selected from the group consisting of melanoma, ovarian cancer, endometrial cancer, thyroid cancer, cervical cancer, non-small-cell lung cancer (NSCLC), lung cancer, bladder cancer, breast cancer, cancer caused by human papilloma virus, head and neck cancer (including head and neck squamous cell carcinoma (HN- SCC)), glioblastoma (including GBM), gastrointestinal cancer, renal cancer, and renal cell carcinoma. In some embodiments, the cancer is selected from the group consisting of melanoma, ovarian cancer, cervical cancer, non-small-cell lung cancer (NSCLC), lung cancer, bladder cancer, breast cancer, cancer caused by human papilloma virus, head and neck cancer (including head and neck squamous cell carcinoma (HNSCC)), glioblastoma (including GBM), gastrointestinal cancer, renal cancer, and renal cell carcinoma. In some embodiments, the donor is suffering from a tumor. In some embodiments, the tumor is a liquid tumor. In some embodiments, the tumor is a solid tumor. In some embodiments, the donor is suffering from a hematologic malignancy.

In certain aspects of the present disclosure, immune effector cells, e.g., T cells, can be obtained from a unit of blood collected from a subject using any number of techniques known to the skilled artisan, such as FICOLL separation. In one preferred aspect, cells from the circulating blood of an individual are obtained by apheresis. The apheresis product typically contains lymphocytes, including T cells, monocytes, granulocytes, B cells, other nucleated white blood cells, red blood cells, and platelets. In one aspect, the cells collected by apheresis may be washed to remove the plasma fraction and, optionally, to place the cells in an appropriate buffer or media for subsequent processing steps. In one embodiment, the cells are washed with phosphate buffered saline (PBS). In an alternative embodiment, the wash solution lacks calcium and may lack magnesium or may lack many if not all divalent cations. In one aspect, T cells are isolated from peripheral blood lymphocytes by lysing the red blood cells and depleting the monocytes, for example, by centrifugation through a PERCOLL gradient or by counterflow centrifugal elutriation.

In some embodiments, the T cells are PBLs separated from whole blood or apheresis product enriched for lymphocytes from a donor. In some embodiments, the donor is suffering from a cancer. In some embodiments, the cancer is the cancer is selected from the group consisting of melanoma, ovarian cancer, endometrial cancer, thyroid cancer, cervical cancer, non-small-cell lung cancer (NSCLC), lung cancer, bladder cancer, breast cancer, cancer caused by human papilloma virus, head and neck cancer (including head and neck squamous cell carcinoma (HNSCC)), glioblastoma (including GBM), gastrointestinal cancer, renal cancer, and renal cell carcinoma. In some embodiments, the cancer is selected from the group consisting of melanoma, ovarian cancer, cervical cancer, non-small-cell lung cancer (NSCLC), lung cancer, bladder cancer, breast cancer, cancer caused by human papilloma virus, head and neck cancer (including head and neck squamous cell carcinoma (HNSCC)), glioblastoma (including GBM), gastrointestinal cancer, renal cancer, and renal cell carcinoma. In some embodiments, the donor is suffering from a tumor. In some embodiments, the tumor is a liquid tumor. In some embodiments, the tumor is a solid tumor. In some embodiments, the donor is suffering from a hematologic malignancy. In some embodiments, the PBLs are isolated from whole blood or apheresis product enriched for lymphocytes by using positive or negative selection methods, i.e., removing the PBLs using a marker(s), e.g., CD3+CD45+, for T cell phenotype, or removing non-T cell phenotype cells, leaving PBLs. In other embodiments, the PBLs are isolated by gradient centrifugation. Upon isolation of PBLs from donor tissue, the priming first expansion of PBLs can be initiated by seeding a suitable number of isolated PBLs (in some embodiments, approximately $1\times10^7$ PBLs) in the priming first expansion culture according to the priming first expansion step of any of the methods described herein.

An exemplary TIL process known as process 3 (also referred to herein as Gen 3) containing some of these features is depicted in FIG. 8 (in particular, e.g., FIG. 8B and/or FIG. 8C), and some of the advantages of this embodiment of the present invention over process 2A are described in FIGS. 1, 2, 8, 30, and 31 (in particular, e.g., FIG. 8A and/or FIG. 8B and/or FIG. 8C and/or FIG. 8D). Embodiments of process 3 (Gen 3) are shown in FIGS. 8 and 30 (in particular, e.g., FIG. 8A and/or FIG. 8B and/or FIG. 8C and/or FIG. 8D). Process 2A or Gen 2 is also described in U.S. Patent Publication No. 2018/0280436, incorporated by reference herein in its entirety. The Gen 3 process is also described in International Patent Publication WO 2020/096988.

As discussed and generally outlined herein, TILs are taken from a patient sample and manipulated to expand their number prior to transplant into a patient using the TIL expansion process described herein and referred to as Gen 3. In some embodiments, the TILs may be optionally genetically manipulated as discussed below. In some embodiments, the TILs may be cryopreserved prior to or after expansion. Once thawed, they may also be restimulated to increase their metabolism prior to infusion into a patient.

In some embodiments, the priming first expansion (including processes referred herein as the pre-Rapid Expansion (Pre-REP), as well as processes shown in FIG. 8 (in particular, e.g., FIG. 8A and/or FIG. 8B and/or FIG. 8C and/or FIG. 8D) as Step B) is shortened to 1 to 8 days and the rapid second expansion (including processes referred to herein as Rapid Expansion Protocol (REP) as well as processes shown in FIG. 1 (in particular, e.g., FIG. 8A and/or FIG. 8B and/or FIG. 8C and/or FIG. 8D) as Step D) is shortened to 1 to 9 days, as discussed in detail below as well as in the examples and figures. In some embodiments, the priming first expansion (including processes referred herein as the pre-Rapid Expansion (Pre-REP), as well as processes shown in FIG. 8 (in particular, e.g., FIG. 8A and/or FIG. 8B and/or FIG. 8C and/or FIG. 8D) as Step B) is shortened to 1 to 8 days and the rapid second expansion (including processes referred to herein as Rapid Expansion Protocol (REP) as well as processes shown in FIG. 8 (in particular, e.g., FIG. 8A and/or FIG. 8B and/or FIG. 8C and/or FIG. 8D) as Step D) is shortened to 1 to 8 days, as discussed in detail below as well as in the examples and figures. In some embodiments, the priming first expansion (including processes referred herein as the pre-Rapid Expansion (Pre-REP), as well as processes shown in FIG. 8 (in particular, e.g., FIG. 8A and/or FIG. 8B and/or FIG. 8C and/or FIG. 8D) as Step B) is shortened to 1 to 7 days and the rapid second expansion (including processes referred to herein as Rapid Expansion Protocol (REP) as well as processes shown in FIG. 8 (in particular, e.g., FIG. 8A and/or FIG. 8B and/or FIG. 8C and/or FIG. 8D) as Step D) is shortened to 1 to 9 days, as discussed in detail below as well as in the examples and figures. In some embodiments, the priming first expansion (including processes referred herein as the pre-Rapid Expansion (Pre-REP), as well as processes shown in FIG. 8 (in particular, e.g., FIG. 8A and/or FIG. 8B and/or FIG. 8C and/or FIG. 8D) as Step B) is 1 to 7 days and the rapid second expansion (including processes referred to herein as Rapid Expansion Protocol (REP) as well as processes shown in FIG. 8 (in particular, e.g., FIG. 8A and/or FIG. 8B and/or FIG. 8C and/or FIG. 8D) as Step D) is 1 to 10 days, as discussed in detail below as well as in the examples and figures. In some embodiments, the priming first expansion (for example, an expansion described as Step B in FIG. 8 (in particular, e.g., FIG. 8A and/or FIG. 8B and/or FIG. 8C and/or FIG. 8D)) is shortened to 8 days and the rapid second expansion (for example, an expansion as described in Step D in FIG. 8 (in particular, e.g., FIG. 8A and/or FIG. 8B and/or FIG. 8C and/or FIG. 8D)) is 7 to 9 days. In some embodiments, the priming first expansion (for example, an expansion described as Step B in FIG. 8 (in particular, e.g., FIG. 8A and/or FIG. 8B and/or FIG. 8C and/or FIG. 8D)) is 8 days and the rapid second expansion (for example, an expansion as described in Step D in FIG. 8 (in particular, e.g., FIG. 8A and/or FIG. 8B and/or FIG. 8C and/or FIG. 8D)) is 8 to 9 days. In some embodiments, the priming first expansion (for example, an expansion described as Step B in FIG. 8 (in particular, e.g., FIG. 8A and/or FIG. 8B and/or FIG. 8C and/or FIG. 8D)) is shortened to 7 days and the rapid second expansion (for example, an expansion as described in Step D in FIG. 1 (in particular, e.g., FIG. 8A and/or FIG. 8B and/or FIG. 8C and/or FIG. 8D)) is 7 to 8 days. In some embodiments, the priming first expansion (for example, an expansion described as Step B in FIG. 8 (in particular, e.g., FIG. 8A and/or FIG. 8B and/or FIG. 8C and/or FIG. 8D)) is shortened to 8 days and the rapid second expansion (for example, an expansion as described in Step D in FIG. 8 (in particular, e.g., FIG. 8A and/or FIG. 8B and/or FIG. 8C and/or FIG. 8D)) is 8 days. In some embodiments, the priming first expansion (for example, an expansion described as Step B in FIG. 8 (in particular, e.g., FIG. 8A and/or FIG. 8B and/or FIG. 8C and/or FIG. 8D)) is 8 days and the rapid second expansion (for example, an expansion as described in Step D in FIG. 8 (in particular, e.g., FIG. 8A and/or FIG. 8B and/or FIG. 8C and/or FIG. 8D)) is 9 days. In some embodiments, the priming first expansion (for example, an expansion described as Step B in FIG. 8 (in particular, e.g., FIG. 8A and/or FIG. 8B and/or FIG. 8C and/or FIG. 8D)) is 8 days and the rapid second expansion (for example, an expansion as described in Step D in FIG. 8 (in particular, e.g., FIG. 8A and/or FIG. 8B and/or FIG. 8C and/or FIG. 8D)) is 10 days. In some embodiments, the priming first expansion (for example, an expansion described as Step B in FIG. 8 (in particular, e.g., FIG. 8A and/or FIG. 8B and/or FIG. 8C and/or FIG. 8D)) is 7 days and the rapid second expansion (for example, an expansion as described in Step D in FIG. 8 (in particular, e.g., FIG. 8A and/or FIG. 8B and/or FIG. 8C and/or FIG. 8D)) is 7 to 10 days. In some embodiments, the priming first expansion (for example, an expansion described as Step B in FIG. 8 (in particular, e.g., FIG. 8A and/or FIG. 8B and/or FIG. 8C and/or FIG. 8D)) is 7 days and the rapid second expansion (for example, an expansion as described in Step D in FIG. 8 (in particular, e.g., FIG. 8A and/or FIG. 8B and/or FIG. 8C and/or FIG. 8D)) is 8 to 10 days. In some embodiments, the priming first expansion (for example, an expansion described as Step B in FIG. 8 (in particular, e.g., FIG. 8A and/or FIG. 8B and/or FIG. 8C and/or FIG. 8D)) is 7 days and the rapid second expansion (for example, an expansion as described in Step D in FIG. 8 (in particular, e.g., FIG. 8A and/or FIG. 8B and/or FIG. 8C and/or FIG. 8D)) is 9 to 10 days. In some embodiments, the priming first expansion (for example, an expansion described as Step B in FIG. 8 (in particular, e.g., FIG. 8A and/or FIG. 8B and/or FIG. 8C and/or FIG. 8D)) is shortened to 7 days and the rapid second expansion (for example, an expansion as described in Step D in FIG. 8 (in particular, e.g., FIG. 8A and/or FIG. 8B and/or FIG. 8C and/or FIG. 8D)) is 7 to 9 days. In some embodiments, the combination of the priming first expansion and rapid second expansion (for example, expansions described as Step B and Step D in FIG. 8 (in particular, e.g., FIG. 8A and/or FIG. 8B and/or FIG. 8C and/or FIG. 8D)) is 14-16 days, as discussed in detail below and in the examples and figures. Particularly, it is considered that certain embodiments of the present invention comprise a priming first expansion step in which TILs are activated by exposure to an anti-CD3 antibody, e.g., OKT-3 in the presence of IL-2 or exposure to an antigen in the presence of at least IL-2 and an anti-CD3 antibody e.g. OKT-3. In certain embodiments, the TILs which are activated in the priming first expansion step as described above are a first population of TILs i.e., which are a primary cell population.

The "Step" Designations A, B, C, etc., below are in reference to the non-limiting example in FIG. 8 (in particular, e.g., FIG. 8A and/or FIG. 8B and/or FIG. 8C and/or FIG. 8D) and in reference to certain non-limiting embodiments described herein. The ordering of the Steps below and in FIG. 8 (in particular, e.g., FIG. 8A and/or FIG. 8B and/or FIG. 8C and/or FIG. 8D) is exemplary and any combination or order of steps, as well as additional steps, repetition of steps, and/or omission of steps is contemplated by the present application and the methods disclosed herein.

A. STEP A: Obtain Patient Tumor Sample

In general, TILs are initially obtained from a patient tumor sample ("primary TILs") or from circulating lymphocytes, such as peripheral blood lymphocytes, including peripheral blood lymphocytes having TIL-like characteristics, and are then expanded into a larger population for further manipulation as described herein, optionally cryopreserved, and optionally evaluated for phenotype and metabolic parameters as an indication of TIL health.

A patient tumor sample may be obtained using methods known in the art, generally via surgical resection, needle biopsy or other means for obtaining a sample that contains a mixture of tumor and TIL cells. In general, the tumor sample may be from any solid tumor, including primary tumors, invasive tumors or metastatic tumors. The tumor sample may also be a liquid tumor, such as a tumor obtained from a hematological malignancy. The solid tumor may be of any cancer type, including, but not limited to skin (including but not limited to squamous cell carcinoma, basal cell carcinoma, and melanoma). In some embodiments, the cancer is melanoma. In some embodiments, useful TILs are obtained from malignant melanoma tumors, as these have been reported to have particularly high levels of TILs.

Once obtained, the tumor sample is generally fragmented using sharp dissection into small pieces of between 1 to about 8 $mm^3$, with from about 2-3 $mm^3$ being particularly useful. The TILs are cultured from these fragments using enzymatic tumor digests. Such tumor digests may be produced by incubation in enzymatic media (e.g., Roswell Park Memorial Institute (RPMI) 1640 buffer, 2 mM glutamate, 10 mcg/mL gentamicin, 30 units/mL of DNase and 1.0 mg/mL of collagenase) followed by mechanical dissociation (e.g., using a tissue dissociator). Tumor digests may be produced by placing the tumor in enzymatic media and mechanically dissociating the tumor for approximately 1 minute, followed by incubation for 30 minutes at 37° C. in 5% $CO_2$, followed by repeated cycles of mechanical dissociation and incubation under the foregoing conditions until only small tissue pieces are present. At the end of this process, if the cell suspension contains a large number of red blood cells or dead cells, a density gradient separation using FICOLL branched hydrophilic polysaccharide may be performed to remove these cells. Alternative methods known in the art may be used, such as those described in U.S. Patent Application Publication No. 2012/0244133 A1, the disclosure of which is incorporated by reference herein. Any of the foregoing methods may be used in any of the embodiments described herein for methods of expanding TILs or methods treating a cancer.

Tumor dissociating enzyme mixtures can include one or more dissociating (digesting) enzymes such as, but not limited to, collagenase (including any blend or type of collagenase), Accutase™, Accumax™, hyaluronidase, neutral protease (dispase), chymotrypsin, chymopapain, trypsin, caseinase, elastase, papain, protease type XIV (pronase), deoxyribonuclease I (DNase), trypsin inhibitor, any other dissociating or proteolytic enzyme, and any combination thereof.

In some embodiments, the dissociating enzymes are reconstituted from lyophilized enzymes. In some embodiments, lyophilized enzymes are reconstituted in an amount of sterile buffer such as HBSS.

In some instances, collagenase (such as animal free-type 1 collagenase) is reconstituted in 10 mL of sterile HBSS or another buffer. The lyophilized stock enzyme may be at a concentration of 2892 PZ U/vial. In some embodiments, collagenase is reconstituted in 5 mL to 15 mL buffer. In some embodiments, after reconstitution the collagenase stock ranges from about 100 PZ U/mL-about 400 PZ U/mL, e.g., about 100 PZ U/mL-about 400 PZ U/mL, about 100 PZ U/mL-about 350 PZ U/mL, about 100 PZ U/mL-about 300 PZ U/mL, about 150 PZ U/mL-about 400 PZ U/mL, about 100 PZ U/mL, about 150 PZ U/mL, about 200 PZ U/mL, about 210 PZ U/mL, about 220 PZ U/mL, about 230 PZ U/mL, about 240 PZ U/mL, about 250 PZ U/mL, about 260 PZ U/mL, about 270 PZ U/mL, about 280 PZ U/mL, about 289.2 PZ U/mL, about 300 PZ U/mL, about 350 PZ U/mL, or about 400 PZ U/mL.

In some embodiments, neutral protease is reconstituted in 1 mL of sterile HBSS or another buffer. The lyophilized stock enzyme may be at a concentration of 175 DMC U/vial. The lyophilized stock enzyme may be at a concentration of 175 DMC/mL. In some embodiments, after reconstitution the neutral protease stock ranges from about 100 DMC/mL to about 400 DMC/mL, e.g., about 100 DMC/mL to about 400 DMC/mL, about 100 DMC/mL to about 350 DMC/mL, about 100 DMC/mL to about 300 DMC/mL, about 150 DMC/mL to about 400 DMC/mL, about 100 DMC/mL, about 110 DMC/mL, about 120 DMC/mL, about 130 DMC/mL, about 140 DMC/mL, about 150 DMC/mL, about 160 DMC/mL, about 170 DMC/mL, about 175 DMC/mL, about 180 DMC/mL, about 190 DMC/mL, about 200 DMC/mL, about 250 DMC/mL, about 300 DMC/mL, about 350 DMC/mL, or about 400 DMC/mL.

In some embodiments, DNAse I is reconstituted in 1 mL of sterile HBSS or another buffer. The lyophilized stock enzyme was at a concentration of 4 KU/vial. In some embodiments, after reconstitution the DNase I stock ranges from about 1 KU/mL to 10 KU/mL, e.g., about 1 KU/mL, about 2 KU/mL, about 3 KU/mL, about 4 KU/mL, about 5 KU/mL, about 6 KU/mL, about 7 KU/mL, about 8 KU/mL, about 9 KU/mL, or about 10 KU/mL.

In some embodiments, the stock of enzymes could change so verify the concentration of the lyophilized stock and amend the final amount of enzyme added to the digest cocktail accordingly.

In some embodiments, the enzyme mixture includes about 10.2-ul of neutral protease (0.36 DMC U/mL), 21.3-ul of collagenase (1.2 PZ/mL) and 250-ul of DNAse I (200 U/mL) in about 4.7 mL of sterile HBSS.

As indicated above, in some embodiments, the TILs are derived from solid tumors. In some embodiments, the solid tumors are not fragmented. In some embodiments, the solid tumors are not fragmented and are subjected to enzymatic digestion as whole tumors. In some embodiments, the tumors are digested in in an enzyme mixture comprising collagenase, DNase, and hyaluronidase. In some embodiments, the tumors are digested in in an enzyme mixture comprising collagenase, DNase, and hyaluronidase for 1-2 hours. In some embodiments, the tumors are digested in in an enzyme mixture comprising collagenase, DNase, and hyaluronidase for 1-2 hours at 37° C., 5% $CO_2$. In some embodiments, the tumors are digested in in an enzyme mixture comprising collagenase, DNase, and hyaluronidase for 1-2 hours at 37° C., 5% $CO_2$ with rotation. In some embodiments, the tumors are digested overnight with constant rotation. In some embodiments, the tumors are digested overnight at 37° C., 5% $CO_2$ with constant rotation. In some embodiments, the whole tumor is combined with the enzymes to form a tumor digest reaction mixture.

In some embodiments, the tumor is reconstituted with the lyophilized enzymes in a sterile buffer. In some embodiments, the buffer is sterile HBSS.

In some embodiments, the enzyme mixture comprises collagenase. In some embodiments, the collagenase is collagenase IV. In some embodiments, the working stock for the collagenase is a 100 mg/mL 10× working stock.

In some embodiments, the enzyme mixture comprises DNAse. In some embodiments, the working stock for the DNAse is a 10,000 IU/mL 10× working stock.

In some embodiments, the enzyme mixture comprises hyaluronidase. In some embodiments, the working stock for the hyaluronidase is a 10 mg/mL 10× working stock.

In some embodiments, the enzyme mixture comprises 10 mg/mL collagenase, 1000 IU/mL DNAse, and 1 mg/mL hyaluronidase.

In some embodiments, the enzyme mixture comprises 10 mg/mL collagenase, 500 IU/mL DNAse, and 1 mg/mL hyaluronidase.

In general, the cell suspension obtained from the tumor is called a "primary cell population" or a "freshly obtained" or a "freshly isolated" cell population. In certain embodiments, the freshly obtained cell population of TILs is exposed to a cell culture medium comprising antigen presenting cells, IL-12 and OKT-3.

In some embodiments, fragmentation includes physical fragmentation, including, for example, dissection as well as digestion. In some embodiments, the fragmentation is physical fragmentation. In some embodiments, the fragmentation is dissection. In some embodiments, the fragmentation is by digestion. In some embodiments, TILs can be initially cultured from enzymatic tumor digests and tumor fragments obtained from patients. In an embodiment, TILs can be initially cultured from enzymatic tumor digests and tumor fragments obtained from patients.

In some embodiments, where the tumor is a solid tumor, the tumor undergoes physical fragmentation after the tumor sample is obtained in, for example, Step A (as provided in FIG. 8 (in particular, e.g., FIG. 8B and/or FIG. 8C)). In some embodiments, the fragmentation occurs before cryopreservation. In some embodiments, the fragmentation occurs after cryopreservation. In some embodiments, the fragmentation occurs after obtaining the tumor and in the absence of any cryopreservation. In some embodiments, the step of fragmentation is an in vitro or ex-vivo process. In some embodiments, the tumor is fragmented and 10, 20, 30, 40 or more fragments or pieces are placed in each container for the priming first expansion. In some embodiments, the tumor is fragmented and 30 or 40 fragments or pieces are placed in each container for the priming first expansion. In some embodiments, the tumor is fragmented and 40 fragments or pieces are placed in each container for the priming first expansion. In some embodiments, the multiple fragments comprise about 4 to about 50 fragments, wherein each fragment has a volume of about 27 $mm^3$. In some embodiments, the multiple fragments comprise about 30 to about 60 fragments with a total volume of about 1300 $mm^3$ to about 1500 $mm^3$. In some embodiments, the multiple fragments comprise about 50 fragments with a total volume of about 1350 $mm^3$. In some embodiments, the multiple fragments comprise about 50 fragments with a total mass of about 1 gram to about 1.5 grams. In some embodiments, the multiple fragments comprise about 4 fragments.

In some embodiments, the TILs are obtained from tumor fragments. In some embodiments, the tumor fragment is obtained by sharp dissection. In some embodiments, the tumor fragment is between about 1 $mm^3$ and 10 $mm^3$. In some embodiments, the tumor fragment is between about 1 $mm^3$ and 8 $mm^3$. In some embodiments, the tumor fragment is about 1 $mm^3$. In some embodiments, the tumor fragment is about 2 $mm^3$. In some embodiments, the tumor fragment is about 3 $mm^3$. In some embodiments, the tumor fragment is about 4 $mm^3$. In some embodiments, the tumor fragment is about 5 $mm^3$. In some embodiments, the tumor fragment is about 6 $mm^3$. In some embodiments, the tumor fragment is about 7 $mm^3$. In some embodiments, the tumor fragment is about 8 $mm^3$. In some embodiments, the tumor fragment is about 9 $mm^3$. In some embodiments, the tumor fragment is about 10 $mm^3$. In some embodiments, the tumor fragments are 1-4 mm×1-4 mm×1-4 mm. In some embodiments, the tumor fragments are 1 mm×1 mm×1 mm. In some embodiments, the tumor fragments are 2 mm×2 mm×2 mm. In some embodiments, the tumor fragments are 3 mm×3 mm×3 mm. In some embodiments, the tumor fragments are 4 mm×4 mm×4 mm.

In some embodiments, the tumors are fragmented in order to minimize the amount of hemorrhagic, necrotic, and/or fatty tissues on each piece. In some embodiments, the tumors are fragmented in order to minimize the amount of hemorrhagic tissue on each piece. In some embodiments, the tumors are fragmented in order to minimize the amount of necrotic tissue on each piece. In some embodiments, the tumors are fragmented in order to minimize the amount of fatty tissue on each piece. In certain embodiments, the step of fragmentation of the tumor is an in vitro or ex-vivo method.

In some embodiments, the tumor fragmentation is performed in order to maintain the tumor internal structure. In some embodiments, the tumor fragmentation is performed without preforming a sawing motion with a scalpel. In some embodiments, the TILs are obtained from tumor digests. In some embodiments, tumor digests were generated by incubation in enzyme media, for example but not limited to RPMI 1640, 2 mM GlutaMAX, 10 mg/mL gentamicin, 30 U/mL DNase, and 1.0 mg/mL collagenase, followed by mechanical dissociation (GentleMACS, Miltenyi Biotec, Auburn, CA). After placing the tumor in enzyme media, the tumor can be mechanically dissociated for approximately 1 minute. The solution can then be incubated for 30 minutes at 37° C. in 5% $CO_2$ and it then mechanically disrupted again for approximately 1 minute. After being incubated again for 30 minutes at 37° C. in 5% $CO_2$, the tumor can be mechanically disrupted a third time for approximately 1 minute. In some embodiments, after the third mechanical disruption if large pieces of tissue were present, 1 or 2 additional mechanical dissociations were applied to the sample, with or without 30 additional minutes of incubation at 37° C. in 5% $CO_2$. In some embodiments, at the end of the final incubation if the cell suspension contained a large number of red blood cells or dead cells, a density gradient separation using Ficoll can be performed to remove these cells.

In some embodiments, the cell suspension prior to the priming first expansion step is called a "primary cell population" or a "freshly obtained" or "freshly isolated" cell population.

In some embodiments, cells can be optionally frozen after sample isolation (e.g., after obtaining the tumor sample and/or after obtaining the cell suspension from the tumor sample) and stored frozen prior to entry into the expansion described in Step B, which is described in further detail below, as well as exemplified in FIG. 8 (in particular, e.g., FIG. 8B).

1. Core/Small Biopsy Derived TILs

In some embodiments, TILs are initially obtained from a patient tumor sample ("primary TILs") obtained by a core biopsy or similar procedure and then expanded into a larger population for further manipulation as described herein, optionally cryopreserved, and optionally evaluated for phenotype and metabolic parameters.

In some embodiments, a patient tumor sample may be obtained using methods known in the art, generally via small biopsy, core biopsy, needle biopsy or other means for obtaining a sample that contains a mixture of tumor and TIL cells. In general, the tumor sample may be from any solid tumor, including primary tumors, invasive tumors or metastatic tumors. The tumor sample may also be a liquid tumor, such as a tumor obtained from a hematological malignancy. In some embodiments, the sample can be from multiple small tumor samples or biopsies. In some embodiments, the sample can comprise multiple tumor samples from a single tumor from the same patient. In some embodiments, the sample can comprise multiple tumor samples from one, two, three, or four tumors from the same patient. In some embodiments, the sample can comprise multiple tumor samples from multiple tumors from the same patient. The solid tumor is melanoma.

In general, the cell suspension obtained from the tumor core or fragment is called a "primary cell population" or a "freshly obtained" or a "freshly isolated" cell population. In certain embodiments, the freshly obtained cell population of TILs is exposed to a cell culture medium comprising antigen presenting cells, IL-2 and OKT-3.

In some embodiments, if the tumor is metastatic and the primary lesion has been efficiently treated/removed in the past, removal of one of the metastatic lesions may be needed. In some embodiments, the least invasive approach is to remove a skin lesion, or a lymph node on the neck or axillary area when available. In some embodiments, a skin lesion is removed or small biopsy thereof is removed. In some embodiments, a lymph node or small biopsy thereof is removed. In some embodiments, the tumor is a melanoma. In some embodiments, the small biopsy for a melanoma comprises a mole or portion thereof.

In some embodiments, the small biopsy is a punch biopsy. In some embodiments, the punch biopsy is obtained with a circular blade pressed into the skin. In some embodiments, the punch biopsy is obtained with a circular blade pressed into the skin. around a suspicious mole. In some embodiments, the punch biopsy is obtained with a circular blade pressed into the skin, and a round piece of skin is removed.

In some embodiments, the small biopsy is a punch biopsy and round portion of the tumor is removed.

In some embodiments, the small biopsy is an excisional biopsy. In some embodiments, the small biopsy is an excisional biopsy and the entire mole or growth is removed. In some embodiments, the small biopsy is an excisional biopsy and the entire mole or growth is removed along with a small border of normal-appearing skin.

In some embodiments, the small biopsy is an incisional biopsy. In some embodiments, the small biopsy is an incisional biopsy and only the most irregular part of a mole or growth is taken. In some embodiments, the small biopsy is an incisional biopsy and the incisional biopsy is used when other techniques can't be completed, such as if a suspicious mole is very large.

The term "solid tumor" refers to an abnormal mass of tissue that usually does not contain cysts or liquid areas. Solid tumors may be benign or malignant. The term "solid tumor cancer refers to malignant, neoplastic, or cancerous solid tumors. In some embodiments, the cancer is melanoma. The tissue structure of solid tumors includes interdependent tissue compartments including the parenchyma (cancer cells) and the supporting stromal cells in which the cancer cells are dispersed and which may provide a supporting microenvironment.

In some embodiments, the sample from the tumor is obtained as a fine needle aspirate (FNA), a core biopsy, a small biopsy (including, for example, a punch biopsy). In some embodiments, sample is placed first into a G-Rex 10. In some embodiments, sample is placed first into a G-Rex 10 when there are 1 or 2 core biopsy and/or small biopsy samples. In some embodiments, sample is placed first into a G-Rex 100 when there are 3, 4, 5, 6, 8, 9, or 10 or more core biopsy and/or small biopsy samples. In some embodiments, sample is placed first into a G-Rex 500 when there are 3, 4, 5, 6, 8, 9, or 10 or more core biopsy and/or small biopsy samples.

The FNA can be obtained from a skin tumor, including, for example, a melanoma. In some cases, the patient with melanoma has previously undergone a surgical treatment.

TILs described herein can be obtained from an FNA sample. In some cases, the FNA sample is obtained or isolated from the patient using a fine gauge needle ranging from an 18 gauge needle to a 25 gauge needle. The fine gauge needle can be 18 gauge, 19 gauge, 20 gauge, 21 gauge, 22 gauge, 23 gauge, 24 gauge, or 25 gauge. In some embodiments, the FNA sample from the patient can contain at least 400,000 TILs, e.g., 400,000 TILs, 450,000 TILs, 500,000 TILs, 550,000 TILs, 600,000 TILs, 650,000 TILs, 700,000 TILs, 750,000 TILs, 800,000 TILs, 850,000 TILs, 900,000 TILs, 950,000 TILs, or more.

In some cases, the TILs described herein are obtained from a core biopsy sample. In some cases, the core biopsy sample is obtained or isolated from the patient using a surgical or medical needle ranging from an 11 gauge needle to a 16 gauge needle. The needle can be 11 gauge, 12 gauge, 13 gauge, 14 gauge, 15 gauge, or 16 gauge. In some embodiments, the core biopsy sample from the patient can contain at least 400,000 TILs, e.g., 400,000 TILs, 450,000 TILs, 500,000 TILs, 550,000 TILs, 600,000 TILs, 650,000 TILs, 700,000 TILs, 750,000 TILs, 800,000 TILs, 850,000 TILs, 900,000 TILs, 950,000 TILs, or more.

In general, the harvested cell suspension is called a "primary cell population" or a "freshly harvested" cell population.

In some embodiments, the TILs are not obtained from tumor digests. In some embodiments, the solid tumor cores are not fragmented.

In some embodiments, the TILs are obtained from tumor digests. In some embodiments, tumor digests were generated by incubation in enzyme media, for example but not limited to RPMI 1640, 2 mM GlutaMAX, 10 mg/mL gentamicin, 30 U/mL DNase, and 1.0 mg/mL collagenase, followed by mechanical dissociation (GentleMACS, Miltenyi Biotec, Auburn, CA). After placing the tumor in enzyme media, the tumor can be mechanically dissociated for approximately 1 minute. The solution can then be incubated for 30 minutes at 37° C. in 5% $CO_2$ and it then mechanically disrupted again for approximately 1 minute. After being incubated again for 30 minutes at 37° C. in 5% $CO_2$, the tumor can be mechanically disrupted a third time for approximately 1 minute. In some embodiments, after the third mechanical disruption if large pieces of tissue were present, 1 or 2 additional mechanical dissociations were applied to the sample, with or without 30 additional minutes of incubation at 37° C. in 5% $CO_2$. In some embodiments, at the end of the final incubation if the cell suspension contained a large number of red blood cells or dead cells, a density gradient separation using Ficoll can be performed to remove these cells.

In some embodiments, obtaining the first population of TILs comprises a multilesional sampling method.

Tumor dissociating enzyme mixtures can include one or more dissociating (digesting) enzymes such as, but not limited to, collagenase (including any blend or type of collagenase), Accutase™, Accumax™, hyaluronidase, neutral protease (dispase), chymotrypsin, chymopapain, trypsin, caseinase, elastase, papain, protease type XIV (pronase), deoxyribonuclease I (DNase), trypsin inhibitor, any other dissociating or proteolytic enzyme, and any combination thereof.

In some embodiments, the dissociating enzymes are reconstituted from lyophilized enzymes. In some embodiments, lyophilized enzymes are reconstituted in an amount of sterile buffer such as HBSS.

In some instances, collagenase (such as animal free type 1 collagenase) is reconstituted in 10 mL of sterile HBSS or another buffer. The lyophilized stock enzyme may be at a concentration of 2892 PZ U/vial. In some embodiments, collagenase is reconstituted in 5 mL to 15 mL buffer. In some embodiments, after reconstitution the collagenase stock ranges from about 100 PZ U/mL to about 400 PZ U/mL, e.g., about 100 PZ U/mL to about 400 PZ U/mL, about 100 PZ U/mL to about 350 PZ U/mL, about 100 PZ U/mL to about 300 PZ U/mL, about 150 PZ U/mL-about 400 PZ U/mL, about 100 PZ U/mL, about 150 PZ U/mL, about 200 PZ U/mL, about 210 PZ U/mL, about 220 PZ U/mL, about 230 PZ U/mL, about 240 PZ U/mL, about 250 PZ U/mL, about 260 PZ U/mL, about 270 PZ U/mL, about 280 PZ U/mL, about 289.2 PZ U/mL, about 300 PZ U/mL, about 350 PZ U/mL, or about 400 PZ U/mL.

In some embodiments neutral protease is reconstituted in 1 mL of sterile HBSS or another buffer. The lyophilized stock enzyme may be at a concentration of 175 DMC U/vial. The lyophilized stock enzyme may be at a concentration of 175 DMC/mL. In some embodiments, after reconstitution the neutral protease stock ranges from about 100 DMC/mL to about 400 DMC/mL, e.g., about 100 DMC/mL to about 400 DMC/mL, about 100 DMC/mL to about 350 DMC/mL, about 100 DMC/mL to about 300 DMC/mL, about 150 DMC/mL-about 400 DMC/mL, about 100 DMC/mL, about 110 DMC/mL, about 120 DMC/mL, about 130 DMC/mL, about 140 DMC/mL, about 150 DMC/mL, about 160 DMC/mL, about 170 DMC/mL, about 175 DMC/mL, about 180 DMC/mL, about 190 DMC/mL, about 200 DMC/mL, about 250 DMC/mL, about 300 DMC/mL, about 350 DMC/mL, or about 400 DMC/mL.

In some embodiments, DNAse I is reconstituted in 1 mL of sterile HBSS or another buffer. The lyophilized stock enzyme was at a concentration of 4 KU/vial. In some embodiments, after reconstitution the DNase I stock ranges from about 1 KU/mL to 10 KU/mL, e.g., about 1 KU/mL, about 2 KU/mL, about 3 KU/mL, about 4 KU/mL, about 5 KU/mL, about 6 KU/mL, about 7 KU/mL, about 8 KU/mL, about 9 KU/mL, or about 10 KU/mL.

In some embodiments, the stock of enzymes could change so verify the concentration of the lyophilized stock and amend the final amount of enzyme added to the digest cocktail accordingly.

In some embodiments, the enzyme mixture includes about 10.2-ul of neutral protease (0.36 DMC U/mL), 21.3-ul of collagenase (1.2 PZ/mL) and 250-ul of DNAse I (200 U/mL) in about 4.7-mL of sterile HBSS.

2. Pleural Effusion TILs

In some embodiments, the sample is a pleural fluid sample. In some embodiments, the source of the TILs for expansion according to the processes described herein is a pleural fluid sample. In some embodiments, the sample is a pleural effusion derived sample. In some embodiments, the source of the TILs for expansion according to the processes described herein is a pleural effusion derived sample. See, for example, methods described in U.S. Patent Publication US 2014/0295426, incorporated herein by reference in its entirety for all purposes.

In some embodiments, any pleural fluid or pleural effusion suspected of and/or containing TILs can be employed. Such a sample may be derived from a primary or metastatic lung cancer, such as NSCLC or SCLC. In some embodiments, the sample may be secondary metastatic cancer cells which originated from another organ, e.g., breast, ovary, colon or prostate. In some embodiments, the sample for use in the expansion methods described herein is a pleural exudate. In some embodiments, the sample for use in the expansion methods described herein is a pleural transudate. Other biological samples may include other serous fluids containing TILs, including, e.g., ascites fluid from the abdomen or pancreatic cyst fluid. Ascites fluid and pleural fluids involve very similar chemical systems; both the abdomen and lung have mesothelial lines and fluid forms in the pleural space and abdominal spaces in the same matter in malignancies and such fluids in some embodiments contain TILs. In some embodiments, wherein the disclosure exemplifies pleural fluid, the same methods may be performed with similar results using ascites or other cyst fluids containing TILs.

In some embodiments, the pleural fluid is in unprocessed form, directly as removed from the patient. In some embodiments, the unprocessed pleural fluid is placed in a standard blood collection tube, such as an EDTA or Heparin tube, prior to the contacting step. In some embodiments, the unprocessed pleural fluid is placed in a standard CellSave® tube (Veridex) prior to the contacting step. In some embodiments, the sample is placed in the CellSave tube immediately after collection from the patient to avoid a decrease in the number of viable TILs. The number of viable TILs can decrease to a significant extent within 24 hours, if left in the untreated pleural fluid, even at 4° C. In some embodiments, the sample is placed in the appropriate collection tube within 1 hour, 5 hours, 10 hours, 15 hours, or up to 24 hours after removal from the patient. In some embodiments, the sample is placed in the appropriate collection tube within 1 hour, 5 hours, 10 hours, 15 hours, or up to 24 hours after removal from the patient at 4° C.

In some embodiments, the pleural fluid sample from the chosen subject may be diluted. In one embodiment, the dilution is 1:10 pleural fluid to diluent. In another embodiment, the dilution is 1:9 pleural fluid to diluent. In another embodiment, the dilution is 1:8 pleural fluid to diluent. In another embodiment, the dilution is 1:5 pleural fluid to diluent. In another embodiment, the dilution is 1:2 pleural fluid to diluent. In another embodiment, the dilution is 1:1 pleural fluid to diluent. In some embodiments, diluents include saline, phosphate buffered saline, another buffer or a physiologically acceptable diluent. In some embodiments, the sample is placed in the CellSave tube immediately after collection from the patient and dilution to avoid a decrease in the viable TILs, which may occur to a significant extent within 24-48 hours, if left in the untreated pleural fluid, even at 4° C. In some embodiments, the pleural fluid sample is placed in the appropriate collection tube within 1 hour, 5 hours, 10 hours, 15 hours, 24 hours, 36 hours, up to 48 hours after removal from the patient, and dilution. In some embodiments, the pleural fluid sample is placed in the appropriate collection tube within 1 hour, 5 hours, 10 hours, 15 hours, 24 hours, 36 hours, up to 48 hours after removal from the patient, and dilution at 4° C.

In still another embodiment, pleural fluid samples are concentrated by conventional means prior further processing steps. In some embodiments, this pre-treatment of the pleural fluid is preferable in circumstances in which the pleural fluid must be cryopreserved for shipment to a laboratory performing the method or for later analysis (e.g., later than 24-48 hours post-collection). In some embodiments, the pleural fluid sample is prepared by centrifuging the pleural fluid sample after its withdrawal from the subject and resuspending the centrifugate or pellet in buffer. In some embodiments, the pleural fluid sample is subjected to multiple centrifugations and resuspensions, before it is cryopreserved for transport or later analysis and/or processing.

In some embodiments, pleural fluid samples are concentrated prior to further processing steps by using a filtration method. In some embodiments, the pleural fluid sample used in the contacting step is prepared by filtering the fluid through a filter containing a known and essentially uniform pore size that allows for passage of the pleural fluid through the membrane but retains the tumor cells. In some embodiments, the diameter of the pores in the membrane may be at least 4 μM. In another embodiment the pore diameter may be 5 μM or more, and in other embodiment, any of 6, 7, 8, 9, or 10 μM. After filtration, the cells, including TILs, retained by the membrane may be rinsed off the membrane into a suitable physiologically acceptable buffer. Cells, including TILs, concentrated in this way may then be used in the contacting step of the method.

In some embodiments, pleural fluid sample (including, for example, the untreated pleural fluid), diluted pleural fluid, or the resuspended cell pellet, is contacted with a lytic reagent that differentially lyses non-nucleated red blood cells present in the sample. In some embodiments, this step is performed prior to further processing steps in circumstances in which the pleural fluid contains substantial numbers of RBCs. Suitable lysing reagents include a single lytic reagent or a lytic reagent and a quench reagent, or a lytic agent, a quench reagent and a fixation reagent. Suitable lytic systems are marketed commercially and include the BD Pharm Lyse™ system (Becton Dickenson). Other lytic systems include the Versalyse™ system, the FACSlyse™ system (Becton Dickenson), the Immunoprep™ system or Erythrolyse II system (Beckman Coulter, Inc.), or an ammonium chloride system. In some embodiments, the lytic reagent can vary with the primary requirements being efficient lysis of the red blood cells, and the conservation of the TILs and phenotypic properties of the TILs in the pleural fluid. In addition to employing a single reagent for lysis, the lytic systems useful in methods described herein can include a second reagent, e.g., one that quenches or retards the effect of the lytic reagent during the remaining steps of the method, e.g., Stabilyse™ reagent (Beckman Coulter, Inc.). A conventional fixation reagent may also be employed depending upon the choice of lytic reagents or the preferred implementation of the method.

In some embodiments, the pleural fluid sample, unprocessed, diluted or multiply centrifuged or processed as described herein above is cryopreserved at a temperature of about −140° C. prior to being further processed and/or expanded as provided herein.

3. Methods of Expanding Peripheral Blood Lymphocytes (PBLs) from Peripheral Blood PBL Method 1. In an embodiment of the invention, PBLs are expanded using the processes described herein. In an embodiment of the invention, the method comprises obtaining a PBMC sample from whole blood. In an embodiment, the method comprises enriching T cells by isolating pure T cells from PBMCs using negative selection of a non-CD19+ fraction. In an embodiment, the method comprises enriching T cells by isolating pure T cells from PBMCs using magnetic bead-based negative selection of a non-CD19+ fraction.

In an embodiment of the invention, PBL Method 1 is performed as follows: On Day 0, a cryopreserved PBMC sample is thawed and PBMCs are counted. T cells are isolated using a Human Pan T-Cell Isolation Kit and LS columns (Miltenyi Biotec).

PBL Method 2. In an embodiment of the invention, PBLs are expanded using PBL Method 2, which comprises obtaining a PBMC sample from whole blood. The T cells from the PBMCs are enriched by incubating the PBMCs for at least three hours at 37° C. and then isolating the non-adherent cells.

In an embodiment of the invention, PBL Method 2 is performed as follows: On Day 0, the cryopreserved PMBC sample is thawed and the PBMC cells are seeded at 6 million cells per well in a 6 well plate in CM-2 media and incubated for 3 hours at 37 degrees Celsius. After 3 hours, the non-adherent cells, which are the PBLs, are removed and counted.

PBL Method 3. In an embodiment of the invention, PBLs are expanded using PBL Method 3, which comprises obtaining a PBMC sample from peripheral blood. B cells are isolated using a CD19+ selection and T cells are selected using negative selection of the non-CD19+ fraction of the PBMC sample.

In an embodiment of the invention, PBL Method 3 is performed as follows: On Day 0, cryopreserved PBMCs derived from peripheral blood are thawed and counted. CD19+ B cells are sorted using a CD19 Multisort Kit, Human (Miltenyi Biotec). Of the non-CD19+ cell fraction, T cells are purified using the Human Pan T cell Isolation Kit and LS Columns (Miltenyi Biotec).

In an embodiment, PBMCs are isolated from a whole blood sample. In an embodiment, the PBMC sample is used as the starting material to expand the PBLs. In an embodiment, the sample is cryopreserved prior to the expansion process. In another embodiment, a fresh sample is used as the starting material to expand the PBLs. In an embodiment of the invention, T cells are isolated from PBMCs using methods known in the art. In an embodiment, the T cells are isolated using a Human Pan T cell isolation kit and LS columns. In an embodiment of the invention, T cells are isolated from PBMCs using antibody selection methods known in the art, for example, CD19 negative selection.

In an embodiment of the invention, the PBMC sample is incubated for a period of time at a desired temperature effective to identify the non-adherent cells. In an embodiment of the invention, the incubation time is about 3 hours. In an embodiment of the invention, the temperature is about 37° Celsius. The non-adherent cells are then expanded using the process described above.

In some embodiments, the PBMC sample is from a subject or patient who has been optionally pre-treated with a regimen comprising a kinase inhibitor or an ITK inhibitor. In some embodiments, the tumor sample is from a subject or patient who has been pre-treated with a regimen comprising a kinase inhibitor or an ITK inhibitor. In some embodiments, the PBMC sample is from a subject or patient who has been pre-treated with a regimen comprising a kinase inhibitor or an ITK inhibitor, has undergone treatment for at least 1 month, at least 2 months, at least 3 months, at least 4 months, at least 5 months, at least 6 months, or 1 year or more. In another embodiment, the PBMCs are derived from a patient who is currently on an ITK inhibitor regimen, such as ibrutinib.

In some embodiments, the PBMC sample is from a subject or patient who has been pre-treated with a regimen comprising a kinase inhibitor or an ITK inhibitor and is refractory to treatment with a kinase inhibitor or an ITK inhibitor, such as ibrutinib.

In some embodiments, the PBMC sample is from a subject or patient who has been pre-treated with a regimen comprising a kinase inhibitor or an ITK inhibitor but is no longer undergoing treatment with a kinase inhibitor or an ITK inhibitor. In some embodiments, the PBMC sample is from a subject or patient who has been pre-treated with a regimen comprising a kinase inhibitor or an ITK inhibitor but is no longer undergoing treatment with a kinase inhibitor or an ITK inhibitor and has not undergone treatment for at least 1 month, at least 2 months, at least 3 months, at least 4 months, at least 5 months, at least 6 months, or at least 1 year or more. In another embodiment, the PBMCs are derived from a patient who has prior exposure to an ITK inhibitor, but has not been treated in at least 3 months, at least 6 months, at least 9 months, or at least 1 year.

In an embodiment of the invention, at Day 0, cells are selected for CD19+ and sorted accordingly. In an embodiment of the invention, the selection is made using antibody binding beads. In an embodiment of the invention, pure T cells are isolated on Day 0 from the PBMCs.

In an embodiment of the invention, for patients that are not pre-treated with ibrutinib or other ITK inhibitor, $10^{-15}$ mL of Buffy Coat will yield about $5\times10^9$ PBMC, which, in turn, will yield about $5.5\times10^7$ PBLs.

In an embodiment of the invention, for patients that are pre-treated with ibrutinib or other ITK inhibitor, the expansion process will yield about $20\times10^9$ PBLs. In an embodiment of the invention, $40.3\times10^6$ PBMCs will yield about $4.7\times10^5$ PBLs.

In any of the foregoing embodiments, PBMCs may be derived from a whole blood sample, by apheresis, from the buffy coat, or from any other method known in the art for obtaining PBMCs.

4. Methods of Expanding Marrow Infiltrating Lymphocytes (MILs) from PBMCs Derived from Bone Marrow MIL Method 3. In an embodiment of the invention, the method comprises obtaining PBMCs from the bone marrow. On Day 0, the PBMCs are selected for CD3+/CD33+/CD20+/CD14+ and sorted, and the non-CD3+/CD33+/CD20+/CD14+ cell fraction is sonicated and a portion of the sonicated cell fraction is added back to the selected cell fraction.

In an embodiment of the invention, MIL Method 3 is performed as follows: On Day 0, a cryopreserved sample of PBMCs is thawed and PBMCs are counted. The cells are stained with CD3, CD33, CD20, and CD14 antibodies and sorted using a S3e cell sorted (Bio-Rad). The cells are sorted into two fractions—an immune cell fraction (or the MIL fraction) (CD3+CD33+CD20+CD14+) and an AML blast cell fraction (non-CD3+CD33+CD20+CD14+).

In an embodiment of the invention, PBMCs are obtained from bone marrow. In an embodiment, the PBMCs are obtained from the bone marrow through apheresis, aspiration, needle biopsy, or other similar means known in the art. In an embodiment, the PBMCs are fresh. In another embodiment, the PBMCs are cryopreserved.

In an embodiment of the invention, MILs are expanded from 10-50 mL of bone marrow aspirate. In an embodiment of the invention, 10 mL of bone marrow aspirate is obtained from the patient. In another embodiment, 20 mL of bone marrow aspirate is obtained from the patient. In another embodiment, 30 mL of bone marrow aspirate is obtained from the patient. In another embodiment, 40 mL of bone marrow aspirate is obtained from the patient. In another embodiment, 50 mL of bone marrow aspirate is obtained from the patient.

In an embodiment of the invention, the number of PBMCs yielded from about 10-50 mL of bone marrow aspirate is about $5\times10^7$ to about $10\times10^7$ PBMCs. In another embodiment, the number of PMBCs yielded is about $7\times10^7$ PBMCs.

In an embodiment of the invention, about $5\times10^7$ to about $10\times10^7$ PBMCs, yields about $0.5\times10^6$ to about $1.5\times10^6$ MILs. In an embodiment of the invention, about $1\times10^6$ MILs is yielded.

In an embodiment of the invention, $12\times10^6$ PBMC derived from bone marrow aspirate yields approximately $1.4\times10^5$ MILs.

In any of the foregoing embodiments, PBMCs may be derived from a whole blood sample, from bone marrow, by apheresis, from the buffy coat, or from any other method known in the art for obtaining PBMCs.

B. STEP B: Priming First Expansion

In some embodiments, the present methods provide for younger TILs, which may provide additional therapeutic benefits over older TILs (i.e., TILs which have further undergone more rounds of replication prior to administration to a subject/patient). Features of young TILs have been described in the literature, for example Donia, at al., *Scandinavian Journal of Immunology,* 75:157-167 (2012); Dudley et al., *Clin Cancer Res,* 16:6122-6131 (2010); Huang et al., *J Immunother,* 28(3):258-267 (2005); Besser et al., *Clin Cancer Res,* 19(17):OF1-OF9 (2013); Besser et al., *J Immunother* 32:415-423 (2009); Robbins, et al., *J Immunol* 2004; 173:7125-7130; Shen et al., J Immunother, 30:123-129 (2007); Zhou, et al., *J Immunother,* 28:53-62 (2005); and Tran, et al., J Immunother, 31:742-751 (2008), all of which are incorporated herein by reference in their entireties.

After dissection or digestion of tumor fragments and/or tumor fragments, for example such as described in Step A of FIG. 1 (in particular, e.g., FIG. 1B and/or FIG. 8C), the resulting cells are cultured in serum containing IL-2, OKT-3, and feeder cells (e.g., antigen-presenting feeder cells), under conditions that favor the growth of TILs over tumor and other cells. In some embodiments, the IL-2, OKT-3, and feeder cells are added at culture initiation along with the tumor digest and/or tumor fragments (e.g., at Day 0). In some embodiments, the tumor digests and/or tumor fragments are incubated in a container with up to 60 fragments per container and with 6000 IU/mL of IL-2. In some embodiments, this primary cell population is cultured for a period of days, generally from 1 to 8 days, resulting in a bulk TIL population, generally about $1\times10^8$ bulk TIL cells. In some embodiments, this primary cell population is cultured for a period of days, generally from 1 to 7 days, resulting in a bulk TIL population, generally about $1\times10^8$ bulk TIL cells. In some embodiments, priming first expansion occurs for a period of 1 to 8 days, resulting in a bulk TIL population, generally about $1\times10^8$ bulk TIL cells. In some embodiments, priming first expansion occurs for a period of 1 to 7 days, resulting in a bulk TIL population, generally about $1\times10^8$ bulk TIL cells. In some embodiments, this priming first expansion occurs for a period of 5 to 8 days, resulting in a bulk TIL population, generally about $1\times10^8$ bulk TIL cells. In some embodiments, this priming first expansion occurs for a period of 5 to 7 days, resulting in a bulk TIL population, generally about $1\times10^8$ bulk TIL cells. In some embodiments, this priming first expansion occurs for a period of about 6 to 8 days, resulting in a bulk TIL population, generally about $1\times10^8$ bulk TIL cells. In some embodiments, this priming first expansion occurs for a period of about 6 to 7 days, resulting in a bulk TIL population, generally about $1\times10^8$ bulk TIL cells. In some embodiments, this priming first expansion occurs for a period of about 7 to 8 days, resulting in a bulk TIL population, generally about $1\times10^8$ bulk TIL cells. In some embodiments, this priming first expansion occurs for a period of about 7 days, resulting in a bulk TIL population, generally about $1\times10^8$ bulk TIL cells. In some embodiments, this priming first expansion occurs for a period of about 8 days, resulting in a bulk TIL population, generally about $1\times10^8$ bulk TIL cells.

In a preferred embodiment, expansion of TILs may be performed using a priming first expansion step (for example such as those described in Step B of FIG. 8 (in particular, e.g., FIG. 8B and/or FIG. 8C), which can include processes referred to as pre-REP or priming REP and which contains feeder cells from Day 0 and/or from culture initiation) as described below and herein, followed by a rapid second expansion (Step D, including processes referred to as rapid expansion protocol (REP) steps) as described below under Step D and herein, followed by optional cryopreservation, and followed by a second Step D (including processes referred to as restimulation REP steps) as described below and herein. The TILs obtained from this process may be optionally characterized for phenotypic characteristics and metabolic parameters as described herein. In some embodiments, the tumor fragment is between about 1 $mm^3$ and 10 $mm^3$.

In some embodiments, the first expansion culture medium is referred to as "CM", an abbreviation for culture media. In some embodiments, CM for Step B consists of RPMI 1640 with GlutaMAX, supplemented with 10% human AB serum, 25 mM Hepes, and 10 mg/mL gentamicin.

In some embodiments, there are less than or equal to 240 tumor fragments. In some embodiments, there are less than or equal to 240 tumor fragments placed in less than or equal to 4 containers. In some embodiments, the containers are G-Rex 100 MCS flasks. In some embodiments, less than or equal to 60 tumor fragments are placed in 1 container. In some embodiments, each container comprises less than or equal to 500 mL of media per container. In some embodiments, the media comprises IL-2. In some embodiments, the media comprises 6000 IU/mL of IL-2. In some embodiments, the media comprises antigen-presenting feeder cells (also referred to herein as "antigen-presenting cells"). In some embodiments, the media comprises $2.5\times10^8$ antigen-presenting feeder cells per container. In some embodiments, the media comprises OKT-3. In some embodiments, the media comprises 30 ng/mL of OKT-3 per container. In some embodiments, the container is a G-Rex 100 MCS flask. In some embodiments, the media comprises 6000 IU/mL of IL-2, 30 ng of OKT-3, and $2.5\times10^8$ antigen-presenting feeder cells. In some embodiments, the media comprises 6000 IU/mL of IL-2, 30 ng/mL of OKT-3, and $2.5\times10^8$ antigen-presenting feeder cells per container.

After preparation of the tumor fragments, the resulting cells (i.e., fragments which is a primary cell population) are cultured in media containing IL-2, antigen-presenting feeder cells and OKT-3 under conditions that favor the growth of TILs over tumor and other cells and which allow for TIL priming and accelerated growth from initiation of the culture on Day 0. In some embodiments, the tumor digests and/or tumor fragments are incubated in with 6000 IU/mL of IL-2, as well as antigen-presenting feeder cells and OKT-3. This primary cell population is cultured for a period of days, generally from 1 to 8 days, resulting in a bulk TIL population, generally about $1\times10^8$ bulk TIL cells. In some embodiments, the growth media during the priming first expansion comprises IL-2 or a variant thereof, as well as antigen-presenting feeder cells and OKT-3. In some embodiments, this primary cell population is cultured for a period of days, generally from 1 to 7 days, resulting in a bulk TIL population, generally about $1\times10^8$ bulk TIL cells. In some embodiments, the growth media during the priming first expansion comprises IL-2 or a variant thereof, as well as antigen-presenting feeder cells and OKT-3. In some embodiments, the IL-2 is recombinant human IL-2 (rhIL-2). In some embodiments the IL-2 stock solution has a specific activity of $20\text{-}30\times10^6$ IU/mg for a 1 mg vial. In some embodiments the IL-2 stock solution has a specific activity of $20\times10^6$ IU/mg for a 1 mg vial. In some embodiments the IL-2 stock solution has a specific activity of $25\times10^6$ IU/mg for a 1 mg vial. In some embodiments the IL-2 stock solution has a specific activity of $30\times10^6$ IU/mg for a 1 mg vial. In some embodiments, the IL-2 stock solution has a final concentration of $4\text{-}8\times10^6$ IU/mg of IL-2. In some embodiments, the IL-2 stock solution has a final concentration of $5\text{-}7\times10^6$ IU/mg of IL-2. In some embodiments, the IL-2 stock solution has a final concentration of $6\times10^6$ IU/mg of IL-2. In some embodiments, the IL-2 stock solution is prepare as described in Example C. In some embodiments, the priming first expansion culture media comprises about 10,000 IU/mL of IL-2, about 9,000 IU/mL of IL-2, about 8,000 IU/mL of IL-2, about 7,000 IU/mL of IL-2, about 6000 IU/mL of IL-2 or about 5,000 IU/mL of IL-2. In some embodiments, the priming first expansion culture media comprises about 9,000 IU/mL of IL-2 to about 5,000 IU/mL of IL-2. In some embodiments, the priming first expansion culture media comprises about 8,000 IU/mL of IL-2 to about 6,000 IU/mL of IL-2. In some embodiments, the priming first expansion culture media comprises about 7,000 IU/mL of IL-2 to about 6,000 IU/mL of IL-2. In some embodiments, the priming first expansion culture media comprises about 6,000 IU/mL of IL-2. In an embodiment, the cell culture medium further comprises IL-2. In some embodiments, the priming first expansion cell culture medium comprises about 3000 IU/mL of IL-2. In an embodiment, the priming first expansion cell culture medium further comprises IL-2. In a preferred embodiment, the priming first expansion cell culture medium comprises about 3000 IU/mL of IL-2. In an embodiment, the priming first expansion cell culture medium comprises about 1000 IU/mL, about 1500 IU/mL, about 2000 IU/mL, about 2500 IU/mL, about 3000 IU/mL, about 3500 IU/mL, about 4000 IU/mL, about 4500 IU/mL, about 5000 IU/mL, about 5500 IU/mL, about 6000 IU/mL, about 6500 IU/mL, about 7000 IU/mL, about 7500 IU/mL, or about 8000 IU/mL of IL-2. In an embodiment, the priming first expansion cell culture medium comprises between 1000 and 2000 IU/mL, between 2000 and 3000 IU/mL, between 3000 and 4000 IU/mL, between 4000 and 5000 IU/mL, between 5000 and 6000 IU/mL, between 6000 and 7000 IU/mL, between 7000 and 8000 IU/mL, or about 8000 IU/mL of IL-2.

In some embodiments, priming first expansion culture media comprises about 500 IU/mL of IL-15, about 400 IU/mL of IL-15, about 300 IU/mL of IL-15, about 200 IU/mL of IL-15, about 180 IU/mL of IL-15, about 160 IU/mL of IL-15, about 140 IU/mL of IL-15, about 120 IU/mL of IL-15, or about 100 IU/mL of IL-15. In some embodiments, the priming first expansion culture media comprises about 500 IU/mL of IL-15 to about 100 IU/mL of IL-15. In some embodiments, the priming first expansion culture media comprises about 400 IU/mL of IL-15 to about 100 IU/mL of IL-15. In some embodiments, the priming first expansion culture media comprises about 300 IU/mL of IL-15 to about 100 IU/mL of IL-15. In some embodiments, the priming first expansion culture media comprises about 200 IU/mL of IL-15. In some embodiments, the priming first expansion cell culture medium comprises about 180 IU/mL of IL-15. In an embodiment, the priming first expansion cell culture medium further comprises IL-15. In a preferred embodiment, the priming first expansion cell culture medium comprises about 180 IU/mL of IL-15.

In some embodiments, priming first expansion culture media comprises about 20 IU/mL of IL-21, about 15 IU/mL of IL-21, about 12 IU/mL of IL-21, about 10 IU/mL of IL-21, about 5 IU/mL of IL-21, about 4 IU/mL of IL-21, about 3 IU/mL of IL-21, about 2 IU/mL of IL-21, about 1 IU/mL of IL-21, or about 0.5 IU/mL of IL-21. In some embodiments, the priming first expansion culture media comprises about 20 IU/mL of IL-21 to about 0.5 IU/mL of IL-21. In some embodiments, the priming first expansion culture media comprises about 15 IU/mL of IL-21 to about 0.5 IU/mL of IL-21. In some embodiments, the priming first expansion culture media comprises about 12 IU/mL of IL-21 to about 0.5 IU/mL of IL-21. In some embodiments, the priming first expansion culture media comprises about 10 IU/mL of IL-21 to about 0.5 IU/mL of IL-21. In some embodiments, the priming first expansion culture media comprises about 5 IU/mL of IL-21 to about 1 IU/mL of IL-21. In some embodiments, the priming first expansion culture media comprises about 2 IU/mL of IL-21. In some embodiments, the priming first expansion cell culture medium comprises about 1 IU/mL of IL-21. In some embodiments, the priming first expansion cell culture medium comprises about 0.5 IU/mL of IL-21. In an embodiment, the cell culture medium further comprises IL-21. In a preferred embodiment, the priming first expansion cell culture medium comprises about 1 IU/mL of IL-21.

In an embodiment, the priming first expansion cell culture medium comprises OKT-3 antibody. In some embodiments, the priming first expansion cell culture medium comprises about 30 ng/mL of OKT-3 antibody. In an embodiment, the priming first expansion cell culture medium comprises about 0.1 ng/mL, about 0.5 ng/mL, about 1 ng/mL, about 2.5 ng/mL, about 5 ng/mL, about 7.5 ng/mL, about 10 ng/mL, about 15 ng/mL, about 20 ng/mL, about 25 ng/mL, about 30 ng/mL, about 35 ng/mL, about 40 ng/mL, about 50 ng/mL, about 60 ng/mL, about 70 ng/mL, about 80 ng/mL, about 90 ng/mL, about 100 ng/mL, about 200 ng/mL, about 500 ng/mL, and about 1 μg/mL of OKT-3 antibody. In an embodiment, the cell culture medium comprises between 0.1 ng/mL and 1 ng/mL, between 1 ng/mL and 5 ng/mL, between 5 ng/mL and 10 ng/mL, between 10 ng/mL and 20 ng/mL, between 20 ng/mL and 30 ng/mL, between 30 ng/mL and 40 ng/mL, between 40 ng/mL and 50 ng/mL, and between 50 ng/mL and 100 ng/mL of OKT-3 antibody. In an embodiment, the cell culture medium comprises between 15 ng/mL and 30 ng/mL of OKT-3 antibody. In an embodiment, the cell culture medium comprises 30 ng/mL of OKT-3 antibody. In some embodiments, the OKT-3 antibody is muromonab.

In some embodiments, the priming first expansion cell culture medium comprises one or more TNFRSF agonists in a cell culture medium. In some embodiments, the TNFRSF agonist comprises a 4-1BB agonist. In some embodiments, the TNFRSF agonist is a 4-1BB agonist, and the 4-1BB agonist is selected from the group consisting of urelumab, utomilumab, EU-101, a fusion protein, and fragments, derivatives, variants, biosimilars, and combinations thereof. In some embodiments, the TNFRSF agonist is added at a concentration sufficient to achieve a concentration in the cell culture medium of between 0.1 μg/mL and 100 μg/mL. In some embodiments, the TNFRSF agonist is added at a concentration sufficient to achieve a concentration in the cell culture medium of between 20 μg/mL and 40 μg/mL.

In some embodiments, in addition to one or more TNFRSF agonists, the priming first expansion cell culture medium further comprises IL-2 at an initial concentration of about 3000 IU/mL and OKT-3 antibody at an initial concentration of about 30 ng/mL, and wherein the one or more TNFRSF agonists comprises a 4-1BB agonist. In some embodiments, in addition to one or more TNFRSF agonists, the priming first expansion cell culture medium further comprises IL-2 at an initial concentration of about 6000 IU/mL and OKT-3 antibody at an initial concentration of about 30 ng/mL, and wherein the one or more TNFRSF agonists comprises a 4-1BB agonist.

In some embodiments, the priming first expansion culture medium is referred to as "CM", an abbreviation for culture media. In some embodiments, it is referred to as CM1 (culture medium 1). In some embodiments, CM consists of RPMI 1640 with GlutaMAX, supplemented with 10% human AB serum, 25 mM Hepes, and 10 mg/mL gentamicin. In some embodiments, the CM is the CM1 described in the Examples, see, Example A. In some embodiments, the priming first expansion occurs in an initial cell culture medium or a first cell culture medium. In some embodiments, the priming first expansion culture medium or the initial cell culture medium or the first cell culture medium comprises IL-2, OKT-3 and antigen-presenting feeder cells (also referred to herein as feeder cells).

In some embodiments, the culture medium used in the expansion processes disclosed herein is a serum-free medium or a defined medium. In some embodiments, the serum-free or defined medium comprises a basal cell medium and a serum supplement and/or a serum replacement. In some embodiments, the serum-free or defined medium is used to prevent and/or decrease experimental variation due in part to the lot-to-lot variation of serum-containing media.

In some embodiments, the serum-free or defined medium comprises a basal cell medium and a serum supplement and/or serum replacement. In some embodiments, the basal cell medium includes, but is not limited to CTS™ OpTmizer™ T cell Expansion Basal Medium, CTS™ OpTmizer™ T-Cell Expansion SFM, CTS™ AIM-V Medium, CTS™ AIM-V SFM, LymphoONE™ T-Cell Expansion Xeno-Free Medium, Dulbecco's Modified Eagle's Medium (DMEM), Minimal Essential Medium (MEM), Basal Medium Eagle (BME), RPMI 1640, F-10, F-12, Minimal Essential Medium (MEM), Glasgow's Minimal Essential Medium (G-MEM), RPMI growth medium, and Iscove's Modified Dulbecco's Medium.

In some embodiments, the serum supplement or serum replacement includes, but is not limited to one or more of CTS™ OpTmizer T-Cell Expansion Serum Supplement, CTS™ Immune Cell Serum Replacement, one or more albumins or albumin substitutes, one or more amino acids, one or more vitamins, one or more transferrins or transferrin substitutes, one or more antioxidants, one or more insulins or insulin substitutes, one or more collagen precursors, one or more antibiotics, and one or more trace elements. In some embodiments, the defined medium comprises albumin and one or more ingredients selected from the group consisting of glycine, L-histidine, L-isoleucine, L-methionine, L-phenylalanine, L-proline, L-hydroxyproline, L-serine, L-threonine, L-tryptophan, L-tyrosine, L-valine, thiamine, reduced glutathione, L-ascorbic acid-2-phosphate, iron saturated transferrin, insulin, and compounds containing the trace element moieties $Ag^{+}$, $Al^{3+}$, $Ba^{2+}$, $Cd^{2+}$, $Co^{2+}$, $Cr^{3+}$, $Ge^{4+}$, $Se^{4+}$, Br, T, $Mn^{2+}$, P, $Si^{4+}$, $V^{5+}$, $Mo^{6+}$, $Ni^{2+}$, $Rb^{+}$, $Sn^{2+}$ and $Zr^{4+}$. In some embodiments, the defined medium further comprises L-glutamine, sodium bicarbonate and/or 2-mercaptoethanol.

In some embodiments, the CTS™ OpTmizer™ T cell Immune Cell Serum Replacement is used with conventional growth media, including but not limited to CTS™ OpTmizer™ T cell Expansion Basal Medium, CTS™ OpTmizer™ T cell Expansion SFM, CTS™ AIM-V Medium, CST™ AIM-V SFM, LymphoONE™ T-Cell Expansion Xeno-Free Medium, Dulbecco's Modified Eagle's Medium (DMEM), Minimal Essential Medium (MEM), Basal Medium Eagle (BME), RPMI 1640, F-10, F-12, Minimal Essential Medium (αMEM), Glasgow's Minimal Essential Medium (G-MEM), RPMI growth medium, and Iscove's Modified Dulbecco's Medium.

In some embodiments, the total serum replacement concentration (vol %) in the serum-free or defined medium is from about 1%, 2%, 3%, 4%, 5%, 6%, 7%, 8%, 9%, 10%, 11%, 12%, 13%, 14%, 15%, 16%, 17%, 18%, 19%, or 20% by volume of the total serum-free or defined medium. In some embodiments, the total serum replacement concentration is about 3% of the total volume of the serum-free or defined medium. In some embodiments, the total serum replacement concentration is about 5% of the total volume of the serum-free or defined medium. In some embodiments, the total serum replacement concentration is about 10% of the total volume of the serum-free or defined medium.

In some embodiments, the serum-free or defined medium is CTS™ OpTmizer™ T cell Expansion SFM (ThermoFisher Scientific). Any formulation of CTS™ OpTmizer™ is useful in the present invention. CTS™ OpTmizer™ T cell Expansion SFM is a combination of 1L CTS™ OpTmizer™ T cell Expansion Basal Medium and 26 mL CTS™ OpTmizer™ T-Cell Expansion Supplement, which are mixed together prior to use. In some embodiments, the CTS™ OpTmizer™ T cell Expansion SFM is supplemented with about 3% of the CTS™ Immune Cell Serum Replacement (SR) (ThermoFisher Scientific). In some embodiments, the CTS™ OpTmizer™ T cell Expansion SFM is supplemented with about 3% of the CTS™ Immune Cell Serum Replacement (SR) (ThermoFisher Scientific), along with 2-mercaptoethanol at 55 mM. In some embodiments, the CTS™ OpTmizer™ T cell Expansion SFM is supplemented with about 3% of the CTS™ Immune Cell Serum Replacement (SR) (ThermoFisher Scientific) and the final concentration of 2-mercaptoethanol in the media is 55 µM.

In some embodiments, the defined medium is CTS™ OpTmizer™ T cell Expansion SFM (ThermoFisher Scientific). Any formulation of CTS™ OpTmizer™ is useful in the present invention. CTS™ OpTmizer™ T cell Expansion SFM is a combination of 1L CTS™ OpTmizer™ T cell Expansion Basal Medium and 26 mL CTS™ OpTmizer™ T-Cell Expansion Supplement, which are mixed together prior to use. In some embodiments, the CTS™ OpTmizer™ T cell Expansion SFM is supplemented with about 3% of the CTS™ Immune Cell Serum Replacement (SR) (ThermoFisher Scientific), along with 2-mercaptoethanol at 55 mM. In some embodiments, the CTS™ OpTmizer™ T cell Expansion SFM is supplemented with about 3% of the CTS™ Immune Cell Serum Replacement (SR) (ThermoFisher Scientific), 55 mM of 2-mercaptoethanol, and 2 mM of L-glutamine. In some embodiments, the CTS™ OpTmizer™ T cell Expansion SFM is supplemented with about 3% of the CTS™ Immune Cell Serum Replacement (SR) (ThermoFisher Scientific), 55 mM of 2-mercaptoethanol, and 2 mM of L-glutamine, and further comprises about 1000 IU/mL to about 8000 IU/mL of IL-2. In some embodiments, the CTS™ OpTmizer™ T cell Expansion SFM is supplemented with about 3% of the CTS™ Immune Cell Serum Replacement (SR) (ThermoFisher Scientific), 55 mM of 2-mercaptoethanol, and 2 mM of L-glutamine, and further comprises about 3000 IU/mL of IL-2. In some embodiments, the CTS™ OpTmizer™ T cell Expansion SFM is supplemented with about 3% of the CTS™ Immune Cell Serum Replacement (SR) (ThermoFisher Scientific), 55 mM of 2-mercaptoethanol, and 2 mM of L-glutamine, and further comprises about 6000 IU/mL of IL-2. In some embodiments, the CTS™ OpTmizer™ T cell Expansion SFM is supplemented with about 3% of the CTS™ Immune Cell Serum Replacement (SR) (ThermoFisher Scientific) and 55 mM of 2-mercaptoethanol, and further comprises about 1000 IU/mL to about 8000 IU/mL of IL-2. In some embodiments, the CTS™ OpTmizer™ T cell Expansion SFM is supplemented with about 3% of the CTS™ Immune Cell Serum Replacement (SR) (ThermoFisher Scientific) and 55 mM of 2-mercaptoethanol, and further comprises about 3000 IU/mL of IL-2. In some embodiments, the CTS™ OpTmizer™ T cell Expansion SFM is supplemented with about 3% of the CTS™ Immune Cell Serum Replacement (SR) (ThermoFisher Scientific) and 55 mM of 2-mercaptoethanol, and further comprises about 1000 IU/mL to about 6000 IU/mL of IL-2. In some embodiments, the CTS™ OpTmizer™ T cell Expansion SFM is supplemented with about 3% of the CTS™ Immune Cell Serum Replacement (SR) (ThermoFisher Scientific) and about 2 mM glutamine, and further comprises about 1000 IU/mL to about 8000 IU/mL of IL-2. In some embodiments, the CTS™ OpTmizer™ T cell Expansion SFM is supplemented with about 3% of the CTS™ Immune Cell Serum Replacement (SR) (ThermoFisher Scientific) and about 2 mM glutamine, and further comprises about 3000 IU/mL of IL-2. In some embodiments, the CTS™ OpTmizer™ T cell Expansion SFM is supplemented with about 3% of the CTS™ Immune Cell Serum Replacement (SR) (ThermoFisher Scientific) and about 2 mM glutamine, and further comprises about 6000 IU/mL of IL-2. In some embodiments, the CTS™ OpTmizer™ T cell Expansion SFM is supplemented with about 3% of the CTS™ Immune Cell Serum Replacement (SR) (ThermoFisher Scientific) and the final concentration of 2-mercaptoethanol in the media is 55 µM.

In some embodiments, the serum-free medium or defined medium is supplemented with glutamine (i.e., GlutaMAX®) at a concentration of from about 0.1 mM to about 10 mM, 0.5 mM to about 9 mM, 1 mM to about 8 mM, 2 mM to about 7 mM, 3 mM to about 6 mM, or 4 mM to about 5 mM. In some embodiments, the serum-free medium or defined medium is supplemented with glutamine (i.e., GlutaMAX®) at a concentration of about 2 mM.

In some embodiments, the serum-free medium or defined medium is supplemented with 2-mercaptoethanol at a concentration of from about 5 mM to about 150 mM, 10 mM to about 140 mM, 15 mM to about 130 mM, 20 mM to about 120 mM, 25 mM to about 110 mM, 30 mM to about 100 mM, 35 mM to about 95 mM, 40 mM to about 90 mM, 45 mM to about 85 mM, 50 mM to about 80 mM, 55 mM to about 75 mM, 60 mM to about 70 mM, or about 65 mM. In some embodiments, the serum-free medium or defined medium is supplemented with 2-mercaptoethanol at a concentration of about 55 mM. In some embodiments, the final concentration of 2-mercaptoethanol in the media is 55 µM.

In some embodiments, the defined media described in International PCT Publication No. WO/1998/030679, which is herein incorporated by reference, are useful in the present invention. In that publication, serum-free eukaryotic cell culture media are described. The serum-free, eukaryotic cell culture medium includes a basal cell culture medium supplemented with a serum-free supplement capable of supporting the growth of cells in serum-free culture. The serum-free eukaryotic cell culture medium supplement comprises or is obtained by combining one or more ingredients selected from the group consisting of one or more albumins or albumin substitutes, one or more amino acids, one or more vitamins, one or more transferrins or transferrin substitutes, one or more antioxidants, one or more insulins or insulin substitutes, one or more collagen precursors, one or more trace elements, and one or more antibiotics. In some embodiments, the defined medium further comprises L-glutamine, sodium bicarbonate and/or beta-mercaptoethanol. In some embodiments, the defined medium comprises an albumin or an albumin substitute and one or more ingredients selected from group consisting of one or more amino acids, one or more vitamins, one or more transferrins or transferrin substitutes, one or more antioxidants, one or more insulins or insulin substitutes, one or more collagen precursors, and one or more trace elements. In some embodiments, the defined medium comprises albumin and one or more ingredients selected from the group consisting of glycine, L-histidine, L-isoleucine, L-methionine, L-phenylalanine, L-proline, L-hydroxyproline, L-serine, L-threonine, L-tryptophan, L-tyrosine, L-valine, thiamine, reduced glutathione, L-ascorbic acid-2-phosphate, iron saturated transferrin, insulin, and compounds containing the trace element moieties $Ag^{+}$, $Al^{3+}$, $Ba^{2+}$, $Cd^{2+}$, $Co^{2+}$, $Cr^{3+}$, $Ge^{4+}$, $Se^{4+}$, Br, T, $Mn^{2+}$, P, $Si^{4+}$, $V^{5+}$, $Mo^{6+}$, $Ni^{2+}$, $Rb^{+}$, $Sn^{2+}$ and $Zr^{4+}$. In some embodiments, the basal cell media is selected from the group consisting of Dulbecco's Modified Eagle's Medium (DMEM), Minimal Essential Medium (MEM), Basal Medium Eagle (BME), RPMI 1640, F-10, F-12, Minimal Essential Medium (αMEM), Glasgow's Minimal Essential Medium (G-MEM), RPMI growth medium, and Iscove's Modified Dulbecco's Medium.

In some embodiments, the concentration of glycine in the defined medium is in the range of from about 5-200 mg/L, the concentration of L-histidine is about 5-250 mg/L, the concentration of L-isoleucine is about 5-300 mg/L, the concentration of L-methionine is about 5-200 mg/L, the concentration of L-phenylalanine is about 5-400 mg/L, the concentration of L-proline is about 1-1000 mg/L, the concentration of L-hydroxyproline is about 1-45 mg/L, the concentration of L-serine is about 1-250 mg/L, the concentration of L-threonine is about $10^{-500}$ mg/L, the concentration of L-tryptophan is about 2-110 mg/L, the concentration of L-tyrosine is about 3-175 mg/L, the concentration of L-valine is about 5-500 mg/L, the concentration of thiamine is about 1-20 mg/L, the concentration of reduced glutathione is about 1-20 mg/L, the concentration of L-ascorbic acid-2-phosphate is about 1-200 mg/L, the concentration of iron saturated transferrin is about 1-50 mg/L, the concentration of insulin is about 1-100 mg/L, the concentration of sodium selenite is about 0.000001-0.0001 mg/L, and the concentration of albumin (e.g., AlbuMAX® I) is about 5000-50,000 mg/L.

In some embodiments, the non-trace element moiety ingredients in the defined medium are present in the concentration ranges listed in the column under the heading "Concentration Range in 1× Medium" in Table 4 below. In other embodiments, the non-trace element moiety ingredients in the defined medium are present in the final concentrations listed in the column under the heading "A Preferred Embodiment of the 1× Medium" in Table 3 below. In other embodiments, the defined medium is a basal cell medium comprising a serum free supplement. In some of these embodiments, the serum free supplement comprises non-trace moiety ingredients of the type and in the concentrations listed in the column under the heading "A Preferred Embodiment in Supplement" in Table 4 below.

TABLE 4

Concentrations of Non-Trace Element Moiety Ingredients

| Ingredient | A preferred embodiment in supplement (mg/L) (About) | Concentration range in 1X medium (mg/L) (About) | A preferred embodiment in 1X medium (mg/L) (About) |
|---|---|---|---|
| Glycine | 150 | 5-200 | 53 |
| L-Histidine | 940 | 5-250 | 183 |
| L-Isoleucine | 3400 | 5-300 | 615 |
| L-Methionine | 90 | 5-200 | 44 |
| L-Phenylalanine | 1800 | 5-400 | 336 |
| L-Proline | 4000 | 1-1000 | 600 |
| L-Hydroxyproline | 100 | 1-45 | 15 |
| L-Serine | 800 | 1-250 | 162 |
| L-Threonine | 2200 | 10-500 | 425 |
| L-Tryptophan | 440 | 2-110 | 82 |
| L-Tyrosine | 77 | 3-175 | 84 |
| L-Valine | 2400 | 5-500 | 454 |
| Thiamine | 33 | 1-20 | 9 |
| Reduced Glutathione | 10 | 1-20 | 1.5 |
| Ascorbic Acid-2-$PO_4$ (Mg Salt) | 330 | 1-200 | 50 |
| Transferrin (iron saturated) | 55 | 1-50 | 8 |
| Insulin | 100 | 1-100 | 10 |
| Sodium Selenite | 0.07 | 0.000001-0.0001 | 0.00001 |
| AlbuMAX ®I | 83,000 | 5000-50,000 | 12,500 |

In some embodiments, the osmolarity of the defined medium is between about 260 and 350 mOsmol. In some embodiments, the osmolarity is between about 280 and 310 mOsmol. In some embodiments, the defined medium is supplemented with up to about 3.7 g/L, or about 2.2 g/L sodium bicarbonate. The defined medium can be further supplemented with L-glutamine (final concentration of about 2 mM), one or more antibiotics, non-essential amino acids (NEAA; final concentration of about 100 μM), 2-mercaptoethanol (final concentration of about 100 μM).

In some embodiments, the defined media described in Smith, et al., "Ex vivo expansion of human T cells for adoptive immunotherapy using the novel Xeno-free CTS Immune Cell Serum Replacement," *Clin. Transl. Immunology,* 4(1) 2015 (doi: 10.1038/cti.2014.31) are useful in the present invention. Briefly, RPMI or CTS™ OpTmizer™ was used as the basal cell medium, and supplemented with either 0, 2%, 5%, or 10% CTS™ Immune Cell Serum Replacement.

In an embodiment, the cell medium in the first and/or second gas permeable container is unfiltered. The use of unfiltered cell medium may simplify the procedures necessary to expand the number of cells. In an embodiment, the cell medium in the first and/or second gas permeable container lacks beta-mercaptoethanol (BME or βME; also known as 2-mercaptoethanol, CAS 60-24-2).

In some embodiments, the priming first expansion (including processes such as for example those described in Step B of FIG. 8 (in particular, e.g., FIG. 8A and/or FIG. 8B and/or FIG. 8C and/or FIG. 8D), which can include those sometimes referred to as the pre-REP or priming REP) process is 1 to 8 days, as discussed in the examples and figures. In some embodiments, the priming first expansion (including processes such as for example those described in Step B of FIG. 8 (in particular, e.g., FIG. 8A and/or FIG. 8B and/or FIG. 8C and/or FIG. 8D), which can include those sometimes referred to as the pre-REP or priming REP) process is 2 to 8 days. In some embodiments, the priming first expansion (including processes such as for example those described in Step B of FIG. 8 (in particular, e.g., FIG. 8A and/or FIG. 8B and/or FIG. 8C and/or FIG. 8D), which can include those sometimes referred to as the pre-REP or priming REP) process is 3 to 8 days. In some embodiments, the priming first expansion (including processes such as for example those described in Step B of FIG. 8 (in particular, e.g., FIG. 8A and/or FIG. 8B and/or FIG. 8C and/or FIG. 8D), which can include those sometimes referred to as the pre-REP or priming REP) process is 4 to 8 days, as discussed in the examples and figures. In some embodiments, the priming first expansion (including processes such as for example those described in Step B of FIG. 8 (in particular, e.g., FIG. 8A and/or FIG. 8B and/or FIG. 8C and/or FIG. 8D), which can include those sometimes referred to as the pre-REP or priming REP) process is 1 to 7 days, as discussed in the examples and figures. In some embodiments, the priming first expansion (including processes such as for example those described in Step B of FIG. 8 (in particular, e.g., FIG. 8A and/or FIG. 8B and/or FIG. 8C and/or FIG. 8D), which can include those sometimes referred to as the pre-REP or priming REP) process is 2 to 8 days. In some embodiments, the priming first expansion (including processes such as for example those described in Step B of FIG. 8 (in particular, e.g., FIG. 8A and/or FIG. 8B and/or FIG. 8C and/or FIG. 8D), which can include those sometimes referred to as the pre-REP or priming REP) process is 2 to 7 days. In some embodiments, the priming first expansion (including processes such as for example those described in Step B of FIG. 8 (in particular, e.g., FIG. 8A and/or FIG. 8B and/or FIG. 8C and/or FIG. 8D), which can include those sometimes referred to as the pre-REP or priming REP) process is 3 to 8 days. In some embodiments, the priming first expansion (including processes such as for example those described in Step B of FIG. 8 (in particular, e.g., FIG. 8A and/or FIG. 8B and/or FIG. 8C and/or FIG. 8D), which can include those sometimes referred to as the pre-REP or priming REP) process is 3 to 7 days. In some embodiments, the priming first expansion (including processes such as for example those described in Step B of FIG. 8 (in particular, e.g., FIG. 8A and/or FIG. 8B and/or FIG. 8C and/or FIG. 8D), which can include those sometimes referred to as the pre-REP or priming REP) process is 4 to 8 days. In some embodiments, the priming first expansion (including processes such as for example those described in Step B of FIG. 8 (in particular, e.g., FIG. 8A and/or FIG. 8B and/or FIG. 8C and/or FIG. 8D), which can include those sometimes referred to as the pre-REP or priming REP) process is 4 to 7 days. In some embodiments, the priming first expansion (including processes such as for example those described in Step B of FIG. 8 (in particular, e.g., FIG. 8A and/or FIG. 8B and/or FIG. 8C and/or FIG. 8D), which can include those sometimes referred to as the pre-REP or priming REP) process is 5 to 8 days. In some embodiments, the priming first expansion (including processes such as for example those described in Step B of FIG. 8 (in particular, e.g., FIG. 8A and/or FIG. 8B and/or FIG. 8C and/or FIG. 8D), which can include those sometimes referred to as the pre-REP or priming REP) process is 5 to 7 days. In some embodiments, the priming first expansion (including processes such as for example those described in Step B of FIG. 8 (in particular, e.g., FIG. 8A and/or FIG. 8B and/or FIG. 8C and/or FIG. 8D), which can include those sometimes referred to as the pre-REP or priming REP) process is 6 to 8 days. In some embodiments, the priming first expansion (including processes such as for example those described in Step B of FIG. 8 (in particular, e.g., FIG. 8A and/or FIG. 8B and/or FIG. 8C and/or FIG. 8D), which can include those sometimes referred to as the pre-REP or priming REP) process is 6 to 7 days. In some embodiments, the priming first expansion (including processes such as for example those provided in Step B of FIG. 1 and/or FIG. 8 (in particular, e.g., FIG. 8A and/or FIG. 8B and/or FIG. 8C and/or FIG. 8D), which can include those sometimes referred to as the pre-REP or priming REP) process is 7 to 8 days. In some embodiments, the priming first expansion (including processes such as for example those provided in Step B of FIG. 8 (in particular, e.g., FIG. 8A and/or FIG. 8B and/or FIG. 8C and/or FIG. 8D), which can include those sometimes referred to as the pre-REP or priming REP) process is 8 days. In some embodiments, the priming first expansion (including processes such as for example those provided in Step B of FIG. 8 (in particular, e.g., FIG. 8A and/or FIG. 8B and/or FIG. 8C and/or FIG. 8D), which can include those sometimes referred to as the pre-REP or priming REP) process is 7 days.

In some embodiments, the priming first TIL expansion can proceed for 1 days to 8 days from when fragmentation occurs and/or when the first priming expansion step is initiated. In some embodiments, the priming first TIL expansion can proceed for 1 days to 7 days from when fragmentation occurs and/or when the first priming expansion step is initiated. In some embodiments, the priming first TIL expansion can proceed for 2 days to 8 days from when fragmentation occurs and/or when the first priming expansion step is initiated. In some embodiments, the priming first TIL expansion can proceed for 2 days to 7 days from when fragmentation occurs and/or when the first priming expansion step is initiated. In some embodiments, the priming first TIL expansion can proceed for 3 days to 8 days from when fragmentation occurs and/or when the first priming expansion step is initiated. In some embodiments, the priming first TIL expansion can proceed for 3 days to 7 days from when fragmentation occurs and/or when the first priming expansion step is initiated. In some embodiments, the priming first TIL expansion can proceed for 4 days to 8 days from when fragmentation occurs and/or when the first priming expansion step is initiated. In some embodiments, the priming first TIL expansion can proceed for 4 days to 7 days from when fragmentation occurs and/or when the first priming expansion step is initiated. In some embodiments, the priming first TIL expansion can proceed for 5 days to 8 days from when fragmentation occurs and/or when the first priming expansion step is initiated. In some embodiments, the priming first TIL expansion can proceed for 5 days to 7 days from when fragmentation occurs and/or when the first priming expansion step is initiated. In some embodiments, the priming first TIL expansion can proceed for 6 days to 8 days from when fragmentation occurs and/or when the first priming expansion step is initiated. In some embodiments, the priming first TIL expansion can proceed for 6 days to 7 days from when fragmentation occurs and/or when the first priming expansion step is initiated. In some embodiments, the priming first TIL expansion can proceed for 7 to 8 days from when fragmentation occurs and/or when the first priming expansion step is initiated. In some embodiments, the priming first TIL expansion can proceed for 8 days from when fragmentation occurs and/or when the first priming expansion step is initiated. In some embodiments, the priming first TIL expansion can proceed for 7 days from when fragmentation occurs and/or when the first priming expansion step is initiated.

In some embodiments, the priming first expansion of the TILs can proceed for 1 day, 2 days, 3 days, 4 days, 5 days, 6 days, 7 days, or 8 days. In some embodiments, the first TIL expansion can proceed for 1 day to 8 days. In some embodiments, the first TIL expansion can proceed for 1 day to 7 days. In some embodiments, the first TIL expansion can proceed for 2 days to 8 days. In some embodiments, the first TIL expansion can proceed for 2 days to 7 days. In some embodiments, the first TIL expansion can proceed for 3 days to 8 days. In some embodiments, the first TIL expansion can proceed for 3 days to 7 days. In some embodiments, the first TIL expansion can proceed for 4 days to 8 days. In some embodiments, the first TIL expansion can proceed for 4 days to 7 days. In some embodiments, the first TIL expansion can proceed for 5 days to 8 days. In some embodiments, the first TIL expansion can proceed for 5 days to 7 days. In some embodiments, the first TIL expansion can proceed for 6 days to 8 days. In some embodiments, the first TIL expansion can proceed for 6 days to 7 days. In some embodiments, the first TIL expansion can proceed for 7 to 8 days. In some embodiments, the first TIL expansion can proceed for 8 days. In some embodiments, the first TIL expansion can proceed for 7 days.

In some embodiments, a combination of IL-2, IL-7, IL-15, and/or IL-21 are employed as a combination during the priming first expansion. In some embodiments, IL-2, IL-7, IL-15, and/or IL-21 as well as any combinations thereof can be included during the priming first expansion, including, for example during Step B processes according to FIG. 8 (in particular, e.g., FIG. 8A and/or FIG. 8B and/or FIG. 8C and/or FIG. 8D), as well as described herein. In some embodiments, a combination of IL-2, IL-15, and IL-21 are employed as a combination during the priming first expansion. In some embodiments, IL-2, IL-15, and IL-21 as well as any combinations thereof can be included during Step B processes according to FIG. 8 (in particular, e.g., FIG. 8A and/or FIG. 8B and/or FIG. 8C and/or FIG. 8D) and as described herein.

In some embodiments, the priming first expansion, for example, Step B according to FIG. 8 (in particular, e.g., FIG. 8A and/or FIG. 8B and/or FIG. 8C and/or FIG. 8D), is performed in a closed system bioreactor. In some embodiments, a closed system is employed for the TIL expansion, as described herein. In some embodiments, a bioreactor is employed. In some embodiments, a bioreactor is employed as the container. In some embodiments, the bioreactor employed is for example a G-Rex-10 or a G-Rex-100. In some embodiments, the bioreactor employed is a G-Rex-100. In some embodiments, the bioreactor employed is a G-Rex-10.

1. Feeder Cells and Antigen Presenting Cells

In an embodiment, the priming first expansion procedures described herein (for example including expansion such as those described in Step B from FIG. 1 (in particular, e.g., FIG. 8A and/or FIG. 8B and/or FIG. 8C and/or FIG. 8D), as well as those referred to as pre-REP or priming REP) does not require feeder cells (also referred to herein as "antigen-presenting cells") at the initiation of the TIL expansion, but rather are added during the priming first expansion. In an embodiment, the priming first expansion procedures described herein (for example including expansion such as those described in Step B from FIG. 8 (in particular, e.g., FIG. 8A and/or FIG. 8B and/or FIG. 8C and/or FIG. 8D), as well as those referred to as pre-REP or priming REP) does not require feeder cells (also referred to herein as "antigen-presenting cells") at the initiation of the TIL expansion, but rather are added during the priming first expansion at any time during days 4-8. In an embodiment, the priming first expansion procedures described herein (for example including expansion such as those described in Step B from FIG. 8 (in particular, e.g., FIG. 8A and/or FIG. 8B and/or FIG. 8C and/or FIG. 8D as well as those referred to as pre-REP or priming REP) does not require feeder cells (also referred to herein as "antigen-presenting cells") at the initiation of the TIL expansion, but rather are added during the priming first expansion at any time during days 4-7. In an embodiment, the priming first expansion procedures described herein (for example including expansion such as those described in Step B from FIG. 8 (in particular, e.g., FIG. 8A and/or FIG. 8B and/or FIG. 8C and/or FIG. 8D), as well as those referred to as pre-REP or priming REP) does not require feeder cells (also referred to herein as "antigen-presenting cells") at the initiation of the TIL expansion, but rather are added during the priming first expansion at any time during days 5-8. In an embodiment, the priming first expansion procedures described herein (for example including expansion such as those described in Step B from FIG. 8 (in particular, e.g., FIG. 8A and/or FIG. 8B and/or FIG. 8C and/or FIG. 8D), as well as those referred to as pre-REP or priming REP) does not require feeder cells (also referred to herein as "antigen-presenting cells") at the initiation of the TIL expansion, but rather are added during the priming first expansion at any time during days 5-7. In an embodiment, the priming first expansion procedures described herein (for example including expansion such as those described in Step B from FIG. 8 (in particular, e.g., FIG. 8A and/or FIG. 8B and/or FIG. 8C and/or FIG. 8D), as well as those referred to as pre-REP or priming REP) does not require feeder cells (also referred to herein as "antigen-presenting cells") at the initiation of the TIL expansion, but rather are added during the priming first expansion at any time during days 6-8. In an embodiment, the priming first expansion procedures described herein (for example including expansion such as those described in Step B from FIG. 8 (in particular, e.g., FIG. 8A and/or FIG. 8B and/or FIG. 8C and/or FIG. 8D), as well as those referred to as pre-REP or priming REP) does not require feeder cells (also referred to herein as "antigen-presenting cells") at the initiation of the TIL expansion, but rather are added during the priming first expansion at any time during days 6-7. In an embodiment, the priming first expansion procedures described herein (for example including expansion such as those described in Step B from FIG. 8 (in particular, e.g., FIG. 8A and/or FIG. 8B and/or FIG. 8C and/or FIG. 8D), as well as those referred to as pre-REP or priming REP) does not require feeder cells (also referred to herein as "antigen-presenting cells") at the initiation of the TIL expansion, but rather are added during the priming first expansion at any time during day 7 or 8. In an embodiment, the priming first expansion procedures described herein (for example including expansion such as those described in Step B from FIG. 8 (in particular, e.g., FIG. 8A and/or FIG. 8B and/or FIG. 8C and/or FIG. 8D), as well as those referred to as pre-REP or priming REP) does not require feeder cells (also referred to herein as "antigen-presenting cells") at the initiation of the TIL expansion, but rather are added during the priming first expansion at any time during day 7. In an embodiment, the priming first expansion procedures described herein (for example including expansion such as those described in Step B from FIG. 8 (in particular, e.g., FIG. 8A and/or FIG. 8B and/or FIG. 8C and/or FIG. 8D), as well as those referred to as pre-REP or priming REP) does not require feeder cells (also referred to herein as "antigen-presenting cells") at the initiation of the TIL expansion, but rather are added during the priming first expansion at any time during day 8.

In an embodiment, the priming first expansion procedures described herein (for example including expansion such as those described in Step B from FIG. 8 (in particular, e.g., FIG. 8B), as well as those referred to as pre-REP or priming REP) require feeder cells (also referred to herein as "antigen-presenting cells") at the initiation of the TIL expansion and during the priming first expansion. In many embodiments, the feeder cells are peripheral blood mononuclear cells (PBMCs) obtained from standard whole blood units from allogeneic healthy blood donors. The PBMCs are obtained using standard methods such as Ficoll-Paque gradient separation. In some embodiments, $2.5\times10^8$ feeder cells are used during the priming first expansion. In some embodiments, $2.5\times10^8$ feeder cells per container are used during the priming first expansion. In some embodiments, $2.5\times10^8$ feeder cells per GREX-10 are used during the priming first expansion. In some embodiments, $2.5\times10^8$ feeder cells per GREX-100 are used during the priming first expansion.

In general, the allogeneic PBMCs are inactivated, either via irradiation or heat treatment, and used in the REP procedures, as described in the examples, which provides an exemplary protocol for evaluating the replication incompetence of irradiate allogeneic PBMCs.

In some embodiments, PBMCs are considered replication incompetent and acceptable for use in the TIL expansion procedures described herein if the total number of viable cells on day 14 is less than the initial viable cell number put into culture on day 0 of the priming first expansion.

In some embodiments, PBMCs are considered replication incompetent and acceptable for use in the TIL expansion procedures described herein if the total number of viable cells, cultured in the presence of OKT3 and IL-2, on day 7 have not increased from the initial viable cell number put into culture on day 0 of the priming first expansion. In some embodiments, the PBMCs are cultured in the presence of 30 ng/mL OKT3 antibody and 3000 IU/mL IL-2. In some embodiments, the PBMCs are cultured in the presence of 30 ng/mL OKT3 antibody and 6000 IU/mL IL-2.

In some embodiments, PBMCs are considered replication incompetent and acceptable for use in the TIL expansion procedures described herein if the total number of viable cells, cultured in the presence of OKT3 and IL-2, on day 7 have not increased from the initial viable cell number put into culture on day 0 of the priming first expansion. In some embodiments, the PBMCs are cultured in the presence of 5-60 ng/mL OKT3 antibody and 1000-6000 IU/mL IL-2. In some embodiments, the PBMCs are cultured in the presence of $10^{-50}$ ng/mL OKT3 antibody and 2000-5000 IU/mL IL-2. In some embodiments, the PBMCs are cultured in the presence of 20-40 ng/mL OKT3 antibody and 2000-4000 IU/mL IL-2. In some embodiments, the PBMCs are cultured in the presence of 25-35 ng/mL OKT3 antibody and 2500-3500 IU/mL IL-2. In some embodiments, the PBMCs are cultured in the presence of 30 ng/mL OKT3 antibody and 6000 IU/mL IL-2. In some embodiments, the PBMCs are cultured in the presence of 15 ng/mL OKT3 antibody and 3000 IU/mL IL-2. In some embodiments, the PBMCs are cultured in the presence of 15 ng/mL OKT3 antibody and 6000 IU/mL IL-2.

In some embodiments, the antigen-presenting feeder cells are PBMCs. In some embodiments, the antigen-presenting feeder cells are artificial antigen-presenting feeder cells. In an embodiment, the ratio of TILs to antigen-presenting feeder cells in the second expansion is about 1 to 25, about 1 to 50, about 1 to 100, about 1 to 125, about 1 to 150, about 1 to 175, about 1 to 200, about 1 to 225, about 1 to 250, about 1 to 275, about 1 to 300, about 1 to 325, about 1 to 350, about 1 to 375, about 1 to 400, or about 1 to 500. In an embodiment, the ratio of TILs to antigen-presenting feeder cells in the second expansion is between 1 to 50 and 1 to 300. In an embodiment, the ratio of TILs to antigen-presenting feeder cells in the second expansion is between 1 to 100 and 1 to 200.

In an embodiment, the priming first expansion procedures described herein require a ratio of about $2.5\times10^8$ feeder cells to about $100\times10^6$ TILs. In another embodiment, the priming first expansion procedures described herein require a ratio of about $2.5\times10^8$ feeder cells to about $50\times10^6$ TILs. In yet another embodiment, the priming first expansion described herein require about $2.5\times10^8$ feeder cells to about $25\times10^6$ TILs. In yet another embodiment, the priming first expansion described herein require about $2.5\times10^8$ feeder cells. In yet another embodiment, the priming first expansion requires one-fourth, one-third, five-twelfths, or one-half of the number of feeder cells used in the rapid second expansion.

In some embodiments, the media in the priming first expansion comprises IL-2. In some embodiments, the media in the priming first expansion comprises 6000 IU/mL of IL-2. In some embodiments, the media in the priming first expansion comprises antigen-presenting feeder cells. In some embodiments, the media in the priming first expansion comprises $2.5\times10^8$ antigen-presenting feeder cells per container. In some embodiments, the media in the priming first expansion comprises OKT-3. In some embodiments, the media comprises 30 ng of OKT-3 per container. In some embodiments, the container is a G-Rex 100 MCS flask. In some embodiments, the media comprises 6000 IU/mL of IL-2, 30 ng/mL of OKT-3, and $2.5\times10^8$ antigen-presenting feeder cells. In some embodiments, the media comprises 6000 IU/mL of IL-2, 30 ng/mL of OKT-3, and $2.5\times10^8$ antigen-presenting feeder cells per container. In some embodiments, the media comprises 500 mL of culture medium and 15 μg of OKT-3 per $2.5\times10^8$ antigen-presenting feeder cells per container. In some embodiments, the media comprises 500 mL of culture medium and 15 μg of OKT-3 per container. In some embodiments, the container is a G-Rex 100 MCS flask. In some embodiments, the media comprises 500 mL of culture medium, 6000 IU/mL of IL-2, 30 ng/mL of OKT-3, and $2.5\times10^8$ antigen-presenting feeder cells. In some embodiments, the media comprises 500 mL of culture medium, 6000 IU/mL of IL-2, 15 μg of OKT-3, and $2.5\times10^8$ antigen-presenting feeder cells per container. In some embodiments, the media comprises 500 mL of culture medium and 15 μg of OKT-3 per $2.5\times10^8$ antigen-presenting feeder cells per container.

In an embodiment, the priming first expansion procedures described herein require an excess of feeder cells over TILs during the second expansion. In many embodiments, the feeder cells are peripheral blood mononuclear cells (PBMCs) obtained from standard whole blood units from allogeneic healthy blood donors. The PBMCs are obtained using standard methods such as Ficoll-Paque gradient separation. In an embodiment, artificial antigen-presenting (aAPC) cells are used in place of PBMCs.

In general, the allogeneic PBMCs are inactivated, either via irradiation or heat treatment, and used in the TIL expansion procedures described herein, including the exemplary procedures described in the figures and examples.

In an embodiment, artificial antigen presenting cells are used in the priming first expansion as a replacement for, or in combination with, PBMCs.

In an embodiment, the antigen presenting cells used in the priming first expansion of a Gen 3 process are monocyte cells. In an embodiment, the antigen presenting cells are B cells. In an embodiment, the antigen presenting cells are B cell lymphoblastoid cells or B-lymphoblastoid cells. In an embodiment, the antigen presenting cells are Burkitt's lymphoma cells. In an embodiment, the antigen presenting cells are myeloid lineage cells. In an embodiment, the antigen presenting cells are monocytes. In an embodiment, the antigen presenting cells are HLA-A-02 positive monocytes. In an embodiment, the antigen presenting cells are acute monocytic leukemia cells. In an embodiment, the antigen presenting cells are M5-subtype acute monocytic leukemia cells. In an embodiment, the antigen presenting cells are Raji cells or a derivative, variant, modification, or progeny thereof. In an embodiment, the antigen presenting cells are Thp1 cells or a derivative, variant, modification, or progeny thereof. In an embodiment, the antigen presenting cells are Ramos cells or a derivative, variant, modification, or progeny thereof. In an embodiment, the antigen presenting cells are U937 cells or a derivative, variant, modification, or progeny thereof. In an embodiment, the antigen presenting cells are Daudi cells or a derivative, variant, modification, or progeny thereof. In an embodiment, the antigen presenting cells are melanocyte cells. In an embodiment, the antigen presenting cells are HLA-A-02 positive melanocyte cells. In an embodiment, the antigen presenting cells are melanoma cells. In an embodiment, the antigen presenting cells are HLA-A-02 positive melanoma cells. In an embodiment, the antigen presenting cells are selected from the group consisting of Sk-MEL-5, Malme-3M, SK-MEL-28, SK-MEL-3, SH-4, SK-MEL-24, RPMI-7951, SK-MEL-1, A375, G-361, and combinations thereof, or derivatives, variants, modifications, or progeny thereof. In any of the foregoing embodiments, the antigen presenting cells may be irradiated as described elsewhere herein or non-irradiated.

In an embodiment, aAPCs are used in the priming first expansion of a Gen 3 process. In an embodiment, the aAPCs are genetically modified monocyte cells. In an embodiment, the aAPCs are genetically modified B cells. In an embodiment, the aAPCs are genetically modified B cell lymphoblastoid cells or B-lymphoblastoid cells. In an embodiment, the aAPCs are genetically modified Burkitt's lymphoma cells. In an embodiment, the aAPCs are genetically modified myeloid lineage cells. In an embodiment, the aAPCs are genetically modified monocytes. In an embodiment, the aAPCs are genetically modified HLA-A-02 positive monocyte cells. In an embodiment, the aAPCs are genetically modified acute monocytic leukemia cells. In an embodiment, the aAPCs are genetically modified M5-subtype acute monocytic leukemia cells. In an embodiment, the aAPCs are genetically modified Raji cells or a derivative, variant, modification, or progeny thereof. In an embodiment, the aAPCs are genetically modified Thp1 cells or a derivative, variant, modification, or progeny thereof. In an embodiment, the aAPCs are genetically modified Ramos cells or a derivative, variant, modification, or progeny thereof. In an embodiment, the aAPCs are genetically modified U937 cells or a derivative, variant, modification, or progeny thereof. In an embodiment, the aAPCs are genetically modified Daudi cells or a derivative, variant, modification, or progeny thereof. In an embodiment, the aAPCs are genetically modified melanocyte cells. In an embodiment, the aAPCs are genetically modified HLA-A-02 positive melanocyte cells. In an embodiment, the aAPCs are genetically modified melanoma cells. In an embodiment, the aAPCs are genetically modified HLA-A-02 positive melanoma cells. In an embodiment, the aAPCs are genetically modified antigen presenting cells selected from the group consisting of Sk-MEL-5, Malme-3M, SK-MEL-28, SK-MEL-3, SH-4, SK-MEL-24, RPMI-7951, SK-MEL-1, A375, G-361, and combinations thereof, or derivatives, variants, modifications, or progeny thereof. In an embodiment, the genetically modified cells are modified to express CD86, OX40L, 4-1BBL, an OX-40 agonistic antibody, a 4-1BB agonistic antibody, an antibody capable of binding the Fc chain of OKT-3, and/or ICOS-L, as described in U.S. Pat. No. 10,415,015, the disclosures of which are incorporated by reference herein. In any of the foregoing embodiments, the genetically modified aAPCs may be irradiated as described elsewhere herein or non-irradiated.

2. Cytokines

The expansion methods described herein generally use culture media with high doses of a cytokine, in particular IL-2, as is known in the art.

Alternatively, using combinations of cytokines for the priming first expansion of TILs is additionally possible, with combinations of two or more of IL-2, IL-15 and IL-21 as is described in U.S. Patent Application Publication No. US 2017/0107490 A1 and International Patent Application Publication No. WO 2015/189357, each of which is hereby expressly incorporated by reference in their entirety. Thus, possible combinations include IL-2 and IL-15, IL-2 and IL-21, IL-15 and IL-21, and IL-2, IL-15 and IL-21, with the latter finding particular use in many embodiments. The use of combinations of cytokines specifically favors the generation of lymphocytes, and in particular T cells as described therein.

C. STEP C: Priming First Expansion to Rapid Second Expansion Transition

In some cases, the bulk TIL population obtained from the priming first expansion (which can include expansions sometimes referred to as pre-REP), including, for example the TIL population obtained from for example, Step B as indicated in FIG. 8 (in particular, e.g., FIG. 8A and/or FIG. 8B and/or FIG. 8C and/or FIG. 8D), can be subjected to a rapid second expansion (which can include expansions sometimes referred to as Rapid Expansion Protocol (REP)) and then cryopreserved as discussed below. Similarly, in the case where genetically modified TILs will be used in therapy, the expanded TIL population from the priming first expansion or the expanded TIL population from the rapid second expansion can be subjected to genetic modifications for suitable treatments prior to the expansion step or after the priming first expansion and prior to the rapid second expansion.

In some embodiments, the TILs obtained from the priming first expansion (for example, from Step B as indicated in FIG. 8 (in particular, e.g., FIG. 8A and/or FIG. 8B and/or FIG. 8C and/or FIG. 8D)) are stored until phenotyped for selection. In some embodiments, the TILs obtained from the priming first expansion (for example, from Step B as indicated in FIG. 8 (in particular, e.g., FIG. 8A and/or FIG. 8B and/or FIG. 8C and/or FIG. 8D)) are not stored and proceed directly to the rapid second expansion. In some embodiments, the TILs obtained from the priming first expansion are not cryopreserved after the priming first expansion and prior to the rapid second expansion. In some embodiments, the transition from the priming first expansion to the second expansion occurs at about 2 days, 3 days, 4, days, 5 days, 6 days, 7 days, or 8 days from when tumor fragmentation occurs and/or when the first priming expansion step is initiated. In some embodiments, the transition from the priming first expansion to the rapid second expansion occurs at about 3 days to 7 days from when fragmentation occurs and/or when the first priming expansion step is initiated. In some embodiments, the transition from the priming first expansion to the rapid second expansion occurs at about 3 days to 8 days from when fragmentation occurs and/or when the first priming expansion step is initiated. In some embodiments, the transition from the priming first expansion to the second expansion occurs at about 4 days to 7 days from when fragmentation occurs and/or when the first priming expansion step is initiated. In some embodiments, the transition from the priming first expansion to the second expansion occurs at about 4 days to 8 days from when fragmentation occurs and/or when the first priming expansion step is initiated. In some embodiments, the transition from the priming first expansion to the second expansion occurs at about 5 days to 7 days from when fragmentation occurs and/or when the first priming expansion step is initiated. In some embodiments, the transition from the priming first expansion to the second expansion occurs at about 5 days to 8 days from when fragmentation occurs and/or when the first priming expansion step is initiated. In some embodiments, the transition from the priming first expansion to the second expansion occurs at about 6 days to 7 days from when fragmentation occurs and/or when the first priming expansion step is initiated. In some embodiments, the transition from the priming first expansion to the second expansion occurs at about 6 days to 8 days from when fragmentation occurs and/or when the first priming expansion step is initiated. In some embodiments, the transition from the priming first expansion to the second expansion occurs at about 7 days to 8 days from when fragmentation occurs and/or when the first priming expansion step is initiated. In some embodiments, the transition from the priming first expansion to the second expansion occurs at about 7 days from when fragmentation occurs and/or when the first priming expansion step is initiated. In some embodiments, the transition from the priming first expansion to the second expansion occurs at about 8 days from when fragmentation occurs and/or when the first priming expansion step is initiated.

In some embodiments, the transition from the priming first expansion to the rapid second expansion occurs at 1 day, 2 days, 3 days, 4 days, 5 days, 6 days, 7 days, or 8 days from when fragmentation occurs and/or when the first priming expansion step is initiated. In some embodiments, the transition from the priming first expansion to the rapid second expansion occurs 1 day to 7 days from when fragmentation occurs and/or when the first priming expansion step is initiated. In some embodiments, the transition from the priming first expansion to the rapid second expansion occurs 1 day to 8 days from when fragmentation occurs and/or when the first priming expansion step is initiated. In some embodiments, the transition from the priming first expansion to the second expansion occurs 2 days to 7 days from when fragmentation occurs and/or when the first priming expansion step is initiated. In some embodiments, the transition from the priming first expansion to the second expansion occurs 2 days to 8 days from when fragmentation occurs and/or when the first priming expansion step is initiated. In some embodiments, the transition from the priming first expansion to the second expansion occurs 3 days to 7 days from when fragmentation occurs and/or when the first priming expansion step is initiated. In some embodiments, the transition from the priming first expansion to the second expansion occurs 3 days to 8 days from when fragmentation occurs and/or when the first priming expansion step is initiated. In some embodiments, the transition from the priming first expansion to the rapid second expansion occurs 4 days to 7 days from when fragmentation occurs and/or when the first priming expansion step is initiated. In some embodiments, the transition from the priming first expansion to the rapid second expansion occurs 4 days to 8 days from when fragmentation occurs and/or when the first priming expansion step is initiated. In some embodiments, the transition from the priming first expansion to the rapid second expansion occurs 5 days to 7 days from when fragmentation occurs and/or when the first priming expansion step is initiated. In some embodiments, the transition from the priming first expansion to the rapid second expansion occurs 5 days to 8 days from when fragmentation occurs and/or when the first priming expansion step is initiated. In some embodiments, the transition from the priming first expansion to the rapid second expansion occurs 6 days to 7 days from when fragmentation occurs and/or when the first priming expansion step is initiated. In some embodiments, the transition from the priming first expansion to the rapid second expansion occurs 6 days to 8 days from when fragmentation occurs and/or when the first priming expansion step is initiated. In some embodiments, the transition from the priming first expansion to the rapid second expansion occurs 7 days to 8 days from when fragmentation occurs and/or when the first priming expansion step is initiated. In some embodiments, the transition from the priming first expansion to the rapid second expansion occurs 7 days from when fragmentation occurs and/or when the first priming expansion step is initiated. In some embodiments, the transition from the priming first expansion to the rapid second expansion occurs 8 days from when fragmentation occurs and/or when the first priming expansion step is initiated.

In some embodiments, the TILs are not stored after the primary first expansion and prior to the rapid second expansion, and the TILs proceed directly to the rapid second expansion (for example, in some embodiments, there is no storage during the transition from Step B to Step D as shown in FIG. 8 (in particular, e.g., FIG. 8A and/or FIG. 8B and/or FIG. 8C and/or FIG. 8D)). In some embodiments, the transition occurs in closed system, as described herein. In some embodiments, the TILs from the priming first expansion, the second population of TILs, proceeds directly into the rapid second expansion with no transition period.

In some embodiments, the transition from the priming first expansion to the rapid second expansion, for example, Step C according to FIG. 8 (in particular, e.g., FIG. 8A and/or FIG. 8B and/or FIG. 8C and/or FIG. 8D), is performed in a closed system bioreactor. In some embodiments, a closed system is employed for the TIL expansion, as described herein. In some embodiments, a single bioreactor is employed. In some embodiments, the single bioreactor employed is for example a GREX-10 or a GREX-100. In some embodiments, the closed system bioreactor is a single bioreactor. In some embodiments, the transition from the priming first expansion to the rapid second expansion involves a scale-up in container size. In some embodiments, the priming first expansion is performed in a smaller container than the rapid second expansion. In some embodiments, the priming first expansion is performed in a GREX-100 and the rapid second expansion is performed in a GREX-500.

D. STEP D: Rapid Second Expansion

In some embodiments, the TIL cell population is further expanded in number after harvest and the priming first expansion, after Step A and Step B, and the transition referred to as Step C, as indicated in FIG. 8 (in particular, e.g., FIG. 8A and/or FIG. 8B and/or FIG. 8C and/or FIG. 8D). This further expansion is referred to herein as the rapid second expansion, which can include expansion processes generally referred to in the art as a rapid expansion process (Rapid Expansion Protocol or REP; as well as processes as indicated in Step D of FIG. 8 (in particular, e.g., FIG. 8A and/or FIG. 8B and/or FIG. 8C and/or FIG. 8D). The rapid second expansion is generally accomplished using a culture media comprising a number of components, including feeder cells, a cytokine source, and an anti-CD3 antibody, in a gas-permeable container. In some embodiments, 1 day, 2 days, 3 days, or 4 days after initiation of the rapid second expansion (i.e., at days 8, 9, 10, or 11 of the overall Gen 3 process), the TILs are transferred to a larger volume container.

In some embodiments, the rapid second expansion (which can include expansions sometimes referred to as REP; as well as processes as indicated in Step D of FIG. 8 (in particular, e.g., FIG. 8A and/or FIG. 8B and/or FIG. 8C and/or FIG. 8D)) of TIL can be performed using any TIL flasks or containers known by those of skill in the art. In some embodiments, the second TIL expansion can proceed for 1 day, 2 days, 3 days, 4, days, 5 days, 6 days, 7 days, 8 days, 9 days or 10 days after initiation of the rapid second expansion. In some embodiments, the second TIL expansion can proceed for about 1 days to about 9 days after initiation of the rapid second expansion. In some embodiments, the second TIL expansion can proceed for about 1 days to about 10 days after initiation of the rapid second expansion. In some embodiments, the second TIL expansion can proceed for about 2 days to about 9 days after initiation of the rapid second expansion. In some embodiments, the second TIL expansion can proceed for about 2 days to about 10 days after initiation of the rapid second expansion. In some embodiments, the second TIL expansion can proceed for about 3 days to about 9 days after initiation of the rapid second expansion. In some embodiments, the second TIL expansion can proceed for about 3 days to about 10 days after initiation of the rapid second expansion. In some embodiments, the second TIL expansion can proceed for about 4 days to about 9 days after initiation of the rapid second expansion. In some embodiments, the second TIL expansion can proceed for about 4 days to about 10 days after initiation of the rapid second expansion. In some embodiments, the second TIL expansion can proceed for about 5 days to about 9 days after initiation of the rapid second expansion. In some embodiments, the second TIL expansion can proceed for about 5 days to about 10 days after initiation of the rapid second expansion. In some embodiments, the second TIL expansion can proceed for about 6 days to about 9 days after initiation of the rapid second expansion. In some embodiments, the second TIL expansion can proceed for about 6 days to about 10 days after initiation of the rapid second expansion. In some embodiments, the second TIL expansion can proceed for about 7 days to about 9 days after initiation of the rapid second expansion. In some embodiments, the second TIL expansion can proceed for about 7 days to about 10 days after initiation of the rapid second expansion. In some embodiments, the second TIL expansion can proceed for about 8 days to about 9 days after initiation of the rapid second expansion. In some embodiments, the second TIL expansion can proceed for about 8 days to about 10 days after initiation of the rapid second expansion. In some embodiments, the second TIL expansion can proceed for about 9 days to about 10 days after initiation of the rapid second expansion. In some embodiments, the second TIL expansion can proceed for about 1 day after initiation of the rapid second expansion. In some embodiments, the second TIL expansion can proceed for about 2 days after initiation of the rapid second expansion. In some embodiments, the second TIL expansion can proceed for about 3 days after initiation of the rapid second expansion. In some embodiments, the second TIL expansion can proceed for about 4 days after initiation of the rapid second expansion. In some embodiments, the second TIL expansion can proceed for about 5 days after initiation of the rapid second expansion. In some embodiments, the second TIL expansion can proceed for about 6 days after initiation of the rapid second expansion. In some embodiments, the second TIL expansion can proceed for about 7 days after initiation of the rapid second expansion. In some embodiments, the second TIL expansion can proceed for about 8 days after initiation of the rapid second expansion. In some embodiments, the second TIL expansion can proceed for about 9 days after initiation of the rapid second expansion. In some embodiments, the second TIL expansion can proceed for about 10 days after initiation of the rapid second expansion.

In an embodiment, the rapid second expansion can be performed in a gas permeable container using the methods of the present disclosure (including, for example, expansions referred to as REP; as well as processes as indicated in Step D of FIG. 8 (in particular, e.g., FIG. 8A and/or FIG. 8B and/or FIG. 8C and/or FIG. 8D). In some embodiments, the TILs are expanded in the rapid second expansion in the presence of IL-2, OKT-3, and feeder cells (also referred herein as "antigen-presenting cells"). In some embodiments, the TILs are expanded in the rapid second expansion in the presence of IL-2, OKT-3, and feeder cells, wherein the feeder cells are added to a final concentration that is twice, 2.4 times, 2.5 times, 3 times, 3.5 times or 4 times the concentration of feeder cells present in the priming first expansion. For example, TILs can be rapidly expanded using non-specific T cell receptor stimulation in the presence of interleukin-2 (IL-2) or interleukin-15 (IL-15). The non-specific T cell receptor stimulus can include, for example, an anti-CD3 antibody, such as about 30 ng/mL of OKT3, a mouse monoclonal anti-CD3 antibody (commercially available from Ortho-McNeil, Raritan, NJ or Miltenyi Biotech, Auburn, CA) or UHCT-1 (commercially available from BioLegend, San Diego, CA, USA). TILs can be expanded to induce further stimulation of the TILs in vitro by including one or more antigens during the second expansion, including antigenic portions thereof, such as epitope(s), of the cancer, which can be optionally expressed from a vector, such as a human leukocyte antigen A2 (HLA-A2) binding peptide, e.g., 0.3 μM MART-1:26-35 (27 L) or gpl 00:209-217 (210M), optionally in the presence of a T cell growth factor, such as 300 IU/mL IL-2 or IL-15. Other suitable antigens may include, e.g., NY-ESO-1, TRP-1, TRP-2, tyrosinase cancer antigen, MAGE-A3, SSX-2, and VEGFR2, or antigenic portions thereof. TIL may also be rapidly expanded by re-stimulation with the same antigen(s) of the cancer pulsed onto HLA-A2-expressing antigen-presenting cells. Alternatively, the TILs can be further re-stimulated with, e.g., example, irradiated, autologous lymphocytes or with irradiated HLA-A2+ allogeneic lymphocytes and IL-2. In some embodiments, the re-stimulation occurs as part of the second expansion. In some embodiments, the second expansion occurs in the presence of irradiated, autologous lymphocytes or with irradiated HLA-A2+ allogeneic lymphocytes and IL-2.

In an embodiment, the cell culture medium further comprises IL-2. In some embodiments, the cell culture medium comprises about 3000 IU/mL of IL-2. In an embodiment, the cell culture medium comprises about 1000 IU/mL, about 1500 IU/mL, about 2000 IU/mL, about 2500 IU/mL, about 3000 IU/mL, about 3500 IU/mL, about 4000 IU/mL, about 4500 IU/mL, about 5000 IU/mL, about 5500 IU/mL, about 6000 IU/mL, about 6500 IU/mL, about 7000 IU/mL, about 7500 IU/mL, or about 8000 IU/mL of IL-2. In an embodiment, the cell culture medium comprises between 1000 and 2000 IU/mL, between 2000 and 3000 IU/mL, between 3000 and 4000 IU/mL, between 4000 and 5000 IU/mL, between 5000 and 6000 IU/mL, between 6000 and 7000 IU/mL, between 7000 and 8000 IU/mL, or between 8000 IU/mL of IL-2.

In an embodiment, the cell culture medium comprises OKT-3 antibody. In some embodiments, the cell culture medium comprises about 30 ng/mL of OKT-3 antibody. In an embodiment, the cell culture medium comprises about 0.1 ng/mL, about 0.5 ng/mL, about 1 ng/mL, about 2.5 ng/mL, about 5 ng/mL, about 7.5 ng/mL, about 10 ng/mL, about 15 ng/mL, about 20 ng/mL, about 25 ng/mL, about 30 ng/mL, about 35 ng/mL, about 40 ng/mL, about 50 ng/mL, about 60 ng/mL, about 70 ng/mL, about 80 ng/mL, about 90 ng/mL, about 100 ng/mL, about 200 ng/mL, about 500 ng/mL, and about 1 μg/mL of OKT-3 antibody. In an embodiment, the cell culture medium comprises between 0.1 ng/mL and 1 ng/mL, between 1 ng/mL and 5 ng/mL, between 5 ng/mL and 10 ng/mL, between 10 ng/mL and 20 ng/mL, between 20 ng/mL and 30 ng/mL, between 30 ng/mL and 40 ng/mL, between 40 ng/mL and 50 ng/mL, and between 50 ng/mL and 100 ng/mL of OKT-3 antibody. In an embodiment, the cell culture medium comprises between 15 ng/mL and 30 ng/mL of OKT-3 antibody. In an embodiment, the cell culture medium comprises between 30 ng/mL and 60 ng/mL of OKT-3 antibody. In an embodiment, the cell culture medium comprises about 30 ng/mL OKT-3. In an embodiment, the cell culture medium comprises about 60 ng/mL OKT-3. In some embodiments, the OKT-3 antibody is muromonab.

In some embodiments, the media in the rapid second expansion comprises IL-2. In some embodiments, the media comprises 6000 IU/mL of IL-2. In some embodiments, the media in the rapid second expansion comprises antigen-presenting feeder cells. In some embodiments, the media in the rapid second expansion comprises $7.5\times10^8$ antigen-presenting feeder cells per container. In some embodiments, the media in the rapid second expansion comprises OKT-3. In some embodiments, the in the rapid second expansion media comprises 500 mL of culture medium and 30 μg of OKT-3 per container. In some embodiments, the container is a G-Rex 100 MCS flask. In some embodiments, the in the rapid second expansion media comprises 6000 IU/mL of IL-2, 60 ng/mL of OKT-3, and $7.5\times10^8$ antigen-presenting feeder cells. In some embodiments, the media comprises 500 mL of culture medium and 6000 IU/mL of IL-2, 30 μg of OKT-3, and $7.5\times10^8$ antigen-presenting feeder cells per container.

In some embodiments, the media in the rapid second expansion comprises IL-2. In some embodiments, the media comprises 6000 IU/mL of IL-2. In some embodiments, the media in the rapid second expansion comprises antigen-presenting feeder cells. In some embodiments, the media comprises between $5\times10^8$ and $7.5\times10^8$ antigen-presenting feeder cells per container. In some embodiments, the media in the rapid second expansion comprises OKT-3. In some embodiments, the media in the rapid second expansion comprises 500 mL of culture medium and 30 μg of OKT-3 per container. In some embodiments, the container is a G-Rex 100 MCS flask. In some embodiments, the media in the rapid second expansion comprises 6000 IU/mL of IL-2, 60 ng/mL of OKT-3, and between $5\times10^8$ and $7.5\times10^8$ antigen-presenting feeder cells. In some embodiments, the media in the rapid second expansion comprises 500 mL of culture medium and 6000 IU/mL of IL-2, 30 μg of OKT-3, and between $5\times10^8$ and $7.5\times10^8$ antigen-presenting feeder cells per container.

In some embodiments, the cell culture medium comprises one or more TNFRSF agonists in a cell culture medium. In some embodiments, the TNFRSF agonist comprises a 4-1BB agonist. In some embodiments, the TNFRSF agonist is a 4-1BB agonist, and the 4-1BB agonist is selected from the group consisting of urelumab, utomilumab, EU-101, a fusion protein, and fragments, derivatives, variants, biosimilars, and combinations thereof. In some embodiments, the TNFRSF agonist is added at a concentration sufficient to achieve a concentration in the cell culture medium of between 0.1 μg/mL and 100 μg/mL. In some embodiments, the TNFRSF agonist is added at a concentration sufficient to achieve a concentration in the cell culture medium of between 20 μg/mL and 40 μg/mL.

In some embodiments, in addition to one or more TNFRSF agonists, the cell culture medium further comprises IL-2 at an initial concentration of about 3000 IU/mL and OKT-3 antibody at an initial concentration of about 30 ng/mL, and wherein the one or more TNFRSF agonists comprises a 4-1BB agonist.

In some embodiments, a combination of IL-2, IL-7, IL-15, and/or IL-21 are employed as a combination during the second expansion. In some embodiments, IL-2, IL-7, IL-15, and/or IL-21 as well as any combinations thereof can be included during the second expansion, including, for example during a Step D processes according to FIG. 8 (in particular, e.g., FIG. 8A and/or FIG. 8B and/or FIG. 8C and/or FIG. 8D), as well as described herein. In some embodiments, a combination of IL-2, IL-15, and IL-21 are employed as a combination during the second expansion. In some embodiments, IL-2, IL-15, and IL-21 as well as any combinations thereof can be included during Step D processes according to FIG. 8 (in particular, e.g., FIG. 8A and/or FIG. 8B and/or FIG. 8C and/or FIG. 8D and as described herein.

In some embodiments, the second expansion can be conducted in a supplemented cell culture medium comprising IL-2, OKT-3, antigen-presenting feeder cells, and optionally a TNFRSF agonist. In some embodiments, the second expansion occurs in a supplemented cell culture medium. In some embodiments, the supplemented cell culture medium comprises IL-2, OKT-3, and antigen-presenting feeder cells. In some embodiments, the second cell culture medium comprises IL-2, OKT-3, and antigen-presenting cells (APCs; also referred to as antigen-presenting feeder cells). In some embodiments, the second expansion occurs in a cell culture medium comprising IL-2, OKT-3, and antigen-presenting feeder cells (i.e., antigen presenting cells).

In some embodiments, the second expansion culture media comprises about 500 IU/mL of IL-15, about 400 IU/mL of IL-15, about 300 IU/mL of IL-15, about 200 IU/mL of IL-15, about 180 IU/mL of IL-15, about 160 IU/mL of IL-15, about 140 IU/mL of IL-15, about 120 IU/mL of IL-15, or about 100 IU/mL of IL-15. In some embodiments, the second expansion culture media comprises about 500 IU/mL of IL-15 to about 100 IU/mL of IL-15. In some embodiments, the second expansion culture media comprises about 400 IU/mL of IL-15 to about 100 IU/mL of IL-15. In some embodiments, the second expansion culture media comprises about 300 IU/mL of IL-15 to about 100 IU/mL of IL-15. In some embodiments, the second expansion culture media comprises about 200 IU/mL of IL-15. In some embodiments, the cell culture medium comprises about 180 IU/mL of IL-15. In an embodiment, the cell culture medium further comprises IL-15. In a preferred embodiment, the cell culture medium comprises about 180 IU/mL of IL-15.

In some embodiments, the second expansion culture media comprises about 20 IU/mL of IL-21, about 15 IU/mL of IL-21, about 12 IU/mL of IL-21, about 10 IU/mL of IL-21, about 5 IU/mL of IL-21, about 4 IU/mL of IL-21, about 3 IU/mL of IL-21, about 2 IU/mL of IL-21, about 1 IU/mL of IL-21, or about 0.5 IU/mL of IL-21. In some embodiments, the second expansion culture media comprises about 20 IU/mL of IL-21 to about 0.5 IU/mL of IL-21. In some embodiments, the second expansion culture media comprises about 15 IU/mL of IL-21 to about 0.5 IU/mL of IL-21. In some embodiments, the second expansion culture media comprises about 12 IU/mL of IL-21 to about 0.5 IU/mL of IL-21. In some embodiments, the second expansion culture media comprises about 10 IU/mL of IL-21 to about 0.5 IU/mL of IL-21. In some embodiments, the second expansion culture media comprises about 5 IU/mL of IL-21 to about 1 IU/mL of IL-21. In some embodiments, the second expansion culture media comprises about 2 IU/mL of IL-21. In some embodiments, the cell culture medium comprises about 1 IU/mL of IL-21. In some embodiments, the cell culture medium comprises about 0.5 IU/mL of IL-21. In an embodiment, the cell culture medium further comprises IL-21. In a preferred embodiment, the cell culture medium comprises about 1 IU/mL of IL-21.

In some embodiments, the antigen-presenting feeder cells (APCs) are PBMCs. In an embodiment, the ratio of TILs to PBMCs and/or antigen-presenting cells in the rapid expansion and/or the second expansion is about 1 to 10, about 1 to 15, about 1 to 20, about 1 to 25, about 1 to 30, about 1 to 35, about 1 to 40, about 1 to 45, about 1 to 50, about 1 to 75, about 1 to 100, about 1 to 125, about 1 to 150, about 1 to 175, about 1 to 200, about 1 to 225, about 1 to 250, about 1 to 275, about 1 to 300, about 1 to 325, about 1 to 350, about 1 to 375, about 1 to 400, or about 1 to 500. In an embodiment, the ratio of TILs to PBMCs in the rapid expansion and/or the second expansion is between 1 to 50 and 1 to 300. In an embodiment, the ratio of TILs to PBMCs in the rapid expansion and/or the second expansion is between 1 to 100 and 1 to 200.

In an embodiment, REP and/or the rapid second expansion is performed in flasks with the bulk TILs being mixed with a 100- or 200-fold excess of inactivated feeder cells, wherein the feeder cell concentration is at least 1.1 times (1.1×), 1.2×, 1.3×, 1.4×, 1.5×, 1.6×, 1.7×, 1.8×, 1.8×, 2×, 2.1×, 2.2×, 2.3×, 2.4×, 2.5×, 2.6×, 2.7×, 2.8×, 2.9×, 3.0×, 3.1×, 3.2×, 3.3×, 3.4×, 3.5×, 3.6×, 3.7×, 3.8×, 3.9× or 4.0× the feeder cell concentration in the priming first expansion, 30 ng/mL OKT3 anti-CD3 antibody and 6000 IU/mL IL-2 in 150 mL media. Media replacement is done (generally 2/3 media replacement via aspiration of 2/3 of spent media and replacement with an equal volume of fresh media) until the cells are transferred to an alternative growth chamber. Alternative growth chambers include G-Rex flasks and gas permeable containers as more fully discussed below.

In some embodiments, the rapid second expansion (which can include processes referred to as the REP process) is 7 to 9 days, as discussed in the examples and figures. In some embodiments, the second expansion is 7 days. In some embodiments, the second expansion is 8 days. In some embodiments, the second expansion is 9 days.

In an embodiment, the second expansion (which can include expansions referred to as REP, as well as those referred to in Step D of FIG. 8 (in particular, e.g., FIG. 8B and/or FIG. 8C) may be performed in 500 mL capacity gas permeable flasks with 100 cm gas-permeable silicon bottoms (G-Rex 100, commercially available from Wilson Wolf Manufacturing Corporation, New Brighton, MN, USA), $5\times10^6$ or $10\times10^6$ TIL may be cultured with PBMCs in 400 mL of 50/50 medium, supplemented with 5% human AB serum, 3000 IU per mL of IL-2 and 30 ng per mL of anti-CD3 (OKT3). The G-Rex 100 flasks may be incubated at 37° C. in 5% $CO_2$. On day 5, 250 mL of supernatant may be removed and placed into centrifuge bottles and centrifuged at 1500 rpm (491× g) for 10 minutes. The TIL pellets may be re-suspended with 150 mL of fresh medium with 5% human AB serum, 6000 IU per mL of IL-2, and added back to the original GREX-100 flasks. When TIL are expanded serially in GREX-100 flasks, on day 10 or 11 the TILs can be moved to a larger flask, such as a GREX-500. The cells may be harvested on day 14 of culture. The cells may be harvested on day 15 of culture. The cells may be harvested on day 16 of culture. In some embodiments, media replacement is done until the cells are transferred to an alternative growth chamber. In some embodiments, 2/3 of the media is replaced by aspiration of spent media and replacement with an equal volume of fresh media. In some embodiments, alternative growth chambers include GREX flasks and gas permeable containers as more fully discussed below.

In some embodiments, the culture medium used in the expansion processes disclosed herein is a serum-free medium or a defined medium. In some embodiments, the serum-free or defined medium comprises a basal cell medium and a serum supplement and/or a serum replacement. In some embodiments, the serum-free or defined medium is used to prevent and/or decrease experimental variation due in part to the lot-to-lot variation of serum-containing media.

In some embodiments, the serum-free or defined medium comprises a basal cell medium and a serum supplement and/or serum replacement. In some embodiments, the basal cell medium includes, but is not limited to CTS™ OpTmizer™ T cell Expansion Basal Medium, CTS™ OpTmizer™ T-Cell Expansion SFM, CTS™ AIM-V Medium, CTS™ AIM-V SFM, LymphoONE™ T-Cell Expansion Xeno-Free Medium, Dulbecco's Modified Eagle's Medium (DMEM), Minimal Essential Medium (MEM), Basal Medium Eagle (BME), RPMI 1640, F-10, F-12, Minimal Essential Medium (αMEM), Glasgow's Minimal Essential Medium (G-MEM), RPMI growth medium, and Iscove's Modified Dulbecco's Medium.

In some embodiments, the serum supplement or serum replacement includes, but is not limited to one or more of CTS™ OpTmizer T-Cell Expansion Serum Supplement, CTS™ Immune Cell Serum Replacement, one or more albumins or albumin substitutes, one or more amino acids, one or more vitamins, one or more transferrins or transferrin substitutes, one or more antioxidants, one or more insulins or insulin substitutes, one or more collagen precursors, one or more antibiotics, and one or more trace elements. In some embodiments, the defined medium comprises albumin and one or more ingredients selected from the group consisting of glycine, L-histidine, L-isoleucine, L-methionine, L-phenylalanine, L-proline, L-hydroxyproline, L-serine, L-threonine, L-tryptophan, L-tyrosine, L-valine, thiamine, reduced glutathione, L-ascorbic acid-2-phosphate, iron saturated transferrin, insulin, and compounds containing the trace element moieties $Ag^+$, $Al^{3+}$, $Ba^{2+}$, $Cd^{2+}$, $Co^{2+}$, $Cr^{3+}$, $Ge^{4+}$, $Se^{4+}$, Br, T, $Mn^{2+}$, P, $Si^{4+}$, $V^{5+}$, $Mo^{6+}$, $Ni^{2+}$, $Rb^+$, $Sn^{2+}$ and $Zr^{4+}$. In some embodiments, the defined medium further comprises L-glutamine, sodium bicarbonate and/or 2-mercaptoethanol.

In some embodiments, the CTS™ OpTmizer™ T cell Immune Cell Serum Replacement is used with conventional growth media, including but not limited to CTS™ OpTmizer™ T cell Expansion Basal Medium, CTS™ OpTmizer™ T cell Expansion SFM, CTS™ AIM-V Medium, CST™ AIM-V SFM, LymphoONE™ T-Cell Expansion Xeno-Free Medium, Dulbecco's Modified Eagle's Medium (DMEM), Minimal Essential Medium (MEM), Basal Medium Eagle (BME), RPMI 1640, F-10, F-12, Minimal Essential Medium (αMEM), Glasgow's Minimal Essential Medium (G-MEM), RPMI growth medium, and Iscove's Modified Dulbecco's Medium.

In some embodiments, the total serum replacement concentration (vol %) in the serum-free or defined medium is from about 1%, 2%, 3%, 4%, 5%, 6%, 7%, 8%, 9%, 10%, 11%, 12%, 13%, 14%, 15%, 16%, 17%, 18%, 19%, or 20% by volume of the total serum-free or defined medium. In some embodiments, the total serum replacement concentration is about 3% of the total volume of the serum-free or defined medium. In some embodiments, the total serum replacement concentration is about 5% of the total volume of the serum-free or defined medium. In some embodiments, the total serum replacement concentration is about 10% of the total volume of the serum-free or defined medium.

In some embodiments, the serum-free or defined medium is CTS™ OpTmizer™ T cell Expansion SFM (ThermoFisher Scientific). Any formulation of CTS™ OpTmizer™ is useful in the present invention. CTS™ OpTmizer™ T cell Expansion SFM is a combination of 1L CTS™ OpTmizer™ T cell Expansion Basal Medium and 26 mL CTS™ OpTmizer™ T-Cell Expansion Supplement, which are mixed together prior to use. In some embodiments, the CTS™ OpTmizer™ T cell Expansion SFM is supplemented with about 3% of the CTS™ Immune Cell Serum Replacement (SR) (ThermoFisher Scientific), along with 2-mercaptoethanol at 55 mM.

In some embodiments, the defined medium is CTS™ OpTmizer™ T cell Expansion SFM (ThermoFisher Scientific). Any formulation of CTS™ OpTmizer™ is useful in the present invention. CTS™ OpTmizer™ T cell Expansion SFM is a combination of 1L CTS™ OpTmizer™ T cell Expansion Basal Medium and 26 mL CTS™ OpTmizer™ T-Cell Expansion Supplement, which are mixed together prior to use. In some embodiments, the CTS™ OpTmizer™ T cell Expansion SFM is supplemented with about 3% of the CTS™ Immune Cell Serum Replacement (SR) (ThermoFisher Scientific), along with 2-mercaptoethanol at 55 mM. In some embodiments, the CTS™ OpTmizer™ T cell Expansion SFM is supplemented with about 3% of the CTS™ Immune Cell Serum Replacement (SR) (ThermoFisher Scientific), 55 mM of 2-mercaptoethanol, and 2 mM of L-glutamine. In some embodiments, the CTS™ OpTmizer™ T cell Expansion SFM is supplemented with about 3% of the CTS™ Immune Cell Serum Replacement (SR) (ThermoFisher Scientific), 55 mM of 2-mercaptoethanol, and 2 mM of L-glutamine, and further comprises about 1000 IU/mL to about 8000 IU/mL of IL-2. In some embodiments, the CTS™ OpTmizer™ T cell Expansion SFM is supplemented with about 3% of the CTS™ Immune Cell Serum Replacement (SR) (ThermoFisher Scientific), 55 mM of 2-mercaptoethanol, and 2 mM of L-glutamine, and further comprises about 3000 IU/mL of IL-2. In some embodiments, the CTS™ OpTmizer™ T cell Expansion SFM is supplemented with about 3% of the CTS™ Immune Cell Serum Replacement (SR) (ThermoFisher Scientific), 55 mM of 2-mercaptoethanol, and 2 mM of L-glutamine, and further comprises about 6000 IU/mL of IL-2. In some embodiments, the CTS™ OpTmizer™ T cell Expansion SFM is supplemented with about 3% of the CTS™ Immune Cell Serum Replacement (SR) (ThermoFisher Scientific) and 55 mM of 2-mercaptoethanol, and further comprises about 1000 IU/mL to about 8000 IU/mL of IL-2. In some embodiments, the CTS™ OpTmizer™ T cell Expansion SFM is supplemented with about 3% of the CTS™ Immune Cell Serum Replacement (SR) (ThermoFisher Scientific) and 55 mM of 2-mercaptoethanol, and further comprises about 3000 IU/mL of IL-2. In some embodiments, the CTS™ OpTmizer™ T cell Expansion SFM is supplemented with about 3% of the CTS™ Immune Cell Serum Replacement (SR) (ThermoFisher Scientific) and 55 mM of 2-mercaptoethanol, and further comprises about 1000 IU/mL to about 6000 IU/mL of IL-2.

In some embodiments, the CTS™ OpTmizer™ T cell Expansion SFM is supplemented with about 3% of the CTS™ Immune Cell Serum Replacement (SR) (ThermoFisher Scientific) and about 2 mM glutamine, and further comprises about 1000 IU/mL to about 8000 IU/mL of IL-2. In some embodiments, the CTS™ OpTmizer™ T cell Expansion SFM is supplemented with about 3% of the CTS™ Immune Cell Serum Replacement (SR) (ThermoFisher Scientific) and about 2 mM glutamine, and further comprises about 3000 IU/mL of IL-2. In some embodiments, the CTS™ OpTmizer™ T cell Expansion SFM is supplemented with about 3% of the CTS™ Immune Cell Serum Replacement (SR) (ThermoFisher Scientific) and about 2 mM glutamine, and further comprises about 6000 IU/mL of IL-2.

In some embodiments, the serum-free medium or defined medium is supplemented with glutamine (i.e., GlutaMAX®) at a concentration of from about 0.1 mM to about 10 mM, 0.5 mM to about 9 mM, 1 mM to about 8 mM, 2 mM to about 7 mM, 3 mM to about 6 mM, or 4 mM to about 5 mM. In some embodiments, the serum-free medium or defined medium is supplemented with glutamine (i.e., GlutaMAX®) at a concentration of about 2 mM.

In some embodiments, the serum-free medium or defined medium is supplemented with 2-mercaptoethanol at a concentration of from about 5 mM to about 150 mM, 10 mM to about 140 mM, 15 mM to about 130 mM, 20 mM to about 120 mM, 25 mM to about 110 mM, 30 mM to about 100 mM, 35 mM to about 95 mM, 40 mM to about 90 mM, 45 mM to about 85 mM, 50 mM to about 80 mM, 55 mM to about 75 mM, 60 mM to about 70 mM, or about 65 mM. In some embodiments, the serum-free medium or defined medium is supplemented with 2-mercaptoethanol at a concentration of about 55 mM.

In some embodiments, the defined media described in International Patent Publication No. WO 1998/030679, which is herein incorporated by reference, are useful in the present invention. In that publication, serum-free eukaryotic cell culture media are described. The serum-free, eukaryotic cell culture medium includes a basal cell culture medium supplemented with a serum-free supplement capable of supporting the growth of cells in serum-free culture. The serum-free eukaryotic cell culture medium supplement comprises or is obtained by combining one or more ingredients selected from the group consisting of one or more albumins or albumin substitutes, one or more amino acids, one or more vitamins, one or more transferrins or transferrin substitutes, one or more antioxidants, one or more insulins or insulin substitutes, one or more collagen precursors, one or more trace elements, and one or more antibiotics. In some embodiments, the defined medium further comprises L-glutamine, sodium bicarbonate and/or beta-mercaptoethanol. In some embodiments, the defined medium comprises an albumin or an albumin substitute and one or more ingredients selected from group consisting of one or more amino acids, one or more vitamins, one or more transferrins or transferrin substitutes, one or more antioxidants, one or more insulins or insulin substitutes, one or more collagen precursors, and one or more trace elements. In some embodiments, the defined medium comprises albumin and one or more ingredients selected from the group consisting of glycine, L-histidine, L-isoleucine, L-methionine, L-phenylalanine, L-proline, L-hydroxyproline, L-serine, L-threonine, L-tryptophan, L-tyrosine, L-valine, thiamine, reduced glutathione, L-ascorbic acid-2-phosphate, iron saturated transferrin, insulin, and compounds containing the trace element moieties $Ag^{+}$, $Al^{3+}$, $Ba^{2+}$, $Cd^{2+}$, $Co^{2+}$, $Cr^{3+}$, $Ge^{4+}$, $Se^{4+}$, Br, T, $Mn^{2+}$, P, $S^{4+}$, $V^{5+}$, $Mo^{6+}$, $Ni^{2+}$, $Rb^{+}$, $Sn^{2+}$ and $Zr^{4+}$. In some embodiments, the basal cell media is selected from the group consisting of Dulbecco's Modified Eagle's Medium (DMEM), Minimal Essential Medium (MEM), Basal Medium Eagle (BME), RPMI 1640, F-10, F-12, Minimal Essential Medium (αMEM), Glasgow's Minimal Essential Medium (G-MEM), RPMI growth medium, and Iscove's Modified Dulbecco's Medium.

In some embodiments, the concentration of glycine in the defined medium is in the range of from about 5-200 mg/L, the concentration of L-histidine is about 5-250 mg/L, the concentration of L-isoleucine is about 5-300 mg/L, the concentration of L-methionine is about 5-200 mg/L, the concentration of L-phenylalanine is about 5-400 mg/L, the concentration of L-proline is about 1-1000 mg/L, the concentration of L-hydroxyproline is about 1-45 mg/L, the concentration of L-serine is about 1-250 mg/L, the concentration of L-threonine is about $10^{-500}$ mg/L, the concentration of L-tryptophan is about 2-110 mg/L, the concentration of L-tyrosine is about 3-175 mg/L, the concentration of L-valine is about 5-500 mg/L, the concentration of thiamine is about 1-20 mg/L, the concentration of reduced glutathione is about 1-20 mg/L, the concentration of L-ascorbic acid-2-phosphate is about 1-200 mg/L, the concentration of iron saturated transferrin is about 1-50 mg/L, the concentration of insulin is about 1-100 mg/L, the concentration of sodium selenite is about 0.000001-0.0001 mg/L, and the concentration of albumin (e.g., AlbuMAX® I) is about 5000-50,000 mg/L.

In some embodiments, the non-trace element moiety ingredients in the defined medium are present in the concentration ranges listed in the column under the heading "Concentration Range in 1× Medium" see Table 4 above. In other embodiments, the non-trace element moiety ingredients in the defined medium are present in the final concentrations listed in the column under the heading "A Preferred Embodiment of the 1× Medium" see Table 4 above. In other embodiments, the defined medium is a basal cell medium comprising a serum free supplement. In some of these embodiments, the serum free supplement comprises non-trace moiety ingredients of the type and in the concentrations listed in the column under the heading "A Preferred Embodiment in Supplement" see, above in Table 4.

In some embodiments, the osmolarity of the defined medium is between about 260 and 350 mOsmol. In some embodiments, the osmolarity is between about 280 and 310 mOsmol. In some embodiments, the defined medium is supplemented with up to about 3.7 g/L, or about 2.2 g/L sodium bicarbonate. The defined medium can be further supplemented with L-glutamine (final concentration of about 2 mM), one or more antibiotics, non-essential amino acids (NEAA; final concentration of about 100 μM), 2-mercaptoethanol (final concentration of about 100 μM).

In some embodiments, the defined media described in Smith, et al., "Ex vivo expansion of human T cells for adoptive immunotherapy using the novel Xeno-free CTS Immune Cell Serum Replacement," *Clin Transl Immunology,* 4(1) 2015 (doi: 10.1038/cti.2014.31) are useful in the present invention. Briefly, RPMI or CTS™ OpTmizer™ was used as the basal cell medium, and supplemented with either 0, 2%, 5%, or 10% CTS™ Immune Cell Serum Replacement.

In an embodiment, the cell medium in the first and/or second gas permeable container is unfiltered. The use of unfiltered cell medium may simplify the procedures necessary to expand the number of cells. In an embodiment, the cell medium in the first and/or second gas permeable container lacks beta-mercaptoethanol (BME or βME; also known as 2-mercaptoethanol, CAS 60-24-2).

In an embodiment, the rapid second expansion (including expansions referred to as REP) is performed and further comprises a step wherein TILs are selected for superior tumor reactivity. Any selection method known in the art may be used. For example, the methods described in U.S. Patent Application Publication No. 2016/0010058 A1, the disclosures of which are incorporated herein by reference, may be used for selection of TILs for superior tumor reactivity.

Optionally, a cell viability assay can be performed after the rapid second expansion (including expansions referred to as the REP expansion), using standard assays known in the art. For example, a trypan blue exclusion assay can be done on a sample of the bulk TILs, which selectively labels dead cells and allows a viability assessment. In some embodiments, TIL samples can be counted and viability determined using a Cellometer K2 automated cell counter (Nexcelom Bioscience, Lawrence, MA). In some embodiments, viability is determined according to the standard Cellometer K2 Image Cytometer Automatic Cell Counter protocol.

The diverse antigen receptors of T and B lymphocytes are produced by somatic recombination of a limited, but large number of gene segments. These gene segments: V (variable), D (diversity), J (joining), and C (constant), determine the binding specificity and downstream applications of immunoglobulins and T cell receptors (TCRs). The present invention provides a method for generating TILs which exhibit and increase the T cell repertoire diversity. In some embodiments, the TILs obtained by the present method exhibit an increase in the T cell repertoire diversity. In some embodiments, the TILs obtained in the second expansion exhibit an increase in the T cell repertoire diversity. In some embodiments, the increase in diversity is an increase in the immunoglobulin diversity and/or the T cell receptor diversity. In some embodiments, the diversity is in the immunoglobulin is in the immunoglobulin heavy chain. In some embodiments, the diversity is in the immunoglobulin is in the immunoglobulin light chain. In some embodiments, the diversity is in the T cell receptor. In some embodiments, the diversity is in one of the T cell receptors selected from the group consisting of alpha, beta, gamma, and delta receptors. In some embodiments, there is an increase in the expression of T cell receptor (TCR) alpha and/or beta. In some embodiments, there is an increase in the expression of T cell receptor (TCR) alpha. In some embodiments, there is an increase in the expression of T cell receptor (TCR) beta. In some embodiments, there is an increase in the expression of TCRab (i.e., TCRα/β).

In some embodiments, the rapid second expansion culture medium (e.g. sometimes referred to as CM2 or the second cell culture medium), comprises IL-2, OKT-3, as well as the antigen-presenting feeder cells (APCs), as discussed in more detail below. In some embodiments, the rapid second expansion culture medium (e.g., sometimes referred to as CM2 or the second cell culture medium), comprises 6000 IU/mL IL-2, 30 ug/flask OKT-3, as well as $7.5\times10^8$ antigen-presenting feeder cells (APCs), as discussed in more detail below. In some embodiments, the rapid second expansion culture medium (e.g., sometimes referred to as CM2 or the second cell culture medium), comprises IL-2, OKT-3, as well as the antigen-presenting feeder cells (APCs), as discussed in more detail below. In some embodiments, the rapid second expansion culture medium (e.g., sometimes referred to as CM2 or the second cell culture medium), comprises 6000 IU/mL IL-2, 30 ug/flask OKT-3, as well as $5\times10^8$ antigen-presenting feeder cells (APCs), as discussed in more detail below.

In some embodiments, the rapid second expansion, for example, Step D according to FIG. 8 (in particular, e.g., FIG. 8A and/or FIG. 8B and/or FIG. 8C and/or FIG. 8D), is performed in a closed system bioreactor. In some embodiments, a closed system is employed for the TIL expansion, as described herein. In some embodiments, a bioreactor is employed. In some embodiments, a bioreactor is employed as the container. In some embodiments, the bioreactor employed is for example a G-Rex-100 or a G-Rex-500. In some embodiments, the bioreactor employed is a G-Rex-100. In some embodiments, the bioreactor employed is a G-Rex-500.

1. Feeder Cells and Antigen Presenting Cells

In an embodiment, the rapid second expansion procedures described herein (for example including expansion such as those described in Step D from FIG. 8 (in particular, e.g., FIG. 8A and/or FIG. 8B and/or FIG. 8C and/or FIG. 8D), as well as those referred to as REP) require an excess of feeder cells during REP TIL expansion and/or during the rapid second expansion. In many embodiments, the feeder cells are peripheral blood mononuclear cells (PBMCs) obtained from standard whole blood units from healthy blood donors. The PBMCs are obtained using standard methods such as Ficoll-Paque gradient separation.

In general, the allogeneic PBMCs are inactivated, either via irradiation or heat treatment, and used in the REP procedures, as described in the examples, which provides an exemplary protocol for evaluating the replication incompetence of irradiate allogeneic PBMCs.

In some embodiments, PBMCs are considered replication incompetent and acceptable for use in the TIL expansion procedures described herein if the total number of viable cells on day 7 or 14 is less than the initial viable cell number put into culture on day 0 of the REP and/or day 0 of the second expansion (i.e., the start day of the second expansion).

In some embodiments, PBMCs are considered replication incompetent and acceptable for use in the TIL expansion procedures described herein if the total number of viable cells, cultured in the presence of OKT3 and IL-2, on day 7 and day 14 has not increased from the initial viable cell number put into culture on day 0 of the REP and/or day 0 of the second expansion (i.e., the start day of the second expansion). In some embodiments, the PBMCs are cultured in the presence of 30 ng/mL OKT3 antibody and 3000 IU/mL IL-2. In some embodiments, the PBMCs are cultured in the presence of 60 ng/mL OKT3 antibody and 6000 IU/mL IL-2. In some embodiments, the PBMCs are cultured in the presence of 60 ng/mL OKT3 antibody and 3000 IU/mL IL-2. In some embodiments, the PBMCs are cultured in the presence of 30 ng/mL OKT3 antibody and 6000 IU/mL IL-2.

In some embodiments, PBMCs are considered replication incompetent and acceptable for use in the TIL expansion procedures described herein if the total number of viable cells, cultured in the presence of OKT3 and IL-2, on day 7 and day 14 has not increased from the initial viable cell number put into culture on day 0 of the REP and/or day 0 of the second expansion (i.e., the start day of the second expansion). In some embodiments, the PBMCs are cultured in the presence of 30-60 ng/mL OKT3 antibody and 1000-6000 IU/mL IL-2. In some embodiments, the PBMCs are cultured in the presence of 30-60 ng/mL OKT3 antibody and 2000-5000 IU/mL IL-2. In some embodiments, the PBMCs are cultured in the presence of 30 to 60 ng/mL OKT3 antibody and 2000-4000 IU/mL IL-2. In some embodiments, the PBMCs are cultured in the presence of 30-60 ng/mL OKT3 antibody and 2500-3500 IU/mL IL-2. In some embodiments, the PBMCs are cultured in the presence of 30 to 60 ng/mL OKT3 antibody and 6000 IU/mL IL-2.

In some embodiments, the antigen-presenting feeder cells are PBMCs. In some embodiments, the antigen-presenting feeder cells are artificial antigen-presenting feeder cells. In an embodiment, the ratio of TILs to antigen-presenting feeder cells in the second expansion is about 1 to 10, about 1 to 25, about 1 to 50, about 1 to 100, about 1 to 125, about 1 to 150, about 1 to 175, about 1 to 200, about 1 to 225, about 1 to 250, about 1 to 275, about 1 to 300, about 1 to 325, about 1 to 350, about 1 to 375, about 1 to 400, or about 1 to 500. In an embodiment, the ratio of TILs to antigen-presenting feeder cells in the second expansion is between 1 to 50 and 1 to 300. In an embodiment, the ratio of TILs to antigen-presenting feeder cells in the second expansion is between 1 to 100 and 1 to 200.

In an embodiment, the second expansion procedures described herein require a ratio of about $5\times10^8$ feeder cells to about $100\times10^6$ TILs. In an embodiment, the second expansion procedures described herein require a ratio of about $7.5\times10^8$ feeder cells to about $100\times10^6$ TILs. In another embodiment, the second expansion procedures described herein require a ratio of about $5\times10^8$ feeder cells to about $50\times10^6$ TILs. In another embodiment, the second expansion procedures described herein require a ratio of about $7.5\times10^8$ feeder cells to about $50\times10^6$ TILs. In yet another embodiment, the second expansion procedures described herein require about $5\times10^8$ feeder cells to about $25\times10^6$ TILs. In yet another embodiment, the second expansion procedures described herein require about $7.5\times10^8$ feeder cells to about $25\times10^6$ TILs. In yet another embodiment, the rapid second expansion requires twice the number of feeder cells as the rapid second expansion. In yet another embodiment, when the priming first expansion described herein requires about $2.5\times10^8$ feeder cells, the rapid second expansion requires about $5\times10^8$ feeder cells. In yet another embodiment, when the priming first expansion described herein requires about $2.5\times10^8$ feeder cells, the rapid second expansion requires about $7.5\times10^8$ feeder cells. In yet another embodiment, the rapid second expansion requires two times (2.0×), 2.5×, 3.0×, 3.5× or 4.0× the number of feeder cells as the priming first expansion.

In an embodiment, the rapid second expansion procedures described herein require an excess of feeder cells during the rapid second expansion. In many embodiments, the feeder cells are peripheral blood mononuclear cells (PBMCs) obtained from standard whole blood units from allogeneic healthy blood donors. The PBMCs are obtained using standard methods such as Ficoll-Paque gradient separation. In an embodiment, artificial antigen-presenting (aAPC) cells are used in place of PBMCs. In some embodiments, the PBMCs are added to the rapid second expansion at twice the concentration of PBMCs that were added to the priming first expansion.

In general, the allogeneic PBMCs are inactivated, either via irradiation or heat treatment, and used in the TIL expansion procedures described herein, including the exemplary procedures described in the figures and examples.

In an embodiment, artificial antigen presenting cells are used in the rapid second expansion as a replacement for, or in combination with, PBMCs.

In an embodiment, the antigen presenting cells used in the rapid second expansion of a Gen 3 process are monocyte cells. In an embodiment, the antigen presenting cells are B cells. In an embodiment, the antigen presenting cells are B cell lymphoblastoid cells or B-lymphoblastoid cells. In an embodiment, the antigen presenting cells are Burkitt's lymphoma cells. In an embodiment, the antigen presenting cells are myeloid lineage cells. In an embodiment, the antigen presenting cells are monocytes. In an embodiment, the antigen presenting cells are HLA-A-02 positive monocytes. In an embodiment, the antigen presenting cells are acute monocytic leukemia cells. In an embodiment, the antigen presenting cells are M5-subtype acute monocytic leukemia cells. In an embodiment, the antigen presenting cells are Raji cells or a derivative, variant, modification, or progeny thereof. In an embodiment, the antigen presenting cells are Thp1 cells or a derivative, variant, modification, or progeny thereof. In an embodiment, the antigen presenting cells are Ramos cells or a derivative, variant, modification, or progeny thereof. In an embodiment, the antigen presenting cells are U937 cells or a derivative, variant, modification, or progeny thereof. In an embodiment, the antigen presenting cells are Daudi cells or a derivative, variant, modification, or progeny thereof. In an embodiment, the antigen presenting cells are melanocyte cells. In an embodiment, the antigen presenting cells are HLA-A-02 positive melanocyte cells. In an embodiment, the antigen presenting cells are melanoma cells. In an embodiment, the antigen presenting cells are HLA-A-02 positive melanoma cells. In an embodiment, the antigen presenting cells are selected from the group consisting of Sk-MEL-5, Malme-3M, SK-MEL-28, SK-MEL-3, SH-4, SK-MEL-24, RPMI-7951, SK-MEL-1, A375, G-361, and combinations thereof, or derivatives, variants, modifications, or progeny thereof. In any of the foregoing embodiments, the antigen presenting cells may be irradiated as described elsewhere herein or non-irradiated.

In an embodiment, aAPCs are used in the rapid second expansion of a Gen 3 process. In an embodiment, the aAPCs are genetically modified monocyte cells. In an embodiment, the aAPCs are genetically modified B cells. In an embodiment, the aAPCs are genetically modified B cell lymphoblastoid cells or B-lymphoblastoid cells. In an embodiment, the aAPCs are genetically modified Burkitt's lymphoma cells. In an embodiment, the aAPCs are genetically modified myeloid lineage cells. In an embodiment, the aAPCs are genetically modified monocytes. In an embodiment, the aAPCs are genetically modified HLA-A-02 positive monocyte cells. In an embodiment, the aAPCs are genetically modified acute monocytic leukemia cells. In an embodiment, the aAPCs are genetically modified M5-subtype acute monocytic leukemia cells. In an embodiment, the aAPCs are genetically modified Raji cells or a derivative, variant, modification, or progeny thereof. In an embodiment, the aAPCs are genetically modified Thp1 cells or a derivative, variant, modification, or progeny thereof. In an embodiment, the aAPCs are genetically modified Ramos cells or a derivative, variant, modification, or progeny thereof. In an embodiment, the aAPCs are genetically modified U937 cells or a derivative, variant, modification, or progeny thereof. In an embodiment, the aAPCs are genetically modified Daudi cells or a derivative, variant, modification, or progeny thereof. In an embodiment, the aAPCs are genetically modified melanocyte cells. In an embodiment, the aAPCs are genetically modified HLA-A-02 positive melanocyte cells. In an embodiment, the aAPCs are genetically modified melanoma cells. In an embodiment, the aAPCs are genetically modified HLA-A-02 positive melanoma cells. In an embodiment, the aAPCs are genetically modified antigen presenting cells selected from the group consisting of Sk-MEL-5, Malme-3M, SK-MEL-28, SK-MEL-3, SH-4, SK-MEL-24, RPMI-7951, SK-MEL-1, A375, G-361, and combinations thereof, or derivatives, variants, modifications, or progeny thereof. In an embodiment, the genetically modified cells are modified to express CD86, OX40L, 4-1BBL, an OX-40 agonistic antibody, a 4-1BB agonistic antibody, an antibody capable of binding the Fc chain of OKT-3, and/or ICOS-L, as described in U.S. Pat. No. 10,415,015, the disclosures of which are incorporated by reference herein. In any of the foregoing embodiments, the genetically modified aAPCs may be irradiated as described elsewhere herein or non-irradiated.

2. Cytokines

The rapid second expansion methods described herein generally use culture media with high doses of a cytokine, in particular IL-2, as is known in the art.

Alternatively, using combinations of cytokines for the rapid second expansion of TILs is additionally possible, with combinations of two or more of IL-2, IL-15 and IL-21 as is generally outlined in WO 2015/189356 and WO 2015/189357, hereby expressly incorporated by reference in their entirety. Thus, possible combinations include IL-2 and IL-15, IL-2 and IL-21, IL-15 and IL-21, and IL-2, IL-15 and IL-21, with the latter finding particular use in many embodiments. The use of combinations of cytokines specifically favors the generation of lymphocytes, and in particular T cells as described therein.

E. STEP E: Harvest TILs

After the rapid second expansion step, cells can be harvested. In some embodiments the TILs are harvested after one, two, three, four or more expansion steps, for example as provided in FIG. 8 (in particular, e.g., FIG. 8A and/or FIG. 8B and/or FIG. 8C and/or FIG. 8D). In some embodiments the TILs are harvested after two expansion steps, for example as provided in FIG. 8 (in particular, e.g., FIG. 8A and/or FIG. 8B and/or FIG. 8C and/or FIG. 8D). In some embodiments the TILs are harvested after two expansion steps, one priming first expansion and one rapid second expansion, for example as provided in FIG. 8 (in particular, e.g., FIG. 8A and/or FIG. 8B and/or FIG. 8C and/or FIG. 8D).

TILs can be harvested in any appropriate and sterile manner, including, for example by centrifugation. Methods for TIL harvesting are well known in the art and any such known methods can be employed with the present process. In some embodiments, TILs are harvested using an automated system.

Cell harvesters and/or cell processing systems are commercially available from a variety of sources, including, for example, Fresenius Kabi, Tomtec Life Science, Perkin Elmer, and Inotech Biosystems International, Inc. Any cell based harvester can be employed with the present methods.

In some embodiments, the cell harvester and/or cell processing system is a membrane-based cell harvester. In some embodiments, cell harvesting is via a cell processing system, such as the LOVO system (manufactured by Fresenius Kabi). The term "LOVO cell processing system" also refers to any instrument or device manufactured by any vendor that can pump a solution comprising cells through a membrane or filter such as a spinning membrane or spinning filter in a sterile and/or closed system environment, allowing for continuous flow and cell processing to remove supernatant or cell culture media without pelletization. In some embodiments, the cell harvester and/or cell processing system can perform cell separation, washing, fluid-exchange, concentration, and/or other cell processing steps in a closed, sterile system.

In some embodiments, the rapid second expansion, for example, Step D according to FIG. 8 (in particular, e.g., FIG. 8B and/or FIG. 8C), is performed in a closed system bioreactor. In some embodiments, a closed system is employed for the TIL expansion, as described herein. In some embodiments, a bioreactor is employed. In some embodiments, a bioreactor is employed as the container. In some embodiments, the bioreactor employed is for example a G-Rex-100 or a G-Rex-500. In some embodiments, the bioreactor employed is a G-Rex-100. In some embodiments, the bioreactor employed is a G-Rex-500.

In some embodiments, Step E according to FIG. 8 (in particular, e.g., FIG. 8A and/or FIG. 8B and/or FIG. 8C and/or FIG. 8D), is performed according to the processes described herein. In some embodiments, the closed system is accessed via syringes under sterile conditions in order to maintain the sterility and closed nature of the system. In some embodiments, a closed system as described herein is employed.

In some embodiments, TILs are harvested according to the methods described in herein. In some embodiments, TILs between days 14 and 16 are harvested using the methods as described herein. In some embodiments, TILs are harvested at 14 days using the methods as described herein. In some embodiments, TILs are harvested at 15 days using the methods as described herein. In some embodiments, TILs are harvested at 16 days using the methods as described herein.

F. STEP F: Assays of Expanded TILs

In some embodiments, the potency and/or functionality of the expanded TILs from the steps provided above is examined using one of the assay methods described herein.

In an embodiment, the invention includes a method of determining the potency of a Gen 3 TIL product as described herein, the method comprising the steps of:

a. performing a co-culture of a target cell with a Gen 3 TIL product cell for a first period;
b. obtaining a harvest from the co-culture; and
c. assessing the harvest for (1) expression of one or more markers on the Gen 3 TIL product or (2) one or more analytes secreted from the Gen 3 TIL product cell to obtain one or more observed values to determine the potency for the Gen 3 TIL product.

Alternatively, in some embodiments, the expanded TILs are analyzed using a combined assay comprising CD3 or CD3/CD28 bead-based stimulation with ELISA or automated ELISA (e.g., ELLA) detection of at least two analytes selected from the group consisting of IFN-γ, granzyme B, perform, and TNF-α. In an embodiment, the product release specification for such combined assay is at least 500 pg/mL for the at least two selected analytes, at least 600 pg/mL for the at least two selected analytes, at least 700 pg/mL for the at least two selected analytes, at least 800 pg/mL for the at least two selected analytes, at least 900 pg/mL for the at least two selected analytes, at least 1000 pg/mL for the at least two selected analytes, at least 1100 pg/mL for the at least two selected analytes, or at least 1200 pg/mL for the at least two selected analytes, wherein each mL of test article contains $1\times10^5$ TILs, $2\times10^5$ TILs, $3\times10^5$ TILs, $4\times10^5$ TILs, $5\times10^5$ TILs, $6\times10^5$ TILs, $7\times10^5$ TILs, $8\times10^5$ TILs, $9\times10^5$ TILs, or $10\times10^5$ TILs.

G. STEP G: Final Formulation and Transfer to Infusion Container

After Steps A through E as provided in an exemplary order in FIG. 8 (in particular, e.g., FIG. 8A and/or FIG. 8B and/or FIG. 8C and/or FIG. 8D) and as outlined in detailed above and herein are complete, cells are transferred to a container, such as an infusion bag or sterile vial, for use in administration to a patient. In some embodiments, once a therapeutically sufficient number of TILs are obtained using the expansion methods described above, they are transferred to a container, which may include an infusion bag or sterile vial, for use in administration to a patient as a pharmaceutical composition, including pharmaceutical compositions described herein. TILs may be assessed for potency after transfer to such a container, which may occur immediately after the transfer or after the container has been stored for a period of time, such as for stability testing.

In an embodiment, TILs expanded using the methods of the present disclosure are administered to a patient as a pharmaceutical composition. In an embodiment, the pharmaceutical composition is a suspension of TILs in a sterile buffer. TILs expanded as disclosed herein may be administered by any suitable route as known in the art. In some embodiments, the TILs are administered as a single intraarterial or intravenous infusion, which preferably lasts approximately 30 to 60 minutes. Other suitable routes of administration include intraperitoneal, intrathecal, and intralymphatic administration.

VI. Further Gen 2, Gen 3, and Other TIL Manufacturing Process Embodiments

A. PBMC Feeder Cell Ratios

In some embodiments, the culture media used in expansion methods described herein (see for example, FIG. 8 (in particular, e.g., FIG. 8B and/or FIG. 8C)) include an anti-CD3 antibody e.g., OKT-3. An anti-CD3 antibody in combination with IL-2 induces T cell activation and cell division in the TIL population. This effect can be seen with full length antibodies as well as Fab and F(ab')2 fragments, with the former being generally preferred; see, e.g., Tsoukas et al., *J. Immunol.* 1985, 135, 1719, hereby incorporated by reference in its entirety.

In an embodiment, the number of PBMC feeder layers is calculated as follows:

A. Volume of a T cell (10 μm diameter): $V=(4/3)\pi r^3=523.6\ \mu m^3$
B. Column of G-Rex 100 (M) with a 40 μm (4 cells) height: $V=(4/3)\pi r^3=4\times10^{12}\ \mu m^3$
C. Number cells required to fill column B: $4\times10^{12}\ \mu m^3/523.6\ \mu m^3=7.6\times10^8\ m^3*0.64=4.86\times10^8$
D. Number cells that can be optimally activated in 4D space: $4.86\times10^8/24=20.25\times10^6$
E. Number of feeders and TIL extrapolated to G-Rex 500: TIL: $100\times10^6$ and Feeder: $2.5\times10^9$ In this calculation, an approximation of the number of mononuclear cells required to provide an icosahedral geometry for activation of TIL in a cylinder with a 100 cm2 base is used. The calculation derives the experimental result of ~5×$10^8$ for threshold activation of T cells which closely mirrors NCI experimental data, as described in Jin, et. al., *J. Immunother.* 2012, 35, 283-292. In (C), the multiplier (0.64) is the random packing density for equivalent spheres as calculated by Jaeger and Nagel, *Science,* 1992, 255, 1523-3. In (D), the divisor 24 is the number of equivalent spheres that could contact a similar object in 4-dimensional space or "the Newton number" as described in Musin, *Russ. Math. Surv.* 2003, 58, 794-795.

In an embodiment, the number of antigen-presenting feeder cells exogenously supplied during the priming first expansion is approximately one-half the number of antigen-presenting feeder cells exogenously supplied during the rapid second expansion. In certain embodiments, the method comprises performing the priming first expansion in a cell culture medium which comprises approximately 50% fewer antigen presenting cells as compared to the cell culture medium of the rapid second expansion.

In another embodiment, the number of antigen-presenting feeder cells (APCs) exogenously supplied during the rapid second expansion is greater than the number of APCs exogenously supplied during the priming first expansion.

In another embodiment, the ratio of the number of APCs exogenously supplied during the rapid second expansion to the number of APCs exogenously supplied during the priming first expansion is selected from a range of from at or about 1.1:1 to at or about 20:1.

In another embodiment, the ratio of the number of APCs exogenously supplied during the rapid second expansion to the number of APCs exogenously supplied during the priming first expansion is selected from a range of from at or about 1.1:1 to at or about 10:1.

In another embodiment, the ratio of the number of APCs exogenously supplied during the rapid second expansion to the number of APCs exogenously supplied during the priming first expansion is selected from a range of from at or about 1.1:1 to at or about 9:1.

In another embodiment, the ratio of the number of APCs exogenously supplied during the rapid second expansion to the number of APCs exogenously supplied during the priming first expansion is selected from a range of from at or about 1.1:1 to at or about 8:1.

In another embodiment, the ratio of the number of APCs exogenously supplied during the rapid second expansion to the number of APCs exogenously supplied during the priming first expansion is selected from a range of from at or about 1.1:1 to at or about 7:1.

In another embodiment, the ratio of the number of APCs exogenously supplied during the rapid second expansion to the number of APCs exogenously supplied during the priming first expansion is selected from a range of from at or about 1.1:1 to at or about 6:1.

In another embodiment, the ratio of the number of APCs exogenously supplied during the rapid second expansion to the number of APCs exogenously supplied during the priming first expansion is selected from a range of from at or about 1.1:1 to at or about 5:1.

In another embodiment, the ratio of the number of APCs exogenously supplied during the rapid second expansion to the number of APCs exogenously supplied during the priming first expansion is selected from a range of from at or about 1.1:1 to at or about 4:1.

In another embodiment, the ratio of the number of APCs exogenously supplied during the rapid second expansion to the number of APCs exogenously supplied during the priming first expansion) is selected from a range of from at or about 1.1:1 to at or about 3:1.

In another embodiment, the ratio of the number of APCs exogenously supplied during the rapid second expansion to the number of APCs exogenously supplied during the priming first expansion is selected from a range of from at or about 1.1:1 to at or about 2.9:1.

In another embodiment, the ratio of the number of APCs exogenously supplied during the rapid second expansion to the number of APCs exogenously supplied during the priming first expansion is selected from a range of from at or about 1.1:1 to at or about 2.8:1.

In another embodiment, the ratio of the number of APCs exogenously supplied during the rapid second expansion to the number of APCs exogenously supplied during the priming first expansion is selected from a range of from at or about 1.1:1 to at or about 2.7:1.

In another embodiment, the ratio of the number of APCs exogenously supplied during the rapid second expansion to the number of APCs exogenously supplied during the priming first expansion is selected from a range of from at or about 1.1:1 to at or about 2.6:1.

In another embodiment, the ratio of the number of APCs exogenously supplied during the rapid second expansion to the number of APCs exogenously supplied during the priming first expansion is selected from a range of from at or about 1.1:1 to at or about 2.5:1.

In another embodiment, the ratio of the number of APCs exogenously supplied during the rapid second expansion to the number of APCs exogenously supplied during the priming first expansion is selected from a range of from at or about 1.1:1 to at or about 2.4:1.

In another embodiment, the ratio of the number of APCs exogenously supplied during the rapid second expansion to the number of APCs exogenously supplied during the priming first expansion is selected from a range of from at or about 1.1:1 to at or about 2.3:1.

In another embodiment, the ratio of the number of APCs exogenously supplied during the rapid second expansion to the number of APCs exogenously supplied during the priming first expansion is selected from a range of from at or about 1.1:1 to at or about 2.2:1.

In another embodiment, the ratio of the number of APCs exogenously supplied during the rapid second expansion to the number of APCs exogenously supplied during the priming first expansion is selected from a range of from at or about 1.1:1 to at or about 2.1:1.

In another embodiment, the ratio of the number of APCs exogenously supplied during the rapid second expansion to the number of APCs exogenously supplied during the priming first expansion is selected from a range of from at or about 1.1:1 to at or about 2:1.

In another embodiment, the ratio of the number of APCs exogenously supplied during the rapid second expansion to the number of APCs exogenously supplied during the priming first expansion is selected from a range of from at or about 2:1 to at or about 10:1.

In another embodiment, the ratio of the number of APCs exogenously supplied during the rapid second expansion to the number of APCs exogenously supplied during the priming first expansion is selected from a range of from at or about 2:1 to at or about 5:1.

In another embodiment, the ratio of the number of APCs exogenously supplied during the rapid second expansion to the number of APCs exogenously supplied during the priming first expansion is selected from a range of from at or about 2:1 to at or about 4:1.

In another embodiment, the ratio of the number of APCs exogenously supplied during the rapid second expansion to the number of APCs exogenously supplied during the priming first expansion is selected from a range of from at or about 2:1 to at or about 3:1.

In another embodiment, the ratio of the number of APCs exogenously supplied during the rapid second expansion to the number of APCs exogenously supplied during the priming first expansion is selected from a range of from at or about 2:1 to at or about 2.9:1.

In another embodiment, the ratio of the number of APCs exogenously supplied during the rapid second expansion to the number of APCs exogenously supplied during the priming first expansion is selected from a range of from at or about 2:1 to at or about 2.8:1.

In another embodiment, the ratio of the number of APCs exogenously supplied during the rapid second expansion to the number of APCs exogenously supplied during the priming first expansion is selected from a range of from at or about 2:1 to at or about 2.7:1.

In another embodiment, the ratio of the number of APCs exogenously supplied during the rapid second expansion to the number of APCs exogenously supplied during the priming first expansion is selected from a range of from at or about 2:1 to at or about 2.6:1.

In another embodiment, the ratio of the number of APCs exogenously supplied during the rapid second expansion to the number of APCs exogenously supplied during the priming first expansion is selected from a range of from at or about 2:1 to at or about 2.5:1.

In another embodiment, the ratio of the number of APCs exogenously supplied during the rapid second expansion to the number of APCs exogenously supplied during the priming first expansion is selected from a range of from at or about 2:1 to at or about 2.4:1.

In another embodiment, the ratio of the number of APCs exogenously supplied during the rapid second expansion to the number of APCs exogenously supplied during the priming first expansion is selected from a range of from at or about 2:1 to at or about 2.3:1.

In another embodiment, the ratio of the number of APCs exogenously supplied during the rapid second expansion to the number of APCs exogenously supplied during the priming first expansion is selected from a range of from at or about 2:1 to at or about 2.2:1.

In another embodiment, the ratio of the number of APCs exogenously supplied during the rapid second expansion to the number of APCs exogenously supplied during the priming first expansion is selected from a range of from at or about 2:1 to at or about 2.1:1.

In another embodiment, the ratio of the number of APCs exogenously supplied during the rapid second expansion to the number of APCs exogenously supplied during the priming first expansion is at or about 2:1.

In another embodiment, the ratio of the number of APCs exogenously supplied during the rapid second expansion to the number of APCs exogenously supplied during the priming first expansion is at or about 1.1:1, 1.2:1, 1.3:1, 1.4:1, 1.5:1, 1.6:1, 1.7:1, 1.8:1, 1.9:1, 2:1, 2.1:1, 2.2:1, 2.3:1, 2.4:1, 2.5:1, 2.6:1, 2.7:1, 2.8:1, 2.9:1, 3:1, 3.1:1, 3.2:1, 3.3:1, 3.4:1, 3.5:1, 3.6:1, 3.7:1, 3.8:1, 3.9:1, 4:1, 4.1:1, 4.2:1, 4.3:1, 4.4:1, 4.5:1, 4.6:1, 4.7:1, 4.8:1, 4.9:1, or 5:1.

In another embodiment, the number of APCs exogenously supplied during the priming first expansion is at or about $1\times10^8$, $1.1\times10^8$, $1.2\times10^8$, $1.3\times10^8$, $1.4\times10^8$, $1.5\times10^8$, $1.6\times10^8$, $1.7\times10^8$, $1.8\times10^8$, $1.9\times10^8$, $2\times10^8$, $2.1\times10^8$, $2.2\times10^8$, $2.3\times10^8$, $2.4\times10^8$, $2.5\times10^8$, $2.6\times10^8$, $2.7\times10^8$, $2.8\times10^8$, $2.9\times10^8$, $3\times10^8$, $3.1\times10^8$, $3.2\times10^8$, $3.3\times10^8$, $3.4\times10^8$ or $3.5\times10^8$ APCs, and the number of APCs exogenously supplied during the rapid second expansion is at or about $3.5\times10^8$, $3.6\times10^8$, $3.7\times10^8$, $3.8\times10^8$, $3.9\times10^8$, $4\times10^8$, $4.1\times10^8$, $4.2\times10^8$, $4.3\times10^8$, $4.4\times10^8$, $4.5\times10^8$, $4.6\times10^8$, $4.7\times10^8$, $4.8\times10^8$, $4.9\times10^8$, $5\times10^8$, $5.1\times10^8$, $5.2\times10^8$, $5.3\times10^8$, $5.4\times10^8$, $5.5\times10^8$, $5.6\times10^8$, $5.7\times10^8$, $5.8\times10^8$, $5.9\times10^8$, $6\times10^8$, $6.1\times10^8$, $6.2\times10^8$, $6.3\times10^8$, $6.4\times10^8$, $6.5\times10^8$, $6.6\times10^8$, $6.7\times10^8$, $6.8\times10^8$, $6.9\times10^8$, $7\times10^8$, $7.1\times10^8$, $7.2\times10^8$, $7.3\times10^8$, $7.4\times10^8$, $7.5\times10^8$, $7.6\times10^8$, $7.7\times10^8$, $7.8\times10^8$, $7.9\times10^8$, $8\times10^8$, $8.1\times10^8$, $8.2\times10^8$, $8.3\times10^8$, $8.4\times10^8$, $8.5\times10^8$, $8.6\times10^8$, $8.7\times10^8$, $8.8\times10^8$, $8.9\times10^8$, $9\times10^8$, $9.1\times10^8$, $9.2\times10^8$, $9.3\times10^8$, $9.4\times10^8$, $9.5\times10^8$, $9.6\times10^8$, $9.7\times10^8$, $9.8\times10^8$, $9.9\times10^8$ or $1\times10^9$ APCs.

In another embodiment, the number of APCs exogenously supplied during the priming first expansion is selected from the range of at or about $1.5\times10^8$ APCs to at or about $3\times10^8$ APCs, and the number of APCs exogenously supplied during the rapid second expansion is selected from the range of at or about $4\times10^8$ APCs to at or about $7.5\times10^8$ APCs.

In another embodiment, the number of APCs exogenously supplied during the priming first expansion is selected from the range of at or about $2\times10^8$ APCs to at or about $2.5\times10^8$ APCs, and the number of APCs exogenously supplied during the rapid second expansion is selected from the range of at or about $4.5\times10^8$ APCs to at or about $5.5\times10^8$ APCs.

In another embodiment, the number of APCs exogenously supplied during the priming first expansion is at or about $2.5\times10^8$ APCs, and the number of APCs exogenously supplied during the rapid second expansion is at or about $5\times10^8$ APCs.

In an embodiment, the number of APCs (including, for example, PBMCs) added at day 0 of the priming first expansion is approximately one-half of the number of PBMCs added at day 7 of the priming first expansion (e.g., day 7 of the method). In certain embodiments, the method comprises adding antigen presenting cells at day 0 of the priming first expansion to the first population of TILs and adding antigen presenting cells at day 7 to the second population of TILs, wherein the number of antigen presenting cells added at day 0 is approximately 50% of the number of antigen presenting cells added at day 7 of the priming first expansion (e.g., day 7 of the method).

In another embodiment, the number of APCs (including, for example, PBMCs) exogenously supplied at day 7 of the rapid second expansion is greater than the number of PBMCs exogenously supplied at day 0 of the priming first expansion.

In another embodiment, the APCs exogenously supplied in the priming first expansion are seeded in the culture flask at a density selected from a range of at or about $1.0\times10^6$ APCs/cm$^2$ to at or about $4.5\times10^6$ APCs/cm$^2$.

In another embodiment, the APCs exogenously supplied in the priming first expansion are seeded in the culture flask at a density selected from a range of at or about $1.5\times10^6$ APCs/cm$^2$ to at or about $3.5\times10^6$ APCs/cm$^2$.

In another embodiment, the APCs exogenously supplied in the priming first expansion are seeded in the culture flask at a density selected from a range of at or about $2\times10^6$ APCs/cm$^2$ to at or about $3\times10^6$ APCs/cm$^2$.

In another embodiment, the APCs exogenously supplied in the priming first expansion are seeded in the culture flask at a density of at or about $2\times10^6$ APCs/cm$^2$.

In another embodiment, the APCs exogenously supplied in the priming first expansion are seeded in the culture flask at a density of at or about $1.0\times10^6$, $1.1\times10^6$, $1.2\times10^6$, $1.3\times10^6$, $1.4\times10^6$, $1.5\times10^6$, $1.6\times10^6$, $1.7\times10^6$, $1.8\times10^6$, $1.9\times$ $10^6$, $2\times10^6$, $2.1\times10^6$, $2.2\times10^6$, $2.3\times10^6$, $2.4\times10^6$, $2.5\times10^6$, $2.6\times10^6$, $2.7\times10^6$, $2.8\times10^6$, $2.9\times10^6$, $3\times10^6$, $3.1\times10^6$, $3.2\times10^6$, $3.3\times10^6$, $3.4\times10^6$, $3.5\times10^6$, $3.6\times10^6$, $3.7\times10^6$, $3.8\times10^6$, $3.9\times10^6$, $4\times10^6$, $4.1\times10^6$, $4.2\times10^6$, $4.3\times10^6$, $4.4\times10^6$ or $4.5\times10^6$ APCs/cm$^2$.

In another embodiment, the APCs exogenously supplied in the rapid second expansion are seeded in the culture flask at a density selected from a range of at or about $2.5\times10^6$ APCs/cm$^2$ to at or about $7.5\times10^6$ APCs/cm$^2$.

In another embodiment, the APCs exogenously supplied in the rapid second expansion are seeded in the culture flask at a density selected from a range of at or about $3.5\times10^6$ APCs/cm$^2$ to about $6.0\times10^6$ APCs/cm$^2$.

In another embodiment, the APCs exogenously supplied in the rapid second expansion are seeded in the culture flask at a density selected from a range of at or about $4.0\times10^6$ APCs/cm$^2$ to about $5.5\times10^6$ APCs/cm$^2$.

In another embodiment, the APCs exogenously supplied in the rapid second expansion are seeded in the culture flask at a density selected from a range of at or about $4.0\times10^6$ APCs/cm$^2$.

In another embodiment, the APCs exogenously supplied in the rapid second expansion are seeded in the culture flask at a density of at or about $2.5\times10^6$ APCs/cm$^2$, $2.6\times10^6$ APCs/cm$^2$, $2.7\times10^6$ APCs/cm$^2$, $2.8\times10^6$, $2.9\times10^6$, $3\times10^6$, $3.1\times10^6$, $3.2\times10^6$, $3.3\times10^6$, $3.4\times10^6$, $3.5\times10^6$, $3.6\times10^6$, $3.7\times10^6$, $3.8\times10^6$, $3.9\times10^6$, $4\times10^6$, $4.1\times10^6$, $4.2\times10^6$, $4.3\times10^6$, $4.4\times10^6$, $4.5\times10^6$, $4.6\times10^6$, $4.7\times10^6$, $4.8\times10^6$, $4.9\times10^6$, $5\times10^6$, $5.1\times10^6$, $5.2\times10^6$, $5.3\times10^6$, $5.4\times10^6$, $5.5\times10^6$, $5.6\times10^6$, $5.7\times10^6$, $5.8\times10^6$, $5.9\times10^6$, $6\times10^6$, $6.1\times10^6$, $6.2\times10^6$, $6.3\times10^6$, $6.4\times10^6$, $6.5\times10^6$, $6.6\times10^6$, $6.7\times10^6$, $6.8\times10^6$, $6.9\times10^6$, $7\times10^6$, $7.1\times10^6$, $7.2\times10^6$, $7.3\times10^6$, $7.4\times10^6$ or $7.5\times10^6$ APCs/cm$^2$.

In another embodiment, the APCs exogenously supplied in the priming first expansion are seeded in the culture flask at a density of at or about $1.0\times10^6$, $1.1\times10^6$, $1.2\times10^6$, $1.3\times10^6$, $1.4\times10^6$, $1.5\times10^6$, $1.6\times10^6$, $1.7\times10^6$, $1.8\times10^6$, $1.9\times10^6$, $2\times10^6$, $2.1\times10^6$, $2.2\times10^6$, $2.3\times10^6$, $2.4\times10^6$, $2.5\times10^6$, $2.6\times10^6$, $2.7\times10^6$, $2.8\times10^6$, $2.9\times10^6$, $3\times10^6$, $3.1\times10^6$, $3.2\times10^6$, $3.3\times10^6$, $3.4\times10^6$, $3.5\times10^6$, $3.6\times10^6$, $3.7\times10^6$, $3.8\times10^6$, $3.9\times10^6$, $4\times10^6$, $4.1\times10^6$, $4.2\times10^6$, $4.3\times10^6$, $4.4\times10^6$ or $4.5\times10^6$ APCs/cm$^2$ and the APCs exogenously supplied in the rapid second expansion are seeded in the culture flask at a density of at or about $2.5\times10^6$ APCs/cm$^2$, $2.6\times10^6$ APCs/cm$^2$, $2.7\times10^6$ APCs/cm$^2$, $2.8\times10^6$, $2.9\times10^6$, $3\times10^6$, $3.1\times10^6$, $3.2\times10^6$, $3.3\times10^6$, $3.4\times10^6$, $3.5\times10^6$, $3.6\times10^6$, $3.7\times10^6$, $3.8\times10^6$, $3.9\times10^6$, $4\times10^6$, $4.1\times10^6$, $4.2\times10^6$, $4.3\times10^6$, $4.4\times10^6$, $4.5\times10^6$, $4.6\times10^6$, $4.7\times10^6$, $4.8\times10^6$, $4.9\times10^6$, $5\times10^6$, $5.1\times10^6$, $5.2\times10^6$, $5.3\times10^6$, $5.4\times10^6$, $5.5\times10^6$, $5.6\times10^6$, $5.7\times10^6$, $5.8\times10^6$, $5.9\times10^6$, $6\times10^6$, $6.1\times10^6$, $6.2\times10^6$, $6.3\times10^6$, $6.4\times10^6$, $6.5\times10^6$, $6.6\times10^6$, $6.7\times10^6$, $6.8\times10^6$, $6.9\times10^6$, $7\times10^6$, $7.1\times10^6$, $7.2\times10^6$, $7.3\times10^6$, $7.4\times10^6$ or $7.5\times10^6$ APCs/cm$^2$.

In another embodiment, the APCs exogenously supplied in the priming first expansion are seeded in the culture flask at a density selected from a range of at or about $1.0\times10^6$ APCs/cm$^2$ to at or about $4.5\times10^6$ APCs/cm$^2$, and the APCs exogenously supplied in the rapid second expansion are seeded in the culture flask at a density selected from a range of at or about $2.5\times10^6$ APCs/cm$^2$ to at or about $7.5\times10^6$ APCs/cm$^2$.

In another embodiment, the APCs exogenously supplied in the priming first expansion are seeded in the culture flask at a density selected from a range of at or about $1.5\times10^6$ APCs/cm$^2$ to at or about $3.5\times10^6$ APCs/cm$^2$, and the APCs exogenously supplied in the rapid second expansion are seeded in the culture flask at a density selected from a range of at or about $3.5\times10^6$ APCs/cm$^2$ to at or about $6\times10^6$ APCs/cm$^2$.

In another embodiment, the APCs exogenously supplied in the priming first expansion are seeded in the culture flask at a density selected from a range of at or about $2\times10^6$ APCs/cm$^2$ to at or about $3\times10^6$ APCs/cm$^2$, and the APCs exogenously supplied in the rapid second expansion are seeded in the culture flask at a density selected from a range of at or about $4\times10^6$ APCs/cm$^2$ to at or about $5.5\times10^6$ APCs/cm$^2$.

In another embodiment, the APCs exogenously supplied in the priming first expansion are seeded in the culture flask at a density at or about $2\times10^6$ APCs/cm$^2$ and the APCs exogenously supplied in the rapid second expansion are seeded in the culture flask at a density of at or about $4\times10^6$ APCs/cm$^2$.

In another embodiment, the ratio of the number of APCs (including, for example, PBMCs) exogenously supplied at day 7 of the rapid second expansion to the number of PBMCs exogenously supplied at day 0 of the priming first expansion is selected from a range of from at or about 1.1:1 to at or about 20:1.

In another embodiment, the ratio of the number of APCs (including, for example, PBMCs) exogenously supplied at day 7 of the rapid second expansion to the number of PBMCs exogenously supplied at day 0 of the priming first expansion is selected from a range of from at or about 1.1:1 to at or about 10:1.

In another embodiment, the ratio of the number of APCs (including, for example, PBMCs) exogenously supplied at day 7 of the rapid second expansion to the number of PBMCs exogenously supplied at day 0 of the priming first expansion is selected from a range of from at or about 1.1:1 to at or about 9:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 8:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 7:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 6:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 5:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 4:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 3:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 2.9:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 2.8:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 2.7:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 2.6:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 2.5:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 2.4:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 2.3:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 2.2:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 2.1:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 1.1:1 to at or about 2:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 2:1 to at or about 10:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 2:1 to at or about 5:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 2:1 to at or about 4:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 2:1 to at or about 3:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 2:1 to at or about 2.9:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 2:1 to at or about 2.8:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 2:1 to at or about 2.7:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 2:1 to at or about 2.6:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 2:1 to at or about 2.5:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 2:1 to at or about 2.4:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 2:1 to at or about 2.3:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 2:1 to at or about 2.2:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is selected from a range of from at or about 2:1 to at or about 2.1:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is at or about 2:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is at or about 1.1:1, 1.2:1, 1.3:1, 1.4:1, 1.5:1, 1.6:1, 1.7:1, 1.8:1, 1.9:1, 2:1, 2.1:1, 2.2:1, 2.3:1, 2.4:1, 2.5:1, 2.6:1, 2.7:1, 2.8:1, 2.9:1, 3:1, 3.1:1, 3.2:1, 3.3:1, 3.4:1, 3.5:1, 3.6:1, 3.7:1, 3.8:1, 3.9:1, 4:1, 4.1:1, 4.2:1, 4.3:1, 4.4:1, 4.5:1, 4.6:1, 4.7:1, 4.8:1, 4.9:1, or 5:1.

In another embodiment, the number of APCs (including, for example, PBMCs) exogenously supplied at day 0 of the priming first expansion is at or about $1\times10^8$, $1.1\times10^8$, $1.2\times10^8$, $1.3\times10^8$, $1.4\times10^8$, $1.5\times10^8$, $1.6\times10^8$, $1.7\times10^8$, $1.8\times10^8$, $1.9\times10^8$, $2\times10^8$, $2.1\times10^8$, $2.2\times10^8$, $2.3\times10^8$, $2.4\times10^8$, $2.5\times10^8$, $2.6\times10^8$, $2.7\times10^8$, $2.8\times10^8$, $2.9\times10^8$, $3\times10^8$, $3.1\times10^8$, $3.2\times10^8$, $3.3\times10^8$, $3.4\times10^8$ or $3.5\times10^8$ APCs (including, for example, PBMCs), and the number of APCs (including, for example, PBMCs) exogenously supplied at day 7 of the rapid second expansion is at or about $3.5\times10^8$, $3.6\times10^8$, $3.7\times10^8$, $3.8\times10^8$, $3.9\times10^8$, $4\times10^8$, $4.1\times10^8$, $4.2\times10^8$, $4.3\times10^8$, $4.4\times10^8$, $4.5\times10^8$, $4.6\times10^8$, $4.7\times10^8$, $4.8\times10^8$, $4.9\times10^8$, $5\times10^8$, $5.1\times10^8$, $5.2\times10^8$, $5.3\times10^8$, $5.4\times10^8$, $5.5\times10^8$, $5.6\times10^8$, $5.7\times10^8$, $5.8\times10^8$, $5.9\times10^8$, $6\times10^8$, $6.1\times10^8$, $6.2\times10^8$, $6.3\times10^8$, $6.4\times10^8$, $6.5\times10^8$, $6.6\times10^8$, $6.7\times10^8$, $6.8\times10^8$, $6.9\times10^8$, $7\times10^8$, $7.1\times10^8$, $7.2\times10^8$, $7.3\times10^8$, $7.4\times10^8$, $7.5\times10^8$, $7.6\times10^8$, $7.7\times10^8$, $7.8\times10^8$, $7.9\times10^8$, $8\times10^8$, $8.1\times10^8$, $8.2\times10^8$, $8.3\times10^8$, $8.4\times10^8$, $8.5\times10^8$, $8.6\times10^8$, $8.7\times10^8$, $8.8\times10^8$, $8.9\times10^8$, $9\times10^8$, $9.1\times10^8$, $9.2\times10^8$, $9.3\times10^8$, $9.4\times10^8$, $9.5\times10^8$, $9.6\times10^8$, $9.7\times10^8$, $9.8\times10^8$, $9.9\times10^8$ or $1\times10^9$ APCs (including, for example, PBMCs).

In another embodiment, the number of APCs (including, for example, PBMCs) exogenously supplied at day 0 of the priming first expansion is selected from the range of at or about $1\times10^8$ APCs (including, for example, PBMCs) to at or about $3.5\times10^8$ APCs (including, for example, PBMCs), and the number of APCs (including, for example, PBMCs) exogenously supplied at day 7 of the rapid second expansion is selected from the range of at or about $3.5\times10^8$ APCs (including, for example, PBMCs) to at or about $1\times10^9$ APCs (including, for example, PBMCs).

In another embodiment, the number of APCs (including, for example, PBMCs) exogenously supplied at day 0 of the priming first expansion is selected from the range of at or about $1.5\times10^8$ APCs to at or about $3\times10^8$ APCs (including, for example, PBMCs), and the number of APCs (including, for example, PBMCs) exogenously supplied at day 7 of the rapid second expansion is selected from the range of at or about $4\times10^8$ APCs (including, for example, PBMCs) to at or about $7.5\times10^8$ APCs (including, for example, PBMCs).

In another embodiment, the number of APCs (including, for example, PBMCs) exogenously supplied at day 0 of the priming first expansion is selected from the range of at or about $2\times10^8$ APCs (including, for example, PBMCs) to at or about $2.5\times10^8$ APCs (including, for example, PBMCs), and the number of APCs (including, for example, PBMCs) exogenously supplied at day 7 of the rapid second expansion is selected from the range of at or about $4.5\times10^8$ APCs (including, for example, PBMCs) to at or about $5.5\times10^8$ APCs (including, for example, PBMCs).

In another embodiment, the number of APCs (including, for example, PBMCs) exogenously supplied at day 0 of the priming first expansion is at or about $2.5\times10^8$ APCs (including, for example, PBMCs) and the number of APCs (including, for example, PBMCs) exogenously supplied at day 7 of the rapid second expansion is at or about $5\times10^8$ APCs (including, for example, PBMCs)

In an embodiment, the number of layers of APCs (including, for example, PBMCs) added at day 0 of the priming first expansion is approximately one-half of the number of layers of APCs (including, for example, PBMCs) added at day 7 of the rapid second expansion. In certain embodiments, the method comprises adding antigen presenting cell layers at day 0 of the priming first expansion to the first population of TILs and adding antigen presenting cell layers at day 7 to the second population of TILs, wherein the number of antigen presenting cell layer added at day 0 is approximately 50% of the number of antigen presenting cell layers added at day 7.

In another embodiment, the number of layers of APCs (including, for example, PBMCs) exogenously supplied at day 7 of the rapid second expansion is greater than the number of layers of APCs (including, for example, PBMCs) exogenously supplied at day 0 of the priming first expansion.

In another embodiment, day 0 of the priming first expansion occurs in the presence of layered APCs (including, for example, PBMCs) with an average thickness of at or about 2 cell layers and day 7 of the rapid second expansion occurs in the presence of layered APCs (including, for example, PBMCs) with an average thickness of at or about 4 cell layers.

In another embodiment, day 0 of the priming first expansion occurs in the presence of layered APCs (including, for example, PBMCs) with an average thickness of at or about one cell layer and day 7 of the rapid second expansion occurs in the presence of layered APCs (including, for example, PBMCs) with an average thickness of at or about 3 cell layers.

In another embodiment, day 0 of the priming first expansion occurs in the presence of layered APCs (including, for example, PBMCs) with an average thickness of at or about 1.5 cell layers to at or about 2.5 cell layers and day 7 of the rapid second expansion occurs in the presence of layered APCs (including, for example, PBMCs) with an average thickness of at or about 3 cell layers.

In another embodiment, day 0 of the priming first expansion occurs in the presence of layered APCs (including, for example, PBMCs) with an average thickness of at or about one cell layer and day 7 of the rapid second expansion occurs in the presence of layered APCs (including, for example, PBMCs) with an average thickness of at or about 2 cell layers.

In another embodiment, day 0 of the priming first expansion occurs in the presence of layered APCs (including, for example, PBMCs) with an average thickness of at or about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9 or 3 cell layers and day 7 of the rapid second expansion occurs in the presence of layered APCs (including, for example, PBMCs) with an average thickness of at or about 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9 or 8 cell layers.

In another embodiment, day 0 of the priming first expansion occurs in the presence of layered APCs (including, for example, PBMCs) with an average thickness of at or about 1 cell layer to at or about 2 cell layers and day 7 of the rapid second expansion occurs in the presence of layered APCs (including, for example, PBMCs) with an average thickness of at or about 3 cell layers to at or about 10 cell layers.

In another embodiment, day 0 of the priming first expansion occurs in the presence of layered APCs (including, for example, PBMCs) with an average thickness of at or about 2 cell layers to at or about 3 cell layers and day 7 of the rapid second expansion occurs in the presence of layered APCs (including, for example, PBMCs) with an average thickness of at or about 4 cell layers to at or about 8 cell layers.

In another embodiment, day 0 of the priming first expansion occurs in the presence of layered APCs (including, for example, PBMCs) with an average thickness of at or about 2 cell layers and day 7 of the rapid second expansion occurs in the presence of layered APCs (including, for example, PBMCs) with an average thickness of at or about 4 cell layers to at or about 8 cell layers.

In another embodiment, day 0 of the priming first expansion occurs in the presence of layered APCs (including, for example, PBMCs) with an average thickness of at or about 1, 2 or 3 cell layers and day 7 of the rapid second expansion occurs in the presence of layered APCs (including, for example, PBMCs) with an average thickness of at or about 3, 4, 5, 6, 7, 8, 9 or 10 cell layers.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.1 to at or about 1:10.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.1 to at or about 1:8.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.1 to at or about 1:7.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.1 to at or about 1:6.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.1 to at or about 1:5.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.1 to at or about 1:4.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.1 to at or about 1:3.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.1 to at or about 1:2.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.2 to at or about 1:8.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.3 to at or about 1:7.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.4 to at or about 1:6.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.5 to at or about 1:5.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.6 to at or about 1:4.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.7 to at or about 1:3.5.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.8 to at or about 1:3.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from the range of at or about 1:1.9 to at or about 1:2.5.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is at or about 1:2.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is selected from at or about 1:1.1, 1:1.2, 1:1.3, 1:1.4, 1:1.5, 1:1.6, 1:1.7, 1:1.8, 1:1.9, 1:2, 1:2.1, 1:2.2, 1:2.3, 1:2.4, 1:2.5, 1:2.6, 1:2.7, 1:2.8, 1:2.9, 1:3, 1:3.1, 1:3.2, 1:3.3, 1:3.4, 1:3.5, 1:3.6, 1:3.7, 1:3.8, 1:3.9, 1:4, 1:4.1, 1:4.2, 1:4.3, 1:4.4, 1:4.5, 1:4.6, 1:4.7, 1:4.8, 1:4.9, 1:5, 1:5.1, 1:5.2, 1:5.3, 1:5.4, 1:5.5, 1:5.6, 1:5.7, 1:5.8, 1:5.9, 1:6, 1:6.1, 1:6.2, 1:6.3, 1:6.4, 1:6.5, 1:6.6, 1:6.7, 1:6.8, 1:6.9, 1:7, 1:7.1, 1:7.2, 1:7.3, 1:7.4, 1:7.5, 1:7.6, 1:7.7, 1:7.8, 1:7.9, 1:8, 1:8.1, 1:8.2, 1:8.3, 1:8.4, 1:8.5, 1:8.6, 1:8.7, 1:8.8, 1:8.9, 1:9, 1:9.1, 1:9.2, 1:9.3, 1:9.4, 1:9.5, 1:9.6, 1:9.7, 1:9.8, 1:9.9 or 1:10.

In some embodiments, the number of APCs in the priming first expansion is selected from the range of about $1.0\times10^6$ APCs/cm$^2$ to about $4.5\times10^6$ APCs/cm$^2$, and the number of APCs in the rapid second expansion is selected from the range of about $2.5\times10^6$ APCs/cm$^2$ to about $7.5\times10^6$ APCs/cm$^2$.

In some embodiments, the number of APCs in the priming first expansion is selected from the range of about $1.5\times10^6$ APCs/cm$^2$ to about $3.5\times10^6$ APCs/cm$^2$, and the number of APCs in the rapid second expansion is selected from the range of about $3.5\times10^6$ APCs/cm$^2$ to about $6.0\times10^6$ APCs/cm$^2$.

In some embodiments, the number of APCs in the priming first expansion is selected from the range of about $2.0\times10^6$ APCs/cm$^2$ to about $3.0\times10^6$ APCs/cm$^2$, and the number of APCs in the rapid second expansion is selected from the range of about $4.0\times10^6$ APCs/cm$^2$ to about $5.5\times10^6$ APCs/cm$^2$.

B. Optional Cell Medium Components

1. Anti-CD3 Antibodies

In some embodiments, the culture media used in expansion methods described herein (including those referred to as REP, see for example, FIGS. 1 and 8 (in particular, e.g., FIG. 8B)) include an anti-CD3 antibody. An anti-CD3 antibody in combination with IL-2 induces T cell activation and cell division in the TIL population. This effect can be seen with full length antibodies as well as Fab and F(ab')2 fragments, with the former being generally preferred; see, e.g., Tsoukas et al., *J. Immunol.* 1985, 135, 1719, hereby incorporated by reference in its entirety.

As will be appreciated by those in the art, there are a number of suitable anti-human CD3 antibodies that find use in the invention, including anti-human CD3 polyclonal and monoclonal antibodies from various mammals, including, but not limited to, murine, human, primate, rat, and canine antibodies. In particular embodiments, the OKT3 anti-CD3 antibody is used (commercially available from Ortho-McNeil, Raritan, NJ or Miltenyi Biotech, Auburn, CA).

2. 4-1BB (CD137) Agonists

In an embodiment, the cell culture medium of the priming first expansion and/or the rapid second expansion comprises a TNFRSF agonist. In an embodiment, the TNFRSF agonist is a 4-1BB (CD137) agonist. The 4-1BB agonist may be any 4-1BB binding molecule known in the art. The 4-1BB binding molecule may be a monoclonal antibody or fusion protein capable of binding to human or mammalian 4-1BB. The 4-1BB agonists or 4-1BB binding molecules may comprise an immunoglobulin heavy chain of any isotype (e.g., IgG, IgE, IgM, IgD, IgA, and IgY), class (e.g., IgG1, IgG2, IgG3, IgG4, IgA1 and IgA2) or subclass of immunoglobulin molecule. The 4-1BB agonist or 4-1BB binding molecule may have both a heavy and a light chain. As used herein, the term binding molecule also includes antibodies (including full length antibodies), monoclonal antibodies (including full length monoclonal antibodies), polyclonal antibodies, multispecific antibodies (e.g., bispecific antibodies), human, humanized or chimeric antibodies, and antibody fragments, e.g., Fab fragments, F(ab') fragments, fragments produced by a Fab expression library, epitope-binding fragments of any of the above, and engineered forms of antibodies, e.g., scFv molecules, that bind to 4-1BB. In an embodiment, the 4-1BB agonist is an antigen binding protein that is a fully human antibody. In an embodiment, the 4-1BB agonist is an antigen binding protein that is a humanized antibody. In some embodiments, 4-1BB agonists for use in the presently disclosed methods and compositions include anti-4-1BB antibodies, human anti-4-1BB antibodies, mouse anti-4-1BB antibodies, mammalian anti-4-1BB antibodies, monoclonal anti-4-1BB antibodies, polyclonal anti-4-1BB antibodies, chimeric anti-4-1BB antibodies, anti-4-1BB adnectins, anti-4-1BB domain antibodies, single chain anti-4-1BB fragments, heavy chain anti-4-1BB fragments, light chain anti-4-1BB fragments, anti-4-1BB fusion proteins, and fragments, derivatives, conjugates, variants, or biosimilars thereof. Agonistic anti-4-1BB antibodies are known to induce strong immune responses. Lee, et al., *PLOS One* 2013, 8, e69677. In a preferred embodiment, the 4-1BB agonist is an agonistic, anti-4-1BB humanized or fully human monoclonal antibody (i.e., an antibody derived from a single cell line). In an embodiment, the 4-1BB agonist is EU-101 (Eutilex Co. Ltd.), utomilumab, or urelumab, or a fragment, derivative, conjugate, variant, or biosimilar thereof. In a preferred embodiment, the 4-1BB agonist is utomilumab or urelumab, or a fragment, derivative, conjugate, variant, or biosimilar thereof.

In a preferred embodiment, the 4-1BB agonist or 4-1BB binding molecule may also be a fusion protein. In a preferred embodiment, a multimeric 4-1BB agonist, such as a trimeric or hexameric 4-1BB agonist (with three or six ligand binding domains), may induce superior receptor (4-1BBL) clustering and internal cellular signaling complex formation compared to an agonistic monoclonal antibody, which typically possesses two ligand binding domains. Trimeric (trivalent) or hexameric (or hexavalent) or greater fusion proteins comprising three TNFRSF binding domains and IgG1-Fc and optionally further linking two or more of these fusion proteins are described, e.g., in Gieffers, et al., *Mol. Cancer Therapeutics* 2013, 12, 2735-47.

Agonistic 4-1BB antibodies and fusion proteins are known to induce strong immune responses. In a preferred embodiment, the 4-1BB agonist is a monoclonal antibody or fusion protein that binds specifically to 4-1BB antigen in a manner sufficient to reduce toxicity. In some embodiments, the 4-1BB agonist is an agonistic 4-1BB monoclonal antibody or fusion protein that abrogates antibody-dependent cellular toxicity (ADCC), for example NK cell cytotoxicity. In some embodiments, the 4-1BB agonist is an agonistic 4-1BB monoclonal antibody or fusion protein that abrogates antibody-dependent cell phagocytosis (ADCP). In some embodiments, the 4-1BB agonist is an agonistic 4-1BB monoclonal antibody or fusion protein that abrogates complement-dependent cytotoxicity (CDC). In some embodiments, the 4-1BB agonist is an agonistic 4-1BB monoclonal antibody or fusion protein which abrogates Fc region functionality.

In some embodiments, the 4-1BB agonists are characterized by binding to human 4-1BB (SEQ ID NO:40) with high affinity and agonistic activity. In an embodiment, the 4-1BB agonist is a binding molecule that binds to human 4-1BB (SEQ ID NO: 40). In an embodiment, the 4-1BB agonist is a binding molecule that binds to murine 4-1BB (SEQ ID NO:41). The amino acid sequences of 4-1BB antigen to which a 4-1BB agonist or binding molecule binds are summarized in Table 5.

TABLE 5

Amino acid sequences of 4-1BB antigens.

| Identifier | Sequence (One-Letter Amino Acid Symbols) |
|---|---|
| SEQ ID NO: 40 human 4-1BB, Tumor necrosis factor receptor superfamily, member 9 (*Homo sapiens*) | MGNSCYNIVA TLLLVLNFER TRSLQDPCSN CPAGTFCDNN RNQICSPCPP NSFSSAGGQR 60<br>TCDICRQCKG VFRTRKECSS TSNAECDCTP GFHCLGAGCS MCEQDCKQGQ ELTKKGCKDC 120<br>CFGTFNDQKR GICRPWTNCS LDGKSVLVNG TKERDVVCGP SPADLSPGAS SVTPPAPARE 180<br>PGHSPQIISF FLALTSTALL FLLFFLTLRF SVVKRGRKKL LYIFKQPFMR PVQTTQEEDG 240<br>CSCRFPEEEE GGCEL 255 |

TABLE 5-continued

| Amino acid sequences of 4-1BB antigens. | |
|---|---|
| Identifier | Sequence (One-Letter Amino Acid Symbols) |
| SEQ ID NO: 41 murine 4-1BB, Tumor necrosis factor receptor superfamily, member 9 (*Mus musculus*) | MGNNCYNVVV IVLLLVGCEK VGAVQNSCDN CQPGTFCRKY NPVCKSCPPS TFSSIGGQPN 60<br>CNICRVCAGY FRFKKFCSST HNAECECIEG FHCLGPQCTR CEKDCRPGQE LTKQGCKTCS 120<br>LGTFNDQNGT GVCRPWTNCS LDGRSVLKTG TTEKDVVCGP PVVSFSPSTT ISVTPEGGPG 180<br>GHSLQVLTLF LALTSALLLA LIFITLLFSV LKWIRKKFPH IFKQPFKKTT GAAQEEDACS 240<br>CRCPQEEEGG GGGYEL 256 |

In some embodiments, the compositions, processes and methods described include a 4-1BB agonist that binds human or murine 4-1BB with a $K_D$ of about 100 pM or lower, binds human or murine 4-1BB with a $K_D$ of about 90 pM or lower, binds human or murine 4-1BB with a $K_D$ of about 80 pM or lower, binds human or murine 4-1BB with a $K_D$ of about 70 pM or lower, binds human or murine 4-1BB with a $K_D$ of about 60 pM or lower, binds human or murine 4-1BB with a $K_D$ of about 50 pM or lower, binds human or murine 4-1BB with a $K_D$ of about 40 pM or lower, or binds human or murine 4-1BB with a $K_D$ of about 30 pM or lower.

In some embodiments, the compositions, processes and methods described include a 4-1BB agonist that binds to human or murine 4-1BB with a $k_{assoc}$ of about $7.5\times10^5$ 1/M·s or faster, binds to human or murine 4-1BB with a $k_{assoc}$ of about $7.5\times10^5$ 1/M·s or faster, binds to human or murine 4-1BB with a $k_{assoc}$ of about $8\times10^5$ 1/M·s or faster, binds to human or murine 4-1BB with a $k_{assoc}$ of about $8.5\times10^5$ 1/M·s or faster, binds to human or murine 4-1BB with a $k_{assoc}$ of about $9\times10^5$ 1/M·s or faster, binds to human or murine 4-1BB with a $k_{assoc}$ of about $9.5\times10^5$ 1/M·s or faster, or binds to human or murine 4-1BB with a $k_{assoc}$ of about $1\times10^6$ 1/M·s or faster.

In some embodiments, the compositions, processes and methods described include a 4-1BB agonist that binds to human or murine 4-1BB with a $k_{dissoc}$ of about $2\times10^{-5}$ 1/s or slower, binds to human or murine 4-1BB with a $k_{dissoc}$ of about $2.1\times10^{-5}$ 1/s or slower, binds to human or murine 4-1BB with a $k_{dissoc}$ of about $2.2\times10^{-5}$ 1/s or slower, binds to human or murine 4-1BB with a $k_{dissoc}$ of about $2.3\times10^{-5}$ 1/s or slower, binds to human or murine 4-1BB with a $k_{dissoc}$ of about $2.4\times10^{-5}$ 1/s or slower, binds to human or murine 4-1BB with a $k_{dissoc}$ of about $2.5\times10^{-5}$ 1/s or slower, binds to human or murine 4-1BB with a $k_{dissoc}$ of about $2.6\times10^{-5}$ 1/s or slower or binds to human or murine 4-1BB with a $k_{dissoc}$ of about $2.7\times10^{-5}$ 1/s or slower, binds to human or murine 4-1BB with a $k_{dissoc}$ of about $2.8\times10^{-5}$ 1/s or slower, binds to human or murine 4-1BB with a $k_{dissoc}$ of about $2.9\times10^{-5}$ 1/s or slower, or binds to human or murine 4-1BB with a $k_{dissoc}$ of about $3\times10^{-5}$ 1/s or slower.

In some embodiments, the compositions, processes and methods described include a 4-1BB agonist that binds to human or murine 4-1BB with an $IC_{50}$ of about 10 nM or lower, binds to human or murine 4-1BB with an $IC_{50}$ of about 9 nM or lower, binds to human or murine 4-1BB with an $IC_{50}$ of about 8 nM or lower, binds to human or murine 4-1BB with an $IC_{50}$ of about 7 nM or lower, binds to human or murine 4-1BB with an $IC_{50}$ of about 6 nM or lower, binds to human or murine 4-1BB with an $IC_{50}$ of about 5 nM or lower, binds to human or murine 4-1BB with an $IC_{50}$ of about 4 nM or lower, binds to human or murine 4-1BB with an $IC_{50}$ of about 3 nM or lower, binds to human or murine 4-1BB with an $IC_{50}$ of about 2 nM or lower, or binds to human or murine 4-1BB with an $IC_{50}$ of about 1 nM or lower.

In a preferred embodiment, the 4-1BB agonist is utomilumab, also known as PF-05082566 or MOR-7480, or a fragment, derivative, variant, or biosimilar thereof. Utomilumab is available from Pfizer, Inc. Utomilumab is an immunoglobulin G2-lambda, anti-[*Homo sapiens* TNFRSF9 (tumor necrosis factor receptor (TNFR) superfamily member 9, 4-1BB, T cell antigen ILA, CD137)], *Homo sapiens* (fully human) monoclonal antibody. The amino acid sequences of utomilumab are set forth in Table 6. Utomilumab comprises glycosylation sites at Asn59 and Asn292; heavy chain intrachain disulfide bridges at positions 22-96 ($V_H$-$V_L$), 143-199 ($C_H1$-$C_L$), 256-316 ($C_H2$) and 362-420 ($C_H3$); light chain intrachain disulfide bridges at positions 22'-87' ($V_H$-$V_L$) and 136'-195' ($C_H1$-$C_L$); interchain heavy chain-heavy chain disulfide bridges at IgG2A isoform positions 218-218, 219-219, 222-222, and 225-225, at IgG2A/B isoform positions 218-130, 219-219, 222-222, and 225-225, and at IgG2B isoform positions 219-130 (2), 222-222, and 225-225; and interchain heavy chain-light chain disulfide bridges at IgG2A isoform positions 130-213' (2), IgG2A/B isoform positions 218-213' and 130-213', and at IgG2B isoform positions 218-213' (2). The preparation and properties of utomilumab and its variants and fragments are described in U.S. Pat. Nos. 8,821,867; 8,337,850; and 9,468,678, and International Patent Application Publication No. WO 2012/032433 A1, the disclosures of each of which are incorporated by reference herein. Preclinical characteristics of utomilumab are described in Fisher, et al., *Cancer Immunolog. & Immunother.* 2012, 61, 1721-33. Current clinical trials of utomilumab in a variety of hematological and solid tumor indications include U.S. National Institutes of Health clinicaltrials.gov identifiers NCT02444793, NCT01307267, NCT02315066, and NCT02554812.

In an embodiment, a 4-1BB agonist comprises a heavy chain given by SEQ ID NO:42 and a light chain given by SEQ ID NO:43. In an embodiment, a 4-1BB agonist comprises heavy and light chains having the sequences shown in SEQ ID NO:42 and SEQ ID NO:43, respectively, or antigen binding fragments, Fab fragments, single-chain variable fragments (scFv), variants, or conjugates thereof. In an embodiment, a 4-1BB agonist comprises heavy and light chains that are each at least 99% identical to the sequences shown in SEQ ID NO:42 and SEQ ID NO:43, respectively. In an embodiment, a 4-1BB agonist comprises heavy and light chains that are each at least 98% identical to the sequences shown in SEQ ID NO:42 and SEQ ID NO:43, respectively. In an embodiment, a 4-1BB agonist comprises heavy and light chains that are each at least 97% identical to the sequences shown in SEQ ID NO:42 and SEQ ID NO:43, respectively. In an embodiment, a 4-1BB agonist comprises heavy and light chains that are each at least 96% identical to the sequences shown in SEQ ID NO:42 and SEQ ID NO:43, respectively. In an embodiment, a 4-1BB agonist comprises heavy and light chains that are each at least 95% identical to the sequences shown in SEQ ID NO:42 and SEQ ID NO:43, respectively.

In an embodiment, the 4-1BB agonist comprises the heavy and light chain CDRs or variable regions (VRs) of utomilumab. In an embodiment, the 4-1BB agonist heavy chain variable region ($V_H$) comprises the sequence shown in SEQ ID NO:44, and the 4-1BB agonist light chain variable region ($V_L$) comprises the sequence shown in SEQ ID NO:45, and conservative amino acid substitutions thereof. In an embodiment, a 4-1BB agonist comprises $V_H$ and $V_L$ regions that are each at least 99% identical to the sequences shown in SEQ ID NO:44 and SEQ ID NO:45, respectively. In an embodiment, a 4-1BB agonist comprises $V_H$ and $V_L$ regions that are each at least 98% identical to the sequences shown in SEQ ID NO:44 and SEQ ID NO:45, respectively. In an embodiment, a 4-1BB agonist comprises $V_H$ and $V_L$ regions that are each at least 97% identical to the sequences shown in SEQ ID NO:44 and SEQ ID NO:45, respectively. In an embodiment, a 4-1BB agonist comprises $V_H$ and $V_L$ regions that are each at least 96% identical to the sequences shown in SEQ ID NO:44 and SEQ ID NO:45, respectively. In an embodiment, a 4-1BB agonist comprises $V_H$ and $V_L$ regions that are each at least 95% identical to the sequences shown in SEQ ID NO:44 and SEQ ID NO:45, respectively. In an embodiment, a 4-1BB agonist comprises an scFv antibody comprising $V_H$ and $V_L$ regions that are each at least 99% identical to the sequences shown in SEQ ID NO:44 and SEQ ID NO:45.

In an embodiment, a 4-1BB agonist comprises heavy chain CDR1, CDR2 and CDR3 domains having the sequences set forth in SEQ ID NO:46, SEQ ID NO:47, and SEQ ID NO:48, respectively, and conservative amino acid substitutions thereof, and light chain CDR1, CDR2 and CDR3 domains having the sequences set forth in SEQ ID NO:49, SEQ ID NO:50, and SEQ ID NO:51, respectively, and conservative amino acid substitutions thereof.

In an embodiment, the 4-1BB agonist is a 4-1BB agonist biosimilar monoclonal antibody approved by drug regulatory authorities with reference to utomilumab. In an embodiment, the biosimilar monoclonal antibody comprises an 4-1BB antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is utomilumab. In some embodiments, the one or more post-translational modifications are selected from one or more of: glycosylation, oxidation, deamidation, and truncation. In some embodiments, the biosimilar is a 4-1BB agonist antibody authorized or submitted for authorization, wherein the 4-1BB agonist antibody is provided in a formulation which differs from the formulations of a reference medicinal product or reference biological product, wherein the reference medicinal product or reference biological product is utomilumab. The 4-1BB agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is utomilumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is utomilumab.

TABLE 6

Amino acid sequences for 4-1BB agonist antibodies related to utomilumab.

| Identifier | Sequence (One-Letter Amino Acid Symbols) |
|---|---|
| SEQ ID NO: 42 heavy chain for utomilumab | EVQLVQSGAE VKKPGESLRI SCKGSGYSFS TYWISWVRQM PGKGLEWMGK IYPGDSYTNY 60<br>SPSFQGQVTI SADKSISTAY LQWSSLKASD TAMYYCARGY GIFDYWGQGT LVTVSSASTK 120<br>GPSVFPLAPC SRSTSESTAA LGCLVKDYFP EPVTVSWNSG ALTSGVHTFP AVLQSSGLYS 180<br>LSSVVTVPSS NFGTQTYTCN VDHKPSNTKV DKTVERKCCV ECPPCPAPPV AGPSVFLFPP 240<br>KPKDTLMISR TPEVTCVVVD VSHEDPEVQF NWYVDGVEVH NAKTKPREEQ FNSTFRVVSV 300<br>LTVVHQDWLN GKEYKCKVSN KGLPAPIEKT ISKTKGQPRE PQVYTLPPSR EEMTKNQVSL 360<br>TCLVKGFYPS DIAVEWESNG QPENNYKTTP PMLDSDGSFF LYSKLTVDKS RWQQGNVFSC 420<br>SVMHEALHNH YTQKSLSLSP G 441 |
| SEQ ID NO: 43 light chain for utomilumab | SYELTQPPSV SVSPGQTASI TCSGDNIGDQ YAHWYQQKPG QSPVLVIYQD KNRPSGIPER 60<br>FSGSNSGNTA TLTISGTQAM DEADYYCATY TGFGSLAVFG GGTKLTVLGQ PKAAPSVTLF 120<br>PPSSEELQAN KATLVCLISD FYPGAVTVAW KADSSPVKAG VETTTPSKQS NNKYAASSYL 180<br>SLTPEQWKSH RSYSCQVTHE GSTVEKTVAP TECS 214 |
| SEQ ID NO: 44 heavy chain variable region for utomilumab | EVQLVQSGAE VKKPGESLRI SCKGSGYSFS TYWISWVRQM PGKGLEWMG KIYPGDSYTN 60<br>YSPSFQGQVT ISADKSISTA YLQWSSLKAS DTAMYYCARG YGIFDYWGQ GTLVTVSS 118 |
| SEQ ID NO: 45 light chain variable region for utomilumab | SYELTQPPSV SVSPGQTASI TCSGDNIGDQ YAHWYQQKPG QSPVLVIYQD KNRPSGIPER 60<br>FSGSNSGNTA TLTISGTQAM DEADYYCATY TGFGSLAVFG GGTKLTVL 108 |
| SEQ ID NO: 46 heavy chain CDR1 for utomilumab | STYWIS 6 |

TABLE 6-continued

Amino acid sequences for 4-1BB agonist antibodies related to utomilumab.

| Identifier | Sequence (One-Letter Amino Acid Symbols) | |
|---|---|---|
| SEQ ID NO: 47 heavy chain CDR2 for utomilumab | KIYPGDSYTN YSPSFQG | 17 |
| SEQ ID NO: 48 heavy chain CDR3 for utomilumab | RGYGIFDY | 8 |
| SEQ ID NO: 49 light chain CDR1 for utomilumab | SGDNIGDQYA H | 11 |
| SEQ ID NO: 50 light chain CDR2 for utomilumab | QDKNRPS | 7 |
| SEQ ID NO: 51 light chain CDR3 for utomilumab | ATYTGFGSLA V | 11 |

In a preferred embodiment, the 4-1BB agonist is the monoclonal antibody urelumab, also known as BMS-663513 and 20H4.9.h4a, or a fragment, derivative, variant, or biosimilar thereof. Urelumab is available from Bristol-Myers Squibb, Inc., and Creative Biolabs, Inc. Urelumab is an immunoglobulin G4-kappa, anti-[*Homo sapiens* TNFRSF9 (tumor necrosis factor receptor superfamily member 9, 4-1BB, T cell antigen ILA, CD137)], *Homo sapiens* (fully human) monoclonal antibody. The amino acid sequences of urelumab are set forth in Table 7. Urelumab comprises N-glycosylation sites at positions 298 (and 298"); heavy chain intrachain disulfide bridges at positions 22-95 (VH-VL), 148-204 (CH1-CL), 262-322 (CH2) and 368-426 (CH3) (and at positions 22"-95", 148"-204", 262"-322", and 368"-426"); light chain intrachain disulfide bridges at positions 23'-88' (VH-VL) and 136'-196' (CH1-CL) (and at positions 23'"-88'" and 136'"-196'"); interchain heavy chain-heavy chain disulfide bridges at positions 227-227" and 230-230"; and interchain heavy chain-light chain disulfide bridges at 135-216' and 135"-216'". The preparation and properties of urelumab and its variants and fragments are described in U.S. Pat. Nos. 7,288,638 and 8,962,804, the disclosures of which are incorporated by reference herein. The preclinical and clinical characteristics of urelumab are described in Segal, et al., Clin. Cancer Res. 2016. Current clinical trials of urelumab in a variety of hematological and solid tumor indications include U.S. National Institutes of Health clinicaltrials.gov identifiers NCT01775631, NCT02110082, NCT02253992, and NCT01471210.

In an embodiment, a 4-1BB agonist comprises a heavy chain given by SEQ ID NO:52 and a light chain given by SEQ ID NO:53. In an embodiment, a 4-1BB agonist comprises heavy and light chains having the sequences shown in SEQ ID NO:52 and SEQ ID NO:53, respectively, or antigen binding fragments, Fab fragments, single-chain variable fragments (scFv), variants, or conjugates thereof. In an embodiment, a 4-1BB agonist comprises heavy and light chains that are each at least 99% identical to the sequences shown in SEQ ID NO:52 and SEQ ID NO:53, respectively. In an embodiment, a 4-1BB agonist comprises heavy and light chains that are each at least 98% identical to the sequences shown in SEQ ID NO:52 and SEQ ID NO:53, respectively. In an embodiment, a 4-1BB agonist comprises heavy and light chains that are each at least 97% identical to the sequences shown in SEQ ID NO:52 and SEQ ID NO:53, respectively. In an embodiment, a 4-1BB agonist comprises heavy and light chains that are each at least 96% identical to the sequences shown in SEQ ID NO:52 and SEQ ID NO:53, respectively. In an embodiment, a 4-1BB agonist comprises heavy and light chains that are each at least 95% identical to the sequences shown in SEQ ID NO:52 and SEQ ID NO:53, respectively.

In an embodiment, the 4-1BB agonist comprises the heavy and light chain CDRs or variable regions (VRs) of urelumab. In an embodiment, the 4-1BB agonist heavy chain variable region ($V_H$) comprises the sequence shown in SEQ ID NO:54, and the 4-1BB agonist light chain variable region ($V_L$) comprises the sequence shown in SEQ ID NO:55, and conservative amino acid substitutions thereof. In an embodiment, a 4-1BB agonist comprises $V_H$ and $V_L$ regions that are each at least 99% identical to the sequences shown in SEQ ID NO:54 and SEQ ID NO:55, respectively. In an embodiment, a 4-1BB agonist comprises $V_H$ and $V_L$ regions that are each at least 98% identical to the sequences shown in SEQ ID NO:54 and SEQ ID NO:55, respectively. In an embodiment, a 4-1BB agonist comprises $V_H$ and $V_L$ regions that are each at least 97% identical to the sequences shown in SEQ ID NO:54 and SEQ ID NO:55, respectively. In an embodiment, a 4-1BB agonist comprises $V_H$ and $V_L$ regions that are each at least 96% identical to the sequences shown in SEQ ID NO:54 and SEQ ID NO:55, respectively. In an embodiment, a 4-1BB agonist comprises $V_H$ and $V_L$ regions that are each at least 95% identical to the sequences shown in SEQ ID NO:54 and SEQ ID NO:55, respectively. In an embodiment, a 4-1BB agonist comprises an scFv antibody comprising $V_H$ and $V_L$ regions that are each at least 99% identical to the sequences shown in SEQ ID NO:54 and SEQ ID NO:55.

In an embodiment, a 4-1BB agonist comprises heavy chain CDR1, CDR2 and CDR3 domains having the sequences set forth in SEQ ID NO:56, SEQ ID NO:57, and SEQ ID NO:58, respectively, and conservative amino acid substitutions thereof, and light chain CDR1, CDR2 and CDR3 domains having the sequences set forth in SEQ ID NO:59, SEQ ID NO:60, and SEQ ID NO:61, respectively, and conservative amino acid substitutions thereof.

In an embodiment, the 4-1BB agonist is a 4-1BB agonist biosimilar monoclonal antibody approved by drug regulatory authorities with reference to urelumab. In an embodiment, the biosimilar monoclonal antibody comprises an 4-1BB antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is urelumab. In some embodiments, the one or more post-translational modifications are selected from one or more of: glycosylation, oxidation, deamidation, and truncation. In some embodiments, the biosimilar is a 4-1BB agonist antibody authorized or submitted for authorization, wherein the 4-1BB agonist antibody is provided in a formulation which differs from the formulations of a reference medicinal product or reference biological product, wherein the reference medicinal product or reference biological product is urelumab. The 4-1BB agonist antibody may be authorized by a drug regulatory authority such as the U. S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is urelumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is urelumab.

TABLE 7

Amino acid sequences for 4-1BB agonist antibodies related to urelumab.

| Identifier | Sequence (One-Letter Amino Acid Symbols) |
| --- | --- |
| SEQ ID NO: 52 heavy chain for urelumab | QVQLQQWGAG LLKPSETLSL TCAVYGGSFS GYYWSWIRQS PEKGLEWIGE INHGGYVTYN 60<br>PSLESRVTIS VDTSKNQFSL KLSSVTAADT AVYYCARDYG PGNYDWYFDL WGRGTLVTVS 120<br>SASTKGPSVF PLAPCSRSTS ESTAALGCLV KDYFPEPVTV SWNSGALTSG VHTFPAVLQS 180<br>SGLYSLSSVV TVPSSSLGTK TYTCNVDHKP SNTKVDKRVE SKYGPPCPPC PAPEFLGGPS 240<br>VFLFPPKPKD TLMISRTPEV TCVVVDVSQE DPEVQFNWYV DGVEVHNAKT KPREEQFNST 300<br>YRVVSVLTVL HQDWLNGKEY KCKVSNKGLP SSIEKTISKA KGQPREPQVY TLPPSQEEMT 360<br>KNQVSLTCLV KGFYPSDIAV EWESNGQPEN NYKTTPPVLD SDGSFFLYSR LTVDKSRWQE 420<br>GNVFSCSVMH EALENHYTQK SLSLSLGK 448 |
| SEQ ID NO: 53 light chain for urelumab | EIVLTQSPAT LSLSPGERAT LSCRASQSVS SYLAWYQQKP GQAPRLLIYD ASNRATGIPA 60<br>RFSGSGSGTD FTLTISSLEP EDFAVYYCQQ RSNWPPALTF CGGTKVEIKR TVAAPSVFIF 120<br>PPSDEQLKSG TASVVCLLNN FYPREAKVQW KVDNALQSGN SQESVTEQDS KDSTYSLSST 180<br>LTLSKADYEK HKVYACEVTH QGLSSPVTKS FNRGEC 216 |
| SEQ ID NO: 54 variable heavy chain for urelumab | MKHLWFFLLL VAAPRWVLSQ VQLQQWGAGL LKPSETLSLT CAVYGGSFSG YYWSWIRQSP 60<br>EKGLEWIGEI NHGGYVTYNP SLESRVTISV DTSFNQFSLK LSSVTAADTA VYYCARDYGP 120 |
| SEQ ID NO: 55 variable light chain for urelumab | MEAPAQLLFL LLLWLPDTTG EIVLTQSPAT LSLSPGERAT LSCRASQSVS SYLAWYQQKP 60<br>GQAPRLLIYD ASNRATGIPA RFSGSGSGTD FTLTISSLEP EDFAVYYCQQ 110 |
| SEQ ID NO: 56 heavy chain CDR1 for urelumab | GYYWS 5 |
| SEQ ID NO: 57 heavy chain CDR2 for urelumab | EINHGGYVTY NPSLES 16 |
| SEQ ID NO: 58 heavy chain CDR3 for urelumab | DYGPGNYDWY FDL 13 |
| SEQ ID NO: 59 light chain CDR1 for urelumab | RASQSVSSYL A 11 |
| SEQ ID NO: 60 light chain CDR2 for urelumab | DASNRAT 7 |
| SEQ ID NO: 61 light chain CDR3 for urelumab | QQRSDWPPAL T 11 |

In an embodiment, the 4-1BB agonist is selected from the group consisting of 1D8, 3Elor, 4B34 (BioLegend 309809), H4-1BB-M127 (BD Pharmingen 552532), BBK2 (Thermo Fisher MS621PABX), 145501 (Leinco Technologies B591), the antibody produced by cell line deposited as ATCC No.

HB-11248 and disclosed in U.S. Pat. No. 6,974,863, 5F4 (BioLegend 31 1503), C65-485 (BD Pharmingen 559446), antibodies disclosed in U.S. Patent Application Publication No. US 2005/0095244, antibodies disclosed in U.S. Pat. No. 7,288,638 (such as 20H4.9-IgG1 (BMS-663031)), antibodies disclosed in U.S. Pat. No. 6,887,673 (such as 4E9 or BMS-554271), antibodies disclosed in U.S. Pat. No. 7,214, 493, antibodies disclosed in U.S. Pat. No. 6,303,121, antibodies disclosed in U.S. Pat. No. 6,569,997, antibodies disclosed in U.S. Pat. No. 6,905,685 (such as 4E9 or BMS-554271), antibodies disclosed in U.S. Pat. No. 6,362, 325 (such as 1D8 or BMS-469492; 3H3 or BMS-469497; or 3E1), antibodies disclosed in U.S. Pat. No. 6,974,863 (such as 53A2); antibodies disclosed in U.S. Pat. No. 6,210,669 (such as 1D8, 3B8, or 3E1), antibodies described in U.S. Pat. No. 5,928,893, antibodies disclosed in U.S. Pat. No. 6,303, 121, antibodies disclosed in U.S. Pat. No. 6,569,997, antibodies disclosed in International Patent Application Publication Nos. WO 2012/177788, WO 2015/119923, and WO 2010/042433, and fragments, derivatives, conjugates, variants, or biosimilars thereof, wherein the disclosure of each of the foregoing patents or patent application publications is incorporated by reference here.

In an embodiment, the 4-1BB agonist is a 4-1BB agonistic fusion protein described in International Patent Application Publication Nos. WO 2008/025516 A1, WO 2009/007120 A1, WO 2010/003766 A1, WO 2010/010051 A1, and WO 2010/078966 A1; U.S. Patent Application Publication Nos. US 2011/0027218 A1, US 2015/0126709 A1, US 2011/0111494 A1, US 2015/0110734 A1, and US 2015/0126710 A1; and U.S. Pat. Nos. 9,359,420, 9,340,599, 8,921,519, and 8,450,460, the disclosures of which are incorporated by reference herein.

Figure 18:
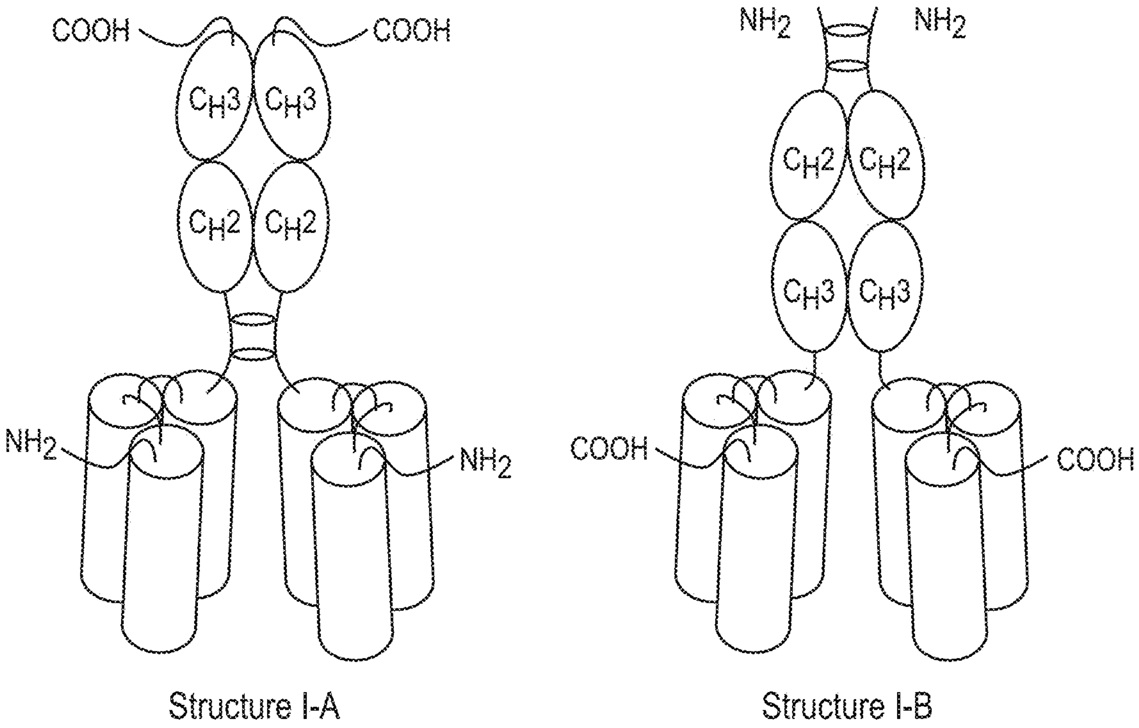
FIG. 18: Provides the structures I-A and I-B. The cylinders refer to individual polypeptide binding domains. Structures I-A and I-B comprise three linearly-linked TNFRSF binding domains derived from e.g., 4-1BBL or an antibody that binds 4-1BB, which fold to form a trivalent protein, which is then linked to a second trivalent protein through IgG1-Fc (including CH3 and CH2 domains) is then used to link two of the trivalent proteins together through disulfide bonds (small elongated ovals), stabilizing the structure and providing an agonists capable of bringing together the intracellular signaling domains of the six receptors and signaling proteins to form a signaling complex. The TNFRSF binding domains denoted as cylinders may be scFv domains comprising, e.g., a $V_H$ and a $V_L$ chain connected by a linker that may comprise hydrophilic residues and Gly and Ser sequences for flexibility, as well as Glu and Lys for solubility.
Figure 19:
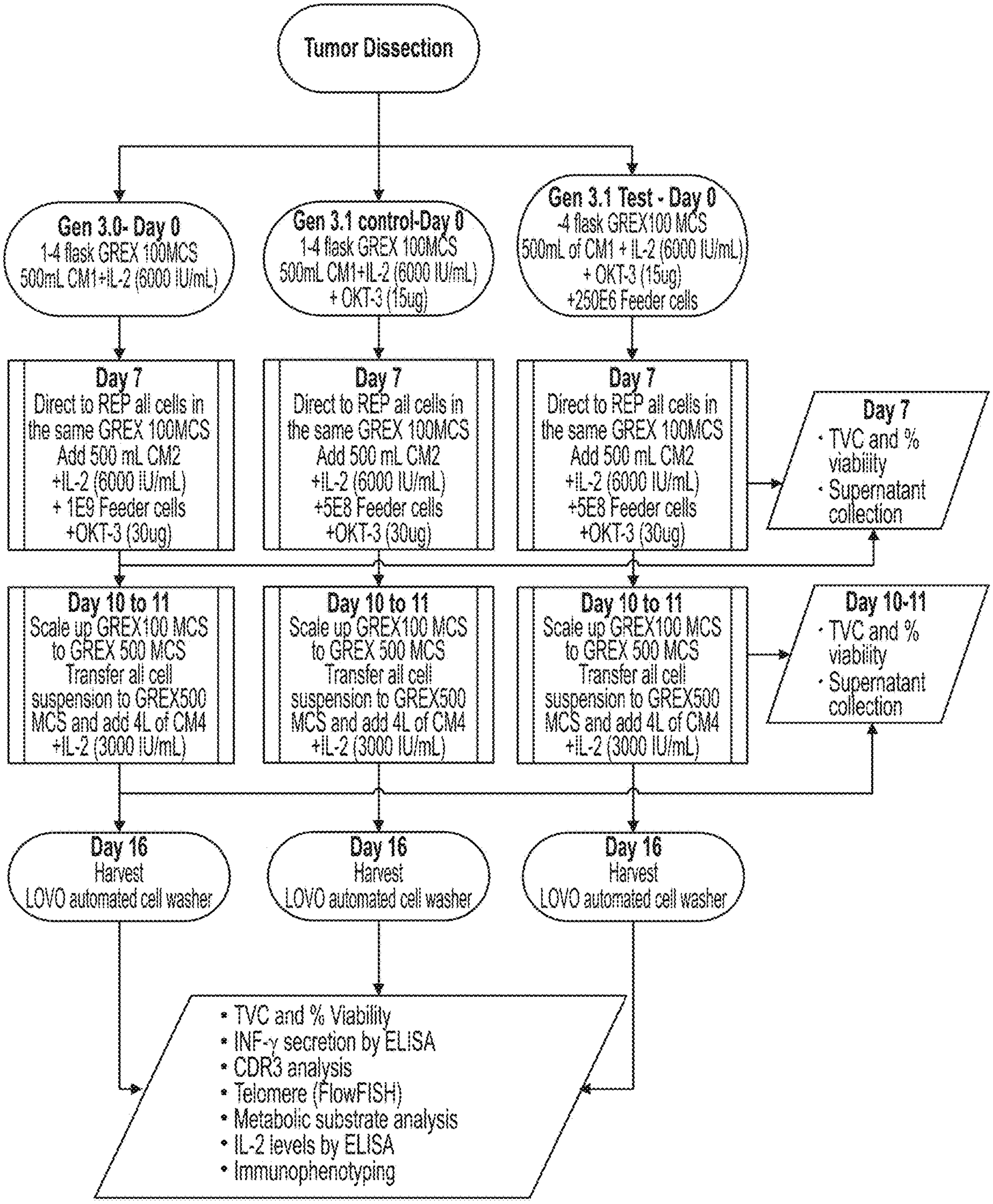
FIG. 19: Schematic of an exemplary embodiment of the Gen 3 process (a 16-day process).
Figure 21:
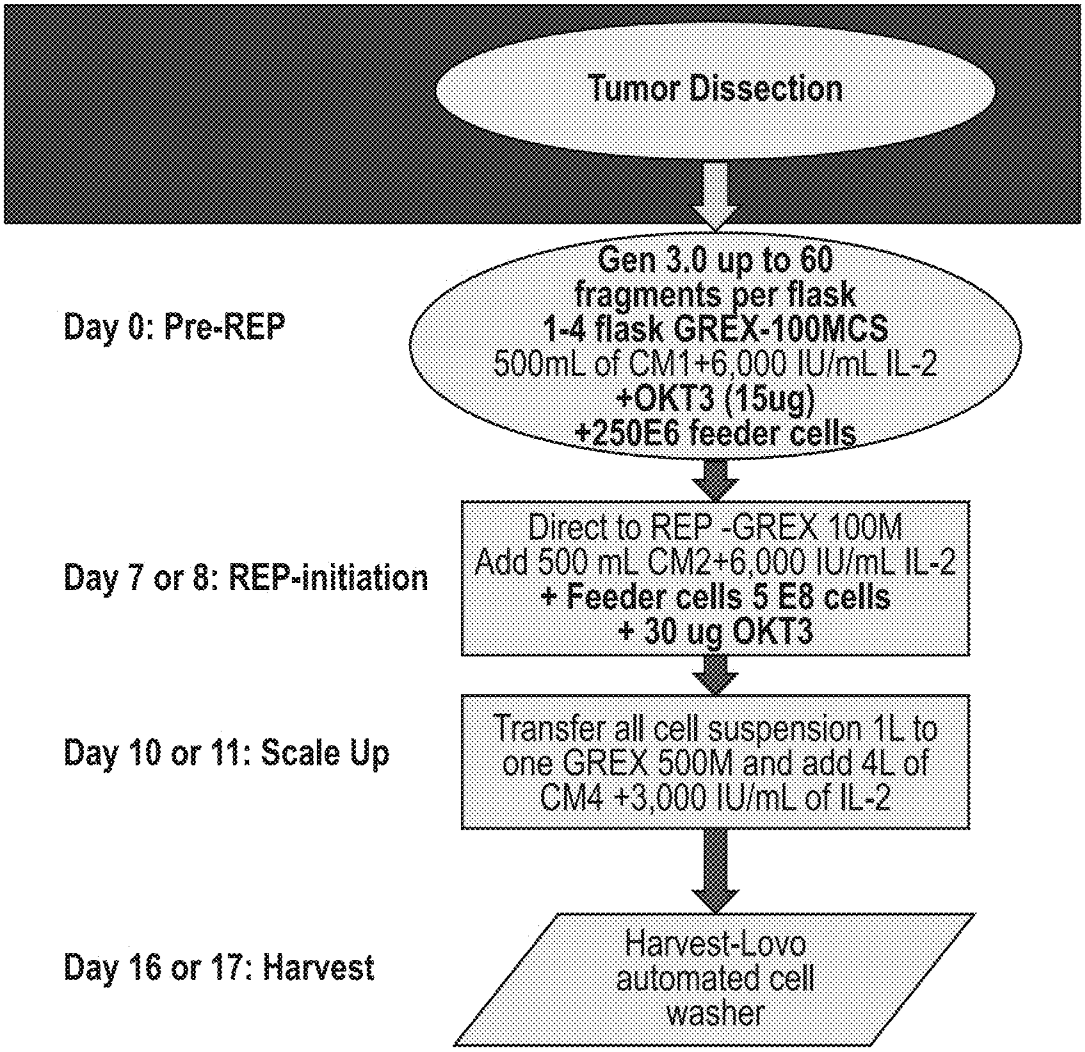
FIG. 21: Schematic of an exemplary embodiment of the Gen 3.1 Test process (a 16-17 day process).
Figure 22:
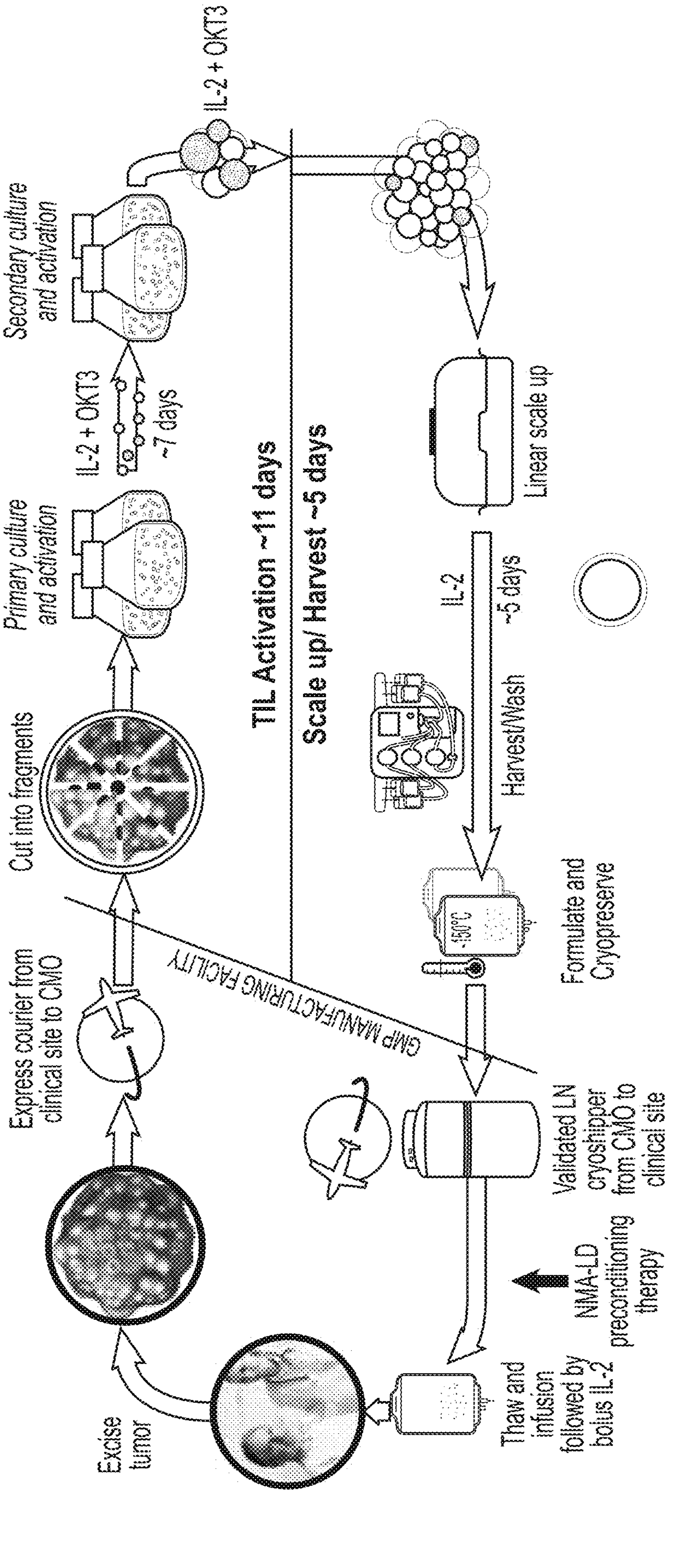
FIG. 22: Schematic of an exemplary embodiment of the Gen 3 process (a 16-day process).
Figure 25:
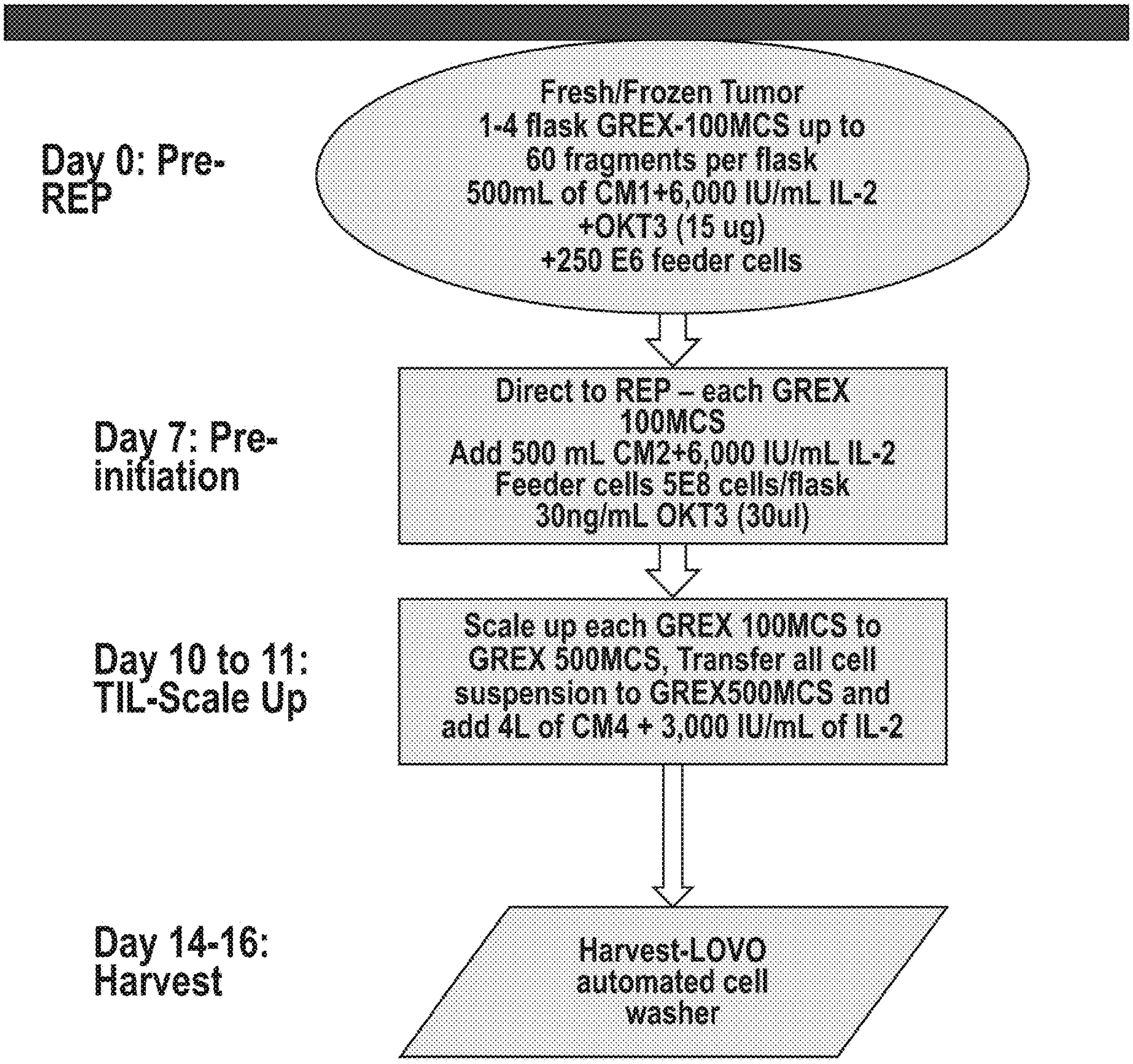
FIG. 25: Schematic of an exemplary embodiment of the Gen 3 process (a 14-16 day process).
Figure 26A:
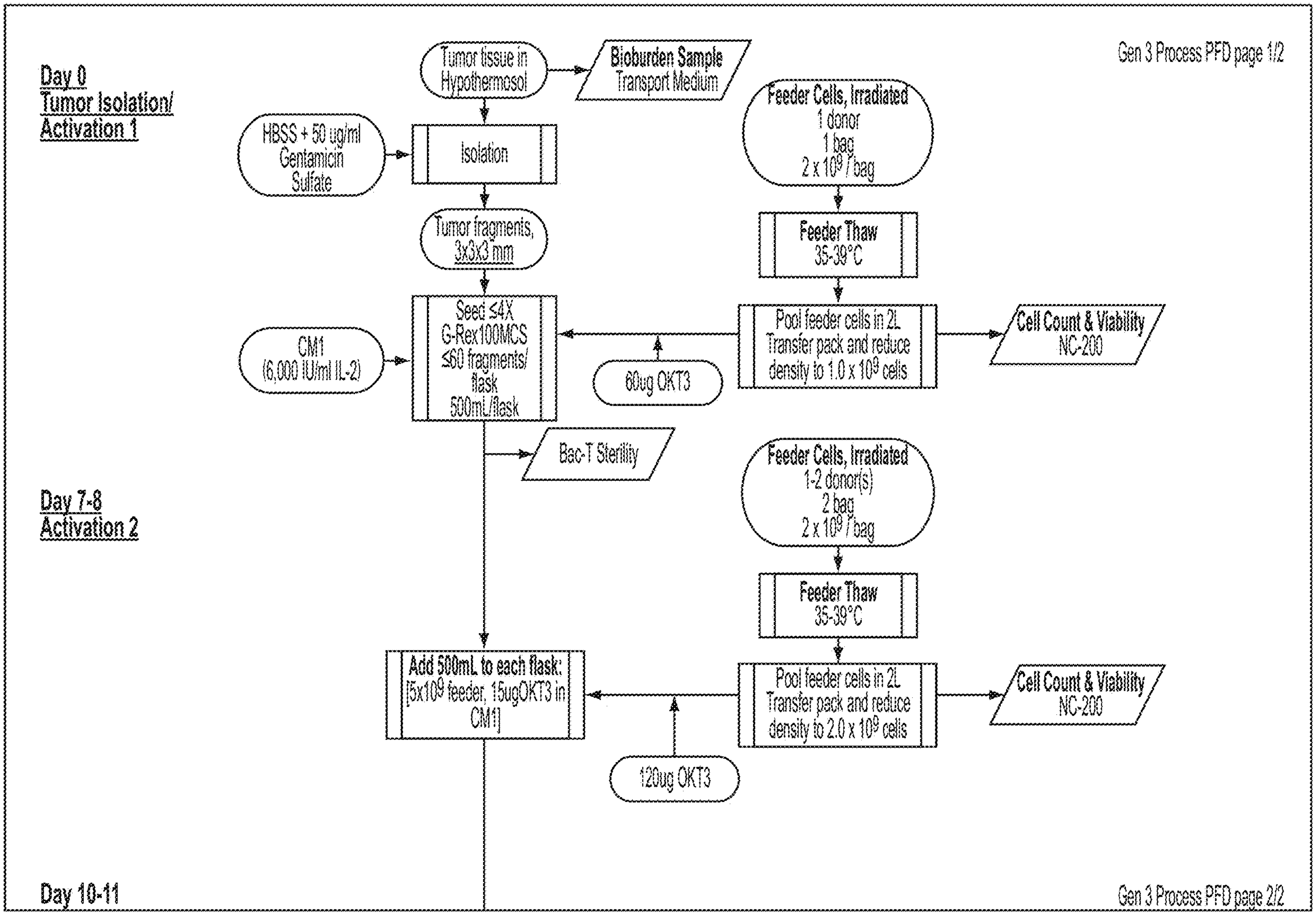
FIG. 26A-26B: Schematic of an exemplary embodiment of the Gen 3 process (a 16 day process).
Figure 26B:
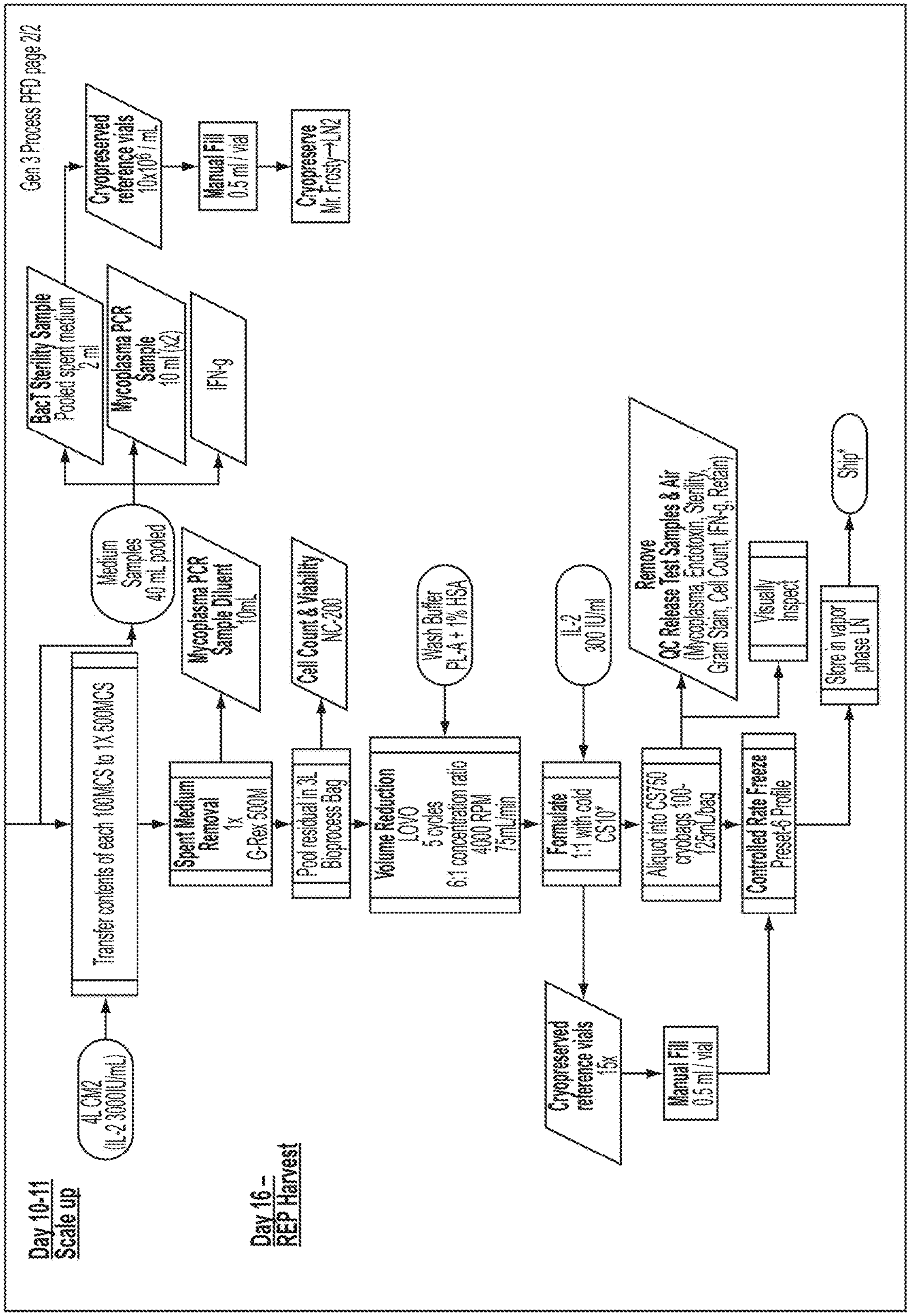
Figure 27:
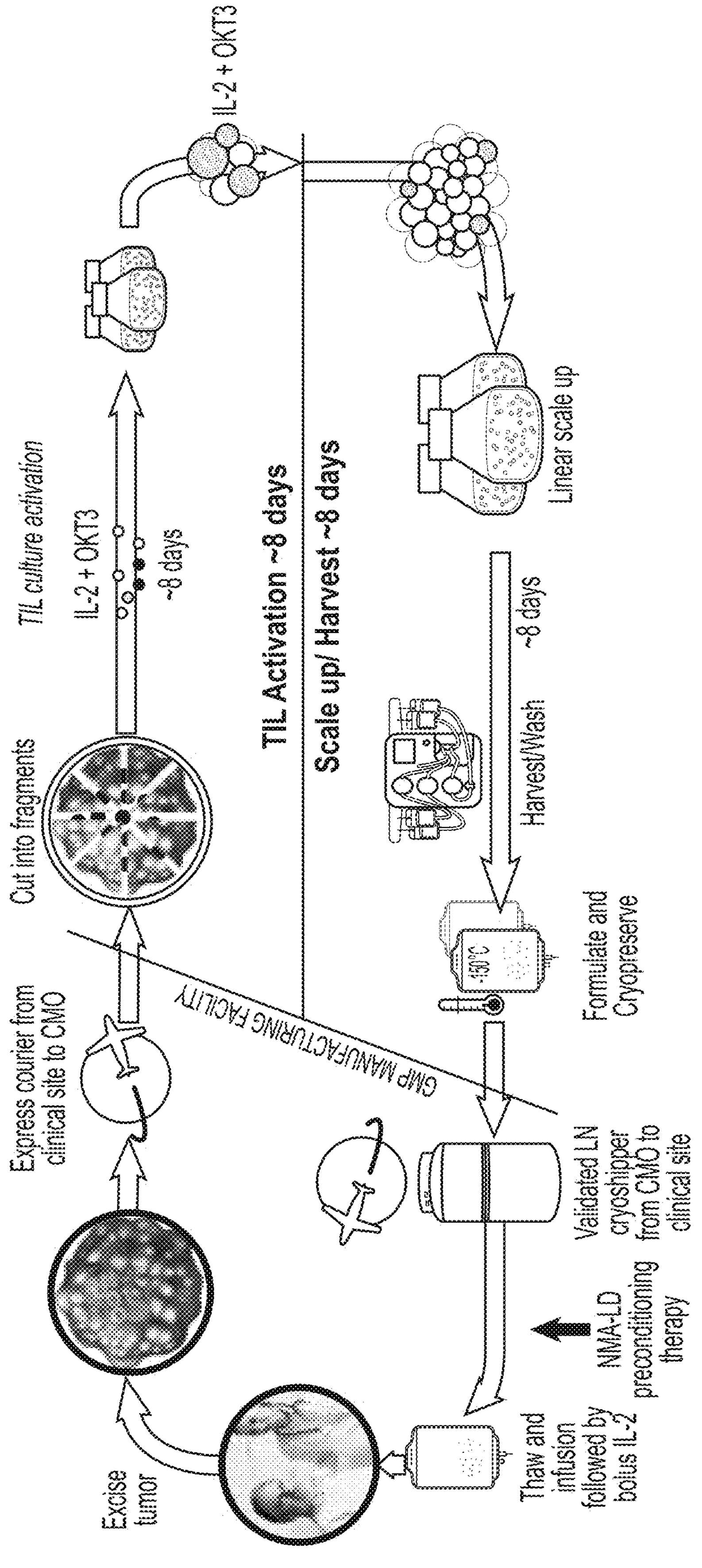
FIG. 27: Schematic of an exemplary embodiment of the Gen 3 process (a 16 day process).
Figure 31:
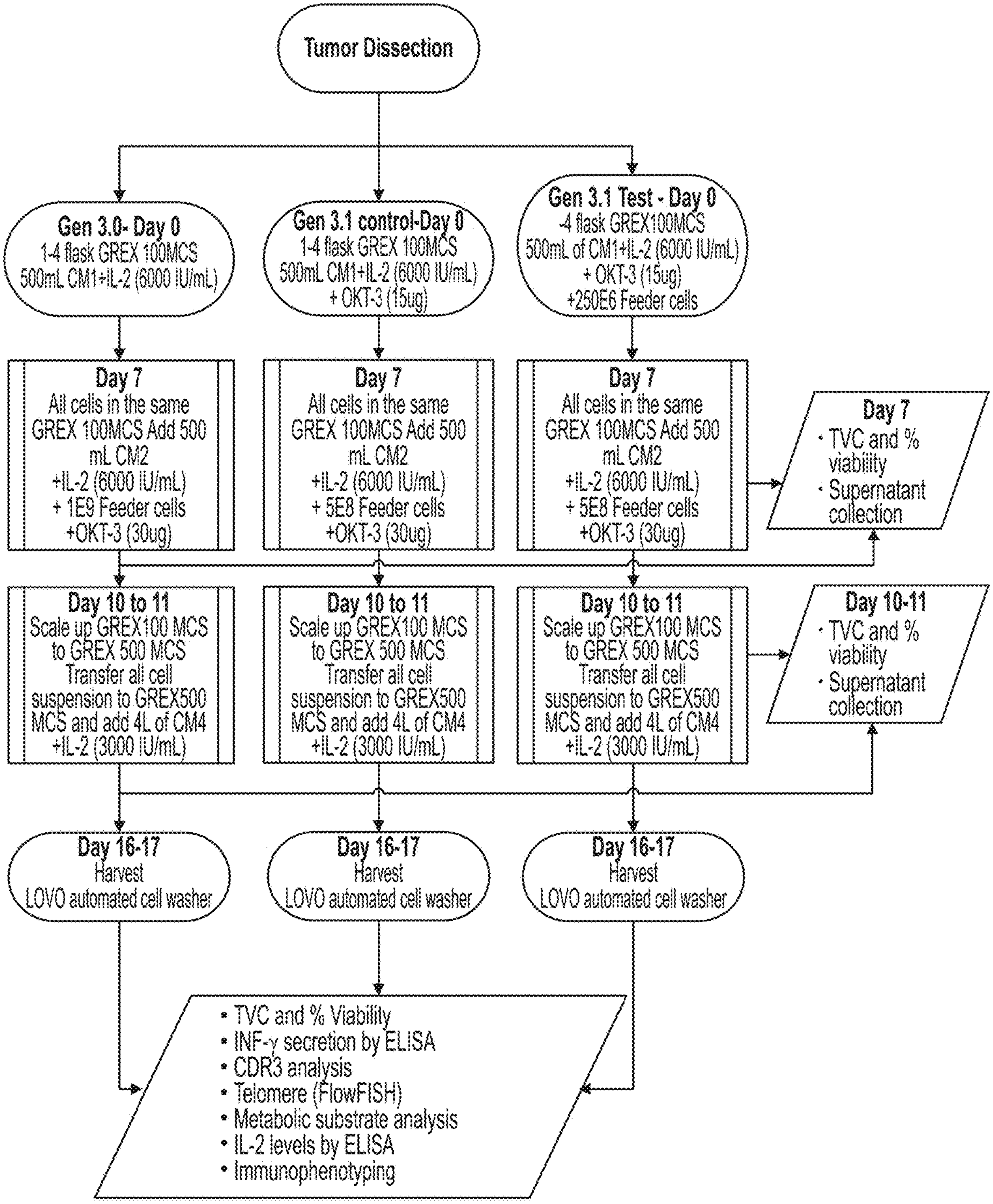
FIG. 31: Gen 3 embodiment flow chart comparison (Gen 3.0, Gen 3.1 control, Gen 3.1 test).

In an embodiment, the 4-1BB agonist is a 4-1BB agonistic fusion protein as depicted in Structure I-A (C-terminal Fc-antibody fragment fusion protein) or Structure I-B (N-terminal Fc-antibody fragment fusion protein), or a fragment, derivative, conjugate, variant, or biosimilar thereof (see, FIG. 18). In structures I-A and I-B, the cylinders refer to individual polypeptide binding domains. Structures I-A and I-B comprise three linearly-linked TNFRSF binding domains derived from e.g., 4-1BBL (4-1BB ligand, CD137 ligand (CD137L), or tumor necrosis factor superfamily member 9 (TNFSF9)) or an antibody that binds 4-1BB, which fold to form a trivalent protein, which is then linked to a second triavelent protein through IgG1-Fc (including $C_H3$ and $C_H2$ domains) is then used to link two of the trivalent proteins together through disulfide bonds (small elongated ovals), stabilizing the structure and providing an agonists capable of bringing together the intracellular signaling domains of the six receptors and signaling proteins to form a signaling complex. The TNFRSF binding domains denoted as cylinders may be scFv domains comprising, e.g., a $V_H$ and a $V_L$ chain connected by a linker that may comprise hydrophilic residues and Gly and Ser sequences for flexibility, as well as Glu and Lys for solubility. Any scFv domain design may be used, such as those described in de Marco, *Microbial Cell Factories,* 2011, 10, 44; Ahmad, et al., *Clin. & Dev. Immunol.* 2012, 980250; Monnier, et al., *Antibodies,* 2013, 2, 193-208; or in references incorporated elsewhere herein. Fusion protein structures of this form are described in U.S. Pat. Nos. 9,359,420, 9,340,599, 8,921,519, and 8,450,460, the disclosures of which are incorporated by reference herein.

Amino acid sequences for the other polypeptide domains of structure I-A given in FIG. 18 are found in Table 8. The Fc domain preferably comprises a complete constant domain (amino acids 17-230 of SEQ ID NO:62) the complete hinge domain (amino acids 1-16 of SEQ ID NO:62) or a portion of the hinge domain (e.g., amino acids 4-16 of SEQ ID NO:62). Preferred linkers for connecting a C-terminal Fc-antibody may be selected from the embodiments given in SEQ ID NO:63 to SEQ ID NO:72, including linkers suitable for fusion of additional polypeptides.

TABLE 8

Amino acid sequences for TNFRSF agonist fusion proteins, including 4-1BB agonist fusion proteins, with C-terminal Fc-antibody fragment fusion protein design (structure I-A).

| Identifier | Sequence (One-Letter Amino Acid Symbols) | |
|---|---|---|
| SEQ ID NO: 62 Fc domain | KSCDKTHTCP PCPAPELLGG PSVFLFPPKP KDTLMISRTP EVTCVVVDVS HEDPEVKFNW | 60 |
| | YVDGVEVHNA KTKPREEQYN STYRVVSVLT VLHQDWLNGK EYKCKVSNKA LPAPIEKTIS | 120 |
| | KAKGQPREPQ VYTLPPSREE MTKNQVSLTC LVKGFYPSDI AVEWESNGQP ENNYKTTPPV | 180 |
| | LDSDGSFFLY SKLTVDKSRW QQGNVFSCSV MHEALHNHYT QKSLSLSPGK | 230 |
| SEQ ID NO: 63 linker | GGPGSSKSCD KTHTCPPCPA PE | 22 |
| SEQ ID NO: 64 linker | GGSGSSKSCD KTHTCPPCPA PE | 22 |
| SEQ ID NO: 65 linker | GGPGSSSSSS SKSCDKTHTC PPCPAPE | 27 |
| SEQ ID NO: 66 linker | GGSGSSSSSS SKSCDKTHTC PPCPAPE | 27 |
| SEQ ID NO: 67 linker | GGPGSSSSSS SSSKSCDKTH TCPPCPAPE | 29 |
| SEQ ID NO: 68 linker | GGSGSSSSSS SSSKSCDKTH TCPPCPAPE | 29 |
| SEQ ID NO: 69 linker | GGPGSSGSGS SDKTHTCPPC PAPE | 24 |

TABLE 8-continued

Amino acid sequences for TNFRSF agonist fusion proteins, including 4-1BB agonist fusion proteins, with C-terminal Fc-antibody fragment fusion protein design (structure I-A).

| Identifier | Sequence (One-Letter Amino Acid Symbols) | |
|---|---|---|
| SEQ ID NO: 70 linker | GGPGSSGSGS DKTHTCPPCP APE | 23 |
| SEQ ID NO: 71 linker | GGPSSSGSDK THTCPPCPAP E | 21 |
| SEQ ID NO: 72 linker | GGSSSSSSSS GSDKTHTCPP CPAPE | 25 |

Amino acid sequences for the other polypeptide domains of structure I-B given in FIG. 18 are found in Table 9. If an Fc antibody fragment is fused to the N-terminus of an TNRFSF fusion protein as in structure I-B, the sequence of the Fc module is preferably that shown in SEQ ID NO:73, and the linker sequences are preferably selected from those embodiments set forth in SED ID NO:74 to SEQ ID NO:76.

TABLE 9

Amino acid sequences for TNFRSF agonist fusion proteins, including 4-1BB agonist fusion proteins, with N-terminal Fc-antibody fragment fusion protein design (structure I-B).

| Identifier | Sequence (One-Letter Amino Acid Symbols) |
|---|---|
| SEQ ID NO: 73 Fc domain | METDTLLLWV LLLWVPAGNG DKTHTCPPCP APELLGGPSV FLFPPKPKDT LMISRTPEVT 60<br>CVVVDVSHED PEVKFNWYVD GVEVHNAKTK PREEQYNSTY RVVSVLTVLH QDWLNGKEYK 120<br>CKVSNKALPA PIEKTISKAK GQPREPQVYT LPPSREEMTK NQVSLTCLVK GFYPSDIAVE 180<br>WESNGQPENN YKTTPPVLDS DGSFFLYSKL TVDKSRWQQG NVFSCSVMHE ALHNHYTQKS 240<br>LSLSPG 246 |
| SEQ ID NO: 74 linker | SGSGSGSGSG S 11 |
| SEQ ID NO: 75 linker | SSSSSSGSGS GS 12 |
| SEQ ID NO: 76 linker | SSSSSSGSGS GSGSGS 16 |

In an embodiment, a 4-1BB agonist fusion protein according to structures I-A or I-B comprises one or more 4-1BB binding domains selected from the group consisting of a variable heavy chain and variable light chain of utomilumab, a variable heavy chain and variable light chain of urelumab, a variable heavy chain and variable light chain of utomilumab, a variable heavy chain and variable light chain selected from the variable heavy chains and variable light chains described in Table 10, any combination of a variable heavy chain and variable light chain of the foregoing, and fragments, derivatives, conjugates, variants, and biosimilars thereof.

In an embodiment, a 4-1BB agonist fusion protein according to structures I-A or I-B comprises one or more 4-1BB binding domains comprising a 4-1BBL sequence. In an embodiment, a 4-1BB agonist fusion protein according to structures I-A or I-B comprises one or more 4-1BB binding domains comprising a sequence according to SEQ ID NO:77. In an embodiment, a 4-1BB agonist fusion protein according to structures I-A or I-B comprises one or more 4-1BB binding domains comprising a soluble 4-1BBL sequence. In an embodiment, a 4-1BB agonist fusion protein according to structures I-A or I-B comprises one or more 4-1BB binding domains comprising a sequence according to SEQ ID NO:78.

In an embodiment, a 4-1BB agonist fusion protein according to structures I-A or I-B comprises one or more 4-1BB binding domains that is a scFv domain comprising $V_H$ and $V_L$ regions that are each at least 95% identical to the sequences shown in SEQ ID NO:43 and SEQ ID NO:44, respectively, wherein the $V_H$ and $V_L$ domains are connected by a linker. In an embodiment, a 4-1BB agonist fusion protein according to structures I-A or I-B comprises one or more 4-1BB binding domains that is a scFv domain comprising $V_H$ and $V_L$ regions that are each at least 95% identical to the sequences shown in SEQ ID NO:54 and SEQ ID NO:55, respectively, wherein the $V_H$ and $V_L$ domains are connected by a linker. In an embodiment, a 4-1BB agonist fusion protein according to structures I-A or I-B comprises one or more 4-1BB binding domains that is a scFv domain comprising $V_H$ and $V_L$ regions that are each at least 95% identical to the $V_H$ and $V_L$ sequences given in Table 10, wherein the $V_H$ and $V_L$ domains are connected by a linker.

TABLE 10

Additional polypeptide domains useful as 4-1BB binding domains in fusion proteins or as scFv 4-1BB agonist antibodies.

| Identifier | Sequence (One-Letter Amino Acid Symbols) | |
|---|---|---|
| SEQ ID NO: 77 4-1BBL | MEYASDASLD PEAPWPPAPR ARACRVLPWA LVAGLLLLLL LAAACAVFLA CPWAVSGARA | 60 |
| | SPGSAASPRL REGPELSPDD PAGLLDLRQG MFAQLVAQNV LLIDGPLSWY SDPGLAGVSL | 120 |
| | TGGLSYKEDT KELVVAKAGV YYVFFQLELR RVVAGEGSGS VSLALHLQPL RSAAGAAALA | 180 |
| | LTVDLPPASS EARNSAFGFQ GRLLHLSAGQ RLGVHLHTEA RARHAWQLTQ GATVLGLFRV | 240 |
| | TPEIPAGLPS PRSE | 254 |
| SEQ ID NO: 78 4-1BBL soluble domain | LRQGMFAQLV AQNVLLIDGP LSWYSDPGLA GVSLTGGLSY KEDTKELVVA KAGVYYVFFQ | 60 |
| | LELRRVVAGE GSGSVSLALH LQPLRSAAGA AALALTVDLP PASSEARNSA FGFQGRLLHL | 120 |
| | SAGQRLGVHL HTEARARHAW QLTQGATVLG LFRVTPEIPA GLPSPRSE | 168 |
| SEQ ID NO: 79 variable heavy chain for 4B4-1-1 version 1 | QVQLQQPGAE LVKPGASVKL SCKASGYTFS SYWMHWVKQR PGQVLEWIGE INPGNGHTNY | 60 |
| | NEKFKSKATL TVDKSSSTAY MQLSSLTSED SAVYYCARSF TTARGFAYWG QGTLVTVS | 118 |
| SEQ ID NO: 80 variable light chain for 4B4-1-1 version 1 | DIVMTQSPAT QSVTPGDRVS LSCRASQTIS DYLHWYQQKS HESPRLLIKY ASQSISGIPS | 60 |
| | RFSGSGSGSD FTLSINSVEP EDVGVYYCQD GHSFPPTFGG GTKLEIK | 107 |
| SEQ ID NO: 81 variable heavy chain for 4B4-1-1 version 2 | QVQLQQPGAE LVKPGASVKL SCKASGYTFS SYWMHWVKQR PGQVLEWIGE INPGNGHTNY | 60 |
| | NEKFKSKATL TVDKSSSTAY MQLSSLTSED SAVYYCARSF TTARGFAYWG QGTLVTVSA | 119 |
| SEQ ID NO: 82 variable light chain for 4B4-1-1 version 2 | DIVMTQSPAT QSVTPGDRVS LSCRASQTIS DYLHWYQQKS HESPRLLIKY ASQSISGIPS | 60 |
| | RFSGSGSGSD FTLSINSVEP EDVGVYYCQD GHSFPPTFGG GTKLEIKR | 108 |
| SEQ ID NO: 83 variable heavy chain for H39E3-2 | MDWTWRILFL VAAATGAHSE VQLVESGGGL VQPGGSLRLS CAASGFTFSD YWMSWVRQAP | 60 |
| | GKGLEWVADI KNDGSYTNYA PSLTNRFTIS RDNAKNSLYL QMNSLRAEDT AVYYCARELT | 120 |
| SEQ ID NO: 84 variable light chain for H39E3-2 | MEAPAQLLFL LLLWLPDTTG DIVMTQSPDS LAVSLGERAT INCKSSQSLL SSGNQKNYL | 60 |
| | WYQQKPGQPP KLLIYYASTR QSGVPDRFSG SGSGTDFTLT ISSLQAEDVA | 110 |

In an embodiment, the 4-1BB agonist is a 4-1BB agonistic single-chain fusion polypeptide comprising (i) a first soluble 4-1BB binding domain, (ii) a first peptide linker, (iii) a second soluble 4-1BB binding domain, (iv) a second peptide linker, and (v) a third soluble 4-1BB binding domain, further comprising an additional domain at the N-terminal and/or C-terminal end, and wherein the additional domain is a Fab or Fc fragment domain. In an embodiment, the 4-1BB agonist is a 4-1BB agonistic single-chain fusion polypeptide comprising (i) a first soluble 4-1BB binding domain, (ii) a first peptide linker, (iii) a second soluble 4-1BB binding domain, (iv) a second peptide linker, and (v) a third soluble 4-1BB binding domain, further comprising an additional domain at the N-terminal and/or C-terminal end, wherein the additional domain is a Fab or Fc fragment domain, wherein each of the soluble 4-1BB domains lacks a stalk region (which contributes to trimerization and provides a certain distance to the cell membrane, but is not part of the 4-1BB binding domain) and the first and the second peptide linkers independently have a length of 3-8 amino acids.

In an embodiment, the 4-1BB agonist is a 4-1BB agonistic single-chain fusion polypeptide comprising (i) a first soluble tumor necrosis factor (TNF) superfamily cytokine domain, (ii) a first peptide linker, (iii) a second soluble TNF superfamily cytokine domain, (iv) a second peptide linker, and (v) a third soluble TNF superfamily cytokine domain, wherein each of the soluble TNF superfamily cytokine domains lacks a stalk region and the first and the second peptide linkers independently have a length of 3-8 amino acids, and wherein each TNF superfamily cytokine domain is a 4-1BB binding domain.

In an embodiment, the 4-1BB agonist is a 4-1BB agonistic scFv antibody comprising any of the foregoing $V_H$ domains linked to any of the foregoing $V_L$ domains.

In an embodiment, the 4-1BB agonist is BPS Bioscience 4-1BB agonist antibody catalog no. 79097-2, commercially available from BPS Bioscience, San Diego, CA, USA. In an embodiment, the 4-1BB agonist is Creative Biolabs 4-1BB agonist antibody catalog no. MOM-18179, commercially available from Creative Biolabs, Shirley, NY, USA.

3. OX40 (CD134) Agonists

In an embodiment, the TNFRSF agonist is an OX40 (CD134) agonist. The OX40 agonist may be any OX40 binding molecule known in the art. The OX40 binding molecule may be a monoclonal antibody or fusion protein capable of binding to human or mammalian OX40. The OX40 agonists or OX40 binding molecules may comprise an immunoglobulin heavy chain of any isotype (e.g., IgG, IgE, IgM, IgD, IgA, and IgY), class (e.g., IgG1, IgG2, IgG3, IgG4, IgA1 and IgA2) or subclass of immunoglobulin molecule. The OX40 agonist or OX40 binding molecule may have both a heavy and a light chain. As used herein, the term binding molecule also includes antibodies (including full length antibodies), monoclonal antibodies (including full length monoclonal antibodies), polyclonal antibodies, multispecific antibodies (e.g., bispecific antibodies), human, humanized or chimeric antibodies, and antibody fragments, e.g., Fab fragments, F(ab') fragments, fragments produced by a Fab expression library, epitope-binding fragments of any of the above, and engineered forms of antibodies, e.g., scFv molecules, that bind to OX40. In an embodiment, the OX40 agonist is an antigen binding protein that is a fully human antibody. In an embodiment, the OX40 agonist is an antigen binding protein that is a humanized antibody. In some embodiments, OX40 agonists for use in the presently disclosed methods and compositions include anti-OX40 antibodies, human anti-OX40 antibodies, mouse anti-OX40 antibodies, mammalian anti-OX40 antibodies, monoclonal anti-OX40 antibodies, polyclonal anti-OX40 antibodies, chimeric anti-OX40 antibodies, anti-OX40 adnectins, anti-OX40 domain antibodies, single chain anti-OX40 fragments, heavy chain anti-OX40 fragments, light chain anti-OX40 fragments, anti-OX40 fusion proteins, and fragments, derivatives, conjugates, variants, or biosimilars thereof. In a preferred embodiment, the OX40 agonist is an agonistic, anti-OX40 humanized or fully human monoclonal antibody (i.e., an antibody derived from a single cell line).

In a preferred embodiment, the OX40 agonist or OX40 binding molecule may also be a fusion protein. OX40 fusion proteins comprising an Fc domain fused to OX40L are described, for example, in Sadun, et al., *J. Immunother.* 2009, 182, 1481-89. In a preferred embodiment, a multimeric OX40 agonist, such as a trimeric or hexameric OX40 agonist (with three or six ligand binding domains), may induce superior receptor (OX40L) clustering and internal cellular signaling complex formation compared to an agonistic monoclonal antibody, which typically possesses two ligand binding domains. Trimeric (trivalent) or hexameric (or hexavalent) or greater fusion proteins comprising three TNFRSF binding domains and IgG1-Fc and optionally further linking two or more of these fusion proteins are described, e.g., in Gieffers, et al., *Mol. Cancer Therapeutics* 2013, 12, 2735-47.

Agonistic OX40 antibodies and fusion proteins are known to induce strong immune responses. Curti, et al., *Cancer Res.* 2013, 73, 7189-98. In a preferred embodiment, the OX40 agonist is a monoclonal antibody or fusion protein that binds specifically to OX40 antigen in a manner sufficient to reduce toxicity. In some embodiments, the OX40 agonist is an agonistic OX40 monoclonal antibody or fusion protein that abrogates antibody-dependent cellular toxicity (ADCC), for example NK cell cytotoxicity. In some embodiments, the OX40 agonist is an agonistic OX40 monoclonal antibody or fusion protein that abrogates antibody-dependent cell phagocytosis (ADCP). In some embodiments, the OX40 agonist is an agonistic OX40 monoclonal antibody or fusion protein that abrogates complement-dependent cytotoxicity (CDC). In some embodiments, the OX40 agonist is an agonistic OX40 monoclonal antibody or fusion protein which abrogates Fc region functionality.

In some embodiments, the OX40 agonists are characterized by binding to human OX40 (SEQ ID NO:85) with high affinity and agonistic activity. In an embodiment, the OX40 agonist is a binding molecule that binds to human OX40 (SEQ ID NO:85). In an embodiment, the OX40 agonist is a binding molecule that binds to murine OX40 (SEQ ID NO:86). The amino acid sequences of OX40 antigen to which an OX40 agonist or binding molecule binds are summarized in Table 11.

TABLE 11

Amino acid sequences of OX40 antigens.

| Identifier | Sequence (One-Letter Amino Acid Symbols) | |
|---|---|---|
| SEQ ID NO: 85 | MCVGARRLGR GPCAALLLLG LGLSTVTGLH CVGDTYPSND RCCHECRPGN GMVSRCSRSQ | 60 |
| human OX40 | NTVCRPCGPG FYNDVVSSKP CKPCTWCNLR SGSERKQLCT ATQDTVCRCR AGTQPLDSYK | 120 |
| (*Homo sapiens*) | PGVDCAPCPP GHFSPGDNQA CKPWTNCTLA GKHTLQPASN SSDAICEDRD PPATQPQETQ | 180 |
| | GPPARPITVQ PTEAWPRTSQ GPSTRPVEVP GGRAVAAILG LGLVLGLLGP LAILLALYLL | 240 |
| | RRDQRLPPDA HKPPGGGSFR TPIQEEQADA HSTLAKI | 277 |
| SEQ ID NO: 86 | MYVWVQQPTA LLLLGLTLGV TARRLNCVKH TYPSGHKCCR ECQPGHGMVS RCDHTRDTLC | 60 |
| murine OX40 | HPCETGFYNE AVNYDTCKQC TQCNHRSGSE LKQNCTPTQD TVCRCRPGTQ PRQDSGYKLG | 120 |
| (*Mus musculus*) | VDCVPCPPGH FSPGNNQACK PWTNCTLSGK QTRHPASDSL DAVCEDRSLL ATLLWETQRP | 180 |
| | TFRPTTVQST TVWPRTSELP SPPTLVTPEG PAFAVLLGLG LGLLAPLTVL LALYLLRKAW | 240 |
| | RLPNTPKPCW GNSFRTPIQE EHTDAHFTLA KI | 272 |

In some embodiments, the compositions, processes and methods described include a OX40 agonist that binds human or murine OX40 with a $K_D$ of about 100 pM or lower, binds human or murine OX40 with a $K_D$ of about 90 pM or lower, binds human or murine OX40 with a $K_D$ of about 80 pM or lower, binds human or murine OX40 with a $K_D$ of about 70 pM or lower, binds human or murine OX40 with a $K_D$ of about 60 pM or lower, binds human or murine OX40 with a $K_D$ of about 50 pM or lower, binds human or murine OX40 with a $K_D$ of about 40 pM or lower, or binds human or murine OX40 with a $K_D$ of about 30 pM or lower.

In some embodiments, the compositions, processes and methods described include a OX40 agonist that binds to human or murine OX40 with a $k_{assoc}$ of about $7.5\times10^5$ l/M·s or faster, binds to human or murine OX40 with a $k_{assoc}$ of about $7.5\times10^5$ l/M·s or faster, binds to human or murine OX40 with a $k_{assoc}$ of about $8\times10^5$ l/M·s or faster, binds to human or murine OX40 with a $k_{assoc}$ of about $8.5\times10^5$ l/M·s or faster, binds to human or murine OX40 with a $k_{assoc}$ of about $9\times10^5$ l/M·s or faster, binds to human or murine OX40 with a $k_{assoc}$ of about $9.5\times10^5$ l/M·s or faster, or binds to human or murine OX40 with a $k_{assoc}$ of about $1\times10^6$ l/M·s or faster.

In some embodiments, the compositions, processes and methods described include a OX40 agonist that binds to human or murine OX40 with a $k_{dissoc}$ of about $2\times10^{-5}$ l/s or slower, binds to human or murine OX40 with a $k_{dissoc}$ of about $2.1\times10^{-5}$ l/s or slower, binds to human or murine OX40 with a $k_{dissoc}$ of about $2.2\times10^{-5}$ l/s or slower, binds to human or murine OX40 with a $k_{dissoc}$ of about $2.3\times10^{-5}$ l/s or slower, binds to human or murine OX40 with a $k_{dissoc}$ of about $2.4\times10^{-5}$ l/s or slower, binds to human or murine OX40 with a $k_{dissoc}$ of about $2.5\times10^{-5}$ l/s or slower, binds to human or murine OX40 with a $k_{dissoc}$ of about $2.6\times10^{-5}$ l/s or slower or binds to human or murine OX40 with a $k_{dissoc}$ of about $2.7\times10^{-5}$ l/s or slower, binds to human or murine OX40 with a $k_{dissoc}$ of about $2.8\times10^{-5}$ l/s or slower, binds to human or murine OX40 with a $k_{dissoc}$ of about $2.9\times10^{-5}$ l/s or slower, or binds to human or murine OX40 with a $k_{dissoc}$ of about $3\times10^{-5}$ l/s or slower.

In some embodiments, the compositions, processes and methods described include OX40 agonist that binds to human or murine OX40 with an $IC_{50}$ of about 10 nM or lower, binds to human or murine OX40 with an $IC_{50}$ of about 9 nM or lower, binds to human or murine OX40 with an $IC_{50}$ of about 8 nM or lower, binds to human or murine OX40 with an $IC_{50}$ of about 7 nM or lower, binds to human or murine OX40 with an $IC_{50}$ of about 6 nM or lower, binds to human or murine OX40 with an $IC_{50}$ of about 5 nM or lower, binds to human or murine OX40 with an $IC_{50}$ of about 4 nM or lower, binds to human or murine OX40 with an $IC_{50}$ of about 3 nM or lower, binds to human or murine OX40 with an $IC_{50}$ of about 2 nM or lower, or binds to human or murine OX40 with an $IC_{50}$ of about 1 nM or lower.

In some embodiments, the OX40 agonist is tavolixizumab, also known as MEDI0562 or MEDI-0562. Tavolixizumab is available from the MedImmune subsidiary of AstraZeneca, Inc. Tavolixizumab is immunoglobulin G1-kappa, anti-[*Homo sapiens* TNFRSF4 (tumor necrosis factor receptor (TNFR) superfamily member 4, OX40, CD134)], humanized and chimeric monoclonal antibody. The amino acid sequences of tavolixizumab are set forth in Table 12. Tavolixizumab comprises N-glycosylation sites at positions 301 and 301", with fucosylated complex bi-antennary CHO-type glycans; heavy chain intrachain disulfide bridges at positions 22-95 ($V_H$-$V_L$), 148-204 ($C_H1$-$C_L$), 265-325 ($C_H2$) and 371-429 ($C_H3$) (and at positions 22"-95", 148"-204", 265"-325", and 371"-429"); light chain intrachain disulfide bridges at positions 23'-88' ($V_H$-$V_L$) and 134'-194' ($C_H1$-$C_L$) (and at positions 23'"-88'" and 134'"-194'"); interchain heavy chain-heavy chain disulfide bridges at positions 230-230" and 233-233"; and interchain heavy chain-light chain disulfide bridges at 224-214' and 224"-214'". Current clinical trials of tavolixizumab in a variety of solid tumor indications include U.S. National Institutes of Health clinicaltrials.gov identifiers NCT02318394 and NCT02705482.

In an embodiment, a OX40 agonist comprises a heavy chain given by SEQ ID NO:87 and a light chain given by SEQ ID NO:88. In an embodiment, a OX40 agonist comprises heavy and light chains having the sequences shown in SEQ ID NO:87 and SEQ ID NO:88, respectively, or antigen binding fragments, Fab fragments, single-chain variable fragments (scFv), variants, or conjugates thereof. In an embodiment, a OX40 agonist comprises heavy and light chains that are each at least 99% identical to the sequences shown in SEQ ID NO:87 and SEQ ID NO:88, respectively. In an embodiment, a OX40 agonist comprises heavy and light chains that are each at least 98% identical to the sequences shown in SEQ ID NO:87 and SEQ ID NO:88, respectively. In an embodiment, a OX40 agonist comprises heavy and light chains that are each at least 97% identical to the sequences shown in SEQ ID NO:87 and SEQ ID NO:88, respectively. In an embodiment, a OX40 agonist comprises heavy and light chains that are each at least 96% identical to the sequences shown in SEQ ID NO:87 and SEQ ID NO:88, respectively. In an embodiment, a OX40 agonist comprises heavy and light chains that are each at least 95% identical to the sequences shown in SEQ ID NO:87 and SEQ ID NO:88, respectively.

In an embodiment, the OX40 agonist comprises the heavy and light chain CDRs or variable regions (VRs) of tavolixizumab. In an embodiment, the OX40 agonist heavy chain variable region ($V_H$) comprises the sequence shown in SEQ ID NO:89, and the OX40 agonist light chain variable region ($V_L$) comprises the sequence shown in SEQ ID NO:90, and conservative amino acid substitutions thereof. In an embodiment, a OX40 agonist comprises $V_H$ and $V_L$ regions that are each at least 99% identical to the sequences shown in SEQ ID NO:89 and SEQ ID NO:90, respectively. In an embodiment, a OX40 agonist comprises $V_H$ and $V_L$ regions that are each at least 98% identical to the sequences shown in SEQ ID NO:89 and SEQ ID NO:90, respectively. In an embodiment, a OX40 agonist comprises $V_H$ and $V_L$ regions that are each at least 97% identical to the sequences shown in SEQ ID NO:89 and SEQ ID NO:90, respectively. In an embodiment, a OX40 agonist comprises $V_H$ and $V_L$ regions that are each at least 96% identical to the sequences shown in SEQ ID NO:89 and SEQ ID NO:90, respectively. In an embodiment, a OX40 agonist comprises $V_H$ and $V_L$ regions that are each at least 95% identical to the sequences shown in SEQ ID NO:89 and SEQ ID NO:90, respectively. In an embodiment, an OX40 agonist comprises an scFv antibody comprising $V_H$ and $V_L$ regions that are each at least 99% identical to the sequences shown in SEQ ID NO:89 and SEQ ID NO:90.

In an embodiment, a OX40 agonist comprises heavy chain CDR1, CDR2 and CDR3 domains having the sequences set forth in SEQ ID NO:91, SEQ ID NO:92, and SEQ ID NO:93, respectively, and conservative amino acid substitutions thereof, and light chain CDR1, CDR2 and CDR3 domains having the sequences set forth in SEQ ID NO:94, SEQ ID NO:95, and SEQ ID NO:96, respectively, and conservative amino acid substitutions thereof.

In an embodiment, the OX40 agonist is a OX40 agonist biosimilar monoclonal antibody approved by drug regulatory authorities with reference to tavolixizumab. In an embodiment, the biosimilar monoclonal antibody comprises an OX40 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is tavolixizumab. In some embodiments, the one or more post-translational modifications are selected from one or more of: glycosylation, oxidation, deamidation, and truncation. In some embodiments, the biosimilar is a OX40 agonist antibody authorized or submitted for authorization, wherein the OX40 agonist antibody is provided in a formulation which differs from the formulations of a reference medicinal product or reference biological product, wherein the reference medicinal product or reference biological product is tavolixizumab. The OX40 agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is tavolixizumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is tavolixizumab.

TABLE 12

Amino acid sequences for OX40 agonist antibodies related to tavolixizumab.

| Identifier | Sequence (One-Letter Amino Acid Symbols) | |
|---|---|---|
| SEQ ID NO: 87 heavy chain for tavolixizumab | QVQLQESGPG LVKPSQTLSL TCAVYGGSFS SGYWNWIRKH PGKGLEYIGY ISYNGITYHN<br>PSLKSRITIN RDTSKNQYSL QLNSVTPEDT AVYYCARYKY DYDGGHAMDY WGQGTLVTVS<br>SASTKGPSVF PLAPSSKSTS GGTAALGCLV KDYFPEPVTV SWNSGALTSG VHTFPAVLQS<br>SGLYSLSSVV TVPSSSLGTQ TYICNVNHKP SNTKVDKRVE PKSCDKTHTC PPCPAPELLG<br>GPSVFLFPPK PKDTLMISRT PEVTCVVVDV SHEDPEVKFN WYVDGVEVHN AKTKPREEQY<br>NSTYRVVSVL TVLHQDWLNG KEYKCKVSNK ALPAPIEKTI SKAKGQPREP QVYTLPPSRE<br>EMTKNQVSLT CLVKGFYPSD IAVEWESNGQ PENNYKTTPP VLDSDGSFFL YSKLTVDKSR<br>WQQGNVFSCS VMHEALHNHY TQKSLSLSPG K | 60<br>120<br>180<br>240<br>300<br>360<br>420<br>451 |
| SEQ ID NO: 88 light chain for tavolixizumab | DIQMTQSPSS LSASVGDRVT ITCRASQDIS NYLNWYQQKP GKAPKLLIYY TSKLHSGVPS<br>RFSGSGSGTD YTLTISSLQP EDFATYYCQQ GSALPWTFGQ GTKVEIKRTV AAPSVFIFPP<br>SDEQLKSGTA SVVCLLNNFY PREAKVQWKV DNALQSGNSQ ESVTEQDSKD STYSLSSTLT<br>LSKADYEKHK VYACEVTHQG LSSPVTKSFN RGEC | 60<br>120<br>180<br>214 |
| SEQ ID NO: 89 heavy chain variable region for tavolixizumab | QVQLQESGPG LVKPSQTLSL TCAVYGGSFS SGYWNWIRKH PGKGLEYIGY ISYNGITYHN<br>PSLKSRITIN RDTSKNQYSL QLNSVTPEDT AVYYCARYKY DYDGGHAMDY WGQGTLVT | 60<br>118 |
| SEQ ID NO: 90 light chain variable region for tavolixizumab | DIQMTQSPSS LSASVGDRVT ITCRASQDIS NYLNWYQQKP GKAPKLLIYY TSKLHSGVPS<br>RFSGSGSGTD YTLTISSLQP EDFATYYCQQ GSALPWTFGQ GTKVEIKR | 60<br>108 |
| SEQ ID NO: 91 heavy chain CDR1 for tavolixizumab | GSFSSGYWN | 9 |
| SEQ ID NO: 92 heavy chain CDR2 for tavolixizumab | YIGYISYNGI TYH | 13 |
| SEQ ID NO: 93 heavy chain CDR3 for tavolixizumab | RYKYDYDGGH AMDY | 14 |
| SEQ ID NO: 94 light chain CDR1 for tavolixizumab | QDISNYLN | 8 |
| SEQ ID NO: 95 light chain CDR2 for tavolixizumab | LLIYYTSKLH S | 11 |
| SEQ ID NO: 96 light chain CDR3 for tavolixizumab | QQGSALPW | 8 |

In some embodiments, the OX40 agonist is 11D4, which is a fully human antibody available from Pfizer, Inc. The preparation and properties of 11D4 are described in U.S. Pat. Nos. 7,960,515; 8,236,930; and 9,028,824, the disclosures of which are incorporated by reference herein. The amino acid sequences of 11D4 are set forth in Table 13.

In an embodiment, a OX40 agonist comprises a heavy chain given by SEQ ID NO:97 and a light chain given by SEQ ID NO:98. In an embodiment, a OX40 agonist comprises heavy and light chains having the sequences shown in SEQ ID NO:97 and SEQ ID NO:98, respectively, or antigen binding fragments, Fab fragments, single-chain variable fragments (scFv), variants, or conjugates thereof. In an embodiment, a OX40 agonist comprises heavy and light chains that are each at least 99% identical to the sequences shown in SEQ ID NO:97 and SEQ ID NO:98, respectively. In an embodiment, a OX40 agonist comprises heavy and light chains that are each at least 98% identical to the sequences shown in SEQ ID NO:97 and SEQ ID NO:98, respectively. In an embodiment, a OX40 agonist comprises heavy and light chains that are each at least 97% identical to the sequences shown in SEQ ID NO:97 and SEQ ID NO:98, respectively. In an embodiment, a OX40 agonist comprises heavy and light chains that are each at least 96% identical to the sequences shown in SEQ ID NO:97 and SEQ ID NO:98, respectively. In an embodiment, a OX40 agonist comprises heavy and light chains that are each at least 95% identical to the sequences shown in SEQ ID NO:97 and SEQ ID NO:98, respectively.

In an embodiment, the OX40 agonist comprises the heavy and light chain CDRs or variable regions (VRs) of 11D4. In an embodiment, the OX40 agonist heavy chain variable region ($V_H$) comprises the sequence shown in SEQ ID NO:99, and the OX40 agonist light chain variable region ($V_L$) comprises the sequence shown in SEQ ID NO:100, and conservative amino acid substitutions thereof. In an embodiment, a OX40 agonist comprises VH and VL regions that are each at least 99% identical to the sequences shown in SEQ ID NO:99 and SEQ ID NO:100, respectively. In an embodiment, a OX40 agonist comprises VH and VL regions that are each at least 98% identical to the sequences shown in SEQ ID NO:99 and SEQ ID NO:100, respectively. In an embodiment, a OX40 agonist comprises VH and VL regions that are each at least 97% identical to the sequences shown in SEQ ID NO:99 and SEQ ID NO:100, respectively. In an embodiment, a OX40 agonist comprises VH and VL regions that are each at least 96% identical to the sequences shown in SEQ ID NO:99 and SEQ ID NO:100, respectively. In an embodiment, a OX40 agonist comprises VH and VL regions that are each at least 95% identical to the sequences shown in SEQ ID NO:99 and SEQ ID NO:100, respectively.

In an embodiment, a OX40 agonist comprises heavy chain CDR1, CDR2 and CDR3 domains having the sequences set forth in SEQ ID NO:101, SEQ ID NO:102, and SEQ ID NO:103, respectively, and conservative amino acid substitutions thereof, and light chain CDR1, CDR2 and CDR3 domains having the sequences set forth in SEQ ID NO:104, SEQ ID NO:105, and SEQ ID NO:106, respectively, and conservative amino acid substitutions thereof.

In an embodiment, the OX40 agonist is a OX40 agonist biosimilar monoclonal antibody approved by drug regulatory authorities with reference to 11D4. In an embodiment, the biosimilar monoclonal antibody comprises an OX40 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is 11D4. In some embodiments, the one or more post-translational modifications are selected from one or more of: glycosylation, oxidation, deamidation, and truncation. In some embodiments, the biosimilar is a OX40 agonist antibody authorized or submitted for authorization, wherein the OX40 agonist antibody is provided in a formulation which differs from the formulations of a reference medicinal product or reference biological product, wherein the reference medicinal product or reference biological product is 11D4. The OX40 agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is 11D4. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is 11D4.

TABLE 13

Amino acid sequences for OX40 agonist antibodies related to 11D4.

| Identifier | Sequence (One-Letter Amino Acid Symbols) | |
|---|---|---|
| SEQ ID NO: 97 heavy chain for 11D4 | EVQLVESGGG LVQPGGSLRL SCAASGFTFS SYSMNWVRQA PGKGLEWVSY ISSSSSTIDY | 60 |
| | ADSVKGRFTI SRDNAKNSLY LQMNSLRDED TAVYYCARES GWYLFDYWGQ GTLVTVSSAS | 120 |
| | TKGPSVFPLA PCSRSTSEST AALGCLVKDY FPEPVTVSWN SGALTSGVHT FPAVLQSSGL | 180 |
| | YSLSSVVTVP SSNFGTQTYT CNVDHKPSNT KVDKTVERKC CVECPPCPAP PVAGPSVFLF | 240 |
| | PPKPKDTLMI SRTPEVTCVV VDVSHEDPEV QFNWYVDGVE VHNAKTKPRE EQFNSTFRVV | 300 |
| | SVLTVVHQDW LNGKEYKCKV SNKGLPAPIE KTISKTKGQP REPQVYTLPP SREEMTKNQV | 360 |
| | SLTCLVKGFY PSDIAVEWES NGQPENNYKT TPPMLDSDGS FFLYSKLTVD KSRWQQGNVF | 420 |
| | SCSVMHEALH NHYTQKSLSL SPGK | 444 |
| SEQ ID NO: 98 light chain for 11D4 | DIQMTQSPSS LSASVGDRVT ITCRASQGIS SWLAWYQQKP EKAPKSLIYA ASSLQSGVPS | 60 |
| | RFSGSGSGTD FTLTISSLQP EDFATYYCQQ YNSYPPTFGG GTKVEIKRTV AAPSVFIFPP | 120 |
| | SDEQLKSGTA SVVCLLNNFY PREAKVQWKV DNALQSGNSQ ESVTEQDSKD STYSLSSTLT | 180 |
| | LSKADYEKHK VYACEVTHQG LSSPVTKSFN RGEC | 214 |
| SEQ ID NO: 99 heavy chain variable region for 11D4 | EVQLVESGGG LVQPGGSLRL SCAASGFTFS SYSMNWVRQA PGKGLEWVSY ISSSSSTIDY | 60 |
| | ADSVKGRFTI SRDNAKNSLY LQMNSLRDED TAVYYCARES GWYLFDYWGQ GTLVTVSS | 118 |
| SEQ ID NO: 100 light chain variable region for 11D4 | DIQMTQSPSS LSASVGDRVT ITCRASQGIS SWLAWYQQKP EKAPKSLIYA ASSLQSGVPS | 60 |
| | RFSGSGSGTD FTLTISSLQP EDFATYYCQQ YNSYPPTFGG GTKVEIK | 107 |
| SEQ ID NO: 101 heavy chain CDR1 for 11D4 | SYSMN | 5 |

TABLE 13-continued

Amino acid sequences for OX40 agonist antibodies related to 11D4.

| Identifier | Sequence (One-Letter Amino Acid Symbols) | |
|---|---|---|
| SEQ ID NO: 102 heavy chain CDR2 for 11D4 | YISSSSSTID YADSVKG | 17 |
| SEQ ID NO: 103 heavy chain CDR3 for 11D4 | ESGWYLFDY | 9 |
| SEQ ID NO: 104 light chain CDR1 for 11D4 | RASQGISSWL A | 11 |
| SEQ ID NO: 105 light chain CDR2 for 11D4 | AASSLQS | 7 |
| SEQ ID NO: 106 light chain CDR3 for 11D4 | QQYNSYPPT | 9 |

In some embodiments, the OX40 agonist is 18D8, which is a fully human antibody available from Pfizer, Inc. The preparation and properties of 18D8 are described in U.S. Pat. Nos. 7,960,515; 8,236,930; and 9,028,824, the disclosures of which are incorporated by reference herein. The amino acid sequences of 18D8 are set forth in Table 14.

In an embodiment, a OX40 agonist comprises a heavy chain given by SEQ ID NO:107 and a light chain given by SEQ ID NO:108. In an embodiment, a OX40 agonist comprises heavy and light chains having the sequences shown in SEQ ID NO:107 and SEQ ID NO:108, respectively, or antigen binding fragments, Fab fragments, single-chain variable fragments (scFv), variants, or conjugates thereof. In an embodiment, a OX40 agonist comprises heavy and light chains that are each at least 99% identical to the sequences shown in SEQ ID NO:107 and SEQ ID NO:108, respectively. In an embodiment, a OX40 agonist comprises heavy and light chains that are each at least 98% identical to the sequences shown in SEQ ID NO:107 and SEQ ID NO:108, respectively. In an embodiment, a OX40 agonist comprises heavy and light chains that are each at least 97% identical to the sequences shown in SEQ ID NO:107 and SEQ ID NO:108, respectively. In an embodiment, a OX40 agonist comprises heavy and light chains that are each at least 96% identical to the sequences shown in SEQ ID NO:107 and SEQ ID NO:108, respectively. In an embodiment, a OX40 agonist comprises heavy and light chains that are each at least 95% identical to the sequences shown in SEQ ID NO:107 and SEQ ID NO:108, respectively.

In an embodiment, the OX40 agonist comprises the heavy and light chain CDRs or variable regions (VRs) of 18D8. In an embodiment, the OX40 agonist heavy chain variable region ($V_H$) comprises the sequence shown in SEQ ID NO:109, and the OX40 agonist light chain variable region ($V_L$) comprises the sequence shown in SEQ ID NO:110, and conservative amino acid substitutions thereof. In an embodiment, a OX40 agonist comprises $V_H$ and $V_L$ regions that are each at least 99% identical to the sequences shown in SEQ ID NO:109 and SEQ ID NO:110, respectively. In an embodiment, a OX40 agonist comprises $V_H$ and $V_L$ regions that are each at least 98% identical to the sequences shown in SEQ ID NO:109 and SEQ ID NO:110, respectively. In an embodiment, a OX40 agonist comprises $V_H$ and $V_L$ regions that are each at least 97% identical to the sequences shown in SEQ ID NO:109 and SEQ ID NO:110, respectively. In an embodiment, a OX40 agonist comprises $V_H$ and $V_L$ regions that are each at least 96% identical to the sequences shown in SEQ ID NO:109 and SEQ ID NO:110, respectively. In an embodiment, a OX40 agonist comprises $V_H$ and $V_L$ regions that are each at least 95% identical to the sequences shown in SEQ ID NO:109 and SEQ ID NO:110, respectively.

In an embodiment, a OX40 agonist comprises heavy chain CDR1, CDR2 and CDR3 domains having the sequences set forth in SEQ ID NO:111, SEQ ID NO:112, and SEQ ID NO:113, respectively, and conservative amino acid substitutions thereof, and light chain CDR1, CDR2 and CDR3 domains having the sequences set forth in SEQ ID NO:114, SEQ ID NO:115, and SEQ ID NO:116, respectively, and conservative amino acid substitutions thereof.

In an embodiment, the OX40 agonist is a OX40 agonist biosimilar monoclonal antibody approved by drug regulatory authorities with reference to 18D8. In an embodiment, the biosimilar monoclonal antibody comprises an OX40 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is 18D8. In some embodiments, the one or more post-translational modifications are selected from one or more of: glycosylation, oxidation, deamidation, and truncation. In some embodiments, the biosimilar is a OX40 agonist antibody authorized or submitted for authorization, wherein the OX40 agonist antibody is provided in a formulation which differs from the formulations of a reference medicinal product or reference biological product, wherein the reference medicinal product or reference biological product is 18D8. The OX40 agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is 18D8.

In some embodiments, the biosimilar is provided as a composition which further comprises one or more excipients, wherein the one or more excipients are the same or different to the excipients comprised in a reference medicinal product or reference biological product, wherein the reference medicinal product or reference biological product is 18D8.

118, and conservative amino acid substitutions thereof. In an embodiment, a OX40 agonist comprises $V_H$ and $V_L$ regions that are each at least 99% identical to the sequences shown in SEQ ID NO:117 and SEQ ID NO:118, respectively. In an embodiment, a OX40 agonist comprises $V_H$ and $V_L$ regions that are each at least 98% identical to the sequences shown in SEQ ID NO:117 and SEQ ID NO:118, respectively. In an

TABLE 14

Amino acid sequences for OX40 agonist antibodies related to 18D8.

| Identifier | Sequence (One-Letter Amino Acid Symbols) | |
|---|---|---|
| SEQ ID NO: 107<br>heavy chain for<br>18D8 | EVQLVESGGG LVQPGRSLRL SCAASGFTFD DYAMHWVRQA PGKGLEWVSG ISWNSGSIGY<br>ADSVKGRFTI SRDNAKNSLY LQMNSLRAED TALYYCAKDQ STADYYFYYG MDVWGQGTTV<br>TVSSASTKGP SVFPLAPCSR STSESTAALG CLVKDYFPEP VTVSWNSGAL TSGVHTFPAV<br>LQSSGLYSLS SVVTVPSSNF GTQTYTCNVD HKPSNTKVDK TVERKCCVEC PPCPAPPVAG<br>PSVFLFPPKP KDTLMISRTP EVTCVVVDVS HEDPEVQFNW YVDGVEVHNA KTKPREEQFN<br>STFRVVSVLT VVHQDWLNGK EYKCKVSNKG LPAPIEKTIS KTKGQPREPQ VYTLPPSREE<br>MTKNQVSLTC LVKGFYPSDI AVEWESNGQP ENNYKTTPPM LDSDGSFFLY SKLTVDKSRW<br>QQGNVFSCSV MHEALHNHYT QKSLSLSPGK | 60<br>120<br>180<br>240<br>300<br>360<br>420<br>450 |
| SEQ ID NO: 108<br>light chain for<br>18D8 | EIVVTQSPAT LSLSPGERAT LSCRASQSVS SYLAWYQQKP GQAPRLLIYD ASNRATGIPA<br>RFSGSGSGTD FTLTISSLEP EDFAVYYCQQ RSNWPTFGQG TKVEIKRTVA APSVFIFPPS<br>DEQLKSGTAS VVCLLNNFYP REAKVQWKVD NALQSGNSQE SVTEQDSKDS TYSLSSTLTL<br>SKADYEKHKV YACEVTHQGL SSPVTKSFNR GEC | 60<br>120<br>180<br>213 |
| SEQ ID NO: 109<br>heavy chain<br>variable region<br>for 18D8 | EVQLVESGGG LVQPGRSLRL SCAASGFTFD DYAMHWVRQA PGKGLEWVSG ISWNSGSIGY<br>ADSVKGRFTI SRDNAKNSLY LQMNSLRAED TALYYCAKDQ STADYYFYYG MDVWGQGTTV<br>TVSS | 60<br>120<br>124 |
| SEQ ID NO: 110<br>light chain<br>variable region<br>for 18D8 | EIVVTQSPAT LSLSPGERAT LSCRASQSVS SYLAWYQQKP GQAPRLLIYD ASNRATGIPA<br>RFSGSGSGTD FTLTISSLEP EDFAVYYCQQ RSNWPTFGQG TKVEIK | 60<br>106 |
| SEQ ID NO: 111<br>heavy chain CDR1<br>for 18D8 | DYAMH | 5 |
| SEQ ID NO: 112<br>heavy chain CDR2<br>for 18D8 | GISWNSGSIG YADSVKG | 17 |
| SEQ ID NO: 113<br>heavy chain CDR3<br>for 18D8 | DQSTADYYFY YGMDV | 15 |
| SEQ ID NO: 114<br>light chain CDR1<br>for 18D8 | RASQSVSSYL A | 11 |
| SEQ ID NO: 115<br>light chain CDR2<br>for 18D8 | DASNRAT | 7 |
| SEQ ID NO: 116<br>light chain CDR3<br>for 18D8 | QQRSNWPT | 8 |

In some embodiments, the OX40 agonist is Hu119-122, which is a humanized antibody available from GlaxoSmithKline plc. The preparation and properties of Hu119-122 are described in U.S. Pat. Nos. 9,006,399 and 9,163,085, and in International Patent Publication No. WO 2012/027328, the disclosures of which are incorporated by reference herein. The amino acid sequences of Hu119-122 are set forth in Table 15.

In an embodiment, the OX40 agonist comprises the heavy and light chain CDRs or variable regions (VRs) of Hu119-122. In an embodiment, the OX40 agonist heavy chain variable region ($V_H$) comprises the sequence shown in SEQ ID NO: 117, and the OX40 agonist light chain variable region ($V_L$) comprises the sequence shown in SEQ ID NO: embodiment, a OX40 agonist comprises $V_H$ and $V_L$ regions that are each at least 97% identical to the sequences shown in SEQ ID NO:117 and SEQ ID NO:118, respectively. In an embodiment, a OX40 agonist comprises $V_H$ and $V_L$ regions that are each at least 96% identical to the sequences shown in SEQ ID NO:117 and SEQ ID NO:118, respectively. In an embodiment, a OX40 agonist comprises $V_H$ and $V_L$ regions that are each at least 95% identical to the sequences shown in SEQ ID NO:117 and SEQ ID NO:118, respectively.

In an embodiment, a OX40 agonist comprises heavy chain CDR1, CDR2 and CDR3 domains having the sequences set forth in SEQ ID NO:119, SEQ ID NO:120, and SEQ ID NO:121, respectively, and conservative amino acid substitutions thereof, and light chain CDR1, CDR2 and CDR3 domains having the sequences set forth in SEQ ID NO:122, SEQ ID NO:123, and SEQ ID NO:124, respectively, and conservative amino acid substitutions thereof.

In an embodiment, the OX40 agonist is a OX40 agonist biosimilar monoclonal antibody approved by drug regulatory authorities with reference to Hu119-122. In an embodiment, the biosimilar monoclonal antibody comprises an product is Hu119-122. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is Hu119-122.

TABLE 15

Amino acid sequences for OX40 agonist antibodies related to Hu119-122.

| Identifier | Sequence (One-Letter Amino Acid Symbols) | |
|---|---|---|
| SEQ ID NO: 117 heavy chain variable region for Hu119-122 | EVQLVESGGG LVQPGGSLRL SCAASEYEFP SHDMSWVRQA PGKGLELVAA INSDGGSTYY<br>PDTMERRFTI SRDNAKNSLY LQMNSLRAED TAVYYCARHY DDYYAWFAYW GQGTMVTVSS | 60<br>120 |
| SEQ ID NO: 118 light chain variable region for Hu119-122 | EIVLTQSPAT LSLSPGERAT LSCRASKSVS TSGYSYMHWY QQKPGQAPRL LIYLASNLES<br>GVPARFSGSG SGTDFTLTIS SLEPEDFAVY YCQHSRELPL TFGGGTKVEI K | 60<br>111 |
| SEQ ID NO: 119 heavy chain CDR1 for Hu119-122 | SHDMS | 5 |
| SEQ ID NO: 120 heavy chain CDR2 for Hu119-122 | AINSDGGSTY YPDTMER | 17 |
| SEQ ID NO: 121 heavy chain CDR3 for Hu119-122 | HYDDYYAWFA Y | 11 |
| SEQ ID NO: 122 light chain CDR1 for Hu119-122 | RASKSVSTSG YSYMH | 15 |
| SEQ ID NO: 123 light chain CDR2 for Hu119-122 | LASNLES | 7 |
| SEQ ID NO: 124 light chain CDR3 for Hu119-122 | QHSRELPLT | 9 |

OX40 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is Hu119-122. In some embodiments, the one or more post-translational modifications are selected from one or more of: glycosylation, oxidation, deamidation, and truncation. In some embodiments, the biosimilar is a OX40 agonist antibody authorized or submitted for authorization, wherein the OX40 agonist antibody is provided in a formulation which differs from the formulations of a reference medicinal product or reference biological product, wherein the reference medicinal product or reference biological product is Hu119-122. The OX40 agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological In some embodiments, the OX40 agonist is Hu106-222, which is a humanized antibody available from GlaxoSmithKline plc. The preparation and properties of Hu106-222 are described in U.S. Pat. Nos. 9,006,399 and 9,163,085, and in International Patent Publication No. WO 2012/027328, the disclosures of which are incorporated by reference herein. The amino acid sequences of Hu106-222 are set forth in Table 16.

In an embodiment, the OX40 agonist comprises the heavy and light chain CDRs or variable regions (VRs) of Hu106-222. In an embodiment, the OX40 agonist heavy chain variable region ($V_H$) comprises the sequence shown in SEQ ID NO:125, and the OX40 agonist light chain variable region ($V_L$) comprises the sequence shown in SEQ ID NO:126, and conservative amino acid substitutions thereof. In an embodiment, a OX40 agonist comprises $V_H$ and $V_L$ regions that are each at least 99% identical to the sequences shown in SEQ ID NO:125 and SEQ ID NO:126, respectively. In an embodiment, a OX40 agonist comprises $V_H$ and $V_L$ regions that are each at least 98% identical to the sequences shown in SEQ ID NO:125 and SEQ ID NO:126, respectively. In an embodiment, a OX40 agonist comprises $V_H$ and $V_L$ regions that are each at least 97% identical to the sequences shown in SEQ ID NO:125 and SEQ ID NO:126, respectively. In an embodiment, a OX40 agonist comprises $V_H$ and $V_L$ regions that are each at least 96% identical to the sequences shown in SEQ ID NO:125 and SEQ ID NO:126, respectively. In an embodiment, a OX40 agonist comprises $V_H$ and $V_L$ regions that are each at least 95% identical to the sequences shown in SEQ ID NO:125 and SEQ ID NO:126, respectively.

In an embodiment, a OX40 agonist comprises heavy chain CDR1, CDR2 and CDR3 domains having the sequences set forth in SEQ ID NO:127, SEQ ID NO:128, and SEQ ID NO:129, respectively, and conservative amino acid substitutions thereof, and light chain CDR1, CDR2 and CDR3 domains having the sequences set forth in SEQ ID NO:130, SEQ ID NO:131, and SEQ ID NO:132, respectively, and conservative amino acid substitutions thereof.

In an embodiment, the OX40 agonist is a OX40 agonist biosimilar monoclonal antibody approved by drug regulatory authorities with reference to Hu106-222. In an embodiment, the biosimilar monoclonal antibody comprises an from the formulations of a reference medicinal product or reference biological product, wherein the reference medicinal product or reference biological product is Hu106-222. The OX40 agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is Hu106-222. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is Hu106-222.

TABLE 16

Amino acid sequences for OX40 agonist antibodies related to Hu106-222.

| Identifier | Sequence (One-Letter Amino Acid Symbols) | |
|---|---|---|
| SEQ ID NO: 125 heavy chain variable region for Hu106-222 | QVQLVQSGSE LKKPGASVKV SCKASGYTFT DYSMHWVRQA PGQGLKWMGW INTETGEPTY<br>ADDFKGRFVF SLDTSVSTAY LQISSLKAED TAVYYCANPY YDYVSYYAMD YWGQGTTVTV<br>SS | 60<br>120<br>122 |
| SEQ ID NO: 126 light chain variable region for Hu106-222 | DIQMTQSPSS LSASVGDRVT ITCKASQDVS TAVAWYQQKP GKAPKLLIYS ASYLYTGVPS<br>RFSGSGSGTD FTFTISSLQP EDIATYYCQQ HYSTPRTFGQ GTKLEIK | 60<br>107 |
| SEQ ID NO: 127 heavy chain CDR1 for Hu106-222 | DYSMH | 5 |
| SEQ ID NO: 128 heavy chain CDR2 for Hu106-222 | WINTETGEPT YADDFKG | 17 |
| SEQ ID NO: 129 heavy chain CDR3 for Hu106-222 | PYYDYVSYYA MDY | 13 |
| SEQ ID NO: 130 light chain CDR1 for Hu106-222 | KASQDVSTAV A | 11 |
| SEQ ID NO: 131 light chain CDR2 for Hu106-222 | SASYLYT | 7 |
| SEQ ID NO: 132 light chain CDR3 for Hu106-222 | QQHYSTPRT | 9 |

OX40 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is Hu106-222. In some embodiments, the one or more post-translational modifications are selected from one or more of: glycosylation, oxidation, deamidation, and truncation. In some embodiments, the biosimilar is a OX40 agonist antibody authorized or submitted for authorization, wherein the OX40 agonist antibody is provided in a formulation which differs In some embodiments, the OX40 agonist antibody is MEDI6469 (also referred to as 9B12). MEDI6469 is a murine monoclonal antibody. Weinberg, et al., *J. Immunother.* 2006, 29, 575-585. In some embodiments the OX40 agonist is an antibody produced by the 9B12 hybridoma, deposited with Biovest Inc. (Malvern, MA, USA), as described in Weinberg, et al., *J. Immunother.* 2006, 29, 575-585, the disclosure of which is hereby incorporated by reference in its entirety. In some embodiments, the antibody comprises the CDR sequences of MEDI6469. In some embodiments, the antibody comprises a heavy chain variable region sequence and/or a light chain variable region sequence of MEDI6469.

In an embodiment, the OX40 agonist is L106 BD (Pharmingen Product #340420). In some embodiments, the OX40 agonist comprises the CDRs of antibody L106 (BD Pharmingen Product #340420). In some embodiments, the OX40 agonist comprises a heavy chain variable region sequence and/or a light chain variable region sequence of antibody L106 (BD Pharmingen Product #340420). In an embodiment, the OX40 agonist is ACT35 (Santa Cruz Biotechnology, Catalog #20073). In some embodiments, the OX40 agonist comprises the CDRs of antibody ACT35 (Santa Cruz Biotechnology, Catalog #20073). In some embodiments, the OX40 agonist comprises a heavy chain variable region sequence and/or a light chain variable region sequence of antibody ACT35 (Santa Cruz Biotechnology, Catalog #20073). In an embodiment, the OX40 agonist is the murine monoclonal antibody anti-mCD134/mOX40 (clone OX86), commercially available from InVivoMAb, BioXcell Inc, West Lebanon, NH.

In an embodiment, the OX40 agonist is selected from the OX40 agonists described in International Patent Application Publication Nos. WO 95/12673, WO 95/21925, WO 2006/121810, WO 2012/027328, WO 2013/028231, WO 2013/038191, and WO 2014/148895; European Patent Application EP 0672141; U.S. Patent Application Publication Nos. US 2010/136030, US 2014/377284, US 2015/190506, and US 2015/132288 (including clones 20E5 and 12H3); and U.S. Pat. Nos. 7,504,101, 7,550,140, 7,622,444, 7,696,175, 7,960,515, 7,961,515, 8,133,983, 9,006,399, and 9,163,085, the disclosure of each of which is incorporated herein by reference in its entirety.

In an embodiment, the OX40 agonist is an OX40 agonistic fusion protein as depicted in Structure I-A (C-terminal Fc-antibody fragment fusion protein) or Structure I-B (N-terminal Fc-antibody fragment fusion protein), or a fragment, derivative, conjugate, variant, or biosimilar thereof. The properties of structures I-A and I-B are described above and in U.S. Pat. Nos. 9,359,420, 9,340,599, 8,921,519, and 8,450,460, the disclosures of which are incorporated by reference herein. Amino acid sequences for the polypeptide domains of structure I-A given in FIG. 18 are found in Table 9. The Fc domain preferably comprises a complete constant domain (amino acids 17-230 of SEQ ID NO:62) the complete hinge domain (amino acids 1-16 of SEQ ID NO:62) or a portion of the hinge domain (e.g., amino acids 4-16 of SEQ ID NO:62). Preferred linkers for connecting a C-terminal Fc-antibody may be selected from the embodiments given in SEQ ID NO:63 to SEQ ID NO:72, including linkers suitable for fusion of additional polypeptides. Likewise, amino acid sequences for the polypeptide domains of structure I-B given in FIG. 18 are found in Table 10. If an Fc antibody fragment is fused to the N-terminus of an TNRFSF fusion protein as in structure I-B, the sequence of the Fc module is preferably that shown in SEQ ID NO:73, and the linker sequences are preferably selected from those embodiments set forth in SED ID NO:74 to SEQ ID NO:76.

In an embodiment, an OX40 agonist fusion protein according to structures I-A or I-B comprises one or more OX40 binding domains selected from the group consisting of a variable heavy chain and variable light chain of tavolixizumab, a variable heavy chain and variable light chain of 11D4, a variable heavy chain and variable light chain of 18D8, a variable heavy chain and variable light chain of Hu119-122, a variable heavy chain and variable light chain of Hu106-222, a variable heavy chain and variable light chain selected from the variable heavy chains and variable light chains described in Table 17, any combination of a variable heavy chain and variable light chain of the foregoing, and fragments, derivatives, conjugates, variants, and biosimilars thereof.

In an embodiment, an OX40 agonist fusion protein according to structures I-A or I-B comprises one or more OX40 binding domains comprising an OX40L sequence. In an embodiment, an OX40 agonist fusion protein according to structures I-A or I-B comprises one or more OX40 binding domains comprising a sequence according to SEQ ID NO:133. In an embodiment, an OX40 agonist fusion protein according to structures I-A or I-B comprises one or more OX40 binding domains comprising a soluble OX40L sequence. In an embodiment, a OX40 agonist fusion protein according to structures I-A or I-B comprises one or more OX40 binding domains comprising a sequence according to SEQ ID NO:134. In an embodiment, a OX40 agonist fusion protein according to structures I-A or I-B comprises one or more OX40 binding domains comprising a sequence according to SEQ ID NO:135.

In an embodiment, an OX40 agonist fusion protein according to structures I-A or I-B comprises one or more OX40 binding domains that is a scFv domain comprising $V_H$ and $V_L$ regions that are each at least 95% identical to the sequences shown in SEQ ID NO:89 and SEQ ID NO:90, respectively, wherein the $V_H$ and $V_L$ domains are connected by a linker. In an embodiment, an OX40 agonist fusion protein according to structures I-A or I-B comprises one or more OX40 binding domains that is a scFv domain comprising $V_H$ and $V_L$ regions that are each at least 95% identical to the sequences shown in SEQ ID NO:99 and SEQ ID NO:100, respectively, wherein the $V_H$ and $V_L$ domains are connected by a linker. In an embodiment, an OX40 agonist fusion protein according to structures I-A or I-B comprises one or more OX40 binding domains that is a scFv domain comprising $V_H$ and $V_L$ regions that are each at least 95% identical to the sequences shown in SEQ ID NO:109 and SEQ ID NO:110, respectively, wherein the $V_H$ and $V_L$ domains are connected by a linker. In an embodiment, an OX40 agonist fusion protein according to structures I-A or I-B comprises one or more OX40 binding domains that is a scFv domain comprising $V_H$ and $V_L$ regions that are each at least 95% identical to the sequences shown in SEQ ID NO:127 and SEQ ID NO: 128, respectively, wherein the $V_H$ and $V_L$ domains are connected by a linker. In an embodiment, an OX40 agonist fusion protein according to structures I-A or I-B comprises one or more OX40 binding domains that is a scFv domain comprising $V_H$ and $V_L$ regions that are each at least 95% identical to the sequences shown in SEQ ID NO:125 and SEQ ID NO: 126, respectively, wherein the $V_H$ and $V_L$ domains are connected by a linker. In an embodiment, an OX40 agonist fusion protein according to structures I-A or I-B comprises one or more OX40 binding domains that is a scFv domain comprising $V_H$ and $V_L$ regions that are each at least 95% identical to the $V_H$ and $V_L$ sequences given in Table 17, wherein the $V_H$ and $V_L$ domains are connected by a linker.

TABLE 17

Additional polypeptide domains useful as OX40 binding domains in fusion proteins (e.g., structures I-A and I-B) or as scFv OX40 agonist antibodies.

| Identifier | Sequence (One-Letter Amino Acid Symbols) | |
|---|---|---|
| SEQ ID NO: 133 OX40L | MERVQPLEEN VGNAARPRFE RNKLLLVASV IQGLGLLLCF TYICLHFSAL QVSHRYPRIQ | 60 |
| | SIKVQFTEYK KEKGFILTSQ KEDEIMKVQN NSVIINCDGF YLISLKGYFS QEVNISLHYQ | 120 |
| | KDEEPLFQLK KVRSVNSLMV ASLTYKDKVY LNVTTDNTSL DDFHVNGGEL ILIHQNPGEF | 180 |
| | CVL | 183 |
| SEQ ID NO: 134 OX40L soluble domain | SHRYPRIQSI KVQFTEYKKE KGFILTSQKE DEIMKVQNNS VIINCDGFYL ISLKGYFSQE | 60 |
| | VNISLHYQKD EEPLFQLKKV RSVNSLMVAS LTYKDKVYLN VTTDNTSLDD FHVNGGELIL | 120 |
| | IHQNPGEFCV L | 131 |
| SEQ ID NO: 135 OX40L soluble domain (alternative) | YPRIQSIKVQ FTEYKKEKGF ILTSQKEDEI MKVQNNSVII NCDGFYLISL KGYFSQEVNI | 60 |
| | SLHYQKDEEP LFQLKKVRSV NSLMVASLTY KDKVYLNVTT DNTSLDDFHV NGGELILIHQ | 120 |
| | NPGEFCVL | 128 |
| SEQ ID NO: 136 variable heavy chain for 008 | EVQLVESGGG LVQPGGSLRL SCAASGFTFS NYTMNWVRQA PGKGLEWVSA ISGSGGSTYY | 60 |
| | ADSVKGRFTI SRDNSKNTLY LQMNSLRAED TAVYYCAKDR YSQVHYALDY WGQGTLVTVS | 120 |
| SEQ ID NO: 137 variable light chain for 008 | DIVMTQSPDS LPVTPGEPAS ISCRSSQSLL HSNGYNYLDW YLQKAGQSPQ LLIYLGSNRA | 60 |
| | SGVPDRFSGS GSGTDFTLKI SRVEAEDVGV YYCQQYYNHP TTFGQGTK | 108 |
| SEQ ID NO: 138 variable heavy chain for 011 | EVQLVESGGG VVQPGRSLRL SCAASGFTFS DYTMNWVRQA PGKGLEWVSS ISGGSTYYAD | 60 |
| | SRKGRFTISR DNSKNTLYLQ MNNLRAEDTA VYYCARDRYF RQQNAFDYWG QGTLVTVSSA | 120 |
| SEQ ID NO: 139 variable light chain for 011 | DIVMTQSPDS LPVTPGEPAS ISCRSSQSLL HSNGYNYLDW YLQKAGQSPQ LLIYLGSNRA | 60 |
| | SGVPDRFSGS GSGTDFTLKI SRVEAEDVGV YYCQQYYNHP TTFGQGTK | 108 |
| SEQ ID NO: 140 variable heavy chain for 021 | EVQLVESGGG LVQPRGSLRL SCAASGFTFS SYAMNWVRQA PGKGLEWVAV ISYDGSNKYY | 60 |
| | ADSVKGRFTI SRDNSKNTLY LQMNSLRAED TAVYYCAKDR YITLPNALDY WGQGTLVTVS | 120 |
| SEQ ID NO: 141 variable light chain for 021 | DIQMTQSPVS LPVTPGEPAS ISCRSSQSLL HSNGYNYLDW YLQKPGQSPQ LLIYLGSNRA | 60 |
| | SGVPDRFSGS GSGTDFTLKI SRVEAEDVGV YYCQQYKSNP PTFGQGTK | 108 |
| SEQ ID NO: 142 variable heavy chain for 023 | EVQLVESGGG LVHPGGSLRL SCAGSGFTFS SYAMHWVRQA PGKGLEWVSA IGTGGGTYYA | 60 |
| | DSVMGRFTIS RDNSKNTLYL QMNSLRAEDT AVYYCARYDN VMGLYWFDYW GQGTLVTVSS | 120 |
| SEQ ID NO: 143 variable light chain for 023 | EIVLTQSPAT LSLSPGERAT LSCRASQSVS SYLAWYQQKP GQAPRLLIYD ASNRATGIPA | 60 |
| | RFSGSGSGTD FTLTISSLEP EDFAVYYCQQ RSNWPPAFGG GTKVEIKR | 108 |
| SEQ ID NO: 144 heavy chain variable region | EVQLQQSGPE LVKPGASVKM SCKASGYTFT SYVMHWVKQK PGQGLEWIGY INPYNDGTKY | 60 |
| | NEKFKGKATL TSDKSSSTAY MELSSLTSED SAVYYCANYY GSSLSMDYWG QGTSVTVSS | 119 |
| SEQ ID NO: 145 light chain variable region | DIQMTQTTSS LSASLGDRVT ISCRASQDIS NYLNWYQQKP DGTVKLLIYY TSRLHSGVPS | 60 |
| | RFSGSGSGTD YSLTISNLEQ EDIATYFCQQ GNTLPWTFGG GTKLEIKR | 108 |
| SEQ ID NO: 146 heavy chain variable region | EVQLQQSGPE LVKPGASVKI SCKTSGYTFK DYTMHWVKQS HGKSLEWIGG IYPNNGGSTY | 60 |
| | NQNFKDKATL TVDKSSSTAY MEFRSLTSED SAVYYCARMG YHGPHLDFDV WGAGTTVTVS | 120 |
| | P | 121 |
| SEQ ID NO: 147 light chain variable region | DIVMTQSHKF MSTSLGDRVS ITCKASQDVG AAVAWYQQKP GQSPKLLIYW ASTRHTGVPD | 60 |
| | RFTGGGSGTD FTLTISNVQS EDLTDYFCQQ YINYPLTFGG GTKLEIKR | 108 |
| SEQ ID NO: 148 heavy chain variable region of humanized antibody | QIQLVQSGPE LKKPGETVKI SCKASGYTFT DYSMHWVKQA PGKGLKWMGW INTETGEPTY | 60 |
| | ADDFKGRFAF SLETSASTAY LQINNLKNED TATYFCANPY YDYVSYYAMD YWGHGTSVTV | 120 |
| | SS | 122 |

TABLE 17-continued

Additional polypeptide domains useful as OX40 binding domains in fusion proteins (e.g., structures I-A and I-B) or as scFv OX40 agonist antibodies.

| Identifier | Sequence (One-Letter Amino Acid Symbols) | |
|---|---|---|
| SEQ ID NO: 149 heavy chain variable region of humanized antibody | QVQLVQSGSE LKKPGASVKV SCKASGYTFT DYSMHWVRQA PGQGLKWMGW INTETGEPTY | 60 |
| | ADDFKGRFVF SLDTSVSTAY LQISSLKAED TAVYYCANPY YDYVSYYAMD YWGQGTTVTV | 120 |
| | SS | 122 |
| SEQ ID NO: 150 light chain variable region of humanized antibody | DIVMTQSHKF MSTSVRDRVS ITCKASQDVS TAVAWYQQKP GQSPKLLIYS ASYLYTGVPD | 60 |
| | RFTGSGSGTD FTFTISSVQA EDLAVYYCQQ HYSTPRTFGG GTKLEIK | 107 |
| SEQ ID NO: 151 light chain variable region of humanized antibody | DIVMTQSHKF MSTSVRDRVS ITCKASQDVS TAVAWYQQKP GQSPKLLIYS ASYLYTGVPD | 60 |
| | RFTGSGSGTD FTFTISSVQA EDLAVYYCQQ HYSTPRTFGG GTKLEIK | 107 |
| SEQ ID NO: 152 heavy chain variable region of humanized antibody | EVQLVESGGG LVQPGESLKL SCESNEYEFP SHDMSWVRKT PEKRLELVAA INSDGGSTYY | 60 |
| | PDTMERRFII SRDNTKKTLY LQMSSLRSED TALYYCARHY DDYYAWFAYW GQGTLVTVSA | 120 |
| SEQ ID NO: 153 heavy chain variable region of humanized antibody | EVQLVESGGG LVQPGGSLRL SCAASEYEFP SHDMSWVRQA PGKGLELVAA INSDGGSTYY | 60 |
| | PDTMERRFTI SRDNAKNSLY LQMNSLRAED TAVYYCARHY DDYYAWFAYW GQGTMVTVSS | 120 |
| SEQ ID NO: 154 light chain variable region of humanized antibody | DIVLTQSPAS LAVSLGQRAT ISCRASKSVS TSGYSYMHWY QQKPGQPPKL LIYLASNLES | 60 |
| | GVPARFSGSG SGTDFTLNIH PVEEEDAATY YCQHSRELPL TFGAGTKLEL K | 111 |
| SEQ ID NO: 155 light chain variable region of humanized antibody | EIVLTQSPAT LSLSPGERAT LSCRASKSVS TSGYSYMHWY QQKPGQAPRL LIYLASNLES | 60 |
| | GVPARFSGSG SGTDFTLTIS SLEPEDFAVY YCQHSRELPL TFGGGTKVEI K | 111 |
| SEQ ID NO: 156 heavy chain variable region | MYLGLNYVFI VFLLNGVQSE VKLEESGGGL VQPGGSMKLS CAASGFTFSD AWMDWVRQSP | 60 |
| | EKGLEWVAEI RSKANNHATY YAESVNGRFT ISRDDSKSSV YLQMNSLRAE DTGIYYCTWG | 120 |
| | EVFYFDYWGQ GTTLTVSS | 138 |
| SEQ ID NO: 157 light chain variable region | MRPSIQFLGL LLFWLHGAQC DIQMTQSPSS LSASLGGKVT ITCKSSQDIN KYIAWYQHKP | 60 |
| | GKGPRLLIHY TSTLQPGIPS RFSGSGSGRD YSFSISNLEP EDIATYYCLQ YDNLLTFGAG | 120 |
| | TKLELK | 126 |

In an embodiment, the OX40 agonist is a OX40 agonistic single-chain fusion polypeptide comprising (i) a first soluble OX40 binding domain, (ii a first peptide linker, (iii) a second soluble OX40 binding domain, (iv) a second peptide linker, and (v) a third soluble OX40 binding domain, further comprising an additional domain at the N-terminal and/or C-terminal end, and wherein the additional domain is a Fab or Fc fragment domain. In an embodiment, the OX40 agonist is a OX40 agonistic single-chain fusion polypeptide comprising (i) a first soluble OX40 binding domain, (ii) a first peptide linker, (iii) a second soluble OX40 binding domain, (iv) a second peptide linker, and (v) a third soluble OX40 binding domain, further comprising an additional domain at the N-terminal and/or C-terminal end, wherein the additional domain is a Fab or Fc fragment domain wherein each of the soluble OX40 binding domains lacks a stalk region (which contributes to trimerisation and provides a certain distance to the cell membrane, but is not part of the OX40 binding domain) and the first and the second peptide linkers independently have a length of 3-8 amino acids.

In an embodiment, the OX40 agonist is an OX40 agonistic single-chain fusion polypeptide comprising (i) a first soluble tumor necrosis factor (TNF) superfamily cytokine domain, (ii) a first peptide linker, (iii) a second soluble TNF superfamily cytokine domain, (iv) a second peptide linker, and (v) a third soluble TNF superfamily cytokine domain, wherein each of the soluble TNF superfamily cytokine domains lacks a stalk region and the first and the second peptide linkers independently have a length of 3-8 amino acids, and wherein the TNF superfamily cytokine domain is an OX40 binding domain.

In some embodiments, the OX40 agonist is MEDI6383. MEDI6383 is an OX40 agonistic fusion protein and can be prepared as described in U.S. Pat. No. 6,312,700, the disclosure of which is incorporated by reference herein.

In an embodiment, the OX40 agonist is an OX40 agonistic scFv antibody comprising any of the foregoing $V_H$ domains linked to any of the foregoing $V_L$ domains.

In an embodiment, the OX40 agonist is Creative Biolabs OX40 agonist monoclonal antibody MOM-18455, commercially available from Creative Biolabs, Inc., Shirley, NY, USA.

In an embodiment, the OX40 agonist is OX40 agonistic antibody clone Ber-ACT35 commercially available from BioLegend, Inc., San Diego, CA, USA.

C. Optional Cell Viability Analyses

Optionally, a cell viability assay can be performed after the priming first expansion (sometimes referred to as the initial bulk expansion), using standard assays known in the art. Thus, in certain embodiments, the method comprises performing a cell viability assay subsequent to the priming first expansion. For example, a trypan blue exclusion assay can be done on a sample of the bulk TILs, which selectively labels dead cells and allows a viability assessment. Other assays for use in testing viability can include but are not limited to the Alamar blue assay; and the MTT assay.

1. Cell Counts, Viability, Flow Cytometry

In some embodiments, cell counts and/or viability are measured. The expression of markers such as but not limited CD3, CD4, CD8, and CD56, as well as any other disclosed or described herein, can be measured by flow cytometry with antibodies, for example but not limited to those commercially available from BD Biosciences, Inc. (San Jose, CA) using a FACSCanto flow cytometer (BD Biosciences, Inc., Franklin Lakes, NJ, USA). The cells can be counted manually using a disposable c-chip hemocytometer (VWR, Batavia, IL, USA) and viability can be assessed using any method known in the art, including but not limited to trypan blue staining. The cell viability can also be assayed based on U.S. Patent Application Publication No. 2018/0282694, incorporated by reference herein in its entirety. Cell viability can also be assayed based on U.S. Patent Application Publication No. 2018/0280436 or International Patent Application Publication No. WO/2018/081473, both of which are incorporate herein in their entireties for all purposes.

In some cases, the bulk TIL population can be cryopreserved immediately, using the protocols discussed below. Alternatively, the bulk TIL population can be subjected to REP and then cryopreserved as discussed below. Similarly, in the case where genetically modified TILs will be used in therapy, the bulk or REP TIL populations can be subjected to genetic modifications for suitable treatments.

2. Cell Cultures

In an embodiment, a method for expanding TILs, including those discussed above as well as exemplified in FIGS. 1 and 8, in particular, e.g., FIG. 8B and/or FIG. 8C, may include using about 5,000 mL to about 25,000 mL of cell medium, about 5,000 mL to about 10,000 mL of cell medium, or about 5,800 mL to about 8,700 mL of cell medium. In some embodiments, the media is a serum free medium. In some embodiments, the media in the priming first expansion is serum free. In some embodiments, the media in the second expansion is serum free. In some embodiments, the media in the priming first expansion and the second expansion (also referred to as rapid second expansion) are both serum free. In an embodiment, expanding the number of TILs uses no more than one type of cell culture medium. Any suitable cell culture medium may be used, e.g., AIM-V cell medium (L-glutamine, 50 μM streptomycin sulfate, and 10 μM gentamicin sulfate) cell culture medium, also referred to as AIM V medium (commercially available from Invitrogen, Carlsbad CA). In this regard, the inventive methods advantageously reduce the amount of medium and the number of types of medium required to expand the number of TIL. In an embodiment, expanding the number of TIL may comprise feeding the cells no more frequently than every third or fourth day. Expanding the number of cells in a gas permeable container simplifies the procedures necessary to expand the number of cells by reducing the feeding frequency necessary to expand the cells.

In an embodiment, the cell culture medium in the first and/or second gas permeable container is unfiltered. The use of unfiltered cell medium may simplify the procedures necessary to expand the number of cells. In an embodiment, the cell medium in the first and/or second gas permeable container lacks beta-mercaptoethanol (BME).

In an embodiment, the duration of the method comprising obtaining a tumor tissue sample from the mammal; culturing the tumor tissue sample in a first gas permeable container containing cell medium including IL-2, 1× antigen-presenting feeder cells, and OKT-3 for a duration of about 1 to 8 days, e.g., about 7 days as a priming first expansion, or about 8 days as a priming first expansion; transferring the TILs to a second gas permeable container and expanding the number of TILs in the second gas permeable container containing cell medium including IL-2, 2× antigen-presenting feeder cells, and OKT-3 for a duration of about 7 to 9 days, e.g., about 7 days, about 8 days, or about 9 days.

In an embodiment, the duration of the method comprising obtaining a tumor tissue sample from the mammal; culturing the tumor tissue sample in a first gas permeable container containing cell medium including IL-2, 1× antigen-presenting feeder cells, and OKT-3 for a duration of about 1 to 7 days, e.g., about 7 days as a priming first expansion; transferring the TILs to a second gas permeable container and expanding the number of TILs in the second gas permeable container containing cell medium including IL-2, 2× antigen-presenting feeder cells, and OKT-3 for a duration of about 7 to 14 days, or about 7 to 9 days, e.g., about 7 days, about 8 days, or about 9 days, about 10 days, or about 11 days.

In an embodiment, the duration of the method comprising obtaining a tumor tissue sample from the mammal; culturing the tumor tissue sample in a first gas permeable container containing cell medium including IL-2, 1× antigen-presenting feeder cells, and OKT-3 for a duration of about 1 to 7 days, e.g., about 7 days as a priming first expansion; transferring the TILs to a second gas permeable container and expanding the number of TILs in the second gas permeable container containing cell medium including IL-2, 2× antigen-presenting feeder cells, and OKT-3 for a duration of about 7 to 11 days, e.g., about 7 days, about 8 days, about 9 days, about 10, or about 11 days.

In an embodiment, TILs are expanded in gas-permeable containers. Gas-permeable containers have been used to expand TILs using PBMCs using methods, compositions, and devices known in the art, including those described in U.S. Patent Application Publication No. 2005/0106717 A1, the disclosures of which are incorporated herein by reference. In an embodiment, TILs are expanded in gas-permeable bags. In an embodiment, TILs are expanded using a cell expansion system that expands TILs in gas permeable bags, such as the Xuri Cell Expansion System W25 (GE Healthcare). In an embodiment, TILs are expanded using a cell expansion system that expands TILs in gas permeable bags, such as the WAVE Bioreactor System, also known as the Xuri Cell Expansion System W5 (GE Healthcare). In an embodiment, the cell expansion system includes a gas permeable cell bag with a volume selected from the group consisting of about 100 mL, about 200 mL, about 300 mL, about 400 mL, about 500 mL, about 600 mL, about 700 mL, about 800 mL, about 900 mL, about 1 L, about 2 L, about 3 L, about 4 L, about 5 L, about 6 L, about 7 L, about 8 L, about 9 L, and about 10 L.

In an embodiment, TILs can be expanded in G-Rex flasks (commercially available from Wilson Wolf Manufacturing). Such embodiments allow for cell populations to expand from about $5\times10^5$ cells/cm$^2$ to between $10\times10^6$ and $30\times10^6$ cells/cm$^2$. In an embodiment this is without feeding. In an embodiment, this is without feeding so long as medium resides at a height of about 10 cm in the G-Rex flask. In an embodiment this is without feeding but with the addition of one or more cytokines. In an embodiment, the cytokine can be added as a bolus without any need to mix the cytokine with the medium. Such containers, devices, and methods are known in the art and have been used to expand TILs, and include those described in U.S. Patent Application Publication No. US 2014/0377739A1, International Publication No. WO 2014/210036 A1, U.S. Patent Application Publication No. us 2013/0115617 A1, International Publication No. WO 2013/188427 A1, U.S. Patent Application Publication No. US 2011/0136228 A1, U.S. Pat. No. 8,809,050 B2, International publication No. WO 2011/072088 A2, U.S. Patent Application Publication No. US 2016/0208216 A1, U.S. Patent Application Publication No. US 2012/0244133 A1, International Publication No. WO 2012/129201 A1, U.S. Patent Application Publication No. US 2013/0102075 A1, U.S. Pat. No. 8,956,860 B2, International Publication No. WO 2013/173835 A1, U.S. Patent Application Publication No. US 2015/0175966 A1, the disclosures of which are incorporated herein by reference. Such processes are also described in Jin et al., *J. Immunotherapy,* 2012, 35:283-292.

D. Optional Genetic Engineering of TILs

In some embodiments, the expanded TILs of the present invention are further manipulated before, during, or after an expansion step, including during closed, sterile manufacturing processes, each as provided herein, in order to alter protein expression in a transient manner. In some embodiments, the transiently altered protein expression is due to transient gene editing. In some embodiments, the expanded TILs of the present invention are treated with transcription factors (TFs) and/or other molecules capable of transiently altering protein expression in the TILs. In some embodiments, the TFs and/or other molecules that are capable of transiently altering protein expression provide for altered expression of tumor antigens and/or an alteration in the number of tumor antigen-specific T cells in a population of TILs.

In certain embodiments, the method comprises genetically editing a population of TILs. In certain embodiments, the method comprises genetically editing the first population of TILs, the second population of TILs and/or the third population of TILs.

In some embodiments, the present invention includes genetic editing through nucleotide insertion, such as through ribonucleic acid (RNA) insertion, including insertion of messenger RNA (mRNA) or small (or short) interfering RNA (siRNA), into a population of TILs for promotion of the expression of one or more proteins or inhibition of the expression of one or more proteins, as well as simultaneous combinations of both promotion of one set of proteins with inhibition of another set of proteins.

In some embodiments, the expanded TILs of the present invention undergo transient alteration of protein expression. In some embodiments, the transient alteration of protein expression occurs in the bulk TIL population prior to first expansion, including, for example in the TIL population obtained from for example, Step A as indicated in FIG. 8 (particularly FIG. 8B and/or FIG. 8C). In some embodiments, the transient alteration of protein expression occurs during the first expansion, including, for example in the TIL population expanded in for example, Step B as indicated in FIG. 8 (for example FIG. 8B and/or FIG. 8C). In some embodiments, the transient alteration of protein expression occurs after the first expansion, including, for example in the TIL population in transition between the first and second expansion (e.g. the second population of TILs as described herein), the TIL population obtained from for example, Step B and included in Step C as indicated in FIG. 8. In some embodiments, the transient alteration of protein expression occurs in the bulk TIL population prior to second expansion, including, for example in the TIL population obtained from for example, Step C and prior to its expansion in Step D as indicated in FIG. 8. In some embodiments, the transient alteration of protein expression occurs during the second expansion, including, for example in the TIL population expanded in for example, Step D as indicated in FIG. 8 (e.g. the third population of TILs). In some embodiments, the transient alteration of protein expression occurs after the second expansion, including, for example in the TIL population obtained from the expansion in for example, Step D as indicated in FIG. 8.

In an embodiment, a method of transiently altering protein expression in a population of TILs includes the step of electroporation. Electroporation methods are known in the art and are described, e.g., in Tsong, *Biophys. J.* 1991, 60, 297-306, and U.S. Patent Application Publication No. 2014/0227237 A1, the disclosures of each of which are incorporated by reference herein. In an embodiment, a method of transiently altering protein expression in population of TILs includes the step of calcium phosphate transfection. Calcium phosphate transfection methods (calcium phosphate DNA precipitation, cell surface coating, and endocytosis) are known in the art and are described in Graham and van der Eb, *Virology* 1973, 52, 456-467; Wigler, et al., *Proc. Nat. Acad. Sci.* 1979, 76, 1373-1376; and Chen and Okayarea, *Mol. Cell. Biol.* 1987, 7, 2745-2752; and in U.S. Pat. No. 5,593,875, the disclosures of each of which are incorporated by reference herein. In an embodiment, a method of transiently altering protein expression in a population of TILs includes the step of liposomal transfection. Liposomal transfection methods, such as methods that employ a 1:1 (w/w) liposome formulation of the cationic lipid N-[1-(2,3-dioleyloxy)propyl]-n,n,n-trimethylammonium chloride (DOTMA) and dioleoyl phophotidylethanolamine (DOPE) in filtered water, are known in the art and are described in Rose, et al., *Biotechniques* 1991, 10, 520-525 and Felgner, et al., *Proc. Nat. Acad. Sci. USA,* 1987, 84, 7413-7417 and in U.S. Pat. Nos. 5,279,833; 5,908,635; 6,056,938; 6,110,490; 6,534,484; and 7,687,070, the disclosures of each of which are incorporated by reference herein. In an embodiment, a method of transiently altering protein expression in a population of TILs includes the step of transfection using methods described in U.S. Pat. Nos. 5,766,902; 6,025,337; 6,410,517; 6,475,994; and 7,189,705; the disclosures of each of which are incorporated by reference herein.

In some embodiments, transient alteration of protein expression results in an increase in stem memory T cells (TSCMs). TSCMs are early progenitors of antigen-experienced central memory T cells. TSCMs generally display the long-term survival, self-renewal, and multipotency abilities that define stem cells, and are generally desirable for the generation of effective TIL products. TSCM have shown enhanced anti-tumor activity compared with other T cell subsets in mouse models of adoptive cell transfer (Gattinoni et al. Nat Med 2009, 2011; Gattinoni, Nature Rev. Cancer, 2012; Cieri et al. Blood 2013). In some embodiments, transient alteration of protein expression results in a TIL population with a composition comprising a high proportion of TSCM. In some embodiments, transient alteration of protein expression results in an at least 5%, at least 10%, at least 10%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% increase in TSCM percentage. In some embodiments, transient alteration of protein expression results in an at least a 1-fold, 2-fold, 3-fold, 4-fold, 5-fold, or 10-fold increase in TSCMs in the TIL population. In some embodiments, transient alteration of protein expression results in a TIL population with at least at least 5%, at least 10%, at least 10%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% TSCMs. In some embodiments, transient alteration of protein expression results in a therapeutic TIL population with at least at least 5%, at least 10%, at least 10%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% TSCMs.

In some embodiments, transient alteration of protein expression results in rejuvenation of antigen-experienced T cells. In some embodiments, rejuvenation includes, for example, increased proliferation, increased T cell activation, and/or increased antigen recognition.

In some embodiments, transient alteration of protein expression alters the expression in a large fraction of the T cells in order to preserve the tumor-derived TCR repertoire. In some embodiments, transient alteration of protein expression does not alter the tumor-derived TCR repertoire. In some embodiments, transient alteration of protein expression maintains the tumor-derived TCR repertoire.

In some embodiments, transient alteration of protein results in altered expression of a particular gene. In some embodiments, the transient alteration of protein expression targets a gene including but not limited to PD-1 (also referred to as PDCD1 or CC279), TGFBR2, CCR4/5, CBLB (CBL-B), CISH, CCRs (chimeric co-stimulatory receptors), IL-2, IL-12, IL-15, IL-21, NOTCH 1/2 ICD, TIM3, LAG3, TIGIT, TGFβ, CCR2, CCR4, CCR5, CXCR1, CXCR2, CSCR3, CCL2 (MCP-1), CCL3 (MIP-1α), CCL4 (MIP1β), CCL5 (RANTES), CXCL1/CXCL8, CCL22, CCL17, CXCL1/CXCL8, VHL, CD44, PIK3CD, SOCS1, and/or cAMP protein kinase A (PKA). In some embodiments, the transient alteration of protein expression targets a gene selected from the group consisting of PD-1, TGFBR2, CCR4/5, CBLB (CBL-B), CISH, CCRs (chimeric co-stimulatory receptors), IL-2, IL-12, IL-15, IL-21, NOTCH 1/2 ICD, TIM3, LAG3, TIGIT, TGFβ, CCR2, CCR4, CCR5, CXCR1, CXCR2, CSCR3, CCL2 (MCP-1), CCL3 (MIP-1α), CCL4 (MIP1β), CCL5 (RANTES), CXCL1/CXCL8, CCL22, CCL17, CXCL1/CXCL8, VHL, CD44, PIK3CD, SOCS1, and/or cAMP protein kinase A (PKA). In some embodiments, the transient alteration of protein expression targets PD-1. In some embodiments, the transient alteration of protein expression targets TGFBR2. In some embodiments, the transient alteration of protein expression targets CCR4/5. In some embodiments, the transient alteration of protein expression targets CBLB. In some embodiments, the transient alteration of protein expression targets CISH. In some embodiments, the transient alteration of protein expression targets CCRs (chimeric co-stimulatory receptors). In some embodiments, the transient alteration of protein expression targets IL-2. In some embodiments, the transient alteration of protein expression targets IL-12. In some embodiments, the transient alteration of protein expression targets IL-15. In some embodiments, the transient alteration of protein expression targets IL-21. In some embodiments, the transient alteration of protein expression targets NOTCH 1/2 ICD. In some embodiments, the transient alteration of protein expression targets TIM3. In some embodiments, the transient alteration of protein expression targets LAG3. In some embodiments, the transient alteration of protein expression targets TIGIT. In some embodiments, the transient alteration of protein expression targets TGFβ. In some embodiments, the transient alteration of protein expression targets CCR1. In some embodiments, the transient alteration of protein expression targets CCR2. In some embodiments, the transient alteration of protein expression targets CCR4. In some embodiments, the transient alteration of protein expression targets CCR5. In some embodiments, the transient alteration of protein expression targets CXCR1. In some embodiments, the transient alteration of protein expression targets CXCR2. In some embodiments, the transient alteration of protein expression targets CSCR3. In some embodiments, the transient alteration of protein expression targets CCL2 (MCP-1). In some embodiments, the transient alteration of protein expression targets CCL3 (MIP-1α). In some embodiments, the transient alteration of protein expression targets CCL4 (MIP1β). In some embodiments, the transient alteration of protein expression targets CCL5 (RANTES). In some embodiments, the transient alteration of protein expression targets CXCL1. In some embodiments, the transient alteration of protein expression targets CXCL8. In some embodiments, the transient alteration of protein expression targets CCL22. In some embodiments, the transient alteration of protein expression targets CCL17. In some embodiments, the transient alteration of protein expression targets VHL. In some embodiments, the transient alteration of protein expression targets CD44. In some embodiments, the transient alteration of protein expression targets PIK3CD. In some embodiments, the transient alteration of protein expression targets SOCS1. In some embodiments, the transient alteration of protein expression targets cAMP protein kinase A (PKA).

In some embodiments, the transient alteration of protein expression results in increased and/or overexpression of a chemokine receptor. In some embodiments, the chemokine receptor that is overexpressed by transient protein expression includes a receptor with a ligand that includes but is not limited to CCL2 (MCP-1), CCL3 (MIP-1α), CCL4 (MIP1β), CCL5 (RANTES), CXCL1, CXCL8, CCL22, and/or CCL17.

In some embodiments, the transient alteration of protein expression results in a decrease and/or reduced expression of PD-1, CTLA-4, TIM3, LAG3, TIGIT, TGFβR2, and/or TGFβ (including resulting in, for example, TGFβ pathway blockade). In some embodiments, the transient alteration of protein expression results in a decrease and/or reduced expression of CBLB (CBL-B). In some embodiments, the transient alteration of protein expression results in a decrease and/or reduced expression of CISH.

In some embodiments, the transient alteration of protein expression results in increased and/or overexpression of chemokine receptors in order to, for example, improve TIL trafficking or movement to the tumor site. In some embodiments, the transient alteration of protein expression results in increased and/or overexpression of a CCR (chimeric co-stimulatory receptor). In some embodiments, the transient alteration of protein expression results in increased and/or overexpression of a chemokine receptor selected from the group consisting of CCR1, CCR2, CCR4, CCR5, CXCR1, CXCR2, and/or CSCR3.

In some embodiments, the transient alteration of protein expression results in increased and/or overexpression of an interleukin. In some embodiments, the transient alteration of protein expression results in increased and/or overexpression of an interleukin selected from the group consisting of IL-2, IL-12, IL-15, and/or IL-21.

In some embodiments, the transient alteration of protein expression results in increased and/or overexpression of NOTCH 1/2 ICD. In some embodiments, the transient alteration of protein expression results in increased and/or overexpression of VHL. In some embodiments, the transient alteration of protein expression results in increased and/or overexpression of CD44. In some embodiments, the transient alteration of protein expression results in increased and/or overexpression of PIK3CD. In some embodiments, the transient alteration of protein expression results in increased and/or overexpression of SOCS1, In some embodiments, the transient alteration of protein expression results in decreased and/or reduced expression of cAMP protein kinase A (PKA).

In some embodiments, the transient alteration of protein expression results in decreased and/or reduced expression of a molecule selected from the group consisting of PD-1, LAG3, TIM3, CTLA-4, TIGIT, CISH, TGFβR2, PKA, CBLB, BAFF (BR3), and combinations thereof. In some embodiments, the transient alteration of protein expression results in decreased and/or reduced expression of two molecules selected from the group consisting of PD-1, LAG3, TIM3, CTLA-4, TIGIT, CISH, TGFβR2, PKA, CBLB, BAFF (BR3), and combinations thereof. In some embodiments, the transient alteration of protein expression results in decreased and/or reduced expression of PD-1 and one molecule selected from the group consisting of LAG3, TIM3, CTLA-4, TIGIT, CISH, TGFβR2, PKA, CBLB, BAFF (BR3), and combinations thereof. In some embodiments, the transient alteration of protein expression results in decreased and/or reduced expression of PD-1, LAG3, CISH, CBLB, TIM3, and combinations thereof. In some embodiments, the transient alteration of protein expression results in decreased and/or reduced expression of PD-1 and one of LAG3, CISH, CBLB, TIM3, and combinations thereof. In some embodiments, the transient alteration of protein expression results in decreased and/or reduced expression of PD-1 and LAG3. In some embodiments, the transient alteration of protein expression results in decreased and/or reduced expression of PD-1 and CISH. In some embodiments, the transient alteration of protein expression results in decreased and/or reduced expression of PD-1 and CBLB. In some embodiments, the transient alteration of protein expression results in decreased and/or reduced expression of LAG3 and CISH. In some embodiments, the transient alteration of protein expression results in decreased and/or reduced expression of LAG3 and CBLB. In some embodiments, the transient alteration of protein expression results in decreased and/or reduced expression of CISH and CBLB. In some embodiments, the transient alteration of protein expression results in decreased and/or reduced expression of TIM3 and PD-1. In some embodiments, the transient alteration of protein expression results in decreased and/or reduced expression of TIM3 and LAG3. In some embodiments, the transient alteration of protein expression results in decreased and/or reduced expression of TIM3 and CISH. In some embodiments, the transient alteration of protein expression results in decreased and/or reduced expression of TIM3 and CBLB.

In some embodiments, an adhesion molecule selected from the group consisting of CCR2, CCR4, CCR5, CXCR2, CXCR3, CX3CR1, and combinations thereof, is inserted by a gammaretroviral or lentiviral method into the first population of TILs, second population of TILs, or harvested population of TILs (e.g., the expression of the adhesion molecule is increased).

In some embodiments, the transient alteration of protein expression results in decreased and/or reduced expression of a molecule selected from the group consisting of PD-1, LAG3, TIM3, CTLA-4, TIGIT, CISH, TGFβR2, PKA, CBLB, BAFF (BR3), and combinations thereof, and increased and/or enhanced expression of CCR2, CCR4, CCR5, CXCR2, CXCR3, CX3CR1, and combinations thereof. In some embodiments, the transient alteration of protein expression results in decreased and/or reduced expression of a molecule selected from the group consisting of PD-1, LAG3, TIM3, CISH, CBLB, and combinations thereof, and increased and/or enhanced expression of CCR2, CCR4, CCR5, CXCR2, CXCR3, CX3CR1, and combinations thereof.

In some embodiments, there is a reduction in expression of about 5%, about 10%, about 10%, about 20%, about 25%, about 30%, about 35%, about 40%, about 45%, about 50%, about 55%, about 60%, about 65%, about 70%, about 75%, about 80%, about 85%, about 90%, or about 95%. In some embodiments, there is a reduction in expression of at least about 65%, about 70%, about 75%, about 80%, about 85%, about 90%, or about 95%. In some embodiments, there is a reduction in expression of at least about 75%, about 80%, about 85%, about 90%, or about 95%. In some embodiments, there is a reduction in expression of at least about 80%, about 85%, about 90%, or about 95%. In some embodiments, there is a reduction in expression of at least about 85%, about 90%, or about 95%. In some embodiments, there is a reduction in expression of at least about 80%. In some embodiments, there is a reduction in expression of at least about 85%, In some embodiments, there is a reduction in expression of at least about 90%. In some embodiments, there is a reduction in expression of at least about 95%. In some embodiments, there is a reduction in expression of at least about 99%.

In some embodiments, there is an increase in expression of about 5%, about 10%, about 10%, about 20%, about 25%, about 30%, about 35%, about 40%, about 45%, about 50%, about 55%, about 60%, about 65%, about 70%, about 75%, about 80%, about 85%, about 90%, or about 95%. In some embodiments, there is an increase in expression of at least about 65%, about 70%, about 75%, about 80%, about 85%, about 90%, or about 95%. In some embodiments, there is an increase in expression of at least about 75%, about 80%, about 85%, about 90%, or about 95%. In some embodiments, there is an increase in expression of at least about 80%, about 85%, about 90%, or about 95%. In some embodiments, there is an increase in expression of at least about 85%, about 90%, or about 95%. In some embodiments, there is an increase in expression of at least about 80%. In some embodiments, there is an increase in expression of at least about 85%, In some embodiments, there is an increase in expression of at least about 90%. In some embodiments, there is an increase in expression of at least about 95%. In some embodiments, there is an increase in expression of at least about 99%.

In some embodiments, transient alteration of protein expression is induced by treatment of the TILs with transcription factors (TFs) and/or other molecules capable of transiently altering protein expression in the TILs. In some embodiments, the SQZ vector-free microfluidic platform is employed for intracellular delivery of the transcription factors (TFs) and/or other molecules capable of transiently altering protein expression. Such methods demonstrating the ability to deliver proteins, including transcription factors, to a variety of primary human cells, including T cells (Sharei et al. PNAS 2013, as well as Sharei et al. PLOS ONE 2015 and Greisbeck et al. J. Immunology vol. 195, 2015) have been described; see, for example, International Patent Publications WO 2013/059343A1, WO 2017/008063A1, and WO 2017/123663A1, all of which are incorporated by reference herein in their entireties. Such methods as described in International Patent Publications WO 2013/059343A1, WO 2017/008063A1, and WO 2017/123663A1 can be employed with the present invention in order to expose a population of TILs to transcription factors (TFs) and/or other molecules capable of inducing transient protein expression, wherein said TFs and/or other molecules capable of inducing transient protein expression provide for increased expression of tumor antigens and/or an increase in the number of tumor antigen-specific T cells in the population of TILs, thus resulting in reprogramming of the TIL population and an increase in therapeutic efficacy of the reprogrammed TIL population as compared to a non-reprogrammed TIL population. In some embodiments, the reprogramming results in an increased subpopulation of effector T cells and/or central memory T cells relative to the starting or prior population (i.e., prior to reprogramming) population of TILs, as described herein.

In some embodiments, the transcription factor (TF) includes but is not limited to TCF-1, NOTCH 1/2 ICD, and/or MYB. In some embodiments, the transcription factor (TF) is TCF-1. In some embodiments, the transcription factor (TF) is NOTCH 1/2 ICD. In some embodiments, the transcription factor (TF) is MYB. In some embodiments, the transcription factor (TF) is administered with induced pluripotent stem cell culture (iPSC), such as the commercially available KNOCKOUT Serum Replacement (Gibco/ThermoFisher), to induce additional TIL reprogramming. In some embodiments, the transcription factor (TF) is administered with an iPSC cocktail to induce additional TIL reprogramming. In some embodiments, the transcription factor (TF) is administered without an iPSC cocktail. In some embodiments, reprogramming results in an increase in the percentage of TSCMs. In some embodiments, reprogramming results in an increase in the percentage of TSCMs by about 5%, about 10%, about 10%, about 20%, about 25%, about 30%, about 35%, about 40%, about 45%, about 50%, about 55%, about 60%, about 65%, about 70%, about 75%, about 80%, about 85%, about 90%, or about 95% TSCMs.

In some embodiments, a method of transient altering protein expression, as described above, may be combined with a method of genetically modifying a population of TILs includes the step of stable incorporation of genes for production of one or more proteins. In certain embodiments, the method comprises a step of genetically modifying a population of TILs. In certain embodiments, the method comprises genetically modifying the first population of TILs, the second population of TILs and/or the third population of TILs. In an embodiment, a method of genetically modifying a population of TILs includes the step of retroviral transduction. In an embodiment, a method of genetically modifying a population of TILs includes the step of lentiviral transduction. Lentiviral transduction systems are known in the art and are described, e.g., in Levine, et al., *Proc. Nat'l Acad. Sci.* 2006, 103, 17372-77; Zufferey, et al., *Nat. Biotechnol.* 1997, 15, 871-75; Dull, et al., *J. Virology* 1998, 72, 8463-71, and U.S. Pat. No. 6,627,442, the disclosures of each of which are incorporated by reference herein. In an embodiment, a method of genetically modifying a population of TILs includes the step of gamma-retroviral transduction. Gamma-retroviral transduction systems are known in the art and are described, e.g., Cepko and Pear, *Cur. Prot. Mol. Biol.* 1996, 9.9.1-9.9.16, the disclosure of which is incorporated by reference herein. In an embodiment, a method of genetically modifying a population of TILs includes the step of transposon-mediated gene transfer. Transposon-mediated gene transfer systems are known in the art and include systems wherein the transposase is provided as DNA expression vector or as an expressible RNA or a protein such that long-term expression of the transposase does not occur in the transgenic cells, for example, a transposase provided as an mRNA (e.g., an mRNA comprising a cap and poly-A tail). Suitable transposon-mediated gene transfer systems, including the salmonid-type Tel-like transposase (SB or Sleeping Beauty transposase), such as SB10, SB11, and SB100×, and engineered enzymes with increased enzymatic activity, are described in, e.g., Hackett, et al., *Mol. Therapy* 2010, 18, 674-83 and U.S. Pat. No. 6,489,458, the disclosures of each of which are incorporated by reference herein.

In some embodiments, transient alteration of protein expression is a reduction in expression induced by self-delivering RNA interference (sdRNA), which is a chemically-synthesized asymmetric siRNA duplex with a high percentage of 2'-OH substitutions (typically fluorine or —$OCH_3$) which comprises a 20-nucleotide antisense (guide) strand and a 13 to 15 base sense (passenger) strand conjugated to cholesterol at its 3' end using a tetraethylenglycol (TEG) linker. In some embodiments, the method comprises transient alteration of protein expression in a population of TILs, comprising the use of self-delivering RNA interference (sdRNA), which is a chemically-synthesized asymmetric siRNA duplex with a high percentage of 2'-OH substitutions (typically fluorine or —$OCH_3$) which comprises a 20-nucleotide antisense (guide) strand and a 13 to 15 base sense (passenger) strand conjugated to cholesterol at its 3' end using a tetraethylenglycol (TEG) linker. Methods of using sdRNA have been described in Khvorova and Watts, *Nat. Biotechnol.* 2017, 35, 238-248; Byrne, et al., *J. Ocul. Pharmacol. Ther.* 2013, 29, 855-864; and Ligtenberg, et al., *Mol. Therapy,* 2018, in press, the disclosures of which are incorporated by reference herein. In an embodiment, delivery of sdRNA to a TIL population is accomplished without use of electroporation, SQZ, or other methods, instead using a 1 to 3 day period in which a TIL population is exposed to sdRNA at a concentration of 1 μM/10,000 TILs in medium. In certain embodiments, the method comprises delivery sdRNA to a TILs population comprising exposing the TILs population to sdRNA at a concentration of 1 μM/10,000 TILs in medium for a period of between 1 to 3 days. In an embodiment, delivery of sdRNA to a TIL population is accomplished using a 1 to 3 day period in which a TIL population is exposed to sdRNA at a concentration of 10 μM/10,000 TILs in medium. In an embodiment, delivery of sdRNA to a TIL population is accomplished using a 1 to 3 day period in which a TIL population is exposed to sdRNA at a concentration of 50 μM/10,000 TILs in medium. In an embodiment, delivery of sdRNA to a TIL population is accomplished using a 1 to 3 day period in which a TIL population is exposed to sdRNA at a concentration of between 0.1 μM/10,000 TILs and 50 μM/10,000 TILs in medium. In an embodiment, delivery of sdRNA to a TIL population is accomplished using a 1 to 3 day period in which a TIL population is exposed to sdRNA at a concentration of between 0.1 μM/10,000 TILs and 50 μM/10,000 TILs in medium, wherein the exposure to sdRNA is performed two, three, four, or five times by addition of fresh sdRNA to the media. Other suitable processes are described, for example, in U.S. Patent Application Publication No. US 2011/0039914 A1, US 2013/0131141 A1, and US 2013/0131142 A1, and U.S. Pat. No. 9,080,171, the disclosures of which are incorporated by reference herein.

In some embodiments, sdRNA is inserted into a population of TILs during manufacturing. In some embodiments, the sdRNA encodes RNA that interferes with NOTCH 1/2 ICD, PD-1, CTLA-4, TIM3, LAG3, TIGIT, TGFβ, TGFBR2, cAMP protein kinase A (PKA), BAFF BR3, CISH, and/or CBLB. In some embodiments, the reduction in expression is determined based on a percentage of gene silencing, for example, as assessed by flow cytometry and/or qPCR. In some embodiments, there is a reduction in expression of about 5%, about 10%, about 10%, about 20%, about 25%, about 30%, about 35%, about 40%, about 45%, about 50%, about 55%, about 60%, about 65%, about 70%, about 75%, about 80%, about 85%, about 90%, or about 95%. In some embodiments, there is a reduction in expression of at least about 65%, about 70%, about 75%, about 80%, about 85%, about 90%, or about 95%. In some embodiments, there is a reduction in expression of at least about 75%, about 80%, about 85%, about 90%, or about 95%. In some embodiments, there is a reduction in expression of at least about 80%, about 85%, about 90%, or about 95%. In some embodiments, there is a reduction in expression of at least about 85%, about 90%, or about 95%. In some embodiments, there is a reduction in expression of at least about 80%. In some embodiments, there is a reduction in expression of at least about 85%, In some embodiments, there is a reduction in expression of at least about 90%. In some embodiments, there is a reduction in expression of at least about 95%. In some embodiments, there is a reduction in expression of at least about 99%.

The self-deliverable RNAi technology based on the chemical modification of siRNAs can be employed with the methods of the present invention to successfully deliver the sdRNAs to the TILs as described herein. The combination of backbone modifications with asymmetric siRNA structure and a hydrophobic ligand (see, for example, Ligtenberg, et al., *Mol. Therapy,* 2018 and US20160304873) allow sdRNAs to penetrate cultured mammalian cells without additional formulations and methods by simple addition to the culture media, capitalizing on the nuclease stability of sdRNAs. This stability allows the support of constant levels of RNAi-mediated reduction of target gene activity simply by maintaining the active concentration of sdRNA in the media. While not being bound by theory, the backbone stabilization of sdRNA provides for extended reduction in gene expression effects which can last for months in non-dividing cells.

In some embodiments, over 95% transfection efficiency of TILs and a reduction in expression of the target by various specific sdRNA occurs. In some embodiments, sdRNAs containing several unmodified ribose residues were replaced with fully modified sequences to increase potency and/or the longevity of RNAi effect. In some embodiments, a reduction in expression effect is maintained for 12 hours, 24 hours, 36 hours, 48 hours, 5 days, 6 days, 7 days, or 8 days or more. In some embodiments, the reduction in expression effect decreases at 10 days or more post sdRNA treatment of the TILs. In some embodiments, more than 70% reduction in expression of the target expression is maintained. In some embodiments, more than 70% reduction in expression of the target expression is maintained TILs. In some embodiments, a reduction in expression in the PD-1/PD-L1 pathway allows for the TILs to exhibit a more potent in vivo effect, which is in some embodiments, due to the avoidance of the suppressive effects of the PD-1/PD-L1 pathway. In some embodiments, a reduction in expression of PD-1 by sdRNA results in an increase TIL proliferation.

Small interfering RNA (siRNA), sometimes known as short interfering RNA or silencing RNA, is a double stranded RNA molecule, generally 19-25 base pairs in length. siRNA is used in RNA interference (RNAi), where it interferes with expression of specific genes with complementary nucleotide sequences.

Double stranded DNA (dsRNA) can be generally used to define any molecule comprising a pair of complementary strands of RNA, generally a sense (passenger) and antisense (guide) strands, and may include single-stranded overhang regions. The term dsRNA, contrasted with siRNA, generally refers to a precursor molecule that includes the sequence of an siRNA molecule which is released from the larger dsRNA molecule by the action of cleavage enzyme systems, including Dicer.

sdRNA (self-deliverable RNA) are a new class of covalently modified RNAi compounds that do not require a delivery vehicle to enter cells and have improved pharmacology compared to traditional siRNAs. "Self-deliverable RNA" or "sdRNA" is a hydrophobically modified RNA interfering-antisense hybrid, demonstrated to be highly efficacious in vitro in primary cells and in vivo upon local administration. Robust uptake and/or silencing without toxicity has been demonstrated. sdRNAs are generally asymmetric chemically modified nucleic acid molecules with minimal double stranded regions. sdRNA molecules typically contain single stranded regions and double stranded regions, and can contain a variety of chemical modifications within both the single stranded and double stranded regions of the molecule. Additionally, the sdRNA molecules can be attached to a hydrophobic conjugate such as a conventional and advanced sterol-type molecule, as described herein. sdRNAs and associated methods for making such sdRNAs have also been described extensively in, for example, US20160304873, WO2010033246, WO2017070151, WO2009102427, WO2011119887, WO2010033247A2, WO2009045457, WO2011119852, all of which are incorporated by reference herein in their entireties for all purposes. To optimize sdRNA structure, chemistry, targeting position, sequence preferences, and the like, a proprietary algorithm has been developed and utilized for sdRNA potency prediction (see, for example, US 20160304873). Based on these analyses, functional sdRNA sequences have been generally defined as having over 70% reduction in expression at 1 μM concentration, with a probability over 40%.

In some embodiments, the sdRNA sequences used in the invention exhibit a 70% reduction in expression of the target gene. In some embodiments, the sdRNA sequences used in the invention exhibit a 75% reduction in expression of the target gene. In some embodiments, the sdRNA sequences used in the invention exhibit an 80% reduction in expression of the target gene. In some embodiments, the sdRNA sequences used in the invention exhibit an 85% reduction in expression of the target gene. In some embodiments, the sdRNA sequences used in the invention exhibit a 90% reduction in expression of the target gene. In some embodiments, the sdRNA sequences used in the invention exhibit a 95% reduction in expression of the target gene. In some embodiments, the sdRNA sequences used in the invention exhibit a 99% reduction in expression of the target gene. In some embodiments, the sdRNA sequences used in the invention exhibit a reduction in expression of the target gene when delivered at a concentration of about 0.25 μM to about 4 μM. In some embodiments, the sdRNA sequences used in the invention exhibit a reduction in expression of the target gene when delivered at a concentration of about 0.25 μM. In some embodiments, the sdRNA sequences used in the invention exhibit a reduction in expression of the target gene when delivered at a concentration of about 0.5 μM. In some embodiments, the sdRNA sequences used in the invention exhibit a reduction in expression of the target gene when delivered at a concentration of about 0.75 μM. In some embodiments, the sdRNA sequences used in the invention exhibit a reduction in expression of the target gene when delivered at a concentration of about 1.0 μM. In some embodiments, the sdRNA sequences used in the invention exhibit a reduction in expression of the target gene when delivered at a concentration of about 1.25 μM. In some embodiments, the sdRNA sequences used in the invention exhibit a reduction in expression of the target gene when delivered at a concentration of about 1.5 μM. In some embodiments, the sdRNA sequences used in the invention exhibit a reduction in expression of the target gene when delivered at a concentration of about 1.75 μM. In some embodiments, the sdRNA sequences used in the invention exhibit a reduction in expression of the target gene when delivered at a concentration of about 2.0 μM. In some embodiments, the sdRNA sequences used in the invention exhibit a reduction in expression of the target gene when delivered at a concentration of about 2.25 μM. In some embodiments, the sdRNA sequences used in the invention exhibit a reduction in expression of the target gene when delivered at a concentration of about 2.5 μM. In some embodiments, the sdRNA sequences used in the invention exhibit a reduction in expression of the target gene when delivered at a concentration of about 2.75 μM. In some embodiments, the sdRNA sequences used in the invention exhibit a reduction in expression of the target gene when delivered at a concentration of about 3.0 μM. In some embodiments, the sdRNA sequences used in the invention exhibit a reduction in expression of the target gene when delivered at a concentration of about 3.25 μM. In some embodiments, the sdRNA sequences used in the invention exhibit a reduction in expression of the target gene when delivered at a concentration of about 3.5 μM. In some embodiments, the sdRNA sequences used in the invention exhibit a reduction in expression of the target gene when delivered at a concentration of about 3.75 μM. In some embodiments, the sdRNA sequences used in the invention exhibit a reduction in expression of the target gene when delivered at a concentration of about 4.0 μM.

In some embodiments, the oligonucleotide agents comprise one or more modification to increase stability and/or effectiveness of the therapeutic agent, and to effect efficient delivery of the oligonucleotide to the cells or tissue to be treated. Such modifications can include a 2'-O-methyl modification, a 2'-O-Fluro modification, a diphosphorothioate modification, 2' F modified nucleotide, a2'-O-methyl modified and/or a 2'deoxy nucleotide. In some embodiments, the oligonucleotide is modified to include one or more hydrophobic modifications including, for example, sterol, cholesterol, vitamin D, naphtyl, isobutyl, benzyl, indol, tryptophane, and/or phenyl. In an additional particular embodiment, chemically modified nucleotides are combination of phosphorothioates, 2'-O-methyl, 2'deoxy, hydrophobic modifications and phosphorothioates. In some embodiments, the sugars can be modified and modified sugars can include but are not limited to D-ribose, 2'-O-alkyl (including 2'-O-methyl and 2'-O-ethyl), i.e., 2'-alkoxy, 2-amino, 2'-S-alkyl, 2'-halo (including 2'-fluoro), T-methoxyethoxy, 2'-allyloxy (—$OCH_2CH$═$CH_2$), 2'-propargyl, 2'-propyl, ethynyl, ethenyl, propenyl, and cyano and the like. In one embodiment, the sugar moiety can be a hexose and incorporated into an oligonucleotide as described in Augustyns, et al., *Nucl. Acids. Res.* 1992, 18, 4711.

In some embodiments, the double-stranded oligonucleotide of the invention is double-stranded over its entire length, i.e., with no overhanging single-stranded sequence at either end of the molecule, i.e., is blunt-ended. In some embodiments, the individual nucleic acid molecules can be of different lengths. In other words, a double-stranded oligonucleotide of the invention is not double-stranded over its entire length. For instance, when two separate nucleic acid molecules are used, one of the molecules, e.g., the first molecule comprising an antisense sequence, can be longer than the second molecule hybridizing thereto (leaving a portion of the molecule single-stranded). In some embodiments, when a single nucleic acid molecule is used a portion of the molecule at either end can remain single-stranded.

In some embodiments, a double-stranded oligonucleotide of the invention contains mismatches and/or loops or bulges, but is double-stranded over at least about 70% of the length of the oligonucleotide. In some embodiments, a double-stranded oligonucleotide of the invention is double-stranded over at least about 80% of the length of the oligonucleotide. In another embodiment, a double-stranded oligonucleotide of the invention is double-stranded over at least about 90%-95% of the length of the oligonucleotide. In some embodiments, a double-stranded oligonucleotide of the invention is double-stranded over at least about 96%-98% of the length of the oligonucleotide. In some embodiments, the double-stranded oligonucleotide of the invention contains at least or up to 1, 2, 3, 4, 5, 6, 7, 8, 9, 10, 11, 12, 13, 14, or 15 mismatches.

In some embodiments, the oligonucleotide can be substantially protected from nucleases e.g., by modifying the 3' or 5' linkages (e.g., U.S. Pat. No. 5,849,902 and WO 98/13526). For example, oligonucleotides can be made resistant by the inclusion of a "blocking group." The term "blocking group" as used herein refers to substituents (e.g., other than OH groups) that can be attached to oligonucleotides or nucleomonomers, either as protecting groups or coupling groups for synthesis (e.g., FITC, propyl ($CH_2$—$CH_2$—$CH_3$), glycol (—O—$CH_2$—$CH_2$—O—) phosphate ($PO_3^{2-}$), hydrogen phosphonate, or phosphoramidite). "Blocking groups" can also include "end blocking groups" or "exonuclease blocking groups" which protect the 5' and 3' termini of the oligonucleotide, including modified nucleotides and non-nucleotide exonuclease resistant structures.

In some embodiments, at least a portion of the contiguous polynucleotides within the sdRNA are linked by a substitute linkage, e.g., a phosphorothioate linkage.

In some embodiments, chemical modification can lead to at least a 1.5, 2, 3, 4, 5, 6, 7, 8, 9, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 225, 250, 275, 300, 325, 350, 375, 400, 425, 450, 475, 500 enhancements in cellular uptake. In some embodiments, at least one of the C or U residues includes a hydrophobic modification. In some embodiments, a plurality of Cs and Us contain a hydrophobic modification. In some embodiments, at least 10%, 15%, 20%, 30%, 40%, 50%, 55%, 60% 65%, 70%, 75%, 80%, 85%, 90% or at least 95% of the Cs and Us can contain a hydrophobic modification. In some embodiments, all of the Cs and Us contain a hydrophobic modification.

In some embodiments, the sdRNA or sd-rxRNAs exhibit enhanced endosomal release of sd-rxRNA molecules through the incorporation of protonatable amines. In some embodiments, protonatable amines are incorporated in the sense strand (in the part of the molecule which is discarded after RISC loading). In some embodiments, the sdRNA compounds of the invention comprise an asymmetric compound comprising a duplex region (required for efficient RISC entry of $10^{-15}$ bases long) and single stranded region of 4-12 nucleotides long; with a 13 nucleotide duplex. In some embodiments, a 6 nucleotide single stranded region is employed. In some embodiments, the single stranded region of the sdRNA comprises 2-12 phosphorothioate internucleotide linkages (referred to as phosphorothioate modifications). In some embodiments, 6-8 phosphorothioate internucleotide linkages are employed. In some embodiments, the sdRNA compounds of the invention also include a unique chemical modification pattern, which provides stability and is compatible with RISC entry.

The guide strand, for example, may also be modified by any chemical modification which confirms stability without interfering with RISC entry. In some embodiments, the chemical modification pattern in the guide strand includes the majority of C and U nucleotides being 2' F modified and the 5' end being phosphorylated.

In some embodiments, at least 30% of the nucleotides in the sdRNA or sd-rxRNA are modified. In some embodiments, at least 30%, 31%, 32%, 33%, 34%, 35%, 36%, 37%, $3^{8}$%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the nucleotides in the sdRNA or sd-rxRNA are modified. In some embodiments, 100% of the nucleotides in the sdRNA or sd-rxRNA are modified.

In some embodiments, the sdRNA molecules have minimal double stranded regions. In some embodiments the region of the molecule that is double stranded ranges from 8-15 nucleotides long. In some embodiments, the region of the molecule that is double stranded is 8, 9, 10, 11, 12, 13, 14 or 15 nucleotides long. In some embodiments the double stranded region is 13 nucleotides long. There can be 100% complementarity between the guide and passenger strands, or there may be one or more mismatches between the guide and passenger strands. In some embodiments, on one end of the double stranded molecule, the molecule is either blunt-ended or has a one-nucleotide overhang. The single stranded region of the molecule is in some embodiments between 4-12 nucleotides long. In some embodiments, the single stranded region can be 4, 5, 6, 7, 8, 9, 10, 11 or 12 nucleotides long. In some embodiments, the single stranded region can also be less than 4 or greater than 12 nucleotides long. In certain embodiments, the single stranded region is 6 or 7 nucleotides long.

In some embodiments, the sdRNA molecules have increased stability. In some instances, a chemically modified sdRNA or sd-rxRNA molecule has a half-life in media that is longer than 1, 2, 3, 4, 5, 6, 7, 8, 9, 10, 11, 12, 13, 14, 15, 16, 17, 18, 19, 20, 21, 22, 23, 24 or more than 24 hours, including any intermediate values. In some embodiments, the sd-rxRNA has a half-life in media that is longer than 12 hours.

In some embodiments, the sdRNA is optimized for increased potency and/or reduced toxicity. In some embodiments, nucleotide length of the guide and/or passenger strand, and/or the number of phosphorothioate modifications in the guide and/or passenger strand, can in some aspects influence potency of the RNA molecule, while replacing 2'-fluoro (2'F) modifications with 2'-O-methyl (2'OMe) modifications can in some aspects influence toxicity of the molecule. In some embodiments, reduction in 2'F content of a molecule is predicted to reduce toxicity of the molecule. In some embodiments, the number of phosphorothioate modifications in an RNA molecule can influence the uptake of the molecule into a cell, for example the efficiency of passive uptake of the molecule into a cell. In some embodiments, the sdRNA has no 2'F modification and yet are characterized by equal efficacy in cellular uptake and tissue penetration.

In some embodiments, a guide strand is approximately 18-19 nucleotides in length and has approximately 2-14 phosphate modifications. For example, a guide strand can contain 2, 3, 4, 5, 6, 7, 8, 9, 10, 11, 12, 13, 14 or more than 14 nucleotides that are phosphate-modified. The guide strand may contain one or more modifications that confer increased stability without interfering with RISC entry. The phosphate modified nucleotides, such as phosphorothioate modified nucleotides, can be at the 3' end, 5' end or spread throughout the guide strand. In some embodiments, the 3' terminal 10 nucleotides of the guide strand contain 1, 2, 3, 4, 5, 6, 7, 8, 9 or 10 phosphorothioate modified nucleotides. The guide strand can also contain 2'F and/or 2'OMe modifications, which can be located throughout the molecule. In some embodiments, the nucleotide in position one of the guide strand (the nucleotide in the most 5' position of the guide strand) is 2'OMe modified and/or phosphorylated. C and U nucleotides within the guide strand can be 2'F modified. For example, C and U nucleotides in positions 2-10 of a 19 nt guide strand (or corresponding positions in a guide strand of a different length) can be 2'F modified. C and U nucleotides within the guide strand can also be 2'OMe modified. For example, C and U nucleotides in positions 11-18 of a 19 nt guide strand (or corresponding positions in a guide strand of a different length) can be 2'OMe modified. In some embodiments, the nucleotide at the most 3' end of the guide strand is unmodified. In certain embodiments, the majority of Cs and Us within the guide strand are 2'F modified and the 5' end of the guide strand is phosphorylated. In other embodiments, position 1 and the Cs or Us in positions 11-18 are 2'OMe modified and the 5' end of the guide strand is phosphorylated. In other embodiments, position 1 and the Cs or Us in positions 11-18 are 2'OMe modified, the 5' end of the guide strand is phosphorylated, and the Cs or Us in position 2-10 are 2'F modified.

The self-deliverable RNAi technology provides a method of directly transfecting cells with the RNAi agent, without the need for additional formulations or techniques. The ability to transfect hard-to-transfect cell lines, high in vivo activity, and simplicity of use, are characteristics of the compositions and methods that present significant functional advantages over traditional siRNA-based techniques, and as such, the sdRNA methods are employed in several embodiments related to the methods of reduction in expression of the target gene in the TILs of the present invention. The sdRNAi methods allows direct delivery of chemically synthesized compounds to a wide range of primary cells and tissues, both ex-vivo and in vivo. The sdRNAs described in some embodiments of the invention herein are commercially available from Advirna LLC, Worcester, MA, USA.

The sdRNA are formed as hydrophobically-modified siRNA-antisense oligonucleotide hybrid structures, and are disclosed, for example in Byrne et al., December 2013, J. Ocular Pharmacology and Therapeutics, 29(10): 855-864, incorporated by reference herein in its entirety.

In some embodiments, the sdRNA oligonucleotides can be delivered to the TILs described herein using sterile electroporation. In certain embodiments, the method comprises sterile electroporation of a population of TILs to deliver sdRNA oligonucleotides.

In some embodiments, the oligonucleotides can be delivered to the cells in combination with a transmembrane delivery system. In some embodiments, this transmembrane delivery system comprises lipids, viral vectors, and the like. In some embodiments, the oligonucleotide agent is a self-delivery RNAi agent, that does not require any delivery agents. In certain embodiments, the method comprises use of a transmembrane delivery system to deliver sdRNA oligonucleotides to a population of TILs.

Oligonucleotides and oligonucleotide compositions are contacted with (e.g., brought into contact with, also referred to herein as administered or delivered to) and taken up by TILs described herein, including through passive uptake by TILs. The sdRNA can be added to the TILs as described herein during the first expansion, for example Step B, after the first expansion, for example, during Step C, before or during the second expansion, for example before or during Step D, after Step D and before harvest in Step E, during or after harvest in Step F, before or during final formulation and/or transfer to infusion Bag in Step F, as well as before any optional cryopreservation step in Step F. Moreover, sdRNA can be added after thawing from any cryopreservation step in Step F. In an embodiment, one or more sdRNAs targeting genes as described herein, including PD-1, LAG3, TIM3, CISH, and CBLB, may be added to cell culture media comprising TILs and other agents at concentrations selected from the group consisting of 100 nM to 20 mM, 200 nM to 10 mM, 500 nm to 1 mM, 1 μM to 100 μM, and 1 μM to 100 μM. In an embodiment, one or more sdRNAs targeting genes as described herein, including PD-1, LAG3, TIM3, CISH, and CBLB, may be added to cell culture media comprising TILs and other agents at amounts selected from the group consisting of 0.1 μM sdRNA/10,000 TILs/100 μL media, 0.5 μM sdRNA/10,000 TILs/100 μL media, 0.75 μM sdRNA/10,000 TILs/100 μL media, 1 μM sdRNA/10,000 TILs/100 μL media, 1.25 μM sdRNA/10,000 TILs/100 μL media, 1.5 μM sdRNA/10,000 TILs/100 μL media, 2 μM sdRNA/10,000 TILs/100 μL media, 5 μM sdRNA/10,000 TILs/100 μL media, or 10 μM sdRNA/10,000 TILs/100 μL media. In an embodiment, one or more sdRNAs targeting genes as described herein, including PD-1, LAG3, TIM3, CISH, and CBLB, may be added to TIL cultures during the pre-REP or REP stages twice a day, once a day, every two days, every three days, every four days, every five days, every six days, or every seven days.

Oligonucleotide compositions of the invention, including sdRNA, can be contacted with TILs as described herein during the expansion process, for example by dissolving sdRNA at high concentrations in cell culture media and allowing sufficient time for passive uptake to occur. In certain embodiments, the method of the present invention comprises contacting a population of TILs with an oligonucleotide composition as described herein. In certain embodiments, the method comprises dissolving an oligonucleotide e.g. sdRNA in a cell culture media and contacting the cell culture media with a population of TILs. The TILs may be a first population, a second population and/or a third population as described herein.

In some embodiments, delivery of oligonucleotides into cells can be enhanced by suitable art recognized methods including calcium phosphate, DMSO, glycerol or dextran, electroporation, or by transfection, e.g., using cationic, anionic, or neutral lipid compositions or liposomes using methods known in the art (see, e.g., WO 90/14074; WO 91/16024; WO 91/17424; U.S. Pat. No. 4,897,355; Bergan et a 1993. Nucleic Acids Research. 21:3567).

In some embodiments, more than one sdRNA is used to reduce expression of a target gene. In some embodiments, one or more of PD-1, TIM3, CBLB, LAG3 and/or CISH targeting sdRNAs are used together. In some embodiments, a PD-1 sdRNA is used with one or more of TIM3, CBLB, LAG3 and/or CISH in order to reduce expression of more than one gene target. In some embodiments, a LAG3 sdRNA is used in combination with a CISH targeting sdRNA to reduce gene expression of both targets. In some embodiments, the sdRNAs targeting one or more of PD-1, TIM3, CBLB, LAG3 and/or CISH herein are commercially available from Advirna LLC, Worcester, MA, USA.

In some embodiments, the sdRNA targets a gene selected from the group consisting of PD-1, LAG3, TIM3, CTLA-4, TIGIT, CISH, TGFβR2, PKA, CBLB, BAFF (BR3), and combinations thereof. In some embodiments, the sdRNA targets a gene selected from the group consisting of PD-1, LAG3, TIM3, CTLA-4, TIGIT, CISH, TGFβR2, PKA, CBLB, BAFF (BR3), and combinations thereof. In some embodiments, one sdRNA targets PD-1 and another sdRNA targets a gene selected from the group consisting of LAG3, TIM3, CTLA-4, TIGIT, CISH, TGFβR2, PKA, CBLB, BAFF (BR3), and combinations thereof. In some embodiments, the sdRNA targets a gene selected from PD-1, LAG3, CISH, CBLB, TIM3, and combinations thereof. In some embodiments, the sdRNA targets a gene selected from PD-1 and one of LAG3, CISH, CBLB, TIM3, and combinations thereof. In some embodiments, one sdRNA targets PD-1 and one sdRNA targets LAG3. In some embodiments, one sdRNA targets PD-1 and one sdRNA targets CISH. In some embodiments, one sdRNA targets PD-1 and one sdRNA targets CBLB. In some embodiments, one sdRNA targets LAG3 and one sdRNA targets CISH. In some embodiments, one sdRNA targets LAG3 and one sdRNA targets CBLB. In some embodiments, one sdRNA targets CISH and one sdRNA targets CBLB. In some embodiments, one sdRNA targets TIM3 and one sdRNA targets PD-1. In some embodiments, one sdRNA targets TIM3 and one sdRNA targets LAG3. In some embodiments, one sdRNA targets TIM3 and one sdRNA targets CISH. In some embodiments, one sdRNA targets TIM3 and one sdRNA targets CBLB.

As discussed above, embodiments of the present invention provide that have been genetically modified via gene-editing to enhance their therapeutic effect. Embodiments of the present invention embrace genetic editing through nucleotide insertion (RNA or DNA) into a population of TILs for both promotion of the expression of one or more proteins and inhibition of the expression of one or more proteins, as well as combinations thereof. Embodiments of the present invention also provide methods for expanding TILs into a therapeutic population, wherein the methods comprise gene-editing the TILs. There are several gene-editing technologies that may be used to genetically modify a population of TILs, which are suitable for use in accordance with the present invention.

In some embodiments, the method comprises a method of genetically modifying a population of TILs which include the step of stable incorporation of genes for production of one or more proteins. In an embodiment, a method of genetically modifying a population of TILs includes the step of retroviral transduction. In an embodiment, a method of genetically modifying a population of TILs includes the step of lentiviral transduction. Lentiviral transduction systems are known in the art and are described, e.g., in Levine, et al., *Proc. Nat'l Acad. Sci.* 2006, 103, 17372-77; Zufferey, et al., *Nat. Biotechnol.* 1997, 15, 871-75; Dull, et al., *J. Virology* 1998, 72, 8463-71, and U.S. Pat. No. 6,627,442, the disclosures of each of which are incorporated by reference herein. In an embodiment, a method of genetically modifying a population of TILs includes the step of gamma-retroviral transduction. Gamma-retroviral transduction systems are known in the art and are described, e.g., Cepko and Pear, *Cur. Prot. Mol. Biol.* 1996, 9.9.1-9.9.16, the disclosure of which is incorporated by reference herein. In an embodiment, a method of genetically modifying a population of TILs includes the step of transposon-mediated gene transfer. Transposon-mediated gene transfer systems are known in the art and include systems wherein the transposase is provided as DNA expression vector or as an expressible RNA or a protein such that long-term expression of the transposase does not occur in the transgenic cells, for example, a transposase provided as an mRNA (e.g., an mRNA comprising a cap and poly-A tail). Suitable transposon-mediated gene transfer systems, including the salmonid-type Tel-like transposase (SB or Sleeping Beauty transposase), such as SB10, SB11, and SB100x, and engineered enzymes with increased enzymatic activity, are described in, e.g., Hackett, et al., *Mol. Therapy* 2010, 18, 674-83 and U.S. Pat. No. 6,489,458, the disclosures of each of which are incorporated by reference herein.

In an embodiment, the method comprises a method of genetically modifying a population of TILs e.g. a first population, a second population and/or a third population as described herein. In an embodiment, a method of genetically modifying a population of TILs includes the step of stable incorporation of genes for production or inhibition (e.g., silencing) of one ore more proteins. In an embodiment, a method of genetically modifying a population of TILs includes the step of electroporation. Electroporation methods are known in the art and are described, e.g., in Tsong, *Biophys. J.* 1991, 60, 297-306, and U.S. Patent Application Publication No. 2014/0227237 A1, the disclosures of each of which are incorporated by reference herein. Other electroporation methods known in the art, such as those described in U.S. Pat. Nos. 5,019,034; 5,128,257; 5,137,817; 5,173,158; 5,232,856; 5,273,525; 5,304,120; 5,318,514; 6,010,613 and 6,078,490, the disclosures of which are incorporated by reference herein, may be used. In an embodiment, the electroporation method is a sterile electroporation method. In an embodiment, the electroporation method is a pulsed electroporation method. In an embodiment, the electroporation method is a pulsed electroporation method comprising the steps of treating TILs with pulsed electrical fields to alter, manipulate, or cause defined and controlled, permanent or temporary changes in the TILs, comprising the step of applying a sequence of at least three single, operator-controlled, independently programmed, DC electrical pulses, having field strengths equal to or greater than 100 V/cm, to the TILs, wherein the sequence of at least three DC electrical pulses has one, two, or three of the following characteristics: (1) at least two of the at least three pulses differ from each other in pulse amplitude; (2) at least two of the at least three pulses differ from each other in pulse width; and (3) a first pulse interval for a first set of two of the at least three pulses is different from a second pulse interval for a second set of two of the at least three pulses. In an embodiment, the electroporation method is a pulsed electroporation method comprising the steps of treating TILs with pulsed electrical fields to alter, manipulate, or cause defined and controlled, permanent or temporary changes in the TILs, comprising the step of applying a sequence of at least three single, operator-controlled, independently programmed, DC electrical pulses, having field strengths equal to or greater than 100 V/cm, to the TILs, wherein at least two of the at least three pulses differ from each other in pulse amplitude. In an embodiment, the electroporation method is a pulsed electroporation method comprising the steps of treating TILs with pulsed electrical fields to alter, manipulate, or cause defined and controlled, permanent or temporary changes in the TILs, comprising the step of applying a sequence of at least three single, operator-controlled, independently programmed, DC electrical pulses, having field strengths equal to or greater than 100 V/cm, to the TILs, wherein at least two of the at least three pulses differ from each other in pulse width. In an embodiment, the electroporation method is a pulsed electroporation method comprising the steps of treating TILs with pulsed electrical fields to alter, manipulate, or cause defined and controlled, permanent or temporary changes in the TILs, comprising the step of applying a sequence of at least three single, operator-controlled, independently programmed, DC electrical pulses, having field strengths equal to or greater than 100 V/cm, to the TILs, wherein a first pulse interval for a first set of two of the at least three pulses is different from a second pulse interval for a second set of two of the at least three pulses. In an embodiment, the electroporation method is a pulsed electroporation method comprising the steps of treating TILs with pulsed electrical fields to induce pore formation in the TILs, comprising the step of applying a sequence of at least three DC electrical pulses, having field strengths equal to or greater than 100 V/cm, to TILs, wherein the sequence of at least three DC electrical pulses has one, two, or three of the following characteristics: (1) at least two of the at least three pulses differ from each other in pulse amplitude; (2) at least two of the at least three pulses differ from each other in pulse width; and (3) a first pulse interval for a first set of two of the at least three pulses is different from a second pulse interval for a second set of two of the at least three pulses, such that induced pores are sustained for a relatively long period of time, and such that viability of the TILs is maintained. In an embodiment, a method of genetically modifying a population of TILs includes the step of calcium phosphate transfection. Calcium phosphate transfection methods (calcium phosphate DNA precipitation, cell surface coating, and endocytosis) are known in the art and are described in Graham and van der Eb, *Virology* 1973, 52, 456-467; Wigler, et al., *Proc. Nat. Acad. Sci.* 1979, 76, 1373-1376; and Chen and Okayarea, *Mol. Cell. Biol.* 1987, 7, 2745-2752; and in U.S. Pat. No. 5,593,875, the disclosures of each of which are incorporated by reference herein. In an embodiment, a method of genetically modifying a population of TILs includes the step of liposomal transfection. Liposomal transfection methods, such as methods that employ a 1:1 (w/w) liposome formulation of the cationic lipid N-[1-(2,3-dioleyloxy)propyl]-n,n,n-trimethylammonium chloride (DOTMA) and dioleoyl phophotidylethanolamine (DOPE) in filtered water, are known in the art and are described in Rose, et al., *Biotechniques* 1991, 10, 520-525 and Felgner, et al., *Proc. Nat. Acad. Sci. USA,* 1987, 84, 7413-7417 and in U.S. Pat. Nos. 5,279,833; 5,908,635; 6,056,938; 6,110,490; 6,534,484; and 7,687,070, the disclosures of each of which are incorporated by reference herein. In an embodiment, a method of genetically modifying a population of TILs includes the step of transfection using methods described in U.S. Pat. Nos. 5,766,902; 6,025,337; 6,410,517; 6,475,994; and 7,189,705; the disclosures of each of which are incorporated by reference herein. The TILs may be a first population, a second population and/or a third population of TILs as described herein.

According to an embodiment, the gene-editing process may comprise the use of a programmable nuclease that mediates the generation of a double-strand or single-strand break at one or more immune checkpoint genes. Such programmable nucleases enable precise genome editing by introducing breaks at specific genomic loci, i.e., they rely on the recognition of a specific DNA sequence within the genome to target a nuclease domain to this location and mediate the generation of a double-strand break at the target sequence. A double-strand break in the DNA subsequently recruits endogenous repair machinery to the break site to mediate genome editing by either non-homologous end-joining (NHEJ) or homology-directed repair (HDR). Thus, the repair of the break can result in the introduction of insertion/deletion mutations that disrupt (e.g., silence, repress, or enhance) the target gene product.

Major classes of nucleases that have been developed to enable site-specific genomic editing include zinc finger nucleases (ZFNs), transcription activator-like nucleases (TALENs), and CRISPR-associated nucleases (e.g., CRISPR/Cas9). These nuclease systems can be broadly classified into two categories based on their mode of DNA recognition: ZFNs and TALENs achieve specific DNA binding via protein-DNA interactions, whereas CRISPR systems, such as Cas9, are targeted to specific DNA sequences by a short RNA guide molecule that base-pairs directly with the target DNA and by protein-DNA interactions. See, e.g., Cox et al., *Nature Medicine,* 2015, Vol. 21, No. 2.

Non-limiting examples of gene-editing methods that may be used in accordance with TIL expansion methods of the present invention include CRISPR methods, TALE methods, and ZFN methods, which are described in more detail below. According to an embodiment, a method for expanding TILs into a therapeutic population may be carried out in accordance with any embodiment of the methods described herein (e.g., GEN 3 process) or as described in PCT/US2017/058610, PCT/US2018/012605, or PCT/US2018/012633, wherein the method further comprises gene-editing at least a portion of the TILs by one or more of a CRISPR method, a TALE method or a ZFN method, in order to generate TILs that can provide an enhanced therapeutic effect. According to an embodiment, gene-edited TILs can be evaluated for an improved therapeutic effect by comparing them to non-modified TILs in vitro, e.g., by evaluating in vitro effector function, cytokine profiles, etc. compared to unmodified TILs. In certain embodiments, the method comprises gene editing a population of TILs using CRISPR, TALE and/or ZFN methods.

In some embodiments of the present invention, electroporation is used for delivery of a gene editing system, such as CRISPR, TALEN, and ZFN systems. In some embodiments of the present invention, the electroporation system is a flow electroporation system. An example of a suitable flow electroporation system suitable for use with some embodiments of the present invention is the commercially-available MaxCyte STX system. There are several alternative commercially-available electroporation instruments which may be suitable for use with the present invention, such as the AgilePulse system or ECM 830 available from BTX-Harvard Apparatus, Cellaxess Elektra (Cellectricon), Nucleofector (Lonza/Amaxa), GenePulser MXcell (BIORAD), iPorator-96 (Primax) or siPORTer96 (Ambion). In some embodiments of the present invention, the electroporation system forms a closed, sterile system with the remainder of the TIL expansion method. In some embodiments of the present invention, the electroporation system is a pulsed electroporation system as described herein, and forms a closed, sterile system with the remainder of the TIL expansion method.

A method for expanding TILs into a therapeutic population may be carried out in accordance with any embodiment of the methods described herein (e.g., process GEN 3) or as described in PCT/US2017/058610, PCT/US2018/012605, or PCT/US2018/012633, wherein the method further comprises gene-editing at least a portion of the TILs by a CRISPR method (e.g., CRISPR/Cas9 or CRISPR/Cpf1). According to particular embodiments, the use of a CRISPR method during the TIL expansion process causes expression of one or more immune checkpoint genes to be silenced or reduced in at least a portion of the therapeutic population of TILs. Alternatively, the use of a CRISPR method during the TIL expansion process causes expression of one or more immune checkpoint genes to be enhanced in at least a portion of the therapeutic population of TILs.

CRISPR stands for "Clustered Regularly Interspaced Short Palindromic Repeats." A method of using a CRISPR system for gene editing is also referred to herein as a CRISPR method. There are three types of CRISPR systems which incorporate RNAs and Cas proteins, and which may be used in accordance with the present invention: Types I, II, and III. The Type II CRISPR (exemplified by Cas9) is one of the most well-characterized systems.

CRISPR technology was adapted from the natural defense mechanisms of bacteria and archaea (the domain of single-celled microorganisms). These organisms use CRISPR-derived RNA and various Cas proteins, including Cas9, to foil attacks by viruses and other foreign bodies by chopping up and destroying the DNA of a foreign invader. A CRISPR is a specialized region of DNA with two distinct characteristics: the presence of nucleotide repeats and spacers. Repeated sequences of nucleotides are distributed throughout a CRISPR region with short segments of foreign DNA (spacers) interspersed among the repeated sequences. In the type II CRISPR/Cas system, spacers are integrated within the CRISPR genomic loci and transcribed and processed into short CRISPR RNA (crRNA). These crRNAs anneal to trans-activating crRNAs (tracrRNAs) and direct sequence-specific cleavage and silencing of pathogenic DNA by Cas proteins. Target recognition by the Cas9 protein requires a "seed" sequence within the crRNA and a conserved dinucleotide-containing protospacer adjacent motif (PAM) sequence upstream of the crRNA-binding region. The CRISPR/Cas system can thereby be retargeted to cleave virtually any DNA sequence by redesigning the crRNA. The crRNA and tracrRNA in the native system can be simplified into a single guide RNA (sgRNA) of approximately 100 nucleotides for use in genetic engineering. The CRISPR/Cas system is directly portable to human cells by co-delivery of plasmids expressing the Cas9 endo-nuclease and the necessary crRNA components. Different variants of Cas proteins may be used to reduce targeting limitations (e.g., orthologs of Cas9, such as Cpf1).

Non-limiting examples of genes that may be silenced or inhibited by permanently gene-editing TILs via a CRISPR method include PD-1, CTLA-4, LAG3, HAVCR2 (TIM3), Cish, TGFβ, PKA, CBL-B, PPP2CA, PPP2CB, PTPN6, PTPN22, PDCD1, BTLA, CD160, TIGIT, CD96, CRTAM, LAIR1, SIGLEC7, SIGLEC9, CD244, TNFRSF10B, TNFRSF10A, CASP8, CASP10, CASP3, CASP6, CASP7, FADD, FAS, SMAD2, SMAD3, SMAD4, SMAD10, SKI, SKIL, TGIF1, IL10RA, IL10RB, HMOX2, IL6R, IL6ST, EIF2AK4, CSK, PAG1, SIT1, FOXP3, PRDM1, BATF, GUCY1A2, GUCY1A3, GUCY1B2, and GUCY1B3.

Non-limiting examples of genes that may be enhanced by permanently gene-editing TILs via a CRISPR method include CCR2, CCR4, CCR5, CXCR2, CXCR3, CX3CR1, IL-2, IL12, IL-15, and IL-21.

Examples of systems, methods, and compositions for altering the expression of a target gene sequence by a CRISPR method, and which may be used in accordance with embodiments of the present invention, are described in U.S. Pat. Nos. 8,697,359; 8,993,233; 8,795,965; 8,771,945; 8,889,356; 8,865,406; 8,999,641; 8,945,839; 8,932,814; 8,871,445; 8,906,616; and 8,895,308, which are incorporated by reference herein. Resources for carrying out CRISPR methods, such as plasmids for expressing CRISPR/Cas9 and CRISPR/Cpf1, are commercially available from companies such as GenScript.

In an embodiment, genetic modifications of populations of TILs, as described herein, may be performed using the CRISPR/Cpf1 system as described in U.S. Pat. No. 9,790,490, the disclosure of which is incorporated by reference herein.

A method for expanding TILs into a therapeutic population may be carried out in accordance with any embodiment of the methods described herein (e.g., Gen 2) or as described in PCT/US2017/058610, PCT/US2018/012605, or PCT/US2018/012633, wherein the method further comprises gene-editing at least a portion of the TILs by a TALE method. According to particular embodiments, the use of a TALE method during the TIL expansion process causes expression of one or more immune checkpoint genes to be silenced or reduced in at least a portion of the therapeutic population of TILs. Alternatively, the use of a TALE method during the TIL expansion process causes expression of one or more immune checkpoint genes to be enhanced in at least a portion of the therapeutic population of TILs.

TALE stands for "Transcription Activator-Like Effector" proteins, which include TALENs ("Transcription Activator-Like Effector Nucleases"). A method of using a TALE system for gene editing may also be referred to herein as a TALE method. TALEs are naturally occurring proteins from the plant pathogenic bacteria genus *Xanthomonas*, and contain DNA-binding domains composed of a series of 33-35-amino-acid repeat domains that each recognizes a single base pair. TALE specificity is determined by two hypervariable amino acids that are known as the repeat-variable di-residues (RVDs). Modular TALE repeats are linked together to recognize contiguous DNA sequences. A specific RVD in the DNA-binding domain recognizes a base in the target locus, providing a structural feature to assemble predictable DNA-binding domains. The DNA binding domains of a TALE are fused to the catalytic domain of a type IIS FokI endonuclease to make a targetable TALE nuclease. To induce site-specific mutation, two individual TALEN arms, separated by a 14-20 base pair spacer region, bring FokI monomers in close proximity to dimerize and produce a targeted double-strand break.

Several large, systematic studies utilizing various assembly methods have indicated that TALE repeats can be combined to recognize virtually any user-defined sequence. Custom-designed TALE arrays are also commercially available through Cellectis Bioresearch (Paris, France), Transposagen Biopharmaceuticals (Lexington, KY, USA), and Life Technologies (Grand Island, NY, USA). TALE and TALEN methods suitable for use in the present invention are described in U.S. Patent Application Publication Nos. US 2011/0201118 A1; US 2013/0117869 A1; US 2013/0315884 A1; US 2015/0203871 A1 and US 2016/0120906 A1, the disclosures of which are incorporated by reference herein.

Non-limiting examples of genes that may be silenced or inhibited by permanently gene-editing TILs via a TALE method include PD-1, CTLA-4, LAG3, HAVCR2 (TIM3), Cish, TGFβ, PKA, CBL-B, PPP2CA, PPP2CB, PTPN6, PTPN22, PDCD1, BTLA, CD160, TIGIT, CD96, CRTAM, LAIR1, SIGLEC7, SIGLEC9, CD244, TNFRSF10B, TNFRSF10A, CASP8, CASP10, CASP3, CASP6, CASP7, FADD, FAS, SMAD2, SMAD3, SMAD4, SMAD10, SKI, SKIL, TGIF1, IL10RA, IL10RB, HMOX2, IL6R, IL6ST, EIF2AK4, CSK, PAG1, SIT1, FOXP3, PRDM1, BATF, GUCY1A2, GUCY1A3, GUCY1B2, and GUCY1B3.

Non-limiting examples of genes that may be enhanced by permanently gene-editing TILs via a TALE method include CCR2, CCR4, CCR5, CXCR2, CXCR3, CX3CR1, IL-2, IL12, IL-15, and IL-21.

Examples of systems, methods, and compositions for altering the expression of a target gene sequence by a TALE method, and which may be used in accordance with embodiments of the present invention, are described in U.S. Pat. No. 8,586,526, which is incorporated by reference herein.

A method for expanding TILs into a therapeutic population may be carried out in accordance with any embodiment of the methods described herein (e.g., process GEN 3) or as described in PCT/US2017/058610, PCT/US2018/012605, or PCT/US2018/012633, wherein the method further comprises gene-editing at least a portion of the TILs by a zinc finger or zinc finger nuclease method. According to particular embodiments, the use of a zinc finger method during the TIL expansion process causes expression of one or more immune checkpoint genes to be silenced or reduced in at least a portion of the therapeutic population of TILs. Alternatively, the use of a zinc finger method during the TIL expansion process causes expression of one or more immune checkpoint genes to be enhanced in at least a portion of the therapeutic population of TILs.

An individual zinc finger contains approximately 30 amino acids in a conserved ββα configuration. Several amino acids on the surface of the α-helix typically contact 3 bp in the major groove of DNA, with varying levels of selectivity. Zinc fingers have two protein domains. The first domain is the DNA binding domain, which includes eukaryotic transcription factors and contain the zinc finger. The second domain is the nuclease domain, which includes the FokI restriction enzyme and is responsible for the catalytic cleavage of DNA.

The DNA-binding domains of individual ZFNs typically contain between three and six individual zinc finger repeats and can each recognize between 9 and 18 base pairs. If the zinc finger domains are specific for their intended target site then even a pair of 3-finger ZFNs that recognize a total of 18 base pairs can, in theory, target a single locus in a mammalian genome. One method to generate new zinc-finger arrays is to combine smaller zinc-finger "modules" of known specificity. The most common modular assembly process involves combining three separate zinc fingers that can each recognize a 3 base pair DNA sequence to generate a 3-finger array that can recognize a 9 base pair target site. Alternatively, selection-based approaches, such as oligomerized pool engineering (OPEN) can be used to select for new zinc-finger arrays from randomized libraries that take into consideration context-dependent interactions between neighboring fingers. Engineered zinc fingers are available commercially; Sangamo Biosciences (Richmond, CA, USA) has developed a propriety platform (CompoZr®) for zinc-finger construction in partnership with Sigma-Aldrich (St. Louis, MO, USA).

Non-limiting examples of genes that may be silenced or inhibited by permanently gene-editing TILs via a zinc finger method include PD-1, CTLA-4, LAG3, HAVCR2 (TIM3), Cish, TGFβ, PKA, CBL-B, PPP2CA, PPP2CB, PTPN6, PTPN22, PDCD1, BTLA, CD160, TIGIT, CD96, CRTAM, LAIR1, SIGLEC7, SIGLEC9, CD244, TNFRSF10B, TNFRSF10A, CASP8, CASP10, CASP3, CASP6, CASP7, FADD, FAS, SMAD2, SMAD3, SMAD4, SMAD10, SKI, SKIL, TGIF1, IL10RA, IL10RB, HMOX2, IL6R, IL6ST, EIF2AK4, CSK, PAG1, SIT1, FOXP3, PRDM1, BATF, GUCY1A2, GUCY1A3, GUCY1B2, and GUCY1B3.

Non-limiting examples of genes that may be enhanced by permanently gene-editing TILs via a zinc finger method include CCR2, CCR4, CCR5, CXCR2, CXCR3, CX3CR1, IL-2, IL12, IL-15, and IL-21.

Examples of systems, methods, and compositions for altering the expression of a target gene sequence by a zinc finger method, which may be used in accordance with embodiments of the present invention, are described in U.S. Pat. Nos. 6,534,261, 6,607,882, 6,746,838, 6,794,136, 6,824,978, 6,866,997, 6,933,113, 6,979,539, 7,013,219, 7,030,215, 7,220,719, 7,241,573, 7,241,574, 7,585,849, 7,595,376, 6,903,185, and 6,479,626, which are incorporated by reference herein.

Other examples of systems, methods, and compositions for altering the expression of a target gene sequence by a zinc finger method, which may be used in accordance with embodiments of the present invention, are described in Beane, et al., *Mol. Therapy,* 2015, 23 1380-1390, the disclosure of which is incorporated by reference herein.

In some embodiments, the TILs are optionally genetically engineered to include additional functionalities, including, but not limited to, a high-affinity T cell receptor (TCR), e.g., a TCR targeted at a tumor-associated antigen such as MAGE-1, HER2, or NY-ESO-1, or a chimeric antigen receptor (CAR) which binds to a tumor-associated cell surface molecule (e.g., mesothelin) or lineage-restricted cell surface molecule (e.g., CD19). In some embodiments, the genetic engineering methods described in International Patent Publication No. WO 2019/160829 A1, the disclosure of which is incorporated by reference herein, may be employed to genetically edit TILs, including knockout of specific target genes such as the genes that code for PD-1 and CTLA-4. In certain embodiments, the method comprises genetically engineering a population of TILs to include a high-affinity T cell receptor (TCR), e.g., a TCR targeted at a tumor-associated antigen such as MAGE-1, HER2, or NY-ESO-1, or a chimeric antigen receptor (CAR) which binds to a tumor-associated cell surface molecule (e.g., mesothelin) or lineage-restricted cell surface molecule (e.g., CD19). Aptly, the population of TILs may be a first population, a second population and/or a third population as described herein.

E. Closed Systems for TIL Manufacturing

The present invention provides for the use of closed systems during the TIL culturing process. Such closed systems allow for preventing and/or reducing microbial contamination, allow for the use of fewer flasks, and allow for cost reductions. In some embodiments, the closed system uses two containers.

Such closed systems are well-known in the art and can be found, for example, in "CBER Guidances/Guidelines/Points to Consider" from world wide web <fda.gov/cber/guidelines.htm> and "Guidance for Industry: Use of Sterile Connecting Devices in Blood Bank Practices" from world wide web <fda.gov/BiologicsBloodVaccines/GuidanceComplianceRegulatoryInformation/Guidances/Blood/ucm3076779.htm>.

Sterile connecting devices (STCDs) produce sterile welds between two pieces of compatible tubing. This procedure permits sterile connection of a variety of containers and tube diameters. In some embodiments, the closed systems include luer lock and heat sealed systems as described in for example, Example 14. In some embodiments, the closed system is accessed via syringes under sterile conditions in order to maintain the sterility and closed nature of the system. In some embodiments, a closed system as described in Example 14 is employed. In some embodiments, the TILs are formulated into a final product formulation container according to the method described in Example 14, section "Final Formulation and Fill".

In some embodiments, the closed system uses one container from the time the tumor fragments are obtained until the TILs are ready for administration to the patient or cryopreserving. In some embodiments when two containers are used, the first container is a closed G-container and the population of TILs is centrifuged and transferred to an infusion bag without opening the first closed G-container. In some embodiments, when two containers are used, the infusion bag is a HypoThermosol-containing infusion bag. A closed system or closed TIL cell culture system is characterized in that once the tumor sample and/or tumor fragments have been added, the system is tightly sealed from the outside to form a closed environment free from the invasion of bacteria, fungi, and/or any other microbial contamination.

In some embodiments, the reduction in microbial contamination is between about 5% and about 100%. In some embodiments, the reduction in microbial contamination is between about 5% and about 95%. In some embodiments, the reduction in microbial contamination is between about 5% and about 90%. In some embodiments, the reduction in microbial contamination is between about 10% and about 90%. In some embodiments, the reduction in microbial contamination is between about 15% and about 85%. In some embodiments, the reduction in microbial contamination is about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 97%, about 98%, about 99%, or about 100%.

The closed system allows for TIL growth in the absence and/or with a significant reduction in microbial contamination.

Moreover, pH, carbon dioxide partial pressure and oxygen partial pressure of the TIL cell culture environment each vary as the cells are cultured. Consequently, even though a medium appropriate for cell culture is circulated, the closed environment still needs to be constantly maintained as an optimal environment for TIL proliferation. To this end, it is desirable that the physical factors of pH, carbon dioxide partial pressure and oxygen partial pressure within the culture liquid of the closed environment be monitored by means of a sensor, the signal whereof is used to control a gas exchanger installed at the inlet of the culture environment, and the that gas partial pressure of the closed environment be adjusted in real time according to changes in the culture liquid so as to optimize the cell culture environment. In some embodiments, the present invention provides a closed cell culture system which incorporates at the inlet to the closed environment a gas exchanger equipped with a monitoring device which measures the pH, carbon dioxide partial pressure and oxygen partial pressure of the closed environment, and optimizes the cell culture environment by automatically adjusting gas concentrations based on signals from the monitoring device.

In some embodiments, the pressure within the closed environment is continuously or intermittently controlled. That is, the pressure in the closed environment can be varied by means of a pressure maintenance device for example, thus ensuring that the space is suitable for growth of TILs in a positive pressure state, or promoting exudation of fluid in a negative pressure state and thus promoting cell proliferation. By applying negative pressure intermittently, moreover, it is possible to uniformly and efficiently replace the circulating liquid in the closed environment by means of a temporary shrinkage in the volume of the closed environment.

In some embodiments, optimal culture components for proliferation of the TILs can be substituted or added, and including factors such as IL-2 and/or OKT3, as well as combination, can be added.

F. Optional Cryopreservation of TILs

Either the bulk TIL population (for example the second population of TILs) or the expanded population of TILs (for example the third population of TILs) can be optionally cryopreserved. In some embodiments, cryopreservation occurs on the therapeutic TIL population. In some embodiments, cryopreservation occurs on the TILs harvested after the second expansion. In some embodiments, cryopreservation occurs on the TILs in exemplary Step F of FIGS. 1 and/or 8 (in particular, e.g., FIG. 8B and/or FIG. 8C). In some embodiments, the TILs are cryopreserved in the infusion bag. In some embodiments, the TILs are cryopreserved prior to placement in an infusion bag. In some embodiments, the TILs are cryopreserved and not placed in an infusion bag. In some embodiments, cryopreservation is performed using a cryopreservation medium. In some embodiments, the cryopreservation media contains dimethylsulfoxide (DMSO). This is generally accomplished by putting the TIL population into a freezing solution, e.g. 85% complement inactivated AB serum and 15% dimethyl sulfoxide (DMSO). The cells in solution are placed into cryogenic vials and stored for 24 hours at −80° C., with optional transfer to gaseous nitrogen freezers for cryopreservation. See, Sadeghi, et al., *Acta Oncologica* 2013, 52, 978-986.

When appropriate, the cells are removed from the freezer and thawed in a 37° C. water bath until approximately 4/5 of the solution is thawed. The cells are generally resuspended in complete media and optionally washed one or more times. In some embodiments, the thawed TILs can be counted and assessed for viability as is known in the art.

In a preferred embodiment, a population of TILs is cryopreserved using CS10 cryopreservation media (CryoStor 10, BioLife Solutions). In a preferred embodiment, a population of TILs is cryopreserved using a cryopreservation media containing dimethylsulfoxide (DMSO). In a preferred embodiment, a population of TILs is cryopreserved using a 1:1 (vol:vol) ratio of CS10 and cell culture media. In a preferred embodiment, a population of TILs is cryopreserved using about a 1:1 (vol:vol) ratio of CS10 and cell culture media, further comprising additional IL-2.

As discussed above, and exemplified in Steps A through E as provided in FIGS. 1 and/or 8 (in particular, e.g., FIG. 8B and/or FIG. 8C), cryopreservation can occur at numerous points throughout the TIL expansion process. In some embodiments, the expanded population of TILs after the first expansion (as provided for example, according to Step B or the expanded population of TILs after the one or more second expansions according to Step D of FIG. 1 or 8 (in particular, e.g., FIG. 8B and/or FIG. 8C) can be cryopreserved. Cryopreservation can be generally accomplished by placing the TIL population into a freezing solution, e.g., 85% complement inactivated AB serum and 15% dimethyl sulfoxide (DMSO). The cells in solution are placed into cryogenic vials and stored for 24 hours at −80° C., with optional transfer to gaseous nitrogen freezers for cryopreservation. See Sadeghi, et al., *Acta Oncologica* 2013, 52, 978-986. In some embodiments, the TILs are cryopreserved in 5% DMSO. In some embodiments, the TILs are cryopreserved in cell culture media plus 5% DMSO. In some embodiments, the TILs are cryopreserved according to the methods provided in Example 6.

When appropriate, the cells are removed from the freezer and thawed in a 37° C. water bath until approximately 4/5 of the solution is thawed. The cells are generally resuspended in complete media and optionally washed one or more times. In some embodiments, the thawed TILs can be counted and assessed for viability as is known in the art.

In some cases, the Step B TIL population can be cryopreserved immediately, using the protocols discussed below. Alternatively, the bulk TIL population can be subjected to Step C and Step D and then cryopreserved after Step D. Similarly, in the case where genetically modified TILs will be used in therapy, the Step B or Step D TIL populations can be subjected to genetic modifications for suitable treatments.

G. Assays and Phenotypic Characteristics of Expanded TILs

In some embodiments, the potency and/or functionality of the TILs from the processes described above are examined using one of the assay methods described herein.

In an embodiment, the invention includes a method of determining the potency of a TIL product as described above, including genetically engineered TIL products and TIL products produced using CD134 (OX40) and/or CD137 (4-1BB) agonists, the method comprising the steps of.

a. performing a co-culture of a target cell with a TIL product cell for a first period;
b. obtaining a harvest from the co-culture; and
c. assessing the harvest for (1) expression of one or more markers on the TIL product or (2) one or more analytes secreted from the TIL product cell to obtain one or more observed values to determine the potency for the TIL product.

Alternatively, in some embodiments, the TILs from the processes described above are analyzed using a combined assay comprising CD3 or CD3/CD28 bead-based stimulation with ELISA or automated ELISA (e.g., ELLA) detection of at least two analytes selected from the group consisting of IFN-γ, granzyme B, perform, and TNF-α. In an embodiment, the product release specification for such combined assay is at least 500 pg/mL for the at least two selected analytes, at least 600 pg/mL for the at least two selected analytes, at least 700 pg/mL for the at least two selected analytes, at least 800 pg/mL for the at least two selected analytes, at least 900 pg/mL for the at least two selected analytes, at least 1000 pg/mL for the at least two selected analytes, at least 1100 pg/mL for the at least two selected analytes, or at least 1200 pg/mL for the at least two selected analytes, wherein each mL of test article contains $1\times10^5$ TILs, $2\times10^5$ TILs, $3\times10^5$ TILs, $4\times10^5$ TILs, $5\times10^5$ TILs, $6\times10^5$ TILs, $7\times10^5$ TILs, $8\times10^5$ TILs, $9\times10^5$ TILs, or $10\times10^5$ TILs.

In some embodiment, the TILs are analyzed for expression of numerous phenotype markers after expansion, including those described herein and in the Examples. In an embodiment, expression of one or more phenotypic markers is examined. In some embodiments, the phenotypic characteristics of the TILs are analyzed after the first expansion in Step B. In some embodiments, the phenotypic characteristics of the TILs are analyzed during the transition in Step C. In some embodiments, the phenotypic characteristics of the TILs are analyzed during the transition according to Step C and after cryopreservation. In some embodiments, the phenotypic characteristics of the TILs are analyzed after the second expansion according to Step D. In some embodiments, the phenotypic characteristics of the TILs are analyzed after two or more expansions according to Step D.

In some embodiments, the marker is selected from the group consisting of CD8 and CD28. In some embodiments, expression of CD8 is examined. In some embodiments, expression of CD28 is examined. In some embodiments, the expression of CD8 and/or CD28 is higher on TILs produced according the current invention process, as compared to other processes (e.g., the Gen 3 process as provided for example in FIG. 8 (in particular, e.g., FIG. 8B and/or FIG. 8C), as compared to the 2A process as provided for example in FIG. 8 (in particular, e.g., FIG. 8B and/or FIG. 8C). In some embodiments, the expression of CD8 is higher on TILs produced according the current invention process, as compared to other processes (e.g., the Gen 3 process as provided for example in FIG. 8 (in particular, e.g., FIG. 8B), as compared to the 2A process as provided for example in FIG. 8 (in particular, e.g., FIG. 8B and/or FIG. 8C). In some embodiments, the expression of CD28 is higher on TILs produced according the current invention process, as compared to other processes (e.g., the Gen 3 process as provided for example in FIG. 8 (in particular, e.g., FIG. 8B and/or FIG. 8C), as compared to the 2A process as provided for example in FIG. 8 (in particular, e.g., FIG. 8A)). In some embodiments, high CD28 expression is indicative of a younger, more persistent TIL phenotype. In an embodiment, expression of one or more regulatory markers is measured.

In an embodiment, no selection of the first population of TILs, second population of TILs, third population of TILs, or harvested TIL population based on CD8 and/or CD28 expression is performed during any of the steps for the method for expanding tumor infiltrating lymphocytes (TILs) described herein.

In some embodiments, the percentage of central memory cells is higher on TILs produced according the current invention process, as compared to other processes (e.g., the Gen 3 process as provided for example in FIG. 8 (in particular, e.g., FIG. 8B and/or FIG. 8C), as compared to the 2A process as provided for example in FIG. 8 (in particular, e.g., FIG. 8A)). In some embodiments the memory marker for central memory cells is selected from the group consisting of CCR7 and CD62L.

In some embodiments, the $CD4^+$ and/or CD8+ TIL Memory subsets can be divided into different memory subsets. In some embodiments, the $CD4^+$ and/or CD8+ TILs comprise the naïve (CD45RA+CD62L+) TILs. In some embodiments, the $CD4^+$ and/or CD8+ TILs comprise the central memory (CM; $CD45RA^-$ CD62L+) TILs. In some embodiments, the $CD4^+$ and/or CD8+ TILs comprise the effector memory (EM; $CD45RA^-$ CD62L−) TILs. In some embodiments, the $CD4^+$ and/or CD8+ TILs comprise the, RA+ effector memory/effector (TEMRA/TEFF; CD45RA+ CD62L+) TILs.

In some embodiments, the TILs express one more markers selected from the group consisting of granzyme B, perform, and granulysin. In some embodiments, the TILs express granzyme B. In some embodiments, the TILs express perforin. In some embodiments, the TILs express granulysin.

In an embodiment, restimulated TILs can also be evaluated for cytokine release, using cytokine release assays. In some embodiments, TILs can be evaluated for interferon-γ (IFN-γ) secretion. In some embodiments, the IFN-γ secretion is measured by an ELISA assay. In some embodiments, the IFN-γ secretion is measured by an ELISA assay after the rapid second expansion step, after Step D as provided in for example, FIG. 8 (in particular, e.g., FIG. 8B and/or FIG. 8C). In some embodiments, TIL health is measured by IFN-gamma (IFN-γ) secretion. In some embodiments, IFN-γ secretion is indicative of active TILs. In some embodiments, a potency assay for IFN-γ production is employed. IFN-γ production is another measure of cytotoxic potential. IFN-γ production can be measured by determining the levels of the cytokine IFN-γ in the media of TIL stimulated with antibodies to CD3, CD28, and CD137/4-1BB. IFN-γ levels in media from these stimulated TIL can be determined using by measuring IFN-γ release. In some embodiments, an increase in IFN-γ production in for example Step D in the Gen 3 process as provided in FIG. 8 (in particular, e.g., FIG. 8B and/or FIG. 8C) TILs as compared to for example Step D in the 2A process as provided in FIG. 8 (in particular, e.g., FIG. 8A) is indicative of an increase in cytotoxic potential of the Step D TILs. In some embodiments, IFN-γ secretion is increased one-fold, two-fold, three-fold, four-fold, or five-fold or more. In some embodiments, IFN-γ secretion is increased one-fold. In some embodiments, IFN-γ secretion is increased two-fold. In some embodiments, IFN-γ secretion is increased three-fold. In some embodiments, IFN-γ secretion is increased four-fold. In some embodiments, IFN-γ secretion is increased five-fold. In some embodiments, IFN-γ is measured using a Quantikine ELISA kit. In some embodiments, IFN-γ is measured in TILs ex vivo. In some embodiments, IFN-γ is measured in TILs ex vivo, including TILs produced by the methods of the present invention, including, for example FIG. 8B methods.

In some embodiments, TILs capable of at least one-fold, two-fold, three-fold, four-fold, or five-fold or more IFN-γ secretion are TILs produced by the expansion methods of the present invention, including, for example FIG. 8A and/or FIG. 8B and/or FIG. 8C and/or FIG. 8D methods. In some embodiments, TILs capable of at least one-fold more IFN-γ secretion are TILs produced by the expansion methods of the present invention, including, for example FIG. 8A and/or FIG. 8B and/or FIG. 8C and/or FIG. 8D methods. In some embodiments, TILs capable of at least two-fold more IFN-γ secretion are TILs produced by the expansion methods of the present invention, including, for example FIG. 8A and/or FIG. 8B and/or FIG. 8C and/or FIG. 8D methods. In some embodiments, TILs capable of at least three-fold more IFN-γ secretion are TILs produced by the expansion methods of the present invention, including, for example FIG. 8A and/or FIG. 8B and/or FIG. 8C and/or FIG. 8D methods. In some embodiments, TILs capable of at least four-fold more IFN-γ secretion are TILs produced by the expansion methods of the present invention, including, for example FIG. 8A and/or FIG. 8B and/or FIG. 8C and/or FIG. 8D methods. In some embodiments, TILs capable of at least five-fold more IFN-γ secretion are TILs produced by the expansion methods of the present invention, including, for example FIG. 8A and/or FIG. 8B and/or FIG. 8C and/or FIG. 8D methods.

In some embodiments, TILs capable of at least 100 pg/mL to about 1000 pg/mL or more IFN-γ secretion are TILs produced by the expansion methods of the present invention, including, for example, FIG. 8A and/or FIG. 8B and/or FIG. 8C and/or FIG. 8D methods. In some embodiments, TILs capable of at least 200 pg/mL, at least 250 pg/mL, at least 300 pg/mL, at least 350 pg/mL, at least 400 pg/mL, at least 450 pg/mL, at least 500 pg/mL, at least 550 pg/mL, at least 600 pg/mL, at least 650 pg/mL, at least 700 pg/mL, at least 750 pg/mL, at least 800 pg/mL, at least 850 pg/mL, at least 900 pg/mL, at least 950 pg/mL, or at least 1000 pg/mL or more IFN-γ secretion are TILs produced by the expansion methods of the present invention, including, for example FIG. 8A and/or FIG. 8B and/or FIG. 8C and/or FIG. 8D methods. In some embodiments, TILs capable of at least 200 pg/mL IFN-γ secretion are TILs produced by the expansion methods of the present invention, including, for example FIG. 8A and/or FIG. 8B and/or FIG. 8C and/or FIG. 8D methods. In some embodiments, TILs capable of at least 200 pg/mL IFN-γ secretion are TILs produced by the expansion methods of the present invention, including, for example FIG. 8A and/or FIG. 8B and/or FIG. 8C and/or FIG. 8D methods. In some embodiments, TILs capable of at least 300 pg/mL IFN-γ secretion are TILs produced by the expansion methods of the present invention, including, for example FIG. 8A and/or FIG. 8B and/or FIG. 8C and/or FIG. 8D methods. In some embodiments, TILs capable of at least 400 pg/mL IFN-γ secretion are TILs produced by the expansion methods of the present invention, including, for example FIG. 8A and/or FIG. 8B and/or FIG. 8C and/or FIG. 8D methods. In some embodiments, TILs capable of at least 500 pg/mL IFN-γ secretion are TILs produced by the expansion methods of the present invention, including, for example FIG. 8A and/or FIG. 8B and/or FIG. 8C and/or FIG. 8D methods. In some embodiments, TILs capable of at least 600 pg/mL IFN-γ secretion are TILs produced by the expansion methods of the present invention, including, for example FIG. 8A and/or FIG. 8B and/or FIG. 8C and/or FIG. 8D methods. In some embodiments, TILs capable of at least 700 pg/mL IFN-γ secretion are TILs produced by the expansion methods of the present invention, including, for example FIG. 8A and/or FIG. 8B and/or FIG. 8C and/or FIG. 8D methods. In some embodiments, TILs capable of at least 800 pg/mL IFN-γ secretion are TILs produced by the expansion methods of the present invention, including, for example FIG. 8A and/or FIG. 8B and/or FIG. 8C and/or FIG. 8D methods. In some embodiments, TILs capable of at least 900 pg/mL IFN-γ secretion are TILs produced by the expansion methods of the present invention, including, for example FIG. 8A and/or FIG. 8B and/or FIG. 8C and/or FIG. 8D methods. In some embodiments, TILs capable of at least 1000 pg/mL IFN-γ secretion are TILs produced by the expansion methods of the present invention, including, for example FIG. 8A and/or FIG. 8B and/or FIG. 8C and/or FIG. 8D methods. In some embodiments, TILs capable of at least 2000 pg/mL IFN-γ secretion are TILs produced by the expansion methods of the present invention, including, for example FIG. 8A and/or FIG. 8B and/or FIG. 8C and/or FIG. 8D methods. In some embodiments, TILs capable of at least 3000 pg/mL IFN-γ secretion are TILs produced by the expansion methods of the present invention, including, for example FIG. 8A and/or FIG. 8B and/or FIG. 8C and/or FIG. 8D methods. In some embodiments, TILs capable of at least 4000 pg/mL IFN-γ secretion are TILs produced by the expansion methods of the present invention, including, for example FIG. 8A and/or FIG. 8B and/or FIG. 8C and/or FIG. 8D methods. In some embodiments, TILs capable of at least 5000 pg/mL IFN-γ secretion are TILs produced by the expansion methods of the present invention, including, for example FIG. 8A and/or FIG. 8B and/or FIG. 8C and/or FIG. 8D methods. In some embodiments, TILs capable of at least 6000 pg/mL IFN-γ secretion are TILs produced by the expansion methods of the present invention, including, for example FIG. 8A and/or FIG. 8B and/or FIG. 8C and/or FIG. 8D methods. In some embodiments, TILs capable of at least 7000 pg/mL IFN-γ secretion are TILs produced by the expansion methods of the present invention, including, for example FIG. 8A and/or FIG. 8B and/or FIG. 8C and/or FIG. 8D methods. In some embodiments, TILs capable of at least 8000 pg/mL IFN-γ secretion are TILs produced by the expansion methods of the present invention, including, for example FIG. 8A and/or FIG. 8B and/or FIG. 8C and/or FIG. 8D methods. In some embodiments, TILs capable of at least 9000 pg/mL IFN-γ secretion are TILs produced by the expansion methods of the present invention, including, for example FIG. 8A and/or FIG. 8B and/or FIG. 8C and/or FIG. 8D methods. In some embodiments, TILs capable of at least 10,000 pg/mL IFN-γ secretion are TILs produced by the expansion methods of the present invention, including, for example FIG. 8A and/or FIG. 8B and/or FIG. 8C and/or FIG. 8D methods. In some embodiments, TILs capable of at least 15,000 pg/mL IFN-γ secretion are TILs produced by the expansion methods of the present invention, including, for example FIG. 8A and/or FIG. 8B and/or FIG. 8C and/or FIG. 8D methods. In some embodiments, TILs capable of at least 20,000 pg/mL IFN-γ secretion are TILs produced by the expansion methods of the present invention, including, for example FIG. 8A and/or FIG. 8B and/or FIG. 8C and/or FIG. 8D methods. In some embodiments, TILs capable of at least 25,000 pg/mL IFN-γ secretion are TILs produced by the expansion methods of the present invention, including, for example FIG. 8A and/or FIG. 8B and/or FIG. 8C and/or FIG. 8D methods. In some embodiments, TILs capable of at least 30,000 pg/mL IFN-γ secretion are TILs produced by the expansion methods of the present invention, including, for example FIG. 8A and/or FIG. 8B and/or FIG. 8C and/or FIG. 8D methods. In some embodiments, TILs capable of at least 35,000 pg/mL IFN-γ secretion are TILs produced by the expansion methods of the present invention, including, for example FIG. 8A and/or FIG. 8B and/or FIG. 8C and/or FIG. 8D methods. In some embodiments, TILs capable of at least 40,000 pg/mL IFN-γ secretion are TILs produced by the expansion methods of the present invention, including, for example FIG. 8A and/or FIG. 8B and/or FIG. 8C and/or FIG. 8D methods. In some embodiments, TILs capable of at least 45,000 pg/mL IFN-γ secretion are TILs produced by the expansion methods of the present invention, including, for example FIG. 8A and/or FIG. 8B and/or FIG. 8C and/or FIG. 8D methods. In some embodiments, TILs capable of at least 50,000 pg/mL IFN-γ secretion are TILs produced by the expansion methods of the present invention, including, for example FIG. 8A and/or FIG. 8B and/or FIG. 8C and/or FIG. 8D methods.

In some embodiments, TILs capable of at least 100 pg/mL/5×10$^5$ cells to about 1000 pg/mL/5×10$^5$ cells or more IFN-γ secretion are TILs produced by the expansion methods of the present invention, including, for example the methods depicted in FIG. 8A and/or FIG. 8B and/or FIG. 8C and/or FIG. 8D. In some embodiments, TILs capable of at least 200 pg/mL/5×10$^5$ cells, at least 250 pg/mL/5×10$^5$ cells, at least 300 pg/mL/5×10$^5$ cells, at least 350 pg/mL/5×10$^5$ cells, at least 400 pg/mL/5×10$^5$ cells, at least 450 pg/mL/5×10$^5$ cells, at least 500 pg/mL/5×10$^5$ cells, at least 550 pg/mL/5×10$^5$ cells, at least 600 pg/mL/5×10$^5$ cells, at least 650 pg/mL/5×10$^5$ cells, at least 700 pg/mL/5×10$^5$ cells, at least 750 pg/mL/5×10$^5$ cells, at least 800 pg/mL/5×10$^5$ cells, at least 850 pg/mL/5×10$^5$ cells, at least 900 pg/mL/5×10$^5$ cells, at least 950 pg/mL/5×10$^5$ cells, or at least 1000 pg/mL/5×10$^5$ cells or more IFN-γ secretion are TILs produced by the expansion methods of the present invention, including, for example FIG. 8A and/or FIG. 8B and/or FIG. 8C and/or FIG. 8D methods. In some embodiments, TILs capable of at least 200 pg/mL/5×10$^5$ cells IFN-γ secretion are TILs produced by the expansion methods of the present invention, including, for example FIG. 8A and/or FIG. 8B and/or FIG. 8C and/or FIG. 8D methods. In some embodiments, TILs capable of at least 200 pg/mL/5×10$^5$ cells IFN-γ secretion are TILs produced by the expansion methods of the present invention, including, for example FIG. 8A and/or FIG. 8B and/or FIG. 8C and/or FIG. 8D methods. In some embodiments, TILs capable of at least 300 pg/mL/5×10$^5$ cells IFN-γ secretion are TILs produced by the expansion methods of the present invention, including, for example FIG. 8A and/or FIG. 8B and/or FIG. 8C and/or FIG. 8D methods. In some embodiments, TILs capable of at least 400 pg/mL/5×10$^5$ cells IFN-γ secretion are TILs produced by the expansion methods of the present invention, including, for example FIG. 8A and/or FIG. 8B and/or FIG. 8C and/or FIG. 8D methods. In some embodiments, TILs capable of at least 500 pg/mL/5×10$^5$ cells IFN-γ secretion are TILs produced by the expansion methods of the present invention, including, for example FIG. 8A and/or FIG. 8B and/or FIG. 8C and/or FIG. 8D methods. In some embodiments, TILs capable of at least 600 pg/mL/5×10$^5$ cells IFN-γ secretion are TILs produced by the expansion methods of the present invention, including, for example FIG. 8A and/or FIG. 8B and/or FIG. 8C and/or FIG. 8D methods. In some embodiments, TILs capable of at least 700 pg/mL/5×10$^5$ cells IFN-γ secretion are TILs produced by the expansion methods of the present invention, including, for example FIG. 8A and/or FIG. 8B and/or FIG. 8C and/or FIG. 8D methods. In some embodiments, TILs capable of at least 800 pg/mL/5×10$^5$ cells IFN-γ secretion are TILs produced by the expansion methods of the present invention, including, for example FIG. 8A and/or FIG. 8B and/or FIG. 8C and/or FIG. 8D methods. In some embodiments, TILs capable of at least 900 pg/mL/5×10$^5$ cells IFN-γ secretion are TILs produced by the expansion methods of the present invention, including, for example FIG. 8A and/or FIG. 8B and/or FIG. 8C and/or FIG. 8D methods. In some embodiments, TILs capable of at least 1000 pg/mL/5×10$^5$ cells IFN-γ secretion are TILs produced by the expansion methods of the present invention, including, for example FIG. 8A and/or FIG. 8B and/or FIG. 8C and/or FIG. 8D methods. In some embodiments, TILs capable of at least 2000 pg/mL/5×10$^5$ cells IFN-γ secretion are TILs produced by the expansion methods of the present invention, including, for example FIG. 8A and/or FIG. 8B and/or FIG. 8C and/or FIG. 8D methods. In some embodiments, TILs capable of at least 3000 pg/mL/5×10$^5$ cells IFN-γ secretion are TILs produced by the expansion methods of the present invention, including, for example the methods depicted in FIG. 8A and/or FIG. 8B and/or FIG. 8C and/or FIG. 8D. In some embodiments, TILs capable of at least 4000 pg/mL/5×10$^5$ cells IFN-γ secretion are TILs produced by the expansion methods of the present invention, including, for example FIG. 8A and/or FIG. 8B and/or FIG. 8C and/or FIG. 8D methods. In some embodiments, TILs capable of at least 5000 pg/mL/5×10$^5$ cells IFN-γ secretion are TILs produced by the expansion methods of the present invention, including, for example FIG. 8A and/or FIG. 8B and/or FIG. 8C and/or FIG. 8D methods. In some embodiments, TILs capable of at least 6000 pg/mL/5×10$^5$ cells IFN-γ secretion are TILs produced by the expansion methods of the present invention, including, for example FIG. 8A and/or FIG. 8B and/or FIG. 8C and/or FIG. 8D methods. In some embodiments, TILs capable of at least 7000 pg/mL/5×10$^5$ cells IFN-γ secretion are TILs produced by the expansion methods of the present invention, including, for example FIG. 8A and/or FIG. 8B and/or FIG. 8C and/or FIG. 8D methods. In some embodiments, TILs capable of at least 8000 pg/mL/5×10$^5$ cells IFN-γ secretion are TILs produced by the expansion methods of the present invention, including, for example FIG. 8A and/or FIG. 8B and/or FIG. 8C and/or FIG. 8D methods. In some embodiments, TILs capable of at least 9000 pg/mL/5×10$^5$ cells IFN-γ secretion are TILs produced by the expansion methods of the present invention, including, for example FIG. 8A and/or FIG. 8B and/or FIG. 8C and/or FIG. 8D methods. In some embodiments, TILs capable of at least 10,000 pg/mL/5×10$^5$ cells IFN-γ secretion are TILs produced by the expansion methods of the present invention, including, for example FIG. 8A and/or FIG. 8B and/or FIG. 8C and/or FIG. 8D methods. In some embodiments, TILs capable of at least 15,000 pg/mL/5×10$^5$ cells IFN-γ secretion are TILs produced by the expansion methods of the present invention, including, for example FIG. 8A and/or FIG. 8B and/or FIG. 8C and/or FIG. 8D methods. In some embodiments, TILs capable of at least 20,000 pg/mL/5×10$^5$ cells IFN-γ secretion are TILs produced by the expansion methods of the present invention, including, for example FIG. 8A and/or FIG. 8B and/or FIG. 8C and/or FIG. 8D methods. In some embodiments, TILs capable of at least 25,000 pg/mL/5×10$^5$ cells IFN-γ secretion are TILs produced by the expansion methods of the present invention, including, for example FIG. 8A and/or FIG. 8B and/or FIG. 8C and/or FIG. 8D methods. In some embodiments, TILs capable of at least 30,000 pg/mL/5×10$^5$ cells IFN-γ secretion are TILs produced by the expansion methods of the present invention, including, for example FIG. 8A and/or FIG. 8B and/or FIG. 8C and/or FIG. 8D methods. In some embodiments, TILs capable of at least 35,000 pg/mL/5×10$^5$ cells IFN-γ secretion are TILs produced by the expansion methods of the present invention, including, for example FIG. 8A and/or FIG. 8B and/or FIG. 8C and/or FIG. 8D methods. In some embodiments, TILs capable of at least 40,000 pg/mL/×10$^5$ cells IFN-γ secretion are TILs produced by the expansion methods of the present invention, including, for example FIG. 8A and/or FIG. 8B and/or FIG. 8C and/or FIG. 8D methods. In some embodiments, TILs capable of at least 45,000 pg/mL/5×10$^5$ cells IFN-γ secretion are TILs produced by the expansion methods of the present invention, including, for example FIG. 8A and/or FIG. 8B and/or FIG. 8C and/or FIG. 8D methods. In some embodiments, TILs capable of at least 50,000 pg/mL/5×$10^5$ cells IFN-γ secretion are TILs produced by the expansion methods of the present invention, including, for example FIG. 8A and/or FIG. 8B and/or FIG. 8C and/or FIG. 8D methods.

The diverse antigen receptors of T and B lymphocytes are produced by somatic recombination of a limited, but large number of gene segments. These gene segments: V (variable), D (diversity), J (joining), and C (constant), determine the binding specificity and downstream applications of immunoglobulins and T cell receptors (TCRs). The present invention provides a method for generating TILs which exhibit and increase the T cell repertoire diversity. In some embodiments, the TILs obtained by the present method exhibit an increase in the T cell repertoire diversity. In some embodiments, the TILs obtained by the present method exhibit an increase in the T cell repertoire diversity as compared to freshly harvested TILs and/or TILs prepared using other methods than those provide herein including, for example, methods other than those embodied in FIG. 8 (in particular, e.g., FIG. 8B and/or FIG. 8C). In some embodiments, the TILs obtained by the present method exhibit an increase in the T cell repertoire diversity as compared to freshly harvested TILs and/or TILs prepared using methods referred to as Gen 2, as exemplified in FIG. 8 (in particular, e.g., FIG. 8A). In some embodiments, the TILs obtained in the first expansion exhibit an increase in the T cell repertoire diversity. In some embodiments, the increase in diversity is an increase in the immunoglobulin diversity and/or the T cell receptor diversity. In some embodiments, the diversity is in the immunoglobulin is in the immunoglobulin heavy chain. In some embodiments, the diversity is in the immunoglobulin is in the immunoglobulin light chain. In some embodiments, the diversity is in the T cell receptor. In some embodiments, the diversity is in one of the T cell receptors selected from the group consisting of alpha, beta, gamma, and delta receptors. In some embodiments, there is an increase in the expression of T cell receptor (TCR) alpha and/or beta. In some embodiments, there is an increase in the expression of T cell receptor (TCR) alpha. In some embodiments, there is an increase in the expression of T cell receptor (TCR) beta. In some embodiments, there is an increase in the expression of TCRαβ (i.e., TCRα/β). In some embodiments, the process as described herein (e.g., the Gen 3 process) shows higher clonal diversity as compared to other processes, for example the process referred to as the Gen 2 based on the number of unique peptide CDRs within the sample (see, for example FIGS. 12-14).

In some embodiments, the activation and exhaustion of TILs can be determined by examining one or more markers. In some embodiments, the activation and exhaustion can be determined using multicolor flow cytometry. In some embodiments, the activation and exhaustion of markers include but not limited to one or more markers selected from the group consisting of CD3, PD-1, 2B4/CD244, CD8, CD25, BTLA, KLRG, TIM3, CD194/CCR4, CD4, TIGIT, CD183, CD69, CD95, CD127, CD103, and/or LAG3). In some embodiments, the activation and exhaustion of markers include but not limited to one or more markers selected from the group consisting of BTLA, CTLA-4, ICOS, Ki67, LAG3, PD-1, TIGIT, and/or TIM3. In some embodiments, the activation and exhaustion of markers include but not limited to one or more markers selected from the group consisting of BTLA, CTLA-4, ICOS, Ki67, LAG3, CD103+/CD69+, CD103+/CD69−, PD-1, TIGIT, and/or TIM3. In some embodiments, the T cell markers (including activation and exhaustion markers) can be determined and/or analyzed to examine T cell activation, inhibition, or function. In some embodiments, the T cell markers can include but are not limited to one or more markers selected from the group consisting of TIGIT, CD3, FoxP3, TIM3, PD-1, CD103, CTLA-4, LAG3, BTLA-4, ICOS, Ki67, CD8, CD25, CD45, CD4, and/or CD59.

In some embodiments, TILs that exhibit greater than 3000 pg/$10^6$ TILs to 300000 pg/$10^6$ TILs or more granzyme B secretion are TILs produced by the expansion methods of the present invention, including for example FIG. 8A and/or FIG. 8B and/or FIG. 8C and/or FIG. 8D. In some embodiments, TILs that exhibit greater than 3000 pg/$10^6$ TILs greater than 5000 pg/$10^6$ TILs, greater than 7000 pg/$10^6$ TILs, greater than 9000 pg/$10^6$ TILs, greater than 11000 pg/$10^6$ TILs, greater than 13000 pg/$10^6$ TILs, greater than 15000 pg/$10^6$ TILs, greater than 17000 pg/$10^6$ TILs, greater than 19000 pg/$10^6$ TILs, greater than 20000 pg/$10^6$ TILs, greater than 40000 pg/$10^6$ TILs, greater than 60000 pg/$10^6$ TILs, greater than 80000 pg/$10^6$ TILs, greater than 100000 pg/$10^6$ TILs, greater than 120000 pg/$10^6$ TILs, greater than 140000 pg/$10^6$ TILs, greater than 160000 pg/$10^6$ TILs, greater than 180000 pg/$10^6$ TILs, greater than 200000 pg/$10^6$ TILs, greater than 220000 pg/$10^6$ TILs, greater than 240000 pg/$10^6$ TILs, greater than 260000 pg/$10^6$ TILs, greater than 280000 pg/$10^6$ TILs, greater than 300000 pg/$10^6$ TILs or more granzyme B secretion are TILs produced by the expansion methods of the present invention, including for example FIG. 8A and/or FIG. 8B and/or FIG. 8C and/or FIG. 8D. In some embodiments, TILs that exhibit greater than 3000 pg/$10^6$ TILs granzyme B secretion are TILs produced by the expansion methods of the present invention, including for example FIG. 8A and/or FIG. 8B and/or FIG. 8C and/or FIG. 8D. In some embodiments, TILs that exhibit greater than 5000 pg/$10^6$ TILs granzyme B secretion are TILs produced by the expansion methods of the present invention, including for example FIG. 8A and/or FIG. 8B and/or FIG. 8C and/or FIG. 8D. In some embodiments, TILs that exhibit greater than 7000 pg/$10^6$ TILs granzyme B secretion are TILs produced by the expansion methods of the present invention, including for example FIG. 8A and/or FIG. 8B and/or FIG. 8C and/or FIG. 8D. In some embodiments, TILs that exhibit greater than 9000 pg/$10^6$ TILs granzyme B secretion are TILs produced by the expansion methods of the present invention, including for example FIG. 8A and/or FIG. 8B and/or FIG. 8C and/or FIG. 8D. In some embodiments, TILs that exhibit greater than 11000 pg/$10^6$ TILs granzyme B secretion are TILs produced by the expansion methods of the present invention, including for example FIG. 8A and/or FIG. 8B and/or FIG. 8C and/or FIG. 8D. In some embodiments, TILs that exhibit greater than 13000 pg/$10^6$ TILs granzyme B secretion are TILs produced by the expansion methods of the present invention, including for example FIG. 8A and/or FIG. 8B and/or FIG. 8C and/or FIG. 8D. In some embodiments, TILs that exhibit greater than 15000 pg/$10^6$ TILs granzyme B secretion are TILs produced by the expansion methods of the present invention, including for example FIG. 8A and/or FIG. 8B and/or FIG. 8C and/or FIG. 8D. In some embodiments, TILs that exhibit greater than 17000 pg/$10^6$ TILs granzyme B secretion are TILs produced by the expansion methods of the present invention, including for example FIG. 8A and/or FIG. 8B and/or FIG. 8C and/or FIG. 8D. In some embodiments, TILs that exhibit greater than 19000 pg/$10^6$ TILs granzyme B secretion are TILs produced by the expansion methods of the present invention, including for example FIG. 8A and/or FIG. 8B and/or FIG. 8C and/or FIG.

8D. In some embodiments, TILs that exhibit greater than 20000 pg/$10^6$ TILs granzyme B secretion are TILs produced by the expansion methods of the present invention, including for example FIG. 8A and/or FIG. 8B and/or FIG. 8C and/or FIG. 8D. In some embodiments, TILs that exhibit greater than 40000 pg/$10^6$ TILs granzyme B secretion are TILs produced by the expansion methods of the present invention, including for example FIG. 8A and/or FIG. 8B and/or FIG. 8C and/or FIG. 8D. In some embodiments, TILs that exhibit greater than 60000 pg/$10^6$ TILs granzyme B secretion are TILs produced by the expansion methods of the present invention, including for example FIG. 8A and/or FIG. 8B and/or FIG. 8C and/or FIG. 8D. In some embodiments, TILs that exhibit greater than 80000 pg/$10^6$ TILs granzyme B secretion are TILs produced by the expansion methods of the present invention, including for example FIG. 8A and/or FIG. 8B and/or FIG. 8C and/or FIG. 8D. In some embodiments, TILs that exhibit greater than 100000 pg/$10^6$ TILs granzyme B secretion are TILs produced by the expansion methods of the present invention, including for example FIG. 8A and/or FIG. 8B and/or FIG. 8C and/or FIG. 8D. In some embodiments, TILs that exhibit greater than 120000 pg/$10^6$ TILs granzyme B secretion are TILs produced by the expansion methods of the present invention, including for example FIG. 8A and/or FIG. 8B and/or FIG. 8C and/or FIG. 8D. In some embodiments, TILs that exhibit greater than 140000 pg/$10^6$ TILs granzyme B secretion are TILs produced by the expansion methods of the present invention, including for example FIG. 8A and/or FIG. 8B and/or FIG. 8C and/or FIG. 8D. In some embodiments, TILs that exhibit greater than 160000 pg/$10^6$ TILs granzyme B secretion are TILs produced by the expansion methods of the present invention, including for example FIG. 8A and/or FIG. 8B and/or FIG. 8C and/or FIG. 8D. In some embodiments, TILs that exhibit greater than 180000 pg/$10^6$ TILs granzyme B secretion are TILs produced by the expansion methods of the present invention, including for example FIG. 8A and/or FIG. 8B and/or FIG. 8C and/or FIG. 8D. In some embodiments, TILs that exhibit greater than 200000 pg/$10^6$ TILs granzyme B secretion are TILs produced by the expansion methods of the present invention, including for example FIG. 8A and/or FIG. 8B and/or FIG. 8C and/or FIG. 8D. In some embodiments, TILs that exhibit greater than 220000 pg/$10^6$ TILs granzyme B secretion are TILs produced by the expansion methods of the present invention, including for example FIG. 8A and/or FIG. 8B and/or FIG. 8C and/or FIG. 8D. In some embodiments, TILs that exhibit greater than 240000 pg/$10^6$ TILs granzyme B secretion are TILs produced by the expansion methods of the present invention, including for example FIG. 8A and/or FIG. 8B and/or FIG. 8C and/or FIG. 8D. In some embodiments, TILs that exhibit greater than 260000 pg/$10^6$ TILs granzyme B secretion are TILs produced by the expansion methods of the present invention, including for example FIG. 8A and/or FIG. 8B and/or FIG. 8C and/or FIG. 8D. In some embodiments, TILs that exhibit greater than 280000 pg/$10^6$ TILs granzyme B secretion are TILs produced by the expansion methods of the present invention, including for example FIG. 8A and/or FIG. 8B and/or FIG. 8C and/or FIG. 8D. In some embodiments, TILs that exhibit greater than 300000 pg/$10^6$ TILs granzyme B secretion are TILs produced by the expansion methods of the present invention, including for example FIG. 8A and/or FIG. 8B and/or FIG. 8C and/or FIG. 8D. In some embodiments, TILs that exhibit greater than 3000 pg/$10^6$ TILs to 300000 pg/$10^6$ TILs or more granzyme B secretion are TILs produced by the expansion methods of the present invention, including for example FIG. 8A and/or FIG. 8B and/or FIG. 8C and/or FIG. 8D. In some embodiments, TILs that exhibit greater than 3000 pg/$10^6$ TILs greater than 5000 pg/$10^6$ TILs, greater than 7000 pg/$10^6$ TILs, greater than 9000 pg/$10^6$ TILs, greater than 11000 pg/$10^6$ TILs, greater than 13000 pg/$10^6$ TILs, greater than 15000 pg/$10^6$ TILs, greater than 17000 pg/$10^6$ TILs, greater than 19000 pg/$10^6$ TILs, greater than 20000 pg/$10^6$ TILs, greater than 40000 pg/$10^6$ TILs, greater than 60000 pg/$10^6$ TILs, greater than 80000 pg/$10^6$ TILs, greater than 100000 pg/$10^6$ TILs, greater than 120000 pg/$10^6$ TILs, greater than 140000 pg/$10^6$ TILs, greater than 160000 pg/$10^6$ TILs, greater than 180000 pg/$10^6$ TILs, greater than 200000 pg/$10^6$ TILs, greater than 220000 pg/$10^6$ TILs, greater than 240000 pg/$10^6$ TILs, greater than 260000 pg/$10^6$ TILs, greater than 280000 pg/$10^6$ TILs, greater than 300000 pg/$10^6$ TILs, or more granzyme B secretion are TILs produced by the expansion methods of the present invention, including for example FIG. 8A and/or FIG. 8B and/or FIG. 8C and/or FIG. 8D. In some embodiments, TILs that exhibit greater than 3000 pg/$10^6$ TILs granzyme B secretion are TILs produced by the expansion methods of the present invention, including for example FIG. 8A and/or FIG. 8B and/or FIG. 8C and/or FIG. 8D. In some embodiments, TILs that exhibit greater than 5000 pg/$10^6$ TILs granzyme B secretion are TILs produced by the expansion methods of the present invention, including for example FIG. 8A and/or FIG. 8B and/or FIG. 8C and/or FIG. 8D. In some embodiments, TILs that exhibit greater than 7000 pg/$10^6$ TILs granzyme B secretion are TILs produced by the expansion methods of the present invention, including for example FIG. 8A and/or FIG. 8B and/or FIG. 8C and/or FIG. 8D. In some embodiments, TILs that exhibit greater than 9000 pg/$10^6$ TILs granzyme B secretion are TILs produced by the expansion methods of the present invention, including for example FIG. 8A and/or FIG. 8B and/or FIG. 8C and/or FIG. 8D. In some embodiments, TILs that exhibit greater than 11000 pg/$10^6$ TILs granzyme B secretion are TILs produced by the expansion methods of the present invention, including for example FIG. 8A and/or FIG. 8B and/or FIG. 8C and/or FIG. 8D. In some embodiments, TILs that exhibit greater than 13000 pg/$10^6$ TILs granzyme B secretion are TILs produced by the expansion methods of the present invention, including for example FIG. 8A and/or FIG. 8B and/or FIG. 8C and/or FIG. 8D. In some embodiments, TILs that exhibit greater than 15000 pg/$10^6$ TILs granzyme B secretion are TILs produced by the expansion methods of the present invention, including for example FIG. 8A and/or FIG. 8B and/or FIG. 8C and/or FIG. 8D. In some embodiments, TILs that exhibit greater than 17000 pg/$10^6$ TILs granzyme B secretion are TILs produced by the expansion methods of the present invention, including for example FIG. 8A and/or FIG. 8B and/or FIG. 8C and/or FIG. 8D. In some embodiments, TILs that exhibit greater than 19000 pg/$10^6$ TILs granzyme B secretion are TILs produced by the expansion methods of the present invention, including for example FIG. 8A and/or FIG. 8B and/or FIG. 8C and/or FIG. 8D. In some embodiments, TILs that exhibit greater than 20000 pg/$10^6$ TILs granzyme B secretion are TILs produced by the expansion methods of the present invention, including for example FIG. 8A and/or FIG. 8B and/or FIG. 8C and/or FIG. 8D. In some embodiments, TILs that exhibit greater than 40000 pg/$10^6$ TILs granzyme B secretion are TILs produced by the expansion methods of the present invention, including for example FIG. 8A and/or FIG. 8B and/or FIG. 8C and/or FIG. 8D. In some embodiments, TILs that exhibit greater than 60000 pg/$10^6$ TILs granzyme B secretion are TILs produced by the expansion methods of the present invention, including for example FIG. 8A and/or FIG. 8B and/or FIG. 8C and/or FIG. 8D. In some embodiments, TILs that exhibit greater than 80000 pg/$10^6$ TILs granzyme B secretion are TILs produced by the expansion methods of the present invention, including for example FIG. 8A and/or FIG. 8B and/or FIG. 8C and/or FIG. 8D. In some embodiments, TILs that exhibit greater than 100000 pg/$10^6$ TILs granzyme B secretion are TILs produced by the expansion methods of the present invention, including for example FIG. 8A and/or FIG. 8B and/or FIG. 8C and/or FIG. 8D. In some embodiments, TILs that exhibit greater than 120000 pg/$10^6$ TILs granzyme B secretion are TILs produced by the expansion methods of the present invention, including for example FIG. 8A and/or FIG. 8B and/or FIG. 8C and/or FIG. 8D. In some embodiments, TILs that exhibit greater than 140000 pg/$10^6$ TILs granzyme B secretion are TILs produced by the expansion methods of the present invention, including for example FIG. 8A and/or FIG. 8B and/or FIG. 8C and/or FIG. 8D. In some embodiments, TILs that exhibit greater than 160000 pg/$10^6$ TILs granzyme B secretion are TILs produced by the expansion methods of the present invention, including for example FIG. 8A and/or FIG. 8B and/or FIG. 8C and/or FIG. 8D. In some embodiments, TILs that exhibit greater than 180000 pg/$10^6$ TILs granzyme B secretion are TILs produced by the expansion methods of the present invention, including for example FIG. 8A and/or FIG. 8B and/or FIG. 8C and/or FIG. 8D. In some embodiments, TILs that exhibit greater than 200000 pg/$10^6$ TILs granzyme B secretion are TILs produced by the expansion methods of the present invention, including for example FIG. 8A and/or FIG. 8B and/or FIG. 8C and/or FIG. 8D. In some embodiments, TILs that exhibit greater than 220000 pg/$10^6$ TILs granzyme B secretion are TILs produced by the expansion methods of the present invention, including for example FIG. 8A and/or FIG. 8B and/or FIG. 8C and/or FIG. 8D. In some embodiments, TILs that exhibit greater than 240000 pg/$10^6$ TILs granzyme B secretion are TILs produced by the expansion methods of the present invention, including for example FIG. 8A and/or FIG. 8B and/or FIG. 8C and/or FIG. 8D. In some embodiments, TILs that exhibit greater than 260000 pg/$10^6$ TILs granzyme B secretion are TILs produced by the expansion methods of the present invention, including for example FIG. 8A and/or FIG. 8B and/or FIG. 8C and/or FIG. 8D. In some embodiments, TILs that exhibit greater than 280000 pg/$10^6$ TILs granzyme B secretion are TILs produced by the expansion methods of the present invention, including for example FIG. 8A and/or FIG. 8B and/or FIG. 8C and/or FIG. 8D. In some embodiments, TILs that exhibit greater than 300000 pg/$10^6$ TILs granzyme B secretion are TILs produced by the expansion methods of the present invention, including for example FIG. 8A and/or FIG. 8B and/or FIG. 8C and/or FIG. 8D.

In some embodiments, TILs that exhibit greater than 1000 pg/mL to 300000 pg/mL or more granzyme B secretion are TILs produced by the expansion methods of the present invention, including for example FIG. 8A and/or FIG. 8B and/or FIG. 8C and/or FIG. 8D. In some embodiments, TILs that exhibit greater than 1000 pg/mL, greater than 2000 pg/mL, greater than 3000 pg/mL, greater than 4000 pg/mL, greater than 5000 pg/mL, greater than 6000 pg/mL, greater than 7000 pg/mL, greater than 8000 pg/mL, greater than 9000 pg/mL, greater than 10000 pg/mL, greater than 20000 pg/mL, greater than 30000 pg/mL, greater than 40000 pg/mL, greater than 50000 pg/mL, greater than 60000 pg/mL, greater than 70000 pg/mL, greater than 80000 pg/mL, greater than 90000 pg/mL, greater than 100000 pg/mL or more granzyme B secretion are TILs produced by the expansion methods of the present invention, including for example FIG. 8A and/or FIG. 8B and/or FIG. 8C and/or FIG. 8D. In some embodiments, TILs that exhibit greater than 1000 pg/mL granzyme B are TILs produced by the expansion methods of the present invention, including for example FIG. 8A and/or FIG. 8B and/or FIG. 8C and/or FIG. 8D. In some embodiments, TILs that exhibit greater than 2000 pg/mL granzyme B are TILs produced by the expansion methods of the present invention, including for example FIG. 8A and/or FIG. 8B and/or FIG. 8C and/or FIG. 8D. In some embodiments, TILs that exhibit greater than 3000 pg/mL granzyme B are TILs produced by the expansion methods of the present invention, including for example FIG. 8A and/or FIG. 8B and/or FIG. 8C and/or FIG. 8D. In some embodiments, TILs that exhibit greater than 4000 pg/mL granzyme B are TILs produced by the expansion methods of the present invention, including for example FIG. 8A and/or FIG. 8B and/or FIG. 8C and/or FIG. 8D. In some embodiments, TILs that exhibit greater than 5000 pg/mL granzyme B are TILs produced by the expansion methods of the present invention, including for example FIG. 8A and/or FIG. 8B and/or FIG. 8C and/or FIG. 8D. In some embodiments, TILs that exhibit greater than 6000 pg/mL granzyme B are TILs produced by the expansion methods of the present invention, including for example FIG. 8A and/or FIG. 8B and/or FIG. 8C and/or FIG. 8D. In some embodiments, TILs that exhibit greater than 7000 pg/mL granzyme B are TILs produced by the expansion methods of the present invention, including for example FIG. 8A and/or FIG. 8B and/or FIG. 8C and/or FIG. 8D. In some embodiments, TILs that exhibit greater than 8000 pg/mL granzyme B are TILs produced by the expansion methods of the present invention, including for example FIG. 8A and/or FIG. 8B and/or FIG. 8C and/or FIG. 8D. In some embodiments, TILs that exhibit greater than 9000 pg/mL granzyme B are TILs produced by the expansion methods of the present invention, including for example FIG. 8A and/or FIG. 8B and/or FIG. 8C and/or FIG. 8D. In some embodiments, TILs that exhibit greater than 10000 pg/mL granzyme B are TILs produced by the expansion methods of the present invention, including for example FIG. 8A and/or FIG. 8B and/or FIG. 8C and/or FIG. 8D. In some embodiments, TILs that exhibit greater than 20000 pg/mL granzyme B are TILs produced by the expansion methods of the present invention, including for example FIG. 8A and/or FIG. 8B and/or FIG. 8C and/or FIG. 8D. In some embodiments, TILs that exhibit greater than 30000 pg/mL granzyme B are TILs produced by the expansion methods of the present invention, including for example FIG. 8A and/or FIG. 8B and/or FIG. 8C and/or FIG. 8D. In some embodiments, TILs that exhibit greater than 40000 pg/mL granzyme B are TILs produced by the expansion methods of the present invention, including for example FIG. 8A and/or FIG. 8B and/or FIG. 8C and/or FIG. 8D. In some embodiments, TILs that exhibit greater than 50000 pg/mL granzyme B are TILs produced by the expansion methods of the present invention, including for example FIG. 8A and/or FIG. 8B and/or FIG. 8C and/or FIG. 8D. In some embodiments, TILs that exhibit greater than 60000 pg/mL granzyme B are TILs produced by the expansion methods of the present invention, including for example FIG. 8A and/or FIG. 8B and/or FIG. 8C and/or FIG. 8D. In some embodiments, TILs that exhibit greater than 70000 pg/mL granzyme B are TILs produced by the expansion methods of the present invention, including for example FIG. 8A and/or FIG. 8B and/or FIG. 8C and/or FIG. 8D. In some embodiments, TILs that exhibit greater than 80000 pg/mL granzyme B are TILs produced by the expansion methods of the present invention, including for example FIG. 8A and/or FIG. 8B and/or FIG. 8C and/or FIG. 8D. In some embodiments, TILs that exhibit greater than 90000 pg/mL granzyme B are TILs produced by the expansion methods of the present invention, including for example FIG. 8A and/or FIG. 8B and/or FIG. 8C and/or FIG. 8D. In some embodiments, TILs that exhibit greater than 100000 pg/mL granzyme B are TILs produced by the expansion methods of the present invention, including for example FIG. 8A and/or FIG. 8B and/or FIG. 8C and/or FIG. 8D. In some embodiments, TILs that exhibit greater than 120000 pg/mL granzyme B secretion are TILs produced by the expansion methods of the present invention, including for example FIG. 8A and/or FIG. 8B and/or FIG. 8C and/or FIG. 8D. In some embodiments, TILs that exhibit greater than 140000 pg/mL granzyme B are TILs granzyme B secretion are TILs produced by the expansion methods of the present invention, including for example FIG. 8A and/or FIG. 8B and/or FIG. 8C and/or FIG. 8D. In some embodiments, TILs that exhibit greater than 160000 pg/mL granzyme B secretion are TILs produced by the expansion methods of the present invention, including for example FIG. 8A and/or FIG. 8B and/or FIG. 8C and/or FIG. 8D. In some embodiments, TILs that exhibit greater than 180000 pg/mL granzyme B secretion are TILs produced by the expansion methods of the present invention, including for example FIG. 8A and/or FIG. 8B and/or FIG. 8C and/or FIG. 8D. In some embodiments, TILs that exhibit greater than 200000 pg/mL granzyme B secretion are TILs produced by the expansion methods of the present invention, including for example FIG. 8A and/or FIG. 8B and/or FIG. 8C and/or FIG. 8D. In some embodiments, TILs that exhibit greater than 220000 pg/mL granzyme B secretion are TILs produced by the expansion methods of the present invention, including for example FIG. 8A and/or FIG. 8B and/or FIG. 8C and/or FIG. 8D. In some embodiments, TILs that exhibit greater than 240000 pg/mL granzyme B secretion are TILs produced by the expansion methods of the present invention, including for example FIG. 8A and/or FIG. 8B and/or FIG. 8C and/or FIG. 8D. In some embodiments, TILs that exhibit greater than 260000 pg/mL granzyme B secretion are TILs produced by the expansion methods of the present invention, including for example FIG. 8A and/or FIG. 8B and/or FIG. 8C and/or FIG. 8D. In some embodiments, TILs that exhibit greater than 280000 pg/mL granzyme B secretion are TILs produced by the expansion methods of the present invention, including for example FIG. 8A and/or FIG. 8B and/or FIG. 8C and/or FIG. 8D. In some embodiments, TILs that exhibit greater than 300000 pg/mL granzyme B secretion are TILs produced by the expansion methods of the present invention, including for example FIG. 8A and/or FIG. 8B and/or FIG. 8C and/or FIG. 8D.

In some embodiments, the expansion methods of the present invention produce an expanded population of TILs that exhibits increased granzyme B secretion in vitro including for example TILs as provided in FIG. 8A and/or FIG. 8B and/or FIG. 8C and/or FIG. 8D, as compared to non-expanded population of TILs. In some embodiments, granzyme B secretion of the expanded population of TILs of the present invention is increased by at least one-fold to fifty-fold or more as compared to non-expanded population of TILs. In some embodiments, IFN-γ secretion is increased by at least one-fold, at least two-fold, at least three-fold, at least four-fold, at least five-fold, at least six-fold, at least seven-fold, at least eight-fold, at least nine-fold, at least ten-fold, at least twenty-fold, at least thirty-fold, at least forty-fold, at least fifty-fold or more as compared to non-expanded population of TILs. In some embodiments, granzyme B secretion of the expanded population of TILs of the present invention is increased by at least one-fold as compared to non-expanded population of TILs. In some embodiments, granzyme B secretion of the expanded population of TILs of the present invention is increased by at least two-fold as compared to non-expanded population of TILs. In some embodiments, granzyme B secretion of the expanded population of TILs of the present invention is increased by at least three-fold as compared to non-expanded population of TILs. In some embodiments, granzyme B secretion of the expanded population of TILs of the present invention is increased by at least four-fold as compared to non-expanded population of TILs. In some embodiments, granzyme B secretion of the expanded population of TILs of the present invention is increased by at least five-fold as compared to non-expanded population of TILs. In some embodiments, granzyme B secretion of the expanded population of TILs of the present invention is increased by at least six-fold as compared to non-expanded population of TILs. In some embodiments, granzyme B secretion of the expanded population of TILs of the present invention is increased by at least seven-fold as compared to non-expanded population of TILs. In some embodiments, granzyme B secretion of the expanded population of TILs of the present invention is increased by at least eight-fold as compared to non-expanded population of TILs. In some embodiments, granzyme B secretion of the expanded population of TILs of the present invention is increased by at least nine-fold as compared to non-expanded population of TILs. In some embodiments, granzyme B secretion of the expanded population of TILs of the present invention is increased by at least ten-fold as compared to non-expanded population of TILs. In some embodiments, granzyme B secretion of the expanded population of TILs of the present invention is increased by at least twenty-fold as compared to non-expanded population of TILs. In some embodiments, granzyme B secretion of the expanded population of TILs of the present invention is increased by at least thirty-fold as compared to non-expanded population of TILs. In some embodiments, granzyme B secretion of the expanded population of TILs of the present invention is increased by at least forty-fold as compared to non-expanded population of TILs. In some embodiments, granzyme B secretion of the expanded population of TILs of the present invention is increased by at least fifty-fold as compared to non-expanded population of TILs.

In some embodiments, TILs capable of at least one-fold, two-fold, three-fold, four-fold, or five-fold or more lower levels of TNF-α (i.e., TNF-alpha) secretion as compared to IFN-γ secretion are TILs produced by the expansion methods of the present invention, including, for example FIG. 8A and/or FIG. 8B and/or FIG. 8C and/or FIG. 8D methods. In some embodiments, TILs capable of at least one-fold lower levels of TNF-α secretion as compared to IFN-γ secretion are TILs produced by the expansion methods of the present invention, including, for example FIG. 8A and/or FIG. 8B and/or FIG. 8C and/or FIG. 8D methods. In some embodiments, TILs capable of at least two-fold lower levels of TNF-α secretion as compared to IFN-γ secretion are TILs produced by the expansion methods of the present invention, including, for example FIG. 8A and/or FIG. 8B and/or FIG. 8C and/or FIG. 8D methods. In some embodiments, TILs capable of at least three-fold lower levels of TNF-α secretion as compared to IFN-γ secretion are TILs produced by the expansion methods of the present invention, including, for example FIG. 8A and/or FIG. 8B and/or FIG. 8C and/or FIG. 8D methods. In some embodiments, TILs capable of at least four-fold lower levels of TNF-α secretion as compared to IFN-γ secretion are TILs produced by the expansion methods of the present invention, including, for example FIG. 8A and/or FIG. 8B and/or FIG. 8C and/or FIG. 8D methods. In some embodiments, TILs capable of at least five-fold lower levels of TNF-α secretion as compared to IFN-γ secretion are TILs produced by the expansion methods of the present invention, including, for example FIG. 8A and/or FIG. 8B and/or FIG. 8C and/or FIG. 8D methods.

In some embodiments, TILs capable of at least 200 pg/mL/5×$10^5$ cells to about 10,000 pg/mL/5×$10^5$ cells or more TNF-α (i.e., TNF-alpha) secretion are TILs produced by the expansion methods of the present invention, including, for example FIG. 8A and/or FIG. 8B and/or FIG. 8C and/or FIG. 8D methods. In some embodiments, TILs capable of at least 500 pg/mL/5×$10^5$ cells to about 10,000 pg/mL/5×$10^5$ cells or more TNF-α secretion are TILs produced by the expansion methods of the present invention, including, for example FIG. 8A and/or FIG. 8B and/or FIG. 8C and/or FIG. 8D methods. In some embodiments, TILs capable of at least 1000 pg/mL/5×$10^5$ cells to about 10,000 pg/mL/5×$10^5$ cells or more TNF-α secretion are TILs produced by the expansion methods of the present invention, including, for example FIG. 8A and/or FIG. 8B and/or FIG. 8C and/or FIG. 8D methods. In some embodiments, TILs capable of at least 2000 pg/mL/5×$10^5$ cells to about 10,000 pg/mL/5×$10^5$ cells or more TNF-α secretion are TILs produced by the expansion methods of the present invention, including, for example FIG. 8A and/or FIG. 8B and/or FIG. 8C and/or FIG. 8D methods. In some embodiments, TILs capable of at least 3000 pg/mL/5×$10^5$ cells to about 10,000 pg/mL/5×$10^5$ cells or more TNF-α secretion are TILs produced by the expansion methods of the present invention, including, for example FIG. 8A and/or FIG. 8B and/or FIG. 8C and/or FIG. 8D methods. In some embodiments, TILs capable of at least 4000 pg/mL/5×$10^5$ cells to about 10,000 pg/mL/5×$10^5$ cells or more TNF-α secretion are TILs produced by the expansion methods of the present invention, including, for example FIG. 8A and/or FIG. 8B and/or FIG. 8C and/or FIG. 8D methods. In some embodiments, TILs capable of at least 5000 pg/mL/5×$10^5$ cells to about 10,000 pg/mL/5×$10^5$ cells or more TNF-α secretion are TILs produced by the expansion methods of the present invention, including, for example FIG. 8A and/or FIG. 8B and/or FIG. 8C and/or FIG. 8D methods. In some embodiments, TILs capable of at least 6000 pg/mL/5×$10^5$ cells to about 10,000 pg/mL/5×$10^5$ cells or more TNF-α secretion are TILs produced by the expansion methods of the present invention, including, for example FIG. 8A and/or FIG. 8B and/or FIG. 8C and/or FIG. 8D methods. In some embodiments, TILs capable of at least 7000 pg/mL/5×$10^5$ cells to about 10,000 pg/mL/5×$10^5$ cells or more TNF-α secretion are TILs produced by the expansion methods of the present invention, including, for example FIG. 8A and/or FIG. 8B and/or FIG. 8C and/or FIG. 8D methods. In some embodiments, TILs capable of at least 8000 pg/mL/5×$10^5$ cells to about 10,000 pg/mL/5×$10^5$ cells or more TNF-α secretion are TILs produced by the expansion methods of the present invention, including, for example FIG. 8A and/or FIG. 8B and/or FIG. 8C and/or FIG. 8D methods. In some embodiments, TILs capable of at least 9000 pg/mL/5×$10^5$ cells to about 10,000 pg/mL/5×$10^5$ cells or more TNF-α secretion are TILs produced by the expansion methods of the present invention, including, for example FIG. 8A and/or FIG. 8B and/or FIG. 8C and/or FIG. 8D methods.

In some embodiments, IFN-γ and granzyme B levels are measured to determine the phenotypic characteristics of the TILs produced by the expansion methods of the present invention, including, for example FIG. 8A and/or FIG. 8B and/or FIG. 8C and/or FIG. 8D methods. In some embodiments, IFN-γ and TNF-α levels are measured to determine the phenotypic characteristics of the TILs produced by the expansion methods of the present invention, including, for example FIG. 8A and/or FIG. 8B and/or FIG. 8C and/or FIG. 8D methods. In some embodiments, granzyme B and TNF-α levels are measured to determine the phenotypic characteristics of the TILs produced by the expansion methods of the present invention, including, for example FIG. 8A and/or FIG. 8B and/or FIG. 8C and/or FIG. 8D methods. In some embodiments, IFN-γ, granzyme B and TNF-α levels are measured to determine the phenotypic characteristics of the TILs produced by the expansion methods of the present invention, including, for example FIG. 8A and/or FIG. 8B and/or FIG. 8C and/or FIG. 8D methods.

In some embodiments, the phenotypic characterization is performed after cryopreservation.

H. Additional Process Embodiments

In some embodiments, the invention provides a method for expanding tumor infiltrating lymphocytes (TILs) into a therapeutic population of TILs comprising: (a) obtaining a first population of TILs from a tumor resected from a subject by processing a tumor sample obtained from the subject into multiple tumor fragments; (b) performing a priming first expansion by culturing the first population of TILs in a cell culture medium comprising IL-2 and OKT-3, wherein the priming first expansion is performed for about 1 to 7 days or about 1 to 8 days to obtain the second population of TILs, wherein the second population of TILs is greater in number than the first population of TILs; (c) performing a rapid second expansion by contacting the second population of TILs with a cell culture medium comprising IL-2, OKT-3 and exogenous antigen presenting cells (APCs) to produce a third population of TILs, wherein the rapid second expansion is performed for about 1 to 11 days or about 1 to 10 days to obtain the third population of TILs, wherein the third population of TILs is a therapeutic population of TILs; and (d) harvesting the therapeutic population of TILs obtained from step (c). In some embodiments, the step of rapid second expansion is split into a plurality of steps to achieve a scaling up of the culture by: (1) performing the rapid second expansion by culturing the second population of TILs in a small scale culture in a first container, e.g., a G-Rex 100MCS container, for a period of about 3 to 4 days, or about 2 to 4 days, and then (2) effecting the transfer of the second population of TILs from the small scale culture to a second container larger than the first container, e.g., a G-Rex 500MCS container, wherein in the second container the second population of TILs from the small scale culture is cultured in a larger scale culture for a period of about 4 to 7 days, or about 4 to 8 days. In some embodiments, the step of rapid expansion is split into a plurality of steps to achieve a scaling out of the culture by: (1) performing the rapid second expansion by culturing the second population of TILs in a first small scale culture in a first container, e.g., a G-Rex 100MCS container, for a period of about 3 to 4 days, and then (2) effecting the transfer and apportioning of the second population of TILs from the first small scale culture into and amongst at least 2, 3, 4, 5, 6, 7, 8, 9, 10, 11, 12, 13, 14, 15, 16, 17, 18, 19, or 20 second containers that are equal in size to the first container, wherein in each second container the portion of the second population of TILs from the first small scale culture transferred to such second container is cultured in a second small scale culture for a period of about 4 to 7 days, or about 4 to 8 days. In some embodiments, the step of rapid expansion is split into a plurality of steps to achieve a scaling out and scaling up of the culture by: (1) performing the rapid second expansion by culturing the second population of TILs in a small scale culture in a first container, e.g., a G-Rex 100MCS container, for a period of about 3 to 4 days, or about 2 to 4 days, and then (2) effecting the transfer and apportioning of the second population of TILs from the first small scale culture into and amongst at least 2, 3, 4, 5, 6, 7, 8, 9, 10, 11, 12, 13, 14, 15, 16, 17, 18, 19, or 20 second containers that are larger in size than the first container, e.g., G-Rex 500MCS containers, wherein in each second container the portion of the second population of TILs transferred from the small scale culture to such second container is cultured in a larger scale culture for a period of about 4 to 7 days, or about 4 to 8 days. In some embodiments, the step of rapid expansion is split into a plurality of steps to achieve a scaling out and scaling up of the culture by: (1) performing the rapid second expansion by culturing the second population of TILs in a small scale culture in a first container, e.g., a G-Rex 100MCS container, for a period of about 3 to 4 days, and then (2) effecting the transfer and apportioning of the second population of TILs from the first small scale culture into and amongst 2, 3 or 4 second containers that are larger in size than the first container, e.g., G-Rex 500MCS containers, wherein in each second container the portion of the second population of TILs transferred from the small scale culture to such second container is cultured in a larger scale culture for a period of about 5 to 7 days.

In some embodiments, the invention provides a method for expanding tumor infiltrating lymphocytes (TILs) into a therapeutic population of TILs comprising: (a) obtaining a first population of TILs from a tumor resected from a subject by processing a tumor sample obtained from the subject into multiple tumor fragments; (b) performing a priming first expansion by culturing the first population of TILs in a cell culture medium comprising IL-2 and OKT-3, wherein the priming first expansion is performed for about 1 to 8 days to obtain the second population of TILs, wherein the second population of TILs is greater in number than the first population of TILs; (c) performing a rapid second expansion by contacting the second population of TILs with a cell culture medium comprising IL-2, OKT-3 and exogenous antigen presenting cells (APCs) to produce a third population of TILs, wherein the rapid second expansion is performed for about 1 to 8 days to obtain the third population of TILs, wherein the third population of TILs is a therapeutic population of TILs; and (d) harvesting the therapeutic population of TILs obtained from step (c). In some embodiments, the step of rapid second expansion is split into a plurality of steps to achieve a scaling up of the culture by: (1) performing the rapid second expansion by culturing the second population of TILs in a small scale culture in a first container, e.g., a G-Rex 100MCS container, for a period of about 2 to 4 days, and then (2) effecting the transfer of the second population of TILs from the small scale culture to a second container larger than the first container, e.g., a G-Rex 500MCS container, wherein in the second container the second population of TILs from the small scale culture is cultured in a larger scale culture for a period of about 4 to 8 days. In some embodiments, the step of rapid expansion is split into a plurality of steps to achieve a scaling out of the culture by: (1) performing the rapid second expansion by culturing the second population of TILs in a first small scale culture in a first container, e.g., a G-Rex 100MCS container, for a period of about 2 to 4 days, and then (2) effecting the transfer and apportioning of the second population of TILs from the first small scale culture into and amongst at least 2, 3, 4, 5, 6, 7, 8, 9, 10, 11, 12, 13, 14, 15, 16, 17, 18, 19, or 20 second containers that are equal in size to the first container, wherein in each second container the portion of the second population of TILs from the first small scale culture transferred to such second container is cultured in a second small scale culture for a period of about 4 to 6 days. In some embodiments, the step of rapid expansion is split into a plurality of steps to achieve a scaling out and scaling up of the culture by: (1) performing the rapid second expansion by culturing the second population of TILs in a small scale culture in a first container, e.g., a G-Rex 100MCS container, for a period of about 2 to 4 days, and then (2) effecting the transfer and apportioning of the second population of TILs from the first small scale culture into and amongst at least 2, 3, 4, 5, 6, 7, 8, 9, 10, 11, 12, 13, 14, 15, 16, 17, 18, 19, or 20 second containers that are larger in size than the first container, e.g., G-Rex 500MCS containers, wherein in each second container the portion of the second population of TILs transferred from the small scale culture to such second container is cultured in a larger scale culture for a period of about 4 to 6 days. In some embodiments, the step of rapid expansion is split into a plurality of steps to achieve a scaling out and scaling up of the culture by: (1) performing the rapid second expansion by culturing the second population of TILs in a small scale culture in a first container, e.g., a G-Rex 100MCS container, for a period of about 3 to 4 days, and then (2) effecting the transfer and apportioning of the second population of TILs from the first small scale culture into and amongst 2, 3 or 4 second containers that are larger in size than the first container, e.g., G-Rex 500MCS containers, wherein in each second container the portion of the second population of TILs transferred from the small scale culture to such second container is cultured in a larger scale culture for a period of about 4 to 5 days.

In some embodiments, the invention provides a method for expanding tumor infiltrating lymphocytes (TILs) into a therapeutic population of TILs comprising: (a) obtaining a first population of TILs from a tumor resected from a subject by processing a tumor sample obtained from the subject into multiple tumor fragments; (b) performing a priming first expansion by culturing the first population of TILs in a cell culture medium comprising IL-2 and OKT-3, wherein the priming first expansion is performed for about 1 to 7 days to obtain the second population of TILs, wherein the second population of TILs is greater in number than the first population of TILs; (c) performing a rapid second expansion by contacting the second population of TILs with a cell culture medium comprising IL-2, OKT-3 and exogenous antigen presenting cells (APCs) to produce a third population of TILs, wherein the rapid second expansion is performed for about 1 to 11 days to obtain the third population of TILs, wherein the third population of TILs is a therapeutic population of TILs; and (d) harvesting the therapeutic population of TILs obtained from step (c). In some embodiments, the step of rapid second expansion is split into a plurality of steps to achieve a scaling up of the culture by: (1) performing the rapid second expansion by culturing the second population of TILs in a small scale culture in a first container, e.g., a G-Rex 100MCS container, for a period of about 3 to 4 days, and then (2) effecting the transfer of the second population of TILs from the small scale culture to a second container larger than the first container, e.g., a G-Rex 500MCS container, wherein in the second container the second population of TILs from the small scale culture is cultured in a larger scale culture for a period of about 4 to 7 days. In some embodiments, the step of rapid expansion is split into a plurality of steps to achieve a scaling out of the culture by: (1) performing the rapid second expansion by culturing the second population of TILs in a first small scale culture in a first container, e.g., a G-Rex 100MCS container, for a period of about 3 to 4 days, and then (2) effecting the transfer and apportioning of the second population of TILs from the first small scale culture into and amongst at least 2, 3, 4, 5, 6, 7, 8, 9, 10, 11, 12, 13, 14, 15, 16, 17, 18, 19, or 20 second containers that are equal in size to the first container, wherein in each second container the portion of the second population of TILs from the first small scale culture transferred to such second container is cultured in a second small scale culture for a period of about 4 to 7 days. In some embodiments, the step of rapid expansion is split into a plurality of steps to achieve a scaling out and scaling up of the culture by: (1) performing the rapid second expansion by culturing the second population of TILs in a small scale culture in a first container, e.g., a G-Rex 100MCS container, for a period of about 3 to 4 days, and then (2) effecting the transfer and apportioning of the second population of TILs from the first small scale culture into and amongst at least 2, 3, 4, 5, 6, 7, 8, 9, 10, 11, 12, 13, 14, 15, 16, 17, 18, 19, or 20 second containers that are larger in size than the first container, e.g., G-Rex 500MCS containers, wherein in each second container the portion of the second population of TILs transferred from the small scale culture to such second container is cultured in a larger scale culture for a period of about 4 to 7 days. In some embodiments, the step of rapid expansion is split into a plurality of steps to achieve a scaling out and scaling up of the culture by: (1) performing the rapid second expansion by culturing the second population of TILs in a small scale culture in a first container, e.g., a G-Rex 100MCS container, for a period of about 4 days, and then (2) effecting the transfer and apportioning of the second population of TILs from the first small scale culture into and amongst 2, 3 or 4 second containers that are larger in size than the first container, e.g., G-Rex 500MCS containers, wherein in each second container the portion of the second population of TILs transferred from the small scale culture to such second container is cultured in a larger scale culture for a period of about 5 days.

In another embodiment, the invention provides the method described in any of the preceding paragraphs as applicable above modified such that in step (b) the primary first expansion is performed by contacting the first population of TILs with a culture medium which further comprises exogenous antigen-presenting cells (APCs), wherein the number of APCs in the culture medium in step (c) is greater than the number of APCs in the culture medium in step (b).

In another embodiment, the invention provides the method described in any of the preceding paragraphs as applicable above modified such that in step (c) the culture medium is supplemented with additional exogenous APCs.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 20:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 10:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 9:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 8:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 7:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 6:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 5:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 4:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 3:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 2.9:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 2.8:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 2.7:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 2.6:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 2.5:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 2.4:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 2.3:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 2.2:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 2.1:1.

In another embodiment, the invention provides the method described in any of the preceding paragraphs as applicable above modified such that the ratio of number of APCs added in the rapid second expansion to the number of APCs added in step (b) is selected from a range of from at or about 1.1:1 to at or about 2:1.

In another embodiment, the invention provides the method described in any of the preceding paragraphs as applicable above modified such that the ratio of number of APCs added in the rapid second expansion to the number of APCs added in step (b) is selected from a range of from at or about 2:1 to at or about 10:1.

In another embodiment, the invention provides the method described in any of the preceding paragraphs as applicable above modified such that the ratio of number of APCs added in the rapid second expansion to the number of APCs added in step (b) is selected from a range of from at or about 2:1 to at or about 5:1.

In another embodiment, the invention provides the method described in any of the preceding paragraphs as applicable above modified such that the ratio of number of APCs added in the rapid second expansion to the number of APCs added in step (b) is selected from a range of from at or about 2:1 to at or about 4:1.

In another embodiment, the invention provides the method described in any of the preceding paragraphs as applicable above modified such that the ratio of number of APCs added in the rapid second expansion to the number of APCs added in step (b) is selected from a range of from at or about 2:1 to at or about 3:1.

In another embodiment, the invention provides the method described in any of the preceding paragraphs as applicable above modified such that the ratio of number of APCs added in the rapid second expansion to the number of APCs added in step (b) is selected from a range of from at or about 2:1 to at or about 2.9:1.

In another embodiment, the invention provides the method described in any of the preceding paragraphs as applicable above modified such that the ratio of number of APCs added in the rapid second expansion to the number of APCs added in step (b) is selected from a range of from at or about 2:1 to at or about 2.8:1.

In another embodiment, the invention provides the method described in any of the preceding paragraphs as applicable above modified such that the ratio of number of APCs added in the rapid second expansion to the number of APCs added in step (b) is selected from a range of from at or about 2:1 to at or about 2.7:1.

In another embodiment, the invention provides the method described in any of the preceding paragraphs as applicable above modified such that the ratio of number of APCs added in the rapid second expansion to the number of APCs added in step (b) is selected from a range of from at or about 2:1 to at or about 2.6:1.

In another embodiment, the invention provides the method described in any of the preceding paragraphs as applicable above modified such that the ratio of number of APCs added in the rapid second expansion to the number of APCs added in step (b) is selected from a range of from at or about 2:1 to at or about 2.5:1.

In another embodiment, the invention provides the method described in any of the preceding paragraphs as applicable above modified such that the ratio of number of APCs added in the rapid second expansion to the number of APCs added in step (b) is selected from a range of from at or about 2:1 to at or about 2.4:1.

In another embodiment, the invention provides the method described in any of the preceding paragraphs as applicable above modified such that the ratio of number of APCs added in the rapid second expansion to the number of APCs added in step (b) is selected from a range of from at or about 2:1 to at or about 2.3:1.

In another embodiment, the invention provides the method described in any of the preceding paragraphs as applicable above modified such that the ratio of number of APCs added in the rapid second expansion to the number of APCs added in step (b) is selected from a range of from at or about 2:1 to at or about 2.2:1.

In another embodiment, the invention provides the method described in any of the preceding paragraphs as applicable above modified such that the ratio of number of APCs added in the rapid second expansion to the number of APCs added in step (b) is selected from a range of from at or about 2:1 to at or about 2.1:1.

In another embodiment, the invention provides the method described in any of the preceding paragraphs as applicable above modified such that the ratio of number of APCs added in the rapid second expansion to the number of APCs added in step (b) is at or about 2:1.

In another embodiment, the invention provides the method described in any of the preceding paragraphs as applicable above modified such that the ratio of number of APCs added in the rapid second expansion to the number of APCs added in step (b) is at or about 1.1:1, 1.2:1, 1.3:1, 1.4:1, 1.5:1, 1.6:1, 1.7:1, 1.8:1, 1.9:1, 2:1, 2.1:1, 2.2:1, 2.3:1, 2.4:1, 2.5:1, 2.6:1, 2.7:1, 2.8:1, 2.9:1, 3:1, 3.1:1, 3.2:1, 3.3:1, 3.4:1, 3.5:1, 3.6:1, 3.7:1, 3.8:1, 3.9:1, 4:1, 4.1:1, 4.2:1, 4.3:1, 4.4:1, 4.5:1, 4.6:1, 4.7:1, 4.8:1, 4.9:1, or 5:1.

In another embodiment, the invention provides the method described in any of the preceding paragraphs as applicable above modified such that the number of APCs added in the primary first expansion is at or about $1\times10^{8}$, 1.1×10', $1.2\times10^{8}$, $1.3\times10^{8}$, 1.4×10', $1.5\times10^{8}$, $1.6\times10^{8}$, $1.7\times10^{8}$, $1.8\times10^{8}$, $1.9\times10^{8}$, $2\times10^{8}$, $2.1\times10^{8}$, $2.2\times10^{8}$, $2.3\times10^{8}$, $2.4\times10^{8}$, $2.5\times10^{8}$, $2.6\times10^{8}$, $2.7\times10^{8}$, $2.8\times10^{8}$, $2.9\times10^{8}$, $3\times10^{8}$, $3.1\times10^{8}$, $3.2\times10^{8}$, $3.3\times10^{8}$, $3.4\times10^{8}$ or $3.5\times10^{8}$ APCs, and such that the number of APCs added in the rapid second expansion is at or about $3.5\times10^{8}$, $3.6\times10^{8}$, $3.7\times10^{8}$, $3.8\times10^{8}$, $3.9\times10^{8}$, $4\times10^{8}$, $4.1\times10^{8}$, $4.2\times10^{8}$, $4.3\times10^{8}$, $4.4\times10^{8}$, $4.5\times10^{8}$, $4.6\times10^{8}$, $4.7\times10^{8}$, $4.8\times10^{8}$, $4.9\times10^{8}$, $5\times10^{8}$, $5.1\times10^{8}$, $5.2\times10^{8}$, $5.3\times10^{8}$, $5.4\times10^{8}$, $5.5\times10^{8}$, $5.6\times10^{8}$, $5.7\times10^{8}$, $5.8\times10^{8}$, $5.9\times10^{8}$, $6\times10^{8}$, $6.1\times10^{8}$, $6.2\times10^{8}$, $6.3\times10^{8}$, $6.4\times10^{8}$, $6.5\times10^{8}$, $6.6\times10^{8}$, $6.7\times10^{8}$, $6.8\times10^{8}$, $6.9\times10^{8}$, $7\times10^{8}$, $7.1\times10^{8}$, $7.2\times10^{8}$, $7.3\times10^{8}$, $7.4\times10^{8}$, $7.5\times10^{8}$, $7.6\times10^{8}$, $7.7\times10^{8}$, $7.8\times10^{8}$, $7.9\times10^{8}$, $8\times10^{8}$, $8.1\times10^{8}$, $8.2\times10^{8}$, $8.3\times10^{8}$, $8.4\times10^{8}$, $8.5\times10^{8}$, $8.6\times10^{8}$, $8.7\times10^{8}$, $8.8\times10^{8}$, $8.9\times10^{8}$, $9\times10^{8}$, $9.1\times10^{8}$, $9.2\times10^{8}$, $9.3\times10^{8}$, $9.4\times10^{8}$, $9.5\times10^{8}$, $9.6\times10^{8}$, $9.7\times10^{8}$, $9.8\times10^{8}$, $9.9\times10^{8}$ or $1\times10^{9}$ APCs.

In another embodiment, the invention provides the method described in any of the preceding paragraphs as applicable above modified such that the number of APCs added in the primary first expansion is selected from the range of at or about $1\times10^{8}$ APCs to at or about $3.5\times10^{8}$ APCs, and wherein the number of APCs added in the rapid second expansion is selected from the range of at or about $3.5\times10^{8}$ APCs to at or about $1\times10^{9}$ APCs.

In another embodiment, the invention provides the method described in any of the preceding paragraphs as applicable above modified such that the number of APCs added in the primary first expansion is selected from the range of at or about $1.5\times10^{8}$ APCs to at or about $3\times10^{8}$ APCs, and wherein the number of APCs added in the rapid second expansion is selected from the range of at or about $4\times10^{8}$ APCs to at or about $7.5\times10^{8}$ APCs.

In another embodiment, the invention provides the method described in any of the preceding paragraphs as applicable above modified such that the number of APCs added in the primary first expansion is selected from the range of at or about $2\times10^{8}$ APCs to at or about $2.5\times10^{8}$ APCs, and wherein the number of APCs added in the rapid second expansion is selected from the range of at or about $4.5\times10^{8}$ APCs to at or about $5.5\times10^{8}$ APCs.

In another embodiment, the invention provides the method described in any of the preceding paragraphs as applicable above modified such that at or about $2.5\times10^{8}$ APCs are added to the primary first expansion and at or about $5\times10^{8}$ APCs are added to the rapid second expansion.

In another embodiment, the invention provides the method described in any of the preceding paragraphs as applicable above modified such that the antigen-presenting cells are peripheral blood mononuclear cells (PBMCs).

In another embodiment, the invention provides the method described in any of the preceding paragraphs as applicable above modified such that the multiple tumor fragments are distributed into a plurality of separate containers, in each of which separate containers the first population of TILs is obtained in step (a), the second population of TILs is obtained in step (b), and the third population of TILs is obtained in step (c), and the therapeutic populations of TILs from the plurality of containers in step (c) are combined to yield the harvested TIL population from step (d).

In another embodiment, the invention provides the method described in any of the preceding paragraphs as applicable above modified such that the multiple tumors are evenly distributed into the plurality of separate containers.

In another embodiment, the invention provides the method described in any of the preceding paragraphs as applicable above modified such that the plurality of separate containers comprises at least two separate containers.

In another embodiment, the invention provides the method described in any of the preceding paragraphs as applicable above modified such that the plurality of separate containers comprises from two to twenty separate containers.

In another embodiment, the invention provides the method described in any of the preceding paragraphs as applicable above modified such that the plurality of separate containers comprises from two to fifteen separate containers.

In another embodiment, the invention provides the method described in any of the preceding paragraphs as applicable above modified such that the plurality of separate containers comprises from two to ten separate containers.

In another embodiment, the invention provides the method described in any of the preceding paragraphs as applicable above modified such that the plurality of separate containers comprises from two to five separate containers.

In another embodiment, the invention provides the method described in any of the preceding paragraphs as applicable above modified such that the plurality of separate containers comprises 2, 3, 4, 5, 6, 7, 8, 9, 10, 11, 12, 13, 14, 15, 16, 17, 18, 19, or 20 separate containers.

In another embodiment, the invention provides the method described in any of the preceding paragraphs as applicable above modified such that for each container in which the priming first expansion is performed on a first population of TILs in step (b) the rapid second expansion in step (c) is performed in the same container on the second population of TILs produced from such first population of TILs.

In another embodiment, the invention provides the method described in any of the preceding paragraphs as applicable above modified such that each of the separate containers comprises a first gas-permeable surface area.

In another embodiment, the invention provides the method described in any of the preceding paragraphs as applicable above modified such that the multiple tumor fragments are distributed in a single container.

In another embodiment, the invention provides the method described in any of the preceding paragraphs as applicable above modified such that the single container comprises a first gas-permeable surface area.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein in step (b) the APCs are layered onto the first gas-permeable surface area at an average thickness of at or about one cell layer to at or about three cell layers.

In another embodiment, the invention provides the method described in any of the preceding paragraphs as applicable above modified such that in step (b) the APCs are layered onto the first gas-permeable surface area at an average thickness of at or about 1.5 cell layers to at or about 2.5 cell layers.

In another embodiment, the invention provides the method described in any of the preceding paragraphs as applicable above modified such that in step (b) the APCs are layered onto the first gas-permeable surface area at an average thickness of at or about 2 cell layers.

In another embodiment, the invention provides the method described in any of the preceding paragraphs as applicable above modified such that in step (b) the APCs are layered onto the first gas-permeable surface area at an average thickness of at or about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9 or 3 cell layers.

In another embodiment, the invention provides the method described in any of the preceding paragraphs as applicable above modified such that in step (c) the APCs are layered onto the first gas-permeable surface area at an average thickness of at or about 3 cell layers to at or about 10 cell layers.

In another embodiment, the invention provides the method described in any of the preceding paragraphs as applicable above modified such that in step (c) the APCs are layered onto the first gas-permeable surface area at an average thickness of at or about 4 cell layers to at or about 8 cell layers.

In another embodiment, the invention provides the method described in any of the preceding paragraphs as applicable above modified such that in step (c) the APCs are layered onto the first gas-permeable surface area at an average thickness of at or about 3, 4, 5, 6, 7, 8, 9 or 10 cell layers.

In another embodiment, the invention provides the method described in any of the preceding paragraphs as applicable above modified such that in step (c) the APCs are layered onto the first gas-permeable surface area at an average thickness of at or about 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9 or 8 cell layers.

In another embodiment, the invention provides the method described in any of the preceding paragraphs as applicable above modified such that in step (b) the priming first expansion is performed in a first container comprising a first gas-permeable surface area and in step (c) the rapid second expansion is performed in a second container comprising a second gas-permeable surface area.

In another embodiment, the invention provides the method described in any of the preceding paragraphs as applicable above modified such that the second container is larger than the first container.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein in step (b) the APCs are layered onto the first gas-permeable surface area at an average thickness of at or about one cell layer to at or about three cell layers.

In another embodiment, the invention provides the method described in any of the preceding paragraphs as applicable above modified such that in step (b) the APCs are layered onto the first gas-permeable surface area at an average thickness of at or about 1.5 cell layers to at or about 2.5 cell layers.

In another embodiment, the invention provides the method described in any of the preceding paragraphs as applicable above modified such that in step (b) the APCs are layered onto the first gas-permeable surface area at an average thickness of at or about 2 cell layers.

In another embodiment, the invention provides the method described in any of the preceding paragraphs as applicable modified such that in step (b) the APCs are layered onto the first gas-permeable surface area at an average thickness of at or about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9 or 3 cell layers.

In another embodiment, the invention provides the method described in any of the preceding paragraphs as applicable above modified such that in step (c) the APCs are layered onto the second gas-permeable surface area at an average thickness of at or about 3 cell layers to at or about 10 cell layers.

In another embodiment, the invention provides the method described in any of the preceding paragraphs as applicable above modified such that in step (c) the APCs are layered onto the second gas-permeable surface area at an average thickness of at or about 4 cell layers to at or about 8 cell layers.

In another embodiment, the invention provides the method described in any of the preceding paragraphs as applicable above modified such that in step (c) the APCs are layered onto the second gas-permeable surface area at an average thickness of at or about 3, 4, 5, 6, 7, 8, 9 or 10 cell layers.

In another embodiment, the invention provides the method described in any of the preceding paragraphs as applicable modified such that in step (c) the APCs are layered onto the second gas-permeable surface area at an average thickness of at or about 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9 or 8 cell layers.

In another embodiment, the invention provides the method described in any of the preceding paragraphs as applicable above modified such that in step (b) the priming first expansion is performed in a first container comprising a first gas-permeable surface area and in step (c) the rapid second expansion is performed in the first container.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein in step (b) the APCs are layered onto the first gas-permeable surface area at an average thickness of at or about one cell layer to at or about three cell layers.

In another embodiment, the invention provides the method described in any of the preceding paragraphs as applicable above modified such that in step (b) the APCs are layered onto the first gas-permeable surface area at an average thickness of at or about 1.5 cell layers to at or about 2.5 cell layers.

In another embodiment, the invention provides the method described in any of the preceding paragraphs as applicable above modified such that in step (b) the APCs are layered onto the first gas-permeable surface area at an average thickness of at or about 2 cell layers.

In another embodiment, the invention provides the method described any of the preceding paragraphs as applicable above modified such that in step (b) the APCs are layered onto the first gas-permeable surface area at an average thickness of at or about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9 or 3 cell layers.

In another embodiment, the invention provides the method described in any of the preceding paragraphs as applicable above modified such that in step (c) the APCs are layered onto the first gas-permeable surface area at an average thickness of at or about 3 cell layers to at or about 10 cell layers.

In another embodiment, the invention provides the method described in any of the preceding paragraphs as applicable above modified such that in step (c) the APCs are layered onto the first gas-permeable surface area at an average thickness of at or about 4 cell layers to at or about 8 cell layers.

In another embodiment, the invention provides the method described in any of the preceding paragraphs as applicable above modified such that in step (c) the APCs are layered onto the first gas-permeable surface area at an average thickness of at or about 3, 4, 5, 6, 7, 8, 9 or 10 cell layers.

In another embodiment, the invention provides the method described in any of the preceding paragraphs as applicable above modified such that in step (c) the APCs are layered onto the first gas-permeable surface area at an average thickness of at or about 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9 or 8 cell layers.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.1 to at or about 1:10.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.1 to at or about 1:9.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.1 to at or about 1:8.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.1 to at or about 1:7.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.1 to at or about 1:6.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.1 to at or about 1:5.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.1 to at or about 1:4.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.1 to at or about 1:3.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.1 to at or about 1:2.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.2 to at or about 1:8.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.3 to at or about 1:7.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.4 to at or about 1:6.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.5 to at or about 1:5.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.6 to at or about 1:4.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.7 to at or about 1:3.5.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.8 to at or about 1:3.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:1.9 to at or about 1:2.5.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from the range of at or about 1:2.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from at or about 1:1.1, 1:1.2, 1:1.3, 1:1.4, 1:1.5, 1:1.6, 1:1.7, 1:1.8, 1:1.9, 1:2, 1:2.1, 1:2.2, 1:2.3, 1:2.4, 1:2.5, 1:2.6, 1:2.7, 1:2.8, 1:2.9, 1:3, 1:3.1, 1:3.2, 1:3.3, 1:3.4, 1:3.5, 1:3.6, 1:3.7, 1:3.8, 1:3.9, 1:4, 1:4.1, 1:4.2, 1:4.3, 1:4.4, 1:4.5, 1:4.6, 1:4.7, 1:4.8, 1:4.9, 1:5, 1:5.1, 1:5.2, 1:5.3, 1:5.4, 1:5.5, 1:5.6, 1:5.7, 1:5.8, 1:5.9, 1:6, 1:6.1, 1:6.2, 1:6.3, 1:6.4, 1:6.5, 1:6.6, 1:6.7, 1:6.8, 1:6.9, 1:7, 1:7.1, 1:7.2, 1:7.3, 1:7.4, 1:7.5, 1:7.6, 1:7.7, 1:7.8, 1:7.9, 1:8, 1:8.1, 1:8.2, 1:8.3, 1:8.4, 1:8.5, 1:8.6, 1:8.7, 1:8.8, 1:8.9, 1:9, 1:9.1, 1:9.2, 1:9.3, 1:9.4, 1:9.5, 1:9.6, 1:9.7, 1:9.8, 1:9.9 or 1:10.

In another embodiment, the invention provides the method described in any of the preceding paragraphs as applicable above modified such that the ratio of the number of TILs in the second population of TILs to the number of TILs in the first population of TILs is at or about 1.5:1 to at or about 100:1.

In another embodiment, the invention provides the method described in any of the preceding paragraphs as applicable above modified such that the ratio of the number of TILs in the second population of TILs to the number of TILs in the first population of TILs is at or about 50:1.

In another embodiment, the invention provides the method described in any of the preceding paragraphs as applicable above modified such that the ratio of the number of TILs in the second population of TILs to the number of TILs in the first population of TILs is at or about 25:1.

In another embodiment, the invention provides the method described in any of the preceding paragraphs as applicable above modified such that the ratio of the number of TILs in the second population of TILs to the number of TILs in the first population of TILs is at or about 20:1.

In another embodiment, the invention provides the method described in any of the preceding paragraphs as applicable above modified such that the ratio of the number of TILs in the second population of TILs to the number of TILs in the first population of TILs is at or about 10:1.

In another embodiment, the invention provides the method described in any of the preceding paragraphs as applicable above modified such that the second population of TILs is at least at or about 50-fold greater in number than the first population of TILs.

In another embodiment, the invention provides the method described in any of the preceding paragraphs as applicable above modified such that the second population of TILs is at least at or about 1-, 2-, 3-, 4-, 5-, 6-, 7-, 8-, 9-, 10-, 11-, 12-, 13-, 14-, 15-, 16-, 17-, 18-, 19-, 20-, 21-, 22-, 23-, 24-, 25-, 26-, 27-, 28-, 29-, 30-, 31-, 32-, 33-, 34-, 35-, 36-, 37-, 38-, 39-, 40-, 41-, 42-, 43-, 44-, 45-, 46-, 47-, 48-, 49- or 50-fold greater in number than the first population of TILs.

In another embodiment, the invention provides the method described in any of the preceding paragraphs as applicable above modified such that at or about 2 days or at or about 3 days after the commencement of the second period in step (c), the cell culture medium is supplemented with additional IL-2.

In another embodiment, the invention provides the method described in any of the preceding paragraphs as applicable above modified to further comprise the step of cryopreserving the harvested TIL population in step (d) using a cryopreservation process.

In another embodiment, the invention provides the method described in any of the preceding paragraphs as applicable above modified to comprise performing after step (d) the additional step of (e) transferring the harvested TIL population from step (d) to an infusion bag that optionally contains HypoThermosol.

In another embodiment, the invention provides the method described in any of the preceding paragraphs as applicable above modified to comprise the step of cryopreserving the infusion bag comprising the harvested TIL population in step (e) using a cryopreservation process.

In another embodiment, the invention provides the method described in any of the preceding paragraphs as applicable above modified such that the cryopreservation process is performed using a 1:1 ratio of harvested TIL population to cryopreservation media.

In another embodiment, the invention provides the method described in any of the preceding paragraphs as applicable above modified such that the antigen-presenting cells are peripheral blood mononuclear cells (PBMCs).

In another embodiment, the invention provides the method described in any of the preceding paragraphs as applicable above modified such that the PBMCs are irradiated and allogeneic.

In another embodiment, the invention provides the method described in any of the preceding paragraphs as applicable above modified such that the total number of APCs added to the cell culture in step (b) is $2.5\times10^8$.

In another embodiment, the invention provides the method described in any of the preceding paragraphs as applicable above modified such that the total number of APCs added to the cell culture in step (c) is $5\times10^8$.

In another embodiment, the invention provides the method described in any of the preceding paragraphs as applicable above modified such that the APCs are PBMCs.

In another embodiment, the invention provides the method described in any of the preceding paragraphs as applicable above modified such that the PBMCs are irradiated and allogeneic.

In another embodiment, the invention provides the method described in any of the preceding paragraphs as applicable above modified such that the antigen-presenting cells are artificial antigen-presenting cells.

In another embodiment, the invention provides the method described in any of the preceding paragraphs as applicable above modified such that the harvesting in step (d) is performed using a membrane-based cell processing system.

In another embodiment, the invention provides the method described in any of the preceding paragraphs as applicable above modified such that the harvesting in step (d) is performed using a LOVO cell processing system.

In another embodiment, the invention provides the method described in any of the preceding paragraphs as applicable above modified such that the multiple fragments comprise at or about 5 to at or about 60 fragments per container in step (b).

In another embodiment, the invention provides the method described in any of the preceding paragraphs as applicable above modified such that the multiple fragments comprise at or about 10 to at or about 60 fragments per container in step (b).

In another embodiment, the invention provides the method described in any of the preceding paragraphs as applicable above modified such that the multiple fragments comprise at or about 15 to at or about 60 fragments per container in step (b).

In another embodiment, the invention provides the method described in any of the preceding paragraphs as applicable above modified such that the multiple fragments comprise at or about 20 to at or about 60 fragments per container in step (b).

In another embodiment, the invention provides the method described in any of the preceding paragraphs as applicable above modified such that the multiple fragments comprise at or about 25 to at or about 60 fragments per container in step (b).

In another embodiment, the invention provides the method described in any of the preceding paragraphs as applicable above modified such that the multiple fragments comprise at or about 30 to at or about 60 fragments per container in step (b).

In another embodiment, the invention provides the method described in any of the preceding paragraphs as applicable above modified such that the multiple fragments comprise at or about 35 to at or about 60 fragments per container in step (b).

In another embodiment, the invention provides the method described in any of the preceding paragraphs as applicable above modified such that the multiple fragments comprise at or about 40 to at or about 60 fragments per container in step (b).

In another embodiment, the invention provides the method described in any of the preceding paragraphs as applicable above modified such that the multiple fragments comprise at or about 45 to at or about 60 fragments per container in step (b).

In another embodiment, the invention provides the method described in any of the preceding paragraphs as applicable above modified such that the multiple fragments comprise at or about 50 to at or about 60 fragments per container in step (b).

In another embodiment, the invention provides the method described in any of the preceding paragraphs as applicable above modified such that the multiple fragments comprise at or about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 fragment(s) per container in step (b).

In another embodiment, the invention provides the method described in any of the preceding paragraphs as applicable above modified such that each fragment has a volume of at or about 27 $mm^3$.

In another embodiment, the invention provides the method described in any of the preceding paragraphs as applicable above modified such that each fragment has a volume of at or about 20 $mm^3$ to at or about 50 $mm^3$.

In another embodiment, the invention provides the method described in any of the preceding paragraphs as applicable above modified such that each fragment has a volume of at or about 21 $mm^3$ to at or about 30 $mm^3$.

In another embodiment, the invention provides the method described in any of the preceding paragraphs as applicable above modified such that each fragment has a volume of at or about 22 $mm^3$ to at or about 29.5 $mm^3$.

In another embodiment, the invention provides the method described in any of the preceding paragraphs as applicable above modified such that each fragment has a volume of at or about 23 $mm^3$ to at or about 29 $mm^3$.

In another embodiment, the invention provides the method described in any of the preceding paragraphs as applicable above modified such that each fragment has a volume of at or about 24 $mm^3$ to at or about 28.5 $mm^3$.

In another embodiment, the invention provides the method described in any of the preceding paragraphs as applicable above modified such that each fragment has a volume of at or about 25 $mm^3$ to at or about 28 $mm^3$.

In another embodiment, the invention provides the method described in any of the preceding paragraphs as applicable above modified such that each fragment has a volume of at or about 26.5 $mm^3$ to at or about 27.5 $mm^3$.

In another embodiment, the invention provides the method described in any of the preceding paragraphs as applicable above modified such that each fragment has a volume of at or about 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 $mm^3$.

In another embodiment, the invention provides the method described in any of the preceding paragraphs as applicable above modified such that the multiple fragments comprise at or about 30 to at or about 60 fragments with a total volume of at or about 1300 $mm^3$ to at or about 1500 $mm^3$.

In another embodiment, the invention provides the method described in any of the preceding paragraphs as applicable above modified such that the multiple fragments comprise at or about 50 fragments with a total volume of at or about 1350 $mm^3$.

In another embodiment, the invention provides the method described in any of the preceding paragraphs as applicable above modified such that the multiple fragments comprise at or about 50 fragments with a total mass of at or about 1 gram to at or about 1.5 grams.

In another embodiment, the invention provides the method described in any of the preceding paragraphs as applicable above modified such that the cell culture medium is provided in a container that is a G-container or a Xuri cellbag.

In another embodiment, the invention provides the method described in any of the preceding paragraphs as applicable above modified such that the IL-2 concentration in the cell culture medium is about 10,000 IU/mL to about 5,000 IU/mL.

In another embodiment, the invention provides the method described in any of the preceding paragraphs as applicable above modified such that the IL-2 concentration in the cell culture medium is about 6,000 IU/mL.

In another embodiment, the invention provides the method described in any of the preceding paragraphs as applicable above modified such that the cryopreservation media comprises dimethlysulfoxide (DMSO).

In another embodiment, the invention provides the method described in any of the preceding paragraphs as applicable above modified such that the cryopreservation media comprises 7% to 10% DMSO.

In another embodiment, the invention provides the method described in any of the preceding paragraphs as applicable above modified such that the first period in step (b) is performed within a period of at or about 1 day, 2 days, 3 days, 4 days, 5 days, 6 days, or 7 days.

In another embodiment, the invention provides the method described in any of the preceding paragraphs as applicable above modified such that the second period in step (c) is performed within a period of at or about 1 day, 2 days, 3 days, 4 days, 5 days, 6 days, 7 days, 8 days, 9 days, 10 days or 11 days.

In another embodiment, the invention provides the method described in any of the preceding paragraphs as applicable above modified such that the first period in step (b) and the second period in step (c) are each individually performed within a period of at or about 1 day, 2 days, 3 days, 4 days, 5 days, 6 days, or 7 days.

In another embodiment, the invention provides the method described in any of the preceding paragraphs as applicable above modified such that the first period in step (b) and the second period in step (c) are each individually performed within a period of at or about 5 days, 6 days, or 7 days.

In another embodiment, the invention provides the method described in any of the preceding paragraphs as applicable above modified such that the first period in step (b) and the second period in step (c) are each individually performed within a period of at or about 7 days.

In another embodiment, the invention provides the method described in any of the preceding paragraphs as applicable above modified such that steps (a) through (d) are performed in a total of at or about 14 days to at or about 18 days.

In another embodiment, the invention provides the method described in any of the preceding paragraphs as applicable above modified such that steps (a) through (d) are performed in a total of at or about 15 days to at or about 18 days.

In another embodiment, the invention provides the method described in any of the preceding paragraphs as applicable above modified such that steps (a) through (d) are performed in a total of at or about 16 days to at or about 18 days.

In another embodiment, the invention provides the method described in any of the preceding paragraphs as applicable above modified such that steps (a) through (d) are performed in a total of at or about 17 days to at or about 18 days.

In another embodiment, the invention provides the method described in any of the preceding paragraphs as applicable above modified such that steps (a) through (d) are performed in a total of at or about 14 days to at or about 17 days.

In another embodiment, the invention provides the method described in any of the preceding paragraphs as applicable above modified such that steps (a) through (d) are performed in a total of at or about 15 days to at or about 17 days.

In another embodiment, the invention provides the method described in any of the preceding paragraphs as applicable above modified such that steps (a) through (d) are performed in a total of at or about 16 days to at or about 17 days.

In another embodiment, the invention provides the method described in any of the preceding paragraphs as applicable above modified such that steps (a) through (d) are performed in a total of at or about 14 days to at or about 16 days.

In another embodiment, the invention provides the method described in any of the preceding paragraphs as applicable above modified such that steps (a) through (d) are performed in a total of at or about 15 days to at or about 16 days.

In another embodiment, the invention provides the method described in any of the preceding paragraphs as applicable above modified such that steps (a) through (d) are performed in a total of at or about 14 days.

In another embodiment, the invention provides the method described in any of the preceding paragraphs as applicable above modified such that steps (a) through (d) are performed in a total of at or about 15 days.

In another embodiment, the invention provides the method described in any of the preceding paragraphs as applicable above modified such that steps (a) through (d) are performed in a total of at or about 16 days.

In another embodiment, the invention provides the method described in any of the preceding paragraphs as applicable above modified such that steps (a) through (d) are performed in a total of at or about 17 days.

In another embodiment, the invention provides the method described in any of the preceding paragraphs as applicable above modified such that steps (a) through (d) are performed in a total of at or about 18 days.

In another embodiment, the invention provides the method described in any of the preceding paragraphs as applicable above modified such that steps (a) through (d) are performed in a total of at or about 14 days or less.

In another embodiment, the invention provides the method described in any of the preceding paragraphs as applicable above modified such that steps (a) through (d) are performed in a total of at or about 15 days or less.

In another embodiment, the invention provides the method described in any of the preceding paragraphs as applicable above modified such that steps (a) through (d) are performed in a total of at or about 16 days or less.

In another embodiment, the invention provides the method described in any of the preceding paragraphs as applicable above modified such that steps (a) through (d) are performed in a total of at or about 18 days or less.

In another embodiment, the invention provides the method described in any of the preceding paragraphs as applicable above modified such that the therapeutic population of TILs harvested in step (d) comprises sufficient TILs for a therapeutically effective dosage of the TILs.

In another embodiment, the invention provides the method described in any of the preceding paragraphs as applicable above modified such that the number of TILs sufficient for a therapeutically effective dosage is from at or about $2.3\times10^{10}$ to at or about $13.7\times10^{10}$.

In another embodiment, the invention provides the method described in any of the preceding paragraphs as applicable above modified such that the third population of TILs in step (c) provides for increased efficacy, increased interferon-gamma production, and/or increased polyclonality.

In another embodiment, the invention provides the method described in any of the preceding paragraphs as applicable above modified such that the third population of TILs in step (c) provides for at least a one-fold to five-fold or more interferon-gamma production as compared to TILs prepared by a process longer than 16 days.

In another embodiment, the invention provides the method described in any of the preceding paragraphs as applicable above modified such that the third population of TILs in step (c) provides for at least a one-fold to five-fold or more interferon-gamma production as compared to TILs prepared by a process longer than 17 days.

In another embodiment, the invention provides the method described in any of the preceding paragraphs as applicable above modified such that the third population of TILs in step (c) provides for at least a one-fold to five-fold or more interferon-gamma production as compared to TILs prepared by a process longer than 18 days.

In another embodiment, the invention provides the method described in any of the preceding paragraphs as applicable above modified such that the effector T cells and/or central memory T cells obtained from the third population of TILs step (c) exhibit increased CD8 and CD28 expression relative to effector T cells and/or central memory T cells obtained from the second population of cells step (b).

In another embodiment, the invention provides the method described in any of the preceding paragraphs as applicable above modified such that each container recited in the method is a closed container.

In another embodiment, the invention provides the method described in any of the preceding paragraphs as applicable above modified such that each container recited in the method is a G-container.

In another embodiment, the invention provides the method described in any of the preceding paragraphs as applicable above modified such that each container recited in the method is a GREX-10.

In another embodiment, the invention provides the method described in any of the preceding paragraphs as applicable above modified such that each container recited in the method is a GREX-100.

In another embodiment, the invention provides the method described in any of the preceding paragraphs as applicable above modified such that each container recited in the method is a GREX-500.

In another embodiment, the invention provides the therapeutic population of tumor infiltrating lymphocytes (TILs) made by the method described in any of the preceding paragraphs as applicable above.

In another embodiment, the invention provides a therapeutic population of tumor infiltrating lymphocytes (TILs) prepared from tumor tissue of a patient, wherein the therapeutic population of TILs provides for increased efficacy, increased interferon-gamma production, and/or increased polyclonality compared to TILs prepared by a process in which the first expansion of TILs is performed without any added antigen-presenting cells (APCs) or OKT3.

In another embodiment, the invention provides a therapeutic population of tumor infiltrating lymphocytes (TILs)

prepared from tumor tissue of a patient, wherein the therapeutic population of TILs provides for increased efficacy, increased interferon-gamma production, and/or increased polyclonality compared to TILs prepared by a process in which the first expansion of TILs is performed without any added antigen-presenting cells (APCs).

In another embodiment, the invention provides a therapeutic population of tumor infiltrating lymphocytes (TILs) prepared from tumor tissue of a patient, wherein the therapeutic population of TILs provides for increased efficacy, increased interferon-gamma production, and/or increased polyclonality compared to TILs prepared by a process in which the first expansion of TILs is performed without any added OKT3.

In another embodiment, the invention provides a therapeutic population of tumor infiltrating lymphocytes (TILs) prepared from tumor tissue of a patient, wherein the therapeutic population of TILs provides for increased efficacy, increased interferon-gamma production, and/or increased polyclonality compared to TILs prepared by a process in which the first expansion of TILs is performed with no added antigen-presenting cells (APCs) and no added OKT3.

In another embodiment, the invention provides a therapeutic population of tumor infiltrating lymphocytes (TILs) prepared from tumor tissue of a patient, wherein the therapeutic population of TILs provides for increased efficacy, increased interferon-gamma production, and/or increased polyclonality compared to TILs prepared by a process by a process longer than 16 days.

In another embodiment, the invention provides a therapeutic population of tumor infiltrating lymphocytes (TILs) prepared from tumor tissue of a patient, wherein the therapeutic population of TILs provides for increased efficacy, increased interferon-gamma production, and/or increased polyclonality compared to TILs prepared by a process by a process longer than 17 days.

In another embodiment, the invention provides a therapeutic population of tumor infiltrating lymphocytes (TILs) prepared from tumor tissue of a patient, wherein the therapeutic population of TILs provides for increased efficacy, increased interferon-gamma production, and/or increased polyclonality compared to TILs prepared by a process by a process longer than 18 days.

In another embodiment, the invention provides for the therapeutic population of TILs described in any of the preceding paragraphs as applicable above that provides for increased interferon-gamma production.

In another embodiment, the invention provides for the therapeutic population of TILs described in any of the preceding paragraphs as applicable above that provides for increased polyclonality.

In another embodiment, the invention provides for the therapeutic population of TILs described in any of the preceding paragraphs as applicable above that provides for increased efficacy.

In another embodiment, the invention provides for the therapeutic population of TILs described in any of the preceding paragraphs as applicable above modified such that the therapeutic population of TILs is capable of at least one-fold more interferon-gamma production as compared to TILs prepared by a process longer than 16 days. In another embodiment, the invention provides for the therapeutic population of TILs described in any of the preceding paragraphs as applicable above modified such that the therapeutic population of TILs is capable of at least one-fold more interferon-gamma production as compared to TILs prepared by a process longer than 17 days. In another embodiment, the invention provides for the therapeutic population of TILs described in any of the preceding paragraphs as applicable above modified such that the therapeutic population of TILs is capable of at least one-fold more interferon-gamma production as compared to TILs prepared by a process longer than 18 days. In some embodiments, the TILs are rendered capable of the at least one-fold more interferon-gamma production due to the expansion process described herein, for example as described in Steps A through F above or according to Steps A through F above (also as shown, for example, in FIG. 8 (in particular, e.g., FIG. 8B and/or FIG. 8C).

In another embodiment, the invention provides for the therapeutic population of TILs described in any of the preceding paragraphs as applicable above modified such that the therapeutic population of TILs is capable of at least two-fold more interferon-gamma production as compared to TILs prepared by a process longer than 16 days. In another embodiment, the invention provides for the therapeutic population of TILs described in any of the preceding paragraphs as applicable above modified such that the therapeutic population of TILs is capable of at least two-fold more interferon-gamma production as compared to TILs prepared by a process longer than 17 days. In another embodiment, the invention provides for the therapeutic population of TILs described in any of the preceding paragraphs as applicable above modified such that the therapeutic population of TILs is capable of at least two-fold more interferon-gamma production as compared to TILs prepared by a process longer than 18 days. In some embodiments, the TILs are rendered capable of the at least two-fold more interferon-gamma production due to the expansion process described herein, for example as described in Steps A through F above or according to Steps A through F above (also as shown, for example, in FIG. 8 (in particular, e.g., FIG. 8B and/or FIG. 8C).

In another embodiment, the invention provides for the therapeutic population of TILs described in any of the preceding paragraphs as applicable above modified such that the therapeutic population of TILs is capable of at least three-fold more interferon-gamma production as compared to TILs prepared by a process longer than 16 days. In another embodiment, the invention provides for the therapeutic population of TILs described in any of the preceding paragraphs as applicable above modified such that the therapeutic population of TILs is capable of at least three-fold more interferon-gamma production as compared to TILs prepared by a process longer than 17 days. In another embodiment, the invention provides for the therapeutic population of TILs described in any of the preceding paragraphs as applicable above modified such that the therapeutic population of TILs is capable of at least three-fold more interferon-gamma production as compared to TILs prepared by a process longer than 18 days. In some embodiments, the TILs are rendered capable of the at least three-fold more interferon-gamma production due to the expansion process described herein, for example as described in Steps A through F above or according to Steps A through F above (also as shown, for example, in FIG. 8 (in particular, e.g., FIG. 8B and/or FIG. 8C).

In another embodiment, the invention provides for a therapeutic population of tumor infiltrating lymphocytes (TILs) that is capable of at least one-fold more interferon-gamma production as compared to TILs prepared by a process in which the first expansion of TILs is performed without any added antigen-presenting cells (APCs). In some embodiments, the TILs are rendered capable of the at least one-fold more interferon-gamma production due to the expansion process described herein, for example as described in Steps A through F above or according to Steps A through F above (also as shown, for example, in FIG. 8 (in particular, e.g., FIG. 8B and/or FIG. 8C).

In another embodiment, the invention provides for a therapeutic population of tumor infiltrating lymphocytes (TILs) that is capable of at least one-fold more interferon-gamma production as compared to TILs prepared by a process in which the first expansion of TILs is performed without any added OKT3. In some embodiments, the TILs are rendered capable of the at least one-fold more interferon-gamma production due to the expansion process described herein, for example as described in Steps A through F above or according to Steps A through F above (also as shown, for example, in FIG. 8 (in particular, e.g., FIG. 8B and/or FIG. 8C).

In another embodiment, the invention provides for a therapeutic population of TILs that is capable of at least two-fold more interferon-gamma production as compared to TILs prepared by a process in which the first expansion of TILs is performed without any added APCs. In some embodiments, the TILs are rendered capable of the at least two-fold more interferon-gamma production due to the expansion process described herein, for example as described in Steps A through F above or according to Steps A through F above (also as shown, for example, in FIG. 8 (in particular, e.g., FIG. 8B and/or FIG. 8C).

In another embodiment, the invention provides for a therapeutic population of TILs that is capable of at least two-fold more interferon-gamma production as compared to TILs prepared by a process in which the first expansion of TILs is performed without any added OKT3. In some embodiments, the TILs are rendered capable of the at least two-fold more interferon-gamma production due to the expansion process described herein, for example as described in Steps A through F above or according to Steps A through F above (also as shown, for example, in FIG. 8 (in particular, e.g., FIG. 8B and/or FIG. 8C).

In another embodiment, the invention provides for a therapeutic population of TILs that is capable of at least three-fold more interferon-gamma production as compared to TILs prepared by a process in which the first expansion of TILs is performed without any added APCs. In some embodiments, the TILs are rendered capable of the at least one-fold more interferon-gamma production due to the expansion process described herein, for example as described in Steps A through F above or according to Steps A through F above (also as shown, for example, in FIG. 8 (in particular, e.g., FIG. 8B and/or FIG. 8C).

In another embodiment, the invention provides for a therapeutic population of TILs that is capable of at least three-fold more interferon-gamma production as compared to TILs prepared by a process in which the first expansion of TILs is performed without any added OKT3. In some embodiments, the TILs are rendered capable of the at least three-fold more interferon-gamma production due to the expansion process described herein, for example as described in Steps A through F above or according to Steps A through F above (also as shown, for example, in FIG. 8 (in particular, e.g., FIG. 8B and/or FIG. 8C).

In another embodiment, the invention provides the method described in any of the preceding paragraphs as applicable above modified such that the tumor fragments are small biopsies (including, for example, a punch biopsy), core biopsies, core needle biopsies or fine needle aspirates.

In another embodiment, the invention provides the method described in any of the preceding paragraphs as applicable above modified such that the tumor fragments are core biopsies.

In another embodiment, the invention provides the method described in any of the preceding paragraphs as applicable above modified such that the tumor fragments are fine needle aspirates.

In another embodiment, the invention provides the method described in any of the preceding paragraphs as applicable above modified such that the tumor fragments are small biopsies (including, for example, a punch biopsy).

In another embodiment, the invention provides the method described in any of the preceding paragraphs as applicable above modified such that the tumor fragments are core needle biopsies.

In another embodiment, the invention provides the method described in any of the preceding paragraphs as applicable above modified such that (i) the method comprises obtaining the first population of TILs from one or more small biopsies (including, for example, a punch biopsy), core biopsies, core needle biopsies or fine needle aspirates of tumor tissue from the subject, (ii) the method comprises performing the step of culturing the first population of TILs in a cell culture medium comprising IL-2 for a period of about 3 days prior to performing the step of the priming first expansion, (iii) the method comprises performing the priming first expansion for a period of about 8 days, and (iv) the method comprises performing the rapid second expansion for a period of about 11 days. In some of the foregoing embodiments, the steps of the method are completed in about 22 days.

In another embodiment, the invention provides the method described in any of the preceding paragraphs as applicable above modified such that (i) the method comprises obtaining the first population of TILs from one or more small biopsies (including, for example, a punch biopsy), core biopsies, core needle biopsies or fine needle aspirates of tumor tissue from the subject, (ii) the method comprises performing the step of culturing the first population of TILs in a cell culture medium comprising IL-2 for a period of about 3 days prior to performing the step of the priming first expansion, (iii) the method comprises performing the priming first expansion for a period of about 8 days, and (iv) the method comprises performing the rapid second expansion by culturing the culture of the second population of TILs for about 5 days, splitting the culture into up to 5 subcultures and culturing the subcultures for about 6 days. In some of the foregoing embodiments, the up to 5 subcultures are each cultured in a container that is the same size or larger than the container in which the culture of the second population of TILs is commenced in the rapid second expansion. In some of the foregoing embodiments, the culture of the second population of TILs is equally divided amongst the up to 5 subcultures. In some of the foregoing embodiments, the steps of the method are completed in about 22 days.

In another embodiment, the invention provides the method described in any of the preceding paragraphs as applicable above modified such that the first population of TILs is obtained from 1 to about 20 small biopsies (including, for example, a punch biopsy), core biopsies, core needle biopsies or fine needle aspirates of tumor tissue from the subject.

In another embodiment, the invention provides the method described in any of the preceding paragraphs as applicable above modified such that the first population of TILs is obtained from 1 to about 10 small biopsies (including, for example, a punch biopsy), core biopsies, core needle biopsies or fine needle aspirates of tumor tissue from the subject.

In another embodiment, the invention provides the method described in any of the preceding paragraphs as applicable above modified such that the first population of TILs is obtained from 1, 2, 3, 4, 5, 6, 7, 8, 9, 10, 11, 12, 13, 14, 15, 16, 17, 18, 19 or 20 small biopsies (including, for example, a punch biopsy), core biopsies, core needle biopsies or fine needle aspirates of tumor tissue from the subject.

In another embodiment, the invention provides the method described in any of the preceding paragraphs as applicable above modified such that the first population of TILs is obtained from 1, 2, 3, 4, 5, 6, 7, 8, 9 or 10 small biopsies (including, for example, a punch biopsy), core biopsies, core needle biopsies or fine needle aspirates of tumor tissue from the subject.

In another embodiment, the invention provides the method described in any of the preceding paragraphs as applicable above modified such that the first population of TILs is obtained from 1 to about 20 core biopsies of tumor tissue from the subject.

In another embodiment, the invention provides the method described in any of the preceding paragraphs as applicable above modified such that the first population of TILs is obtained from 1 to about 10 core biopsies of tumor tissue from the subject.

In another embodiment, the invention provides the method described in any of the preceding paragraphs as applicable above modified such that the first population of TILs is obtained from 1, 2, 3, 4, 5, 6, 7, 8, 9, 10, 11, 12, 13, 14, 15, 16, 17, 18, 19 or 20 core biopsies of tumor tissue from the subject.

In another embodiment, the invention provides the method described in any of the preceding paragraphs as applicable above modified such that the first population of TILs is obtained from 1, 2, 3, 4, 5, 6, 7, 8, 9 or 10 core biopsies of tumor tissue from the subject.

In another embodiment, the invention provides the method described in any of the preceding paragraphs as applicable above modified such that the first population of TILs is obtained from 1 to about 20 fine needle aspirates of tumor tissue from the subject.

In another embodiment, the invention provides the method described in any of the preceding paragraphs as applicable above modified such that the first population of TILs is obtained from 1 to about 10 fine needle aspirates of tumor tissue from the subject.

In another embodiment, the invention provides the method described in any of the preceding paragraphs as applicable above modified such that the first population of TILs is obtained from 1, 2, 3, 4, 5, 6, 7, 8, 9, 10, 11, 12, 13, 14, 15, 16, 17, 18, 19 or 20 fine needle aspirates of tumor tissue from the subject.

In another embodiment, the invention provides the method described in any of the preceding paragraphs as applicable above modified such that the first population of TILs is obtained from 1, 2, 3, 4, 5, 6, 7, 8, 9 or 10 fine needle aspirates of tumor tissue from the subject.

In another embodiment, the invention provides the method described in any of the preceding paragraphs as applicable above modified such that the first population of TILs is obtained from 1 to about 20 core needle biopsies of tumor tissue from the subject.

In another embodiment, the invention provides the method described in any of the preceding paragraphs as applicable above modified such that the first population of TILs is obtained from 1 to about 10 core needle biopsies of tumor tissue from the subject.

In another embodiment, the invention provides the method described in any of the preceding paragraphs as applicable above modified such that the first population of TILs is obtained from 1, 2, 3, 4, 5, 6, 7, 8, 9, 10, 11, 12, 13, 14, 15, 16, 17, 18, 19 or 20 core needle biopsies of tumor tissue from the subject.

In another embodiment, the invention provides the method described in any of the preceding paragraphs as applicable above modified such that the first population of TILs is obtained from 1, 2, 3, 4, 5, 6, 7, 8, 9 or 10 core needle biopsies of tumor tissue from the subject.

In another embodiment, the invention provides the method described in any of the preceding paragraphs as applicable above modified such that the first population of TILs is obtained from 1 to about 20 small biopsies (including, for example, a punch biopsy) of tumor tissue from the subject.

In another embodiment, the invention provides the method described in any of the preceding paragraphs as applicable above modified such that the first population of TILs is obtained from 1 to about 10 small biopsies (including, for example, a punch biopsy) of tumor tissue from the subject.

In another embodiment, the invention provides the method described in any of the preceding paragraphs as applicable above modified such that the first population of TILs is obtained from 1, 2, 3, 4, 5, 6, 7, 8, 9, 10, 11, 12, 13, 14, 15, 16, 17, 18, 19 or 20 small biopsies (including, for example, a punch biopsy) of tumor tissue from the subject.

In another embodiment, the invention provides the method described in any of the preceding paragraphs as applicable above modified such that the first population of TILs is obtained from 1, 2, 3, 4, 5, 6, 7, 8, 9 or 10 small biopsies (including, for example, a punch biopsy) of tumor tissue from the subject.

In another embodiment, the invention provides the method described in any of the preceding paragraphs as applicable above modified such that (i) the method comprises obtaining the first population of TILs from 1 to about 10 core biopsies of tumor tissue from the subject, (ii) the method comprises performing the step of culturing the first population of TILs in a cell culture medium comprising IL-2 for a period of about 3 days prior to performing the step of the priming first expansion, (iii) the method comprises performing the priming first expansion step by culturing the first population of TILs in a culture medium comprising IL-2, OKT-3 and antigen presenting cells (APCs) for a period of about 8 days to obtain the second population of TILs, and (iv) the method comprises performing the rapid second expansion step by culturing the second population of TILs in a culture medium comprising IL-2, OKT-3 and APCs for a period of about 11 days. In some of the foregoing embodiments, the steps of the method are completed in about 22 days.

In another embodiment, the invention provides the method described in any of the preceding paragraphs as applicable above modified such that (i) the method comprises obtaining the first population of TILs from 1 to about 10 core biopsies of tumor tissue from the subject, (ii) the method comprises performing the step of culturing the first population of TILs in a cell culture medium comprising IL-2 for a period of about 3 days prior to performing the step of the priming first expansion, (iii) the method comprises performing the priming first expansion step by culturing the first population of TILs in a culture medium comprising IL-2, OKT-3 and antigen presenting cells (APCs) for a period of about 8 days to obtain the second population of TILs, and (iv) the method comprises performing the rapid second expansion by culturing the culture of the second population of TILs in a culture medium comprising IL-2, OKT-3 and APCs for about 5 days, splitting the culture into up to 5 subcultures and culturing each of the subcultures in a culture medium comprising IL-2 for about 6 days. In some of the foregoing embodiments, the up to 5 subcultures are each cultured in a container that is the same size or larger than the container in which the culture of the second population of TILs is commenced in the rapid second expansion. In some of the foregoing embodiments, the culture of the second population of TILs is equally divided amongst the up to 5 subcultures. In some of the foregoing embodiments, the steps of the method are completed in about 22 days.

In another embodiment, the invention provides the method described in any of the preceding paragraphs as applicable above modified such that (i) the method comprises obtaining the first population of TILs from 1 to about 10 core biopsies of tumor tissue from the subject, (ii) the method comprises performing the step of culturing the first population of TILs in a cell culture medium comprising 6000 IU IL-2/mL in 0.5 L of CM1 culture medium in a G-Rex 100M flask for a period of about 3 days prior to performing the step of the priming first expansion, (iii) the method comprises performing the priming first expansion by adding 0.5 L of CM1 culture medium containing 6000 IU/mL IL-2, 30 ng/mL OKT-3, and about 108 feeder cells and culturing for a period of about 8 days, and (iv) the method comprises performing the rapid second expansion by (a) transferring the second population of TILs to a G-Rex 500MCS flask containing 5 L of CM2 culture medium with 3000 IU/mL IL-2, 30 ng/mL OKT-3, and $5\times10^9$ feeder cells and culturing for about 5 days (b) splitting the culture into up to 5 subcultures by transferring 109 TILs into each of up to 5 G-Rex 500MCS flasks containing 5 L of AIM-V medium with 3000 IU/mL IL-2, and culturing the subcultures for about 6 days. In some of the foregoing embodiments, the steps of the method are completed in about 22 days.

In another embodiment, the invention provides a method of expanding T cells comprising: (a) performing a priming first expansion of a first population of T cells obtained from a donor by culturing the first population of T cells to effect growth and to prime an activation of the first population of T cells; (b) after the activation of the first population of T cells primed in step (a) begins to decay, performing a rapid second expansion of the first population of T cells by culturing the first population of T cells to effect growth and to boost the activation of the first population of T cells to obtain a second population of T cells; and (c) harvesting the second population of T cells. In another embodiment, the step of rapid second expansion is split into a plurality of steps to achieve a scaling up of the culture by: (a) performing the rapid second expansion by culturing the first population of T cells in a small scale culture in a first container, e.g., a G-Rex 100MCS container, for a period of about 3 to 4 days, and then (b) effecting the transfer of the first population of T cells from the small scale culture to a second container larger than the first container, e.g., a G-Rex 500MCS container, and culturing the first population of T cells from the small scale culture in a larger scale culture in the second container for a period of about 4 to 7 days. In another embodiment, the step of rapid expansion is split into a plurality of steps to achieve a scaling out of the culture by: (a) performing the rapid second expansion by culturing the first population of T cells in a first small scale culture in a first container, e.g., a G-Rex 100MCS container, for a period of about 3 to 4 days, and then (b) effecting the transfer and apportioning of the first population of T cells from the first small scale culture into and amongst at least 2, 3, 4, 5, 6, 7, 8, 9, 10, 11, 12, 13, 14, 15, 16, 17, 18, 19, or 20 second containers that are equal in size to the first container, wherein in each second container the portion of the first population of T cells from first small scale culture transferred to such second container is cultured in a second small scale culture for a period of about 4 to 7 days. In another embodiment, the step of rapid expansion is split into a plurality of steps to achieve a scaling out and scaling up of the culture by: (a) performing the rapid second expansion by culturing the first population of T cells in a small scale culture in a first container, e.g., a G-Rex 100MCS container, for a period of about 3 to 4 days, and then (b) effecting the transfer and apportioning of the first population of T cells from the small scale culture into and amongst at least 2, 3, 4, 5, 6, 7, 8, 9, 10, 11, 12, 13, 14, 15, 16, 17, 18, 19, or 20 second containers that are larger in size than the first container, e.g., G-Rex 500MCS containers, wherein in each second container the portion of the first population of T cells from the small scale culture transferred to such second container is cultured in a larger scale culture for a period of about 4 to 7 days. In another embodiment, the step of rapid expansion is split into a plurality of steps to achieve a scaling out and scaling up of the culture by: (a) performing the rapid second expansion by culturing the first population of T cells in a small scale culture in a first container, e.g., a G-Rex 100MCS container, for a period of about 4 days, and then (b) effecting the transfer and apportioning of the first population of T cells from the small scale culture into and amongst 2, 3 or 4 second containers that are larger in size than the first container, e.g., G-Rex 500MCS containers, wherein in each second container the portion of the first population of T cells from the small scale culture transferred to such second container is cultured in a larger scale culture for a period of about 5 days.

In another embodiment, the invention provides the method described in any of the preceding paragraphs as applicable above modified such that the step of rapid second expansion is split into a plurality of steps to achieve a scaling up of the culture by: (a) performing the rapid second expansion by culturing the first population of T cells in a small scale culture in a first container, e.g., a G-Rex 100MCS container, for a period of about 2 to 4 days, and then (b) effecting the transfer of the first population of T cells from the small scale culture to a second container larger than the first container, e.g., a G-Rex 500MCS container, and culturing the first population of T cells from the small scale culture in a larger scale culture in the second container for a period of about 5 to 7 days.

In another embodiment, the invention provides the method described in any of the preceding paragraphs as applicable above modified such that the step of rapid expansion is split into a plurality of steps to achieve a scaling out of the culture by: (a) performing the rapid second expansion by culturing the first population of T cells in a first small scale culture in a first container, e.g., a G-Rex 100MCS container, for a period of about 2 to 4 days, and then (b) effecting the transfer and apportioning of the first population of T cells from the first small scale culture into and amongst at least 2, 3, 4, 5, 6, 7, 8, 9, 10, 11, 12, 13, 14, 15, 16, 17, 18, 19, or 20 second containers that are equal in size to the first container, wherein in each second container the portion of the first population of T cells from first small scale culture transferred to such second container is cultured in a second small scale culture for a period of about 5 to 7 days.

In another embodiment, the invention provides the method described in any of the preceding paragraphs as applicable above modified such that the step of rapid expansion is split into a plurality of steps to achieve a scaling out and scaling up of the culture by: (a) performing the rapid second expansion by culturing the first population of T cells in a small scale culture in a first container, e.g., a G-Rex 100MCS container, for a period of about 2 to 4 days, and then (b) effecting the transfer and apportioning of the first population of T cells from the small scale culture into and amongst at least 2, 3, 4, 5, 6, 7, 8, 9, 10, 11, 12, 13, 14, 15, 16, 17, 18, 19, or 20 second containers that are larger in size than the first container, e.g., G-Rex 500MCS containers, wherein in each second container the portion of the first population of T cells from the small scale culture transferred to such second container is cultured in a larger scale culture for a period of about 5 to 7 days.

In another embodiment, the invention provides the method described in any of the preceding paragraphs as applicable above modified such that the step of rapid expansion is split into a plurality of steps to achieve a scaling out and scaling up of the culture by: (a) performing the rapid second expansion by culturing the first population of T cells in a small scale culture in a first container, e.g., a G-Rex 100MCS container, for a period of about 3 to 4 days, and then (b) effecting the transfer and apportioning of the first population of T cells from the small scale culture into and amongst 2, 3 or 4 second containers that are larger in size than the first container, e.g., G-Rex 500MCS containers, wherein in each second container the portion of the first population of T cells from the small scale culture transferred to such second container is cultured in a larger scale culture for a period of about 5 to 6 days.

In another embodiment, the invention provides the method described in any of the preceding paragraphs as applicable above modified such that the step of rapid expansion is split into a plurality of steps to achieve a scaling out and scaling up of the culture by: (a) performing the rapid second expansion by culturing the first population of T cells in a small scale culture in a first container, e.g., a G-Rex 100MCS container, for a period of about 3 to 4 days, and then (b) effecting the transfer and apportioning of the first population of T cells from the small scale culture into and amongst 2, 3 or 4 second containers that are larger in size than the first container, e.g., G-Rex 500MCS containers, wherein in each second container the portion of the first population of T cells from the small scale culture transferred to such second container is cultured in a larger scale culture for a period of about 5 days.

In another embodiment, the invention provides the method described in any of the preceding paragraphs as applicable above modified such that the step of rapid expansion is split into a plurality of steps to achieve a scaling out and scaling up of the culture by: (a) performing the rapid second expansion by culturing the first population of T cells in a small scale culture in a first container, e.g., a G-Rex 100MCS container, for a period of about 3 to 4 days, and then (b) effecting the transfer and apportioning of the first population of T cells from the small scale culture into and amongst 2, 3 or 4 second containers that are larger in size than the first container, e.g., G-Rex 500MCS containers, wherein in each second container the portion of the first population of T cells from the small scale culture transferred to such second container is cultured in a larger scale culture for a period of about 6 days.

In another embodiment, the invention provides the method described in any of the preceding paragraphs as applicable above modified such that the step of rapid expansion is split into a plurality of steps to achieve a scaling out and scaling up of the culture by: (a) performing the rapid second expansion by culturing the first population of T cells in a small scale culture in a first container, e.g., a G-Rex 100MCS container, for a period of about 3 to 4 days, and then (b) effecting the transfer and apportioning of the first population of T cells from the small scale culture into and amongst 2, 3 or 4 second containers that are larger in size than the first container, e.g., G-Rex 500MCS containers, wherein in each second container the portion of the first population of T cells from the small scale culture transferred to such second container is cultured in a larger scale culture for a period of about 7 days.

In another embodiment, the invention provides the method described in any of the preceding paragraphs as applicable above modified such that the priming first expansion of step (a) is performed during a period of up to 7 days.

In another embodiment, the invention provides the method described in any of the preceding paragraphs as applicable above modified such that the rapid second expansion of step (b) is performed during a period of up to 8 days.

In another embodiment, the invention provides the method described in any of the preceding paragraphs as applicable above modified such that the rapid second expansion of step (b) is performed during a period of up to 9 days.

In another embodiment, the invention provides the method described in any of the preceding paragraphs as applicable above modified such that the rapid second expansion of step (b) is performed during a period of up to 10 days.

In another embodiment, the invention provides the method described in any of the preceding paragraphs as applicable above modified such that the rapid second expansion of step (b) is performed during a period of up to 11 days.

In another embodiment, the invention provides the method described in any of the preceding paragraphs as applicable above modified such that the priming first expansion in step (a) is performed during a period of 7 days and the rapid second expansion of step (b) is performed during a period of up to 9 days.

In another embodiment, the invention provides the method described in any of the preceding paragraphs as applicable above modified such that the priming first expansion in step (a) is performed during a period of 7 days and the rapid second expansion of step (b) is performed during a period of up to 10 days.

In another embodiment, the invention provides the method described in any of the preceding paragraphs as applicable above modified such that the priming first expansion in step (a) is performed during a period of 7 days or 8 days and the rapid second expansion of step (b) is performed during a period of up to 9 days.

In another embodiment, the invention provides the method described in any of the preceding paragraphs as applicable above modified such that the priming first expansion in step (a) is performed during a period of 7 days or 8 days and the rapid second expansion of step (b) is performed during a period of up to 10 days.

In another embodiment, the invention provides the method described in any of the preceding paragraphs as applicable above modified such that the priming first expansion in step (a) is performed during a period of 8 days and the rapid second expansion of step (b) is performed during a period of up to 9 days.

In another embodiment, the invention provides the method described in any of the preceding paragraphs as applicable above modified such that the priming first expansion in step (a) is performed during a period of 8 days and the rapid second expansion of step (b) is performed during a period of up to 8 days.

In another embodiment, the invention provides the method described in any of the preceding paragraphs as applicable above modified such that in step (a) the first population of T cells is cultured in a first culture medium comprising OKT-3 and IL-2.

In another embodiment, the invention provides the method described in any of the preceding paragraphs as applicable above modified such that the first culture medium comprises 4-1BB agonist, OKT-3 and IL-2.

In another embodiment, the invention provides the method described in any of the preceding paragraphs as applicable above modified such that the first culture medium comprises OKT-3, IL-2 and antigen-presenting cells (APCs).

In another embodiment, the invention provides the method described in any of the preceding paragraphs as applicable above modified such that the first culture medium comprises 4-1BB agonist, OKT-3, IL-2 and antigen-presenting cells (APCs).

In another embodiment, the invention provides the method described in any of the preceding paragraphs as applicable above modified such that in step (b) the first population of T cells is cultured in a second culture medium comprising OKT-3, IL-2 and antigen-presenting cells (APCs).

In another embodiment, the invention provides the method described in any of the preceding paragraphs as applicable above modified such that the second culture medium comprises 4-1BB agonist, OKT-3, IL-2 and antigen-presenting cells (APCs).

In another embodiment, the invention provides the method described in any of the preceding paragraphs as applicable above modified such that in step (a) the first population of T cells is cultured in a first culture medium in a container comprising a first gas-permeable surface, wherein the first culture medium comprises OKT-3, IL-2 and a first population of antigen-presenting cells (APCs), wherein the first population of APCs is exogenous to the donor of the first population of T cells and the first population of APCs is layered onto the first gas-permeable surface, wherein in step (b) the first population of T cells is cultured in a second culture medium in the container, wherein the second culture medium comprises OKT-3, IL-2 and a second population of APCs, wherein the second population of APCs is exogenous to the donor of the first population of T cells and the second population of APCs is layered onto the first gas-permeable surface, and wherein the second population of APCs is greater than the first population of APCs.

In another embodiment, the invention provides the method described in any of the preceding paragraphs as applicable above modified such that in step (a) the first population of T cells is cultured in a first culture medium in a container comprising a first gas-permeable surface, wherein the first culture medium comprises 4-1BB agonist, OKT-3, IL-2 and a first population of antigen-presenting cells (APCs), wherein the first population of APCs is exogenous to the donor of the first population of T cells and the first population of APCs is layered onto the first gas-permeable surface, wherein in step (b) the first population of T cells is cultured in a second culture medium in the container, wherein the second culture medium comprises OKT-3, IL-2 and a second population of APCs, wherein the second population of APCs is exogenous to the donor of the first population of T cells and the second population of APCs is layered onto the first gas-permeable surface, and wherein the second population of APCs is greater than the first population of APCs.

In another embodiment, the invention provides the method described in any of the preceding paragraphs as applicable above modified such that in step (a) the first population of T cells is cultured in a first culture medium in a container comprising a first gas-permeable surface, wherein the first culture medium comprises OKT-3, IL-2 and a first population of antigen-presenting cells (APCs), wherein the first population of APCs is exogenous to the donor of the first population of T cells and the first population of APCs is layered onto the first gas-permeable surface, wherein in step (b) the first population of T cells is cultured in a second culture medium in the container, wherein the second culture medium comprises 4-1BB agonist, OKT-3, IL-2 and a second population of APCs, wherein the second population of APCs is exogenous to the donor of the first population of T cells and the second population of APCs is layered onto the first gas-permeable surface, and wherein the second population of APCs is greater than the first population of APCs.

In another embodiment, the invention provides the method described in any of the preceding paragraphs as applicable above modified such that in step (a) the first population of T cells is cultured in a first culture medium in a container comprising a first gas-permeable surface, wherein the first culture medium comprises 4-1BB agonist, OKT-3, IL-2 and a first population of antigen-presenting cells (APCs), wherein the first population of APCs is exogenous to the donor of the first population of T cells and the first population of APCs is layered onto the first gas-permeable surface, wherein in step (b) the first population of T cells is cultured in a second culture medium in the container, wherein the second culture medium comprises 4-1BB agonist, OKT-3, IL-2 and a second population of APCs, wherein the second population of APCs is exogenous to the donor of the first population of T cells and the second population of APCs is layered onto the first gas-permeable surface, and wherein the second population of APCs is greater than the first population of APCs.

In another embodiment, the invention provides the method described in any of the preceding paragraphs as applicable above modified such that the ratio of the number of APCs in the second population of APCs to the number of APCs in the first population of APCs is about 2:1.

In another embodiment, the invention provides the method described in any of the preceding paragraphs as applicable above modified such that the number of APCs in the first population of APCs is about $2.5\times10^8$ and the number of APCs in the second population of APCs is about $5\times10^8$.

In another embodiment, the invention provides the method described in any of the preceding paragraphs as applicable above modified such that in step (a) the first population of APCs is layered onto the first gas-permeable surface at an average thickness of 2 layers of APCs.

In another embodiment, the invention provides the method described in any of the preceding paragraphs as applicable above modified such that in step (b) the second population of APCs is layered onto the first gas-permeable surface at an average thickness selected from the range of 4 to 8 layers of APCs.

In another embodiment, the invention provides the method described in any of the preceding paragraphs as applicable above modified such that the ratio of the average number of layers of APCs layered onto the first gas-permeable surface in step (b) to the average number of layers of APCs layered onto the first gas-permeable surface in step (a) is 2:1.

In another embodiment, the invention provides the method described in any of the preceding paragraphs as applicable above modified such that in step (a) the first population of APCs is seeded on the first gas permeable surface at a density selected from the range of at or about $1.0\times10^6$ APCs/cm$^2$ to at or about $4.5\times10^6$ APCs/cm$^2$.

In another embodiment, the invention provides the method described in any of the preceding paragraphs as applicable above modified such that in step (a) the first population of APCs is seeded on the first gas permeable surface at a density selected from the range of at or about $1.5\times10^6$ APCs/cm$^2$ to at or about $3.5\times10^6$ APCs/cm$^2$.

In another embodiment, the invention provides the method described in any of the preceding paragraphs as applicable above modified such that in step (a) the first population of APCs is seeded on the first gas permeable surface at a density selected from the range of at or about $2.0\times10^6$ APCs/cm$^2$ to at or about $3.0\times10^6$ APCs/cm$^2$.

In another embodiment, the invention provides the method described in any of the preceding paragraphs as applicable above modified such that in step (a) the first population of APCs is seeded on the first gas permeable surface at a density of at or about $2.0\times10^6$ APCs/cm$^2$.

In another embodiment, the invention provides the method described in any of the preceding paragraphs as applicable above modified such that in step (b) the second population of APCs is seeded on the first gas permeable surface at a density selected from the range of at or about $2.5\times10^6$ APCs/cm$^2$ to at or about $7.5\times10^6$ APCs/cm$^2$.

In another embodiment, the invention provides the method described in any of the preceding paragraphs as applicable above modified such that in step (b) the second population of APCs is seeded on the first gas permeable surface at a density selected from the range of at or about $3.5\times10^6$ APCs/cm$^2$ to at or about $6.0\times10^6$ APCs/cm$^2$.

In another embodiment, the invention provides the method described in any of the preceding paragraphs as applicable above modified such that in step (b) the second population of APCs is seeded on the first gas permeable surface at a density selected from the range of at or about $4.0\times10^6$ APCs/cm$^2$ to at or about $5.5\times10^6$ APCs/cm$^2$.

In another embodiment, the invention provides the method described in any of the preceding paragraphs as applicable above modified such that in step (b) the second population of APCs is seeded on the first gas permeable surface at a density of at or about $4.0\times10^6$ APCs/cm$^2$.

In another embodiment, the invention provides the method described in any of the preceding paragraphs as applicable above modified such that in step (a) the first population of APCs is seeded on the first gas permeable surface at a density selected from the range of at or about $1.0\times10^6$ APCs/cm$^2$ to at or about $4.5\times10^6$ APCs/cm$^2$ and in step (b) the second population of APCs is seeded on the first gas permeable surface at a density selected from the range of at or about $2.5\times10^6$ APCs/cm$^2$ to at or about $7.5\times10^6$ APCs/cm$^2$.

In another embodiment, the invention provides the method described in any of the preceding paragraphs as applicable modified such that in step (a) the first population of APCs is seeded on the first gas permeable surface at a density selected from the range of at or about $1.5\times10^6$ APCs/cm$^2$ to at or about $3.5\times10^6$ APCs/cm$^2$ and in step (b) the second population of APCs is seeded on the first gas permeable surface at a density selected from the range of at or about $3.5\times10^6$ APCs/cm$^2$ to at or about $6.0\times10^6$ APCs/cm$^2$.

In another embodiment, the invention provides the method described in any of the preceding paragraphs as applicable above modified such that in step (a) the first population of APCs is seeded on the first gas permeable surface at a density selected from the range of at or about $2.0\times10^6$ APCs/cm$^2$ to at or about $3.0\times10^6$ APCs/cm$^2$ and in step (b) the second population of APCs is seeded on the first gas permeable surface at a density selected from the range of at or about $4.0\times10^6$ APCs/cm$^2$ to at or about $5.5\times10^6$ APCs/cm$^2$.

In another embodiment, the invention provides the method described in any of the preceding paragraphs as applicable above modified such that in step (a) the first population of APCs is seeded on the first gas permeable surface at a density of at or about $2.0\times10^6$ APCs/cm$^2$ and in step (b) the second population of APCs is seeded on the first gas permeable surface at a density of at or about $4.0\times10^6$ APCs/cm$^2$.

In another embodiment, the invention provides the method described in any of the preceding paragraphs as applicable above modified such that the APCs are peripheral blood mononuclear cells (PBMCs).

In another embodiment, the invention provides the method described in any of the preceding paragraphs as applicable above modified such that the PBMCs are irradiated and exogenous to the donor of the first population of T cells.

In another embodiment, the invention provides the method described in any of the preceding paragraphs as applicable above modified such that the T cells are tumor infiltrating lymphocytes (TILs).

In another embodiment, the invention provides the method described in any of the preceding paragraphs as applicable above modified such that the T cells are marrow infiltrating lymphocytes (MILs).

In another embodiment, the invention provides the method described in any of the preceding paragraphs as applicable above modified such that the T cells are peripheral blood lymphocytes (PBLs).

In another embodiment, the invention provides the method described in any of the preceding paragraphs as applicable above modified such that the first population of T cells is obtained by separation from the whole blood of the donor.

In another embodiment, the invention provides the method described in any of the preceding paragraphs as applicable above modified such that the first population of T cells is obtained by separation from the apheresis product of the donor.

In another embodiment, the invention provides the method described in any of the preceding paragraphs as applicable above modified such that the first population of T cells is separated from the whole blood or apheresis product of the donor by positive or negative selection of a T cell phenotype.

In another embodiment, the invention provides the method described in any of the preceding paragraphs as applicable above modified such that the T cell phenotype is CD3+ and CD45+.

In another embodiment, the invention provides the method described in any of the preceding paragraphs as applicable above modified such that before performing the priming first expansion of the first population of T cells the T cells are separated from NK cells. In another embodiment, the T cells are separated from NK cells in the first population of T cells by removal of CD3− CD56+ cells from the first population of T cells. In another embodiment, the CD3− CD56+ cells are removed from the first population of T cells by subjecting the first population of T cells to cell sorting using a gating strategy that removes the CD3− CD56+ cell fraction and recovers the negative fraction. In another embodiment, the foregoing method is utilized for the expansion of T cells in a first population of T cells characterized by a high percentage of NK cells. In another embodiment, the foregoing method is utilized for the expansion of T cells in a first population of T cells characterized by a high percentage of CD3− CD56+ cells. In another embodiment, the foregoing method is utilized for the expansion of T cells in tumor tissue characterized by the present of a high number of NK cells. In another embodiment, the foregoing method is utilized for the expansion of T cells in tumor tissue characterized by a high number of CD3− CD56+ cells. In another embodiment, the foregoing method is utilized for the expansion of T cells in tumor tissue obtained from a patient suffering from a tumor characterized by the presence of a high number of NK cells. In another embodiment, the foregoing method is utilized for the expansion of T cells in tumor tissue obtained from a patient suffering from a tumor characterized by the presence of a high number of CD3− CD56+ cells. In another embodiment, the foregoing method is utilized for the expansion of T cells in tumor tissue obtained from a patient suffering from ovarian cancer.

In another embodiment, the invention provides the method described in any of the preceding paragraphs as applicable above modified such that at or about $1\times10^7$ T cells from the first population of T cells are seeded in a container to initiate the primary first expansion culture in such container.

In another embodiment, the invention provides the method described in any of the preceding paragraphs as applicable above modified such that the first population of T cells is distributed into a plurality of containers, and in each container at or about $1\times10^7$ T cells from the first population of T cells are seeded to initiate the primary first expansion culture in such container.

In another embodiment, the invention provides the method described in any of the preceding paragraphs as applicable above modified such that the second population of T cells harvested in step (c) is a therapeutic population of TILs.

In another embodiment, the invention provides the method described in any of the preceding paragraphs as applicable above modified such that the first population of T cells is obtained from one or more small biopsies (including, for example, a punch biopsy), core biopsies, core needle biopsies or fine needle aspirates of tumor tissue from the donor.

In another embodiment, the invention provides the method described in any of the preceding paragraphs as applicable above modified such that the first population of T cells is obtained from 1 to 20 small biopsies (including, for example, a punch biopsy), core biopsies, core needle biopsies or fine needle aspirates of tumor tissue from the donor.

In another embodiment, the invention provides the method described in any of the preceding paragraphs as applicable above modified such that the first population of T cells is obtained from 1 to 10 small biopsies (including, for example, a punch biopsy), core biopsies, core needle biopsies or fine needle aspirates of tumor tissue from the donor.

In another embodiment, the invention provides the method described in any of the preceding paragraphs as applicable above modified such that the first population of T cells is obtained from 1, 2, 3, 4, 5, 6, 7, 8, 9, 10, 11, 12, 13, 14, 15, 16, 17, 18, 19 or 20 small biopsies (including, for example, a punch biopsy), core biopsies, core needle biopsies or fine needle aspirates of tumor tissue from the donor.

In another embodiment, the invention provides the method described in any of the preceding paragraphs as applicable above modified such that the first population of T cells is obtained from 1, 2, 3, 4, 5, 6, 7, 8, 9, or 10 small biopsies (including, for example, a punch biopsy), core biopsies, core needle biopsies or fine needle aspirates of tumor tissue from the donor.

In another embodiment, the invention provides the method described in any of the preceding paragraphs as applicable above modified such that the first population of T cells is obtained from one or more core biopsies of tumor tissue from the donor.

In another embodiment, the invention provides the method described in any of the preceding paragraphs as applicable above modified such that the first population of T cells is obtained from 1 to 20 core biopsies of tumor tissue from the donor.

In another embodiment, the invention provides the method described in any of the preceding paragraphs as applicable above modified such that the first population of T cells is obtained from 1 to 10 core biopsies of tumor tissue from the donor.

In another embodiment, the invention provides the method described in any of the preceding paragraphs as applicable above modified such that the first population of T cells is obtained from 1, 2, 3, 4, 5, 6, 7, 8, 9, 10, 11, 12, 13, 14, 15, 16, 17, 18, 19 or 20 core biopsies of tumor tissue from the donor.

In another embodiment, the invention provides the method described in any of the preceding paragraphs as applicable above modified such that the first population of T cells is obtained from 1, 2, 3, 4, 5, 6, 7, 8, 9, or 10 core biopsies of tumor tissue from the donor.

In another embodiment, the invention provides the method described in any of the preceding paragraphs as applicable above modified such that the first population of T cells is obtained from one or more fine needle aspirates of tumor tissue from the donor.

In another embodiment, the invention provides the method described in any of the preceding paragraphs as applicable above modified such that the first population of T cells is obtained from 1 to 20 fine needle aspirates of tumor tissue from the donor.

In another embodiment, the invention provides the method described in any of the preceding paragraphs as applicable above modified such that the first population of T cells is obtained from 1 to 10 fine needle aspirates of tumor tissue from the donor.

In another embodiment, the invention provides the method described in any of the preceding paragraphs as applicable above modified such that the first population of T cells is obtained from 1, 2, 3, 4, 5, 6, 7, 8, 9, 10, 11, 12, 13, 14, 15, 16, 17, 18, 19 or 20 fine needle aspirates of tumor tissue from the donor.

In another embodiment, the invention provides the method described in any of the preceding paragraphs as applicable above modified such that the first population of T cells is obtained from 1, 2, 3, 4, 5, 6, 7, 8, 9, or 10 fine needle aspirates of tumor tissue from the donor.

In another embodiment, the invention provides the method described in any of the preceding paragraphs as applicable above modified such that the first population of T cells is obtained from one or more small biopsies (including, for example, a punch biopsy) of tumor tissue from the donor.

In another embodiment, the invention provides the method described in any of the preceding paragraphs as applicable above modified such that the first population of T cells is obtained from 1 to 20 small biopsies (including, for example, a punch biopsy) of tumor tissue from the donor.

In another embodiment, the invention provides the method described in any of the preceding paragraphs as applicable above modified such that the first population of T cells is obtained from 1 to 10 small biopsies (including, for example, a punch biopsy) of tumor tissue from the donor.

In another embodiment, the invention provides the method described in any of the preceding paragraphs as applicable above modified such that the first population of T cells is obtained from 1, 2, 3, 4, 5, 6, 7, 8, 9, 10, 11, 12, 13, 14, 15, 16, 17, 18, 19 or 20 small biopsies (including, for example, a punch biopsy) of tumor tissue from the donor.

In another embodiment, the invention provides the method described in any of the preceding paragraphs as applicable above modified such that the first population of T cells is obtained from 1, 2, 3, 4, 5, 6, 7, 8, 9, or 10 small biopsies (including, for example, a punch biopsy) of tumor tissue from the donor.

In another embodiment, the invention provides the method described in any of the preceding paragraphs as applicable above modified such that the first population of T cells is obtained from one or more core needle biopsies of tumor tissue from the donor.

In another embodiment, the invention provides the method described in any of the preceding paragraphs as applicable above modified such that the first population of T cells is obtained from 1 to 20 core needle biopsies of tumor tissue from the donor.

In another embodiment, the invention provides the method described in any of the preceding paragraphs as applicable above modified such that the first population of T cells is obtained from 1 to 10 core needle biopsies of tumor tissue from the donor.

In another embodiment, the invention provides the method described in any of the preceding paragraphs as applicable above modified such that the first population of T cells is obtained from 1, 2, 3, 4, 5, 6, 7, 8, 9, 10, 11, 12, 13, 14, 15, 16, 17, 18, 19 or 20 core needle biopsies of tumor tissue from the donor.

In another embodiment, the invention provides the method described in any of the preceding paragraphs as applicable above modified such that the first population of T cells is obtained from 1, 2, 3, 4, 5, 6, 7, 8, 9, or 10 core needle biopsies of tumor tissue from the donor.

In another embodiment, the invention provides a method for expanding tumor infiltrating lymphocytes (TILs) into a therapeutic population of TILs comprising: i) obtaining and/or receiving a first population of TILs from a tumor sample obtained from one or more small biopsies, core biopsies, or needle biopsies of a tumor in a subject by culturing the tumor sample in a first cell culture medium comprising IL-2 for about 3 days; (ii) performing a priming first expansion by culturing the first population of TILs in a second cell culture medium comprising IL-2, OKT-3, and antigen presenting cells (APCs) to produce a second population of TILs, wherein the priming first expansion is performed in a container comprising a first gas-permeable surface area, wherein the priming first expansion is performed for first period of about 7 or 8 days to obtain the second population of TILs, wherein the second population of TILs is greater in number than the first population of TILs; (iii) performing a rapid second expansion by supplementing the second cell culture medium of the second population of TILs with additional IL-2, OKT-3, and APCs, to produce a third population of TILs, wherein the number of APCs added in the rapid second expansion is at least twice the number of APCs added in step (ii), wherein the rapid second expansion is performed for a second period of about 11 days to obtain the third population of TILs, wherein the third population of TILs is a therapeutic population of TILs, wherein the rapid second expansion is performed in a container comprising a second gas-permeable surface area; (iv) harvesting the therapeutic population of TILs obtained from step (iii); and (v) transferring the harvested TIL population from step (iv) to an infusion bag.

In another embodiment, the invention provides a method for expanding tumor infiltrating lymphocytes (TILs) into a therapeutic population of TILs comprising: (i) obtaining and/or receiving a first population of TILs from a tumor sample obtained from one or more small biopsies, core biopsies, or needle biopsies of a tumor in a subject by culturing the tumor sample in a first cell culture medium comprising IL-2 for about 3 days; (ii) performing a priming first expansion by culturing the first population of TILs in a second cell culture medium comprising IL-2, OKT-3, and antigen presenting cells (APCs) to produce a second population of TILs, wherein the priming first expansion is performed for first period of about 7 or 8 days to obtain the second population of TILs, wherein the second population of TILs is greater in number than the first population of TILs; (iii) performing a rapid second expansion by contacting the second population of TILs with a third cell culture medium comprising IL-2, OKT-3, and APCs, to produce a third population of TILs, wherein the rapid second expansion is performed for a second period of about 11 days to obtain the third population of TILs, wherein the third population of TILs is a therapeutic population of TILs; and (iv) harvesting the therapeutic population of TILs obtained from step (iii).

In another embodiment, the invention provides the method described in any of the preceding paragraphs as applicable above modified such that after day 5 of the second period the culture is split into 2 or more subcultures, and each subculture is supplemented with an additional quantity of the third culture medium and cultured for about 6 days.

In another embodiment, the invention provides the method described in any of the preceding paragraphs as applicable above modified such that after day 5 of the second period the culture is split into 2 or more subcultures, and each subculture is supplemented with a fourth culture medium comprising IL-2 and cultured for about 6 days.

In another embodiment, the invention provides the method described in any of the preceding paragraphs as applicable above modified such that after day 5 of the second period the culture is split into up to 5 subcultures.

In another embodiment, the invention provides the method described in any of the preceding paragraphs as applicable above modified such that all steps in the method are completed in about 22 days.

In another embodiment, the invention provides a method of expanding T cells comprising: (i) performing a priming first expansion of a first population of T cells from a tumor sample obtained from one or more small biopsies, core biopsies, or needle biopsies of a tumor in a donor by culturing the first population of T cells to effect growth and to prime an activation of the first population of T cells; (ii) after the activation of the first population of T cells primed in step (a) begins to decay, performing a rapid second expansion of the first population of T cells by culturing the first population of T cells to effect growth and to boost the activation of the first population of T cells to obtain a second population of T cells; and (iv) harvesting the second population of T cells. In some embodiments, the tumor sample is obtained from a plurality of core biopsies. In some embodiments, the plurality of core biopsies is selected from the group consisting of 2, 3, 4, 5, 6, 7, 8, 9 and 10 core biopsies.

In some embodiments, the invention the method described in any of the preceding paragraphs as applicable above modified such that T cells or TILs are obtained from tumor digests. In some embodiments, tumor digests are generated by incubating the tumor in enzyme media, for example but not limited to RPMI 1640, 2 mM GlutaMAX, 10 mg/mL gentamicin, 30 U/mL DNase, and 1.0 mg/mL collagenase, followed by mechanical dissociation (GentleMACS, Miltenyi Biotec, Auburn, CA). In some embodiments, the tumor is placed in a tumor dissociating enzyme mixture including one or more dissociating (digesting) enzymes such as, but not limited to, collagenase (including any blend or type of collagenase), Accutase™, Accumax™, hyaluronidase, neutral protease (dispase), chymotrypsin, chymopapain, trypsin, caseinase, elastase, papain, protease type XIV (pronase), deoxyribonuclease I (DNase), trypsin inhibitor, any other dissociating or proteolytic enzyme, and any combination thereof. In other embodiments, the tumor is placed in a tumor dissociating enzyme mixture including collagenase (including any blend or type of collagenase), neutral protease (dispase) and deoxyribonuclease I (DNase).

Pharmaceutical Compositions, Dosages, and Dosing Regimens

In an embodiment, TILs expanded using the methods of the present disclosure are administered to a patient as a pharmaceutical composition. In an embodiment, the pharmaceutical composition is a suspension of TILs in a sterile buffer. TILs expanded using PBMCs of the present disclosure may be administered by any suitable route as known in the art. In some embodiments, the T cells are administered as a single intra-arterial or intravenous infusion, which preferably lasts approximately 30 to 60 minutes. Other suitable routes of administration include intraperitoneal, intrathecal, and intralymphatic administration.

Any suitable dose of TILs can be administered. In some embodiments, from about $2.3\times10^{10}$ to about $13.7\times10^{101}$ TILs are administered, with an average of around $7.8\times10^{101}$ TILs, particularly if the cancer is melanoma. In an embodiment, about $1.2\times10^{10}$ to about $4.3\times10^{10}$ of TILs are administered. In some embodiments, about $3\times10^{10}$ to about $12\times10^{10}$ TILs are administered. In some embodiments, about $4\times10^{10}$ to about $10\times10^{10}$ TILs are administered. In some embodiments, about $5\times10^{10}$ to about $8\times10^{10}$ TILs are administered. In some embodiments, about $6\times10^{10}$ to about $8\times10^{10}$ TILs are administered. In some embodiments, about $7\times10^{10}$ to about $8\times10^{10}$ TILs are administered. In some embodiments, the therapeutically effective dosage is about $2.3\times10^{10}$ to about $13.7\times10^{10}$. In some embodiments, the therapeutically effective dosage is about $7.8\times10^{10}$ TILs, particularly of the cancer is melanoma. In some embodiments, the therapeutically effective dosage is about $1.2\times10^{10}$ to about $4.3\times10^{10}$ of TILs. In some embodiments, the therapeutically effective dosage is about $3\times10^{10}$ to about $12\times10^{10}$ TILs. In some embodiments, the therapeutically effective dosage is about $4\times10^{10}$ to about $10\times10^{10}$ TILs. In some embodiments, the therapeutically effective dosage is about $5\times10^{10}$ to about $8\times10^{10}$ TILs. In some embodiments, the therapeutically effective dosage is about $6\times10^{10}$ to about $8\times10^{10}$ TILs. In some embodiments, the therapeutically effective dosage is about $7\times10^{10}$ to about $8\times10^{10}$ TILs.

In some embodiments, the number of the TILs provided in the pharmaceutical compositions of the invention is about $1\times10^{6}$, $2\times10^{6}$, $3\times10^{6}$, $4\times10^{6}$, $5\times10^{6}$, $6\times10^{6}$, $7\times10^{6}$, $8\times10^{6}$, $9\times10^{6}$, $1\times10^{7}$, $2\times10^{7}$, $3\times10^{7}$, $4\times10^{7}$, $5\times10^{7}$, $6\times10^{7}$, $7\times10^{7}$, $8\times10^{7}$, $9\times10^{7}$, $1\times10^{8}$, $2\times10^{8}$, $3\times10^{8}$, $4\times10^{8}$, $5\times10^{8}$, $6\times10^{8}$, $7\times10^{8}$, $8\times10^{8}$, $9\times10^{8}$, $1\times10^{9}$, $2\times10^{9}$, $3\times10^{9}$, $4\times10^{9}$, $5\times10^{9}$, $6\times10^{9}$, $7\times10^{9}$, $8\times10^{9}$, $9\times10^{9}$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{1}$, $3\times10^{1}$, $4\times10^{1}$, $5\times10^{1}$, $6\times10^{1}$, $7\times10^{1}$, $8\times10^{1}$, $9\times10^{1}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, $9\times10^{12}$, $1\times10^{13}$, $2\times10^{13}$, $3\times10^{13}$, $4\times10^{13}$, $5\times10^{13}$, $6\times10^{13}$, $7\times10^{13}$, $8\times10^{13}$, and $9\times10^{13}$. In an embodiment, the number of the TILs provided in the pharmaceutical compositions of the invention is in the range of $1\times10^{6}$ to $5\times10^{6}$, $5\times10^{6}$ to $1\times10^{7}$, $1\times10^{7}$ to $5\times10^{7}$, $5\times10^{7}$ to $1\times10^{8}$, $1\times10^{8}$ to $5\times10^{8}$, $5\times10^{8}$ to $1\times10^{9}$, $1\times10^{9}$ to $5\times10^{9}$, $5\times10^{9}$ to $1\times10^{10}$, $1\times10^{10}$ to $5\times10^{10}$, $5\times10^{10}$ to $1\times10^{11}$, $5\times10^{11}$ to $1\times10^{12}$, $1\times10^{12}$ to $5\times10^{12}$, and $5\times10^{12}$ to $1\times10^{13}$.

In some embodiments, the concentration of the TILs provided in the pharmaceutical compositions of the invention is less than, for example, 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v or v/v of the pharmaceutical composition.

In some embodiments, the concentration of the TILs provided in the pharmaceutical compositions of the invention is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.00010% w/w, w/v, or v/v of the pharmaceutical composition.

In some embodiments, the concentration of the TILs provided in the pharmaceutical compositions of the invention is in the range from about 0.0001% to about 50%, about 0.001% to about 40%, about 0.01% to about 30%, about 0.02% to about 29%, about 0.03% to about 28%, about 0.04% to about 27%, about 0.05% to about 26%, about 0.06% to about 25%, about 0.07% to about 24%, about 0.08% to about 23%, about 0.09% to about 22%, about 0.10% to about 21%, about 0.2% to about 20%, about 0.3% to about 19%, about 0.4% to about 18%, about 0.5% to about 17%, about 0.6% to about 16%, about 0.7% to about 15%, about 0.8% to about 14%, about 0.9% to about 12% or about 1% to about 10% w/w, w/v or v/v of the pharmaceutical composition.

In some embodiments, the concentration of the TILs provided in the pharmaceutical compositions of the invention is in the range from about 0.001% to about 10%, about 0.01% to about 5%, about 0.02% to about 4.5%, about 0.03% to about 4%, about 0.04% to about 3.5%, about 0.05% to about 3%, about 0.06% to about 2.5%, about 0.07% to about 2%, about 0.08% to about 1.5%, about 0.09% to about 1%, about 0.1% to about 0.9% w/w, w/v or v/v of the pharmaceutical composition.

In some embodiments, the amount of the TILs provided in the pharmaceutical compositions of the invention is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of the TILs provided in the pharmaceutical compositions of the invention is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

The TILs provided in the pharmaceutical compositions of the invention are effective over a wide dosage range. The exact dosage will depend upon the route of administration, the form in which the compound is administered, the gender and age of the subject to be treated, the body weight of the subject to be treated, and the preference and experience of the attending physician. The clinically-established dosages of the TILs may also be used if appropriate. The amounts of the pharmaceutical compositions administered using the methods herein, such as the dosages of TILs, will be dependent on the human or mammal being treated, the severity of the disorder or condition, the rate of administration, the disposition of the active pharmaceutical ingredients and the discretion of the prescribing physician.

In some embodiments, TILs may be administered in a single dose. Such administration may be by injection, e.g., intravenous injection. In some embodiments, TILs may be administered in multiple doses. Dosing may be once, twice, three times, four times, five times, six times, or more than six times per year. Dosing may be once a month, once every two weeks, once a week, or once every other day. Administration of TILs may continue as long as necessary.

In some embodiments, an effective dosage of TILs is about $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, $9\times10^{12}$, $1\times10^{13}$, $2\times10^{13}$, $3\times10^{13}$, $4\times10^{13}$, $5\times10^{13}$, $6\times10^{13}$, $7\times10^{13}$, $8\times10^{13}$, and $9\times10^{13}$. In some embodiments, an effective dosage of TILs is in the range of $1\times10^6$ to $5\times10^6$, $5\times10^6$ to $1\times10^7$, $1\times10^7$ to $5\times10^7$, $5\times10^7$ to $1\times10^8$, $1\times10^8$ to $5\times10^8$, $5\times10^8$ to Ix 109, $1\times10^9$ to $5\times10^9$, $5\times10^9$ to $1\times10^{10}$, $1\times10^{10}$ to $5\times10^{10}$, $5\times10^{10}$ to $1\times10^{11}$, $5\times10^{11}$ to $1\times10^{12}$, $1\times10^{12}$ to $5\times10^{12}$, and $5\times10^{12}$ to $1\times10^{13}$.

In some embodiments, an effective dosage of TILs is in the range of about 0.01 mg/kg to about 4.3 mg/kg, about 0.15 mg/kg to about 3.6 mg/kg, about 0.3 mg/kg to about 3.2 mg/kg, about 0.35 mg/kg to about 2.85 mg/kg, about 0.15 mg/kg to about 2.85 mg/kg, about 0.3 mg to about 2.15 mg/kg, about 0.45 mg/kg to about 1.7 mg/kg, about 0.15 mg/kg to about 1.3 mg/kg, about 0.3 mg/kg to about 1.15 mg/kg, about 0.45 mg/kg to about 1 mg/kg, about 0.55 mg/kg to about 0.85 mg/kg, about 0.65 mg/kg to about 0.8 mg/kg, about 0.7 mg/kg to about 0.75 mg/kg, about 0.7 mg/kg to about 2.15 mg/kg, about 0.85 mg/kg to about 2 mg/kg, about 1 mg/kg to about 1.85 mg/kg, about 1.15 mg/kg to about 1.7 mg/kg, about 1.3 mg/kg mg to about 1.6 mg/kg, about 1.35 mg/kg to about 1.5 mg/kg, about 2.15 mg/kg to about 3.6 mg/kg, about 2.3 mg/kg to about 3.4 mg/kg, about 2.4 mg/kg to about 3.3 mg/kg, about 2.6 mg/kg to about 3.15 mg/kg, about 2.7 mg/kg to about 3 mg/kg, about 2.8 mg/kg to about 3 mg/kg, or about 2.85 mg/kg to about 2.95 mg/kg.

In some embodiments, an effective dosage of TILs is in the range of about 1 mg to about 500 mg, about 10 mg to about 300 mg, about 20 mg to about 250 mg, about 25 mg to about 200 mg, about 1 mg to about 50 mg, about 5 mg to about 45 mg, about 10 mg to about 40 mg, about 15 mg to about 35 mg, about 20 mg to about 30 mg, about 23 mg to about 28 mg, about 50 mg to about 150 mg, about 60 mg to about 140 mg, about 70 mg to about 130 mg, about 80 mg to about 120 mg, about 90 mg to about 110 mg, or about 95 mg to about 105 mg, about 98 mg to about 102 mg, about 150 mg to about 250 mg, about 160 mg to about 240 mg, about 170 mg to about 230 mg, about 180 mg to about 220 mg, about 190 mg to about 210 mg, about 195 mg to about 205 mg, or about 198 to about 207 mg.

An effective amount of the TILs may be administered in either single or multiple doses by any of the accepted modes of administration of agents having similar utilities, including intranasal and transdermal routes, by intra-arterial injection, intravenously, intraperitoneally, parenterally, intramuscularly, subcutaneously, topically, by transplantation, or by inhalation.

In another embodiment, the invention provides an infusion bag comprising the therapeutic population of TILs described in any of the preceding paragraphs above.

In another embodiment, the invention provides a tumor infiltrating lymphocyte (TIL) composition comprising the therapeutic population of TILs described in any of the preceding paragraphs above and a pharmaceutically acceptable carrier.

In another embodiment, the invention provides an infusion bag comprising the TIL composition described in any of the preceding paragraphs above.

In another embodiment, the invention provides a cryopreserved preparation of the therapeutic population of TILs described in any of the preceding paragraphs above.

In another embodiment, the invention provides a tumor infiltrating lymphocyte (TIL) composition comprising the therapeutic population of TILs described in any of the preceding paragraphs above and a cryopreservation media.

In another embodiment, the invention provides the TIL composition described in any of the preceding paragraphs above modified such that the cryopreservation media contains DMSO.

In another embodiment, the invention provides the TIL composition described in any of the preceding paragraphs above modified such that the cryopreservation media contains 7-10% DMSO.

In another embodiment, the invention provides a cryopreserved preparation of the TIL composition described in any of the preceding paragraphs above.

In an embodiment, TILs expanded using the methods of the present disclosure are administered to a patient as a pharmaceutical composition. In an embodiment, the pharmaceutical composition is a suspension of TILs in a sterile buffer. TILs expanded using PBMCs of the present disclosure may be administered by any suitable route as known in the art. In some embodiments, the T cells are administered as a single intra-arterial or intravenous infusion, which preferably lasts approximately 30 to 60 minutes. Other suitable routes of administration include intraperitoneal, intrathecal, and intralymphatic administration.

Any suitable dose of TILs can be administered. In some embodiments, from about $2.3\times10^{10}$ to about $13.7\times10^{10}$ TILs are administered, with an average of around $7.8\times10^{10}$ TILs, particularly if the cancer is melanoma. In an embodiment, about $1.2\times10^{10}$ to about $4.3\times10^{10}$ of TILs are administered. In some embodiments, about $3\times10^{10}$ to about $12\times10^{10}$ TILs are administered. In some embodiments, about $4\times10^{10}$ to about $10\times10^{10}$ TILs are administered. In some embodiments, about $5\times10^{10}$ to about $8\times10^{10}$ TILs are administered. In some embodiments, about $6\times10^{10}$ to about $8\times10^{10}$ TILs are administered. In some embodiments, about $7\times10^{10}$ to about $8\times10^{10}$ TILs are administered. In some embodiments, therapeutically effective dosage is about $2.3\times10^{10}$ to about $13.7\times10^{10}$. In some embodiments, therapeutically effective dosage is about $7.8\times10^{10}$ TILs, particularly of the cancer is melanoma. In some embodiments, therapeutically effective dosage is about $1.2\times10^{10}$ to about $4.3\times10^{10}$ of TILs. In some embodiments, therapeutically effective dosage is about $3\times10^{10}$ to about $12\times10^{10}$ TILs. In some embodiments, therapeutically effective dosage is about $4\times10^{10}$ to about $10\times10^{10}$ TILs. In some embodiments, therapeutically effective dosage is about $5\times10^{10}$ to about $8\times10^{10}$ TILs. In some embodiments, therapeutically effective dosage is about $6\times10^{10}$ to about $8\times10^{10}$ TILs. In some embodiments, therapeutically effective dosage is about $7\times10^{10}$ to about $8\times10^{10}$ TILs.

In some embodiments, the number of the TILs provided in the pharmaceutical compositions of the invention is about $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, $9\times10^{12}$, $1\times10^{13}$, $2\times10^{13}$, $3\times10^{13}$, $4\times10^{13}$, $5\times10^{13}$, $6\times10^{13}$, $7\times10^{13}$, $8\times10^{13}$, and $9\times10^{13}$. In an embodiment, the number of the TILs provided in the pharmaceutical compositions of the invention is in the range of $1\times10^6$ to $5\times10^6$, $5\times10^6$ to $1\times10^7$, $1\times10^7$ to $5\times10^7$, $5\times10^7$ to $1\times10^8$, $1\times10^8$ to $5\times10^8$, $5\times10^8$ to $1\times10^9$, $1\times10^9$ to $5\times10^9$, $5\times10^9$ to $1\times10^{10}$, $1\times10^{10}$ to $5\times10^{10}$, $5\times10^{10}$ to $1\times10^{11}$, $5\times10^{11}$ to $1\times10^{12}$, $1\times10^{12}$ to $5\times10^{12}$, and $5\times10^{12}$ to $1\times10^{13}$.

In some embodiments, the concentration of the TILs provided in the pharmaceutical compositions of the invention is less than, for example, 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v or v/v of the pharmaceutical composition.

In some embodiments, the concentration of the TILs provided in the pharmaceutical compositions of the invention is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.00010% w/w, w/v, or v/v of the pharmaceutical composition.

In some embodiments, the concentration of the TILs provided in the pharmaceutical compositions of the invention is in the range from about 0.00010% to about 50%, about 0.001% to about 40%, about 0.01% to about 30%, about 0.02% to about 29%, about 0.03% to about 28%, about 0.04% to about 27%, about 0.05% to about 26%, about 0.06% to about 25%, about 0.07% to about 24%, about 0.08% to about 23%, about 0.09% to about 22%, about 0.10% to about 21%, about 0.2% to about 20%, about 0.3% to about 19%, about 0.4% to about 18%, about 0.5% to about 17%, about 0.6% to about 16%, about 0.7% to about 15%, about 0.8% to about 14%, about 0.9% to about 12% or about 1% to about 10% w/w, w/v or v/v of the pharmaceutical composition.

In some embodiments, the concentration of the TILs provided in the pharmaceutical compositions of the invention is in the range from about 0.0010% to about 10%, about 0.010% to about 5%, about 0.02% to about 4.5%, about 0.03% to about 4%, about 0.04% to about 3.5%, about 0.05% to about 3%, about 0.06% to about 2.5%, about 0.07% to about 2%, about 0.08% to about 1.5%, about 0.09% to about 1%, about 0.1% to about 0.9% w/w, w/v or v/v of the pharmaceutical composition.

In some embodiments, the amount of the TILs provided in the pharmaceutical compositions of the invention is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of the TILs provided in the pharmaceutical compositions of the invention is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

The TILs provided in the pharmaceutical compositions of the invention are effective over a wide dosage range. The exact dosage will depend upon the route of administration, the form in which the compound is administered, the gender and age of the subject to be treated, the body weight of the subject to be treated, and the preference and experience of the attending physician. The clinically-established dosages of the TILs may also be used if appropriate. The amounts of the pharmaceutical compositions administered using the methods herein, such as the dosages of TILs, will be dependent on the human or mammal being treated, the severity of the disorder or condition, the rate of administration, the disposition of the active pharmaceutical ingredients and the discretion of the prescribing physician.

In some embodiments, TILs may be administered in a single dose. Such administration may be by injection, e.g., intravenous injection. In some embodiments, TILs may be administered in multiple doses. Dosing may be once, twice, three times, four times, five times, six times, or more than six times per year. Dosing may be once a month, once every two weeks, once a week, or once every other day. Administration of TILs may continue as long as necessary.

In some embodiments, an effective dosage of TILs is about $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, $9\times10^{12}$, $1\times10^{13}$, $2\times10^{13}$, $3\times10^{13}$, $4\times10^{13}$, $5\times10^{13}$, $6\times10^{13}$, $7\times10^{13}$, $8\times10^{13}$, and $9\times10^{13}$. In some embodiments, an effective dosage of TILs is in the range of $1\times10^6$ to $5\times10^6$, $5\times10^6$ to $1\times10^7$, $1\times10^7$ to $5\times10^7$, $5\times10^7$ to $1\times10^8$, $1\times10^8$ to $5\times10^8$, $5\times10^8$ to Ix 109, $1\times10^9$ to $5\times10^9$, $5\times10^9$ to $1\times10^{10}$, $1\times10^{10}$ to $5\times10^{10}$, $5\times10^{10}$ to $1\times10^{11}$, $5\times10^{11}$ to $1\times10^{12}$, $1\times10^{12}$ to $5\times10^{12}$, and $5\times10^{12}$ to $1\times10^{13}$.

In some embodiments, an effective dosage of TILs is in the range of about 0.01 mg/kg to about 4.3 mg/kg, about 0.15 mg/kg to about 3.6 mg/kg, about 0.3 mg/kg to about 3.2 mg/kg, about 0.35 mg/kg to about 2.85 mg/kg, about 0.15 mg/kg to about 2.85 mg/kg, about 0.3 mg to about 2.15 mg/kg, about 0.45 mg/kg to about 1.7 mg/kg, about 0.15 mg/kg to about 1.3 mg/kg, about 0.3 mg/kg to about 1.15 mg/kg, about 0.45 mg/kg to about 1 mg/kg, about 0.55 mg/kg to about 0.85 mg/kg, about 0.65 mg/kg to about 0.8 mg/kg, about 0.7 mg/kg to about 0.75 mg/kg, about 0.7 mg/kg to about 2.15 mg/kg, about 0.85 mg/kg to about 2 mg/kg, about 1 mg/kg to about 1.85 mg/kg, about 1.15 mg/kg to about 1.7 mg/kg, about 1.3 mg/kg mg to about 1.6 mg/kg, about 1.35 mg/kg to about 1.5 mg/kg, about 2.15 mg/kg to about 3.6 mg/kg, about 2.3 mg/kg to about 3.4 mg/kg, about 2.4 mg/kg to about 3.3 mg/kg, about 2.6 mg/kg to about 3.15 mg/kg, about 2.7 mg/kg to about 3 mg/kg, about 2.8 mg/kg to about 3 mg/kg, or about 2.85 mg/kg to about 2.95 mg/kg.

In some embodiments, an effective dosage of TILs is in the range of about 1 mg to about 500 mg, about 10 mg to about 300 mg, about 20 mg to about 250 mg, about 25 mg to about 200 mg, about 1 mg to about 50 mg, about 5 mg to about 45 mg, about 10 mg to about 40 mg, about 15 mg to about 35 mg, about 20 mg to about 30 mg, about 23 mg to about 28 mg, about 50 mg to about 150 mg, about 60 mg to about 140 mg, about 70 mg to about 130 mg, about 80 mg to about 120 mg, about 90 mg to about 110 mg, or about 95 mg to about 105 mg, about 98 mg to about 102 mg, about 150 mg to about 250 mg, about 160 mg to about 240 mg, about 170 mg to about 230 mg, about 180 mg to about 220 mg, about 190 mg to about 210 mg, about 195 mg to about 205 mg, or about 198 to about 207 mg.

An effective amount of the TILs may be administered in either single or multiple doses by any of the accepted modes of administration of agents having similar utilities, including intranasal and transdermal routes, by intra-arterial injection, intravenously, intraperitoneally, parenterally, intramuscularly, subcutaneously, topically, by transplantation, or by inhalation.

I. Improved Artificial Antigen Presenting Cell Process Embodiments

In some embodiments, the invention includes a method for expanding TILs, MILs, or PBLs using APCs selected from the group consisting of Raji cells, Ramos cells, Daudi cells, U937 cells, Thp1 cells, and derivatives, variants, modifications, or progeny thereof. In some embodiments, the invention includes a method for expanding TILs, MILs, or PBLs using APCs, wherein the APCs are irradiated or non-irradiated monocyte lineage cells, such as U937 or Thp1 cells or derivatives, variants, modifications, or progeny thereof. In some embodiments, the APCs are artificial APCs. In some embodiments, the APCs are genetically modified as described elsewhere herein, for example to express 4-1BBL or OX40L. In an embodiment, the genetically modified cells are modified to express CD86, OX40L, 4-1BBL, an OX-40 agonistic antibody, a 4-1BB agonistic antibody, an antibody capable of binding the Fc chain of OKT-3, and/or ICOS-L, as described in U.S. Pat. No. 10,415,015, the disclosures of which are incorporated by reference herein. In any of the foregoing embodiments, the genetically modified aAPCs may be irradiated as described elsewhere herein or non-irradiated. The foregoing Gen 2, Gen 3, and other TIL manufacturing processes, including processes based on select of cell surface markers, may be employed.

In some embodiments, the invention includes a method for treating a subject with cancer, the method comprising administering expanded tumor infiltrating lymphocytes (TILs) comprising:

(a) obtaining a first population of TILs from a tumor resected from a subject by processing a tumor sample obtained from the subject into multiple tumor fragments;
(b) adding the tumor fragments into a closed system;
(c) performing a first expansion by culturing the first population of TILs in a cell culture medium comprising IL-2 to produce a second population of TILs, wherein the first expansion is performed in a closed container providing a first gas-permeable surface area, wherein the first expansion is performed for about 3-11 days to obtain the second population of TILs, wherein the second population of TILs is at least 10-fold greater in number than the first population of TILs, and wherein the transition from step (b) to step (c) occurs without opening the system;

(d) performing a second expansion by supplementing the cell culture medium of the second population of TILs with additional IL-2, OKT-3, and antigen presenting cells (APCs), to produce a third population of TILs, wherein the second expansion is performed for about 7-11 days to obtain the third population of TILs, wherein the second expansion is performed in a closed container providing a second gas-permeable surface area, and wherein the transition from step (c) to step (d) occurs without opening the system;

(e) harvesting the therapeutic population of TILs obtained from step (d), wherein the transition from step (d) to step (e) occurs without opening the system;

(f) transferring the harvested TIL population from step (e) to an infusion bag, wherein the transfer from step (e) to (f) occurs without opening the system;

(g) cryopreserving the infusion bag comprising the harvested TIL population from step (f) using a cryopreservation process; and (h) administering a therapeutically effective dosage of the third population of TILs from the infusion bag in step (g) to the subject;

wherein the APCs are selected from the group consisting of Raji cells, Ramos cells, Daudi cells, U937 cells, Thp1 cells, and derivatives, variants, modifications, or progeny thereof.

In some embodiments, the invention includes a method for treating a subject with cancer, the method comprising administering expanded tumor infiltrating lymphocytes (TILs) comprising:

(a) obtaining a first population of TILs from a tumor resected from a subject by processing a tumor sample obtained from the subject into multiple tumor fragments;

(b) adding the tumor fragments into a closed system;

(c) performing a first expansion by culturing the first population of TILs in a cell culture medium comprising IL-2 to produce a second population of TILs, wherein the first expansion is performed in a closed container providing a first gas-permeable surface area, wherein the first expansion is performed for about 3-11 days to obtain the second population of TILs, wherein the second population of TILs is at least 10-fold greater in number than the first population of TILs, and wherein the transition from step (b) to step (c) occurs without opening the system;

(d) performing a second expansion by supplementing the cell culture medium of the second population of TILs with additional IL-2, OKT-3, and antigen presenting cells (APCs), to produce a third population of TILs, wherein the second expansion is performed for about 7-11 days to obtain the third population of TILs, wherein the second expansion is performed in a closed container providing a second gas-permeable surface area, and wherein the transition from step (c) to step (d) occurs without opening the system;

(e) harvesting the therapeutic population of TILs obtained from step (d), wherein the transition from step (d) to step (e) occurs without opening the system;

(f) transferring the harvested TIL population from step (e) to an infusion bag, wherein the transfer from step (e) to (f) occurs without opening the system;

(g) cryopreserving the infusion bag comprising the harvested TIL population from step (f) using a cryopreservation process; and (h) administering a therapeutically effective dosage of the third population of TILs from the infusion bag in step (g) to the subject;

wherein the APCs are irradiated or non-irradiated monocyte lineage cells, such as U937 or Thp1 cells or derivatives, variants, modifications, or progeny thereof.

In some embodiments, the invention includes a population of expanded tumor infiltrating lymphocytes (TILs), wherein the population of expanded TILs is a third population of TILs obtainable by a method comprising:

(a) obtaining a first population of TILs from a tumor resected from a subject by processing a tumor sample obtained from the patient into multiple tumor fragments;

(b) adding the tumor fragments into a closed system;

(c) performing a first expansion by culturing the first population of TILs in a cell culture medium comprising IL-2 to produce a second population of TILs, wherein the first expansion is performed in a closed container providing a first gas-permeable surface area, wherein the first expansion is performed for about 3-11 days to obtain the second population of TILs, and wherein the transition from step (b) to step (c) occurs without opening the system;

(d) performing a second expansion by supplementing the cell culture medium of the second population of TILs with additional IL-2, OKT-3, and antigen presenting cells (APCs), to produce a third population of TILs, wherein the second expansion is performed for about 7-11 days to obtain the third population of TILs, wherein the third population of TILs is a therapeutic population of TILs, wherein the second expansion is performed in a closed container providing a second gas-permeable surface area, and wherein the transition from step (c) to step (d) occurs without opening the system; and (e) harvesting the therapeutic population of TILs obtained from step (d), wherein the transition from step (d) to step (e) occurs without opening the system;

wherein the APCs are selected from the group consisting of Raji cells, Ramos cells, Daudi cells, U937 cells, Thp1 cells, and derivatives, variants, modifications, or progeny thereof.

In some embodiments, the invention includes a population of expanded tumor infiltrating lymphocytes (TILs), wherein the population of expanded TILs is a third population of TILs obtainable by a method comprising:

(a) obtaining a first population of TILs from a tumor resected from a subject by processing a tumor sample obtained from the patient into multiple tumor fragments;

(b) adding the tumor fragments into a closed system;

(c) performing a first expansion by culturing the first population of TILs in a cell culture medium comprising IL-2 to produce a second population of TILs, wherein the first expansion is performed in a closed container providing a first gas-permeable surface area, wherein the first expansion is performed for about 3-11 days to obtain the second population of TILs, and wherein the transition from step (b) to step (c) occurs without opening the system;

(d) performing a second expansion by supplementing the cell culture medium of the second population of TILs with additional IL-2, OKT-3, and antigen presenting cells (APCs), to produce a third population of TILs, wherein the second expansion is performed for about 7-11 days to obtain the third population of TILs, wherein the third population of TILs is a therapeutic population of TILs, wherein the second expansion is performed in a closed container providing a second gas-permeable surface area, and wherein the transition from step (c) to step (d) occurs without opening the system; and (e) harvesting the therapeutic population of TILs obtained from step (d), wherein the transition from step (d) to step (e) occurs without opening the system;

wherein the APCs are irradiated or non-irradiated monocyte lineage cells, such as U937 or Thp1 cells or derivatives, variants, modifications, or progeny thereof.

In some embodiments, the invention includes a cryopreserved tumor infiltrating lymphocyte (TIL) composition comprising a therapeutic population of tumor infiltrating lymphocytes (TILs), wherein the cryopreserved TIL composition is produced by a method comprising:

(a) obtaining a first population of TILs from a tumor resected from a subject by processing a tumor sample obtained from the subject into multiple tumor fragments;

(b) adding the tumor fragments into a closed system;

(c) performing a first expansion by culturing the first population of TILs in a cell culture medium comprising IL-2 to produce a second population of TILs, wherein the first expansion is performed in a closed container providing a first gas-permeable surface area, wherein the first expansion is performed for about 7-11 days to obtain the second population of TILs, wherein the second population of TILs is at least 10-fold greater in number than the first population of TILs, and wherein the transition from step (b) to step (c) occurs without opening the system;

(d) performing a second expansion by supplementing the cell culture medium of the second population of TILs with additional IL-2, OKT-3, and antigen presenting cells (APCs), to produce a third population of TILs, wherein the second expansion is performed for about 7-11 days to obtain the third population of TILs, wherein the second expansion is performed in a closed container providing a second gas-permeable surface area, and wherein the transition from step (c) to step (d) occurs without opening the system; (e) harvesting the therapeutic population of TILs obtained from step (d), wherein the transition from step (d) to step (e) occurs without opening the system;

(e) transferring the harvested TIL population from step (e) to an infusion bag, wherein the transfer from step (e) to (f) occurs without opening the system; and (f) cryopreserving the infusion bag comprising the harvested TIL population from step (f) using a cryopreservation process to obtain the cryopreserved TIL composition;

wherein the APCs are selected from the group consisting of Raji cells, Ramos cells, Daudi cells, U937 cells, Thp1 cells, and derivatives, variants, modifications, or progeny thereof.

In some embodiments, the invention includes a cryopreserved tumor infiltrating lymphocyte (TIL) composition comprising a therapeutic population of tumor infiltrating lymphocytes (TILs), wherein the cryopreserved TIL composition is produced by a method comprising:

(a) obtaining a first population of TILs from a tumor resected from a subject by processing a tumor sample obtained from the subject into multiple tumor fragments;

(b) adding the tumor fragments into a closed system;

(c) performing a first expansion by culturing the first population of TILs in a cell culture medium comprising IL-2 to produce a second population of TILs, wherein the first expansion is performed in a closed container providing a first gas-permeable surface area, wherein the first expansion is performed for about 7-11 days to obtain the second population of TILs, wherein the second population of TILs is at least 10-fold greater in number than the first population of TILs, and wherein the transition from step (b) to step (c) occurs without opening the system;

(d) performing a second expansion by supplementing the cell culture medium of the second population of TILs with additional IL-2, OKT-3, and antigen presenting cells (APCs), to produce a third population of TILs, wherein the second expansion is performed for about 7-11 days to obtain the third population of TILs, wherein the second expansion is performed in a closed container providing a second gas-permeable surface area, and wherein the transition from step (c) to step (d) occurs without opening the system; (e) harvesting the therapeutic population of TILs obtained from step (d), wherein the transition from step (d) to step (e) occurs without opening the system;

(e) transferring the harvested TIL population from step (e) to an infusion bag, wherein the transfer from step (e) to (f) occurs without opening the system; and (f) cryopreserving the infusion bag comprising the harvested TIL population from step (f) using a cryopreservation process to obtain the cryopreserved TIL composition;

wherein the APCs are irradiated or non-irradiated monocyte lineage cells, such as U937 or Thp1 cells or derivatives, variants, modifications, or progeny thereof.

In some embodiments, the invention includes a method for treating a subject with a cancer, the method comprising administering expanded tumor infiltrating lymphocytes (TILs) comprising:

(a) obtaining a first population of TILs from a tumor resected from a subject by processing a tumor sample obtained from the subject into a tumor digest;

(b) adding the tumor digest into a closed system (c) performing a first expansion by culturing the first population of TILs in a cell culture medium comprising IL-2 to produce a second population of TILs, wherein the first expansion is performed in a closed container providing a first gas-permeable surface area, wherein the first expansion is performed for about 3-11 days to obtain the second population of TILs, and wherein the transition from step (b) to step (c) occurs without opening the system;

(d) performing a second expansion by supplementing the cell culture medium of the second population of TILs with additional IL-2, OKT-3, and antigen presenting cells (APCs), to produce a third population of TILs, wherein the second expansion is performed for about 7-11 days to obtain the third population of TILs, wherein the second expansion is performed in a closed container providing a second gas-permeable surface area, and wherein the transition from step (c) to step (d) occurs without opening the system;

(e) harvesting the third population of TILs obtained from step (d), wherein the transition from step (d) to step (e) occurs without opening the system;

(f) transferring the harvested third TIL population from step (e) to an infusion bag, wherein the transfer from step (e) to (f) occurs without opening the system;

(g) cryopreserving the infusion bag comprising the harvested TIL population from step (f) using a cryopreservation process; and (h) administering a therapeutically effective dosage of the third population of TILs from the infusion bag in step (g) to the subject;

wherein the APCs are selected from the group consisting of Raji cells, Ramos cells, Daudi cells, U937 cells, Thp1 cells, and derivatives, variants, modifications, or progeny thereof.

In some embodiments, the invention includes a method for treating a subject with a cancer, the method comprising administering expanded tumor infiltrating lymphocytes (TILs) comprising:

(a) obtaining a first population of TILs from a tumor resected from a subject by processing a tumor sample obtained from the subject into a tumor digest;

(b) adding the tumor digest into a closed system (c) performing a first expansion by culturing the first population of TILs in a cell culture medium comprising IL-2 to produce a second population of TILs, wherein the first expansion is performed in a closed container providing a first gas-permeable surface area, wherein the first expansion is performed for about 3-11 days to obtain the second population of TILs, and wherein the transition from step (b) to step (c) occurs without opening the system;

(d) performing a second expansion by supplementing the cell culture medium of the second population of TILs with additional IL-2, OKT-3, and antigen presenting cells (APCs), to produce a third population of TILs, wherein the second expansion is performed for about 7-11 days to obtain the third population of TILs, wherein the second expansion is performed in a closed container providing a second gas-permeable surface area, and wherein the transition from step (c) to step (d) occurs without opening the system;

(e) harvesting the third population of TILs obtained from step (d), wherein the transition from step (d) to step (e) occurs without opening the system;

(f) transferring the harvested third TIL population from step (e) to an infusion bag, wherein the transfer from step (e) to (f) occurs without opening the system;

(g) cryopreserving the infusion bag comprising the harvested TIL population from step (f) using a cryopreservation process; and (h) administering a therapeutically effective dosage of the third population of TILs from the infusion bag in step (g) to the subject;

wherein the APCs are irradiated or non-irradiated monocyte lineage cells, such as U937 or Thp1 cells or derivatives, variants, modifications, or progeny thereof.

In some embodiments, the invention includes a method for treating a subject with a cancer, the method comprising administering expanded tumor infiltrating lymphocytes (TILs) comprising:

(a) obtaining a first population of TILs from a tumor resected from a patient by processing a tumor sample obtained from the patient into multiple tumor fragments;

(b) adding the tumor fragments into a closed system;

(c) performing a first expansion by culturing the first population of TILs in a cell culture medium comprising IL-2, and optionally OKT-3, and optionally antigen-presenting cells (APCs), to produce a second population of TILs, wherein the first expansion is performed in a closed container providing a first gas-permeable surface area, wherein the first expansion is performed for about 3-14 days to obtain the second population of TILs, wherein the transition from step (b) to step (c) occurs without opening the system;

(d) performing a second expansion by supplementing the cell culture medium of the second population of TILs with additional IL-2, OKT-3, and APCs to produce a third population of TILs, wherein the second expansion is performed for about 4-6 days to obtain the third population of TILs, wherein the second expansion is performed in a closed container providing a second gas-permeable surface area, and wherein the transition from step (c) to step (d) occurs without opening the system;

(e) dividing the third population of TILs into a first plurality of 2-5 subpopulations of TILs, wherein at least $1.0\times10^9$ TILs are present in each subpopulation, wherein the transition from step (d) to (e) occurs without opening the system;

(f) performing a third expansion of the first plurality of subpopulations of TILs by optionally supplementing the cell culture medium of each subpopulation of TILs with additional IL-2, OKT-3, and APCs to produce a second plurality of subpopulations of TILs, wherein the third expansion is performed for about 5-7 days, wherein the third expansion for each subpopulation is performed in a closed container providing a third gas-permeable surface area, and wherein the transition from step (e) to step (f) occurs without opening the system;

(g) harvesting the second plurality of subpopulations of TILs obtained from step (f), wherein the transition from step (f) to step (g) occurs without opening the system;

(h) transferring the harvested subpopulations of TILs from step (g) to one or more infusion bags, wherein the transition from step (g) to (h) occurs without opening the system;

(i) cryopreserving the one or more infusion bags comprising the harvested subpopulations of TILs from step (h) using a cryopreservation process; and (j) administering a therapeutically effective dosage of the harvested subpopulation of TILs from the one or more infusion bags in step (i) to the subject;

wherein the APCs are selected from the group consisting of Raji cells, Ramos cells, Daudi cells, U937 cells, Thp1 cells, and derivatives, variants, modifications, or progeny thereof.

In some embodiments, the invention includes a method for treating a subject with a cancer, the method comprising administering expanded tumor infiltrating lymphocytes (TILs) comprising:

(a) obtaining a first population of TILs from a tumor resected from a patient by processing a tumor sample obtained from the patient into multiple tumor fragments;

(b) adding the tumor fragments into a closed system;

(c) performing a first expansion by culturing the first population of TILs in a cell culture medium comprising IL-2, and optionally OKT-3, and optionally antigen-presenting cells (APCs), to produce a second population of TILs, wherein the first expansion is performed in a closed container providing a first gas-permeable surface area, wherein the first expansion is performed for about 3-14 days to obtain the second population of TILs, wherein the transition from step (b) to step (c) occurs without opening the system;

(d) performing a second expansion by supplementing the cell culture medium of the second population of TILs with additional IL-2, OKT-3, and APCs to produce a third population of TILs, wherein the second expansion is performed for about 4-6 days to obtain the third population of TILs, wherein the second expansion is performed in a closed container providing a second gas-permeable surface area, and wherein the transition from step (c) to step (d) occurs without opening the system;

(e) dividing the third population of TILs into a first plurality of 2-5 subpopulations of TILs, wherein at least $1.0\times10^9$ TILs are present in each subpopulation, wherein the transition from step (d) to (e) occurs without opening the system;

(f) performing a third expansion of the first plurality of subpopulations of TILs by optionally supplementing the cell culture medium of each subpopulation of TILs with additional IL-2, OKT-3, and APCs to produce a second plurality of subpopulations of TILs, wherein the third expansion is performed for about 5-7 days, wherein the third expansion for each subpopulation is performed in a closed container providing a third gas-permeable surface area, and wherein the transition from step (e) to step (f) occurs without opening the system;

(g) harvesting the second plurality of subpopulations of TILs obtained from step (f), wherein the transition from step (f) to step (g) occurs without opening the system;

(h) transferring the harvested subpopulations of TILs from step (g) to one or more infusion bags, wherein the transition from step (g) to (h) occurs without opening the system;

(i) cryopreserving the one or more infusion bags comprising the harvested subpopulations of TILs from step (h) using a cryopreservation process; and (j) administering a therapeutically effective dosage of the harvested subpopulation of TILs from the one or more infusion bags in step (i) to the subject;

wherein the APCs are irradiated or non-irradiated monocyte lineage cells, such as U937 or Thp1 cells or derivatives, variants, modifications, or progeny thereof.

VII. Methods of Treating Patients

Methods of treatment begin with the initial TIL collection and culture of TILs. Such methods have been both described in the art by, for example, Jin, et al., *J. Immunother.,* 2012, 35(3), 283-292, incorporated by reference herein in its entirety. Embodiments of methods of treatment are described throughout the sections below, including the Examples.

The expanded TILs produced according the methods described herein, including for example as described in Steps A through F above or according to Steps A through F above (also as shown, for example, in FIG. 1 and or FIG. 8) find particular use in the treatment of patients with cancer (for example, as described in Goff, et al., *J. Clin. Oncol.,* 2016, 34(20), 2389-239, as well as the supplemental content; incorporated by reference herein in its entirety. In some embodiments, TILs were grown from resected deposits of metastatic melanoma as previously described (see, Dudley, et al., *J. Immunother.,* 2003, 26, 332-342; incorporated by reference herein in its entirety). Fresh tumor can be dissected under sterile conditions. A representative sample can be collected for formal pathologic analysis. Single fragments of 2 $mm^3$ to 3 $mm^3$ may be used. In some embodiments, 5, 10, 15, 20, 25 or 30 samples per patient are obtained. In some embodiments, 20, 25, or 30 samples per patient are obtained. In some embodiments, 20, 22, 24, 26, or 28 samples per patient are obtained. In some embodiments, 24 samples per patient are obtained. Samples can be placed in individual wells of a 24-well plate, maintained in growth media with high-dose IL-2 (6,000 IU/mL), and monitored for destruction of tumor and/or proliferation of TIL. Any tumor with viable cells remaining after processing can be enzymatically digested into a single cell suspension and cryopreserved, as described herein.

In some embodiments, successfully grown TIL can be sampled for phenotype analysis (CD3, CD4, CD8, and CD56) and tested against autologous tumor when available. TIL can be considered reactive if overnight coculture yielded interferon-gamma (IFN-γ) levels >200 pg/mL and twice background. (Goff, et al., *J. Immunother.,* 2010, 33, 840-847; incorporated by reference herein in its entirety). In some embodiments, cultures with evidence of autologous reactivity or sufficient growth patterns can be selected for a second expansion (for example, a second expansion as provided in according to Step D of FIG. 1 and/or FIG. 8), including second expansions that are sometimes referred to as rapid expansion (REP). In some embodiments, expanded TILs with high autologous reactivity (for example, high proliferation during a second expansion), are selected for an additional second expansion. In some embodiments, TILs with high autologous reactivity (for example, high proliferation during second expansion as provided in Step D of FIG. 1 and/or FIG. 8), are selected for an additional second expansion according to Step D of FIG. 1 and/or FIG. 8.

Cell phenotypes of cryopreserved samples of infusion bag TIL can be analyzed by flow cytometry (e.g., FlowJo) for surface markers CD3, CD4, CD8, CCR7, and CD45RA (BD BioSciences), as well as by any of the methods described herein. Serum cytokines were measured by using standard enzyme-linked immunosorbent assay techniques. A rise in serum IFN-g was defined as >100 pg/mL and greater than 43 baseline levels.

In some embodiments, the TILs produced by the methods provided herein, for example those exemplified in FIG. 1 and/or FIG. 8, provide for a surprising improvement in clinical efficacy of the TILs. In some embodiments, the TILs produced by the methods provided herein, for example those exemplified in FIG. 1 and/or FIG. 8, exhibit increased clinical efficacy as compared to TILs produced by methods other than those described herein, including for example, methods other than those exemplified in FIG. 1 and/or FIG. 8. In some embodiments, the methods other than those described herein include methods referred to as process 1C and/or Generation 1 (Gen 1). In some embodiments, the increased efficacy is measured by DCR, ORR, and/or other clinical responses. In some embodiments, the TILs produced by the methods provided herein, for example those exemplified in FIG. 1, exhibit a similar time to response and safety profile compared to TILs produced by methods other than those described herein, including for example, methods other than those exemplified in FIG. 1 and/or FIG. 8, for example the Gen 1 process.

In some embodiments, IFN-gamma (IFN-γ) is indicative of treatment efficacy and/or increased clinical efficacy. In some embodiments, IFN-γ in the blood of subjects treated with TILs is indicative of active TILs. In some embodiments, a potency assay for IFN-γ production is employed. IFN-γ production is another measure of cytotoxic potential. IFN-γ production can be measured by determining the levels of the cytokine IFN-γ in the blood, serum, or TILs ex vivo of a subject treated with TILs prepared by the methods of the present invention, including those as described for example in FIG. 1 and/or FIG. 8. In some embodiments, an increase in IFN-γ is indicative of treatment efficacy in a patient treated with the TILs produced by the methods of the present invention. In some embodiments, IFN-γ is increased one-fold, two-fold, three-fold, four-fold, or five-fold or more as compared to an untreated patient and/or as compared to a patient treated with TILs prepared using other methods than those provide herein including for example, methods other than those embodied in FIG. 1 and/or FIG. 8. In some embodiments, IFN-γ secretion is increased one-fold as compared to an untreated patient and/or as compared to a patient treated with TILs prepared using other methods than those provide herein including for example, methods other than those embodied in FIG. 1 and/or FIG. 8. In some embodiments, IFN-γ secretion is increased two-fold as compared to an untreated patient and/or as compared to a patient treated with TILs prepared using other methods than those provide herein including for example, methods other than those embodied in FIG. 1 and/or FIG. 8. In some embodiments, IFN-γ secretion is increased three-fold as compared to an untreated patient and/or as compared to a patient treated with TILs prepared using other methods than those provide herein including for example, methods other than those embodied in FIG. 1 and/or FIG. 8. In some embodiments, IFN-γ secretion is increased four-fold as compared to an untreated patient and/or as compared to a patient treated with TILs prepared using other methods than those provide herein including for example, methods other than those embodied in FIG. 1 and/or FIG. 8. In some embodiments, IFN-γ secretion is increased five-fold as compared to an untreated patient and/or as compared to a patient treated with TILs prepared using other methods than those provide herein including for example, methods other than those embodied in FIG. 1 and/or FIG. 8. In some embodiments, IFN-γ is measured using a Quantikine ELISA kit. In some embodiments, IFN-γ is measured in TILs ex vivo of a subject treated with TILs prepared by the methods of the present invention, including those as described for example in FIG. 1 and/or FIG. 8. In some embodiments, IFN-γ is measured in blood of a subject treated with TILs prepared by the methods of the present invention, including those as described for example in FIG. 1 and/or FIG. 8. In some embodiments, IFN-γ is measured in TILs from serum of a subject treated with TILs prepared by the methods of the present invention, including those as described for example in FIG. 1 and/or FIG. 8.

In some embodiments, IFN-gamma (IFN-γ) is indicative of treatment efficacy and/or increased clinical efficacy. In some embodiments, IFN-γ in the blood of subjects treated with TILs is indicative of active TILs. In some embodiments, a potency assay for IFN-γ production is employed. IFN-γ production is another measure of cytotoxic potential. IFN-γ production can be measured by determining the levels of the cytokine IFN-γ in the blood, serum, or other tissue of a subject treated with TILs prepared by the methods of the present invention, including those as described for example in FIG. 1 and/or FIG. 8. In some embodiments, an increase in IFN-γ is indicative of treatment efficacy in a patient treated with the TILs produced by the methods of the present invention. In some embodiments, IFN-γ is increased one-fold, two-fold, three-fold, four-fold, or five-fold or more IFN-γ as compared to an untreated patient and/or as compared to a patient treated with TILs prepared using other methods than those provide herein including for example, methods other than those embodied in FIG. 1 and/or FIG. 8.

In some embodiments, the TILs prepared by the methods of the present invention, including those as described for example in FIG. 1 and/or FIG. 8, exhibit increased polyclonality as compared to TILs produced by other methods, including those not exemplified in FIG. 1 and/or FIG. 8, including for example, methods referred to as process 1C methods. In some embodiments, significantly improved polyclonality and/or increased polyclonality is indicative of treatment efficacy and/or increased clinical efficacy. In some embodiments, polyclonality refers to the T cell repertoire diversity. In some embodiments, an increase in polyclonality can be indicative of treatment efficacy with regard to administration of the TILs produced by the methods of the present invention. In some embodiments, polyclonality is increased one-fold, two-fold, ten-fold, 100-fold, 500-fold, or 1000-fold as compared to TILs prepared using methods than those provide herein including for example, methods other than those embodied in FIG. 1 and/or FIG. 8. In some embodiments, polyclonality is increased one-fold as compared to an untreated patient and/or as compared to a patient treated with TILs prepared using other methods than those provide herein including for example, methods other than those embodied in FIG. 1 and/or FIG. 8. In some embodiments, polyclonality is increased two-fold as compared to an untreated patient and/or as compared to a patient treated with TILs prepared using other methods than those provide herein including for example, methods other than those embodied in FIG. 1 and/or FIG. 8. In some embodiments, polyclonality is increased ten-fold as compared to an untreated patient and/or as compared to a patient treated with TILs prepared using other methods than those provide herein including for example, methods other than those embodied in FIG. 1 and/or FIG. 8. In some embodiments, polyclonality is increased 100-fold as compared to an untreated patient and/or as compared to a patient treated with TILs prepared using other methods than those provide herein including for example, methods other than those embodied in FIG. 1 and/or FIG. 8. In some embodiments, polyclonality is increased 500-fold as compared to an untreated patient and/or as compared to a patient treated with TILs prepared using other methods than those provide herein including for example, methods other than those embodied in FIG. 1 and/or FIG. 8. In some embodiments, polyclonality is increased 1000-fold as compared to an untreated patient and/or as compared to a patient treated with TILs prepared using other methods than those provide herein including for example, methods other than those embodied in FIG. 1 and/or FIG. 8.

Measures of efficacy can include the disease control rate (DCR) as well as overall response rate (ORR), as known in the art as well as described herein.

1. Methods of Treating Cancers and Other Diseases

The compositions and methods described herein can be used in a method for treating diseases. In an embodiment, they are for use in treating hyperproliferative disorders.

They may also be used in treating other disorders as described herein and in the following paragraphs.

In some embodiments, the hyperproliferative disorder is cancer. In some embodiments, the hyperproliferative disorder is a solid tumor cancer. In some embodiments, the solid tumor cancer is selected from the group consisting of sarcoma, pancreatic cancer, liver cancer, glioblastoma, glioma, gastrointestinal cancer, melanoma, ovarian cancer, endometrial cancer, thyroid cancer, colorectal cancer, cervical cancer, non-small-cell lung cancer (NSCLC), lung cancer, bladder cancer, breast cancer, stomach cancer, esophageal cancer, cancer caused by human papilloma virus, head and neck cancer (including head and neck squamous cell carcinoma (HNSCC)), renal cancer, prostate cancer, and renal cell carcinoma. In some embodiments, the hyperproliferative disorder is a hematological malignancy. In some embodiments, the solid tumor cancer is selected from the group consisting of chronic lymphocytic leukemia, acute lymphoblastic leukemia, diffuse large B cell lymphoma, non-Hodgkin's lymphoma, Hodgkin's lymphoma, follicular lymphoma, and mantle cell lymphoma. In some embodiments, the solid tumor cancer is selected from the group consisting of anal cancer, bladder cancer, breast cancer (including triple-negative breast cancer), bone cancer, cancer caused by human papilloma virus (HPV), central nervous system associated cancer (including ependymoma, medulloblastoma, neuroblastoma, pineoblastoma, and primitive neuroectodermal tumor), cervical cancer (including squamous cell cervical cancer, adenosquamous cervical cancer, and cervical adenocarcinoma), colon cancer, colorectal cancer, endometrial cancer, esophageal cancer, esophagogastric junction cancer, gastric cancer, gastrointestinal cancer, gastrointestinal stromal tumor, glioblastoma, glioma, head and neck cancer (including head and neck squamous cell carcinoma (HNSCC), hypopharynx cancer, larynx cancer, nasopharynx cancer, oropharynx cancer, and pharynx cancer), kidney cancer, liver cancer, lung cancer (including non-small-cell lung cancer (NSCLC) and small-cell lung cancer), melanoma (including uveal melanoma, choroidal melanoma, ciliary body melanoma, or iris melanoma), mesothelioma (including malignant pleural mesothelioma), ovarian cancer, pancreatic cancer (including pancreatic ductal adenocarcinoma), penile cancer, rectal cancer, renal cancer, renal cell carcinoma, sarcoma (including Ewing sarcoma, osteosarcoma, rhabdomyosarcoma, and other bone and soft tissue sarcomas), thyroid cancer (including anaplastic thyroid cancer), uterine cancer, and vaginal cancer.

In some embodiments, the cancer is melanoma. In some embodiments, the cancer is melanoma stages IIB to IV.

In some embodiments, the invention provides a method for treating a subject with cancer wherein the cancer is melanoma, ovarian cancer, cervical cancer, non-small-cell lung cancer (NSCLC), lung cancer, bladder cancer, breast cancer, cancer caused by human papilloma virus, head and neck cancer (including head and neck squamous cell carcinoma (HNSCC)), glioblastoma (including GBM), gastrointestinal cancer, renal cancer, or renal cell carcinoma.

In another embodiment, the invention provides a method for treating a subject with cancer described herein, wherein the cancer is melanoma, HNSCC, cervical cancers, NSCLC, glioblastoma (including GBM), and gastrointestinal cancer.

In another embodiment, the invention provides a method for treating a subject with cancer described herein, wherein the cancer is melanoma.

In another embodiment, the invention provides a method for treating a subject with cancer described herein, wherein the cancer is HNSCC.

In another embodiment, the invention provides a method for treating a subject with cancer described herein, wherein the cancer is cervical cancer.

In another embodiment, the invention provides a method for treating a subject with cancer described herein, wherein the cancer is NSCLC.

In another embodiment, the invention provides a method for treating a subject with cancer described herein, wherein the cancer is glioblastoma (including GBM).

In another embodiment, the invention provides a method for treating a subject with cancer described herein, wherein the cancer is gastrointestinal cancer.

In another embodiment, the invention provides a method for treating a subject with cancer described herein, wherein the cancer is a hypermutated cancer.

In another embodiment, the invention provides a method for treating a subject with cancer described herein, wherein the cancer is a pediatric hypermutated cancer.

In some embodiments, the hyperproliferative disorder is a hematological malignancy. In some embodiments, the hematological malignancy is selected from the group consisting of chronic lymphocytic leukemia, acute lymphoblastic leukemia, diffuse large B cell lymphoma, non-Hodgkin's lymphoma, Hodgkin's lymphoma, follicular lymphoma, mantle cell lymphoma, and multiple myeloma. In some embodiments, the present invention includes a method of treating a patient with a cancer, wherein the cancer is a hematological malignancy. In some embodiments, the present invention includes a method of treating a patient with a cancer using TILs, MILs, or PBLs modified to express one or more CCRs, wherein the cancer is a hematological malignancy. In some embodiments, the present invention includes a method of treating a patient with a cancer using MILs or PBLs modified to express one or more CCRs, wherein the cancer is a hematological malignancy.

In some embodiments, the cancer is a hypermutated cancer or hypermutated cancer phenotype. Hypermutated cancers are extensively described in Campbell, et al., *Cell* 2017, 171, 1042-1056; incorporated by reference herein in its entirety for all purposes). In some embodiments, a hypermutated tumors comprise between 9 and 10 mutations per megabase (Mb). In some embodiments, pediatric hypermutated tumors comprise 9.91 mutations per megabase (Mb). In some embodiments, adult hypermutated tumors comprise 9 mutations per megabase (Mb). In some embodiments, enhanced hypermutated tumors comprise between 10 and 100 mutations per megabase (Mb). In some embodiments, enhanced pediatric hypermutated tumors comprise between 10 and 100 mutations per megabase (Mb). In some embodiments, enhanced adult hypermutated tumors comprise between 10 and 100 mutations per megabase (Mb). In some embodiments, an ultra-hypermutated tumors comprise greater than 100 mutations per megabase (Mb). In some embodiments, pediatric ultra-hypermutated tumors comprise greater than 100 mutations per megabase (Mb). In some embodiments, adult ultra-hypermutated tumors comprise greater than 100 mutations per megabase (Mb).

In some embodiments, the hypermutated tumors have mutations in replication repair pathways. In some embodiments, the hypermutated tumors have mutations in replication repair associated DNA polymerases. In some embodiments, the hypermutated tumors have microsatellite instability. In some embodiments, the ultra-hypermutated tumors have mutations in replication repair associated DNA polymerases and have microsatellite instability. In some embodiments, hypermutation in the tumor is correlated with response to immune checkpoint inhibitors. In some embodiments, hypermutated tumors are resistant to treatment with immune checkpoint inhibitors. In some embodiments, hypermutated tumors can be treated using the TILs of the present invention. In some embodiments, hypermutation in the tumor is caused by environmental factors (extrinsic exposures). For example, UV light can be the primary cause of the high numbers of mutations in malignant melanoma (see, for example, Pfeifer, et al. *Mutat. Res.* 2005, 571, 19-31; Sage, *Photochem. Photobiol.* 1993, 57, 163-174). In some embodiments, hypermutation in the tumor can be caused by the greater than 60 carcinogens in tobacco smoke for tumors of the lung and larynx, as well as other tumors, due to direct mutagen exposure (see, for example, Pleasance, et al., *Nature* 2010, 463, 184-190). In some embodiments, hypermutation in the tumor is caused by dysregulation of apolipoprotein B mRNA editing enzyme, catalytic polypeptide-like (APOBEC) family members, which has been shown to result in increased levels of C to T transitions in a wide range of cancers (see, for example, Roberts, et al., *Nat. Genet.* 2013, 45, 970-976). In some embodiments, hypermutation in the tumor is caused by defective DNA replication repair by mutations that compromise proofreading, which is performed by the major replicative enzymes Pol3 and Pold1. In some embodiments, hypermutation in the tumor is caused by defects in DNA mismatch repair, which are associated with hypermutation in colorectal, endometrial, and other cancers (see, for example, Kandoth, et al., *Nature* 2013, 497, 67-73; Muzny, et al., *Nature* 2012, 487, 330-337). In some embodiments, DNA replication repair mutations are also found in cancer predisposition syndromes, such as constitutional or biallelic mismatch repair deficiency (CMMRD), Lynch syndrome, and polymerase proofreading-associated polyposis (PPAP).

In an embodiment, the invention includes a method of treating a cancer with a population of TILs, wherein the cancer is a hypermutated cancer. In an embodiment, the invention includes a method of treating a cancer with a population of TILs, wherein the cancer is an enhanced hypermutated cancer. In an embodiment, the invention includes a method of treating a cancer with a population of TILs, wherein the cancer is an ultra-hypermutated cancer.

In an embodiment, the invention includes a method of treating a cancer with a population of TILs, wherein a patient is pre-treated with non-myeloablative chemotherapy prior to an infusion of TILs according to the present disclosure. In an embodiment, the non-myeloablative chemotherapy is cyclophosphamide 60 mg/kg/d for 2 days (days 27 and 26 prior to TIL infusion) and fludarabine 25 mg/m2/d for 5 days (days 27 to 23 prior to TIL infusion). In some embodiments, the non-myeloablative chemotherapy is cyclophosphamide 60 mg/kg/d for 2 days (days 27 and 26 prior to TIL infusion) and fludarabine 25 $mg/m^2/d$ for 3 days (days 27 to 25 prior to TIL infusion). In some embodiments, the non-myeloablative chemotherapy is cyclophosphamide 60 mg/kg/d for 2 days (days 27 and 26 prior to TIL infusion) followed by fludarabine 25 $mg/m^2/d$ for 3 days (days 25 to 23 prior to TIL infusion). In an embodiment, after non-myeloablative chemotherapy and TIL infusion (at day 0) according to the present disclosure, the patient receives an intravenous infusion of IL-2 intravenously at 720,000 IU/kg every 8 hours to physiologic tolerance.

Efficacy of the compounds and combinations of compounds described herein in treating, preventing and/or managing the indicated diseases or disorders can be tested using various models known in the art, which provide guidance for treatment of human disease. For example, models for determining efficacy of treatments for ovarian cancer are described, e.g., in Mullany, et al., *Endocrinology* 2012, 153, 1585-92; and Fong, et al., *J. Ovarian Res.* 2009, 2, 12. Models for determining efficacy of treatments for pancreatic cancer are described in Herreros-Villanueva, et al., *World J. Gastroenterol.* 2012, 18, 1286-1294. Models for determining efficacy of treatments for breast cancer are described, e.g., in Fantozzi, *Breast Cancer Res.* 2006, 8, 212. Models for determining efficacy of treatments for melanoma are described, e.g., in Damsky, et al., *Pigment Cell & Melanoma Res.* 2010, 23, 853-859. Models for determining efficacy of treatments for lung cancer are described, e.g., in Meuwissen, et al., *Genes & Development,* 2005, 19, 643-664. Models for determining efficacy of treatments for lung cancer are described, e.g., in Kim, *Clin. Exp. Otorhinolaryngol.* 2009, 2, 55-60; and Sano, *Head Neck Oncol.* 2009, 1, 32.

In some embodiments, IFN-gamma (IFN-γ) is indicative of treatment efficacy for hyperproliferative disorder treatment. In some embodiments, IFN-γ in the blood of subjects treated with TILs is indicative of active TILs. In some embodiments, a potency assay for IFN-γ production is employed. IFN-γ production is another measure of cytotoxic potential. IFN-γ production can be measured by determining the levels of the cytokine IFN-γ in the blood of a subject treated with TILs prepared by the methods of the present invention, including those as described for example in FIG. 8 (in particular, e.g., FIG. 8A and/or FIG. 8B and/or FIG. 8C and/or FIG. 8D). In some embodiments, the TILs obtained by the present method provide for increased IFN-γ in the blood of subjects treated with the TILs of the present method as compared subjects treated with TILs prepared using methods referred to as the Gen 3 process, as exemplified FIG. 8 (in particular, e.g., FIG. 8A and/or FIG. 8B and/or FIG. 8C and/or FIG. 8D) and throughout this application. In some embodiments, an increase in IFN-γ is indicative of treatment efficacy in a patient treated with the TILs produced by the methods of the present invention. In some embodiments, IFN-γ is increased one-fold, two-fold, three-fold, four-fold, or five-fold or more as compared to an untreated patient and/or as compared to a patient treated with TILs prepared using other methods than those provide herein including, for example, methods other than those embodied in FIG. 8 (in particular, e.g., FIG. 8A and/or FIG. 8B and/or FIG. 8C and/or FIG. 8D). In some embodiments, IFN-γ secretion is increased one-fold as compared to an untreated patient and/or as compared to a patient treated with TILs prepared using other methods than those provide herein including, for example, methods other than those embodied in FIG. 8 (in particular, e.g., FIG. 8A and/or FIG. 8B and/or FIG. 8C and/or FIG. 8D). In some embodiments, IFN-γ secretion is increased two-fold as compared to an untreated patient and/or as compared to a patient treated with TILs prepared using other methods than those provide herein including, for example, methods other than those embodied in FIG. 8 (in particular, e.g., FIG. 8A and/or FIG. 8B and/or FIG. 8C and/or FIG. 8D). In some embodiments, IFN-γ secretion is increased three-fold as compared to an untreated patient and/or as compared to a patient treated with TILs prepared using other methods than those provide herein including, for example, methods other than those embodied in FIG. 8 (in particular, e.g., FIG. 8A and/or FIG. 8B and/or FIG. 8C and/or FIG. 8D). In some embodiments, IFN-γ secretion is increased four-fold as compared to an untreated patient and/or as compared to a patient treated with TILs prepared using other methods than those provide herein including, for example, methods other than those embodied in FIG. 8 (in particular, e.g., FIG. 8A and/or FIG. 8B and/or FIG. 8C and/or FIG. 8D). In some embodiments, IFN-γ secretion is increased five-fold as compared to an untreated patient and/or as compared to a patient treated with TILs prepared using other methods than those provide herein including, for example, methods other than those embodied in FIG. 8 (in particular, e.g., FIG. 8A and/or FIG. 8B and/or FIG. 8C and/or FIG. 8D). In some embodiments, IFN-γ is measured using a Quantikine ELISA kit. In some embodiments, IFN-γ is measured using a Quantikine ELISA kit. In some embodiments, IFN-γ is measured in TILs ex vivo from a patient treated with the TILs produced by the methods of the present invention. In some embodiments, IFN-γ is measured in blood in a patient treated with the TILs produced by the methods of the present invention. In some embodiments, IFN-γ is measured in serum in a patient treated with the TILs produced by the methods of the present invention.

In some embodiments, the TILs prepared by the methods of the present invention, including those as described for example in FIG. 8 (in particular, e.g., FIG. 8A and/or FIG. 8B and/or FIG. 8C and/or FIG. 8D), exhibit increased polyclonality as compared to TILs produced by other methods, including those not exemplified in FIG. 8 (in particular, e.g., FIG. 8A and/or FIG. 8B and/or FIG. 8C and/or FIG. 8D), such as for example, methods referred to as process 1C methods. In some embodiments, significantly improved polyclonality and/or increased polyclonality is indicative of treatment efficacy and/or increased clinical efficacy for cancer treatment. In some embodiments, polyclonality refers to the T cell repertoire diversity. In some embodiments, an increase in polyclonality can be indicative of treatment efficacy with regard to administration of the TILs produced by the methods of the present invention. In some embodiments, polyclonality is increased one-fold, two-fold, ten-fold, 100-fold, 500-fold, or 1000-fold as compared to TILs prepared using methods than those provide herein including, for example, methods other than those embodied in FIG. 8 (in particular, e.g., FIG. 8A and/or FIG. 8B and/or FIG. 8C and/or FIG. 8D). In some embodiments, polyclonality is increased one-fold as compared to an untreated patient and/or as compared to a patient treated with TILs prepared using other methods than those provide herein including, for example, methods other than those embodied in FIG. 8 (in particular, e.g., FIG. 8A and/or FIG. 8B and/or FIG. 8C and/or FIG. 8D). In some embodiments, polyclonality is increased two-fold as compared to an untreated patient and/or as compared to a patient treated with TILs prepared using other methods than those provide herein including, for example, methods other than those embodied in FIG. 8 (in particular, e.g., FIG. 8A and/or FIG. 8B and/or FIG. 8C and/or FIG. 8D). In some embodiments, polyclonality is increased ten-fold as compared to an untreated patient and/or as compared to a patient treated with TILs prepared using other methods than those provide herein including, for example, methods other than those embodied in FIG. 8 (in particular, e.g., FIG. 8A and/or FIG. 8B and/or FIG. 8C and/or FIG. 8D). In some embodiments, polyclonality is increased 100-fold as compared to an untreated patient and/or as compared to a patient treated with TILs prepared using other methods than those provide herein including, for example, methods other than those embodied in FIG. 8 (in particular, e.g., FIG. 8A and/or FIG. 8B and/or FIG. 8C and/or FIG. 8D). In some embodiments, polyclonality is increased 500-fold as compared to an untreated patient and/or as compared to a patient treated with TILs prepared using other methods than those provide herein including, for example, methods other than those embodied in FIG. 8 (in particular, e.g., FIG. 8A and/or FIG. 8B and/or FIG. 8C and/or FIG. 8D). In some embodiments, polyclonality is increased 1000-fold as compared to an untreated patient and/or as compared to a patient treated with TILs prepared using other methods than those provide herein including, for example, methods other than those embodied in FIG. 8 (in particular, e.g., FIG. 8A and/or FIG. 8B and/or FIG. 8C and/or FIG. 8D).

2. Combinations with PD-1 and PD-L1 Inhibitors

In some embodiments, the TIL therapy provided to patients with cancer may include treatment with therapeutic populations of TILs alone or may include a combination treatment including TILs and one or more PD-1 and/or PD-L1 inhibitors. For example, antibodies that target PD-1 and which can be co-administered with the TILs of the present invention include, e.g., but are not limited to nivolumab (BMS-936558, Bristol-Myers Squibb; Opdivo®), pembrolizumab (lambrolizumab, MK03475 or MK-3475, Merck; Keytruda®), humanized anti-PD-1 antibody JS001 (ShangHai JunShi), monoclonal anti-PD-1 antibody TSR-042 (Tesaro, Inc.), Pidilizumab (anti-PD-1 mAb CT-011, Medivation), anti-PD-1 monoclonal Antibody BGB-A317 (BeiGene), and/or anti-PD-1 antibody SHR-1210 (ShangHai HengRui), human monoclonal antibody REGN2810 (Regeneron), human monoclonal antibody MDX-1106 (Bristol-Myers Squibb), and/or humanized anti-PD-1 IgG4 antibody PDR001 (Novartis). In some embodiments, the PD-1 antibody is from clone: RMP1-14 (rat IgG)-BioXcell cat #BP0146. Other suitable antibodies suitable for use in co-administration methods with TILs produced according to Steps A through F as described herein are anti-PD-1 antibodies disclosed in U.S. Pat. No. 8,008,449, herein incorporated by reference. In some embodiments, the antibody or antigen-binding portion thereof binds specifically to PD-L1 and inhibits its interaction with PD-1, thereby increasing immune activity. Any antibodies known in the art which bind to PD-L1 and disrupt the interaction between the PD-1 and PD-L1, and stimulates an anti-tumor immune response, are suitable for use in co-administration methods with TILs produced according to Steps A through F as described herein. For example, antibodies that target PD-L1 and are in clinical trials, include BMS-936559 (Bristol-Myers Squibb) and MPDL3280A (Genentech). Other suitable antibodies that target PD-L1 are disclosed in U.S. Pat. No. 7,943,743, herein incorporated by reference. It will be understood by one of ordinary skill that any antibody which binds to PD-1 or PD-L1, disrupts the PD-1/PD-L1 interaction, and stimulates an anti-tumor immune response, are suitable for use in co-administration methods with TILs produced according to Steps A through F as described herein. In some embodiments, the subject administered the combination of TILs produced according to Steps A through F is co administered with a and anti-PD-1 antibody when the patient has a cancer type that is refractory to administration of the anti-PD-1 antibody alone. In some embodiments, the patient is administered TILs in combination with an anti-PD-1 when the patient has refractory melanoma.

Programmed death 1 (PD-1) is a 288-amino acid transmembrane immunocheckpoint receptor protein expressed by T cells, B cells, natural killer (NK) T cells, activated monocytes, and dendritic cells. PD-1, which is also known as CD279, belongs to the CD28 family, and in humans is encoded by the Pdcd1 gene on chromosome 2. PD-1 consists of one immunoglobulin (Ig) superfamily domain, a transmembrane region, and an intracellular domain containing an immunoreceptor tyrosine-based inhibitory motif (ITIM) and an immunoreceptor tyrosine-based switch motif (ITSM). PD-1 and its ligands (PD-L1 and PD-L2) are known to play a key role in immune tolerance, as described in Keir, et al., *Annu. Rev. Immunol.* 2008, 26, 677-704. PD-1 provides inhibitory signals that negatively regulate T cell immune responses. PD-L1 (also known as B7-H1 or CD274) and PD-L2 (also known as B7-DC or CD273) are expressed on tumor cells and stromal cells, which may be encountered by activated T cells expressing PD-1, leading to immunosuppression of the T cells. PD-L1 is a 290 amino acid transmembrane protein encoded by the Cd274 gene on human chromosome 9. Blocking the interaction between PD-1 and its ligands PD-L1 and PD-L2 by use of a PD-1 inhibitor, a PD-L1 inhibitor, and/or a PD-L2 inhibitor can overcome immune resistance, as demonstrated in recent clinical studies, such as that described in Topalian, et al., *N. Eng. J. Med.* 2012, 366, 2443-54. PD-L1 is expressed on many tumor cell lines, while PD-L2 is expressed is expressed mostly on dendritic cells and a few tumor lines. In addition to T cells (which inducibly express PD-1 after activation), PD-1 is also expressed on B cells, natural killer cells, macrophages, activated monocytes, and dendritic cells.

In an embodiment, the PD-1 inhibitor may be any PD-1 inhibitor or PD-1 blocker known in the art. In particular, it is one of the PD-1 inhibitors or blockers described in more detail in the following paragraphs. The terms "inhibitor," "antagonist," and "blocker" are used interchangeably herein in reference to PD-1 inhibitors. For avoidance of doubt, references herein to a PD-1 inhibitor that is an antibody may refer to a compound or antigen-binding fragments, variants, conjugates, or biosimilars thereof. For avoidance of doubt, references herein to a PD-1 inhibitor may also refer to a small molecule compound or a pharmaceutically acceptable salt, ester, solvate, hydrate, cocrystal, or prodrug thereof.

In a preferred embodiment, the PD-1 inhibitor is an antibody (i.e., an anti-PD-1 antibody), a fragment thereof, including Fab fragments, or a single-chain variable fragment (scFv) thereof. In some embodiments the PD-1 inhibitor is a polyclonal antibody. In a preferred embodiment, the PD-1 inhibitor is a monoclonal antibody. In some embodiments, the PD-1 inhibitor competes for binding with PD-1, and/or binds to an epitope on PD-1. In an embodiment, the antibody competes for binding with PD-1, and/or binds to an epitope on PD-1.

In some embodiments, the PD-1 inhibitor is one that binds human PD-1 with a KD of about 100 μM or lower, binds human PD-1 with a KD of about 90 μM or lower, binds human PD-1 with a KD of about 80 μM or lower, binds human PD-1 with a KD of about 70 pM or lower, binds human PD-1 with a KD of about 60 μM or lower, binds human PD-1 with a KD of about 50 μM or lower, binds human PD-1 with a KD of about 40 μM or lower, binds human PD-1 with a KD of about 30 μM or lower, binds human PD-1 with a KD of about 20 μM or lower, binds human PD-1 with a KD of about 10 μM or lower, or binds human PD-1 with a KD of about 1 μM or lower.

In some embodiments, the PD-1 inhibitor is one that binds to human PD-1 with a kassoc of about 7.5×105 l/M·s or faster, binds to human PD-1 with a kassoc of about 7.5×105 l/M·s or faster, binds to human PD-1 with a kassoc of about 8×105 l/M·s or faster, binds to human PD-1 with a kassoc of about 8.5×105 l/M·s or faster, binds to human PD-1 with a kassoc of about 9×105 l/M·s or faster, binds to human PD-1 with a kassoc of about 9.5×105 l/M·s or faster, or binds to human PD-1 with a kassoc of about 1×106 l/M·s or faster.

In some embodiments, the PD-1 inhibitor is one that binds to human PD-1 with a kdissoc of about 2×10−5 l/s or slower, binds to human PD-1 with a kdissoc of about 2.1×10−5 l/s or slower, binds to human PD-1 with a kdissoc of about 2.2×10−5 l/s or slower, binds to human PD-1 with a kdissoc of about 2.3×10−5 l/s or slower, binds to human PD-1 with a kdissoc of about 2.4×10−5 l/s or slower, binds to human PD-1 with a kdissoc of about 2.5×10−5 l/s or slower, binds to human PD-1 with a kdissoc of about 2.6×10−5 l/s or slower or binds to human PD-1 with a kdissoc of about 2.7×10−5 l/s or slower, binds to human PD-1 with a kdissoc of about 2.8×10−5 l/s or slower, binds to human PD-1 with a kdissoc of about 2.9×10−5 l/s or slower, or binds to human PD-1 with a kdissoc of about 3×10−5 l/s or slower.

In some embodiments, the PD-1 inhibitor is one that blocks or inhibits binding of human PD-L1 or human PD-L2 to human PD-1 with an IC50 of about 10 nM or lower, blocks or inhibits binding of human PD-L1 or human PD-L2 to human PD-1 with an IC50 of about 9 nM or lower, blocks or inhibits binding of human PD-L1 or human PD-L2 to human PD-1 with an IC50 of about 8 nM or lower, blocks or inhibits binding of human PD-L1 or human PD-L2 to human PD-1 with an IC50 of about 7 nM or lower, blocks or inhibits binding of human PD-L1 or human PD-L2 to human PD-1 with an IC50 of about 6 nM or lower, blocks or inhibits binding of human PD-L1 or human PD-L2 to human PD-1 with an IC50 of about 5 nM or lower, blocks or inhibits binding of human PD-L1 or human PD-L2 to human PD-1 with an IC50 of about 4 nM or lower, blocks or inhibits binding of human PD-L1 or human PD-L2 to human PD-1 with an IC50 of about 3 nM or lower, blocks or inhibits binding of human PD-L1 or human PD-L2 to human PD-1 with an IC50 of about 2 nM or lower, or blocks or inhibits binding of human PD-L1 or human PD-L2 to human PD-1 with an IC50 of about 1 nM or lower.

In an embodiment, the PD-1 inhibitor is nivolumab (commercially available as OPDIVO from Bristol-Myers Squibb Co.), or biosimilars, antigen-binding fragments, conjugates, or variants thereof. Nivolumab is a fully human IgG4 antibody blocking the PD-1 receptor. In an embodiment, the anti-PD-1 antibody is an immunoglobulin G4 kappa, anti-(human CD274) antibody. Nivolumab is assigned Chemical Abstracts Service (CAS) registry number 946414-94-4 and is also known as 5C4, BMS-936558, MDX-1106, and ONO-4538. The preparation and properties of nivolumab are described in U.S. Pat. No. 8,008,449 and International Patent Publication No. WO 2006/121168, the disclosures of which are incorporated by reference herein. The clinical safety and efficacy of nivolumab in various forms of cancer has been described in Wang, et al., *Cancer Immunol. Res.* 2014, 2, 846-56; Page, et al., *Ann. Rev. Med.,* 2014, 65, 185-202; and Weber, et al., *J Clin. Oncology,* 2013, 31, 4311-4318, the disclosures of which are incorporated by reference herein. The amino acid sequences of nivolumab are set forth in Table 18. Nivolumab has intra-heavy chain disulfide linkages at 22-96, 140-196, 254-314, 360-418, 22"-96", 140"-196", 254"-314", and 360"-418"; intra-light chain disulfide linkages at 23'-88', 134'-194', 23'"-88'", and 134'"-194'"; inter-heavy-light chain disulfide linkages at 127-214', 127"-214'", inter-heavy-heavy chain disulfide linkages at 219-219" and 222-222"; and N-glycosylation sites (H $C_H2$ 84.4) at 290, 290".

In an embodiment, a PD-1 inhibitor comprises a heavy chain given by SEQ ID NO:158 and a light chain given by SEQ ID NO:159. In an embodiment, a PD-1 inhibitor comprises heavy and light chains having the sequences shown in SEQ ID NO:158 and SEQ ID NO:159, respectively, or antigen binding fragments, Fab fragments, single-chain variable fragments (scFv), variants, or conjugates thereof. In an embodiment, a PD-1 inhibitor comprises heavy and light chains that are each at least 99% identical to the sequences shown in SEQ ID NO:158 and SEQ ID NO:159, respectively. In an embodiment, a PD-1 inhibitor comprises heavy and light chains that are each at least 98% identical to the sequences shown in SEQ ID NO:158 and SEQ ID NO:159, respectively. In an embodiment, a PD-1 inhibitor comprises heavy and light chains that are each at least 97% identical to the sequences shown in SEQ ID NO:158 and SEQ ID NO:159, respectively. In an embodiment, a PD-1 inhibitor comprises heavy and light chains that are each at least 96% identical to the sequences shown in SEQ ID NO:158 and SEQ ID NO:159, respectively. In an embodiment, a PD-1 inhibitor comprises heavy and light chains that are each at least 95% identical to the sequences shown in SEQ ID NO:463 and SEQ ID NO:159, respectively.

In an embodiment, the PD-1 inhibitor comprises the heavy and light chain CDRs or variable regions (VRs) of nivolumab. In an embodiment, the PD-1 inhibitor heavy chain variable region (VH) comprises the sequence shown in SEQ ID NO:160, and the PD-1 inhibitor light chain variable region (VL) comprises the sequence shown in SEQ ID NO:161, and conservative amino acid substitutions thereof. In an embodiment, a PD-1 inhibitor comprises VH and VL regions that are each at least 99% identical to the sequences shown in SEQ ID NO:160 and SEQ ID NO:161, respectively. In an embodiment, a PD-1 inhibitor comprises VH and VL regions that are each at least 98% identical to the sequences shown in SEQ ID NO:160 and SEQ ID NO:161, respectively. In an embodiment, a PD-1 inhibitor comprises VH and VL regions that are each at least 97% identical to the sequences shown in SEQ ID NO:160 and SEQ ID NO:161, respectively. In an embodiment, a PD-1 inhibitor comprises VH and VL regions that are each at least 96% identical to the sequences shown in SEQ ID NO:160 and SEQ ID NO:161, respectively. In an embodiment, a PD-1 inhibitor comprises VH and VL regions that are each at least 95% identical to the sequences shown in SEQ ID NO:160 and SEQ ID NO:161, respectively.

In an embodiment, a PD-1 inhibitor comprises heavy chain CDR1, CDR2 and CDR3 domains having the sequences set forth in SEQ ID NO:162, SEQ ID NO:163, and SEQ ID NO:164, respectively, and conservative amino acid substitutions thereof, and light chain CDR1, CDR2 and CDR3 domains having the sequences set forth in SEQ ID NO:165, SEQ ID NO:166, and SEQ ID NO:167, respectively, and conservative amino acid substitutions thereof. In an embodiment, the antibody competes for binding with, and/or binds to the same epitope on PD-1 as any of the aforementioned antibodies.

In an embodiment, the PD-1 inhibitor is an anti-PD-1 biosimilar monoclonal antibody approved by drug regulatory authorities with reference to nivolumab. In an embodiment, the biosimilar comprises an anti-PD-1 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is nivolumab. In some embodiments, the one or more post-translational modifications are selected from one or more of glycosylation, oxidation, deamidation, and truncation. In some embodiments, the biosimilar is an anti-PD-1 antibody authorized or submitted for authorization, wherein the anti-PD-1 antibody is provided in a formulation which differs from the formulations of a reference medicinal product or reference biological product, wherein the reference medicinal product or reference biological product is nivolumab. The anti-PD-1 antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is nivolumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is nivolumab.

TABLE 18

Amino acid sequences for PD-1 inhibitors related to nivolumab.

| Identifier | Sequence (One-Letter Amino Acid Symbols) | |
|---|---|---|
| SEQ ID NO: 158 nivolumab heavy chain | QVQLVESGGG VVQPGRSLRL DCKASGITFS NSGMHWVRQA PGKGLEWVAV IWYDGSKRYY | 60 |
| | ADSVKGRFTI SRDNSKNTLF LQMNSLRAED TAVYYCATND DYWGQGTLVT VSSASTKGPS | 120 |
| | VFPLAPCSRS TSESTAALGC LVKDYFPEPV TVSWNSGALT SGVHTFPAVL QSSGLYSLSS | 180 |
| | VVTVPSSSLG TKTYTCNVDH KPSNTKVDKR VESKYGPPCP PCPAPEFLGG PSVFLFPPKP | 240 |
| | KDTLMISRTP EVTCVVVDVS QEDPEVQFNW YVDGVEVHNA KTKPREEQFN STYRVVSVLT | 300 |
| | VLHQDWLNGK EYKCKVSNKG LPSSIEKTIS KAKGQPREPQ VYTLPPSQEE MTKNQVSLTC | 360 |
| | LVKGFYPSDI AVEWESNGQP ENNYKTTPPV LDSDGSFFLY SRLTVDKSRW QEGNVFSCSV | 420 |
| | MHEALHNHYT QKSLSLSLGK | 440 |
| SEQ ID NO: 159 nivolumab light chain | EIVLTQSPAT LSLSPGERAT LSCRASQSVS SYLAWYQQKP GQAPRLLIYD ASNRATGIPA | 60 |
| | RFSGSGSGTD FTLTISSLEP EDFAVYYCQQ SSNWPRTFGQ GTKVEIKRTV AAPSVFIFPP | 120 |
| | SDEQLKSGTA SVVCLLNNFY PREAKVQWKV DNALQSGNSQ ESVTEQDSKD STYSLSSTLT | 180 |
| | LSKADYEKHK VYACEVTHQG LSSPVTKSFN RGEC | 214 |
| SEQ ID NO: 160 nivolumab variable heavy chain | QVQLVESGGG VVQPGRSLRL DCKASGITFS NSGMHWVRQA PGKGLEWVAV IWYDGSKRYY | 60 |
| | ADSVKGRFTI SRDNSKNTLF LQMNSLRAED TAVYYCATND DYWGQGTLVT VSS | 113 |
| SEQ ID NO: 161 nivolumab variable light chain | EIVLTQSPAT LSLSPGERAT LSCRASQSVS SYLAWYQQKP GQAPRLLIYD ASNRATGIPA | 60 |
| | RFSGSGSGTD FTLTISSLEP EDFAVYYCQQ SSNWPRTFGQ GTKVEIK | 107 |
| SEQ ID NO: 162 nivolumab heavy chain CDR1 | NSGMH | 5 |

TABLE 18-continued

| Amino acid sequences for PD-1 inhibitors related to nivolumab. | | |
|---|---|---|
| Identifier | Sequence (One-Letter Amino Acid Symbols) | |
| SEQ ID NO: 163 nivolumab heavy chain CDR2 | VIWYDGSKRY YADSVKG | 17 |
| SEQ ID NO: 164 nivolumab heavy chain CDR3 | NDDY | 4 |
| SEQ ID NO: 165 nivolumab light chain CDR1 | RASQSVSSYL A | 11 |
| SEQ ID NO: 166 nivolumab light chain CDR2 | DASNRAT | 7 |
| SEQ ID NO: 167 nivolumab light chain CDR3 | QQSSNWPRT | 9 |

In some embodiments, the PD-1 inhibitor is nivolumab or a biosimilar thereof, and the nivolumab is administered at a dose of about 0.5 mg/kg to about 10 mg/kg. In some embodiments, the PD-1 inhibitor is nivolumab or a biosimilar thereof, and the nivolumab is administered at a dose of about 0.5 mg/kg, about 1 mg/kg, about 1.5 mg/kg, about 2 mg/kg, about 2.5 mg/kg, about 3 mg/kg, about 3.5 mg/kg, about 4 mg/kg, about 4.5 mg/kg, about 5 mg/kg, about 5.5 mg/kg, about 6 mg/kg, about 6.5 mg/kg, about 7 mg/kg, about 7.5 mg/kg, about 8 mg/kg, about 8.5 mg/kg, about 9 mg/kg, about 9.5 mg/kg, or about 10 mg/kg. In some embodiments, the nivolumab administration is begun 1, 2, 3, 4, or 5 days post IL-2 administration. In some embodiments, the nivolumab administration is begun 1, 2, or 3 days post IL-2 administration. In some embodiments, the nivolumab can also be administered 1, 2, 3, 4 or 5 weeks pre-resection (i.e., before obtaining a tumor sample from the subject or patient). In some embodiments, the nivolumab can also be administered 1, 2, or 3 weeks pre-resection (i.e., before obtaining a tumor sample from the subject or patient).

In some embodiments, the PD-1 inhibitor is nivolumab or a biosimilar thereof, and the nivolumab is administered at a dose of about 200 mg to about 500 mg. In some embodiments, the PD-1 inhibitor is nivolumab or a biosimilar thereof, and the nivolumab is administered at a dose of about 200 mg, about 220 mg, about 240 mg, about 260 mg, about 280 mg, about 300 mg, about 320 mg, about 340 mg, about 360 mg, about 380 mg, about 400 mg, about 420 mg, about 440 mg, about 460 mg, about 480 mg, or about 500 mg. In some embodiments, the nivolumab administration is begun 1, 2, 3, 4, or 5 days post IL-2 administration. In some embodiments, the nivolumab administration is begun 1, 2, or 3 days post IL-2 administration. In some embodiments, the nivolumab can also be administered 1, 2, 3, 4 or 5 weeks pre-resection (i.e., before obtaining a tumor sample from the subject or patient). In some embodiments, the nivolumab can also be administered 1, 2, or 3 weeks pre-resection (i.e., before obtaining a tumor sample from the subject or patient).

In some embodiments, the PD-1 inhibitor is nivolumab or a biosimilar thereof, and the nivolumab is administered every 2 weeks, every 3 weeks, every 4 weeks, every 5 weeks, or every 6 weeks. In some embodiments, the nivolumab administration is begun 1, 2, 3, 4, or 5 days post IL-2 administration. In some embodiments, the nivolumab administration is begun 1, 2, or 3 days post IL-2 administration. In some embodiments, the nivolumab can also be administered 1, 2, 3, 4 or 5 weeks pre-resection (i.e., before obtaining a tumor sample from the subject or patient). In some embodiments, the nivolumab can also be administered 1, 2, or 3 weeks pre-resection (i.e., before obtaining a tumor sample from the subject or patient).

In some embodiments, the nivolumab is administered to treat unresectable or metastatic melanoma. In some embodiments, the nivolumab is administered to treat unresectable or metastatic melanoma and is administered at about 240 mg every 2 weeks. In some embodiments, the nivolumab is administered to treat unresectable or metastatic melanoma and is administered at about 480 mg every 4 weeks. In some embodiments, the nivolumab is administered to treat unresectable or metastatic melanoma and is administered at about 1 mg/kg followed by ipilimumab 3 mg/kg on the same day every 3 weeks for 4 doses, then 240 mg every 2 weeks or 480 mg every 4 weeks. In some embodiments, the nivolumab administration is begun 1, 2, 3, 4, or 5 days post IL-2 administration. In some embodiments, the nivolumab administration is begun 1, 2, or 3 days post IL-2 administration. In some embodiments, the nivolumab can also be administered 1, 2, 3, 4 or 5 weeks pre-resection (i.e., before obtaining a tumor sample from the subject or patient). In some embodiments, the nivolumab can also be administered 1, 2, or 3 weeks pre-resection (i.e., before obtaining a tumor sample from the subject or patient).

In some embodiments, the nivolumab is administered for the adjuvant treatment of melanoma. In some embodiments, the nivolumab is administered for the adjuvant treatment of melanoma at about 240 mg every 2 weeks. In some embodiments, the nivolumab is administered for the adjuvant treatment of melanoma at about 480 mg every 4 weeks. In some embodiments, the nivolumab administration is begun 1, 2, 3, 4, or 5 days post IL-2 administration. In some embodiments, the nivolumab administration is begun 1, 2, or 3 days post IL-2 administration. In some embodiments, the nivolumab can also be administered 1, 2, 3, 4 or 5 weeks pre-resection (i.e., before obtaining a tumor sample from the subject or patient). In some embodiments, the nivolumab can also be administered 1, 2, or 3 weeks pre-resection (i.e., before obtaining a tumor sample from the subject or patient).

In some embodiments, the nivolumab is administered to treat metastatic non-small cell lung cancer. In some embodiments, the nivolumab is administered to treat metastatic non-small cell lung cancer at about 3 mg/kg every 2 weeks along with ipilimumab at about 1 mg/kg every 6 weeks. In some embodiments, the nivolumab is administered to treat metastatic non-small cell lung cancer at about 360 mg every 3 weeks with ipilimumab 1 mg/kg every 6 weeks and 2 cycles of platinum-doublet chemotherapy. In some embodiments, the nivolumab is administered to treat metastatic non-small cell lung cancer at about 240 mg every 2 weeks or 480 mg every 4 weeks. In some embodiments, the nivolumab administration is begun 1, 2, 3, 4, or 5 days post IL-2 administration. In some embodiments, the nivolumab administration is begun 1, 2, or 3 days post IL-2 administration. In some embodiments, the nivolumab can also be administered 1, 2, 3, 4 or 5 weeks pre-resection (i.e., before obtaining a tumor sample from the subject or patient). In some embodiments, the nivolumab can also be administered 1, 2, or 3 weeks pre-resection (i.e., before obtaining a tumor sample from the subject or patient).

In some embodiments, the nivolumab is administered to treat small cell lung cancer. In some embodiments, the nivolumab is administered to treat small cell lung cancer at about 240 mg every 2 weeks. In some embodiments, the nivolumab administration is begun 1, 2, 3, 4, or 5 days post IL-2 administration. In some embodiments, the nivolumab administration is begun 1, 2, or 3 days post IL-2 administration. In some embodiments, the nivolumab can also be administered 1, 2, 3, 4 or 5 weeks pre-resection (i.e., before obtaining a tumor sample from the subject or patient). In some embodiments, the nivolumab can also be administered 1, 2, or 3 weeks pre-resection (i.e., before obtaining a tumor sample from the subject or patient).

In some embodiments, the nivolumab is administered to treat malignant pleural mesothelioma at about 360 mg every 3 weeks with ipilimumab 1 mg/kg every 6 weeks. In some embodiments, the nivolumab administration is begun 1, 2, 3, 4, or 5 days post IL-2 administration. In some embodiments, the nivolumab administration is begun 1, 2, or 3 days post IL-2 administration. In some embodiments, the nivolumab can also be administered 1, 2, 3, 4 or 5 weeks pre-resection (i.e., before obtaining a tumor sample from the subject or patient). In some embodiments, the nivolumab can also be administered 1, 2, or 3 weeks pre-resection (i.e., before obtaining a tumor sample from the subject or patient).

In some embodiments, the nivolumab is administered to treat advanced renal cell carcinoma. In some embodiments, the nivolumab is administered to treat advanced renal cell carcinoma at about 240 mg every 2 weeks. In some embodiments, the nivolumab is administered to treat advanced renal cell carcinoma at about 480 mg every 4 weeks. In some embodiments, the nivolumab is administered to treat advanced renal cell carcinoma at about 3 mg/kg followed by ipilimumab at about 1 mg/kg on the same day every 3 weeks for 4 doses, then 240 mg every 2 weeks. In some embodiments, the nivolumab is administered to treat advanced renal cell carcinoma at about 3 mg/kg followed by ipilimumab at about 1 mg/kg on the same day every 3 weeks for 4 doses, then 240 mg every 2 weeks 480 mg every 4 weeks. In some embodiments, the nivolumab administration is begun 1, 2, 3, 4, or 5 days post IL-2 administration. In some embodiments, the nivolumab administration is begun 1, 2, or 3 days post IL-2 administration. In some embodiments, the nivolumab can also be administered 1, 2, 3, 4 or 5 weeks pre-resection (i.e., before obtaining a tumor sample from the subject or patient). In some embodiments, the nivolumab can also be administered 1, 2, or 3 weeks pre-resection (i.e., before obtaining a tumor sample from the subject or patient).

In some embodiments, the nivolumab is administered to treat classical Hodgkin lymphoma. In some embodiments, the nivolumab is administered to treat classical Hodgkin lymphoma at about 240 mg every 2 weeks. In some embodiments, the nivolumab is administered to treat classical Hodgkin lymphoma at about 480 mg every 4 weeks. In some embodiments, the nivolumab administration is begun 1, 2, 3, 4, or 5 days post IL-2 administration. In some embodiments, the nivolumab administration is begun 1, 2, or 3 days post IL-2 administration. In some embodiments, the nivolumab can also be administered 1, 2, 3, 4 or 5 weeks pre-resection (i.e., before obtaining a tumor sample from the subject or patient). In some embodiments, the nivolumab can also be administered 1, 2, or 3 weeks pre-resection (i.e., before obtaining a tumor sample from the subject or patient).

In some embodiments, the nivolumab is administered to treat Recurrent or metastatic squamous cell carcinoma of the head and neck. In some embodiments, the nivolumab is administered to treat recurrent or metastatic squamous cell carcinoma of the head and neck at about 240 mg every 2 weeks. In some embodiments, the nivolumab is administered to treat recurrent or metastatic squamous cell carcinoma of the head and neck at about 480 mg every 4 weeks. In some embodiments, the nivolumab administration is begun 1, 2, 3, 4, or 5 days post IL-2 administration. In some embodiments, the nivolumab administration is begun 1, 2, or 3 days post IL-2 administration. In some embodiments, the nivolumab can also be administered 1, 2, 3, 4 or 5 weeks pre-resection (i.e., before obtaining a tumor sample from the subject or patient). In some embodiments, the nivolumab can also be administered 1, 2, or 3 weeks pre-resection (i.e., before obtaining a tumor sample from the subject or patient).

In some embodiments, the nivolumab is administered to treat locally advanced or metastatic urothelial carcinoma at about 240 mg every 2 weeks. In some embodiments, the nivolumab is administered to treat locally advanced or metastatic urothelial carcinoma at about 480 mg every 4 weeks. In some embodiments, the nivolumab administration is begun 1, 2, 3, 4, or 5 days post IL-2 administration. In some embodiments, the nivolumab administration is begun 1, 2, or 3 days post IL-2 administration. In some embodiments, the nivolumab can also be administered 1, 2, 3, 4 or 5 weeks pre-resection (i.e., before obtaining a tumor sample from the subject or patient). In some embodiments, the nivolumab can also be administered 1, 2, or 3 weeks pre-resection (i.e., before obtaining a tumor sample from the subject or patient).

In some embodiments, the nivolumab is administered to treat microsatellite instability-high (MSI-H) or mismatch repair deficient (dMMR) metastatic colorectal cancer. In some embodiments, the nivolumab is administered to treat Microsatellite instability-high (MSI-H) or mismatch repair deficient (dMMR) metastatic colorectal cancer in adult and pediatric patients. In some embodiments, the nivolumab is administered to treat microsatellite instability-high (MSI-H)

or mismatch repair deficient (dMMR) metastatic colorectal cancer in adult and pediatric patients ≥40 kg at about 240 mg every 2 weeks. In some embodiments, the nivolumab is administered to treat microsatellite instability-high (MSI-H) or mismatch repair deficient (dMMR) metastatic colorectal cancer in adult and pediatric patients ≥40 kg at about 480 mg every 4 weeks. In some embodiments, the nivolumab administration is begun 1, 2, 3, 4, or 5 days post IL-2 administration. In some embodiments, the nivolumab administration is begun 1, 2, or 3 days post IL-2 administration. In some embodiments, the nivolumab can also be administered 1, 2, 3, 4 or 5 weeks pre-resection (i.e., before obtaining a tumor sample from the subject or patient). In some embodiments, the nivolumab can also be administered 1, 2, or 3 weeks pre-resection (i.e., before obtaining a tumor sample from the subject or patient).

In some embodiments, the nivolumab is administered to treat microsatellite instability-high (MSI-H) or mismatch repair deficient (dMMR) metastatic colorectal cancer in pediatric patients <40 kg at about 3 mg/kg every 2 weeks. In some embodiments, the nivolumab is administered to treat microsatellite instability-high (MSI-H) or mismatch repair deficient (dMMR) metastatic colorectal cancer in adult and pediatric patients ≥40 kg at about 3 mg/kg followed by ipilimumab 1 mg/kg on the same day every 3 weeks for 4 doses, then 240 mg every 2 weeks. In some embodiments, the nivolumab is administered to treat microsatellite instability-high (MSI-H) or mismatch repair deficient (dMMR) metastatic colorectal cancer in adult and pediatric patients ≥40 kg at about 3 mg/kg followed by ipilimumab 1 mg/kg on the same day every 3 weeks for 4 doses, then 480 mg every 4 weeks. In some embodiments, the nivolumab administration is begun 1, 2, 3, 4, or 5 days post IL-2 administration. In some embodiments, the nivolumab administration is begun 1, 2, or 3 days post IL-2 administration. In some embodiments, the nivolumab can also be administered 1, 2, 3, 4 or 5 weeks pre-resection (i.e., before obtaining a tumor sample from the subject or patient). In some embodiments, the nivolumab can also be administered 1, 2, or 3 weeks pre-resection (i.e., before obtaining a tumor sample from the subject or patient).

In some embodiments, the nivolumab is administered to treat hepatocellular carcinoma. In some embodiments, the nivolumab is administered to treat hepatocellular carcinoma at about 240 mg every 2 weeks. In some embodiments, the nivolumab is administered to treat hepatocellular carcinoma at about 480 mg every 4 weeks. In some embodiments, the nivolumab is administered to treat hepatocellular carcinoma at about 1 mg/kg followed by ipilimumab 3 mg/kg on the same day every 3 weeks for 4 doses, then 240 mg every 2 weeks. In some embodiments, the nivolumab is administered to treat hepatocellular carcinoma at about 1 mg/kg followed by ipilimumab 3 mg/kg on the same day every 3 weeks for 4 doses, then 480 mg every 4 weeks. In some embodiments, the nivolumab administration is begun 1, 2, 3, 4, or 5 days post IL-2 administration. In some embodiments, the nivolumab administration is begun 1, 2, or 3 days post IL-2 administration. In some embodiments, the nivolumab can also be administered 1, 2, 3, 4 or 5 weeks pre-resection (i.e., before obtaining a tumor sample from the subject or patient). In some embodiments, the nivolumab can also be administered 1, 2, or 3 weeks pre-resection (i.e., before obtaining a tumor sample from the subject or patient).

In some embodiments, the nivolumab is administered to treat esophageal squamous cell carcinoma. In some embodiments, the nivolumab is administered to treat esophageal squamous cell carcinoma at about 240 mg every 2 weeks. In some embodiments, the nivolumab is administered to treat esophageal squamous cell carcinoma at about 480 mg every 4 weeks. In some embodiments, the nivolumab administration is begun 1, 2, 3, 4, or 5 days post IL-2 administration. In some embodiments, the nivolumab administration is begun 1, 2, or 3 days post IL-2 administration. In some embodiments, the nivolumab can also be administered 1, 2, 3, 4 or 5 weeks pre-resection (i.e., before obtaining a tumor sample from the subject or patient). In some embodiments, the nivolumab can also be administered 1, 2, or 3 weeks pre-resection (i.e., before obtaining a tumor sample from the subject or patient).

In another embodiment, the PD-1 inhibitor comprises pembrolizumab (commercially available as KEYTRUDA from Merck & Co., Inc., Kenilworth, NJ, USA), or antigen-binding fragments, conjugates, or variants thereof. Pembrolizumab is assigned CAS registry number 1374853-91-4 and is also known as lambrolizumab, MK-3475, and SCH-900475. Pembrolizumab has an immunoglobulin G4, anti-(human protein PDCD1 (programmed cell death 1)) (human-*Mus musculus* monoclonal heavy chain), disulfide with human-*Mus musculus* monoclonal light chain, dimer structure. The structure of pembrolizumab may also be described as immunoglobulin G4, anti-(human programmed cell death 1); humanized mouse monoclonal [228-L-proline(H10-S>P)]γ4 heavy chain (134-218')-disulfide with humanized mouse monoclonal κ light chain dimer (226-226":229-229")-bisdisulfide. The properties, uses, and preparation of pembrolizumab are described in International Patent Publication No. WO 2008/156712 A1, U.S. Pat. No. 8,354,509 and U.S. Patent Application Publication Nos. US 2010/0266617 A1, US 2013/0108651 A1, and US 2013/0109843 A2, the disclosures of which are incorporated herein by reference. The clinical safety and efficacy of pembrolizumab in various forms of cancer is described in Fuerst, *Oncology Times,* 2014, 36, 35-36; Robert, et al., *Lancet,* 2014, 384, 1109-17; and Thomas, et al., *Exp. Opin. Biol. Ther.,* 2014, 14, 1061-1064. The amino acid sequences of pembrolizumab are set forth in Table 19. Pembrolizumab includes the following disulfide bridges: 22-96, 22"-96", 23'-92', 23'"-92'", 134-218', 134"-218'", 138'-198', 138'-198'", 147-203, 147"-203", 226-226", 229-229", 261-321, 261"-321", 367-425, and 367"-425", and the following glycosylation sites (N): Asn-297 and Asn-297". Pembrolizumab is an IgG4/kappa isotype with a stabilizing S228P mutation in the Fc region; insertion of this mutation in the IgG4 hinge region prevents the formation of half molecules typically observed for IgG4 antibodies. Pembrolizumab is heterogeneously glycosylated at Asn297 within the Fc domain of each heavy chain, yielding a molecular weight of approximately 149 kDa for the intact antibody. The dominant glycoform of pembrolizumab is the fucosylated agalacto diantennary glycan form (GOF).

In an embodiment, a PD-1 inhibitor comprises a heavy chain given by SEQ ID NO:168 and a light chain given by SEQ ID NO:169. In an embodiment, a PD-1 inhibitor comprises heavy and light chains having the sequences shown in SEQ ID NO:168 and SEQ ID NO:169, respectively, or antigen binding fragments, Fab fragments, single-chain variable fragments (scFv), variants, or conjugates thereof. In an embodiment, a PD-1 inhibitor comprises heavy and light chains that are each at least 99% identical to the sequences shown in SEQ ID NO:168 and SEQ ID NO:169, respectively. In an embodiment, a PD-1 inhibitor comprises heavy and light chains that are each at least 98% identical to the sequences shown in SEQ ID NO:168 and SEQ ID NO:169, respectively. In an embodiment, a PD-1 inhibitor comprises heavy and light chains that are each at least 97% identical to the sequences shown in SEQ ID NO:168 and SEQ ID NO:169, respectively. In an embodiment, a PD-1 inhibitor comprises heavy and light chains that are each at least 96% identical to the sequences shown in SEQ ID NO:168 and SEQ ID NO:169, respectively. In an embodiment, a PD-1 inhibitor comprises heavy and light chains that are each at least 95% identical to the sequences shown in SEQ ID NO:168 and SEQ ID NO:169, respectively.

In an embodiment, the PD-1 inhibitor comprises the heavy and light chain CDRs or variable regions (VRs) of pembrolizumab. In an embodiment, the PD-1 inhibitor heavy chain variable region (VH) comprises the sequence shown in SEQ ID NO:170, and the PD-1 inhibitor light chain variable region (VL) comprises the sequence shown in SEQ ID NO:171, and conservative amino acid substitutions thereof. In an embodiment, a PD-1 inhibitor comprises VH and VL regions that are each at least 99% identical to the sequences shown in SEQ ID NO:170 and SEQ ID NO:171, respectively. In an embodiment, a PD-1 inhibitor comprises VH and VL regions that are each at least 98% identical to the sequences shown in SEQ ID NO:170 and SEQ ID NO:171, respectively. In an embodiment, a PD-1 inhibitor comprises VH and VL regions that are each at least 97% identical to the sequences shown in SEQ ID NO:170 and SEQ ID NO:171, respectively. In an embodiment, a PD-1 inhibitor comprises VH and VL regions that are each at least 96% identical to the sequences shown in SEQ ID NO:170 and SEQ ID NO:171, respectively. In an embodiment, a PD-1 inhibitor comprises VH and VL regions that are each at least 95% identical to the sequences shown in SEQ ID NO:170 and SEQ ID NO:171, respectively.

In an embodiment, a PD-1 inhibitor comprises the heavy chain CDR1, CDR2 and CDR3 domains having the sequences set forth in SEQ ID NO:172, SEQ ID NO:173, and SEQ ID NO:174, respectively, and conservative amino acid substitutions thereof, and light chain CDR1, CDR2 and CDR3 domains having the sequences set forth in SEQ ID NO:175, SEQ ID NO:176, and SEQ ID NO:177, respectively, and conservative amino acid substitutions thereof. In an embodiment, the antibody competes for binding with, and/or binds to the same epitope on PD-1 as any of the aforementioned antibodies.

In an embodiment, the PD-1 inhibitor is an anti-PD-1 biosimilar monoclonal antibody approved by drug regulatory authorities with reference to pembrolizumab. In an embodiment, the biosimilar comprises an anti-PD-1 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is pembrolizumab. In some embodiments, the one or more post-translational modifications are selected from one or more of: glycosylation, oxidation, deamidation, and truncation. In some embodiments, the biosimilar is an anti-PD-1 antibody authorized or submitted for authorization, wherein the anti-PD-1 antibody is provided in a formulation which differs from the formulations of a reference medicinal product or reference biological product, wherein the reference medicinal product or reference biological product is pembrolizumab. The anti-PD-1 antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is pembrolizumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is pembrolizumab.

TABLE 19

Amino acid sequences for PD-1 inhibitors related to pembrolizumab.

| Identifier | Sequence (One-Letter Amino Acid Symbols) | |
|---|---|---|
| SEQ ID NO: 168 pembrolizumab heavy chain | QVQLVQSGVE VKKPGASVKV SCKASGYTFT NYYMYWVRQA PGQGLEWMGG INPSNGGTNF | 60 |
| | NEKFKNRVTL TTDSSTTTAY MELKSLQFDD TAVYYCARRD YRFDMGFDYW GQGTTVTVSS | 120 |
| | ASTKGPSVFP LAPCSRSTSE STAALGCLVK DYFPEPVTVS WNSGALTSGV HTFPAVLQSS | 180 |
| | GLYSLSSVVT VPSSSLGTKT YTCNVDHKPS NTKVDKRVES KYGPPCPPCP APEFLGGPSV | 240 |
| | FLFPPKPKDT LMISRTPEVT CVVVDVSQED PEVQFNWYVD GVEVHNAKTK PREEQFNSTY | 300 |
| | RVVSVLTVLH QDWLNGKEYK CKVSNKGLPS SIEKTISKAK GQPREPQVYT LPPSQEEMTK | 360 |
| | NQVSLTCLVK GFYPSDIAVE WESNGQPENN YKTTPPVLDS DGSFFLYSRL TVDKSRWQEG | 420 |
| | NVFSCSVMHE ALHNHYTQKS LSLSLGK | 447 |
| SEQ ID NO: 169 pembrolizumab light chain | EIVLTQSPAT LSLSPGERAT LSCRASKGVS TSGYSYLHWY QQKPGQAPRL LIYLASYLES | 60 |
| | GVPARFSGSG SGTDFTLTIS SLEPEDFAVY YCQHSRDLPL TFGGGTKVEI KRTVAAPSVF | 120 |
| | IFPPSDEQLK SGTASVVCLL NNFYPREAKV QWKVDNALQS GNSQESVTEQ DSKDSTYSLS | 180 |
| | STLTLSKADY EKHKVYACEV THQGLSSPVT KSFNRGEC | 218 |
| SEQ ID NO: 170 pembrolizumab variable heavy chain | QVQLVQSGVE VKKPGASVKV SCKASGYTFT NYYMYWVRQA PGQGLEWMGG INPSNGGTNF | 60 |
| | NEKFKNRVTL TTDSSTTTAY MELKSLQFDD TAVYYCARRD YRFDMGFDYW GQGTTVTVSS | 120 |
| SEQ ID NO: 171 pembrolizumab variable light chain | EIVLTQSPAT LSLSPGERAT LSCRASKGVS TSGYSYLHWY QQKPGQAPRL LIYLASYLES | 60 |
| | GVPARFSGSG SGTDFTLTIS SLEPEDFAVY YCQHSRDLPL TFGGGTKVEI K | 111 |

TABLE 19-continued

| Amino acid sequences for PD-1 inhibitors related to pembrolizumab. | | |
|---|---|---|
| Identifier | Sequence (One-Letter Amino Acid Symbols) | |
| SEQ ID NO: 172 pembrolizumab heavy chain CDR1 | NYYMY | 5 |
| SEQ ID NO: 173 pembrolizumab heavy chain CDR2 | GINPSNGGTN FNEKFK | 16 |
| SEQ ID NO: 174 pembrolizumab heavy chain CDR3 | RDYRFDMGFD Y | 11 |
| SEQ ID NO: 175 pembrolizumab light chain CDR1 | RASKGVSTSG YSYLH | 15 |
| SEQ ID NO: 176 pembrolizumab light chain CDR2 | LASYLES | 7 |
| SEQ ID NO: 177 pembrolizumab light chain CDR3 | QHSRDLPLT | 9 |

In some embodiments, the PD-1 inhibitor is pembrolizumab or a biosimilar thereof, and the pembrolizumab is administered at a dose of about 0.5 mg/kg to about 10 mg/kg. In some embodiments, the PD-1 inhibitor is pembrolizumab or a biosimilar thereof, and the pembrolizumab is administered at a dose of about 0.5 mg/kg, about 1 mg/kg, about 1.5 mg/kg, about 2 mg/kg, about 2.5 mg/kg, about 3 mg/kg, about 3.5 mg/kg, about 4 mg/kg, about 4.5 mg/kg, about 5 mg/kg, about 5.5 mg/kg, about 6 mg/kg, about 6.5 mg/kg, about 7 mg/kg, about 7.5 mg/kg, about 8 mg/kg, about 8.5 mg/kg, about 9 mg/kg, about 9.5 mg/kg, or about 10 mg/kg. In some embodiments, the pembrolizumab administration is begun 1, 2, 3, 4, or 5 days post IL-2 administration. In some embodiments, the pembrolizumab administration 15 begun 1, 2, or 3 days post IL-2 administration. In some embodiments, the pembrolizumab can also be administered 1, 2, 3, 4 or 5 weeks pre-resection (i.e., before obtaining a tumor sample from the subject or patient). In some embodiments, the pembrolizumab can also be administered 1, 2, or 3 weeks pre-resection (i.e., before obtaining a tumor sample from the subject or patient).

In some embodiments, the PD-1 inhibitor is pembrolizumab or a biosimilar thereof, wherein the pembrolizumab is administered at a dose of about 200 mg to about 500 mg. In some embodiments, the PD-1 inhibitor is pembrolizumab or a biosimilar thereof, and the nivolumab is administered at a dose of about 200 mg, about 220 mg, about 240 mg, about 260 mg, about 280 mg, about 300 mg, about 320 mg, about 340 mg, about 360 mg, about 380 mg, about 400 mg, about 420 mg, about 440 mg, about 460 mg, about 480 mg, or about 500 mg. In some embodiments, the pembrolizumab administration is begun 1, 2, 3, 4, or 5 days post IL-2 administration. In some embodiments, the pembrolizumab administration is begun 1, 2, or 3 days post IL-2 administration. In some embodiments, the pembrolizumab can also be administered 1, 2, 3, 4 or 5 weeks pre-resection (i.e., before obtaining a tumor sample from the subject or patient). In some embodiments, the pembrolizumab can also be administered 1, 2, or 3 weeks pre-resection (i.e., before obtaining a tumor sample from the subject or patient).

In some embodiments, the PD-1 inhibitor is pembrolizumab or a biosimilar thereof, wherein the pembrolizumab is administered every 2 weeks, every 3 weeks, every 4 weeks, every 5 weeks, or every 6 weeks. In some embodiments, the pembrolizumab administration is begun 1, 2, 3, 4, or 5 days post IL-2 administration. In some embodiments, the pembrolizumab administration is begun 1, 2, or 3 days post IL-2 administration. In some embodiments, the pembrolizumab can also be administered 1, 2, 3, 4 or 5 weeks pre-resection (i.e., before obtaining a tumor sample from the subject or patient). In some embodiments, the pembrolizumab can also be administered 1, 2, or 3 weeks pre-resection (i.e., before obtaining a tumor sample from the subject or patient).

In some embodiments, the pembrolizumab is administered to treat melanoma. In some embodiments, the pembrolizumab is administered to treat melanoma at about 200 mg every 3 weeks. In some embodiments, the pembrolizumab is administered to treat melanoma at about 400 mg every 6 weeks. In some embodiments, the pembrolizumab administration is begun 1, 2, 3, 4, or 5 days post IL-2 administration. In some embodiments, the pembrolizumab administration is begun 1, 2, or 3 days post IL-2 administration. In some embodiments, the pembrolizumab can also be administered 1, 2, 3, 4 or 5 weeks pre-resection (i.e., before obtaining a tumor sample from the subject or patient). In some embodiments, the pembrolizumab can also be administered 1, 2, or 3 weeks pre-resection (i.e., before obtaining a tumor sample from the subject or patient).

In some embodiments, the pembrolizumab is administered to treat NSCLC. In some embodiments, the pembrolizumab is administered to treat NSCLC at about 200 mg every 3 weeks. In some embodiments, the pembrolizumab is administered to treat NSCLC at about 400 mg every 6 weeks. In some embodiments, the pembrolizumab administration is begun 1, 2, 3, 4, or 5 days post IL-2 administration. In some embodiments, the pembrolizumab administration is begun 1, 2, or 3 days post IL-2 administration. In some embodiments, the pembrolizumab can also be administered 1, 2, 3, 4 or 5 weeks pre-resection (i.e., before obtaining a tumor sample from the subject or patient). In some embodiments, the pembrolizumab can also be administered 1, 2, or 3 weeks pre-resection (i.e., before obtaining a tumor sample from the subject or patient).

In some embodiments, the pembrolizumab is administered to treat small cell lung cancer (SCLC). In some embodiments, the pembrolizumab is administered to treat SCLC at about 200 mg every 3 weeks. In some embodiments, the pembrolizumab is administered to treat SCLC at about 400 mg every 6 weeks. In some embodiments, the pembrolizumab administration is begun 1, 2, 3, 4, or 5 days post IL-2 administration. In some embodiments, the pembrolizumab administration is begun 1, 2, or 3 days post IL-2 administration. In some embodiments, the pembrolizumab can also be administered 1, 2, 3, 4 or 5 weeks pre-resection (i.e., before obtaining a tumor sample from the subject or patient). In some embodiments, the pembrolizumab can also be administered 1, 2, or 3 weeks pre-resection (i.e., before obtaining a tumor sample from the subject or patient).

In some embodiments, the pembrolizumab is administered to treat head and neck squamous cell cancer (HNSCC). In some embodiments, the pembrolizumab is administered to treat HNSCC at about 200 mg every 3 weeks. In some embodiments, the pembrolizumab is administered to treat HNSCC at about 400 mg every 6 weeks. In some embodiments, the pembrolizumab administration is begun 1, 2, 3, 4, or 5 days post IL-2 administration. In some embodiments, the pembrolizumab administration is begun 1, 2, or 3 days post IL-2 administration. In some embodiments, the pembrolizumab can also be administered 1, 2, 3, 4 or 5 weeks pre-resection (i.e., before obtaining a tumor sample from the subject or patient). In some embodiments, the pembrolizumab can also be administered 1, 2, or 3 weeks pre-resection (i.e., before obtaining a tumor sample from the subject or patient).

In some embodiments, the pembrolizumab is administered to treat Classical Hodgkin Lymphoma (cHL) or Primary Mediastinal Large B-Cell Lymphoma (PMBCL) at about 200 mg every 3 weeks. In some embodiments, the pembrolizumab is administered to treat Classical Hodgkin Lymphoma (cHL) or Primary Mediastinal Large B-Cell Lymphoma (PMBCL) at about 400 mg every 6 weeks for adults. In some embodiments, the pembrolizumab is administered to treat Classical Hodgkin Lymphoma (cHL) or Primary Mediastinal Large B-Cell Lymphoma (PMBCL) at about 2 mg/kg (up to 200 mg) every 3 weeks for pediatrics. In some embodiments, the pembrolizumab administration is begun 1, 2, 3, 4, or 5 days post IL-2 administration. In some embodiments, the pembrolizumab administration is begun 1, 2, or 3 days post IL-2 administration. In some embodiments, the pembrolizumab can also be administered 1, 2, 3, 4 or 5 weeks pre-resection (i.e., before obtaining a tumor sample from the subject or patient). In some embodiments, the pembrolizumab can also be administered 1, 2, or 3 weeks pre-resection (i.e., before obtaining a tumor sample from the subject or patient).

In some embodiments, the pembrolizumab is administered to treat urothelial carcinoma at about 200 mg every 3 weeks. In some embodiments, the pembrolizumab is administered to treat urothelial carcinoma at about 400 mg every 6 weeks. In some embodiments, the pembrolizumab administration is begun 1, 2, 3, 4, or 5 days post IL-2 administration. In some embodiments, the pembrolizumab administration is begun 1, 2, or 3 days post IL-2 administration. In some embodiments, the pembrolizumab can also be administered 1, 2, 3, 4 or 5 weeks pre-resection (i.e., before obtaining a tumor sample from the subject or patient). In some embodiments, the pembrolizumab can also be administered 1, 2, or 3 weeks pre-resection (i.e., before obtaining a tumor sample from the subject or patient).

In some embodiments, the pembrolizumab is administered to treat microsatellite instability-high (MSI-H) or mismatch repair deficient (dMMR) cancer at about 200 mg every 3 weeks. In some embodiments, the pembrolizumab is administered to treat MSI-H or dMMR cancer at about 400 mg every 6 weeks for adults. In some embodiments, the pembrolizumab is administered to treat MSI-H or dMMR cancer at about 2 mg/kg (up to 200 mg) every 3 weeks for pediatrics. In some embodiments, the pembrolizumab administration is begun 1, 2, 3, 4, or 5 days post IL-2 administration. In some embodiments, the pembrolizumab administration is begun 1, 2, or 3 days post IL-2 administration. In some embodiments, the pembrolizumab can also be administered 1, 2, 3, 4 or 5 weeks pre-resection (i.e., before obtaining a tumor sample from the subject or patient). In some embodiments, the pembrolizumab can also be administered 1, 2, or 3 weeks pre-resection (i.e., before obtaining a tumor sample from the subject or patient). In some embodiments, the pembrolizumab administration is begun 1, 2, 3, 4, or 5 days post IL-2 administration. In some embodiments, the pembrolizumab administration is begun 1, 2, or 3 days post IL-2 administration. In some embodiments, the pembrolizumab can also be administered 1, 2, 3, 4 or 5 weeks pre-resection (i.e., before obtaining a tumor sample from the subject or patient). In some embodiments, the pembrolizumab can also be administered 1, 2, or 3 weeks pre-resection (i.e., before obtaining a tumor sample from the subject or patient).

In some embodiments, the pembrolizumab is administered to treat microsatellite instability-high (MSI-H) or mismatch repair deficient colorectal cancer (dMMR CRC at about 200 mg every 3 weeks. In some embodiments, the pembrolizumab is administered to treat MSI-H or dMMR CRC at about 400 mg every 6 weeks. In some embodiments, the pembrolizumab administration is begun 1, 2, 3, 4, or 5 days post IL-2 administration. In some embodiments, the pembrolizumab administration is begun 1, 2, or 3 days post IL-2 administration. In some embodiments, the pembrolizumab can also be administered 1, 2, 3, 4 or 5 weeks pre-resection (i.e., before obtaining a tumor sample from the subject or patient). In some embodiments, the pembrolizumab can also be administered 1, 2, or 3 weeks pre-resection (i.e., before obtaining a tumor sample from the subject or patient).

In some embodiments, the pembrolizumab is administered to treat gastric cancer at about 200 mg every 3 weeks. In some embodiments, the pembrolizumab is administered to treat gastric cancer at about 400 mg every 6 weeks. In some embodiments, the pembrolizumab administration is begun 1, 2, 3, 4, or 5 days post IL-2 administration. In some embodiments, the pembrolizumab administration is begun 1, 2, or 3 days post IL-2 administration. In some embodiments, the pembrolizumab can also be administered 1, 2, 3, 4 or 5 weeks pre-resection (i.e., before obtaining a tumor sample from the subject or patient). In some embodiments, the pembrolizumab can also be administered 1, 2, or 3 weeks pre-resection (i.e., before obtaining a tumor sample from the subject or patient).

In some embodiments, the pembrolizumab is administered to treat Esophageal Cancer at about 200 mg every 3 weeks. In some embodiments, the pembrolizumab is administered to treat Esophageal Cancer at about 400 mg every 6 weeks. In some embodiments, the pembrolizumab administration is begun 1, 2, 3, 4, or 5 days post IL-2 administration. In some embodiments, the pembrolizumab administration is begun 1, 2, or 3 days post IL-2 administration. In some embodiments, the pembrolizumab can also be administered 1, 2, 3, 4 or 5 weeks pre-resection (i.e., before obtaining a tumor sample from the subject or patient). In some embodiments, the pembrolizumab can also be administered 1, 2, or 3 weeks pre-resection (i.e., before obtaining a tumor sample from the subject or patient).

In some embodiments, the pembrolizumab is administered to treat cervical cancer at about 200 mg every 3 weeks. In some embodiments, the pembrolizumab is administered to treat cervical cancer at about 400 mg every 6 weeks. In some embodiments, the pembrolizumab administration is begun 1, 2, 3, 4, or 5 days post IL-2 administration. In some embodiments, the pembrolizumab administration is begun 1, 2, or 3 days post IL-2 administration. In some embodiments, the pembrolizumab can also be administered 1, 2, 3, 4 or 5 weeks pre-resection (i.e., before obtaining a tumor sample from the subject or patient). In some embodiments, the pembrolizumab can also be administered 1, 2, or 3 weeks pre-resection (i.e., before obtaining a tumor sample from the subject or patient).

In some embodiments, the pembrolizumab is administered to treat hepatocellular carcinoma (HCC) at about 200 mg every 3 weeks. In some embodiments, the pembrolizumab is administered to treat HCC at about 400 mg every 6 weeks. In some embodiments, the pembrolizumab administration is begun 1, 2, 3, 4, or 5 days post IL-2 administration. In some embodiments, the pembrolizumab administration is begun 1, 2, or 3 days post IL-2 administration. In some embodiments, the pembrolizumab can also be administered 1, 2, 3, 4 or 5 weeks pre-resection (i.e., before obtaining a tumor sample from the subject or patient). In some embodiments, the pembrolizumab can also be administered 1, 2, or 3 weeks pre-resection (i.e., before obtaining a tumor sample from the subject or patient).

In some embodiments, the pembrolizumab is administered to treat Merkel cell carcinoma (MCC) at about 200 mg every 3 weeks for adults. In some embodiments, the pembrolizumab is administered to treat MCC at about 400 mg every 6 weeks for adults. In some embodiments, the pembrolizumab is administered to treat MCC at about 2 mg/kg (up to 200 mg) every 3 weeks for pediatrics. In some embodiments, the pembrolizumab administration is begun 1, 2, 3, 4, or 5 days post IL-2 administration. In some embodiments, the pembrolizumab administration is begun 1, 2, or 3 days post IL-2 administration. In some embodiments, the pembrolizumab can also be administered 1, 2, 3, 4 or 5 weeks pre-resection (i.e., before obtaining a tumor sample from the subject or patient). In some embodiments, the pembrolizumab can also be administered 1, 2, or 3 weeks pre-resection (i.e., before obtaining a tumor sample from the subject or patient). In some embodiments, the pembrolizumab administration is begun 1, 2, 3, 4, or 5 days post IL-2 administration. In some embodiments, the pembrolizumab administration is begun 1, 2, or 3 days post IL-2 administration. In some embodiments, the pembrolizumab can also be administered 1, 2, 3, 4 or 5 weeks pre-resection (i.e., before obtaining a tumor sample from the subject or patient). In some embodiments, the pembrolizumab can also be administered 1, 2, or 3 weeks pre-resection (i.e., before obtaining a tumor sample from the subject or patient).

In some embodiments, the pembrolizumab is administered to treat renal cell carcinoma (RCC) at about 200 mg every 3 weeks. In some embodiments, the pembrolizumab is administered to treat RCC at about 400 mg every 6 weeks with axitinib 5 mg orally twice daily. In some embodiments, the pembrolizumab administration is begun 1, 2, 3, 4, or 5 days post IL-2 administration. In some embodiments, the pembrolizumab administration is begun 1, 2, or 3 days post IL-2 administration. In some embodiments, the pembrolizumab can also be administered 1, 2, 3, 4 or 5 weeks pre-resection (i.e., before obtaining a tumor sample from the subject or patient). In some embodiments, the pembrolizumab can also be administered 1, 2, or 3 weeks pre-resection (i.e., before obtaining a tumor sample from the subject or patient).

In some embodiments, the pembrolizumab is administered to treat endometrial carcinoma at about 200 mg every 3 weeks. In some embodiments, the pembrolizumab is administered to treat Endometrial Carcinoma at about 400 mg every 6 weeks with lenvatinib 20 mg orally once daily for tumors that are not MSI-H or dMMR. In some embodiments, the pembrolizumab administration is begun 1, 2, 3, 4, or 5 days post IL-2 administration. In some embodiments, the pembrolizumab administration is begun 1, 2, or 3 days post IL-2 administration. In some embodiments, the pembrolizumab can also be administered 1, 2, 3, 4 or 5 weeks pre-resection (i.e., before obtaining a tumor sample from the subject or patient). In some embodiments, the pembrolizumab can also be administered 1, 2, or 3 weeks pre-resection (i.e., before obtaining a tumor sample from the subject or patient).

In some embodiments, the pembrolizumab is administered to treat tumor mutational burden-high (TMB-H) Cancer at about 200 mg every 3 weeks for adults. In some embodiments, the pembrolizumab is administered to treat TMB-H Cancer at about 400 mg every 6 weeks for adults. In some embodiments, the pembrolizumab is administered to treat TMB-H Cancer at about 2 mg/kg (up to 200 mg) every 3 weeks for pediatrics. In some embodiments, the pembrolizumab administration is begun 1, 2, 3, 4, or 5 days post IL-2 administration. In some embodiments, the pembrolizumab administration is begun 1, 2, or 3 days post IL-2 administration. In some embodiments, the pembrolizumab can also be administered 1, 2, 3, 4 or 5 weeks pre-resection (i.e., before obtaining a tumor sample from the subject or patient). In some embodiments, the pembrolizumab can also be administered 1, 2, or 3 weeks pre-resection (i.e., before obtaining a tumor sample from the subject or patient).

In some embodiments, the pembrolizumab is administered to treat cutaneous squamous cell carcinoma (cSCC) at about 200 mg every 3 weeks. In some embodiments, the pembrolizumab is administered to treat cSCC at about 400 mg every 6 weeks. In some embodiments, the pembrolizumab administration is begun 1, 2, 3, 4, or 5 days post IL-2 administration. In some embodiments, the pembrolizumab administration is begun 1, 2, or 3 days post IL-2 administration. In some embodiments, the pembrolizumab can also be administered 1, 2, 3, 4 or 5 weeks pre-resection (i.e., before obtaining a tumor sample from the subject or patient). In some embodiments, the pembrolizumab can also be administered 1, 2, or 3 weeks pre-resection (i.e., before obtaining a tumor sample from the subject or patient).

In some embodiments, the pembrolizumab is administered to treat triple-negative breast cancer (TNBC) at about 200 mg every 3 weeks. In some embodiments, the pembrolizumab is administered to treat TNBC at about 400 mg every 6 weeks. In some embodiments, the pembrolizumab administration is begun 1, 2, 3, 4, or 5 days post IL-2 administration. In some embodiments, the pembrolizumab administration is begun 1, 2, or 3 days post IL-2 administration. In some embodiments, the pembrolizumab can also be administered 1, 2, 3, 4 or 5 weeks pre-resection (i.e., before obtaining a tumor sample from the subject or patient). In some embodiments, the pembrolizumab can also be administered 1, 2, or 3 weeks pre-resection (i.e., before obtaining a tumor sample from the subject or patient).

In an embodiment, if the patient or subject is an adult, i.e., treatment of adult indications, and additional dosing regimen of 400 mg every 6 weeks can be employed. In some embodiments, the pembrolizumab administration is begun 1, 2, 3, 4, or 5 days post IL-2 administration. In some embodiments, the pembrolizumab administration is begun 1, 2, or 3 days post IL-2 administration. In some embodiments, the pembrolizumab can also be administered 1, 2, 3, 4 or 5 weeks pre-resection (i.e., before obtaining a tumor sample from the subject or patient). In some embodiments, the pembrolizumab can also be administered 1, 2, or 3 weeks pre-resection (i.e., before obtaining a tumor sample from the subject or patient).

In an embodiment, the PD-1 inhibitor or anti-PD-1 antibody is cemiplimab, or a fragment, variant, conjugate, or biosimilar thereof, which is commercially available from Regeneron, Inc. In an embodiment, the PD-1 inhibitor or anti-PD-1 antibody is tislelizumab, or a fragment, variant, conjugate, or biosimilar thereof, which is available from Novartis AG and Beigene Co., Ltd. In an embodiment, the PD-1 inhibitor or anti-PD-1 antibody is sintilimab, or a fragment, variant, conjugate, or biosimilar thereof, which is available from Eli Lilly and Co. In an embodiment, the PD-1 inhibitor or anti-PD-1 antibody is toripalimab, or a fragment, variant, conjugate, or biosimilar thereof, which is available from Junshi Biosciences Co., Ltd. and Coherus BioSciences, Inc. In an embodiment, the PD-1 inhibitor or anti-PD-1 antibody is dostarlimab, or a fragment, variant, conjugate, or biosimilar thereof, which is available from GlaxoSmithKline plc.

In an embodiment, the PD-1 inhibitor is a commercially-available anti-PD-1 monoclonal antibody, such as anti-m-PD-1 clones J43 (Cat #BE0033-2) and RMP1-14 (Cat #BE0146) (Bio X Cell, Inc., West Lebanon, NH, USA). A number of commercially-available anti-PD-1 antibodies are known to one of ordinary skill in the art.

In an embodiment, the PD-1 inhibitor is an antibody disclosed in U.S. Pat. No. 8,354,509 or U.S. Patent Application Publication Nos. 2010/0266617 A1, 2013/0108651 A1, 2013/0109843 A2, the disclosures of which are incorporated by reference herein. In an embodiment, the PD-1 inhibitor is an anti-PD-1 antibody described in U.S. Pat. Nos. 8,287,856, 8,580,247, and 8,168,757 and U.S. Patent Application Publication Nos. 2009/0028857 A1, 2010/0285013 A1, 2013/0022600 A1, and 2011/0008369 A1, the teachings of which are hereby incorporated by reference. In another embodiment, the PD-1 inhibitor is an anti-PD-1 antibody disclosed in U.S. Pat. No. 8,735,553 B1, the disclosure of which is incorporated herein by reference. In an embodiment, the PD-1 inhibitor is pidilizumab, also known as CT-011, which is described in U.S. Pat. No. 8,686,119, the disclosure of which is incorporated by reference herein.

In an embodiment, the PD-1 inhibitor may be a small molecule or a peptide, or a peptide derivative, such as those described in U.S. Pat. Nos. 8,907,053; 9,096,642; and 9,044,442 and U.S. Patent Application Publication No. US 2015/0087581; 1,2,4-oxadiazole compounds and derivatives such as those described in U.S. Patent Application Publication No. 2015/0073024; cyclic peptidomimetic compounds and derivatives such as those described in U.S. Patent Application Publication No. US 2015/0073042; cyclic compounds and derivatives such as those described in U.S. Patent Application Publication No. US 2015/0125491; 1,3,4-oxadiazole and 1,3,4-thiadiazole compounds and derivatives such as those described in International Patent Application Publication No. WO 2015/033301; peptide-based compounds and derivatives such as those described in International Patent Application Publication Nos. WO 2015/036927 and WO 2015/04490, or a macrocyclic peptide-based compounds and derivatives such as those described in U.S. Patent Application Publication No. US 2014/0294898; the disclosures of each of which are hereby incorporated by reference in their entireties. In an embodiment, the PD-1 inhibitor is cemiplimab, which is commercially available from Regeneron, Inc. In an embodiment, the PD-1 inhibitor is tislelizumab, which is available from Novartis AG and Beigene Co., Ltd. In an embodiment, the PD-1 inhibitor is sintilimab, which is available from Eli Lilly and Co. In an embodiment, the PD-1 inhibitor is toripalimab, which is available from Junshi Biosciences Co., Ltd. and Coherus BioSciences, Inc.

In an embodiment, the PD-L1 or PD-L2 inhibitor may be any PD-L1 or PD-L2 inhibitor, antagonist, or blocker known in the art. In particular, it is one of the PD-L1 or PD-L2 inhibitors, antagonist, or blockers described in more detail in the following paragraphs. The terms "inhibitor," "antagonist," and "blocker" are used interchangeably herein in reference to PD-L1 and PD-L2 inhibitors. For avoidance of doubt, references herein to a PD-L1 or PD-L2 inhibitor that is an antibody may refer to a compound or antigen-binding fragments, variants, conjugates, or biosimilars thereof. For avoidance of doubt, references herein to a PD-L1 or PD-L2 inhibitor may refer to a compound or a pharmaceutically acceptable salt, ester, solvate, hydrate, cocrystal, or prodrug thereof.

In some embodiments, the compositions, processes and methods described herein include a PD-L1 or PD-L2 inhibitor. In some embodiments, the PD-L1 or PD-L2 inhibitor is a small molecule. In a preferred embodiment, the PD-L1 or PD-L2 inhibitor is an antibody (i.e., an anti-PD-1 antibody), a fragment thereof, including Fab fragments, or a single-chain variable fragment (scFv) thereof. In some embodiments the PD-L1 or PD-L2 inhibitor is a polyclonal antibody. In a preferred embodiment, the PD-L1 or PD-L2 inhibitor is a monoclonal antibody. In some embodiments, the PD-L1 or PD-L2 inhibitor competes for binding with PD-L1 or PD-L2, and/or binds to an epitope on PD-L1 or PD-L2. In an embodiment, the antibody competes for binding with PD-L1 or PD-L2, and/or binds to an epitope on PD-L1 or PD-L2.

In some embodiments, the PD-L1 inhibitors provided herein are selective for PD-L1, in that the compounds bind or interact with PD-L1 at substantially lower concentrations than they bind or interact with other receptors, including the PD-L2 receptor. In certain embodiments, the compounds bind to the PD-L1 receptor at a binding constant that is at least about a 2-fold higher concentration, about a 3-fold higher concentration, about a 5-fold higher concentration, about a 10-fold higher concentration, about a 20-fold higher concentration, about a 30-fold higher concentration, about a 50-fold higher concentration, about a 100-fold higher concentration, about a 200-fold higher concentration, about a 300-fold higher concentration, or about a 500-fold higher concentration than to the PD-L2 receptor.

In some embodiments, the PD-L2 inhibitors provided herein are selective for PD-L2, in that the compounds bind or interact with PD-L2 at substantially lower concentrations than they bind or interact with other receptors, including the PD-L1 receptor. In certain embodiments, the compounds bind to the PD-L2 receptor at a binding constant that is at least about a 2-fold higher concentration, about a 3-fold higher concentration, about a 5-fold higher concentration, about a 10-fold higher concentration, about a 20-fold higher concentration, about a 30-fold higher concentration, about a 50-fold higher concentration, about a 100-fold higher concentration, about a 200-fold higher concentration, about a 300-fold higher concentration, or about a 500-fold higher concentration than to the PD-L1 receptor.

Without being bound by any theory, it is believed that tumor cells express PD-L1, and that T cells express PD-1. However, PD-L1 expression by tumor cells is not required for efficacy of PD-1 or PD-L1 inhibitors or blockers. In an embodiment, the tumor cells express PD-L1. In another embodiment, the tumor cells do not express PD-L1. In some embodiments, the methods can include a combination of a PD-1 and a PD-L1 antibody, such as those described herein, in combination with a TIL. The administration of a combination of a PD-1 and a PD-L1 antibody and a TIL may be simultaneous or sequential.

In some embodiments, the PD-L1 and/or PD-L2 inhibitor is one that binds human PD-L1 and/or PD-L2 with a KD of about 100 pM or lower, binds human PD-L1 and/or PD-L2 with a KD of about 90 pM or lower, binds human PD-L1 and/or PD-L2 with a KD of about 80 pM or lower, binds human PD-L1 and/or PD-L2 with a KD of about 70 pM or lower, binds human PD-L1 and/or PD-L2 with a KD of about 60 pM or lower, a KD of about 50 pM or lower, binds human PD-L1 and/or PD-L2 with a KD of about 40 pM or lower, or binds human PD-L1 and/or PD-L2 with a KD of about 30 pM or lower, In some embodiments, the PD-L1 and/or PD-L2 inhibitor is one that binds to human PD-L1 and/or PD-L2 with a kassoc of about 7.5×105 l/M·s or faster, binds to human PD-L1 and/or PD-L2 with a kassoc of about 8×105 l/M·s or faster, binds to human PD-L1 and/or PD-L2 with a kassoc of about 8.5×105 l/M·s or faster, binds to human PD-L1 and/or PD-L2 with a kassoc of about 9×105 l/M·s or faster, binds to human PD-L1 and/or PD-L2 with a kassoc of about 9.5×105 l/M·s and/or faster, or binds to human PD-L1 and/or PD-L2 with a kassoc of about 1×106 l/M·s or faster.

In some embodiments, the PD-L1 and/or PD-L2 inhibitor is one that binds to human PD-L1 or PD-L2 with a kdissoc of about 2×10−5 l/s or slower, binds to human PD-1 with a kdissoc of about 2.1×10−5 l/s or slower, binds to human PD-1 with a kdissoc of about 2.2×10−5 l/s or slower, binds to human PD-1 with a kdissoc of about 2.3×10−5 l/s or slower, binds to human PD-1 with a kdissoc of about 2.4×10−5 l/s or slower, binds to human PD-1 with a kdissoc of about 2.5×10−5 l/s or slower, binds to human PD-1 with a kdissoc of about 2.6×10−5 l/s or slower, binds to human PD-L1 or PD-L2 with a kdissoc of about 2.7×10−5 l/s or slower, or binds to human PD-L1 or PD-L2 with a kdissoc of about 3×10−5 l/s or slower.

In some embodiments, the PD-L1 and/or PD-L2 inhibitor is one that blocks or inhibits binding of human PD-L1 or human PD-L2 to human PD-1 with an IC50 of about 10 nM or lower; blocks or inhibits binding of human PD-L1 or human PD-L2 to human PD-1 with an IC50 of about 9 nM or lower; blocks or inhibits binding of human PD-L1 or human PD-L2 to human PD-1 with an IC50 of about 8 nM or lower; blocks or inhibits binding of human PD-L1 or human PD-L2 to human PD-1 with an IC50 of about 7 nM or lower; blocks or inhibits binding of human PD-L1 or human PD-L2 to human PD-1 with an IC50 of about 6 nM or lower; blocks or inhibits binding of human PD-L1 or human PD-L2 to human PD-1 with an IC50 of about 5 nM or lower; blocks or inhibits binding of human PD-L1 or human PD-L2 to human PD-1 with an IC50 of about 4 nM or lower; blocks or inhibits binding of human PD-L1 or human PD-L2 to human PD-1 with an IC50 of about 3 nM or lower; blocks or inhibits binding of human PD-L1 or human PD-L2 to human PD-1 with an IC50 of about 2 nM or lower; or blocks human PD-1, or blocks binding of human PD-L1 or human PD-L2 to human PD-1 with an IC50 of about 1 nM or lower.

In an embodiment, the PD-L1 inhibitor is durvalumab, also known as MEDI4736 (which is commercially available from Medimmune, LLC, Gaithersburg, Maryland, a subsidiary of AstraZeneca plc.), or antigen-binding fragments, conjugates, or variants thereof. In an embodiment, the PD-L1 inhibitor is an antibody disclosed in U.S. Pat. No. 8,779,108 or U.S. Patent Application Publication No. 2013/0034559, the disclosures of which are incorporated by reference herein. The clinical efficacy of durvalumab has been described in Page, et al., Ann. Rev. Med., 2014, 65, 185-202; Brahmer, et al., J. Clin. Oncol. 2014, 32, 5s (supplement, abstract 8021); and McDermott, et al., Cancer Treatment Rev., 2014, 40, 1056-64. The preparation and properties of durvalumab are described in U.S. Pat. No. 8,779,108, the disclosure of which is incorporated by reference herein. The amino acid sequences of durvalumab are set forth in Table 20. The durvalumab monoclonal antibody includes disulfide linkages at 22-96, 22"-96", 23'-89', 23'"-89'", 135'-195', 135'-195'", 148-204, 148"-204", 215'-224, 215'-224", 230-230", 233-233", 265-325, 265"-325", 371-429, and 371"-429'; and N-glycosylation sites at Asn-301 and Asn-301".

In an embodiment, a PD-L1 inhibitor comprises a heavy chain given by SEQ ID NO:178 and a light chain given by SEQ ID NO:179. In an embodiment, a PD-L1 inhibitor comprises heavy and light chains having the sequences shown in SEQ ID NO:178 and SEQ ID NO:179, respectively, or antigen binding fragments, Fab fragments, single-chain variable fragments (scFv), variants, or conjugates thereof. In an embodiment, a PD-L1 inhibitor comprises heavy and light chains that are each at least 99% identical to the sequences shown in SEQ ID NO:178 and SEQ ID NO:179, respectively. In an embodiment, a PD-L1 inhibitor comprises heavy and light chains that are each at least 98% identical to the sequences shown in SEQ ID NO:178 and SEQ ID NO:179, respectively. In an embodiment, a PD-L1 inhibitor comprises heavy and light chains that are each at least 97% identical to the sequences shown in SEQ ID NO:178 and SEQ ID NO:179, respectively. In an embodiment, a PD-L1 inhibitor comprises heavy and light chains that are each at least 96% identical to the sequences shown in SEQ ID NO:178 and SEQ ID NO:179, respectively. In an embodiment, a PD-L1 inhibitor comprises heavy and light chains that are each at least 95% identical to the sequences shown in SEQ ID NO:178 and SEQ ID NO:179, respectively.

In an embodiment, the PD-L1 inhibitor comprises the heavy and light chain CDRs or variable regions (VRs) of durvalumab. In an embodiment, the PD-L1 inhibitor heavy chain variable region (VH) comprises the sequence shown in SEQ ID NO:180, and the PD-L1 inhibitor light chain variable region (VL) comprises the sequence shown in SEQ ID NO:181, and conservative amino acid substitutions thereof. In an embodiment, a PD-L1 inhibitor comprises VH and VL regions that are each at least 99% identical to the sequences shown in SEQ ID NO:180 and SEQ ID NO:181, respectively. In an embodiment, a PD-L1 inhibitor comprises VH and VL regions that are each at least 98% identical to the sequences shown in SEQ ID NO:180 and SEQ ID NO:181, respectively. In an embodiment, a PD-L1 inhibitor comprises VH and VL regions that are each at least 97% identical to the sequences shown in SEQ ID NO:180 and SEQ ID NO:181, respectively. In an embodiment, a PD-L1 inhibitor comprises VH and VL regions that are each at least 96% identical to the sequences shown in SEQ ID NO:180 and SEQ ID NO:181, respectively. In an embodiment, a PD-L1 inhibitor comprises VH and VL regions that are each at least 95% identical to the sequences shown in SEQ ID NO:180 and SEQ ID NO:181, respectively.

In an embodiment, a PD-L1 inhibitor comprises heavy chain CDR1, CDR2 and CDR3 domains having the sequences set forth in SEQ ID NO:182, SEQ ID NO: 183, and SEQ ID NO:184, respectively, and conservative amino acid substitutions thereof, and light chain CDR1, CDR2 and CDR3 domains having the sequences set forth in SEQ ID NO:185, SEQ ID NO:186, and SEQ ID NO:187, respectively, and conservative amino acid substitutions thereof. In an embodiment, the antibody competes for binding with, and/or binds to the same epitope on PD-L1 as any of the aforementioned antibodies.

In an embodiment, the PD-L1 inhibitor is an anti-PD-L1 biosimilar monoclonal antibody approved by drug regulatory authorities with reference to durvalumab. In an embodiment, the biosimilar comprises an anti-PD-L1 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is durvalumab. In some embodiments, the one or more post-translational modifications are selected from one or more of: glycosylation, oxidation, deamidation, and truncation. In some embodiments, the biosimilar is an anti-PD-L1 antibody authorized or submitted for authorization, wherein the anti-PD-L1 antibody is provided in a formulation which differs from the formulations of a reference medicinal product or reference biological product, wherein the reference medicinal product or reference biological product is durvalumab. The anti-PD-L1 antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is durvalumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is durvalumab.

TABLE 20

Amino acid sequences for PD-L1 inhibitors related to durvalumab.

| Identifier | Sequence (One-Letter Amino Acid Symbols) | |
|---|---|---|
| SEQ ID NO: 178<br>durvalumab<br>heavy chain | EVQLVESGGG LVQPGGSLRL SCAASGFTFS RYWMSWVRQA PGKGLEWVAN IKQDGSEKYY<br>VDSVKGRFTI SRDNAKNSLY LQMNSLRAED TAVYYCAREG GWFGELAFDY WGQGTLVTVS<br>SASTKGPSVF PLAPSSKSTS GGTAALGCLV KDYFPEPVTV SWNSGALTSG VHTFPAVLQS<br>SGLYSLSSVV TVPSSSLGTQ TYICNVNHKP SNTKVDKRVE PKSCDKTHTC PPCPAPEFEG<br>GPSVFLFPPK PKDTLMISRT PEVTCVVVDV SHEDPEVKFN WYVDGVEVEN AKTKPREEQY<br>NSTYRVVSVL TVLHQDWLNG KEYKCKVSNK ALPASIEKTI SKAKGQPREP QVYTLPPSRE<br>EMTKNQVSLT CLVKGFYPSD IAVEWESNGQ PENNYKTTPP VLDSDGSFFL YSKLTVDKSR<br>WQQGNVFSCS VMHEALHNHY TQKSLSLSPG K | 60<br>120<br>180<br>240<br>300<br>360<br>420<br>451 |
| SEQ ID NO: 179<br>durvalumab<br>light chain | EVQLVESGGG LVQPGGSLRL SCAASGFTFS RYWMSWVRQA PGKGLEWVAN EIVLTQSPGT<br>LSLSPGERAT LSCRASQRVS SSYLAWYQQK PGQAPRLLIY DASSRATGIP DRFSGSGSGT<br>DFTLTISRLE PEDFAVYYCQ QYGSLPWTFG QGTKVEIKRT VAAPSVFIFP PSDEQLKSGT<br>ASVVCLLNNF YPREAKVQWK VDNALQSGNS QESVTEQDSK DSTYSLSSTL TLSKADYEKH<br>KVYACEVTHQ GLSSPVTKSF NRGEC | 60<br>120<br>180<br>240<br>265 |
| SEQ ID NO: 180<br>durvalumab<br>variable<br>heavy chain | EVQLVESGGG LVQPGGSLRL SCAASGFTFS RYWMSWVRQA PGKGLEWVAN IKQDGSEKYY<br>VDSVKGRFTI SRDNAKNSLY LQMNSLRAED TAVYYCAREG GWFGELAFDY WGQGTLVTVS<br>S | 60<br>120<br>121 |
| SEQ ID NO: 181<br>durvalumab<br>variable<br>light chain | EIVLTQSPGT LSLSPGERAT LSCRASQRVS SSYLAWYQQK PGQAPRLLIY DASSRATGIP<br>DRFSGSGSGT DFTLTISRLE PEDFAVYYCQ QYGSLPWTFG QGTKVEIK | 60<br>108 |
| SEQ ID NO: 182<br>durvalumab<br>heavy chain<br>CDR1 | RYWMS | 5 |

TABLE 20-continued

| Amino acid sequences for PD-L1 inhibitors related to durvalumab. | | |
|---|---|---|
| Identifier | Sequence (One-Letter Amino Acid Symbols) | |
| SEQ ID NO: 183 durvalumab heavy chain CDR2 | NIKQDGSEKY YVDSVKG | 17 |
| SEQ ID NO: 184 durvalumab heavy chain CDR3 | EGGWFGELAF DY | 12 |
| SEQ ID NO: 185 durvalumab light chain CDR1 | RASQRVSSSY LA | 12 |
| SEQ ID NO: 186 durvalumab light chain CDR2 | DASSRAT | 7 |
| SEQ ID NO: 187 durvalumab light chain CDR3 | QQYGSLPWT | 9 |

In an embodiment, the PD-L1 inhibitor is avelumab, also known as MSB0010718C (commercially available from Merck KGaA/EMD Serono), or antigen-binding fragments, conjugates, or variants thereof. The preparation and properties of avelumab are described in U.S. Patent Application Publication No. US 2014/0341917 A1, the disclosure of which is specifically incorporated by reference herein. The amino acid sequences of avelumab are set forth in Table 21. Avelumab has intra-heavy chain disulfide linkages (C23-C104) at 22-96, 147-203, 264-324, 370-428, 22"-96", 147"-203", 264"-324", and 370"-428"; intra-light chain disulfide linkages (C23-C104) at 22'-90', 138'-197', 22"-90'", and 138"-197'"; intra-heavy-light chain disulfide linkages (h 5-CL 126) at 223-215' and 223"-215'"; intra-heavy-heavy chain disulfide linkages (h 11, h 14) at 229-229" and 232-232"; N-glycosylation sites (H CH2 N84.4) at 300, 300"; fucosylated complex bi-antennary CHO-type glycans; and H CHS K2 C-terminal lysine clipping at 450 and 450'.

In an embodiment, a PD-L1 inhibitor comprises a heavy chain given by SEQ ID NO:188 and a light chain given by SEQ ID NO:189. In an embodiment, a PD-L1 inhibitor comprises heavy and light chains having the sequences shown in SEQ ID NO:188 and SEQ ID NO:189, respectively, or antigen binding fragments, Fab fragments, single-chain variable fragments (scFv), variants, or conjugates thereof. In an embodiment, a PD-L1 inhibitor comprises heavy and light chains that are each at least 99% identical to the sequences shown in SEQ ID NO:188 and SEQ ID NO:189, respectively. In an embodiment, a PD-L1 inhibitor comprises heavy and light chains that are each at least 98% identical to the sequences shown in SEQ ID NO:188 and SEQ ID NO:189, respectively. In an embodiment, a PD-L1 inhibitor comprises heavy and light chains that are each at least 97% identical to the sequences shown in SEQ ID NO:188 and SEQ ID NO:189, respectively. In an embodiment, a PD-L1 inhibitor comprises heavy and light chains that are each at least 96% identical to the sequences shown in SEQ ID NO:188 and SEQ ID NO:189, respectively. In an embodiment, a PD-L1 inhibitor comprises heavy and light chains that are each at least 95% identical to the sequences shown in SEQ ID NO:188 and SEQ ID NO:189, respectively.

In an embodiment, the PD-L1 inhibitor comprises the heavy and light chain CDRs or variable regions (VRs) of avelumab. In an embodiment, the PD-L1 inhibitor heavy chain variable region (VH) comprises the sequence shown in SEQ ID NO:190, and the PD-L1 inhibitor light chain variable region (VL) comprises the sequence shown in SEQ ID NO:191, and conservative amino acid substitutions thereof. In an embodiment, a PD-L1 inhibitor comprises VH and VL regions that are each at least 99% identical to the sequences shown in SEQ ID NO:190 and SEQ ID NO:191, respectively. In an embodiment, a PD-L1 inhibitor comprises VH and VL regions that are each at least 98% identical to the sequences shown in SEQ ID NO:190 and SEQ ID NO:191, respectively. In an embodiment, a PD-L1 inhibitor comprises VH and VL regions that are each at least 97% identical to the sequences shown in SEQ ID NO:190 and SEQ ID NO:191, respectively. In an embodiment, a PD-L1 inhibitor comprises VH and VL regions that are each at least 96% identical to the sequences shown in SEQ ID NO:190 and SEQ ID NO:191, respectively. In an embodiment, a PD-L1 inhibitor comprises VH and VL regions that are each at least 95% identical to the sequences shown in SEQ ID NO:190 and SEQ ID NO:191, respectively.

In an embodiment, a PD-L1 inhibitor comprises heavy chain CDR1, CDR2 and CDR3 domains having the sequences set forth in SEQ ID NO:192, SEQ ID NO:193, and SEQ ID NO:194, respectively, and conservative amino acid substitutions thereof, and light chain CDR1, CDR2 and CDR3 domains having the sequences set forth in SEQ ID NO:195, SEQ ID NO:196, and SEQ ID NO:197, respectively, and conservative amino acid substitutions thereof. In an embodiment, the antibody competes for binding with, and/or binds to the same epitope on PD-L1 as any of the aforementioned antibodies.

In an embodiment, the PD-L1 inhibitor is an anti-PD-L1 biosimilar monoclonal antibody approved by drug regulatory authorities with reference to avelumab. In an embodiment, the biosimilar comprises an anti-PD-L1 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is avelumab. In some embodiments, the one or more post-translational modifications are selected from one or more of: glycosylation, oxidation, deamidation, and truncation. In some embodiments, the biosimilar is an anti-PD-L1 antibody authorized or submitted for authorization, wherein the anti-PD-L1 antibody is provided in a formulation which differs from the formulations of a reference medicinal product or reference biological product, wherein the reference medicinal product or reference biological product is avelumab. The anti-PD-L1 antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is avelumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is avelumab.

TABLE 21

Amino acid sequences for PD-L1 inhibitors related to avelumab.

| Identifier | Sequence (One-Letter Amino Acid Symbols) | |
|---|---|---|
| SEQ ID NO: 188 avelumab heavy chain | EVQLLESGGG LVQPGGSLRL SCAASGFTFS SYIMMWVRQA PGKGLEWVSS IYPSGGITFY | 60 |
| | ADTVKGRFTI SRDNSKNTLY LQMNSLRAED TAVYYCARIK LGTVTTVDYW GQGTLVTVSS | 120 |
| | ASTKGPSVFP LAPSSKSTSG GTAALGCLVK DYFPEPVTVS WNSGALTSGV HTFPAVLQSS | 180 |
| | GLYSLSSVVT VPSSSLGTQT YICNVNHKPS NTKVDKKVEP KSCDKTHTCP PCPAPELLGG | 240 |
| | PSVFLFPPKP KDTLMISRTP EVTCVVVDVS HEDPEVKFNW YVDGVEVHNA KTKPREEQYN | 300 |
| | STYRVVSVLT VLHQDWLNGK EYKCKVSNKA LPAPIEKTIS KAKGQPREPQ VYTLPPSRDE | 360 |
| | LTKNQVSLTC LVKGFYPSDI AVEWESNGQP ENNYKTTPPV LDSDGSFFLY SKLTVDKSRW | 420 |
| | QQGNVFSCSV MHEALHNHYT QKSLSLSPGK | 450 |
| SEQ ID NO: 189 avelumab light chain | QSALTQPASV SGSPGQSITI SCTGTSSDVG GYNYVSWYQQ HPGKAPKLMI YDVSNRPSGV | 60 |
| | SNRFSGSKSG NTASLTISGL QAEDEADYYC SSYTSSSTRV FGTGTKVTVL GQPKANPTVT | 120 |
| | LFPPSSEELQ ANKATLVCLI SDFYPGAVTV AWKADGSPVK AGVETTKPSK QSNNKYAASS | 180 |
| | YLSLTPEQWK SHRSYSCQVT HEGSTVEKTV APTECS | 216 |
| SEQ ID NO: 190 avelumab variable heavy chain | EVQLLESGGG LVQPGGSLRL SCAASGFTFS SYIMMWVRQA PGKGLEWVSS IYPSGGITFY | 60 |
| | ADTVKGRFTI SRDNSKNTLY LQMNSLRAED TAVYYCARIK LGTVTTVDYW GQGTLVTVSS | 120 |
| SEQ ID NO: 191 avelumab variable light chain | QSALTQPASV SGSPGQSITI SCTGTSSDVG GYNYVSWYQQ HPGKAPKLMI YDVSNRPSGV | 60 |
| | SNRFSGSKSG NTASLTISGL QAEDEADYYC SSYTSSSTRV FGTGTKVTVL | 110 |
| SEQ ID NO: 192 avelumab heavy chain CDR1 | SYIMM | 5 |
| SEQ ID NO: 193 avelumab heavy chain CDR2 | SIYPSGGITF YADTVKG | 17 |
| SEQ ID NO: 194 avelumab heavy chain CDR3 | IKLGTVTTVD Y | 11 |
| SEQ ID NO: 195 avelumab light chain CDR1 | TGTSSDVGGY NYVS | 14 |
| SEQ ID NO: 196 avelumab light chain CDR2 | DVSNRPS | 7 |
| SEQ ID NO: 197 avelumab light chain CDR3 | SSYTSSSTRV | 10 |

an embodiment, the PD-L1 inhibitor is atezolizumab, also known as MPDL3280A or RG7446 (commercially available as TECENTRIQ from Genentech, Inc., a subsidiary of Roche Holding AG, Basel, Switzerland), or antigen-binding fragments, conjugates, or variants thereof. In an embodiment, the PD-L1 inhibitor is an antibody disclosed in U.S. Pat. No. 8,217,149, the disclosure of which is specifically incorporated by reference herein. In an embodiment, the PD-L1 inhibitor is an antibody disclosed in U.S. Patent Application Publication Nos. 2010/0203056 A1, 2013/0045200 A1, 2013/0045201 A1, 2013/0045202 A1, or 2014/0065135 A1, the disclosures of which are specifically incorporated by reference herein. The preparation and properties of atezolizumab are described in U.S. Pat. No. 8,217,149, the disclosure of which is incorporated by reference herein. The amino acid sequences of atezolizumab are set forth in Table 22. Atezolizumab has intra-heavy chain disulfide linkages (C23-C104) at 22-96, 145-201, 262-322, 368-426, 22"-96", 145"-201", 262"-322", and 368"-426"; intra-light chain disulfide linkages (C23-C104) at 23'-88', 134'-194', 23'"-88'", and 134'"-194'"; intra-heavy-light chain disulfide linkages (h 5-CL 126) at 221-214' and 221"-214'"; intra-heavy-heavy chain disulfide linkages (h 11, h 14) at 227-227" and 230-230"; and N-glycosylation sites (H $C_H2$ N84.4>A) at 298 and 298'.

In an embodiment, a PD-L1 inhibitor comprises a heavy chain given by SEQ ID NO:198 and a light chain given by SEQ ID NO:199. In an embodiment, a PD-L1 inhibitor comprises heavy and light chains having the sequences shown in SEQ ID NO:198 and SEQ ID NO:199, respectively, or antigen binding fragments, Fab fragments, single-chain variable fragments (scFv), variants, or conjugates thereof. In an embodiment, a PD-L1 inhibitor comprises heavy and light chains that are each at least 99% identical to the sequences shown in SEQ ID NO:198 and SEQ ID NO:199, respectively. In an embodiment, a PD-L1 inhibitor comprises heavy and light chains that are each at least 98% identical to the sequences shown in SEQ ID NO:198 and SEQ ID NO:199, respectively. In an embodiment, a PD-L1 inhibitor comprises heavy and light chains that are each at least 97% identical to the sequences shown in SEQ ID NO:198 and SEQ ID NO:199, respectively. In an embodiment, a PD-L1 inhibitor comprises heavy and light chains that are each at least 96% identical to the sequences shown in SEQ ID NO:198 and SEQ ID NO:199, respectively. In an embodiment, a PD-L1 inhibitor comprises heavy and light chains that are each at least 95% identical to the sequences shown in SEQ ID NO:198 and SEQ ID NO:199, respectively.

In an embodiment, the PD-L1 inhibitor comprises the heavy and light chain CDRs or variable regions (VRs) of atezolizumab. In an embodiment, the PD-L1 inhibitor heavy chain variable region (VH) comprises the sequence shown in SEQ ID NO:200, and the PD-L1 inhibitor light chain variable region (VL) comprises the sequence shown in SEQ ID NO:201, and conservative amino acid substitutions thereof. In an embodiment, a PD-L1 inhibitor comprises VH and VL regions that are each at least 99% identical to the sequences shown in SEQ ID NO:200 and SEQ ID NO:201, respectively. In an embodiment, a PD-L1 inhibitor comprises VH and VL regions that are each at least 98% identical to the sequences shown in SEQ ID NO:200 and SEQ ID NO:201, respectively. In an embodiment, a PD-L1 inhibitor comprises VH and VL regions that are each at least 97% identical to the sequences shown in SEQ ID NO:200 and SEQ ID NO:201, respectively. In an embodiment, a PD-L1 inhibitor comprises VH and VL regions that are each at least 96% identical to the sequences shown in SEQ ID NO:200 and SEQ ID NO:201, respectively. In an embodiment, a PD-L1 inhibitor comprises VH and VL regions that are each at least 95% identical to the sequences shown in SEQ ID NO:200 and SEQ ID NO:201, respectively.

In an embodiment, a PD-L1 inhibitor comprises heavy chain CDR1, CDR2 and CDR3 domains having the sequences set forth in SEQ ID NO:202, SEQ ID NO:203, and SEQ ID NO:204, respectively, and conservative amino acid substitutions thereof, and light chain CDR1, CDR2 and CDR3 domains having the sequences set forth in SEQ ID NO:205, SEQ ID NO:206, and SEQ ID NO:207, respectively, and conservative amino acid substitutions thereof. In an embodiment, the antibody competes for binding with, and/or binds to the same epitope on PD-L1 as any of the aforementioned antibodies.

In an embodiment, the anti-PD-L1 antibody is an anti-PD-L1 biosimilar monoclonal antibody approved by drug regulatory authorities with reference to atezolizumab. In an embodiment, the biosimilar comprises an anti-PD-L1 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is atezolizumab. In some embodiments, the one or more post-translational modifications are selected from one or more of: glycosylation, oxidation, deamidation, and truncation. In some embodiments, the biosimilar is an anti-PD-L1 antibody authorized or submitted for authorization, wherein the anti-PD-L1 antibody is provided in a formulation which differs from the formulations of a reference medicinal product or reference biological product, wherein the reference medicinal product or reference biological product is atezolizumab. The anti-PD-L1 antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is atezolizumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is atezolizumab.

TABLE 22

Amino acid sequences for PD-L1 inhibitors related to atezolizumab.

| Identifier | Sequence (One-Letter Amino Acid Symbols) | |
|---|---|---|
| SEQ ID NO: 198 atezolizumab heavy chain | EVQLVESGGG LVQPGGSLRL SCAASGFTFS DSWIHWVRQA PGKGLEWVAW ISPYGGSTYY | 60 |
| | ADSVKGRFTI SADTSKNTAY LQMNSLRAED TAVYYCARRH WPGGFDYWGQ GTLVTVSSAS | 120 |
| | TKGPSVFPLA PSSKSTSGGT AALGCLVKDY FPEPVTVSWN SGALTSGVHT FPAVLQSSGL | 180 |
| | YSLSSVVTVP SSSLGTQTYI CNVNHKPSNT KVDKKVEPKS CDKTHTCPPC PAPELLGGPS | 240 |
| | VFLFPPKPKD TLMISRTPEV TCVVVDVSHE DPEVKFNWYV DGVEVHNAKT KPREEQYAST | 300 |
| | YRVVSVLTVL HQDWLNGKEY KCKVSNKALP APIEKTISKA KGQPREPQVY TLPPSREEMT | 360 |
| | KNQVSLTCLV KGFYPSDIAV EWESNGQPEN NYKTTPPVLD SDGSFFLYSK LTVDKSRWQQ | 420 |
| | GNVFSCSVMH EALENHYTQK SLSLSPGK | 448 |
| SEQ ID NO: 199 atezolizumab light chain | DIQMTQSPSS LSASVGDRVT ITCRASQDVS TAVAWYQQKP GKAPKLLIYS ASFLYSGVPS | 60 |
| | RFSGSGSGTD FTLTISSLQP EDFATYYCQQ YLYHPATFGQ GTKVEIKRTV AAPSVFIFPP | 120 |
| | SDEQLKSGTA SVVCLLNNFY PREAKVQWKV DNALQSGNSQ ESVTEQDSKD STYSLSSTLT | 180 |
| | LSKADYEKHK VYACEVTHQG LSSPVTKSFN RGEC | 214 |
| SEQ ID NO: 200 atezolizumab variable heavy chain | EVQLVESGGG LVQPGGSLRL SCAASGFTFS DSWIHWVRQA PGKGLEWVAW ISPYGGSTYY | 60 |
| | ADSVKGRFTI SADTSKNTAY LQMNSLRAED TAVYYCARRH WPGGFDYWGQ GTLVTVSA | 118 |
| SEQ ID NO: 201 atezolizumab variable light chain | DIQMTQSPSS LSASVGDRVT ITCRASQDVS TAVAWYQQKP GKAPKLLIYS ASFLYSGVPS | 60 |
| | RFSGSGSGTD FTLTISSLQP EDFATYYCQQ YLYHPATFGQ GTKVEIKR | 108 |
| SEQ ID NO: 202 atezolizumab heavy chain CDR1 | GFTFSDSWIH | 10 |
| SEQ ID NO: 203 atezolizumab heavy chain CDR2 | AWISPYGGST YYADSVKG | 18 |
| SEQ ID NO: 204 atezolizumab heavy chain CDR3 | RHWPGGFDY | 9 |
| SEQ ID NO: 205 atezolizumab light chain CDR1 | RASQDVSTAV A | 11 |
| SEQ ID NO: 206 atezolizumab light chain CDR2 | SASFLYS | 7 |
| SEQ ID NO: 207 atezolizumab light chain CDR3 | QQYLYHPAT | 9 |

In an embodiment, the PD-L1 inhibitor or anti-PD-L1 antibody is retifanlimab, or a fragment, variant, conjugate, or biosimilar thereof, which is available from Incyte, Inc.

In an embodiment, PD-L11 inhibitors include those antibodies described in U. S. Patent Application Publication No. US 2014/0341917 A1, the disclosure of which is incorporated by reference herein. In another embodiment, antibodies that compete with any of these antibodies for binding to PD-L1 are also included. In an embodiment, the anti-PD-L1 antibody is MDX-1105, also known as BMS-935559, which is disclosed in U. S. Patent No. U.S. Pat. No. 7,943,743, the disclosures of which are incorporated by reference herein. In an embodiment, the anti-PD-L1 antibody is selected from the anti-PD-L1 antibodies disclosed in U.S. Pat. No. 7,943, 743, which are incorporated by reference herein.

In an embodiment, the PD-L1 inhibitor is a commercially-available monoclonal antibody, such as INVIVOMAB anti-m-PD-L1 clone 10F.9G2 (Catalog #BE0101, Bio X Cell, Inc., West Lebanon, NH, USA). In an embodiment, the anti-PD-L1 antibody is a commercially-available monoclonal antibody, such as AFFYMETRIX EBIOSCIENCE (MIH1). A number of commercially-available anti-PD-L1 antibodies are known to one of ordinary skill in the art.

In an embodiment, the PD-L2 inhibitor is a commercially-available monoclonal antibody, such as BIOLEGEND 24F.10C12 Mouse IgG2a, κ isotype (catalog #329602 Biolegend, Inc., San Diego, CA), SIGMA anti-PD-L2 antibody (catalog #SAB3500395, Sigma-Aldrich Co., St. Louis, MO), or other commercially-available anti-PD-L2 antibodies known to one of ordinary skill in the art.

3. Combinations with CTLA-4 Inhibitors

In some embodiments, the TIL therapy provided to patients with cancer may include treatment with therapeutic populations of TILs alone or may include a combination treatment including TILs and one or more CTLA-4 inhibitors.

Cytotoxic T lymphocyte antigen 4 (CTLA-4) is a member of the immunoglobulin superfamily and is expressed on the surface of helper T cells. CTLA-4 is a negative regulator of CD28-dependent T cell activation and acts as a checkpoint for adaptive immune responses. Similar to the T cell costimulatory protein CD28, the CTLA-4 binding antigen presents CD80 and CD86 on the cells. CTLA-4 delivers a suppressor signal to T cells, while CD28 delivers a stimulus signal. Human antibodies against human CTLA-4 have been described as immunostimulatory modulators in many disease conditions, such as treating or preventing viral and bacterial infections and for treating cancer (WO 01/14424 and WO 00/37504). A number of fully human anti-human CTLA-4 monoclonal antibodies (mAbs) have been studied in clinical trials for the treatment of various types of solid tumors, including, but not limited to, ipilimumab (MDX-010) and tremelimumab (CP-675,206).

In some embodiments, a CTLA-4 inhibitor may be any CTLA-4 inhibitor or CTLA-4 blocker known in the art. In particular, it is one of the CTLA-4 inhibitors or blockers described in more detail in the following paragraphs. The terms "inhibitor," "antagonist," and "blocker" are used interchangeably herein in reference to CTLA-4 inhibitors. For avoidance of doubt, references herein to a CTLA-4 inhibitor that is an antibody may refer to a compound or antigen-binding fragments, variants, conjugates, or biosimilars thereof. For avoidance of doubt, references herein to a CTLA-4 inhibitor may also refer to a small molecule compound or a pharmaceutically acceptable salt, ester, solvate, hydrate, cocrystal, or prodrug thereof.

Suitable CTLA-4 inhibitors for use in the methods of the invention, include, without limitation, anti-CTLA-4 antibodies, human anti-CTLA-4 antibodies, mouse anti-CTLA-4 antibodies, mammalian anti-CTLA-4 antibodies, humanized anti-CTLA-4 antibodies, monoclonal anti-CTLA-4 antibodies, polyclonal anti-CTLA-4 antibodies, chimeric anti-CTLA-4 antibodies, MDX-010 (ipilimumab), tremelimumab, anti-CD28 antibodies, anti-CTLA-4 adnectins, anti-CTLA-4 domain antibodies, single chain anti-CTLA-4 fragments, heavy chain anti-CTLA-4 fragments, light chain anti-CTLA-4 fragments, inhibitors of CTLA-4 that agonize the co-stimulatory pathway, the antibodies disclosed in PCT Publication No. WO 2001/014424, the antibodies disclosed in PCT Publication No. WO 2004/035607, the antibodies disclosed in U.S. Publication No. 2005/0201994, and the antibodies disclosed in granted European Patent No. EP 1212422 B1, the disclosures of each of which are incorporated herein by reference. Additional CTLA-4 antibodies are described in U.S. Pat. Nos. 5,811,097, 5,855,887, 6,051,227, and 6,984,720; in PCT Publication Nos. WO 01/14424 and WO 00/37504; and in U.S. Publication Nos. 2002/0039581 and 2002/086014, the disclosures of each of which are incorporated herein by reference. Other anti-CTLA-4 antibodies that can be used in a method of the present invention include, for example, those disclosed in: WO 98/42752; U.S. Pat. Nos. 6,682,736 and 6,207,156; Hurwitz et al., Proc. Natl. Acad. Sci. USA, 95(17):10067-10071 (1998); Camacho et al., J. Clin. Oncology, 22(145): Abstract No. 2505 (2004) (antibody CP-675206); Mokyr et al., Cancer Res., 58:5301-5304 (1998), and U.S. Pat. Nos. 5,977,318, 6,682,736, 7,109,003, and 7,132,281, the disclosures of each of which are incorporated herein by reference.

Additional CTLA-4 inhibitors include, but are not limited to, the following: any inhibitor that is capable of disrupting the ability of CD28 antigen to bind to its cognate ligand, to inhibit the ability of CTLA-4 to bind to its cognate ligand, to augment T cell responses via the co-stimulatory pathway, to disrupt the ability of B7 to bind to CD28 and/or CTLA-4, to disrupt the ability of B7 to activate the co-stimulatory pathway, to disrupt the ability of CD80 to bind to CD28 and/or CTLA-4, to disrupt the ability of CD80 to activate the co-stimulatory pathway, to disrupt the ability of CD86 to bind to CD28 and/or CTLA-4, to disrupt the ability of CD86 to activate the co-stimulatory pathway, and to disrupt the co-stimulatory pathway, in general from being activated. This necessarily includes small molecule inhibitors of CD28, CD80, CD86, CTLA-4, among other members of the co-stimulatory pathway; antibodies directed to CD28, CD80, CD86, CTLA-4, among other members of the co-stimulatory pathway; antisense molecules directed against CD28, CD80, CD86, CTLA-4, among other members of the co-stimulatory pathway; adnectins directed against CD28, CD80, CD86, CTLA-4, among other members of the co-stimulatory pathway, RNAi inhibitors (both single and double stranded) of CD28, CD80, CD86, CTLA-4, among other members of the co-stimulatory pathway, among other CTLA-4 inhibitors.

In some embodiments a CTLA-4 inhibitor binds to CTLA-4 with a $K_d$ of about $10^{-6}$ M or less, $10^{-7}$ M or less, $10^{-8}$ M or less, $10^{-9}$ M or less, $10^{-10}$ M or less, $10^{-11}$ M or less, $10^{-12}$ M or less, e.g., between $10^{-13}$ M and $10^{-16}$ M, or within any range having any two of the afore-mentioned values as endpoints. In some embodiments a CTLA-4 inhibitor binds to CTLA-4 with a $K_d$ of no more than 10-fold that of ipilimumab, when compared using the same assay. In some embodiments a CTLA-4 inhibitor binds to CTLA-4 with a Kd of about the same as, or less (e.g., up to 10-fold lower, or up to 100-fold lower) than that of ipilimumab, when compared using the same assay. In some embodiments, the $IC_{50}$ values for inhibition by a CTLA-4 inhibitor of CTLA-4 binding to CD80 or CD86 is no more than 10-fold greater than that of ipilimumab-mediated inhibition of CTLA-4 binding to CD80 or CD86, respectively, when compared using the same assay. In some embodiments, the $IC_{50}$ values for inhibition by a CTLA-4 inhibitor of CTLA-4 binding to CD80 or CD86 is about the same or less (e.g., up to 10-fold lower, or up to 100-fold lower) than that of ipilimumab-mediated inhibition of CTLA-4 binding to CD80 or CD86, respectively, when compared using the same assay.

In some embodiments a CTLA-4 inhibitor is used in an amount sufficient to inhibit expression and/or decrease biological activity of CTLA-4 by at least 20%, 30%, 40%, 50%, 60%, 70%, 80%, 90%, 95%, or 100% relative to a suitable control, e.g., between 50% and 75%, 75% and 90%, or 90% and 100%. In some embodiments a CTLA-4 pathway inhibitor is used in an amount sufficient to decrease the biological activity of CTLA-4 by reducing binding of CTLA-4 to CD80, CD86, or both by at least 20%, 30%, 40%, 50%, 60%, 70%, 80%, 90%, 95%, or 100% relative to a suitable control, e.g., between 50% and 75%, 75% and 90%, or 90% and 100% relative to a suitable control. A suitable control in the context of assessing or quantifying the effect of an agent of interest is typically a comparable biological system (e.g., cells or a subject) that has not been exposed to or treated with the agent of interest, e.g., CTLA-4 pathway inhibitor (or has been exposed to or treated with a negligible amount). In some embodiments a biological system may serve as its own control (e.g., the biological system may be assessed before exposure to or treatment with the agent and compared with the state after exposure or treatment has started or finished. In some embodiments a historical control may be used.

In an embodiment, the CTLA-4 inhibitor is ipilimumab (commercially available as Yervoy from Bristol-Myers Squibb Co.), or biosimilars, antigen-binding fragments, conjugates, or variants thereof. As is known in the art, ipilimumab refers to an anti-CTLA-4 antibody, a fully human IgG 1κ antibody derived from a transgenic mouse with human genes encoding heavy and light chains to generate a functional human repertoire. is there. Ipilimumab can also be referred to by its CAS Registry Number 477202-00-9, and in PCT Publication Number WO 01/14424, which is incorporated herein by reference in its entirety for all purposes. It is disclosed as antibody 10DI. Specifically, ipilimumab contains a light chain variable region and a heavy chain variable region (having a light chain variable region comprising SEQ ID NO:211 and having a heavy chain variable region comprising SEQ ID NO:210). A pharmaceutical composition of ipilimumab includes all pharmaceutically acceptable compositions containing ipilimumab and one or more diluents, vehicles, or excipients. An example of a pharmaceutical composition containing ipilimumab is described in International Patent Application Publication No. WO 2007/67959. Ipilimumab can be administered intravenously (IV).

In an embodiment, a CTLA-4 inhibitor comprises a heavy chain given by SEQ ID NO:208 and a light chain given by SEQ ID NO:209. In an embodiment, a CTLA-4 inhibitor comprises heavy and light chains having the sequences shown in SEQ ID NO:208 and SEQ ID NO:209, respectively, or antigen binding fragments, Fab fragments, single-chain variable fragments (scFv), variants, or conjugates thereof. In an embodiment, a CTLA-4 inhibitor comprises heavy and light chains that are each at least 99% identical to the sequences shown in SEQ ID NO:208 and SEQ ID NO:209, respectively. In an embodiment, a CTLA-4 inhibitor comprises heavy and light chains that are each at least 98% identical to the sequences shown in SEQ ID NO:208 and SEQ ID NO:209, respectively. In an embodiment, a CTLA-4 inhibitor comprises heavy and light chains that are each at least 97% identical to the sequences shown in SEQ ID NO:208 and SEQ ID NO:209, respectively. In an embodiment, a CTLA-4 inhibitor comprises heavy and light chains that are each at least 96% identical to the sequences shown in SEQ ID NO:208 and SEQ ID NO:209, respectively. In an embodiment, a CTLA-4 inhibitor comprises heavy and light chains that are each at least 95% identical to the sequences shown in SEQ ID NO:208 and SEQ ID NO:209, respectively.

In an embodiment, the CTLA-4 inhibitor comprises the heavy and light chain CDRs or variable regions (VRs) of ipilimumab. In an embodiment, the CTLA-4 inhibitor heavy chain variable region ($V_H$) comprises the sequence shown in SEQ ID NO:210, and the CTLA-4 inhibitor light chain variable region ($V_L$) comprises the sequence shown in SEQ ID NO:211, and conservative amino acid substitutions thereof. In an embodiment, a CTLA-4 inhibitor comprises $V_H$ and $V_L$ regions that are each at least 99% identical to the sequences shown in SEQ ID NO:210 and SEQ ID NO:211, respectively. In an embodiment, a CTLA-4 inhibitor comprises $V_H$ and $V_L$ regions that are each at least 98% identical to the sequences shown in SEQ ID NO:210 and SEQ ID NO:211, respectively. In an embodiment, a CTLA-4 inhibitor comprises $V_H$ and $V_L$ regions that are each at least 97% identical to the sequences shown in SEQ ID NO:210 and SEQ ID NO:211, respectively. In an embodiment, a CTLA-4 inhibitor comprises $V_H$ and $V_L$ regions that are each at least 96% identical to the sequences shown in SEQ ID NO:210 and SEQ ID NO:211, respectively. In an embodiment, a CTLA-4 inhibitor comprises $V_H$ and $V_L$ regions that are each at least 95% identical to the sequences shown in SEQ ID NO:210 and SEQ ID NO:211, respectively.

In an embodiment, a CTLA-4 inhibitor comprises the heavy chain CDR1, CDR2 and CDR3 domains having the sequences set forth in SEQ ID NO:212, SEQ ID NO:213, and SEQ ID NO:214, respectively, and conservative amino acid substitutions thereof, and light chain CDR1, CDR2 and CDR3 domains having the sequences set forth in SEQ ID NO:215, SEQ ID NO:216, and SEQ ID NO:217, respectively, and conservative amino acid substitutions thereof. In an embodiment, the antibody competes for binding with, and/or binds to the same epitope on CTLA-4 as any of the aforementioned antibodies.

In an embodiment, the CTLA-4 inhibitor is a CTLA-4 biosimilar monoclonal antibody approved by drug regulatory authorities with reference to ipilimumab. In an embodiment, the biosimilar comprises an anti-CTLA-4 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is ipilimumab. In some embodiments, the one or more post-translational modifications are selected from one or more of glycosylation, oxidation, deamidation, and truncation. The amino acid sequences of ipilimumab are set forth in Table 23. In some embodiments, the biosimilar is an anti-CTLA-4 antibody authorized or submitted for authorization, wherein the anti-CTLA-4 antibody is provided in a formulation which differs from the formulations of a reference medicinal product or reference biological product, wherein the reference medicinal product or reference biological product is ipilimumab. The anti-CTLA-4 antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is ipilimumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is ipilimumab.

TABLE 23

Amino acid sequences for ipilimumab.

| Identifier | Sequence (One-Letter Amino Acid Symbols) | |
|---|---|---|
| SEQ ID NO: 208 ipilimumab heavy chain | QVQLVESGGG VVQPGRSLRL SCAASGFTFS SYTMHWVRQA PGKGLEWVTF ISYDGNNKYY | 60 |
| | ADSVKGRFTI SRDNSKNTLY LQMNSLRAED TAIYYCARTG WLGPFDYWGQ GTLVTVSSAS | 120 |
| | TKGPSVFPLA PSSKSTSGGT AALGCLVKDY FPEPVTVSWN SGALTSGVHT FPAVLQSSGL | 180 |
| | YSLSSVVTVP SSSLGTQTYI CNVNHKPSNT KVDKRVEPKS CDKTH | 225 |
| SEQ ID NO: 209 ipilimumab light chain | EIVLTQSPGT LSLSPGERAT LSCRASQSVG SSYLAWYQQK PGQAPRLLIY GAFSRATGIP | 60 |
| | DRFSGSGSGT DFTLTISRLE PEDFAVYYCQ QYGSSPWTFG QGTKVEIKRT VAAPSVFIFP | 120 |
| | PSDEQLKSGT ASVVCLLNNF YPREAKVQWK VDNALQSGNS QESVTEQDSK DSTYSLSSTL | 180 |
| | TLSKADYEKH KVYACEVTHQ GLSSPVTKSF NRGEC | 215 |
| SEQ ID NO: 210 ipilimumab variable heavy chain | QVQLVESGGG VVQPGRSLRL SCAASGFTFS SYTMHWVRQA PGKGLEWVTF ISYDGNNKYY | 60 |
| | ADSVKGRFTI SRDNSKNTLY LQMNSLRAED TAIYYCARTG WLGPFDYWGQ GTLVTVSS | 118 |
| SEQ ID NO: 211 ipilimumab variable light chain | EIVLTQSPGT LSLSPGERAT LSCRASQSVG SSYLAWYQQK PGQAPRLLIY GAFSRATGIP | 60 |
| | DRFSGSGSGT DFTLTISRLE PEDFAVYYCQ QYGSSPWTFG QGTKVEIK | 108 |
| SEQ ID NO: 212 ipilimumab heavy chain CDR1 | GFTFSSYT | 8 |
| SEQ ID NO: 213 ipilimumab heavy chain CDR2 | TFISYDGNNK | 10 |
| SEQ ID NO: 214 ipilimumab heavy chain CDR3 | ARTGWLGPFD Y | 11 |
| SEQ ID NO: 215 ipilimumab light chain CDR1 | QSVGSSY | 7 |
| SEQ ID NO: 216 ipilimumab light chain CDR2 | GAF | 3 |
| SEQ ID NO: 217 ipilimumab light chain CDR3 | QQYGSSPWT | 9 |

In some embodiments, the CTLA-4 inhibitor is ipilimumab or a biosimilar thereof, and the ipilimumab is administered at a dose of about 0.5 mg/kg to about 10 mg/kg. In some embodiments, the CTLA-4 inhibitor is ipilimumab or a biosimilar thereof, and the ipilimumab is administered at a dose of about 0.5 mg/kg, about 1 mg/kg, about 1.5 mg/kg, about 2 mg/kg, about 2.5 mg/kg, about 3 mg/kg, about 3.5 mg/kg, about 4 mg/kg, about 4.5 mg/kg, about 5 mg/kg, about 5.5 mg/kg, about 6 mg/kg, about 6.5 mg/kg, about 7 mg/kg, about 7.5 mg/kg, about 8 mg/kg, about 8.5 mg/kg, about 9 mg/kg, about 9.5 mg/kg, or about 10 mg/kg. In some embodiments, the ipilimumab administration is begun 1, 2, 3, 4, or 5 weeks pre-resection (i.e., prior to obtaining the tumor sample from the subject or patient). In some embodiments, the ipilimumab administration is begun 1, 2, or 3 weeks pre-resection (i.e., prior to obtaining the tumor sample from the subject or patient).

In some embodiments, the CTLA-4 inhibitor is ipilimumab or a biosimilar thereof, and the ipilimumab is administered at a dose of about 200 mg to about 500 mg. In some embodiments, the CTLA-4 inhibitor is ipilimumab or a biosimilar thereof, and the ipilimumab is administered at a dose of about 200 mg, about 220 mg, about 240 mg, about 260 mg, about 280 mg, about 300 mg, about 320 mg, about 340 mg, about 360 mg, about 380 mg, about 400 mg, about 420 mg, about 440 mg, about 460 mg, about 480 mg, or about 500 mg. In some embodiments, the ipilimumab administration is begun 1, 2, 3, 4, or 5 weeks pre-resection (i.e., prior to obtaining the tumor sample from the subject or patient). In some embodiments, the ipilimumab administration is begun 1, 2, or 3 weeks pre-resection (i.e., prior to obtaining the tumor sample from the subject or patient).

In some embodiments, the CTLA-4 inhibitor is ipilimumab or a biosimilar thereof, and the ipilimumab is administered every 2 weeks, every 3 weeks, every 4 weeks, every 5 weeks, or every 6 weeks. In some embodiments, the ipilimumab administration is begun 1, 2, 3, 4, or 5 weeks pre-resection (i.e., prior to obtaining the tumor sample from the subject or patient). In some embodiments, the ipilimumab administration is begun 1, 2, or 3 weeks pre-resection (i.e., prior to obtaining the tumor sample from the subject or patient).

In some embodiments, the ipilimumab is administered to treat unresectable or metastatic melanoma. In some embodiments, the ipilimumab is administered to treat Unresectable or Metastatic Melanoma at about mg/kg every 3 weeks for a maximum of 4 doses. In some embodiments, the ipilimumab administration is begun 1, 2, 3, 4, or 5 weeks pre-resection (i.e., prior to obtaining the tumor sample from the subject or patient). In some embodiments, the ipilimumab administration is begun 1, 2, or 3 weeks pre-resection (i.e., prior to obtaining the tumor sample from the subject or patient).

In some embodiments, the ipilimumab is administered for the adjuvant treatment of melanoma. In some embodiments, the ipilimumab is administered to for the adjuvant treatment of melanoma at about 10 mg/kg every 3 weeks for 4 doses, followed by 10 mg/kg every 12 weeks for up to 3 years. In some embodiments, the ipilimumab administration is begun 1, 2, 3, 4, or 5 weeks pre-resection (i.e., prior to obtaining the tumor sample from the subject or patient). In some embodiments, the ipilimumab administration is begun 1, 2, or 3 weeks pre-resection (i.e., prior to obtaining the tumor sample from the subject or patient).

In some embodiments, the ipilimumab is administered to treat advanced renal cell carcinoma. In some embodiments, the ipilimumab is administered to treat advanced renal cell carcinoma at about 1 mg/kg immediately following nivolumab 3 mg/kg on the same day, every 3 weeks for 4 doses. In some embodiments, after completing 4 doses of the combination, nivolumab can be administered as a single agent according to standard dosing regimens for advanced renal cell carcinoma and/or renal cell carcinoma. In some embodiments, the ipilimumab administration is begun 1, 2, 3, 4, or 5 weeks pre-resection (i.e., prior to obtaining the tumor sample from the subject or patient). In some embodiments, the ipilimumab administration is begun 1, 2, or 3 weeks pre-resection (i.e., prior to obtaining the tumor sample from the subject or patient).

In some embodiments, the ipilimumab is administered to treat microsatellite instability-high (MSI-H) or mismatch repair deficient (dMMR) metastatic colorectal cancer. In some embodiments, the ipilimumab is administered to treat microsatellite instability-high (MSI-H) or mismatch repair deficient (dMMR) metastatic colorectal cancer at about 1 mg/kg intravenously over 30 minutes immediately following nivolumab 3 mg/kg intravenously over 30 minutes on the same day, every 3 weeks for 4 doses. In some embodiments, after completing 4 doses of the combination, administer nivolumab as a single agent as recommended according to standard dosing regimens for microsatellite instability-high (MSI-H) or mismatch repair deficient (dMMR) metastatic colorectal cancer. In some embodiments, the ipilimumab administration is begun 1, 2, 3, 4, or 5 weeks pre-resection (i.e., prior to obtaining the tumor sample from the subject or patient). In some embodiments, the ipilimumab administration is begun 1, 2, or 3 weeks pre-resection (i.e., prior to obtaining the tumor sample from the subject or patient).

In some embodiments, the ipilimumab is administered to treat hepatocellular carcinoma. In some embodiments, the ipilimumab is administered to treat hepatocellular carcinoma at about 3 mg/kg intravenously over 30 minutes immediately following nivolumab 1 mg/kg intravenously over 30 minutes on the same day, every 3 weeks for 4 doses. In some embodiments, after completion 4 doses of the combination, administer nivolumab as a single agent according to standard dosing regimens for hepatocellular carcinoma. In some embodiments, the ipilimumab administration is begun 1, 2, 3, 4, or 5 weeks pre-resection (i.e., prior to obtaining the tumor sample from the subject or patient). In some embodiments, the ipilimumab administration is begun 1, 2, or 3 weeks pre-resection (i.e., prior to obtaining the tumor sample from the subject or patient).

In some embodiments, the ipilimumab is administered to treat metastatic non-small cell lung cancer. In some embodiments, the ipilimumab is administered to treat metastatic non-small cell lung cancer at about 1 mg/kg every 6 weeks with nivolumab 3 mg/kg every 2 weeks. In some embodiments, the ipilimumab is administered to treat metastatic non-small cell lung cancer at about 1 mg/kg every 6 weeks with nivolumab 360 mg every 3 weeks and 2 cycles of platinum-doublet chemotherapy. In some embodiments, the ipilimumab administration is begun 1, 2, 3, 4, or 5 weeks pre-resection (i.e., prior to obtaining the tumor sample from the subject or patient). In some embodiments, the ipilimumab administration is begun 1, 2, or 3 weeks pre-resection (i.e., prior to obtaining the tumor sample from the subject or patient).

In some embodiments, the ipilimumab is administered to treat malignant pleural mesothelioma. In some embodiments, the ipilimumab is administered to treat malignant pleural mesothelioma at about 1 mg/kg every 6 weeks with nivolumab 360 mg every 3 weeks. In some embodiments, the ipilimumab administration is begun 1, 2, 3, 4, or 5 weeks pre-resection (i.e., prior to obtaining the tumor sample from the subject or patient). In some embodiments, the ipilimumab administration is begun 1, 2, or 3 weeks pre-resection (i.e., prior to obtaining the tumor sample from the subject or patient).

Tremelimumab (also known as CP-675,206) is a fully human IgG2 monoclonal antibody and has the CAS number 745013-59-6. Tremelimumab is disclosed as antibody 11.2.1 in U.S. Pat. No. 6,682,736 (incorporated herein by reference). The amino acid sequences of the heavy chain and light chain of tremelimumab are set forth in SEQ ID NOs:218 and 219, respectively. Tremelimumab has been investigated in clinical trials for the treatment of various tumors, including melanoma and breast cancer; in which Tremelimumab was administered intravenously either as single dose or multiple doses every 4 or 12 weeks at the dose range of 0.01 and 15 mg/kg. In the regimens provided by the present invention, tremelimumab is administered locally, particularly intradermally or subcutaneously. The effective amount of tremelimumab administered intradermally or subcutaneously is typically in the range of 5-200 mg/dose per person. In some embodiments, the effective amount of tremelimumab is in the range of $10^{-150}$ mg/dose per person per dose. In some particular embodiments, the effective amount of tremelimumab is about 10, 25, 37.5, 40, 50, 75, 100, 125, 150, 175, or 200 mg/dose per person.

In an embodiment, a CTLA-4 inhibitor comprises a heavy chain given by SEQ ID NO:218 and a light chain given by SEQ ID NO:219. In an embodiment, a CTLA-4 inhibitor comprises heavy and light chains having the sequences shown in SEQ ID NO:218 and SEQ ID NO:219, respectively, or antigen binding fragments, Fab fragments, single-chain variable fragments (scFv), variants, or conjugates thereof. In an embodiment, a CTLA-4 inhibitor comprises heavy and light chains that are each at least 99% identical to the sequences shown in SEQ ID NO:218 and SEQ ID NO:219, respectively. In an embodiment, a CTLA-4 inhibitor comprises heavy and light chains that are each at least 98% identical to the sequences shown in SEQ ID NO:218 and SEQ ID NO:219, respectively. In an embodiment, a CTLA-4 inhibitor comprises heavy and light chains that are each at least 97% identical to the sequences shown in SEQ ID NO:218 and SEQ ID NO:219, respectively. In an embodiment, a CTLA-4 inhibitor comprises heavy and light chains that are each at least 96% identical to the sequences shown in SEQ ID NO:218 and SEQ ID NO:219, respectively. In an embodiment, a CTLA-4 inhibitor comprises heavy and light chains that are each at least 95% identical to the sequences shown in SEQ ID NO:218 and SEQ ID NO:219, respectively.

In an embodiment, the CTLA-4 inhibitor comprises the heavy and light chain CDRs or variable regions (VRs) of tremelimumab. In an embodiment, the CTLA-4 inhibitor heavy chain variable region ($V_H$) comprises the sequence shown in SEQ ID NO:220, and the CTLA-4 inhibitor light chain variable region ($V_L$) comprises the sequence shown in SEQ ID NO:221, and conservative amino acid substitutions thereof. In an embodiment, a CTLA-4 inhibitor comprises $V_H$ and $V_L$ regions that are each at least 99% identical to the sequences shown in SEQ ID NO:220 and SEQ ID NO:221, respectively. In an embodiment, a CTLA-4 inhibitor comprises $V_H$ and $V_L$ regions that are each at least 98% identical to the sequences shown in SEQ ID NO:220 and SEQ ID NO:221, respectively. In an embodiment, a CTLA-4 inhibitor comprises $V_H$ and $V_L$ regions that are each at least 97% identical to the sequences shown in SEQ ID NO:220 and SEQ ID NO:221, respectively. In an embodiment, a CTLA-4 inhibitor comprises $V_H$ and $V_L$ regions that are each at least 96% identical to the sequences shown in SEQ ID NO:220 and SEQ ID NO:221, respectively. In an embodiment, a CTLA-4 inhibitor comprises $V_H$ and $V_L$ regions that are each at least 95% identical to the sequences shown in SEQ ID NO:220 and SEQ ID NO:221, respectively.

In an embodiment, a CTLA-4 inhibitor comprises the heavy chain CDR1, CDR2 and CDR3 domains having the sequences set forth in SEQ ID NO:222, SEQ ID NO:223, and SEQ ID NO:224, respectively, and conservative amino acid substitutions thereof, and light chain CDR1, CDR2 and CDR3 domains having the sequences set forth in SEQ ID NO:225, SEQ ID NO:226, and SEQ ID NO:227, respectively, and conservative amino acid substitutions thereof. In an embodiment, the antibody competes for binding with, and/or binds to the same epitope on CTLA-4 as any of the aforementioned antibodies.

In an embodiment, the CTLA-4 inhibitor is an anti-CTLA-4 biosimilar monoclonal antibody approved by drug regulatory authorities with reference to tremelimumab. In an embodiment, the biosimilar comprises an anti-CTLA-4 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is tremelimumab. In some embodiments, the one or more post-translational modifications are selected from one or more of: glycosylation, oxidation, deamidation, and truncation. The amino acid sequences of tremelimumab are set forth in Table 24. In some embodiments, the biosimilar is an anti-CTLA-4 antibody authorized or submitted for authorization, wherein the anti-CTLA-4 antibody is provided in a formulation which differs from the formulations of a reference medicinal product or reference biological product, wherein the reference medicinal product or reference biological product is tremelimumab. The anti-CTLA-4 antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is tremelimumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is tremelimumab.

TABLE 24

Amino acid sequences for tremelimumab.

| Identifier | Sequence (One-Letter Amino Acid Symbols) | |
|---|---|---|
| SEQ ID NO: 218 tremelimumab heavy chain | QVQLVESGGG VVQPGRSLRL SCAASGFTFS SYGMHWVRQA PGKGLEWVAV IWYDGSNKYY | 60 |
| | ADSVKGRFTI SRDNSKNTLY LQMNSLRAED TAVYYCARDP RGATLYYYYY GMDVWGQGTT | 120 |
| | VTVSSASTKG PSVFPLAPCS RSTSESTAAL GCLVKDYFPE PVTVSWNSGA LTSGVHTFPA | 180 |
| | VLQSSGLYSL SSVVTVPSSN FGTQTYTCNV DHKPSNTKVD KTVERKCCVE CPPCPAPPVA | 240 |
| | GPSVFLFPPK PKDTLMISRT PEVTCVVVDV SHEDPEVQFN WYVDGVEVHN AKTKPREEQF | 300 |
| | NSTFRVVSVL TVVHQDWLNG KEYKCKVSNK GLPAPIEKTI SKTKGQPREP QVYTLPPSRE | 360 |
| | EMTKNQVSLT CLVKGFYPSD IAVEWESNGQ PENNYKTTPP MLDSDGSFFL YSKLTVDKSR | 420 |
| | WQQGNVFSCS VMHEALHNHY TQKSLSLSPG K | 451 |
| SEQ ID NO: 219 tremelimumab light chain | DIQMTQSPSS LSASVGDRVT ITCRASQSIN SYLDWYQQKP GKAPKLLIYA ASSLQSGVPS | 60 |
| | RFSGSGSGTD FTLTISSLQP EDFATYYCQQ YYSTPFTFGP GTKVEIKRTV AAPSVFIFPP | 120 |
| | SDEQLKSGTA SVVCLLNNFY PREAKVQWKV DNALQSGNSQ ESVTEQDSKD STYSLSSTLT | 180 |
| | LSKADYEKHK VYACEVTHQG LSSPVTKSFN RGEC | 214 |
| SEQ ID NO: 220 tremelimumab variable heavy chain | GVVQPGRSLR LSCAASGFTF SSYGMHWVRQ APGKGLEWVA VIWYDGSNKY YADSVKGRFT | 60 |
| | ISRDNSKNTL YLQMNSLRAE DTAVYYCARD PRGATLYYYY YGMDVWGQGT TVTVSSASTK | 120 |
| | GPSVFPLAPC SRSTSESTAA LGCLVKDYFP EPVTVSWNSG ALTSGVH | 167 |
| SEQ ID NO: 221 tremelimumab variable light chain | PSSLSASVGD RVTITCRASQ SINSYLDWYQ QKPGKAPKLL IYAASSLQSG VPSRFSGSGS | 60 |
| | GTDFTLTISS LQPEDFATYY CQQYYSTPFT FGPGTKVEIK RTVAAPSVFI FPPSDEQLKS | 120 |
| | GTASVVCLLN NFYPREAKV | 139 |

TABLE 24-continued

Amino acid sequences for tremelimumab.

| Identifier | Sequence (One-Letter Amino Acid Symbols) | |
|---|---|---|
| SEQ ID NO: 222 tremelimumab heavy chain CDR1 | GFTFSSYGMH | 10 |
| SEQ ID NO: 223 tremelimumab heavy chain CDR2 | VIWYDGSNKY YADSV | 15 |
| SEQ ID NO: 224 tremelimumab heavy chain CDR3 | DPRGATLYYY YYGMDV | 16 |
| SEQ ID NO: 225 tremelimumab light chain CDR1 | RASQSINSYL D | 11 |
| SEQ ID NO: 226 tremelimumab light chain CDR2 | AASSLQS | 7 |
| SEQ ID NO: 227 tremelimumab light chain CDR3 | QQYYSTPFT | 9 |

In some embodiments, the CTLA-4 inhibitor is tremelimumab or a biosimilar thereof, and the tremelimumab is administered at a dose of about 0.5 mg/kg to about 10 mg/kg. In some embodiments, the CTLA-4 inhibitor is tremelimumab or a biosimilar thereof, and the tremelimumab is administered at a dose of about 0.5 mg/kg, about 1 mg/kg, about 1.5 mg/kg, about 2 mg/kg, about 2.5 mg/kg, about 3 mg/kg, about 3.5 mg/kg, about 4 mg/kg, about 4.5 mg/kg, about 5 mg/kg, about 5.5 mg/kg, about 6 mg/kg, about 6.5 mg/kg, about 7 mg/kg, about 7.5 mg/kg, about 8 mg/kg, about 8.5 mg/kg, about 9 mg/kg, about 9.5 mg/kg, or about 10 mg/kg. In some embodiments, the tremelimumab administration is begun 1, 2, 3, 4, or 5 weeks pre-resection (i.e., prior to obtaining the tumor sample from the subject or patient). In some embodiments, the tremelimumab administration is begun 1, 2, or 3 weeks pre-resection (i.e., prior to obtaining the tumor sample from the subject or patient).

In some embodiments, the CTLA-4 inhibitor is tremelimumab or a biosimilar thereof, and the tremelimumab is administered at a dose of about 200 mg to about 500 mg. In some embodiments, the CTLA-4 inhibitor is tremelimumab or a biosimilar thereof, and the tremelimumab is administered at a dose of about 200 mg, about 220 mg, about 240 mg, about 260 mg, about 280 mg, about 300 mg, about 320 mg, about 340 mg, about 360 mg, about 380 mg, about 400 mg, about 420 mg, about 440 mg, about 460 mg, about 480 mg, or about 500 mg. In some embodiments, the tremelimumab administration is begun 1, 2, 3, 4, or 5 weeks pre-resection (i.e., prior to obtaining the tumor sample from the subject or patient). In some embodiments, the tremelimumab administration is begun 1, 2, or 3 weeks pre-resection (i.e., prior to obtaining the tumor sample from the subject or patient).

In some embodiments, the CTLA-4 inhibitor is tremelimumab or a biosimilar thereof, and the tremelimumab is administered every 2 weeks, every 3 weeks, every 4 weeks, every 5 weeks, or every 6 weeks. In some embodiments, the tremelimumab administration is begun 1, 2, 3, 4, or 5 weeks pre-resection (i.e., prior to obtaining the tumor sample from the subject or patient). In some embodiments, the tremelimumab administration is begun 1, 2, or 3 weeks pre-resection (i.e., prior to obtaining the tumor sample from the subject or patient).

In an embodiment, the CTLA-4 inhibitor is zalifrelimab from Agenus, or biosimilars, antigen-binding fragments, conjugates, or variants thereof. Zalifrelimab is a fully human monoclonal antibody. Zalifrelimab is assigned Chemical Abstracts Service (CAS) registry number 2148321-69-9 and is also known as also known as AGEN1884. The preparation and properties of zalifrelimab are described in U.S. Pat. No. 10,144,779 and US Patent Application Publication No. US2020/0024350 A1, the disclosures of which are incorporated by reference herein.

In an embodiment, a CTLA-4 inhibitor comprises a heavy chain given by SEQ ID NO:228 and a light chain given by SEQ ID NO:229. In an embodiment, a CTLA-4 inhibitor comprises heavy and light chains having the sequences shown in SEQ ID NO:228 and SEQ ID NO:229, respectively, or antigen binding fragments, Fab fragments, single-chain variable fragments (scFv), variants, or conjugates thereof. In an embodiment, a CTLA-4 inhibitor comprises heavy and light chains that are each at least 99% identical to the sequences shown in SEQ ID NO:228 and SEQ ID NO:229, respectively. In an embodiment, a CTLA-4 inhibitor comprises heavy and light chains that are each at least 98% identical to the sequences shown in SEQ ID NO:228 and SEQ ID NO:229, respectively. In an embodiment, a CTLA-4 inhibitor comprises heavy and light chains that are each at least 97% identical to the sequences shown in SEQ ID NO:228 and SEQ ID NO:229, respectively. In an embodiment, a CTLA-4 inhibitor comprises heavy and light chains that are each at least 96% identical to the sequences shown in SEQ ID NO:228 and SEQ ID NO:229, respectively. In an embodiment, a CTLA-4 inhibitor comprises heavy and light chains that are each at least 95% identical to the sequences shown in SEQ ID NO:228 and SEQ ID NO:229, respectively.

In an embodiment, the CTLA-4 inhibitor comprises the heavy and light chain CDRs or variable regions (VRs) of zalifrelimab. In an embodiment, the CTLA-4 inhibitor heavy chain variable region ($V_H$) comprises the sequence shown in SEQ ID NO:230, and the CTLA-4 inhibitor light chain variable region ($V_L$) comprises the sequence shown in SEQ ID NO:231, and conservative amino acid substitutions thereof. In an embodiment, a CTLA-4 inhibitor comprises $V_H$ and $V_L$ regions that are each at least 99% identical to the sequences shown in SEQ ID NO:230 and SEQ ID NO:231, respectively. In an embodiment, a CTLA-4 inhibitor comprises $V_H$ and $V_L$ regions that are each at least 98% identical to the sequences shown in SEQ ID NO:230 and SEQ ID NO:231, respectively. In an embodiment, a CTLA-4 inhibitor comprises $V_H$ and $V_L$ regions that are each at least 97% identical to the sequences shown in SEQ ID NO:230 and SEQ ID NO:231, respectively. In an embodiment, a CTLA-4 inhibitor comprises $V_H$ and $V_L$ regions that are each at least 96% identical to the sequences shown in SEQ ID NO:230 and SEQ ID NO:231, respectively. In an embodiment, a CTLA-4 inhibitor comprises $V_H$ and $V_L$ regions that are each at least 95% identical to the sequences shown in SEQ ID NO:230 and SEQ ID NO:231, respectively.

In an embodiment, a CTLA-4 inhibitor comprises the heavy chain CDR1, CDR2 and CDR3 domains having the sequences set forth in SEQ ID NO:231, SEQ ID NO:233, and SEQ ID NO:234, respectively, and conservative amino acid substitutions thereof, and light chain CDR1, CDR2 and CDR3 domains having the sequences set forth in SEQ ID NO:235, SEQ ID NO:236, and SEQ ID NO:237, respectively, and conservative amino acid substitutions thereof. In an embodiment, the antibody competes for binding with, and/or binds to the same epitope on CTLA-4 as any of the aforementioned antibodies.

In an embodiment, the CTLA-4 inhibitor is a CTLA-4 biosimilar monoclonal antibody approved by drug regulatory authorities with reference to zalifrelimab. In an embodiment, the biosimilar comprises an anti-CTLA-4 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is zalifrelimab. In some embodiments, the one or more post-translational modifications are selected from one or more of: glycosylation, oxidation, deamidation, and truncation. The amino acid sequences of zalifrelimab are set forth in Table 25. In some embodiments, the biosimilar is an anti-CTLA-4 antibody authorized or submitted for authorization, wherein the anti-CTLA-4 antibody is provided in a formulation which differs from the formulations of a reference medicinal product or reference biological product, wherein the reference medicinal product or reference biological product is zalifrelimab. The anti-CTLA-4 antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is zalifrelimab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is zalifrelimab.

TABLE 25

Amino acid sequences for zalifrelimab.

| Identifier | Sequence (One-Letter Amino Acid Symbols) | |
|---|---|---|
| SEQ ID NO: 228 zalifrelimab heavy chain | EVQLVESGGG LVKPGGSLRL SCAASGFTFS SYSMNWVRQA PGKGLEWVSS ISSSSSYIYY | 60 |
| | ADSVKGRFTI SRDNAKNSLY LQMNSLRAED TAVYYCARVG LMGPFDIWGQ GTMVTVSSAS | 120 |
| | TKGPSVFPLA PSSKSTSGGT AALGCLVKDY FPEPVTVSWN SGALTSGVHT FPAVLQSSGL | 180 |
| | YSLSSVVTVP SSSLGTQTYI CNVNHKPSNT KVDKRVEPKS CDKTHTCPPC PAPELLGGPS | 240 |
| | VFLFPPKPKD TLMISRTPEV TCVVVDVSHE DPEVKFNWYV DGVEVHNAKT KPREEQYNST | 300 |
| | YRVVSVLTVL HQDWLNGKEY KCKVSNKALP APIEKTISKA KGQPREPQVY TLPPSREEMT | 360 |
| | KNQVSLTCLV KGFYPSDIAV EWESNGQPEN NYKTTPPVLD SDGSFFLYSK LTVDKSRWQQ | 420 |
| | GNVFSCSVMH EALHNHYTQK SLSLSPGK | 448 |
| SEQ ID NO: 229 zalifrelimab light chain | EIVLTQSPGT LSLSPGERAT LSCRASQSVS RYLGWYQQKP GQAPRLLIYG ASTRATGIPD | 60 |
| | RFSGSGSGTD FTLTITRLEP EDFAVYYCQQ YGSSPWTFGQ GTKVEIKRTV AAPSVFIFPP | 120 |
| | SDEQLKSGTA SVVCLLNNFY PREAKVQWKV DNALQSGNSQ ESVTEQDSKD STYSLSSTLT | 180 |
| | LSKADYEKHK VYACEVTHQG LSSPVTKSFN RGEC | 214 |
| SEQ ID NO: 230 zalifrelimab variable heavy chain | EVOLVESGGG LVKPGGSLRL SCAASGFTFS SYSMNWVROA PGKGLEWVSS ISSSSSYIYY | 60 |
| | ADSVKGRFTI SRDNAKNSLY LOMNSLRAED TAVYYCARVG LMGPFDIWGQ GTMVTVSS | 118 |
| SEQ ID NO: 231 zalifrelimab variable light chain | EIVLTOSPGT LSLSPGERAT LSCRASQSVS RYLGWYQQKP GQAPRLLIYG ASTRATGIPD | 60 |
| | RFSGSGSGTD FTLTITRLEP EDFAVYYCQQ YGSSPWTFGQ GTKVEIK | 107 |

TABLE 25-continued

| Amino acid sequences for zalifrelimab. | | |
|---|---|---|
| Identifier | Sequence (One-Letter Amino Acid Symbols) | |
| SEQ ID NO: 232 zalifrelimab heavy chain CDR1 | GFTFSSYS | 8 |
| SEQ ID NO: 233 zalifrelimab heavy chain CDR2 | ISSSSSYI | 8 |
| SEQ ID NO: 234 zalifrelimab heavy chain CDR3 | ARVGLMGPFD I | 11 |
| SEQ ID NO: 235 zalifrelimab light chain CDR1 | QSVSRY | 6 |
| SEQ ID NO: 236 zalifrelimab light chain CDR2 | GAS | 3 |
| SEQ ID NO: 237 zalifrelimab light chain CDR3 | QQYGSSPWT | 9 |

Examples of additional anti-CTLA-4 antibodies includes, but are not limited to: AGEN1181, BMS-986218, BCD-145, ONC-392, CS1002, REGN4659, and ADG116, which are known to one of ordinary skill in the art.

In some embodiments, the anti-CTLA-4 antibody is an anti-CTLA-4 antibody disclosed in any of the following patent publications (incorporated herein by reference): US 2019/0048096 A1; US 2020/0223907; US 2019/0201334; US 2019/0201334; US 2005/0201994; EP 1212422 BT; WO 2018/204760; WO 2018/204760; WO 2001/014424; WO 2004/035607; WO 2003/086459; WO 2012/120125; WO 2000/037504; WO 2009/100140; WO 2006/09649; WO2005092380; WO 2007/123737; WO 2006/029219; WO 2010/0979597; WO 2006/12168; and WO1997020574. Additional CTLA-4 antibodies are described in U.S. Pat. Nos. 5,811,097, 5,855,887, 6,051,227, and 6,984,720; in PCT Publication Nos. WO 01/14424 and WO 00/37504; and in U.S. Publication Nos. 2002/0039581 and 2002/086014; and/or U.S. Pat. Nos. 5,977,318, 6,682,736, 7,109,003, and 7,132,281, incorporated herein by reference). In some embodiments, the anti-CTLA-4 antibody is an, for example, those disclosed in: WO 98/42752; U.S. Pat. Nos. 6,682,736 and 6,207,156; Hurwitz et al., Proc. Natl. Acad. Sci. USA, 95(17): 10067-10071 (1998); Camacho et al., J. Clin. Oncol., 22(145): Abstract No. 2505 (2004) (antibody CP-675206); Mokyr et al., Cancer Res., 58:5301-5304 (1998) (incorporated herein by reference).

In some embodiments, the CTLA-4 inhibitor is a CTLA-4 ligand as disclosed in WO1996040915 (incorporated herein by reference).

In some embodiments, the CTLA-4 inhibitor is a nucleic acid inhibitor of CTLA-4 expression. For example, anti-CTLA-4 RNAi molecules may take the form of the molecules described by Mello and Fire in PCT Publication Nos. WO 1999/032619 and WO 2001/029058; U.S. Publication Nos. 2003/0051263, 2003/0055020, 2003/0056235, 2004/265839, 2005/0100913, 2006/0024798, 2008/0050342, 2008/0081373, 2008/0248576, and 2008/055443; and/or U.S. Pat. Nos. 6,506,559, 7,282,564, 7,538,095, and 7,560,438 (incorporated herein by reference). In some instances, the anti-CTLA-4 RNAi molecules take the form of double stranded RNAi molecules described by Tuschl in European Patent No. EP 1309726 (incorporated herein by reference). In some instances, the anti-CTLA-4 RNAi molecules take the form of double stranded RNAi molecules described by Tuschl in U.S. Pat. Nos. 7,056,704 and 7,078,196 (incorporated herein by reference). In some embodiments, the CTLA-4 inhibitor is an aptamer described in PCT Publication No. WO2004081021 (incorporated herein by reference).

In other embodiments, the anti-CTLA-4 RNAi molecules of the present invention are RNA molecules described by Crooke in U.S. Pat. Nos. 5,898,031, 6,107,094, 7,432,249, and 7,432,250, and European Application No. EP 0928290 (incorporated herein by reference).

4. Optional Lymphodepletion Preconditioning of Patients

In an embodiment, the invention includes a method of treating a cancer with a population of TILs, wherein a patient is pre-treated with non-myeloablative chemotherapy prior to an infusion of TILs according to the present disclosure. In an embodiment, the invention includes a population of TILs for use in the treatment of cancer in a patient which has been pre-treated with non-myeloablative chemotherapy. In an embodiment, the population of TILs is for administration by infusion. In an embodiment, the non-myeloablative chemotherapy is cyclophosphamide 60 mg/kg/d for 2 days (days 27 and 26 prior to TIL infusion) and fludarabine 25 mg/m$^2$/d for 5 days (days 27 to 23 prior to TIL infusion). In some embodiments, the non-myeloablative chemotherapy is cyclophosphamide 60 mg/kg/d for 2 days (days 27 and 26 prior to TIL infusion) and fludarabine 25 mg/m2/d for 3 days (days 27 to 25 prior to TIL infusion). In some embodiments, the non-myeloablative chemotherapy is cyclophosphamide 60 mg/kg/d for 2 days (days 27 and 26 prior to TIL infusion) followed by fludarabine 25 mg/m2/d for 3 days (days 25 to 23 prior to TIL infusion). In an embodiment, after non-myeloablative chemotherapy and TIL infusion (at day 0) according to the present disclosure, the patient receives an intravenous infusion of IL-2 (aldesleukin, commercially available as PROLEUKIN) intravenously at 720,000 IU/kg every 8 hours to physiologic tolerance. In certain embodiments, the population of TILs is for use in treating cancer in combination with IL-2, wherein the IL-2 is administered after the population of TILs.

Experimental findings indicate that lymphodepletion prior to adoptive transfer of tumor-specific T lymphocytes plays a key role in enhancing treatment efficacy by eliminating regulatory T cells and competing elements of the immune system ('cytokine sinks'). Accordingly, some embodiments of the invention utilize a lymphodepletion step (sometimes also referred to as "immunosuppressive conditioning") on the patient prior to the introduction of the TILs of the invention.

In general, lymphodepletion is achieved using administration of fludarabine or cyclophosphamide (the active form being referred to as mafosfamide) and combinations thereof. Such methods are described in Gassner, et al., *Cancer Immunol. Immunother.* 2011, 60, 75-85, Muranski, et al., *Nat. Clin. Pract. Oncol.,* 2006, 3, 668-681, Dudley, et al., *J. Clin. Oncol.* 2008, 26, 5233-5239, and Dudley, et al., *J. Clin. Oncol.* 2005, 23, 2346-2357, all of which are incorporated by reference herein in their entireties.

In some embodiments, the fludarabine is administered at a concentration of 0.5 μg/mL-10 μg/mL fludarabine. In some embodiments, the fludarabine is administered at a concentration of 1 μg/mL fludarabine. In some embodiments, the fludarabine treatment is administered for 1 day, 2 days, 3 days, 4 days, 5 days, 6 days, or 7 days or more. In some embodiments, the fludarabine is administered at a dosage of 10 mg/kg/day, 15 mg/kg/day, 20 mg/kg/day, 25 mg/kg/day, 30 mg/kg/day, 35 mg/kg/day, 40 mg/kg/day, or 45 mg/kg/day. In some embodiments, the fludarabine treatment is administered for 2-7 days at 35 mg/kg/day. In some embodiments, the fludarabine treatment is administered for 4-5 days at 35 mg/kg/day. In some embodiments, the fludarabine treatment is administered for 4-5 days at 25 mg/kg/day.

In some embodiments, the mafosfamide, the active form of cyclophosphamide, is obtained at a concentration of 0.5 μg/mL-10 μg/mL by administration of cyclophosphamide. In some embodiments, mafosfamide, the active form of cyclophosphamide, is obtained at a concentration of 1 μg/mL by administration of cyclophosphamide. In some embodiments, the cyclophosphamide treatment is administered for 1 day, 2 days, 3 days, 4 days, 5 days, 6 days, or 7 days or more. In some embodiments, the cyclophosphamide is administered at a dosage of 100 mg/m$^2$/day, 150 mg/m$^2$/day, 175 mg/m$^2$/day, 200 mg/m$^2$/day, 225 mg/m$^2$/day, 250 mg/m$^2$/day, 275 mg/m$^2$/day, or 300 mg/m$^2$/day. In some embodiments, the cyclophosphamide is administered intravenously (i.e., i.v.) In some embodiments, the cyclophosphamide treatment is administered for 2-7 days at 35 mg/kg/day. In some embodiments, the cyclophosphamide treatment is administered for 4-5 days at 250 mg/m$^2$/day i.v. In some embodiments, the cyclophosphamide treatment is administered for 4 days at 250 mg/m$^2$/day i.v.

In some embodiments, lymphodepletion is performed by administering the fludarabine and the cyclophosphamide together to a patient. In some embodiments, fludarabine is administered at 25 mg/m$^2$/day i.v. and cyclophosphamide is administered at 250 mg/m$^2$/day i.v. over 4 days.

In an embodiment, the lymphodepletion is performed by administration of cyclophosphamide at a dose of 60 mg/m$^2$/day for two days followed by administration of fludarabine at a dose of 25 mg/m$^2$/day for five days.

In an embodiment, the lymphodepletion is performed by administration of cyclophosphamide at a dose of 60 mg/m$^2$/day for two days and administration of fludarabine at a dose of 25 mg/m$^2$/day for five days, wherein cyclophosphamide and fludarabine are both administered on the first two days, and wherein the lymphodepletion is performed in five days in total.

In an embodiment, the lymphodepletion is performed by administration of cyclophosphamide at a dose of about 50 mg/m$^2$/day for two days and administration of fludarabine at a dose of about 25 mg/m$^2$/day for five days, wherein cyclophosphamide and fludarabine are both administered on the first two days, and wherein the lymphodepletion is performed in five days in total.

In an embodiment, the lymphodepletion is performed by administration of cyclophosphamide at a dose of about 50 mg/m$^2$/day for two days and administration of fludarabine at a dose of about 20 mg/m$^2$/day for five days, wherein cyclophosphamide and fludarabine are both administered on the first two days, and wherein the lymphodepletion is performed in five days in total.

In an embodiment, the lymphodepletion is performed by administration of cyclophosphamide at a dose of about 40 mg/m$^2$/day for two days and administration of fludarabine at a dose of about 20 mg/m$^2$/day for five days, wherein cyclophosphamide and fludarabine are both administered on the first two days, and wherein the lymphodepletion is performed in five days in total.

In an embodiment, the lymphodepletion is performed by administration of cyclophosphamide at a dose of about 40 mg/m$^2$/day for two days and administration of fludarabine at a dose of about 15 mg/m$^2$/day for five days, wherein cyclophosphamide and fludarabine are both administered on the first two days, and wherein the lymphodepletion is performed in five days in total.

In an embodiment, the lymphodepletion is performed by administration of cyclophosphamide at a dose of 60 mg/m$^2$/day and fludarabine at a dose of 25 mg/m$^2$/day for two days followed by administration of fludarabine at a dose of 25 mg/m$^2$/day for three days.

In an embodiment, the cyclophosphamide is administered with mesna. In an embodiment, mesna is administered at 15 mg/kg. In an embodiment where mesna is infused, and if infused continuously, mesna can be infused over approximately 2 hours with cyclophosphamide (on Days −5 and/or −4), then at a rate of 3 mg/kg/hour for the remaining 22 hours over the 24 hours starting concomitantly with each cyclophosphamide dose.

In an embodiment, the lymphodepletion comprises the step of treating the patient with an IL-2 regimen starting on the day after administration of the third population of TILs to the patient.

In an embodiment, the lymphodepletion comprises the step of treating the patient with an IL-2 regimen starting on the same day as administration of the third population of TILs to the patient.

In some embodiments, the lymphodeplete comprises 5 days of preconditioning treatment. In some embodiments, the days are indicated as days −5 through −1, or Day 0 through Day 4. In some embodiments, the regimen comprises cyclophosphamide on days −5 and −4 (i.e., days 0 and 1). In some embodiments, the regimen comprises intravenous cyclophosphamide on days −5 and −4 (i.e., days 0 and 1). In some embodiments, the regimen comprises 60 mg/kg intravenous cyclophosphamide on days −5 and −4 (i.e., days 0 and 1). In some embodiments, the cyclophosphamide is administered with mesna. In some embodiments, the regimen further comprises fludarabine. In some embodiments, the regimen further comprises intravenous fludarabine. In some embodiments, the regimen further comprises 25 $mg/m^2$ intravenous fludarabine. In some embodiments, the regimen further comprises 25 $mg/m^2$ intravenous fludarabine on days −5 and −1 (i.e., days 0 through 4). In some embodiments, the regimen further comprises 25 $mg/m^2$ intravenous fludarabine on days −5 and −1 (i.e., days 0 through 4).

In some embodiments, the non-myeloablative lymphodepletion regimen comprises the steps of administration of cyclophosphamide at a dose of 60 mg/m2/day and fludarabine at a dose of 25 $mg/m^2$/day for two days followed by administration of fludarabine at a dose of 25 $mg/m^2$/day for five days.

In some embodiments, the non-myeloablative lymphodepletion regimen comprises the steps of administration of cyclophosphamide at a dose of 60 mg/m2/day and fludarabine at a dose of 25 $mg/m^2$/day for two days followed by administration of fludarabine at a dose of 25 $mg/m^2$/day for three days.

In some embodiments, the non-myeloablative lymphodepletion regimen comprises the steps of administration of cyclophosphamide at a dose of 60 $mg/m^2$/day and fludarabine at a dose of 25 $mg/m^2$/day for two days along with administration of fludarabine at a dose of 25 $mg/m^2$/day for two days, followed by fludarabine at a dose of 25 $mg/m^2$/day for one day.

In some embodiments, the non-myeloablative lymphodepletion regimen comprises the steps of administration of cyclophosphamide at a dose of 60 $mg/m^2$/day and fludarabine at a dose of 25 $mg/m^2$/day for two days along with administration of fludarabine at a dose of 25 $mg/m^2$/day for two days, followed by fludarabine at a dose of 25 $mg/m^2$/day for two days.

In some embodiments, the non-myeloablative lymphodepletion regimen comprises the steps of administration of cyclophosphamide at a dose of 60 $mg/m^2$/day and fludarabine at a dose of 25 $mg/m^2$/day for two days along with administration of fludarabine at a dose of 25 $mg/m^2$/day for two days, followed by fludarabine at a dose of 25 $mg/m^2$/day for three days.

In some embodiments, the non-myeloablative lymphodepletion regimen comprises 5 days of preconditioning treatment. In some embodiments, the days are indicated as days −5 through −1, or Day 0 through Day 4. In some embodiments, the regimen comprises cyclophosphamide on days −5 and −4 (i.e., days 0 and 1). In some embodiments, the regimen comprises intravenous cyclophosphamide on days −5 and −4 (i.e., days 0 and 1). In some embodiments, the regimen comprises 300 mg/kg intravenous cyclophosphamide on days −5 and −4 (i.e., days 0 and 1). In some embodiments, the cyclophosphamide is administered with mesna. In some embodiments, the regimen further comprises fludarabine. In some embodiments, the regimen further comprises intravenous fludarabine. In some embodiments, the regimen further comprises 30 $mg/m^2$ intravenous fludarabine. In some embodiments, the regimen further comprises 30 $mg/m^2$ intravenous fludarabine on days −5 and −1 (i.e., days 0 through 4). In some embodiments, the regimen further comprises 30 $mg/m^2$ intravenous fludarabine on days −5 and −1 (i.e., days 0 through 4).

In some embodiments, the non-myeloablative lymphodepletion regimen comprises the steps of administration of cyclophosphamide at a dose of 300 $mg/m^2$/day and fludarabine at a dose of 30 $mg/m^2$/day for two days followed by administration of fludarabine at a dose of 30 $mg/m^2$/day for five days.

In some embodiments, the non-myeloablative lymphodepletion regimen comprises the steps of administration of cyclophosphamide at a dose of 60 $mg/m^2$/day and fludarabine at a dose of 30 $mg/m^2$/day for two days followed by administration of fludarabine at a dose of 30 $mg/m^2$/day for three days.

In some embodiments, the non-myeloablative lymphodepletion regimen comprises the steps of administration of cyclophosphamide at a dose of 60 $mg/m^2$/day and fludarabine at a dose of 30 $mg/m^2$/day for two days along with administration of fludarabine at a dose of 30 $mg/m^2$/day for two days, followed by fludarabine at a dose of 30 $mg/m^2$/day for one day.

In some embodiments, the non-myeloablative lymphodepletion regimen comprises the steps of administration of cyclophosphamide at a dose of 300 $mg/m^2$/day and fludarabine at a dose of 30 $mg/m^2$/day for two days along with administration of fludarabine at a dose of 30 $mg/m^2$/day for two days, followed by fludarabine at a dose of 30 $mg/m^2$/day for two days.

In some embodiments, the non-myeloablative lymphodepletion regimen comprises the steps of administration of cyclophosphamide at a dose of 300 $mg/m^2$/day and fludarabine at a dose of 30 $mg/m^2$/day for two days along with administration of fludarabine at a dose of 30 $mg/m^2$/day for two days, followed by fludarabine at a dose of 30 $mg/m^2$/day for three days.

In some embodiments, the non-myeloablative lymphodepletion regimen is administered according to Table 26.

TABLE 26

Exemplary lymphodepletion and treatment regimen.

| | Day | | | | | | | | | |
|---|---|---|---|---|---|---|---|---|---|---|
| | −5 | −4 | −3 | −2 | −1 | 0 | 1 | 2 | 3 | 4 |
| Cyclophosphamide 60 mg/kg | X | X | | | | | | | | |
| Mesna (as needed) | X | X | | | | | | | | |
| Fludarabine 25 $mg/m^2$/day | X | X | X | X | X | | | | | |
| TIL infusion | | | | | | X | | | | |

In some embodiments, the non-myeloablative lymphodepletion regimen is administered according to Table 27.

TABLE 27

Exemplary lymphodepletion and treatment regimen.

| | Day | | | | | | | | |
|---|---|---|---|---|---|---|---|---|---|
| | −4 | −3 | −2 | −1 | 0 | 1 | 2 | 3 | 4 |
| Cyclophosphamide 60 mg/kg | X | X | | | | | | | |
| Mesna (as needed) | X | X | | | | | | | |
| Fludarabine 25 $mg/m^2$/day | X | X | X | X | | | | | |
| TIL infusion | | | | | X | | | | |

In some embodiments, the non-myeloablative lymphodepletion regimen is administered according to Table 28.

TABLE 28

Exemplary lymphodepletion and treatment regimen.

| | Day | | | | | | | |
|---|---|---|---|---|---|---|---|---|
| | −3 | −2 | −1 | 0 | 1 | 2 | 3 | 4 |
| Cyclophosphamide 60 mg/kg | X | X | | | | | | |
| Mesna (as needed) | X | X | | | | | | |
| Fludarabine 25 mg/m$^2$/day | X | X | X | | | | | |
| TIL infusion | | | | X | | | | |

In some embodiments, the non-myeloablative lymphodepletion regimen is administered according to Table 29.

TABLE 29

Exemplary lymphodepletion and treatment regimen.

| | Day | | | | | | | | | |
|---|---|---|---|---|---|---|---|---|---|---|
| | −5 | −4 | −3 | −2 | −1 | 0 | 1 | 2 | 3 | 4 |
| Cyclophosphamide 60 mg/kg | X | X | | | | | | | | |
| Mesna (as needed) | X | X | | | | | | | | |
| Fludarabine 25 mg/m$^2$/day | | | X | X | X | | | | | |
| TIL infusion | | | | | | X | | | | |

In some embodiments, the non-myeloablative lymphodepletion regimen is administered according to Table 30.

TABLE 30

Exemplary lymphodepletion and treatment regimen.

| | Day | | | | | | | | | |
|---|---|---|---|---|---|---|---|---|---|---|
| | −5 | −4 | −3 | −2 | −1 | 0 | 1 | 2 | 3 | 4 |
| Cyclophosphamide 300 mg/kg | X | X | | | | | | | | |
| Mesna (as needed) | X | X | | | | | | | | |
| Fludarabine 30 mg/m$^2$/day | X | X | X | X | X | | | | | |
| TIL infusion | | | | | | X | | | | |

In some embodiments, the non-myeloablative lymphodepletion regimen is administered according to Table 31.

TABLE 32

Exemplary lymphodepletion and treatment regimen.

| | Day | | | | | | | | |
|---|---|---|---|---|---|---|---|---|---|
| | −4 | −3 | −2 | −1 | 0 | 1 | 2 | 3 | 4 |
| Cyclophosphamide 300 mg/kg | X | X | | | | | | | |
| Mesna (as needed) | X | X | | | | | | | |
| Fludarabine 30 mg/m$^2$/day | X | X | X | X | | | | | |
| TIL infusion | | | | | X | | | | |

In some embodiments, the non-myeloablative lymphodepletion regimen is administered according to Table 32.

TABLE 32

Exemplary lymphodepletion and treatment regimen.

| | Day | | | | | | | |
|---|---|---|---|---|---|---|---|---|
| | −3 | −2 | −1 | 0 | 1 | 2 | 3 | 4 |
| Cyclophosphamide 300 mg/kg | X | X | | | | | | |
| Mesna (as needed) | X | X | | | | | | |
| Fludarabine 30 mg/m$^2$/day | X | X | X | | | | | |
| TIL infusion | | | | X | | | | |

In some embodiments, the non-myeloablative lymphodepletion regimen is administered according to Table 33.

TABLE 33

Exemplary lymphodepletion and treatment regimen.

| | Day | | | | | | | | | |
|---|---|---|---|---|---|---|---|---|---|---|
| | −5 | −4 | −3 | −2 | −1 | 0 | 1 | 2 | 3 | 4 |
| Cyclophosphamide 300 mg/kg | X | X | | | | | | | | |
| Mesna (as needed) | X | X | | | | | | | | |
| Fludarabine 30 mg/m$^2$/day | | | X | X | X | | | | | |
| TIL infusion | | | | | | X | | | | |

In some embodiments, the non-myeloablative lymphodepletion regimen comprises melphalan administered to a total dose of 100 mg/m$^2$ over the course of 1, 2, or 3 days prior to the day of TIL infusion. In some embodiments, the non-myeloablative lymphodepletion regimen comprises melphalan administered to a total dose of 200 mg/m$^2$ over the course of 1, 2, or 3 days prior to the day of TIL infusion. In some embodiments, the non-myeloablative lymphodepletion regimen comprises melphalan administered to a total dose of 100 mg/m$^2$ and fludarabine administered at a dose of 30 mg/m$^2$/day over the course of 1, 2, or 3 days prior to the day of TIL infusion. In some embodiments, the non-myeloablative lymphodepletion regimen comprises melphalan administered to a total dose of 200 mg/m$^2$ and fludarabine administered at a dose of 30 mg/m$^2$/day over the course of 1, 2, or 3 days prior to the day of TIL infusion.

In some embodiments, the TIL infusion used with the foregoing embodiments of myeloablative lymphodepletion regimens may be any TIL composition described herein and may also include infusions of MILs and PBLs in place of the TIL infusion, as well as the addition of IL-2 regimens and administration of co-therapies (such as PD-1 and PD-L1 inhibitors) as described herein.

5. IL-2 Regimens

In an embodiment, the IL-2 regimen comprises a high-dose IL-2 regimen, wherein the high-dose IL-2 regimen comprises aldesleukin, or a biosimilar or variant thereof, administered intravenously starting on the day after administering a therapeutically effective portion of therapeutic population of TILs, wherein the aldesleukin or a biosimilar or variant thereof is administered at a dose of 0.037 mg/kg or 0.044 mg/kg IU/kg (patient body mass) using 15-minute bolus intravenous infusions every eight hours until tolerance, for a maximum of 14 doses. Following 9 days of rest, this schedule may be repeated for another 14 doses, for a maximum of 28 doses in total. In some embodiments, IL-2 is administered in 1, 2, 3, 4, 5, or 6 doses. In some embodiments, IL-2 is administered at a maximum dosage of up to 6 doses. In some embodiments, the high-dose IL-2 regimen is adapted for pediatric use. In some embodiments, a dose of 600,000 international units (IU)/kg of aldesleukin every 8-12 hours for up to a maximum of 6 doses is used. In some embodiments, a dose of 500,000 international units (IU)/kg of aldesleukin every 8-12 hours for up to a maximum of 6 doses is used. In some embodiments, a dose of 400,000 international units (IU)/kg of aldesleukin every 8-12 hours for up to a maximum of 6 doses is used. In some embodiments, a dose of 500,000 international units (IU)/kg of aldesleukin every 8-12 hours for up to a maximum of 6 doses is used. In some embodiments, a dose of 300,000 international units (IU)/kg of aldesleukin every 8-12 hours for up to a maximum of 6 doses is used. In some embodiments, a dose of 200,000 international units (IU)/kg of aldesleukin every 8-12 hours for up to a maximum of 6 doses is used. In some embodiments, a dose of 100,000 international units (IU)/kg of aldesleukin every 8-12 hours for up to a maximum of 6 doses is used.

In an embodiment, the IL-2 regimen comprises a decrescendo IL-2 regimen. Decrescendo IL-2 regimens have been described in O'Day, et al., *J. Clin. Oncol.* 1999, 17, 2752-61 and Eton, et al., *Cancer* 2000, 88, 1703-9, the disclosures of which are incorporated herein by reference. In an embodiment, a decrescendo IL-2 regimen comprises $18\times10^6$ IU/$m^2$ administered intravenously over 6 hours, followed by $18\times10^6$ IU/$m^2$ administered intravenously over 12 hours, followed by $18\times10^6$ IU/$m^2$ administered intravenously over 24 hours, followed by $4.5\times10^6$ IU/$m^2$ administered intravenously over 72 hours. This treatment cycle may be repeated every 28 days for a maximum of four cycles. In an embodiment, a decrescendo IL-2 regimen comprises 18,000,000 IU/$m^2$ on day 1, 9,000,000 IU/$m^2$ on day 2, and 4,500,000 IU/$m^2$ on days 3 and 4.

In an embodiment, the IL-2 regimen comprises administration of pegylated IL-2 every 1, 2, 4, 6, 7, 14 or 21 days at a dose of 0.10 mg/day to 50 mg/day.

In an embodiment, the IL-2 regimen comprises administration of an IL-2 fragment engrafted onto an antibody backbone. In an embodiment, the IL-2 regimen comprises administration of an antibody-cytokine engrafted protein that binds the IL-2 low affinity receptor. In an embodiment, the IL-2 regimen comprises administration of an antibody-cytokine engrafted protein that exhibits enhanced binding to the IL-2Rβ and/or IL-2Rγ receptors, in comparison to aldesleukin, without an effect on the binding to the IL-2Rα receptor.

In some embodiments, the antibody cytokine engrafted protein described herein has a longer serum half-life that a wild-type IL-2 molecule such as, but not limited to, aldeskeukin (Proleukin®) or a comparable molecule.

6. Additional Methods of Treatment

In another embodiment, the invention provides a method for treating a subject with cancer comprising administering to the subject a therapeutically effective dosage of the therapeutic TIL population described in any of the preceding paragraphs above.

In another embodiment, the invention provides a method for treating a subject with cancer comprising administering to the subject a therapeutically effective dosage of the TIL composition described in any of the preceding paragraphs above.

In another embodiment, the invention provides the method for treating a subject with cancer described in any of the preceding paragraphs above modified such that prior to administering the therapeutically effective dosage of the therapeutic TIL population and the TIL composition described in any of the preceding paragraphs above, respectively, a non-myeloablative lymphodepletion regimen has been administered to the subject.

In another embodiment, the invention provides the method for treating a subject with cancer described in any of the preceding paragraphs above modified such that the non-myeloablative lymphodepletion regimen comprises the steps of administration of cyclophosphamide at a dose of 60 mg/$m^2$/day for two days followed by administration of fludarabine at a dose of 25 mg/$m^2$/day for five days.

In another embodiment, the invention provides the method for treating a subject with cancer described in any of the preceding paragraphs above modified to further comprise the step of treating the subject with a high-dose IL-2 regimen starting on the day after administration of the TIL cells to the subject.

In another embodiment, the invention provides the method for treating a subject with cancer described in any of the preceding paragraphs above modified such that the high-dose IL-2 regimen comprises 600,000 or 720,000 IU/kg administered as a 15-minute bolus intravenous infusion every eight hours until tolerance.

In another embodiment, the invention provides the method for treating a subject with cancer described in any of the preceding paragraphs above modified such that the cancer is a solid tumor.

In another embodiment, the invention provides the method for treating a subject with cancer described in any of the preceding paragraphs above modified such that the cancer is melanoma.

In another embodiment, the invention provides the method for treating a subject with cancer described in any of the preceding paragraphs above modified such that the cancer is a pediatric hypermutated cancer.

In another embodiment, the invention provides the therapeutic TIL population described in any of the preceding paragraphs above for use in a method for treating a subject with cancer comprising administering to the subject a therapeutically effective dosage of the therapeutic TIL population.

In another embodiment, the invention provides the TIL composition described in any of the preceding paragraphs above for use in a method for treating a subject with cancer comprising administering to the subject a therapeutically effective dosage of the TIL composition.

In another embodiment, the invention provides the therapeutic TIL population described in any of the preceding paragraphs above or the TIL composition described in any of the preceding paragraphs above modified such that prior to administering to the subject the therapeutically effective dosage of the therapeutic TIL population described in any of the preceding paragraphs above or the TIL composition described in any of the preceding paragraphs above, a non-myeloablative lymphodepletion regimen has been administered to the subject.

In another embodiment, the invention provides the therapeutic TIL population or the TIL composition described in any of the preceding paragraphs above modified such that the non-myeloablative lymphodepletion regimen comprises the steps of administration of cyclophosphamide at a dose of 60 mg/$m^2$/day for two days followed by administration of fludarabine at a dose of 25 mg/$m^2$/day for five days.

In another embodiment, the invention provides the therapeutic TIL population or the TIL composition described in any of the preceding paragraphs above modified to further comprise the step of treating patient with a high-dose IL-2 regimen starting on the day after administration of the TIL cells to the patient.

In another embodiment, the invention provides the therapeutic TIL population or the TIL composition described in any of the preceding paragraphs above modified such that the high-dose IL-2 regimen comprises 600,000 or 720,000 IU/kg administered as a 15-minute bolus intravenous infusion every eight hours until tolerance.

In another embodiment, the invention provides the therapeutic TIL population or the TIL composition described in any of the preceding paragraphs above modified such that the cancer is a solid tumor.

In another embodiment, the invention provides the therapeutic TIL population or the TIL composition described in any of the preceding paragraphs above modified such that the cancer is melanoma.

In another embodiment, the invention provides the therapeutic TIL population or the TIL composition described in any of the preceding paragraphs above modified such that the cancer is a hypermutated cancer.

In another embodiment, the invention provides the therapeutic TIL population or the TIL composition described in any of the preceding paragraphs above modified such that the cancer is a pediatric hypermutated cancer.

In another embodiment, the invention provides the use of the therapeutic TIL population described in any of any of the preceding paragraphs above in a method of treating cancer in a subject comprising administering to the subject a therapeutically effective dosage of the therapeutic TIL population.

In another embodiment, the invention provides the use of the TIL composition described in any of the preceding paragraphs above in a method of treating cancer in a subject comprising administering to the subject a therapeutically effective dosage of the TIL composition.

In another embodiment, the invention provides the use of the therapeutic TIL population described in any of the preceding paragraphs above or the TIL composition described in any of the preceding paragraphs above in a method of treating cancer in a subject comprising administering to the subject a non-myeloablative lymphodepletion regimen and then administering to the subject the therapeutically effective dosage of the therapeutic TIL population described in any of the preceding paragraphs above or the therapeutically effective dosage of the TIL composition described in any of the preceding paragraphs above.

EXAMPLES

The embodiments encompassed herein are now described with reference to the following examples. These examples are provided for the purpose of illustration only and the disclosure encompassed herein should in no way be construed as being limited to these examples, but rather should be construed to encompass any and all variations which become evident as a result of the teachings provided herein.

Example 1: Preparation of Media for Pre-Rep and Rep Processes

This Example describes the procedure for the preparation of tissue culture media for use in protocols involving the culture of TILs derived from various tumor types including melanoma. This media can be used for preparation of any of the TILs described in the present application and Examples.

Preparation of CM1. Removed the following reagents from cold storage and warmed them in a 37° C. water bath: (RPMI1640, Human AB serum, 200 mM L-glutamine). Prepared CM1 medium according to Table 34 below by adding each of the ingredients into the top section of a 0.2 um filter unit appropriate to the volume to be filtered. Store at 4° C.

TABLE 34

Preparation of CM1

| Ingredient | Final concentration | Final Volume 500 mL | Final Volume IL |
|---|---|---|---|
| RPMI1640 | NA | 450 mL | 900 mL |
| Human AB serum, heat-inactivated 10% | 50 mL | 100 mL | |
| 200 mM L-glutamine | 2 mM | 5 mL | 10 mL |
| 55 mM BME | 55 μM | 0.5 mL | 1 mL |
| 50 mg/mL gentamicin sulfate | 50 μg/mL | 0.5 mL | 1 mL |

On the day of use, prewarmed required amount of CM1 in a 37° C. water bath and add 6000 IU/mL IL-2.

Additional supplementation may be performed as needed according to Table 35.

TABLE 35

Additional supplementation of CM1, as needed.

| Supplement | Stock concentration | Dilution | Final concentration |
|---|---|---|---|
| GlutaMAX ™ | 200 mM | 1:100 | 2 mM |
| Penicillin/ streptomycin | 10,000 U/mL penicillin 10,000 μg/mL streptomycin | 1:100 | 100 U/mL penicillin 100 μg/mL streptomycin |
| Amphotericin B | 250 μg/mL | 1:100 | 2.5 μg/mL |

Preparation of CM2. Removed prepared CM1 from refrigerator or prepare fresh CM1. Removed AIM-V® from refrigerator and prepared the amount of CM2 needed by mixing prepared CM1 with an equal volume of AIM-V® in a sterile media bottle. Added 3000 IU/mL IL-2 to CM2 medium on the day of usage. Made sufficient amount of CM2 with 3000 IU/mL IL-2 on the day of usage. Labeled the CM2 media bottle with its name, the initials of the preparer, the date it was filtered/prepared, the two-week expiration date and store at 4° C. until needed for tissue culture.

Preparation of CM3. Prepared CM3 on the day it was required for use. CM3 was the same as AIM-V® medium, supplemented with 3000 IU/mL IL-2 on the day of use. Prepared an amount of CM3 sufficient to experimental needs by adding IL-2 stock solution directly to the bottle or bag of AIM-V. Mixed well by gentle shaking. Label bottle with “3000 IU/mL IL-2” immediately after adding to the AIM-V. If there was excess CM3, stored it in bottles at 4° C. labeled with the media name, the initials of the preparer, the date the media was prepared, and its expiration date (7 days after preparation). Discarded media supplemented with IL-2 after 7 days storage at 4° C.

Preparation of CM4. CM4 was the same as CM3, with the additional supplement of 2 mM GlutaMAX™ (final concentration). For every 1L of CM3, added 10 ml of 200 mM GlutaMAX™. Prepared an amount of CM4 sufficient to experimental needs by adding IL-2 stock solution and GlutaMAX™ stock solution directly to the bottle or bag of AIM-V. Mixed well by gentle shaking. Labeled bottle with “3000 IL/nil IL-2 and GlutaMAX” immediately after adding to the AIM-V. If there was excess CM4, stored it in bottles at 4° C. labeled with the media name, "GlutaMAX", and its expiration date (7 days after preparation). Discarded media supplemented with IL-2 after 7-days storage at 4° C.

Example 2: Qualifying Individual Lots of Gamma-Irradiated Peripheral Mononuclear Cells This Example describes an abbreviated procedure for qualifying individual lots of gamma-irradiated peripheral mononuclear cells (PBMCs, also known as mononuclear cells or MNCs) for use as allogeneic feeder cells in the exemplary methods described herein.

Each irradiated MNC feeder lot was prepared from an individual donor. Each lot or donor was screened individually for its ability to expand TIL in the REP in the presence of purified anti-CD3 (clone OKT3) antibody and interleukin-2 (IL-2). In addition, each lot of feeder cells was tested without the addition of TIL to verify that the received dose of gamma radiation was sufficient to render them replication incompetent.

Gamma-irradiated, growth-arrested MNC feeder cells are required for REP of TILs. Membrane receptors on the feeder MNCs bind to anti-CD3 (clone OKT3) antibody and crosslink to TILs in the REP flask, stimulating the TIL to expand. Feeder lots were prepared from the leukapheresis of whole blood taken from individual donors. The leukapheresis product was subjected to centrifugation over Ficoll-Hypaque, washed, irradiated, and cryopreserved under GMP conditions.

It is important that patients who received TIL therapy not be infused with viable feeder cells as this can result in graft-versus-host disease (GVHD). Feeder cells are therefore growth-arrested by dosing the cells with gamma-irradiation, resulting in double strand DNA breaks and the loss of cell viability of the MNC cells upon re-culture.

Feeder lots were evaluated on two criteria: (1) their ability to expand TILs in co-culture >100-fold and (2) their replication incompetency.

Feeder lots were tested in mini-REP format utilizing two primary pre-REP TIL lines grown in upright T25 tissue culture flasks. Feeder lots were tested against two distinct TIL lines, as each TIL line is unique in its ability to proliferate in response to activation in a REP. As a control, a lot of irradiated MNC feeder cells which has historically been shown to meet the criteria above was run alongside the test lots.

To ensure that all lots tested in a single experiment receive equivalent testing, sufficient stocks of the same pre-REP TIL lines were available to test all conditions and all feeder lots.

For each lot of feeder cells tested, there was a total of six T25 flasks: Pre-REP TIL line #1 (2 flasks); Pre-REP TIL line #2 (2 flasks); and feeder control (2 flasks). Flasks containing TIL lines #1 and #2 evaluated the ability of the feeder lot to expand TIL. The feeder control flasks evaluated the replication incompetence of the feeder lot.

A. Experimental Protocol

Day −2/3, Thaw of TIL lines. Prepare CM2 medium and warm CM2 in 37° C. water bath. Prepare 40 mL of CM2 supplemented with 3000 IU/mL IL-2. Keep warm until use. Place 20 mL of pre-warmed CM2 without IL-2 into each of two 50 mL conical tubes labeled with names of the TIL lines used. Removed the two designated pre-REP TIL lines from LN2 storage and transferred the vials to the tissue culture room. Thawed vials by placing them inside a sealed zipper storage bag in a 37° C. water bath until a small amount of ice remains.

Using a sterile transfer pipet, the contents of each vial were immediately transferred into the 20 mL of CM2 in the prepared, labeled 50 mL conical tube. QS to 40 mL using CM2 without IL-2 to wash cells and centrifuged at 400× CF for 5 minutes. Aspirated the supernatant and resuspend in 5 mL warm CM2 supplemented with 3000 IU/mL IL-2.

A small aliquot (20 μL) was removed in duplicate for cell counting using an automated cell counter. The counts were recorded. While counting, the 50 mL conical tube with TIL cells was placed into a humidified 37° C., 5% $CO_2$ incubator, with the cap loosened to allow for gas exchange. The cell concentration was determined, and the TILs were diluted to $1\times10^6$ cells/mL in CM2 supplemented with IL-2 at 3000 IU/mL.

Cultured in 2 mL/well of a 24-well tissue culture plate in as many wells as needed in a humidified 37° C. incubator until Day 0 of the mini-REP. The different TIL lines were cultured in separate 24-well tissue culture plates to avoid confusion and potential cross-contamination.

Day 0, initiate Mini-REP. Prepared enough CM2 medium for the number of feeder lots to be tested. (e.g., for testing 4 feeder lots at one time, prepared 800 mL of CM2 medium). Aliquoted a portion of the CM2 prepared above and supplemented it with 3000 IU/mL IL-2 for the culturing of the cells. (e.g., for testing 4 feeder lots at one time, prepare 500 mL of CM2 medium with 3000 IU/mL IL-2).

Working with each TIL line separately to prevent cross-contamination, the 24-well plate with TIL culture was removed from the incubator and transferred to the BSC.

Using a sterile transfer pipet or 100-1000 μL pipettor and tip, about 1 mL of medium was removed from each well of TILs to be used and placed in an unused well of the 24-well tissue culture plate.

Using a fresh sterile transfer pipet or 100-1000 μL pipettor and tip, the remaining medium was mixed with TILs in wells to resuspend the cells and then transferred the cell suspension to a 50 mL conical tube labeled with the TIL lot name and recorded the volume.

Washed the wells with the reserved media and transferred that volume to the same 50 mL conical tube. Spun the cells at 400× CF to collect the cell pellet. Aspirated off the media supernatant and resuspend the cell pellet in 2-5 mL of CM2 medium containing 3000 IU/mL IL-2, volume to be used based on the number of wells harvested and the size of the pellet—volume should be sufficient to ensure a concentration of $>1.3\times10^6$ cells/mL.

Using a serological pipet, the cell suspension was mixed thoroughly and the volume was recorded. Removed 200 μL for a cell count using an automated cell counter. While counting, placed the 50 mL conical tube with TIL cells into a humidified, 5% $CO_2$, 37° C. incubator, with the cap loosened to allow gas exchange. Recorded the counts.

Removed the 50 mL conical tube containing the TIL cells from the incubator and resuspend them cells at a concentration of $1.3\times10^6$ cells/mL in warm CM2 supplemented with 3000 IU/mL IL-2. Returned the 50 mL conical tube to the incubator with a loosened cap.

The steps above were repeated for the second TIL line.

Just prior to plating the TIL into the T25 flasks for the experiment, TILs were diluted 1:10 for a final concentration of $1.3\times10^5$ cells/mL as per below.

Prepare MACS GMP CD3 pure (OKT3) working solution. Took out stock solution of OKT3 (1 mg/mL) from 4° C. refrigerator and placed in BSC. A final concentration of 30 ng/mL OKT3 was used in the media of the mini-REP.

600 ng of OKT3 were needed for 20 mL in each T25 flask of the experiment; this was the equivalent of 60 μL of a 10 μg/mL solution for each 20 mL, or 360 μL for all 6 flasks tested for each feeder lot.

For each feeder lot tested, made 400 μL of a 1:100 dilution of 1 mg/mL OKT3 for a working concentration of 10 μg/mL (e.g., for testing 4 feeder lots at one time, make 1600 μL of a 1:100 dilution of 1 mg/mL OKT3: 16 μL of 1 mg/mL OKT3+1.584 mL of CM2 medium with 3000 IU/mL IL-2.)

Prepare T25 flasks. Labeled each flask and filled flask with the CM2 medium prior to preparing the feeder cells. Placed flasks into 37° C. humidified 5% $CO_2$ incubator to keep media warm while waiting to add the remaining components. Once feeder cells were prepared, the components will be added to the CM2 in each flask.

TABLE 36

| Solutions | | |
|---|---|---|
| Component | Volume in co-culture flasks | Volume in control (feeder only) flasks |
| CM2 + 3000 IU/mL IL-2 | 18 mL | 19 mL |
| MNC: 1.3 × $10^7$/mL in CM2 + 3000 IU IL-2 (final concentration 1.3 × $10^7$/flask) | 1 mL | 1 mL |
| OKT3: 10 μL/mL in CM2 = 3000 IU IL-2 | 60 μL | 60 μL |
| TIL: 1.3 × $10^5$/mL in CM2 with 3000 IU of IL-2 (final concentration 1.3 × $10^5$/flask) | 1 mL | 0 |

Prepare Feeder Cells. A minimum of 78×$10^6$ feeder cells were needed per lot tested for this protocol. Each 1 mL vial frozen by SDBB had 100×$10^6$ viable cells upon freezing. Assuming a 50% recovery upon thaw from liquid $N_2$ storage, it was recommended to thaw at least two 1 mL vials of feeder cells per lot giving an estimated 100×$10^6$ viable cells for each REP. Alternately, if supplied in 1.8 mL vials, only one vial provided enough feeder cells.

Before thawing feeder cells, approximately 50 mL of CM2 without IL-2 was pre-warmed for each feeder lot to be tested. The designated feeder lot vials were removed from LN2 storage, placed in zipper storage bag, and placed on ice. Vials were thawed inside closed zipper storage bag by immersing in a 37° C. water bath. Vials were removed from zipper bag, sprayed or wiped with 70% EtOH, and transferred to a BSC.

Using a transfer pipet, the contents of feeder vials were immediately transferred into 30 mL of warm CM2 in a 50 mL conical tube. The vial was washed with a small volume of CM2 to remove any residual cells in the vial, and centrifuged at 400× CF for 5 minutes. Aspirated the supernatant and resuspended in 4 mL warm CM2 plus 3000 IU/mL IL-2. Removed 200 μL for cell counting using the automated cell counter. Recorded the counts.

Resuspended cells at 1.3×$10^7$ cells/mL in warm CM2 plus 3000 IU/mL IL-2. Diluted TIL cells from 1.3×$10^6$ cells/mL to 1.3×$10^5$ cells/mL.

Setup Co-Culture. Diluted TIL cells from 1.3×$10^6$ cells/mL to 1.3×$10^5$ cells/mL. Added 4.5 mL of CM2 medium to a 15 mL conical tube. Removed TIL cells from incubator and resuspended well using a 10 mL serological pipet. Removed 0.5 mL of cells from the 1.3×$10^6$ cells/mL TIL suspension and added to the 4.5 mL of medium in the 15 mL conical tube. Returned TIL stock vial to incubator. Mixed well. Repeated for the second TIL line.

Transferred flasks with pre-warmed media for a single feeder lot from the incubator to the BSC. Mixed feeder cells by pipetting up and down several times with a 1 mL pipet tip and transferred 1 mL (1.3×$10^7$ cells) to each flask for that feeder lot. Added 60 μL of OKT3 working stock (10 μg/mL) to each flask. Returned the two control flasks to the incubator.

Transferred 1 mL (1.3×$10^5$) of each TIL lot to the correspondingly labeled T25 flask. Returned flasks to the incubator and incubate upright. Did not disturb until Day 5. This procedure was repeated for all feeder lots tested.

Day 5, Media change. Prepared CM2 with 3000 IU/mL IL-2. 10 mL is needed for each flask. With a 10 mL pipette, transferred 10 mL warm CM2 with 3000 IU/mL IL-2 to each flask. Returned flasks to the incubator and incubated upright until day 7. Repeated for all feeder lots tested.

Day 7, Harvest. Removed flasks from the incubator and transfer to the BSC, care as taken not to disturb the cell layer on the bottom of the flask. Without disturbing the cells growing on the bottom of the flasks, 10 mL of medium was removed from each test flask and 15 mL of medium from each of the control flasks.

Using a 10 mL serological pipet, the cells were resuspended in the remaining medium and mix well to break up any clumps of cells. After thoroughly mixing cell suspension by pipetting, removed 200 μL for cell counting. Counted the TIL using the appropriate standard operating procedure in conjunction with the automatic cell counter equipment. Recorded counts in day 7. This procedure was repeated for all feeder lots tested.

Feeder control flasks were evaluated for replication incompetence and flasks containing TILs were evaluated for fold expansion from day 0.

Day 7, Continuation of Feeder Control Flasks to Day 14. After completing the day 7 counts of the feeder control flasks, 15 mL of fresh CM2 medium containing 3000 IU/mL IL-2 was added to each of the control flasks. The control flasks were returned to the incubator and incubated in an upright position until day 14.

Day 14, Extended Non-proliferation of Feeder Control Flasks. Removed flasks from the incubator and transfer to the BSC, care was taken not to disturb the cell layer on the bottom of the flask. Without disturbing the cells growing on the bottom of the flasks, approximately 17 mL of medium was removed from each control flasks. Using a 5 mL serological pipet, the cells were resuspended in the remaining medium and mixed well to break up any clumps of cells. The volumes were recorded for each flask.

After thoroughly mixing the cell suspension by pipetting, 200 μL was removed for cell counting. The TILs were counted using the appropriate standard operating procedure in conjunction with the automatic cell counter equipment and the counts were recorded. This procedure was repeated for all feeder lots tested.

B. Results and Acceptance Criteria Protocol

Results. The dose of gamma irradiation was sufficient to render the feeder cells replication incompetent. All lots were expected to meet the evaluation criteria and also demonstrated a reduction in the total viable number of feeder cells remaining on day 7 of the REP culture compared to day 0. All feeder lots were expected to meet the evaluation criteria of 100-fold expansion of TIL growth by day 7 of the REP culture. Day 14 counts of Feeder Control flasks were expected to continue the non-proliferative trend seen on day 7.

Acceptance Criteria. The following acceptance criteria were met for each replicate TIL line tested for each lot of feeder cells. Acceptance criteria were two-fold, as shown in Table 37 below, which may be combined with potency assay acceptance criteria using the methods set forth herein.

TABLE 37

| Acceptance Criteria | |
|---|---|
| Test | Acceptance criteria |
| Irradiation of MNC and Replication Incompetence | No growth observed at 7 and 14 days |
| TIL expansion | At least a 100-fold expansion of each TIL (minimum of $1.3 \times 10^7$ viable cells) |

The dose of radiation was evaluated for its sufficiency to render the MNC feeder cells replication incompetent when cultured in the presence of 30 ng/mL OKT3 antibody and 3000 IU/mL IL-2. Replication incompetence was evaluated by total viable cell count (TVC) as determined by automated cell counting on day 7 and day 14 of the REP.

The acceptance criteria was "No Growth," meaning the total viable cell number has not increased on day 7 and day 14 from the initial viable cell number put into culture on Day 0 of the REP.

The ability of the feeder cells to support TIL expansion was evaluated. TIL growth was measured in terms of fold expansion of viable cells from the onset of culture on day 0 of the REP to day 7 of the REP. On day 7, TIL cultures achieved a minimum of 100-fold expansion, (i.e., greater than 100 times the number of total viable TIL cells put into culture on REP day 0), as evaluated by automated cell counting.

Contingency Testing of MNC Feeder Lots that do not meet acceptance criteria. In the event that an MNC feeder lot did not meet the either of the acceptance criteria outlined above, the following steps will be taken to retest the lot to rule out simple experimenter error as its cause.

If there are two or more remaining satellite testing vials of the lot, then the lot was retested. If there were one or no remaining satellite testing vials of the lot, then the lot was failed according to the acceptance criteria listed above.

In order to be qualified, the lot in question and the control lot had to achieve the acceptance criteria above. Upon meeting these criteria, the lot is released for use.

Example 3: Qualifying Individual Lots of Gamma-Irradiated Peripheral Blood Mononuclear Cells This Example describes a novel abbreviated procedure for qualifying individual lots of gamma-irradiated peripheral blood mononuclear cells (PBMC) for use as allogeneic feeder cells in the exemplary methods described herein. This example provides a protocol for the evaluation of irradiated PBMC cell lots for use in the production of clinical lots of TIL. Each irradiated PBMC lot was prepared from an individual donor. Over the course of more than 100 qualification protocols, it has been shown that, in all cases, irradiated PBMC lots from SDBB (San Diego Blood Bank) expand TIL >100-fold on Day 7 of a REP. This modified qualification protocol was intended to apply to irradiated donor PBMC lots from SDBB which were then further tested to verify that the received dose of gamma radiation was sufficient to render them replication incompetent. Once demonstrated that they maintained replication incompetence over the course of 14 days, donor PBMC lots were considered "qualified" for usage to produce clinical lots of TIL.

Gamma-irradiated, growth-arrested PBMC were required for current standard REP of TIL. Membrane receptors on the PBMCs bind to anti-CD3 (clone OKT3) antibody and cross-link to TIL in culture, stimulating the TIL to expand. PBMC lots were prepared from the leukapheresis of whole blood taken from individual donors. The leukapheresis product was subjected to centrifugation over Ficoll-Hypaque, washed, irradiated, and cryopreserved under GMP conditions.

It is important that patients who received TIL therapy not be infused with viable PBMCs as this could result in Graft-Versus-Host Disease (GVHD). Donor PBMCs are therefore growth-arrested by dosing the cells with gamma-irradiation, resulting in double strand DNA breaks and the loss of cell viability of the PBMCs upon reculture.

The evaluation criterion for irradiated PBMC lots was their replication incompetency.

Feeder lots were tested in mini-REP format as if they were to be co-cultured with TIL, using upright T25 tissue culture flasks. The control lot was one lot of irradiated PBMCs, which had historically been shown to meet the evaluation criterion, was run alongside the experimental lots as a control. For each lot of irradiated donor PBMC tested, duplicate flasks were run.

Experimental Protocol—Day 0. Prepared ~90 mL of CM2 medium for each lot of donor PBMC to be tested. Kept CM2 warm in 37° C. water bath. Thawed an aliquot of $6\times10^6$ IU/mL IL-2. Returned the CM2 medium to the BSC, wiping with 70% EtOH prior to placing in hood. For each lot of PBMC tested, removed about 60 mL of CM2 to a separate sterile bottle. Added IL-2 from the thawed $6\times10^6$ IU/mL stock solution to this medium for a final concentration of 3000 IU/mL. Labeled this bottle as "CM2/IL2" (or similar) to distinguish it from the unsupplemented CM2.

Prepare OKT3. Took out the stock solution of anti-CD3 (OKT3) from the 4° C. refrigerator and placed in the BSC. A final concentration of 30 ng/mL OKT3 was used in the media of the mini-REP. Prepared a 10 μg/mL working solution of anti-CD3 (OKT3) from the 1 mg/mL stock solution. Placed in refrigerator until needed.

For each PBMC lot tested, prepare 150 μL of a 1:100 dilution of the anti-CD3 (OKT3) stock. For example, for testing 4 PBMC lots at one time, prepare 600 μl of 10 μg/mL anti-CD3 (OKT3) by adding 6 μL of the 1 mg/mL stock solution to 594 μl of CM2 supplemented with 3000 IU/mL IL-2.

Prepare Flasks. Added 19 mL per flask of CM2/IL-2 to the labeled T25 flasks and placed flasks into 37° C., humidified, 5% $CO_2$ incubator while preparing cells.

Prepare Irradiated PBMCs. Retrieved vials of PBMC lots to be tested from LN2 storage. These were placed at −80° C. or kept on dry ice prior to thawing. Placed 30 mL of CM2 (without IL-2 supplement) into 50 mL conical tubes for each lot to be thawed. Labeled each tube with the different lot numbers of the PBMC to be thawed. Capped tubes tightly and place in 37° C. water bath prior to use. As needed, returned 50 mL conical tubes to the BSC, wiping with 70% EtOH prior to placing in the hood.

Removed a vial PBMC from cold storage and place in a floating tube rack in a 37° C. water bath to thaw. Allowed thaw to proceed until a small amount of ice remains in the vial. Using a sterile transfer pipet, immediately transferred the contents of the vial into the 30 mL of CM2 in the 50 mL conical tube. Removed about 1 mL of medium from the tube to rinse the vial; returned rinse to the 50 mL conical tube. Capped tightly and swirl gently to wash cells.

Centrifuged at 400× g for 5 minutes at room temperature. Aspirated the supernatant and resuspend the cell pellet in 1 mL of warm CM2/IL-2 using a 1000 μL pipet tip. Alternately, prior to adding medium, resuspended cell pellet by dragging capped tube along an empty tube rack. After resuspending the cell pellet, brought volume to 4 mL using CM2/IL-2 medium. Recorded volume.

Removed a small aliquot (e.g., 100 μL) for cell counting using an automated cell counter. Performed counts in duplicate according to the particular automated cell counter SOP. It most likely was necessary to perform a dilution of the PBMC prior to performing the cell counts. A recommended starting dilution was 1:10, but this varied depending on the type of cell counter used. Recorded the counts.

Adjusted concentration of PBMC to $1.3\times10^7$ cells/mL using CM2/IL-2 medium. Mixed well by gentle swirling or by gently aspirating up-and-down using a serological pipet.

Set up Culture Flasks. Returned two labeled T25 flasks to the BSC from the tissue culture incubator. Returned the 10 μg/mL vial of anti-CD3/OKT3 to the BSC. Added 1 mL of the $1.3\times10^7$ PBMC cell suspension to each flask. Added 60 μL of the 10 μg/mL anti-CD3/OKT3 to each flask. Returned capped flasks to the tissue culture incubators for 14 days of growth without disturbance. Placed anti-CD3/OKT3 vial back into the refrigerator until needed for the next lot. Repeated for each lot of PBMC to be evaluated.

Day 14, Measurement of Non-proliferation of PBMC. Returned the duplicate T25 flasks to the BSC. For each flask, using a fresh 10 mL serological pipet, removed ~17 mL from each of the flasks, then carefully pulled up the remaining media to measure the volume remaining in the flasks. Recorded volume.

Mixed sample well by pipetting up and down using the same serological pipet.

Removed a 200 μL sample from each flask for counting. Counted cells using an automated cell counter. Repeat each step for each lot of PBMC being evaluated.

Results. The dose of gamma irradiation was expected to be sufficient to render the feeder cells replication incompetent. All lots were expected to meet the evaluation criterion, demonstrating a reduction in the total viable number of feeder cells remaining on Day 14 of the REP culture compared to Day 0.

Acceptance Criterion. The following acceptance criterion were met for each irradiated donor PBMC lot tested: "No growth"—meant that the total number of viable cells on Day 14 was less than the initial viable cell number put into culture on Day 0 of the REP.

Contingency Testing of MNC Feeder Lots that do not meet acceptance criteria. In the event than an irradiated donor PBMC lot did not meet the acceptance criterion above, the following steps were taken to retest the lot to rule out simple experimental error as the cause of its failure. If there were two or more remaining satellite vials of the lot, then the lot was retested. If there are one or no remaining satellite vials of the lot, then the lot was failed according to the acceptance criterion above.

To be qualified, a PBMC lot going through contingency testing had both the control lot and both replicates of the lot in question achieve the acceptance criterion. Upon meeting this criterion, the lot was then released for use.

Example 4: Preparation of IL-2 Stock Solution

This Example describes the process of dissolving purified, lyophilized recombinant human interleukin-2 into stock samples suitable for use in further tissue culture protocols, including all of those described in the present application and Examples, including those that involve using rhIL-2.

Procedure. Prepared 0.2% Acetic Acid solution (HAc). Transferred 29 mL sterile water to a 50 mL conical tube. Added 1 mL TN acetic acid to the 50 mL conical tube. Mixed well by inverting tube 2-3 times. Sterilized the HAc solution by filtration using a Steriflip filter Prepare 1% HSA in PBS. Added 4 mL of 25% HSA stock solution to 96 mL PBS in a 150 mL sterile filter unit. Filtered solution. Stored at 4° C. For each vial of rhIL-2 prepared, fill out forms.

Prepared rhIL-2 stock solution ($6\times10^6$ IU/mL final concentration). Each lot of rhIL-2 was different and required information found in the manufacturer's Certificate of Analysis (COA), such as: 1) Mass of rhIL-2 per vial (mg), 2) Specific activity of rhIL-2 (IU/mg) and 3) Recommended 0.2% HAc reconstitution volume (mL).

Calculated the volume of 1% HSA required for rhIL-2 lot by using the equation below:

$$\left(\frac{\text{Vial Mass (mg)} \times \text{Biological Activity} \left(\frac{IU}{\text{mg}}\right)}{6\times10^6\ \frac{IU}{\text{mL}}}\right) - HAc\ \text{vol (mL)} = 1\%\ HSA\ \text{vol (mL)}$$

For example, according to the COA of rhIL-2 lot 10200121 (Cellgenix), the specific activity for a 1 mg vial is $25\times10^6$ IU/mg. It recommends reconstituting the rhIL-2 in 2 mL 0.2% HAc.

$$\left(\frac{1\ \text{mg} \times 25\times10^6\ \frac{IU}{\text{mg}}}{6\times10^6\ \frac{IU}{\text{mL}}}\right) - 2\ \text{mL} = 2.167\ \text{mL}\ HSA$$

Wiped rubber stopper of IL-2 vial with alcohol wipe. Using a 16G needle attached to a 3 mL syringe, injected recommended volume of 0.2% HAc into vial. Took care to not dislodge the stopper as the needle is withdrawn. Inverted vial 3 times and swirled until all powder is dissolved. Carefully removed the stopper and set aside on an alcohol wipe. Added the calculated volume of 1% HSA to the vial.

Storage of rhIL-2 solution: for short-term storage (<72 hours), stored vial at 4° C. For long-term storage (>72 hours), aliquoted vial into smaller volumes and stored in cryovials at −20° C. until ready to use. Avoided freeze/thaw cycles. Expired 6 months after date of preparation. RhIL-2 labels included vendor and catalog number, lot number, expiration date, operator initials, concentration and volume of aliquot.

Example 5: Cryopreservation Process

This example describes a cryopreservation process method for TILs prepared with the procedures described herein using the CryoMed Controlled Rate Freezer, Model 7454 (Thermo Scientific).

The equipment used was as follows: aluminum cassette holder rack (compatible with CS750 freezer bags), cryostorage cassettes for 750 mL bags, low pressure (22 psi) liquid nitrogen tank, refrigerator, thermocouple sensor (ribbon type for bags), and CryoStore CS750 Freezing bags (OriGen Scientific).

The freezing process provides for a 0.5° C. rate from nucleation to −20° C. and 1° C. per minute cooling rate to −80° C. end temperature. The program parameters are as follows: Step 1—wait at 4° C.; Step 2: 1.0° C./min (sample temperature) to −4° C.; Step 3: 20.0° C./min (chamber temperature) to −45° C.; Step 4: 10.0° C./min (chamber temperature) to −10.0° C.; Step 5: 0.5° C./min (chamber temperature) to −20° C.; and Step 6: 1.0° C./min (sample temperature) to −80° C.

Example 6: Gen 2 and Gen 3 Exemplary Processes

This example demonstrates the Gen 2 and Gen 3 processes. Process Gen 2 and Gen 3 TILs are generally composed of autologous TIL derived from an individual patient through surgical resection of a tumor and then expanded ex vivo. The priming first expansion step of the Gen 3 process was a cell culture in the presence of interleukin-2 (IL-2) and the monoclonal antibody OKT3, which targets the T cell co-receptor CD3 on a scaffold of irradiated peripheral blood mononuclear cells (PBMCs). Exemplary Gen 2 processes are described in U.S. Pat. Nos. 11,083,752 and 11,168,304, the disclosures of which are incorporated by reference herein, and wherein the disclosures of which may be modified to replace PBMCs with aAPCs or antigen presenting cells described elsewhere herein, such as Thp1 or U937 cells, optionally genetically modified and optionally irradiated.

The manufacture of Gen 2 TIL products consists of two phases: 1) pre-Rapid Expansion (Pre-REP) and 2) Rapid Expansion Protocol (REP). During the Pre-REP resected tumors were cut up into ≤50 fragments 2-3 mm in each dimension which were cultured with serum-containing culture medium (RPMI 1640 media containing 10% HuSAB supplemented) and 6,000 IU/mL of interleukin-2 (IL-2) for a period of 11 days. On day 11 TILs were harvested and introduced into the large-scale secondary REP expansion. The REP consists of activation of ≤200×10$^6$ of the viable cells from pre-REP in a co-culture of 5×10$^9$ irradiated allogeneic PBMC feeder cells (or aAPCs or antigen presenting cells described elsewhere herein, such as Thp1 or U937 cells, optionally genetically modified and optionally irradiated) loaded with 150 μg of monoclonal anti-CD3 antibody (OKT3) in a 5 L volume of CM2 supplemented with 3000 IU/mL of rhIL-2 for 5 days. On day 16 the culture is volume reduced 90% and the cell fraction is split into multiple G-Rex-500 flasks at ≥1×10$^9$ viable lymphocytes/flask and QS to 5L with CM4. TILs are incubated an additional 6 days. The REP is harvested on day 22, washed, formulated, and cryo-preserved prior to shipping at −150° C. to the clinical site for infusion.

The manufacture of Gen 3 TIL products consists of three phases: 1) Priming First Expansion Protocol, 2) Rapid Second Expansion Protocol (also referred to as rapid expansion phase or REP), and 3) Subculture Split. To effect the Priming First Expansion TIL propagation, resected tumor was cut up into ≤120 fragments 2-3 mm in each dimension. On day 0 of the Priming First Expansion, a feeder layer of approximately 2.5×10$^8$ allogeneic irradiated PBMCs feeder cells loaded with OKT-3 was established on a surface area of approximately 100 cm$^2$ in each of 3 100 MCS vessels. The tumor fragments were distributed among and cultured in the 3 100 MCS vessels each with 500 mL serum-containing CM1 culture medium and 6,000 IU/mL of Interleukin-2 (IL-2) and 15 ug OKT-3 for a period of 7 days. On day 7, REP was initiated by incorporating an additional feeder cell layer of approximately 5×10$^8$ allogeneic irradiated PBMCs feeder cells loaded with OKT-3 into the tumor fragmented culture phase in each of the three 100 MCS vessels and culturing with 500 mL CM2 culture medium and 6,000 IU/mL IL-2 and 30 μg OKT-3. The REP initiation was enhanced by activating the entire Priming First Expansion culture in the same vessel using closed system fluid transfer of OKT3 loaded feeder cells into the 100MCS vessel. For Gen 3, the TIL scale up or split involved process steps where the whole cell culture was scaled to a larger vessel through closed system fluid transfer and was transferred (from 100 M flask to a 500 M flask) and additional 4 L of CM4 media was added. The REP cells were harvested on day 16, washed, formulated, and cryo-preserved prior to shipping at −150° C. to the clinical site for infusion. In place of PBMCs, aAPCs or antigen presenting cells described elsewhere herein may be employed, such as Thp1 or U937 cells, optionally genetically modified and optionally irradiated.

Overall, the Gen 3 process is a shorter, more scalable, and easily modifiable expansion platform that will accommodate to fit robust manufacturing and process comparability.

TABLE 38

Comparison of Exemplary Gen 2 and Exemplary Gen 3 manufacturing process.

| Step | Process (Gen 2) | Process (Gen 3) |
|---|---|---|
| Pre REP-day 0 | Up to 50 fragments, 1 G-Rex 100MCS, 11 days<br>In 1 L of CM1 media + IL-2 (6000 IU/mL) | Whole tumor up to 120 fragments divided evenly among up to 3 flasks. 1 flask: 1-60 fragments<br>2 flasks: 61-89 fragments<br>3 flasks 90-120 fragments<br>7 days in 500 mL of CM1 media + IL-2 (6000 IU/mL)<br>2.5 × 10$^8$ feeder cells/flask<br>15 ug OKT-3/flask |
| REP Initiation | Direct to REP, Day 11, <200 × 10$^6$ TIL<br>(1)G-Rex 500MCS in 5 L CM2 media<br>IL-2 (3000 IU/mL)<br>5 × 10$^9$ feeder cells<br>150 ug OKT-3 | Direct to REP, Day 7, all cells, same G-Rex 100MCS<br>Add 500 CM2 media<br>IL-2 (6000 IU/mL)<br>5 × 10$^8$ feeder cells/flask<br>30 ug OKT-3/flask |
| TIL propagation or Scale up | Volume reduce and split cell fraction in up to 5 G-Rex 500MCS<br>4.5 L CM4 media + IL-2 (3000 IU/mL)<br>≥1 × 10$^9$ TVC/flask<br>Split day 16 | Each G-Rex 100MCS(1 L) transfers to 1 G-Rex 500MCS<br>Add 4 L CM4 media + IL-2 (3000 IU/mL)<br>Scale up on day 9 to 11 |

TABLE 38-continued

| Comparison of Exemplary Gen 2 and Exemplary Gen 3 manufacturing process. | | |
|---|---|---|
| Step | Process (Gen 2) | Process (Gen 3) |
| Harvest | Harvest day 22, LOVO-automated cell washer | Harvest day 16 LOVO-automated cell washer |
| Final formulation | Cryopreserved Product 300 IU/mL IL2- CS10 in $LN_2$, multiple aliquots | Cryopreserved product 300 IU/mL IL-2-CS10 in $LN_2$, multiple aliquots |
| Process time | 22 days | 16 days |

On day 0, for both processes, the tumor was washed 3 times and the fragments were randomized and divided into two pools; one pool per process. For the Gen 2 Process, the fragments were transferred to one –GREX 100MCS flask with 1 L of CM1 media containing 6,000 IU/mL rhIL-2. For the Gen 3 Process, fragments were transferred to one G-Rex 100MCS flask with 500 mL of CM1 containing 6,000 IU/mL rhIL-2, 15 ug OKT-3 and $2.5\times10^8$ feeder cells. Seeding of TIL for Rep initiation day occurred on different days according to each process. For the Gen 2 Process, in which the G-Rex 100MCS flask was 90% volume reduced, collected cell suspension was transferred to a new G-Rex 500MCS to start REP initiation on day 11 in CM2 media containing IL-2 (3000 IU/mL), plus $5\times10^9$ feeder cells and OKT-3 (30 ng/mL). Cells were expanded and split on day 16 into multiple G-Rex 500 MCS flasks with CM4 media with IL-2 (3000 IU/mL) per protocol. The culture was then harvested and cryopreserved on day 22 per protocol. For the Gen 3 process, the REP initiation occurred on day 7, in which the same G-Rex 100MCS used for REP initiation. Briefly, 500 mL of CM2 media containing IL-2 (6000 IU/mL) and $5\times10^8$ feeder cells with 30 ug OKT-3 was added to each flask. On day 9-11 the culture was scaled up. The entire volume of the G-Rex 100M (1L) was transferred to a G-Rex 500MCS and 4L of CM4 containing IL-2 (3000 IU/mL) was added. Flasks were incubated 5 days. Cultures were harvested and cryopreserved on Day 16.

Three different tumors were included in the comparison, two lung tumors (L4054 and L4055) and one melanoma tumor (M1085T).

CM1 (culture media 1), CM2 (culture media 2), and CM4 (culture media 4) media were prepared in advance and held at 4° C. for L4054 and L4055. CM1 and CM2 media were prepared without filtration to compare cell growth with and without filtration of media.

Media was warmed at 37° C. up to 24 hours in advance for L4055 tumor on REP initiation and scale-up.

Results. Gen 3 results fell within 30% of Gen 2 for total viable cells achieved. Gen 3 final product exhibited higher production of IFN-γ after restimulation. Gen 3 final product exhibited increased clonal diversity as measured by total unique CDR3 sequences present. Gen 3 final product exhibited longer mean telomere length.

Pre-REP and REP expansion on Gen 2 and Gen 3 processes followed the procedures described above. For each tumor, the two pools contained equal number of fragments. Due to the small size of tumors, the maximum number of fragments per flask was not achieved. Total pre-REP cells (TVC) were harvested and counted at day 11 for the Gen 2 process and at day 7 for the Gen 3 process. To compare the two pre-REP arms, the cell count was divided over the number of fragments provided in the culture in order to calculate an average of viable cells per fragment. As indicated in Table 39 below, the Gen 2 process consistently grew more cells per fragment compared to the Gen 3 Process. An extrapolated calculation of the number of TVC expected for Gen 3 process at day 11, which was calculated dividing the pre-REP TVC by 7 and then multiply by 11.

TABLE 39

| Pre-REP cell counts | | | | | | |
|---|---|---|---|---|---|---|
| | Tumor ID | | | | | |
| | L4054 | | L4055* | | M1085T | |
| Process | Gen 2 | Gen 3 | Gen 2 | Gen 3 | Gen 2 | Gen 3 |
| pre-REP TVC | 1.42E+08 | 4.32E+07 | 2.68E+07 | 1.38E+07 | 1.23E+07 | 3.50E+06 |
| Number of fragments | 21 | 21 | 24 | 24 | 16 | 16 |
| Average TVC per fragment at pre-REP | 6.65E+06 | 2.06E+06 | 1.12E+06 | 5.75E+05 | 7.66E+05 | 2.18E+05 |
| Gen 3 extrapolated value at pre REP day 11 | N/A | 6.79E+07 | N/A | 2.17E+07 | N/A | 5.49E+06 |

*L4055, unfiltered media.

For the Gen 2 and Gen 3 processes, TVC was counted per process condition and percent viable cells was generated for each day of the process. On harvest, day 22 (Gen 2) and day 16 (Gen 3) cells were collected and the TVC count was established. The TVC was then divided by the number of fragments provided on day 0, to calculate an average of viable cells per fragment. Fold expansion was calculated by dividing harvest TVC by over the REP initiation TVC. As exhibited in Table 40, comparing Gen 2 and the Gen 3, fold expansions were similar for L4054; in the case of L4055, the fold expansion was higher for the Gen 2 process. Specifically, in this case, the media was warmed up 24 in advance of REP initiation day. A higher fold expansion was also observed in Gen 3 for M1085T. An extrapolated calculation of the number of TVC expected for Gen 3 process at day 22, which was calculated dividing the REP TVC by 16 and then multiply by 22.

TABLE 40

Total viable cell count and fold expansion on TIL final product

| | Tumor ID | | | | | |
|---|---|---|---|---|---|---|
| | L4054 | | L4055 | | M1085T | |
| Process | Gen 2 | Gen 3 | Gen 2 | Gen 3 | Gen 2 | Gen 3 |
| # Fragments | 21 | 21 | 24 | 24 | 16 | 16 |
| TVC/fragment (at harvest) | 3.18E+09 | 8.77E+08 | 2.30E+09 | 3.65E+08 | 7.09E+08 | 4.80E+08 |
| REP initiation | 1.42E+08 | 4.32E+07 | 2.68E+07 | 1.38E+07 | 1.23E+07 | 3.50E+06 |
| Scale up | 3.36E+09 | 9.35E+08 | 3.49E+09 | 8.44E+08 | 1.99E+09 | 3.25E+08 |
| Harvest | 6.67E+10 | 1.84E+10 | 5.52E+10 | 8.76E+09 | 1.13E+10 | 7.68E+09 |
| Fold Expansion Harvest/REP initiation | 468.4 | 425.9 | 2056.8 | 634.6 | 925.0 | 2197.2 |
| Gen 3 extrapolated value at REP harvest day 22 | N/A | 2.53E+10 | N/A | 1.20E+10 | N/A | 1.06E+10 |

* L4055, unfiltered media.

Upon harvest, the final TIL REP products were compared against release criteria for % viability. All of the conditions for the Gen 2 and Gen 3 processes surpassed the 70% viability criterion and were comparable across processes and tumors.

TABLE 41

% Viability of REP (TIL final product).

| | Tumor ID | | | | | |
|---|---|---|---|---|---|---|
| | L4054 | | L4055 | | M1085T | |
| Process | Gen 2 | Gen 3 | Gen 2 | Gen 3 | Gen 2 | Gen 3 |
| REP initiation | 98.23% | 97.97% | 97.43% | 92.03% | 81.85% | 68.27% |
| Scale up | 94.00% | 93.57% | 90.50% | 95.93% | 78.55% | 71.15% |
| Harvest | 87.95% | 89.85% | 87.50% | 86.70% | 86.10% | 87.45% |

Due to the number of fragments per flask below the maximum required number, an estimated cell count at harvest day was calculated for each tumor. The estimation was based on the expectation that clinical tumors were large enough to seed 2 or 3 flasks on day 0.

TABLE 42

Extrapolated estimated cell count calculation to full scale (2 and 3 flasks) for the Gen 3 process.

| | Tumor ID | | | | | |
|---|---|---|---|---|---|---|
| | L4054 | | L4055 | | M1085T | |
| Gen 3 Process | 2 flasks | 3 flasks | 2 flasks | 3 flasks | 2 flasks | 3 flasks |
| Estimate Harvest | 3.68E+10 | 5.52E+10 | 1.75E+10 | 2.63E+10 | 1.54E+10 | 2.30E+10 |

Activation and exhaustion markers were analyzed in TIL from two, tumors L4054 and L4055 to compare the final TIL product by from the Gen 2 and Gen 3 TIL expansion processes. Activation and exhaustion markers were comparable between the Gen 2 and Gen 3 processes.

Interferon gamma secretion upon restimulation. On harvest day, day 22 for Gen 2 and day 16 for Gen 3, TIL underwent an overnight restimulation with coated anti-CD3 plates for L4054 and L4055. The restimulation on M1085T was performed using anti-CD3, CD28, and CD137 beads. Supernatant was collected after 24 hours of the restimulation in all conditions and the supernatant was frozen. IFN-γ analysis by ELISA was assessed on the supernatant from both processes at the same time using the same ELISA plate. Higher production of IFN-γ from the Gen 3 process was observed in the three tumors analyzed.

Measurement of IL-2 levels in culture media. To compare the IL-2 consumption between Gen 2 and Gen 3 process, cell supernatant was collected on REP initiation, scale up, and harvest day, on tumor L4054 and L4055. The quantity of IL-2 in cell culture supernatant was measured by Quantitate ELISA Kit from R&D. The general trend indicates that the IL-2 concentration remains higher in the Gen 3 process when compared to the Gen 2 process. This is likely due to the higher concentration of IL-2 on REP initiation (6000 IU/mL) for Gen 3 coupled with the carryover of the media throughout the process.

Immunophenotyping—phenotypic marker comparisons on TIL final product. Three tumors L4054, L4055, and M1085T underwent TIL expansion in both the Gen 2 and Gen 3 processes. Upon harvest, the REP TIL final products were subjected to flow cytometry analysis to test purity, differentiation, and memory markers. For all the conditions the percentage of TCR a/b+ cells was over 90%.

TIL harvested from the Gen 3 process showed a higher expression of CD8 and CD28 compared to TIL harvested from the Gen 2 process. The Gen 2 process showed a higher percentage of CD4+.

TIL harvested from the Gen 3 process showed a higher expression on central memory compartments compared to TIL from the Gen 2 process.

Metabolic substrate and metabolite analysis. The levels of metabolic substrates such as D-glucose and L-glutamine were measured as surrogates of overall media consumption. Their reciprocal metabolites, such lactic acid and ammonia, were measured. Glucose is a simple sugar in media that is utilized by mitochondria to produce energy in the form of ATP. When glucose is oxidized, lactic acid is produced (lactate is an ester of lactic acid). Lactate is strongly produced during the cells exponential growth phase. High levels of lactate have a negative impact on cell culture processes.

Spent media for L4054 and L4055 was collected at REP initiation, scale up, and harvest days for both process Gen 2 and Gen 3. The spent media collection was for Gen 2 on Day 11, day 16 and day 22; for Gen 3 was on day 7, day 11 and day 16. Supernatant was analyzed on a CEDEX Bio-analyzer for concentrations of glucose, lactic acid, glutamine, GlutaMax, and ammonia.

L-glutamine is an unstable essential amino acid required in cell culture media formulations. Glutamine contains an amine, and this amide structural group can transport and deliver nitrogen to cells. When L-glutamine oxidizes, a toxic ammonia by-product is produced by the cell. To counteract the degradation of L-glutamine the media for the Gen 2 and Gen 3 processes was supplemented with Glutamax, which is more stable in aqueous solutions and does not spontaneously degrade. In the two tumor lines, the Gen 3 arm showed a decrease in L-glutamine and Glutamax during the process and an increase in ammonia throughout the REP. In the Gen 2 arm a constant concentration of L-glutamine and Glutamax, and a slight increase in the ammonia production was observed. The Gen 2 and Gen 3 processes were comparable at harvest day for ammonia and showed a slight difference in L-glutamine degradation.

Telomere repeats by Flow-FISH. Flow-FISH technology was used to measure the average length of the telomere repeat on L4054 and L4055 under Gen 2 and Gen 3 process. The determination of a relative telomere length (RTL) was calculated using Telomere PNA kit/FITC for flow cytometry analysis from DAKO. Gen 3 showed comparable telomere length to Gen 2.

CD3 Analysis. To determine the clonal diversity of the cell products generated in each process, TIL final product harvested for L4054 and L4055, were sampled and assayed for clonal diversity analysis through sequencing of the CDR3 portion of the T cell receptors.

Table 43 shows a comparison between Gen 2 and Gen 3 of percentage shared unique CDR3 sequences on L4054 on TIL harvested cell product. 199 sequences are shared between Gen 3 and Gen 2 final product, corresponding to 97.07% of top 80% of unique CDR3 sequences from Gen 2 shared with Gen 3 final product.

TABLE 43

Comparison of shared uCDR3 sequences between Gen 2 and Gen 3 processes on L4054.

| # uCDR3 | All uCDR3's | | Top 80% uCDR3's | |
|---|---|---|---|---|
| (% Overlap) | Gen 2 | Gen 3 | Gen 2 | Gen 3 |
| Gen 2-L4054 | 8915 | 4355 (48.85%) | 205 | 199 (97.07%) |
| Gen 3-L4054 | — | 18130 | — | 223 |

Table 44 shows a comparison between Gen 2 and Gen 3 of percentage shared unique CDR3 sequences on L4055 on TIL harvested cell product. 1833 sequences are shared between Gen 3 and Gen 2 final product, corresponding to 99.45% of top 80% of unique CDR3 sequences from Gen 2 shared with Gen 3 final product.

TABLE 44

Comparison of shared uCDR3 sequences between Gen 2 and Gen 3 processes on L4055.

| # uCDR3 | All uCDR3's | | Top 80% uCDR3's | |
|---|---|---|---|---|
| (% Overlap) | Gen 2 | Gen 3 | Gen 2 | Gen 3 |
| Gen 2-L4055 | 12996 | 6599 (50.77%) | 1843 | 1833 (99.45%) |
| Gen 3-L4055 | — | 27246 | — | 2616 |

CM1 and CM2 media was prepared in advanced without filtration and held at 4 degree C. until use for tumor L4055 to use on Gen 2 and Gen 3 process.

Media was warmed up at 37 degree C. for 24 hours in advance for tumor L4055 on REP initiation day for Gen 2 and Gen 3 process.

LDH was not measured in the supernatants collected on the processes.

M1085T TIL cell count was executed with K2 cellometer cell counter.

On tumor M1085T, samples were not available such as supernatant for metabolic analysis, TIL product for activation and exhaustion markers analysis, telomere length and CD3-TCR vb Analysis.

Conclusions. This example compares 3 independent donor tumors tissue in terms of functional quality attributes, plus extended phenotypic characterization and media consumption among Gen 2 and Gen 3 processes.

Gen 2 and Gen 3 pre-REP and REP expansion comparison were evaluated in terms of total viable cells generated and viability of the total nucleated cell population. TVC cell doses at harvest day was not comparable between Gen 2 (22 days) and Gen 3 (16 days). Gen 3 cell doses were lower than Gen 2 at around 40% of total viable cells collected at harvest.

An extrapolated cell number was calculated for Gen 3 process assuming the pre-REP harvest occurred at day 11 instead day 7 and REP Harvest at Day 22 instead day 16. In both cases, Gen 3 shows a closer number on TVC compared to the Gen 2 process, indicating that the early activation could allow an overall better performance on TIL growth.

In the case of extrapolated value for extra flasks (2 or 3) on Gen 3 process assuming a bigger size of tumor processed, and reaching the maximum number of fragments required per process as described. It was observed that a similar dose can be reachable on TVC at Day 16 Harvest for Gen 3 process compared to Gen 2 process at Day 22. This observation is important and indicates an early activation of the culture can allow better performance of TIL in less processing time.

Gen 2 and Gen 3 pre-REP and REP expansion comparison were evaluated in terms of total viable cells generated and viability of the total nucleated cell population. TVC cell doses at harvest day was not comparable between Gen 2 (22 days) and Gen 3 (16 days). Gen 3 cell doses were lower than Gen 2 at around 40% of total viable cells collected at harvest.

In terms of phenotypic characterization, a higher CD8+ and CD28+ expression was observed on three tumors on Gen 3 process compared to Gen 2 process. This data indicates the Gen 3 process has improved attributes of final TIL product compared to Gen 2.

Gen 3 process showed slightly higher central memory compartments compared to Gen 2 process.

Gen 2 and Gen 3 process showed comparable activation and exhaustion markers, despite the shorter duration of the Gen 3 process.

IFN gamma (IFN-γ) production was 3 times higher on Gen 3 final product compared to Gen 2 in the three tumors analyzed. This data indicates the Gen 3 process generated a highly functional and more potent TIL product as compared to the Gen 2 process, possibly due to the higher expression of CD8 and CD28 expression on Gen 3. Phenotypic characterization suggested positive trends in Gen 3 toward CD8+, CD28+ expression on three tumors compared to Gen 2 process.

Telomere length on TIL final product between Gen 2 and Gen 3 were comparable.

Glucose and Lactate levels were comparable between Gen 2 and Gen 3 final product, suggesting the levels of nutrients on the media of Gen 3 process were not affected due to the non-execution of volume reduction removal in each day of the process and less volume media overall in the process, compared to Gen 2.

Overall Gen 3 process showed a reduction almost two times of the processing time compared to Gen 2 process, which would yield a substantial reduction on the cost of goods (COGs) for TIL product expanded by the Gen 3 process.

IL-2 consumption indicates a general trend of IL-2 consumption on Gen 2 process, and in Gen 3 process IL-2 was higher due to the non-removal of the old media.

The Gen 3 process showed a higher clonal diversity measured by CDR3 TCRab sequence analysis.

The addition of feeders and OKT-3 on day 0 of the pre-REP allowed an early activation of TIL and overall a better growth TIL performance using the Gen 3 process.

Table 45 describes various embodiments and outcomes for the Gen 3 process as compared to the current Gen 2 process.

TABLE 45

Exemplary Gen 3 process features.

| Step | Process Gen 2 | Process Gen 3 embodiment |
|---|---|---|
| Pre REP-day 0 | ≤50 fragments | ≤240 fragments |
| | 1X G-Rex 100MCS | ≤60 fragments/flask |
| | 1 L media | ≤4 flasks |
| | IL-2 (6000 IU/mL) | ≤2 L media (500 mL/flask) |
| | 11 days | IL-2 (6000 IU/mL) |
| | | 2.5 × $10^8$ feeder cells/flask |
| | | 15 ug OKT3/flask |
| REP | Fresh TIL direct to REP | Fresh TIL direct to REP |
| Initiation | Day 11 | Day 7 |
| | ≤200 × $10^6$ viable cells | Activate entire culture |
| | 5 × $10^9$ feeder cells | 5 × $10^8$ feeder cells |
| | G-Rex 500MCS | 30 ug OKT3/flask |
| | 5 L CM2 media + IL-2 (3000 IU/mL) | G-Rex 100MCS |
| | 150 ug OKT3 | 500 mL media + IL-2(6000 IU/mL) |
| TIL Sub-culture or | ≤5 G-Rex 500MCS | ≤4 G-Rex 500MCS |
| Scale up | ≤1 × 10 viable cells/flask | Scale up entire culture |
| | 5 L/flask | 4 L/flask |
| | Day 16 | Day 10-11 |
| Harvest | Harvest Day 22, | Harvest Day 16 |
| | LOVO-automated cell washer | LOVO-automated cell washer |
| | 2 wash cycles | 5 wash cycles |
| Final formulation | Cryopreserved Product | Cryopreserved product |
| | 300 IU/mL IL2- CS10 in $LN_2$, | 300 IU/mL IL-2-CS10 in $LN_2$, |
| | multiple aliquots | multiple aliquots |
| Process time | 22 days | 16 days |

Example 7: An Exemplary Embodiment of the Gen 3 Expansion Process at Day 0

Prepared tumor wash media. Media warmed prior to start. Added 5 mL of gentamicin (50 mg/mL) to the 500 mL bottle of HBSS. Added 5 mL of Tumor Wash Media to a 15 mL conical to be used for OKT3 dilution. Store at room temperature (RT).

Prepared feeder cell (PBMC) bags. Sterilely transferred feeder cells to feeder cell bags and stored at 37° C. until use or freeze. Counted feeder cells if at 37° C. Thawed and then counted feeder cells if frozen. In place of PBMCs, aAPCs or antigen presenting cells described elsewhere herein may be employed, such as Thp1 or U937 cells, optionally genetically modified and optionally irradiated.

Optimal range for the feeder cell concentration is between $5\times10^4$ and $5\times10^6$ cells/mL. Prepared four conical tubes with 4.5 mL of AIM-V. Added 0.5 mL of cell fraction for each cell count.

If total viable feeder cell number was ≥$1\times10^+$ cells, proceeded to the next step to adjust the feeder cell concentration. Calculated the volume of feeder cells to remove from the first feeder cell bag in order to add $1\times10^+$ cells to a second feeder cell bag.

Using the p1000 micropipette, transferred 900 μL of Tumor Wash Media to the OKT3 aliquot (100 μL). Using a syringe and sterile technique, drew up 0.6 mL of OKT3 and added into the second feeder cell bag. Adjusted media volume to a total volume of 2L. Transferred the second feeder cells bag to the incubator.

OKT3 formulation details: OKT3 may be aliquoted and frozen in original stock concentration from the vial (1 mg/mL) in 100 μL aliquots. ~10× aliquots per 1 mL vial. Stored at −80° C. Day 0: 15 μg/flask, i.e. 30 ng/mL in 500 mL-60 μL max ~ 1 aliquot.

Prepared tumor samples. Obtained 6-well plate and 100 mm petri dishes (4 total). Labeled the 6 well plate 'Excess Tumor Pieces'. Labeled one each of the four 100 mm petri dishes as 'Wash_01', 'Wash_02', 'Wash_03', 'Wash_04', and 'Holding'.

Added 5 mL of Tumor Wash Medium into all wells of the 6-well plate labelled Excess Tumor Pieces. Kept the Tumor Wash Medium available for further use in keeping the tumor hydrated during dissection.

Added 50 mL of Tumor Wash Medium to each 100 mm petri dish labelled Wash_01, Wash_02, Wash_03, and Holding. Using a marker, label each petri dish as Dissection 1 through Dissection 4. Incubated the tumor at ambient temperature in Wash_01 for ≥3 min. Incubated the tumor at ambient temperature in Wash_02 for ≥3 min. Incubated the tumor at ambient temperature in Wash_03 for ≥3 min. After washes were completed, moved tumor to the 'Holding' dish to ensure tissue stays hydrated.

While tumor incubations were in progress, transferred 10 mL of tumor shipping medium into a tube labelled Tumor Shipping Medium. Drew 10 mL of the Tumor Shipping Medium into a syringe and inoculated one each anaerobic and aerobic sterility bottle with 5 mL of tumor shipping medium.

Placed ruler under the petri dish lid for the entirety of the dissection process. Measured and recorded length of the tumor and the number of fragments. Dissected the tumor into four intermediate pieces or group into four groups of equivalent volume and conserving the tumor structure of each intermediate piece. Keep tumor pieces hydrated.

Transferred any intermediate tumor pieces not being actively dissected to the Holding dish to keep the tissue hydrated.

Dissected the tumor into 27 $mm^3$ fragments (3×3×3 mm), using the ruler under the Dissection dish lid as a reference. Dissected intermediate fragment until 60 fragments were reached. Counted total number of final fragments and prepared G-Rex 100MCS flasks according to the number of final fragments generated (generally 60 fragments per flask).

Retained favorable tissue fragments in the conical tubes labeled as Fragments Tube 1 through Fragments Tube 4. Calculated the number of G-Rex 100MCS flasks to seed with feeder cell suspension according to the number of fragments tubes originated.

Removed feeder cells bag from the incubator and seed the G-Rex 100MCS. Label as D0 (Day 0).

Tumor fragment addition to culture in G-Rex 100 MCS. Under sterile conditions, unscrewed the cap of the G-Rex 100MCS labelled Tumor Fragments Culture (DO) 1 and the 50 mL conical tube labelled Fragments Tube. Swirled the opened Fragments Tube 1 and, at the same time, slightly lifted the cap of the G-Rex 100MCS. Added the medium with the fragments to the G-Rex 100MCS while being swirled. Recorded the number of fragments transferred into the G-Rex 100MCS.

Once the fragments were located at the bottom of the GREX flask, drew 7 mL of media and created seven 1 mL aliquots-5 mL for extended characterization and 2 mL for sterility samples. Stored the 5 aliquots (final fragment culture supernatant) for extended characterization at −20° C. until needed.

Inoculated one anaerobic BacT/Alert bottle and one aerobic BacT/Alert bottle each with 1 mL of final fragment culture supernatant. Repeat for each flask sampled.

Example 8: An Exemplary Embodiment of the Gen 3 Expansion Process at Day 7-8

Prepared feeder cell bags. Thawed feeder bags for 3-5 minutes in 37° C. water bath when frozen. Counted feeder cells if frozen.

Optimal range for the feeder cell concentration is between $5\times10^4$ and $5\times10^6$ cells/mL. Prepared four conical tubes with 4.5 mL of AIM-V. Added 0.5 mL of cell fraction for each cell count into a new cryovial tube. Mixed the samples well and proceeded with the cell count.

If total viable feeder cell number was $\geq2\times10^+$ cells, proceeded to the next step to adjust the feeder cell concentration. Calculated the volume of feeder cells to remove from the first feeder cell bag in order to add $2\times10^9$ cells to the second feeder cell bag.

Using the p1000 micropipette, transfer 900 μL of HBSS to a 100 μL OKT3 aliquot. Mix by pipetting up and down 3 times. Prepared two aliquots.

OKT3 formulation details: OKT3 may be aliquoted and frozen in original stock concentration from the vial (1 mg/mL) in 100 μL aliquots. ~10× aliquots per 1 mL vial. Stored at −80 C. Day 7/8: 30 μg/flask, i.e. 60 ng/mL in 500 mL-120 μl max ~2 aliquots.

Using a syringe and sterile technique, drew up 0.6 mL of OKT3 and added into the feeder cell bag, ensuring all added. Adjusted media volume to a total volume of 2 L. Repeated with second OKT3 aliquot and added to the feeder cell bag. Transferred the second feeder cells bag to the incubator.

Preparation of G-Rex 100MCS flask with feeder cell suspension. Recorded the number of G-Rex 100MCS flasks to process according to the number of G-Rex flasks generated on Day 0. Removed G-Rex flask from incubator and removed second feeder cells bag from incubator.

Removal of supernatant prior to feeder cell suspension addition. Connected one 10 mL syringe to the G-Rex 100 flask and drew up 5 mL of media. Created five 1 mL aliquots ~5 mL for extended characterization and stored the 5 aliquots (final fragment culture supernatant) for extended characterization at −20° C. until requested for analysis. Labeled and repeated for each G-Rex 100 flask.

Prepare 5-20×1 mL samples for characterization, depending on number of flasks:

5 mL=1 flask
10 mL=2 flasks
15 mL=3 flasks
20 mL=4 flasks

Continued seeding feeder cells into the G-Rex 100 MCS and repeated for each G-Rex 100 MCS flask. Using sterile transfer methods, gravity transferred 500 mL of the second feeder cells bag by weight (assume 1 g=1 mL) into each G-Rex 100 MCS flask and recorded amount. Labeled as Day 7 culture and repeated for each G-Rex 100 flask. Transferred G-Rex 100MCS flasks to the incubator.

Example 9: An Exemplary Embodiment of the Gen 3 Expansion Process at Day 10-11

Removed the first G-Rex 100MCS flask and using sterile conditions removed 7 mL of pre-process culture supernatant using a 10 mL syringe. Created seven 1 mL aliquots-5 mL for extended characterization and 2 mL for sterility samples.

Mixed the flask carefully and using a new 10 mL syringe remove 10 mL supernatant and transfer to a 15 mL tube labelled as D10/11 mycoplasma supernatant.

Mixed the flask carefully and using a new syringe removed the volume below according to how many flasks were to be processed:

1 flask=40 mL
2 flask=20 mL/flask
3 flask=13.3 mL/flask
4 flask=10 mL/flask

A total of 40 mL should be pulled from all flasks and pooled in a 50 mL conical tube labeled 'Day 10/11 QC Sample' and stored in the incubator until needed. Performed a cell count and allocated the cells.

Stored the 5 aliquots (pre-process culture supernatant) for extended characterization at ≤−20° C. until needed. Inoculated one anaerobic BacT/Alert bottle and one aerobic BacT/Alert bottle each with 1 mL of pre-process culture supernatant.

Continued with cell suspension transferred to the G-Rex 500MCS and repeated for each G-Rex 100MCS. Using sterile conditions, transferred the contents of each G-Rex 100MCS into a G-Rex 500MCS, monitoring about 100 mL of fluid transfer at a time. Stopped transfer when the volume of the G-Rex 100MCS was reduced to 500 mL.

During transfer step, used 10 mL syringe and drew 10 mL of cell suspension into the syringe from the G-Rex 100MCS. Followed the instructions according to the number of flasks in culture. If only 1 flask: Removed 20 mL total using two syringes. If 2 flasks: removed 10 mL per flask. If 3 flasks: removed 7 mL per flask. If 4 flasks: removed 5 mL per flask. Transferred the cell suspension to one common 50 mL conical tube. Keep in the incubator until the cell count step and QC sample. Total number of cells needed for QC was $20\times10^6$ cells: 4×0.5 mL cell counts (cell counts were undiluted first).

The quantities of cells needed for assays are as follows:

$10\times10^6$ cells minimum for potency assays, such as those described herein, or for an IFN-γ or granzyme B assay
$1\times10^6$ cells for mycoplasma
$5\times10^6$ cells for flow cytometry for CD3+/CD45+

Transferred the G-Rex 500MCS flasks to the incubator.

Prepared QC Samples. At least $15\times10^8$ cells were needed for the assays in this embodiment. Assays included: cell count and viability; mycoplasma ($1\times10^6$ cells/average viable concentration;) flow ($5\times10^6$ cells/average viable concentration;) and IFN-γ assay ($5\times10^6$ cells-$1\times10^6$ cells; 8-$10\times10^6$ cells are required for the IFN-γ assay.

Calculated the volume of cells fraction for cryopreservation at $10\times10^6$ cells/mL and calculated the number of vials to prepare.

Example 10: An Exemplary Embodiment of the Gen 3 Expansion Process at Day 16-17

Wash Buffer preparation (1% HSA Plasmalyte A). Transfer HSA and Plasmalyte to 5 L bag to make LOVO wash buffer. Using sterile conditions, transferred a total volume of 125 mL of 25% HSA to the 5 L bag, which was stored at room temperature.

Removed and transferred 10 mL or 40 mL of wash buffer in the 'IL-2 $6\times10^4$ IU/mL' tube (10 mL if IL-2 was prepared in advance or 40 mL if IL-2 was prepared fresh).

Calculated volume of reconstituted IL-2 to add to Plasmalyte+1% HSA: volume of reconstituted IL-2=(Final concentration of IL-2×Final volume)/specific activity of the IL-2 (based on standard assay). The final concentration of IL-2 was $6\times10^4$ IU/mL. The final volume was 40 mL.

Removed calculated initial volume of IL-2 needed of reconstituted IL-2 and transfer to the 'IL-2 $6\times10^4$ IU/mL' tube. Added 100 μL of IL-2 $6\times10^6$ IU/mL from the aliquot prepared in advance to the tube labelled 'IL-2 $6\times10^4$ IU/mL' containing 10 mL of LOVO wash buffer.

Removed about 4500 mL of supernatant from the G-Rex 500MCS flasks. Swirled the remaining supernatant and transferred cells to the Cell Collection Pool bag. Repeated with all G-Rex 500MCS flasks.

Removed 60 mL of supernatant and add to supernatant tubes for quality control assays, including mycoplasma detection. Stored at +2-8° C.

Cell collection. Counted cells. Prepare four 15 mL conicals with 4.5 mL of AIM-V. These may be prepared in advance. Optimal range=is between $5\times10^4$ and $5\times10^6$ cells/mL. (1:10 dilution was recommended). For 1:10 dilution, to 4500 μL of AIM-V prepared previously, add 500 μL of CF. Recorded dilution factor.

$$\text{Calculated the TC (Total Cells) pre-}\mathit{LOVO}\text{ (live + dead)} = \text{Average Total Cell Concentration } (\mathit{TC\ conc}\text{ pre }\mathit{LOVO})\text{ (live + dead)} \times \text{Volume of Source bag}$$

$$\text{Calculated the TVC (Total Viable Cells) pre-}\mathit{LOVO}\text{ (live)} = \text{Average Total Viable Cell Concentration } (\mathit{TVC}\text{ pre }\mathit{LOVO})\text{ (live)} \times \text{Volume of LOVO Source bag}$$

When the total cell (TC) number was $>5\times10^9$, remove $5\times10^8$ cells to be cryopreserved as MDA retention samples. $5\times10^8$÷average TC concentration (step 14.44)=volume to remove.

When the total cell (TC) number was $\leq5\times10^9$, remove $4\times10^6$ cells to be cryopreserved as MDA retention samples. $4\times10^6$÷average TC concentration=volume to remove.

Used an appropriately sized syringe to remove the required volume from the LOVO Source Bag. Retained in incubator until cryopreservation steps.

When the total cell number was determined, the number of cells to remove should allow retention of $150\times10^9$ viable cells. Confirm TVC pre-LOVO $5\times10^8$ or $4\times10^6$ or not applicable. Calculate the volume of cells to remove.

Calculate the remaining total cells remaining in bag. Calculate the TC (Total Cells) pre-LOVO as [Avg. Total cell concentration×Remaining Volume=TC pre-LOVO Remaining].

According to the total number of cells remaining, the corresponding process in Table 46 is selected.

TABLE 46

Total number of cells.

| Total cells | Retentate (mL) |
|---|---|
| $0 < \text{Total cells} \leq 31\times10^9$ | 115 |
| $31\times10^9 < \text{Total cells} \leq 71\times10^9$ | 165 |
| $71\times10^9 < \text{Total Cells} \leq 110\times10^9$ | 215 |
| $110\times10^9 < \text{Total Cells} \leq 115\times10^9$ | 265 |

Chose the volume of IL-2 to add corresponding to the used process. Volume calculated as: Retentate Volume×2×300 IU/mL=IU of IL-2 required. IU of IL-2 required/$6\times10^4$IU/mL=Volume of IL-2 to add post-LOVO bag. Recorded all volumes added. Obtained samples in cryovial for further analyses.

Mixed the cell product well. Sealed all bags for further processing, included cryopreservation when applicable.

Performed endotoxin, IFN-γ, sterility, and other assays as needed on cryovial samples obtained.

Example 11: An Exemplary Gen 3 Process (Also Referred to as Gen 3.1)

This example describes further studies regarding the "Comparability between the Gen 2 and Gen 3 processes for TIL expansion". The Gen 3 process was modified to include an activation step early in the process with the goal of increasing the final total viable cell (TVC) output to be comparable (or better) to that in Gen 2, while maintaining the phenotypic and functional profiles as previously seen.

The scope of this example involves assessment of TVC output through introduction of an activation step to the cultured tumor fragments on Day 0; demonstrating comparability in terms of functional and extended phenotypic characterization with the Gen 3 standard, as well as a control arm, across two independent patient tumors; and analysis of media consumption and metabolite production to confirm processing parameters were maintained at physiologic conditions.

All runs for this example were performed at full-scale platform using commercial donor tumor tissue as the starting material.

A Gen 3 embodiment was modified as a further embodiment and is referred to herein in this example as Gen 3.1.

In an embodiment, the Gen 3.1 TIL manufacturing process has four operator interventions:

1. Tumor Fragment Isolation and Activation: On Day 0 of the process the tumor was dissected and the final fragments generated were ~3×3 mm each (up to 240 fragments total) and cultured in 1-4 G-Rex 100 MCS flasks. Each flask contained up to 60 fragments, 500 mL of CM1 or DM1 media, and supplemented with 6,000 IU rhIL-2, 15 μg OKT3, and $2.5\times10^8$ irradiated allogeneic mononuclear cells (PBMCs). The culture was incubated at 37° C. for 6-8 days. In place of PBMCs, aAPCs or antigen presenting cells described elsewhere herein may be employed, such as Thp1 or U937 cells, optionally genetically modified and optionally irradiated.
2. TIL Culture Reactivation: On Day 7-8 the culture was supplemented through slow addition of CM2 or DM1 media supplemented with 6,000 IU rhIL-2, 30 μg OKT3, and $5\times10^8$ irradiated allogeneic mononuclear cells in both cases. Care was taken to not disturb the existing cells at the bottom of the flask. The culture was incubated at 37° C. for 3-4 days.
3. Culture Scale Up: Occurs on day $10^{-11}$. During the culture scale-up, the entire contents of the G-Rex 100 MCS was transferred to a G-Rex 500 MCS flask containing 4L of CM4 or DM2 supplemented with 3,000 IU/mL of IL-2 in both cases. Flasks were incubated at 37° C. for 5-6 days until harvest.
4. Harvest/Wash/Formulate: On day 16-17 the flasks are volume reduced and pooled. Cells were concentrated and washed with PlasmaLyte A pH 7.4 containing 1% HSA. The washed cell suspension was formulated at a 1:1 ratio with CryoStor10 and supplemented with rhIL-2 to a final concentration of 300 IU/mL.

The DP was cryopreserved with a controlled rate freeze and stored in vapor phase liquid nitrogen. Complete Standard TIL media 1, 2, or 4 (CM1, CM2, CM4) may be substituted for CTS™ OpTmizer™ T-Cell serum free expansion medium, referred to as Defined Medium (DM1 or DM2), as noted above.

Process description. On day 0, the tumor was washed 3 times, then fragmented in 3×3×3 final fragments. Once the whole tumor was fragmented, then the final fragments were randomized equally and divided into three pools. One randomized fragment pool was introduced to each arm, adding the same number of fragments per the three experimental matrices.

Tumor L4063 expansion was performed with Standard Media and tumor L4064 expansion was performed with Defined Media (CTS OpTmizer) for the entire TIL expansion process. Components of the media are described herein.

CM1 Complete Media 1: RPMI+ Glutamine supplemented with 2 mM Glutamax, 10% Human AB Serum, Gentamicin (50 ug/mL), 2-Mercaptoethanol (55 uM). Final media formulation supplemented with 60001 U/mL IL-2.

CM2 Complete Media 2: 50% CM1 medium+50% AIM-V medium. Final media formulation supplemented with 60001 U/mL IL-2.

CM4 Complete Media 4: AIM-V supplemented with Glutamax (2 mM). Final media formulation supplemented with 30001 U/mL IL-2.

CTS OpTmizer CTS™ OpTmizer™ T-Cell Expansion Basal Medium supplemented with CTS™ OpTmizer™ T-Cell Expansion Supplement (26 mL/L).

DM1: CTS™ OpTmizer™ T-Cell Expansion Basal Medium supplemented with CTS™ OpTmizer™ T-Cell Expansion Supplement (26 mL/L), and CTS™ Immune Cell SR (3%), with Glutamax (2 mM). Final formulation supplemented with 6,000 IU/mL of IL-2.

DM2: CTS™ OpTmizer™ T-Cell Expansion Basal Medium supplemented with CTS™ OpTmizer™ T-Cell Expansion Supplement (26 mL/L), and CTS™ Immune Cell SR (3%), with Glutamax (2 mM). Final formulation supplemented with 3,000 IU/mL of IL-2.

All types of media used, i.e., Complete (CM) and Defined (DM) media, were prepared in advance, held at 4° C. degree until the day before use, and warmed at 37° C. in an incubator for up to 24 hours in advance prior to process day.

TIL culture reactivation occurred on Day 7 for both tumors. Scale-up occurred on day 10 for L4063 and day 11 for L4064. Both cultures were harvested and cryopreserved on Day 16.

Results Achieved. Cells counted and % viability for Gen 3.0 and Gen 3.1 processes were determined. Expansion in all the conditions followed details described in this example.

For each tumor, the fragments were divided into three pools of equal numbers. Due to the small size of the tumors, the maximum number of fragments per flask was not achieved. For the three different processes, the total viable cells and cell viability were assessed for each condition. Cell counts were determined as TVC on day 7 for reactivation, TVC on day 10 (L4064) or day 11 (L4063) for scale-up, and TVC at harvest on day 16/17.

Cell counts for Day 7 and Day 10/11 were taken FIO. Fold expansion was calculated by dividing the harvest day 16/17 TVC by the day 7 reactivation day TVC. To compare the three arms, the TVC on harvest day was divided by the number of fragments added in the culture on Day 0 in order to calculate an average of viable cells per fragment.

Cell counts and viability assays were performed for L4063 and L4064. The Gen 3.1-Test process yielded more cells per fragment than the Gen 3.0 Process on both tumors.

Total viable cell count and fold expansion; % Viability during the process. On reactivation, scale up and harvest the percent viability was performed on all conditions. On day 16/17 harvest, the final TVC were compared against release criteria for % viability. All of the conditions assessed surpassed the 70% viability criterion and were comparable across processes and tumors.

Immunophenotyping—Phenotypic characterization on TIL final product. The final products were subjected to flow cytometry analysis to test purity, differentiation, and memory markers. Percent populations were consistent for TCRα/β, CD4+ and CD8+ cells for all conditions.

Extended phenotypic analysis of REP TIL was performed. TIL product showed a higher percentage of CD4+ cells for Gen 3.1 conditions compared to Gen 3.0 on both tumors, and higher percentage of CD28+ cells from CD8+ population for Gen 3.0 compared to Gen 3.1 conditions on both conditions.

TIL harvested from the Gen 3.0 and Gen 3.1 processes showed comparable phenotypic markers as CD27 and CD56 expression on CD4+ and CD8+ cells, and a comparable CD28 expression on CD4+ gated cells population. Memory markers comparison on TIL final product:

Frozen samples of TIL harvested on day 16 were stained for analysis. TIL memory status was comparable between Gen 3.0 and Gen 3.1 processes. Activation and exhaustion markers comparison on TIL final product:

Activation and exhaustion markers were comparable between the Gen 3.0 and Gen 3.1 processes gated on CD4+ and CD8+ cells.

Interferon gamma secretion upon restimulation. Harvested TIL underwent an overnight restimulation with coated anti-CD3 plates for L4063 and L4064. Higher production of IFN-γ from the Gen 3.1 process was observed in the two tumors analyzed compared to Gen 3.0 process.

Measurement of IL-2 levels in culture media. To compare the levels of IL-2 consumption between all of the conditions and processes, cell supernatants were collected at initiation of reactivation on Day 7, at scale-up Day 10 (L4064)/11 (L4063), and at harvest Day 16/17, and frozen. The supernatants were subsequently thawed and then analyzed. The quantity of IL-2 in cell culture supernatant was measured by the manufacturer protocol.

Overall Gen 3 and Gen 3.1 processes were comparable in terms of IL-2 consumption during the complete process assessed across same media conditions. IL-2 concentration (pg/mL) analysis on spent media collected for L4063 and L4064.

Metabolite analysis. Spent media supernatants was collected from L4063 and L4064 at reactivation initiation on day 7, scale-up on day 10 (L4064) or day 11 (L4063), and at harvest on days 16/17 for L4063 and L4064, for every condition. Supernatants were analyzed on a CEDEX Bioanalyzer for concentrations of glucose, lactate, glutamine, GlutaMax, and ammonia.

Defined media has a higher glucose concentration of 4.5 g/L compared to complete media (2 g/L). Overall, the concentration and consumption of glucose were comparable for Gen 3.0 and Gen 3.1 processes within each media type.

An increase in lactate was observed for both tumors, L4063 and L4064, for all test conditions. The increase in lactate was comparable between the Gen 3.0 and Gen 3.1 conditions and between the two media used for reactivation expansion (complete media for L4063 and defined media for L4064).

In the case of L4063, the standard basal media contained 2 mM L-glutamine and was supplemented with 2 mM GlutaMax to compensate for the natural degradation of L-glutamine in culture conditions to L-glutamate and ammonia.

For L4064 tumor, defined (serum free) media used did not contain L-glutamine on the basal media, and was supplemented only with GlutaMax to a final concentration of 2 mM. GlutaMax is a dipeptide of L-alanine and L-glutamine, is more stable than L-glutamine in aqueous solutions and does not spontaneously degrade into glutamate and ammonia. Instead, the dipeptide is gradually dissociated into the individual amino acids, thereby maintaining a lower but sufficient concentration of L-glutamine to sustain robust cell growth.

For L4063, the concentration of glutamine and GlutaMax slightly decreased on the scale-up day, but at harvest day showed an increase to similar or closer levels compared to reactivation day. For L4064, glutamine and GlutaMax concentration showed a slight degradation in a similar rate between different conditions, during the whole process.

As expected, ammonia concentrations were higher for L4063 (grown in standard media containing 2 mM glutamine+2 mM GlutaMax) than L4064 (grown in defined media containing 2 mM GlutaMax). Further, as expected, there was a gradual increase or accumulation of ammonia over the course of the culture. There were no differences in ammonia concentrations across the three different test conditions.

Telomere repeats by Flow—FISH. Flow-FISH technology was used to measure the average length of the telomere repeat on L4063 and L4064 under Gen 3 and Gen 3.1 processes. The determination of a relative telomere length (RTL) was calculated using Telomere PNA kit/FITC for flow cytometry analysis from DAKO. Telomere assay was performed. Telomere length in samples of L4063 and L4064 were compared to a control cell line (1301 leukemia). The control cell line is a tetraploid cell line having long stable telomeres that allows calculation of a relative telomere length. Gen 3 and Gen 3.1 processes assessed in both tumors showed comparable telomere length. TCR Vβ repertoire Analysis To determine the clonal diversity of the cell products generated in each process, TIL final products were assayed for clonal diversity analysis through sequencing of the CDR3 portion of the T cell receptors.

Three parameters were compared between the three conditions:

Diversity index of Unique CDR3 (uCDR3)

% shared uCDR3

For the top 80% of uCDR3:

- Compare the % shared uCDR3 copies
- Compare the frequency of unique clonotypes Control and Gen 3.1 Test, percentage shared unique CDR3 sequences on L4063 on TIL harvested cell product for: 975 sequences are shared between Gen 3 and Gen 3.1 Test final product, equivalent to 88% of top 80% of unique CDR3 sequences from Gen 3 shared with Gen 3.1 Test final product.

Control and Gen 3.1 Test, percentage shared unique CDR3 sequences on L4064 on TIL harvested cell product for: 2163 sequences are shared between Gen 3 and Gen 3.1 Test final product, equivalent to 87% of top 80% of unique CDR3 sequences from Gen 3 shared with Gen 3.1 Test final product.

The number of unique CD3 sequences identified from $1\times10^6$ cells collected on Harvest day 16, for the different processes. Gen 3.1 Test condition showed a slightly higher clonal diversity compared to Gen 3.0 based on the number of unique peptide CDRs within the sample.

The Shannon entropy diversity index is a more reliable and common metric for comparison, because Gen 3.1 conditions on both tumors showed slightly higher diversity than Gen 3 process, suggesting that TCR VP repertoire for Gen 3.1 Test condition is more polyclonal than the Gen 3.0 process.

Additionally, the TCR VP repertoire for Gen 3.1 Test condition showed more than 87% overlap with the corresponding repertoire for Gen 3.0 process on both tumor L4063 and L4064.

The value of IL-2 concentration on spent media for Gen 3.1 Test L4064 on reactivation day was below to the expected value (similar to Gen 3.1 control and Gen 3.0 condition).

The low value could be due to a pipetting error, but because of the minimal sample taken it was not possible to repeat the assay.

Spent media from scale up day 10/11 on sample L4064 was not collected, and not included in the analysis of IL-2 concentration and metabolite analysis on supernatant.

Conclusions. Gen 3.1 test condition including feeders and OKT-3 on Day 0 showed a higher TVC of cell doses at Harvest day 16 compared to Gen 3.0 and Gen 3.1 control. TVC on the final product for Gen 3.1 test condition was around 2.5 times higher than Gen 3.0.

Gen 3.1 test condition with the addition of OKT-3 and feeders on day 0, for both tumors L4063 and L4064, reached a maximum capacity of the flask at harvest. Under these conditions, if a maximum of 4 flasks on day 0 is initiated, the final cell dose could be between 80-100×$10^9$ TILs.

All the quality attributes such as phenotypic characterization including purity, exhaustion, activation and memory markers on final TIL product were maintained and comparable between Gen 3.1 Test and Gen 3.0 process. Telomere length on TIL final product and IL-2 consumption on spent media were comparable between Gen 3.0 and Gen 3.1 processes.

IFN-γ production on final TIL product was 3 times higher on Gen 3.1 with feeder and OKT-3 addition on day 0, compared to Gen 3.0 in the two tumors analyzed, suggesting Gen 3.1 process generated a potent TIL product.

Gen 3.0 optimized process can have flexibility on processing days, thereby facilitating flexibility in the manufacturing schedule.

Gen 3.1 process with feeder and OKT-3 addition on day 0 showed a higher clonal diversity measured by CDR3 TCRab sequence analysis compared to Gen 3.0.

FIG. 32 describes an embodiment of the Gen 3 process (Gen 3 Optimized process). Standard media and CTS Optimizer serum free media can be used for Gen 3 Optimized process TIL expansion. In case of CTS Optimizer serum free media is recommended to increase the GlutaMax on the media to final concentration 4 mM.

Feasibility was established for all study conditions in all experiments. Across all the experiments and conditions and between the donor tumor tissue, all the experiments were performed utilizing the same lots of critical raw material such as IL-2, Human Serum-AB, allogeneic feeder cells, OKT-3.

Comparability was determined by the ability of any arm of the study to meet release criteria of the clinical product according to prior specifications for cryopreserved day 22 TIL products.

Example 12: Tumor Expansion Processes with Defined Medium

The processes disclosed above may be performed substituting the CM1 and CM2 media with a defined medium according (e.g., CTS™ OpTmizer™ T-Cell Expansion SFM, ThermoFisher, including for example DM1 and DM2).

Example 13: Exemplary Production of a Cryopreserved TIL Cell Therapy

This example describes an exemplary cGMP manufacture of TIL Cell Therapy Process in G-Rex Flasks according to current Good Tissue Practices and current Good Manufacturing Practices.

TABLE 47

Process Expansion Exemplary Plan.

| Estimated Day (post-seed) | Activity | Target Criteria | Anticipated Vessels | Estimated Total Volume (mL) |
|---|---|---|---|---|
| 0 | Tumor Dissection | ≤50 desirable tumor fragments per G-Rex 100MCS | G-Rex 100MCS 1 flask | ≤1000 |
| 11 | REP Seed | 5-200 × $10^6$ viable cells per G-Rex 500MCS | G-Rex 500MCS 1 flasks | ≤5000 |
| 16 | REP Split | 1 × $10^9$ viable cells per G-Rex 500MCS | G-Rex 500MCS ≤5 flasks | ≤25000 |
| 22 | Harvest | Total available cells | 3-4 CS-750 bags | ≤530 |

No differences observed in glucose or lactate levels across test conditions. No differences observed on glutamine and ammonia between Gen 3.0 and Gen 3.1 processes across media conditions. The low levels of glutamine on the media are not limiting cell growth and suggest the addition of GlutaMax only in media is sufficient to give the nutrients needed to make cells proliferate.

The scale up day for L4063 and L4064 was on day 11 and day 10 respectively and did not show major differences in terms of cell number reached on the harvest day of the process and metabolite consumption was comparable in both cases during the whole process. This observation suggests of

TABLE 48

Flask Volumes.

| Flask Type | Working Volume/Flask (mL) |
|---|---|
| G-Rex 100MCS | 1000 |
| G-Rex 500MCS | 5000 |

Day 0 CM1 Media Preparation. In the BSC added reagents to RPMI 1640 Media bottle. Added the following reagents t Added per bottle: Heat Inactivated Human AB Serum (100.0 mL); GlutaMax (10.0 mL); Gentamicin sulfate, 50 mg/mL (1.0 mL); 2-mercaptoethanol (1.0 mL)

Removed unnecessary materials from BSC. Passed out media reagents from BSC, left Gentamicin Sulfate and HBSS in BSC for Formulated Wash Media preparation.

Thawed IL-2 aliquot. Thawed one 1.1 mL IL-2 aliquot ($6\times10^6$ IU/mL) (BR71424) until all ice had melted. Recorded IL-2: Lot # and Expiry Transferred IL-2 stock solution to media. In the BSC, transferred 1.0 mL of IL-2 stock solution to the CM1 Day 0 Media Bottle prepared. Added CM1 Day 0 Media 1 bottle and IL-2 ($6\times10^6$ IU/mL) 1.0 mL.

Passed G-Rex 100MCS into BSC. Aseptically passed G-Rex1 00MCS (W3013130) into the BSC.

Pumped all Complete CM1 Day 0 Media into G-Rex 100 MCS flask. Tissue Fragments Conical or G-Rex 100 MCS Day 0 Tumor Wash Media Preparation. In the BSC, added 5.0 mL Gentamicin (W3009832 or W3012735) to 1×500 mL HBSS Media (W3013128) bottle. Added per bottle: HBSS (500.0 mL); Gentamicin sulfate, 50 mg/mL (5.0 mL). Filtered HBSS containing gentamicin prepared through a 1L 0.22-micron filter unit (W1218810).

Day 0 Tumor Processing. Obtained tumor specimen and transferred into suite at 2-8° C. immediately for processing.

Aliquoted tumor wash media. Tumor wash 1 is performed using 8" forceps (W3009771). The tumor is removed from the specimen bottle and transferred to the "Wash 1" dish prepared. This is followed by tumor wash 2 and tumor wash 3.

Measured and assessed tumor. Assessed whether >30% of entire tumor area observed to be necrotic and/or fatty tissue. Clean up dissection if applicable. If tumor was large and >30% of tissue exterior was observed to be necrotic/fatty, performed "clean up dissection" by removing necrotic/fatty tissue while preserving tumor inner structure using a combination of scalpel and/or forceps.

Dissect tumor. Using a combination of scalpel and/or forceps, cut the tumor specimen into even, appropriately sized fragments (up to 6 intermediate fragments). Transferred intermediate tumor fragments. Dissected tumor fragments into pieces approximately 3×3×3 mm in size. Stored Intermediate Fragments to prevent drying.

Repeated intermediate fragment dissection. Determined number of pieces collected. If desirable tissue remains, selected additional favorable tumor pieces from the "favorable intermediate fragments" 6-well plate to fill the drops for a maximum of 50 pieces.

Prepared conical tube. Transferred tumor pieces to 50 mL conical tube. Prepared BSC for G-Rex 100 MCS. Removed G-Rex 100 MCS from incubator. Aseptically passed G-Rex 100 MCS flask into the BSC. Added tumor fragments to G-Rex 100 MCS flask. Evenly distributed pieces.

Incubated G-Rex 100 MCS at the following parameters: Incubated G-Rex flask: Temperature LED Display: 37.0±2.0° C.; $CO_2$ Percentage: 5.0±1.5% $CO_2$. Calculations: Time of incubation; lower limit=time of incubation+252 hours; upper limit=time of incubation+276 hours.

After process was complete, discarded any remaining warmed media and thawed aliquots of IL-2.

Day 11—Media Preparation. Monitored incubator. Incubator parameters: Temperature LED Display: 37.0±2.0° C.; $CO_2$ Percentage: 5.0±1.5% $CO_2$.

Warmed 3×1000 mL RPMI 1640 Media (W3013112) bottles and 3×1000 mL AIM-V (W3009501) bottles in an incubator for ≥30 minutes. Removed RPMI 1640 Media from incubator. Prepared RPMI 1640 Media. Filter Media. Thawed 3×1.1 mL aliquots of IL-2 ($6\times10^6$ IU/mL) (BR71424). Removed AIM-V Media from the incubator. Add IL-2 to AIM-V. Aseptically transferred a 10 L Labtainer Bag and a repeater pump transfer set into the BSC.

Prepared 10 L Labtainer media bag. Prepared Baxa pump. Prepared 10 L Labtainer media bag. Pumped media into 10 L Labtainer. Removed pumpmatic from Labtainer bag.

Mixed media. Gently massaged the bag to mix. Sample media per sample plan. Removed 20.0 mL of media and place in a 50 mL conical tube. Prepared cell count dilution tubes. In the BSC, added 4.5 mL of AIM-V Media that had been labelled with "For Cell Count Dilutions" and lot number to four 15 mL conical tubes. Transferred reagents from the BSC to 2-8° C. Prepared 1 L Transfer Pack. Outside of the BSC weld (per Process Note 5.11) a 1L Transfer Pack to the transfer set attached to the "Complete CM2 Day 11 Media" bag prepared. Prepared feeder cell transfer pack. Incubated Complete CM2 Day 11 Media.

Day 11—TIL Harvest. Preprocessing table. Incubator parameters: Temperature LED display: 37.0±2.0° C.; $CO_2$ Percentage: 5.0±1.5% $CO_2$. Removed G-Rex 100 MCS from incubator. Prepared 300 mL Transfer Pack. Welded transfer packs to G-Rex 100 MCS.

Prepare flask for TIL Harvest and initiation of TIL Harvest. TIL Harvested. Using the GatheRex pump, transferred the cell suspension through the blood filter into the 300 mL transfer pack. Inspect membrane for adherent cells.

Rinsed flask membrane. Closed clamps on G-Rex 100 MCS. Ensured all clamps are closed. Heat sealed the TIL and the "Supernatant" transfer pack. Calculated volume of TIL suspension. Prepared supernatant transfer pack for sampling.

Pulled Bac-T Sample. In the BSC, draw up approximately 20.0 mL of supernatant from the 1 L "Supernatant" transfer pack and dispense into a sterile 50 mL conical tube.

Inoculated BacT per Sample Plan. Removed a 1.0 mL sample from the 50 mL conical labeled BacT prepared using an appropriately sized syringe and inoculated the anaerobic bottle.

Incubated TIL. Placed TIL transfer pack in incubator until needed. Performed cell counts and calculations. Determined the Average of viable cell concentration and viability of the cell counts performed. Viability÷2. Viable Cell Concentration÷2. Determined Upper and Lower Limit for counts. Lower Limit: average of viable cell concentration×0.9. Upper Limit: average of viable cell concentration×1.1. Confirmed both counts within acceptable limits. Determined an average viable cell concentration from all four counts performed.

Adjusted Volume of TIL Suspension: Calculate the adjusted volume of TIL suspension after removal of cell count samples. Total TIL Cell Volume (A). Volume of Cell Count Sample Removed (4.0 mL) (B) Adjusted Total TIL Cell Volume C=A−B.

Calculated Total Viable TIL Cells. Average viable cell concentration: Total Volume; Total Viable Cells: C=A×B.

Calculation for flow cytometry: if the Total Viable TIL Cell count from was $\geq4.0\times10^7$, calculated the volume to obtain $1.0\times10^7$ cells for the flow cytometry sample.

Total viable cells required for flow cytometry: $1.0\times10^7$ cells. Volume of cells required for flow cytometry: Viable cell concentration divided by $1.0\times10^7$ cells A.

Calculated the volume of TIL suspension equal to $2.0\times10^8$ viable cells. As needed, calculated the excess volume of TIL cells to remove and removed excess TIL and placed TIL in incubator as needed. Calculated total excess TIL removed, as needed.

Calculated amount of CS-10 media to add to excess TIL cells with the target cell concentration for freezing is 1.0×$10^8$ cells/mL. Centrifuged excess TILs, as needed. Observed conical tube and added CS-10.

Filled Vials. Aliquoted 1.0 mL cell suspension, into appropriately sized cryovials. Aliquoted residual volume into appropriately sized cryovial. If volume is ≤0.5 mL, add CS10 to vial until volume is 0.5 mL.

Calculated the volume of cells required to obtain 1×$10^7$ cells for cryopreservation. Removed sample for cryopreservation. Placed TIL in incubator.

Cryopreservation of sample. Observed conical tube and added CS-10 slowly and record volume of 0.5 mL of CS10 added.

Day 11—Feeder Cells. Obtained feeder cells. Obtained 3 bags of feeder cells with at least two different lot numbers from LN2 freezer. Kept cells on dry ice until ready to thaw. Prepared water bath or cryotherm. Thawed feeder cells at 37.0±2.0° C. in the water bath or cytotherm for ~3-5 minutes or until ice has just disappeared. Removed media from incubator. Pooled thawed feeder cells. Added feeder cells to transfer pack. Dispensed the feeder cells from the syringe into the transfer pack. Mixed pooled feeder cells and labeled transfer pack.

Calculated total volume of feeder cell suspension in transfer pack. Removed cell count samples. Using a separate 3 mL syringe for each sample, pulled 4×1.0 mL cell count samples from Feeder Cell Suspension Transfer Pack using the needless injection port. Aliquoted each sample into the cryovials labeled. Performed cell counts and determine multiplication factors, elected protocols and entered multiplication factors. Determined the average of viable cell concentration and viability of the cell counts performed. Determined upper and lower limit for counts and confirm within limits.

Adjusted volume of feeder cell suspension. Calculated the adjusted volume of feeder cell suspension after removal of cell count samples. Calculated total viable feeder cells. Obtained additional feeder cells as needed. Thawed additional feeder cells as needed. Placed the 4th feeder cell bag into a zip top bag and thaw in a 37.0±2.0° C. water bath or cytotherm for ~3-5 minutes and pooled additional feeder cells. Measured volume. Measured the volume of the feeder cells in the syringe and recorded below (B). Calculated the new total volume of feeder cells. Added feeder cells to transfer pack.

Prepared dilutions as needed, adding 4.5 mL of AIM-V Media to four 15 mL conical tubes. Prepared cell counts. Using a separate 3 mL syringe for each sample, removed 4×1.0 mL cell count samples from Feeder Cell Suspension transfer pack, using the needless injection port. Performed cell counts and calculations. Determined an average viable cell concentration from all four counts performed. Adjusted volume of feeder cell suspension and calculated the adjusted volume of feeder cell suspension after removal of cell count samples. Total Feeder Cell Volume minutes 4.0 mL removed. Calculated the volume of Feeder Cell Suspension that was required to obtain 5×$10^9$ viable feeder cells. Calculated excess feeder cell volume. Calculated the volume of excess feeder cells to remove. Removed excess feeder cells.

Using a 1.0 mL syringe and 16 G needle, drew up 0.15 mL of OKT3 and added OKT3. Heat sealed the feeder cell suspension transfer pack.

Day 11 G-Rex Fill and Seed Set up G-Rex500MCS. Removed "Complete CM2 Day 11 Media", from incubator and pumped media into G-Rex500MCS. Pumped 4.5 L of media into the G-Rex500MCS, filling to the line marked on the flask. Heat sealed and incubated flask as needed. Welded the Feeder Cell suspension transfer pack to the G-Rex500MCS. Added Feeder Cells to G-Rex500MCS. Heat sealed. Welded the TIL Suspension transfer pack to the flask. Added TIL to G-Rex500MCS. Heat sealed. Incubated G-Rex500MCS at 37.0±2.0° C., $CO_2$ Percentage: 5.0±1.5% $CO_2$.

Calculated incubation window. Performed calculations to determine the proper time to remove G-Rex500MCS from incubator on Day 16. Lower limit: Time of incubation+108 hours. Upper limit: Time of incubation+132 hours.

Day 11 Excess TIL Cryopreservation. Applicable: Froze Excess TIL Vials. Verified the CRF has been set up prior to freeze. Perform Cryopreservation. Transferred vials from Controlled Rate Freezer to the appropriate storage. Upon completion of freeze, transfer vials from CRF to the appropriate storage container. Transferred vials to appropriate storage. Recorded storage location in LN2.

Day 16 Media Preparation. Pre-warmed AIM-V Media. Calculated time Media was warmed for media bags 1, 2, and 3. Ensured all bags have been warmed for a duration between 12 and 24 hours. Setup 10 L Labtainer for Supernatant. Attached the larger diameter end of a fluid pump transfer set to one of the female ports of a 10 L Labtainer bag using the Luer connectors. Setup 10 L Labtainer for Supernatant and label. Setup 10 L Labtainer for Supernatant. Ensure all clamps were closed prior to removing from the BSC. NOTE: Supernatant bag was used during TIL Harvest, which may be performed concurrently with media preparation.

Thawed IL-2. Thawed 5×1.1 mL aliquots of IL-2 (6×$10^6$ IU/mL) (BR71424) per bag of CTS AIM-V media until all ice had melted. Aliquoted 100.0 mL GlutaMax. Added IL-2 to GlutaMax. Prepared CTS AIM-V media bag for formulation. Prepared CTS AIM-V media bag for formulation. Stage Baxa Pump. Prepared to formulate media. Pumped GlutaMax +IL-2 into bag. Monitored parameters: Temperature LED Display: 37.0±2.0° C., $CO_2$ Percentage: 5.0±1.5% $CO_2$. Warmed Complete CM4 Day 16 Media. Prepared Dilutions.

Day 16 REP Spilt. Monitored Incubator parameters: Temperature LED display: 37.0±2.0° C., $CO_2$ Percentage: 5.0±1.5% $CO_2$. Removed G-Rex500MCS from the incubator. Prepared and labeled 1 L Transfer Pack as TIL Suspension and weighed 1L.

Volume Reduction of G-Rex500MCS. Transferred ~4.5 L of culture supernatant from the G-Rex500MCS to the 10 L Labtainer.

Prepared flask for TIL harvest. After removal of the supernatant, closed all clamps to the red line.

Initiation of TIL Harvest. Vigorously tap flask and swirl media to release cells and ensure all cells have detached.

TIL Harvest. Released all clamps leading to the TIL suspension transfer pack. Using the GatheRex transferred the cell suspension into the TIL Suspension transfer pack. NOTE: Be sure to maintain the tilted edge until all cells and media are collected. Inspected membrane for adherent cells. Rinsed flask membrane. Closed clamps on G-Rex500MCS. Heat sealed the Transfer Pack containing the TIL. Heat sealed the 10 L Labtainer containing the supernatant. Recorded weight of Transfer Pack with cell suspension and calculate the volume suspension. Prepared transfer pack for sample removal. Removed testing samples from cell supernatant.

Sterility & BacT testing sampling. Removed a 1.0 mL sample from the 15 mL conical labeled BacT prepared. Removed Cell Count Samples. In the BSC, using separate 3 mL syringes for each sample, removed 4×1.0 mL cell count samples from "TIL Suspension" transfer pack.

Removed mycoplasma samples. Using a 3 mL syringe, removed 1.0 mL from TIL Suspension transfer pack and place into 15 mL conical labeled "Mycoplasma diluent" prepared.

Prepared transfer pack for seeding. Placed TIL in incubator. Removed cell suspension from the BSC and place in incubator until needed. Performed cell counts and calculations. Diluted cell count samples initially by adding 0.5 mL of cell suspension into 4.5 mL of AIM-V media prepared which gave a 1:10 dilution. Determined the average of viable cell concentration and viability of the cell counts performed. Determined upper and lower limit for counts. Note: dilution may be adjusted according based off the expected concentration of cells. Determined an average viable cell concentration from all four counts performed. Adjusted volume of TIL suspension. Calculated the adjusted volume of TIL suspension after removal of cell count samples. Total TIL cell volume minus 5.0 mL removed for testing.

Calculated total viable TIL cells. Calculated the total number of flasks to seed. NOTE: The maximum number of G-Rex500MCS flasks to seed was five. If the calculated number of flasks to seed exceeded five, only five were seeded using the entire volume of cell suspension available.

Calculate number of flasks for subculture. Calculated the number of media bags required in addition to the bag prepared. Prepared one 10 L bag of "CM4 Day 16 Media" for every two G-Rex-500M flask needed as calculated. Proceeded to seed the first GREX-500M flask(s) while additional media is prepared and warmed. Prepared and warmed the calculated number of additional media bags determined. Filled G-Rex500MCS. Prepared to pump media and pumped 4.5 L of media into G-Rex500MCS. Heat Sealed. Repeated Fill. Incubated flask. Calculated the target volume of TIL suspension to add to the new G-Rex500MCS flasks. If the calculated number of flasks exceeds five only five will be seeded, USING THE ENTIRE VOLUME OF CELL SUSPENSION. Prepared Flasks for Seeding. Removed G-Rex500MCS from the incubator. Prepared G-Rex500MCS for pumping. Closed all clamps on except large filter line. Removed TIL from incubator. Prepared cell suspension for seeding. Sterile welded (per Process Note 5.11) "TIL Suspension" transfer pack to pump inlet line. Placed TIL suspension bag on a scale.

Seeded flask with TIL Suspension. Pump the volume of TIL suspension calculated into flask. Heat sealed. Filled remaining flasks.

Monitored Incubator. Incubator parameters: Temperature LED Display: 37.0±2.0° C., $CO_2$ Percentage: 5.0±1.5% $CO_2$. Incubated Flasks.

Determined the time range to remove G-Rex500MCS from incubator on Day 22.

Day 22 Wash Buffer Preparation. Prepared 10 L Labtainer Bag. In BSC, attach a 4" plasma transfer set to a 10 L Labtainer Bag via luer connection. Prepared 10 L Labtainer Bag. Closed all clamps before transferring out of the BSC. NOTE: Prepared one 10 L Labtainer Bag for every two G-Rex500MCS flasks to be harvested. Pumped Plasmalyte into 3000 mL bag and removed air from 3000 mL Origen bag by reversing the pump and manipulating the position of the bag. Added human albumin 25% to 3000 mL Bag. Obtain a final volume of 120.0 mL of human albumin 25%.

Prepared IL-2 diluent. Using a 10 mL syringe, removed 5.0 mL of LOVO Wash Buffer using the needleless injection port on the LOVO Wash Buffer bag. Dispensed LOVO wash buffer into a 50 mL conical tube.

CRF blank bag LOVO wash buffer aliquoted. Using a 100 mL syringe, drew up 70.0 mL of LOVO Wash Buffer from the needleless injection port.

Thawed one 1.1 mL of IL-2 ($6\times10^6$ IU/mL), until all ice has melted. Added 50 µL IL-2 stock ($6\times10^6$ IU/mL) to the 50 mL conical tube labeled "IL-2 Diluent."

Cryopreservation preparation. Placed 5 cryo-cassettes at 2-8° C. to precondition them for final product cryopreservation.

Prepared cell count dilutions. In the BSC, added 4.5 mL of AIM-V Media that has been labelled with lot number and "For Cell Count Dilutions" to 4 separate 15 mL conical tubes. Prepared cell counts. Labeled 4 cryovials with vial number (1-4). Kept vials under BSC to be used.

Day 22 TIL Harvest. Monitored Incubator. Incubator Parameters Temperature LED display: 37±2.0° C., CO2 Percentage: 5%±1.5%. Removed G-Rex500MCS Flasks from Incubator. Prepared TIL collection bag and labeled. Sealed off extra connections. Volume Reduction: Transferred ~4.5 L of supernatant from the G-Rex500MCS to the Supernatant bag.

Prepared flask for TIL harvest. Initiated collection of TIL. Vigorously tap flask and swirl media to release cells. Ensure all cells have detached. Initiated collection of TIL. Released all clamps leading to the TIL suspension collection bag. TIL Harvest. Using the GatheRex, transferred the TIL suspension into the 3000 mL collection bag. Inspect membrane for adherent cells. Rinsed flask membrane. Closed clamps on G-Rex500MCS and ensured all clamps are closed. Transferred cell suspension into LOVO source bag. Closed all clamps. Heat Sealed. Removed 4×1.0 mL Cell Counts Samples Performed Cell Counts. Performed cell counts and calculations utilizing NC-200 and Process Note 5.14. Diluted cell count samples initially by adding 0.5 mL of cell suspension into 4.5 mL of AIM-V media prepared. This gave a 1:10 dilution. Determined the average viability, viable cell concentration, and total nucleated cell concentration of the cell counts performed. Determined Upper and Lower Limit for counts. Determined the average viability, viable cell concentration, and total nucleated cell concentration of the cell counts performed. Weighed LOVO source bag. Calculated total viable TIL Cells. Calculated total nucleated cells.

Prepared Mycoplasma Diluent. Removed 10.0 mL from one supernatant bag via luer sample port and placed in a 15 mL conical.

Performed "TIL G-Rex Harvest" protocol and determined the final product target volume. Loaded disposable kit. Removed filtrate bag. Entered Filtrate capacity. Placed Filtrate container on benchtop. Attached PlasmaLyte. Verified that the PlasmaLyte was attached and observed that the PlasmaLyte is moving. Attached Source container to tubing and verified Source container was attached. Confirmed PlasmaLyte was moving.

Final Formulation and Fill. Target volume/bag calculation. Calculated volume of CS-10 and LOVO wash buffer to formulate blank bag. Prepared CRF Blank.

Calculated the volume of IL-2 to add to the Final Product. Final IL-2 Concentration desired (IU/mL)—300 IU/mL. IL-2 working stock: $6\times10^4$ IU/mL. Assembled connect apparatus. Sterile welded a 4S-4M60 to a CC2 cell connection. Sterile welded the CS750 cryobags to the harness prepared. Welded CS-10 bags to spikes of the 4S-4M60. Prepared TIL with IL-2. Using an appropriately sized syringe, removed amount of IL-2 determined from the "IL-2 $6\times10^4$" aliquot.

Labeled formulated TIL Bag. Added the formulated TIL bag to the apparatus. Added CS10. Switched Syringes. Drew ~10 mL of air into a 100 mL syringe and replaced the 60 mL syringe on the apparatus. Added CS10. Prepared CS-750 bags. Dispensed cells.

Removed air from final product bags and take retain. Once the last final product bag was filled, closed all clamps. Drew 10 mL of air into a new 100 mL syringe and replace the syringe on the apparatus. Dispensed retain into a 50 mL conical tube and label tube as "Retain" and lot number. Repeat air removal step for each bag.

Prepared final product for cryopreservation, including visual inspection. Held the cryobags on cold pack or at 2-8° C. until cryopreservation.

Removed cell count sample. Using an appropriately sized pipette, remove 2.0 mL of retain and place in a 15 mL conical tube to be used for cell counts. Performed cell counts and calculations. NOTE: Diluted only one sample to appropriate dilution to verify dilution is sufficient. Diluted additional samples to appropriate dilution factor and proceed with counts. Determined the Average of Viable Cell Concentration and Viability of the cell counts performed. Determined Upper and Lower Limit for counts. NOTE: Dilution may be adjusted according based off the expected concentration of cells. Determined the Average of Viable Cell Concentration and Viability. Determined Upper and Lower Limit for counts. Calculated IFN-γ. Heat Sealed Final Product bags.

Labeled and collected samples per exemplary sample plan below.

TABLE 49

Sample plan.

| Sample | Number of Containers | Sample Volume to Add to Each | Container Type |
|---|---|---|---|
| *Mycoplasma | 1 | 1.0 mL | 15 mL Conical |
| Endotoxin | 2 | 1.0 mL | 2 mL Cryovial |
| Gram Stain | 1 | 1.0 mL | 2 mL Cryovial |
| IFN-γ | 1 | 1.0 mL | 2 mL Cryovial |
| Flow Cytometry | 1 | 1.0 mL | 2 mL Cryovial |
| **Bac-T Sterility | 2 | 1.0 mL | Bac-T Bottle |
| QC Retain | 4 | 1.0 mL | 2 mL Cryovial |
| Satellite Vials | 10 | 0.5 mL | 2 mL Cryovial |

Sterility and BacT testing. Testing Sampling. In the BSC, remove a 1.0 mL sample from the retained cell suspension collected using an appropriately sized syringe and inoculate the anaerobic bottle. Repeat the above for the aerobic bottle.

Final Product Cryopreservation. Prepared controlled rate freezer (CRF). Verified the CRF had been set up. Set up CRF probes. Placed final product and samples in CRF. Determined the time needed to reach 4° C.±1.5° C. and proceed with the CRF run. CRF completed and stored. Stopped the CRF after the completion of the run. Remove cassettes and vials from CRF. Transferred cassettes and vials to vapor phase LN2 for storage. Recorded storage location.

Post-Processing and analysis of final drug product included the following tests: (Day 22) Determination of $CD3^+$ cells on Day 22 REP by flow cytometry; (Day 22) Gram staining method (GMP); (Day 22) Bacterial endotoxin test by Gel Clot LAL Assay (GMP); (Day 16) BacT Sterility Assay (GMP); (Day 16) Mycoplasma DNA detection by TD-PCR (GMP); Acceptable appearance attributes; (Day 22) BacT sterility assay (GMP)(Day 22); (Day 22) IFN-gamma assay. Other potency assay as described herein are also employed to analyze TIL products.

Example 14: TIL Potency Assay Pilot Study

Figure 34:
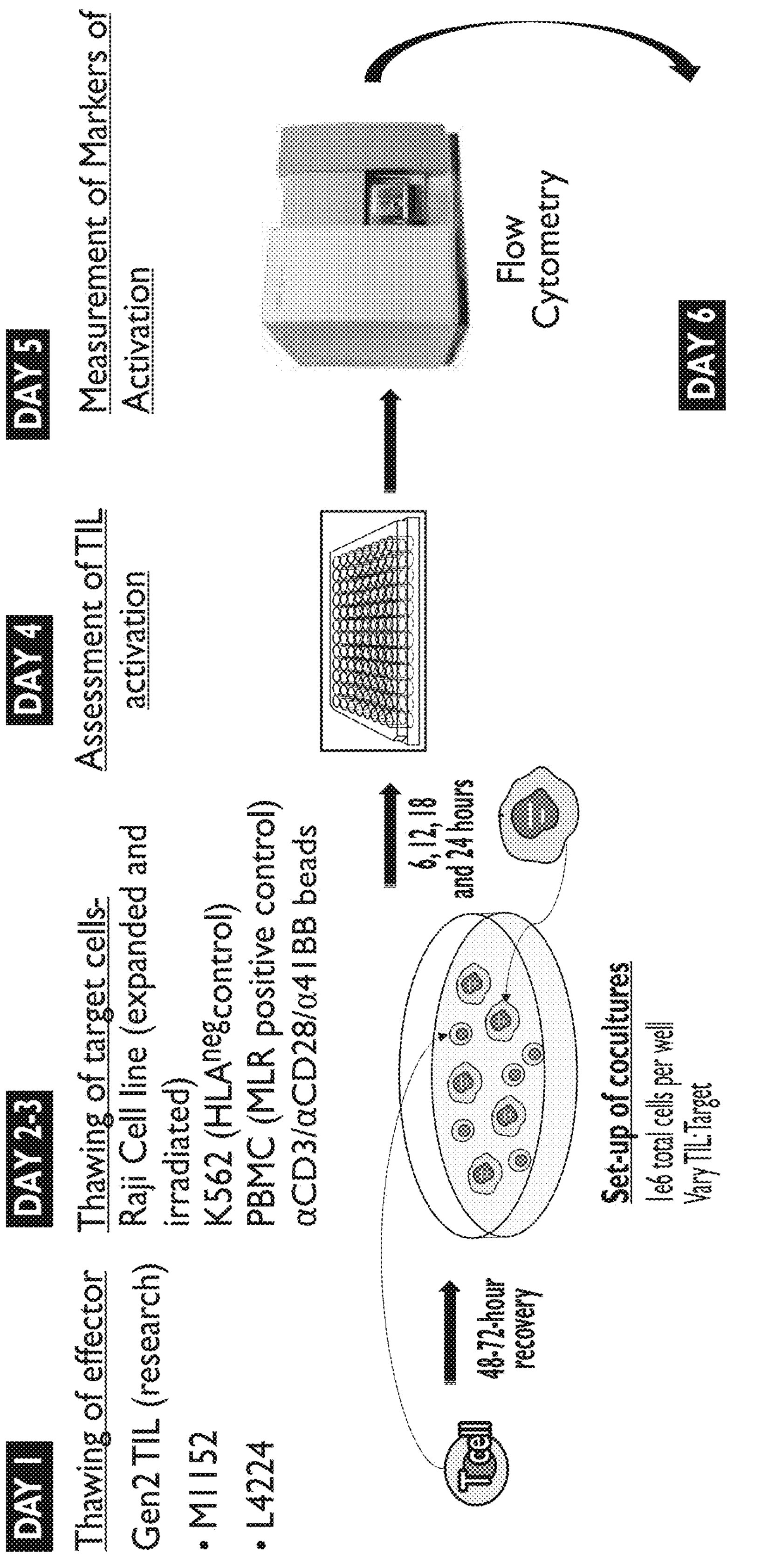
FIG. 34: Diagram of an embodiment of the TIL-Raji co-culture assay with a TIL-K562 negative control, and MLR (patient-matched PBMC) and bead-based positive controls.
Figure 35:
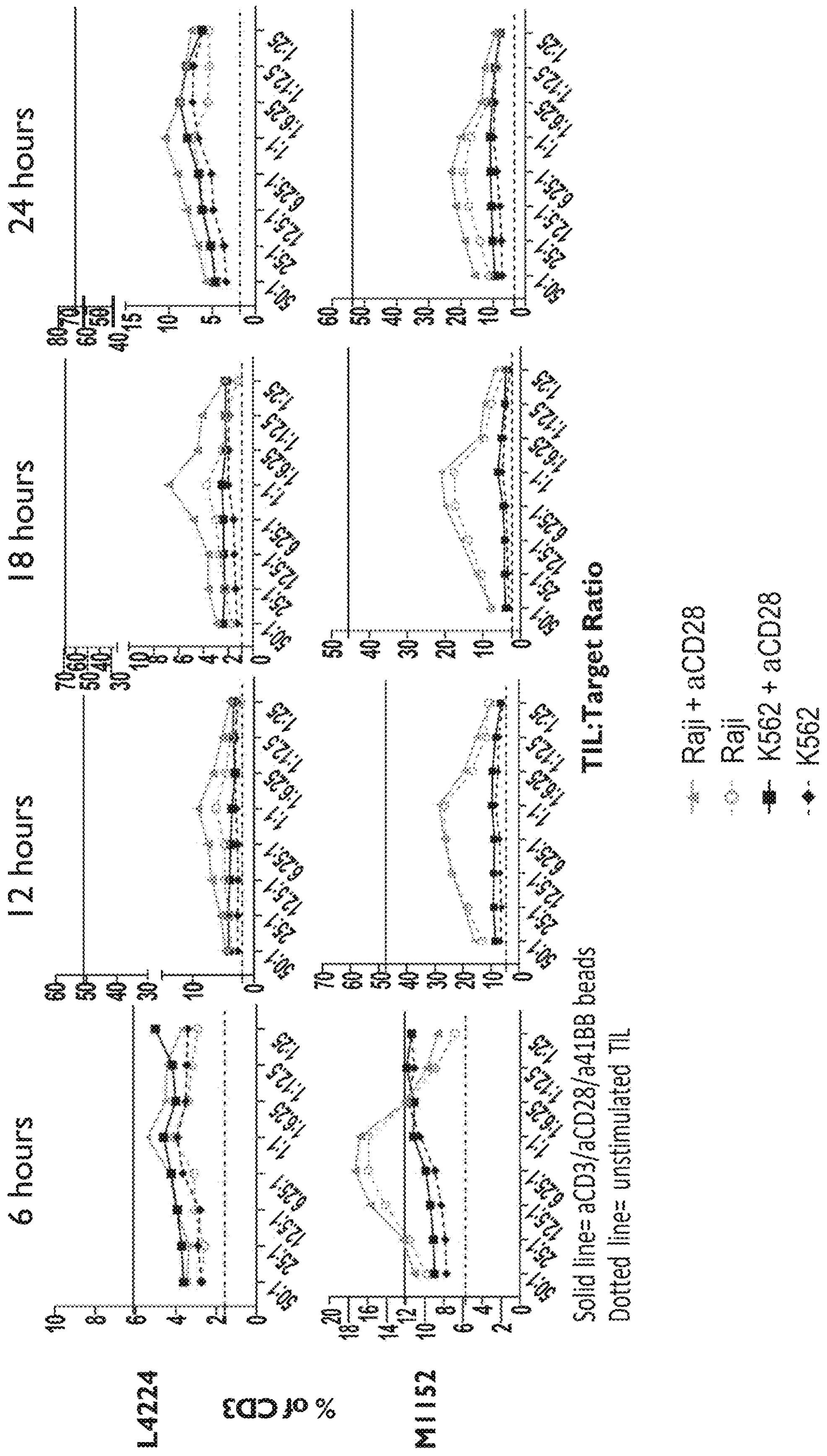
FIG. 35: CD25 levels observed by flow cytometry (% of CD3) for different co-culture periods and TIL:target ratios for a lung tumor (L4224) and a melanoma tumor (M1152) using the TIL-Raji co-culture assay.
Figure 36:
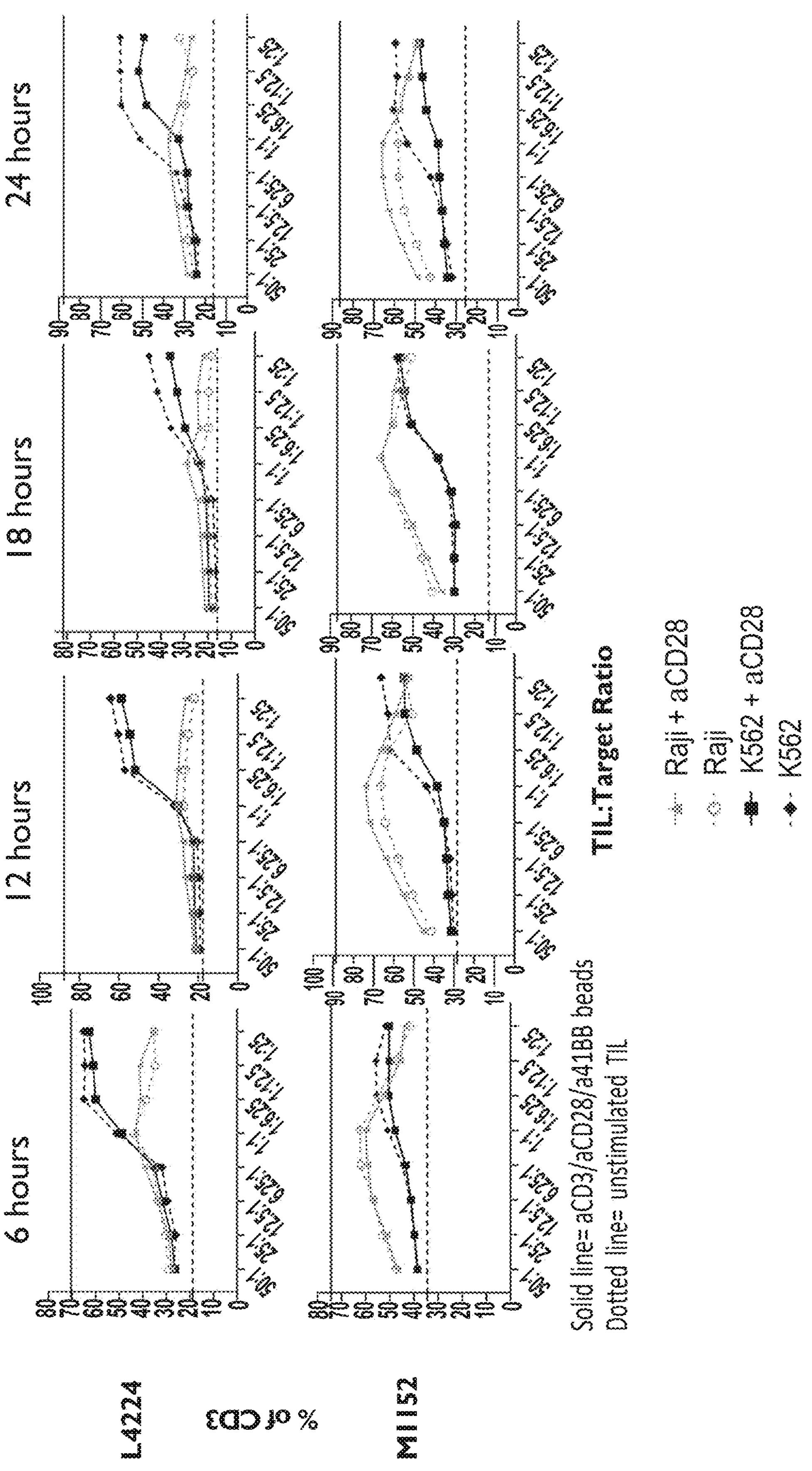
FIG. 36: CD69 levels observed by flow cytometry (% of CD3) for different co-culture periods and TIL:target ratios for a lung tumor (L4224) and a melanoma tumor (M1152) using the TIL-Raji co-culture assay.
Figure 37:
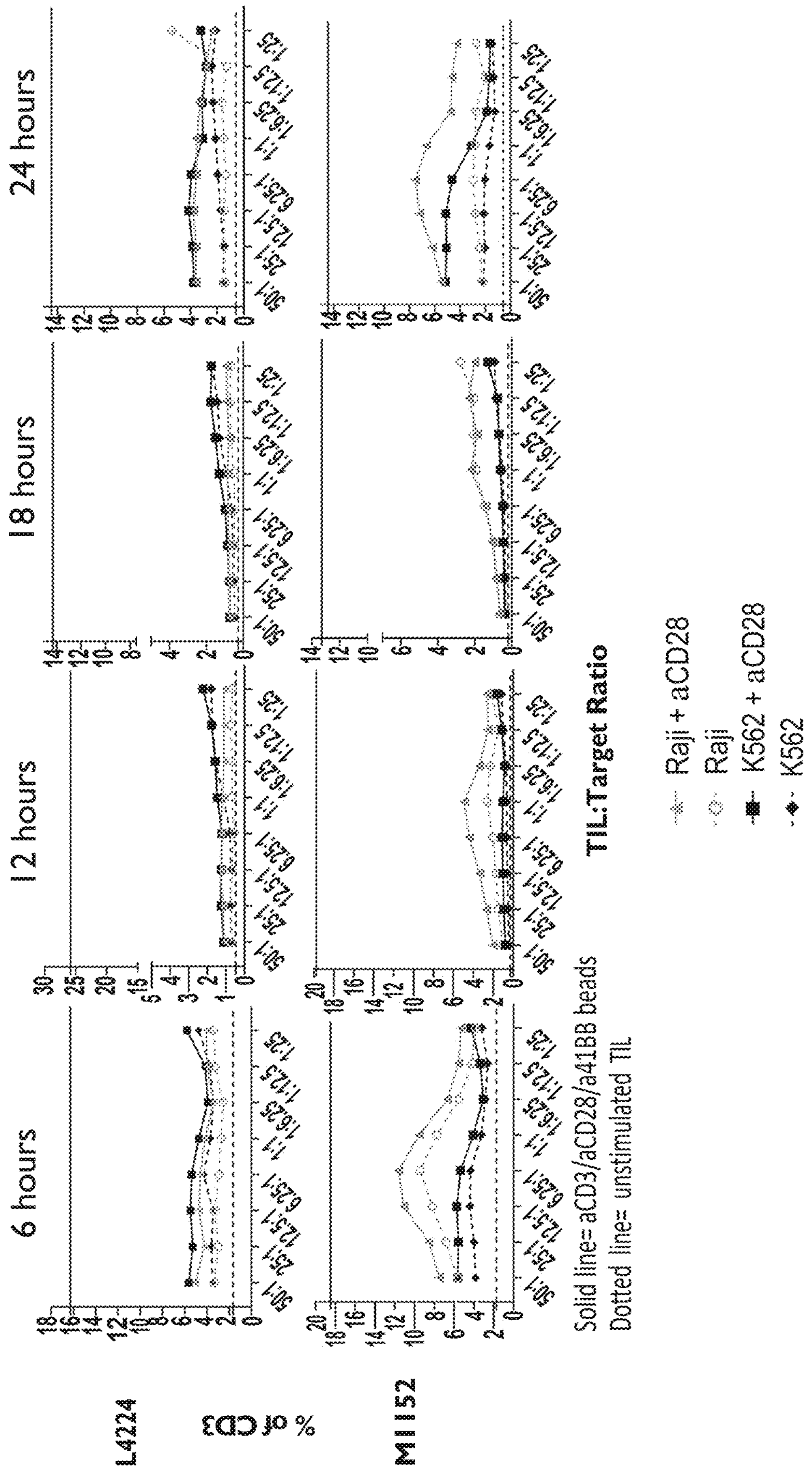
FIG. 37: CD137 (4-1BB) levels observed by flow cytometry (% of CD3) for different co-culture periods and TIL: target ratios for a lung tumor (L4224) and a melanoma tumor (M1152) using the TIL-Raji co-culture assay.
Figure 38:
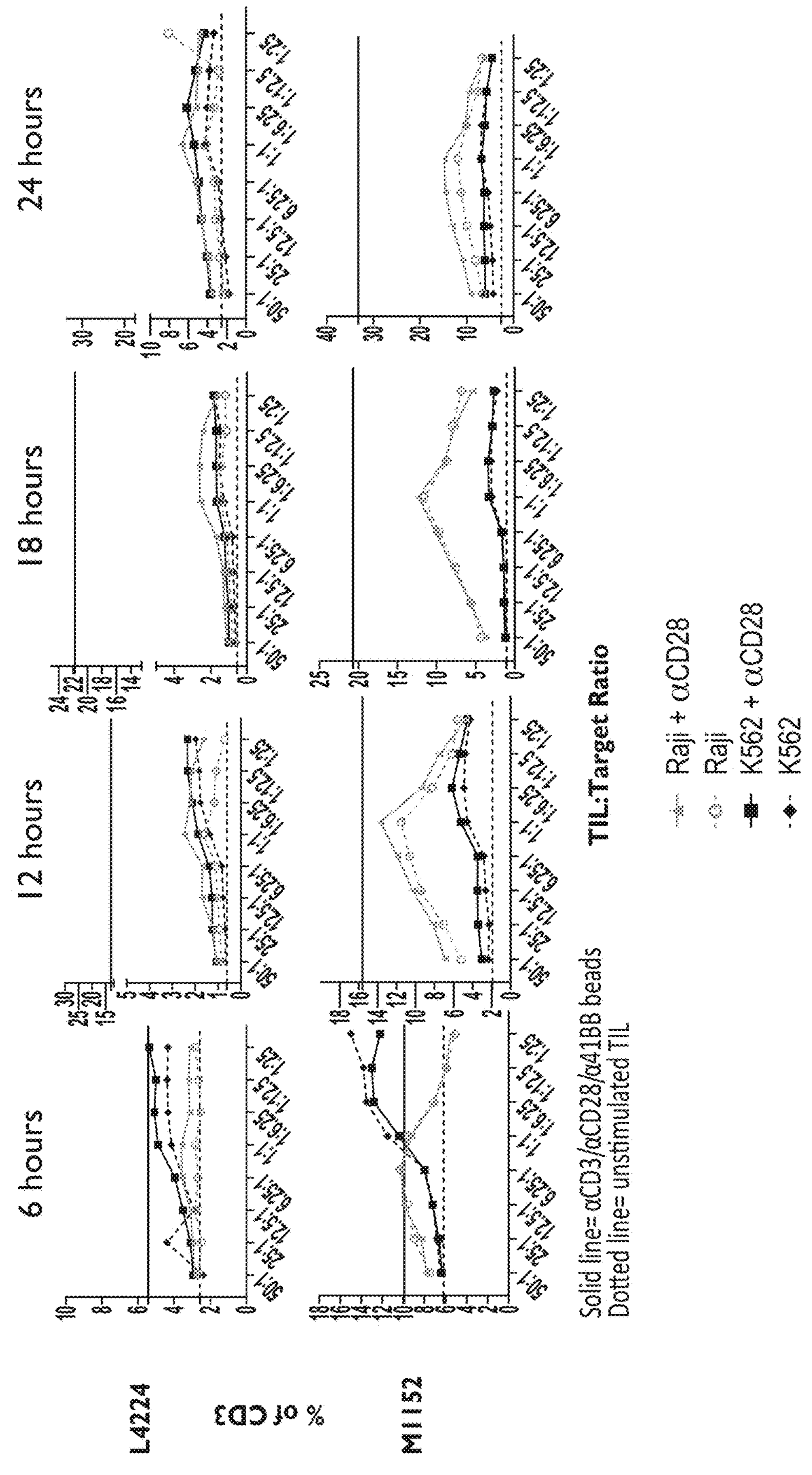
FIG. 38: CD134 (OX40) levels observed by flow cytometry (% of CD3) for different co-culture periods and TIL: target ratios for a lung tumor (L4224) and a melanoma tumor (M1152) using the TIL-Raji co-culture assay.

This example describes a potency assay for characterization of clinical TIL product lots. The protocol described in this example was applied to two TIL samples generated by the Gen 2 manufacturing process, which were prepared from a lung tumor (L4224) and a melanoma tumor (M1154). The TILs were co-cultured with irradiated Raji cells. K562 cells and PBMCs beads were used as negative and positive controls, respectively. The general experimental scheme is illustrated in FIG. 34. Functionality of the TIL was verified with anti-CD3/anti-CD28/anti-4-1BB-coated beads. Addition of an anti-CD28 antibody to provide co-stimulation was also tested to determine if it provided any benefit or had no effect. Different co-culture durations were observed.

K562 and Raji cells were thawed, counted, and expanded in 6-well plates or T25 flasks for 10-14 days. Once the cell numbers reached >$160\times10^6$, cells were irradiated at 35 Gy, aliquoted, and frozen back for later use. Gen 2 expanded TILs were thawed and counted, and put into culture for recovery for 48-72 hours prior to co-culture.

Irradiated Raji cells and irradiated K562 controls were thawed, and co-cultured with TIL using the following TIL: target ratios: 50:1, 25:1, 12.5:1, 6.25:1, 1:1, 1:6.25, 1:12.5, and 1:25, +/− anti-CD28 antibody. TILs were also stimulated with magnetic beads coated with anti-CD3/CD28/4-1BB to provide a positive activation control. TIL and tumor cell line only controls were also included.

Supernatants were harvested 6-24 hours post-initiation of the coculture and frozen at −80° C. Cells were harvested at the same point and stained for the expression of surface markers of T cell activation. Thawed supernatants were assessed for cytokines, using the Ella platform. Stained samples were analyzed by flow cytometry, using a Ze5 instrument.

Three different cell lines were used to coculture with the TIL. Wild-type Raji (Cat #CCL-86) and K562 (Cat #CCL-243) cells were obtained commercially from ATCC. Raji cells are a human B lymphoblastoid cell line derived from a patient with Burkitt's lymphoma, and K562 is a myelogenous leukemia cell line. Irradiated human PBMC were received from the San Diego Blood Bank.

Two Gen 2 TIL lots were tested for activation upon coculture with irradiated Raji cells, K562 cells, and PBMC cells. TIL activation was defined as increased expression of select surface markers expressed as percentage of marker-positive cells or mean fluorescence intensity (MFI) upon coculture with Raji cells, compared to K562 cells. Alternatively, Raji cells, K562 and TIL may be cultured alone. If PBMC was used as a control, CD3/CD28 may also be used. TIL activation is expected to result from the expression of different MHC between the target and effector cells. The allogeneic interaction of the TIL TCR complex with the target cells HLA-peptide complex is referred to as MHC dominant recognition. Felix and Allen, *Nat. Rev. Immunol.,* 2007, 7(12), 942-53; Matzinger and Bevan, *Cell Immunol.* 1977, 29, 1-5; and Janeway, The major histocompatibility complex and its functions in Immunobiology: The Immune System in Health and Disease. 5th edition G. Science, Editor. 2001, Garland Science.

Due to a lack of MHC I and II expression, K562 cells provide a baseline activation level to which the coculture of TIL with Raji cells will be compared. Addition of a mouse monoclonal antibody against CD28, was added to provide co-stimulation to amplify the T cell response. PBMCs were co-cultured with each TIL lot as a positive control for the MLR response.

Raji cells were expanded to over 160×10$^6$ million, prior to irradiation, to ensure that enough cells were available for the pilot experiments.

Thawing and Culturing of Tumor Cell Samples. The K562 and Raji tumor cells were thawed and cultured for 10-14 days to allow the cells to recover from the thaw, adapt to the media, and expand to appropriate numbers prior to the experiment. 200 mL media was warmed in a 37° C. water bath for 15±5 min. For each of the tumor cell samples, a 50 mL conical tube was prepared with 10 mL of warm media and labeled with the tumor line name.

Thawed a single vial of cells, containing between 2×10$^6$ to 10×10$^6$ cells/i mL vial, in a 37° C. water bath until only small chunks of ice remain. Transferred the partially thawed vials into the BSC. Transferred the contents of the thawed tumor cells to the designated conical tube. Slowly add 0.5 mL of warm media dropwise into the cryovial, swirling the vial while adding the media to mix. Mixed the contents of cryovial by pipetting up and down gently 5-6 times. Transferred the contents of the vial to the 50 mL conical tube.

Centrifuged the conical tubes together at 400× g for 5 minutes at room temperature (RT). Removed the supernatant from each tube, avoiding the cell pellet. Loosen the cell pellet by scraping the tube gently against the tube rack. Checked the cells daily and split 1:4 when the cells are about 70-80% confluent.

Tumor Cell Harvesting. Removed the tumor cells in suspension from the flask or plate and add to a 50-mL conical tube with tumor media. Rinse the flask with 1×PBS or tumor media and add the contents to the 50 mL conical tube.

Centrifuged the conical tubes together at 400× g for 5 minutes at RT. Carefully removed the supernatant from each tube, avoiding the cell pellet. Loosen the cell pellet by scraping the tube gently against the tube rack. Using a 1 mL pipettor, resuspended TIL in 1 mL media and pipette up and down gently to further break pellet. Using a serological pipette, brought the cell suspension to 5 mL with media. Pipetted cell suspension up and down with the serological pipette to mix thoroughly. Removed two 200 μL aliquots of cell suspension to count on the K2 Cell Counter.

Irradiation of K562 and Raji Cells. Once the tumor cells have were expanded to greater than 160×10$^6$ cells, cells were irradiated at 35 Gy using standard operating procedures.

Post irradiation, cells are counted and assessed for viability using the K2 cell counter. The cells are then frozen in a dewar at 10×10$^6$ cells/mL in CryoStor CS10 Freeze Media (BioLife Solutions, Washington, Cat #210373).

Thawing and Recovery of TIL. Warmed 200 mL of TIL media (CM1) in a 37° C. water bath for 15±5 minutes before placing into the BSC. Prepared IL-2 stock solution (6×10$^6$ IU/mL). Transferred the warm media and IL-2 stock solution to the BSC. Supplement media with 300 IU/mL IL-2 by adding 10 μL of IL-2 stock solution (6×10$^6$ IU/mL) into the media.

For each TIL lot, prepared a 50 mL conical tube with 10 mL of warm media. Label the tubes with the TIL number. Based upon the availability of the TIL product and the number of cells per vial, thaw enough vials to obtain 60×10$^6$ total cells per TIL lot.

Thawed frozen TIL vials in a 37° C. water bath until only small chunks of ice remain. Transfer the thawed vial into the BSC. Transferred the contents of the thawed TIL vial and PBMCs to the designated conical tube. Slowly added 0.5 mL of warm media dropwise into the TIL vial, swirling the vial while adding the media to mix. Mixed the contents of the TIL vial by pipetting up and down gently 5-6 times. Transferred the TIL vial contents to the 50 mL conical tube.

The conical tubes were centrifuged together at 400× g for 5 minutes at RT. Carefully removed the supernatant from each tube, avoiding the cell pellet. Loosen the cell pellet by scraping the tube gently against the tube rack. Using a 1 mL pipettor, resuspended TIL in 1 mL TIL media and pipette up and down gently to further break pellet. Using a serological pipette, brought the cell suspension to 5 mL with media.

Cell suspensions were pipetted up and down with the serological pipette to mix thoroughly. Removed two 200 μL aliquots of cell suspension to count on the K2 cell counter. Resuspended the TIL to a concentration of 1.5×10$^6$/3×10$^6$ cells/mL in CM1 media and 3000 IU/mL of IL-2. Allowed the cells to recover at 37° C./5% $CO_2$ for 48-72 hours using either a G-Rex 10 flask or G-Rex 6-well plate.

TIL Preparation for Coculture. Warmed 200 mL of media in a 37° C. water bath for 15±5 minutes before placing it into the BSC. Prepared a 50 mL conical tubes with 10 mL of warm media. Harvest the TIL from the G-Rex 10 flasks or G-Rex 6-well plates and transfer the cells to the designated conical tube. Centrifuged the conical tubes together at 400× g for 5 minutes at RT.

Carefully removed the supernatant from each tube, avoiding the cell pellet. Loosen the cell pellet by scraping the tube gently against the tube rack. Using a 1 mL pipettor, resuspend TIL in 1 mL media and pipette up and down gently to further break pellet. Using a serological pipette, brought the cell suspension to 2 mL with media. Pipetted cell suspension up and down with the serological pipette to mix thoroughly. Removed two 200 μL aliquots of cell suspension to count on the K2 cell counter.

Resuspended the TIL to 5×10$^5$ cells/mL in TIL media. Thawed irradiated K562 cells, Raji cells, and PBMCs for coculture. Warmed 200 mL of media in a 37° C. water bath for 15±5 min. Transferred the warm media to the BSC. For each and cell lines, prepared a 50 mL conical tube with 10 mL of warm media.

Thawed frozen tumor cell lines in a 37° C. water bath until only small chunks of ice remain. Transferred the thawed satellite vial into the BSC. Transferred the contents of the thawed tumor cell lines to the designated conical tube. Slowly added 0.5 mL of warm media dropwise into the cryovial, swirling the vial while adding the media to mix. Mixed the contents of the vial by pipetting up and down gently 5-6 times. Transferred the cell contents to the 50-mL conical tube.

Centrifuged the conical tubes together at 400× g for 5 minutes at room temperature (RT). Carefully removed the supernatant from each tube, avoiding the cell pellet. Loosen the cell pellet by scraping the tube gently against the tube rack. Using a 1 mL pipettor, resuspended TIL in 1 mL media and pipette up and down gently to further break pellet. Using a serological pipette, brought the cell suspension to 5 mL with media. Pipetted cell suspension up and down with the serological pipette to mix thoroughly. Removed two 200-μL aliquots of cell suspension to count on the K2 cell counter. Resuspended the cells to a concentration of 5×10$^5$ cells/mL in tumor media and place in the incubator for coculture once the TIL are prepared.

Figure 47:
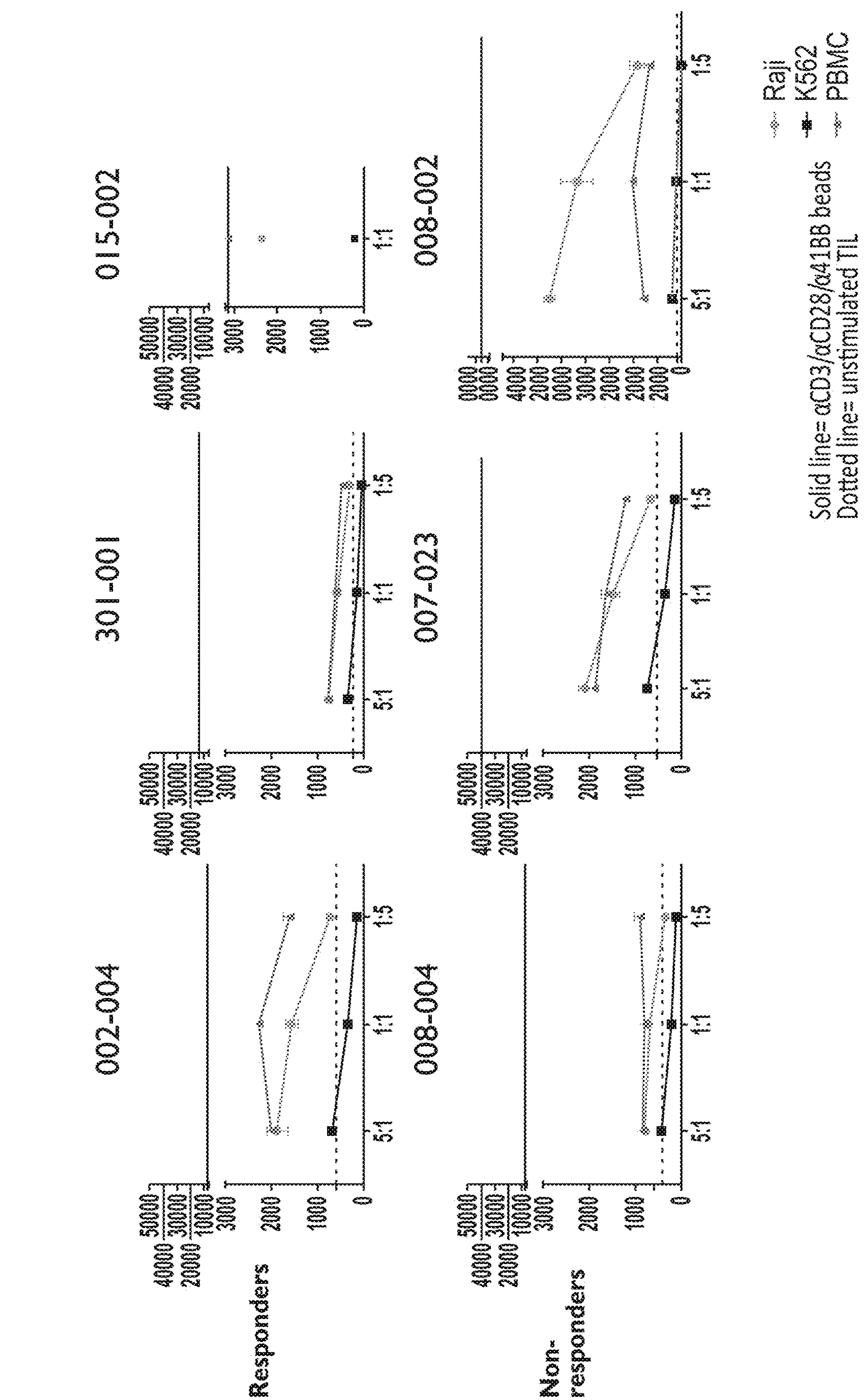
FIG. 47: Granzyme B secretion levels in pg/mL.
Figure 48:
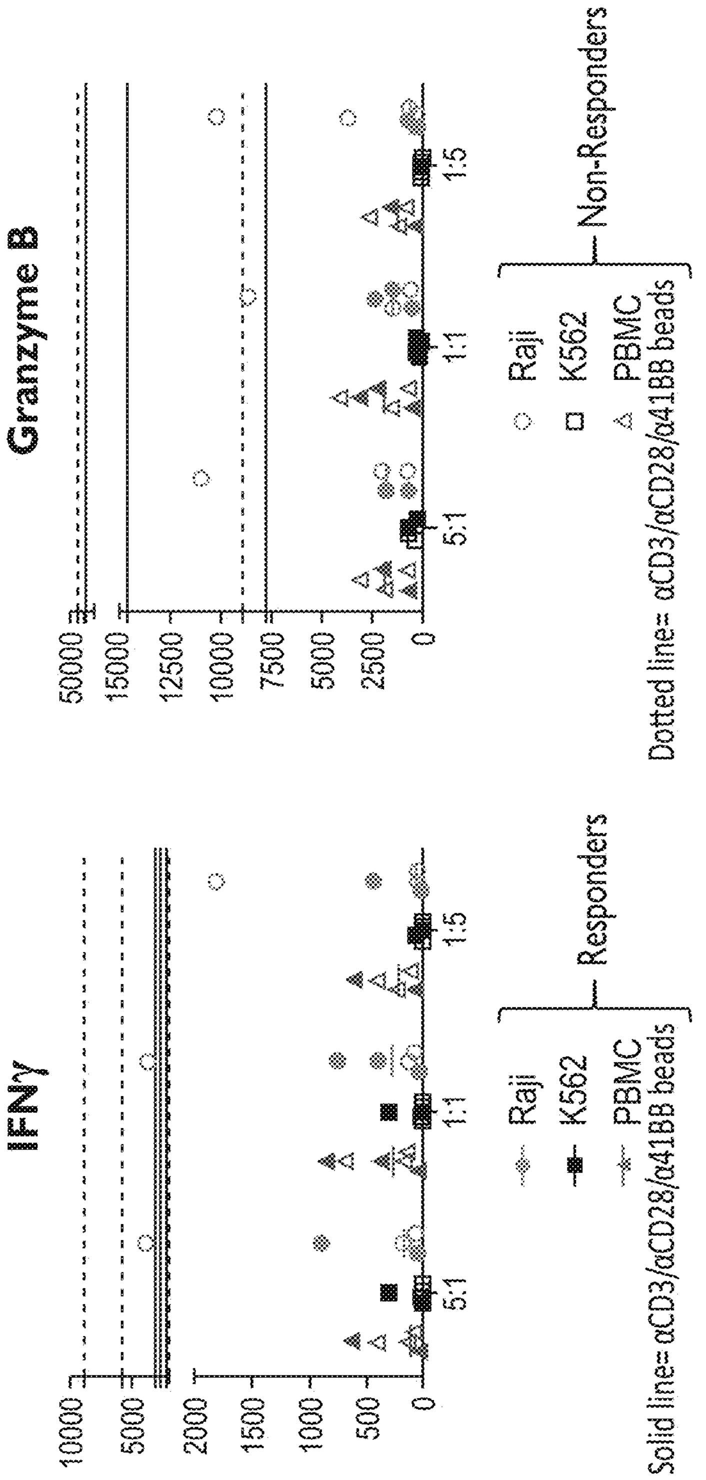
FIG. 48: IFN-γ and granzyme B secretion levels.
Figure 49:
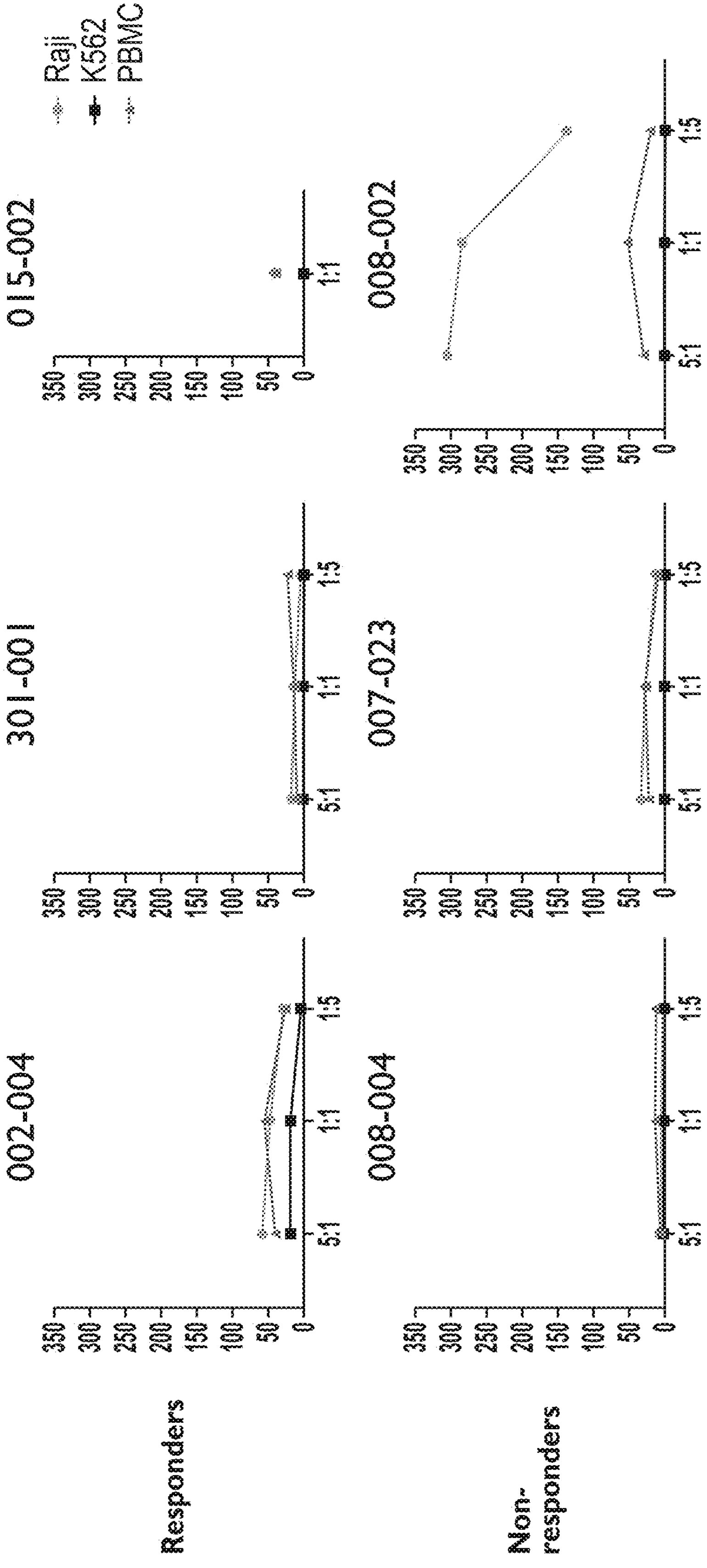
FIG. 49: Fold changes in IFN-γ release: TIL+ cell line/TIL alone.
Figure 50:
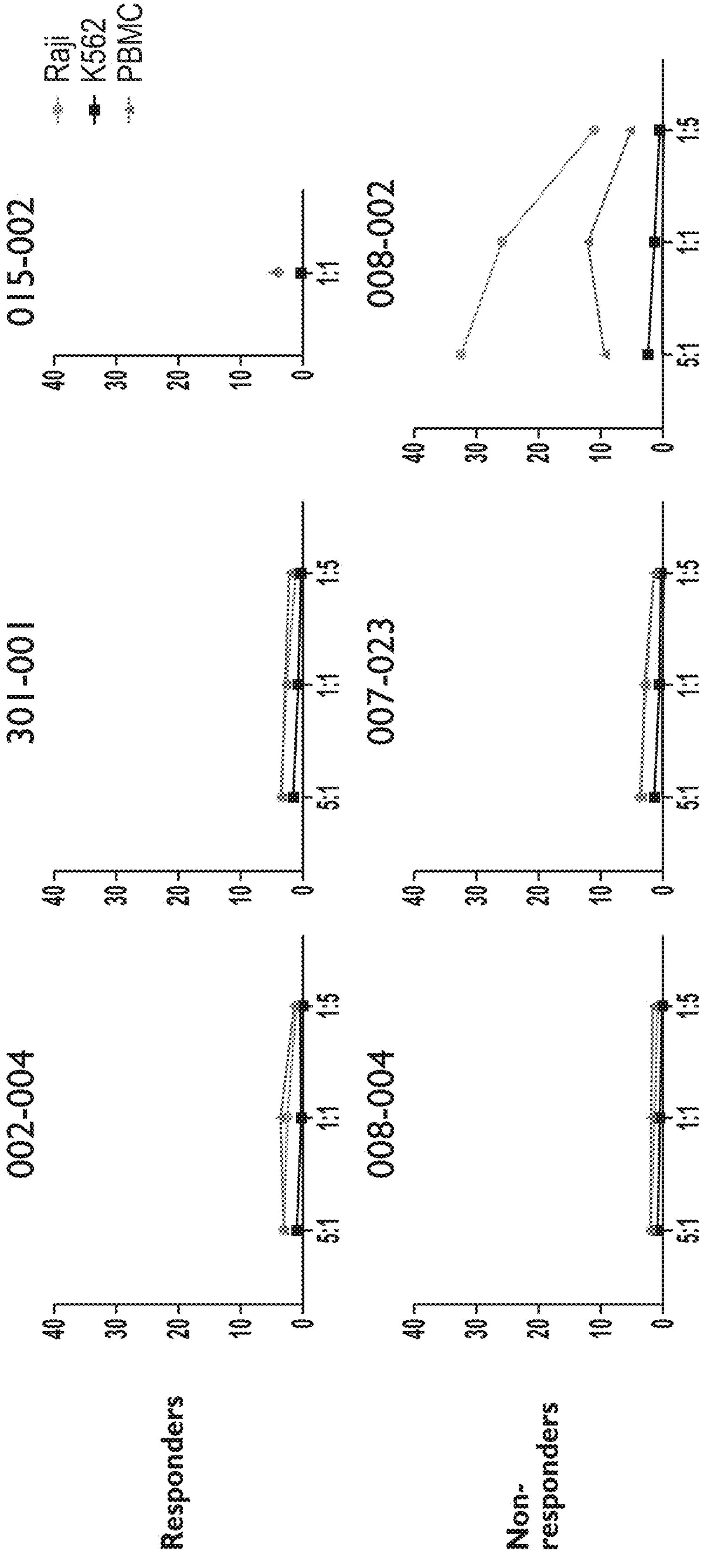
FIG. 50: Fold changes in granzyme: TIL+ cell line/TIL alone.
Figure 51:
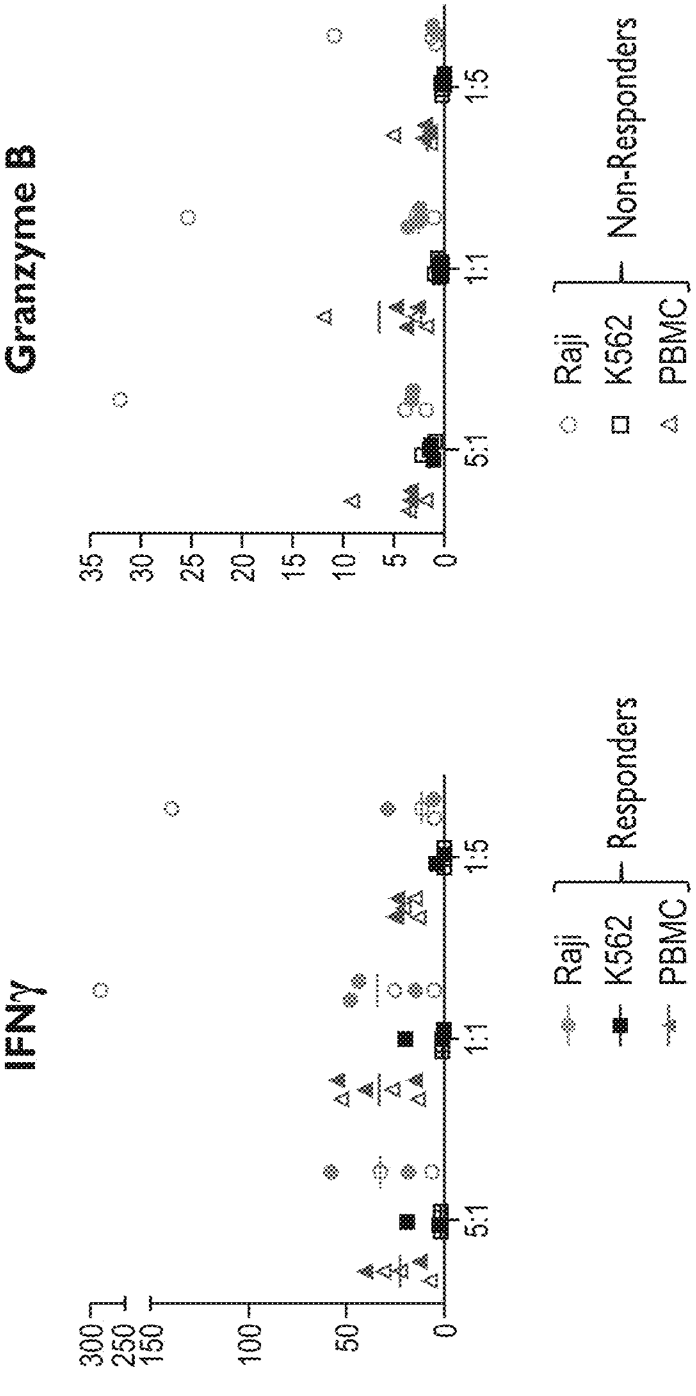
FIG. 51: Fold changes in cytokine release: TIL+ cell line/TIL alone.
Figure 52:
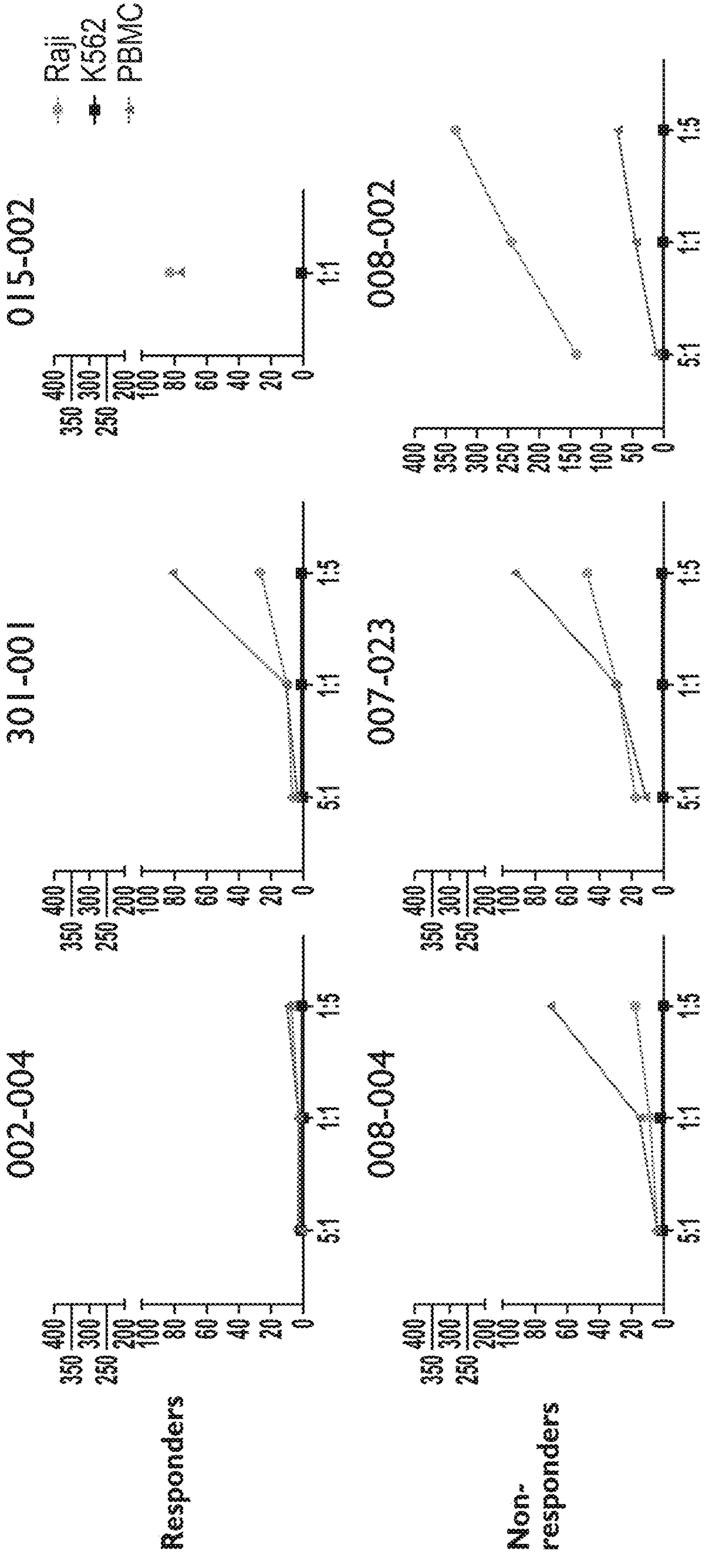
FIG. 52: Fold changes in IFN-γ release: TIL+ cell line/TIL+K562.
Figure 53:
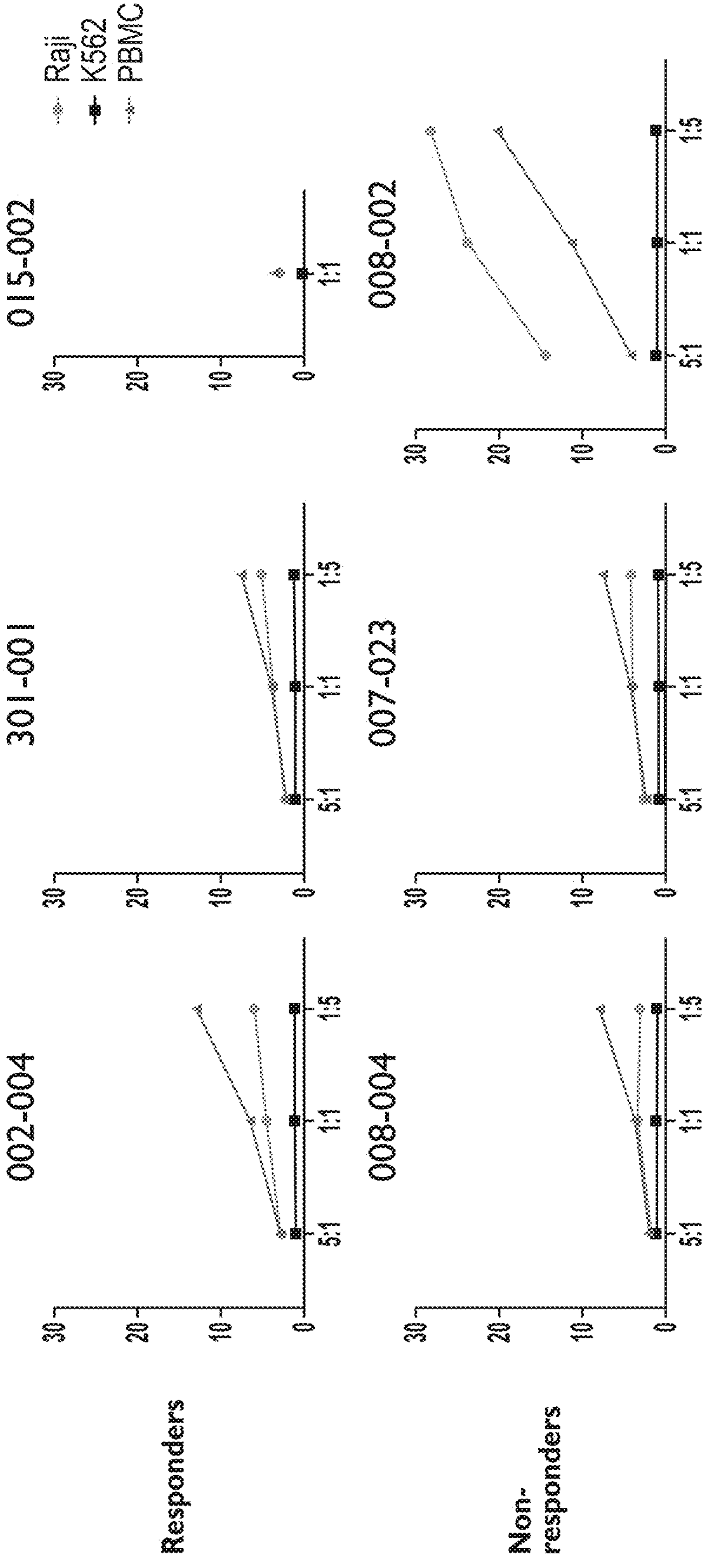
FIG. 53: Fold changes in granzyme B release: TIL+ cell line/TIL+K562.
Figure 54:
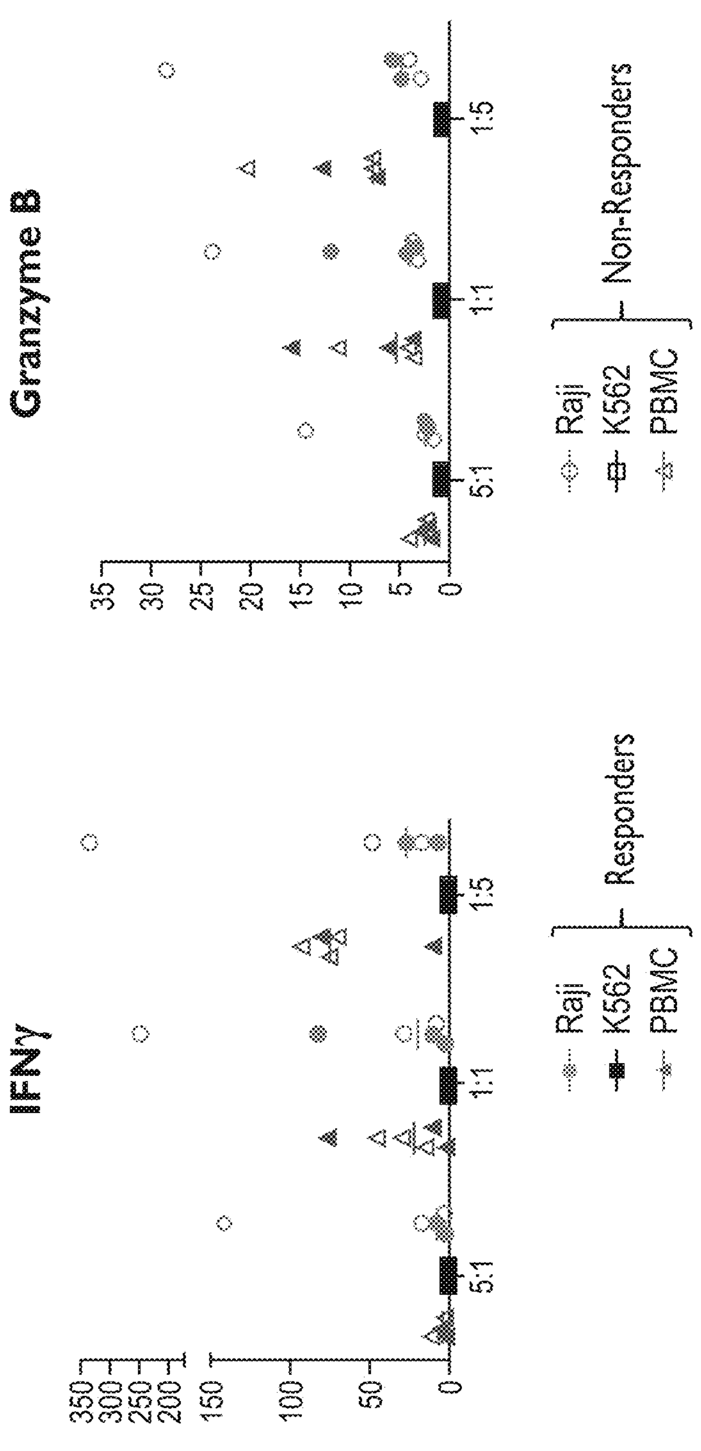
FIG. 54: Fold changes in cytokine release: TIL+ cell line/TIL+K562.

TIL and Tumor Cell Coculture Set-up. Each TIL lot was cocultured separately with irradiated K562 cells, Raji cells, and PBMCs (3-4 donors) or bead stimulation, using the TIL:target ratios and cell numbers indicated below +/− anti-CD28 (5 μg/mL) antibody. 1×10$^6$ total cells will be plated in 1 mL in 1 well of a 48-well plate. The experimental set-up is the same for the pilot and the main study. One plate was required per TIL lot, plus additional control wells will be run on an additional plate, as can be seen in FIG. 47.

50:1 ($9.8\times10^5$ TIL:$2\times10^4$ target cells)
25:1 ($9.6\times10^5$ TIL:$4\times10^4$ target cells)
12.5:1 ($9.2\times10^5$ TIL:$8\times10^4$ target cells)
6.25:1 ($8.4\times10^5$ TIL:$1.5\times10^5$ target cells)
1:1 ($5\times10^5$ TIL:$5\times10^5$ target cells)
1:6.25 ($1.5\times10^5$ TIL:$8.4\times10^5$ target cells)
1:12.5 ($8\times10^4$ TIL:$9.2\times10^5$ target cells)
1:25 ($4\times10^4$ TIL:$9.6\times10^5$ target cells)

Added 5 mg/mL of anti-CD28 to the indicated wells. Brought up the volume of the wells to 1000 μL with TIL media. For the wells containing the αCD3/αCD28/α4-1BB beads, washed, prepared, and added the beads according to the manufacturer's directions. Approximately $27.0\times10^6$ TIL and $9\times10^6$ target cells are required per TIL lot.

The plates were incubated in the incubator (5% $CO_2$, 37° C.) for the selected culture duration. For the pilot study with the two Gen 2 research samples, the plates will be incubated at various time points (i.e., 6, 12, 18, and 24 hours). The optimal coculture duration was to be defined as the one yielding the highest Raji/K562 activation values and applied to the six Gen 2 TIL clinical samples.

Collection of Cells to Assess Expression of Markers of Activation. The cell suspension was removed from the 48-well plates, and placed into prelabeled FACS tubes. Approximately 3 mL of 1×PBS was added to each tube. The tubes were spun at 400×g, high acceleration and brake, for 5 minutes at RT. The supernatant was decanted. The cells were stained with the exemplary antibody panel shown in Table 50.

TABLE 50

Activation (DIG1) Flow Cytometry Antibodies and Stains.

| Marker | Format | Clone | Company | Catalog |
|---|---|---|---|---|
| CD3 | BUV395 | UCHT1 | BD Bioscience | 563546 |
| Live/Dead Fix Blue | Live/Dead Fix Blue | N/A | Thermo Fisher | L34962 |
| CD8 | Pacific Blue | RPA-T8 | BioLegend | 301033 |
| CD4 | VioGreen | M-T466 | Miltenyi | 130-106-655 |
| CD25 | BUV563 | 2A3 | BD Bioscience | 565699 |
| PD-1 | PE | EH12.2H7 | BioLegend | 329906 |
| KLRG1 | PE-Dazzle 594 | SA231A2 | BioLegend | 367710 |
| CD137/4-1BB | PerCP-Cy5.5 | 4B4-1 | BioLegend | 309814 |
| CD69 | APC-R700 | FN50 | BD Bioscience | 565154 |
| CD134/OX40 | BUV737 | Ber-ACT35 | BD Bioscience | 749286 |

Upon completion of staining, samples were stored at 40° C. in the dark until ready to collect on the flow cytometer, and data was acquired on the Ze5 within 24 hours. The flow cytometry data was analyzed using FlowJo software. Results were expressed as percent marker-positive cells of live CD3+CD4+ and CD3+CD8+ cells.

Collection of Supernatants and Assessment for Cytokines. Removed the plates from incubator. Do not disturb the cells on the bottom of the plate. From the top of each well, removed 80 μL of supernatant and transfer 80 μL of sample to a 96-well U plate. Repeated this step with two more 96-well plates to create two back-up plates. Sealed each 96-well plate with an adhesive seal and store plates in a −80° C. freezer. The results are shown in FIG. 35 through FIG. 38.

Figure 39:
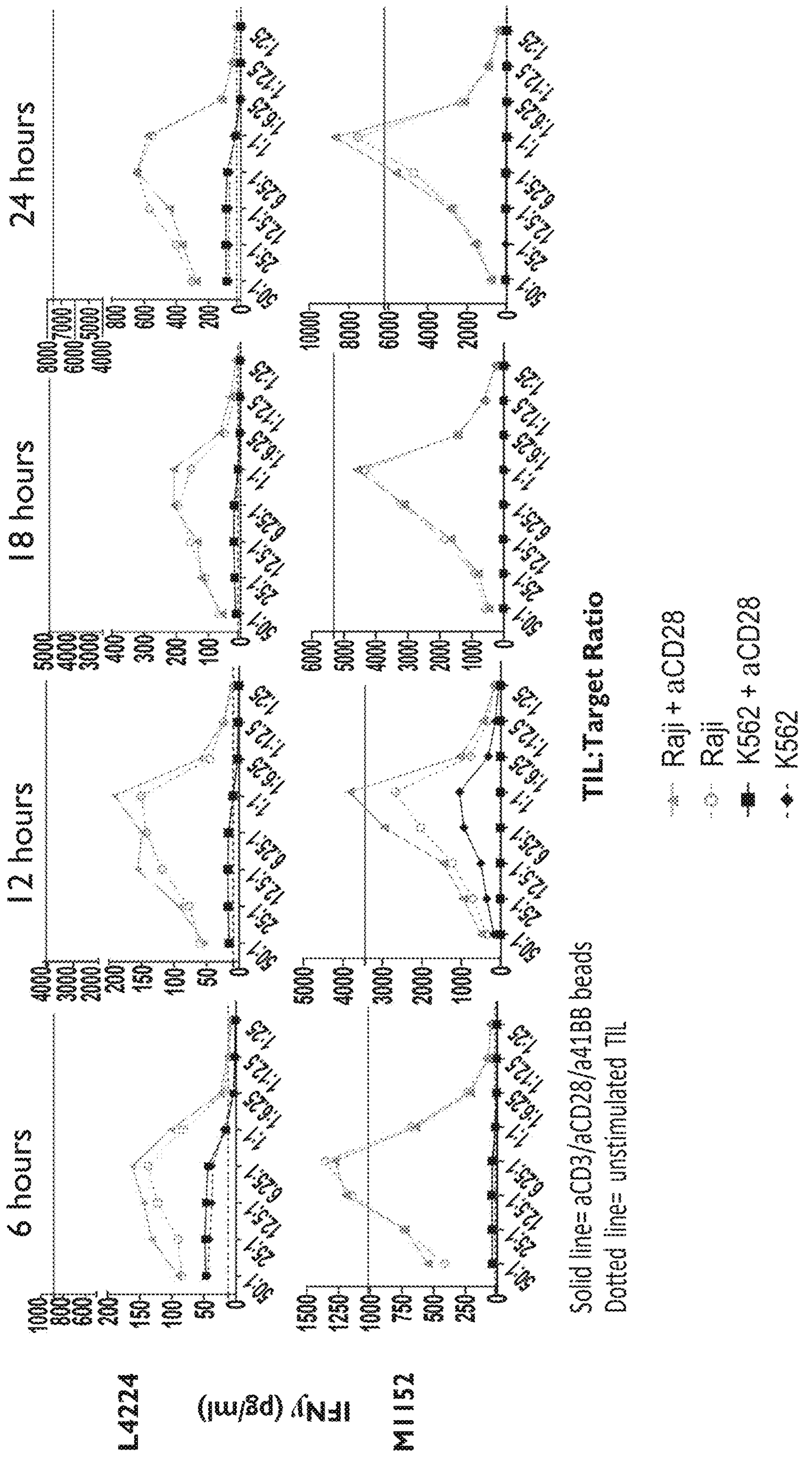
FIG. 39: IFN-γ secretion for different co-culture periods and TIL:target ratios for a lung tumor (L4224) and a melanoma tumor (M1152) using the TIL-Raji co-culture assay.
Figure 40:
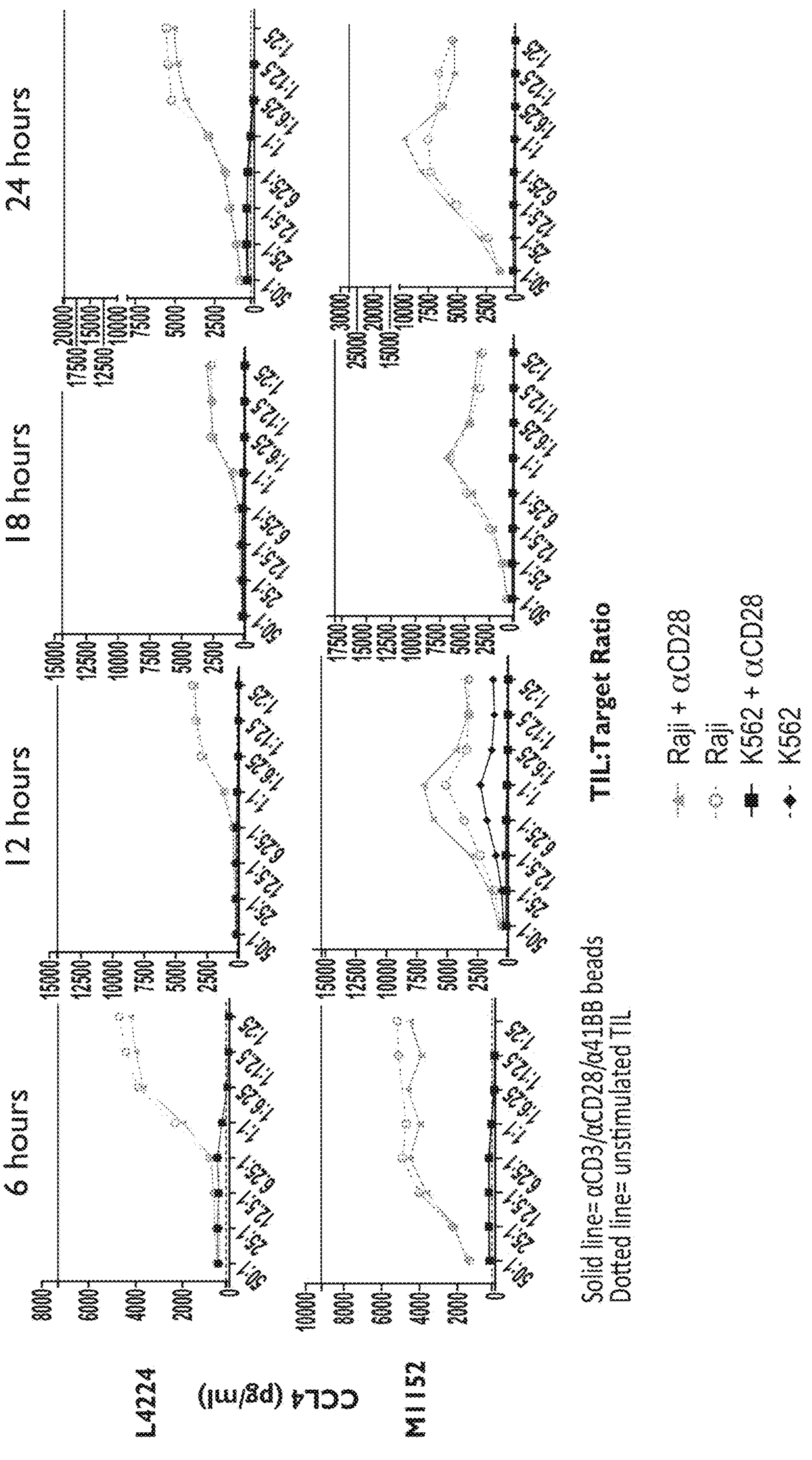
FIG. 40: CCL4 secretion for different co-culture periods and TIL:target ratios for a lung tumor (L4224) and a melanoma tumor (M1152) using the TIL-Raji co-culture assay.
Figure 41:
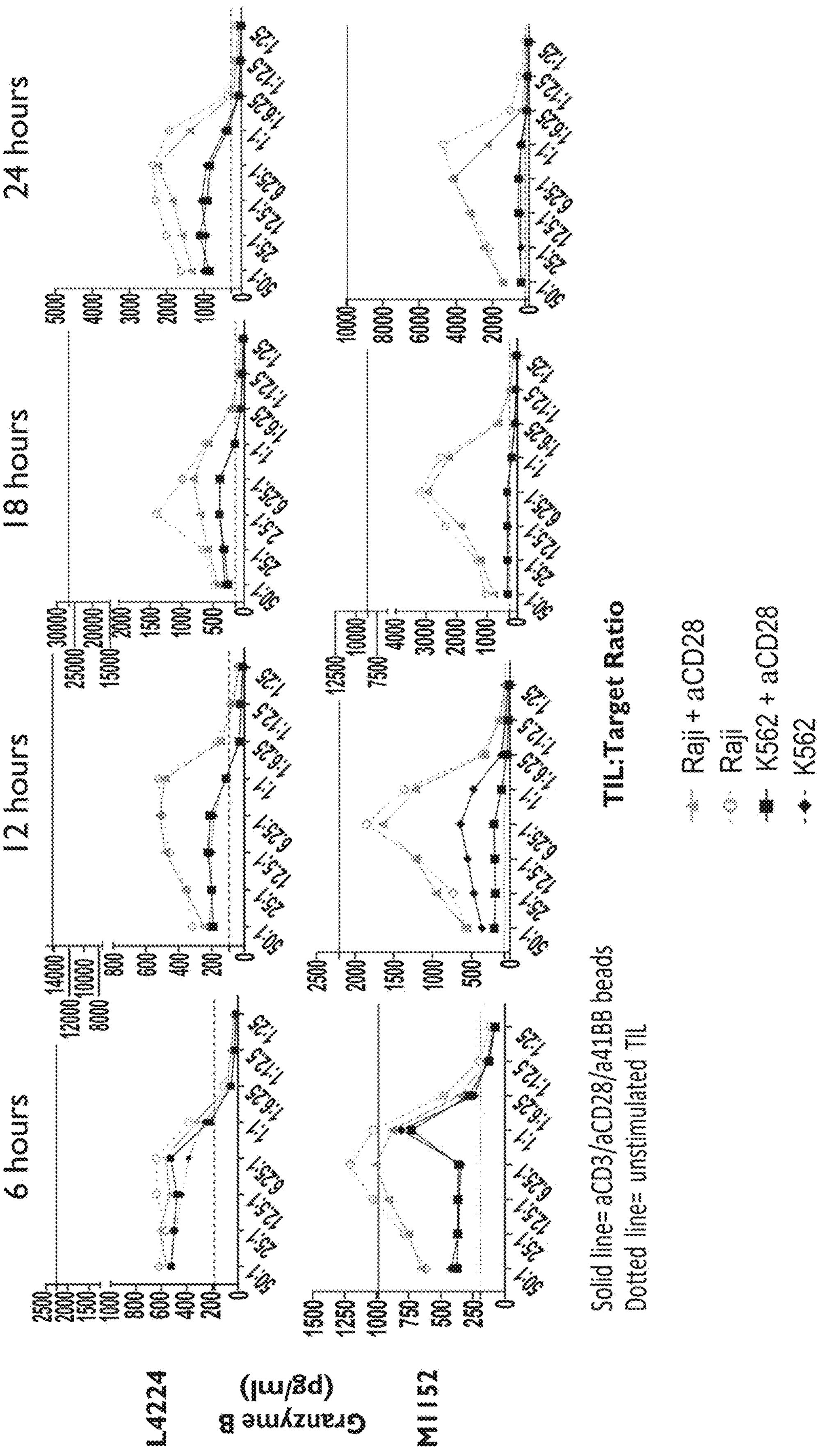
FIG. 41: Granzyme B secretion for different co-culture periods and TIL:target ratios different co-culture periods and TIL:target ratios for a lung tumor (L4224) and a melanoma tumor (M1152) using the TIL-Raji co-culture assay.
Figure 42:
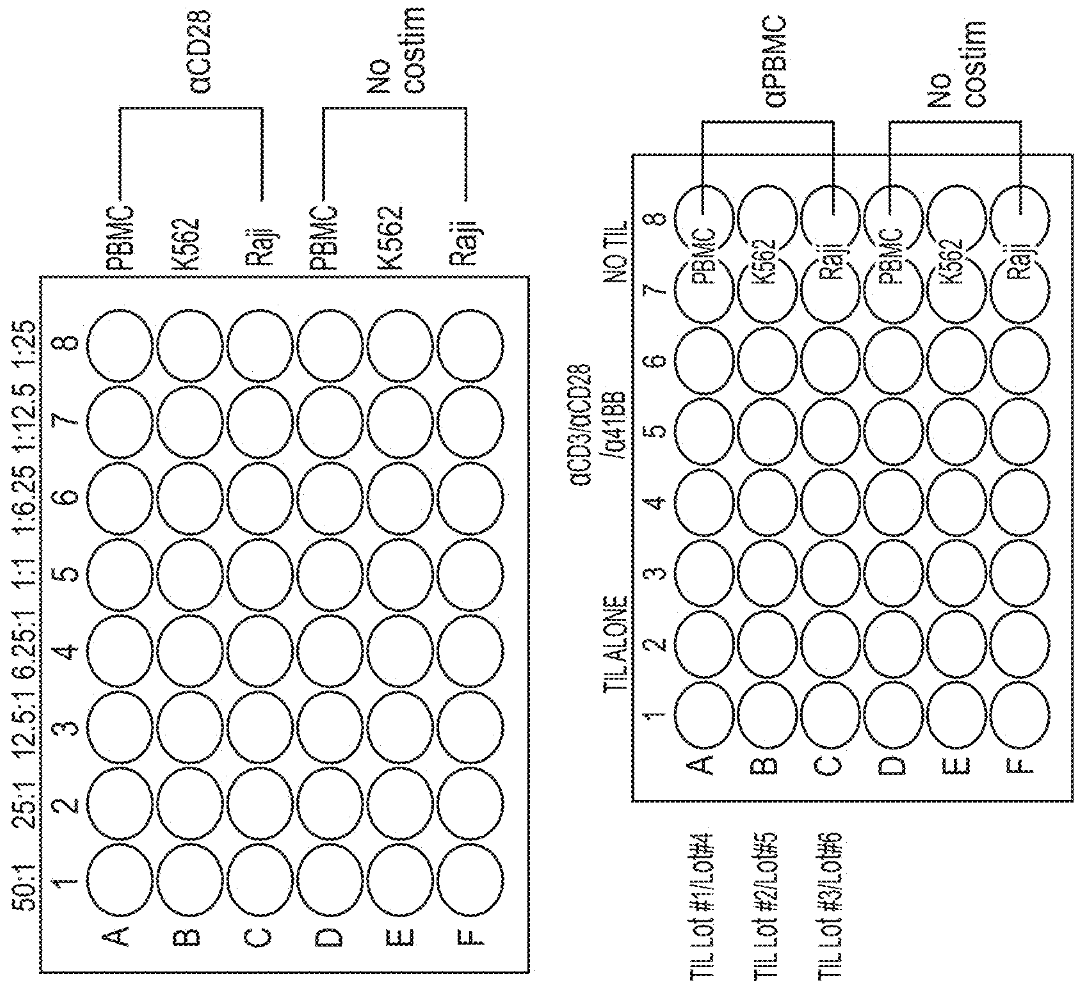
FIG. 42: Diagram of an embodiment of the TIL-Raji co-culture assay with a TIL-K562 negative control.
Figure 43:
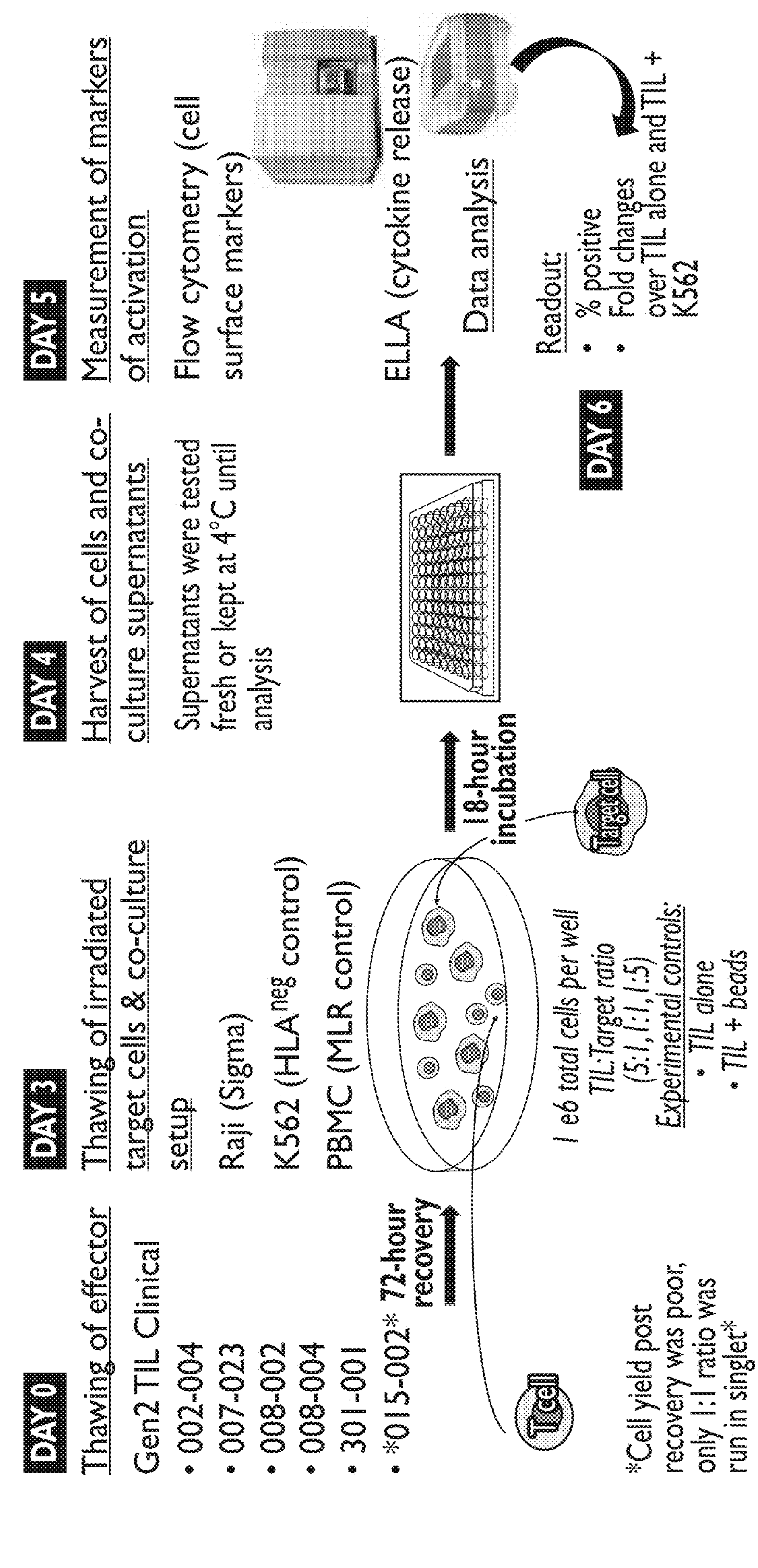
FIG. 43: Co-culture experimental setup for an exemplary embodiment of a TIL-Raji cell-based potency assay.
Figure 44:
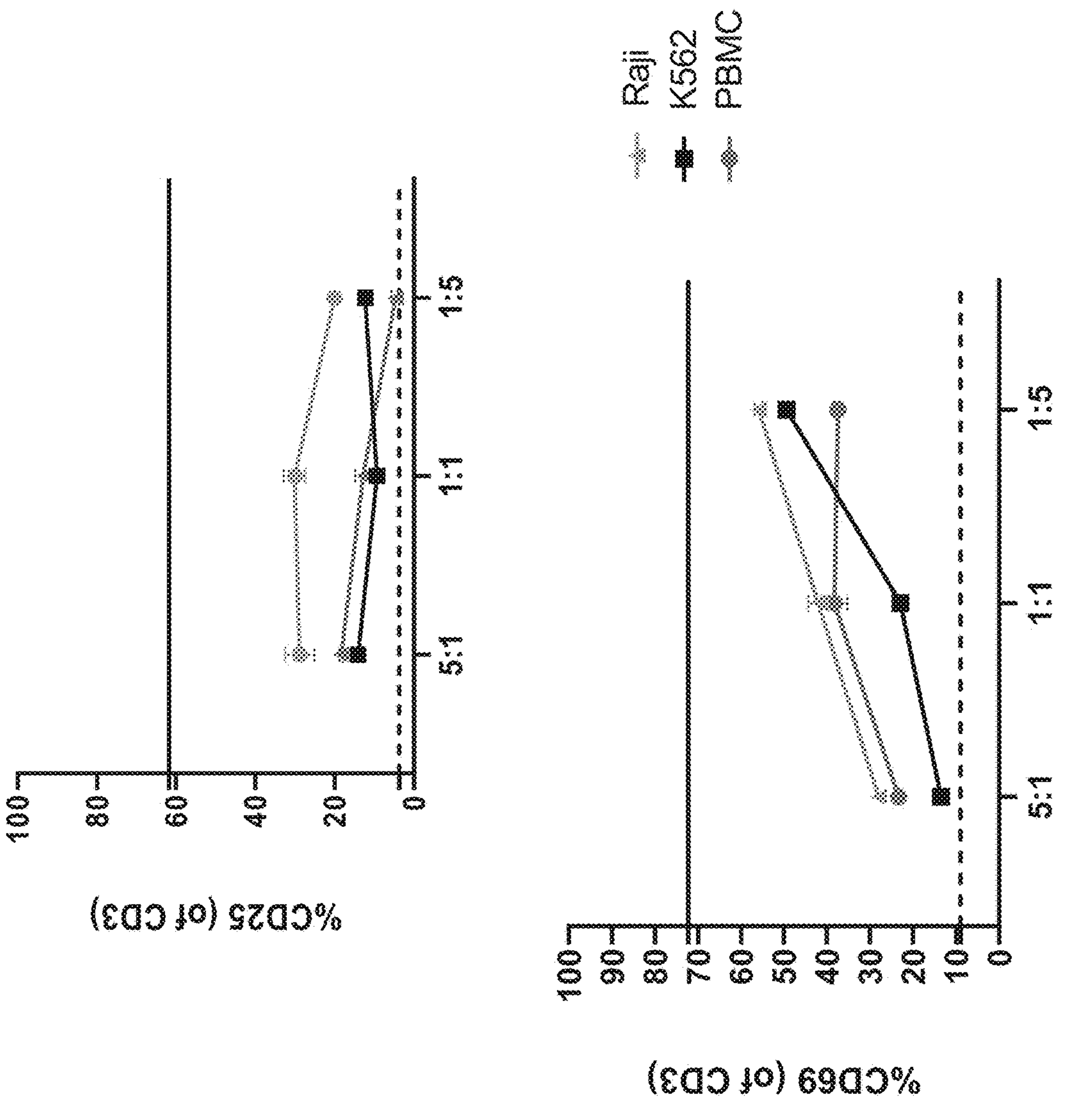
FIG. 44: Phenotypic expression of markers of activation in the TIL-Raji co-culture assay.
Figure 45:
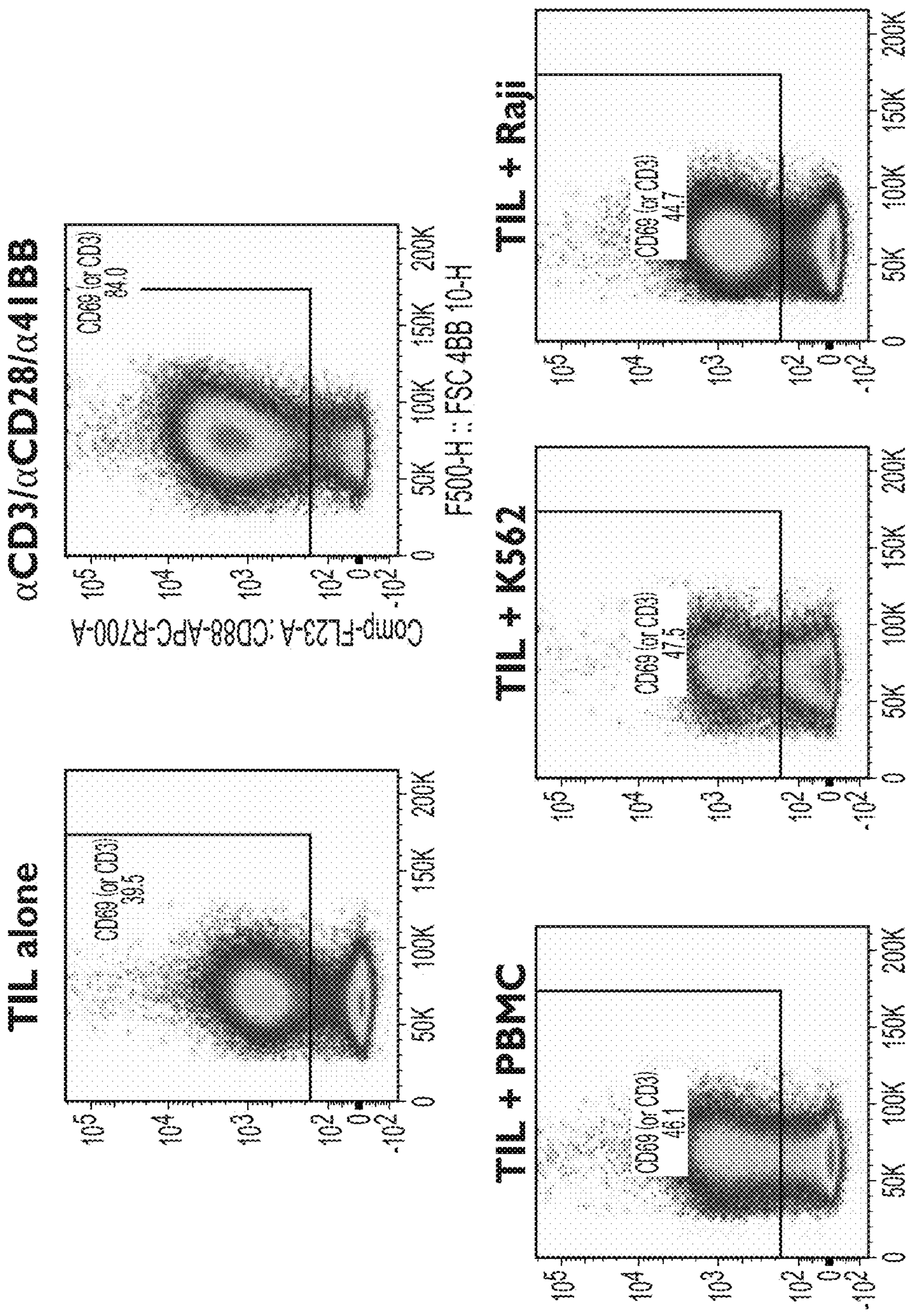
FIG. 45: Phenotypic expression of CD69 (Gen 2 TIL: 301-001) in TIL-Raji co-culture.
Figure 46:
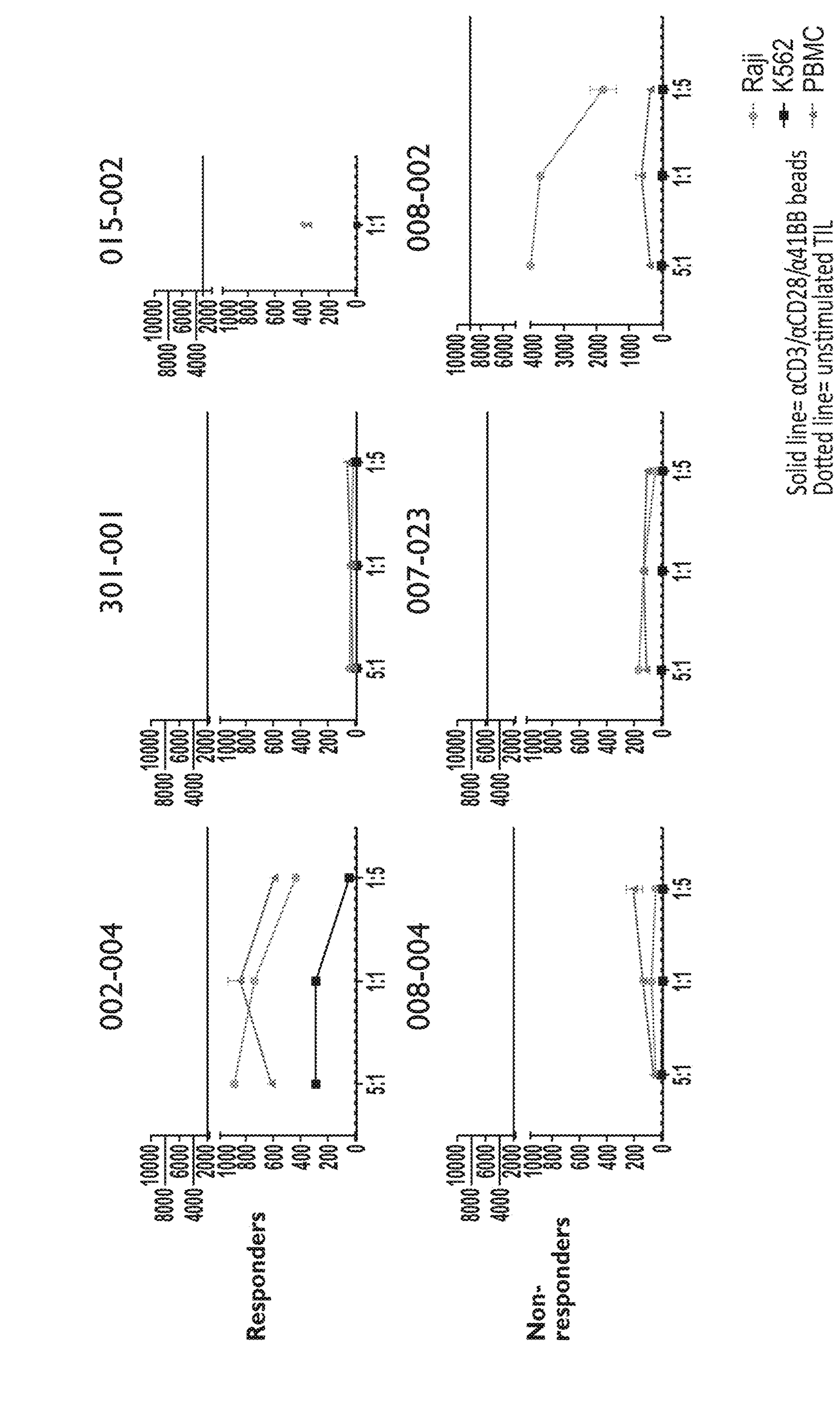
FIG. 46: IFN-γ secretion levels in pg/mL.

The supernatants were then assessed for IFN-γ, CCL4, granzyme B, TNF-α and MIP-1β secretion using the ELLA platform. The results for IFN-γ are shown in FIG. 39. The results for CCL4 are shown in FIG. 40. The results for granzyme B are shown in FIG. 41. The plate layout is shown in FIG. 42.

Example 15: TIL Potency Assessment for Six TIL Samples

A Raji-cell based co-culture system, as described in Example 14, was used to assess a total of six Gen 2 melanoma TIL lots. K562 cells were used as an HLA-negative control. TIL samples were analyzed for phenotypic markers of activation and secreted cytokines. Multiple additional cytokines or other secreted proteins can be monitored using ELISA or automated ELISA methods. The general experimental scheme is shown in FIG. 42.

FIG. 43 through FIG. 54 show the results of experiments with the co-culture potency assay on this set of TIL samples. Patients with clinical responses are separated by the criteria used in accompanying study are separated from those that did not respond; however, the response status of a patient does not limit the use of the assay or analysis of the data. The experiments demonstrated the ability of the assay to detect IFN-γ and granzyme B secretion upon co-culture with Raji cells. Across the six Gen 2 TIL samples, the range of IFN-γ determined by the TIL-Raji cell coculture assay was 42.1 pg/mL (301-001) to 3708 pg/mL (patient 008-002). The range of granzyme B determined by the TIL-Raji cell coculture assay was 568.3 pg/mL (301-001) to 8721.33 pg/mL (008-002).

Example 16: Polyfunctional TIL Potency Assessment for Twenty-Two TIL Samples

In this example, various embodiments of a polyfunctional TIL potency assay are demonstrated using a Raji-cell based co-culture system used in conjunction with a K562-cell based negative control co-culture system to assess TIL lots for potency. K562 and Raji cells were be thawed, counted and expanded in 6-well plates or T25 flasks for 10-14 days. Once the cell numbers reached $>160\times10^6$, cells were irradiated at 35 Gy, aliquoted, and frozen back for later use. Gen 2 TIL lots were thawed and counted, and put into culture for recovery for 48-72 hours prior to co-culture. Irradiated K562 and Raji cells were thawed and co-cultured with TIL using three TIL:target ratios (3:1, 1:1, 1:3), with a constant number of TILs (500,000 cells). TIL lots will also be stimulated with magnetic beads coated with anti-CD3/CD28/41BB to provide an optional positive activation control. TIL and tumor cell line only controls will also be included. Supernatants will be harvested at 12 and 18 hours post-initiation of the coculture. Supernatants will be assessed for cytokines, using the ELLA automated ELISA-based platform. Two cell lines will be co-cultured with the TIL. Wild-type Raji (Cat.

#CCL-86) and K562 (Cat. #CCL-243) cells were obtained commercially from ATCC. Raji cells are a human B lymphoblastoid cell line derived from a patient with Burkitt's lymphoma. K562 is a myelogenous leukemia cell line. The HLA type for the Raji cells was verified prior to use.

The following materials were used for this example, in addition to generally-available laboratory materials known to one of skill in the art: RPMI 1640 medium (ATCC, VA, USA, Cat. #ATCC 30-2001); glutamate (Gibco, MA, USA Cat. #30050-061); beta-mercaptoethanol (Gibco, MA, USA, Cat. #21985-023); human AB serum for TIL (Gemini, CA, USA, Cat. #100-512); fetal bovine serum for tumor cell lines (ATCC, VA, USA, Cat. #ATCC 30-2020); gentamycin (Gibco, MA, USA, Cat. #15750-060); GMP recombinant IL-2 (CellGenix, Germany, Cat. #1020-1000); Hank's balanced salt solution, or HBSS (Gibco, MA, USA, Cat. #14175-095); CELLSTAR T25 flasks (Fisher Scientific, MA, USA, Cat. #07-000-225); G-Rex 6, 24 well plates, and 10 flasks (Wilson Wolf, MN, USA, Cat. #P/N 80240M, P/N 80192M; #80040S); ELLA human multianalyte cartridges for IFN-γ (3rd generation), granzyme B, TNF-α (second generation) and MIP-1α (BioAgilytix, NC, USA, Kit ID 127725); human cytokine lyophilized controls (BioAgilytix, NC, USA, Cat. #89077); and CryoStor CS10 freeze media (BioLife Solutions, WA, USA, Cat. #210373).

The following equipment was used for this example, in addition to generally-available laboratory equipment known to one of skill in the art: Protein Simple ELLA (BioAgilytix, NC, USA, Cat. #500-140); K2 Cell Counter (Nexcelom, MA, USA); K2 Counting Chambers (Nexcelom, MA, USA, Cat. #SD100); JUN-AIR, model 84R-RP vacuum pump (Sony, NY, USA); and Steri-Cycle i160 CO2 incubator (ThermoFisher Scientific, MA, USA, Cat. #51030301).

Twenty-two randomly selected melanoma Gen 2 TIL lots were tested for activation upon co-culture with irradiated Raji and K562 cells.

Figure 56:
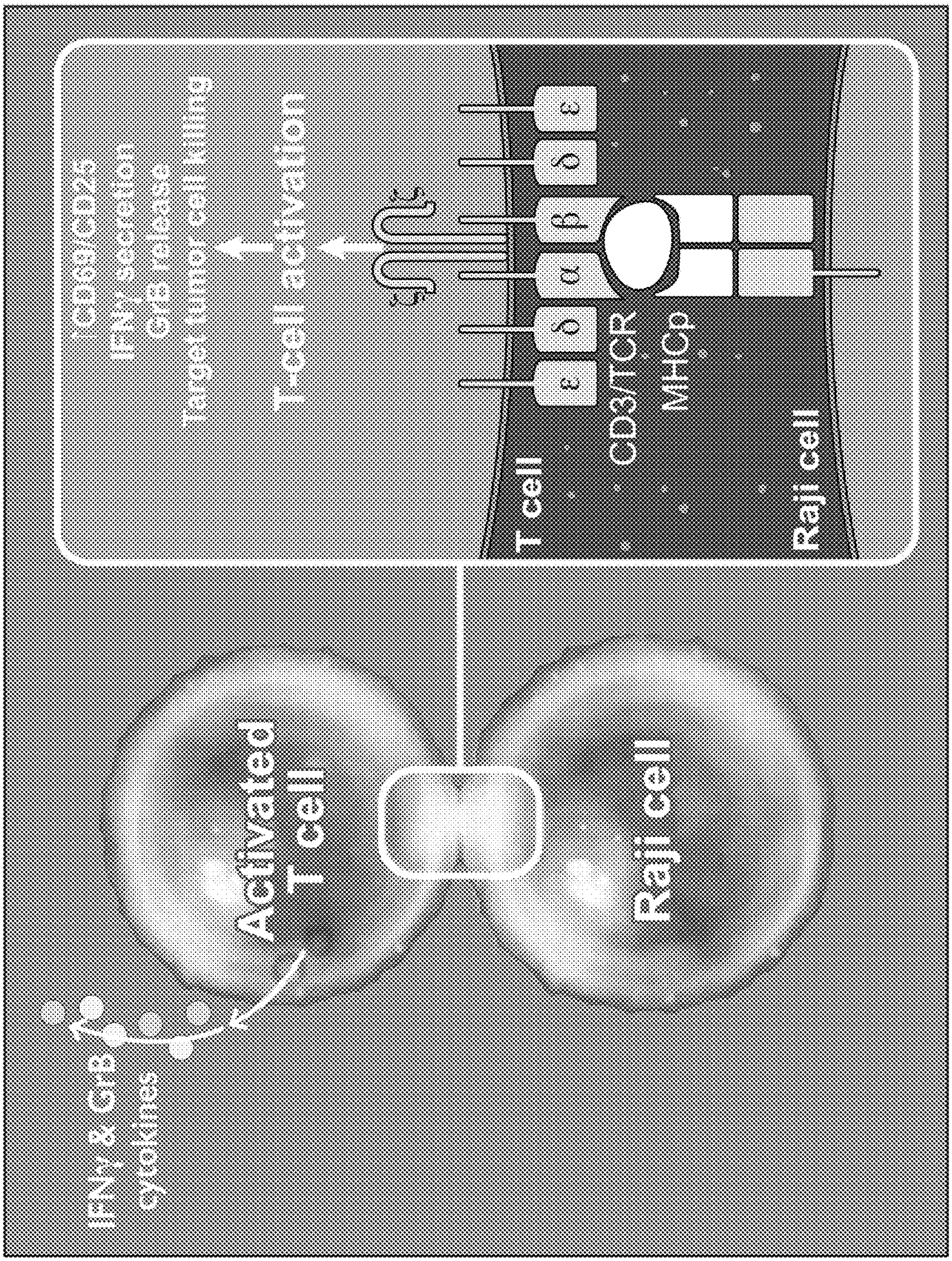
FIG. 56: Schematic of an embodiment of a TIL-Raji cell-based potency assay showing TIL activation by MHC dominant recognition.

Without being bound by theory, in an embodiment of the present invention, the allogeneic interaction of the TIL TCR complex with the target cells HLA-peptide complex to as MHC dominant recognition, as depicted in FIG. 56 and also described elsewhere herein. Due to a lack of MHC I and II expression, K562 cells are expected to provide a baseline activation level to which the co-culture of TIL with Raji cells can be compared. A culture of TIL alone may also be used as a baseline.

Thawing and Culturing of Tumor Cell Samples. The K562 and Raji tumor cells were thawed and cultured for 10-14 days to allow the cells to recover from the thaw, adapt to the media, and expand to appropriate numbers prior to the study. Media (200 mL) was warmed in a 37° C. water bath for 15±5 minutes before placing it into the BSC. For each of the tumor cell samples, a 50 mL conical tube was prepared with 10 mL of warm media. The tubes are labelled with the tumor line name. A single vial of cells was thawed, containing between $2\times10^6$ and $10\times10^6$ cells/1 mL vial, in a 37° C. water bath until only small chunks of ice remained. The partially thawed vials were transferred into a biological safety cabinet. The contents of the thawed tumor cells were transferred to the designated conical tube, and 0.5 mL of warm media was slowly added dropwise into the cryovial, swirling the vial while adding the media to mix. The contents of cryovial were then mixed by pipetting up and down gently 5-6 times. The contents of the vial were transferred to the 50 mL conical tube. The conical tubes were centrifuged at 400×g for 5 minutes at room temperature (RT). The supernatant was carefully removed from each tube, avoiding the cell pellet. The cell pellet was loosened by scraping the tube gently against the tube rack. The cells were checked daily and split 1:4 when the cells are about 70-80% confluent.

Harvesting of Tumor Cells. The tumor cells in suspension were removed from the flask or plate and added to a 50 mL conical tube with tumor media. The flask was rinsed with 1×PBS or tumor media and the contents were added to the 50 mL conical tube. The conical tubes were centrifuged together at 400× g for 5 minutes at RT. The supernatant was carefully removed from each tube, avoiding the cell pellet. The cell pellet was loosened by scraping the tube gently against the tube rack. Using a 1 mL pipettor, the TILs were resuspended in 1 mL media and pipetted up and down gently to further break the pellet. The cell suspension was brought to 5 mL with media using a serological pipette. The cell suspension was pipetted up and down with the serological pipette to mix thoroughly. Two 200 μL aliquots of cell suspension were then removed for counting on the K2 cell counter.

Irradiation of K562 and Raji Cells. Once the Raji and K562 cells have been expanded to $>160\times10^6$ cells, the cells were irradiated at 35 Gy. Post irradiation, cells were be counted and assessed for viability using the K2 cell counter. The cells were frozen at $10\times10^6$ cells/mL in CryoStor CS10.

Thawing and Recovery of TIL. 200 mL of TIL media (CM1) is warmed in a 37° C. water bath for 15±5 minutes before placing into the biological safety cabinet (BSC). An IL-2 stock solution ($6\times10^6$ IU/mL) is prepared and transferred into the BSC with the warm media. The media is supplemented with 300 IU/mL IL-2 by adding 10 μL of IL-2 stock solution ($6\times10^6$ IU/mL) into the media. For each TIL lot, a 50 mL conical tube is prepared with 10 mL of warm media and is labelled with the TIL lot number. Based upon the availability of the TIL product and the number of cells per vial, enough vials are thawed to obtain $60\times10^6$ total cells per TIL lot. Frozen TIL vials are thawed in a 37° C. water bath until only small chunks of ice remain. The thawed vials are transferred into the BSC. The contents of the thawed TIL vials and PBMCs (the latter used as a MLR positive control) are then transferred to the designated conical tube. Warm media (0.5 mL) is slowly added dropwise into the TIL vial, while swirling the vial and adding the media to mix. The contents of each TIL vial are mixed by pipetting up and down gently 5-6 times. The TIL vial contents are transferred to the 50 mL conical tubes. The conical tubes are centrifuged together at 400× g for 5 minutes at RT. The supernatant is carefully removed from each tube, avoiding the cell pellet. The cell pellet is loosened by scraping the tube gently against the tube rack. Using a 1 mL pipettor, TIL lots are resuspended in 1 mL TIL media and pipetted up and down gently to further break the pellet. Using a serological pipette, the cell suspension is brought to 5 mL with media, and the suspension is pipetted up and down to mix thoroughly. Two 200 μL aliquots of cell suspension are removed for counting on the K2 cell counter. The TIL lots are resuspended to a concentration of $1.5\times10^6/3\times10^6$ cells/mL in CM1 media and 3000 IU/mL of IL-2. The cells are allowed to recover at 37° C./5% $CO_2$ for 48-72 hours using either a G-Rex 10 flask or G-Rex 6-well plate.

TIL Preparation for Co-culture. 200 mL of media is warmed in a 37° C. water bath for 15±5 minutes before placing it into the BSC. 50 mL conical tubes are prepared with 10 mL of warm media. The TIL samples are harvested from the G-Rex 10 flasks or G-Rex 6-well plates and transferred the designated conical tube. The conical tubes are centrifuged together at 400× g for 5 minutes at RT. The supernatant is carefully from each tube, avoiding the cell pellet. The cell pellet is loosened by scraping the tube gently against the tube rack. Using a 1 mL pipettor, TIL lots are resuspended in 1 mL media and pipetted up and down gently to further break the pellet. Using a serological pipette, the cell suspension is brought to 2 mL with media, and pipetted up and down to mix thoroughly. Two 200 μL aliquots of cell suspension are removed for counting on the K2 cell counter. The TIL lots are resuspended at $5\times10^5$ cells/mL in TIL media.

Thawing Irradiated K562 cells, Raji cells, and PBMCs for Co-Culture. 200 mL of media is warmed in a 37° C. water bath for 15±5 min before placing it into the BSC. The warm media is transferred to the BSC. For each cell line, a 50 mL conical tube is prepared with 10 mL of warm media and labelled appropriately. Frozen K562 and Raji cells are thawed in a 37° C. water bath until only small chunks of ice remain. The thawed satellite vial is transferred into the BSC. The contents of the thawed K562 and Raji cell lines are transferred to the designated conical tube, and 0.5 mL of warm media is slowly added dropwise into the cryovial, swirling the vial while adding the media to mix. The contents of the vial are mixed by pipetting up and down gently 5-6 times. The cell contents are transferred to the 50 mL conical tube. The conical tubes are centrifuged together at 400× g for 5 minutes at RT. The supernatant is carefully removed from each tube, avoiding the cell pellet. The cell pellet is loosened by scraping the tube gently against the tube rack. Using a 1 mL pipettor, TILs are resuspended in 1 mL media and pipetted up and down gently to further break the pellet. Using a serological pipette, the cell suspension is brought to 5 mL with media, and pipetted up and down with the serological pipette to mix thoroughly. Two 200 μL aliquots of cell suspension are removed for counting on the K2 cell counter. The cells are resuspended to a concentration of $5\times10^5$ cells/mL in tumor media and placed in the incubator for co-culture once the TIL samples are prepared.

Figure 57:
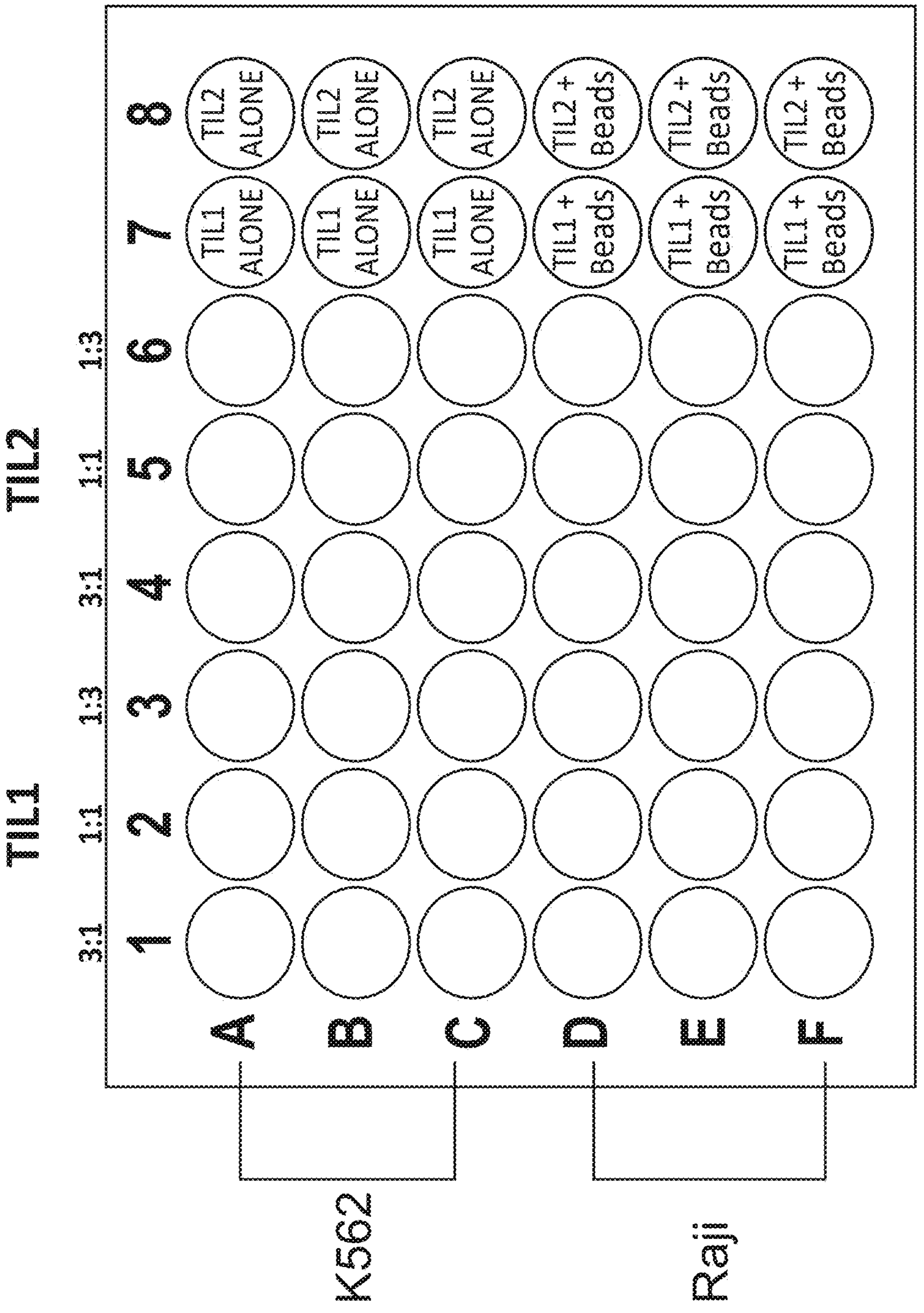
FIG. 57: Co-culture experimental plate setup for an exemplary embodiment of a TIL-Raji cell-based potency assay.
Figure 58:
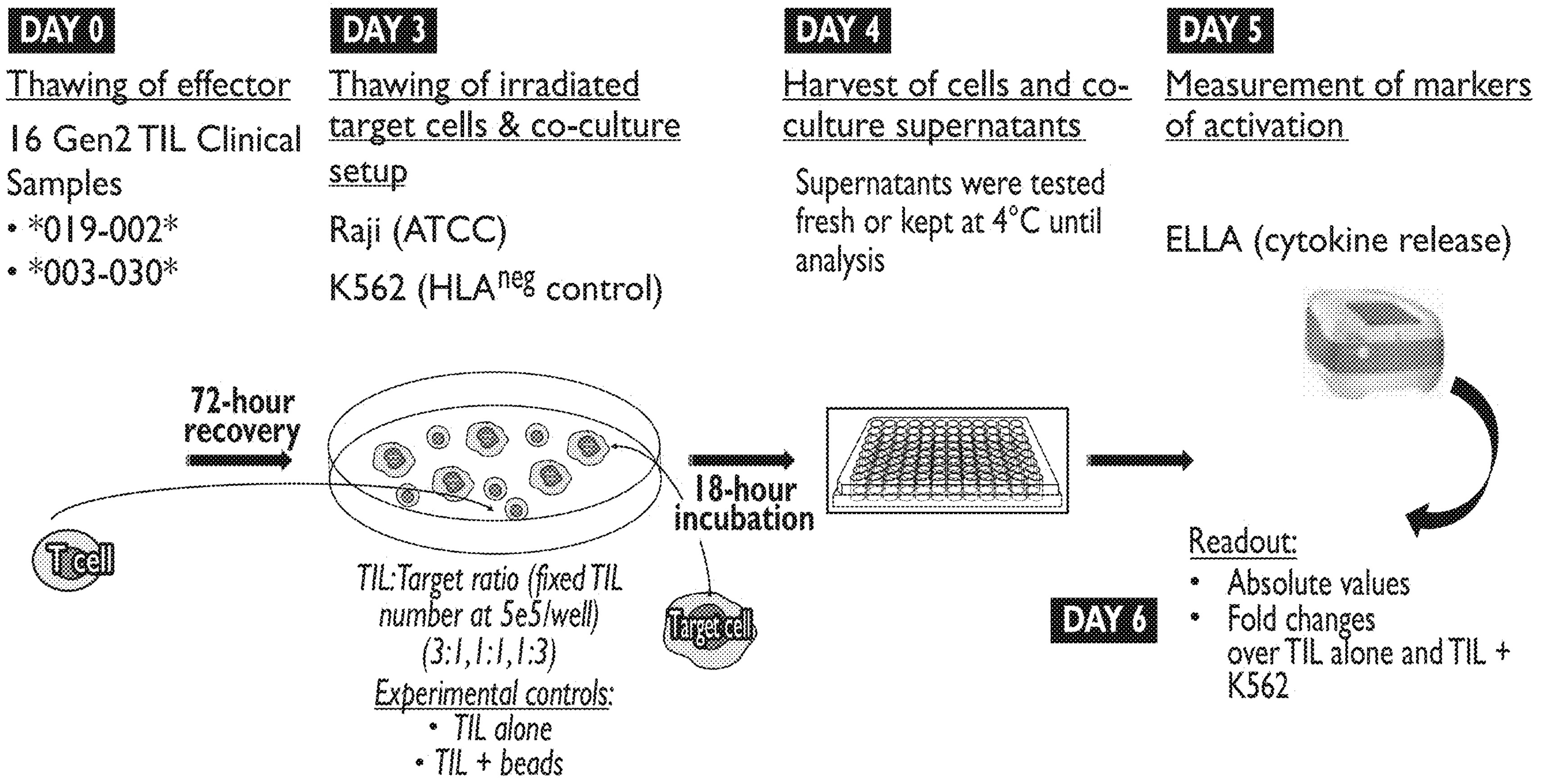
FIG. 58: Diagram of an embodiment of the TIL-Raji co-culture assay with an optional TIL-K562 negative control.
Figure 59:
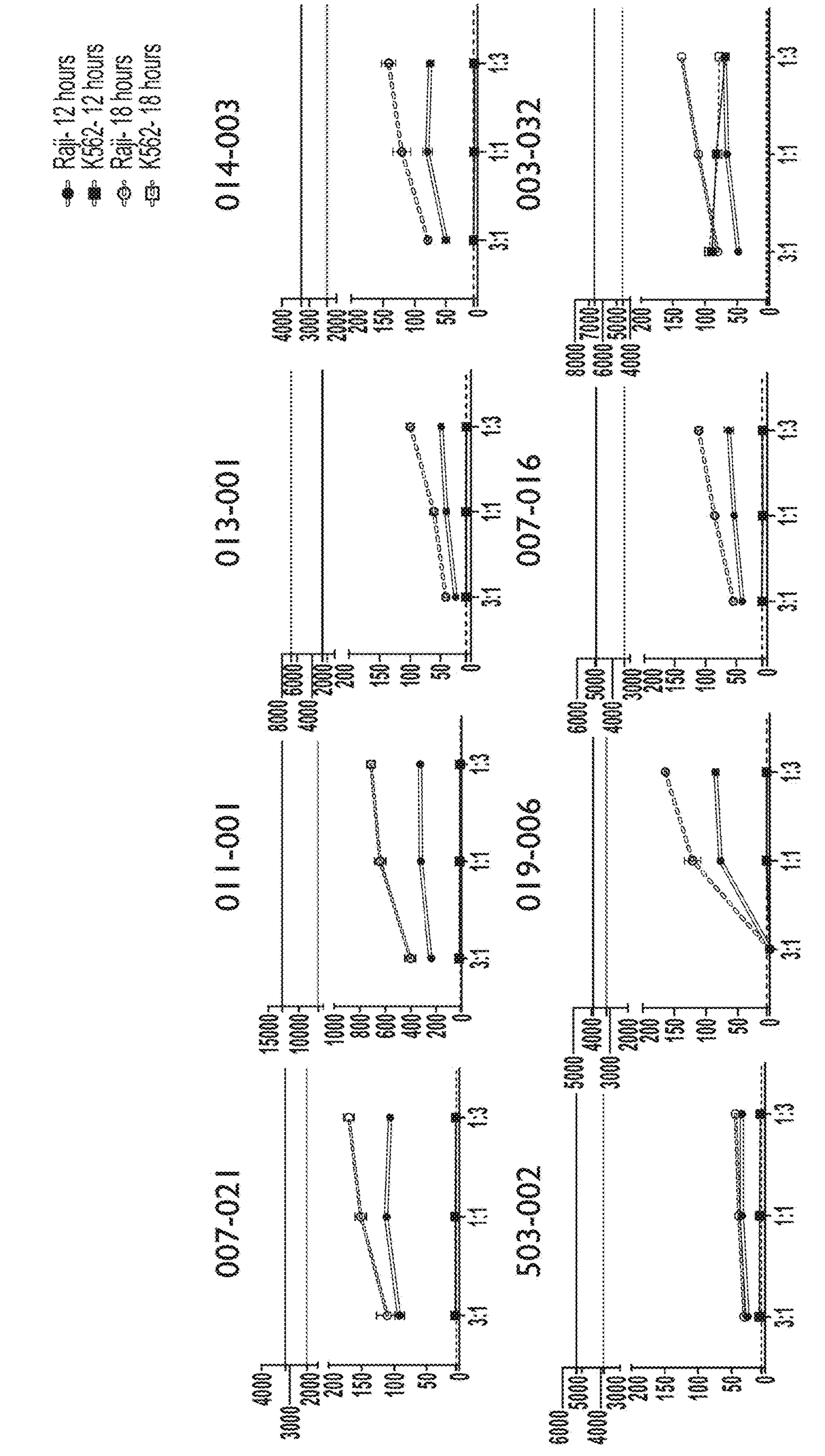
FIG. 59: IFN-γ secretion (pg/mL) for melanoma TIL lots for 3:1, 1:1, and 1:3 TIL:Raji or TIL:K562 ratios. Secretion levels in pg/mL are shown on the y-axes and TIL:target ratios are shown on the x-axes.
Figure 60:
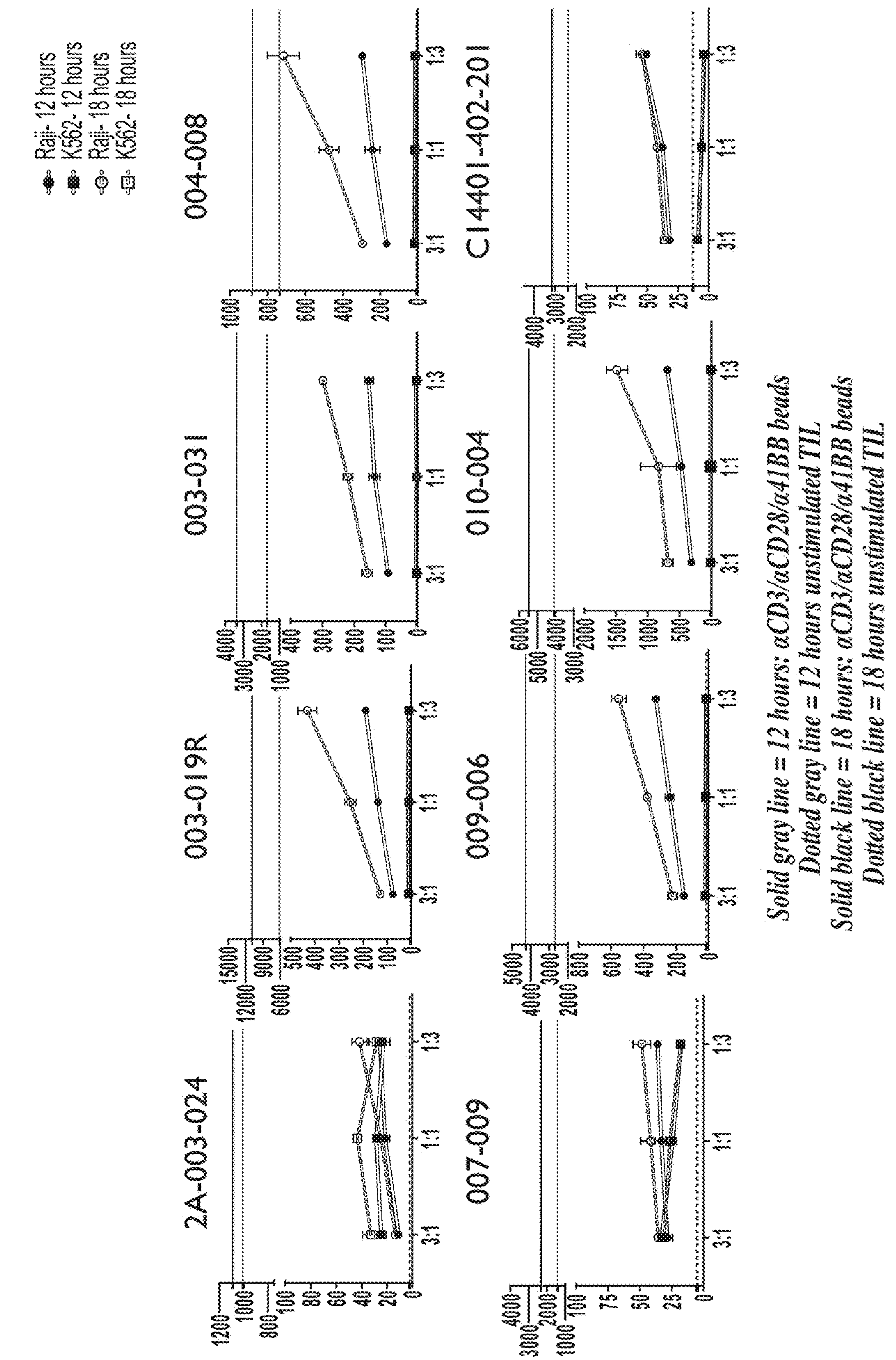
FIG. 60: IFN-γ secretion (pg/mL) for melanoma TIL lots for 3:1, 1:1, and 1:3 TIL:Raji or TIL:K562 ratios. Secretion levels in pg/mL are shown on the y-axes and TIL:target ratios are shown on the x-axes.
Figure 61:
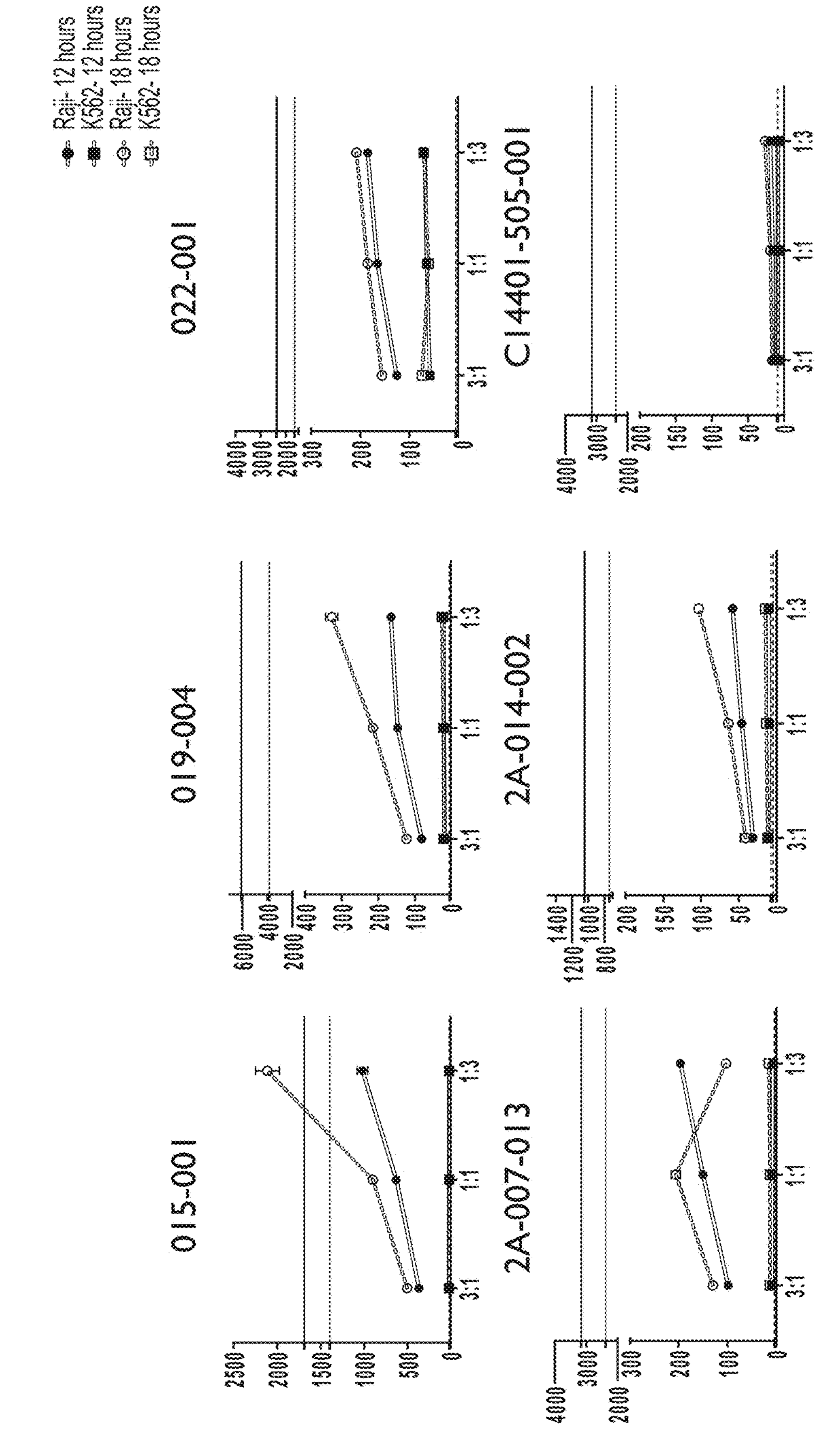
FIG. 61: IFN-γ secretion (pg/mL) for melanoma TIL lots for 3:1, 1:1, and 1:3 TIL:Raji or TIL:K562 ratios. Secretion levels in pg/mL are shown on the y-axes and TIL:target ratios are shown on the x-axes.
Figure 62:
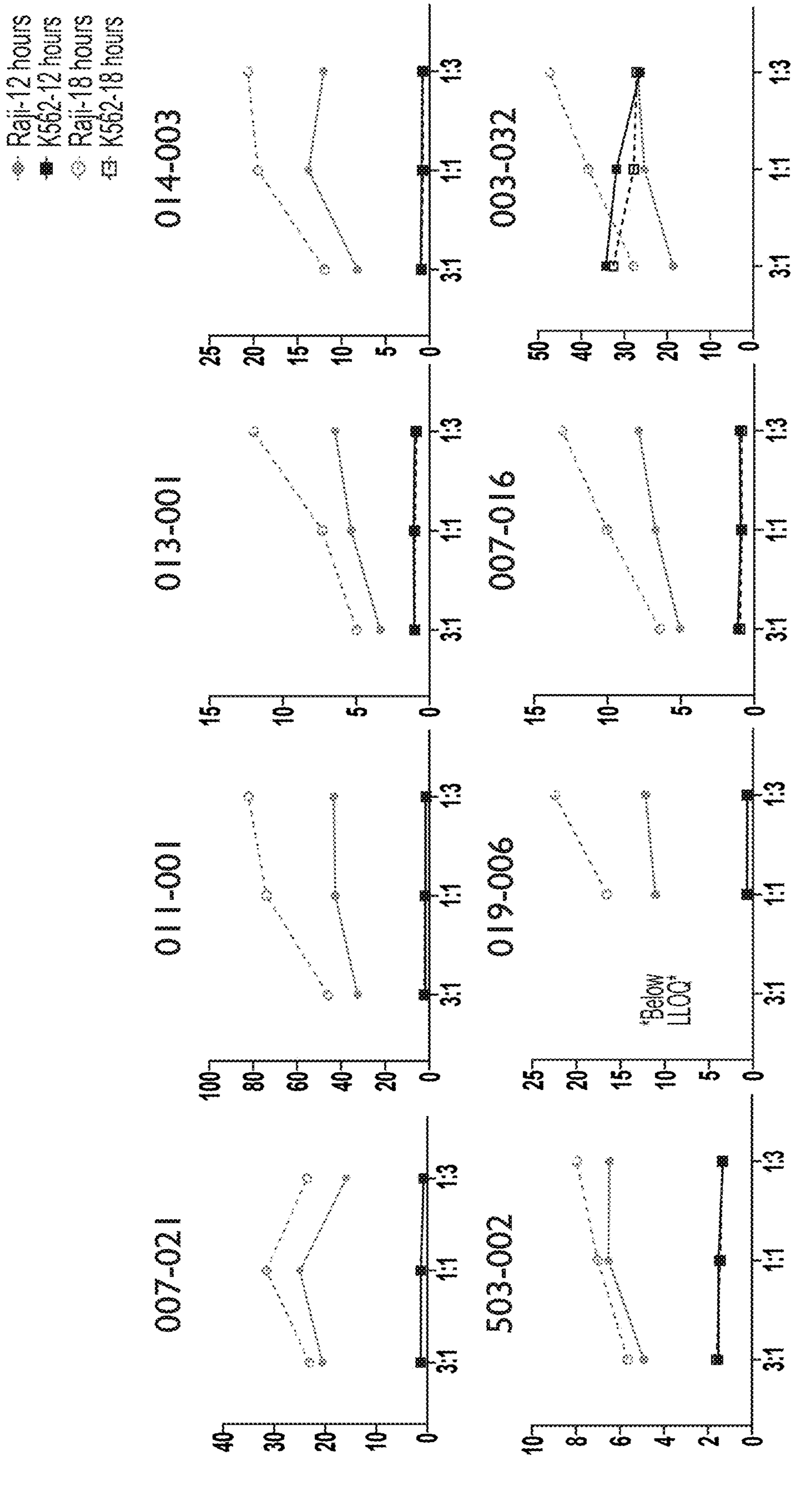
FIG. 62: Fold changes in IFN-γ release for TILs plus Raji or K562 cells over IFN-γ release from TILs alone for melanoma TIL lots for 3:1, 1:1, and 1:3 TIL:Raji or TIL:K562 ratios. Fold changes are shown on the y-axes and TIL:target ratios are shown on the x-axes.
Figure 63:
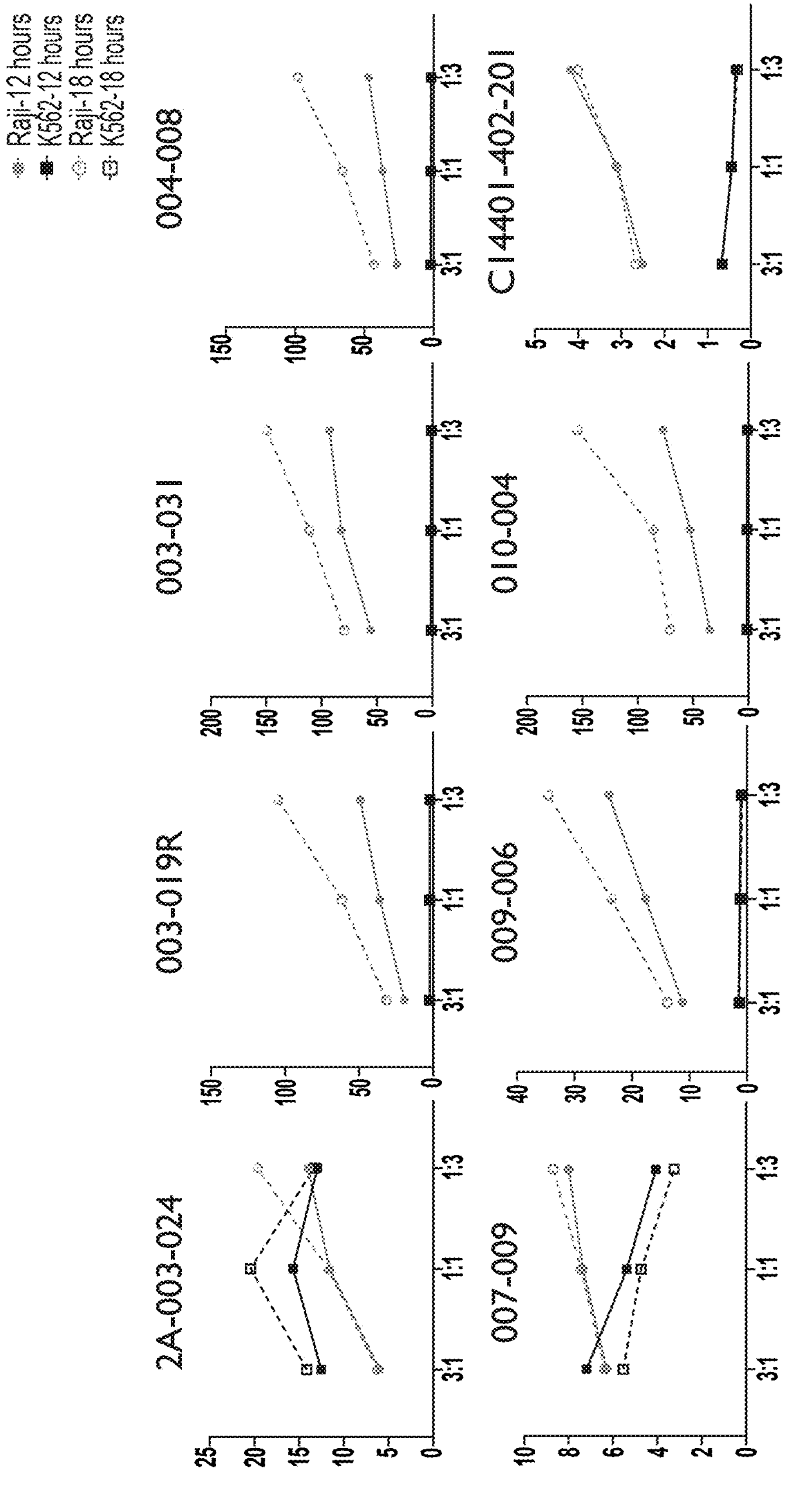
FIG. 63: Fold changes in IFN-γ release for TILs plus Raji or K562 cells over IFN-γ release from TILs alone for melanoma TIL lots for 3:1, 1:1, and 1:3 TIL:Raji or TIL:K562 ratios. Fold changes are shown on the y-axes and TIL:target ratios are shown on the x-axes.
Figure 64:
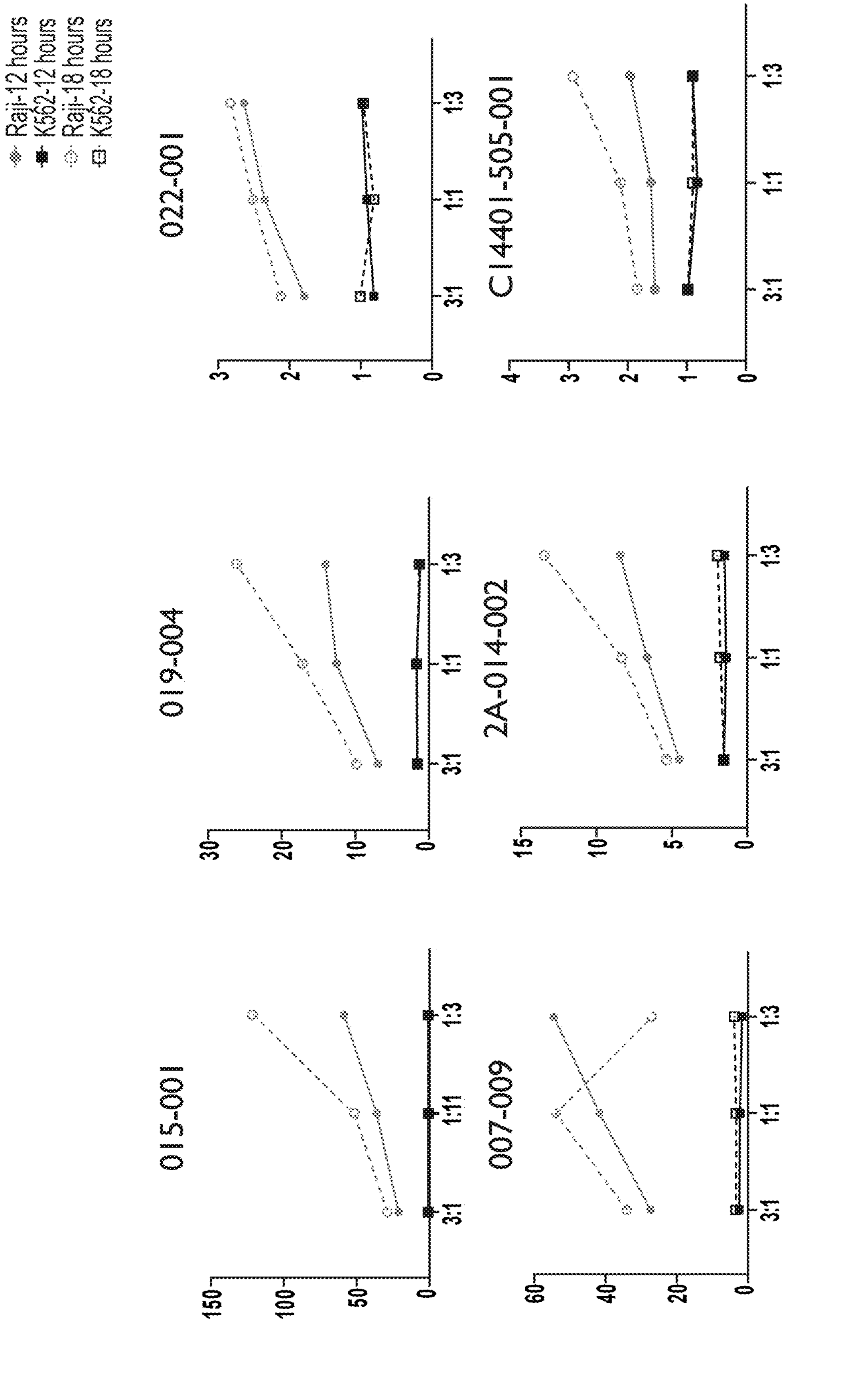
FIG. 64: Fold changes in IFN-γ release for TILs plus Raji or K562 cells over IFN-γ release from TILs alone for melanoma TIL lots for 3:1, 1:1, and 1:3 TIL:Raji or TIL:K562 ratios. Fold changes are shown on the y-axes and TIL:target ratios are shown on the x-axes.
Figure 65:
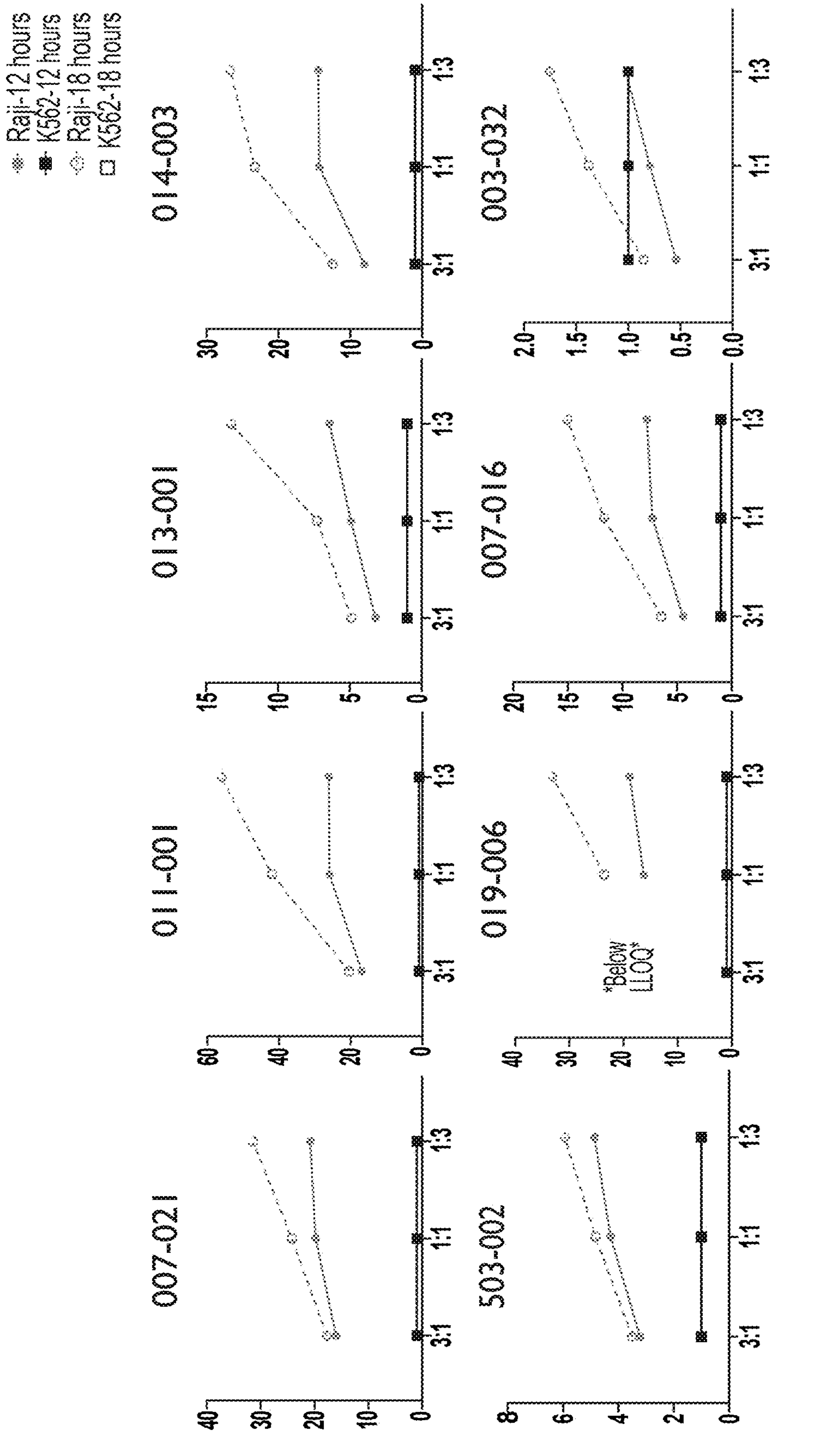
FIG. 65: Fold changes in IFN-γ release for TILs plus Raji or K562 cells over IFN-γ release from TILs plus K562 cells for melanoma TIL lots for 3:1, 1:1, and 1:3 TIL:Raji or TIL:K562 ratios. Fold changes are shown on the y-axes and TIL:target ratios are shown on the x-axes.
Figure 66:
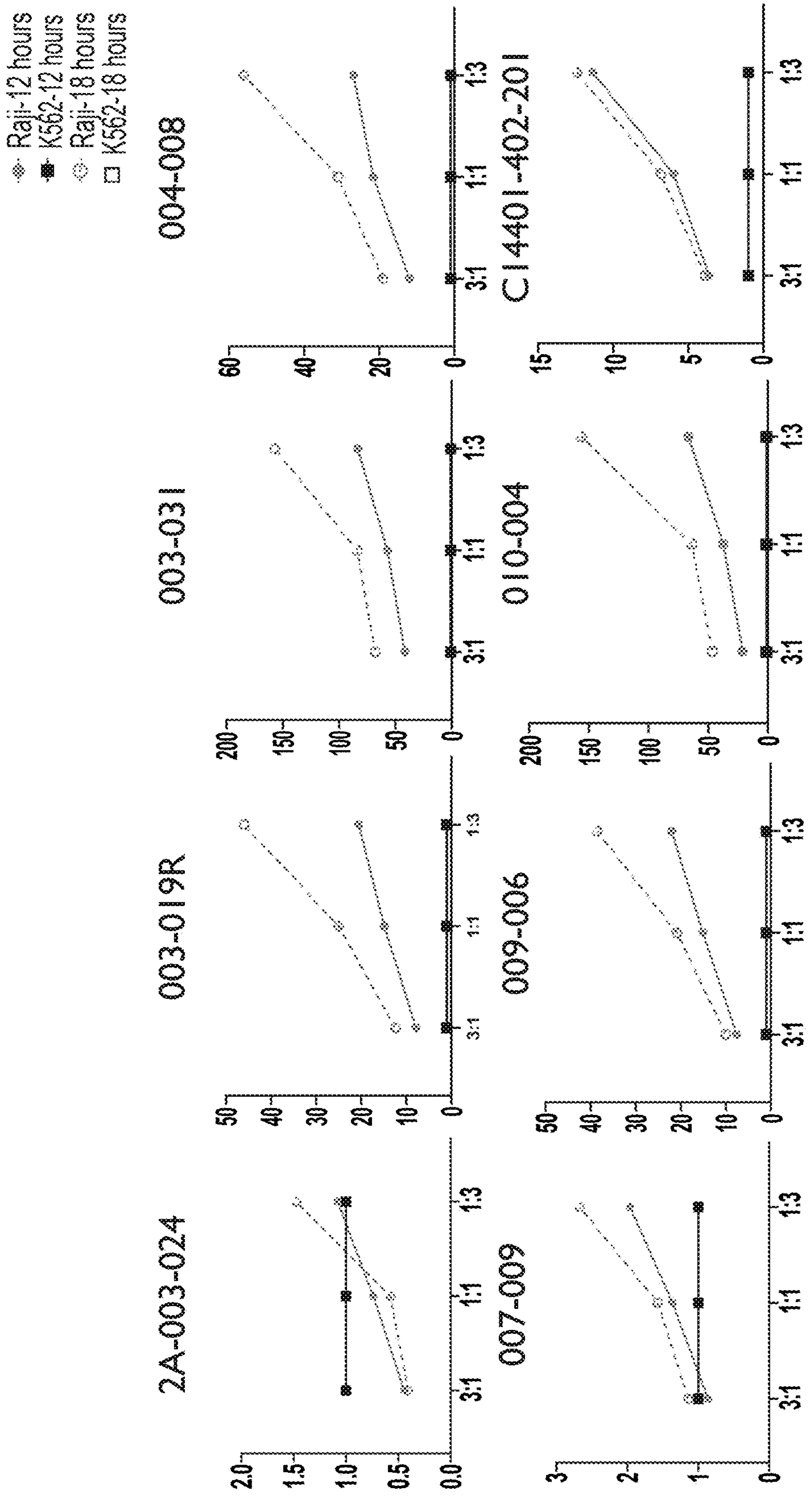
FIG. 66: Fold changes in IFN-γ release for TILs plus Raji or K562 cells over IFN-γ release from TILs plus K562 cells for melanoma TIL lots for 3:1, 1:1, and 1:3 TIL:Raji or TIL:K562 ratios. Fold changes are shown on the y-axes and TIL:target ratios are shown on the x-axes.
Figure 67:
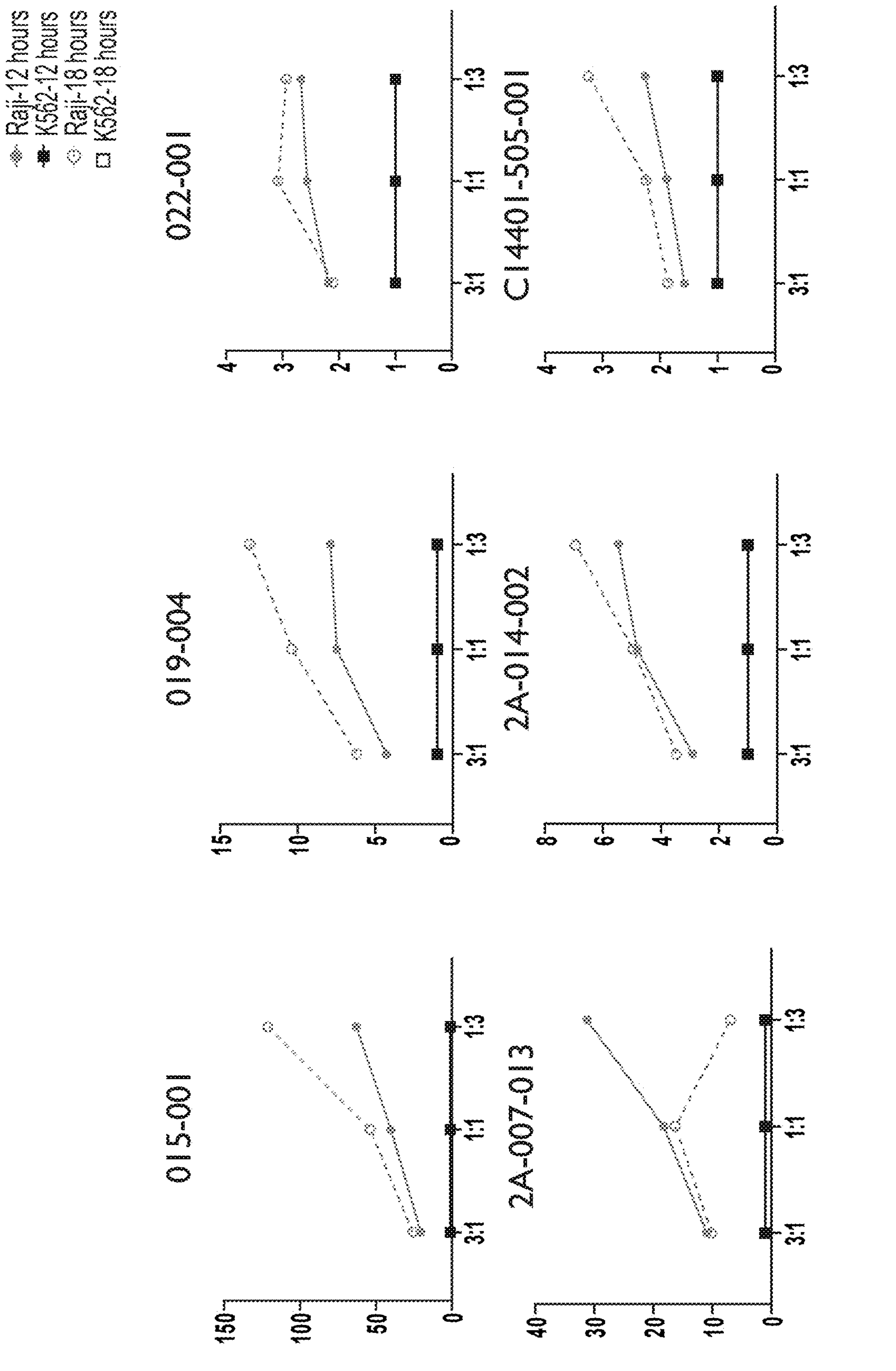
FIG. 67: Fold changes in IFN-γ release for TILs plus Raji or K562 cells over IFN-γ release from TILs plus K562 cells for melanoma TIL lots for 3:1, 1:1, and 1:3 TIL:Raji or TIL:K562 ratios. Fold changes are shown on the y-axes and TIL:target ratios are shown on the x-axes.
Figure 68:
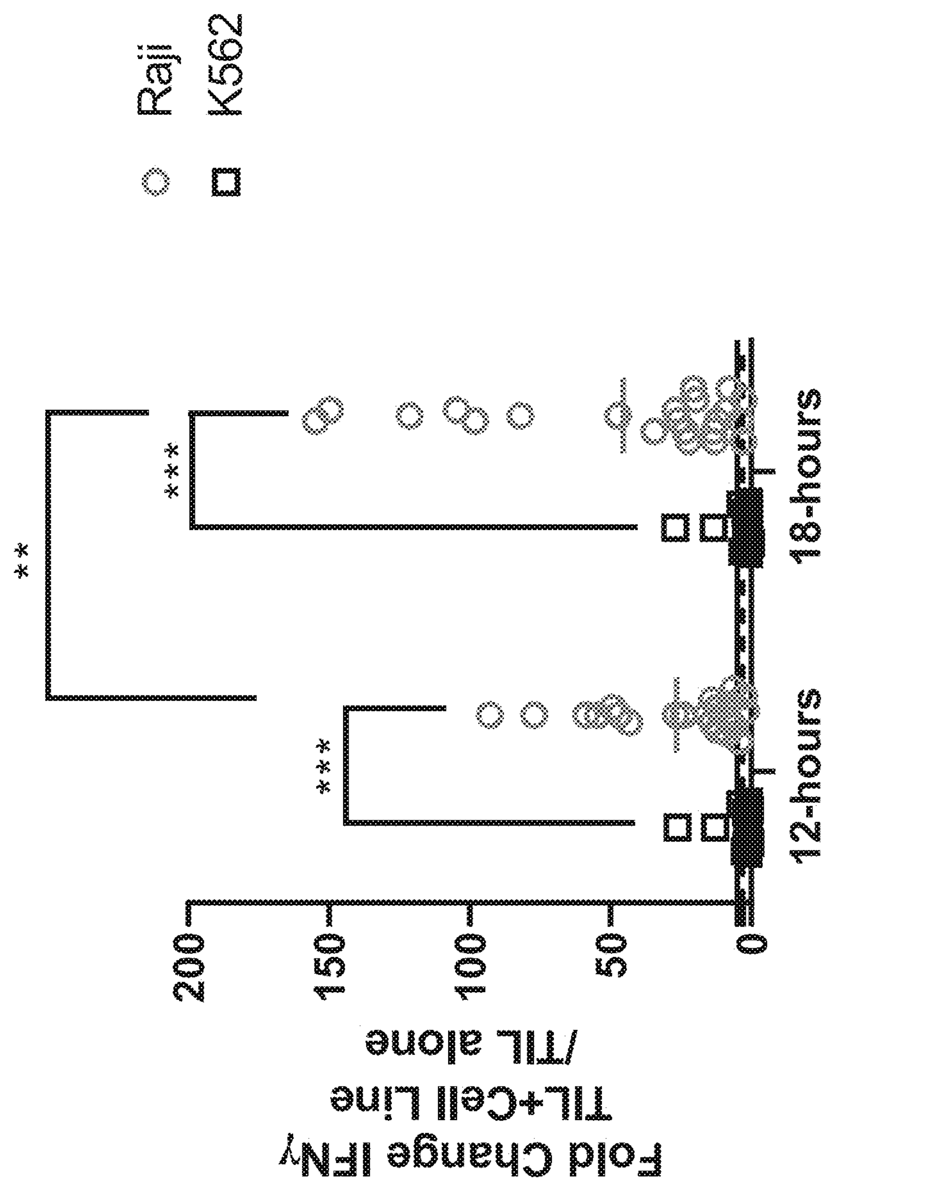
FIG. 68: Fold changes in IFN-γ release for TILs plus Raji or K562 cells over TILs alone at 12 and 18 hours of incubation time, showing the cumulative data set at a 1:3 TIL:Raji or TIL:K562 cell ratio, wherein * denotes a p-value of ≤0.05:  denotes a p-value of ≤0.01; and * denotes a p-value of ≤0.001.
Figure 69:
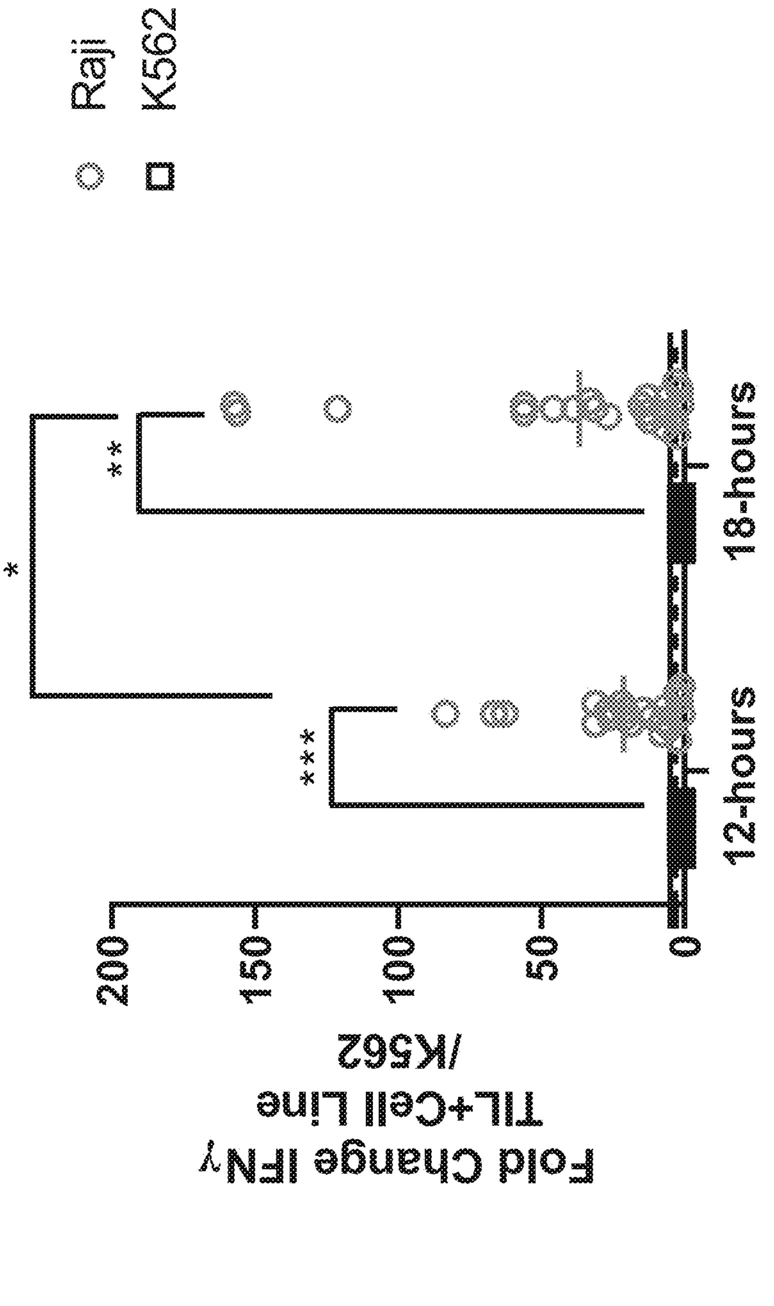
FIG. 69: Fold changes in IFN-γ release for TILs plus Raji or K562 cells over TILs alone or over K562 cells at 12 and 18 hours of incubation time, showing the cumulative data set at a 1:3 TIL:Raji or TIL:K562 cell ratio, wherein * denotes a p-value of ≤0.05:  denotes a p-value of ≤0.01; and * denotes a p-value of ≤0.001.
Figure 70:
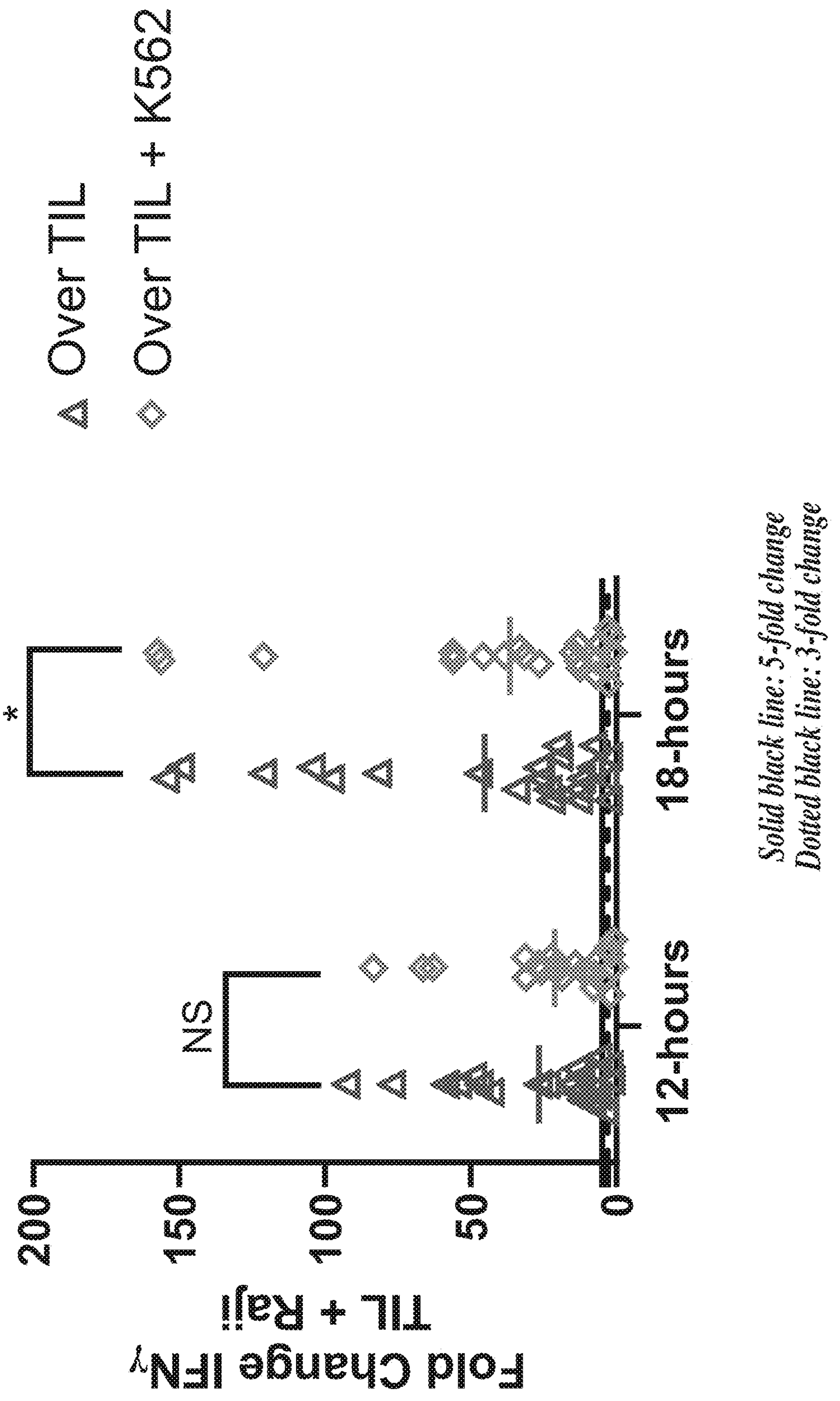
FIG. 70: Fold changes in IFN-γ release for TILs plus Raji cells over TILs plus K562 cells or over TILs at 12 and 18 hours of incubation time, showing the cumulative data set at a 1:3 TIL:Raji or TIL:K562 cell ratio, wherein * denotes a p-value of ≤0.05 and NS denotes not significant, at full scale.
Figure 71:
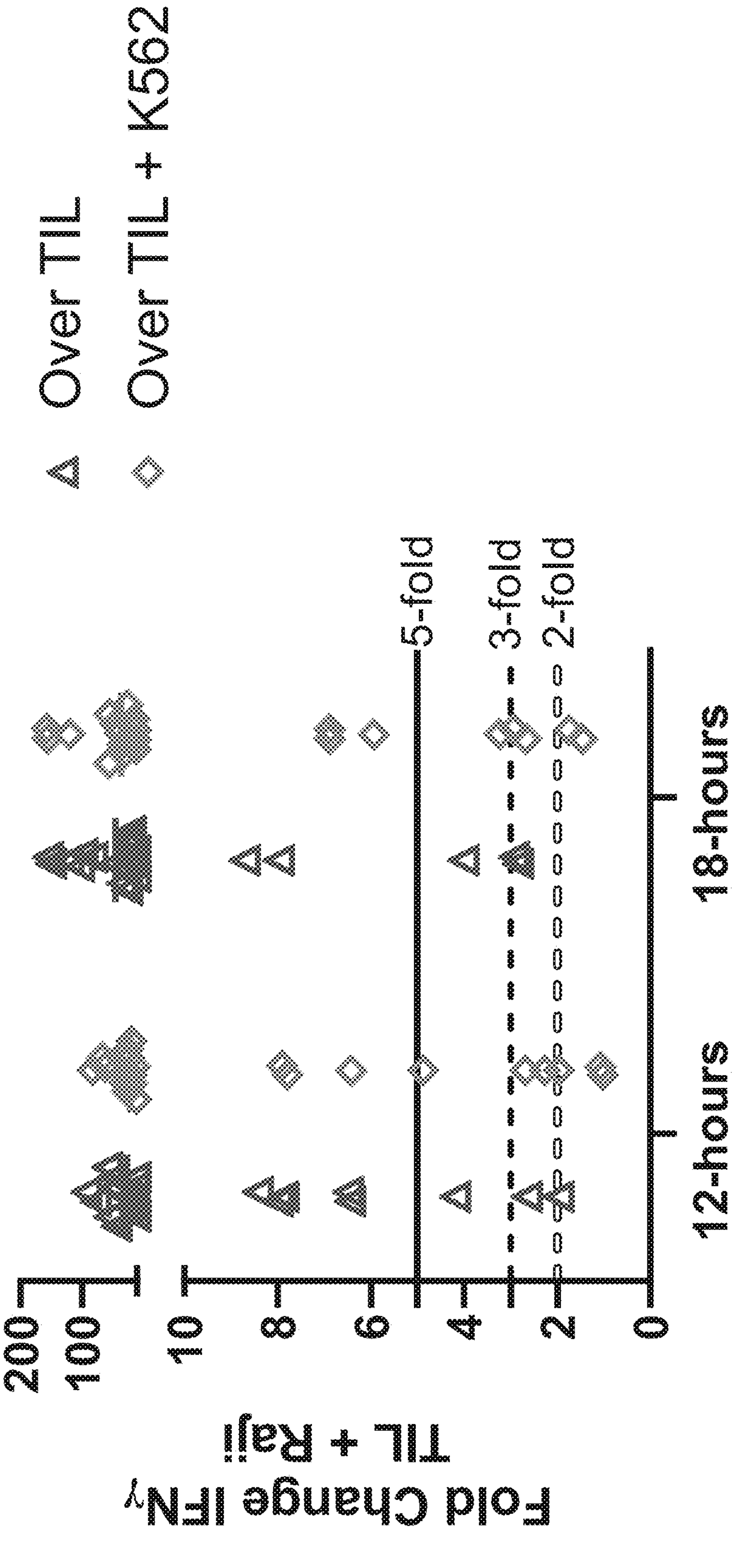
FIG. 71: Fold changes in IFN-γ release for TILs plus Raji cells over TILs plus K562 cells or over TILs at 12 and 18 hours of incubation time, showing the cumulative data set at a 1:3 TIL:Raji or TIL:K562 cell ratio, expanded to show detail of lower fold-change levels.
Figure 72:
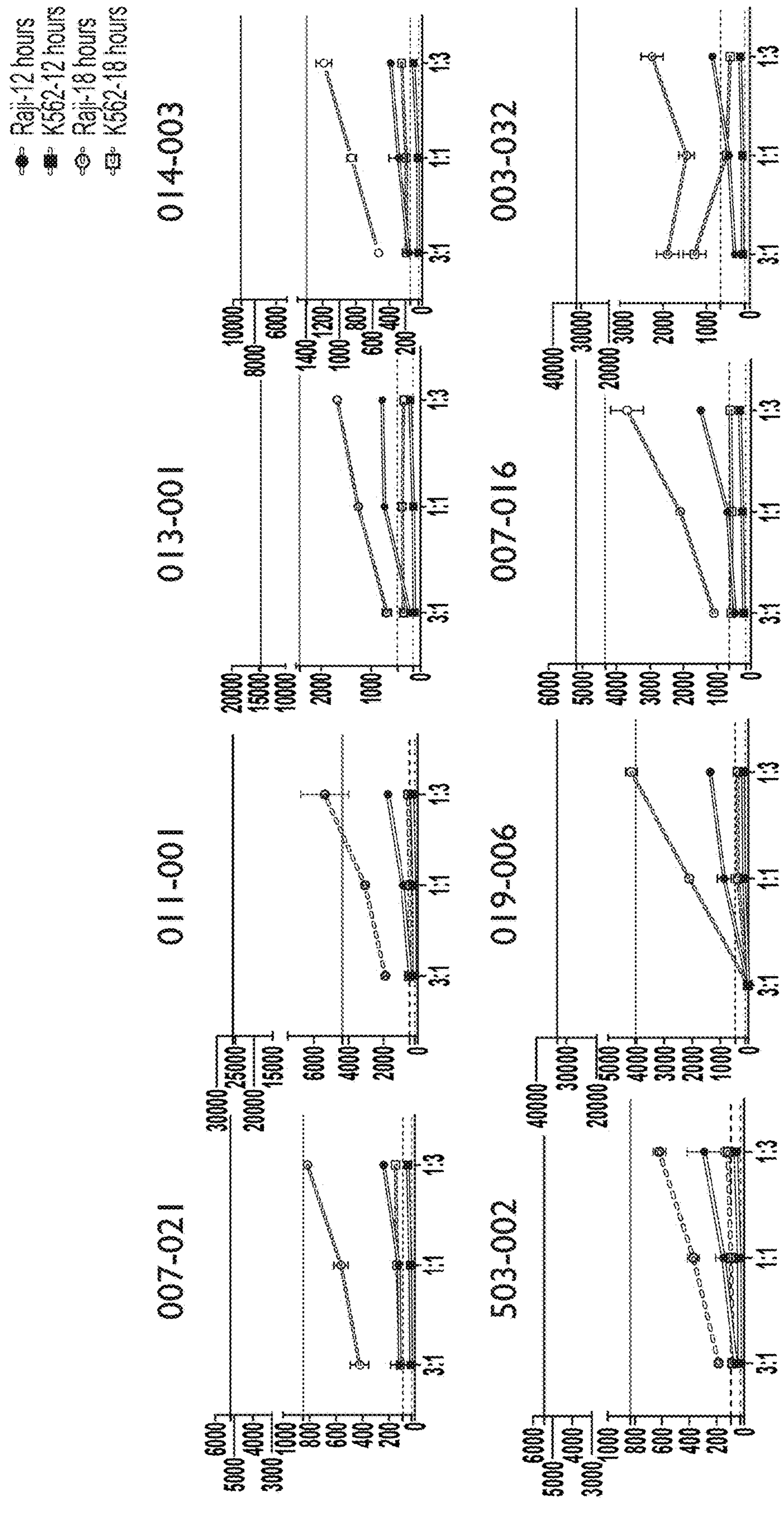
FIG. 72: Granzyme B secretion (pg/mL) for melanoma TIL lots for 3:1, 1:1, and 1:3 TIL:Raji or TIL:K562 ratios. Secretion levels in pg/mL are shown on the y-axes and TIL:target ratios are shown on the x-axes.
Figure 73:
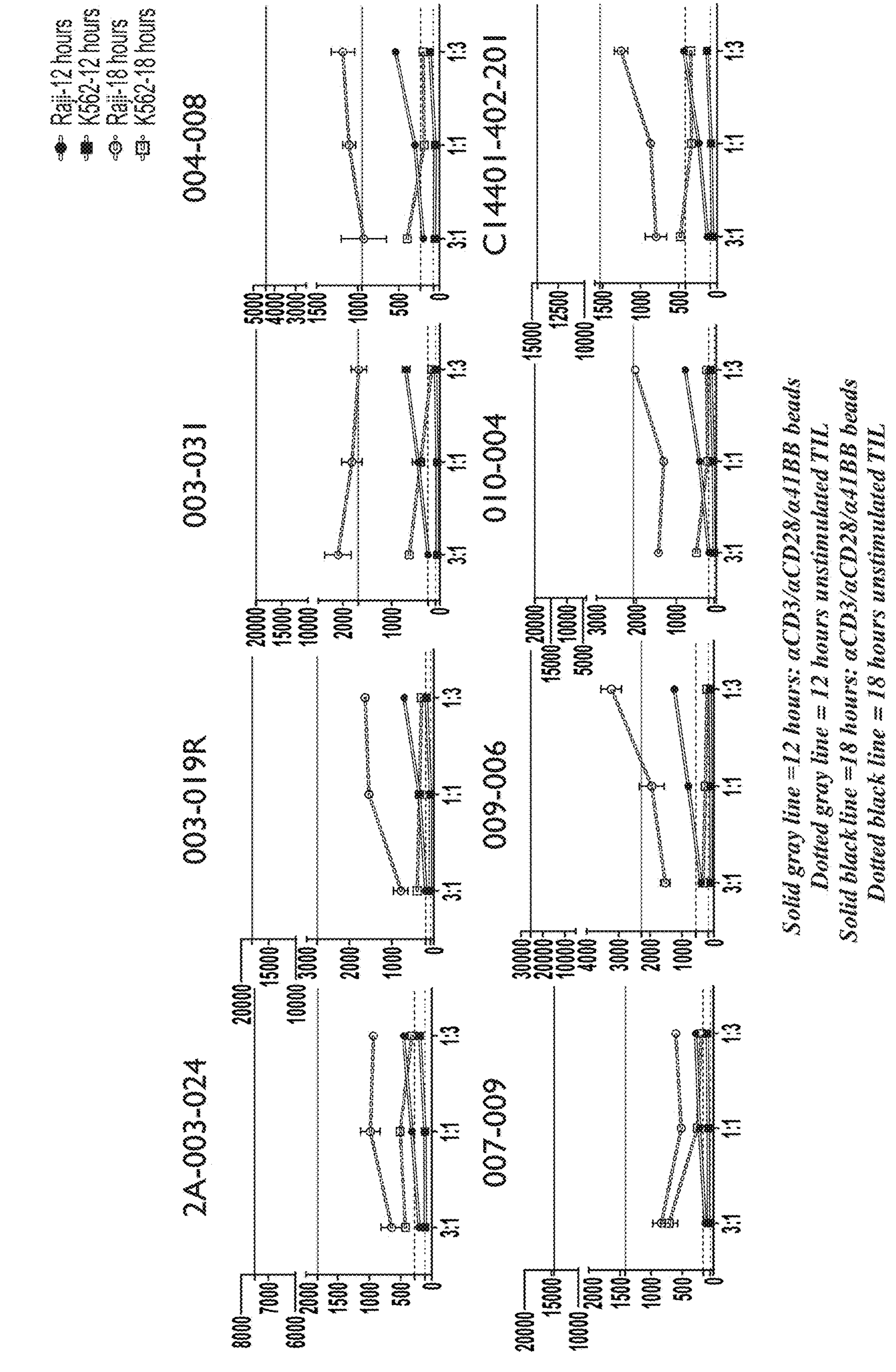
FIG. 73: Granzyme B secretion (pg/mL) for melanoma TIL lots for 3:1, 1:1, and 1:3 TIL:Raji or TIL:K562 ratios. Secretion levels in pg/mL are shown on the y-axes and TIL:target ratios are shown on the x-axes.
Figure 74:
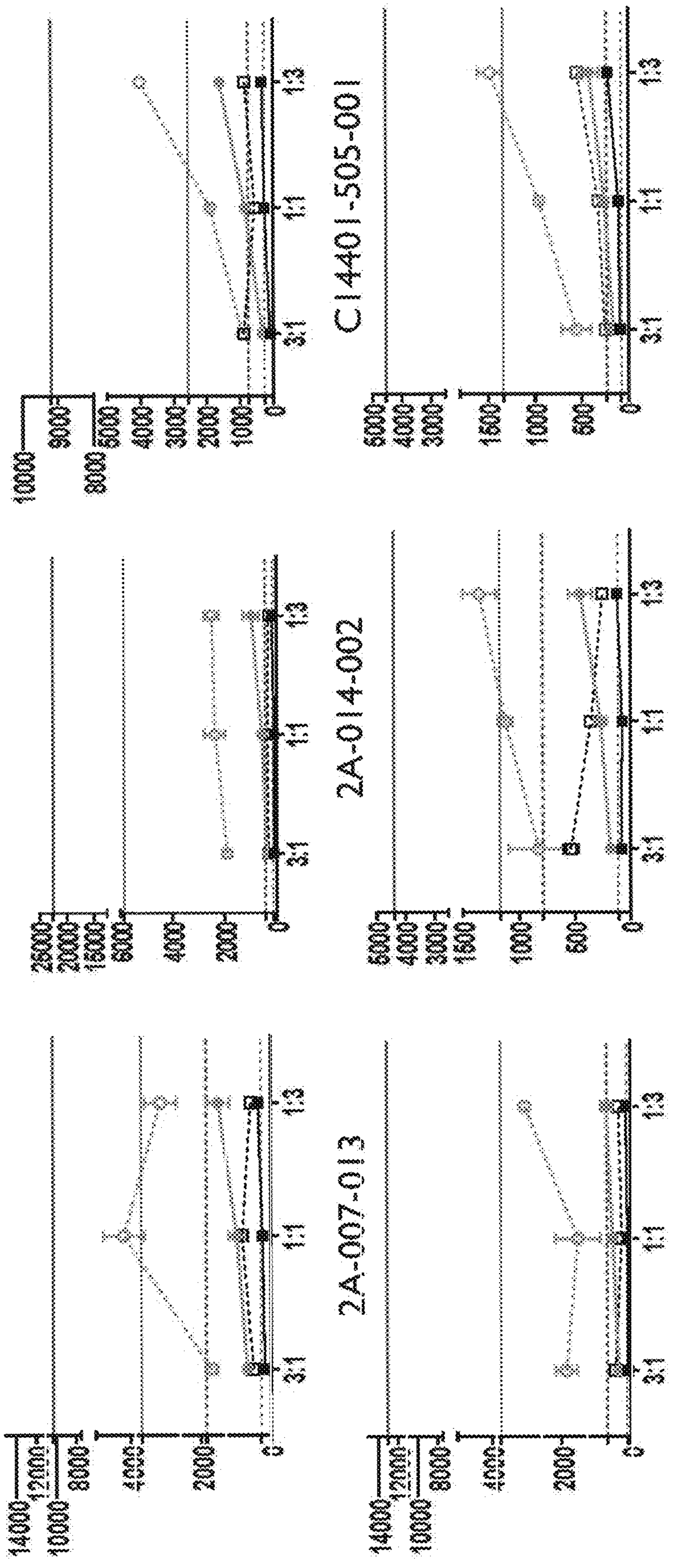
FIG. 74: Granzyme B secretion (pg/mL) for melanoma TIL lots for 3:1, 1:1, and 1:3 TIL:Raji or TIL:K562 ratios. Secretion levels in pg/mL are shown on the y-axes and TIL:target ratios are shown on the x-axes.
Figure 75:
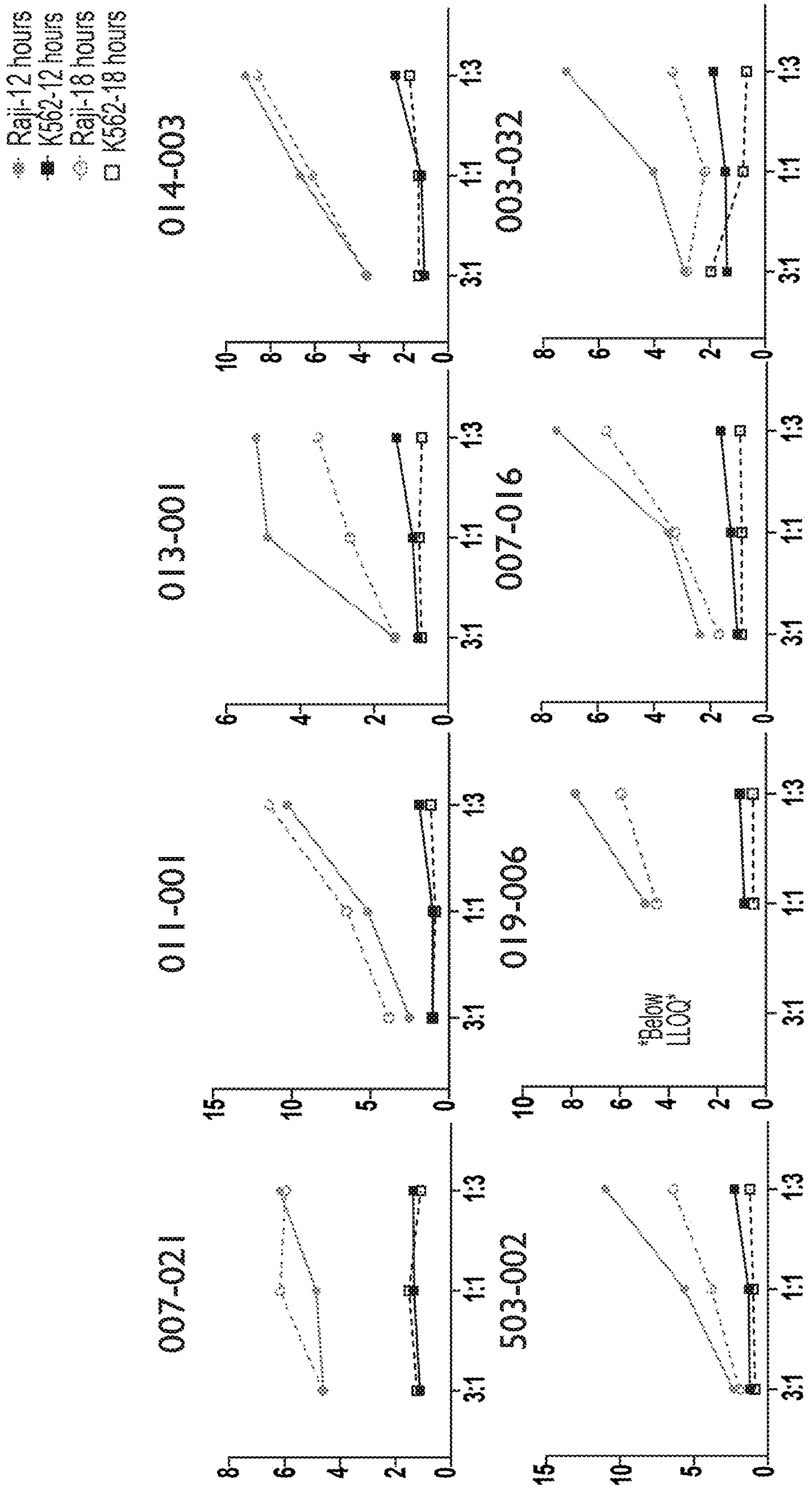
FIG. 75: Fold changes in granzyme B release for TILs plus Raji or K562 cells over granzyme B release from TILs alone for melanoma TIL lots for 3:1, 1:1, and 1:3 TIL:Raji or TIL:K562 ratios. Fold changes are shown on the y-axes and TIL:target ratios are shown on the x-axes.
Figure 76:
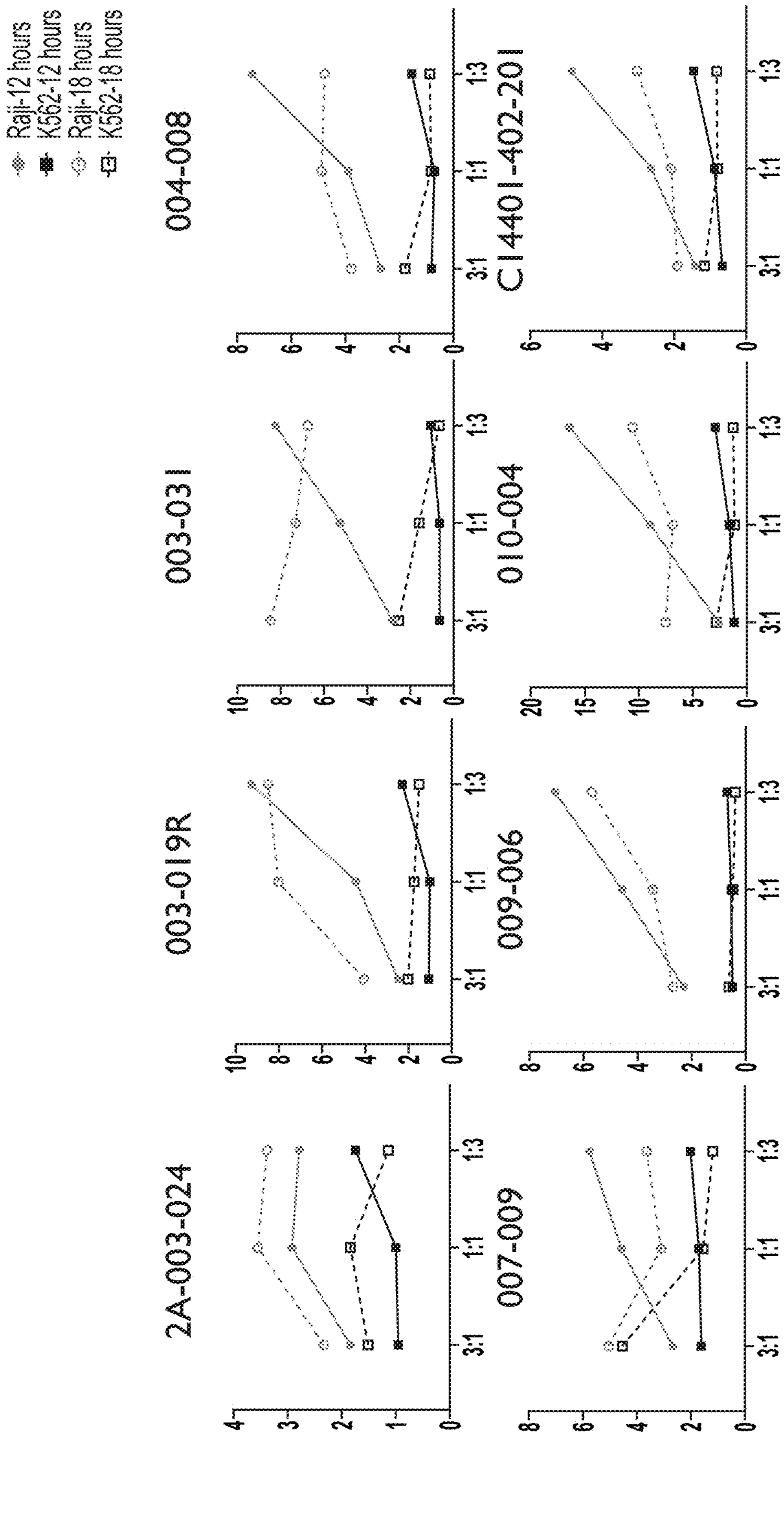
FIG. 76: Fold changes in granzyme B release for TILs plus Raji or K562 cells over granzyme B release from TILs alone for melanoma TIL lots for 3:1, 1:1, and 1:3 TIL:Raji or TIL:K562 ratios. Fold changes are shown on the y-axes and TIL:target ratios are shown on the x-axes.
Figure 77:
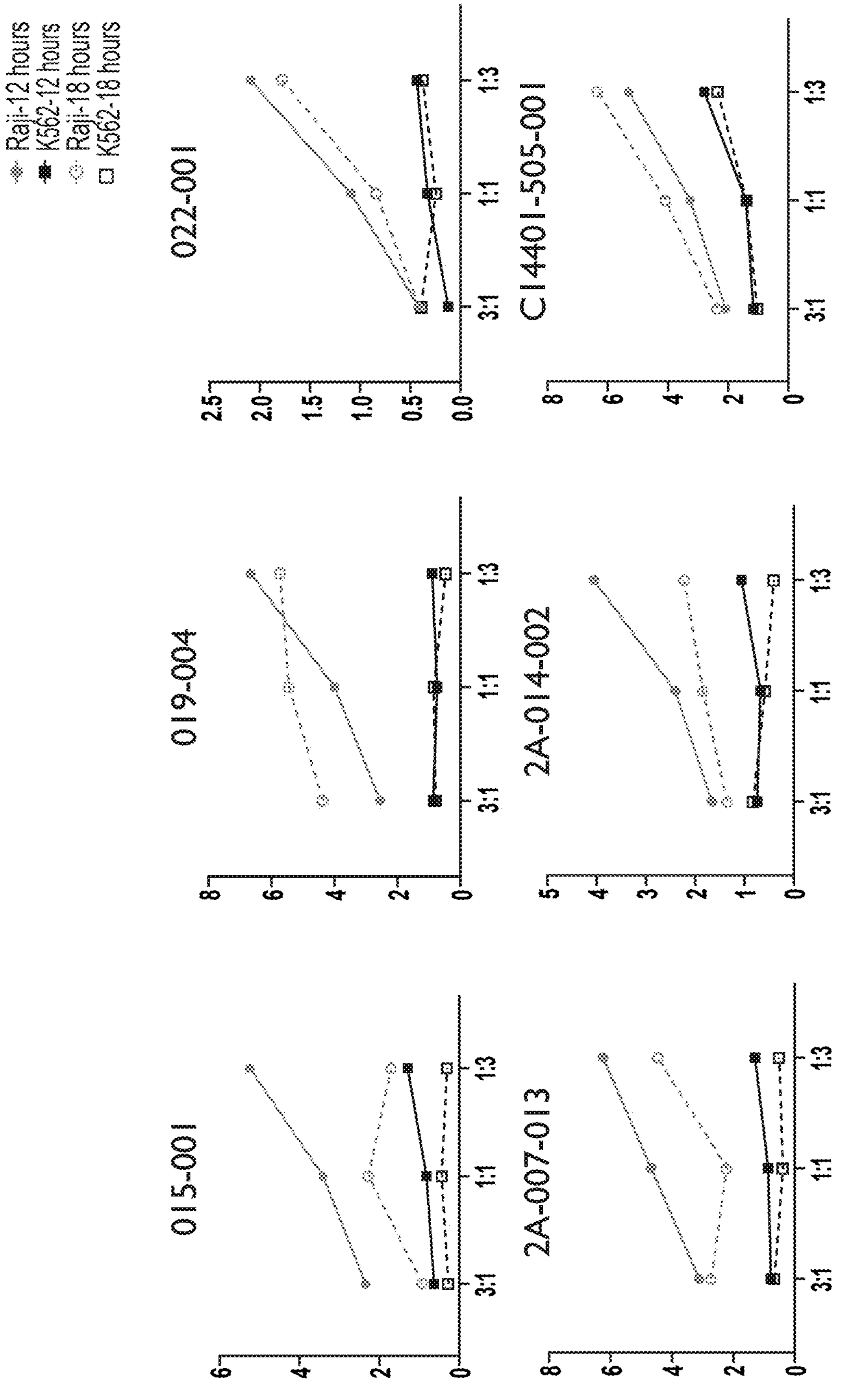
FIG. 77: Fold changes in granzyme B release for TILs plus Raji or K562 cells over granzyme B release from TILs alone for melanoma TIL lots for 3:1, 1:1, and 1:3 TIL:Raji or TIL:K562 ratios. Fold changes are shown on the y-axes and TIL:target ratios are shown on the x-axes.
Figure 78:
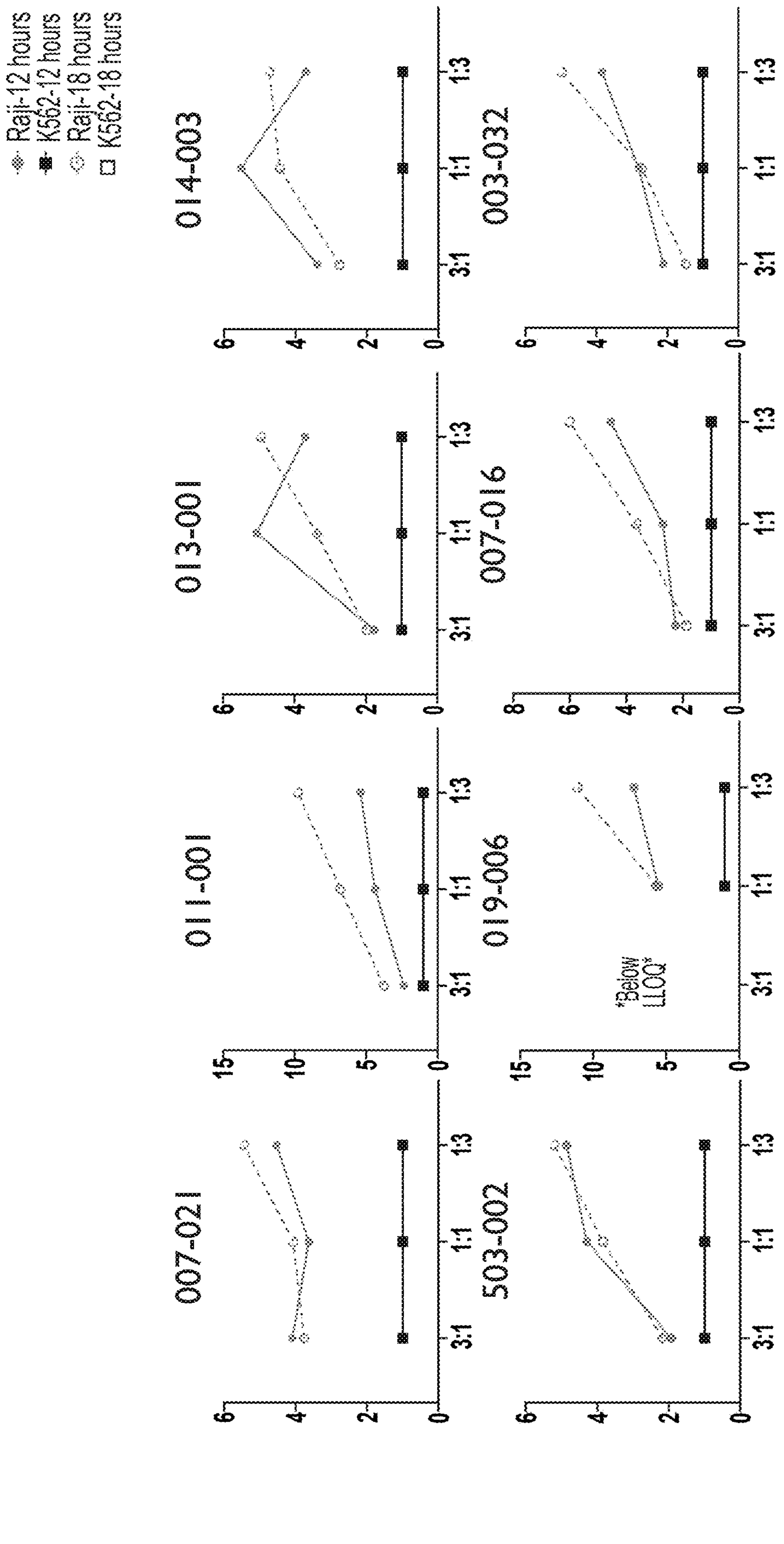
FIG. 78: Fold changes in granzyme B release for TILs plus Raji or K562 cells over granzyme B release from TILs plus K562 cells for melanoma TIL lots for 3:1, 1:1, and 1:3 TIL:Raji or TIL:K562 ratios. Fold changes are shown on the y-axes and TIL:target ratios are shown on the x-axes.
Figure 79:
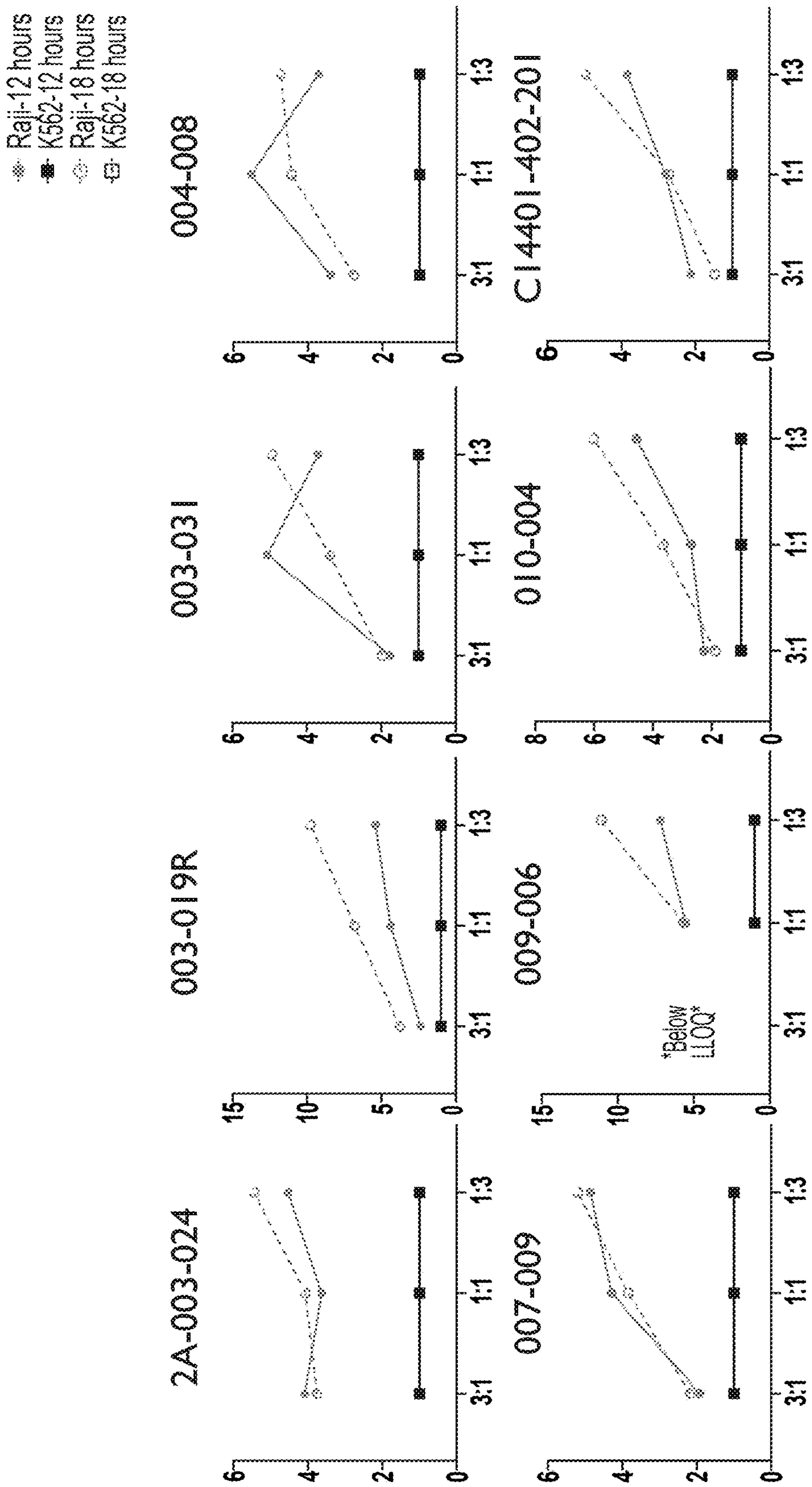
FIG. 79: Fold changes in granzyme B release for TILs plus Raji or K562 cells over granzyme B release from TILs plus K562 cells for melanoma TIL lots for 3:1, 1:1, and 1:3 TIL:Raji or TIL:K562 ratios. Fold changes are shown on the y-axes and TIL:target ratios are shown on the x-axes.
Figure 80:
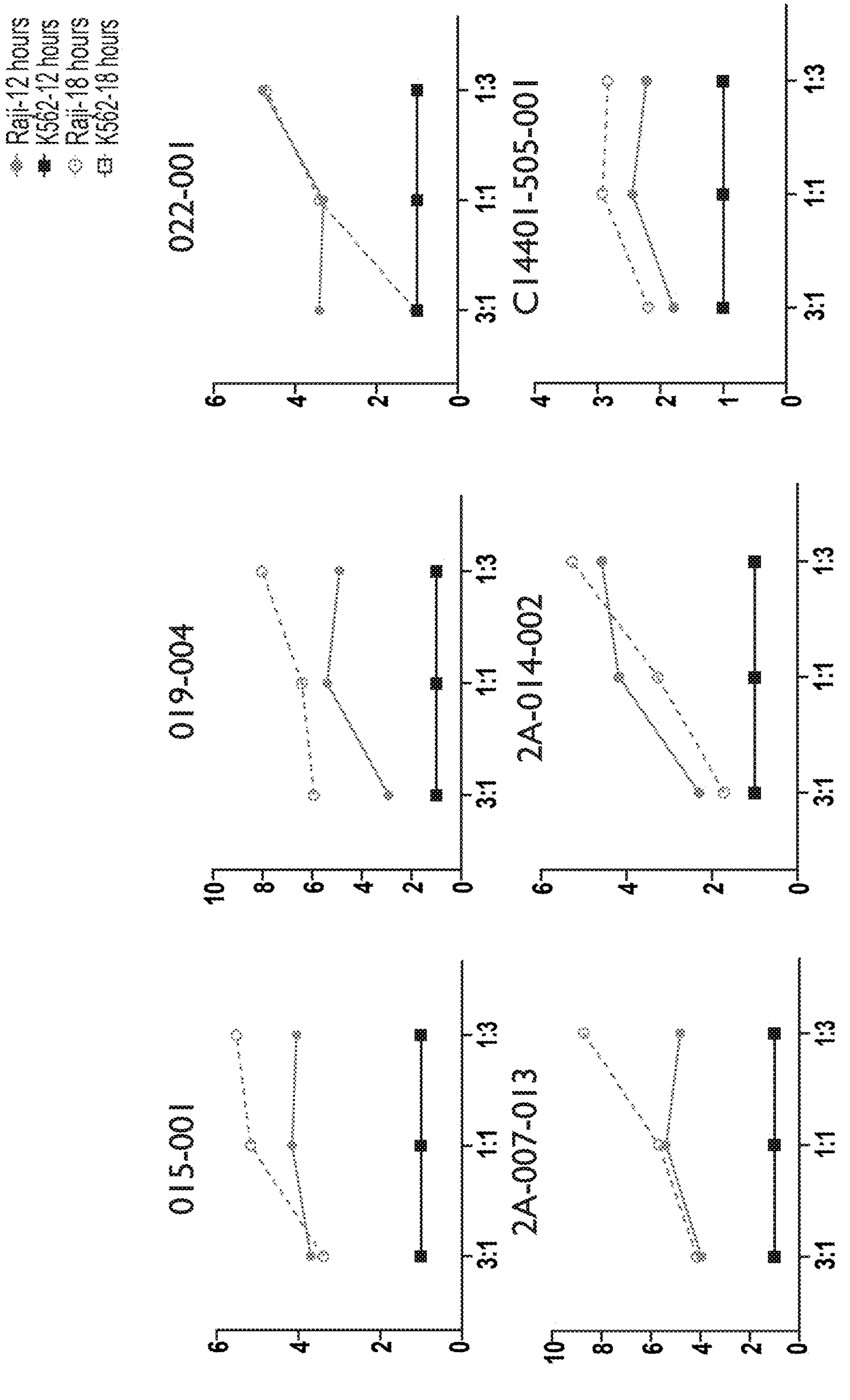
FIG. 80: Fold changes in granzyme B release for TILs plus Raji or K562 cells over granzyme B release from TILs plus K562 cells for melanoma TIL lots for 3:1, 1:1, and 1:3 TIL:Raji or TIL:K562 ratios. Fold changes are shown on the y-axes and TIL:target ratios are shown on the x-axes.
Figure 81:
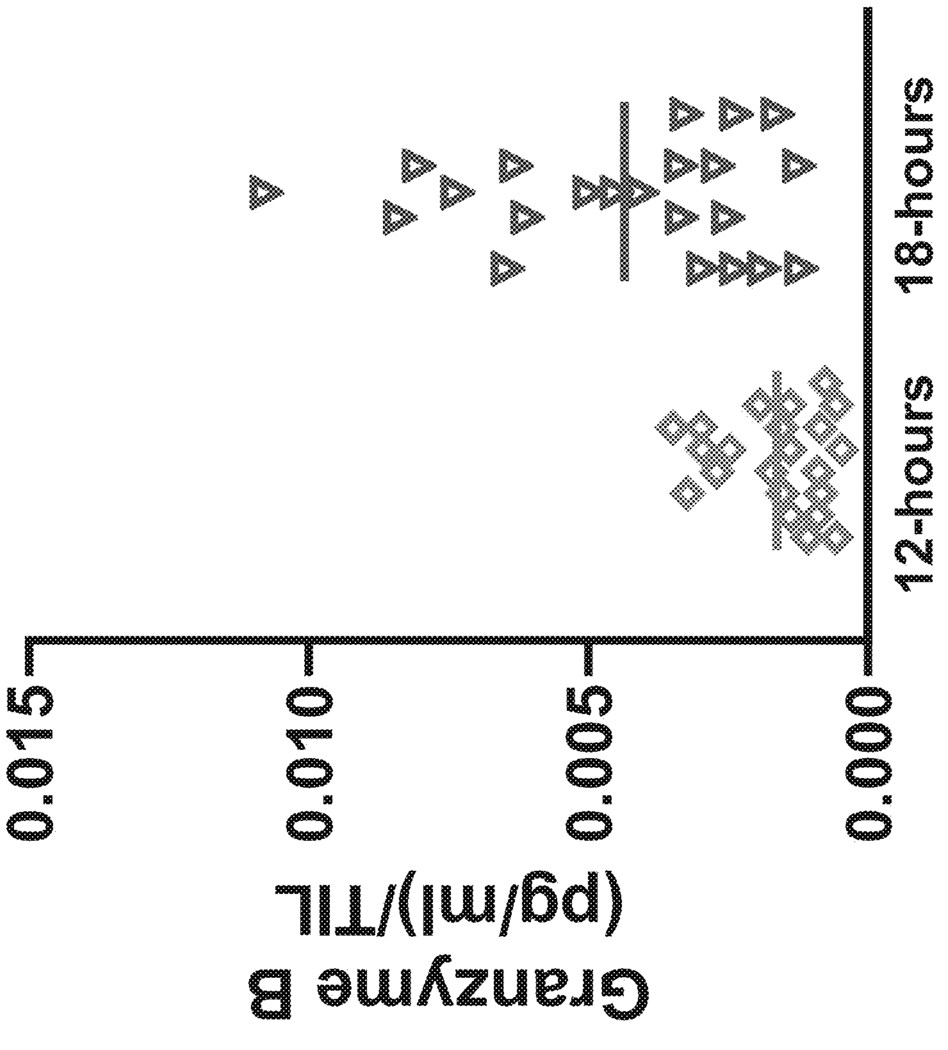
FIG. 81: Granzyme B release for TILs in pg/mL/TIL at incubation times of 12 and 18 hours.
Figure 82:
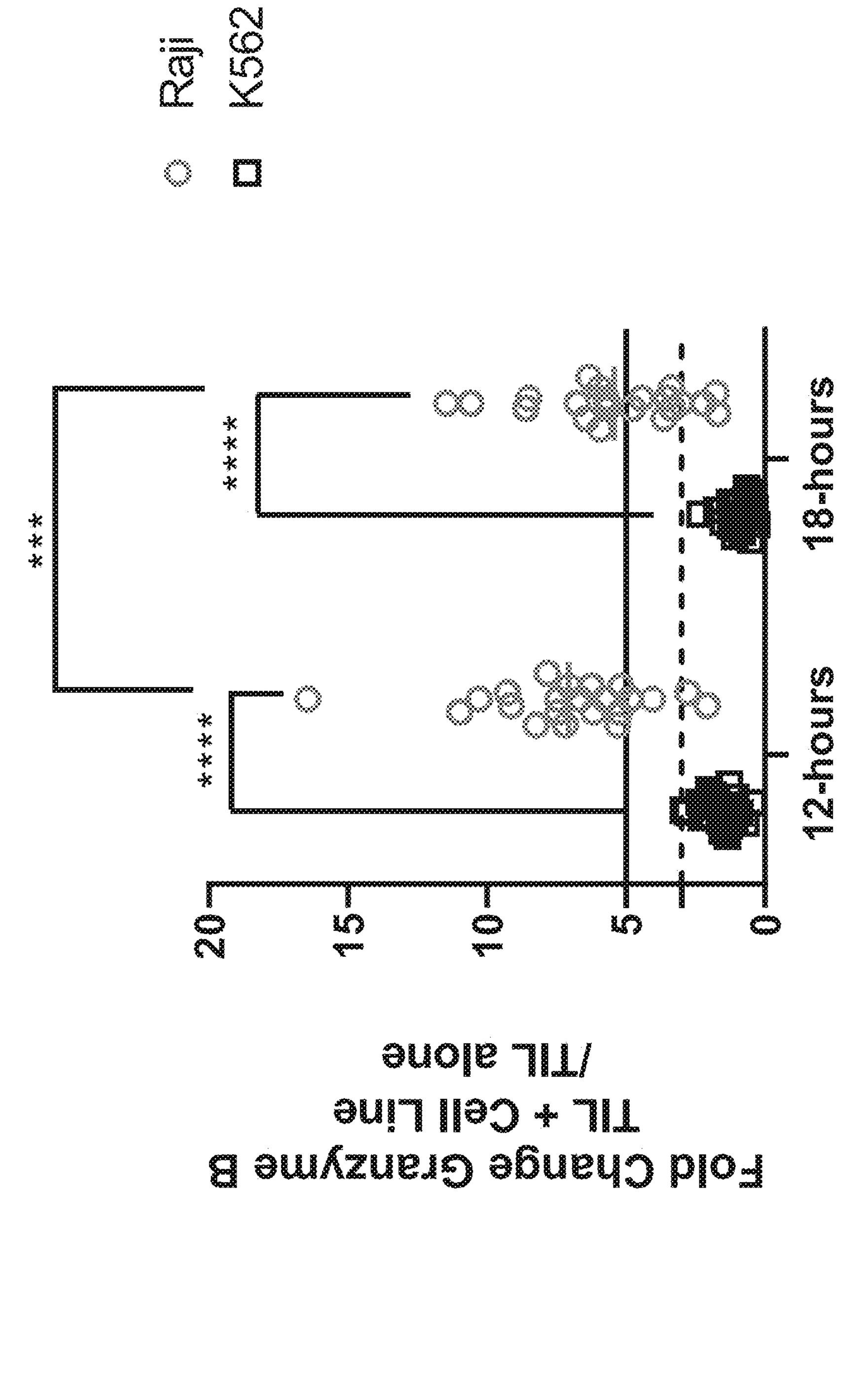
FIG. 82: Granzyme B release for TILs plus Raji or K562 cells over TILs alone at 12 and 18 hours of incubation time, showing the cumulative data set at a 1:3 TIL:Raji or TIL:K562 cell ratio, wherein * denotes a p-value of ≤0.001 and ** denotes a p-value of ≤0.0001.
Figure 83:
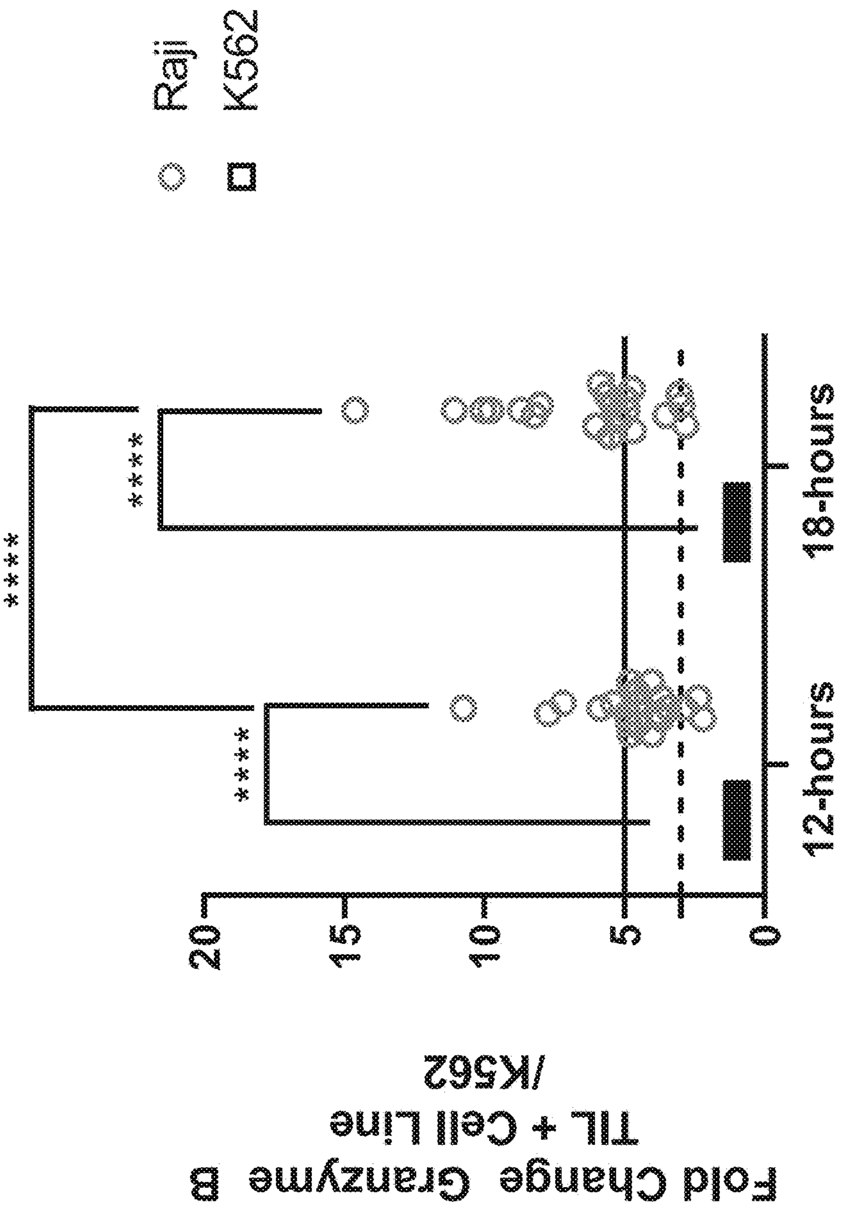
FIG. 83: Granzyme B release for TILs plus Raji or K562 cells over K562 cells at 12 and 18 hours of incubation time, showing the cumulative data set at a 1:3 TIL:Raji cell or TIL:K562 ratio, wherein **** denotes a p-value of ≤0.0001.
Figure 84:
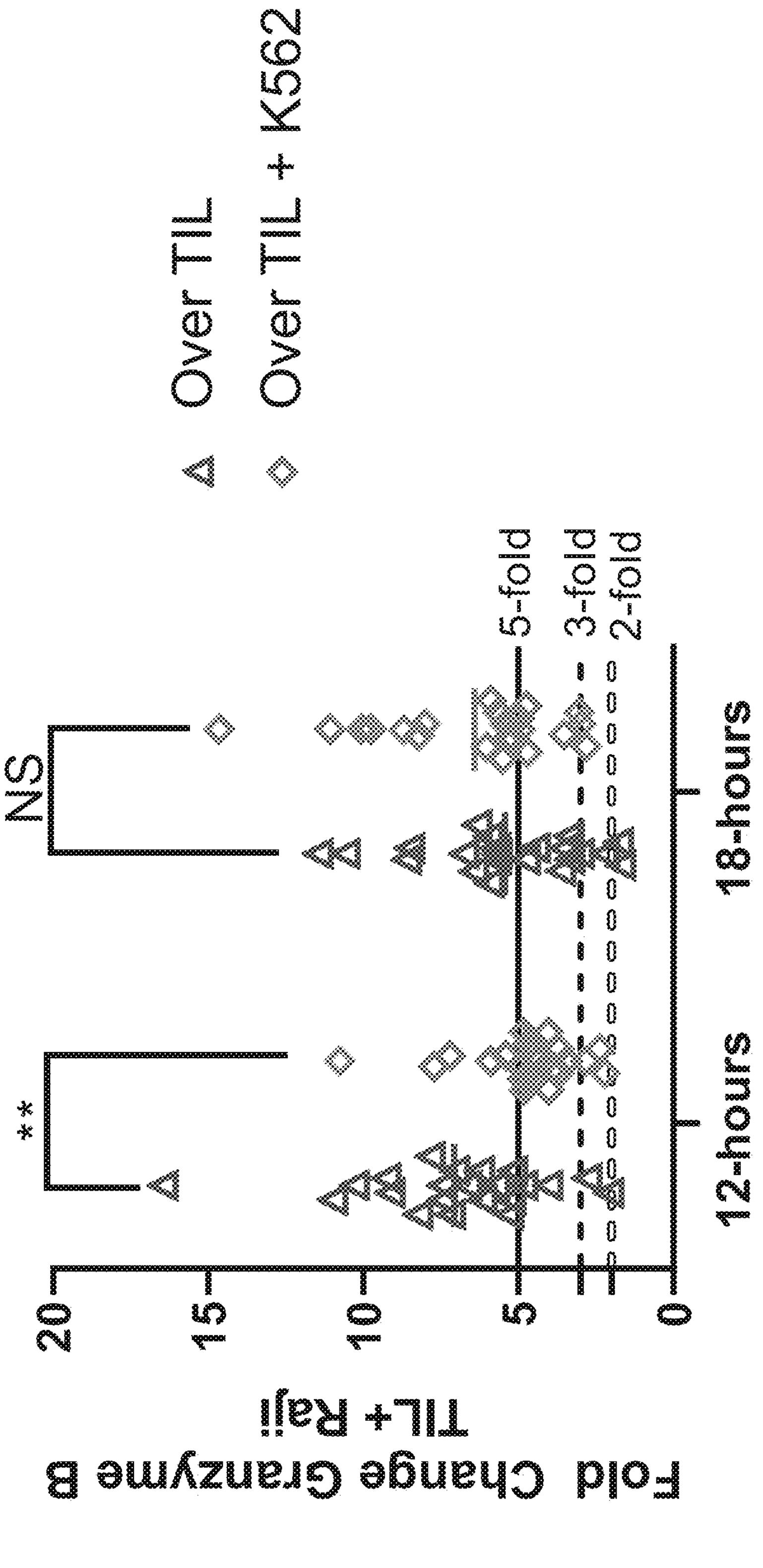
FIG. 84: Fold changes in granzyme B release for TILs plus Raji cells over TILs plus K562 cells or over TILs at 12 and 18 hours of incubation time, showing the cumulative data set at a 1:3 TIL:Raji or TIL:K562 cell ratio, wherein ** denotes a p-value of ≤0.01 and NS denotes not significant.
Figure 85:
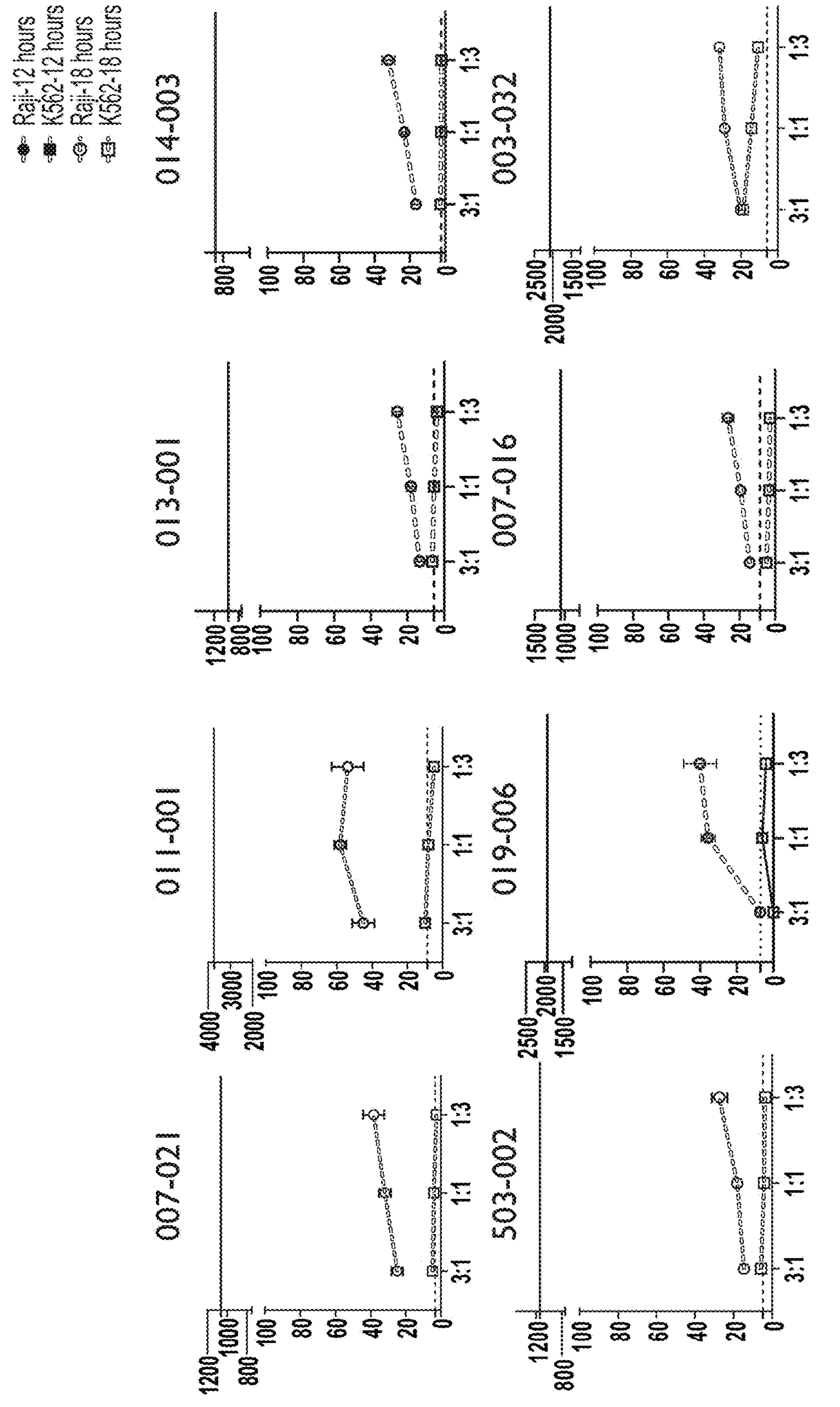
FIG. 85: TNF-α secretion (pg/mL) for melanoma TIL lots for 3:1, 1:1, and 1:3 TIL:Raji or TIL:K562 ratios. Secretion levels in pg/mL are shown on the y-axes and TIL:target ratios are shown on the x-axes.
Figure 86:
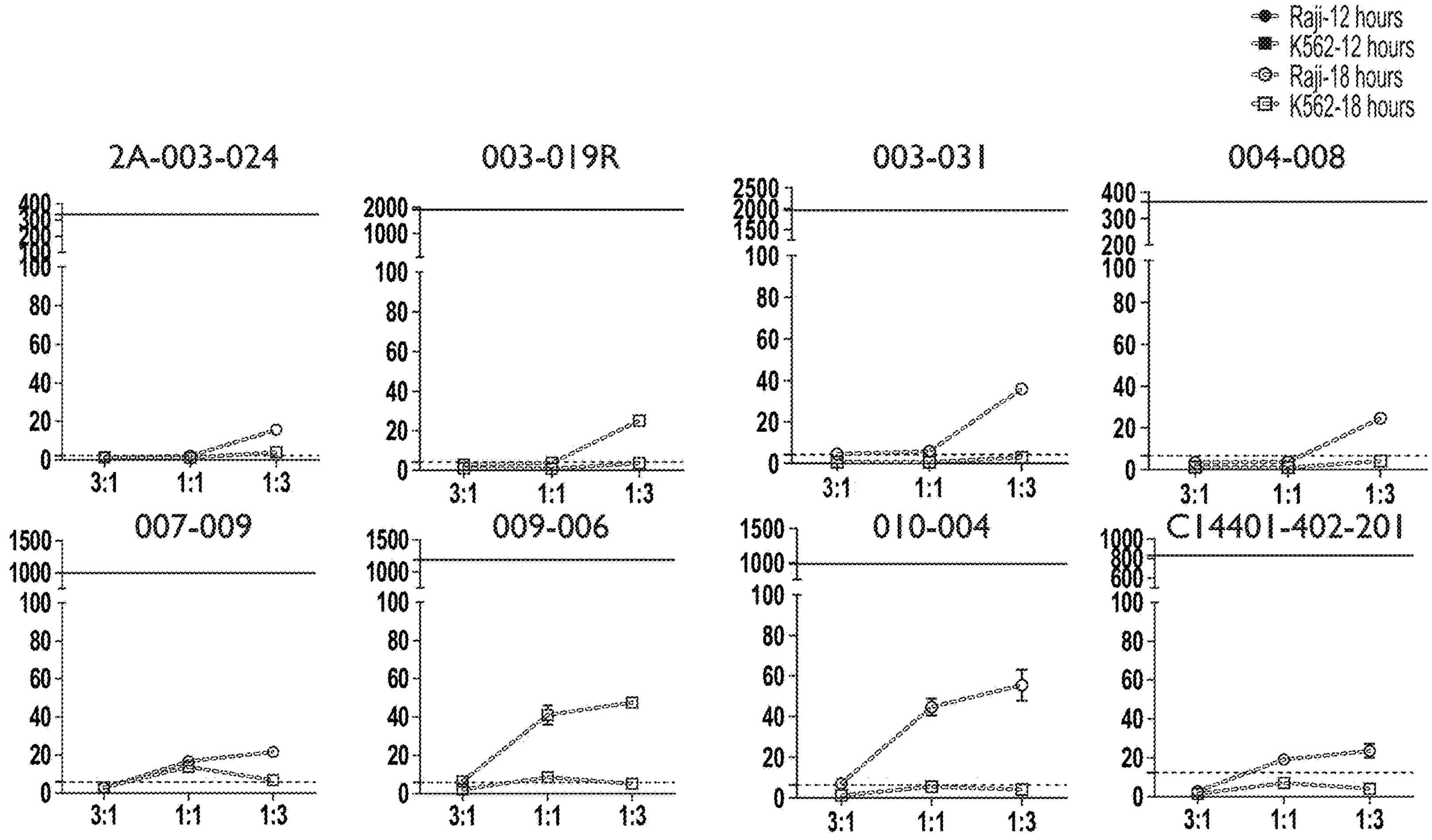
FIG. 86: TNF-α secretion (pg/mL) for melanoma TIL lots for 3:1, 1:1, and 1:3 TIL:Raji or TIL:K562 ratios. Secretion levels in pg/mL are shown on the y-axes and TIL:target ratios are shown on the x-axes.
Figure 87:
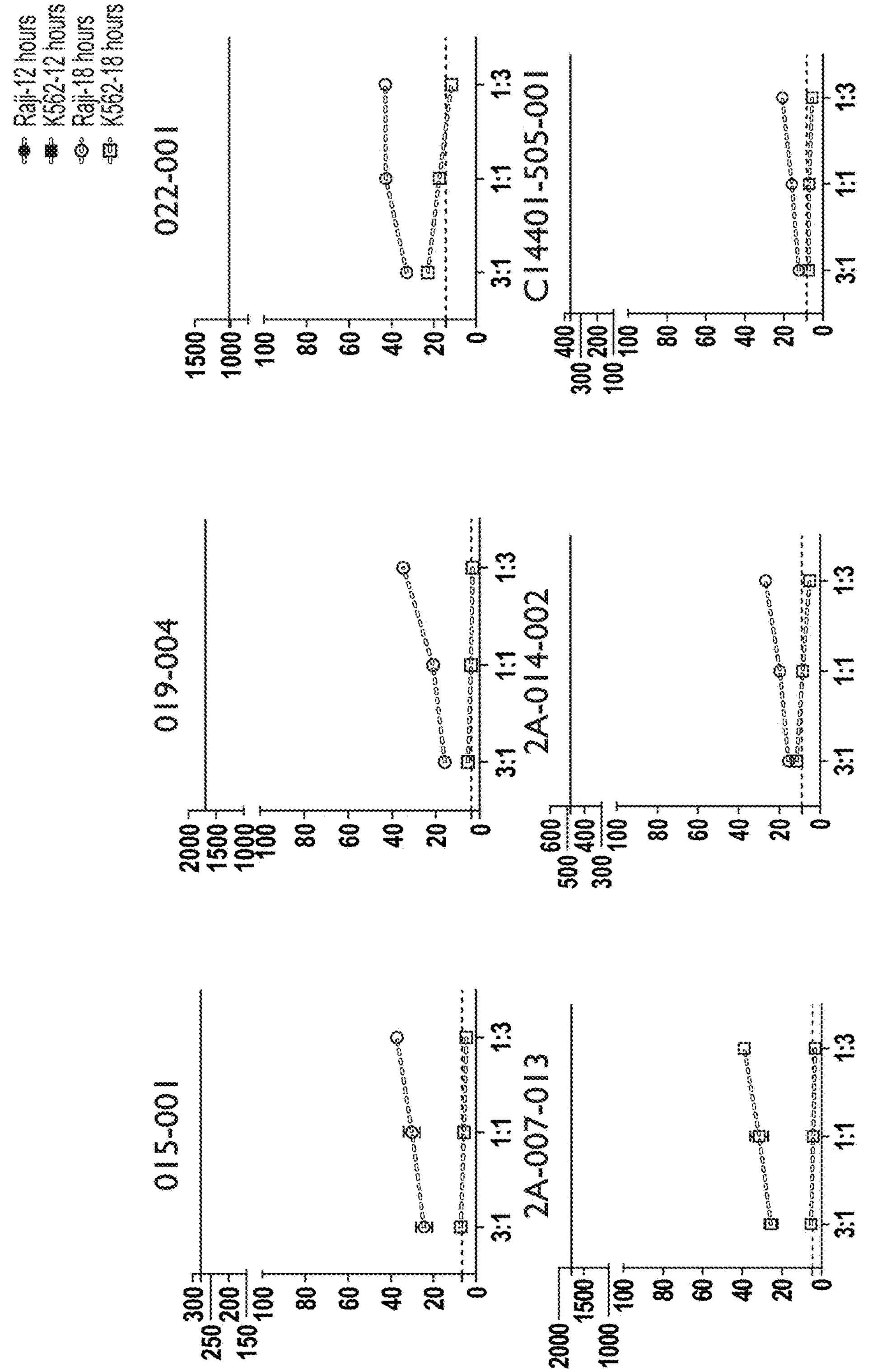
FIG. 87: TNF-α secretion (pg/mL) for melanoma TIL lots for 3:1, 1:1, and 1:3 TIL:Raji or TIL:K562 ratios. Secretion levels in pg/mL are shown on the y-axes and TIL:target ratios are shown on the x-axes.
Figure 88:
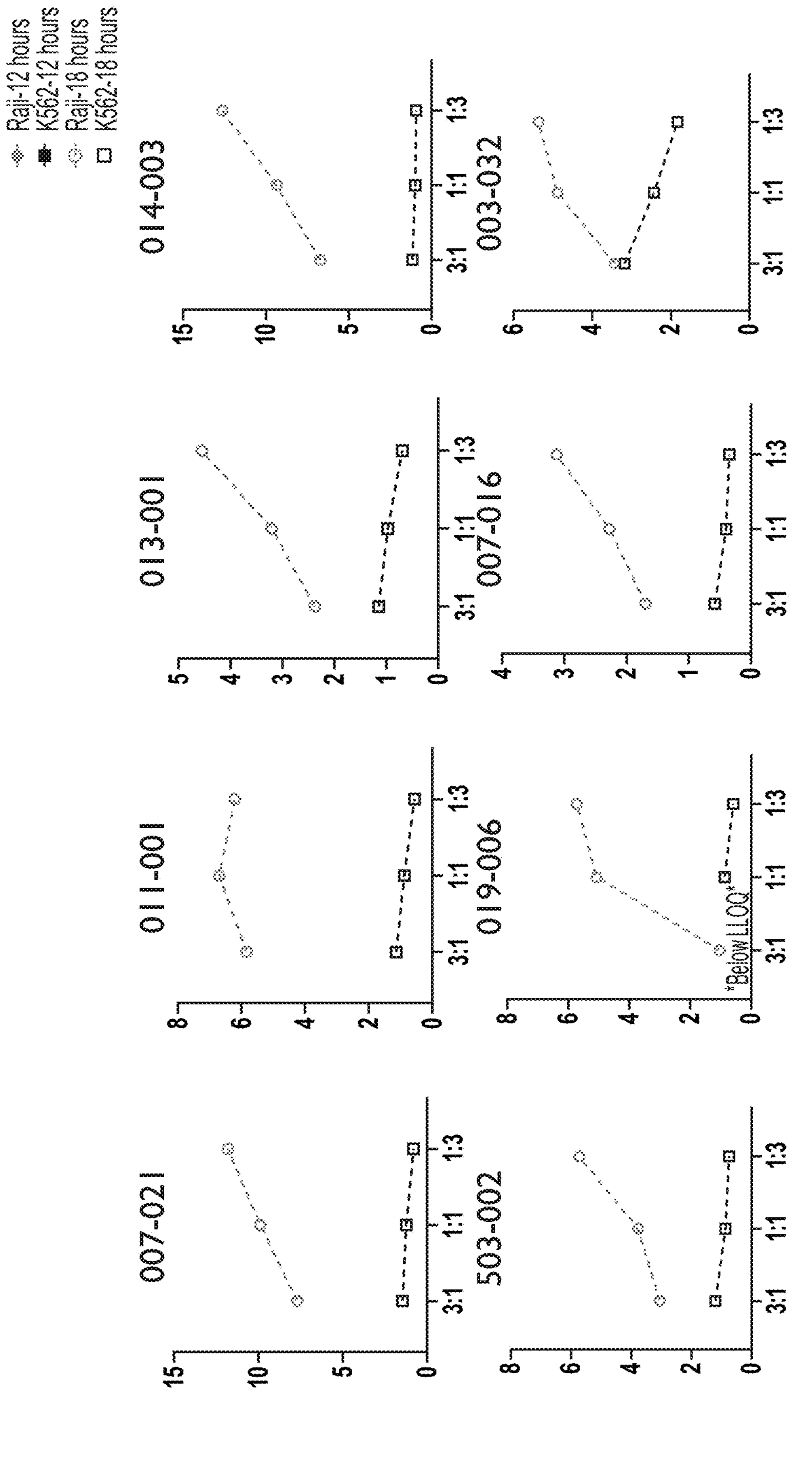
FIG. 88: Fold changes in TNF-α release for TILs plus Raji or K562 cells over granzyme B release from TILs alone for melanoma TIL lots for 3:1, 1:1, and 1:3 TIL:Raji or TIL: K562 ratios. Fold changes are shown on the y-axes and TIL:target ratios are shown on the x-axes.
Figure 89:
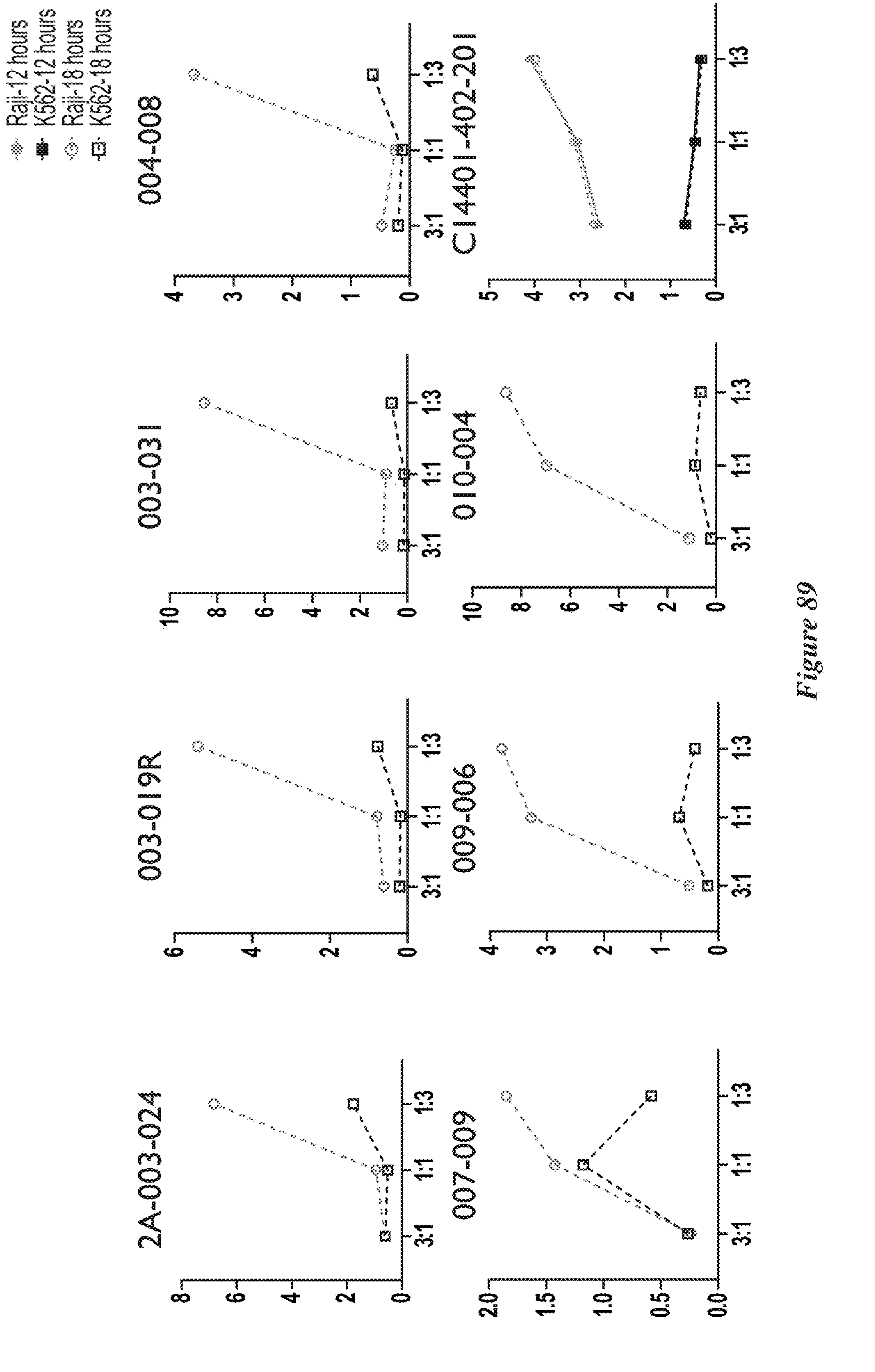
FIG. 89: Fold changes in TNF-α release for TILs plus Raji or K562 cells over granzyme B release from TILs alone for melanoma TIL lots for 3:1, 1:1, and 1:3 TIL:Raji or TIL: K562 ratios. Fold changes are shown on the y-axes and TIL:target ratios are shown on the x-axes.
Figure 90:
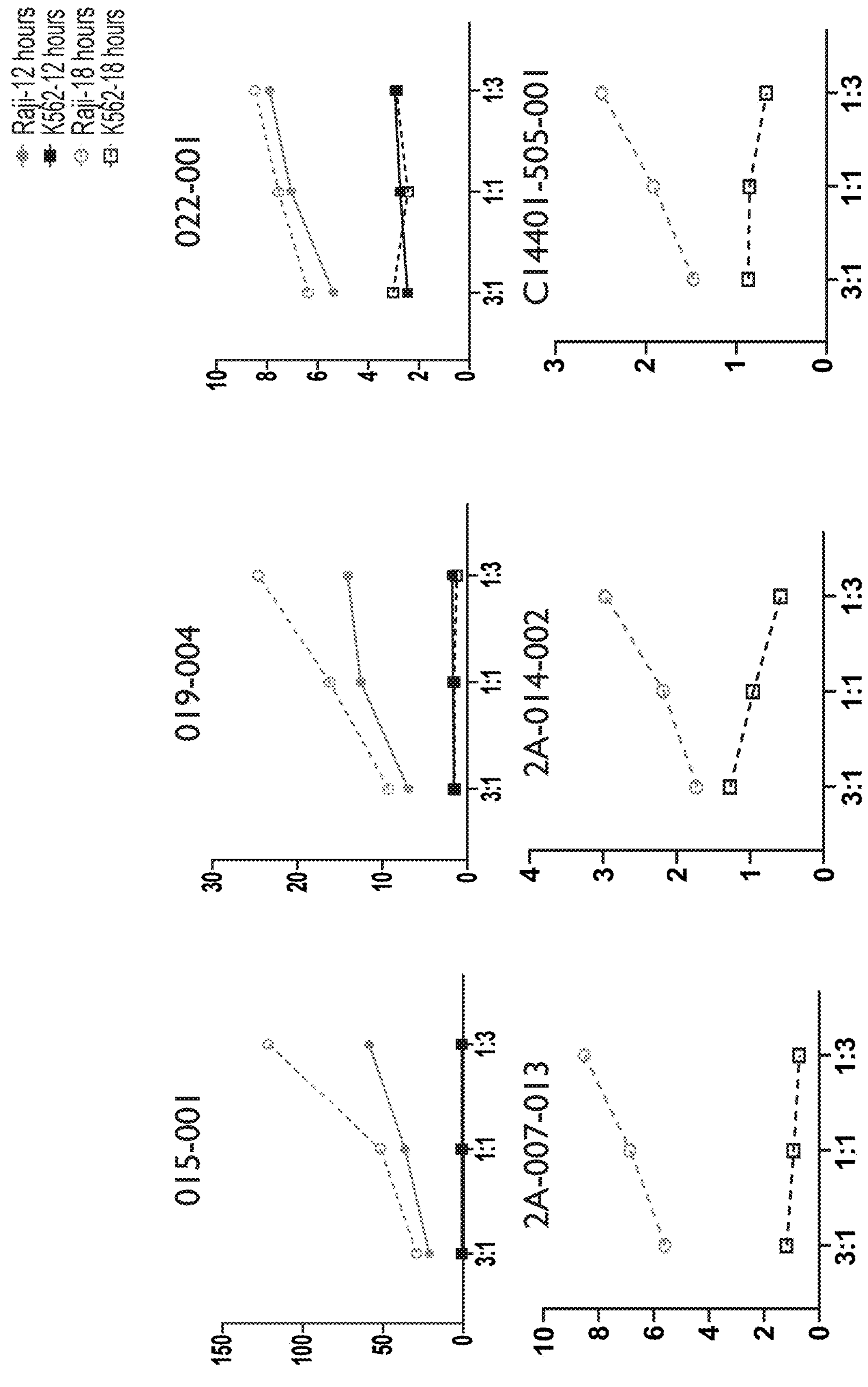
FIG. 90: Fold changes in TNF-α release for TILs plus Raji or K562 cells over granzyme B release from TILs alone for melanoma TIL lots for 3:1, 1:1, and 1:3 TIL:Raji or TIL: K562 ratios. Fold changes are shown on the y-axes and TIL:target ratios are shown on the x-axes.
Figure 91:
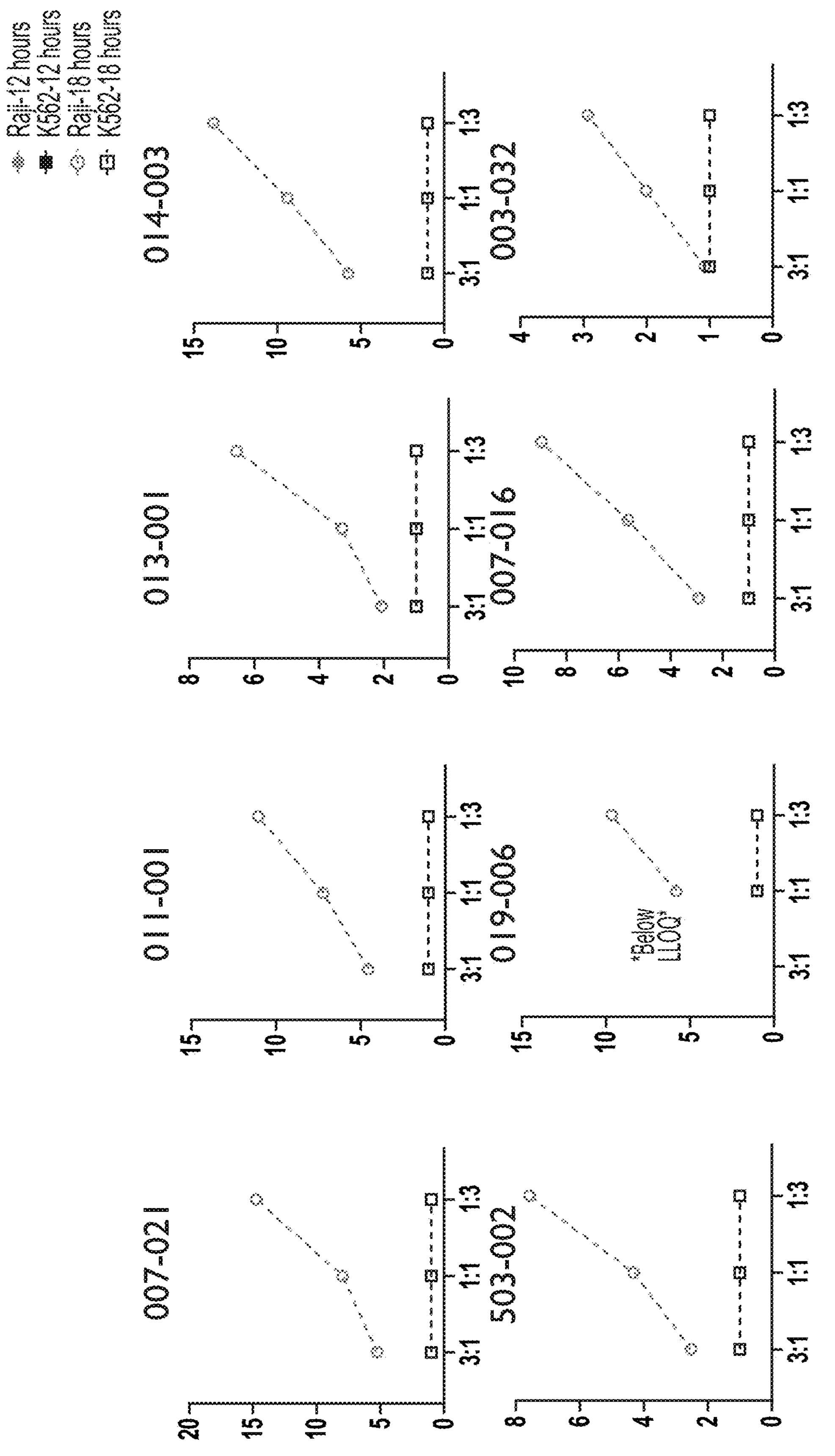
FIG. 91: Fold changes in TNF-α release for TILs plus Raji or K562 cells over granzyme B release from TILs plus K562 cells for melanoma TIL lots for 3:1, 1:1, and 1:3 TIL:Raji or TIL:K562 ratios. Fold changes are shown on the y-axes and TIL:target ratios are shown on the x-axes.
Figure 92:
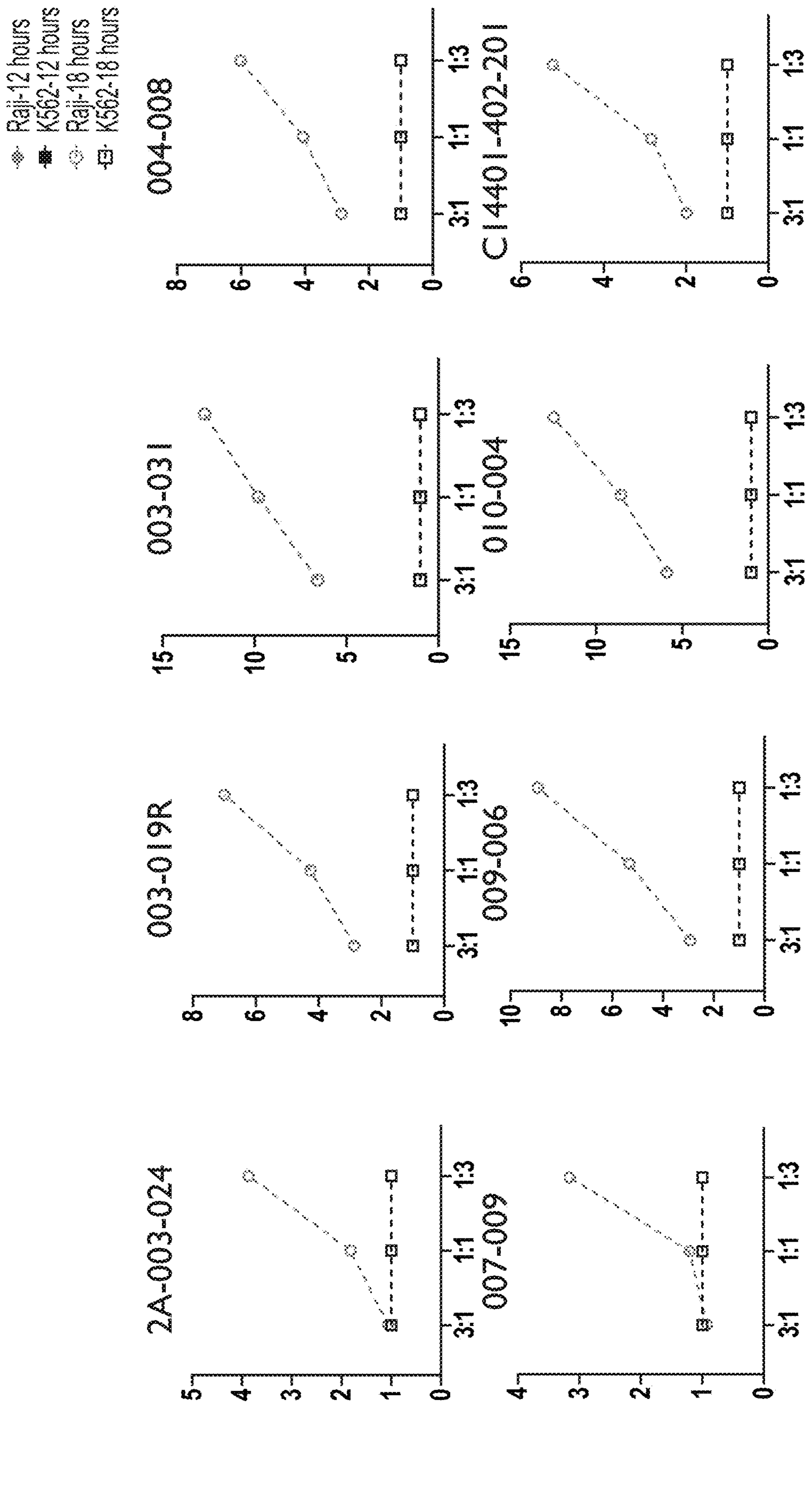
FIG. 92: Fold changes in TNF-α release for TILs plus Raji or K562 cells over granzyme B release from TILs plus K562 cells for melanoma TIL lots for 3:1, 1:1, and 1:3 TIL:Raji or TIL:K562 ratios. Fold changes are shown on the y-axes and TIL:target ratios are shown on the x-axes.
Figure 93:
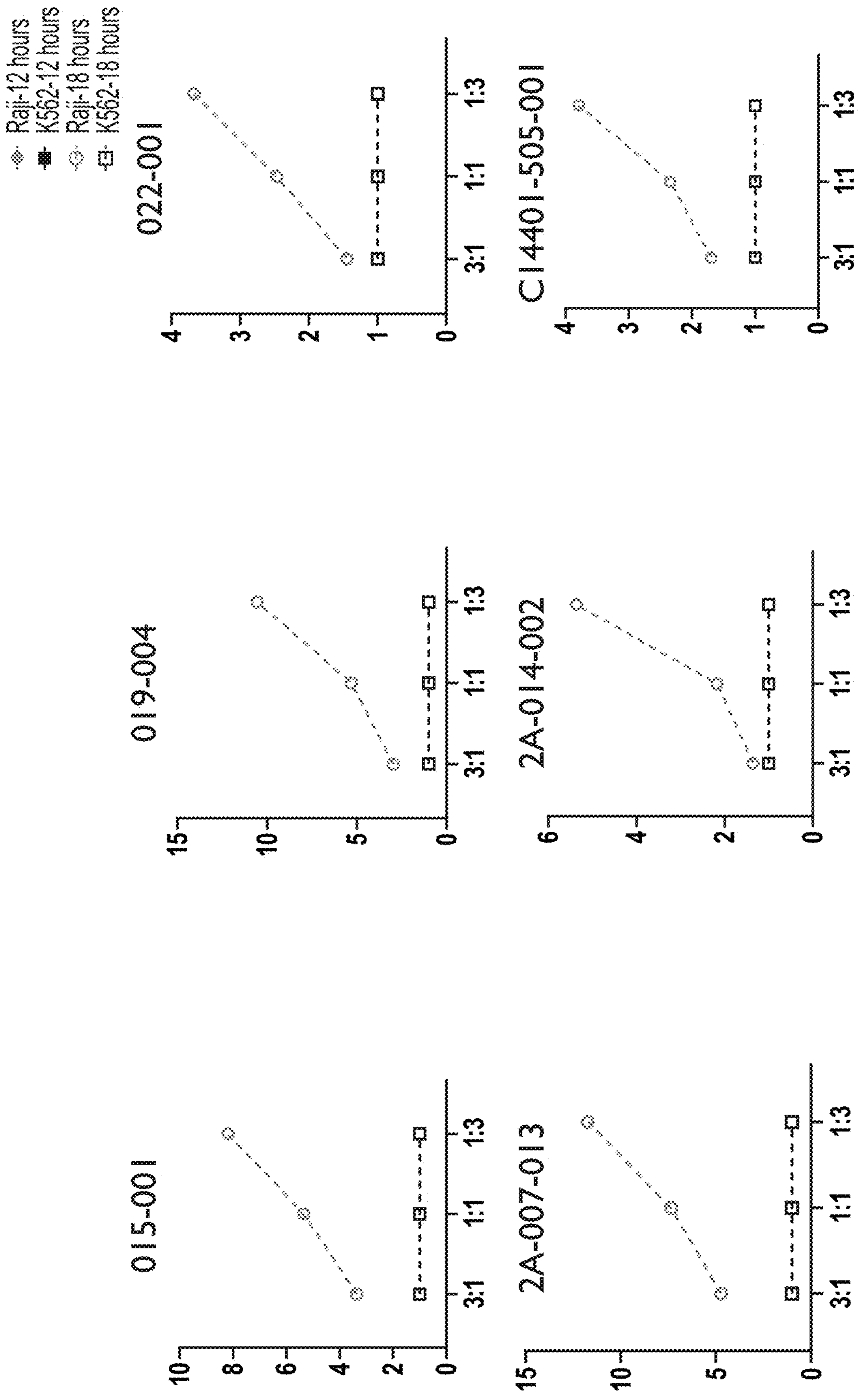
FIG. 93: Fold changes in TNF-α release for TILs plus Raji or K562 cells over granzyme B release from TILs plus K562 cells for melanoma TIL lots for 3:1, 1:1, and 1:3 TIL:Raji or TIL:K562 ratios. Fold changes are shown on the y-axes and TIL:target ratios are shown on the x-axes.
Figure 94:
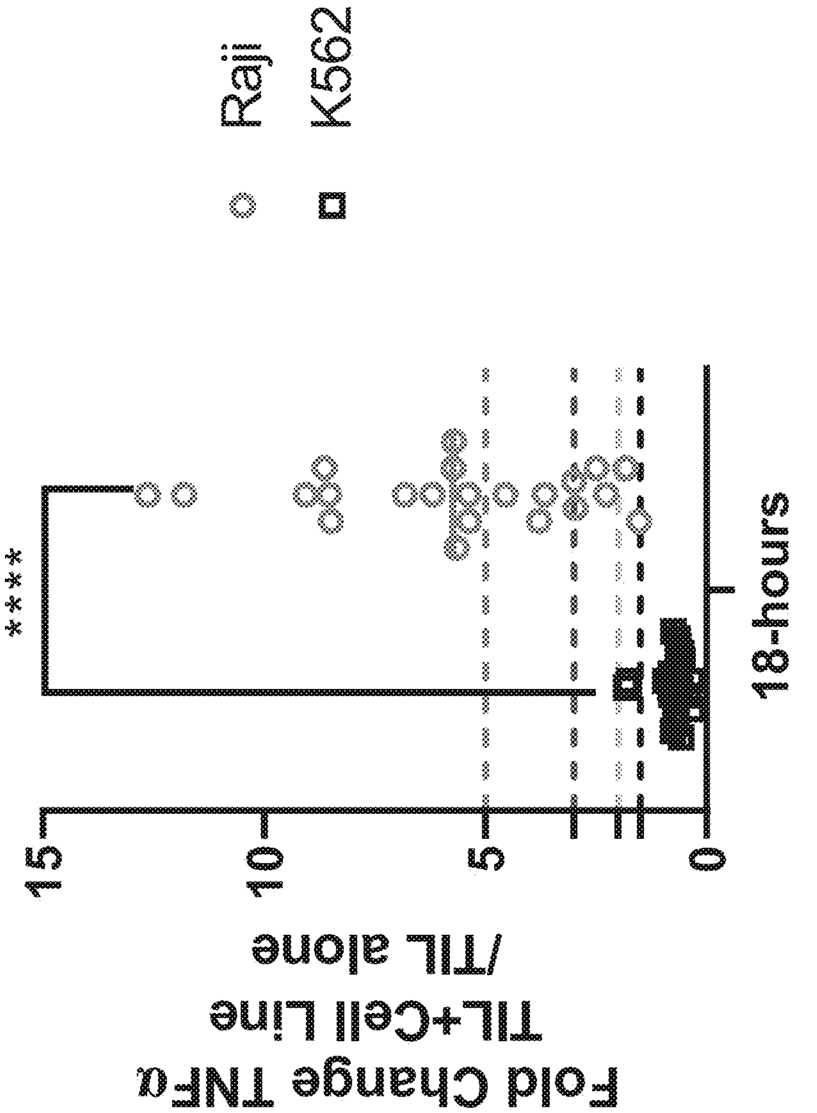
FIG. 94: Fold changes in TNF-α release for TILs plus Raji or K562 cells over TILs alone at 18 hours of incubation time, showing the cumulative data set at a 1:3 TIL:Raji or TIL: K562 cell ratio, wherein **** denotes a p-value of ≤0.0001.
Figure 95:
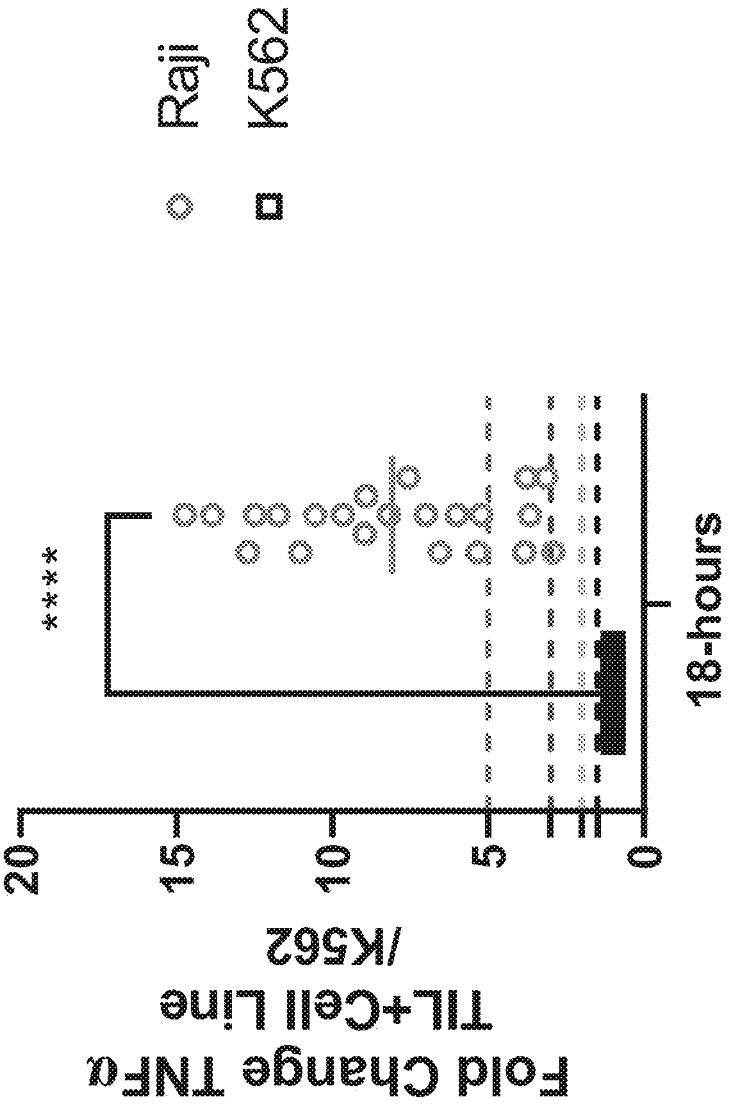
FIG. 95: Fold changes for TNF-α release for TILs plus Raji or K562 cells over K562 cells at 18 hours of incubation time, showing the cumulative data set at a 1:3 TIL:Raji or TIL:K562 cell ratio, wherein **** denotes a p-value of ≤0.0001.
Figure 96:
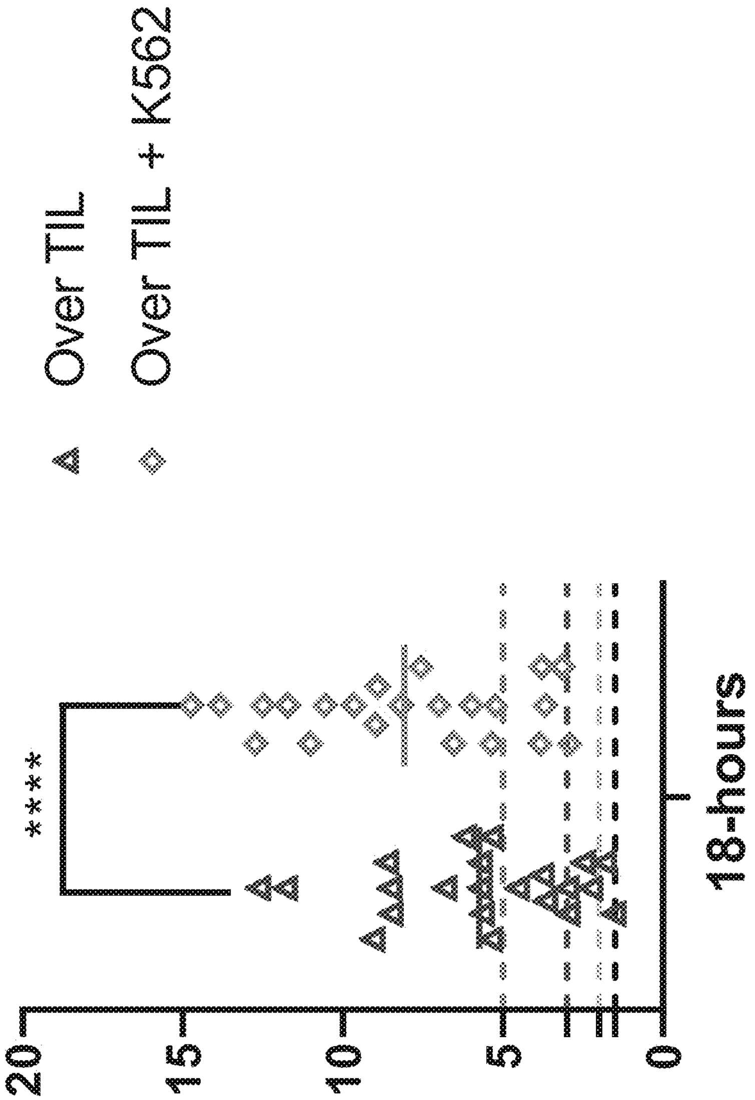
FIG. 96: Fold changes in TNF-α release for TILs plus Raji cells over TILs alone or over TILs plus K562 cells at 18 hours of incubation time, showing the cumulative data set at a 1:3 TIL:Raji or TIL:K562 cell ratio, wherein **** denotes a p-value of ≤0.0001.

TIL and Tumor Cells Co-culture Setup. Each TIL lot is be co-cultured separately with irradiated K562 cells and Raji cells, using the following TIL:target ratios: 3:1 ($5.0\times10^5$:$1.67\times10^5$); 1:1 ($5.0\times10^5$:$5.0\times10^5$); and 1:3 ($5.0\times10^5$:$1.5\times10^6$). TIL samples for co-culture are be plated at 500,000 cells for all conditions, in triplicate, in 1 mL in 1 well of a 48-well plate, for a total of 24 conditions, as can be seen below. Two Gen 2 TIL lines can be run per plate. A maximum of 3 plates are setup at one time. 1 mL of media is added for a total of 2 mL per well. For the wells containing the αCD3/αCD28/α41BB beads (used as an optional control as described elsewhere herein), the beads are washed, prepared and added according to the manufacturer's directions. The plates are incubated (5% $CO_2$, 37° C.) for the selected culture duration. The plate layout is shown in FIG. 57 and the general experimental scheme is shown in FIG. 58.

Collection of Supernatants and Assessment for Cytokines. The plates are removed from the incubator without disturbing the cells on the bottom of the plate. At 12- and 18-hours of co-culture, 50 μL of supernatant is removed and transferred to either Eppendorf tubes or a 96-well U plate. This step is repeated with two more 96-well plates to create two back-up plates. The plates are labelled to identify samples. The back-up plates are stored at −80° C. Each 96-well plate is sealed with an adhesive seal and stored at 4° C. until use. The supernatants are assessed for IFN-γ and granzyme B using the ELLA platform. Additional flow cytometry experiments may be performed to assess markers of interest as described herein, such as CD25, CD69, CD134, CD137, or CD150.

Results. The results of the 22 TIL samples are shown in FIG. 59 to FIG. 97. All experiments were performed in triplicate with the exception of sample 007-016 (performed once, except at the 1:3 ratio condition with Raji and K562 cells, which was in duplicate), sample 019-006 (performed in duplicate for all conditions), and 022-001 (performed once for all conditions). Both 12 hour and 18 hour co-culture periods are shown for IFN-γ and granzyme B results, and 18 hour co-culture periods are shown for TNF-α results. The results illustrate the surprisingly good performance of the assay for a variety of TIL samples, including when used with the K562 negative control cell line to show fold-increase in production of IFN-γ and granzyme, and demonstrate that the co-culture system was used to activate the TILs via allogeneic MHC-TCR engagement and provide a measure of the potency of the TIL products after Gen 2 manufacturing, cryopreservation and thawing. The assay is polyfunctional in nature, allowing for the selection of one analyte or a combination of analytes in an efficient manner. In general, the 18-hour coculture timepoint was a more robust timepoint when considering both IFN-γ and granzyme B. TNF-α may also be assessed at the 12-hour timepoint and utilized if suitable. The 1:3 (TIL:target) ratio resulted in the greatest cytokine secretion in this example. The dose response across the TIL:target ratio range was surprisingly notable for TNF-α. The TIL:target ratio may be increased, e.g., to 1:5, 1:10, or 1:20.

Example 17: Recovery Time Evaluation

Figure 98:
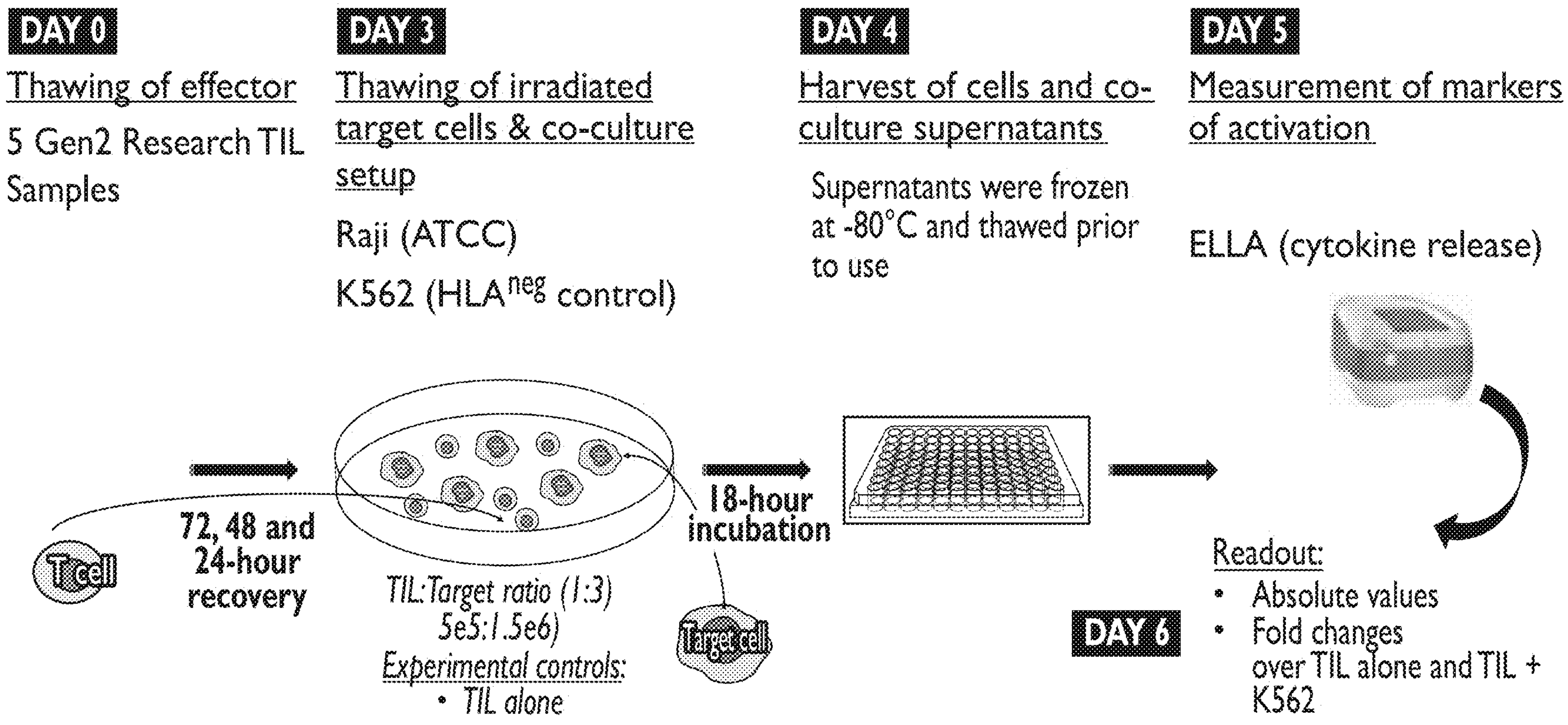
FIG. 98: Diagram of an embodiment of the TIL-Raji co-culture assay with an optional TIL-K562 negative control.
Figure 99:
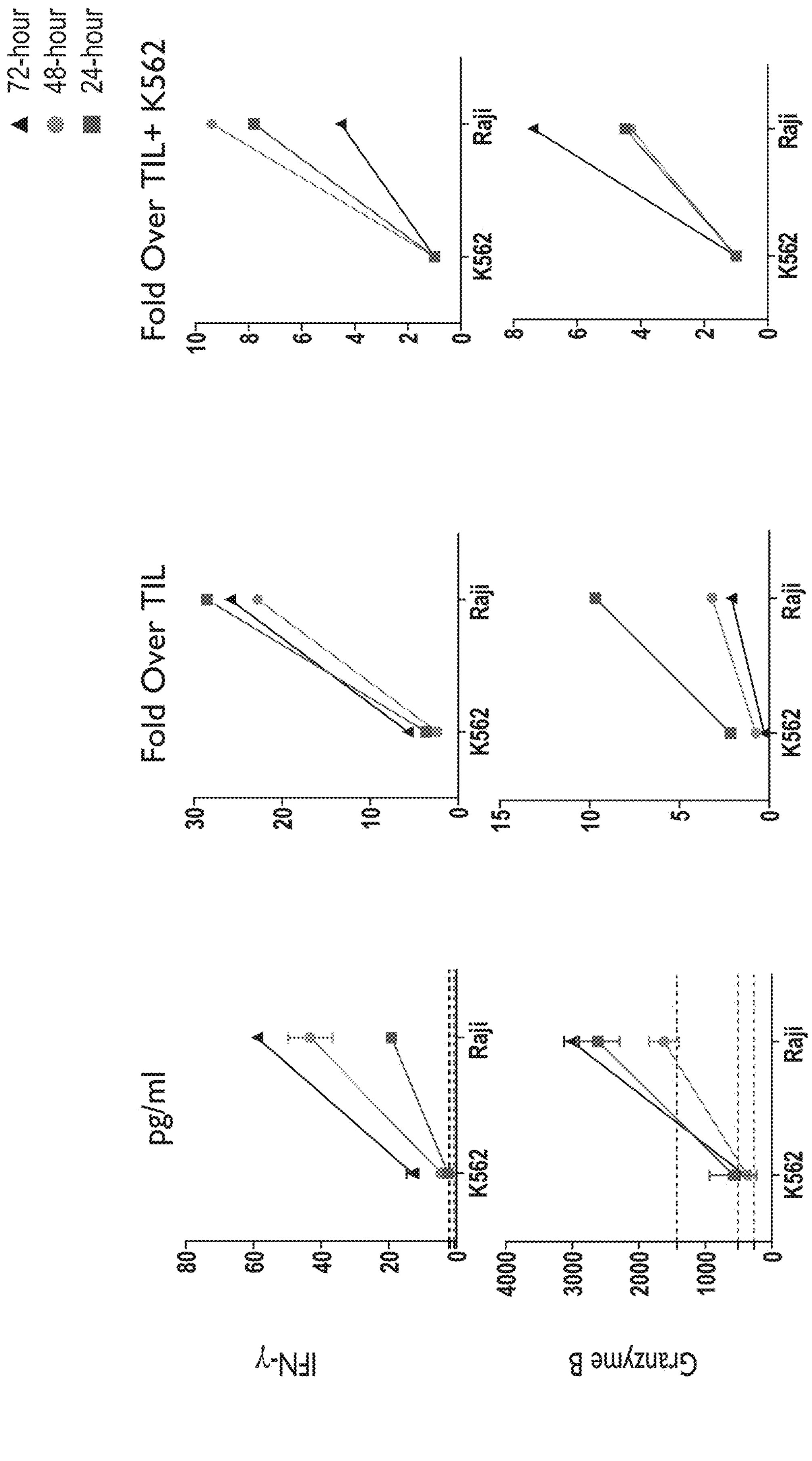
FIG. 99: Assay results for TIL lot M1173.
Figure 100:
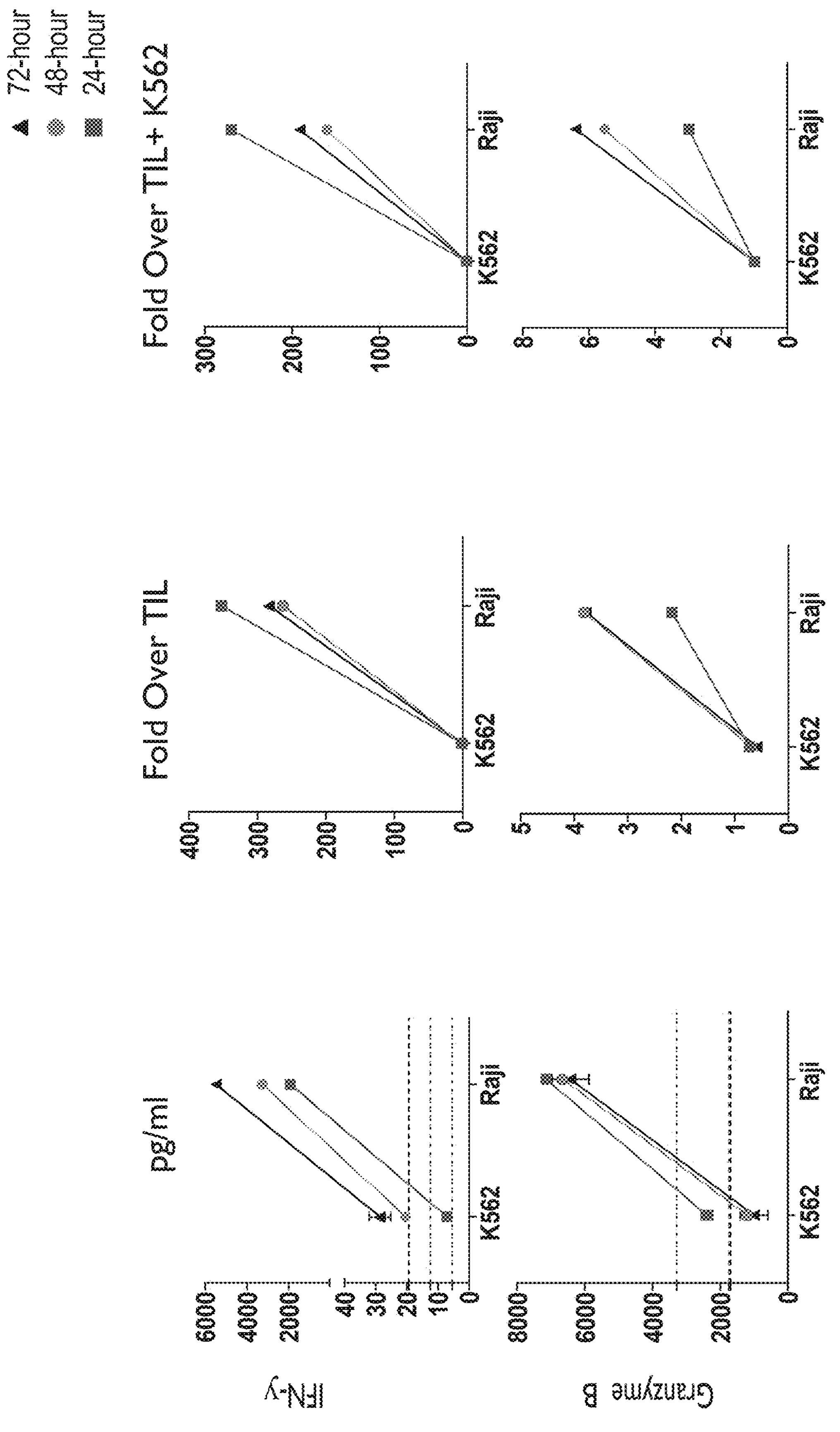
FIG. 100: Assay results for TIL lot M1152.
Figure 101:
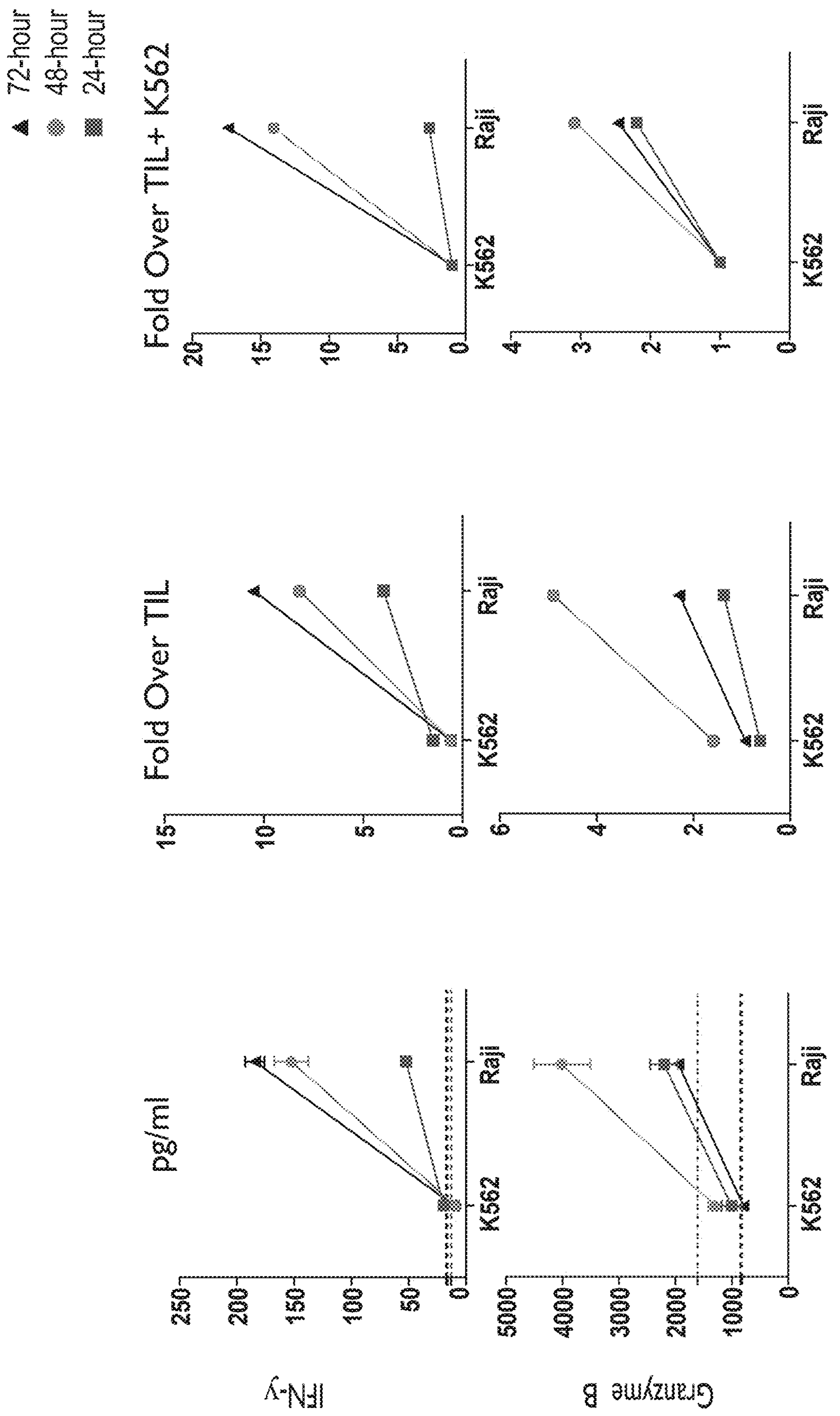
FIG. 101: Assay results for TIL lot M1187.
Figure 102:
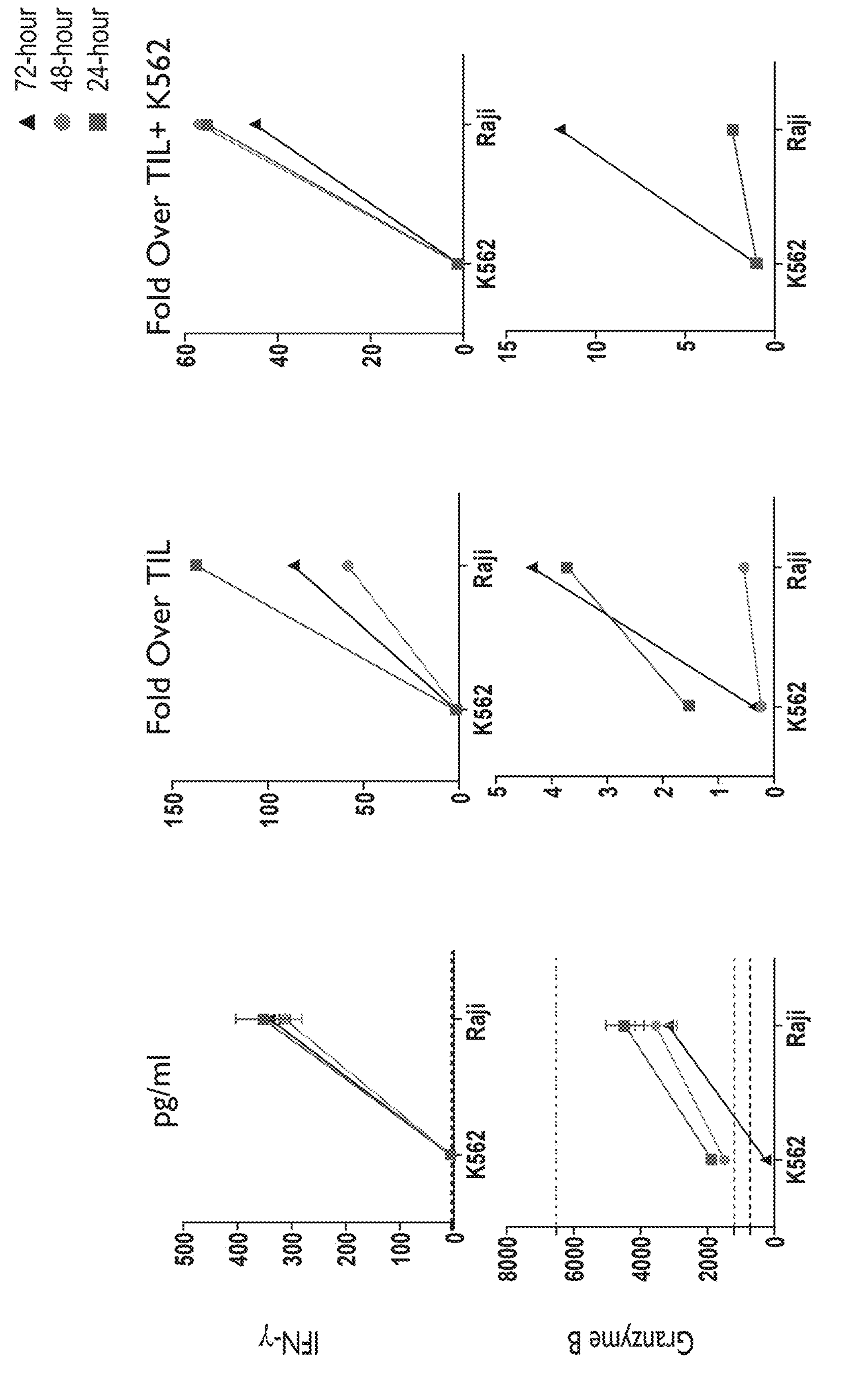
FIG. 102: Assay results for TIL lot M1179.
Figure 103:
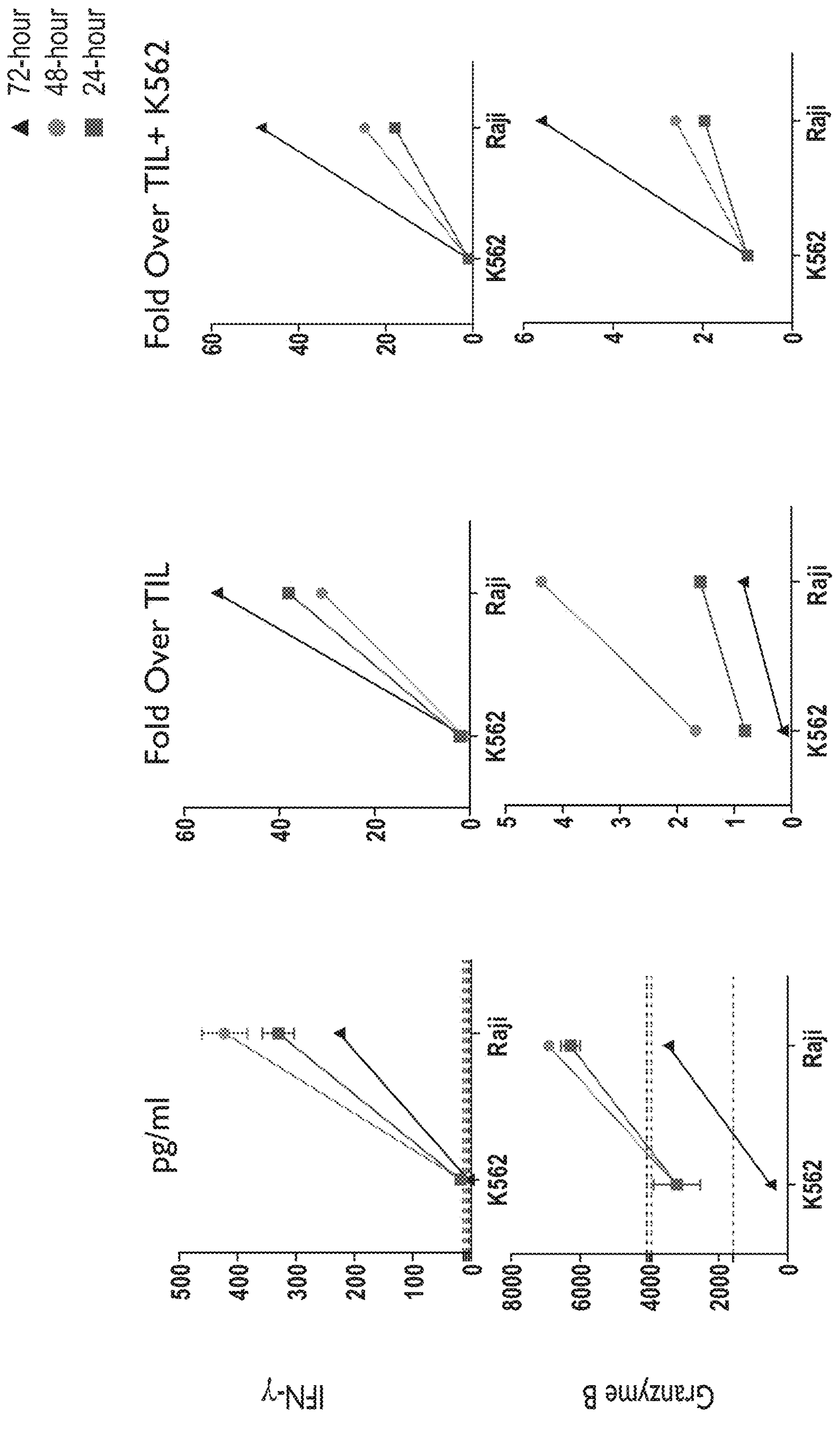
FIG. 103: Assay results for TIL lot M1183.
Figure 104:
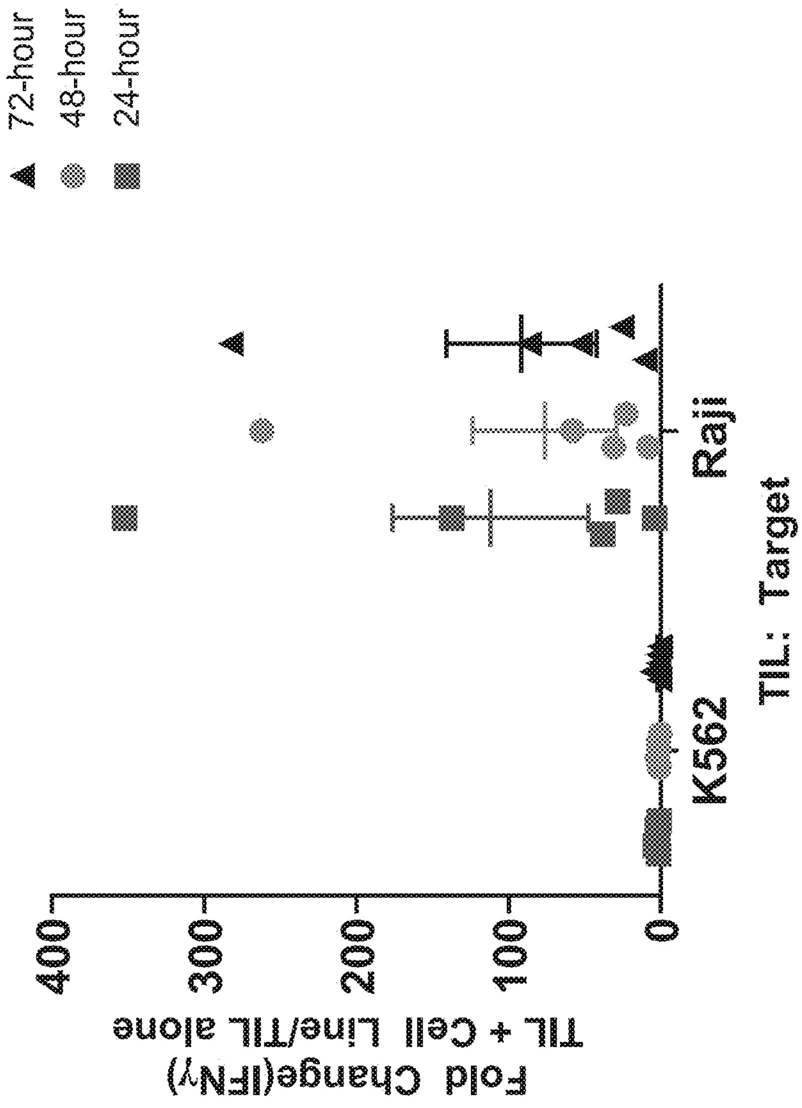
FIG. 104: Cytokine secretion results for IFN-γ showing fold change over TILs plus K562 or Raji cells over TILs alone at different post-thaw recovery times.
Figure 105:
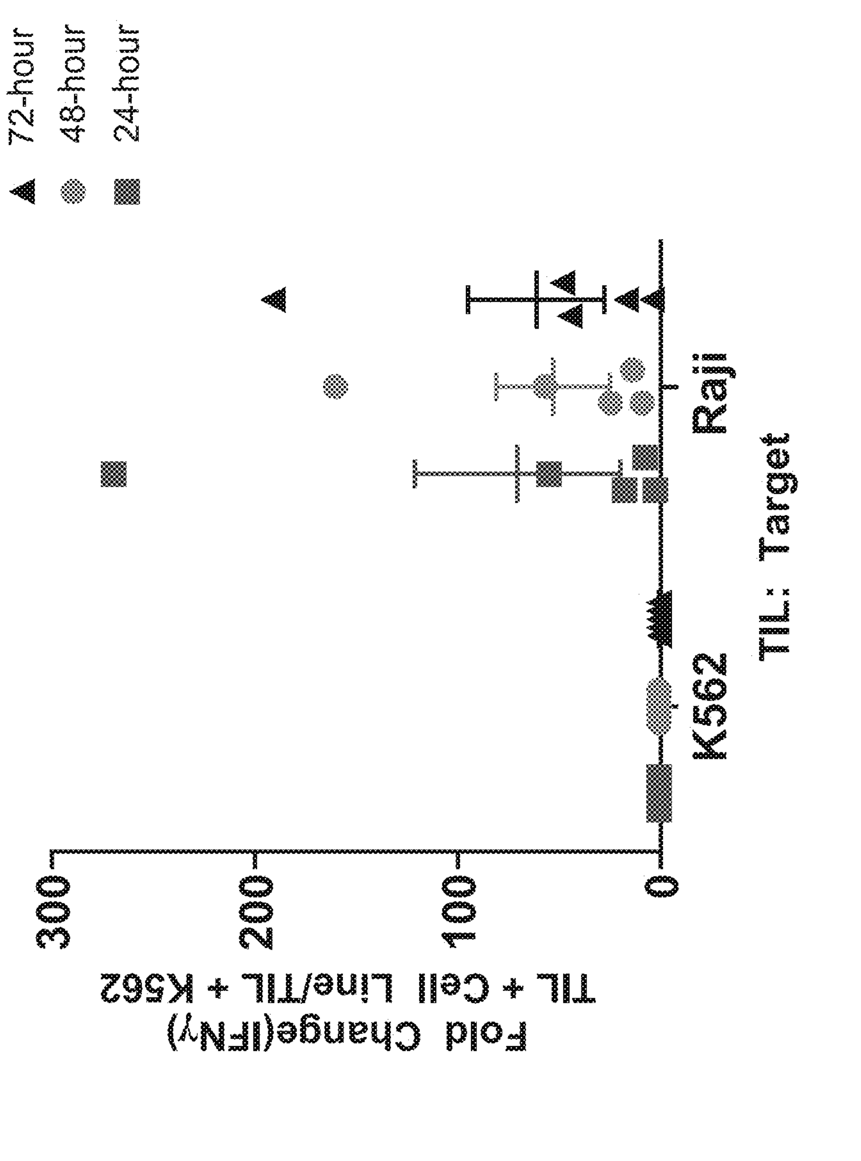
FIG. 105: Cytokine secretion results for IFN-γ showing fold change over TILs plus K562 or Raji cells over TILs plus K562 cells at different post-thaw recovery times.
Figure 106:
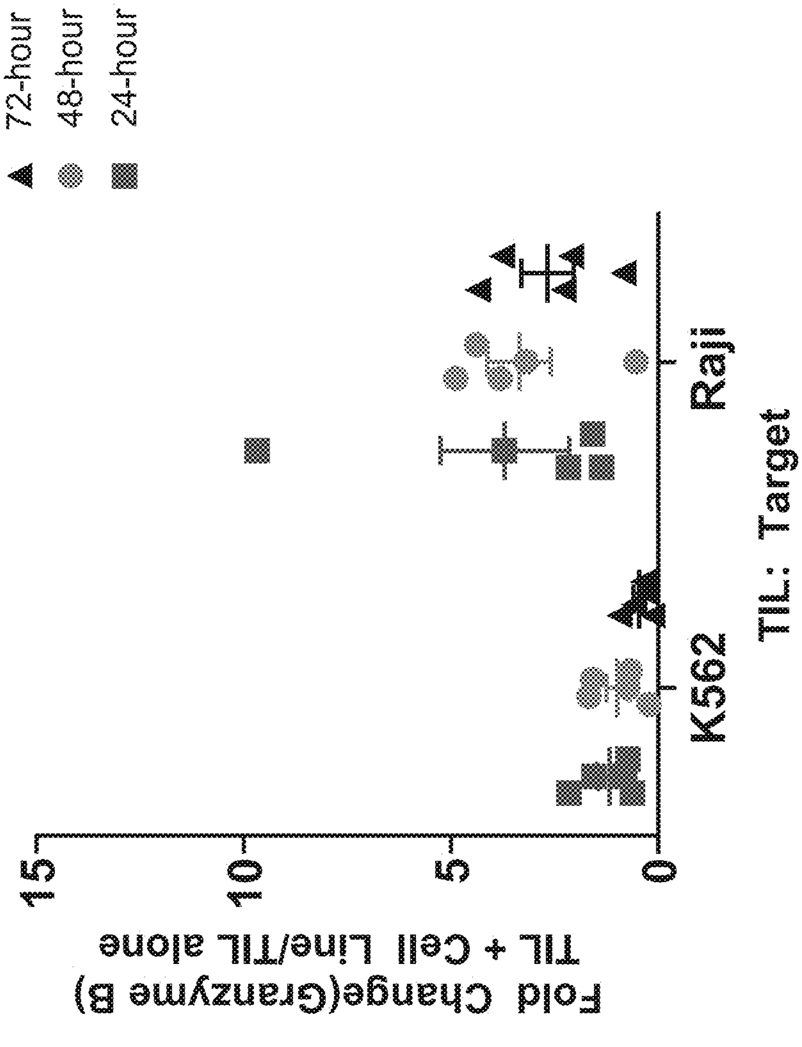
FIG. 106: Cytokine secretion results for granzyme B showing fold change over TILs plus K562 or Raji cells over TILs alone at different post-thaw recovery times.
Figure 107:
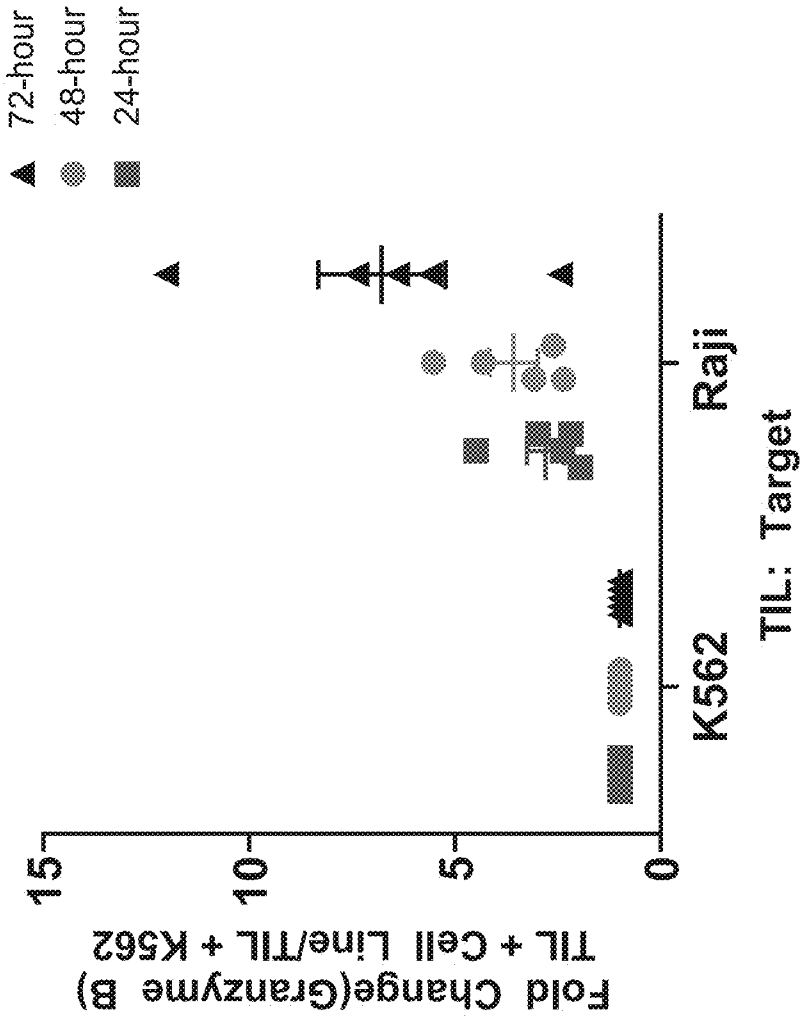
FIG. 107: Cytokine secretion results for granzyme B showing fold change over TILs plus K562 or Raji cells over TILs plus K562 cells at different post-thaw recovery times.

In this example, the recovery time after thawing of frozen TIL products is investigated. The experimental scheme, which is also an embodiment of the present invention, is depicted in FIG. 98. Five research TIL lots prepared using the Gen 2 process were thawed and allowed to recover for either 72, 48 or 24 hours after thawing, and assessed for IFN-γ and granzyme B upon co-culture with Raji and K562 cells at a 1:3 TIL:target ratio using the method described in Example 16. The results are shown in FIG. 99 for lot M1173, FIG. 100 for lot M1152, FIG. 101 for lot M1187, FIG. 102 for lot M1179, and FIG. 103 for lot M1183. The results for IFN-γ are summarized in FIGS. 104 and 105, and the results for granzyme B are summarized in FIGS. 106 and 107. All three readouts for IFN-γ (absolute values, fold over TILs, and fold over TILs plus K562 cells), were similar across the recovery conditions. The 72-hour TIL recovery resulted in a greater fold induction of TILs plus Raji over TIL plus K562 for granzyme B secretion. Reduced cell yield and viability was observed in the 24-hour recovery samples.

Example 18: Master Cell Bank Preparation

In this example, master cell banks are prepared for Raji and K562 cell lines. Such master cell banks are suitable for use in an assay for release and/or stability testing of TIL, MIL, or PBL products for human use, where such products are regulated by health authorities such as the United States Food and Drug Administration. A pilot study is performed first, using 25 vials, which are then assessed for performance in one or more potency assays of the present invention. The master cell banks for the Raji and K562 cell lines are then prepared using 500 vials containing between $5\times10^6$ and $5\times10^6$ cells per mL, in 1 mL volumes per vial. Cell culture expansions are performed as necessary. Characterization and release are then performed, including method suitability testing by direct inoculation, sterility by direct inoculation, interference testing for rapid mycoplasma detection by DNA amplification, rapid mycoplasma detection by DNA amplification, in vitro adventitious viral assay detection (cell lines MRC-5, Vero, and HeLa, virus PIV-5), and identification by cytochrome C oxidase subunit 1. Certificates of analysis and batch records are prepared. The Raji and K562 cell lines are then suitably qualified for use in method validation and testing procedures. Master cell banks for Ramos, U937, Thp1, and Daudi cells may be similarly prepared.

Example 19: Alloreactivity Co-Culture Assay with Thp1 Cells

Figure 108:
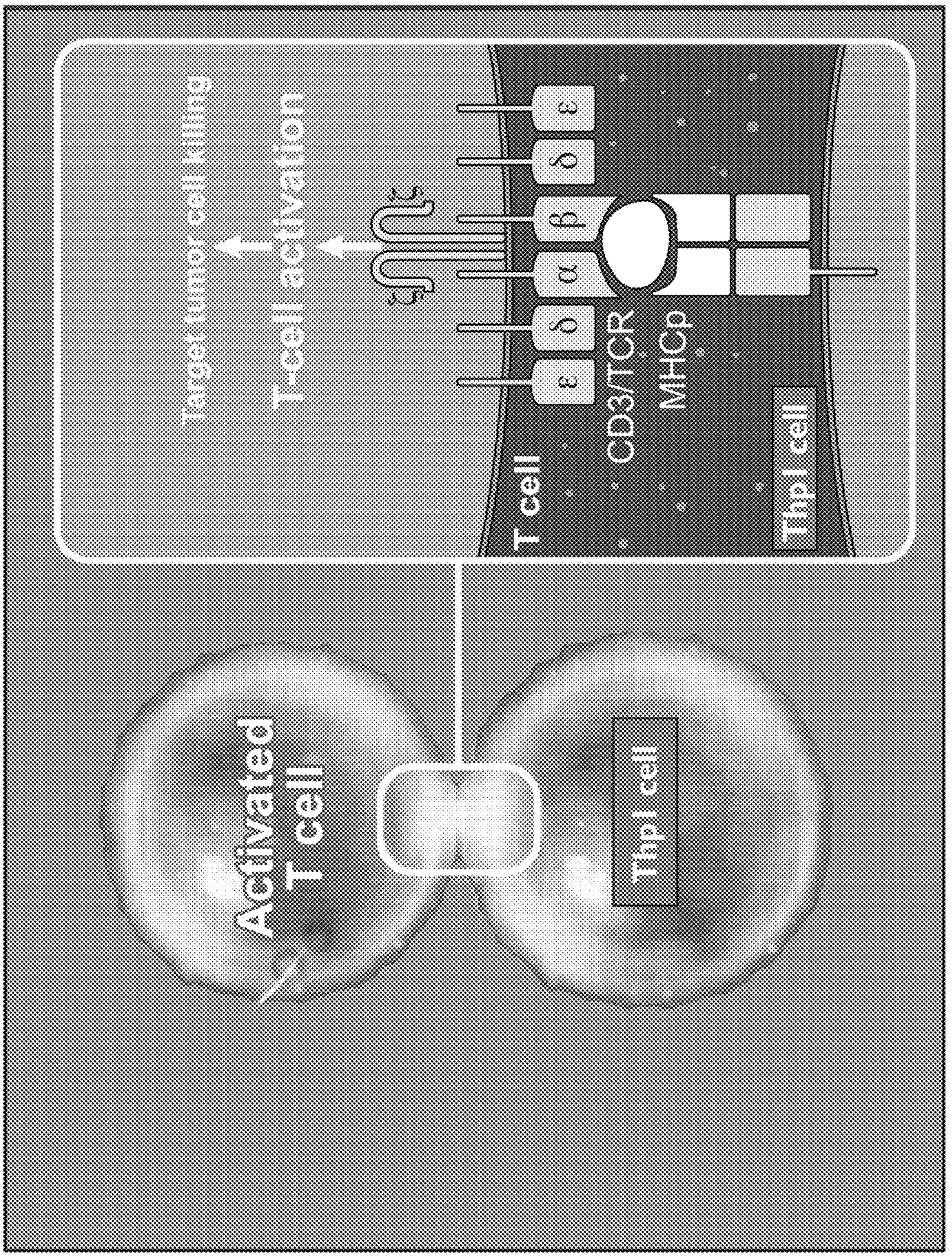
FIG. 108: Embodiment of an allogeneic recognition assay.
Figure 109:
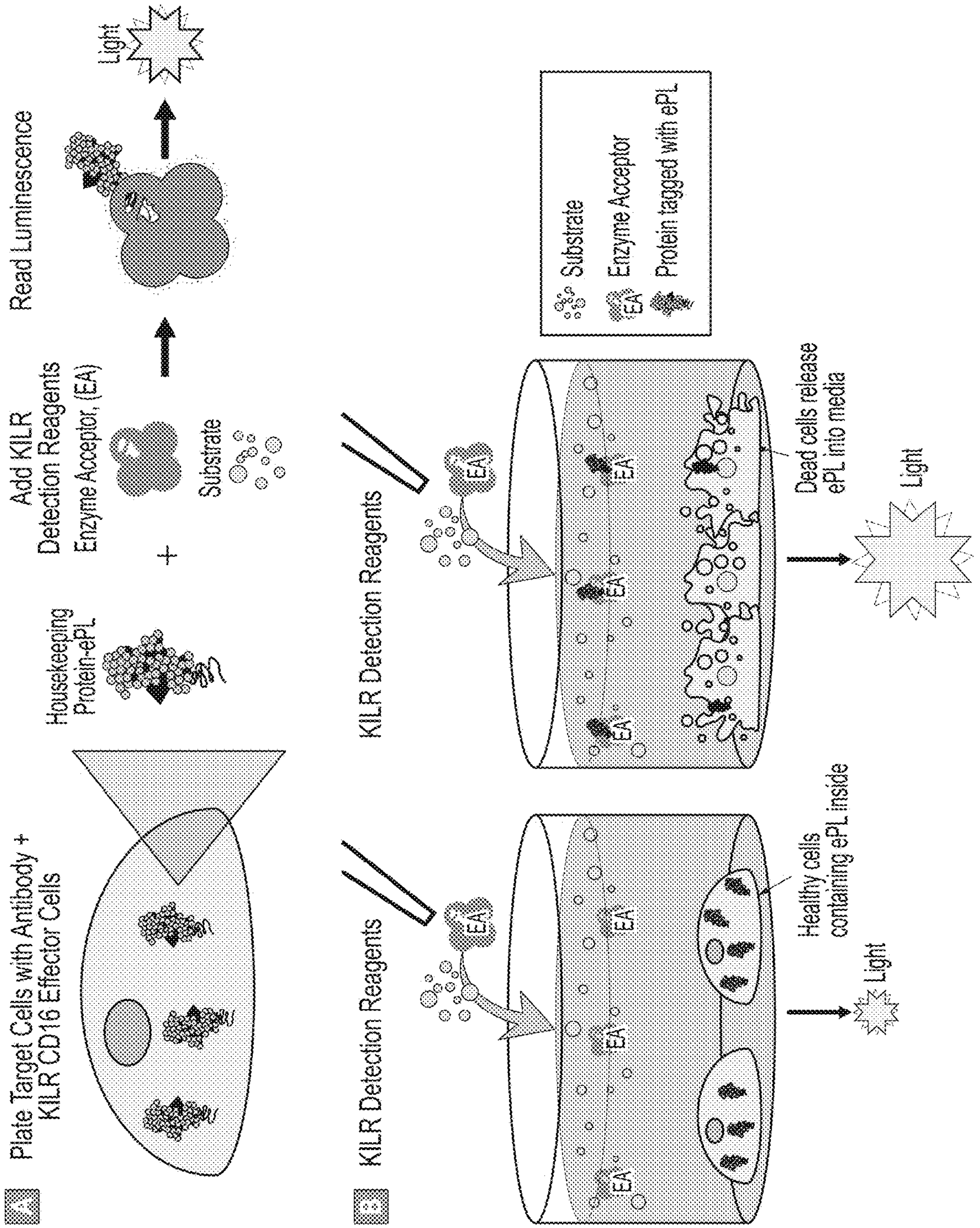
FIG. 109: Embodiment of an allogeneic recognition assay detection method.

In this example, an embodiment of an alloreactive co-culture assay using co-cultures of TILs with the Thp1 (also known as THP-1) target cell line, a human monocytic leukemia cell line, is demonstrated. Without being bound by theory, TIL activation is believed to be induced upon allorecognition by the TCR of an unmatched peptide-MHC complex (MHCp) at the surface of the Thp1 cells, as shown in FIG. 108. The read out for this assay is the killing of the target cells, which can be detected by release of a reporter chemiluminescent protein. The assay requires the use of target cell lines to be produced under GMP conditions to create a master cell bank and working cell banks, for example, as described elsewhere herein. Target cells are engineered to stably express a housekeeping protein tagged with ProLabel® (ePL), a β-gal enzyme fragment. Upon co-culture with T cells, including TILs, MILs, or PBLs, and following cytotoxicity mediated membrane disruption, the ePL β-gal fragment is released to the media. Following co-culture, an enzyme acceptor fragment of the β-gal enzyme is added, forming an active β-gal enzyme that hydrolyzes an added substrate, producing a chemiluminescent signal that is proportional to the number of dead target cells. The readout is specific for and directly measures target cell death, for example, cell death for Thp1 or Raji cells. The foregoing process is illustrated in FIG. 109. The mechanism of action of this assay is allogeneic response (for example, a mixed lymphocyte reaction, or MLR), such as the ability of T cells to recognize peptide-allogeneic MHC complexes.

The genetically modified Thp1 cell line was tested using two TIL post-thaw conditions (starting from frozen TIL lots): (1) rested overnight for 18 to 24 hours after thawing and (2) no resting post-thaw. The effector:target (E:T) ratios tested were 35:1 to 2.5:1 for the first condition and 10:1 to 1:10 for the second condition. Both conditions used 10,000 target cells per well. The coculture durations tested were 4 hours, 8 hours, 16 hours, and 36 hours for the first condition and overnight (16 to 24 hours) for the second condition. For both conditions, 0% cytotoxicity signal corresponds to no effector cells, and 100% cytotoxicity signal corresponds to totally lysed target cells.

Example 20: TIL Potency Methods Using IL-2 During Co-Culture

Figure 112:
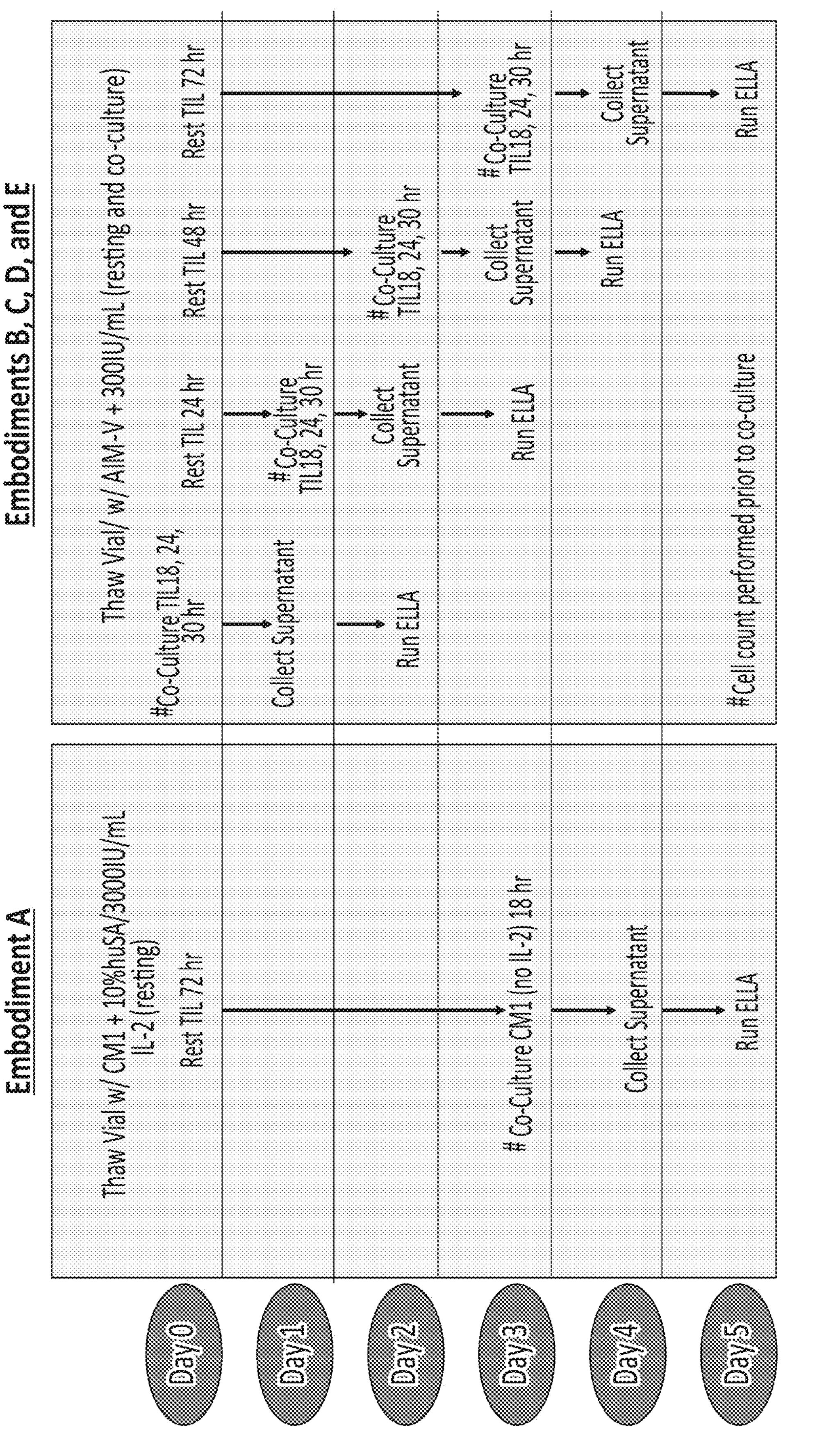
FIG. 112: Exemplary embodiments of a TIL-Raji cell-based potency assay.

In this example, potency methods of the present invention are further evaluated using AIM-V media with 300 IU/mL IL-2 added continuously during the co-culture (as illustrated in FIG. 112 as embodiments B, C, D, and E) in comparison to CM1 media with initial addition of IL-2 at 3000 IU/mL, as described above and illustrated in FIG. 112 as embodiment A. Embodiments B, C, D, and E include 300 IU/mL IL-2 in AIM-V added during co-culture, which matches an embodiment of the final Gen 2 and Gen 3 product formulation and provides for better system suitability. The AIM-V culture medium is serum-free to match final cell expansion and also provides for better system suitability. Adding IL-2 during co-culture increases cytokine concentration. Initiation of co-culture immediately post-thaw (i.e., no resting period for TIL recovery) may also offer advantages, because it more closely represents TIL drug products upon administration. Longer resting periods promote the recovery of TILs and may not be stability indicating, and also may mask manufacturing process failures.

Figure 113:
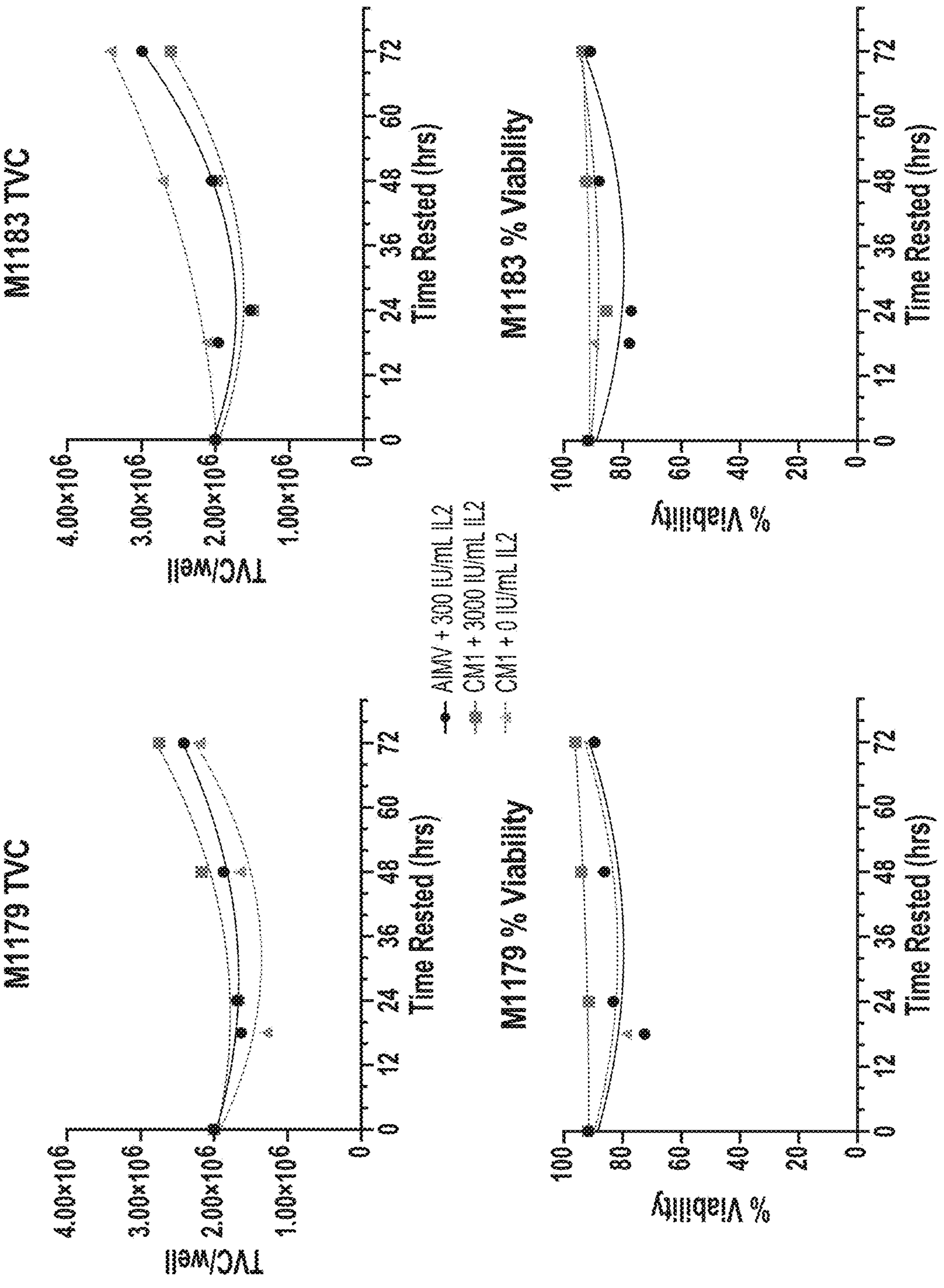
FIG. 113: Total viable cells (TVC, top plots) and % viability (bottom plots) versus resting time.

FIG. 113 shows the results of an evaluation of total viable cell count (TVC) and percent viability for two different TIL cell lines, M1179 and M1183, under different co-culture media conditions, as a function of resting period after thawing of the TIL cell lines. A decrease in percent viability and was observed in the first 24-hour period, and an increase in TVC and proliferation was observed in TILs resting for >24 hours (~1 doubling/day). These results suggest that TILs recovered after 24 hours of resting may not represent the same cell population of the drug product. For both TIL cell lines, a slight decrease is observed after thawing, after which recovery commences.

Figure 114:
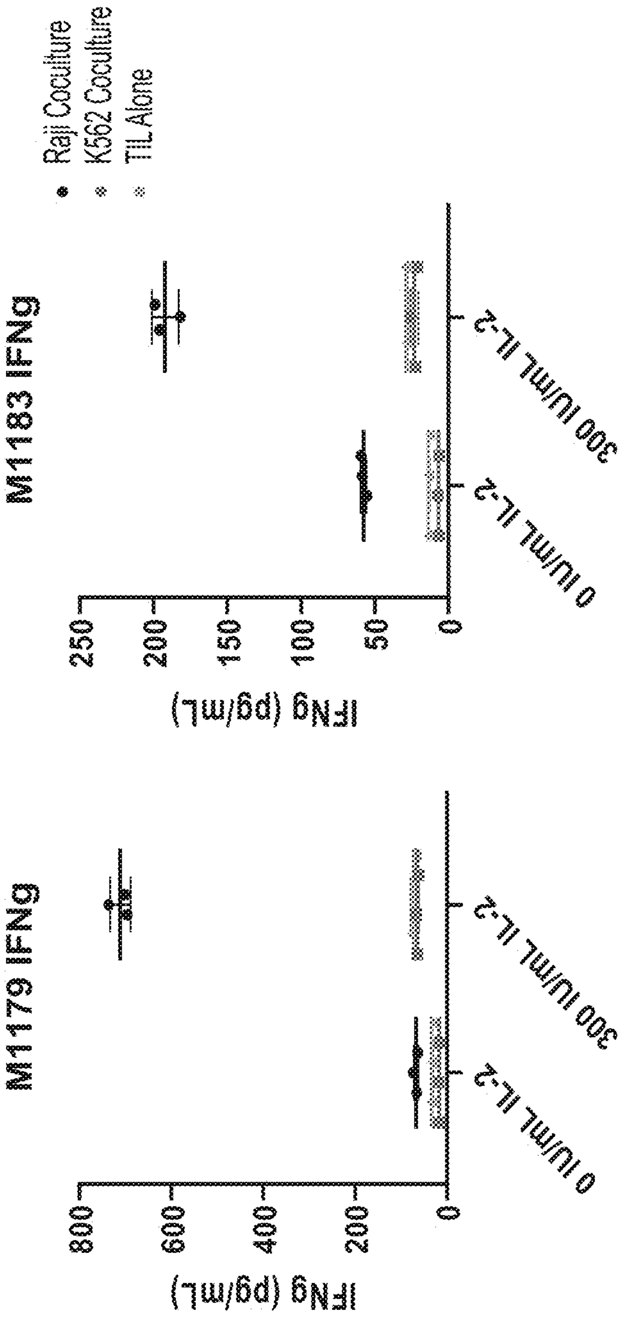
FIG. 114: Results of Raji and K562 co-culture experiments with two TIL cell lines with and without 300 IU/mL IL-2, showing IFN-γ secretion in pg/mL.
Figure 115:
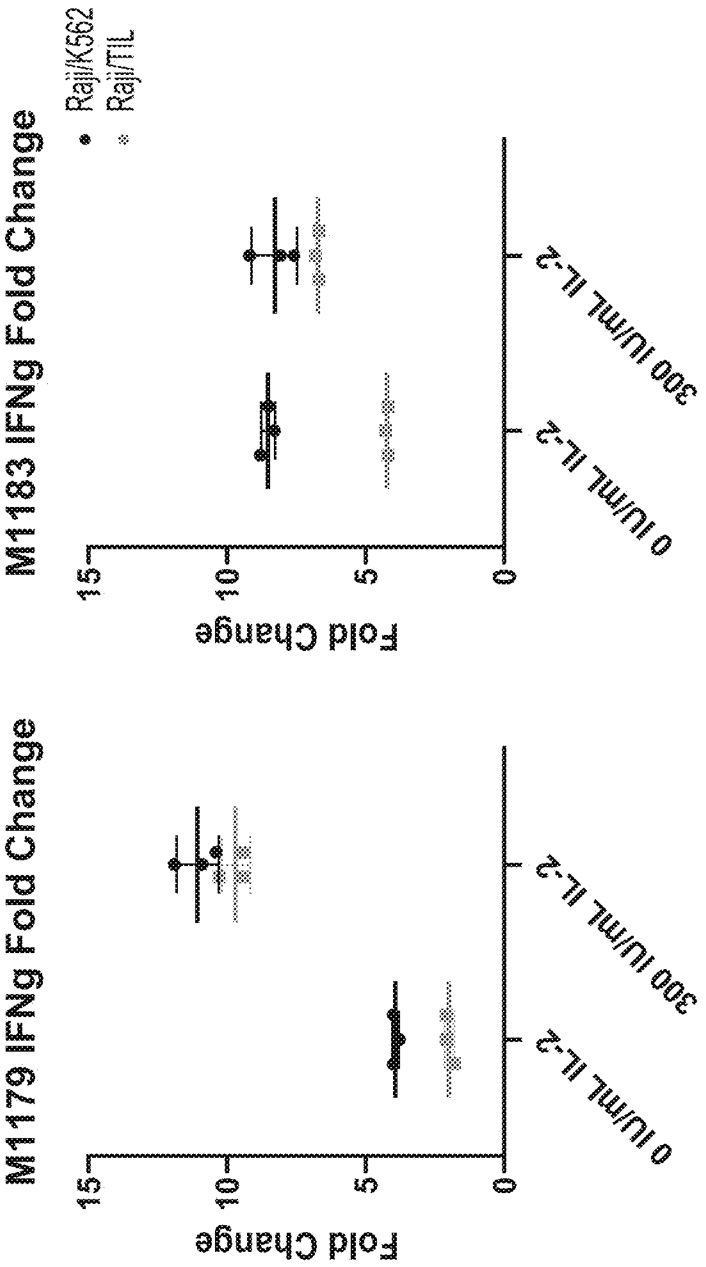
FIG. 115: Results of Raji and K562 co-culture experiments with two TIL cell lines with and without 300 IU/mL IL-2, showing IFN-γ secretion in units of fold change.

The results of a comparison of co-culture with Raji and K562 cells with and without 300 IU/mL of IL-2 are given in Table 51, FIG. 114, and FIG. 115. Experiments were performed in AIM-V media immediately after thawing of TIL lines M1179 and M1183 (that is, with no rest period). The results demonstrate that the addition of IL-2 enhances IFN-γ secretion. Absolute concentration values of IFN-γ and fold change increase with adding IL-2. IL-2 was observed to increase the baseline of the control performed using TIL alone. Repeatability was assessed across co-culture replicates during these experiments. A single vial coefficient of variation (CV) % of 11% was obtained.

TABLE 51

Results of Raji and K562 co-culture experiments with two TIL cell lines with and without 300 IU/mL IL-2.

| | | Raji Coculture | | | | K562 Coculture | | | | TIL Alone | | | |
|---|---|---|---|---|---|---|---|---|---|---|---|---|---|
| TIL Lot | IL-2 Conc. | Average | St. Dev | % CV | N | Average | St. Dev | % CV | N | Average | St. Dev | % CV | N |
| M1179 | 0 IU/mL | 68 | 5 | 7 | 3 | 17 | 1 | 7 | 3 | 33 | 2 | 7 | 3 |
| | 300 IU/mL | 711 | 22 | 3 | 3 | 64 | 3 | 4 | 3 | 73 | 6 | 8 | 3 |
| M1183 | 0 IU/mL | 58 | 2 | 4 | 3 | 7 | 0 | 5 | 3 | 14 | 1 | 5 | 3 |
| | 300 IU/mL | 192 | 9 | 5 | 3 | 23 | 3 | 11 | 3 | 28 | 1 | 5 | 3 |

Figure 110:
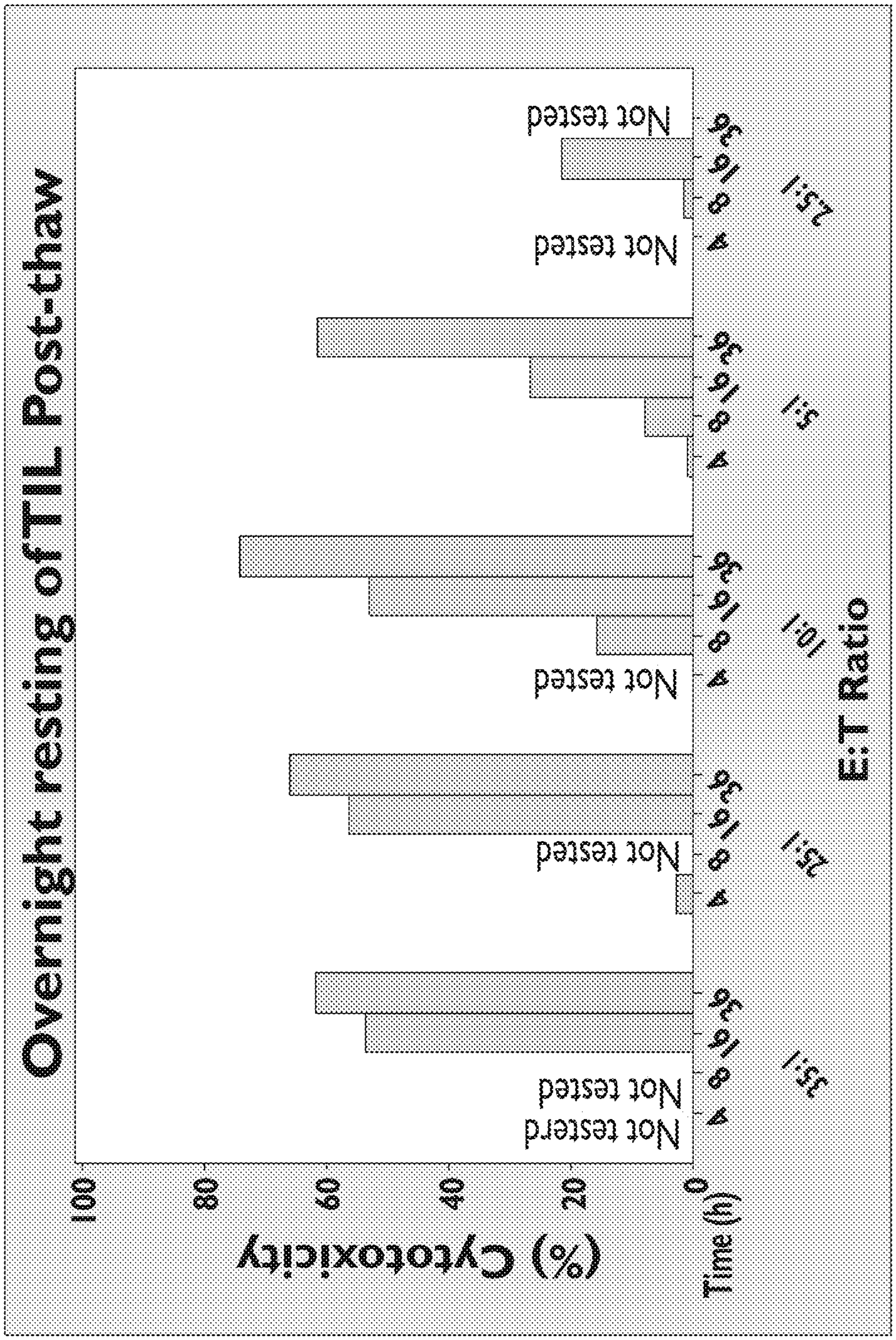
FIG. 110: Results for post-thaw condition 1 (rested overnight for 18 to 24 hours after thawing). The effector:target (E:T) ratios tested ranged from 35:1 to 2.5:1, and the coculture durations tested were 4 hours, 8 hours, 16 hours, and 36 hours.
Figure 111:
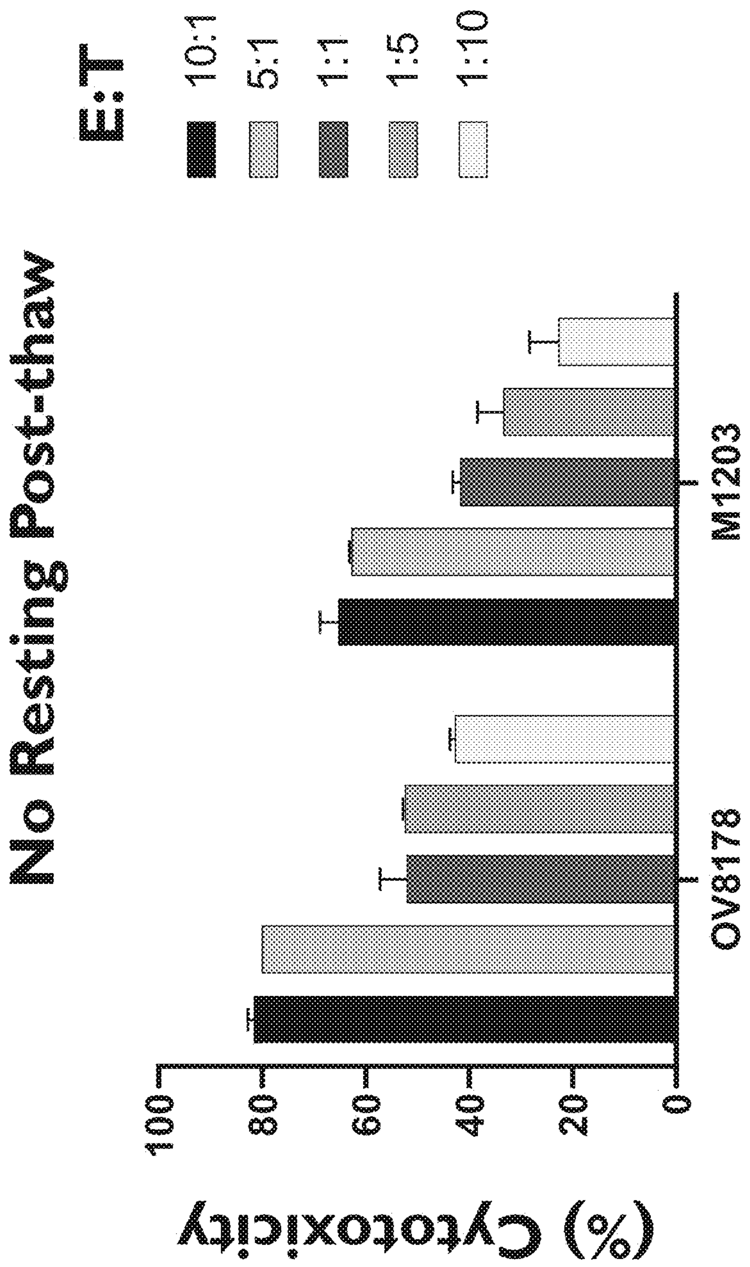
FIG. 111: Results for post-thaw condition 2 (no resting post-thaw). The effector:target (E:T) ratios tested ranged from 10:1 to 1:10 and the coculture duration was overnight (16 to 24 hours). TILs produced from an ovarian cancer tumor (OV8178) and a melanoma tumor (M1203) were tested.

Cytotoxicity was observed by dose- and time-dependent response for the first condition and dose-dependent response for the second condition. FIG. 110 shows the results from the first condition. The data shown are averages from 3 experiments. FIG. 111 shows the results from the second condition.

Figure 116:
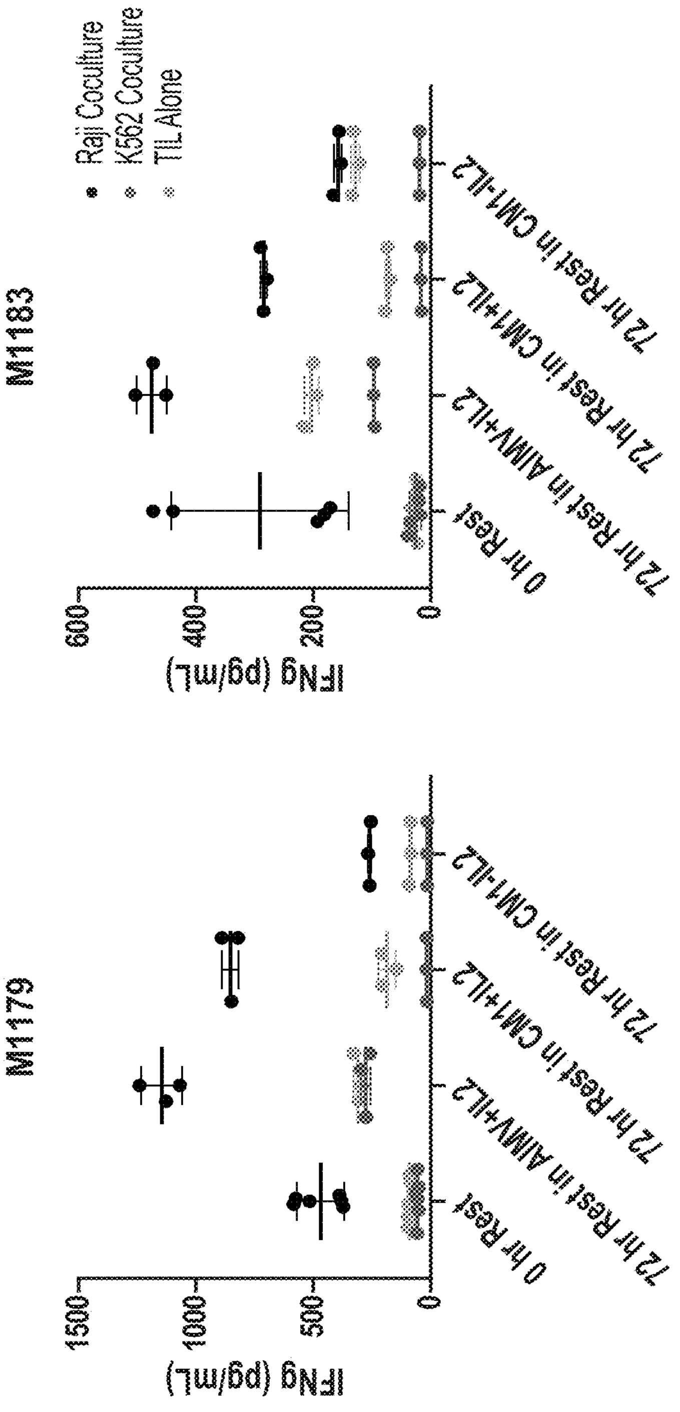
FIG. 116: Results of Raji and K562 co-culture experiments with two TIL cell lines under different co-culture conditions, showing IFN-γ secretion in pg/mL.
Figure 117:
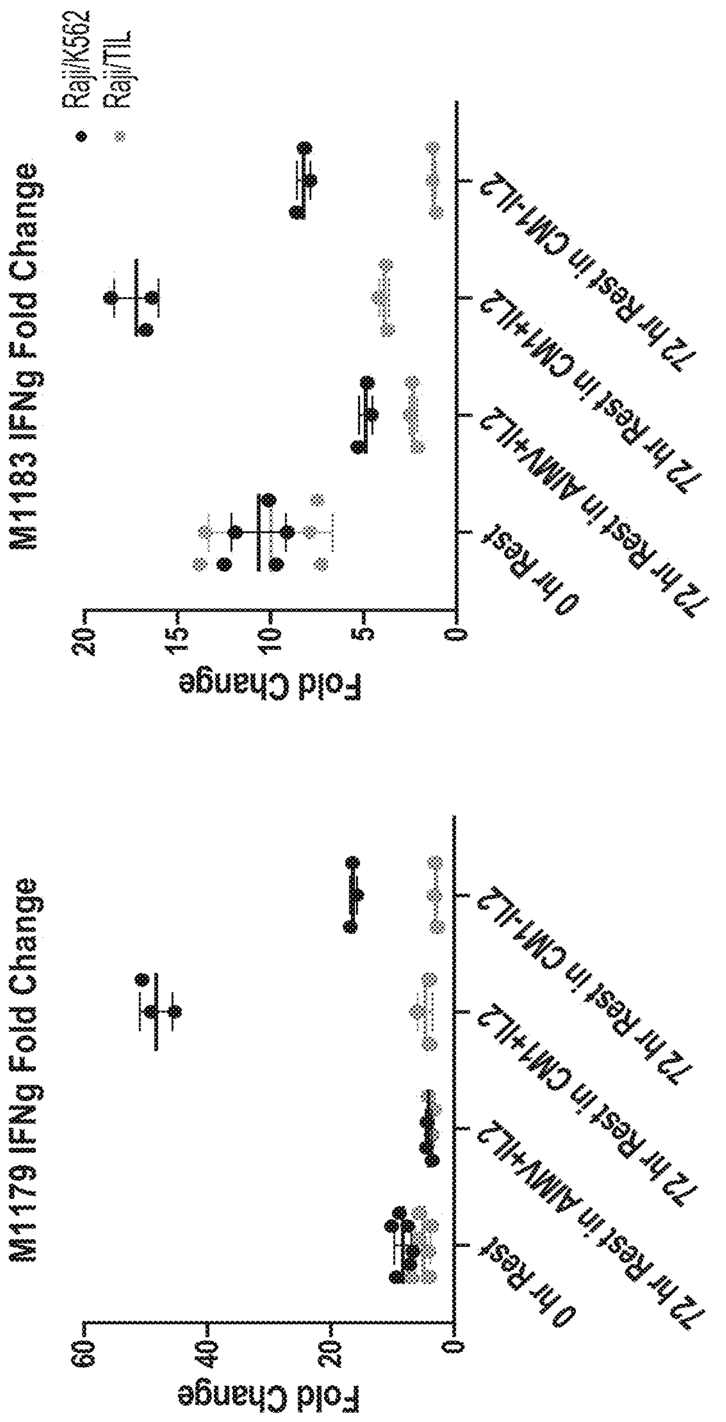
FIG. 117: Results of Raji and K562 co-culture experiments with two TIL cell lines under different co-culture conditions, showing IFN-γ secretion in units of fold change.

Different culture conditions and rest periods were also explored, with the results given in Table 52, FIG. 116, and FIG. 117. The results show that 72 hours of recovery is not required for good IFN-γ secretion when AIM-V and IL-2 are used in the co-culture media.

TABLE 52

Results of Raji and K562 co-culture experiments with different media culture conditions for two TIL cell lines (M1179 and M1183), including no rest after TIL thawing ("0 hr rest"), after 72 hours of rest in AIM-V media with 300 IU/mL of IL-2 ("72 hr rest in AIM-V + IL2"), after 72 hours of rest in CM1 media with 300 IU/mL of IL-2 ("72 hr rest in CM1 + IL2"), and after 72 hours of rest in CM1 media without 300 IU/mL of IL-2 ("72 hr rest in CM − IL2").

| | | Raji Coculture | | | | K562 Coculture | | | | TIL Alone | | | |
|---|---|---|---|---|---|---|---|---|---|---|---|---|---|
| TIL Lot | Condition | Average | St. Dev | % CV | N | Average | St. Dev | % CV | N | Average | St. Dev | % CV | N |
| M1179 | 0 hr rest + IL2 | 470 | 101 | 21 | 6 | 56 | 4 | 7 | 6 | 93 | 5 | 6 | 6 |
| | 72 hr rest in AIM-V + IL2 | 1146 | 87 | 8 | 3 | 277 | 20 | 7 | 3 | 311 | 16 | 5 | 3 |
| | 72 hr rest in CM1 + IL2 | 854 | 35 | 4 | 3 | 18 | 0 | 2 | 3 | 187 | 36 | 20 | 3 |
| | 72 hr rest in CM1 − IL2 | 261 | 6 | 2 | 3 | 16 | 0 | 1 | 3 | 87 | 5 | 6 | 3 |
| M1183 | 0 hr rest + IL2 | 291 | 151 | 52 | 5 | 26 | 10 | 39 | 5 | 28 | 5 | 19 | 5 |
| | 72 hr rest in AIM-V + IL2 | 476 | 26 | 6 | 3 | 97 | 1 | 1 | 3 | 204 | 12 | 6 | 3 |
| | 72 hr rest in CM1 + IL2 | 285 | 6 | 2 | 3 | 17 | 1 | 5 | 3 | 73 | 5 | 6 | 3 |
| | 72 hr rest in CM1 − IL2 | 158 | 7 | 4 | 3 | 19 | 0 | 1 | 3 | 129 | 7 | 5 | 3 |

Figure 118:
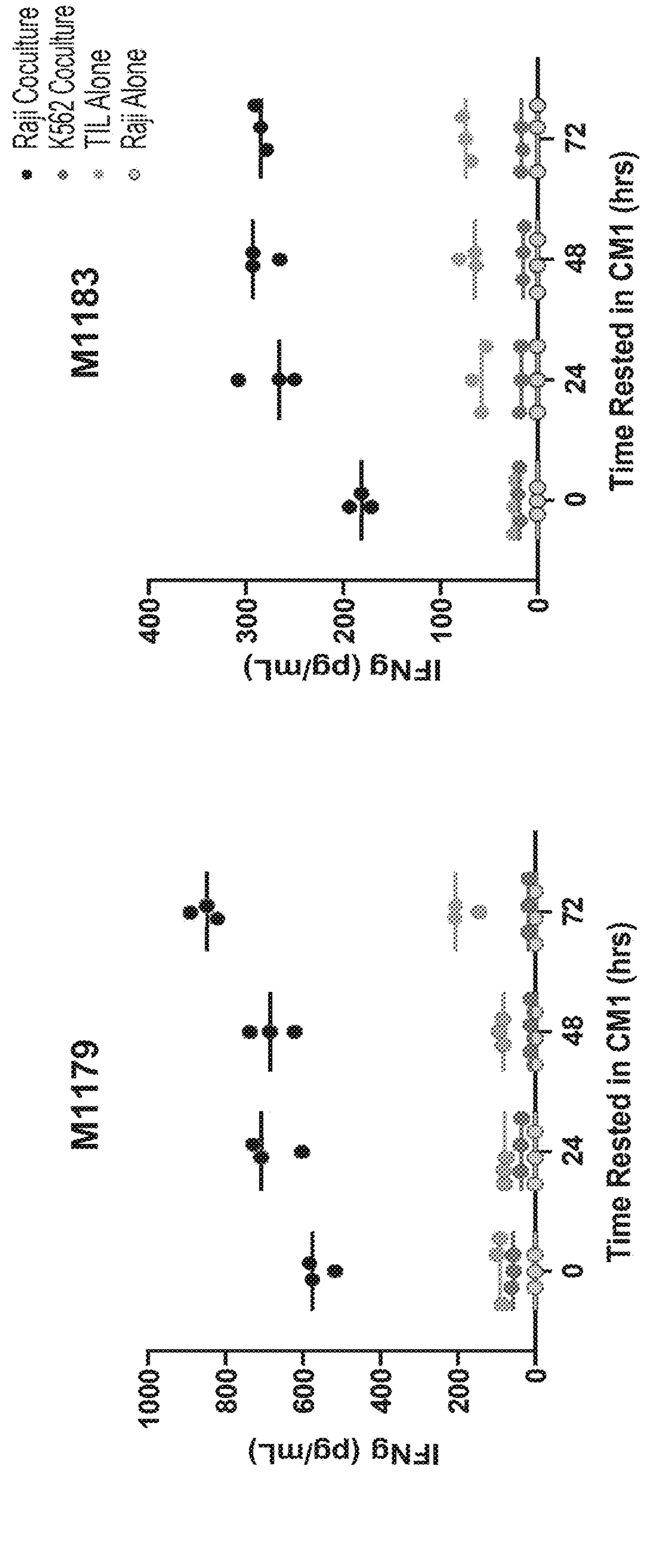
FIG. 118: Results of Raji and K562 co-culture experiments with two TIL cell lines under different co-culture conditions for evaluation of cytokine secretion effects as the TIL post-thaw recovery period is extended, showing IFN-γ secretion in pg/mL.
Figure 119:
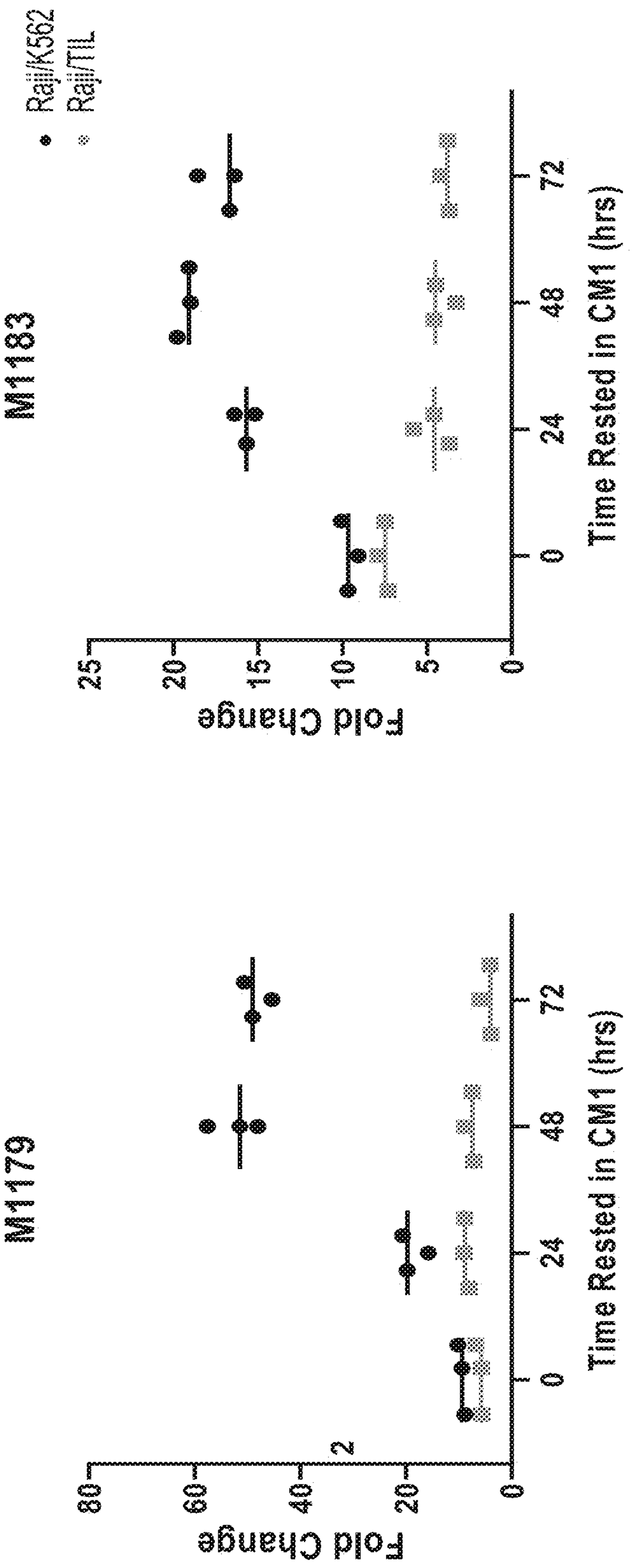
FIG. 119: Results of Raji and K562 co-culture experiments with two TIL cell lines under different co-culture conditions, which are embodiments of the present invention, for evaluation of cytokine secretion effects as the TIL post-thaw recovery period is extended, showing IFN-γ secretion in units of fold change.

Experiments to determine cytokine secretion effects as the post-thaw recovery period is extended were also performed, with results summarized in Table 53, FIG. 118, and FIG. 119. In these experiments, the resting media was CM1 with 3000 IU/mL IL-2, and the co-culture media was AIM-V with 300 AU/m IL-2. Absolute IFN-γ secretion was detected across all conditions for co-cultures with Raji cells. Fold change in IFN-γ over TIL alone was consistent across all resting conditions. Differences in fold change between TIL alone and with use of the K562 negative control was observed at time points greater than 24 hours, and may be indicative of cell population changes.

TABLE 53

Results of Raji and K562 co-culture experiments performed with different TIL post-thaw recovery periods two TIL cell lines (M1179 and M1183).

| | Time rested in | Raji Coculture | | | | K562 Coculture | | | | TIL Alone | | | |
|---|---|---|---|---|---|---|---|---|---|---|---|---|---|
| TIL Lot | CM1 (hrs) | Avg. (pg/mL) | St. Dev. | % CV | N | Avg. | St. Dev | % CV | N | Avg. (pg/mL) | St. Dev | % CV | N |
| M1179 | 0 | 559 | 37 | 7 | 3 | 59 | 3 | 5 | 3 | 92 | 7 | 8 | 3 |
| | 24 | 679 | 68 | 10 | 3 | 36 | 2 | 5 | 3 | 79 | 4 | 5 | 3 |
| | 48 | 681 | 58 | 9 | 3 | 13 | 0 | 2 | 3 | 87 | 6 | 7 | 3 |
| | 72 | 854 | 35 | 4 | 3 | 18 | 0 | 2 | 3 | 187 | 36 | 20 | 3 |
| M1183 | 0 | 182 | 11 | 6 | 3 | 19 | 1 | 6 | 3 | 24 | 1 | 4 | 3 |
| | 24 | 275 | 30 | 11 | 3 | 17 | 1 | 7 | 3 | 59 | 7 | 12 | 3 |
| | 48 | 284 | 16 | 6 | 3 | 15 | 1 | 5 | 3 | 69 | 10 | 14 | 3 |
| | 72 | 285 | 6 | 2 | 3 | 17 | 1 | 5 | 3 | 73 | 5 | 6 | 3 |

Flow cytometry analysis was performed to determine cell population characteristics over a 72-hour period. Time studies were performed in two experiments, as provided in Table 54 and Table 55.

TABLE 54

Experiment 1 design.

| Timepoints | Media | |
|---|---|---|
| 0 hour | AIM-V + 300 IU/mL IL-2 | N/A |
| 24 hours rest | AIM-V + 300 IU/mL IL-2 | CM1 − No IL-2 |
| 48 hours rest | AIM-V + 300 IU/mL IL-2 | CM1 − No IL-2 |
| 72 hours rest | AIM-V + 300 IU/mL IL-2 | CM1 − No IL-2 |

TABLE 55

| Experiment 2 design. | | |
|---|---|---|
| Timepoints | Media | |
| 0 hour | AIM-V + 300 IU/mL IL-2 | N/A |
| 24 hours rest | AIM-V + 300 IU/mL IL-2 | CM1 + IL-2 |
| 48 hours rest | AIM-V + 300 IU/mL IL-2 | CM1 + IL-2 |
| 72 hours rest | AIM-V + 300 IU/mL IL-2 | CM1 + IL-2 |

Following these designs, cells were seeded at a concentration of 1×10$^6$/mL in 24-well plates and were rested at 37° C. with 500 $CO_2$. Cells were harvested at each specific timepoint +/−1 hour. Viability and TVC were performed at each time point. Cells were stained using a qualified residual flow assay with FMO controls and acquired on a BD FACSCanto flow cytometer with same day acquisition (BD Biosciences, Inc., Franklin Lakes, NJ, USA). Results are summarized in Table 56 and Table 57, where AIM-V+IL2 results were averaged from Experiment 1 and Experiment 2.

TABLE 56

T lymphocyte population changes across resting conditions (0 to 72 hours, IL-2 and serum).

| | % Lymphocytes | | | % Live | | |
|---|---|---|---|---|---|---|
| Cell Populations | AIM-V + IL2 (no serum) | CM1 No IL2 (serum) | CM1 + IL2 (serum) | AIM-V + IL2 (no serum) | CM1 No IL2 (serum) | CM1 + IL2 (serum) |
| M1179 (0 hr) | 96 | N/A | N/A | 94.35 | N/A | N/A |
| M1179 (24 hr) | 91.00 | 85.80 | 94.80 | 33.80 | 36.00 | 67.10 |
| M1179 (48 hr) | 92.80 | 85.90 | 93.90 | 56.45 | 38.60 | 89.90 |
| M1179 (72 hr) | 90.20 | 77.70 | 99.20 | 42.40 | 94.90 | 74.70 |
| M1183 (0 hr) | 92.80 | N/A | N/A | 92.85 | N/A | N/A |
| M1183 (24 hr) | 93.30 | 86.90 | 92.00 | 44.85 | 60.30 | 46.30 |
| M1183 (48 hr) | 92.95 | 83.60 | 98.30 | 74.30 | 69.00 | 79.90 |
| M1183 (72 hr) | 91.75 | 87.70 | 98.60 | 50.80 | 93.50 | 59.40 |

The results show that % CD45+ and % CD3+ cell populations of the total population were consistent across 72 hours with IL-2 in all media. However, 00 CD45+ and CD3+ populations of the live population decreases by about 50% after 24 hours of resting for all conditions. Results are variable across media conditions (IL-2, serum) with greater than 24 hours of resting.

TABLE 57

Residual cells (B cells, NK cells and monocytes) changes across resting conditions (0 to 72 hours, IL-2, and serum).

| | % CD45+/CD3+ | | | % CD19+/CD20+ | | | % CD16+/CD56+ | | | % CD14+ | | |
|---|---|---|---|---|---|---|---|---|---|---|---|---|
| Cell Populations | AIM-V + IL2 | CM1 No IL2 | CM1 + IL2 | AIM-V + IL2 | CM1 No IL2 | CM1 + IL2 | AIM-V + IL2 | CM1 No IL2 | CM1 + IL2 | AIM-V + IL2 | CM1 No IL2 | CM1 + IL2 |
| M1179 (0 hr) | 98.10 | N/A | N/A | 0.76 | N/A | N/A | 0.37 | N/A | N/A | 0.01 | N/A | N/A |
| M1179 (24 hr) | 95.60 | 89.90 | 93.00 | 1.50 | 1.39 | 1.30 | 0.47 | 0.22 | 0.48 | 0.07 | 0.01 | 0.03 |
| M1179 (48 hr) | 97.40 | 96.10 | 92.90 | 0.40 | 0.47 | 0.02 | 4.87 | 0.15 | 5.91 | 0.03 | 0.03 | 0.00 |
| M1179 (72 hr) | 94.60 | 50.30 | 98.40 | 3.56 | 20.30 | 0.05 | 4.75 | 3.55 | 4.03 | 0.03 | 0.73 | 0.00 |
| M1183 (0 hr) | 98.00 | N/A | N/A | 0.59 | N/A | N/A | 0.24 | N/A | N/A | 0.01 | N/A | N/A |
| M1183 (24 hr) | 96.40 | 92.30 | 89.80 | 1.03 | 0.74 | 0.95 | 0.37 | 0.16 | 0.33 | 0.04 | 0.00 | 0.01 |
| M1183 (48 hr) | 98.70 | 96.40 | 97.40 | 0.18 | 0.20 | 0.10 | 3.47 | 0.12 | 3.52 | 0.01 | 0.02 | 0.01 |
| M1183 (72 hr) | 95.20 | 64.10 | 97.40 | 3.26 | 13.20 | 0.14 | 3.59 | 2.30 | 1.76 | 0.04 | 1.28 | 0.01 |

Residual cell populations are observed to increase with longer resting post-thaw. For example, B cell populations increase ~20% at 72 hours of resting with no IL-2, while NK cells increase 4-5% after 24 hours of resting. Average residual cell populations for drug product are typically <10%.

FIG. 120 shows the flow cytometry analysis of residual cell populations of parent live population for TIL line M1179. FIGS. 121 and 122 show proliferation profiles of Raji and K562 cell lines, respectively.

In conclusion, the addition of IL-2 at 300 IU/mL in co-culture increases the cytokine signal and fold change for IFN-γ over media without IL-2. The cell population in co-culture is observed to change in CM1 media after 24 hours of resting (including growth, differentiation, and heterogeneity), such that 72 hours of rest for TILs after thawing and before beginning the co-culture assay renders this version of the assay less sensitive to manufacturing process failures, as the product is given the availability to recover and expand during recovery period. AIM-V and IL-2 are more suitable for matrix suitability with Gen 2 and Gen 3 TIL products. Serum is not recommended in ligand binding assays due to interference.

Example 21: Alloreactivity Co-Culture Assays with Melanoma TIL Lines and Raji, Thp1, Ramos, and U937 Target Cells This example explores the use of multiple target cell lines, including Raji, Thp1, Ramos, and U937 target cell lines, in the potency assays of the present invention including with the K562 cell line negative control. The experimental protocol is summarized in FIG. 123.

The co-culture system was used to activate the TILs via allogeneic MHC-TCR engagement. Four research melanoma Gen 2 TIL products were assessed for IFN-γ and TNF-α upon co-culture with Raji, Ramos, Thp1, and U937 cells, and K562 cells, at a ratio of 3:1, 1:1 and 1:3 (TIL to tumor cells). Results are shown in FIG. 124 to FIG. 129. Cytokine secretion and fold inductions for both TNF-α and IFN-γ were variable across the assessed tumor cells. In general, the responsiveness to the tumor lines across the four TIL cell lines selected here, from greatest to least, was as follows: Thp1, U937, Raji, and Ramos. Two of the four assessed Gen 2 TIL lines which secreted similar levels of IFN-γ in response to Raji cells compared to TIL alone or K562 cells secreted greater cytokines when co-cultured in the presence of either U937 or Thp1. It was observed that TNF-α was secreted by Raji, Ramos, Thp1, and U937 cells, but not by K562 cells, when co-cultured without the TILs. The amount of TNF-α secreted by the tumor lines varied across the different lines and increased with increasing numbers of tumor cells, with the most significant effect observed at 1:3 in this example.

HLA properties of exemplary target cells lines for use with the potency assays of the present invention are provided in Table 58. Variable degrees of HLA diversity and/or immunogenicity are available from the use of these cell lines and other suitable target cell lines known in the art.

TABLE 58

HLA-A, -B and -C Properties of Exemplary Potency Assay Target Cell Lines.

| Tumor Line | HLA-A | HLA-B | HLA-C |
|---|---|---|---|
| Raji | 03:01, 03:01 | 15:10, 15:10 | 04:01, 03:04 |
| Ramos | 03:01, 03:01 | 44:03, 51:01 | 16:01, 16:01 |
| Daudi | 66:01, 01:02 | 58:01, 35:01 | 03:02, 06:02 |
| THP-1 | 02:01; 24:02 | 15:11, 35:01 | 03:03 |
| U937 | 03:01, 31:01 | 18:01, 51:01 | 01:02, 07:02 |

FIG. 134 summarizes the IFN-gamma performance of the different target cell lines and cell line combinations for the four tested melanoma TIL lines.

FIG. 135 shows TNF-α secretion (pg/mL) for tested target and negative control cell lines, including combination target cell lines, for melanoma TIL lines M1152, M1187, M1198, and M1200. FIG. 136 shows TNF-α secretion as fold change of (TIL+tumor cell line or combination)/TIL alone, while FIG. 137 shows TNF-α secretion as fold change of (TIL+tumor cell line or combination)/(TIL+K562), for the same four melanoma TIL lines.

FIG. 138 shows granzyme B secretion (pg/mL) for tested target and negative control cell lines, including combination target cell lines, for melanoma TIL lines M1152, M1187, M1198, and M1200. FIG. 139 shows granzyme B secretion as fold change of (TIL+tumor cell line or combination)/TIL alone, while FIG. 140 shows granzyme B secretion as fold change of (TIL+tumor cell line or combination)/(TIL+K562), for the same four melanoma TIL lines.

The results demonstrate the effectiveness of different target cell lines and combinations thereof in the assessment of TIL potency.

Example 22: Alloreactivity Co-Culture Assays with Non-Small Cell Lung Cancer TIL Lines and Raji, Thp1, Ramos, and U937 Target Cells Ten non-small cell lung cancer (NSCLC) TIL lines were evaluated using different target cell lines and combinations of target cell lines using the experimental protocol of FIG. 141.

Four of the ten NSCLC TIL lines were research cell lines grown from commercially sourced donor tumors. The results from these four TIL lines are shown in FIG. 142 to 144.

The other six of the ten NSCLC TIL lines were clinical cell lines obtained from clinical trial participants in non-registrational studies of TIL therapy in NSCLC patients after treatment with anti-PD-1 antibodies sponsored by Iovance Biotherapeutics, Inc. The results from these six TIL lines shown in FIG. 145 to 147.

A summary of clinical NSCLC results for IFN-γ secretion as fold over TIL alone is shown in FIG. 148, and for IFN-γ secretion as fold over TILs cocultured with K562 negative control cells as FIG. 149.

A summary of 19 lots, including the ten NSCLC lots of this example and nine melanoma lots, as fold over TIL alone, is shown in FIG. 150, and for IFN-γ secretion as fold over TILs co-cultured with K562 negative control cells in FIG. 151.

Example 23: Comparison of Irradiated and Non-Irradiated Target Cells

The use of irradiated Raji and K562 cells were compared with non-irradiated Raji and K562 cells by observing proliferation (total viable cells), IFN-γ secretion using the co-culture method described in Example 20 with 300 IU/mL IL-2 and AIM-V media, and flow cytometry properties including morphology by scattering and cell surface markers and annexin V staining for apoptosis. Irradiation was performed using an X-Rad 160 irradiator (Precision X-ray, North Branford, CT, USA) at conditions of 5000 rads at 30 cm and at 420 rads/min.

FIG. 152 shows that irradiation of Raji and K562 cells generally had a minimal impact on proliferation during 24 hours of co-culture time. Irradiated Raji cells increased proliferation by 18 to 27% across concentrations in a 24-hour culture. Non-irradiated Raji cells increased proliferation by 2 to 14% across concentrations in a 24-hour culture. Irradiated K562 cells varied with a 15% decrease to 8% increase across concentrations in a 24-hour culture. Non-irradiated K562 cells increased proliferation by 14 to 34% across concentrations in a 24-hour culture.

FIG. 153 shows that TIL lines were found to secrete greater concentrations of IFN-γ when stimulated with non-irradiated versus irradiated Raji cells using the two cervical cancer TIL lots tested.

The flow cytometry results in Table 59 and FIG. 154 demonstrate that irradiation was observed to decrease the two monitored cell surface markers as well as HLA class I expression.

TABLE 59

Effects of Irradiation on Cell Surface Markers and HLA Class I Expression.

| Condition | Live | CD33+ (live) | CD33+ (MFI) | CD19+ (live) | CD19+ (MFI) | HLA-ABC+ (live) | HLA-ABC+ (MFI) |
|---|---|---|---|---|---|---|---|
| K562 | 83.4% | 82.4% | 1191.0 | 0.54% | 71.7 | 0.90% | 560 |
| Irr. K562 | 97.3% | 59.4% | 541.0 | 0.51% | 68.7 | 0.048% | 485 |
| Raji | 74.9% | 0.51% | 48.2 | 97.0% | 6267.0 | 96.0% | 12943 |
| Irr. Raji | 97.4% | 0.17% | 61.2 | 99.8% | 4727.0 | 98.4% | 9499 |

The results showed that proliferation of non-irradiated Raji and K562 cells are negligible during 24 hours, a period of co-culture suitable for performance of a potency assay. Proliferation of non-irradiated Raji cells over 24 hours (<14%) was less than proliferation of irradiated Raji cells (<27%) and therefore, irradiation had little impact on increased proliferation during the 24-hour culture period for Raji cells with the TIL lines used here. IFN-γ secretion was decreased in the irradiation condition versus non-irradiation, which was generally correlated to the down-regulation of HLA-ABC on irradiated Raji cells ($-^{26}$% by MFI). Irradiation was also observed to induce morphological changes in both K562 and Raji using forward versus side scatter observation by flow cytometry. Finally, late-stage apoptosis was increased using the irradiation condition for Raji cells and increased across all stages of apoptosis for K562 compared to non-irradiated condition as observed by annexin V staining.

In summary, the results demonstrated that non-irradiated Raji and K562 cells may be used with the potency assays of the present invention, or alternatively, only Raji (or other target cells) may be irradiated, or only K562 cells may be irradiated.

Example 24: Evaluation of Co-Culture Conditions

Using the co-culture method described in Example 20 with 300 IU/mL IL-2 and AIM-V media, with non-irradiated Raji target cells, TILs seeded at a density within the range of MX $10^6$ to $2\times10^6$ TILs per well, and Raji cells at a concentration range specific to a mid-point of 1:1 and 3:1 ratios (500,000 cells). IFN-γ release was assessed in triplicate for three co-culture periods of 18, 24, and 30 hours. Results are given in Table 60 and FIG. 155.

TABLE 60

Effects of Irradiation on Cell Surface Markers and HLA Class I Expression. TIL lots that begin with an "M", "L", and "C" represent melanoma, NSCLC, and cervical TIL lines, respectively.

| TIL Lot | Co-culture Period | Average | St. Dev. | % CV | Fold Change TIL | (pg/mL)/h | Rate increase (pg/mL)/6 hr |
|---|---|---|---|---|---|---|---|
| M40231 | 18 h | 199.7 | 6.5 | 3.3 | 5.1 | 11.1 | — |
| M40231 | 24 h | 252.0 | 4.4 | 1.7 | 6.0 | 10.5 | 8.7 |
| M40231 | 30 h | 309.3 | 7.1 | 2.3 | 7.0 | 10.3 | 9.6 |
| M1802 | 18 h | 298.0 | 32.4 | 10.9 | 2.7 | 16.6 | — |
| M1802 | 24 h | 368.3 | 4.5 | 1.2 | 3.4 | 15.3 | 11.7 |
| M1802 | 30 h | 454.0 | 45.7 | 10.1 | 3.8 | 15.1 | 14.3 |
| M1172a | 18 h | 508.7 | 15.5 | 3.1 | 4.0 | 28.3 | — |
| M1172a | 24 h | 820.0 | 44.6 | 5.4 | 3.4 | 34.2 | 51.9 |
| M1172a | 30 h | 1128.3 | 58.5 | 5.2 | 2.4 | 37.6 | 51.4 |
| L4262 | 18 h | 1347.0 | 67.0 | 5.0 | 2.4 | 74.8 | — |
| L4262 | 24 h | 1581.3 | 49.5 | 3.1 | 2.4 | 65.9 | 39.1 |
| L4262 | 30 h | 1875.3 | 61.6 | 3.3 | 2.4 | 62.5 | 49.0 |
| C172071358-H | 18 h | 506.7 | 67.2 | 13.3 | 6.4 | 28.2 | — |
| C172071358-H | 24 h | 518.0 | 42.9 | 8.3 | 4.7 | 21.6 | 1.9 |
| C172071358-H | 30 h | 650.0 | 34.4 | 5.3 | 4.4 | 21.7 | 22.0 |
| C170971358-J | 18 h | 173.3 | 3.8 | 2.2 | 3.6 | 9.6 | — |
| C170971358-J | 24 h | 248.3 | 5.9 | 2.4 | 4.9 | 10.3 | 12.5 |
| C170971358-J | 30 h | 307.0 | 14.7 | 4.8 | 4.8 | 10.2 | 9.8 |

The results showed no evidence of signal saturation at 30 hours, and that fold change over TIL values were relatively insensitive to timepoint. The IFN-γ signal from TIL alone showed minimal increase at 30 hours.

Example 25: Comparison of Tumor Target Cell Lines

Using the co-culture method generally described in Example 20 with 300 IU/mL IL-2 and AIM-V media, additional comparisons of tumor target cell lines were performed in this example. Non-irradiated Thp1, U937, and Raji cell lines were used. Similar comparisons can be performed using other methods, tumor target cell lines, and negative controls based on the teachings provided herein. FIG. 156 shows the experimental design for a study of twelve melanoma TIL lines. Table 61 summarizes the number of TIL and target cells for each experiment.

TABLE 61

Number of TIL and target cells per well, and total viable cells (TVC) per well, for the experimental design.

| | 3:1 Ratio | | 1:1 Ratio | | 1:3 Ratio | |
|---|---|---|---|---|---|---|
| TVC/well | TIL | Target | TIL | Target | TIL | Target |
| $5 \times 10^5$ | $3.75 \times 10^5$ | $1.25 \times 10^5$ | $2.5 \times 10^5$ | $2.5 \times 10^5$ | $1.25 \times 10^5$ | $3.75 \times 10^5$ |
| $1.0 \times 10^6$ | $7.50 \times 10^5$ | $2.50 \times 10^5$ | $5.0 \times 10^5$ | $5.0 \times 10^5$ | $2.50 \times 10^5$ | $7.50 \times 10^5$ |
| $2.0 \times 10^6$ | $1.5 \times 10^6$ | $5.0 \times 10^5$ | $1.0 \times 10^6$ | $1.0 \times 10^6$ | $5.0 \times 10^5$ | $1.5 \times 10^6$ |
| $3.0 \times 10^6$ | $2.25 \times 10^6$ | $7.50 \times 10^5$ | $1.50 \times 10^6$ | $1.50 \times 10^6$ | $7.50 \times 10^5$ | $2.25 \times 10^6$ |

Results are summarized in FIG. 157 for 1. Ox 10 TVC/well (over TIL alone as a control), in FIG. 158 for $2.0\times10^6$ TVC/well (over TIL alone as a control), in FIG. 159 for $1.0\times10^6$ TVC/well (over K562 cells as a control), and in FIG. 160 for $2.0\times10^6$ TVC/well (over K562 cells as a control). In general, increasing the total TIL per well enhanced the IFN-γ signal. For the majority of TIL lots tested, the 3:1 ratio demonstrated the greatest signal for IFN-γ for all three tumor cell lines tested. The optimal seeding density in this study was found to be approximately $2\times10^6$ (TVC/well or total cells per well). In general, Thp1 surprisingly requires less TIL cells and lower TVC to induce a robust IFN-γ signal.

A comparison of wildtype and genetically modified Thp1 (also referred to as THP-1) cells was also performed. Genetically modified Thp1 cells may be used for killing assays, as described in Example 19. The experimental procedure shown in FIG. 161 was performed. Results are shown for seven TIL lines in FIG. 162 for absolute values of IFN-γ in pg/mL, and in FIG. 163 for fold change over TIL alone. The results indicate that wildtype and genetically modified Thp1 perform similarly using the co-culture method, and either may be used for analysis of TIL samples, depending on whether IFN-γ or other cytokines are to be measured or if cell killing by luminescence is to be measured (using a genetic modification as described elsewhere herein or known in the art).

Example 26: Negative Control Using HLA Blocking Antibodies

The co-culture assays of the present invention may also be supplemented or supported by a negative control using HLA blocking antibodies, in place or in addition to use of a K562 cell, genetic knockout of a target cell, or other cell-based negative controls. This example demonstrates the use of HLA blocking antibodies. Without being bound by theory, the proposed blockade of HLA in the assays of the present invention is depicted in FIG. 164.

The HLA-I blocking antibody used in this example was Clone W6/32 (anti-HLA-ABC), obtained from Biolegend, Inc. (San Diego, CA, USA), and is in ultra-leaf purified format. The HLA-II blocking antibody used in this example was Clone TU39 (HLA-DR, DP, DQ), obtained from BD Biosciences, Inc. (Franklin Lakes, NJ, USA), and is in functional grade format with no azide and low endotoxin (≤0.01 EU/μg (≤0.001 ng/μg)), supplied in aqueous buffered solution containing no preservative, and 0.2 μm sterile filtered.

The general experimental procedure was as follows. The target cells were plated plus HLA Class I and/or Class II antibodies, and incubate for at least 1-2 hours, prior to adding the TILs. The TIL:target ratio is 3:1 ($1.5\times10^6$ TILs to $5\times10^5$ target cells), however initial experiments were performed at a 1:1 TIL:target ratio. Each condition was generally performed in triplicate. Target cells were thawed and resuspended in AIM-V and counted with an NC200 or K2 cell counter. Cells were seeded into 48 well culture plates at $1\times10^6$ in 1 mL of AIM-V media with 300 IU/mL IL-2. HLA blocking antibodies were immediately added at the concentrations noted in the following paragraphs (in the range of 1-20 μg/mL; stock concentrations were 1 mg/mL). Cells were incubated at 37° C. for 24 hours. Cells were then collected and unbound antibody was washed away with phosphate-buffered saline. Cells were stained for HLA antibody binding or apoptosis, where indicated below, and analyzed on a BD FACSCanto II flow cytometer (BD Biosciences, Inc., Franklin Lakes, NJ, USA).

The effects of HLA-I and HLA-II blocking antibodies on the viability of assay target cells were assessed first. The results of HLA-I blocking antibody added to cultures of Thp1 and U937 cells as described above, with the additional step of staining cells with fixable live/dead viability dye, are shown in FIG. 165. The results indicate no loss of viability. Similarly, the results of HLA-II blocking antibody added to cultures of Thp1 and U937 cells as described above, again with the additional step of staining cells with fixable live/dead viability dye, are shown in FIG. 166, and also indicate no loss of viability. In FIG. 167, Raji wildtype cells were observed to show loss of viability upon addition of anti-HLA-II antibody and live/dead viability staining. However, the Raji B2M (beta-2 microglobulin) knockout cell line (Sigma-Aldrich, Inc., St. Louis, MO, USA), which does not express HLA-I, did not show the same effect upon addition of anti-HLA-II antibody and staining with live/dead viability dye.

Using the foregoing general procedure, the effects of HLA-I and HLA-II blocking antibodies on the viability of TILs were then assessed. Cell apoptosis was detected by flow cytometry after staining for 7AAD and Annexin V: necrotic cells were detected via 7AAD+ Annexin V−; late apoptotic cells were detected via 7AAD+ Annexin V+; early apoptotic cells were detected via 7AAD− Annexin V+; and live cells were detected by 7AAD− Annexin V−. Results are shown in FIGS. 168, 169, and 170. No toxicity was observed in TILs cocultured with HLA Class I and II blocking antibodies for three different TIL lines.

Titration experiments to assess the concentrations of HLA-I and HLA-II antibodies were performed for Thp1 and U937 cell lines at concentrations of 0 to 20 μg/mL against a target cell concentration of $1\times10^6$ TILs per 1 mL. The binding of the HLA antibodies was analyzed by staining the cells with fluorophore conjugated antibodies of the same clone as the blocking antibody using the agents in Table 62.

TABLE 62

| Panel used for HLA binding studies. | |
|---|---|
| Stain | Fluor |
| CD45 | PerCP-Cy5.5 |
| CD19 | APC-H7 |
| CD33 | APC |
| HLA-I (W6/32) | BB515 |
| HLA-II (TU39) | PE |

The results are shown in FIG. 171. Loss of binding of flow antibody (as reported by mean fluorescence intensity or MFI) indicates the amount of binding sites occupied by the blocking antibody. The red dashed lines in FIG. 171 indicate the fluorescence minus one level.

The IFN-γ ELLA results of TIL cultures with HLA-I and HLA-II blocking antibodies are shown in FIG. 172. The top plots in FIG. 172 depict results from cultures with $1\times10^{6}$ TILs after 18 hours of incubation, while the bottom plots depict results from $1.5\times10^{6}$ TILs after 24 hours of incubation. The results also showed that HLA-II blocking antibody effects on TIL lines were less pronounced at 5 μg/mL.

Certain embodiments of the potency assays of the present invention using HLA-I, HLA-II, or both blocking antibodies as negative controls is illustrated in FIG. 173, and the results of this approach are shown in FIG. 174 to FIG. 178 for absolute values of IFN-γ and in FIG. 179 to FIG. 183 for fold enhancement over TIL alone. Further embodiments of the potency assays of the present invention using HLA-I, HLA-II, or both blocking antibodies as negative controls is provided in FIG. 184, and the results of this approach are shown in FIG. 185 to FIG. 189 for absolute values of IFN-γ and in FIG. 190 to FIG. 194 for fold enhancement over TIL alone. The results illustrate the effectiveness of the HLA-I and HLA-II blocking antibodies as negative controls. Blockade with anti-HLA-I (A, B, C) resulted in abrogated IFN-γ secretion upon coculture of TIL with THP-1 or U937 target cells, similar to TIL alone plus anti-HLA A, B, C antibody controls, and demonstrating a viable negative control for the potency assays. Treatment with anti-HLA-II (DP, DQ, DR) also resulted in reduced IFN-γ secretion from U937 and THP-1 target cells. Anti-HLA-I treatment alone (at 10 μg/mL) is sufficient to downregulate the induced activation of TILs by U937 and THP-1 target cells; however, addition of anti-HLA-II also performs well as a negative control. The $CD4^{+}/CD8^{+}$ ratio was variable in the assessed TIL lines (see the figure descriptions for FIG. 185 to FIG. 194). The effects of HLA-I and HLA-II blockade on TIL was independent of the ratio of $CD4^{+}$ and $CD8^{+}$ TILs. Addition of HLA blocking antibodies had negligible toxicity on TIL samples, nor did it cause deleterious activation of TIL alone in cultures. The Raji B2M cells alone or in combination with HLA-II antibody blockade also serves as a useful negative control.

The effectiveness of HLA blockade (Class I and II) as a negative control and the surprising specificity of the potency assays described herein towards MHC-peptide activation of the TIL through the TCR complex was further assessed in 15 melanoma TIL cell lines. FIG. 195 shows further embodiments of the potency assays of the present invention using anti-HLA-I, anti-HLA-II, or both blocking antibodies as negative controls. Tumor cell lines were pretreated for 1-2 hours with +/−10 μg/mL HLA Class I (anti-HLA A, B, C) and/or +/−5 μg/mL HLA Class II (anti-HLA DP, DQ, DR) blocking antibodies. The 15 melanoma TIL lines, all produced using the Gen 2 process, were cocultured with non-irradiated Raji, Raji β2M KO, THP-1 and U937 tumor cells at a 3:1 TIL:target ratio at $2\times10^{6}$ TVC for 24 hours.

Results are summarized in FIG. 196 for U937 and in FIG. 197 for Thp1. Blockade with anti-HLA A, B, C antibody resulted in abrogated IFN-γ secretion upon coculture of TILs with THP-1 or U937 (similar to TIL alone plus anti-HLA A, B, C controls). Anti-HLA A, B, C treatment alone (at 10 μg/mL) was found to be sufficient to abrogate U937 and THP-1 induced activation of TILs. Treatment with anti-HLA DP, DQ, DR antibody (5 μg/mL) resulted in: reduced IFN-γ secretion in THP-1 cells, but not to the extent of blockade with anti-HLA A, B, C; and complete blockade of IFN-γ secretion in U937 cells, similar to blockade with anti-HLA A, B, C. The $CD4^{+}/CD8^{+}$ ratio was variable in the assessed TIL lines. The effects of HLA Class I and II blockade is independent of the ratio of $CD4^{+}/CD8^{+}$ cells, indicating that activation of TILs upon coculture with allogeneic tumor cell lines is not HLA restricted. Abrogation of IFNγ secretion with HLA blockade demonstrated that non-autologous tumor cell line induced activation of TILs is mediated directly through TCR-HLA engagement.

Example 27: Parallel Line Analysis of Monocyte Cell Line Assay Data

In this example, the use of parallel line analysis is demonstrated for several assays and assay conditions that are embodiments of the present invention. Six melanoma TIL lots were used in this study: M1150A, M1164, M1174, M1163, M1169, and M1218. Seven concentrations of each TIL lot ($2\times10^{6}$ or 2e6, $1.5\times10^{6}$ or 1.5e6, $1\times10^{6}$ or 1e6, $5\times10^{5}$ or 5e5, $2.5\times10^{5}$ or 2.5e5, $1.25\times10^{5}$ or 1.25e5, and $6.25\times10^{4}$ or 6.25e4) were tested across seven target concentrations (1e6, 5e5, 2.5e5, 1.25e5, 6.25e4, $3.13\times10^{4}$ or 3.13e4, $1.56\times10^{4}$ or 1.56e4) for each of two targets (U937 and Thp1 cells). Statistical analysis was performed to determine the best TIL concentration for an assay method. Four parameter logistic (4PL) analysis was used to determine Hills slope, range, and EC50. Parallel line analysis (PLA) was used for regression (linearity).

Details of the PLA method can be found in the literature, including in USP Chapter <1032> Design and Development of Biological Assays. USP Pharmacopeial Convention: Rockville, MD, 2013; USP Chapter <111> Design and Analysis of Biological Assays. US Pharmacopeial Convention: Rockville, MD, 2014; USP Chapter <1033> Biological Assay Validation. USP Pharmacopeial Convention: Rockville, MD, 2013; USP Chapter <1034> Analysis of Biological Assays. US Pharmacopeial Convention: Rockville, MD, 2013; Hauck, et al., *PDA J. Pharma. Sci. Technol.* 2005, 59(2), 127-137; Callahan and Sajjadi, *BioProcessing J.* 2003, 2(2), 71-77; Findlay, et al., *J. Pharm. Biomed. Anal.* 2000, 21, 1249-1273; and Gottschalk and Dunn, *J. Biopharm. Stat.* 2005, 15(3), 437-463; the disclosures of each of which are incorporated by reference herein.

To determine conditions for stimulation of TIL product for two target cell lines (U937 and Thp1), two non-limiting factors were considered: (i) repeatability and linearity with the greatest number of concentrations on the linear portion of the dose curve and (ii) the greatest signal of IFN-γ, which potentially may also result in the best signal to noise. IFN-γ was measured as a function of effective TIL concentration for Thp1 (FIG. 198) and U937 (FIG. 199). A noticeable decrease in signal correlating to target concentration was seen for all 6 TIL lots. Only the $1.5\times10^{6}$ and $2.0\times10^{6}$ TIL concentrations demonstrated a dose response with greater than four (4) concentrations of target cell concentration in linear range. U937 showed a higher IFN-γ signal and greater signal to noise than Thp1.

FIG. 200 and FIG. 201 show dose response curves for six melanoma TIL lines using the assay. A TIL concentration of $1.5\times10^{6}$ or $2.0\times10^{6}$ provides acceptable results for use in assay methods. This offers increased signal, better signal to noise, and a greater number of target concentrations on the linear dose curve. FIG. 202 shows parallel line analysis for six TIL lots using U937 target cells at a TIL concentration of $1.5\times10^{6}$ cells All six TILs are seen to show a clear dose response with this target cell line. In FIG. 203, the parallel line analysis for the same six TIL lots under the same conditions is shown using Thp1 target cells, wherein only TIL M1173 and TIL M1213 demonstrate a clear dose response. FIGS. 204 and 205 illustrate that blocking antibodies demonstrate assay specificity with U937 cells across six TIL lots with anti-HLA-I (10 μg/mL) and anti-HLA-II (5 μg/mL). Surprisingly, the U937 cell line performed better than the Thp1 cell line. For given target concentration, U937 cells offer greater IFN-γ signal than Thp1 cells in this embodiment of an assay method. U937 cells also offered more concentrations on the linear portion of the dose-response curve. A 4-point dose curve may be used with a linear fit with the option to remove one outlier per curve and mask for curve saturation (which will provide at least three points on curve that is needed for final analysis). Screening for and removing outliers and masking for curve saturation may be performed as performed as described in USP Chapter <1032> Design and Development of Biological Assays, US Pharmacopeial Convention: Rockville, MD, 2013, the disclosure of which is incorporated by reference herein. In addition, TIL lots tested with Thp1 cells required masking at lower concentrations to be linear on most TIL lots, while U937 cells did not have this requirement. The upper asymptote was not always resolved with Thp1 cells; therefore, the upper range may not be defined across TIL lots tested with Thp1 cells.

Example 28: Potency and Identity Assay Matrix

In this example, the use of a potency and identity assay matrix is demonstrated. A potency and identity assay matrix can be used for release and stability testing of TIL, MIL, and PBL products, and can include the potency assays described herein as a component of the matrix. An exemplary and non-limiting assay matrix is given in Table 63, which is also an embodiment of the present invention and may be modified to remove or add members of the matrix. Assays are qualified for precision, accuracy, specificity and linearity where appropriate and/or required.

TABLE 63

An exemplary, non-limiting potency and identity assay matrix.

| | Attribute Measured | Assay | Purpose |
|---|---|---|---|
| Potency | TCR-HLA engagement and function; U937 or Thp1 cell target | Cell coculture assay with IFN-γ detection for relative potency | TIL activation and functionality by a highly specific mechanism relevant to lifileucel's MoA |
| | CD3, CD28, and CD137 costimulation and TIL activation | Bead-based assay with detection of IFN-γ secretion level | TIL activation and functionality by an orthogonal T cell activation mechanism |
| | Percentage of viable cells | Cell counter | Reports percentage of functional TIL in dose |
| | Total viable cells | Cell counter | Reports total viable cells and thus functional TIL dose |
| Potency and Identity | Percentage of cells with LAG3 expression | Flow cytometry | Exhaustion marker that is highly relevant to lifileucel's potency and identity |
| | Percentage of cells with KLRG1 expression | Flow cytometry | Differentiation marker that is highly relevant to lifileucel's potency and identity |
| | Total viable $CD4^{+}$ and $CD8^{+}$ cell population | Flow cytometry and cell counter | Both $CD4^{+}$ and $CD8^{+}$ cell populations are involved in TIL responses and are relevant to lifileucel's potency and identity |
| | Percentage of $CD4^{+}$ cells | Flow cytometry | Reflects the key role of $CD4^{+}$ lineage cells in lifileucel's potency and identity |
| | Percentage of $CD8^{+}$ cells | Flow cytometry | Reflects the key role of $CD8^{+}$ lineage cells in lifileucel's potency and identity |
| | Total viable $T_{CM}$ and $T_{EM}$ cell population | Flow cytometry and cell counter | Both $T_{CM}$ and $T_{EM}$ cell populations contribute to TIL effector function and are relevant to lifileucel's potency and identity |
| | Percentage of $T_{CM}$ cells | Flow cytometry | Reflects the key role of $T_{CM}$ cells, which differentiate into $T_{EM}$ cells, in lifileucel's potency and identity |
| | Percentage of $T_{EM}$ cells | Flow cytometry | Reflects the key role of $T_{EM}$ cells and their effector function in lifileucel's potency and identity |
| Identity | Percentage of $CD45^{+}/CD3^{+}$ cells | Flow cytometry | Identity test for lifileucel product |
| | Percentage of $CD16^{+}/CD56^{+}$ cells | Flow cytometry | Detects the presence of NK and NKT cells in lifileucel product |

The allogeneic co-culture assays described herein, for example in Examples 14 to 27, are used to assess TCR-HLA interactions. The matrix shown in Table 63 presents one example, using U937 or Thp1 cells in conjunction with relative potency against a positive control and a parallel line analysis method as described in Example 27 and elsewhere herein. A negative control using HLA blocking antibodies was used to demonstrate specificity for TCR-HLA interactions during qualification and may also be used during routine testing as an alternative to the relative potency measure versus a positive control reference standard as described herein. Positive controls are prepared using known TIL, MIL, or PBL cell line(s) that have been banked and characterized for this purpose.

For example, using the U937 co-culture assay, the following procedure was used. U937 cells were sourced from ATCC and used to create two-tier GMP cell banks (MCB, 250 vials, and WCB, 500 vials). The WCB was manufactured as a ready-to-use (RTU) GMP non-production bank for bioassay, where thawed cells straight from vial are used in the assay, thereby eliminating the need for cell expansion and associated risks for contamination or variability. The MCB was tested for viable cell count, % viability, identity, sterility, mycoplasma, and in vitro adventitious agents. The WCB was tested for viable cell count, % viability, sterility, mycoplasma, and in vitro adventitious agents. The MCB and WCB were assessed for passage dependent impact on the co-culture potency assay within the qualification parameter for robustness and were found to have no significant difference. A positive control TIL lot is manufactured under GMP using the same Gen 2 manufacturing process that is used for clinical TIL product and will also be used as the reference standard. After formulation, the entirety of the drug product for the reference standard is filled into vials, which are then frozen at a controlled rate using the same equipment and program used for clinical TIL drug product manufacturing. The vials are stored cryopreserved in vapor phase liquid nitrogen. Representative vials are tested for several attributes including sterility, mycoplasma, cell count, viability, identity, and potency, and to qualify the TIL lot for use as a reference standard. Once qualified, single-use vial(s) of the reference standard are thawed and tested alongside the test articles on each assay. The assay assesses TIL product lots for relative potency to a reference standard TIL lot at a defined set-point of $1.5\times10^6$ TIL per well to respond reliably and in a dose-dependent manner to co-culture with four dose-concentrations ($4\times10^5$, $2\times10^5$, $1\times10^5$, and $0.5\times10^5$ cells per well; performed in triplicate at each dose-concentration) of U937 cells for a period of 24 hours. The concentration of IFN-γ released into the supernatant from each replicate at each U937 dose-concentration is measured. An ELLA system (as described elsewhere herein) was used to measure IFN-γ concentration post activation of the co-culture assay of TIL product and U937. A Simple Plex 72-well IFN-γ 3rd Gen Version 5 cartridge (available from the ProteinSimple division of BioTechne, Inc., San Jose, CA, USA, catalog number #SPCKB-CS-002697) is used. Cultivation and storage of media for the subsequent measurement of secreted IFN-γ is performed immediately preceding the co-culture. Supernatants are transferred to three replicate 96-well plates and stored <60° C. The plate is then thawed and measured for IFN-γ. Supernatants collected from the co-culture are screened for IFN-γ production on each 72-well commercially validated cartridge. Data analysis is performed per USP <1032>, USP Pharmacopeial Convention: Rockville, MD, 2013. Data are log transformed according to USP <1032> and USP <1033> Biological Assay Validation, USP Pharmacopeial Convention: Rockville, MD, 2013, to meet requirements for symmetry, normal distribution, and homogeneity of variability in measurements across the potency range. Outliers are assessed and omitted from analysis as described in USP <1034> Analysis of Biological Assays, USP Pharmacopeial Convention: Rockville, MD, 2013. Linear regression is performed across the four-point dose curve with masking (if needed) of either the highest or lowest concentration due to saturation of the curve. Per USP<1032>, it is advised to "use at least three and preferably four adjacent [dose-]concentrations; require that the slope of the linear segment is sufficiently steep; and require that the lines fit to Standard and Test samples are straight and that the lines are parallel." Parallel line analysis is performed between the TIL test article and the RS, per USP<1032>. Statistical similarity between the reference standard and the TIL test article measured by parallelism demonstrates the biological similarity of the TIL test article to the reference standard. The parallelism slope ratio, linearity ratio, regression ($R^2$) and root mean square error (RMSE) are calculated and reported. Assay suitability and validity of parallelism and linearity is ranked and determined to either "pass" or "fail" the validity criterion within limits per USP<1033>. The relative potency within the 95% confidence interval as a range of percent of tolerance is determined as "reportable" or "inconclusive". Per USP<1032>, relative potency may be preferred over potency, which is derived from an absolute value, because it is a calibrator that nulls out the effect of variability inherent of biological samples and cellular behavior over time. Finally, the predicted IFN-γ concentration is reported at each U937 cell density. The fold-increase in absolute IFN-γ concentration produced by TIL in co-culture with U937 cells versus TIL alone (unstimulated) is evaluated for use as an alternative or additional reportable value for each TIL lot. Analysis is performed using JMP software from JMP Statistical Discovery LLC (Cary, NC, USA) with suitable validation. Additional assay details and embodiments of the present invention are also provided in Table 64.

TABLE 64

An exemplary, non-limiting summary of co-culture method conditions and an embodiment of the present invention.

| Step | Parameter | Description |
|---|---|---|
| Stimulation | Assay format | 4-point dose U937 vs. IFN-γ concentration curve |
| | Assay throughput | 48-well plate |
| | Activation cell line | U937, ATCC CRL-1593.2 (lot no. 70036658) |
| | Number of TILs per well | $1.5\times10^6$ |
| | Number of U937 cells per well | $4.0\times10^5$, $2.0\times10^5$, $1.0\times10^5$, $0.5\times10^5$ |
| | Co-culture media | AIM-V (serum-free medium) containing IL-2 (300 IU/mL) |
| | Volume of media | 1000 μL |
| | Number of replicate wells per sample/per plate/per run | 3 (all three wells are sourced from the same thawed vial of test article; an average of 3 wells is used to determine IFNγ concentration). |
| | Period of stimulation | 24 ± 0.5 hours at 37° C. in an incubator with 5% $CO_2$ |
| | Positive control | Qualified TIL line |
| | Negative control | Anti-HLA I&II antibodies |
| Analysis | Assay throughput | 72-well plate |
| | Instrument | ELLA automated ELISA |
| | System Software | Simple Plex Runner and Simple Plex Explorer |
| | ELLA parameters | Simple Plex 72-well IFN-γ 3rd generation Version 5 cartridge (cat. no. SPCKB-CS-002697), ProteinSimple, paired capture and detection antibodies conjugated to three (3) glass microtubes in series for triplicate repeated readout within each well. |

TABLE 64-continued

An exemplary, non-limiting summary of co-culture method conditions and an embodiment of the present invention.

| Step | Parameter | Description |
|---|---|---|
| | System suitability control, IFN-γ immune control standard | Protein Simple Human IFN-γ 3rd Gen Lyophilized Control (Protein Simple cat. no. 899077) |
| | Replicates per sample, per plate, per run | 3 |

The matrix shown in Table 63 also includes an orthogonal activation assay using the measurement of IFN-γ secreted by TIL in response to activation by beads coated with anti-CD3/CD28/CD137 antibodies. When TIL product is exposed to these beads, the antibodies will bind the CD3ε contained within the CD3 signaling complex and the T cell co-stimulatory receptors, CD28 and CD137. The stimulation of TIL with the anti-CD3 mitogen antibody OKIT3 is used to assess the functionality of TIL products, as described in Borovsky, et al. *J. Biol. Chem.* 2002, 277, 21529-36, the disclosure of which is incorporated by reference herein. Anti-CD28 activity is known to augment in vitro T cell proliferation and cytokine production. CD137 (4-1BB) is a member of the tumor necrosis factor family. An agonistic anti-CD137 antibody acts as an activating costimulatory molecule especially important for effector and memory T cells and promotes the survival and proliferation of T lymphocytes. The design of the bead-based IFN-γ assay is thus intended to mimic the biological activity of the TIL cells in response to in vivo T cell activation by professional antigen-presenting cells by utilizing the three activation signals involved in physiological re-stimulation and expansion of antigen-specific T cells.

Total viable cells and percentage viable cells are also included in Table 63. Total viable cell count is a parameter that is correlated with objective tumor responses to TIL product infusion in the literature. Seitter, et al. *Clin. Cancer Res.* 2021, 27, 5289-98. Cell viability is a parameter that is intrinsic to total viable cell count. The ability of cells to maintain or recover viability is a necessary pre-requisite for TIL functionality, and demonstration of cell viability thus serves as an additional measure of activity. The importance of these parameters to the performance of TIL products is supported by preclinical studies as well as the substantial clinical experience with TIL therapy in studies that have to date enrolled several hundred patients with metastatic melanoma. Although investigators have reported statistically significant positive correlations between the objective tumor response rate and total viable cells administered, there remained substantial overlap in the total cell number distributions between responders and non-responders in these studies Seitter, et al., *Clin. Cancer Res.* 2021, 27, 5289-98; Goff, et al., *J. Clin. Oncol.* 2016, 34, 2389-97. Exemplary results for total viable cell count and percentage viability are given in Table 65.

TABLE 65

Summary statistics for total viable cells and percentage viability for clinical melanoma TIL lots.

| Attribute | N | Mean | Std Dev | Minimum | Median | Maximum |
|---|---|---|---|---|---|---|
| Total viable cells | 149 | 25.74 | 17.54 | 1.19 | 21.89 | 99.60 |
| Viability (%) | 149 | 89.55 | 4.20 | 74.70 | 87.50 | 90.50 |

The lineage markers in the matrix of Table 63 include total viable $CD4^+$ and $CD8^+$ cell population, percentage of $CD4^+$ cells, and percentage of $CD8^+$ cells, which are measured by flow cytometry and cell counter. TILs are composed of a mixture of lymphocytes, including $CD4^+$ and $CD8^+$ T cells. $CD8^+$ and $CD4^+$ T cells are present in variable proportions in TIL products, and both cell lineages appear to contribute to anti-tumor immune responses. Topalian, et al., *J. Immunological Methods* 1987, 102, 127-41; Andersen, et al. *Clin. Cancer Res.* 2016, 22, 3734-45; Goff, et al. *J. Clin. Oncol.* 2016, 34, 2389-97. $CD8^+$ T cells have been associated with tumor regression, while $CD4^+$ T cells are critical to the function of the immune system, and augment $CD8^+$ T cell function by enhancing $CD8^+$ T cell proliferation and IFN-γ secretion. Shedlock and Shen, *Science* 2003, 300, 337-9; Sun and Bevan, *Science* 2003, 300, 339-42. Seitter, et al., have analyzed the consolidated data from studies in TIL therapy that have to date enrolled several hundred patients with metastatic melanoma and have shown statistically significant positive correlations between the objective tumor response rate and total viable $CD8^+$ cells administered, as well as a substantial overlap in the total cell number distributions between responders and non-responders. Seitter, et al. *Clin. Cancer Res.* 2021, 27, 5289-98. Without being bound by theory, a TIL product with a population of $CD8^+$ and $CD4^+$ T cells may be the most favorable product for adoptive cell therapy, and one that is most likely to have clinical efficacy. Exemplary results for $CD4^+$ and $CD8^+$ expression for clinical melanoma TIL lots are given in Table 66.

TABLE 66

Summary statistics for $CD4^+$ and $CD8^+$ expression for clinical melanoma TIL lots.

| Attribute[1] | N | Mean | Std Dev | Minimum | Median | Maximum |
|---|---|---|---|---|---|---|
| % $CD8^+$ | 147 | 53.98 | 29.66 | 0.93 | 58.20 | 97.60 |
| % $CD4^+$ | 147 | 40.21 | 29.08 | 0.32 | 33.00 | 97.50 |

TABLE 66-continued

| Summary statistics for CD4+ and CD8+ expression for clinical melanoma TIL lots. | | | | | | |
|---|---|---|---|---|---|---|
| Attribute[1] | N | Mean | Std Dev | Minimum | Median | Maximum |
| Total viable $CD4^+$ and $CD8^+$ cells ($\times 10^6$) | 147 | 24520.35 | 17176.11 | 1057.61 | 11921.25 | 20342.07 |

[1]% $CD8^+$ and % $CD4^+$ cells are expressed as a percentage of $CD3^+$ cells

Table 63 also includes several memory markers, the total viable central memory ($T_{CM}$) and effector memory ($T_{EM}$) cell populations, percentage of $T_{CM}$ cells, and percentage of $T_{EM}$ cells, which are measured by flow cytometry and a cell counter. Memory T cells exist as multiple subsets, which differ by their trafficking patterns, functional capacity, and lineage relationship. Farber, et al. *Nature Rev. Immunol.* 2014, 14, 24-35; Sallusto, et al. *Ann. Rev. Immunol.* 2004, 22, 745-63. Main subsets include $T_{CM}$ cells, which retain the ability to traffic to lymphoid tissues; and $T_{EM}$ cells, which migrate to peripheral tissue sites. Both subsets have effector capacities. $T_{EM}$ cells are defined as $CD45RA^-CCR7^-$, and $T_{CM}$ cells are defined as $CD45RA^-CCR7^+$ by flow cytometry. The majority of cells in TIL products have an effector memory T cell phenotype consistent with a high level of functionality. Goff, et al. *J. Clin. Oncol.* 2016, 34, 2389-97. Similarly, $T_{EM}$ cells are often the predominant population in TIL samples produced by the Gen 2 process in day 22 samples, because of their efficient expansion during the 22-day process. Exemplary results for $T_{EM}$ and $T_{CM}$ content in clinical melanoma TIL lots are given in Table 67.

TABLE 67

| Summary statistics for $T_{EM}$ and $T_{CM}$ cells for clinical melanoma TIL lots. | | | | | | |
|---|---|---|---|---|---|---|
| Attribute[1] | N | Mean | Std Dev | Minimum | Median | Maximum |
| % $T_{EM}$ | 147 | 81.47 | 17.90 | 3.23 | 87.50 | 99.50 |
| % $T_{CM}$ | 147 | 15.45 | 15.09 | 0.36 | 10.00 | 73.40 |
| Total viable $T_{EM}$ and $T_{CM}$ cells ($\times 10^6$) | 147 | 24690.57 | 17571.59 | 1055.39 | 11800.69 | 20686.78 |

[1]% $T_{EM}$ and % $T_{CM}$ cells are expressed as a percentage of $CD3^+$ cells The percentage of cells with KLRG1 expression is also included in the matrix of Table 63 as a marker for differentiation, and thus potency, in the final lifileucel product. KLRG1 expression is measured by flow cytometry. KLRG1 is a marker of terminal differentiation and senescence of T cells, which was shown to be down-regulated upon the differentiation of memory T cells. Henson, et al., *Blood* 2009, 113, 6619-28; Herndler-Brandstetter, et al., *Immunity* 2018, 48, 716-729. Exemplary statistics for clinical melanoma TIL lots are given in Table 69.

TABLE 69

| Summary statistics for KLRG1 expression for clinical melanoma TIL lots. | | | | | | |
|---|---|---|---|---|---|---|
| Attribute | N | Mean | Std Dev | Minimum | Median | Maximum |
| % $KLRG1^+$ | 141 | 13.19 | 13.32 | 0.76 | 8.48 | 58.30 |

[1] % $KLRG1^+$ cells are expressed as a percentage of $CD3^+$ cells

The percentage of cells with LAG3 expression is also included in the matrix of Table 63 as a marker for exhaustion, and thus potency, in the final TIL product. LAG3 expression is measured by flow cytometry. LAG3 levels are generally upregulated by the Gen 2 process, for example. This upregulation has been associated with T cell activation and effector function and indicates that LAG3 is likely to be a sensitive and representative exhaustion marker for monitoring. Annunziato, et al., *FASEB J.* 1996, 10, 769-76. Exemplary statistics for clinical melanoma TIL lots are given in Table 68.

TABLE 68

| Summary statistics for LAG3 expression for clinical melanoma TIL lots. | | | | | | |
|---|---|---|---|---|---|---|
| Attribute | N | Mean | Std Dev | Minimum | Median | Maximum |
| % $LAG3^+$ | 147 | 15.15 | 8.63 | 1.31 | 13.00 | 45.20 |

[1] % $LAG3^+$ cells are expressed as a percentage of $CD3^+$ cells

A histogram of LAG3 expression across these clinical data sets is shown in FIG. 206.

A histogram of KLRG1 expression across the clinical data sets is shown in FIG. 207.

A $CD14^+/CD19^+/CD16^+/CD56^+$ flow cytometry assay may be substituted for the $CD16^+/CD56^+$ assay shown in Table 63 to detect NK, NKT, B cells, and monocytes.

The U937 co-culture described herein, and incorporated in the matrix of Table 63, may be used to assess the relative potency of clinical melanoma TIL lots as described above. Results are shown in Table 70, where several lots are observed to not exhibit a dose-dependent response, indicating a potential loss of potency.

TABLE 70

| Relative potency results for clinical melanoma TIL lots. | |
|---|---|
| Lot Number | Relative Potency (%) |
| 170171423 | 21.6[1] |
| 187371423 | 125.2 |
| 186871423 | 34.0[1] |
| 170271423 | 48.4 |
| 1810271423 | 33.3[1] |
| 187071423 | 435.8 |

TABLE 70-continued

Relative potency results for clinical melanoma TIL lots.

| Lot Number | Relative Potency (%) |
|---|---|
| 187471423 | 87.5 |
| 182671423 | 38.3[1] |
| 185571423 | 238.3 |
| 186371423 | 226.4 |
| 171171423 | 284.9 |
| 185671423 | 100.0 |
| 189171423 | 222.0 |
| 186471423 | 261.7 |
| 189571423 | 377.9 |
| 183271423 | 25.2 |
| 170871423 | 1393.8 |
| 180171423 | 42.5 |
| 187971423 | 165.4 |
| 183871423 | 68.8 |
| 185171423 | 515.5 |
| 181071423 | 180.7 |
| 186271423 | 1268.5 |
| 181171423 | 166.3 |
| 185071423 | 455.6 |
| 181271423 | 303.6 |
| 189071423 | 399.7 |
| ECT170087 | 115.3 |
| 171271423 | 2022.9 |
| 171071423 | 103.9 |
| 184271423 | 360.2 |
| 183171423 | 444.6 |

[1]Lots did not display a dose-dependent response

The results of Table 70 are plotted in FIG. 208 as a histogram, where a log-normal distribution is observed.

Additional markers and corresponding flow cytometry assays may be utilized, including an assay for $CD101^+$ cell content, an assay for $CD69^+$ cell content, an assay for $T_{SCM}$ cell content, an assay for $T_{EMRA}$ cell content, an assay for $T_{reg}$ cell content, an assay for PD-1 cell content, an assay for $TIM3^+$ cell content, an assay for $CD25^+$ cell content, an assay for $CD27^+$ cell content, an assay for $CD28^+$ cell content, an assay for $CD56^+$ cell content, an assay for CTLA-$4^+$ cell content, an assay for $TIGIT^+$ cell content, and/or an assay for $CD57^+$ cell content. The statistical significance of certain markers in the reinvigoration of TIL products during the Gen 2 manufacturing process is described in Simpson-Abelson, et al., *Ann. Oncol.,* 2020, 31, S720, and Simpson-Abelson, et al., Iovance Generation-2 Tumor-infiltrating Lymphocyte (TIL) Product Is Reinvigorated During the Manufacturing Process ESMO Congress, Sep. 19-21, 2020, poster 1053P, the disclosures of each of which are incorporated by reference herein.

Example 29: Expansion of TIL Products Using U937 Cells

Irradiated U937 cells may be used as artificial antigen processing cells (aAPCs) for the REP stage of a Gen 2 process or similar processes (or activation stage of Gen 3 or similar processes, or similar stages in genetically edited TIL processes and selected TIL processes). Three melanoma pre-REP TIL lots were thawed and incubated with irradiated U937 cells or allogenic PBMC feeder cells (three donors) with anti-CD3 (OKT-3) for 11 days using a procedure as described elsewhere herein (e.g., Example 6) and evaluated for expansion. Results are shown in FIG. 209. U937 cells are capable of inducting the expansion of the TIL cells. After stimulation beads to CD3 and CD28, the TILs secreted IFN-γ in response, as shown in FIG. 210, indicating that they were capable of activation. The use of U937 cells as aAPCs may support the growth or preservation of lower frequency TCR clones, as assessed by TCR repertoire analysis (e.g., for unique CDR3 domains). In some embodiments of the present invention, TILs, MILs, or PBLs expanded by use of U937 aAPCs (including genetically modified U937 aAPCs) using Gen 2, Gen 3, or other processes described herein may show increased growth or preservation of lower frequency TCR clones.

The examples set forth above are provided to give those of ordinary skill in the art a complete disclosure and description of how to make and use the embodiments of the compositions, processes, assays, systems, and methods of the invention, and are not intended to limit the scope of what the inventors regard as their invention. Modifications of the above-described modes for carrying out the invention that are obvious to persons of skill in the art are intended to be within the scope of the following claims. All patents, patent applications, and publications mentioned in the specification are indicative of the levels of skill of those skilled in the art to which the invention pertains.

All headings and section designations are used for clarity and reference purposes only and are not to be considered limiting in any way. For example, those of skill in the art will appreciate the usefulness of combining various aspects from different headings and sections as appropriate according to the spirit and scope of the invention described herein.

All references cited herein are hereby incorporated by reference herein in their entireties and for all purposes to the same extent as if each individual publication or patent or patent application was specifically and individually indicated to be incorporated by reference in its entirety for all purposes.

Many modifications and variations of this application can be made without departing from its spirit and scope, as will be apparent to those skilled in the art. The specific embodiments and examples described herein are offered by way of example only, and the application is to be limited only by the terms of the appended claims, along with the full scope of equivalents to which the claims are entitled.

SEQUENCE LISTING

```
Sequence total quantity: 237
SEQ ID NO: 1          moltype = AA  length = 450
FEATURE               Location/Qualifiers
REGION                1..450
                      note = Synthetic Muromonab heavy chain
source                1..450
                      mol_type = protein
                      organism = synthetic construct
SEQUENCE: 1
QVQLQQSGAE LARPGASVKM SCKASGYTFT RYTMHWVKQR PGQGLEWIGY INPSRGYTNY  60
NQKFKDKATL TTDKSSSTAY MQLSSLTSED SAVYYCARYY DDHYCLDYWG QGTTLTVSSA  120
```

```
KTTAPSVYPL APVCGGTTGS SVTLGCLVKG YFPEPVTLTW NSGSLSSGVH TFPAVLQSDL  180
YTLSSSVTVT SSTWPSQSIT CNVAHPASST KVDKKIEPRP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                   450

SEQ ID NO: 2            moltype = AA  length = 213
FEATURE                 Location/Qualifiers
REGION                  1..213
                        note = Synthetic Muromonab light chain
source                  1..213
                        mol_type = protein
                        organism = synthetic construct
SEQUENCE: 2
QIVLTQSPAI MSASPGEKVT MTCSASSSVS YMNWYQQKSG TSPKRWIYDT SKLASGVPAH  60
FRGSGSGTSY SLTISGMEAE DAATYYCQQW SSNPFTFGSG TKLEINRADT APTVSIFPPS  120
SEQLTSGGAS VVCFLNNFYP KDINVKWKID GSERQNGVLN SWTDQDSKDS TYSMSSTLTL  180
TKDEYERHNS YTCEATHKTS TSPIVKSFNR NEC                               213

SEQ ID NO: 3            moltype = AA  length = 134
FEATURE                 Location/Qualifiers
REGION                  1..134
                        note = Synthetic recombinant human IL-2 (rhIL-2)
source                  1..134
                        mol_type = protein
                        organism = synthetic construct
SEQUENCE: 3
MAPTSSSTKK TQLQLEHLLL DLQMILNGIN NYKNPKLTRM LTFKFYMPKK ATELKHLQCL  60
EEELKPLEEV LNLAQSKNFH LRPRDLISNI NVIVLELKGS ETTFMCEYAD ETATIVEFLN  120
RWITFCQSII STLT                                                    134

SEQ ID NO: 4            moltype = AA  length = 132
FEATURE                 Location/Qualifiers
REGION                  1..132
                        note = Synthetic Aldesleukin
source                  1..132
                        mol_type = protein
                        organism = synthetic construct
SEQUENCE: 4
PTSSSTKKTQ LQLEHLLLDL QMILNGINNY KNPKLTRMLT FKFYMPKKAT ELKHLQCLEE  60
ELKPLEEVLN LAQSKNFHLR PRDLISNINV IVLELKGSET TFMCEYADET ATIVEFLNRW  120
ITFSQSIIST LT                                                      132

SEQ ID NO: 5            moltype = AA  length = 133
FEATURE                 Location/Qualifiers
REGION                  1..133
                        note = Synthetic IL-2 form
source                  1..133
                        mol_type = protein
                        organism = synthetic construct
SEQUENCE: 5
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLT                                                     133

SEQ ID NO: 6            moltype = AA  length = 303
FEATURE                 Location/Qualifiers
REGION                  1..303
                        note = Synthetic IL-2 form
source                  1..303
                        mol_type = protein
                        organism = synthetic construct
SEQUENCE: 6
SKNFHLRPRD LISNINVIVL ELKGSETTFM CEYADETATI VEFLNRWITF SQSIISTLTG  60
GSSSTKKTQL QLEHLLLDLQ MILNGINNYK NPKLTRMLTF KFYMPKKATE LKHLQCLEEE  120
LKPLEEVLNL AQGSGGGSEL CDDDPPEIPH ATFKAMAYKE GTMLNCECKR GFRRIKSGSL  180
YMLCTGNSSH SSWDNQCQCT SSATRNTTKQ VTPQPEEQKE RKTTEMQSPM QPVDQASLPG  240
HCREPPPWEN EATERIYHFV VGQMVYYQCV QGYRALHRGP AESVCKMTHG KTRWTQPQLI  300
CTG                                                                303

SEQ ID NO: 7            moltype = AA  length = 452
FEATURE                 Location/Qualifiers
REGION                  1..452
                        note = Synthetic IL-2 form
source                  1..452
                        mol_type = protein
                        organism = synthetic construct
SEQUENCE: 7
```

```
MDAMKRGLCC VLLLCGAVFV SARRPSGRKS SKMQAFRIWD VNQKTFYLRN NQLVAGYLQG  60
PNVNLEEKID VVPIEPHALF LGIHGGKMCL SCVKSGDETR LQLEAVNITD LSENRKQDKR  120
FAFIRSDSGP TTSFESAACP GWFLCTAMEA DQPVSLTNMP DEGVMVTKFY FQEDESGSGG  180
ASSESSASSD GPHPVITESR ASSESSASSD GPHPVITESR EPKSSDKTHT CPPCPAPELL  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP GK                                452

SEQ ID NO: 8           moltype = AA  length = 16
FEATURE                Location/Qualifiers
REGION                 1..16
                       note = Synthetic mucin domain polypeptide
source                 1..16
                       mol_type = protein
                       organism = synthetic construct
SEQUENCE: 8
SESSASSDGP HPVITP                                                  16

SEQ ID NO: 9           moltype = AA  length = 130
FEATURE                Location/Qualifiers
REGION                 1..130
                       note = Synthetic recombinant human IL-4 (rhIL-4)
source                 1..130
                       mol_type = protein
                       organism = synthetic construct
SEQUENCE: 9
MHKCDITLQE IIKTLNSLTE QKTLCTELTV TDIFAASKNT TEKETFCRAA TVLRQFYSHH  60
EKDTRCLGAT AQQFHRHKQL IRFLKRLDRN LWGLAGLNSC PVKEANQSTL ENFLERLKTI  120
MREKYSKCSS                                                         130

SEQ ID NO: 10          moltype = AA  length = 153
FEATURE                Location/Qualifiers
REGION                 1..153
                       note = Synthetic recombinant human IL-7 (rhIL-7)
source                 1..153
                       mol_type = protein
                       organism = synthetic construct
SEQUENCE: 10
MDCDIEGKDG KQYESVLMVS IDQLLDSMKE IGSNCLNNEF NFFKRHICDA NKEGMFLFRA  60
ARKLRQFLKM NSTGDFDLHL LKVSEGTTIL LNCTGQVKGR KPAALGEAQP TKSLEENKSL  120
KEQKKLNDLC FLKRLLQEIK TCWNKILMGT KEH                               153

SEQ ID NO: 11          moltype = AA  length = 115
FEATURE                Location/Qualifiers
REGION                 1..115
                       note = Synthetic recombinant human IL-15 (rhIL-15)
source                 1..115
                       mol_type = protein
                       organism = synthetic construct
SEQUENCE: 11
MNWVNVISDL KKIEDLIQSM HIDATLYTES DVHPSCKVTA MKCFLLELQV ISLESGDASI  60
HDTVENLIIL ANNSLSSNGN VTESGCKECE ELEEKNIKEF LQSFVHIVQM FINTS       115

SEQ ID NO: 12          moltype = AA  length = 132
FEATURE                Location/Qualifiers
REGION                 1..132
                       note = Synthetic recombinant human IL-21 (rhIL-21)
source                 1..132
                       mol_type = protein
                       organism = synthetic construct
SEQUENCE: 12
MQDRHMIRMR QLIDIVDQLK NYVNDLVPEF LPAPEDVETN CEWSAFSCFQ KAQLKSANTG  60
NNERIINVSI KKLKRKPPST NAGRRQKHRL TCPSCDSYEK KPPKEFLERF KSLLQKMIHQ  120
HLSSRTHGSE DS                                                      132

SEQ ID NO: 13          moltype = AA  length = 153
FEATURE                Location/Qualifiers
REGION                 1..153
                       note = Synthetic IL-2
source                 1..153
                       mol_type = protein
                       organism = synthetic construct
SEQUENCE: 13
MYRMQLLSCI ALSLALVTNS APTSSSTKKT QLQLEHLLLD LQMILNGINN YKNPKLTRML  60
TFKFYMPKKA TELKHLQCLE EELKPLEEVL NLAQSKNFHL RPRDLISNIN VIVLELKGSE  120
TTFMCEYADE TATIVEFLNR WITFCQSIIS TLT                               153

SEQ ID NO: 14          moltype = AA  length = 133
```

```
FEATURE                Location/Qualifiers
REGION                 1..133
                       note = Synthetic IL-2 mutein
source                 1..133
                       mol_type = protein
                       organism = synthetic construct
SEQUENCE: 14
APTSSSTKKT QLQLEHLLLD LQMILNGINN YKNPKLTAML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLT                                                     133

SEQ ID NO: 15          moltype = AA  length = 133
FEATURE                Location/Qualifiers
REGION                 1..133
                       note = Synthetic IL-2 mutein
source                 1..133
                       mol_type = protein
                       organism = synthetic construct
SEQUENCE: 15
APTSSSTKKT QLQLEHLLLD LQMILNGINN YKNPKLTRML TAKFYMPKKA TELKHLQCLE  60
EELKPLEEVL NLAQSKNFHL RPRDLISNIN VIVLELKGSE TTFMCEYADE TATIVEFLNR  120
WITFCQSIIS TLT                                                     133

SEQ ID NO: 16          moltype = AA  length = 145
FEATURE                Location/Qualifiers
REGION                 1..145
                       note = Synthetic HCDR1_IL-2
source                 1..145
                       mol_type = protein
                       organism = synthetic construct
SEQUENCE: 16
GFSLAPTSSS TKKTQLQLEH LLLDLQMILN GINNYKNPKL TAMLTFKFYM PKKATELKHL  60
QCLEEELKPL EEVLNLAQSK NFHLRPRDLI SNINVIVLEL KGSETTFMCE YADETATIVE  120
FLNRWITFCQ SIISTLTSTS GMSVG                                        145

SEQ ID NO: 17          moltype = AA  length = 16
FEATURE                Location/Qualifiers
REGION                 1..16
                       note = Synthetic HCDR2
source                 1..16
                       mol_type = protein
                       organism = synthetic construct
SEQUENCE: 17
DIWWDDKKDY NPSLKS                                                  16

SEQ ID NO: 18          moltype = AA  length = 10
FEATURE                Location/Qualifiers
REGION                 1..10
                       note = Synthetic HCDR3
source                 1..10
                       mol_type = protein
                       organism = synthetic construct
SEQUENCE: 18
SMITNWYFDV                                                         10

SEQ ID NO: 19          moltype = AA  length = 141
FEATURE                Location/Qualifiers
REGION                 1..141
                       note = Synthetic HCDR1_IL-2 kabat
source                 1..141
                       mol_type = protein
                       organism = synthetic construct
SEQUENCE: 19
APTSSSTKKT QLQLEHLLLD LQMILNGINN YKNPKLTAML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSTSGMSV G                                            141

SEQ ID NO: 20          moltype = AA  length = 16
FEATURE                Location/Qualifiers
REGION                 1..16
                       note = Synthetic HCDR2 kabat
source                 1..16
                       mol_type = protein
                       organism = synthetic construct
SEQUENCE: 20
DIWWDDKKDY NPSLKS                                                  16

SEQ ID NO: 21          moltype = AA  length = 10
FEATURE                Location/Qualifiers
```

```
REGION                  1..10
                        note = Synthetic HCDR3 kabat
source                  1..10
                        mol_type = protein
                        organism = synthetic construct
SEQUENCE: 21
SMITNWYFDV                                                            10

SEQ ID NO: 22           moltype = AA  length = 142
FEATURE                 Location/Qualifiers
REGION                  1..142
                        note = Synthetic HCDR1_IL-2 clothia
source                  1..142
                        mol_type = protein
                        organism = synthetic construct
SEQUENCE: 22
GFSLAPTSSS TKKTQLQLEH LLLDLQMILN GINNYKNPKL TAMLTFKFYM PKKATELKHL  60
QCLEEELKPL EEVLNLAQSK NFHLRPRDLI SNINVIVLEL KGSETTFMCE YADETATIVE  120
FLNRWITFCQ SIISTLTSTS GM                                              142

SEQ ID NO: 23           moltype = AA  length = 5
FEATURE                 Location/Qualifiers
REGION                  1..5
                        note = Synthetic HCDR2 clothia
source                  1..5
                        mol_type = protein
                        organism = synthetic construct
SEQUENCE: 23
WWDDK                                                                 5

SEQ ID NO: 24           moltype = AA  length = 10
FEATURE                 Location/Qualifiers
REGION                  1..10
                        note = Synthetic HCDR3 clothia
source                  1..10
                        mol_type = protein
                        organism = synthetic construct
SEQUENCE: 24
SMITNWYFDV                                                            10

SEQ ID NO: 25           moltype = AA  length = 143
FEATURE                 Location/Qualifiers
REGION                  1..143
                        note = Synthetic HCDR1_IL-2 IMGT
source                  1..143
                        mol_type = protein
                        organism = synthetic construct
SEQUENCE: 25
GFSLAPTSSS TKKTQLQLEH LLLDLQMILN GINNYKNPKL TAMLTFKFYM PKKATELKHL  60
QCLEEELKPL EEVLNLAQSK NFHLRPRDLI SNINVIVLEL KGSETTFMCE YADETATIVE  120
FLNRWITFCQ SIISTLTSTS GMS                                             143

SEQ ID NO: 26           moltype = AA  length = 7
FEATURE                 Location/Qualifiers
REGION                  1..7
                        note = Synthetic HCDR2 IMGT
source                  1..7
                        mol_type = protein
                        organism = synthetic construct
SEQUENCE: 26
IWWDDKK                                                               7

SEQ ID NO: 27           moltype = AA  length = 12
FEATURE                 Location/Qualifiers
REGION                  1..12
                        note = Synthetic HCDR3 IMGT
source                  1..12
                        mol_type = protein
                        organism = synthetic construct
SEQUENCE: 27
ARSMITNWYF DV                                                         12

SEQ ID NO: 28           moltype = AA  length = 253
FEATURE                 Location/Qualifiers
REGION                  1..253
                        note = Synthetic VH
source                  1..253
                        mol_type = protein
                        organism = synthetic construct
```

```
SEQUENCE: 28
QVTLRESGPA LVKPTQTLTL TCTFSGFSLA PTSSSTKKTQ LQLEHLLLDL QMILNGINNY  60
KNPKLTAMLT FKFYMPKKAT ELKHLQCLEE ELKPLEEVLN LAQSKNFHLR PRDLISNINV  120
IVLELKGSET TFMCEYADET ATIVEFLNRW ITFCQSIIST LTSTSGMSVG WIRQPPGKAL  180
EWLADIWWDD KKDYNPSLKS RLTISKDTSK NQVVLKVTNM DPADTATYYC ARSMITNWYF  240
DVWGAGTTVT VSS                                                    253

SEQ ID NO: 29           moltype = AA  length = 533
FEATURE                 Location/Qualifiers
REGION                  1..533
                        note = Synthetic Heavy chain
source                  1..533
                        mol_type = protein
                        organism = synthetic construct
SEQUENCE: 29
QMILNGINNY KNPKLTAMLT FKFYMPKKAT ELKHLQCLEE ELKPLEEVLN LAQSKNFHLR  60
PRDLISNINV IVLELKGSET TFMCEYADET ATIVEFLNRW ITFCQSIIST LTSTSGMSVG  120
WIRQPPGKAL EWLADIWWDD KKDYNPSLKS RLTISKDTSK NQVVLKVTNM DPADTATYYC  180
ARSMITNWYF DVWGAGTTVT VSSASTKGPS VFPLAPSSKS TSGGTAALGC LVKDYFPEPV  240
TVSWNSGALT SGVHTFPAVL QSSGLYSLSS VVTVPSSSLG TQTYICNVNH KPSNTKVDKR  300
VEPKSCDKTH TCPPCPAPEL LGGPSVFLFP PKPKDTLMIS RTPEVTCVVV AVSHEDPEVK  360
FNWYVDGVEV HNAKTKPREE QYNSTYRVVS VLTVLHQDWL NGKEYKCKVS NKALAAPIEK  420
TISKAKGQPR EPQVYTLPPS REEMTKNQVS LTCLVKGFYP SDIAVEWESN GQPENNYKTT  480
PPVLDSDGSF FLYSKLTVDK SRWQQGNVFS CSVMHEALHN HYTQKSLSLS PGK         533

SEQ ID NO: 30           moltype = AA  length = 10
FEATURE                 Location/Qualifiers
REGION                  1..10
                        note = Synthetic LCDR1 kabat
source                  1..10
                        mol_type = protein
                        organism = synthetic construct
SEQUENCE: 30
KAQLSVGYMH                                                        10

SEQ ID NO: 31           moltype = AA  length = 7
FEATURE                 Location/Qualifiers
REGION                  1..7
                        note = Synthetic LCDR2 kabat
source                  1..7
                        mol_type = protein
                        organism = synthetic construct
SEQUENCE: 31
DTSKLAS                                                           7

SEQ ID NO: 32           moltype = AA  length = 9
FEATURE                 Location/Qualifiers
REGION                  1..9
                        note = Synthetic LCDR3 kabat
source                  1..9
                        mol_type = protein
                        organism = synthetic construct
SEQUENCE: 32
FQGSGYPFT                                                         9

SEQ ID NO: 33           moltype = AA  length = 6
FEATURE                 Location/Qualifiers
REGION                  1..6
                        note = Synthetic LCDR1 chothia
source                  1..6
                        mol_type = protein
                        organism = synthetic construct
SEQUENCE: 33
QLSVGY                                                            6

SEQ ID NO: 34           moltype =   length =
SEQUENCE: 34
000

SEQ ID NO: 35           moltype = AA  length = 6
FEATURE                 Location/Qualifiers
REGION                  1..6
                        note = Synthetic LCDR3 chothia
source                  1..6
                        mol_type = protein
                        organism = synthetic construct
SEQUENCE: 35
GSGYPF                                                            6
```

```
SEQ ID NO: 36          moltype = AA  length = 106
FEATURE                Location/Qualifiers
REGION                 1..106
                       note = Synthetic VL
source                 1..106
                       mol_type = protein
                       organism = synthetic construct
SEQUENCE: 36
DIQMTQSPST LSASVGDRVT ITCKAQLSVG YMHWYQQKPG KAPKLLIYDT SKLASGVPSR  60
FSGSGSGTEF TLTISSLQPD DFATYYCFQG SGYPFTFGGG TKLEIK                 106

SEQ ID NO: 37          moltype = AA  length = 213
FEATURE                Location/Qualifiers
REGION                 1..213
                       note = Synthetic Light chain
source                 1..213
                       mol_type = protein
                       organism = synthetic construct
SEQUENCE: 37
DIQMTQSPST LSASVGDRVT ITCKAQLSVG YMHWYQQKPG KAPKLLIYDT SKLASGVPSR  60
FSGSGSGTEF TLTISSLQPD DFATYYCFQG SGYPFTFGGG TKLEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                               213

SEQ ID NO: 38          moltype = AA  length = 583
FEATURE                Location/Qualifiers
REGION                 1..583
                       note = Synthetic Light chain
source                 1..583
                       mol_type = protein
                       organism = synthetic construct
SEQUENCE: 38
QVTLRESGPA LVKPTQTLTL TCTFSGFSLA PTSSSTKKTQ LQLEHLLLDL QMILNGINNY  60
KNPKLTRMLT AKFYMPKKAT ELKHLQCLEE ELKPLEEVLN LAQSKNFHLR PRDLISNINV  120
IVLELKGSET TFMCEYADET ATIVEFLNRW ITFCQSIIST LTSTSGMSVG WIRQPPGKAL  180
EWLADIWWDD KKDYNPSLKS RLTISKDTSK NQVVLKVTNM DPADTATYYC ARSMITNWYF  240
DVWGAGTTVT VSSASTKGPS VFPLAPSSKS TSGGTAALGC LVKDYFPEPV TVSWNSGALT  300
SGVHTFPAVL QSSGLYSLSS VVTVPSSSLG TQTYICNVNH KPSNTKVDKR VEPKSCDKTH  360
TCPPCPAPEL LGGPSVFLFP PKPKDTLMIS RTPEVTCVVV AVSHEDPEVK FNWYVDGVEV  420
HNAKTKPREE QYNSTYRVVS VLTVLHQDWL NGKEYKCKVS NKALAAPIEK TISKAKGQPR  480
EPQVYTLPPS REEMTKNQVS LTCLVKGFYP SDIAVEWESN GQPENNYKTT PPVLDSDGSF  540
FLYSKLTVDK SRWQQGNVFS CSVMHEALHN HYTQKSLSLS PGK                    583

SEQ ID NO: 39          moltype = AA  length = 213
FEATURE                Location/Qualifiers
REGION                 1..213
                       note = Synthetic Light chain
source                 1..213
                       mol_type = protein
                       organism = synthetic construct
SEQUENCE: 39
DIQMTQSPST LSASVGDRVT ITCKAQLSVG YMHWYQQKPG KAPKLLIYDT SKLASGVPSR  60
FSGSGSGTEF TLTISSLQPD DFATYYCFQG SGYPFTFGGG TKLEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                               213

SEQ ID NO: 40          moltype = AA  length = 255
FEATURE                Location/Qualifiers
REGION                 1..255
                       note = Synthetic human 4-1BB, Tumor necrosis factor
                        receptor superfamily, member 9 (Homo sapiens)
source                 1..255
                       mol_type = protein
                       organism = synthetic construct
SEQUENCE: 40
MGNSCYNIVA TLLLVLNFER TRSLQDPCSN CPAGTFCDNN RNQICSPCPP NSFSSAGGQR  60
TCDICRQCKG VFRTRKECSS TSNAECDCTP GFHCLGAGCS MCEQDCKQGQ ELTKKGCKDC  120
CFGTFNDQKR GICRPWTNCS LDGKSVLVNG TKERDVVCGP SPADLSPGAS SVTPPAPARE  180
PGHSPQIISF FLALTSTALL FLLFFLTLRF SVVKRGRKKL LYIFKQPFMR PVQTTQEEDG  240
CSCRFPEEEE GGCEL                                                   255

SEQ ID NO: 41          moltype = AA  length = 256
FEATURE                Location/Qualifiers
REGION                 1..256
                       note = Synthetic murine 4-1BB, Tumor necrosis factor
                        receptor superfamily, member 9 (Mus musculus)
source                 1..256
                       mol_type = protein
                       organism = synthetic construct
```

```
SEQUENCE: 41
MGNNCYNVVV IVLLLVGCEK VGAVQNSCDN CQPGTFCRKY NPVCKSCPPS TFSSIGGQPN  60
CNICRVCAGY FRFKKFCSST HNAECECIEG FHCLGPQCTR CEKDCRPGQE LTKQGCKTCS  120
LGTFNDQNGT GVCRPWTNCS LDGRSVLKTG TTEKDVVCGP PVVSFSPSTT ISVTPEGGPG  180
GHSLQVLTLF LALTSALLLA LIFITLLFSV LKWIRKKFPH IFKQPFKKTT GAAQEEDACS  240
CRCPQEEEGG GGGYEL                                                 256

SEQ ID NO: 42           moltype = AA  length = 441
FEATURE                 Location/Qualifiers
REGION                  1..441
                        note = Synthetic heavy chain for utomilumab
source                  1..441
                        mol_type = protein
                        organism = synthetic construct
SEQUENCE: 42
EVQLVQSGAE VKKPGESLRI SCKGSGYSFS TYWISWVRQM PGKGLEWMGK IYPGDSYTNY  60
SPSFQGQVTI SADKSISTAY LQWSSLKASD TAMYYCARGY GIFDYWGQGT LVTVSSASTK  120
GPSVFPLAPC SRSTSESTAA LGCLVKDYFP EPVTVSWNSG ALTSGVHTFP AVLQSSGLYS  180
LSSVVTVPSS NFGTQTYTCN VDHKPSNTKV DKTVERKCCV ECPPCPAPPV AGPSVFLFPP  240
KPKDTLMISR TPEVTCVVVD VSHEDPEVQF NWYVDGVEVH NAKTKPREEQ FNSTFRVVSV  300
LTVVHQDWLN GKEYKCKVSN KGLPAPIEKT ISKTKGQPRE PQVYTLPPSR EEMTKNQVSL  360
TCLVKGFYPS DIAVEWESNG QPENNYKTTP PMLDSDGSFF LYSKLTVDKS RWQQGNVFSC  420
SVMHEALHNH YTQKSLSLSP G                                           441

SEQ ID NO: 43           moltype = AA  length = 214
FEATURE                 Location/Qualifiers
REGION                  1..214
                        note = Synthetic light chain for utomilumab
source                  1..214
                        mol_type = protein
                        organism = synthetic construct
SEQUENCE: 43
SYELTQPPSV SVSPGQTASI TCSGDNIGDQ YAHWYQQKPG QSPVLVIYQD KNRPSGIPER  60
FSGSNSGNTA TLTISGTQAM DEADYYCATY TGFGSLAVFG GGTKLTVLGQ PKAAPSVTLF  120
PPSSEELQAN KATLVCLISD FYPGAVTVAW KADSSPVKAG VETTTPSKQS NNKYAASSYL  180
SLTPEQWKSH RSYSCQVTHE GSTVEKTVAP TECS                             214

SEQ ID NO: 44           moltype = AA  length = 116
FEATURE                 Location/Qualifiers
REGION                  1..116
                        note = Synthetic heavy chain variable region for utomilumab
source                  1..116
                        mol_type = protein
                        organism = synthetic construct
SEQUENCE: 44
EVQLVQSGAE VKKPGESLRI SCKGSGYSFS TYWISWVRQM PGKGLEWMGK IYPGDSYTNY  60
SPSFQGQVTI SADKSISTAY LQWSSLKASD TAMYYCARGY GIFDYWGQGT LVTVSS      116

SEQ ID NO: 45           moltype = AA  length = 108
FEATURE                 Location/Qualifiers
REGION                  1..108
                        note = Synthetic light chain variable region for utomilumab
source                  1..108
                        mol_type = protein
                        organism = synthetic construct
SEQUENCE: 45
SYELTQPPSV SVSPGQTASI TCSGDNIGDQ YAHWYQQKPG QSPVLVIYQD KNRPSGIPER  60
FSGSNSGNTA TLTISGTQAM DEADYYCATY TGFGSLAVFG GGTKLTVL              108

SEQ ID NO: 46           moltype = AA  length = 6
FEATURE                 Location/Qualifiers
REGION                  1..6
                        note = Synthetic heavy chain CDR1 for utomilumab
source                  1..6
                        mol_type = protein
                        organism = synthetic construct
SEQUENCE: 46
STYWIS                                                            6

SEQ ID NO: 47           moltype = AA  length = 17
FEATURE                 Location/Qualifiers
REGION                  1..17
                        note = Synthetic heavy chain CDR2 for utomilumab
source                  1..17
                        mol_type = protein
                        organism = synthetic construct
SEQUENCE: 47
KIYPGDSYTN YSPSFQG                                                17
```

```
SEQ ID NO: 48          moltype = AA  length = 8
FEATURE                Location/Qualifiers
REGION                 1..8
                       note = Synthetic heavy chain CDR3 for utomilumab
source                 1..8
                       mol_type = protein
                       organism = synthetic construct
SEQUENCE: 48
RGYGIFDY                                                    8

SEQ ID NO: 49          moltype = AA  length = 11
FEATURE                Location/Qualifiers
REGION                 1..11
                       note = Synthetic light chain CDR1 for utomilumab
source                 1..11
                       mol_type = protein
                       organism = synthetic construct
SEQUENCE: 49
SGDNIGDQYA H                                                11

SEQ ID NO: 50          moltype = AA  length = 7
FEATURE                Location/Qualifiers
REGION                 1..7
                       note = Synthetic light chain CDR2 for utomilumab
source                 1..7
                       mol_type = protein
                       organism = synthetic construct
SEQUENCE: 50
QDKNRPS                                                     7

SEQ ID NO: 51          moltype = AA  length = 11
FEATURE                Location/Qualifiers
REGION                 1..11
                       note = Synthetic light chain CDR3 for utomilumab
source                 1..11
                       mol_type = protein
                       organism = synthetic construct
SEQUENCE: 51
ATYTGFGSLA V                                                11

SEQ ID NO: 52          moltype = AA  length = 448
FEATURE                Location/Qualifiers
REGION                 1..448
                       note = Synthetic heavy chain for urelumab
source                 1..448
                       mol_type = protein
                       organism = synthetic construct
SEQUENCE: 52
QVQLQQWGAG LLKPSETLSL TCAVYGGSFS GYYWSWIRQS PEKGLEWIGE INHGGYVTYN  60
PSLESRVTIS VDTSKNQFSL KLSSVTAADT AVYYCARDYG PGNYDWYFDL WGRGTLVTVS  120
SASTKGPSVF PLAPCSRSTS ESTAALGCLV KDYFPEPVTV SWNSGALTSG VHTFPAVLQS  180
SGLYSLSSVV TVPSSSLGTK TYTCNVDHKP SNTKVDKRVE SKYGPPCPPC PAPEFLGGPS  240
VFLFPPKPKD TLMISRTPEV TCVVVDVSQE DPEVQFNWYV DGVEVHNAKT KPREEQFNST  300
YRVVSVLTVL HQDWLNGKEY KCKVSNKGLP SSIEKTISKA KGQPREPQVY TLPPSQEEMT  360
KNQVSLTCLV KGFYPSDIAV EWESNGQPEN NYKTTPPVLD SDGSFFLYSR LTVDKSRWQE  420
GNVFSCSVMH EALHNHYTQK SLSLSLGK                              448

SEQ ID NO: 53          moltype = AA  length = 216
FEATURE                Location/Qualifiers
REGION                 1..216
                       note = Synthetic light chain for urelumab
source                 1..216
                       mol_type = protein
                       organism = synthetic construct
SEQUENCE: 53
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWPPALTF CGGTKVEIKR TVAAPSVFIF  120
PPSDEQLKSG TASVVCLLNN FYPREAKVQW KVDNALQSGN SQESVTEQDS KDSTYSLSST  180
LTLSKADYEK HKVYACEVTH QGLSSPVTKS FNRGEC                      216

SEQ ID NO: 54          moltype = AA  length = 120
FEATURE                Location/Qualifiers
REGION                 1..120
                       note = Synthetic variable heavy chain for urelumab
source                 1..120
                       mol_type = protein
                       organism = synthetic construct
SEQUENCE: 54
MKHLWFFLLL VAAPRWVLSQ VQLQQWGAGL LKPSETLSLT CAVYGGSFSG YYWSWIRQSP  60
```

```
EKGLEWIGEI NHGGYVTYNP SLESRVTISV DTSKNQFSLK LSSVTAADTA VYYCARDYGP  120

SEQ ID NO: 55           moltype = AA  length = 110
FEATURE                 Location/Qualifiers
REGION                  1..110
                        note = Synthetic variable light chain for urelumab
source                  1..110
                        mol_type = protein
                        organism = synthetic construct
SEQUENCE: 55
MEAPAQLLFL LLLWLPDTTG EIVLTQSPAT LSLSPGERAT LSCRASQSVS SYLAWYQQKP  60
GQAPRLLIYD ASNRATGIPA RFSGSGSGTD FTLTISSLEP EDFAVYYCQQ             110

SEQ ID NO: 56           moltype = AA  length = 5
FEATURE                 Location/Qualifiers
REGION                  1..5
                        note = Synthetic heavy chain CDR1 for urelumab
source                  1..5
                        mol_type = protein
                        organism = synthetic construct
SEQUENCE: 56
GYYWS                                                              5

SEQ ID NO: 57           moltype = AA  length = 16
FEATURE                 Location/Qualifiers
REGION                  1..16
                        note = Synthetic heavy chain CDR2 for urelumab
source                  1..16
                        mol_type = protein
                        organism = synthetic construct
SEQUENCE: 57
EINHGGYVTY NPSLES                                                  16

SEQ ID NO: 58           moltype = AA  length = 13
FEATURE                 Location/Qualifiers
REGION                  1..13
                        note = Synthetic heavy chain CDR3 for urelumab
source                  1..13
                        mol_type = protein
                        organism = synthetic construct
SEQUENCE: 58
DYGPGNYDWY FDL                                                     13

SEQ ID NO: 59           moltype = AA  length = 11
FEATURE                 Location/Qualifiers
REGION                  1..11
                        note = Synthetic light chain CDR1 for urelumab
source                  1..11
                        mol_type = protein
                        organism = synthetic construct
SEQUENCE: 59
RASQSVSSYL A                                                       11

SEQ ID NO: 60           moltype = AA  length = 7
FEATURE                 Location/Qualifiers
REGION                  1..7
                        note = Synthetic light chain CDR2 for urelumab
source                  1..7
                        mol_type = protein
                        organism = synthetic construct
SEQUENCE: 60
DASNRAT                                                            7

SEQ ID NO: 61           moltype = AA  length = 11
FEATURE                 Location/Qualifiers
REGION                  1..11
                        note = Synthetic light chain CDR3 for urelumab
source                  1..11
                        mol_type = protein
                        organism = synthetic construct
SEQUENCE: 61
QQRSDWPPAL T                                                       11

SEQ ID NO: 62           moltype = AA  length = 230
FEATURE                 Location/Qualifiers
REGION                  1..230
                        note = Synthetic Fc domain
source                  1..230
                        mol_type = protein
```

```
                      organism = synthetic construct
SEQUENCE: 62
KSCDKTHTCP PCPAPELLGG PSVFLFPPKP KDTLMISRTP EVTCVVVDVS HEDPEVKFNW  60
YVDGVEVHNA KTKPREEQYN STYRVVSVLT VLHQDWLNGK EYKCKVSNKA LPAPIEKTIS  120
KAKGQPREPQ VYTLPPSREE MTKNQVSLTC LVKGFYPSDI AVEWESNGQP ENNYKTTPPV  180
LDSDGSFFLY SKLTVDKSRW QQGNVFSCSV MHEALHNHYT QKSLSLSPGK             230

SEQ ID NO: 63         moltype = AA  length = 22
FEATURE               Location/Qualifiers
REGION                1..22
                      note = Synthetic linker
source                1..22
                      mol_type = protein
                      organism = synthetic construct
SEQUENCE: 63
GGPGSSKSCD KTHTCPPCPA PE                                           22

SEQ ID NO: 64         moltype = AA  length = 22
FEATURE               Location/Qualifiers
REGION                1..22
                      note = Synthetic linker
source                1..22
                      mol_type = protein
                      organism = synthetic construct
SEQUENCE: 64
GGSGSSKSCD KTHTCPPCPA PE                                           22

SEQ ID NO: 65         moltype = AA  length = 27
FEATURE               Location/Qualifiers
REGION                1..27
                      note = Synthetic linker
source                1..27
                      mol_type = protein
                      organism = synthetic construct
SEQUENCE: 65
GGPGSSSSSS SKSCDKTHTC PPCPAPE                                      27

SEQ ID NO: 66         moltype = AA  length = 27
FEATURE               Location/Qualifiers
REGION                1..27
                      note = Synthetic linker
source                1..27
                      mol_type = protein
                      organism = synthetic construct
SEQUENCE: 66
GGSGSSSSSS SKSCDKTHTC PPCPAPE                                      27

SEQ ID NO: 67         moltype = AA  length = 29
FEATURE               Location/Qualifiers
REGION                1..29
                      note = Synthetic linker
source                1..29
                      mol_type = protein
                      organism = synthetic construct
SEQUENCE: 67
GGPGSSSSSS SSSKSCDKTH TCPPCPAPE                                    29

SEQ ID NO: 68         moltype = AA  length = 29
FEATURE               Location/Qualifiers
REGION                1..29
                      note = Synthetic linker
source                1..29
                      mol_type = protein
                      organism = synthetic construct
SEQUENCE: 68
GGSGSSSSSS SSSKSCDKTH TCPPCPAPE                                    29

SEQ ID NO: 69         moltype = AA  length = 24
FEATURE               Location/Qualifiers
REGION                1..24
                      note = Synthetic linker
source                1..24
                      mol_type = protein
                      organism = synthetic construct
SEQUENCE: 69
GGPGSSGSGS SDKTHTCPPC PAPE                                         24

SEQ ID NO: 70         moltype = AA  length = 23
FEATURE               Location/Qualifiers
```

```
REGION                  1..23
                        note = Synthetic linker
source                  1..23
                        mol_type = protein
                        organism = synthetic construct
SEQUENCE: 70
GGPGSSGSGS DKTHTCPPCP APE                                          23

SEQ ID NO: 71           moltype = AA  length = 21
FEATURE                 Location/Qualifiers
REGION                  1..21
                        note = Synthetic linker
source                  1..21
                        mol_type = protein
                        organism = synthetic construct
SEQUENCE: 71
GGPSSSGSDK THTCPPCPAP E                                            21

SEQ ID NO: 72           moltype = AA  length = 25
FEATURE                 Location/Qualifiers
REGION                  1..25
                        note = Synthetic linker
source                  1..25
                        mol_type = protein
                        organism = synthetic construct
SEQUENCE: 72
GGSSSSSSSS GSDKTHTCPP CPAPE                                        25

SEQ ID NO: 73           moltype = AA  length = 246
FEATURE                 Location/Qualifiers
REGION                  1..246
                        note = Synthetic Fc domain
source                  1..246
                        mol_type = protein
                        organism = synthetic construct
SEQUENCE: 73
METDTLLLWV LLLWVPAGNG DKTHTCPPCP APELLGGPSV FLFPPKPKDT LMISRTPEVT  60
CVVVDVSHED PEVKFNWYVD GVEVHNAKTK PREEQYNSTY RVVSVLTVLH QDWLNGKEYK  120
CKVSNKALPA PIEKTISKAK GQPREPQVYT LPPSREEMTK NQVSLTCLVK GFYPSDIAVE  180
WESNGQPENN YKTTPPVLDS DGSFFLYSKL TVDKSRWQQG NVFSCSVMHE ALHNHYTQKS  240
LSLSPG                                                             246

SEQ ID NO: 74           moltype = AA  length = 11
FEATURE                 Location/Qualifiers
REGION                  1..11
                        note = Synthetic linker
source                  1..11
                        mol_type = protein
                        organism = synthetic construct
SEQUENCE: 74
SGSGSGSGSG S                                                       11

SEQ ID NO: 75           moltype = AA  length = 12
FEATURE                 Location/Qualifiers
REGION                  1..12
                        note = Synthetic linker
source                  1..12
                        mol_type = protein
                        organism = synthetic construct
SEQUENCE: 75
SSSSSSGSGS GS                                                      12

SEQ ID NO: 76           moltype = AA  length = 16
FEATURE                 Location/Qualifiers
REGION                  1..16
                        note = Synthetic linker
source                  1..16
                        mol_type = protein
                        organism = synthetic construct
SEQUENCE: 76
SSSSSSGSGS GSGSGS                                                  16

SEQ ID NO: 77           moltype = AA  length = 254
FEATURE                 Location/Qualifiers
REGION                  1..254
                        note = Synthetic 4-1BBL
source                  1..254
                        mol_type = protein
                        organism = synthetic construct
```

```
SEQUENCE: 77
MEYASDASLD PEAPWPPAPR ARACRVLPWA LVAGLLLLLL LAAACAVFLA CPWAVSGARA  60
SPGSAASPRL REGPELSPDD PAGLLDLRQG MFAQLVAQNV LLIDGPLSWY SDPGLAGVSL  120
TGGLSYKEDT KELVVAKAGV YYVFFQLELR RVVAGEGSGS VSLALHLQPL RSAAGAAALA  180
LTVDLPPASS EARNSAFGFQ GRLLHLSAGQ RLGVHLHTEA RARHAWQLTQ GATVLGLFRV  240
TPEIPAGLPS PRSE                                                   254

SEQ ID NO: 78          moltype = AA  length = 168
FEATURE                Location/Qualifiers
REGION                 1..168
                       note = Synthetic 4-1BBL soluble domain
source                 1..168
                       mol_type = protein
                       organism = synthetic construct
SEQUENCE: 78
LRQGMFAQLV AQNVLLIDGP LSWYSDPGLA GVSLTGGLSY KEDTKELVVA KAGVYYVFFQ  60
LELRRVVAGE GSGSVSLALH LQPLRSAAGA AALALTVDLP PASSEARNSA FGFQGRLLHL  120
SAGQRLGVHL HTEARARHAW QLTQGATVLG LFRVTPEIPA GLPSPRSE              168

SEQ ID NO: 79          moltype = AA  length = 118
FEATURE                Location/Qualifiers
REGION                 1..118
                       note = Synthetic variable heavy chain for 4B4-1-1 version 1
source                 1..118
                       mol_type = protein
                       organism = synthetic construct
SEQUENCE: 79
QVQLQQPGAE LVKPGASVKL SCKASGYTFS SYWMHWVKQR PGQVLEWIGE INPGNGHTNY  60
NEKFKSKATL TVDKSSSTAY MQLSSLTSED SAVYYCARSF TTARGFAYWG QGTLVTVS    118

SEQ ID NO: 80          moltype = AA  length = 107
FEATURE                Location/Qualifiers
REGION                 1..107
                       note = Synthetic variable light chain for 4B4-1-1 version 1
source                 1..107
                       mol_type = protein
                       organism = synthetic construct
SEQUENCE: 80
DIVMTQSPAT QSVTPGDRVS LSCRASQTIS DYLHWYQQKS HESPRLLIKY ASQSISGIPS  60
RFSGSGSGSD FTLSINSVEP EDVGVYYCQD GHSFPPTFGG GTKLEIK               107

SEQ ID NO: 81          moltype = AA  length = 119
FEATURE                Location/Qualifiers
REGION                 1..119
                       note = Synthetic variable heavy chain for 4B4-1-1 version 2
source                 1..119
                       mol_type = protein
                       organism = synthetic construct
SEQUENCE: 81
QVQLQQPGAE LVKPGASVKL SCKASGYTFS SYWMHWVKQR PGQVLEWIGE INPGNGHTNY  60
NEKFKSKATL TVDKSSSTAY MQLSSLTSED SAVYYCARSF TTARGFAYWG QGTLVTVSA   119

SEQ ID NO: 82          moltype = AA  length = 108
FEATURE                Location/Qualifiers
REGION                 1..108
                       note = Synthetic variable light chain for 4B4-1-1 version 2
source                 1..108
                       mol_type = protein
                       organism = synthetic construct
SEQUENCE: 82
DIVMTQSPAT QSVTPGDRVS LSCRASQTIS DYLHWYQQKS HESPRLLIKY ASQSISGIPS  60
RFSGSGSGSD FTLSINSVEP EDVGVYYCQD GHSFPPTFGG GTKLEIKR              108

SEQ ID NO: 83          moltype = AA  length = 120
FEATURE                Location/Qualifiers
REGION                 1..120
                       note = Synthetic variable heavy chain for H39E3-2
source                 1..120
                       mol_type = protein
                       organism = synthetic construct
SEQUENCE: 83
MDWTWRILFL VAAATGAHSE VQLVESGGGL VQPGGSLRLS CAASGFTFSD YWMSWVRQAP  60
GKGLEWVADI KNDGSYTNYA PSLTNRFTIS RDNAKNSLYL QMNSLRAEDT AVYYCARELT  120

SEQ ID NO: 84          moltype = AA  length = 109
FEATURE                Location/Qualifiers
REGION                 1..109
                       note = Synthetic variable light chain for H39E3-2
source                 1..109
```

```
                         mol_type = protein
                         organism = synthetic construct
SEQUENCE: 84
MEAPAQLLFL LLLWLPDTTG DIVMTQSPDS LAVSLGERAT INCKSSQSLL SSGNQKNYLW  60
YQQKPGQPPK LLIYYASTRQ SGVPDRFSGS GSGTDFTLTI SSLQAEDVA             109

SEQ ID NO: 85            moltype = AA  length = 277
FEATURE                  Location/Qualifiers
REGION                   1..277
                         note = Synthetic human OX40 (Homo sapiens)
source                   1..277
                         mol_type = protein
                         organism = synthetic construct
SEQUENCE: 85
MCVGARRLGR GPCAALLLLG LGLSTVTGLH CVGDTYPSND RCCHECRPGN GMVSRCSRSQ  60
NTVCRPCGPG FYNDVVSSKP CKPCTWCNLR SGSERKQLCT ATQDTVCRCR AGTQPLDSYK  120
PGVDCAPCPP GHFSPGDNQA CKPWTNCTLA GKHTLQPASN SSDAICEDRD PPATQPQETQ  180
GPPARPITVQ PTEAWPRTSQ GPSTRPVEVP GGRAVAAILG LGLVLGLLGP LAILLALYLL  240
RRDQRLPPDA HKPPGGGSFR TPIQEEQADA HSTLAKI                          277

SEQ ID NO: 86            moltype = AA  length = 272
FEATURE                  Location/Qualifiers
REGION                   1..272
                         note = Synthetic murine OX40 (Mus musculus)
source                   1..272
                         mol_type = protein
                         organism = synthetic construct
SEQUENCE: 86
MYVWVQQPTA LLLLGLTLGV TARRLNCVKH TYPSGHKCCR ECQPGHGMVS RCDHTRDTLC  60
HPCETGFYNE AVNYDTCKQC TQCNHRSGSE LKQNCTPTQD TVCRCRPGTQ PRQDSGYKLG  120
VDCVPCPPGH FSPGNNQACK PWTNCTLSGK QTRHPASDSL DAVCEDRSLL ATLLWETQRP  180
TFRPTTVQST TVWPRTSELP SPPTLVTPEG PAFAVLLGLG LGLLAPLTVL LALYLLRKAW  240
RLPNTPKPCW GNSFRTPIQE EHTDAHFTLA KI                               272

SEQ ID NO: 87            moltype = AA  length = 451
FEATURE                  Location/Qualifiers
REGION                   1..451
                         note = Synthetic heavy chain for tavolixizumab
source                   1..451
                         mol_type = protein
                         organism = synthetic construct
SEQUENCE: 87
QVQLQESGPG LVKPSQTLSL TCAVYGGSFS SGYWNWIRKH PGKGLEYIGY ISYNGITYHN  60
PSLKSRITIN RDTSKNQYSL QLNSVTPEDT AVYYCARYKY DYDGGHAMDY WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKRVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRE  360
EMTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                451

SEQ ID NO: 88            moltype = AA  length = 214
FEATURE                  Location/Qualifiers
REGION                   1..214
                         note = Synthetic light chain for tavolixizumab
source                   1..214
                         mol_type = protein
                         organism = synthetic construct
SEQUENCE: 88
DIQMTQSPSS LSASVGDRVT ITCRASQDIS NYLNWYQQKP GKAPKLLIYY TSKLHSGVPS  60
RFSGSGSGTD YTLTISSLQP EDFATYYCQQ GSALPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 89            moltype = AA  length = 118
FEATURE                  Location/Qualifiers
REGION                   1..118
                         note = Synthetic heavy chain variable region for
                          tavolixizumab
source                   1..118
                         mol_type = protein
                         organism = synthetic construct
SEQUENCE: 89
QVQLQESGPG LVKPSQTLSL TCAVYGGSFS SGYWNWIRKH PGKGLEYIGY ISYNGITYHN  60
PSLKSRITIN RDTSKNQYSL QLNSVTPEDT AVYYCARYKY DYDGGHAMDY WGQGTLVT    118

SEQ ID NO: 90            moltype = AA  length = 108
FEATURE                  Location/Qualifiers
REGION                   1..108
```

```
                        note = Synthetic light chain variable region for
                         tavolixizumab
source                  1..108
                        mol_type = protein
                        organism = synthetic construct
SEQUENCE: 90
DIQMTQSPSS LSASVGDRVT ITCRASQDIS NYLNWYQQKP GKAPKLLIYY TSKLHSGVPS  60
RFSGSGSGTD YTLTISSLQP EDFATYYCQQ GSALPWTFGQ GTKVEIKR              108

SEQ ID NO: 91           moltype = AA  length = 9
FEATURE                 Location/Qualifiers
REGION                  1..9
                        note = Synthetic heavy chain CDR1 for tavolixizumab
source                  1..9
                        mol_type = protein
                        organism = synthetic construct
SEQUENCE: 91
GSFSSGYWN                                                          9

SEQ ID NO: 92           moltype = AA  length = 13
FEATURE                 Location/Qualifiers
REGION                  1..13
                        note = Synthetic heavy chain CDR2 for tavolixizumab
source                  1..13
                        mol_type = protein
                        organism = synthetic construct
SEQUENCE: 92
YIGYISYNGI TYH                                                     13

SEQ ID NO: 93           moltype = AA  length = 14
FEATURE                 Location/Qualifiers
REGION                  1..14
                        note = Synthetic heavy chain CDR3 for tavolixizumab
source                  1..14
                        mol_type = protein
                        organism = synthetic construct
SEQUENCE: 93
RYKYDYDGGH AMDY                                                    14

SEQ ID NO: 94           moltype = AA  length = 8
FEATURE                 Location/Qualifiers
REGION                  1..8
                        note = Synthetic light chain CDR1 for tavolixizumab
source                  1..8
                        mol_type = protein
                        organism = synthetic construct
SEQUENCE: 94
QDISNYLN                                                           8

SEQ ID NO: 95           moltype = AA  length = 11
FEATURE                 Location/Qualifiers
REGION                  1..11
                        note = Synthetic light chain CDR2 for tavolixizumab
source                  1..11
                        mol_type = protein
                        organism = synthetic construct
SEQUENCE: 95
LLIYYTSKLH S                                                       11

SEQ ID NO: 96           moltype = AA  length = 8
FEATURE                 Location/Qualifiers
REGION                  1..8
                        note = Synthetic light chain CDR3 for tavolixizumab
source                  1..8
                        mol_type = protein
                        organism = synthetic construct
SEQUENCE: 96
QQGSALPW                                                           8

SEQ ID NO: 97           moltype = AA  length = 444
FEATURE                 Location/Qualifiers
REGION                  1..444
                        note = Synthetic heavy chain for 11D4
source                  1..444
                        mol_type = protein
                        organism = synthetic construct
SEQUENCE: 97
EVQLVESGGG LVQPGGSLRL SCAASGFTFS SYSMNWVRQA PGKGLEWVSY ISSSSSTIDY  60
ADSVKGRFTI SRDNAKNSLY LQMNSLRDED TAVYYCARES GWYLFDYWGQ GTLVTVSSAS  120
```

```
TKGPSVFPLA PCSRSTSEST AALGCLVKDY FPEPVTVSWN SGALTSGVHT FPAVLQSSGL  180
YSLSSVVTVP SSNFGTQTYT CNVDHKPSNT KVDKTVERKC CVECPPCPAP PVAGPSVFLF  240
PPKPKDTLMI SRTPEVTCVV VDVSHEDPEV QFNWYVDGVE VHNAKTKPRE EQFNSTFRVV  300
SVLTVVHQDW LNGKEYKCKV SNKGLPAPIE KTISKTKGQP REPQVYTLPP SREEMTKNQV  360
SLTCLVKGFY PSDIAVEWES NGQPENNYKT TPPMLDSDGS FFLYSKLTVD KSRWQQGNVF  420
SCSVMHEALH NHYTQKSLSL SPGK                                        444

SEQ ID NO: 98           moltype = AA  length = 214
FEATURE                 Location/Qualifiers
REGION                  1..214
                        note = Synthetic light chain for 11D4
source                  1..214
                        mol_type = protein
                        organism = synthetic construct
SEQUENCE: 98
DIQMTQSPSS LSASVGDRVT ITCRASQGIS SWLAWYQQKP EKAPKSLIYA ASSLQSGVPS  60
RFSGSGSGTD FTLTISSLQP EDFATYYCQQ YNSYPPTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 99           moltype = AA  length = 118
FEATURE                 Location/Qualifiers
REGION                  1..118
                        note = Synthetic heavy chain variable region for 11D4
source                  1..118
                        mol_type = protein
                        organism = synthetic construct
SEQUENCE: 99
EVQLVESGGG LVQPGGSLRL SCAASGFTFS SYSMNWVRQA PGKGLEWVSY ISSSSSTIDY  60
ADSVKGRFTI SRDNAKNSLY LQMNSLRDED TAVYYCARES GWYLFDYWGQ GTLVTVSS    118

SEQ ID NO: 100          moltype = AA  length = 107
FEATURE                 Location/Qualifiers
REGION                  1..107
                        note = Synthetic light chain variable region for 11D4
source                  1..107
                        mol_type = protein
                        organism = synthetic construct
SEQUENCE: 100
DIQMTQSPSS LSASVGDRVT ITCRASQGIS SWLAWYQQKP EKAPKSLIYA ASSLQSGVPS  60
RFSGSGSGTD FTLTISSLQP EDFATYYCQQ YNSYPPTFGG GTKVEIK                107

SEQ ID NO: 101          moltype = AA  length = 5
FEATURE                 Location/Qualifiers
REGION                  1..5
                        note = Synthetic heavy chain CDR1 for 11D4
source                  1..5
                        mol_type = protein
                        organism = synthetic construct
SEQUENCE: 101
SYSMN                                                             5

SEQ ID NO: 102          moltype = AA  length = 17
FEATURE                 Location/Qualifiers
REGION                  1..17
                        note = Synthetic heavy chain CDR2 for 11D4
source                  1..17
                        mol_type = protein
                        organism = synthetic construct
SEQUENCE: 102
YISSSSSTID YADSVKG                                                17

SEQ ID NO: 103          moltype = AA  length = 9
FEATURE                 Location/Qualifiers
REGION                  1..9
                        note = Synthetic heavy chain CDR3 for 11D4
source                  1..9
                        mol_type = protein
                        organism = synthetic construct
SEQUENCE: 103
ESGWYLFDY                                                         9

SEQ ID NO: 104          moltype = AA  length = 11
FEATURE                 Location/Qualifiers
REGION                  1..11
                        note = Synthetic light chain CDR1 for 11D4
source                  1..11
                        mol_type = protein
                        organism = synthetic construct
```

-continued

```
SEQUENCE: 104
RASQGISSWL A                                                 11

SEQ ID NO: 105          moltype = AA  length = 7
FEATURE                 Location/Qualifiers
REGION                  1..7
                        note = Synthetic light chain CDR2 for 11D4
source                  1..7
                        mol_type = protein
                        organism = synthetic construct
SEQUENCE: 105
AASSLQS                                                      7

SEQ ID NO: 106          moltype = AA  length = 9
FEATURE                 Location/Qualifiers
REGION                  1..9
                        note = Synthetic light chain CDR3 for 11D4
source                  1..9
                        mol_type = protein
                        organism = synthetic construct
SEQUENCE: 106
QQYNSYPPT                                                    9

SEQ ID NO: 107          moltype = AA  length = 450
FEATURE                 Location/Qualifiers
REGION                  1..450
                        note = Synthetic heavy chain for 18D8
source                  1..450
                        mol_type = protein
                        organism = synthetic construct
SEQUENCE: 107
EVQLVESGGG LVQPGRSLRL SCAASGFTFD DYAMHWVRQA PGKGLEWVSG ISWNSGSIGY  60
ADSVKGRFTI SRDNAKNSLY LQMNSLRAED TALYYCAKDQ STADYYFYYG MDVWGQGTTV  120
TVSSASTKGP SVFPLAPCSR STSESTAALG CLVKDYFPEP VTVSWNSGAL TSGVHTFPAV  180
LQSSGLYSLS SVVTVPSSNF GTQTYTCNVD HKPSNTKVDK TVERKCCVEC PPCPAPPVAG  240
PSVFLFPPKP KDTLMISRTP EVTCVVVDVS HEDPEVQFNW YVDGVEVHNA KTKPREEQFN  300
STFRVVSVLT VVHQDWLNGK EYKCKVSNKG LPAPIEKTIS KTKGQPREPQ VYTLPPSREE  360
MTKNQVSLTC LVKGFYPSDI AVEWESNGQP ENNYKTTPPM LDSDGSFFLY SKLTVDKSRW  420
QQGNVFSCSV MHEALHNHYT QKSLSLSPGK                                450

SEQ ID NO: 108          moltype = AA  length = 213
FEATURE                 Location/Qualifiers
REGION                  1..213
                        note = Synthetic light chain for 18D8
source                  1..213
                        mol_type = protein
                        organism = synthetic construct
SEQUENCE: 108
EIVVTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWPTFGQG TKVEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                            213

SEQ ID NO: 109          moltype = AA  length = 124
FEATURE                 Location/Qualifiers
REGION                  1..124
                        note = Synthetic heavy chain variable region for 18D8
source                  1..124
                        mol_type = protein
                        organism = synthetic construct
SEQUENCE: 109
EVQLVESGGG LVQPGRSLRL SCAASGFTFD DYAMHWVRQA PGKGLEWVSG ISWNSGSIGY  60
ADSVKGRFTI SRDNAKNSLY LQMNSLRAED TALYYCAKDQ STADYYFYYG MDVWGQGTTV  120
TVSS                                                            124

SEQ ID NO: 110          moltype = AA  length = 106
FEATURE                 Location/Qualifiers
REGION                  1..106
                        note = Synthetic light chain variable region for 18D8
source                  1..106
                        mol_type = protein
                        organism = synthetic construct
SEQUENCE: 110
EIVVTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWPTFGQG TKVEIK              106

SEQ ID NO: 111          moltype = AA  length = 5
FEATURE                 Location/Qualifiers
REGION                  1..5
```

```
                        note = Synthetic heavy chain CDR1 for 18D8
source                  1..5
                        mol_type = protein
                        organism = synthetic construct
SEQUENCE: 111
DYAMH                                                                   5

SEQ ID NO: 112          moltype = AA  length = 17
FEATURE                 Location/Qualifiers
REGION                  1..17
                        note = Synthetic heavy chain CDR2 for 18D8
source                  1..17
                        mol_type = protein
                        organism = synthetic construct
SEQUENCE: 112
GISWNSGSIG YADSVKG                                                      17

SEQ ID NO: 113          moltype = AA  length = 15
FEATURE                 Location/Qualifiers
REGION                  1..15
                        note = Synthetic heavy chain CDR3 for 18D8
source                  1..15
                        mol_type = protein
                        organism = synthetic construct
SEQUENCE: 113
DQSTADYYFY YGMDV                                                        15

SEQ ID NO: 114          moltype = AA  length = 11
FEATURE                 Location/Qualifiers
REGION                  1..11
                        note = Synthetic light chain CDR1 for 18D8
source                  1..11
                        mol_type = protein
                        organism = synthetic construct
SEQUENCE: 114
RASQSVSSYL A                                                            11

SEQ ID NO: 115          moltype = AA  length = 7
FEATURE                 Location/Qualifiers
REGION                  1..7
                        note = Synthetic light chain CDR2 for 18D8
source                  1..7
                        mol_type = protein
                        organism = synthetic construct
SEQUENCE: 115
DASNRAT                                                                 7

SEQ ID NO: 116          moltype = AA  length = 8
FEATURE                 Location/Qualifiers
REGION                  1..8
                        note = Synthetic light chain CDR3 for 18D8
source                  1..8
                        mol_type = protein
                        organism = synthetic construct
SEQUENCE: 116
QQRSNWPT                                                                8

SEQ ID NO: 117          moltype = AA  length = 120
FEATURE                 Location/Qualifiers
REGION                  1..120
                        note = Synthetic heavy chain variable region for Hu119-122
source                  1..120
                        mol_type = protein
                        organism = synthetic construct
SEQUENCE: 117
EVQLVESGGG LVQPGGSLRL SCAASEYEFP SHDMSWVRQA PGKGLELVAA INSDGGSTYY  60
PDTMERRFTI SRDNAKNSLY LQMNSLRAED TAVYYCARHY DDYYAWFAYW GQGTMVTVSS  120

SEQ ID NO: 118          moltype = AA  length = 111
FEATURE                 Location/Qualifiers
REGION                  1..111
                        note = Synthetic light chain variable region for Hu119-122
source                  1..111
                        mol_type = protein
                        organism = synthetic construct
SEQUENCE: 118
EIVLTQSPAT LSLSPGERAT LSCRASKSVS TSGYSYMHWY QQKPGQAPRL LIYLASNLES  60
GVPARFSGSG SGTDFTLTIS SLEPEDFAVY YCQHSRELPL TFGGGTKVEI K           111
```

```
SEQ ID NO: 119          moltype = AA  length = 5
FEATURE                 Location/Qualifiers
REGION                  1..5
                        note = Synthetic heavy chain CDR1 for Hu119-122
source                  1..5
                        mol_type = protein
                        organism = synthetic construct
SEQUENCE: 119
SHDMS                                                                5

SEQ ID NO: 120          moltype = AA  length = 17
FEATURE                 Location/Qualifiers
REGION                  1..17
                        note = Synthetic heavy chain CDR2 for Hu119-122
source                  1..17
                        mol_type = protein
                        organism = synthetic construct
SEQUENCE: 120
AINSDGGSTY YPDTMER                                                   17

SEQ ID NO: 121          moltype = AA  length = 11
FEATURE                 Location/Qualifiers
REGION                  1..11
                        note = Synthetic heavy chain CDR3 for Hu119-122
source                  1..11
                        mol_type = protein
                        organism = synthetic construct
SEQUENCE: 121
HYDDYYAWFA Y                                                         11

SEQ ID NO: 122          moltype = AA  length = 15
FEATURE                 Location/Qualifiers
REGION                  1..15
                        note = Synthetic light chain CDR1 for Hu119-122
source                  1..15
                        mol_type = protein
                        organism = synthetic construct
SEQUENCE: 122
RASKSVSTSG YSYMH                                                     15

SEQ ID NO: 123          moltype = AA  length = 7
FEATURE                 Location/Qualifiers
REGION                  1..7
                        note = Synthetic light chain CDR2 for Hu119-122
source                  1..7
                        mol_type = protein
                        organism = synthetic construct
SEQUENCE: 123
LASNLES                                                              7

SEQ ID NO: 124          moltype = AA  length = 9
FEATURE                 Location/Qualifiers
REGION                  1..9
                        note = Synthetic light chain CDR3 for Hu119-122
source                  1..9
                        mol_type = protein
                        organism = synthetic construct
SEQUENCE: 124
QHSRELPLT                                                            9

SEQ ID NO: 125          moltype = AA  length = 122
FEATURE                 Location/Qualifiers
REGION                  1..122
                        note = Synthetic heavy chain variable region for Hu106-222
source                  1..122
                        mol_type = protein
                        organism = synthetic construct
SEQUENCE: 125
QVQLVQSGSE LKKPGASVKV SCKASGYTFT DYSMHWVRQA PGQGLKWMGW INTETGEPTY  60
ADDFKGRFVF SLDTSVSTAY LQISSLKAED TAVYYCANPY YDYVSYYAMD YWGQGTTVTV  120
SS                                                                   122

SEQ ID NO: 126          moltype = AA  length = 107
FEATURE                 Location/Qualifiers
REGION                  1..107
                        note = Synthetic light chain variable region for Hu106-222
source                  1..107
                        mol_type = protein
                        organism = synthetic construct
```

```
SEQUENCE: 126
DIQMTQSPSS LSASVGDRVT ITCKASQDVS TAVAWYQQKP GKAPKLLIYS ASYLYTGVPS  60
RFSGSGSGTD FTFTISSLQP EDIATYYCQQ HYSTPRTFGQ GTKLEIK               107

SEQ ID NO: 127         moltype = AA  length = 5
FEATURE                Location/Qualifiers
REGION                 1..5
                       note = Synthetic heavy chain CDR1 for Hu106-222
source                 1..5
                       mol_type = protein
                       organism = synthetic construct
SEQUENCE: 127
DYSMH                                                             5

SEQ ID NO: 128         moltype = AA  length = 17
FEATURE                Location/Qualifiers
REGION                 1..17
                       note = Synthetic heavy chain CDR2 for Hu106-222
source                 1..17
                       mol_type = protein
                       organism = synthetic construct
SEQUENCE: 128
WINTETGEPT YADDFKG                                                17

SEQ ID NO: 129         moltype = AA  length = 13
FEATURE                Location/Qualifiers
REGION                 1..13
                       note = Synthetic heavy chain CDR3 for Hu106-222
source                 1..13
                       mol_type = protein
                       organism = synthetic construct
SEQUENCE: 129
PYYDYVSYYA MDY                                                    13

SEQ ID NO: 130         moltype = AA  length = 11
FEATURE                Location/Qualifiers
REGION                 1..11
                       note = Synthetic light chain CDR1 for Hu106-222
source                 1..11
                       mol_type = protein
                       organism = synthetic construct
SEQUENCE: 130
KASQDVSTAV A                                                      11

SEQ ID NO: 131         moltype = AA  length = 7
FEATURE                Location/Qualifiers
REGION                 1..7
                       note = Synthetic light chain CDR2 for Hu106-222
source                 1..7
                       mol_type = protein
                       organism = synthetic construct
SEQUENCE: 131
SASYLYT                                                           7

SEQ ID NO: 132         moltype = AA  length = 9
FEATURE                Location/Qualifiers
REGION                 1..9
                       note = Synthetic light chain CDR3 for Hu106-222
source                 1..9
                       mol_type = protein
                       organism = synthetic construct
SEQUENCE: 132
QQHYSTPRT                                                         9

SEQ ID NO: 133         moltype = AA  length = 183
FEATURE                Location/Qualifiers
REGION                 1..183
                       note = Synthetic OX40L
source                 1..183
                       mol_type = protein
                       organism = synthetic construct
SEQUENCE: 133
MERVQPLEEN VGNAARPRFE RNKLLLVASV IQGLGLLLCF TYICLHFSAL QVSHRYPRIQ  60
SIKVQFTEYK KEKGFILTSQ KEDEIMKVQN NSVIINCDGF YLISLKGYFS QEVNISLHYQ  120
KDEEPLFQLK KVRSVNSLMV ASLTYKDKVY LNVTTDNTSL DDFHVNGGEL ILIHQNPGEF  180
CVL                                                               183

SEQ ID NO: 134         moltype = AA  length = 131
FEATURE                Location/Qualifiers
```

```
REGION                  1..131
                        note = Synthetic OX40L soluble domain
source                  1..131
                        mol_type = protein
                        organism = synthetic construct
SEQUENCE: 134
SHRYPRIQSI KVQFTEYKKE KGFILTSQKE DEIMKVQNNS VIINCDGFYL ISLKGYFSQE  60
VNISLHYQKD EEPLFQLKKV RSVNSLMVAS LTYKDKVYLN VTTDNTSLDD FHVNGGELIL  120
IHQNPGEFCV L                                                      131

SEQ ID NO: 135          moltype = AA  length = 128
FEATURE                 Location/Qualifiers
REGION                  1..128
                        note = Synthetic OX40L soluble domain (alternative)
source                  1..128
                        mol_type = protein
                        organism = synthetic construct
SEQUENCE: 135
YPRIQSIKVQ FTEYKKEKGF ILTSQKEDEI MKVQNNSVII NCDGFYLISL KGYFSQEVNI  60
SLHYQKDEEP LFQLKKVRSV NSLMVASLTY KDKVYLNVTT DNTSLDDFHV NGGELILIHQ  120
NPGEFCVL                                                          128

SEQ ID NO: 136          moltype = AA  length = 120
FEATURE                 Location/Qualifiers
REGION                  1..120
                        note = Synthetic variable heavy chain for 008
source                  1..120
                        mol_type = protein
                        organism = synthetic construct
SEQUENCE: 136
EVQLVESGGG LVQPGGSLRL SCAASGFTFS NYTMNWVRQA PGKGLEWVSA ISGSGGSTYY  60
ADSVKGRFTI SRDNSKNTLY LQMNSLRAED TAVYYCAKDR YSQVHYALDY WGQGTLVTVS  120

SEQ ID NO: 137          moltype = AA  length = 108
FEATURE                 Location/Qualifiers
REGION                  1..108
                        note = Synthetic variable light chain for 008
source                  1..108
                        mol_type = protein
                        organism = synthetic construct
SEQUENCE: 137
DIVMTQSPDS LPVTPGEPAS ISCRSSQSLL HSNGYNYLDW YLQKAGQSPQ LLIYLGSNRA  60
SGVPDRFSGS GSGTDFTLKI SRVEAEDVGV YYCQQYYNHP TTFGQGTK              108

SEQ ID NO: 138          moltype = AA  length = 120
FEATURE                 Location/Qualifiers
REGION                  1..120
                        note = Synthetic variable heavy chain for 011
source                  1..120
                        mol_type = protein
                        organism = synthetic construct
SEQUENCE: 138
EVQLVESGGG VVQPGRSLRL SCAASGFTFS DYTMNWVRQA PGKGLEWVSS ISGGSTYYAD  60
SRKGRFTISR DNSKNTLYLQ MNNLRAEDTA VYYCARDRYF RQQNAFDYWG QGTLVTVSSA  120

SEQ ID NO: 139          moltype = AA  length = 108
FEATURE                 Location/Qualifiers
REGION                  1..108
                        note = Synthetic variable light chain for 011
source                  1..108
                        mol_type = protein
                        organism = synthetic construct
SEQUENCE: 139
DIVMTQSPDS LPVTPGEPAS ISCRSSQSLL HSNGYNYLDW YLQKAGQSPQ LLIYLGSNRA  60
SGVPDRFSGS GSGTDFTLKI SRVEAEDVGV YYCQQYYNHP TTFGQGTK              108

SEQ ID NO: 140          moltype = AA  length = 120
FEATURE                 Location/Qualifiers
REGION                  1..120
                        note = Synthetic variable heavy chain for 021
source                  1..120
                        mol_type = protein
                        organism = synthetic construct
SEQUENCE: 140
EVQLVESGGG LVQPRGSLRL SCAASGFTFS SYAMNWVRQA PGKGLEWVAV ISYDGSNKYY  60
ADSVKGRFTI SRDNSKNTLY LQMNSLRAED TAVYYCAKDR YITLPNALDY WGQGTLVTVS  120

SEQ ID NO: 141          moltype = AA  length = 108
FEATURE                 Location/Qualifiers
```

```
REGION                  1..108
                        note = Synthetic variable light chain for 021
source                  1..108
                        mol_type = protein
                        organism = synthetic construct
SEQUENCE: 141
DIQMTQSPVS LPVTPGEPAS ISCRSSQSLL HSNGYNYLDW YLQKPGQSPQ LLIYLGSNRA  60
SGVPDRFSGS GSGTDFTLKI SRVEAEDVGV YYCQQYKSNP PTFGQGTK              108

SEQ ID NO: 142          moltype = AA  length = 120
FEATURE                 Location/Qualifiers
REGION                  1..120
                        note = Synthetic variable heavy chain for 023
source                  1..120
                        mol_type = protein
                        organism = synthetic construct
SEQUENCE: 142
EVQLVESGGG LVHPGGSLRL SCAGSGFTFS SYAMHWVRQA PGKGLEWVSA IGTGGGTYYA  60
DSVMGRFTIS RDNSKNTLYL QMNSLRAEDT AVYYCARYDN VMGLYWFDYW GQGTLVTVSS  120

SEQ ID NO: 143          moltype = AA  length = 108
FEATURE                 Location/Qualifiers
REGION                  1..108
                        note = Synthetic variable light chain for 023
source                  1..108
                        mol_type = protein
                        organism = synthetic construct
SEQUENCE: 143
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWPPAFGG GTKVEIKR              108

SEQ ID NO: 144          moltype = AA  length = 119
FEATURE                 Location/Qualifiers
REGION                  1..119
                        note = Synthetic heavy chain variable region
source                  1..119
                        mol_type = protein
                        organism = synthetic construct
SEQUENCE: 144
EVQLQQSGPE LVKPGASVKM SCKASGYTFT SYVMHWVKQK PGQGLEWIGY INPYNDGTKY  60
NEKFKGKATL TSDKSSSTAY MELSSLTSED SAVYYCANYY GSSLSMDYWG QGTSVTVSS   119

SEQ ID NO: 145          moltype = AA  length = 108
FEATURE                 Location/Qualifiers
REGION                  1..108
                        note = Synthetic light chain variable region
source                  1..108
                        mol_type = protein
                        organism = synthetic construct
SEQUENCE: 145
DIQMTQTTSS LSASLGDRVT ISCRASQDIS NYLNWYQQKP DGTVKLLIYY TSRLHSGVPS  60
RFSGSGSGTD YSLTISNLEQ EDIATYFCQQ GNTLPWTFGG GTKLEIKR              108

SEQ ID NO: 146          moltype = AA  length = 121
FEATURE                 Location/Qualifiers
REGION                  1..121
                        note = Synthetic heavy chain variable region
source                  1..121
                        mol_type = protein
                        organism = synthetic construct
SEQUENCE: 146
EVQLQQSGPE LVKPGASVKI SCKTSGYTFK DYTMHWVKQS HGKSLEWIGG IYPNNGGSTY  60
NQNFKDKATL TVDKSSSTAY MEFRSLTSED SAVYYCARMG YHGPHLDFDV WGAGTTVTVS  120
P                                                                 121

SEQ ID NO: 147          moltype = AA  length = 108
FEATURE                 Location/Qualifiers
REGION                  1..108
                        note = Synthetic light chain variable region
source                  1..108
                        mol_type = protein
                        organism = synthetic construct
SEQUENCE: 147
DIVMTQSHKF MSTSLGDRVS ITCKASQDVG AAVAWYQQKP GQSPKLLIYW ASTRHTGVPD  60
RFTGGGSGTD FTLTISNVQS EDLTDYFCQQ YINYPLTFGG GTKLEIKR              108

SEQ ID NO: 148          moltype = AA  length = 122
FEATURE                 Location/Qualifiers
REGION                  1..122
```

```
                        note = Synthetic heavy chain variable region of humanized
                         antibody
source                  1..122
                        mol_type = protein
                        organism = synthetic construct
SEQUENCE: 148
QIQLVQSGPE LKKPGETVKI SCKASGYTFT DYSMHWVKQA PGKGLKWMGW INTETGEPTY  60
ADDFKGRFAF SLETSASTAY LQINNLKNED TATYFCANPY YDYVSYYAMD YWGHGTSVTV  120
SS                                                                122

SEQ ID NO: 149          moltype = AA  length = 122
FEATURE                 Location/Qualifiers
REGION                  1..122
                        note = Synthetic heavy chain variable region of humanized
                         antibody
source                  1..122
                        mol_type = protein
                        organism = synthetic construct
SEQUENCE: 149
QVQLVQSGSE LKKPGASVKV SCKASGYTFT DYSMHWVRQA PGQGLKWMGW INTETGEPTY  60
ADDFKGRFVF SLDTSVSTAY LQISSLKAED TAVYYCANPY YDYVSYYAMD YWGQGTTVTV  120
SS                                                                122

SEQ ID NO: 150          moltype = AA  length = 107
FEATURE                 Location/Qualifiers
REGION                  1..107
                        note = Synthetic light chain variable region of humanized
                         antibody
source                  1..107
                        mol_type = protein
                        organism = synthetic construct
SEQUENCE: 150
DIVMTQSHKF MSTSVRDRVS ITCKASQDVS TAVAWYQQKP GQSPKLLIYS ASYLYTGVPD  60
RFTGSGSGTD FTFTISSVQA EDLAVYYCQQ HYSTPRTFGG GTKLEIK               107

SEQ ID NO: 151          moltype = AA  length = 107
FEATURE                 Location/Qualifiers
REGION                  1..107
                        note = Synthetic light chain variable region of humanized
                         antibody
source                  1..107
                        mol_type = protein
                        organism = synthetic construct
SEQUENCE: 151
DIVMTQSHKF MSTSVRDRVS ITCKASQDVS TAVAWYQQKP GQSPKLLIYS ASYLYTGVPD  60
RFTGSGSGTD FTFTISSVQA EDLAVYYCQQ HYSTPRTFGG GTKLEIK               107

SEQ ID NO: 152          moltype = AA  length = 120
FEATURE                 Location/Qualifiers
REGION                  1..120
                        note = Synthetic heavy chain variable region of humanized
                         antibody
source                  1..120
                        mol_type = protein
                        organism = synthetic construct
SEQUENCE: 152
EVQLVESGGG LVQPGESLKL SCESNEYEFP SHDMSWVRKT PEKRLELVAA INSDGGSTYY  60
PDTMERRFII SRDNTKKTLY LQMSSLRSED TALYYCARHY DDYYAWFAYW GQGTLVTVSA  120

SEQ ID NO: 153          moltype = AA  length = 120
FEATURE                 Location/Qualifiers
REGION                  1..120
                        note = Synthetic heavy chain variable region of humanized
                         antibody
source                  1..120
                        mol_type = protein
                        organism = synthetic construct
SEQUENCE: 153
EVQLVESGGG LVQPGGSLRL SCAASEYEFP SHDMSWVRQA PGKGLELVAA INSDGGSTYY  60
PDTMERRFTI SRDNAKNSLY LQMNSLRAED TAVYYCARHY DDYYAWFAYW GQGTMVTVSS  120

SEQ ID NO: 154          moltype = AA  length = 111
FEATURE                 Location/Qualifiers
REGION                  1..111
                        note = Synthetic light chain variable region of humanized
                         antibody
source                  1..111
                        mol_type = protein
                        organism = synthetic construct
```

```
SEQUENCE: 154
DIVLTQSPAS LAVSLGQRAT ISCRASKSVS TSGYSYMHWY QQKPGQPPKL LIYLASNLES  60
GVPARFSGSG SGTDFTLNIH PVEEEDAATY YCQHSRELPL TFGAGTKLEL K           111

SEQ ID NO: 155         moltype = AA  length = 111
FEATURE                Location/Qualifiers
REGION                 1..111
                       note = Synthetic light chain variable region of humanized
                        antibody
source                 1..111
                       mol_type = protein
                       organism = synthetic construct
SEQUENCE: 155
EIVLTQSPAT LSLSPGERAT LSCRASKSVS TSGYSYMHWY QQKPGQAPRL LIYLASNLES  60
GVPARFSGSG SGTDFTLTIS SLEPEDFAVY YCQHSRELPL TFGGGTKVEI K           111

SEQ ID NO: 156         moltype = AA  length = 138
FEATURE                Location/Qualifiers
REGION                 1..138
                       note = Synthetic heavy chain variable region
source                 1..138
                       mol_type = protein
                       organism = synthetic construct
SEQUENCE: 156
MYLGLNYVFI VFLLNGVQSE VKLEESGGGL VQPGGSMKLS CAASGFTFSD AWMDWVRQSP  60
EKGLEWVAEI RSKANNHATY YAESVNGRFT ISRDDSKSSV YLQMNSLRAE DTGIYYCTWG  120
EVFYFDYWGQ GTTLTVSS                                                138

SEQ ID NO: 157         moltype = AA  length = 126
FEATURE                Location/Qualifiers
REGION                 1..126
                       note = Synthetic light chain variable region
source                 1..126
                       mol_type = protein
                       organism = synthetic construct
SEQUENCE: 157
MRPSIQFLGL LLFWLHGAQC DIQMTQSPSS LSASLGGKVT ITCKSSQDIN KYIAWYQHKP  60
GKGPRLLIHY TSTLQPGIPS RFSGSGSGRD YSFSISNLEP EDIATYYCLQ YDNLLTFGAG  120
TKLELK                                                             126

SEQ ID NO: 158         moltype = AA  length = 440
FEATURE                Location/Qualifiers
REGION                 1..440
                       note = Synthetic nivolumab heavy chain
source                 1..440
                       mol_type = protein
                       organism = synthetic construct
SEQUENCE: 158
QVQLVESGGG VVQPGRSLRL DCKASGITFS NSGMHWVRQA PGKGLEWVAV IWYDGSKRYY  60
ADSVKGRFTI SRDNSKNTLF LQMNSLRAED TAVYYCATND DYWGQGTLVT VSSASTKGPS  120
VFPLAPCSRS TSESTAALGC LVKDYFPEPV TVSWNSGALT SGVHTFPAVL QSSGLYSLSS  180
VVTVPSSSLG TKTYTCNVDH KPSNTKVDKR VESKYGPPCP PCPAPEFLGG PSVFLFPPKP  240
KDTLMISRTP EVTCVVVDVS QEDPEVQFNW YVDGVEVHNA KTKPREEQFN STYRVVSVLT  300
VLHQDWLNGK EYKCKVSNKG LPSSIEKTIS KAKGQPREPQ VYTLPPSQEE MTKNQVSLTC  360
LVKGFYPSDI AVEWESNGQP ENNYKTTPPV LDSDGSFFLY SRLTVDKSRW QEGNVFSCSV  420
MHEALHNHYT QKSLSLSLGK                                              440

SEQ ID NO: 159         moltype = AA  length = 214
FEATURE                Location/Qualifiers
REGION                 1..214
                       note = Synthetic nivolumab light chain
source                 1..214
                       mol_type = protein
                       organism = synthetic construct
SEQUENCE: 159
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ SSNWPRTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 160         moltype = AA  length = 113
FEATURE                Location/Qualifiers
REGION                 1..113
                       note = Synthetic nivolumab variable heavy chain
source                 1..113
                       mol_type = protein
                       organism = synthetic construct
SEQUENCE: 160
QVQLVESGGG VVQPGRSLRL DCKASGITFS NSGMHWVRQA PGKGLEWVAV IWYDGSKRYY  60
```

```
ADSVKGRFTI SRDNSKNTLF LQMNSLRAED TAVYYCATND DYWGQGTLVT VSS         113

SEQ ID NO: 161          moltype = AA  length = 107
FEATURE                 Location/Qualifiers
REGION                  1..107
                        note = Synthetic nivolumab variable light chain
source                  1..107
                        mol_type = protein
                        organism = synthetic construct
SEQUENCE: 161
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ SSNWPRTFGQ GTKVEIK                107

SEQ ID NO: 162          moltype = AA  length = 5
FEATURE                 Location/Qualifiers
REGION                  1..5
                        note = Synthetic nivolumab heavy chain CDR1
source                  1..5
                        mol_type = protein
                        organism = synthetic construct
SEQUENCE: 162
NSGMH                                                              5

SEQ ID NO: 163          moltype = AA  length = 17
FEATURE                 Location/Qualifiers
REGION                  1..17
                        note = Synthetic nivolumab heavy chain CDR2
source                  1..17
                        mol_type = protein
                        organism = synthetic construct
SEQUENCE: 163
VIWYDGSKRY YADSVKG                                                 17

SEQ ID NO: 164          moltype = AA  length = 4
FEATURE                 Location/Qualifiers
REGION                  1..4
                        note = Synthetic nivolumab heavy chain CDR3
source                  1..4
                        mol_type = protein
                        organism = synthetic construct
SEQUENCE: 164
NDDY                                                               4

SEQ ID NO: 165          moltype = AA  length = 11
FEATURE                 Location/Qualifiers
REGION                  1..11
                        note = Synthetic nivolumab light chain CDR1
source                  1..11
                        mol_type = protein
                        organism = synthetic construct
SEQUENCE: 165
RASQSVSSYL A                                                       11

SEQ ID NO: 166          moltype = AA  length = 7
FEATURE                 Location/Qualifiers
REGION                  1..7
                        note = Synthetic nivolumab light chain CDR2
source                  1..7
                        mol_type = protein
                        organism = synthetic construct
SEQUENCE: 166
DASNRAT                                                            7

SEQ ID NO: 167          moltype = AA  length = 9
FEATURE                 Location/Qualifiers
REGION                  1..9
                        note = Synthetic nivolumab light chain CDR3
source                  1..9
                        mol_type = protein
                        organism = synthetic construct
SEQUENCE: 167
QQSSNWPRT                                                          9

SEQ ID NO: 168          moltype = AA  length = 447
FEATURE                 Location/Qualifiers
REGION                  1..447
                        note = Synthetic pembrolizumab heavy chain
source                  1..447
                        mol_type = protein
```

```
                          organism = synthetic construct
SEQUENCE: 168
QVQLVQSGVE VKKPGASVKV SCKASGYTFT NYYMYWVRQA PGQGLEWMGG INPSNGGTNF  60
NEKFKNRVTL TTDSSTTTAY MELKSLQFDD TAVYYCARRD YRFDMGFDYW GQGTTVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
NVFSCSVMHE ALHNHYTQKS LSLSLGK                                     447

SEQ ID NO: 169            moltype = AA  length = 218
FEATURE                   Location/Qualifiers
REGION                    1..218
                          note = Synthetic pembrolizumab light chain
source                    1..218
                          mol_type = protein
                          organism = synthetic construct
SEQUENCE: 169
EIVLTQSPAT LSLSPGERAT LSCRASKGVS TSGYSYLHWY QQKPGQAPRL LIYLASYLES  60
GVPARFSGSG SGTDFTLTIS SLEPEDFAVY YCQHSRDLPL TFGGGTKVEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                         218

SEQ ID NO: 170            moltype = AA  length = 120
FEATURE                   Location/Qualifiers
REGION                    1..120
                          note = Synthetic pembrolizumab variable heavy chain
source                    1..120
                          mol_type = protein
                          organism = synthetic construct
SEQUENCE: 170
QVQLVQSGVE VKKPGASVKV SCKASGYTFT NYYMYWVRQA PGQGLEWMGG INPSNGGTNF  60
NEKFKNRVTL TTDSSTTTAY MELKSLQFDD TAVYYCARRD YRFDMGFDYW GQGTTVTVSS  120

SEQ ID NO: 171            moltype = AA  length = 111
FEATURE                   Location/Qualifiers
REGION                    1..111
                          note = Synthetic pembrolizumab variable light chain
source                    1..111
                          mol_type = protein
                          organism = synthetic construct
SEQUENCE: 171
EIVLTQSPAT LSLSPGERAT LSCRASKGVS TSGYSYLHWY QQKPGQAPRL LIYLASYLES  60
GVPARFSGSG SGTDFTLTIS SLEPEDFAVY YCQHSRDLPL TFGGGTKVEI K           111

SEQ ID NO: 172            moltype = AA  length = 5
FEATURE                   Location/Qualifiers
REGION                    1..5
                          note = Synthetic pembrolizumab heavy chain CDR1
source                    1..5
                          mol_type = protein
                          organism = synthetic construct
SEQUENCE: 172
NYYMY                                                             5

SEQ ID NO: 173            moltype = AA  length = 16
FEATURE                   Location/Qualifiers
REGION                    1..16
                          note = Synthetic pembrolizumab heavy chain CDR2
source                    1..16
                          mol_type = protein
                          organism = synthetic construct
SEQUENCE: 173
GINPSNGGTN FNEKFK                                                 16

SEQ ID NO: 174            moltype = AA  length = 11
FEATURE                   Location/Qualifiers
REGION                    1..11
                          note = Synthetic pembrolizumab heavy chain CDR3
source                    1..11
                          mol_type = protein
                          organism = synthetic construct
SEQUENCE: 174
RDYRFDMGFD Y                                                      11

SEQ ID NO: 175            moltype = AA  length = 15
FEATURE                   Location/Qualifiers
REGION                    1..15
```

```
                        note = Synthetic pembrolizumab light chain CDR1
source                  1..15
                        mol_type = protein
                        organism = synthetic construct
SEQUENCE: 175
RASKGVSTSG YSYLH                                                  15

SEQ ID NO: 176          moltype = AA  length = 7
FEATURE                 Location/Qualifiers
REGION                  1..7
                        note = Synthetic pembrolizumab light chain CDR2
source                  1..7
                        mol_type = protein
                        organism = synthetic construct
SEQUENCE: 176
LASYLES                                                           7

SEQ ID NO: 177          moltype = AA  length = 9
FEATURE                 Location/Qualifiers
REGION                  1..9
                        note = Synthetic pembrolizumab light chain CDR3
source                  1..9
                        mol_type = protein
                        organism = synthetic construct
SEQUENCE: 177
QHSRDLPLT                                                         9

SEQ ID NO: 178          moltype = AA  length = 451
FEATURE                 Location/Qualifiers
REGION                  1..451
                        note = Synthetic durvalumab heavy chain
source                  1..451
                        mol_type = protein
                        organism = synthetic construct
SEQUENCE: 178
EVQLVESGGG LVQPGGSLRL SCAASGFTFS RYWMSWVRQA PGKGLEWVAN IKQDGSEKYY  60
VDSVKGRFTI SRDNAKNSLY LQMNSLRAED TAVYYCAREG GWFGELAFDY WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKRVE PKSCDKTHTC PPCPAPEFEG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPASIEKTI SKAKGQPREP QVYTLPPSRE  360
EMTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                451

SEQ ID NO: 179          moltype = AA  length = 265
FEATURE                 Location/Qualifiers
REGION                  1..265
                        note = Synthetic durvalumab light chain
source                  1..265
                        mol_type = protein
                        organism = synthetic construct
SEQUENCE: 179
EVQLVESGGG LVQPGGSLRL SCAASGFTFS RYWMSWVRQA PGKGLEWVAN EIVLTQSPGT  60
LSLSPGERAT LSCRASQRVS SSYLAWYQQK PGQAPRLLIY DASSRATGIP DRFSGSGSGT  120
DFTLTISRLE PEDFAVYYCQ QYGSLPWTFG QGTKVEIKRT VAAPSVFIFP PSDEQLKSGT  180
ASVVCLLNNF YPREAKVQWK VDNALQSGNS QESVTEQDSK DSTYSLSSTL TLSKADYEKH  240
KVYACEVTHQ GLSSPVTKSF NRGEC                                       265

SEQ ID NO: 180          moltype = AA  length = 121
FEATURE                 Location/Qualifiers
REGION                  1..121
                        note = Synthetic durvalumab variable heavy chain
source                  1..121
                        mol_type = protein
                        organism = synthetic construct
SEQUENCE: 180
EVQLVESGGG LVQPGGSLRL SCAASGFTFS RYWMSWVRQA PGKGLEWVAN IKQDGSEKYY  60
VDSVKGRFTI SRDNAKNSLY LQMNSLRAED TAVYYCAREG GWFGELAFDY WGQGTLVTVS  120
S                                                                 121

SEQ ID NO: 181          moltype = AA  length = 108
FEATURE                 Location/Qualifiers
REGION                  1..108
                        note = Synthetic durvalumab variable light chain
source                  1..108
                        mol_type = protein
                        organism = synthetic construct
SEQUENCE: 181
EIVLTQSPGT LSLSPGERAT LSCRASQRVS SSYLAWYQQK PGQAPRLLIY DASSRATGIP  60
```

```
DRFSGSGSGT DFTLTISRLE PEDFAVYYCQ QYGSLPWTFG QGTKVEIK              108

SEQ ID NO: 182         moltype = AA  length = 5
FEATURE                Location/Qualifiers
REGION                 1..5
                       note = Synthetic durvalumab heavy chain CDR1
source                 1..5
                       mol_type = protein
                       organism = synthetic construct
SEQUENCE: 182
RYWMS                                                             5

SEQ ID NO: 183         moltype = AA  length = 17
FEATURE                Location/Qualifiers
REGION                 1..17
                       note = Synthetic durvalumab heavy chain CDR2
source                 1..17
                       mol_type = protein
                       organism = synthetic construct
SEQUENCE: 183
NIKQDGSEKY YVDSVKG                                                17

SEQ ID NO: 184         moltype = AA  length = 12
FEATURE                Location/Qualifiers
REGION                 1..12
                       note = Synthetic durvalumab heavy chain CDR3
source                 1..12
                       mol_type = protein
                       organism = synthetic construct
SEQUENCE: 184
EGGWFGELAF DY                                                     12

SEQ ID NO: 185         moltype = AA  length = 12
FEATURE                Location/Qualifiers
REGION                 1..12
                       note = Synthetic durvalumab light chain CDR1
source                 1..12
                       mol_type = protein
                       organism = synthetic construct
SEQUENCE: 185
RASQRVSSSY LA                                                     12

SEQ ID NO: 186         moltype = AA  length = 7
FEATURE                Location/Qualifiers
REGION                 1..7
                       note = Synthetic durvalumab light chain CDR2
source                 1..7
                       mol_type = protein
                       organism = synthetic construct
SEQUENCE: 186
DASSRAT                                                           7

SEQ ID NO: 187         moltype = AA  length = 9
FEATURE                Location/Qualifiers
REGION                 1..9
                       note = Synthetic durvalumab light chain CDR3
source                 1..9
                       mol_type = protein
                       organism = synthetic construct
SEQUENCE: 187
QQYGSLPWT                                                         9

SEQ ID NO: 188         moltype = AA  length = 450
FEATURE                Location/Qualifiers
REGION                 1..450
                       note = Synthetic avelumab heavy chain
source                 1..450
                       mol_type = protein
                       organism = synthetic construct
SEQUENCE: 188
EVQLLESGGG LVQPGGSLRL SCAASGFTFS SYIMMWVRQA PGKGLEWVSS IYPSGGITFY  60
ADTVKGRFTI SRDNSKNTLY LQMNSLRAED TAVYYCARIK LGTVTTVDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                  450
```

```
SEQ ID NO: 189         moltype = AA  length = 216
FEATURE                Location/Qualifiers
REGION                 1..216
                       note = Synthetic avelumab light chain
source                 1..216
                       mol_type = protein
                       organism = synthetic construct
SEQUENCE: 189
QSALTQPASV SGSPGQSITI SCTGTSSDVG GYNYVSWYQQ HPGKAPKLMI YDVSNRPSGV  60
SNRFSGSKSG NTASLTISGL QAEDEADYYC SSYTSSSTRV FGTGTKVTVL GQPKANPTVT  120
LFPPSSEELQ ANKATLVCLI SDFYPGAVTV AWKADGSPVK AGVETTKPSK QSNNKYAASS  180
YLSLTPEQWK SHRSYSCQVT HEGSTVEKTV APTECS                            216

SEQ ID NO: 190         moltype = AA  length = 120
FEATURE                Location/Qualifiers
REGION                 1..120
                       note = Synthetic avelumab variable heavy chain
source                 1..120
                       mol_type = protein
                       organism = synthetic construct
SEQUENCE: 190
EVQLLESGGG LVQPGGSLRL SCAASGFTFS SYIMMWVRQA PGKGLEWVSS IYPSGGITFY  60
ADTVKGRFTI SRDNSKNTLY LQMNSLRAED TAVYYCARIK LGTVTTVDYW GQGTLVTVSS  120

SEQ ID NO: 191         moltype = AA  length = 110
FEATURE                Location/Qualifiers
REGION                 1..110
                       note = Synthetic avelumab variable light chain
source                 1..110
                       mol_type = protein
                       organism = synthetic construct
SEQUENCE: 191
QSALTQPASV SGSPGQSITI SCTGTSSDVG GYNYVSWYQQ HPGKAPKLMI YDVSNRPSGV  60
SNRFSGSKSG NTASLTISGL QAEDEADYYC SSYTSSSTRV FGTGTKVTVL            110

SEQ ID NO: 192         moltype = AA  length = 5
FEATURE                Location/Qualifiers
REGION                 1..5
                       note = Synthetic avelumab heavy chain CDR1
source                 1..5
                       mol_type = protein
                       organism = synthetic construct
SEQUENCE: 192
SYIMM                                                              5

SEQ ID NO: 193         moltype = AA  length = 17
FEATURE                Location/Qualifiers
REGION                 1..17
                       note = Synthetic avelumab heavy chain CDR2
source                 1..17
                       mol_type = protein
                       organism = synthetic construct
SEQUENCE: 193
SIYPSGGITF YADTVKG                                                 17

SEQ ID NO: 194         moltype = AA  length = 11
FEATURE                Location/Qualifiers
REGION                 1..11
                       note = Synthetic avelumab heavy chain CDR3
source                 1..11
                       mol_type = protein
                       organism = synthetic construct
SEQUENCE: 194
IKLGTVTTVD Y                                                       11

SEQ ID NO: 195         moltype = AA  length = 14
FEATURE                Location/Qualifiers
REGION                 1..14
                       note = Synthetic avelumab light chain CDR1
source                 1..14
                       mol_type = protein
                       organism = synthetic construct
SEQUENCE: 195
TGTSSDVGGY NYVS                                                    14

SEQ ID NO: 196         moltype = AA  length = 7
FEATURE                Location/Qualifiers
REGION                 1..7
                       note = Synthetic avelumab light chain CDR2
```

```
source                  1..7
                        mol_type = protein
                        organism = synthetic construct
SEQUENCE: 196
DVSNRPS                                                             7

SEQ ID NO: 197          moltype = AA  length = 10
FEATURE                 Location/Qualifiers
REGION                  1..10
                        note = Synthetic avelumab light chain CDR3
source                  1..10
                        mol_type = protein
                        organism = synthetic construct
SEQUENCE: 197
SSYTSSSTRV                                                          10

SEQ ID NO: 198          moltype = AA  length = 448
FEATURE                 Location/Qualifiers
REGION                  1..448
                        note = Synthetic atezolizumab heavy chain
source                  1..448
                        mol_type = protein
                        organism = synthetic construct
SEQUENCE: 198
EVQLVESGGG LVQPGGSLRL SCAASGFTFS DSWIHWVRQA PGKGLEWVAW ISPYGGSTYY  60
ADSVKGRFTI SADTSKNTAY LQMNSLRAED TAVYYCARRH WPGGFDYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPELLGGPS  240
VFLFPPKPKD TLMISRTPEV TCVVVDVSHE DPEVKFNWYV DGVEVHNAKT KPREEQYAST  300
YRVVSVLTVL HQDWLNGKEY KCKVSNKALP APIEKTISKA KGQPREPQVY TLPPSREEMT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                      448

SEQ ID NO: 199          moltype = AA  length = 214
FEATURE                 Location/Qualifiers
REGION                  1..214
                        note = Synthetic atezolizumab light chain
source                  1..214
                        mol_type = protein
                        organism = synthetic construct
SEQUENCE: 199
DIQMTQSPSS LSASVGDRVT ITCRASQDVS TAVAWYQQKP GKAPKLLIYS ASFLYSGVPS  60
RFSGSGSGTD FTLTISSLQP EDFATYYCQQ YLYHPATFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                                214

SEQ ID NO: 200          moltype = AA  length = 118
FEATURE                 Location/Qualifiers
REGION                  1..118
                        note = Synthetic atezolizumab variable heavy chain
source                  1..118
                        mol_type = protein
                        organism = synthetic construct
SEQUENCE: 200
EVQLVESGGG LVQPGGSLRL SCAASGFTFS DSWIHWVRQA PGKGLEWVAW ISPYGGSTYY  60
ADSVKGRFTI SADTSKNTAY LQMNSLRAED TAVYYCARRH WPGGFDYWGQ GTLVTVSA    118

SEQ ID NO: 201          moltype = AA  length = 108
FEATURE                 Location/Qualifiers
REGION                  1..108
                        note = Synthetic atezolizumab variable light chain
source                  1..108
                        mol_type = protein
                        organism = synthetic construct
SEQUENCE: 201
DIQMTQSPSS LSASVGDRVT ITCRASQDVS TAVAWYQQKP GKAPKLLIYS ASFLYSGVPS  60
RFSGSGSGTD FTLTISSLQP EDFATYYCQQ YLYHPATFGQ GTKVEIKR              108

SEQ ID NO: 202          moltype = AA  length = 10
FEATURE                 Location/Qualifiers
REGION                  1..10
                        note = Synthetic atezolizumab heavy chain CDR1
source                  1..10
                        mol_type = protein
                        organism = synthetic construct
SEQUENCE: 202
GFTFSDSWIH                                                          10

SEQ ID NO: 203          moltype = AA  length = 18
```

```
FEATURE                Location/Qualifiers
REGION                 1..18
                       note = Synthetic atezolizumab heavy chain CDR2
source                 1..18
                       mol_type = protein
                       organism = synthetic construct
SEQUENCE: 203
AWISPYGGST YYADSVKG                                              18

SEQ ID NO: 204         moltype = AA  length = 9
FEATURE                Location/Qualifiers
REGION                 1..9
                       note = Synthetic atezolizumab heavy chain CDR3
source                 1..9
                       mol_type = protein
                       organism = synthetic construct
SEQUENCE: 204
RHWPGGFDY                                                        9

SEQ ID NO: 205         moltype = AA  length = 11
FEATURE                Location/Qualifiers
REGION                 1..11
                       note = Synthetic atezolizumab light chain CDR1
source                 1..11
                       mol_type = protein
                       organism = synthetic construct
SEQUENCE: 205
RASQDVSTAV A                                                     11

SEQ ID NO: 206         moltype = AA  length = 7
FEATURE                Location/Qualifiers
REGION                 1..7
                       note = Synthetic atezolizumab light chain CDR2
source                 1..7
                       mol_type = protein
                       organism = synthetic construct
SEQUENCE: 206
SASFLYS                                                          7

SEQ ID NO: 207         moltype = AA  length = 9
FEATURE                Location/Qualifiers
REGION                 1..9
                       note = Synthetic atezolizumab light chain CDR3
source                 1..9
                       mol_type = protein
                       organism = synthetic construct
SEQUENCE: 207
QQYLYHPAT                                                        9

SEQ ID NO: 208         moltype = AA  length = 225
FEATURE                Location/Qualifiers
REGION                 1..225
                       note = Synthetic ipilimumab heavy chain
source                 1..225
                       mol_type = protein
                       organism = synthetic construct
SEQUENCE: 208
QVQLVESGGG VVQPGRSLRL SCAASGFTFS SYTMHWVRQA PGKGLEWVTF ISYDGNNKYY  60
ADSVKGRFTI SRDNSKNTLY LQMNSLRAED TAIYYCARTG WLGPFDYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKRVEPKS CDKTH                  225

SEQ ID NO: 209         moltype = AA  length = 215
FEATURE                Location/Qualifiers
REGION                 1..215
                       note = Synthetic ipilimumab light chain
source                 1..215
                       mol_type = protein
                       organism = synthetic construct
SEQUENCE: 209
EIVLTQSPGT LSLSPGERAT LSCRASQSVG SSYLAWYQQK PGQAPRLLIY GAFSRATGIP  60
DRFSGSGSGT DFTLTISRLE PEDFAVYYCQ QYGSSPWTFG QGTKVEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                             215

SEQ ID NO: 210         moltype = AA  length = 118
FEATURE                Location/Qualifiers
REGION                 1..118
                       note = Synthetic ipilimumab variable heavy chain
```

```
source                 1..118
                       mol_type = protein
                       organism = synthetic construct
SEQUENCE: 210
QVQLVESGGG VVQPGRSLRL SCAASGFTFS SYTMHWVRQA PGKGLEWVTF ISYDGNNKYY  60
ADSVKGRFTI SRDNSKNTLY LQMNSLRAED TAIYYCARTG WLGPFDYWGQ GTLVTVSS    118

SEQ ID NO: 211         moltype = AA  length = 108
FEATURE                Location/Qualifiers
REGION                 1..108
                       note = Synthetic ipilimumab variable light chain
source                 1..108
                       mol_type = protein
                       organism = synthetic construct
SEQUENCE: 211
EIVLTQSPGT LSLSPGERAT LSCRASQSVG SSYLAWYQQK PGQAPRLLIY GAFSRATGIP  60
DRFSGSGSGT DFTLTISRLE PEDFAVYYCQ QYGSSPWTFG QGTKVEIK               108

SEQ ID NO: 212         moltype = AA  length = 8
FEATURE                Location/Qualifiers
REGION                 1..8
                       note = Synthetic ipilimumab heavy chain CDR1
source                 1..8
                       mol_type = protein
                       organism = synthetic construct
SEQUENCE: 212
GFTFSSYT                                                           8

SEQ ID NO: 213         moltype = AA  length = 10
FEATURE                Location/Qualifiers
REGION                 1..10
                       note = Synthetic ipilimumab heavy chain CDR2
source                 1..10
                       mol_type = protein
                       organism = synthetic construct
SEQUENCE: 213
TFISYDGNNK                                                         10

SEQ ID NO: 214         moltype = AA  length = 11
FEATURE                Location/Qualifiers
REGION                 1..11
                       note = Synthetic ipilimumab heavy chain CDR3
source                 1..11
                       mol_type = protein
                       organism = synthetic construct
SEQUENCE: 214
ARTGWLGPFD Y                                                       11

SEQ ID NO: 215         moltype = AA  length = 7
FEATURE                Location/Qualifiers
REGION                 1..7
                       note = Synthetic ipilimumab light chain CDR1
source                 1..7
                       mol_type = protein
                       organism = synthetic construct
SEQUENCE: 215
QSVGSSY                                                            7

SEQ ID NO: 216         moltype =   length =
SEQUENCE: 216
000

SEQ ID NO: 217         moltype = AA  length = 9
FEATURE                Location/Qualifiers
REGION                 1..9
                       note = Synthetic ipilimumab light chain CDR3
source                 1..9
                       mol_type = protein
                       organism = synthetic construct
SEQUENCE: 217
QQYGSSPWT                                                          9

SEQ ID NO: 218         moltype = AA  length = 451
FEATURE                Location/Qualifiers
REGION                 1..451
                       note = Synthetic tremelimumab heavy chain
source                 1..451
                       mol_type = protein
                       organism = synthetic construct
```

```
SEQUENCE: 218
QVQLVESGGG VVQPGRSLRL SCAASGFTFS SYGMHWVRQA PGKGLEWVAV IWYDGSNKYY  60
ADSVKGRFTI SRDNSKNTLY LQMNSLRAED TAVYYCARDP RGATLYYYYY GMDVWGQGTT  120
VTVSSASTKG PSVFPLAPCS RSTSESTAAL GCLVKDYFPE PVTVSWNSGA LTSGVHTFPA  180
VLQSSGLYSL SSVVTVPSSN FGTQTYTCNV DHKPSNTKVD KTVERKCCVE CPPCPAPPVA  240
GPSVFLFPPK PKDTLMISRT PEVTCVVVDV SHEDPEVQFN WYVDGVEVHN AKTKPREEQF  300
NSTFRVVSVL TVVHQDWLNG KEYKCKVSNK GLPAPIEKTI SKTKGQPREP QVYTLPPSRE  360
EMTKNQVSLT CLVKGFYPSD IAVEWESNGQ PENNYKTTPP MLDSDGSFFL YSKLTVDKSR  420
WQQGNVFSCS VMHEALHNHY TQKSLSLSPG K                                 451

SEQ ID NO: 219         moltype = AA  length = 214
FEATURE                Location/Qualifiers
REGION                 1..214
                       note = Synthetic tremelimumab light chain
source                 1..214
                       mol_type = protein
                       organism = synthetic construct
SEQUENCE: 219
DIQMTQSPSS LSASVGDRVT ITCRASQSIN SYLDWYQQKP GKAPKLLIYA ASSLQSGVPS  60
RFSGSGSGTD FTLTISSLQP EDFATYYCQQ YYSTPFTFGP GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 220         moltype = AA  length = 167
FEATURE                Location/Qualifiers
REGION                 1..167
                       note = Synthetic tremelimumab variable heavy chain
source                 1..167
                       mol_type = protein
                       organism = synthetic construct
SEQUENCE: 220
GVVQPGRSLR LSCAASGFTF SSYGMHWVRQ APGKGLEWVA VIWYDGSNKY YADSVKGRFT  60
ISRDNSKNTL YLQMNSLRAE DTAVYYCARD PRGATLYYYY YGMDVWGQGT TVTVSSASTK  120
GPSVFPLAPC SRSTSESTAA LGCLVKDYFP EPVTVSWNSG ALTSGVH                167

SEQ ID NO: 221         moltype = AA  length = 139
FEATURE                Location/Qualifiers
REGION                 1..139
                       note = Synthetic tremelimumab variable light chain
source                 1..139
                       mol_type = protein
                       organism = synthetic construct
SEQUENCE: 221
PSSLSASVGD RVTITCRASQ SINSYLDWYQ QKPGKAPKLL IYAASSLQSG VPSRFSGSGS  60
GTDFTLTISS LQPEDFATYY CQQYYSTPFT FGPGTKVEIK RTVAAPSVFI FPPSDEQLKS  120
GTASVVCLLN NFYPREAKV                                               139

SEQ ID NO: 222         moltype = AA  length = 10
FEATURE                Location/Qualifiers
REGION                 1..10
                       note = Synthetic tremelimumab heavy chain CDR1
source                 1..10
                       mol_type = protein
                       organism = synthetic construct
SEQUENCE: 222
GFTFSSYGMH                                                        10

SEQ ID NO: 223         moltype = AA  length = 15
FEATURE                Location/Qualifiers
REGION                 1..15
                       note = Synthetic tremelimumab heavy chain CDR2
source                 1..15
                       mol_type = protein
                       organism = synthetic construct
SEQUENCE: 223
VIWYDGSNKY YADSV                                                  15

SEQ ID NO: 224         moltype = AA  length = 16
FEATURE                Location/Qualifiers
REGION                 1..16
                       note = Synthetic tremelimumab heavy chain CDR3
source                 1..16
                       mol_type = protein
                       organism = synthetic construct
SEQUENCE: 224
DPRGATLYYY YYGMDV                                                 16

SEQ ID NO: 225         moltype = AA  length = 11
FEATURE                Location/Qualifiers
```

```
REGION                  1..11
                        note = Synthetic tremelimumab light chain CDR1
source                  1..11
                        mol_type = protein
                        organism = synthetic construct
SEQUENCE: 225
RASQSINSYL D                                                     11

SEQ ID NO: 226          moltype = AA  length = 7
FEATURE                 Location/Qualifiers
REGION                  1..7
                        note = Synthetic tremelimumab light chain CDR2
source                  1..7
                        mol_type = protein
                        organism = synthetic construct
SEQUENCE: 226
AASSLQS                                                          7

SEQ ID NO: 227          moltype = AA  length = 9
FEATURE                 Location/Qualifiers
REGION                  1..9
                        note = Synthetic tremelimumab light chain CDR3
source                  1..9
                        mol_type = protein
                        organism = synthetic construct
SEQUENCE: 227
QQYYSTPFT                                                        9

SEQ ID NO: 228          moltype = AA  length = 448
FEATURE                 Location/Qualifiers
REGION                  1..448
                        note = Synthetic zalifrelimab heavy chain
source                  1..448
                        mol_type = protein
                        organism = synthetic construct
SEQUENCE: 228
EVQLVESGGG LVKPGGSLRL SCAASGFTFS SYSMNWVRQA PGKGLEWVSS ISSSSSYIYY  60
ADSVKGRFTI SRDNAKNSLY LQMNSLRAED TAVYYCARVG LMGPFDIWGQ GTMVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKRVEPKS CDKTHTCPPC PAPELLGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSREEMT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                   448

SEQ ID NO: 229          moltype = AA  length = 214
FEATURE                 Location/Qualifiers
REGION                  1..214
                        note = Synthetic zalifrelimab light chain
source                  1..214
                        mol_type = protein
                        organism = synthetic construct
SEQUENCE: 229
EIVLTQSPGT LSLSPGERAT LSCRASQSVS RYLGWYQQKP GQAPRLLIYG ASTRATGIPD  60
RFSGSGSGTD FTLTITRLEP EDFAVYYCQQ YGSSPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 230          moltype = AA  length = 118
FEATURE                 Location/Qualifiers
REGION                  1..118
                        note = Synthetic zalifrelimab variable heavy chain
source                  1..118
                        mol_type = protein
                        organism = synthetic construct
SEQUENCE: 230
EVQLVESGGG LVKPGGSLRL SCAASGFTFS SYSMNWVRQA PGKGLEWVSS ISSSSSYIYY  60
ADSVKGRFTI SRDNAKNSLY LQMNSLRAED TAVYYCARVG LMGPFDIWGQ GTMVTVSS    118

SEQ ID NO: 231          moltype = AA  length = 107
FEATURE                 Location/Qualifiers
REGION                  1..107
                        note = Synthetic zalifrelimab variable light chain
source                  1..107
                        mol_type = protein
                        organism = synthetic construct
SEQUENCE: 231
EIVLTQSPGT LSLSPGERAT LSCRASQSVS RYLGWYQQKP GQAPRLLIYG ASTRATGIPD  60
RFSGSGSGTD FTLTITRLEP EDFAVYYCQQ YGSSPWTFGQ GTKVEIK                107
```

-continued

```
SEQ ID NO: 232          moltype = AA  length = 8
FEATURE                 Location/Qualifiers
REGION                  1..8
                        note = Synthetic zalifrelimab heavy chain CDR1
source                  1..8
                        mol_type = protein
                        organism = synthetic construct
SEQUENCE: 232
GFTFSSYS                                                            8

SEQ ID NO: 233          moltype = AA  length = 8
FEATURE                 Location/Qualifiers
REGION                  1..8
                        note = Synthetic zalifrelimab heavy chain CDR2
source                  1..8
                        mol_type = protein
                        organism = synthetic construct
SEQUENCE: 233
ISSSSSYI                                                            8

SEQ ID NO: 234          moltype = AA  length = 11
FEATURE                 Location/Qualifiers
REGION                  1..11
                        note = Synthetic zalifrelimab heavy chain CDR3
source                  1..11
                        mol_type = protein
                        organism = synthetic construct
SEQUENCE: 234
ARVGLMGPFD I                                                        11

SEQ ID NO: 235          moltype = AA  length = 6
FEATURE                 Location/Qualifiers
REGION                  1..6
                        note = Synthetic zalifrelimab light chain CDR1
source                  1..6
                        mol_type = protein
                        organism = synthetic construct
SEQUENCE: 235
QSVSRY                                                              6

SEQ ID NO: 236          moltype =   length =
SEQUENCE: 236
000

SEQ ID NO: 237          moltype = AA  length = 9
FEATURE                 Location/Qualifiers
REGION                  1..9
                        note = Synthetic zalifrelimab light chain CDR3
source                  1..9
                        mol_type = protein
                        organism = synthetic construct
SEQUENCE: 237
QQYGSSPWT                                                           9
```

What is claimed is:

1. A method for determining the potency and/or functionality of a tumor infiltrating lymphocyte (TIL) product comprising TIL cells, the method comprising:

(a) measuring interferon gamma (IFN-γ) release from the TIL product by a co-culture assay, wherein the co-culture assay comprises (i) co-culturing TIL cells from the TIL product with U937 target cells, and (ii) detecting IFN-γ released by the TIL cells, wherein the U937 target cells express a major histocompatibility complex (MHC) and the TIL cells express a T cell receptor (TCR), wherein the TIL cells are activated via allogeneic MHC-TCR engagement between the MHC of the U937 target cells and the TCR of the TIL cells during the co-culture assay;

(b) measuring IFN-γ release from the TIL product by a bead-based assay; and (c) measuring, using a flow cytometry assay, $LAG3^+$ cell content, $KLRG1^+$ cell content, the sum of $CD4^+$ cell content and $CD8^+$ cell content, total viable TCM and TEM cell population, and $CD45^+/CD3^+$ cell content of the TIL product.

2. The method of claim 1, wherein the bead-based assay comprises stimulating TIL cells from the TIL product with an anti-CD3 antibody, an anti-CD28 antibody, and/or an anti-CD137 antibody, and detecting IFN-γ released by the TIL cells.

3. The method of claim 1, wherein the co-culture assay for IFN-γ release comprises the steps of:

a) co-culturing the U937 target cells with the TIL cells to provide a co-culture;

b) extracting supernatant from the co-culture; and c) assessing the supernatant for IFN-γ.

4. The method of claim 3, wherein the co-culturing is performed for a time period selected from the group consisting of about 6 hours, about 12 hours, about 18 hours, about 24 hours, about 30 hours, about 36 hours, about 42 hours, and about 48 hours.

5. The method of claim 3, wherein the ratio of TIL cell:U937 target cell is about 15:4, about 15:2, about 15:1, or about 30:1.

6. The method of claim 3, wherein the co-culturing is performed in a cell culture medium comprising IL-2.

7. The method of claim 6, wherein the cell culture medium comprises IL-2 at a concentration of about 300 IU/mL.

8. The method of claim 3, wherein an HLA blocking antibody is added in the co-culture as a negative control.

9. The method of claim 8, wherein the HLA blocking antibody is used at a concentration of about 1-20 μg/mL.

10. The method of claim 1, wherein the TIL product is produced by a method comprising:

(i) performing a first expansion by culturing a first population of TILs in a cell culture medium comprising IL-2 to produce a second population of TILs, wherein the first expansion is performed for about 3-14 days to obtain the second population of TILs;

(ii) performing a second expansion by supplementing the cell culture medium of the second population of TILs with additional IL-2, OKT-3, and antigen presenting cells (APCs), to produce a third population of TILs, wherein the second expansion is performed for about 7-14 days to obtain the third population of TILs, wherein the third population of TILs is a therapeutic population of TILs;

(iii) harvesting the therapeutic population of TILs obtained from step (ii);

(iv) transferring the therapeutic population of TILs from step (iii) to an infusion bag; and (v) cryopreserving the infusion bag.

11. The method of claim 10, wherein steps (a)-(c) are performed after cryopreservation.

12. The method of claim 1, wherein the TIL product comprises CD8+ TILs and CD4+ TILs.

13. The method of claim 1, wherein the co-culture assay for IFN-γ release comprises the steps of:

a) performing at least three different co-cultures of U937 target cells with the TIL cells at different U937 target cell concentrations;

b) extracting supernatants from each of the co-cultures; and c) assessing the supernatants from each of the co-cultures for IFN-γ secreted from the TIL cells to determine the potency of the TIL product.

* * * * *